US012697024B2

(12) United States Patent
Singh et al.

(10) Patent No.: US 12,697,024 B2
(45) Date of Patent: Aug. 4, 2026

(54) METHOD OF AND SYSTEM FOR AUTOMATED MACHINE-ASSISTED DETECTION OF OCULAR DISEASE CONDITIONS IN HUMAN EYES CAPTURED USING VISIBLE ILLUMINATION LIGHT SOURCES AND DIGITAL CAMERA SYSTEMS

(71) Applicant: CorneaCare Inc., Philadelphia, PA (US)

(72) Inventors: Ranjodh Singh, Philadelphia, PA (US); Carl Van Alen Murray, Southhampton, NY (US)

(73) Assignee: CORNEACARE, INC., Philadelphia, PA (US)

( * ) Notice: Subject to any disclaimer, the term of this patent is extended or adjusted under 35 U.S.C. 154(b) by 905 days.

(21) Appl. No.: 17/220,535

(22) Filed: Apr. 1, 2021

(65) Prior Publication Data

US 2022/0313077 A1     Oct. 6, 2022

(51) Int. Cl.
*A61B 3/14* (2006.01)
*A61B 3/00* (2006.01)
(Continued)

(52) U.S. Cl.
CPC ............ *A61B 3/101* (2013.01); *A61B 3/0025* (2013.01); *A61B 3/14* (2013.01); *A61B 5/0022* (2013.01);
(Continued)

(58) Field of Classification Search
CPC ......... A61B 3/101; A61B 3/0025; A61B 3/14; A61B 5/0022; A61B 5/4848;
(Continued)

(56) References Cited

U.S. PATENT DOCUMENTS

| | | | |
|---|---|---|---|
| 4,837,831 A | 6/1989 | Gillick | |
| 5,027,406 A | 6/1991 | Roberts | |

(Continued)

FOREIGN PATENT DOCUMENTS

| | | |
|---|---|---|
| CN | 201986004 U | 9/2011 |
| CN | 204618187 U | 9/2015 |

(Continued)

OTHER PUBLICATIONS

Abdullah Kaya, "Ophthoselfie: Detailed Self-imaging of Cornea and Anterior Segment by Smartphone", Turkish Journal of Ophthalmology, vol. 47, 2017 (pp. 3).

(Continued)

*Primary Examiner* — Mahidere S Sahle
(74) *Attorney, Agent, or Firm* — Thomas J Perkowski ESQ., PC

(57) ABSTRACT

Digital imaging processing system and methods for automatically recognizing ocular diseases including dry eye disease, and other ocular conditions in the eyes of humans by automatically (i) processing 2D in vivo digital images of the human eyes formed, captured and detected using a visible-wavelength operating digital camera system, and (ii) using machine-vision image processing subsystems (e.g. engines) to automatically detect the presence and location of specific objects in the ocular surfaces in the human eye, and confirm that specific conditions have been satisfied during image processing to support automated recognition of a specific ocular disease and other ocular conditions indicative of ocular pathology.

13 Claims, 374 Drawing Sheets

(51) Int. Cl.

| | | |
|---|---|---|
| *A61B 3/10* | (2006.01) | |
| *A61B 5/00* | (2006.01) | |
| *G06V 10/143* | (2022.01) | |
| *G06V 10/75* | (2022.01) | |
| *G06V 40/18* | (2022.01) | |

(52) U.S. Cl.
CPC .......... *A61B 5/4848* (2013.01); *G06V 10/143* (2022.01); *G06V 10/751* (2022.01); *G06V 40/18* (2022.01); *A61B 2576/02* (2013.01); *G06V 2201/03* (2022.01)

(58) Field of Classification Search
CPC ............. A61B 2576/02; G06V 10/143; G06V 10/751; G06V 40/18; G06V 2201/03
USPC ................................................. 351/206, 246
See application file for complete search history.

(56) References Cited

U.S. PATENT DOCUMENTS

| | | | |
|---|---|---|---|
| 5,202,952 | A | 4/1993 | Gillick |
| 5,526,463 | A | 6/1996 | Gillick |
| 5,765,132 | A | 6/1998 | Roberts |
| 5,794,189 | A | 8/1998 | Gould |
| 5,909,666 | A | 6/1999 | Gould |
| 7,403,805 | B2 | 7/2008 | Abreu |
| 7,465,049 | B2 | 12/2008 | Maeda |
| 7,654,957 | B2 | 2/2010 | Abreu |
| 7,897,363 | B2 | 3/2011 | McGrath |
| 8,388,136 | B2 | 3/2013 | Huth |
| 8,594,389 | B2 | 11/2013 | Cohen |
| 8,733,937 | B2 | 5/2014 | Huth |
| 8,820,931 | B2 | 9/2014 | Walsh |
| 8,868,155 | B2 | 10/2014 | Debuc |
| 8,881,254 | B2 | 11/2014 | Applewhite |
| 9,149,182 | B2 | 10/2015 | Walsh |
| 9,795,290 | B2 | 10/2017 | Grenon |
| 9,808,155 | B2 | 11/2017 | Verdooner |
| 9,888,839 | B2 | 2/2018 | Korb |
| 9,898,659 | B2 | 2/2018 | Kanagasingam |
| 9,962,077 | B2 | 5/2018 | Farrer |
| 9,996,555 | B1 | 6/2018 | Malpani |
| 10,016,178 | B2 | 7/2018 | Su |
| 10,129,450 | B2 | 11/2018 | Nabhan |
| 10,165,941 | B2 | 1/2019 | Walsh |
| 10,185,147 | B2 | 1/2019 | Lewis |
| 10,258,309 | B2 | 4/2019 | Su |
| 10,314,486 | B2 | 6/2019 | Wang |
| 10,467,992 | B2 | 11/2019 | Deering |
| 10,468,142 | B1 * | 11/2019 | Abou Shousha ...... G16H 30/20 |
| 10,492,680 | B2 | 12/2019 | Farrer |
| 10,512,396 | B2 | 12/2019 | Grenon |
| 10,527,847 | B1 | 1/2020 | Lewis |
| 10,582,848 | B2 | 3/2020 | Korb |
| 10,984,508 | B2 | 4/2021 | Kim |
| 11,004,565 | B2 | 5/2021 | Abramoff |
| 2010/0097573 | A1 | 4/2010 | Verdooner |
| 2010/0145180 | A1 | 6/2010 | Abreu |
| 2013/0144790 | A1 | 6/2013 | Clements |
| 2014/0129240 | A1 | 5/2014 | Zhang |
| 2015/0116569 | A1 | 4/2015 | Mercado |
| 2015/0141837 | A1 | 5/2015 | Arita |
| 2015/0313462 | A1 | 11/2015 | Reis |
| 2017/0042421 | A1 | 2/2017 | Wallace |
| 2017/0115742 | A1 | 4/2017 | Xing |
| 2017/0188814 | A1 | 7/2017 | Hamrah |
| 2017/0192511 | A1 | 7/2017 | Lawrenson |
| 2017/0265739 | A1 | 9/2017 | Korb |
| 2017/0280992 | A1 | 10/2017 | Huth |
| 2018/0190244 | A1 | 7/2018 | Deering |
| 2018/0344512 | A1 | 12/2018 | Badawi |
| 2019/0090733 | A1 | 3/2019 | Walsh |
| 2019/0110753 | A1 * | 4/2019 | Zhang .................. A61B 3/0025 |
| 2019/0191995 | A1 | 6/2019 | Giovinazzo |

| | | | |
|---|---|---|---|
| 2020/0107719 | A1 | 4/2020 | Schneider |
| 2020/0107720 | A1 | 4/2020 | Xiong |
| 2020/0202529 | A1 * | 6/2020 | Hart ...................... A61B 3/1241 |
| 2020/0405148 | A1 * | 12/2020 | Tran ...................... A61B 3/0016 |
| 2022/0039654 | A1 * | 2/2022 | Fitzgibbons ........... A61B 50/00 |
| 2022/0207729 | A1 * | 6/2022 | Boyd ................... G06V 10/774 |
| 2022/0218198 | A1 * | 7/2022 | Devani ............... A61B 5/4088 |
| 2022/0313077 | A1 | 10/2022 | Singh |

FOREIGN PATENT DOCUMENTS

| | | |
|---|---|---|
| CN | 205163030 U | 4/2016 |
| CN | 107582022 | 1/2018 |
| CN | 107645921 | 1/2018 |
| CN | 305014464 S | 1/2019 |
| CN | 208910212 U | 5/2019 |
| EP | 2312994 | 4/2011 |
| EP | 3164058 A1 | 5/2017 |
| GB | 2442339 | 4/2008 |
| JP | 2002197195 A2 | 7/2002 |
| KR | 101690539 B1 | 12/2016 |
| KR | 20170137726 | 12/2017 |
| WO | 04017825 | 3/2004 |
| WO | 08142697 | 11/2008 |
| WO | 09094587 | 7/2009 |
| WO | 09120543 | 10/2009 |
| WO | 09122114 | 10/2009 |
| WO | 2010009447 A2 | 1/2010 |
| WO | 2010009447 A3 | 1/2010 |
| WO | 2010009450 A1 | 1/2010 |
| WO | 2010118292 A1 | 10/2010 |
| WO | 12061078 | 5/2012 |
| WO | 14072342 | 5/2014 |
| WO | 14144918 A3 | 9/2014 |
| WO | 14144940 A3 | 9/2014 |
| WO | 16004131 | 1/2016 |
| WO | 2016004385 A | 1/2016 |
| WO | 16022215 | 2/2016 |
| WO | 16093750 | 6/2016 |
| WO | 2017031019 A2 | 2/2017 |
| WO | 17054847 | 4/2017 |
| WO | 18127782 | 7/2018 |
| WO | 18191784 | 10/2018 |
| WO | 2019146792 | 8/2019 |
| WO | 2020023959 A1 | 1/2020 |
| WO | 20072994 | 4/2020 |
| WO | 2020176039 A1 | 9/2020 |
| WO | 2020200087 | 10/2020 |
| WO | 2020210891 A1 | 10/2020 |
| WO | 2022212799 A2 | 10/2022 |

OTHER PUBLICATIONS

Amr Elsawy, Mohamed Abdel-Mottaleb, Mohamed Abou-Shousha, "Diagnosis of corneal pathologies using deep learning", SPIE Digital Library, Feb. 9, 2019 (pp. 12).

Aston Zhang, Zachary C. Lipton, Mu Li, Alexander J. Smola, "Dive into Deep Learning," Release 0.14.3, Aug. 11, 2020 (pp. 987).

Behnam Askarian, Fatemehsadat Tabei, Amin Askarian, Jo Woon Chong, "An affordable and easy-to-use diagnostic method for keraconus detection using a smartphone," SPIE Digital Library, Feb. 27, 2018 (pp. 7).

Ben Dickson, "What are artificial neural networks (ANN)?", Techtalks, Aug. 5, 2019 (pp. 9).

Ben Dickson, "What are convolutional neural networks (CNN)?", Techtalks, Jan. 6, 2020 (pp. 13).

Ben Dickson, "What is computer vision?", Techtalks, Jan. 14, 2019 (pp. 9).

Ben Dickson, Techtalks, "Computer vision: Why it's hard to compare AI and human perception", published at https://bdtechtalks. com/2020/08/10/computer-vision-deep-learning-vs-human-perception/, Aug. 10, 2020 (pp. 10).

Bernardo T. Lopes, Ashkan Eliasy, Renato Ambrosio Jr., "Artificial Intelligence in Corneal Diagnosis: Where are we?", Current Ophthalmology Reports (2019) vol. 7, pp. 204-211, Jul. 9, 2019 (pp. 8).

(56)  References Cited

OTHER PUBLICATIONS

Cassie A. Ludwig et al., "The Future of Automated Mobile Eye Diagnosis", Journal of Mobile Technology in Medicine, vol. 5, No. 2 , pp. 44-50, Jul. 2016 (pp. 7).

Christina M. Funke, Judy Borowski, Karolina Stosio, Wieland Brendel, Thomas S. A. Wallis, Matthias Bethge, "The Notorious Difficulty of Comparing Human and Machine Perception", Published on arXiv:2004.09406v3 [cs.CV] Apr. 20, 2020, (pp. 34).

Christopher Kent, Review of Ophthamology, "Dry-Eye Diagnosis: 21st-Century Tools", published in https://www.reviewofophthalmology.com/article/dry-eye-diagnosis . . . , Oct. 8, 2013 (pp. 13).

Clara Llorens-Quintana, Dorota Szczesna-Iskander, Robert Iskander, "Supporting dry eye diagnosis with a new method for non-invasive tear film quality assessment", Optomological Vision Science vol. 96(2), Feb. 2019, (pp. 23).

Devrim Toslak, Damber Thapa, Muhammet Kazim Erol, Yanjun Chen, Xicheng Yao, "Smartphone-based imaging of the corneal endothelium at sub-cellular resolution", Journal Modern Optics, vol. 64, published online https://doi.org/10.1080/09500340.2016.126781, Dec. 25, 2016 (pp. 10).

Eisuke Shimizu, Yoko Ogawa, Hiroyuki Yazu, Naohiko Aketa, Fan Yang, Mio Yamane, Yasunori Sato, Yutaka Kawakami, Kazuo Tsubota, "'Smart Eye Camera': An innovative technique to evaluate tear film breakup time in a murine dry eye disease model", PLOS One, May 9, 2019 (pp. 13).

Ekaterina Sirazitdiinova, Marlies Gijs, Christian J. F. Bertens, Tos T. J. M. Berendschot, Rudy M. M. A. Nuijts, Thomas M. Deserno, "Validation of Computerized Quantification of Ocular, Redness", Dec. 12, 2019 (pp. 13).

Erin Boyle, "How Artificial intelligence Is Primed to Change Opthamology", Opthamology Advisor, May 14, 2021 (pp. 9).

Fei-Fei Li, Justin Johnson, Serena Yeung, "Welcome to CS231n", Stanford University, Apr. 4, 2017 (pp. 48).

Francisco Amparo, Jia Yin, Antonio Di Zazzo, Tulio Abud, Ula V. Jurkunas, Pedram Hamrah, Reza Dana, "Evaluating Changes in Ocular Redness Using a Novel Automated Method", TVST, vol. 6, No. 7, Article 13, Jul. 20, 2017 (pp. 7).

Hillary K. Rono, Andrew Bastawrous, David Macleod, Emmanuel Wanjala, Gian Luca Di Tanna, Helen A Weiss, Matthew J Burton, "Smartphone-based screening for visual impairment in Kenyan school children: a cluster randomised controlled trial", The Lancet, 2018, (pp. 9).

Hung-Yin Lai, Ming-Tse Kuo, Po-Chiung Fang, Chi-Chang Lin, Chun-Chih Chien, Wan-Hua Cho, Alexander Chen, and Ing-Chou Lai, "Tracking the Reflective Light Particles Spreading on the Cornea: An Emerging Assessment for Tear Film Homeostasis", TVST, Jun. 4, 2019 (pp. 9).

Hyeonha Hwang, Hee-Jae Jeon, Jin Choong Yow, Ho Sik Hwang, Euiheon Chung, "Image-Based quantitative analysis of tear film lipid layer thickness for meibomian gland evaluation", BioMedical Engineering Online, vol. 16, Nov. 17, 2017 (pp. 15).

Joanna Mylona, Emmanouil S. Deres, Georgianna-Despoina S. Dere, Ioannis Tsinopolous, Mikes Glynatsis, "The Impact of Internet and Videogaming Addiction on Adolescent Vision: A Review of the Literature", Frontiers in Public Health, 5, 2020 (pp. 6).

J. Daniel Nelson et. al., "TFOS DEWS II Introduction", The Ocular Surface, May 3, 2017 (pp. 7).

James Vincent, "Deep Mind's AI can detect over 50 diseases as accurately as a doctor", The Verge, Aug. 13, 2018 (pp. 7).

Jason Brownlee, "Deep Learning for Computer Vision: Image Classification, Object Detection and Face Recognition in Python", Edition v1.20, Machine Learning Mastery, Jason Brownlee, 2020 (pp. 563).

Jason Brownlee, "Deep Learning With Python: Develop Deep Learning Models on Theano and TensorFlow Using Keras", Jan. 2020 (pp. 266).

Jeannine Ditas, Nan Ma, Yuxuan Zhang, Denise Assmann, Marco Neumaier, Hella Riede. Einar Karu, Jonathan Williams, et al., "Strong impact of wildfires on the abundance and aging of black carbon in the lowermost stratosphere", PNAS, Nov. 26, 2018 (pp. 9).

Jennifer P. Craig et al., "TFOS DEWS II Report Executive Summary", The Ocular Surface, Aug. 2017 (pp. 11).

Jennifer Rayner, "Using the Oculus Keratograph 5M and Jenvis Pro Dry Eye Report to Diagnose Dry Eye", Oculus 2021, Optikgerate GmbH, 2021 (pp. 3).

John Daugman , "How Iris Recognition Works", University of Cambridge, The Computer Laboratory, Jan. 2001 (pp. 10).

John Rodriguez, Patrick Johnston, Keith Lane, George Ousler, "Automated Detection and Enumeration of Corneal Superficial Punctate Keratitis", Investigative Ophthalmology & Visual Science, Jun. 2013, vol. 54, 4341 (pp. 2).

Kara L. Maki, William D. Henshaw, Alex Mcmanus, Richard J. Braun, Dylan M. Chapp, Tobin A. Driscoll, "A model for tear film dynamics during a realistic blink", Journal for Modeling in Opthamology, 2019 (pp. 7).

Katsumi Yabusaki, Reiko Arita, Takanori Yamauchi, "Automated classification of dry eye type analyzing interference fringe color images of tear film using machine learning techniques, Journal for Modeling in Opthamology,". 2019 (pp. 7).

Masatoshi Miyamoto, Takayuki Sassa, Megumi Sawai, Akio Kihara., "Lipid polarity gradient formed by w-hydroxy lipids in tear film prevents dry eye disease", eLIFE, Apr. 7, 2020 (pp. 22).

Michael A. Lemp et al., "Definition and Classification of Dry Eye Disease: Report of the Definition and Classification Subcommittee of the Interntional Dry Eye Workshop", The Ocular Surface, 2007 (pp. 18).

Mikel Aldaba, Alejandro Mira-Agudelo, John Fredy Barrera Ramirez, Carlos Enrique Garcia-Guerra, Jaume Pujol Ramo, "Tear film stability assessment by corneal reflex image degradation", Journal of the Optical Society of America, Mar. 26, 2019, (pp. 6).

Mostafa Langarizadeh, Banafshe Maghsoudi, Navid Nilforushan, "Decision Support System for Age-Related Macular Degeneration Using Convolutional Neural Networks", Iranian Journal of Medical Physics, Mar. 29, 2017 (pp. 8).

Parvin Dibajnia , Mohadaseh Mohammadinia, Maryam Moghadasin, Mohammad Aghazade Amiri, "Tear Film Break-up Time in Bipolar Disorder", Iranian Journal Psychiatry vol. 7, No. 4, Fall 2012 (pp. 3).

Pin-I Fu, Po-Chiung Fang, Ren-Wen Ho, Tsai-Ling Chao, Wan-Hua Cho, Hung-Yin Lai, Yu-Ting Hsiao, Ming-Tse Kuo, "Determination of Tear Lipid Film Thickness Based on a Reflected Placido Disk Tear Film Analyzer", Diagnostics 2020, vol. 10, 353 (pp. 14).

Priyanka Chhadva, Raquel Goldhardt, Anat Galor, "Meibomian gland disease: the role of gland dysfunction in dry eye disease", Ophthalmology, vol. 124 (11 Suppl), Nov. 2017, ( pp. 17).

Raja Narayanan, Baruch Kuppermann, "Corticosteroids and Anti-Complement Therapy in Retinal Diseases", Handbook of Experimenteal Pharmacology, Jan. 2017 (pp. 389).

Raul Martin, "Cornea and anterior eye assessment with plidoo-disc keratoscopy, sli scanning evalution topography, and scheimpflug imaging tomography", Indian Journal of Opthamology, 2018 (pp. 9).

Reiko Arita, Katsumi Yabusaki, Taisuke Hirono, Takanori Yamuachi, Tadashi Ichihashi, Shima Fukuoka, Naoyuki Morishige, "Automated Measurement of Tear Meniscus Height with the Kowa DR-1a Tear Interferometer in Both Healthy Subjects and Dry Eye Patients", Arvo Journals, Apr. 16, 2019 (pp. 10).

Richmond Alake, "6 Months as a Machine Learning/Computer Vision Engineer", Towards Data Science, Sep. 6, 2020, 26 pages.

Sanyukta Chetia, S.R. Nirmala, "Image processing-base model for tortuosity measurement of retinal blood vessels", Journal for Modeling in Opthamology, 2019 (pp. 25).

Shizukah Koh, Chikako Ikeda, Shinya Watanabe, Yoshinori Oie, Takeshi Soma, Hitoshi Watanabe, Naoyuki Maeda, Kohji Nishida, "Effect of non-invasive tear stability assessment on tear meniscus height", Acta Ophthalmology 2015, vol. 93, pp. 135-139 (pp. 5).

Sunpreet S. Arora, Mayank Vatsa, Richa Singh, "Iris Recognition under Alcohol Influence: A Preliminary Study", IEEE, Jan. 2012 (pp. 6).

(56)                    References Cited

OTHER PUBLICATIONS

Tai Yuan Su, Chen Kerh Hwa, Po Hsuan Liu, Ming Hong Wu, David O. Chang, Po Fang Su, Shu Wen Chang, Huihua Kenny Chiang, Journal of Biomedical Optics, "Noncontact detection of dry eye using a custom designed infrared thermal image system", Journal of Biomedical Optics, Apr. 20, 2011 (pp. 7).

Tamir Yedidya, Richard Hartley, Jean-Pierre Guillon, Yogesan Kanagasingam, "Automatic Dry Eye Detection", N. Ayache, S. Ourselin, A. Maeder (Eds.): Miccai 2007, Part I, LNCS 4791, pp. 792-799, Springer-Verlag, Berlin Heidelberg 2007, (pp. 8).

Tim Bezemer, Marc CH. De Groot, Enja Blasse, Maarten J. Ten Berg, Teus H. Kappen, Annelien L. Bredenoord, Wouter W. Van Solinge, Imo E. Hoefer, Saskia Haitjema, "A Human(e) Factor in Clinical Decision Support Systems", Journal of Medical Internet Research, Mar. 19, 2019 (pp. 14).

Tyson N. Kim, Frank Myers, Clay Reber, PJ Loury, Panagiota Loumou, Doug Webster, Chris Echanique, Patrick Li, Jose R Davila, Robi N Maamari, at al., "A Smartphone-Based Tool for Rapid, Portable, and Automated Wide-Field Retinal Imaging", TVST, Oct. 1, 2018 (pp. 15).

Webmd LLC, "Dry Eyes: How Screen Time Parches Your Peepers", Jun. 17, 2019 (pp. 2).

Willem A Van Den Bosch, Ineke Leenders, Paul Mulder, "Topographic anatomy of the eyelids, and the effects of sex and age", British Journal Ophthalmology 1999, vol. 83, pp. 347-352, Mar. 1, 1999 (pp. 6).

Xiaohang Wu, Lixue Liu, Lanqin Zhao, Chong Guo, Ruiyang Li, Ting Wang, Xioanan Yang, Piechen Xie, Yizhi Liu, Haotian Lin, "Application of artificial intelligence in anterior segment ophthalmic diseases: diversity and standardization", Annals of Translational Medicine, 2020 (pp. 12).

Xiaoyue Jiang, Abdenour Hadid, Yanwei Pang, Eric Granger, Xiaoyi Feng (Editors), "Deep Learning in Object Detection and Recognition", Springer, 2019 (pp. 237).

Yeoun Sook Chun, Woong Bae Yoon, Kwang Gi Kim, In Ki Park, "Objective Assessment of Corneal Staining Using Digital Image Analysis", Association for Research in Vision and Ophtalmology Inc., pp. 7896-7903, Oct. 25, 2014 (pp. 8).

Young-Gon Kim, Gyuheon Choi, Heounjeong Go, Yongwon Cho, Hyunna Lee, A-Reum Lee, Beomhee Park, Namkug Kim, "A Fully Automated System Using A Convolutional Neural Network to Predict Renal Allograft Rejection: Extra-validation with Giga-pixel Immunostained Slides", Scientific Reports, Mar. 26, 2019 (pp. 10).

Yue-Fang Dong, Lei-Lei Shi, Wei-Wei Fu, Zhe Zhou, "Design and Implementation of Dry Eye Detection Illumination Imaging System Based on Placido Disc", Elsevier, 2018, (pp. 6).

Yureeda Qazi, Shruti Aggarwal, Pedram Hamrah, National Institutes of Health, "Image-Guided Evaluation and Monitoring of Treatment Response in Patients with Dry Eye Disease", Graefes Archives Clinical Experimental Ophthalmology, Jun. 2014 , 252(6), pp. 857-872, (pp. 30).

Amr Elsawy, Tiarnan D. L. Keenan, Qingyu Chen, Alisa T. Thavikulwat, Sanjeeb Bhandari, Ten Cheer Quek, Jocelyn Hui Lin Goh, Yih- Chung Tham, Ching-Yu Cheng, Emily Y. Chew & Zhiyong Lu, "A deep network DeepOpacityNet for detection of cataracts from color fundus photographs", Communications Medicine (2023), vol. 3, No. 184 (11 Pages).

Article 34 Amendment dated Feb. 23, 2023, filed in International Patent Application No. PCT/US2022/022967—ISR-WO (50 Pages).

Ashish Vaswani, Noam Shazeer, Niki Parmar, Jakob Uszkoreit, Llion Jones, Aidan N. Gomez, Łukasz Kaiser, and Illia Polosukhin, "Attention Is All You Need", 31st Conference on Neural Information Processing Systems (NIPS), 2017, Long Beach, CA, USA (15 Pages).

Benjamin Fassbind, Achim Langenbucher & Andreas Streich, "Cornea topography maps allow ophthalmologists to screen and diagnose cornea", Springer Nature, Scientific Reports, (2023) vol. 13, p. 6566 (9 Pages).

Christine Yue Leonard, "Artificial Intelligence for the Cornea Specialist", published at Review of Ophthalmology, https://www.reviewofophthalmology.com/article/artificial-intelligence-f . . . on Sep. 14, 2022, captured on Jan. 2, 2026, (13 Pages).

Eisuke Shimizu, Yoko Ogawa, Hiroyuki Yazu , Naohiko Aketa, Fan Yang, Mio Yamane, Yasunori Sato, Yutaka Kawakami, and Kazuo Tsubota, "Smart Eye Camera: An innovative technique to evaluate tear film breakup time in a murine dry eye disease model", published in PLOS One on May 9, 2019, vol. 14(5) (13 Pages).

European Search Report dated Jan. 24, 2025, and issued in European Patent Application No. 22782269.9 which was filed as Regional Stage Entry Application from International Patent Application No. PCT/US2022/022967 (11 Pages).

International Search Report (ISR) and Written Opinion (WO) dated Dec. 2, 2022, and issued in International Patent Application No. PCT/US2022/022967(23 Pages).

Reply to Search Opinion/Written Opinion/IPEA and Amended Claims dated Aug. 8, 2025, filed in European Patent Application No. 22782269.9 (25 Pages).

Reply to Written Opinion (RW) dated Feb. 26, 2023, filed in International Patent Application No. PCT/US2022/022967 (6 Pages).

Response to the Communication pursuant to Rules 161(2) and 162 EPC dated Nov. 10, 2023, filed in European Patent Application No. 22782269.9 on May 10, 2024 (132 Pages).

Shubo Tian, et al, "Opportunities and challenges for ChatGPT and large language models in biomedicine and health", Briefings in Bioinformatics, Oxford, 2024, vol. 25(1), pp. 1-13 (13 Pages).

Umezawa Akira, "Diagnosing Diseases of the Eye with a Smartphone", Series: Science & Technology, Highlighting Japan, p. 26, Dec. 2021, republished at https://www.gov-online.go.jp/pdf/hlj/20211201/hlj202112_26-27_Diagnosing_Diseases_of_the_Eye_with_a_Smartphone.pdf, captured on Jan. 2, 2026 (26 Pages).

Xiaohang Wu, Lixue Liu, Lanqin Zhao, Chong Guo, Ruiyang Li, Ting Wang, Xiaonan Yang, Peichen Xie, Yizhi Liu, and Haotian Lin, "Application of artificial intelligence in anterior segment ophthalmic diseases: diversity and standardization", Annals of Translational Medicine, Apr. 2020, vol. 8(11) p. 714 (12 Pages).

* cited by examiner

Tear film:

Lipid Layer
(Meibomian glands)

Aqueous Layer
(Lacrimal glands)

Mucin Layer
(Epithelial cells)

Lacrimal
gland

Meibomian
glands

Goblet cells
(Conjunctiva)

SOME COMMON SYMPTOMS OF DRY EYE DISEASE

| Image modalities | Image features | Application |
|---|---|---|
| 1A | Slit light | Catarcat detection and grading |
| 1B  1C | Slit-lamp images  Diffuse light | Conjunctival hyperemia grading  Catarcat detection and grading  High intraocular pressure detection  Identification, localization of conjunctiva, cornea and lens diseases |
| 1D | Retro-illumination | Posterior capsule opacification progress prediction |
| 1E | AS-OCT images | Angle-closure detection |
| 1F | Tear film layer interference images | Tear Film Lipid Layer Classification  Dry eye diagnosis |
| 1G | Frontal eye videos after fluorescein instillation | Dry eye detection,  BUT calculation |
| 1H | Retinal fundus images | Cataract grading |
| 1I | Visible wavelength image by digital camera | Corneal arcus and cataract detection |

FIG. 5
(PRIOR ART)

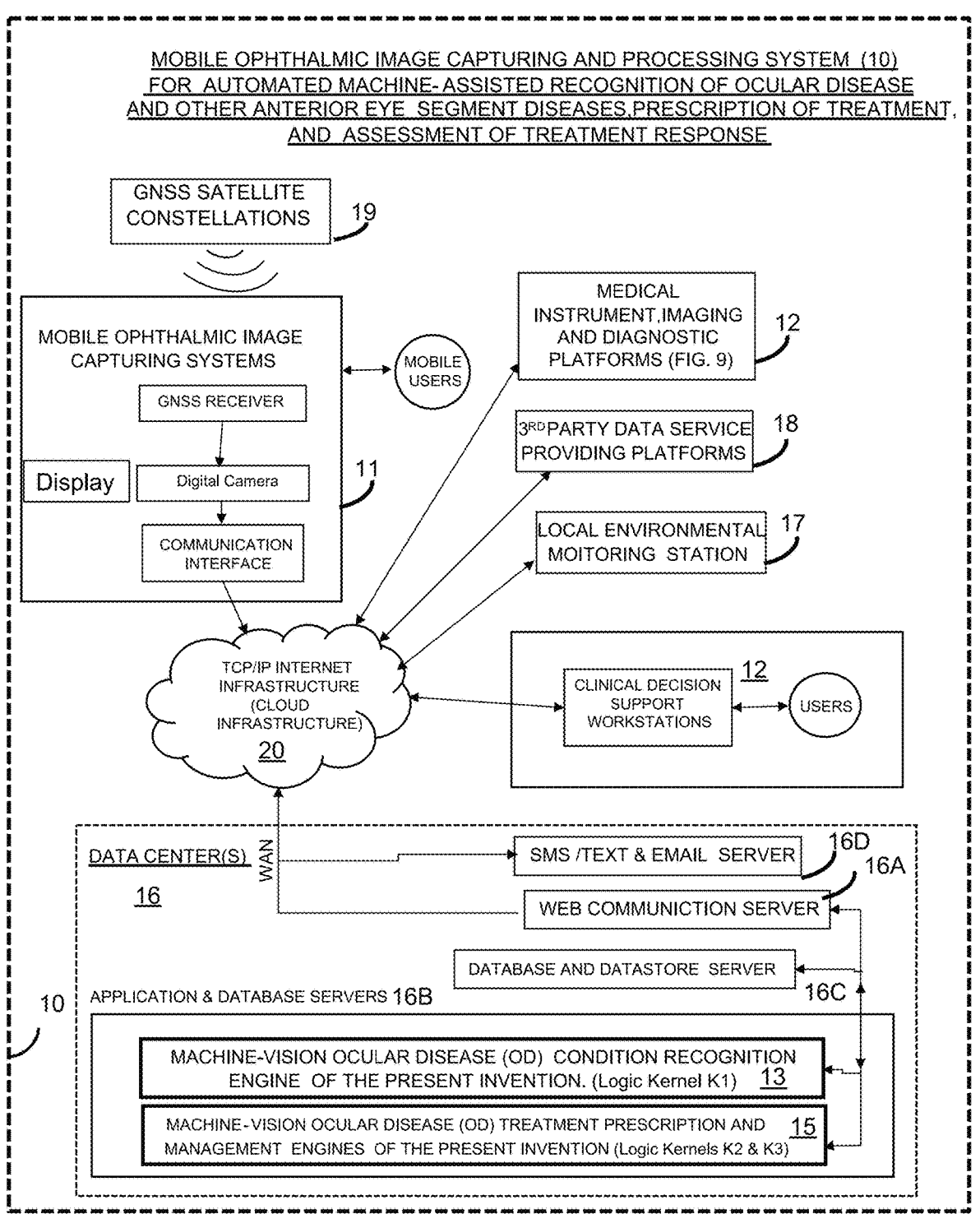

MOBILE OPHTHALMIC IMAGE CAPTURING AND PROCESSING SYSTEM (10)
FOR AUTOMATED MACHINE-ASSISTED RECOGNITION OF OCULAR DISEASE
AND OTHER ANTERIOR EYE SEGMENT DISEASES,PRESCRIPTION OF TREATMENT,
AND ASSESSMENT OF TREATMENT RESPONSE

GNSS SATELLITE CONSTELLATIONS      19

MOBILE OPHTHALMIC IMAGE CAPTURING SYSTEMS

GNSS RECEIVER

Display      Digital Camera      11

COMMUNICATION INTERFACE

MOBILE USERS

MEDICAL INSTRUMENT,IMAGING AND DIAGNOSTIC PLATFORMS (FIG. 9)      12

3RD PARTY DATA SERVICE PROVIDING PLATFORMS      18

LOCAL ENVIRONMENTAL MOITORING STATION      17

TCP/IP INTERNET INFRASTRUCTURE (CLOUD INFRASTRUCTURE) 20

CLINICAL DECISION SUPPORT WORKSTATIONS      12

USERS

DATA CENTER(S)      16

WAN

SMS /TEXT & EMAIL SERVER      16D      16A

WEB COMMUNICTION SERVER

DATABASE AND DATASTORE SERVER      16C

APPLICATION & DATABASE SERVERS 16B

10

MACHINE-VISION OCULAR DISEASE (OD) CONDITION RECOGNITION ENGINE OF THE PRESENT INVENTION. (Logic Kernel K1)      13

MACHINE-VISION OCULAR DISEASE (OD) TREATMENT PRESCRIPTION AND      15 MANAGEMENT ENGINES OF THE PRESENT INVENTION (Logic Kernels K2 & K3)

FIG. 8A

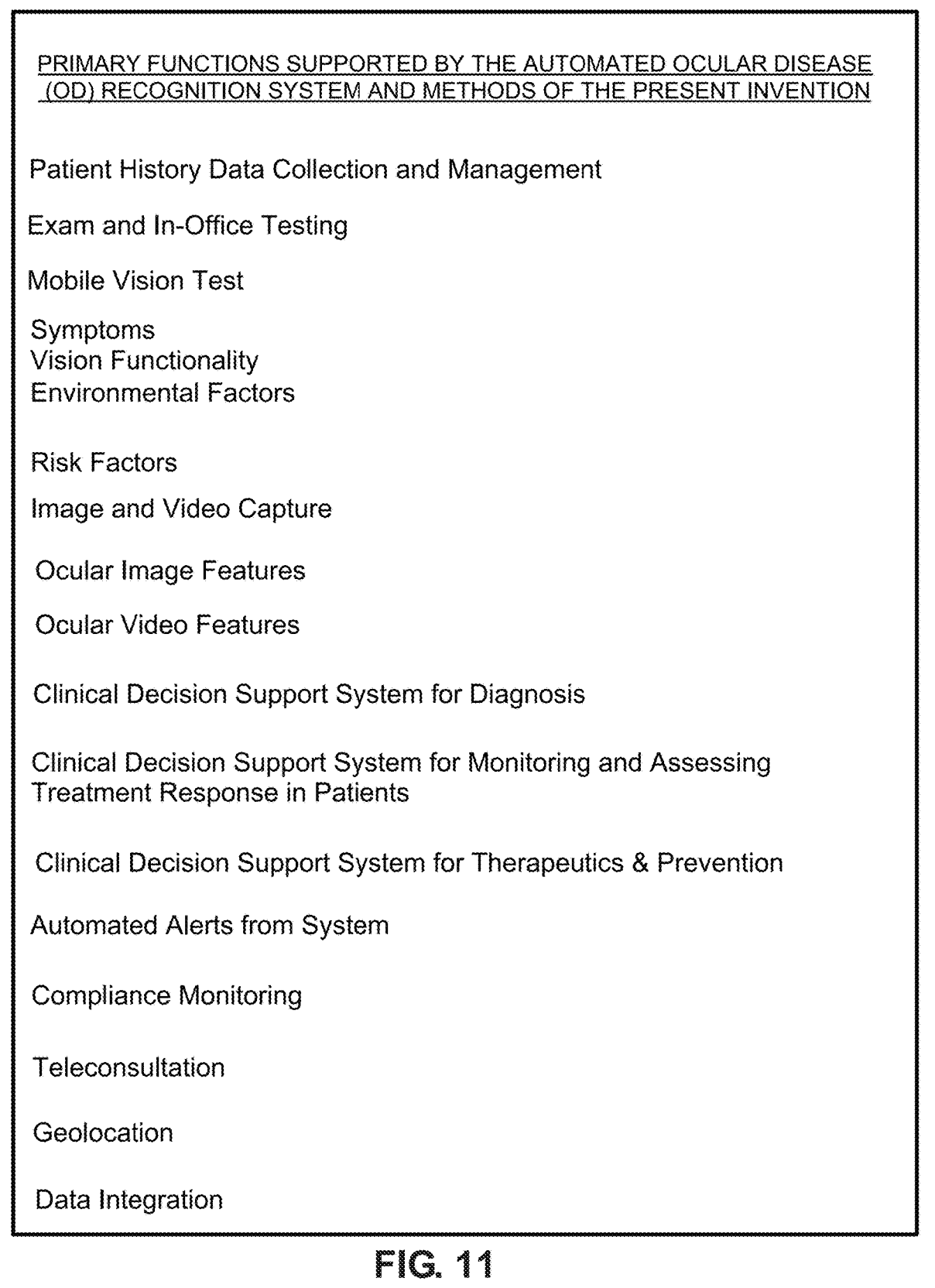

PRIMARY FUNCTIONS SUPPORTED BY THE AUTOMATED OCULAR DISEASE (OD) RECOGNITION SYSTEM AND METHODS OF THE PRESENT INVENTION

Patient History Data Collection and Management

Exam and In-Office Testing

Mobile Vision Test

Symptoms
Vision Functionality
Environmental Factors

Risk Factors

Image and Video Capture

Ocular Image Features

Ocular Video Features

Clinical Decision Support System for Diagnosis

Clinical Decision Support System for Monitoring and Assessing Treatment Response in Patients Clinical Decision Support System for Therapeutics & Prevention Automated Alerts from System Compliance Monitoring Teleconsultation Geolocation Data Integration

FIG. 11

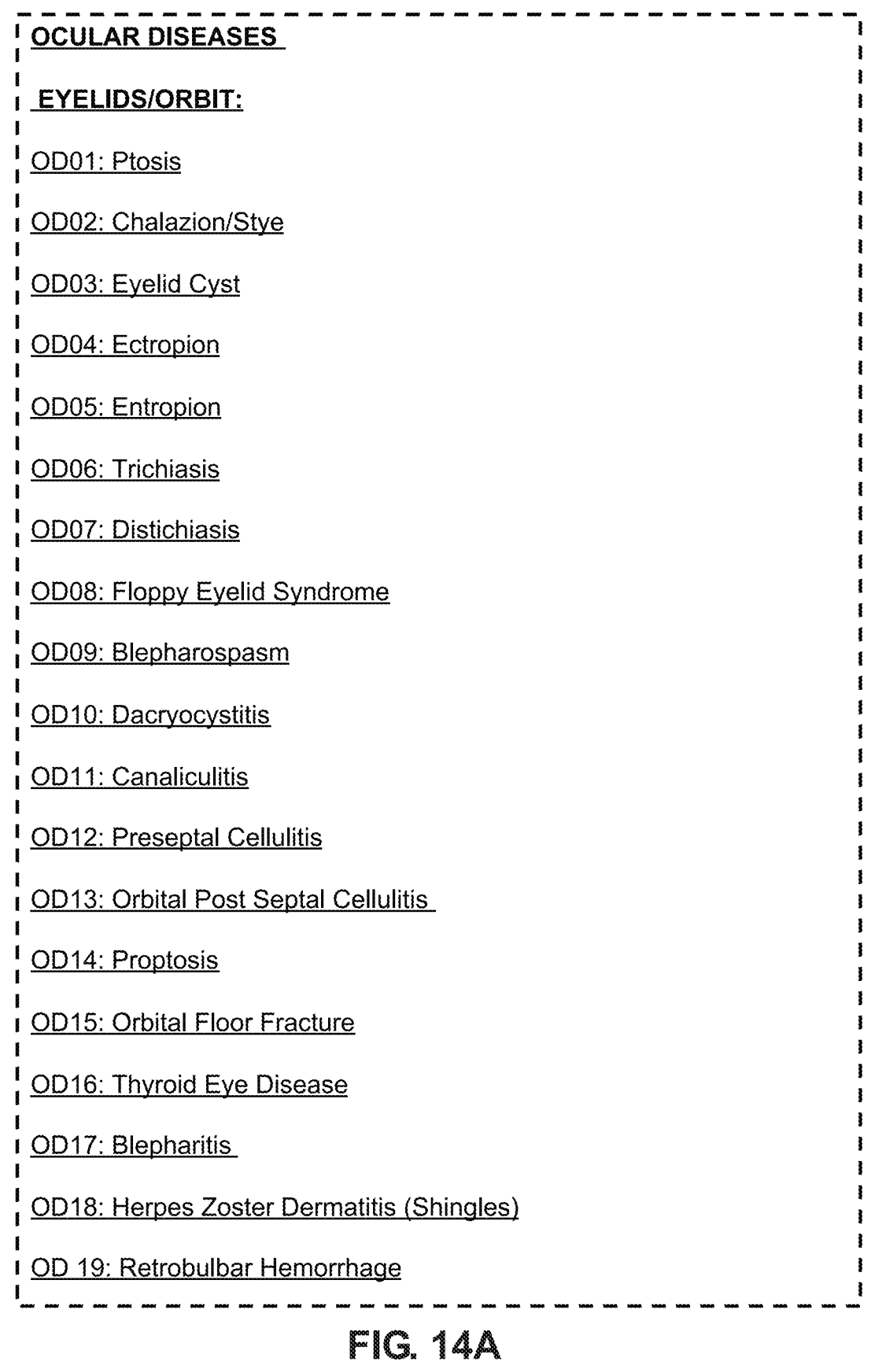

OCULAR DISEASES

EYELIDS/ORBIT:

OD01: Ptosis

OD02: Chalazion/Stye

OD03: Eyelid Cyst

OD04: Ectropion

OD05: Entropion

OD06: Trichiasis

OD07: Distichiasis

OD08: Floppy Eyelid Syndrome

OD09: Blepharospasm

OD10: Dacryocystitis

OD11: Canaliculitis

OD12: Preseptal Cellulitis

OD13: Orbital Post Septal Cellulitis

OD14: Proptosis

OD15: Orbital Floor Fracture

OD16: Thyroid Eye Disease

OD17: Blepharitis

OD18: Herpes Zoster Dermatitis (Shingles)

OD 19: Retrobulbar Hemorrhage

FIG. 14A

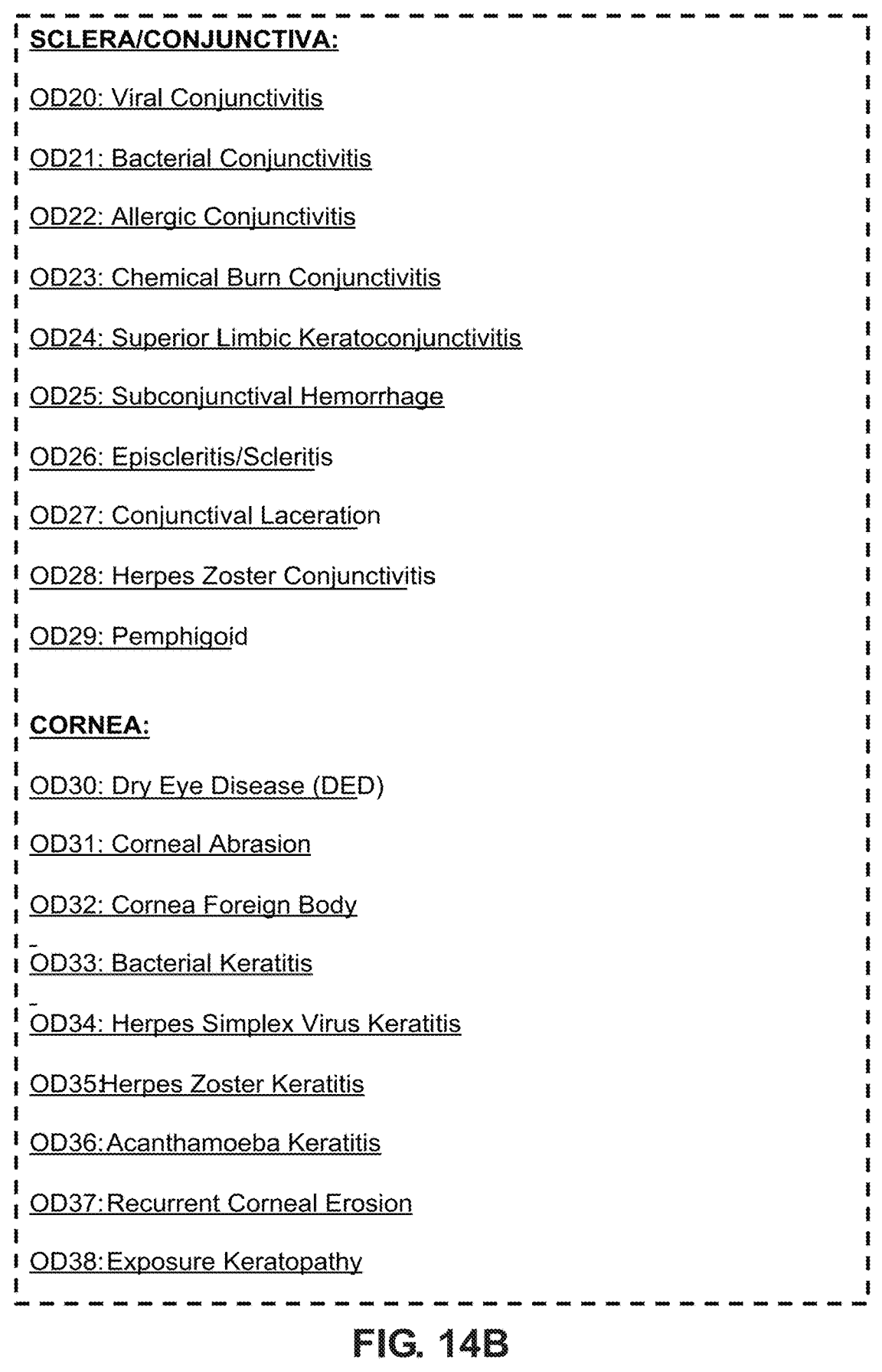

SCLERA/CONJUNCTIVA:

OD20: Viral Conjunctivitis

OD21: Bacterial Conjunctivitis

OD22: Allergic Conjunctivitis

OD23: Chemical Burn Conjunctivitis

OD24: Superior Limbic Keratoconjunctivitis

OD25: Subconjunctival Hemorrhage

OD26: Episcleritis/Scleritis

OD27: Conjunctival Laceration

OD28: Herpes Zoster Conjunctivitis

OD29: Pemphigoid

CORNEA:

OD30: Dry Eye Disease (DED)

OD31: Corneal Abrasion

OD32: Cornea Foreign Body

OD33: Bacterial Keratitis

OD34: Herpes Simplex Virus Keratitis

OD35:Herpes Zoster Keratitis

OD36:Acanthamoeba Keratitis

OD37:Recurrent Corneal Erosion

OD38:Exposure Keratopathy

FIG. 14B

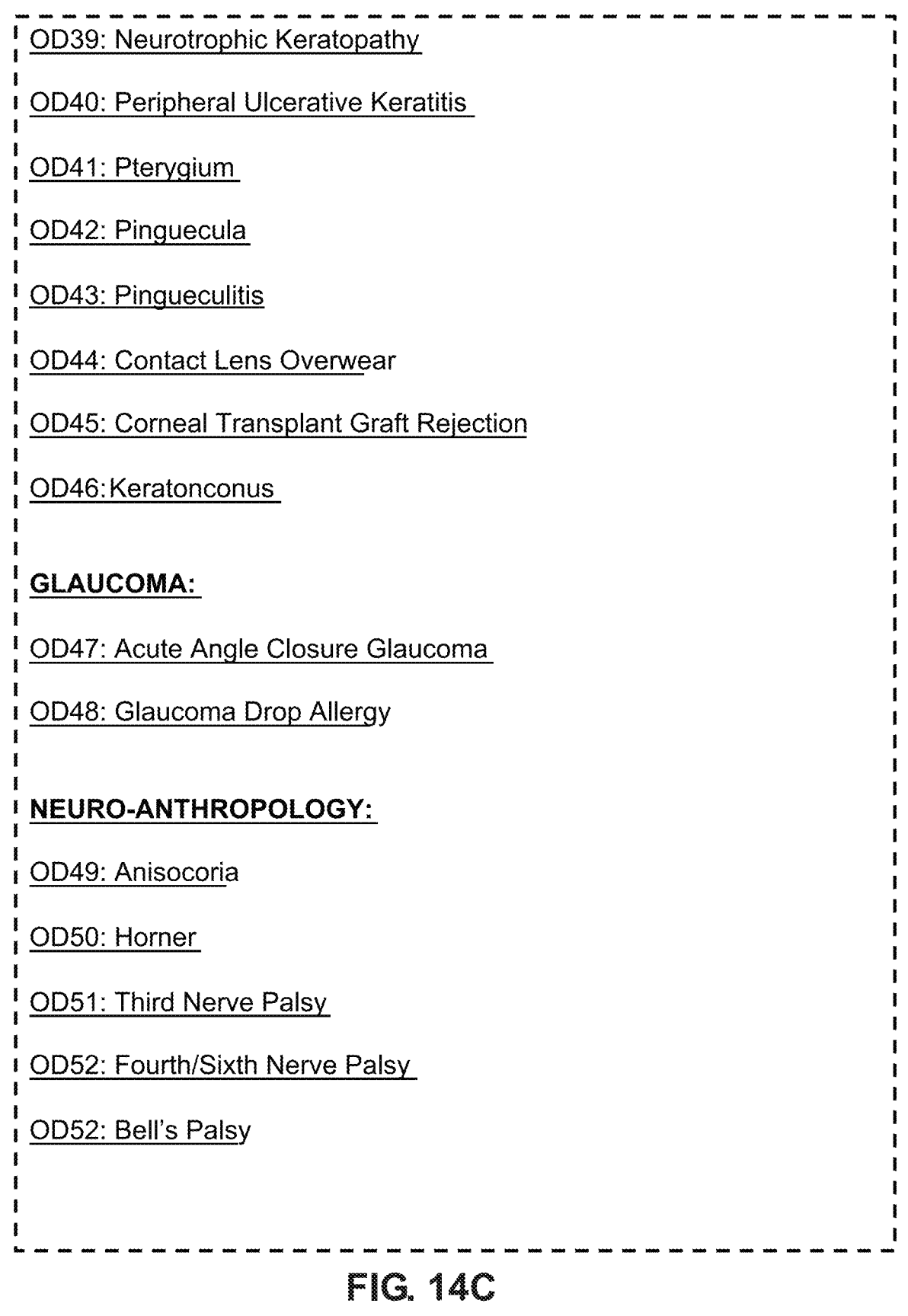

OD39: Neurotrophic Keratopathy

OD40: Peripheral Ulcerative Keratitis

OD41: Pterygium

OD42: Pinguecula

OD43: Pingueculitis

OD44: Contact Lens Overwear

OD45: Corneal Transplant Graft Rejection

OD46: Keratonconus

GLAUCOMA:

OD47: Acute Angle Closure Glaucoma

OD48: Glaucoma Drop Allergy

NEURO-ANTHROPOLOGY:

OD49: Anisocoria

OD50: Horner

OD51: Third Nerve Palsy

OD52: Fourth/Sixth Nerve Palsy

OD52: Bell's Palsy

FIG. 14C

IRIS:

OD54: Iritis

LENS:

OD55: Cataract

OD56: Ophthalmic Post Operative Complications

FIG. 14D

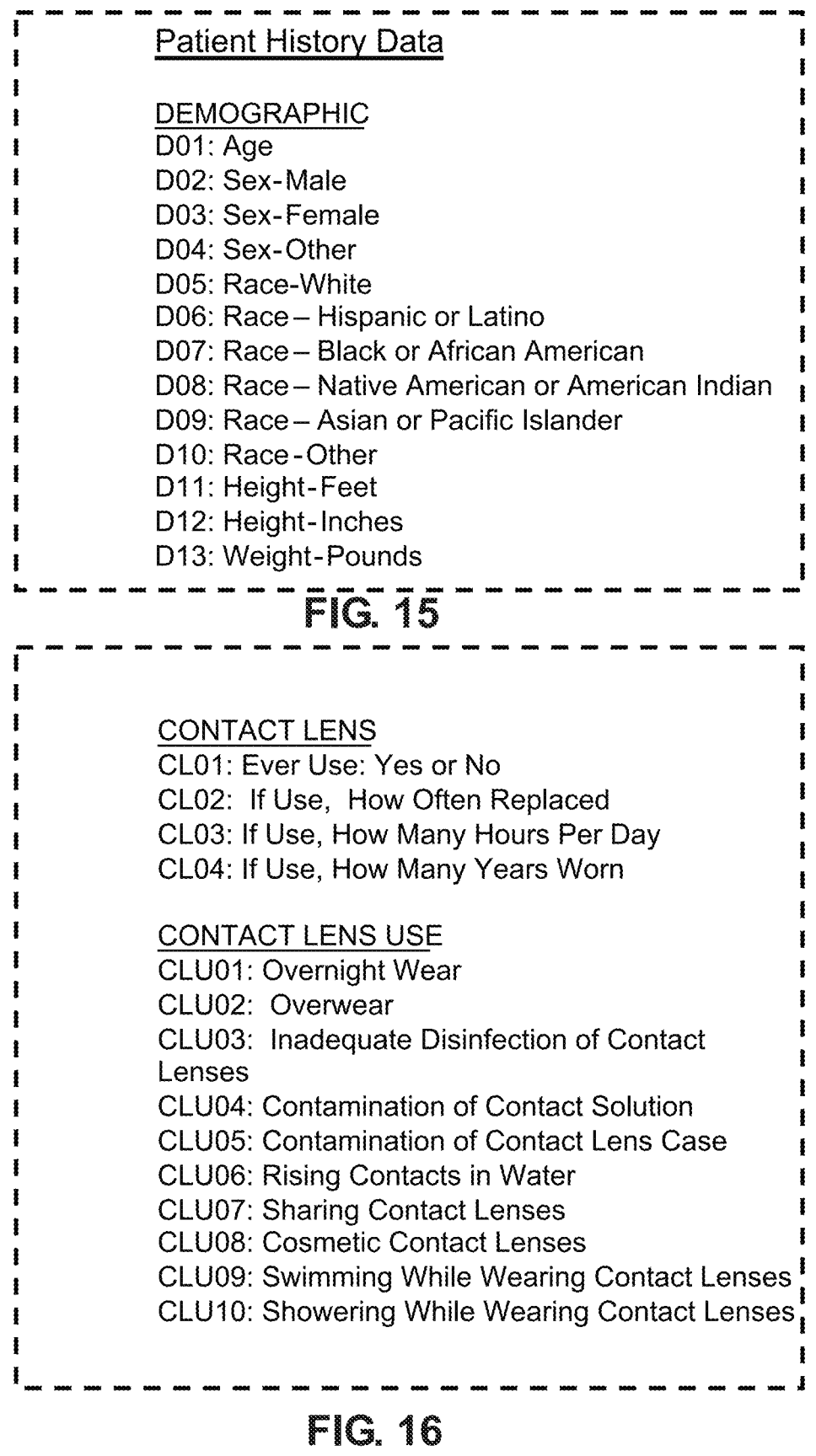

Patient History Data

DEMOGRAPHIC
D01: Age
D02: Sex-Male
D03: Sex-Female
D04: Sex-Other
D05: Race-White
D06: Race – Hispanic or Latino
D07: Race – Black or African American
D08: Race – Native American or American Indian
D09: Race – Asian or Pacific Islander
D10: Race-Other
D11: Height-Feet
D12: Height-Inches
D13: Weight-Pounds

FIG. 15

CONTACT LENS
CL01: Ever Use: Yes or No
CL02:  If Use,  How Often Replaced
CL03: If Use, How Many Hours Per Day
CL04: If Use, How Many Years Worn CONTACT LENS USE
CLU01: Overnight Wear
CLU02:  Overwear
CLU03:  Inadequate Disinfection of Contact Lenses
CLU04: Contamination of Contact Solution
CLU05: Contamination of Contact Lens Case
CLU06: Rising Contacts in Water
CLU07: Sharing Contact Lenses
CLU08: Cosmetic Contact Lenses
CLU09: Swimming While Wearing Contact Lenses
CLU10: Showering While Wearing Contact Lenses

FIG. 16

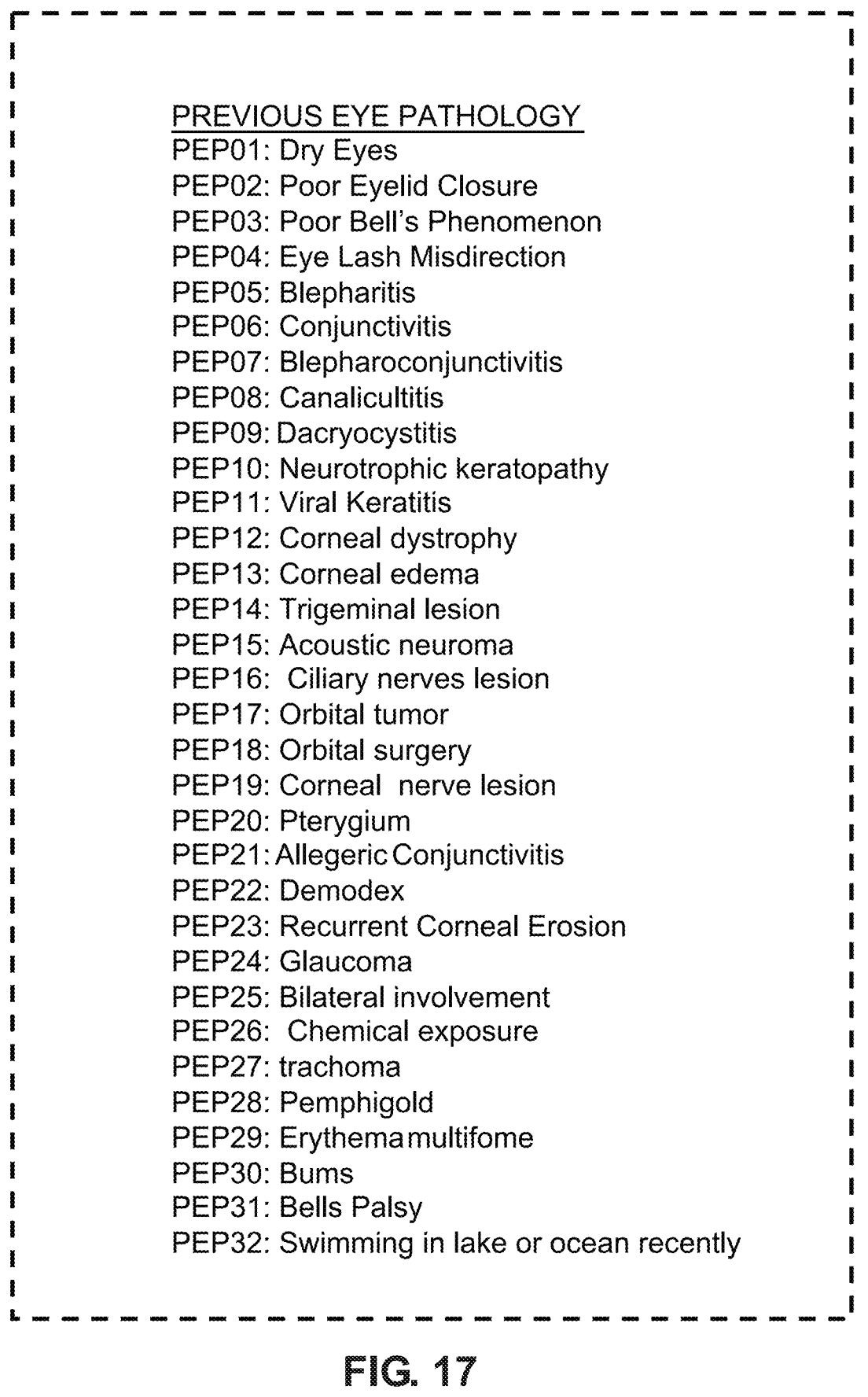

PREVIOUS EYE PATHOLOGY
PEP01: Dry Eyes
PEP02: Poor Eyelid Closure
PEP03: Poor Bell's Phenomenon
PEP04: Eye Lash Misdirection
PEP05: Blepharitis
PEP06: Conjunctivitis
PEP07: Blepharoconjunctivitis
PEP08: Canalicultitis
PEP09: Dacryocystitis
PEP10: Neurotrophic keratopathy
PEP11: Viral Keratitis
PEP12: Corneal dystrophy
PEP13: Corneal edema
PEP14: Trigeminal lesion
PEP15: Acoustic neuroma
PEP16:  Ciliary nerves lesion
PEP17: Orbital tumor
PEP18: Orbital surgery
PEP19: Corneal  nerve lesion
PEP20: Pterygium
PEP21: Allegeric Conjunctivitis
PEP22: Demodex
PEP23: Recurrent Corneal Erosion
PEP24: Glaucoma
PEP25: Bilateral involvement
PEP26:  Chemical exposure
PEP27: trachoma
PEP28: Pemphigold
PEP29: Erythema multifome
PEP30: Bums
PEP31: Bells Palsy
PEP32: Swimming in lake or ocean recently

FIG. 17

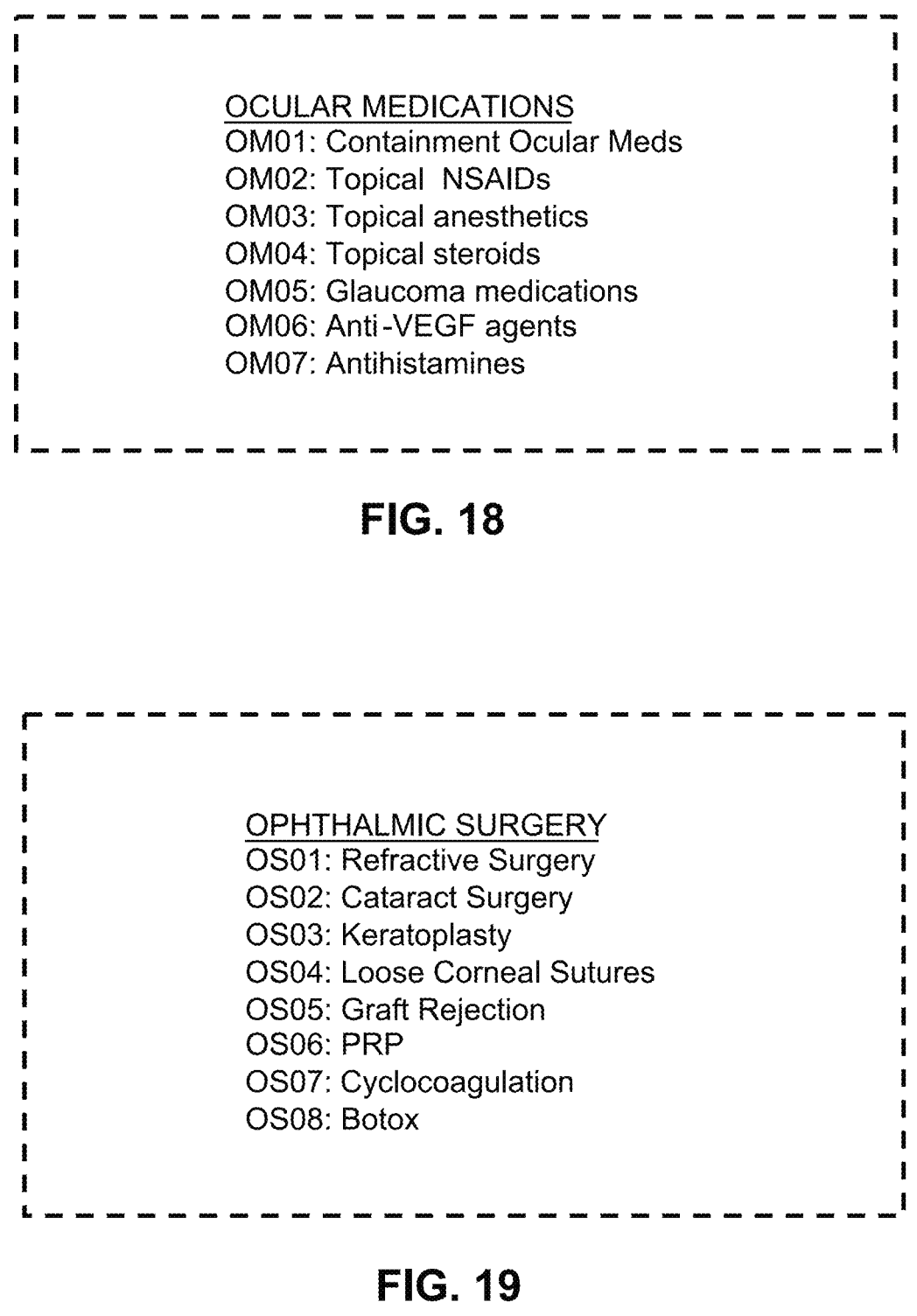

OCULAR MEDICATIONS
OM01: Containment Ocular Meds
OM02: Topical NSAIDs
OM03: Topical anesthetics
OM04: Topical steroids
OM05: Glaucoma medications
OM06: Anti-VEGF agents
OM07: Antihistamines

FIG. 18

OPHTHALMIC SURGERY
OS01: Refractive Surgery
OS02: Cataract Surgery
OS03: Keratoplasty
OS04: Loose Corneal Sutures
OS05: Graft Rejection
OS06: PRP
OS07: Cyclocoagulation
OS08: Botox

FIG. 19

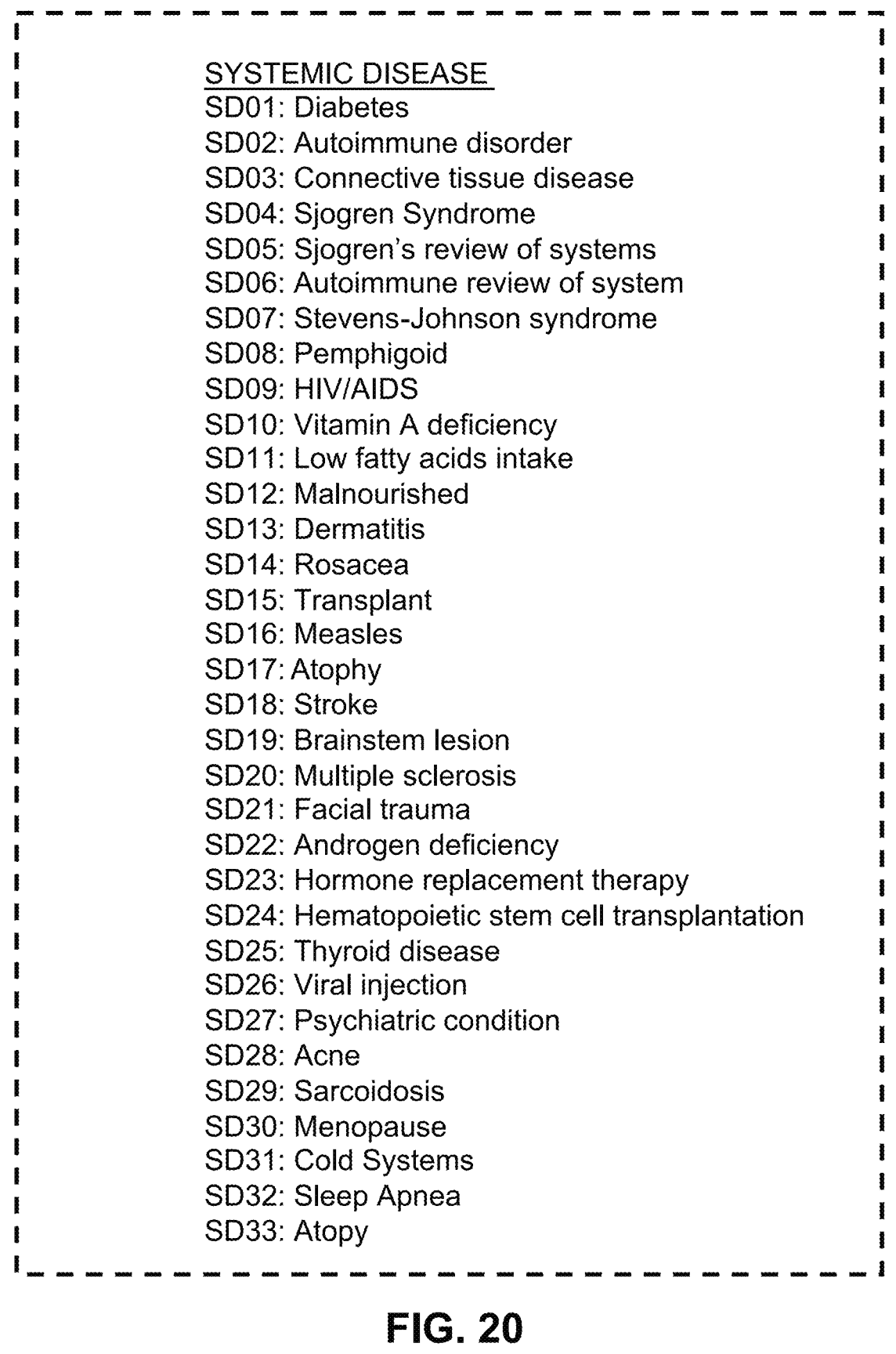

SYSTEMIC DISEASE
SD01: Diabetes
SD02: Autoimmune disorder
SD03: Connective tissue disease
SD04: Sjogren Syndrome
SD05: Sjogren's review of systems
SD06: Autoimmune review of system
SD07: Stevens-Johnson syndrome
SD08: Pemphigoid
SD09: HIV/AIDS
SD10: Vitamin A deficiency
SD11: Low fatty acids intake
SD12: Malnourished
SD13: Dermatitis
SD14: Rosacea
SD15: Transplant
SD16: Measles
SD17: Atophy
SD18: Stroke
SD19: Brainstem lesion
SD20: Multiple sclerosis
SD21: Facial trauma
SD22: Androgen deficiency
SD23: Hormone replacement therapy
SD24: Hematopoietic stem cell transplantation
SD25: Thyroid disease
SD26: Viral injection
SD27: Psychiatric condition
SD28: Acne
SD29: Sarcoidosis
SD30: Menopause
SD31: Cold Systems
SD32: Sleep Apnea
SD33: Atopy

FIG. 20

<u>SYSTEMIC SURGERY</u>
SS01: Heart Surgery
SS02: Joint Surgery
SS03: Endocrine Surgery
SS04: Lung Surgery
SS05: Breast Surgery
SS06: Colorectal Surgery

FIG. 21

<u>SYSTEMIC MEDICATIONS</u>
SM01: Immunosuppressive medication
SM02: Antihistamines
SM03: Antidepressants
SM04: Anxiolytics
SM05: Isotretinoin
SM06: Anticholinergics
SM07: Diuretics
SM08: Beta Blockers
SM09: Oral Contraception

FIG. 22

EYE TRAUMA
ET01: Corneal foreign body
ET02: Corneal abrasion
ET03: Chemical injury
ET04: Burn or thermal injury LIVING SITUATION
LST01: Sleep Under Fan
LST02: Humidified Air at Home
LST03: Humidified Air at Work
LST04: Geolocation: Urban
LST05: Geolocation: Suburban
LST06: Rural
LST07: High Pollution Area
LST08: Dry Climate Area
LST09: Low Humidity Area ENVIRONMENT
EV01: Discomfort in Windy Conditions
EV02: Discomfort in Low Humidity (Very Dry)
EV03:  Discomfort in Air Conditioned Areas
EV04: Discomfort in the Sun
EV05: Discomfort in Crowded Areas
EV06: Discomfort in Urban Areas

FIG. 25

PATIENT VISION FUNCTIONALITY
FT01: Difficulty Reading on Paper
FT02: Difficulty Reading on Computer or Phone
FT03: Difficulty with Car Headlights at Night
FT04: Difficulty Reading Driving Signs
FT05: Difficulty Watching TV
FT06: Difficulty With Work Related Activities
FT07: Difficulty with Household Activities (e.g.
Bills, Cooking, etc.)

FIG. 26

SUMMARY OF RISK FACTORS

TABLE : Risk Factors

| Demographic | Contact lens | Trauma | Surgery | Ocular medications | Systemic medications |
|---|---|---|---|---|---|
| Age > 50 | Overnight wear | Corneal foreign body | Refractive surgery | Contaminated occular meds | Immunosuppresive medication |
| Female | Overwear | Corneal abrasion | Cataract surgery | Topical NSAIDS | Antihistamines |
| Asian race | Inadequate disinfection of contact lenses | Chemical injury | Keratoplasty | Topical anesthetics | Antidepressants |
| Hispanic race | Contamination of contact solution | Burn or thermal injury | Loose corneal sutures | topical steroids | Anxiolytics |
| Menopause | Contamination of contact lens case | | Graft rejection | Glaucoma medications | Isotretinoin |
| | Rinsing contacts in water | | Pan-retinal photocaogulation | Anti-VEGF agents | Anticholinergics |
| | Sharing contact lenses | | Cyclocoagulation | Antihistamines | Diuretics |
| | Cosmetic contact lenses | | Botox | | Beta-blockers |
| | Swimming in contact lenses | | | | Oral contraception |
| | Showering in contact lenses | | | | |

| Eye Disease | | Systemic disease | | Other |
|---|---|---|---|---|
| Dry eyes | Viral Keratitis | Diabetes | Dermatitis | Screen time |
| Poor eyelid closure | Corneal dystrophy | Autoimmune disorder | Rosacea | Pollution |
| Poor Bell's phenomenon | Corneal edema | Connective tissue disease | Transplant | Humidity |
| Eye lash misdirection | Trigeminal lesion | Sjogren Syndrome | Measles | Sick building syndrome |
| Blepharitis | Acoustic neuroma | Stevens-Johnson syndrome | Atopy | Smoking |
| Conjunctivitis | Ciliary nerves lesion | Pemphigoid | Stroke | Alcohol |
| Blepharoconjunctivitis | Orbital tumor | HIV / AIDS | Brainstem lesion | Pregnancy |
| Canaliculitis | Orbital surgery | Vitamin A deficiency | Multiple sclerosis | |
| Dacryocystitis | Corneal nerve lesion | Low fatty acids intake | Facial trauma | |
| Neurotrophic keratopathy | Pterygium | Malnourished | Androgren deficiency | |
| Allergic conjunctivitis | Demodex | Psychiatric condition | Hormone replacement therapy | |
| | | Acne | Heatopoietic stem cell transplantation | |
| | | Sarcoidosis | Thyroid disease | |

FIG. 27

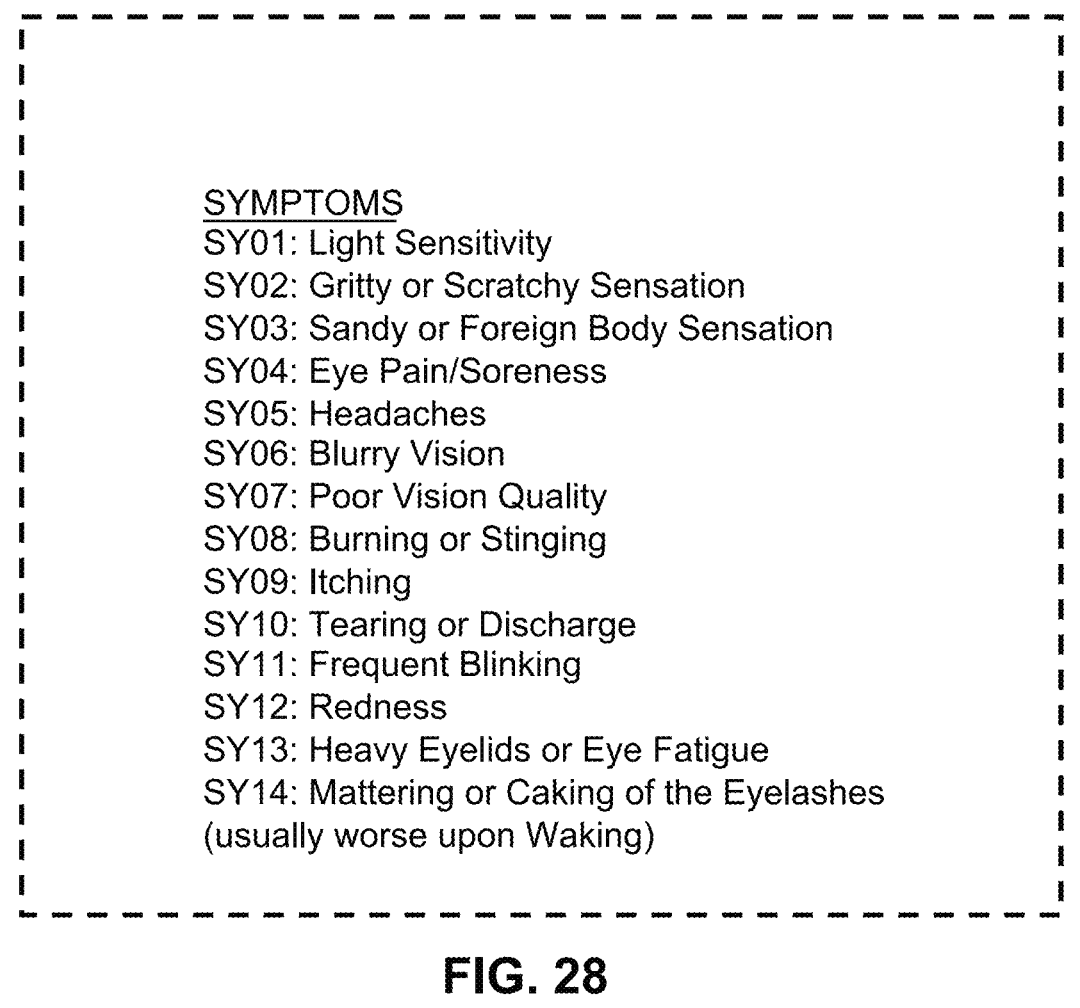

SYMPTOMS
SY01: Light Sensitivity
SY02: Gritty or Scratchy Sensation
SY03: Sandy or Foreign Body Sensation
SY04: Eye Pain/Soreness
SY05: Headaches
SY06: Blurry Vision
SY07: Poor Vision Quality
SY08: Burning or Stinging
SY09: Itching
SY10: Tearing or Discharge
SY11: Frequent Blinking
SY12: Redness
SY13: Heavy Eyelids or Eye Fatigue
SY14: Mattering or Caking of the Eyelashes
(usually worse upon Waking)

FIG. 28

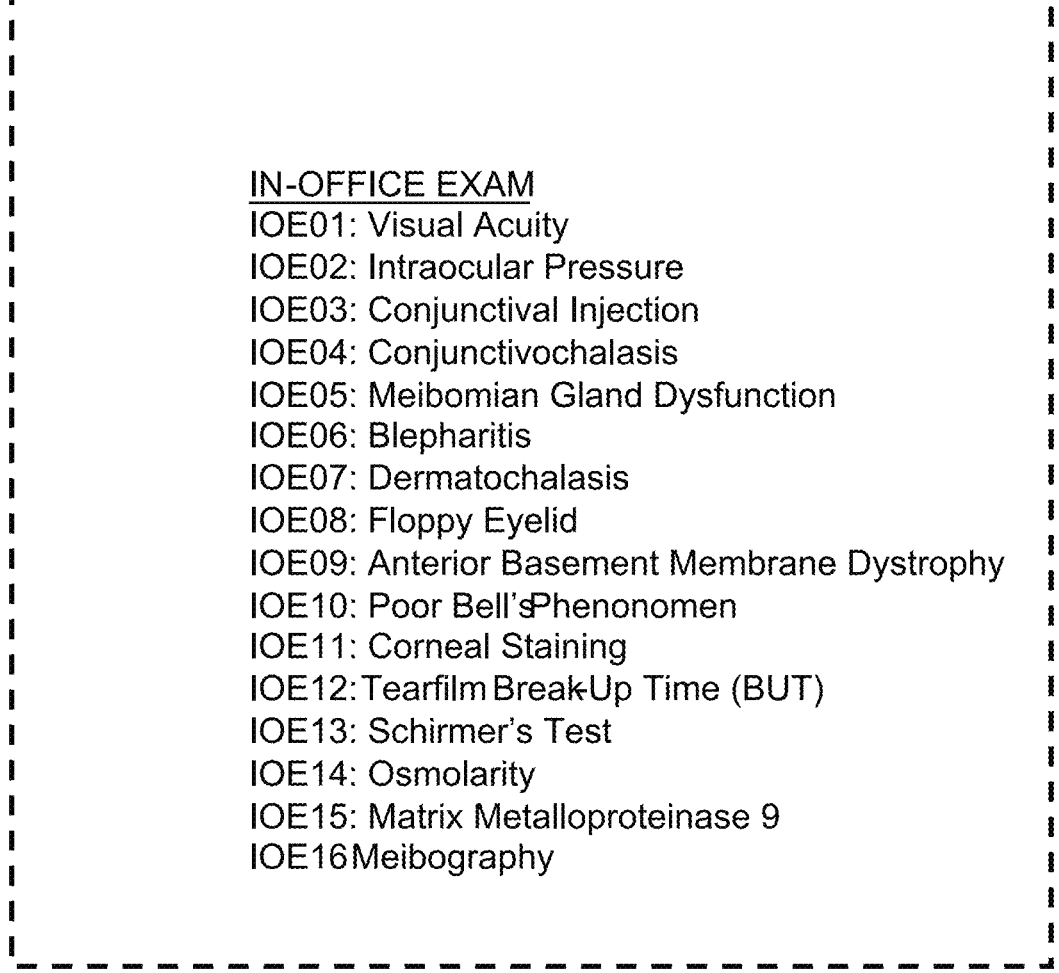

IN-OFFICE EXAM
IOE01: Visual Acuity
IOE02: Intraocular Pressure
IOE03: Conjunctival Injection
IOE04: Conjunctivochalasis
IOE05: Meibomian Gland Dysfunction
IOE06: Blepharitis
IOE07: Dermatochalasis
IOE08: Floppy Eyelid
IOE09: Anterior Basement Membrane Dystrophy
IOE10: Poor Bell'sPhenonomen
IOE11: Corneal Staining
IOE12: Tearfilm Break-Up Time (BUT)
IOE13: Schirmer's Test
IOE14: Osmolarity
IOE15: Matrix Metalloproteinase 9
IOE16 Meibography

FIG. 29

COLLECTING AND PROCESSING EXAM AND IN-OFFICE TESTING DATA

TABLE : Exam and In-office Testing

| | Range | |
|---|---|---|
| Exam | | |
| Vision | 20/20 - No light perception | - |
| Intraocular pressure | 0-99 mmHg | - |
| Conjunctival injection | 0-4+ injection | 0 = No, 1 = any inection |
| Conjunctivochalasis | +/- | +0 = No, 1 = Yes |
| MGD | Mild to Severe | 0 = No, 1 = any MGD |
| Blepharitis | Mild to Severe | 0 = No, 1 = any Bleph |
| Dermatochalasis | +/- | 0 = No, 1 = Yes |
| Floppy eyelids | +/- | 0 = No, 1 = Yes |
| Corneal dystrophy | +/- | 0 = No, 1 = Yes |
| Poor Bell's phenomenon | +/- | 0 = No, 1 = Yes |
| Testing | | |
| Corneal staining | Grade 0-3 | 0 = No staining, 1 = any staining |
| Tearfilm break-up time | <5s: severe; 5-10s: mild-mod; >10s normal | 0 = >10sec; 1 = ≤10sec |
| Schirmer's test | <5s: severe; 5-10s: mild-mod; >10s normal | 0 = >10mm; 1 = ≤10mm |
| Osmolarity test | 0-1000mOsm/L (>308 is abnormal \|\| 302 +/- 8: normal; 315 +/- 11: mild-mod; 336 +/- 22: severe \|\| intereye variability of 8) | 0 = <308, 1 = ≥308 |
| Matrix metalloproteinase 9 | +/- | 0 = No, 1= Yes |
| Meibography | Grade 0 - 4 (0: no MG dropout, 1: 1-25% 2: 25-50, 3: 50-75%, 4: >75%) | 0 = No, 1+ any MGD dropout |

FIG. 30

VISION
V1: Vision

FIGURE : Mobile Vision Test

| Weight | Numbers | Letters |
|---|---|---|
| W₁ | 6 | A |
| W₂ | 5 3 | D K |
| W₃ | 6 2 4 | E T S |
| W₄ | 9 7 5 1 | V B F R |
| W₅ | 7 3 9 4 0 | C H X W U |
| W₆ | 8 4 0 9 7 | Q E C S M |
| W₇ | | |
| W₈ | | |
| W₉ | | |
| W₁₀ | | |

| Weight | Low Vision |
|---|---|
| W₁₁ | Unable to see anything |
| W₁₂ | Able to see light/shadows |
| W₁₃ | Able to see hand motion |
| W₁₄ | Able to count fingers |

COMPLIANCE FACTOR
CP01: Medication
CP02: Image/Video
CP03: Symptoms
CP04: Vision
CP05: Depression

FIG. 33

<u>CAPTURING DIGITAL IMAGES OF HUMAN EYES USING A MOBILE SMARTPHONE CAMERA SYSTEM AND TRANSMITTING TO REAL-TIME OPHTHALMIC IMAGING PROCESSING ENGINE OF THE PRESENT INVENTION FOR PROCESSING BY METHODS M1 THROUGH M48</u>

<u>IMAGE–BASED METHODS (Mi)</u>

M1: Conjunctival Injection
M2: Tear Meniscus Height (TMH)
M3: Meibomian Gland Dysfunction (MGD)
M4: Conjunctivochalasis
M5: Dermatochalasis
M10: Corneal Abrasion
M11: Palpebral
M12: Margin Reflex Distance (MRD)
M13: Scleral Show (SS)
M14: Levator Function (LF)
M15: Contact Lens Over Wear (CLOW)
M16: Corneal Transplant Graft Rejection (CTGR)
M17: Cataract
M18: Viral Conjunctivitis
M19: Bacterial Conjunctivis
M20: Allergic Conjunctivis
M21: Chemical Burn Conjunctivis
M22: Pterygium/Pinguecula
M23: Subconjunctival Hemmorhage
M24: Conjunctival Laceration
M25: Episcleritis/ Scleritis
M26: Superior Limbic Keratoconjunctivitis
M27: Blepharitis
M28: Chalazion/Stye
M29: Eyelid Cysts
M30: Preseptal Cellulitis
M31: Ptosis
M32: Ophthalmoplegia

FIG. 34A

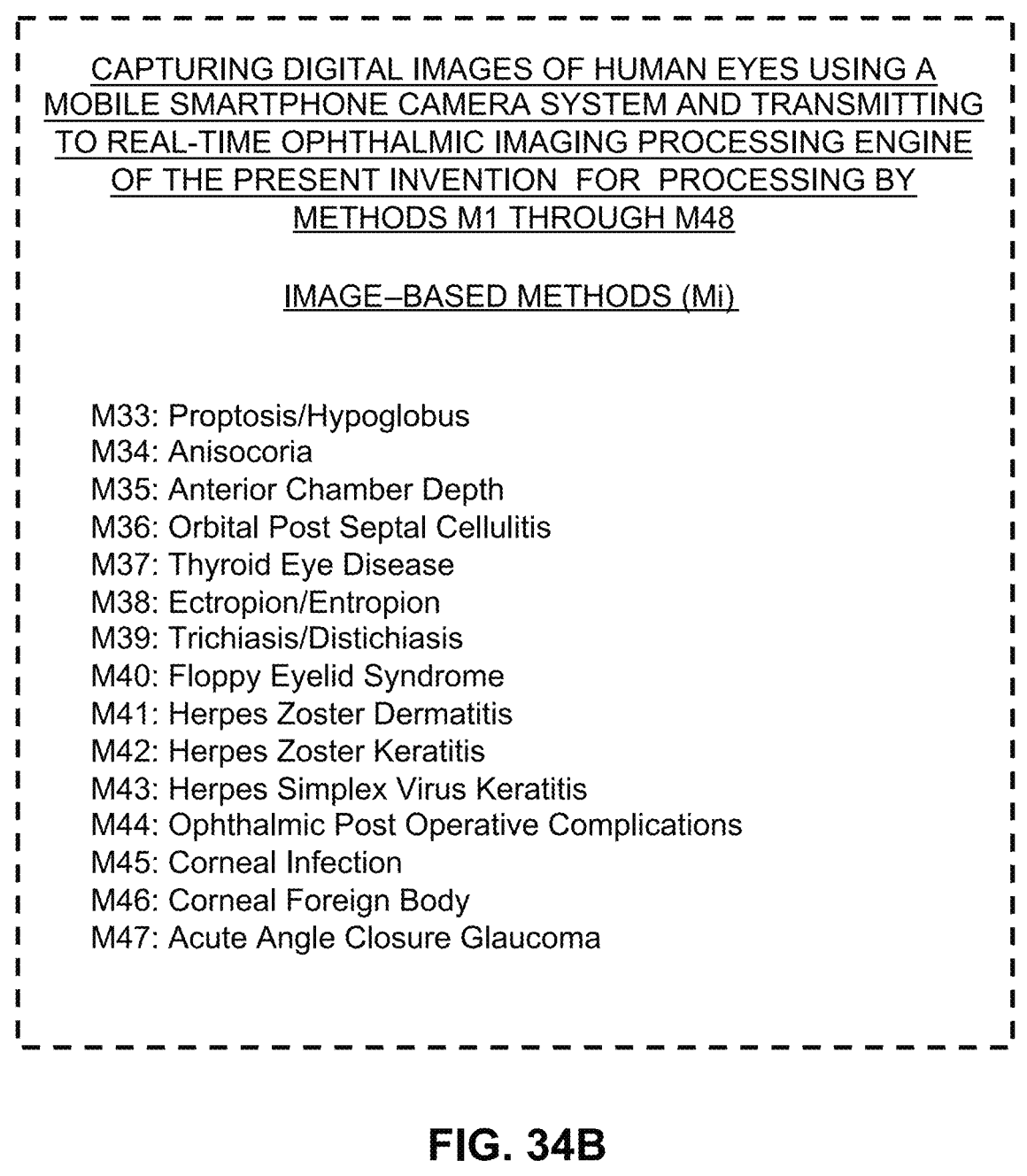

CAPTURING DIGITAL IMAGES OF HUMAN EYES USING A MOBILE SMARTPHONE CAMERA SYSTEM AND TRANSMITTING TO REAL-TIME OPHTHALMIC IMAGING PROCESSING ENGINE OF THE PRESENT INVENTION FOR PROCESSING BY METHODS M1 THROUGH M48

IMAGE-BASED METHODS (Mi)

M33: Proptosis/Hypoglobus
M34: Anisocoria
M35: Anterior Chamber Depth
M36: Orbital Post Septal Cellulitis
M37: Thyroid Eye Disease
M38: Ectropion/Entropion
M39: Trichiasis/Distichiasis
M40: Floppy Eyelid Syndrome
M41: Herpes Zoster Dermatitis
M42: Herpes Zoster Keratitis
M43: Herpes Simplex Virus Keratitis
M44: Ophthalmic Post Operative Complications
M45: Corneal Infection
M46: Corneal Foreign Body
M47: Acute Angle Closure Glaucoma

FIG. 34B

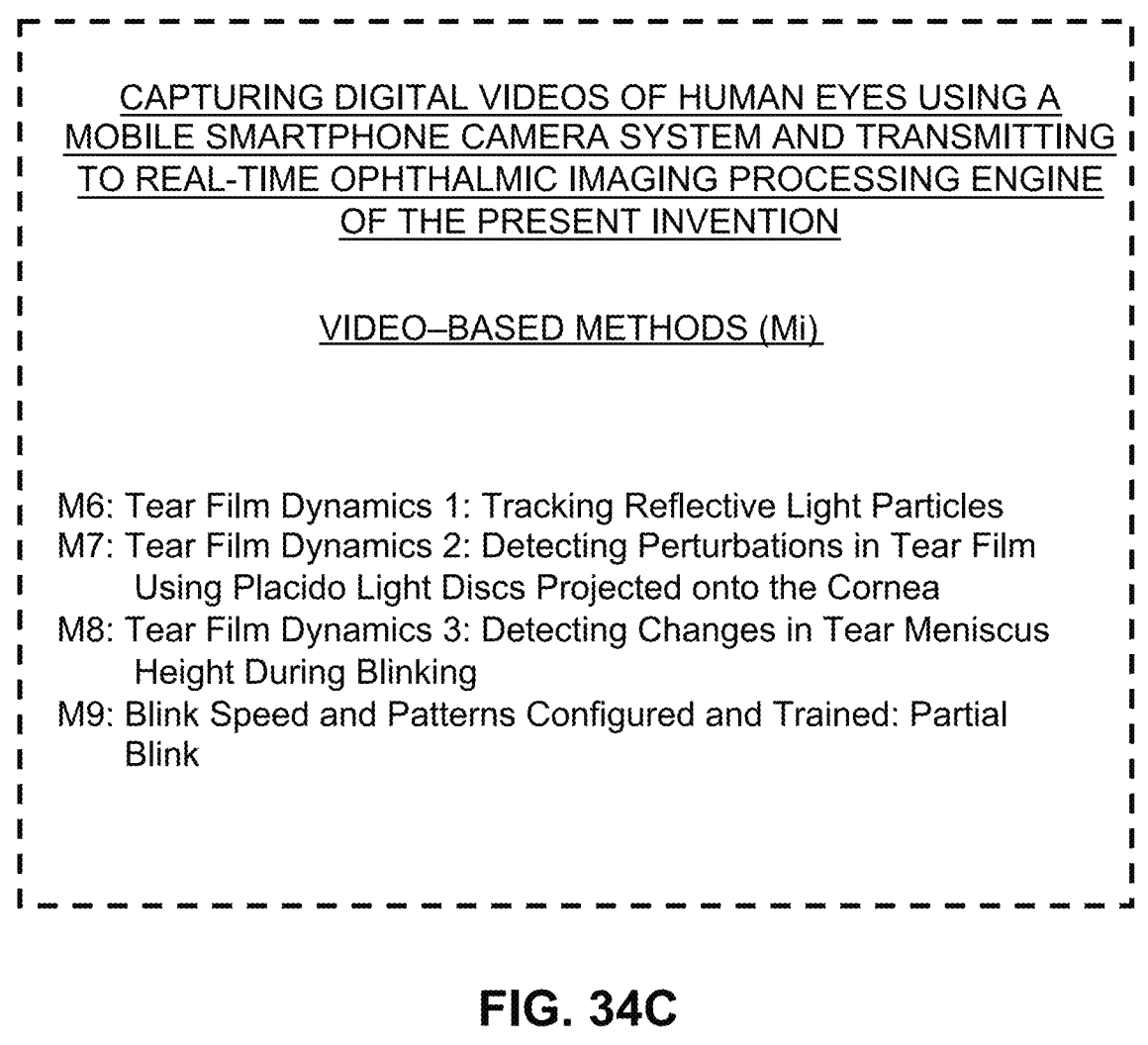

CAPTURING DIGITAL VIDEOS OF HUMAN EYES USING A MOBILE SMARTPHONE CAMERA SYSTEM AND TRANSMITTING TO REAL-TIME OPHTHALMIC IMAGING PROCESSING ENGINE OF THE PRESENT INVENTION

VIDEO-BASED METHODS (Mi)

M6: Tear Film Dynamics 1: Tracking Reflective Light Particles
M7: Tear Film Dynamics 2: Detecting Perturbations in Tear Film Using Placido Light Discs Projected onto the Cornea
M8: Tear Film Dynamics 3: Detecting Changes in Tear Meniscus Height During Blinking
M9: Blink Speed and Patterns Configured and Trained: Partial Blink

FIG. 34C

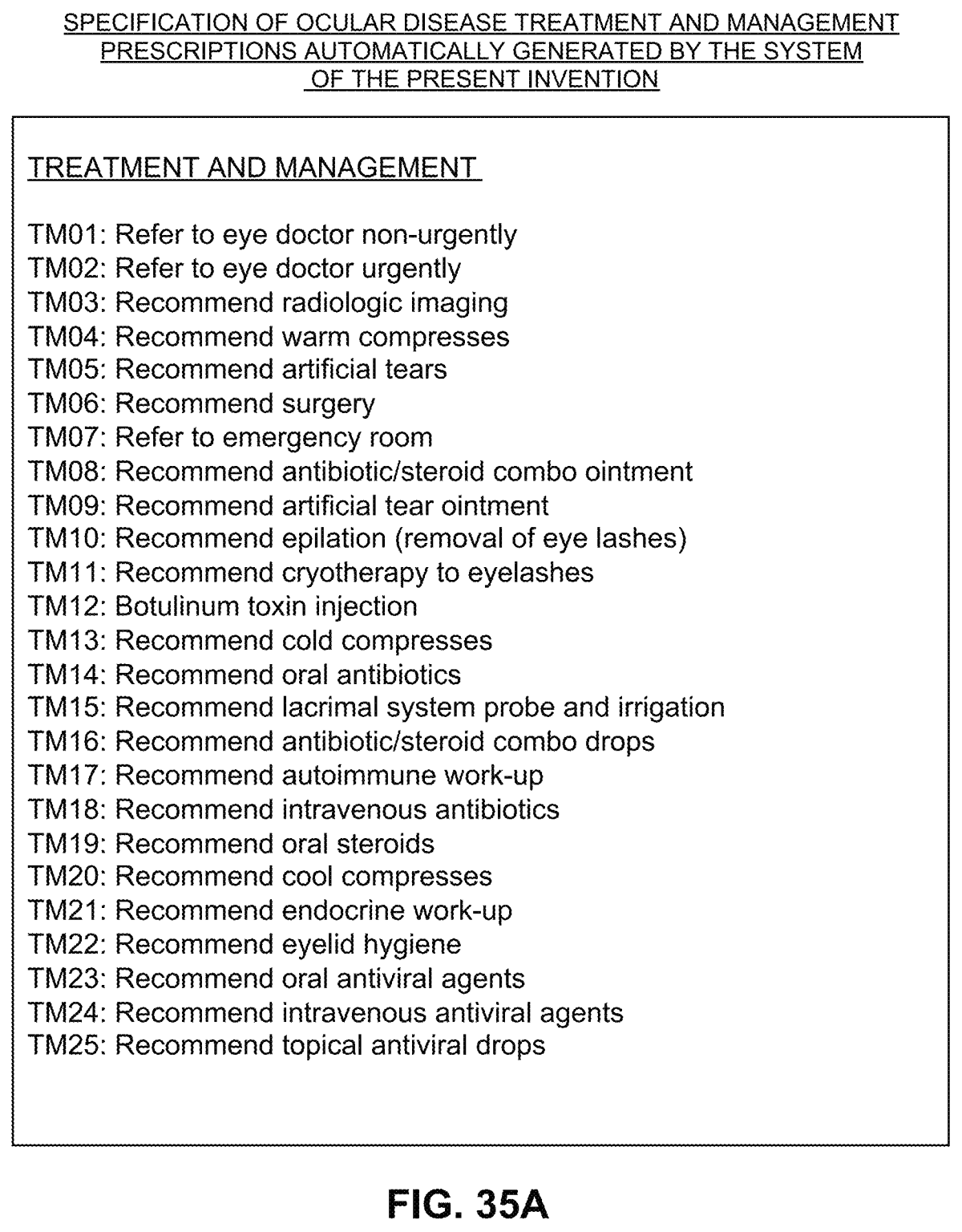

SPECIFICATION OF OCULAR DISEASE TREATMENT AND MANAGEMENT
PRESCRIPTIONS AUTOMATICALLY GENERATED BY THE SYSTEM
OF THE PRESENT INVENTION

TREATMENT AND MANAGEMENT

TM01: Refer to eye doctor non-urgently
TM02: Refer to eye doctor urgently
TM03: Recommend radiologic imaging
TM04: Recommend warm compresses
TM05: Recommend artificial tears
TM06: Recommend surgery
TM07: Refer to emergency room
TM08: Recommend antibiotic/steroid combo ointment
TM09: Recommend artificial tear ointment
TM10: Recommend epilation (removal of eye lashes)
TM11: Recommend cryotherapy to eyelashes
TM12: Botulinum toxin injection
TM13: Recommend cold compresses
TM14: Recommend oral antibiotics
TM15: Recommend lacrimal system probe and irrigation
TM16: Recommend antibiotic/steroid combo drops
TM17: Recommend autoimmune work-up
TM18: Recommend intravenous antibiotics
TM19: Recommend oral steroids
TM20: Recommend cool compresses
TM21: Recommend endocrine work-up
TM22: Recommend eyelid hygiene
TM23: Recommend oral antiviral agents
TM24: Recommend intravenous antiviral agents
TM25: Recommend topical antiviral drops

FIG. 35A

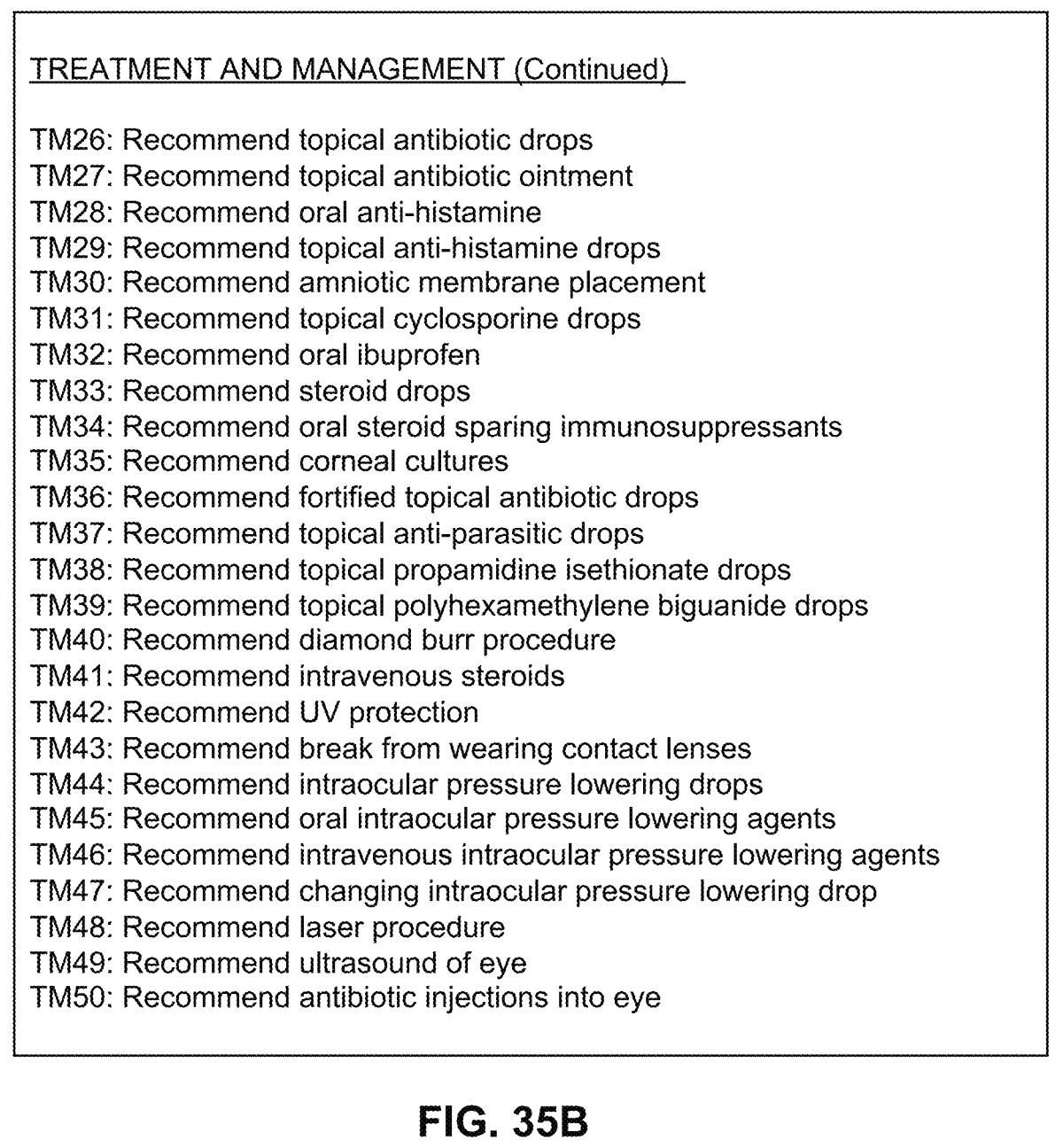

TREATMENT AND MANAGEMENT (Continued)

TM26: Recommend topical antibiotic drops
TM27: Recommend topical antibiotic ointment
TM28: Recommend oral anti-histamine
TM29: Recommend topical anti-histamine drops
TM30: Recommend amniotic membrane placement
TM31: Recommend topical cyclosporine drops
TM32: Recommend oral ibuprofen
TM33: Recommend steroid drops
TM34: Recommend oral steroid sparing immunosuppressants
TM35: Recommend corneal cultures
TM36: Recommend fortified topical antibiotic drops
TM37: Recommend topical anti-parasitic drops
TM38: Recommend topical propamidine isethionate drops
TM39: Recommend topical polyhexamethylene biguanide drops
TM40: Recommend diamond burr procedure
TM41: Recommend intravenous steroids
TM42: Recommend UV protection
TM43: Recommend break from wearing contact lenses
TM44: Recommend intraocular pressure lowering drops
TM45: Recommend oral intraocular pressure lowering agents
TM46: Recommend intravenous intraocular pressure lowering agents
TM47: Recommend changing intraocular pressure lowering drop
TM48: Recommend laser procedure
TM49: Recommend ultrasound of eye
TM50: Recommend antibiotic injections into eye

FIG. 35B

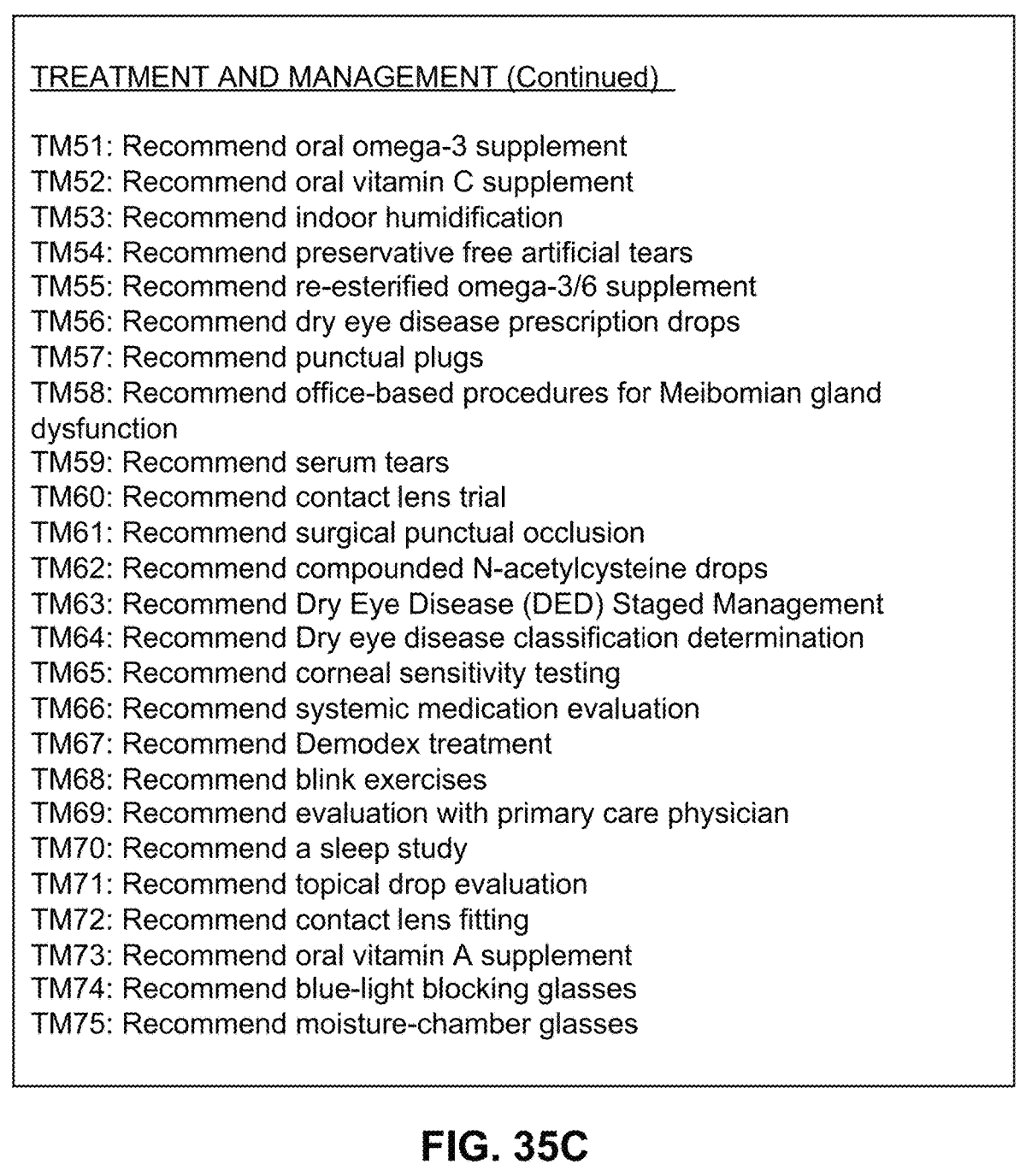

TREATMENT AND MANAGEMENT (Continued)

TM51: Recommend oral omega-3 supplement
TM52: Recommend oral vitamin C supplement
TM53: Recommend indoor humidification
TM54: Recommend preservative free artificial tears
TM55: Recommend re-esterified omega-3/6 supplement
TM56: Recommend dry eye disease prescription drops
TM57: Recommend punctual plugs
TM58: Recommend office-based procedures for Meibomian gland dysfunction
TM59: Recommend serum tears
TM60: Recommend contact lens trial
TM61: Recommend surgical punctual occlusion
TM62: Recommend compounded N-acetylcysteine drops
TM63: Recommend Dry Eye Disease (DED) Staged Management
TM64: Recommend Dry eye disease classification determination
TM65: Recommend corneal sensitivity testing
TM66: Recommend systemic medication evaluation
TM67: Recommend Demodex treatment
TM68: Recommend blink exercises
TM69: Recommend evaluation with primary care physician
TM70: Recommend a sleep study
TM71: Recommend topical drop evaluation
TM72: Recommend contact lens fitting
TM73: Recommend oral vitamin A supplement
TM74: Recommend blue-light blocking glasses
TM75: Recommend moisture-chamber glasses

FIG. 35C

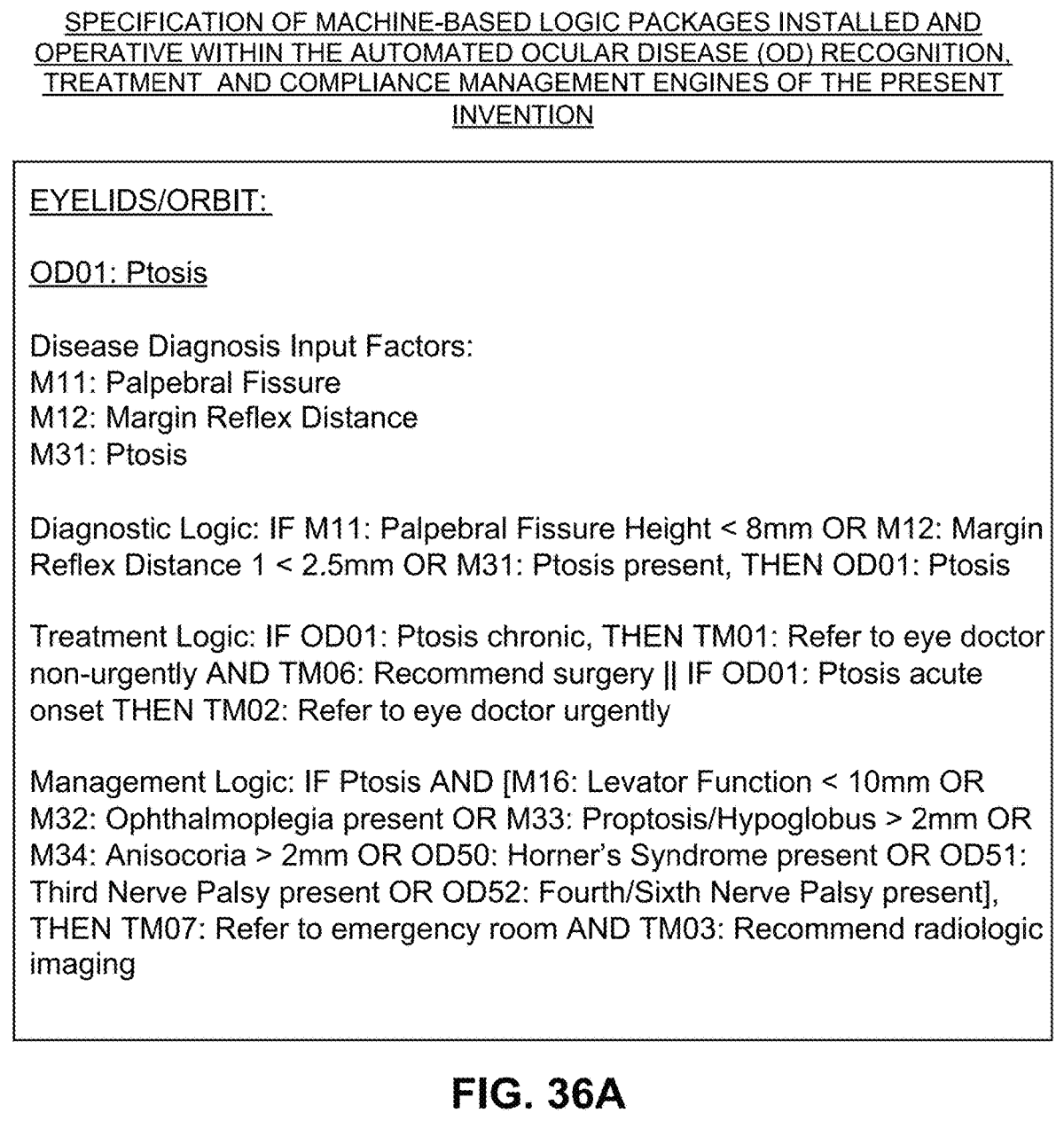

SPECIFICATION OF MACHINE-BASED LOGIC PACKAGES INSTALLED AND OPERATIVE WITHIN THE AUTOMATED OCULAR DISEASE (OD) RECOGNITION, TREATMENT  AND COMPLIANCE MANAGEMENT ENGINES OF THE PRESENT INVENTION

EYELIDS/ORBIT:

OD01: Ptosis

Disease Diagnosis Input Factors:
M11: Palpebral Fissure
M12: Margin Reflex Distance
M31: Ptosis Diagnostic Logic: IF M11: Palpebral Fissure Height < 8mm OR M12: Margin Reflex Distance 1 < 2.5mm OR M31: Ptosis present, THEN OD01: Ptosis Treatment Logic: IF OD01: Ptosis chronic, THEN TM01: Refer to eye doctor non-urgently AND TM06: Recommend surgery || IF OD01: Ptosis acute onset THEN TM02: Refer to eye doctor urgently Management Logic: IF Ptosis AND [M16: Levator Function < 10mm OR M32: Ophthalmoplegia present OR M33: Proptosis/Hypoglobus > 2mm OR M34: Anisocoria > 2mm OR OD50: Horner's Syndrome present OR OD51: Third Nerve Palsy present OR OD52: Fourth/Sixth Nerve Palsy present], THEN TM07: Refer to emergency room AND TM03: Recommend radiologic imaging

FIG. 36A

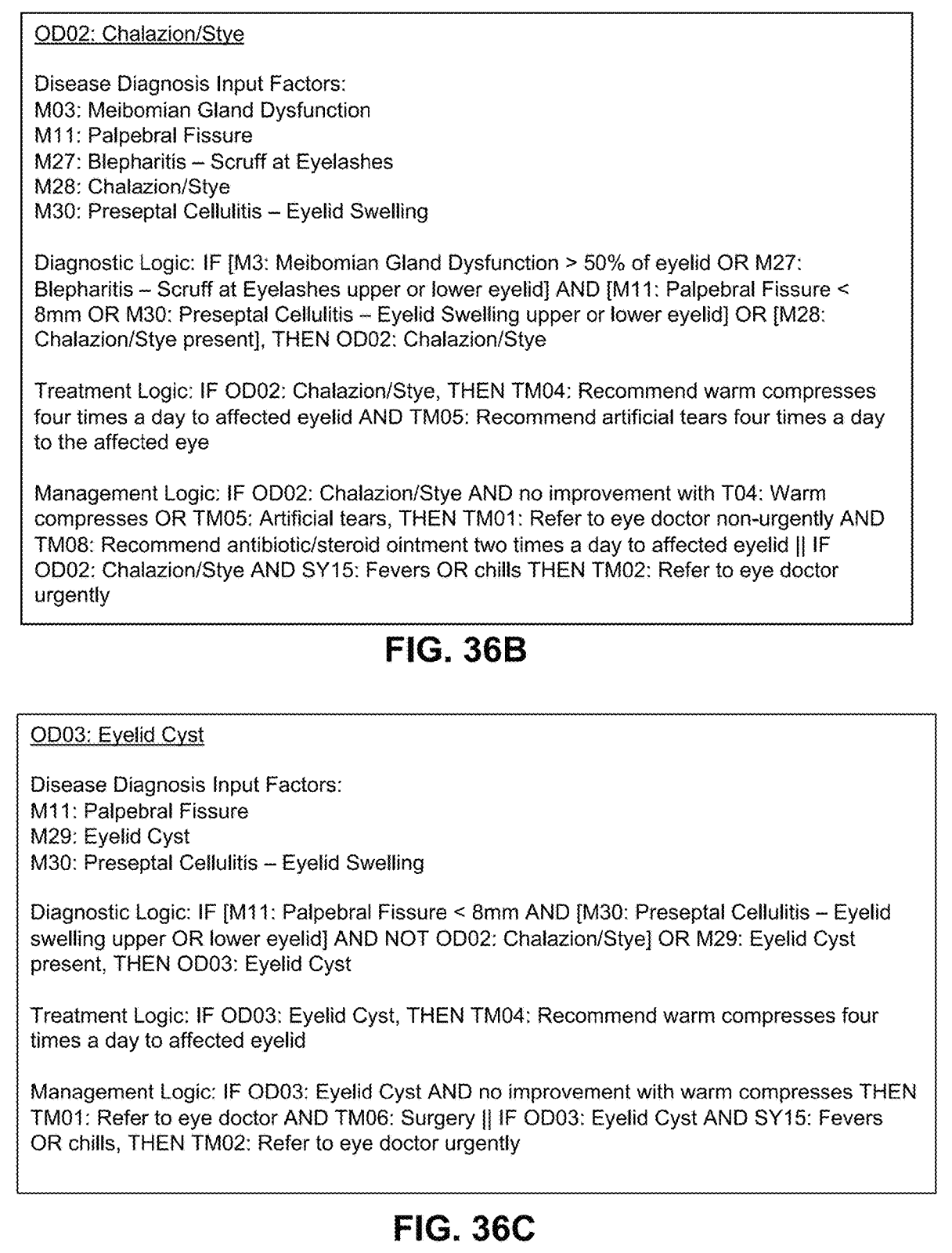

OD02: Chalazion/Stye

Disease Diagnosis Input Factors:
M03: Meibomian Gland Dysfunction
M11: Palpebral Fissure
M27: Blepharitis – Scruff at Eyelashes
M28: Chalazion/Stye
M30: Preseptal Cellulitis – Eyelid Swelling Diagnostic Logic: IF [M3: Meibomian Gland Dysfunction > 50% of eyelid OR M27: Blepharitis – Scruff at Eyelashes upper or lower eyelid] AND [M11: Palpebral Fissure < 8mm OR M30: Preseptal Cellulitis – Eyelid Swelling upper or lower eyelid] OR [M28: Chalazion/Stye present], THEN OD02: Chalazion/Stye Treatment Logic: IF OD02: Chalazion/Stye, THEN TM04: Recommend warm compresses four times a day to affected eyelid AND TM05: Recommend artificial tears four times a day to the affected eye Management Logic: IF OD02: Chalazion/Stye AND no improvement with T04: Warm compresses OR TM05: Artificial tears, THEN TM01: Refer to eye doctor non-urgently AND TM08: Recommend antibiotic/steroid ointment two times a day to affected eyelid || IF OD02: Chalazion/Stye AND SY15: Fevers OR chills THEN TM02: Refer to eye doctor urgently

FIG. 36B

OD03: Eyelid Cyst

Disease Diagnosis Input Factors:
M11: Palpebral Fissure
M29: Eyelid Cyst
M30: Preseptal Cellulitis – Eyelid Swelling Diagnostic Logic: IF [M11: Palpebral Fissure < 8mm AND [M30: Preseptal Cellulitis – Eyelid swelling upper OR lower eyelid] AND NOT OD02: Chalazion/Stye] OR M29: Eyelid Cyst present, THEN OD03: Eyelid Cyst Treatment Logic: IF OD03: Eyelid Cyst, THEN TM04: Recommend warm compresses four times a day to affected eyelid Management Logic: IF OD03: Eyelid Cyst AND no improvement with warm compresses THEN TM01: Refer to eye doctor AND TM06: Surgery || IF OD03: Eyelid Cyst AND SY15: Fevers OR chills, THEN TM02: Refer to eye doctor urgently

FIG. 36C

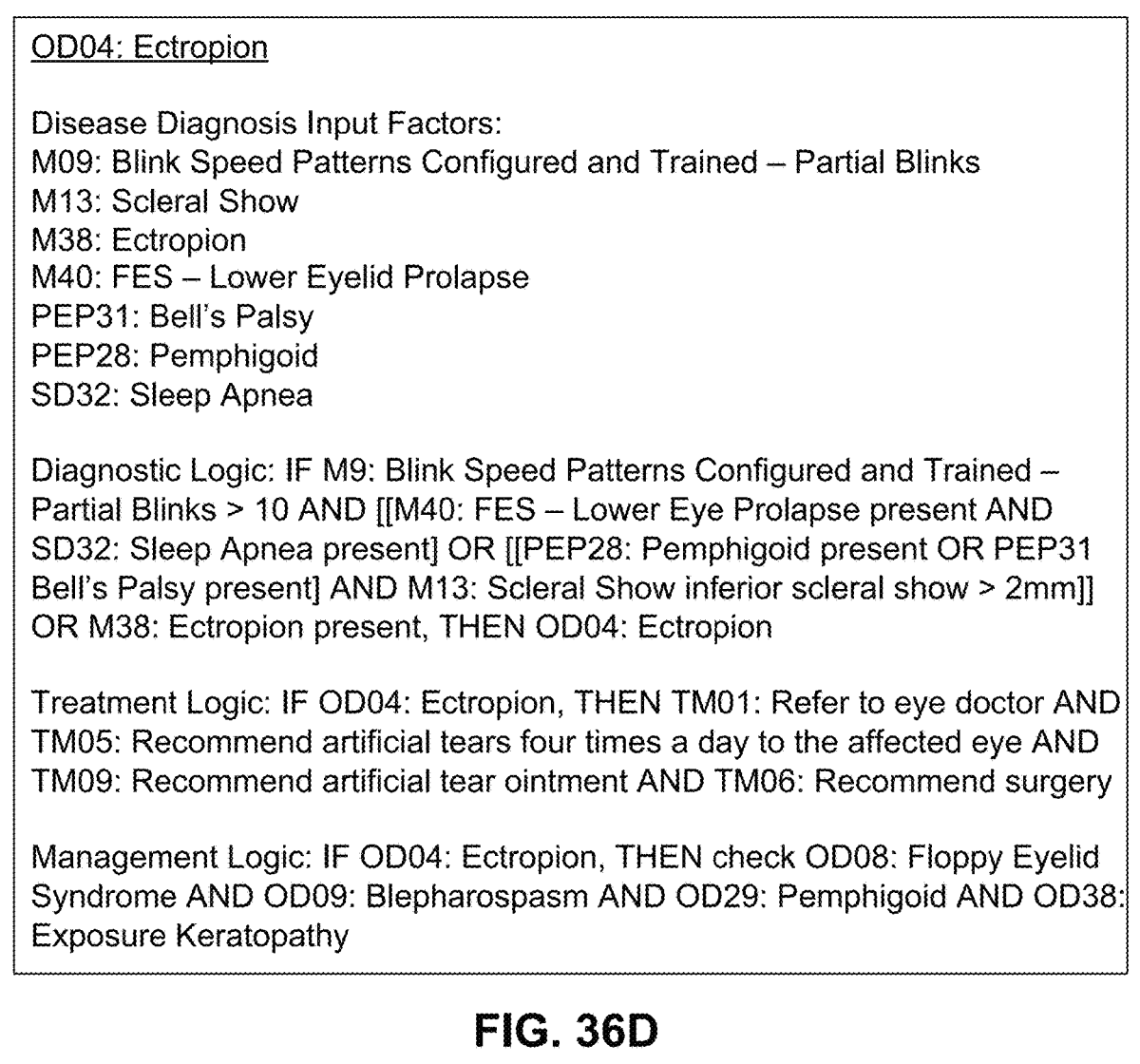

OD04: Ectropion

Disease Diagnosis Input Factors:
M09: Blink Speed Patterns Configured and Trained – Partial Blinks
M13: Scleral Show
M38: Ectropion
M40: FES – Lower Eyelid Prolapse
PEP31: Bell's Palsy
PEP28: Pemphigoid
SD32: Sleep Apnea Diagnostic Logic: IF M9: Blink Speed Patterns Configured and Trained – Partial Blinks > 10 AND [[M40: FES – Lower Eye Prolapse present AND SD32: Sleep Apnea present] OR [[PEP28: Pemphigoid present OR PEP31 Bell's Palsy present] AND M13: Scleral Show inferior scleral show > 2mm]] OR M38: Ectropion present, THEN OD04: Ectropion Treatment Logic: IF OD04: Ectropion, THEN TM01: Refer to eye doctor AND TM05: Recommend artificial tears four times a day to the affected eye AND TM09: Recommend artificial tear ointment AND TM06: Recommend surgery Management Logic: IF OD04: Ectropion, THEN check OD08: Floppy Eyelid Syndrome AND OD09: Blepharospasm AND OD29: Pemphigoid AND OD38: Exposure Keratopathy

FIG. 36D

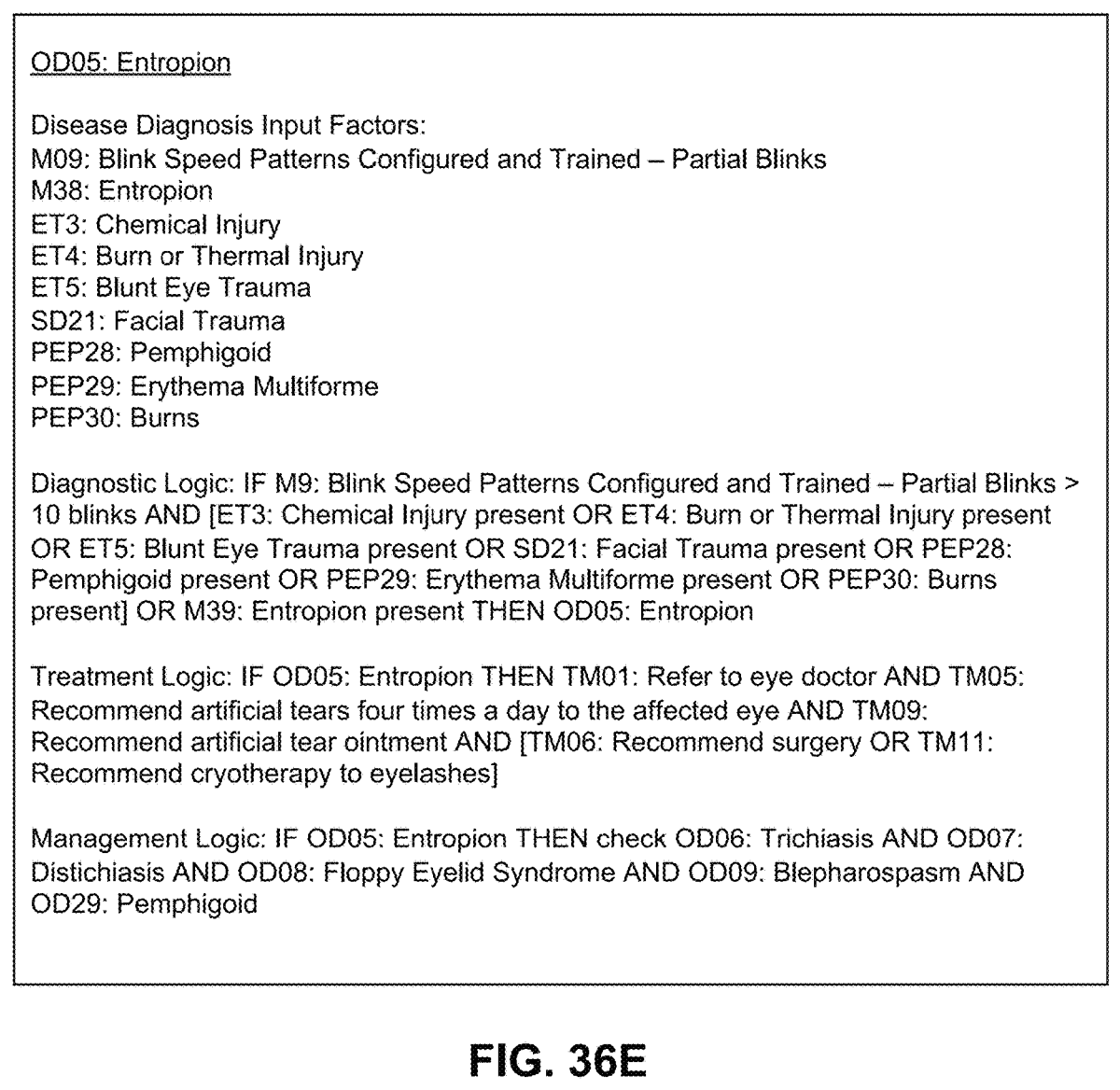

OD05: Entropion

Disease Diagnosis Input Factors:
M09: Blink Speed Patterns Configured and Trained – Partial Blinks
M38: Entropion
ET3: Chemical Injury
ET4: Burn or Thermal Injury
ET5: Blunt Eye Trauma
SD21: Facial Trauma
PEP28: Pemphigoid
PEP29: Erythema Multiforme
PEP30: Burns Diagnostic Logic: IF M9: Blink Speed Patterns Configured and Trained – Partial Blinks >
10 blinks AND [ET3: Chemical Injury present OR ET4: Burn or Thermal Injury present
OR ET5: Blunt Eye Trauma present OR SD21: Facial Trauma present OR PEP28:
Pemphigoid present OR PEP29: Erythema Multiforme present OR PEP30: Burns
present] OR M39: Entropion present THEN OD05: Entropion Treatment Logic: IF OD05: Entropion THEN TM01: Refer to eye doctor AND TM05:
Recommend artificial tears four times a day to the affected eye AND TM09:
Recommend artificial tear ointment AND [TM06: Recommend surgery OR TM11:
Recommend cryotherapy to eyelashes]

Management Logic: IF OD05: Entropion THEN check OD06: Trichiasis AND OD07:
Distichiasis AND OD08: Floppy Eyelid Syndrome AND OD09: Blepharospasm AND
OD29: Pemphigoid

FIG. 36E

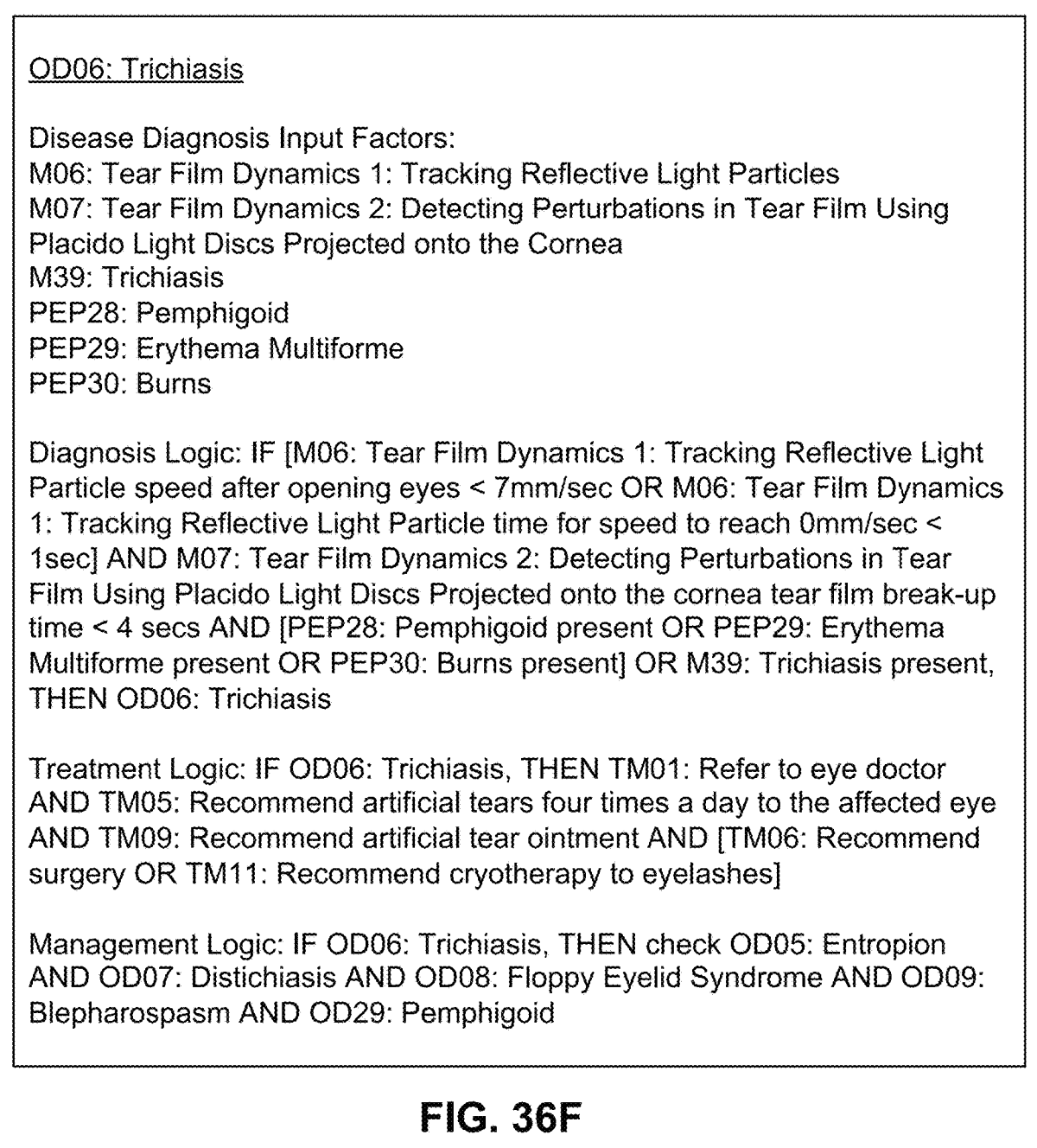

OD06: Trichiasis

Disease Diagnosis Input Factors:
M06: Tear Film Dynamics 1: Tracking Reflective Light Particles
M07: Tear Film Dynamics 2: Detecting Perturbations in Tear Film Using
Placido Light Discs Projected onto the Cornea
M39: Trichiasis
PEP28: Pemphigoid
PEP29: Erythema Multiforme
PEP30: Burns Diagnosis Logic: IF [M06: Tear Film Dynamics 1: Tracking Reflective Light
Particle speed after opening eyes < 7mm/sec OR M06: Tear Film Dynamics
1: Tracking Reflective Light Particle time for speed to reach 0mm/sec <
1sec] AND M07: Tear Film Dynamics 2: Detecting Perturbations in Tear
Film Using Placido Light Discs Projected onto the cornea tear film break-up
time < 4 secs AND [PEP28: Pemphigoid present OR PEP29: Erythema
Multiforme present OR PEP30: Burns present] OR M39: Trichiasis present,
THEN OD06: Trichiasis Treatment Logic: IF OD06: Trichiasis, THEN TM01: Refer to eye doctor
AND TM05: Recommend artificial tears four times a day to the affected eye
AND TM09: Recommend artificial tear ointment AND [TM06: Recommend
surgery OR TM11: Recommend cryotherapy to eyelashes]

Management Logic: IF OD06: Trichiasis, THEN check OD05: Entropion
AND OD07: Distichiasis AND OD08: Floppy Eyelid Syndrome AND OD09:
Blepharospasm AND OD29: Pemphigoid

FIG. 36F

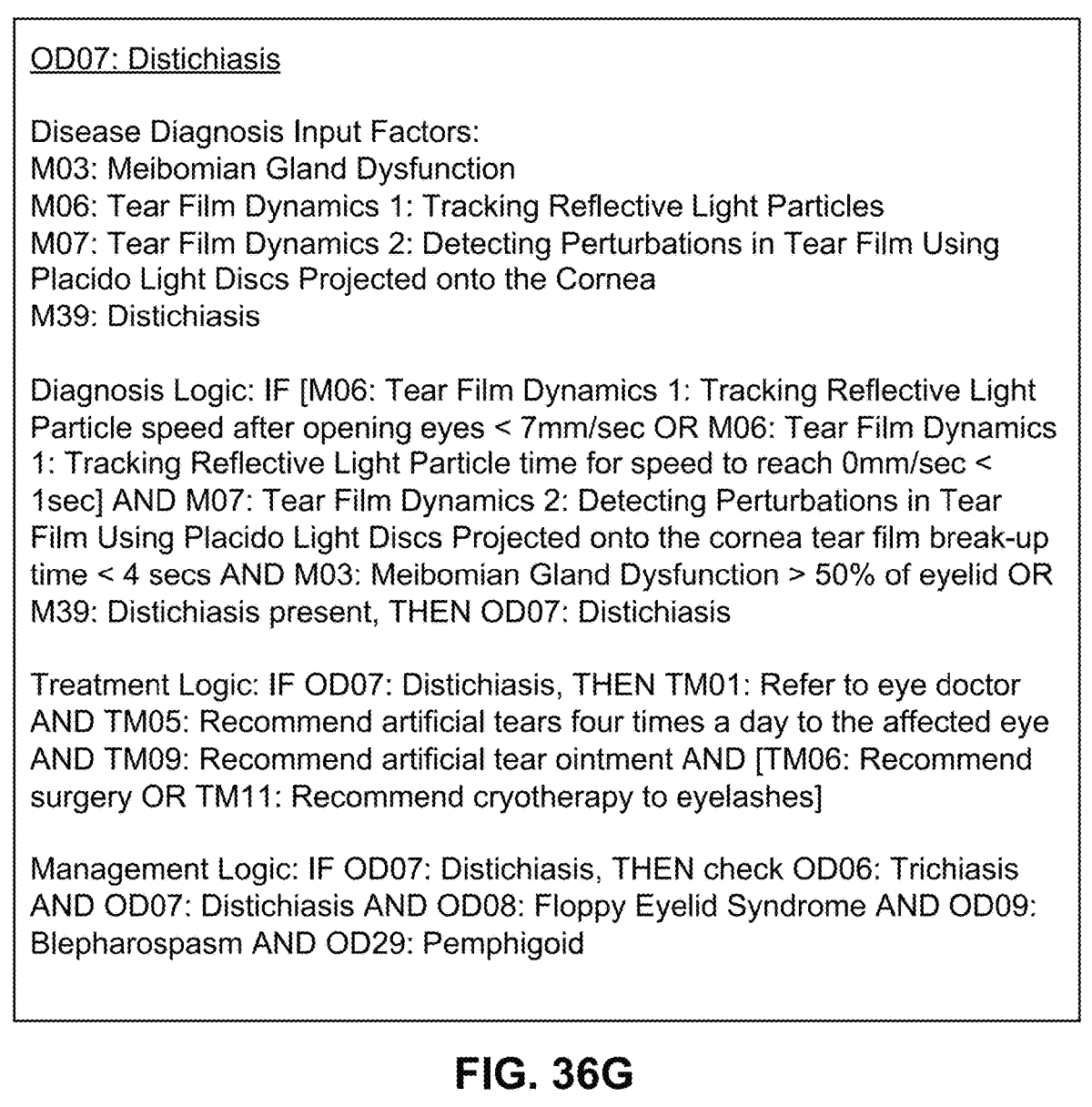

OD07: Distichiasis

Disease Diagnosis Input Factors:
M03: Meibomian Gland Dysfunction
M06: Tear Film Dynamics 1: Tracking Reflective Light Particles
M07: Tear Film Dynamics 2: Detecting Perturbations in Tear Film Using Placido Light Discs Projected onto the Cornea
M39: Distichiasis Diagnosis Logic: IF [M06: Tear Film Dynamics 1: Tracking Reflective Light Particle speed after opening eyes < 7mm/sec OR M06: Tear Film Dynamics 1: Tracking Reflective Light Particle time for speed to reach 0mm/sec < 1sec] AND M07: Tear Film Dynamics 2: Detecting Perturbations in Tear Film Using Placido Light Discs Projected onto the cornea tear film break-up time < 4 secs AND M03: Meibomian Gland Dysfunction > 50% of eyelid OR M39: Distichiasis present, THEN OD07: Distichiasis Treatment Logic: IF OD07: Distichiasis, THEN TM01: Refer to eye doctor AND TM05: Recommend artificial tears four times a day to the affected eye AND TM09: Recommend artificial tear ointment AND [TM06: Recommend surgery OR TM11: Recommend cryotherapy to eyelashes]

Management Logic: IF OD07: Distichiasis, THEN check OD06: Trichiasis AND OD07: Distichiasis AND OD08: Floppy Eyelid Syndrome AND OD09: Blepharospasm AND OD29: Pemphigoid

FIG. 36G

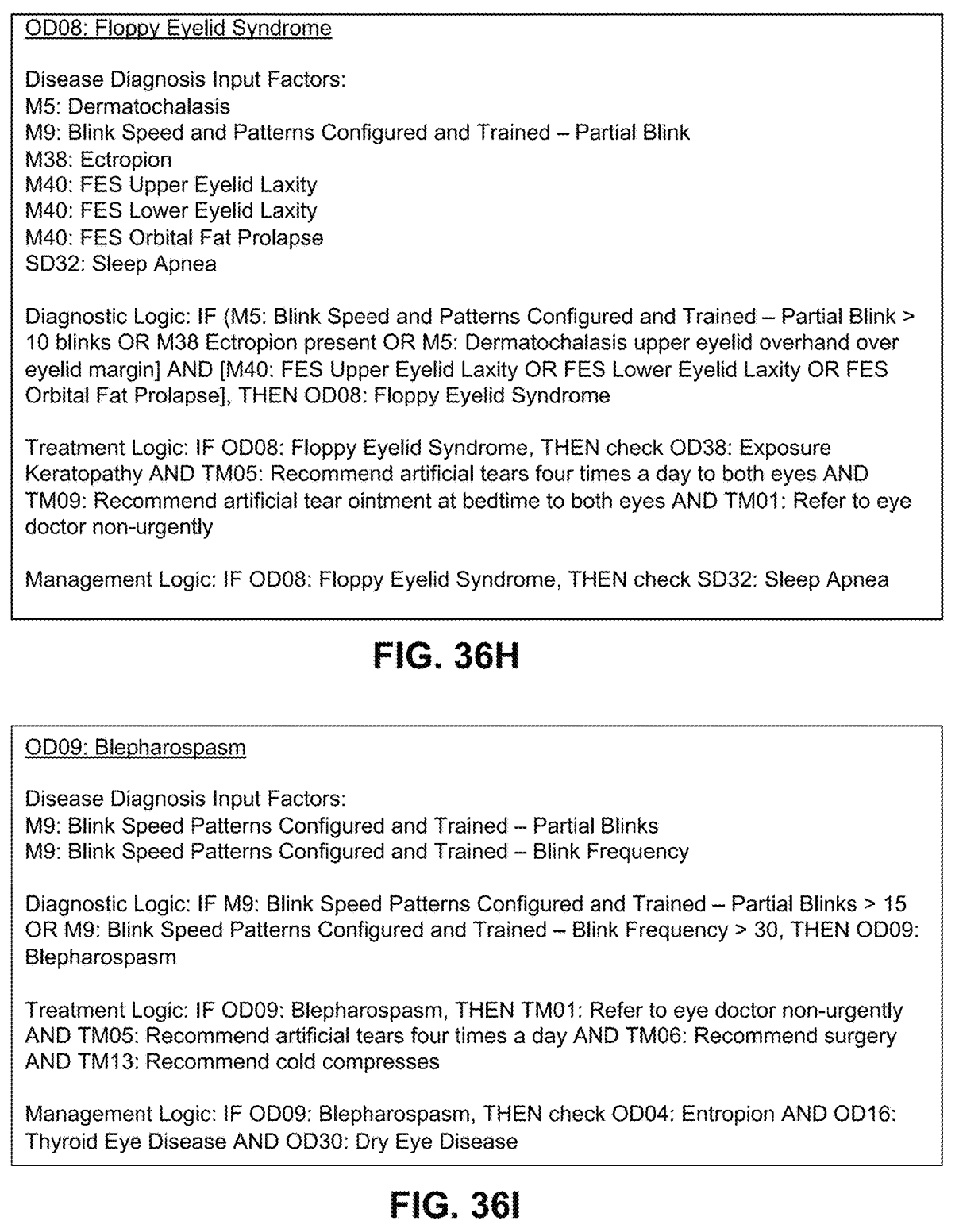

OD08: Floppy Eyelid Syndrome

Disease Diagnosis Input Factors:
M5: Dermatochalasis
M9: Blink Speed and Patterns Configured and Trained – Partial Blink
M38: Ectropion
M40: FES Upper Eyelid Laxity
M40: FES Lower Eyelid Laxity
M40: FES Orbital Fat Prolapse
SD32: Sleep Apnea Diagnostic Logic: IF (M5: Blink Speed and Patterns Configured and Trained – Partial Blink > 10 blinks OR M38 Ectropion present OR M5: Dermatochalasis upper eyelid overhand over eyelid margin] AND [M40: FES Upper Eyelid Laxity OR FES Lower Eyelid Laxity OR FES Orbital Fat Prolapse], THEN OD08: Floppy Eyelid Syndrome Treatment Logic: IF OD08: Floppy Eyelid Syndrome, THEN check OD38: Exposure Keratopathy AND TM05: Recommend artificial tears four times a day to both eyes AND TM09: Recommend artificial tear ointment at bedtime to both eyes AND TM01: Refer to eye doctor non-urgently Management Logic: IF OD08: Floppy Eyelid Syndrome, THEN check SD32: Sleep Apnea

FIG. 36H

OD09: Blepharospasm

Disease Diagnosis Input Factors:
M9: Blink Speed Patterns Configured and Trained – Partial Blinks
M9: Blink Speed Patterns Configured and Trained – Blink Frequency Diagnostic Logic: IF M9: Blink Speed Patterns Configured and Trained – Partial Blinks > 15 OR M9: Blink Speed Patterns Configured and Trained – Blink Frequency > 30, THEN OD09: Blepharospasm Treatment Logic: IF OD09: Blepharospasm, THEN TM01: Refer to eye doctor non-urgently AND TM05: Recommend artificial tears four times a day AND TM06: Recommend surgery AND TM13: Recommend cold compresses Management Logic: IF OD09: Blepharospasm, THEN check OD04: Entropion AND OD16: Thyroid Eye Disease AND OD30: Dry Eye Disease

FIG. 36I

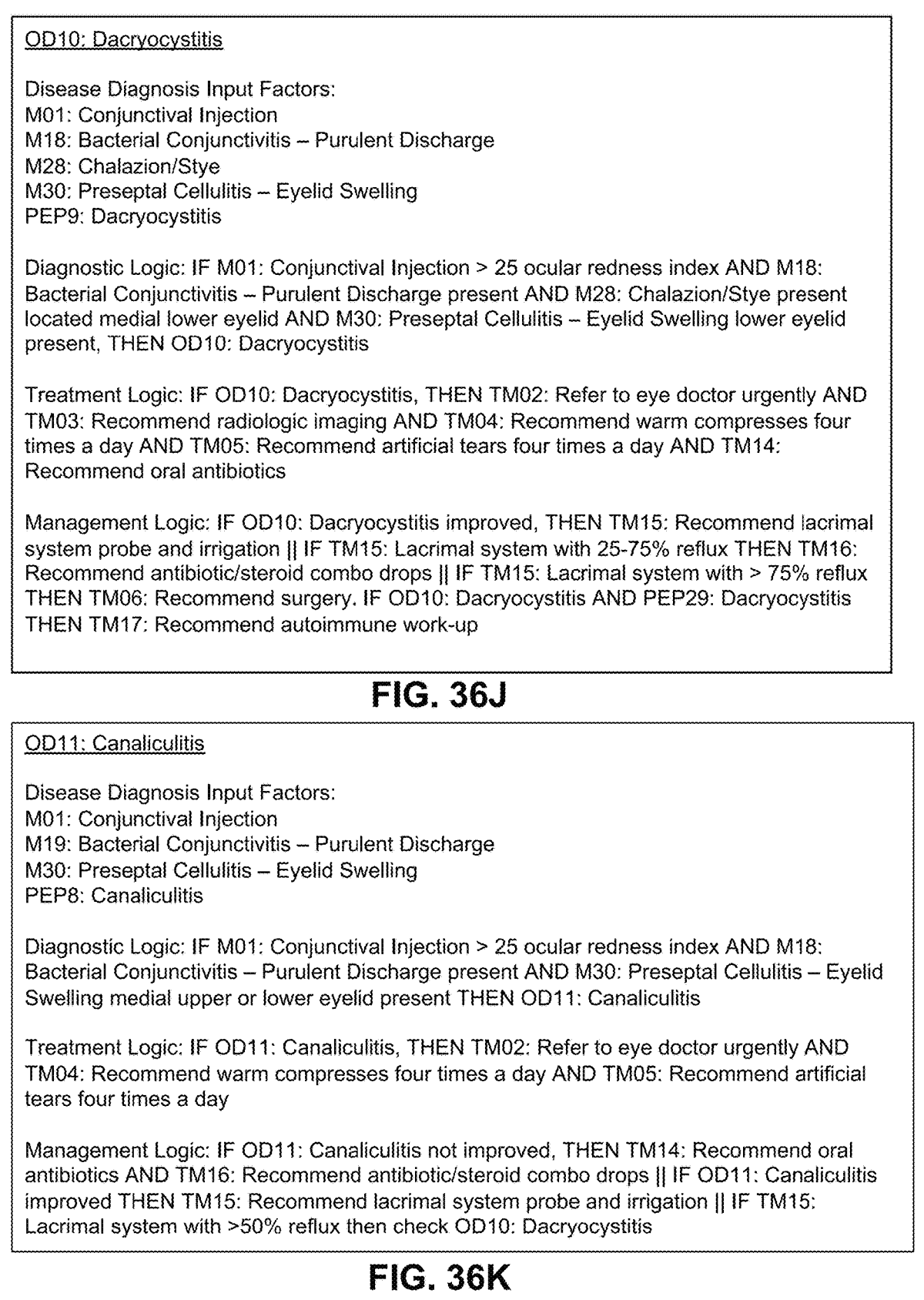

OD10: Dacryocystitis

Disease Diagnosis Input Factors:
M01: Conjunctival Injection
M18: Bacterial Conjunctivitis – Purulent Discharge
M28: Chalazion/Stye
M30: Preseptal Cellulitis – Eyelid Swelling
PEP9: Dacryocystitis Diagnostic Logic: IF M01: Conjunctival Injection > 25 ocular redness index AND M18: Bacterial Conjunctivitis – Purulent Discharge present AND M28: Chalazion/Stye present located medial lower eyelid AND M30: Preseptal Cellulitis – Eyelid Swelling lower eyelid present, THEN OD10: Dacryocystitis Treatment Logic: IF OD10: Dacryocystitis, THEN TM02: Refer to eye doctor urgently AND TM03: Recommend radiologic imaging AND TM04: Recommend warm compresses four times a day AND TM05: Recommend artificial tears four times a day AND TM14: Recommend oral antibiotics Management Logic: IF OD10: Dacryocystitis improved, THEN TM15: Recommend lacrimal system probe and irrigation || IF TM15: Lacrimal system with 25-75% reflux THEN TM16: Recommend antibiotic/steroid combo drops || IF TM15: Lacrimal system with > 75% reflux THEN TM06: Recommend surgery. IF OD10: Dacryocystitis AND PEP29: Dacryocystitis THEN TM17: Recommend autoimmune work-up

FIG. 36J

OD11: Canaliculitis

Disease Diagnosis Input Factors:
M01: Conjunctival Injection
M19: Bacterial Conjunctivitis – Purulent Discharge
M30: Preseptal Cellulitis – Eyelid Swelling
PEP8: Canaliculitis Diagnostic Logic: IF M01: Conjunctival Injection > 25 ocular redness index AND M18: Bacterial Conjunctivitis – Purulent Discharge present AND M30: Preseptal Cellulitis – Eyelid Swelling medial upper or lower eyelid present THEN OD11: Canaliculitis Treatment Logic: IF OD11: Canaliculitis, THEN TM02: Refer to eye doctor urgently AND TM04: Recommend warm compresses four times a day AND TM05: Recommend artificial tears four times a day Management Logic: IF OD11: Canaliculitis not improved, THEN TM14: Recommend oral antibiotics AND TM16: Recommend antibiotic/steroid combo drops || IF OD11: Canaliculitis improved THEN TM15: Recommend lacrimal system probe and irrigation || IF TM15: Lacrimal system with >50% reflux then check OD10: Dacryocystitis

FIG. 36K

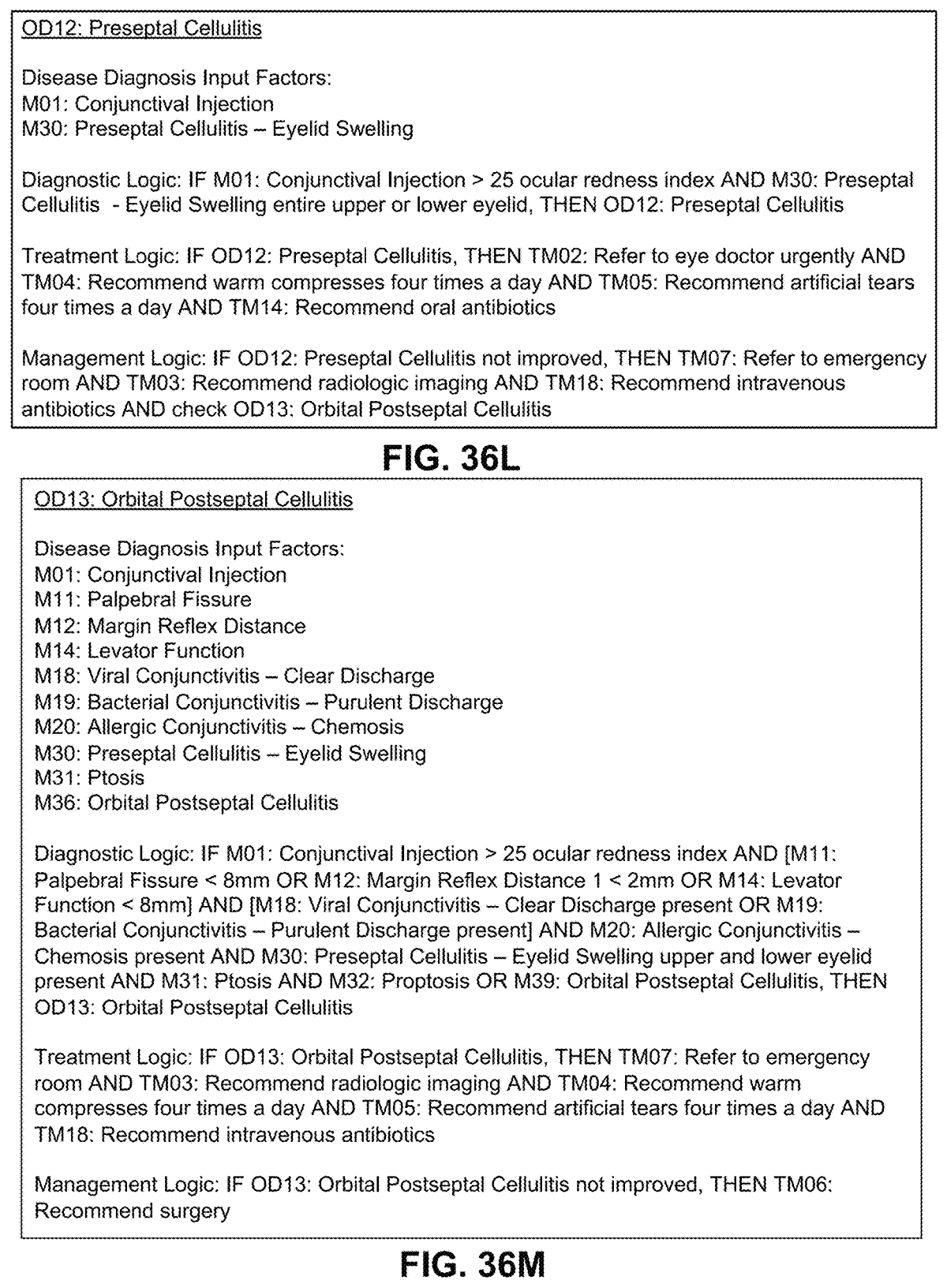

OD12: Preseptal Cellulitis

Disease Diagnosis Input Factors:
M01: Conjunctival Injection
M30: Preseptal Cellulitis – Eyelid Swelling Diagnostic Logic: IF M01: Conjunctival Injection > 25 ocular redness index AND M30: Preseptal Cellulitis - Eyelid Swelling entire upper or lower eyelid, THEN OD12: Preseptal Cellulitis Treatment Logic: IF OD12: Preseptal Cellulitis, THEN TM02: Refer to eye doctor urgently AND TM04: Recommend warm compresses four times a day AND TM05: Recommend artificial tears four times a day AND TM14: Recommend oral antibiotics Management Logic: IF OD12: Preseptal Cellulitis not improved, THEN TM07: Refer to emergency room AND TM03: Recommend radiologic imaging AND TM18: Recommend intravenous antibiotics AND check OD13: Orbital Postseptal Cellulitis

FIG. 36L

OD13: Orbital Postseptal Cellulitis

Disease Diagnosis Input Factors:
M01: Conjunctival Injection
M11: Palpebral Fissure
M12: Margin Reflex Distance
M14: Levator Function
M18: Viral Conjunctivitis – Clear Discharge
M19: Bacterial Conjunctivitis – Purulent Discharge
M20: Allergic Conjunctivitis – Chemosis
M30: Preseptal Cellulitis – Eyelid Swelling
M31: Ptosis
M36: Orbital Postseptal Cellulitis Diagnostic Logic: IF M01: Conjunctival Injection > 25 ocular redness index AND [M11: Palpebral Fissure < 8mm OR M12: Margin Reflex Distance 1 < 2mm OR M14: Levator Function < 8mm] AND [M18: Viral Conjunctivitis – Clear Discharge present OR M19: Bacterial Conjunctivitis – Purulent Discharge present] AND M20: Allergic Conjunctivitis – Chemosis present AND M30: Preseptal Cellulitis – Eyelid Swelling upper and lower eyelid present AND M31: Ptosis AND M32: Proptosis OR M39: Orbital Postseptal Cellulitis, THEN OD13: Orbital Postseptal Cellulitis Treatment Logic: IF OD13: Orbital Postseptal Cellulitis, THEN TM07: Refer to emergency room AND TM03: Recommend radiologic imaging AND TM04: Recommend warm compresses four times a day AND TM05: Recommend artificial tears four times a day AND TM18: Recommend intravenous antibiotics Management Logic: IF OD13: Orbital Postseptal Cellulitis not improved, THEN TM06: Recommend surgery

FIG. 36M

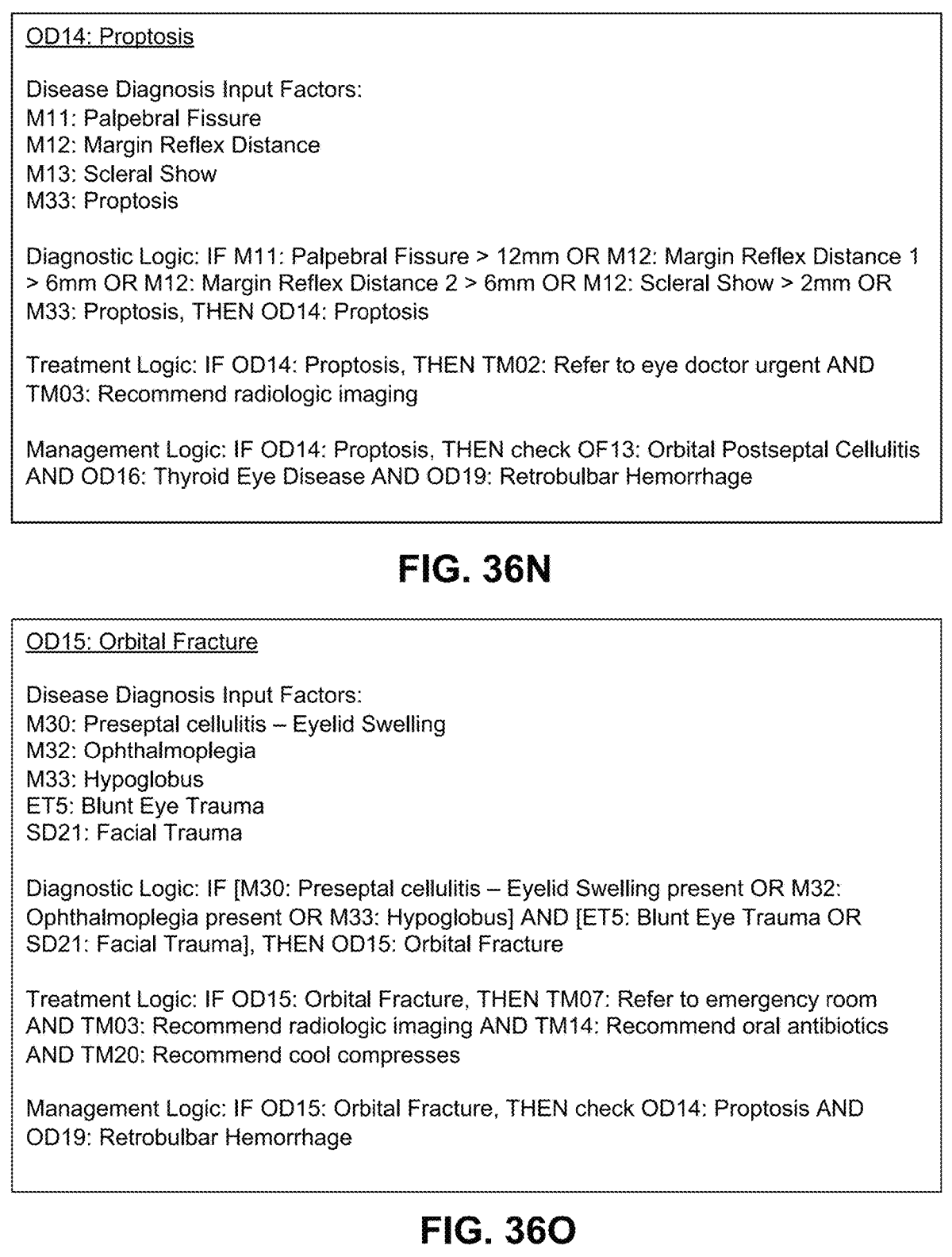

OD14: Proptosis

Disease Diagnosis Input Factors:
M11: Palpebral Fissure
M12: Margin Reflex Distance
M13: Scleral Show
M33: Proptosis Diagnostic Logic: IF M11: Palpebral Fissure > 12mm OR M12: Margin Reflex Distance 1 > 6mm OR M12: Margin Reflex Distance 2 > 6mm OR M12: Scleral Show > 2mm OR M33: Proptosis, THEN OD14: Proptosis Treatment Logic: IF OD14: Proptosis, THEN TM02: Refer to eye doctor urgent AND TM03: Recommend radiologic imaging Management Logic: IF OD14: Proptosis, THEN check OF13: Orbital Postseptal Cellulitis AND OD16: Thyroid Eye Disease AND OD19: Retrobulbar Hemorrhage

FIG. 36N

OD15: Orbital Fracture

Disease Diagnosis Input Factors:
M30: Preseptal cellulitis – Eyelid Swelling
M32: Ophthalmoplegia
M33: Hypoglobus
ET5: Blunt Eye Trauma
SD21: Facial Trauma Diagnostic Logic: IF [M30: Preseptal cellulitis – Eyelid Swelling present OR M32: Ophthalmoplegia present OR M33: Hypoglobus] AND [ET5: Blunt Eye Trauma OR SD21: Facial Trauma], THEN OD15: Orbital Fracture Treatment Logic: IF OD15: Orbital Fracture, THEN TM07: Refer to emergency room AND TM03: Recommend radiologic imaging AND TM14: Recommend oral antibiotics AND TM20: Recommend cool compresses Management Logic: IF OD15: Orbital Fracture, THEN check OD14: Proptosis AND OD19: Retrobulbar Hemorrhage

FIG. 36O

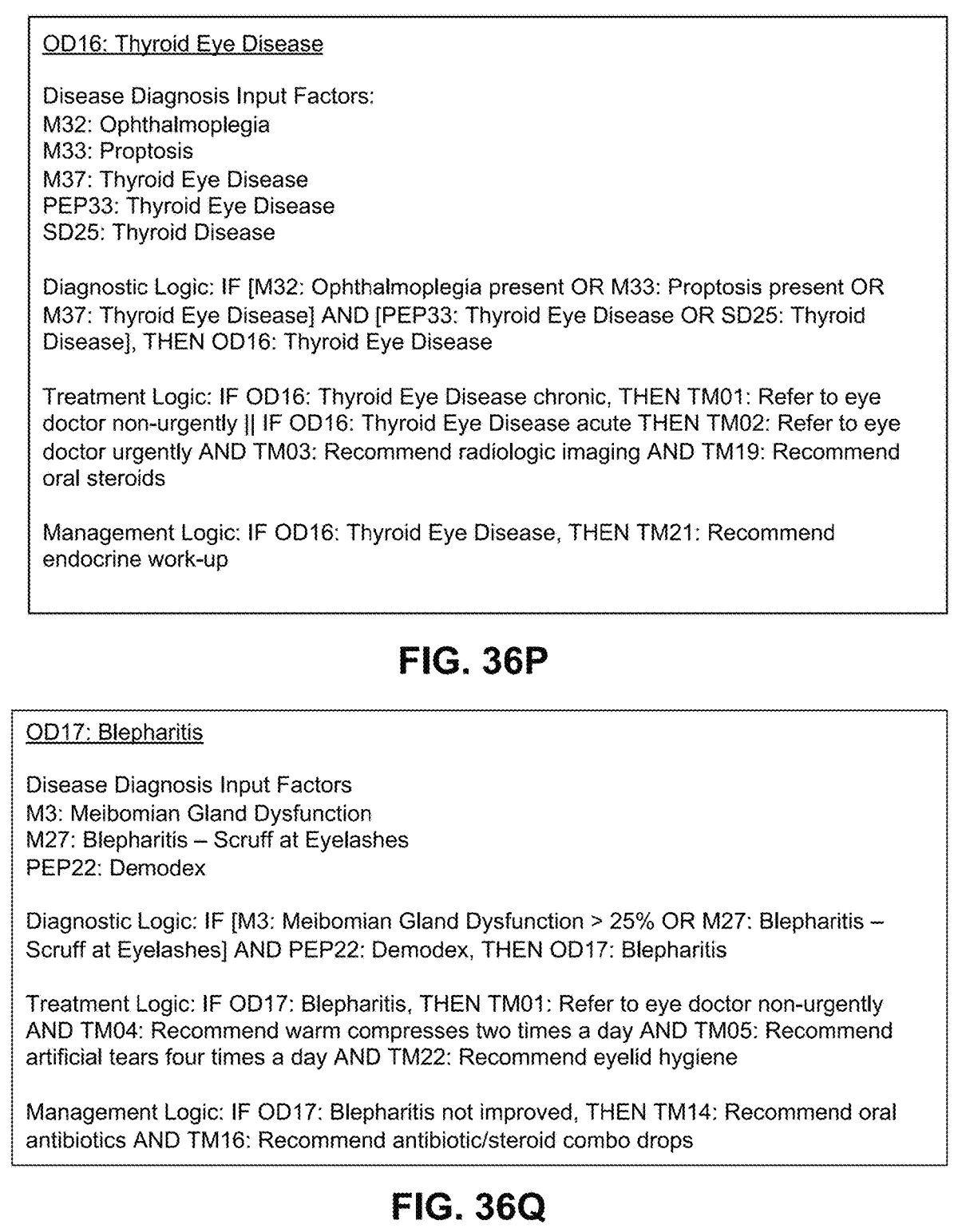

OD16: Thyroid Eye Disease

Disease Diagnosis Input Factors:
M32: Ophthalmoplegia
M33: Proptosis
M37: Thyroid Eye Disease
PEP33: Thyroid Eye Disease
SD25: Thyroid Disease Diagnostic Logic: IF [M32: Ophthalmoplegia present OR M33: Proptosis present OR M37: Thyroid Eye Disease] AND [PEP33: Thyroid Eye Disease OR SD25: Thyroid Disease], THEN OD16: Thyroid Eye Disease Treatment Logic: IF OD16: Thyroid Eye Disease chronic, THEN TM01: Refer to eye doctor non-urgently || IF OD16: Thyroid Eye Disease acute THEN TM02: Refer to eye doctor urgently AND TM03: Recommend radiologic imaging AND TM19: Recommend oral steroids Management Logic: IF OD16: Thyroid Eye Disease, THEN TM21: Recommend endocrine work-up

FIG. 36P

OD17: Blepharitis

Disease Diagnosis Input Factors
M3: Meibomian Gland Dysfunction
M27: Blepharitis – Scruff at Eyelashes
PEP22: Demodex Diagnostic Logic: IF [M3: Meibomian Gland Dysfunction > 25% OR M27: Blepharitis – Scruff at Eyelashes] AND PEP22: Demodex, THEN OD17: Blepharitis Treatment Logic: IF OD17: Blepharitis, THEN TM01: Refer to eye doctor non-urgently AND TM04: Recommend warm compresses two times a day AND TM05: Recommend artificial tears four times a day AND TM22: Recommend eyelid hygiene Management Logic: IF OD17: Blepharitis not improved, THEN TM14: Recommend oral antibiotics AND TM16: Recommend antibiotic/steroid combo drops

FIG. 36Q

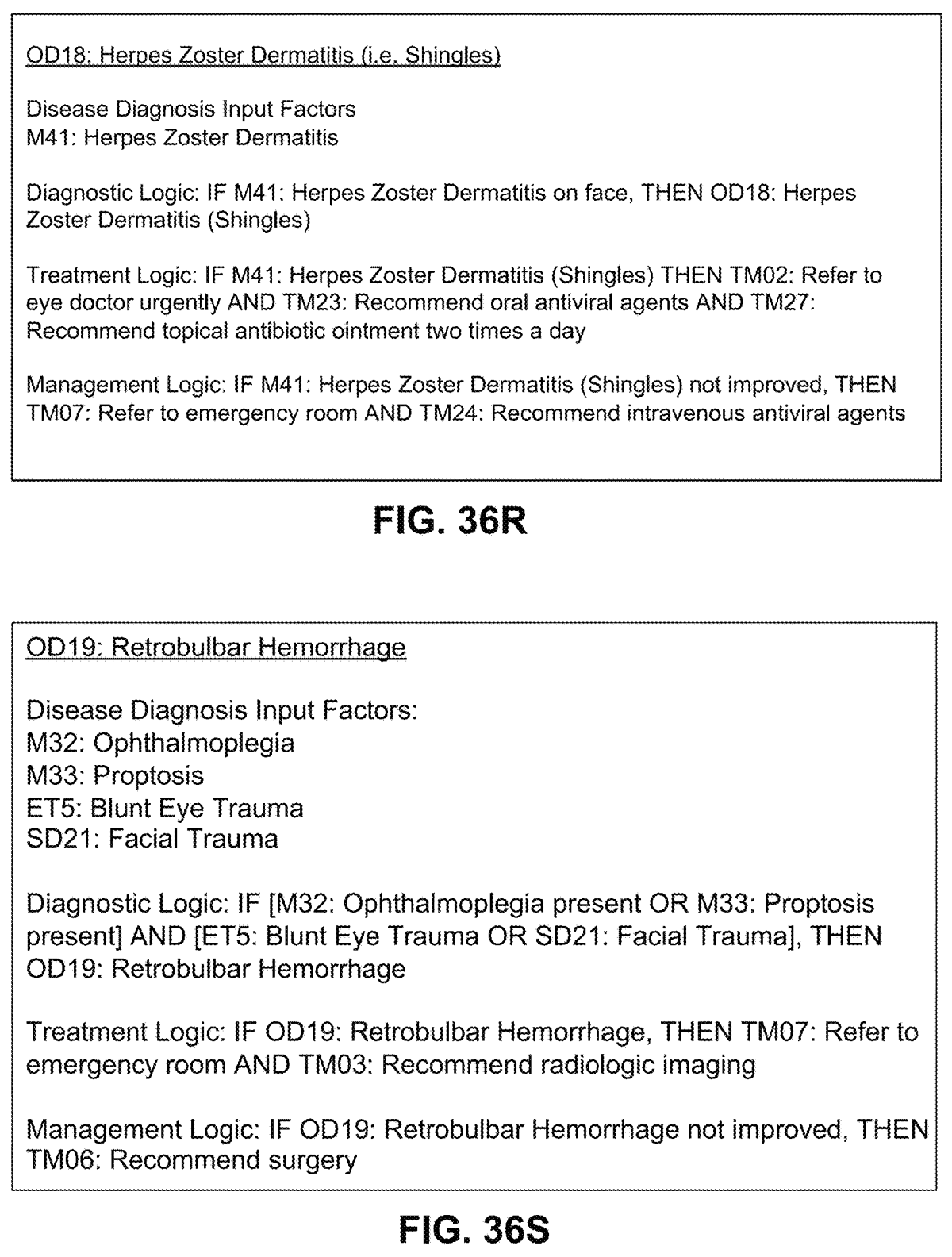

OD18: Herpes Zoster Dermatitis (i.e. Shingles)

Disease Diagnosis Input Factors
M41: Herpes Zoster Dermatitis

Diagnostic Logic: IF M41: Herpes Zoster Dermatitis on face, THEN OD18: Herpes Zoster Dermatitis (Shingles)

Treatment Logic: IF M41: Herpes Zoster Dermatitis (Shingles) THEN TM02: Refer to eye doctor urgently AND TM23: Recommend oral antiviral agents AND TM27: Recommend topical antibiotic ointment two times a day Management Logic: IF M41: Herpes Zoster Dermatitis (Shingles) not improved, THEN TM07: Refer to emergency room AND TM24: Recommend intravenous antiviral agents

FIG. 36R

OD19: Retrobulbar Hemorrhage

Disease Diagnosis Input Factors:
M32: Ophthalmoplegia
M33: Proptosis
ET5: Blunt Eye Trauma
SD21: Facial Trauma Diagnostic Logic: IF [M32: Ophthalmoplegia present OR M33: Proptosis present] AND [ET5: Blunt Eye Trauma OR SD21: Facial Trauma], THEN OD19: Retrobulbar Hemorrhage Treatment Logic: IF OD19: Retrobulbar Hemorrhage, THEN TM07: Refer to emergency room AND TM03: Recommend radiologic imaging Management Logic: IF OD19: Retrobulbar Hemorrhage not improved, THEN TM06: Recommend surgery

FIG. 36S

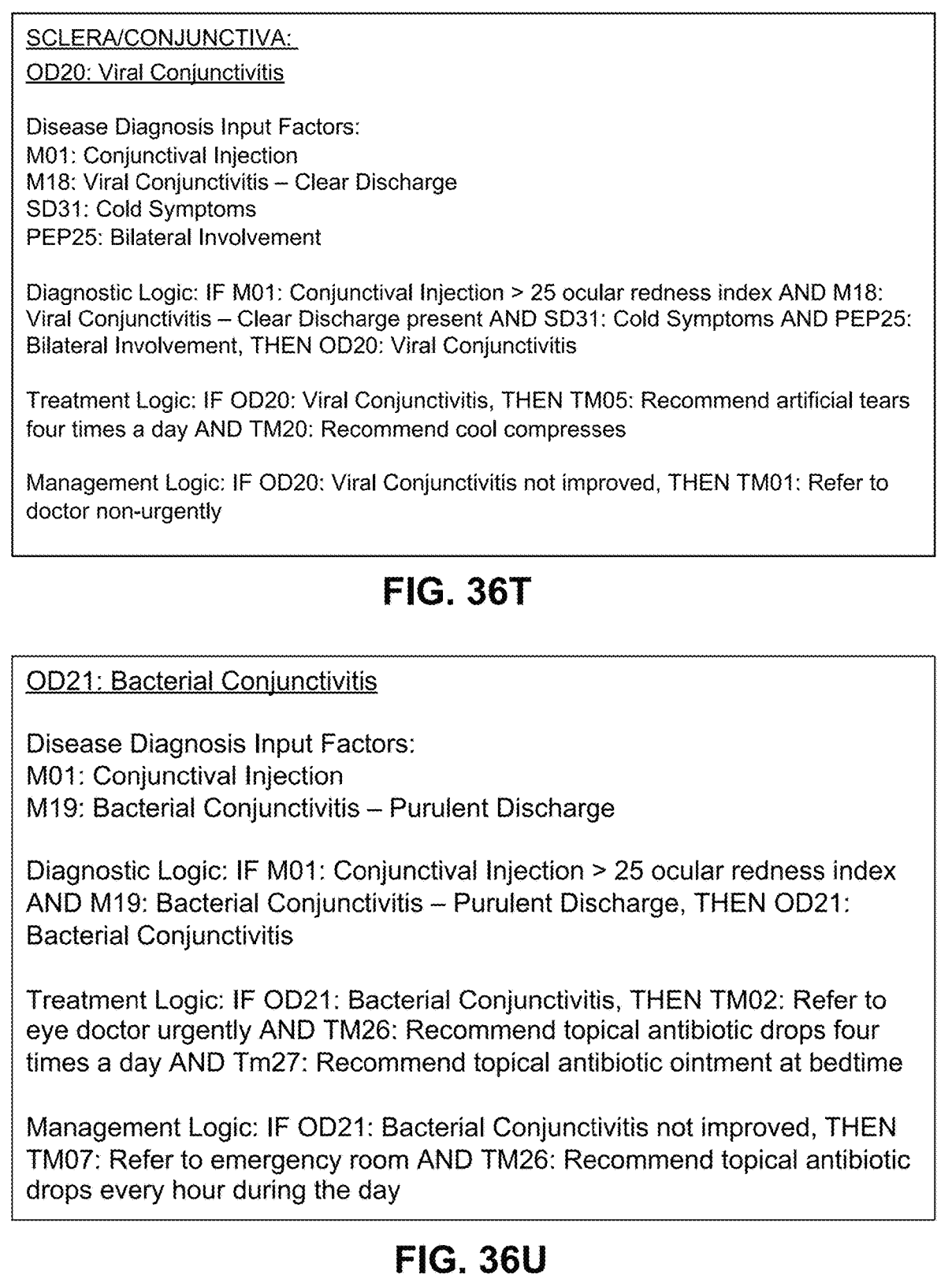

SCLERA/CONJUNCTIVA:

OD20: Viral Conjunctivitis

Disease Diagnosis Input Factors:
M01: Conjunctival Injection
M18: Viral Conjunctivitis – Clear Discharge
SD31: Cold Symptoms
PEP25: Bilateral Involvement Diagnostic Logic: IF M01: Conjunctival Injection > 25 ocular redness index AND M18: Viral Conjunctivitis – Clear Discharge present AND SD31: Cold Symptoms AND PEP25: Bilateral Involvement, THEN OD20: Viral Conjunctivitis Treatment Logic: IF OD20: Viral Conjunctivitis, THEN TM05: Recommend artificial tears four times a day AND TM20: Recommend cool compresses Management Logic: IF OD20: Viral Conjunctivitis not improved, THEN TM01: Refer to doctor non-urgently

FIG. 36T

OD21: Bacterial Conjunctivitis

Disease Diagnosis Input Factors:
M01: Conjunctival Injection
M19: Bacterial Conjunctivitis – Purulent Discharge Diagnostic Logic: IF M01: Conjunctival Injection > 25 ocular redness index AND M19: Bacterial Conjunctivitis – Purulent Discharge, THEN OD21: Bacterial Conjunctivitis Treatment Logic: IF OD21: Bacterial Conjunctivitis, THEN TM02: Refer to eye doctor urgently AND TM26: Recommend topical antibiotic drops four times a day AND Tm27: Recommend topical antibiotic ointment at bedtime Management Logic: IF OD21: Bacterial Conjunctivitis not improved, THEN TM07: Refer to emergency room AND TM26: Recommend topical antibiotic drops every hour during the day

FIG. 36U

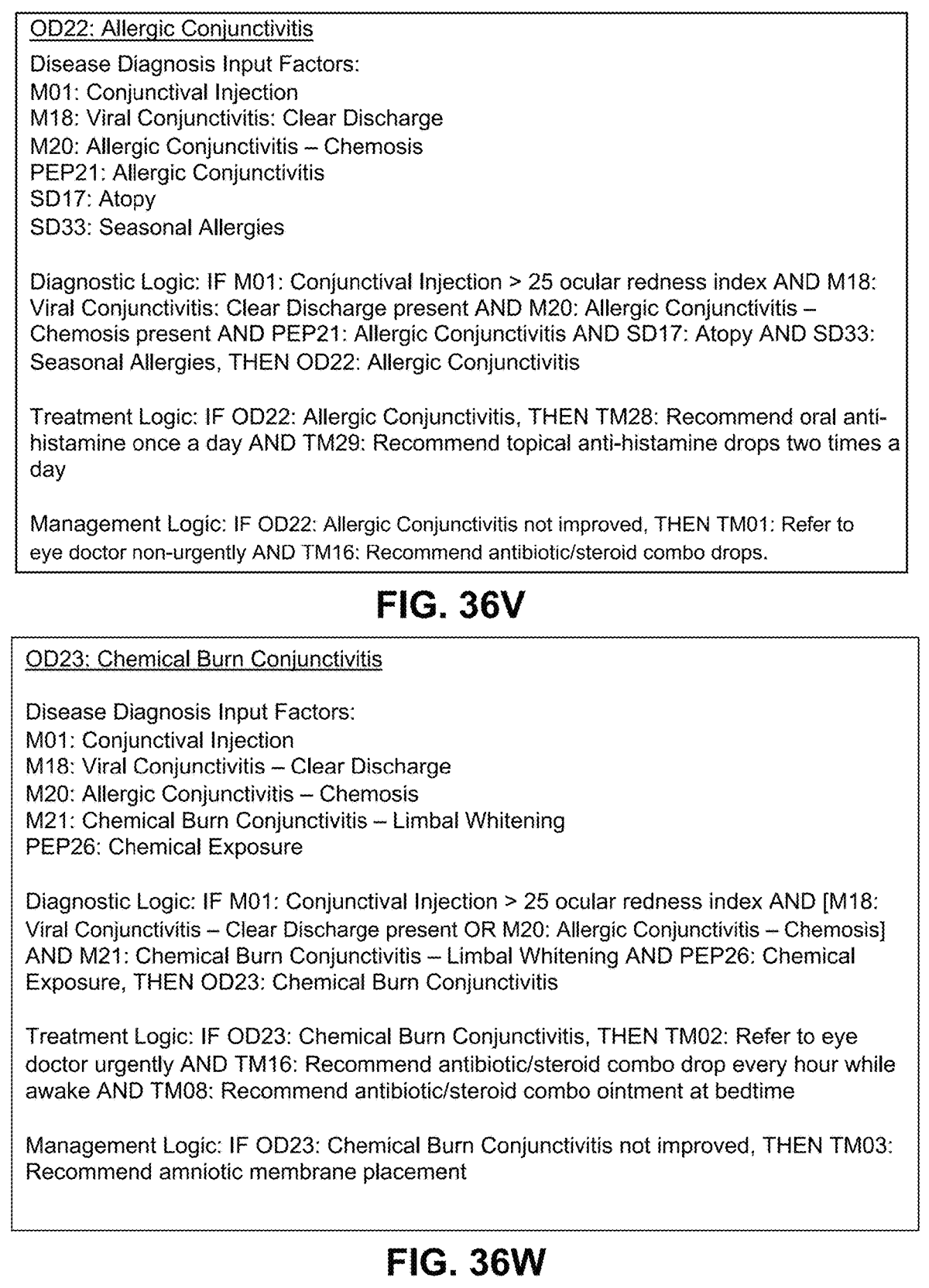

OD22: Allergic Conjunctivitis
Disease Diagnosis Input Factors:
M01: Conjunctival Injection
M18: Viral Conjunctivitis: Clear Discharge
M20: Allergic Conjunctivitis – Chemosis
PEP21: Allergic Conjunctivitis
SD17: Atopy
SD33: Seasonal Allergies Diagnostic Logic: IF M01: Conjunctival Injection > 25 ocular redness index AND M18: Viral Conjunctivitis: Clear Discharge present AND M20: Allergic Conjunctivitis – Chemosis present AND PEP21: Allergic Conjunctivitis AND SD17: Atopy AND SD33: Seasonal Allergies, THEN OD22: Allergic Conjunctivitis Treatment Logic: IF OD22: Allergic Conjunctivitis, THEN TM28: Recommend oral anti-histamine once a day AND TM29: Recommend topical anti-histamine drops two times a day Management Logic: IF OD22: Allergic Conjunctivitis not improved, THEN TM01: Refer to eye doctor non-urgently AND TM16: Recommend antibiotic/steroid combo drops.

FIG. 36V

OD23: Chemical Burn Conjunctivitis

Disease Diagnosis Input Factors:
M01: Conjunctival Injection
M18: Viral Conjunctivitis – Clear Discharge
M20: Allergic Conjunctivitis – Chemosis
M21: Chemical Burn Conjunctivitis – Limbal Whitening
PEP26: Chemical Exposure Diagnostic Logic: IF M01: Conjunctival Injection > 25 ocular redness index AND [M18: Viral Conjunctivitis – Clear Discharge present OR M20: Allergic Conjunctivitis – Chemosis] AND M21: Chemical Burn Conjunctivitis – Limbal Whitening AND PEP26: Chemical Exposure, THEN OD23: Chemical Burn Conjunctivitis Treatment Logic: IF OD23: Chemical Burn Conjunctivitis, THEN TM02: Refer to eye doctor urgently AND TM16: Recommend antibiotic/steroid combo drop every hour while awake AND TM08: Recommend antibiotic/steroid combo ointment at bedtime Management Logic: IF OD23: Chemical Burn Conjunctivitis not improved, THEN TM03: Recommend amniotic membrane placement

FIG. 36W

OD24: Superior Limbic Keratoconjunctivitis

Disease Diagnosis Input Factors:
M01: Conjunctival Injection
M10: Corneal Abrasion
M18: Viral Conjunctivitis – Clear Discharge
M26: Superior Limbic Keratoconjunctivitis (SLK)

Diagnostic Logic: IF [M01: Conjunctival Injection > 50 in superior conjunctiva AND M10: Corneal abrasion present superior cornea AND M18: Viral Conjunctivitis – Clear Discharge present] OR M26: Superior Limbic Keratoconjunctivitis (SLK),THEN OD24: Superior Limbic Keratoconjunctivitis (SLK)

Treatment Logic: IF OD24: Superior Limbic Keratoconjunctivitis (SLK), THEN TM02: Refer to eye doctor urgently AND TM05: Recommend artificial tears four times a day AND TM09: Recommend artificial tear ointment at bedtime Management Logic: IF OD24: Superior Limbic Keratoconjunctivitis (SLK) not improved, THEN TM31: Recommend topical cyclosporine drops OR TM16: Recommend antibiotic/steroid combo drops || IF OD24: Superior Limbic Keratoconjunctivitis (SLK), THEN check SD25: Thyroid Disease AND TM21: Recommend endocrine work-up

FIG. 36X

OD25: Subconjunctival Hemorrhage

Disease Diagnosis Input Factors:
M25: Episcleritis/Scleritis – Sectoral Conjunctival Injection
M23: Subconjunctival Hemorrhage
ET5: Blunt Eye Trauma
SD21: Facial Trauma Diagnostic Logic: IF [M25: Episcleritis/Scleritis – Sectoral Conjunctival Injection > 75 ocular redness index in one sector without vessel differentiation AND [ET5: Blunt Eye Trauma OR SD21: Facial Trauma]] OR M23: Subconjunctival Hemorrhage, THEN OD25: Subconjunctival Hemorrhage Treatment Logic: IF OD25: Subconjunctival Hemorrhage, THEN TM05: Recommend artificial tears four times a day AND TM20: Recommend cool compresses Management Logic: IF OD25: Subconjunctival Hemorrhage, THEN check OD27: Conjunctival Laceration

FIG. 36Y

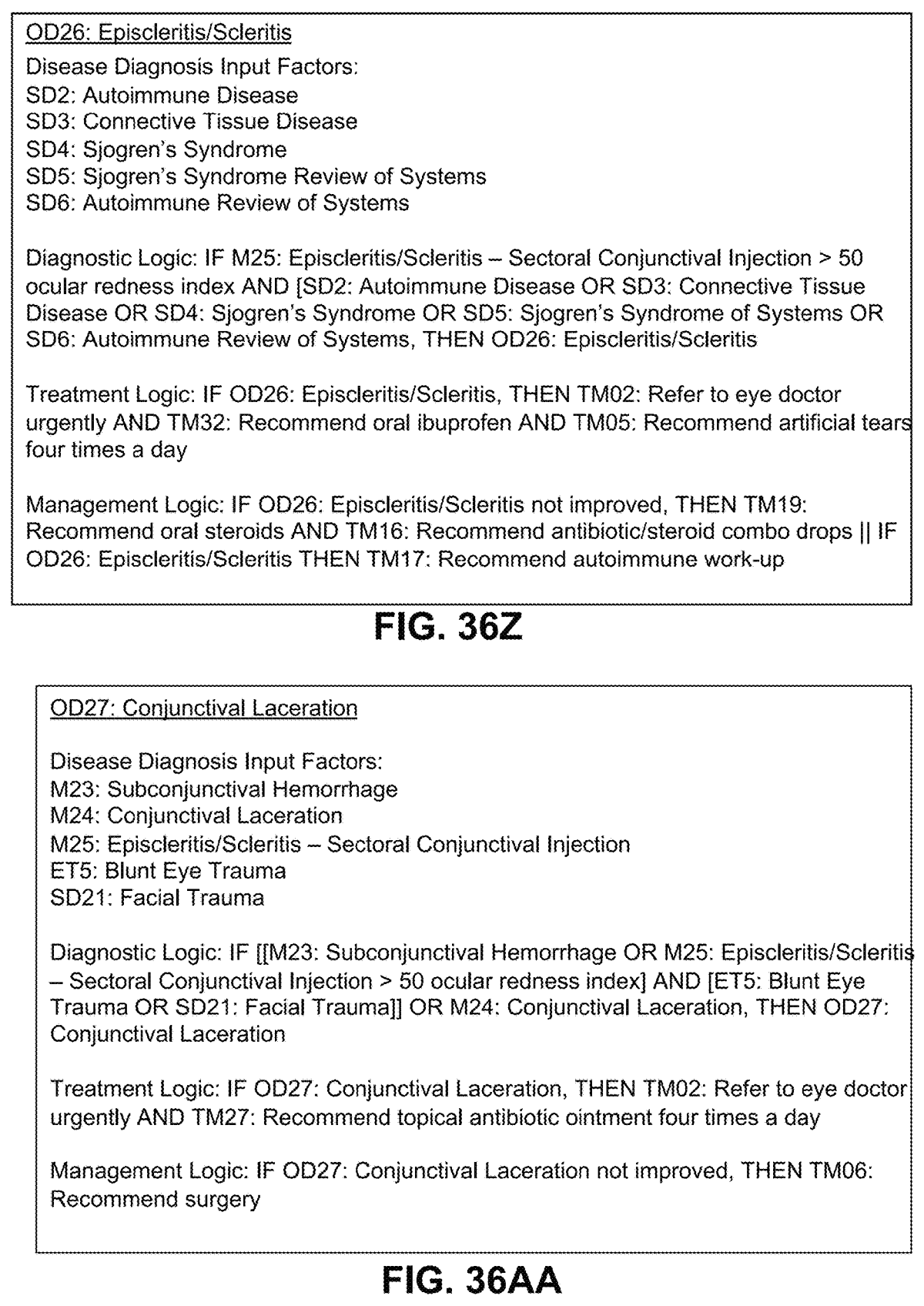

OD26: Episcleritis/Scleritis

Disease Diagnosis Input Factors:
SD2: Autoimmune Disease
SD3: Connective Tissue Disease
SD4: Sjogren's Syndrome
SD5: Sjogren's Syndrome Review of Systems
SD6: Autoimmune Review of Systems Diagnostic Logic: IF M25: Episcleritis/Scleritis – Sectoral Conjunctival Injection > 50 ocular redness index AND [SD2: Autoimmune Disease OR SD3: Connective Tissue Disease OR SD4: Sjogren's Syndrome OR SD5: Sjogren's Syndrome of Systems OR SD6: Autoimmune Review of Systems, THEN OD26: Episcleritis/Scleritis Treatment Logic: IF OD26: Episcleritis/Scleritis, THEN TM02: Refer to eye doctor urgently AND TM32: Recommend oral ibuprofen AND TM05: Recommend artificial tears four times a day Management Logic: IF OD26: Episcleritis/Scleritis not improved, THEN TM19: Recommend oral steroids AND TM16: Recommend antibiotic/steroid combo drops || IF OD26: Episcleritis/Scleritis THEN TM17: Recommend autoimmune work-up

FIG. 36Z

OD27: Conjunctival Laceration

Disease Diagnosis Input Factors:
M23: Subconjunctival Hemorrhage
M24: Conjunctival Laceration
M25: Episcleritis/Scleritis – Sectoral Conjunctival Injection
ET5: Blunt Eye Trauma
SD21: Facial Trauma Diagnostic Logic: IF [[M23: Subconjunctival Hemorrhage OR M25: Episcleritis/Scleritis – Sectoral Conjunctival Injection > 50 ocular redness index] AND [ET5: Blunt Eye Trauma OR SD21: Facial Trauma]] OR M24: Conjunctival Laceration, THEN OD27: Conjunctival Laceration Treatment Logic: IF OD27: Conjunctival Laceration, THEN TM02: Refer to eye doctor urgently AND TM27: Recommend topical antibiotic ointment four times a day Management Logic: IF OD27: Conjunctival Laceration not improved, THEN TM06: Recommend surgery

FIG. 36AA

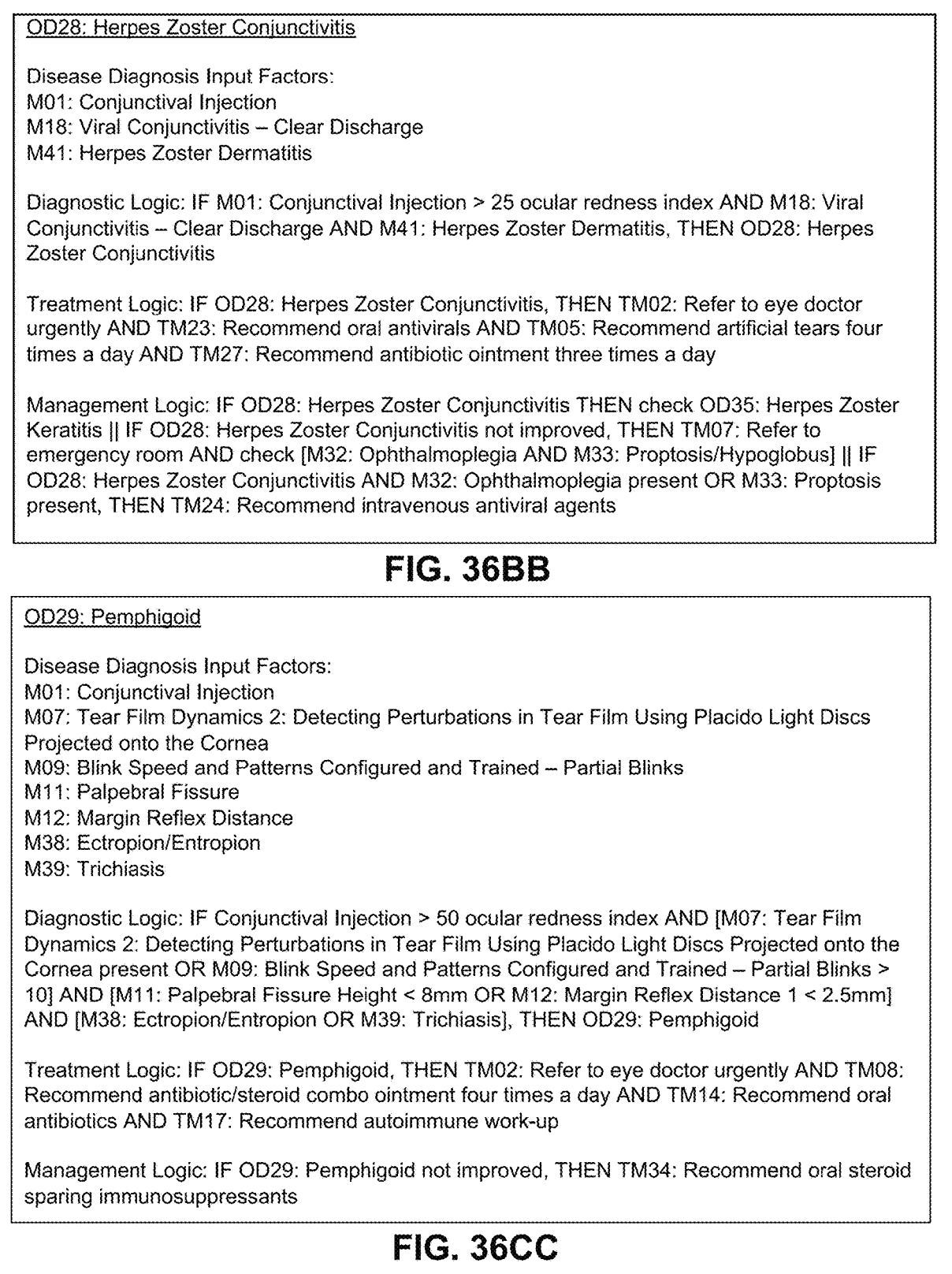

OD28: Herpes Zoster Conjunctivitis

Disease Diagnosis Input Factors:
M01: Conjunctival Injection
M18: Viral Conjunctivitis – Clear Discharge
M41: Herpes Zoster Dermatitis Diagnostic Logic: IF M01: Conjunctival Injection > 25 ocular redness index AND M18: Viral Conjunctivitis – Clear Discharge AND M41: Herpes Zoster Dermatitis, THEN OD28: Herpes Zoster Conjunctivitis Treatment Logic: IF OD28: Herpes Zoster Conjunctivitis, THEN TM02: Refer to eye doctor urgently AND TM23: Recommend oral antivirals AND TM05: Recommend artificial tears four times a day AND TM27: Recommend antibiotic ointment three times a day Management Logic: IF OD28: Herpes Zoster Conjunctivitis THEN check OD35: Herpes Zoster Keratitis || IF OD28: Herpes Zoster Conjunctivitis not improved, THEN TM07: Refer to emergency room AND check [M32: Ophthalmoplegia AND M33: Proptosis/Hypoglobus] || IF OD28: Herpes Zoster Conjunctivitis AND M32: Ophthalmoplegia present OR M33: Proptosis present, THEN TM24: Recommend intravenous antiviral agents

FIG. 36BB

OD29: Pemphigoid

Disease Diagnosis Input Factors:
M01: Conjunctival Injection
M07: Tear Film Dynamics 2: Detecting Perturbations in Tear Film Using Placido Light Discs Projected onto the Cornea
M09: Blink Speed and Patterns Configured and Trained – Partial Blinks
M11: Palpebral Fissure
M12: Margin Reflex Distance
M38: Ectropion/Entropion
M39: Trichiasis Diagnostic Logic: IF Conjunctival Injection > 50 ocular redness index AND [M07: Tear Film Dynamics 2: Detecting Perturbations in Tear Film Using Placido Light Discs Projected onto the Cornea present OR M09: Blink Speed and Patterns Configured and Trained – Partial Blinks > 10] AND [M11: Palpebral Fissure Height < 8mm OR M12: Margin Reflex Distance 1 < 2.5mm] AND [M38: Ectropion/Entropion OR M39: Trichiasis], THEN OD29: Pemphigoid Treatment Logic: IF OD29: Pemphigoid, THEN TM02: Refer to eye doctor urgently AND TM08: Recommend antibiotic/steroid combo ointment four times a day AND TM14: Recommend oral antibiotics AND TM17: Recommend autoimmune work-up Management Logic: IF OD29: Pemphigoid not improved, THEN TM34: Recommend oral steroid sparing immunosuppressants

FIG. 36CC

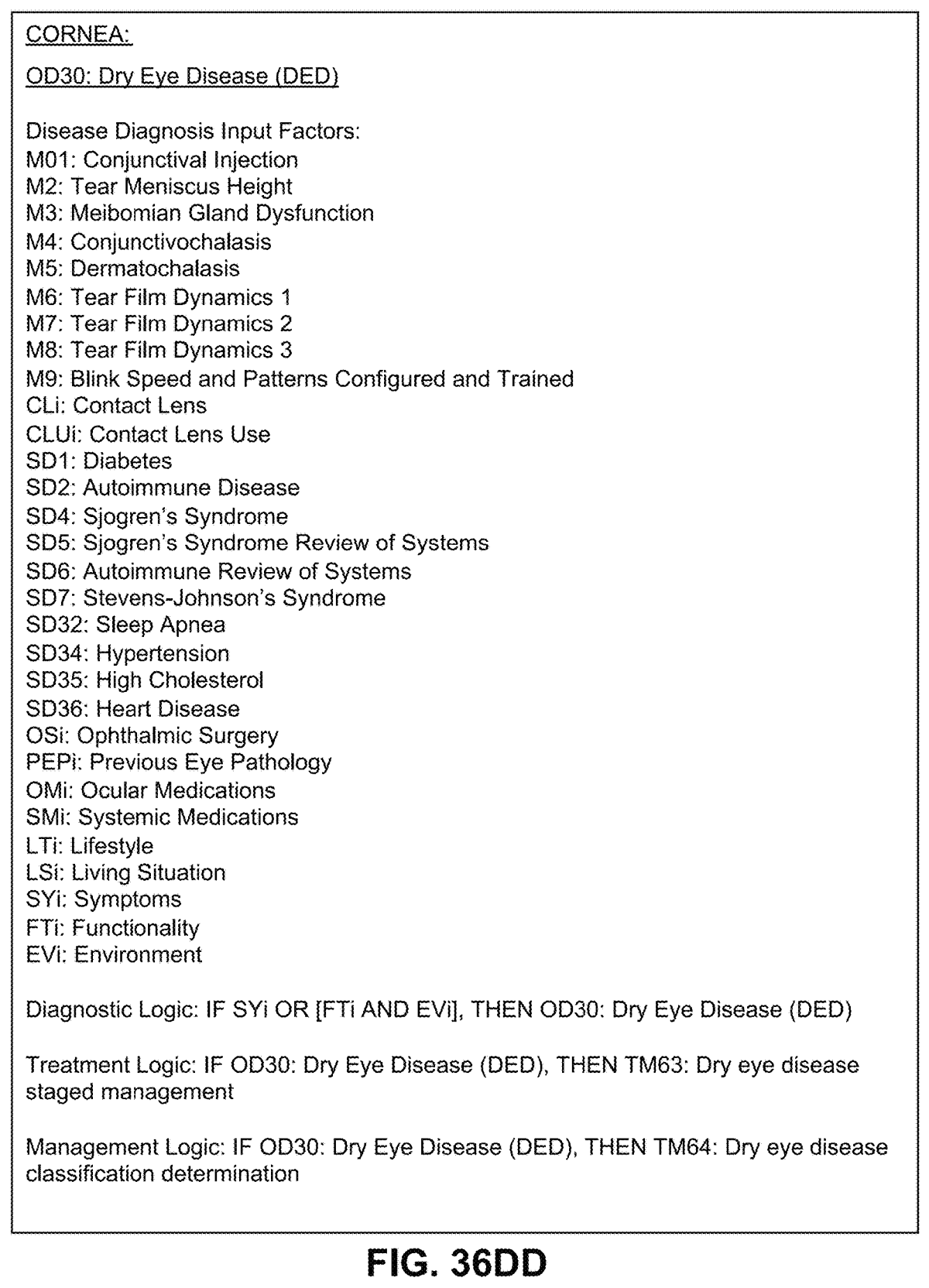

CORNEA:

OD30: Dry Eye Disease (DED)

Disease Diagnosis Input Factors:
M01: Conjunctival Injection
M2: Tear Meniscus Height
M3: Meibomian Gland Dysfunction
M4: Conjunctivochalasis
M5: Dermatochalasis
M6: Tear Film Dynamics 1
M7: Tear Film Dynamics 2
M8: Tear Film Dynamics 3
M9: Blink Speed and Patterns Configured and Trained
CLi: Contact Lens
CLUi: Contact Lens Use
SD1: Diabetes
SD2: Autoimmune Disease
SD4: Sjogren's Syndrome
SD5: Sjogren's Syndrome Review of Systems
SD6: Autoimmune Review of Systems
SD7: Stevens-Johnson's Syndrome
SD32: Sleep Apnea
SD34: Hypertension
SD35: High Cholesterol
SD36: Heart Disease
OSi: Ophthalmic Surgery
PEPi: Previous Eye Pathology
OMi: Ocular Medications
SMi: Systemic Medications
LTi: Lifestyle
LSi: Living Situation
SYi: Symptoms
FTi: Functionality
EVi: Environment Diagnostic Logic: IF SYi OR [FTi AND EVi], THEN OD30: Dry Eye Disease (DED)

Treatment Logic: IF OD30: Dry Eye Disease (DED), THEN TM63: Dry eye disease staged management Management Logic: IF OD30: Dry Eye Disease (DED), THEN TM64: Dry eye disease classification determination

FIG. 36DD

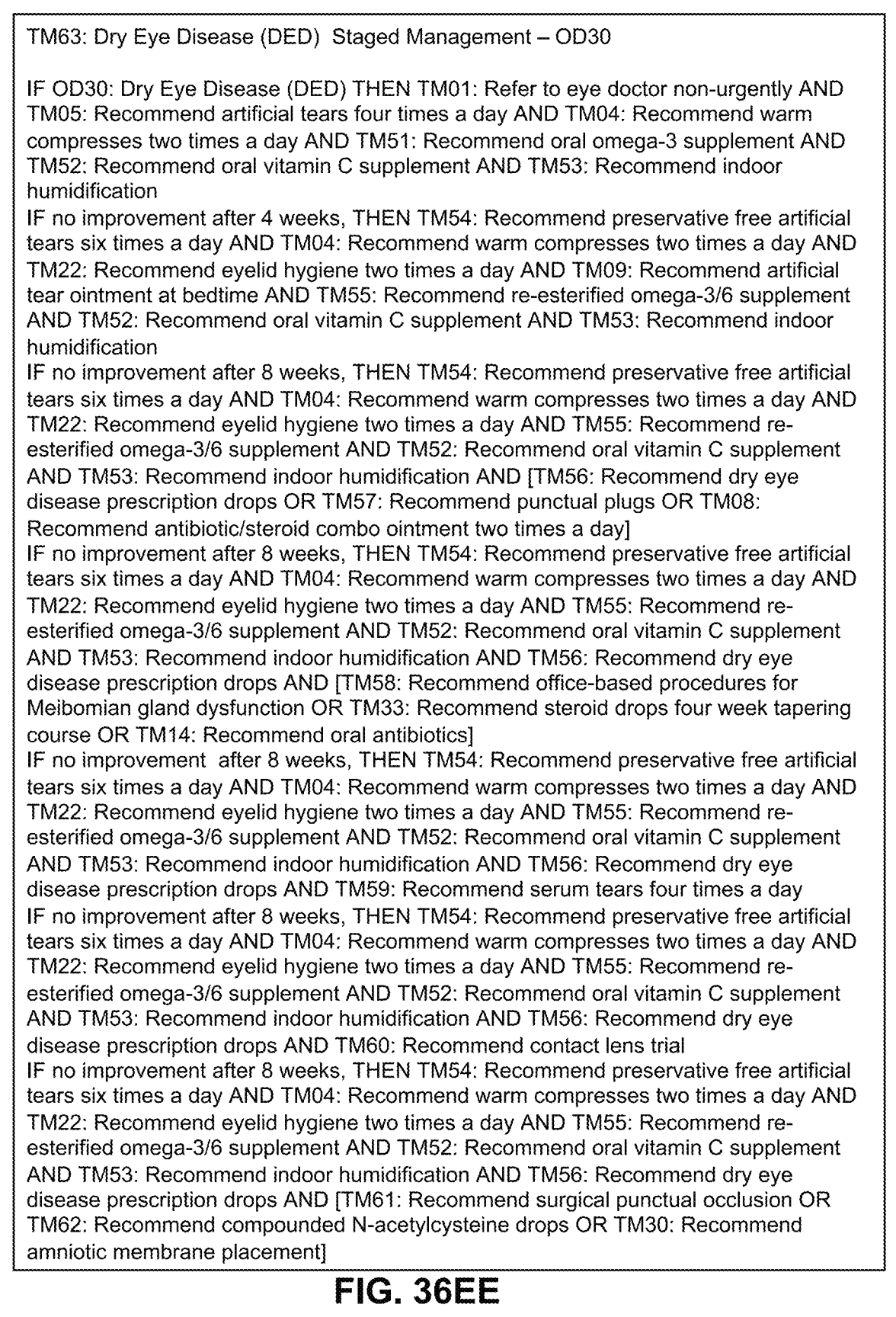

TM63: Dry Eye Disease (DED)  Staged Management – OD30

IF OD30: Dry Eye Disease (DED) THEN TM01: Refer to eye doctor non-urgently AND TM05: Recommend artificial tears four times a day AND TM04: Recommend warm compresses two times a day AND TM51: Recommend oral omega-3 supplement AND TM52: Recommend oral vitamin C supplement AND TM53: Recommend indoor humidification IF no improvement after 4 weeks, THEN TM54: Recommend preservative free artificial tears six times a day AND TM04: Recommend warm compresses two times a day AND TM22: Recommend eyelid hygiene two times a day AND TM09: Recommend artificial tear ointment at bedtime AND TM55: Recommend re-esterified omega-3/6 supplement AND TM52: Recommend oral vitamin C supplement AND TM53: Recommend indoor humidification IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND [TM56: Recommend dry eye disease prescription drops OR TM57: Recommend punctual plugs OR TM08: Recommend antibiotic/steroid combo ointment two times a day]

IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND [TM58: Recommend office-based procedures for Meibomian gland dysfunction OR TM33: Recommend steroid drops four week tapering course OR TM14: Recommend oral antibiotics]

IF no improvement  after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND TM59: Recommend serum tears four times a day IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND TM60: Recommend contact lens trial IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND [TM61: Recommend surgical punctual occlusion OR TM62: Recommend compounded N-acetylcysteine drops OR TM30: Recommend amniotic membrane placement]

FIG. 36EE

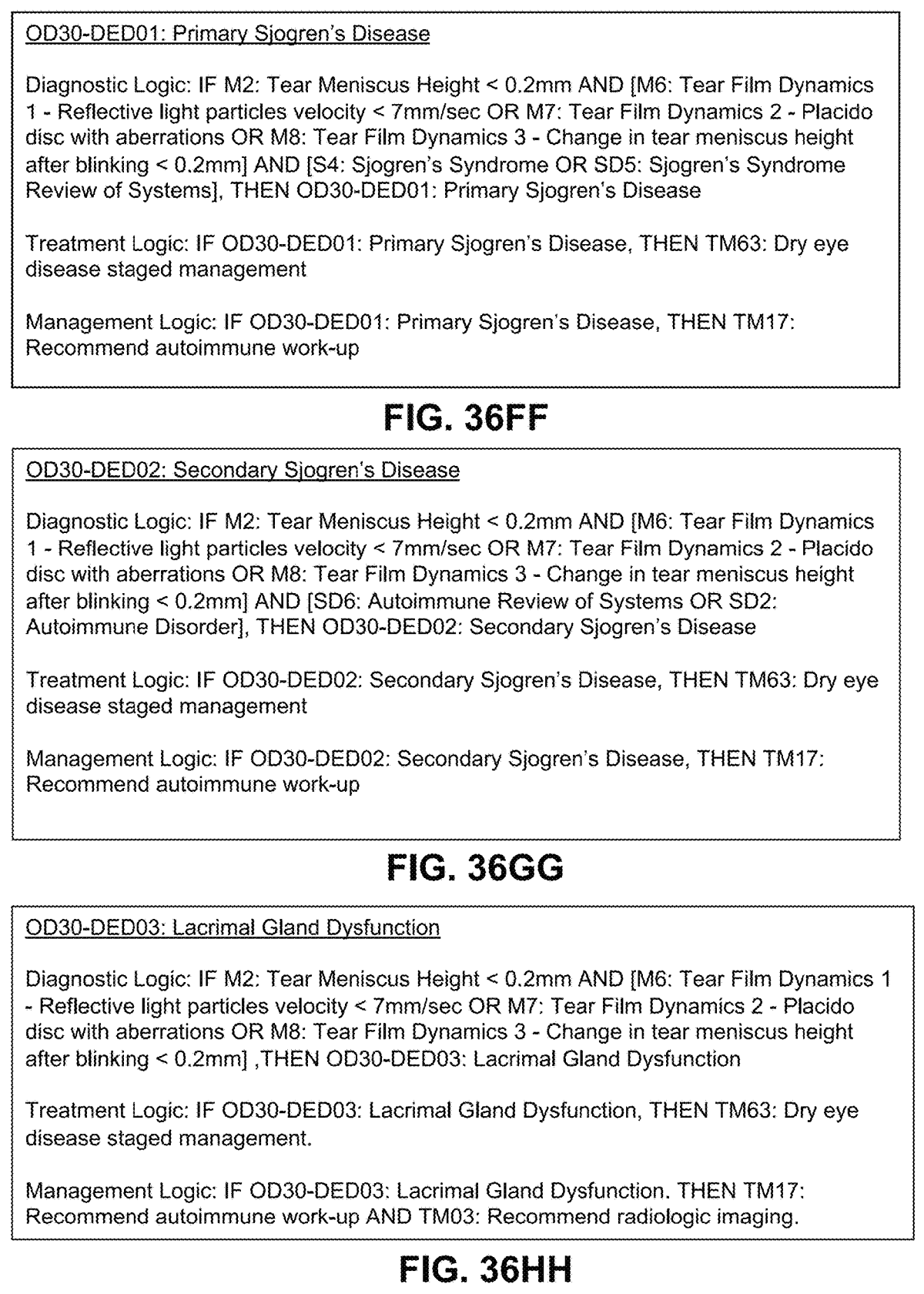

OD30-DED01: Primary Sjogren's Disease

Diagnostic Logic: IF M2: Tear Meniscus Height < 0.2mm AND [M6: Tear Film Dynamics 1 - Reflective light particles velocity < 7mm/sec OR M7: Tear Film Dynamics 2 - Placido disc with aberrations OR M8: Tear Film Dynamics 3 - Change in tear meniscus height after blinking < 0.2mm] AND [S4: Sjogren's Syndrome OR SD5: Sjogren's Syndrome Review of Systems], THEN OD30-DED01: Primary Sjogren's Disease Treatment Logic: IF OD30-DED01: Primary Sjogren's Disease, THEN TM63: Dry eye disease staged management Management Logic: IF OD30-DED01: Primary Sjogren's Disease, THEN TM17: Recommend autoimmune work-up

FIG. 36FF

OD30-DED02: Secondary Sjogren's Disease

Diagnostic Logic: IF M2: Tear Meniscus Height < 0.2mm AND [M6: Tear Film Dynamics 1 - Reflective light particles velocity < 7mm/sec OR M7: Tear Film Dynamics 2 - Placido disc with aberrations OR M8: Tear Film Dynamics 3 - Change in tear meniscus height after blinking < 0.2mm] AND [SD6: Autoimmune Review of Systems OR SD2: Autoimmune Disorder], THEN OD30-DED02: Secondary Sjogren's Disease Treatment Logic: IF OD30-DED02: Secondary Sjogren's Disease, THEN TM63: Dry eye disease staged management Management Logic: IF OD30-DED02: Secondary Sjogren's Disease, THEN TM17: Recommend autoimmune work-up

FIG. 36GG

OD30-DED03: Lacrimal Gland Dysfunction

Diagnostic Logic: IF M2: Tear Meniscus Height < 0.2mm AND [M6: Tear Film Dynamics 1 - Reflective light particles velocity < 7mm/sec OR M7: Tear Film Dynamics 2 - Placido disc with aberrations OR M8: Tear Film Dynamics 3 - Change in tear meniscus height after blinking < 0.2mm] ,THEN OD30-DED03: Lacrimal Gland Dysfunction Treatment Logic: IF OD30-DED03: Lacrimal Gland Dysfunction, THEN TM63: Dry eye disease staged management.

Management Logic: IF OD30-DED03: Lacrimal Gland Dysfunction. THEN TM17: Recommend autoimmune work-up AND TM03: Recommend radiologic imaging.

FIG. 36HH

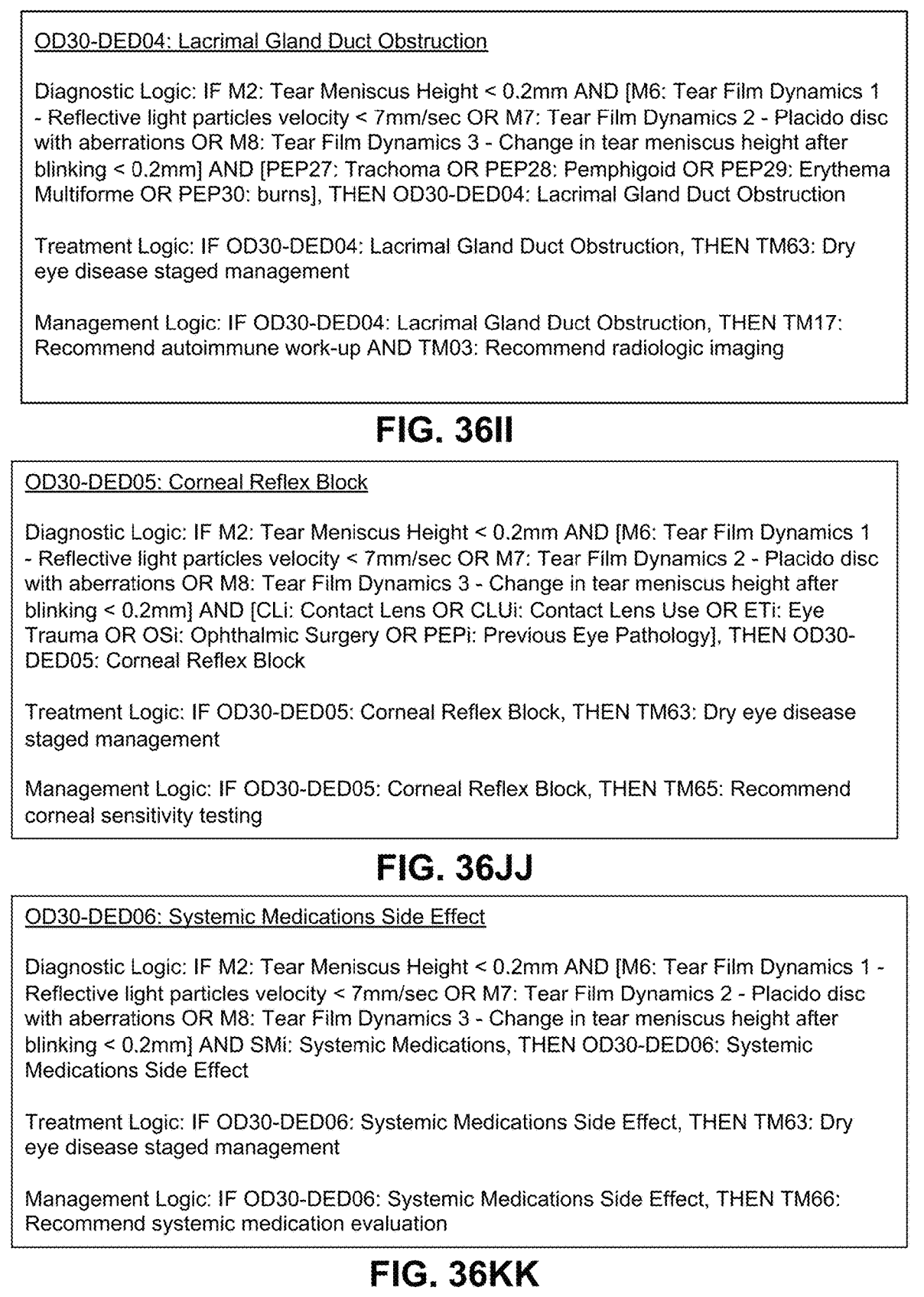

OD30-DED04: Lacrimal Gland Duct Obstruction

Diagnostic Logic: IF M2: Tear Meniscus Height < 0.2mm AND [M6: Tear Film Dynamics 1 - Reflective light particles velocity < 7mm/sec OR M7: Tear Film Dynamics 2 - Placido disc with aberrations OR M8: Tear Film Dynamics 3 - Change in tear meniscus height after blinking < 0.2mm] AND [PEP27: Trachoma OR PEP28: Pemphigoid OR PEP29: Erythema Multiforme OR PEP30: burns], THEN OD30-DED04: Lacrimal Gland Duct Obstruction Treatment Logic: IF OD30-DED04: Lacrimal Gland Duct Obstruction, THEN TM63: Dry eye disease staged management Management Logic: IF OD30-DED04: Lacrimal Gland Duct Obstruction, THEN TM17: Recommend autoimmune work-up AND TM03: Recommend radiologic imaging

FIG. 36II

OD30-DED05: Corneal Reflex Block

Diagnostic Logic: IF M2: Tear Meniscus Height < 0.2mm AND [M6: Tear Film Dynamics 1 - Reflective light particles velocity < 7mm/sec OR M7: Tear Film Dynamics 2 - Placido disc with aberrations OR M8: Tear Film Dynamics 3 - Change in tear meniscus height after blinking < 0.2mm] AND [CLi: Contact Lens OR CLUi: Contact Lens Use OR ETi: Eye Trauma OR OSi: Ophthalmic Surgery OR PEPi: Previous Eye Pathology], THEN OD30-DED05: Corneal Reflex Block Treatment Logic: IF OD30-DED05: Corneal Reflex Block, THEN TM63: Dry eye disease staged management Management Logic: IF OD30-DED05: Corneal Reflex Block, THEN TM65: Recommend corneal sensitivity testing

FIG. 36JJ

OD30-DED06: Systemic Medications Side Effect

Diagnostic Logic: IF M2: Tear Meniscus Height < 0.2mm AND [M6: Tear Film Dynamics 1 - Reflective light particles velocity < 7mm/sec OR M7: Tear Film Dynamics 2 - Placido disc with aberrations OR M8: Tear Film Dynamics 3 - Change in tear meniscus height after blinking < 0.2mm] AND SMi: Systemic Medications, THEN OD30-DED06: Systemic Medications Side Effect Treatment Logic: IF OD30-DED06: Systemic Medications Side Effect, THEN TM63: Dry eye disease staged management Management Logic: IF OD30-DED06: Systemic Medications Side Effect, THEN TM66: Recommend systemic medication evaluation

FIG. 36KK

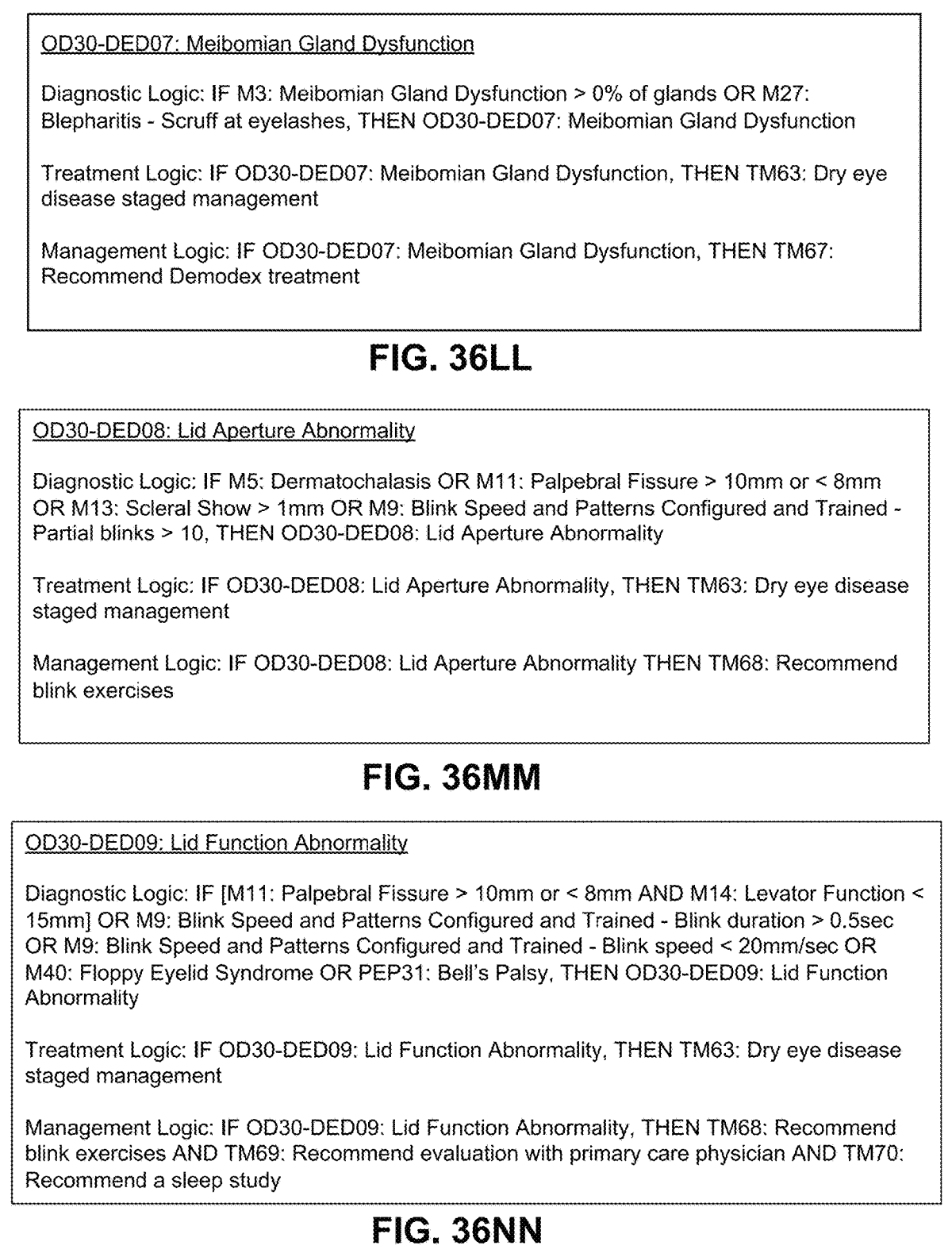

OD30-DED07: Meibomian Gland Dysfunction

Diagnostic Logic: IF M3: Meibomian Gland Dysfunction > 0% of glands OR M27: Blepharitis - Scruff at eyelashes, THEN OD30-DED07: Meibomian Gland Dysfunction Treatment Logic: IF OD30-DED07: Meibomian Gland Dysfunction, THEN TM63: Dry eye disease staged management Management Logic: IF OD30-DED07: Meibomian Gland Dysfunction, THEN TM67: Recommend Demodex treatment

FIG. 36LL

OD30-DED08: Lid Aperture Abnormality

Diagnostic Logic: IF M5: Dermatochalasis OR M11: Palpebral Fissure > 10mm or < 8mm OR M13: Scleral Show > 1mm OR M9: Blink Speed and Patterns Configured and Trained - Partial blinks > 10, THEN OD30-DED08: Lid Aperture Abnormality Treatment Logic: IF OD30-DED08: Lid Aperture Abnormality, THEN TM63: Dry eye disease staged management Management Logic: IF OD30-DED08: Lid Aperture Abnormality THEN TM68: Recommend blink exercises

FIG. 36MM

OD30-DED09: Lid Function Abnormality

Diagnostic Logic: IF [M11: Palpebral Fissure > 10mm or < 8mm AND M14: Levator Function < 15mm] OR M9: Blink Speed and Patterns Configured and Trained - Blink duration > 0.5sec OR M9: Blink Speed and Patterns Configured and Trained - Blink speed < 20mm/sec OR M40: Floppy Eyelid Syndrome OR PEP31: Bell's Palsy, THEN OD30-DED09: Lid Function Abnormality Treatment Logic: IF OD30-DED09: Lid Function Abnormality, THEN TM63: Dry eye disease staged management Management Logic: IF OD30-DED09: Lid Function Abnormality, THEN TM68: Recommend blink exercises AND TM69: Recommend evaluation with primary care physician AND TM70: Recommend a sleep study

FIG. 36NN

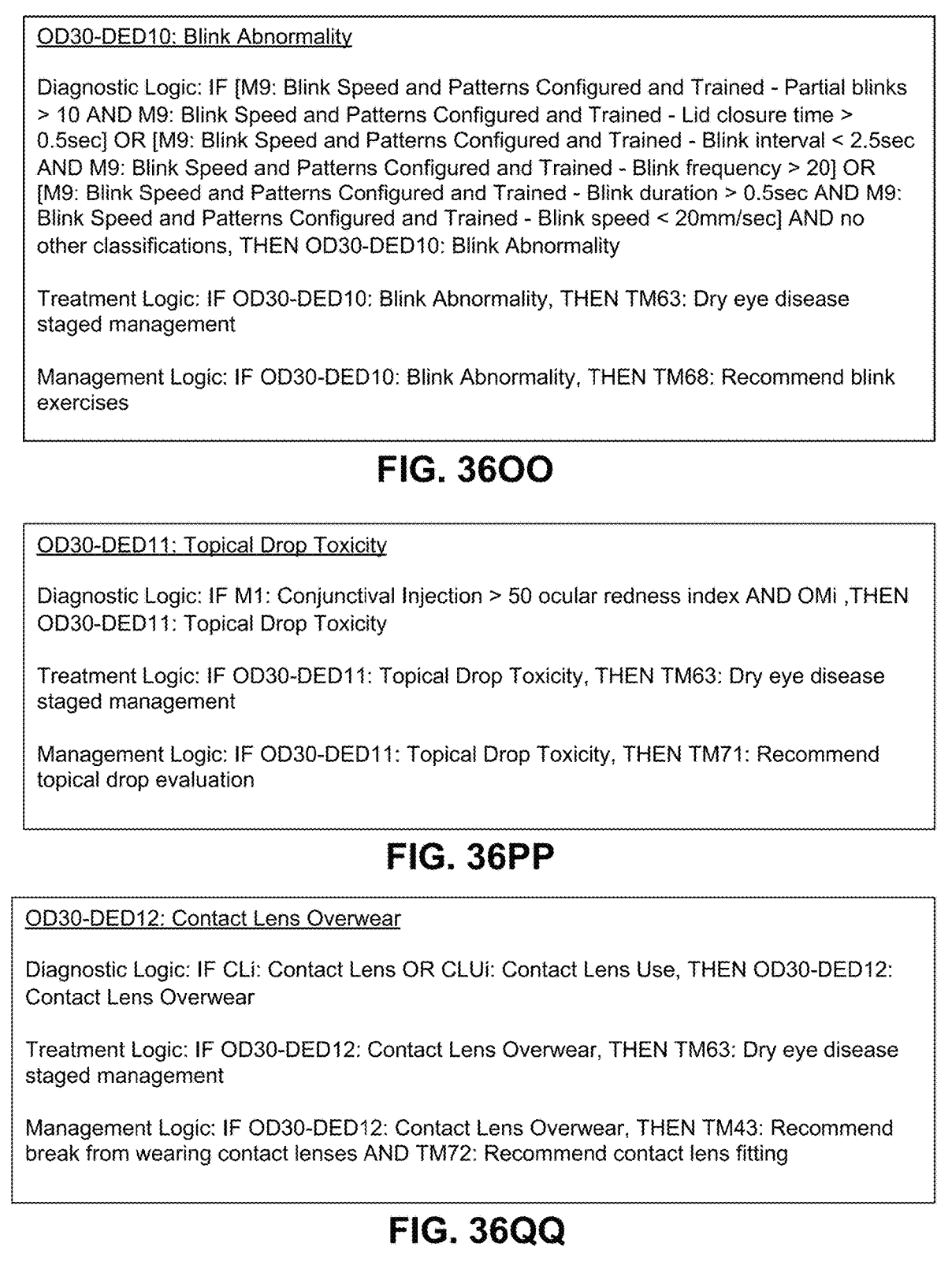

OD30-DED10: Blink Abnormality

Diagnostic Logic: IF [M9: Blink Speed and Patterns Configured and Trained - Partial blinks > 10 AND M9: Blink Speed and Patterns Configured and Trained - Lid closure time > 0.5sec] OR [M9: Blink Speed and Patterns Configured and Trained - Blink interval < 2.5sec AND M9: Blink Speed and Patterns Configured and Trained - Blink frequency > 20] OR [M9: Blink Speed and Patterns Configured and Trained - Blink duration > 0.5sec AND M9: Blink Speed and Patterns Configured and Trained - Blink speed < 20mm/sec] AND no other classifications, THEN OD30-DED10: Blink Abnormality Treatment Logic: IF OD30-DED10: Blink Abnormality, THEN TM63: Dry eye disease staged management Management Logic: IF OD30-DED10: Blink Abnormality, THEN TM68: Recommend blink exercises

FIG. 36OO

OD30-DED11: Topical Drop Toxicity

Diagnostic Logic: IF M1: Conjunctival Injection > 50 ocular redness index AND OMi ,THEN OD30-DED11: Topical Drop Toxicity Treatment Logic: IF OD30-DED11: Topical Drop Toxicity, THEN TM63: Dry eye disease staged management Management Logic: IF OD30-DED11: Topical Drop Toxicity, THEN TM71: Recommend topical drop evaluation

FIG. 36PP

OD30-DED12: Contact Lens Overwear

Diagnostic Logic: IF CLi: Contact Lens OR CLUi: Contact Lens Use, THEN OD30-DED12: Contact Lens Overwear Treatment Logic: IF OD30-DED12: Contact Lens Overwear, THEN TM63: Dry eye disease staged management Management Logic: IF OD30-DED12: Contact Lens Overwear, THEN TM43: Recommend break from wearing contact lenses AND TM72: Recommend contact lens fitting

FIG. 36QQ

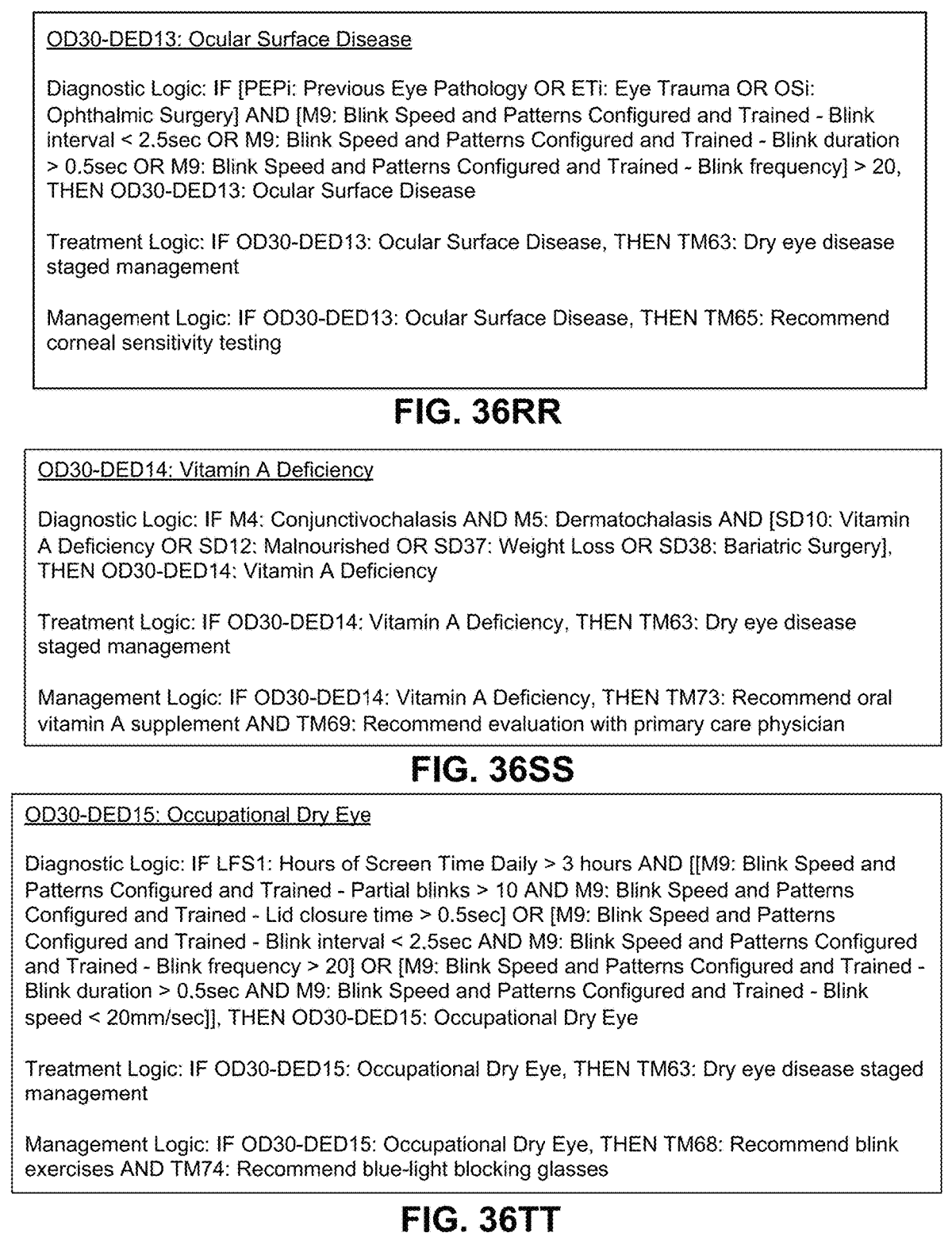

OD30-DED13: Ocular Surface Disease

Diagnostic Logic: IF [PEPi: Previous Eye Pathology OR ETi: Eye Trauma OR OSi: Ophthalmic Surgery] AND [M9: Blink Speed and Patterns Configured and Trained - Blink interval < 2.5sec OR M9: Blink Speed and Patterns Configured and Trained - Blink duration > 0.5sec OR M9: Blink Speed and Patterns Configured and Trained - Blink frequency] > 20, THEN OD30-DED13: Ocular Surface Disease Treatment Logic: IF OD30-DED13: Ocular Surface Disease, THEN TM63: Dry eye disease staged management Management Logic: IF OD30-DED13: Ocular Surface Disease, THEN TM65: Recommend corneal sensitivity testing

FIG. 36RR

OD30-DED14: Vitamin A Deficiency

Diagnostic Logic: IF M4: Conjunctivochalasis AND M5: Dermatochalasis AND [SD10: Vitamin A Deficiency OR SD12: Malnourished OR SD37: Weight Loss OR SD38: Bariatric Surgery], THEN OD30-DED14: Vitamin A Deficiency Treatment Logic: IF OD30-DED14: Vitamin A Deficiency, THEN TM63: Dry eye disease staged management Management Logic: IF OD30-DED14: Vitamin A Deficiency, THEN TM73: Recommend oral vitamin A supplement AND TM69: Recommend evaluation with primary care physician

FIG. 36SS

OD30-DED15: Occupational Dry Eye

Diagnostic Logic: IF LFS1: Hours of Screen Time Daily > 3 hours AND [[M9: Blink Speed and Patterns Configured and Trained - Partial blinks > 10 AND M9: Blink Speed and Patterns Configured and Trained - Lid closure time > 0.5sec] OR [M9: Blink Speed and Patterns Configured and Trained - Blink interval < 2.5sec AND M9: Blink Speed and Patterns Configured and Trained - Blink frequency > 20] OR [M9: Blink Speed and Patterns Configured and Trained - Blink duration > 0.5sec AND M9: Blink Speed and Patterns Configured and Trained - Blink speed < 20mm/sec]], THEN OD30-DED15: Occupational Dry Eye Treatment Logic: IF OD30-DED15: Occupational Dry Eye, THEN TM63: Dry eye disease staged management Management Logic: IF OD30-DED15: Occupational Dry Eye, THEN TM68: Recommend blink exercises AND TM74: Recommend blue-light blocking glasses

FIG. 36TT

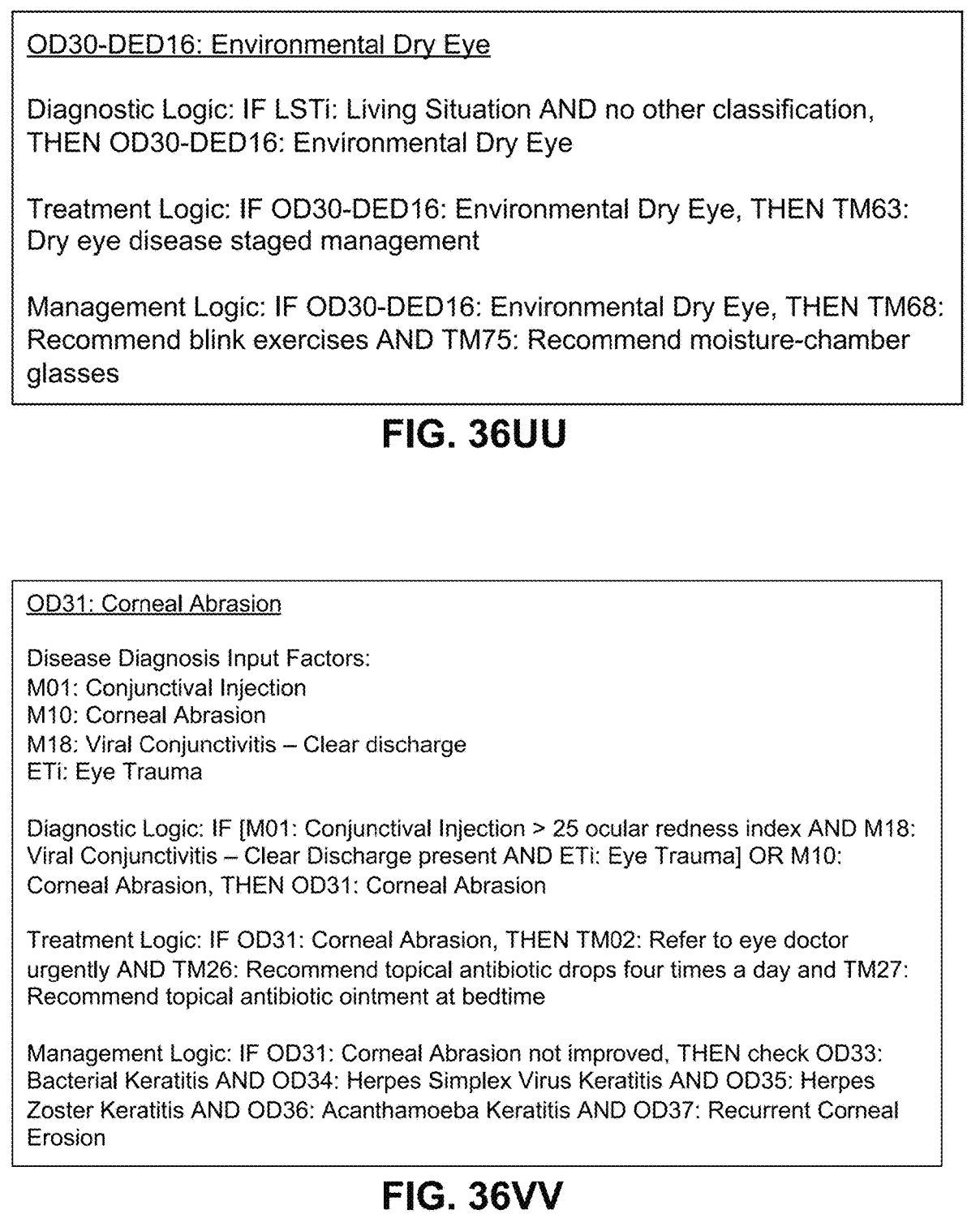

OD30-DED16: Environmental Dry Eye

Diagnostic Logic: IF LSTi: Living Situation AND no other classification, THEN OD30-DED16: Environmental Dry Eye Treatment Logic: IF OD30-DED16: Environmental Dry Eye, THEN TM63: Dry eye disease staged management Management Logic: IF OD30-DED16: Environmental Dry Eye, THEN TM68: Recommend blink exercises AND TM75: Recommend moisture-chamber glasses

FIG. 36UU

OD31: Corneal Abrasion

Disease Diagnosis Input Factors:
M01: Conjunctival Injection
M10: Corneal Abrasion
M18: Viral Conjunctivitis – Clear discharge
ETi: Eye Trauma Diagnostic Logic: IF [M01: Conjunctival Injection > 25 ocular redness index AND M18: Viral Conjunctivitis – Clear Discharge present AND ETi: Eye Trauma] OR M10: Corneal Abrasion, THEN OD31: Corneal Abrasion Treatment Logic: IF OD31: Corneal Abrasion, THEN TM02: Refer to eye doctor urgently AND TM26: Recommend topical antibiotic drops four times a day and TM27: Recommend topical antibiotic ointment at bedtime Management Logic: IF OD31: Corneal Abrasion not improved, THEN check OD33: Bacterial Keratitis AND OD34: Herpes Simplex Virus Keratitis AND OD35: Herpes Zoster Keratitis AND OD36: Acanthamoeba Keratitis AND OD37: Recurrent Corneal Erosion

FIG. 36VV

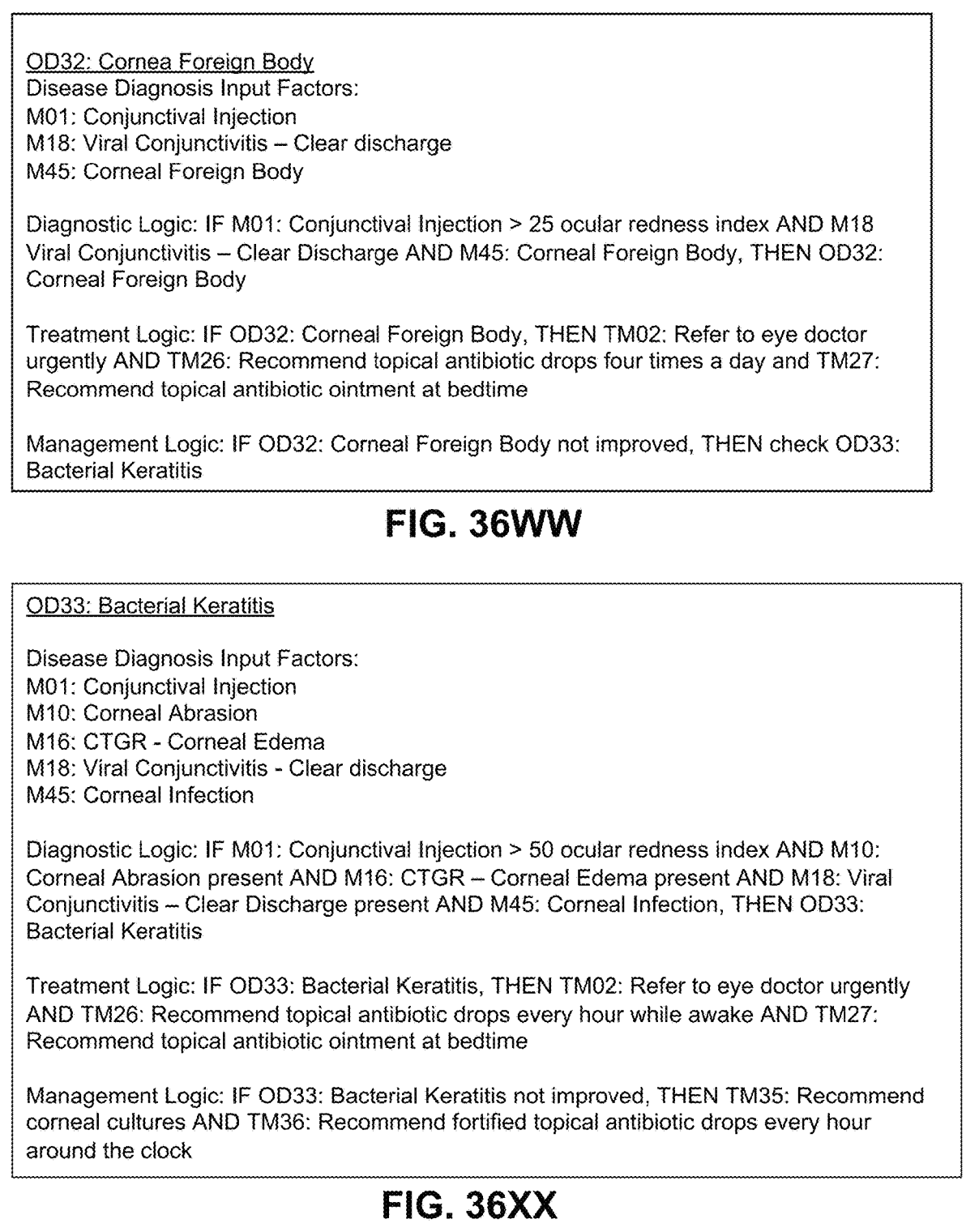

OD32: Cornea Foreign Body
Disease Diagnosis Input Factors:
M01: Conjunctival Injection
M18: Viral Conjunctivitis – Clear discharge
M45: Corneal Foreign Body Diagnostic Logic: IF M01: Conjunctival Injection > 25 ocular redness index AND M18 Viral Conjunctivitis – Clear Discharge AND M45: Corneal Foreign Body, THEN OD32: Corneal Foreign Body Treatment Logic: IF OD32: Corneal Foreign Body, THEN TM02: Refer to eye doctor urgently AND TM26: Recommend topical antibiotic drops four times a day and TM27: Recommend topical antibiotic ointment at bedtime Management Logic: IF OD32: Corneal Foreign Body not improved, THEN check OD33: Bacterial Keratitis

FIG. 36WW

OD33: Bacterial Keratitis

Disease Diagnosis Input Factors:
M01: Conjunctival Injection
M10: Corneal Abrasion
M16: CTGR - Corneal Edema
M18: Viral Conjunctivitis - Clear discharge
M45: Corneal Infection Diagnostic Logic: IF M01: Conjunctival Injection > 50 ocular redness index AND M10: Corneal Abrasion present AND M16: CTGR – Corneal Edema present AND M18: Viral Conjunctivitis – Clear Discharge present AND M45: Corneal Infection, THEN OD33: Bacterial Keratitis Treatment Logic: IF OD33: Bacterial Keratitis, THEN TM02: Refer to eye doctor urgently AND TM26: Recommend topical antibiotic drops every hour while awake AND TM27: Recommend topical antibiotic ointment at bedtime Management Logic: IF OD33: Bacterial Keratitis not improved, THEN TM35: Recommend corneal cultures AND TM36: Recommend fortified topical antibiotic drops every hour around the clock

FIG. 36XX

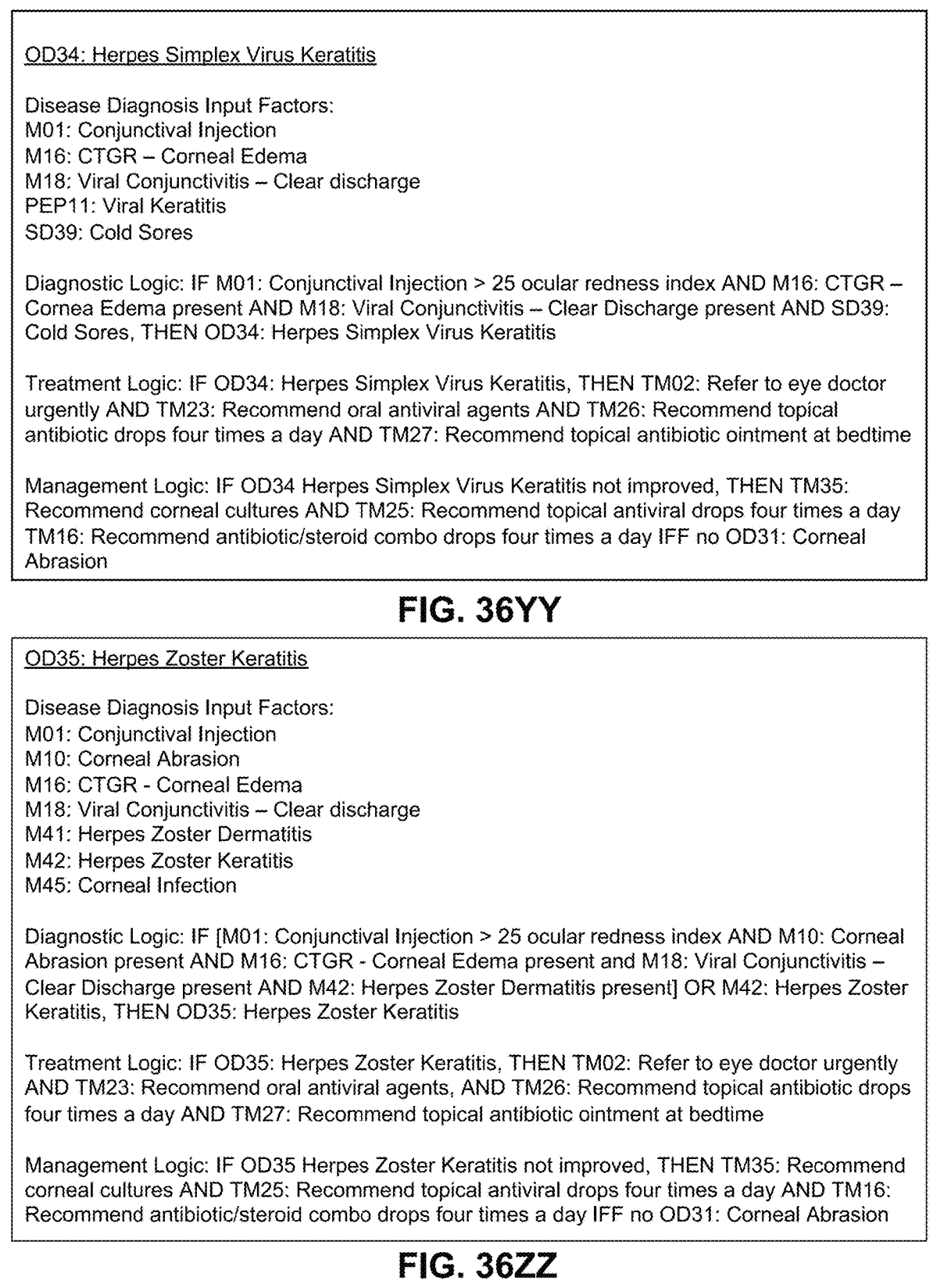

OD34: Herpes Simplex Virus Keratitis

Disease Diagnosis Input Factors:
M01: Conjunctival Injection
M16: CTGR – Corneal Edema
M18: Viral Conjunctivitis – Clear discharge
PEP11: Viral Keratitis
SD39: Cold Sores Diagnostic Logic: IF M01: Conjunctival Injection > 25 ocular redness index AND M16: CTGR – Cornea Edema present AND M18: Viral Conjunctivitis – Clear Discharge present AND SD39: Cold Sores, THEN OD34: Herpes Simplex Virus Keratitis Treatment Logic: IF OD34: Herpes Simplex Virus Keratitis, THEN TM02: Refer to eye doctor urgently AND TM23: Recommend oral antiviral agents AND TM26: Recommend topical antibiotic drops four times a day AND TM27: Recommend topical antibiotic ointment at bedtime Management Logic: IF OD34 Herpes Simplex Virus Keratitis not improved, THEN TM35: Recommend corneal cultures AND TM25: Recommend topical antiviral drops four times a day TM16: Recommend antibiotic/steroid combo drops four times a day IFF no OD31: Corneal Abrasion

FIG. 36YY

OD35: Herpes Zoster Keratitis

Disease Diagnosis Input Factors:
M01: Conjunctival Injection
M10: Corneal Abrasion
M16: CTGR - Corneal Edema
M18: Viral Conjunctivitis – Clear discharge
M41: Herpes Zoster Dermatitis
M42: Herpes Zoster Keratitis
M45: Corneal Infection Diagnostic Logic: IF [M01: Conjunctival Injection > 25 ocular redness index AND M10: Corneal Abrasion present AND M16: CTGR - Corneal Edema present and M18: Viral Conjunctivitis – Clear Discharge present AND M42: Herpes Zoster Dermatitis present] OR M42: Herpes Zoster Keratitis, THEN OD35: Herpes Zoster Keratitis Treatment Logic: IF OD35: Herpes Zoster Keratitis, THEN TM02: Refer to eye doctor urgently AND TM23: Recommend oral antiviral agents, AND TM26: Recommend topical antibiotic drops four times a day AND TM27: Recommend topical antibiotic ointment at bedtime Management Logic: IF OD35 Herpes Zoster Keratitis not improved, THEN TM35: Recommend corneal cultures AND TM25: Recommend topical antiviral drops four times a day AND TM16: Recommend antibiotic/steroid combo drops four times a day IFF no OD31: Corneal Abrasion

FIG. 36ZZ

Figure 36:
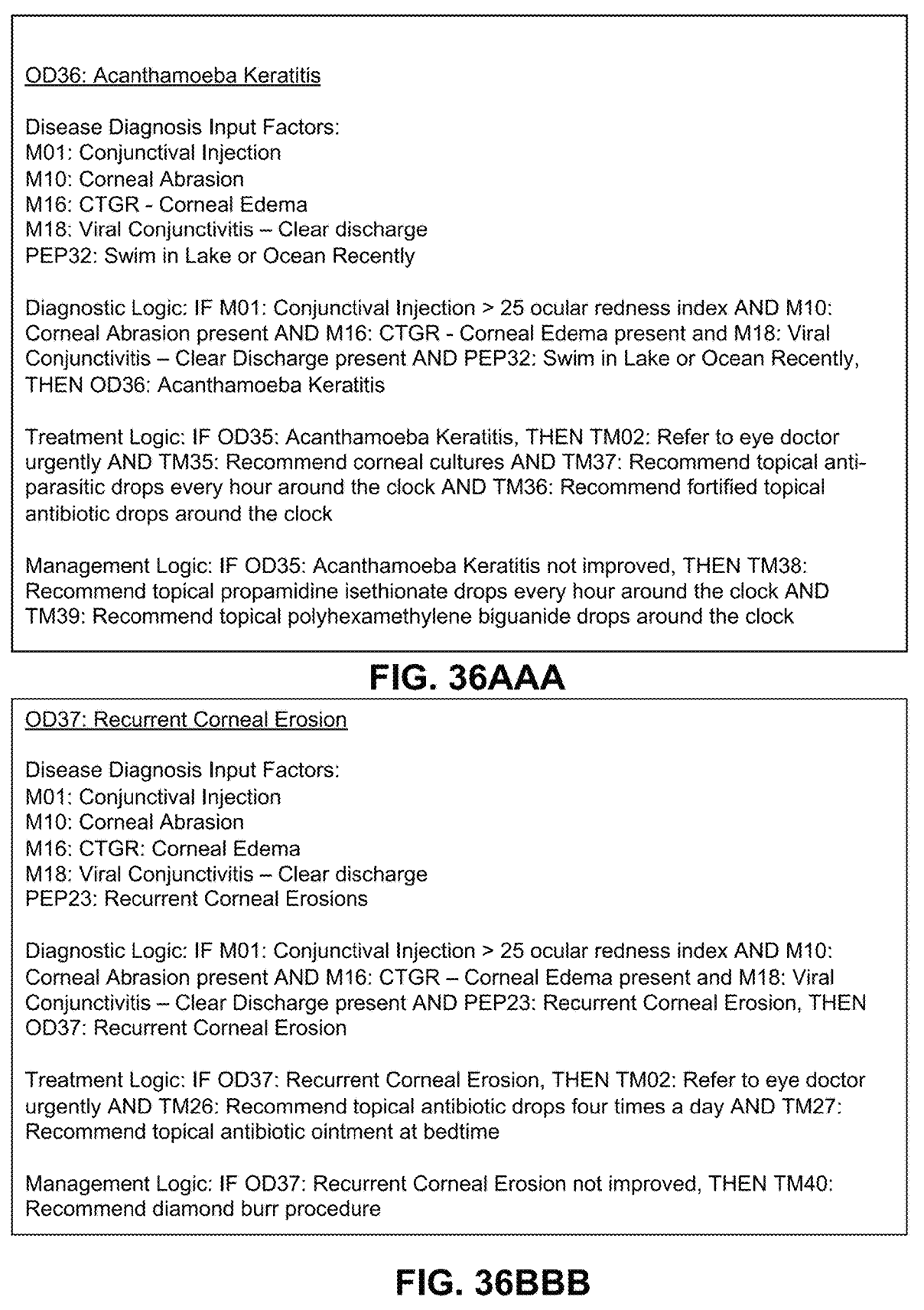

OD36: Acanthamoeba Keratitis

Disease Diagnosis Input Factors:
M01: Conjunctival Injection
M10: Corneal Abrasion
M16: CTGR - Corneal Edema
M18: Viral Conjunctivitis – Clear discharge
PEP32: Swim in Lake or Ocean Recently Diagnostic Logic: IF M01: Conjunctival Injection > 25 ocular redness index AND M10: Corneal Abrasion present AND M16: CTGR - Corneal Edema present and M18: Viral Conjunctivitis – Clear Discharge present AND PEP32: Swim in Lake or Ocean Recently, THEN OD36: Acanthamoeba Keratitis Treatment Logic: IF OD35: Acanthamoeba Keratitis, THEN TM02: Refer to eye doctor urgently AND TM35: Recommend corneal cultures AND TM37: Recommend topical anti-parasitic drops every hour around the clock AND TM36: Recommend fortified topical antibiotic drops around the clock Management Logic: IF OD35: Acanthamoeba Keratitis not improved, THEN TM38: Recommend topical propamidine isethionate drops every hour around the clock AND TM39: Recommend topical polyhexamethylene biguanide drops around the clock

FIG. 36AAA

OD37: Recurrent Corneal Erosion

Disease Diagnosis Input Factors:
M01: Conjunctival Injection
M10: Corneal Abrasion
M16: CTGR: Corneal Edema
M18: Viral Conjunctivitis – Clear discharge
PEP23: Recurrent Corneal Erosions Diagnostic Logic: IF M01: Conjunctival Injection > 25 ocular redness index AND M10: Corneal Abrasion present AND M16: CTGR – Corneal Edema present and M18: Viral Conjunctivitis – Clear Discharge present AND PEP23: Recurrent Corneal Erosion, THEN OD37: Recurrent Corneal Erosion Treatment Logic: IF OD37: Recurrent Corneal Erosion, THEN TM02: Refer to eye doctor urgently AND TM26: Recommend topical antibiotic drops four times a day AND TM27: Recommend topical antibiotic ointment at bedtime Management Logic: IF OD37: Recurrent Corneal Erosion not improved, THEN TM40: Recommend diamond burr procedure

FIG. 36BBB

<u>OD38: Exposure Keratopathy</u>

Disease Diagnosis Input Factors:
OD30: Dry Eye Disease (DED)
M09: Blink Speed and Patterns Configured and Trained
M10: Cornea Abrasion
M33: Proptosis/Hypoglobus
M37: Ectropion/Entropion
M38: Ectropion/Entropion
M39: Trichiasis/Distichiasis
M40: Floppy Eyelid Syndrome
M45: Corneal Infection
PEP28: Pemphigoid
PEP29: Erythema Multiforme
PEP30: Burns
PEP31: Bells Palsy
PEP33: Thyroid Eye Disease
SD32: Sleep Apnea Diagnostic Logic: IF OD30: Dry Eye Disease (DED) present AND [M10: Cornea Abrasion present OR M45: Corneal Infection present] AND [M09: Blink Speed and Patterns Configured and Trained – Partial Blinks > 10 OR M33: Proptosis/Hypoglobus OR M38: Ectropion/Entropion OR M39: Trichiasis/Distichiasis OR M40: Floppy Eyelid Syndrome] AND [PEP28: Pemphigoid OR PEP29: Erythema Multiforme OR PEP30: Burns OR PEP31: Bells Palsy OR PEP33: Thyroid Eye Disease AND SD32: Sleep Apnea], THEN OD38: Exposure Keratopathy Treatment Logic: IF OD38: Exposure Keratopathy, THEN TM01: Refer to eye doctor non-urgently AND TM05: Recommend artificial tears four times a day AND TM09: Recommend artificial tear ointment at bedtime Management Logic: IF OD38: Exposure Keratopathy, THEN check OD39: Neurotrophic Keratopathy AND OD14: Proptosis AND OD16: Thyroid Eye Disease AND OD31: Corneal Abrasion AND OD33: Bacterial Keratitis AND OD53: Bell's Palsy || IF OD38: Exposure Keratopathy not improved THEN TM02: Refer to eye doctor urgently AND TM27: Recommend topical antibiotic ointment four times a day

FIG. 36CCC

Figure 36:
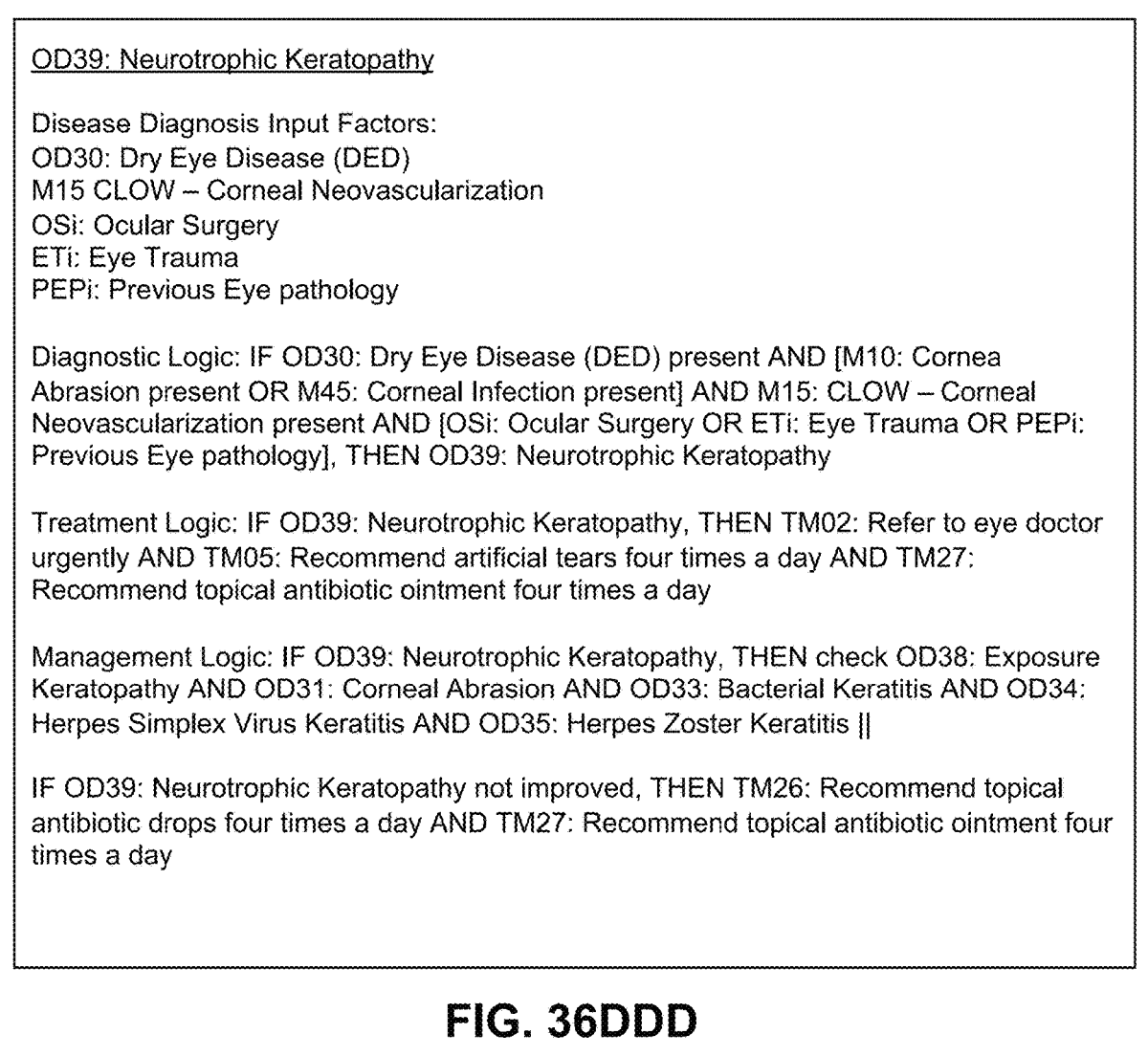

OD39: Neurotrophic Keratopathy

Disease Diagnosis Input Factors:
OD30: Dry Eye Disease (DED)
M15 CLOW – Corneal Neovascularization
OSi: Ocular Surgery
ETi: Eye Trauma
PEPi: Previous Eye pathology Diagnostic Logic: IF OD30: Dry Eye Disease (DED) present AND [M10: Cornea Abrasion present OR M45: Corneal Infection present] AND M15: CLOW – Corneal Neovascularization present AND [OSi: Ocular Surgery OR ETi: Eye Trauma OR PEPi: Previous Eye pathology], THEN OD39: Neurotrophic Keratopathy Treatment Logic: IF OD39: Neurotrophic Keratopathy, THEN TM02: Refer to eye doctor urgently AND TM05: Recommend artificial tears four times a day AND TM27: Recommend topical antibiotic ointment four times a day Management Logic: IF OD39: Neurotrophic Keratopathy, THEN check OD38: Exposure Keratopathy AND OD31: Corneal Abrasion AND OD33: Bacterial Keratitis AND OD34: Herpes Simplex Virus Keratitis AND OD35: Herpes Zoster Keratitis ||

IF OD39: Neurotrophic Keratopathy not improved, THEN TM26: Recommend topical antibiotic drops four times a day AND TM27: Recommend topical antibiotic ointment four times a day

FIG. 36DDD

Figure 36:
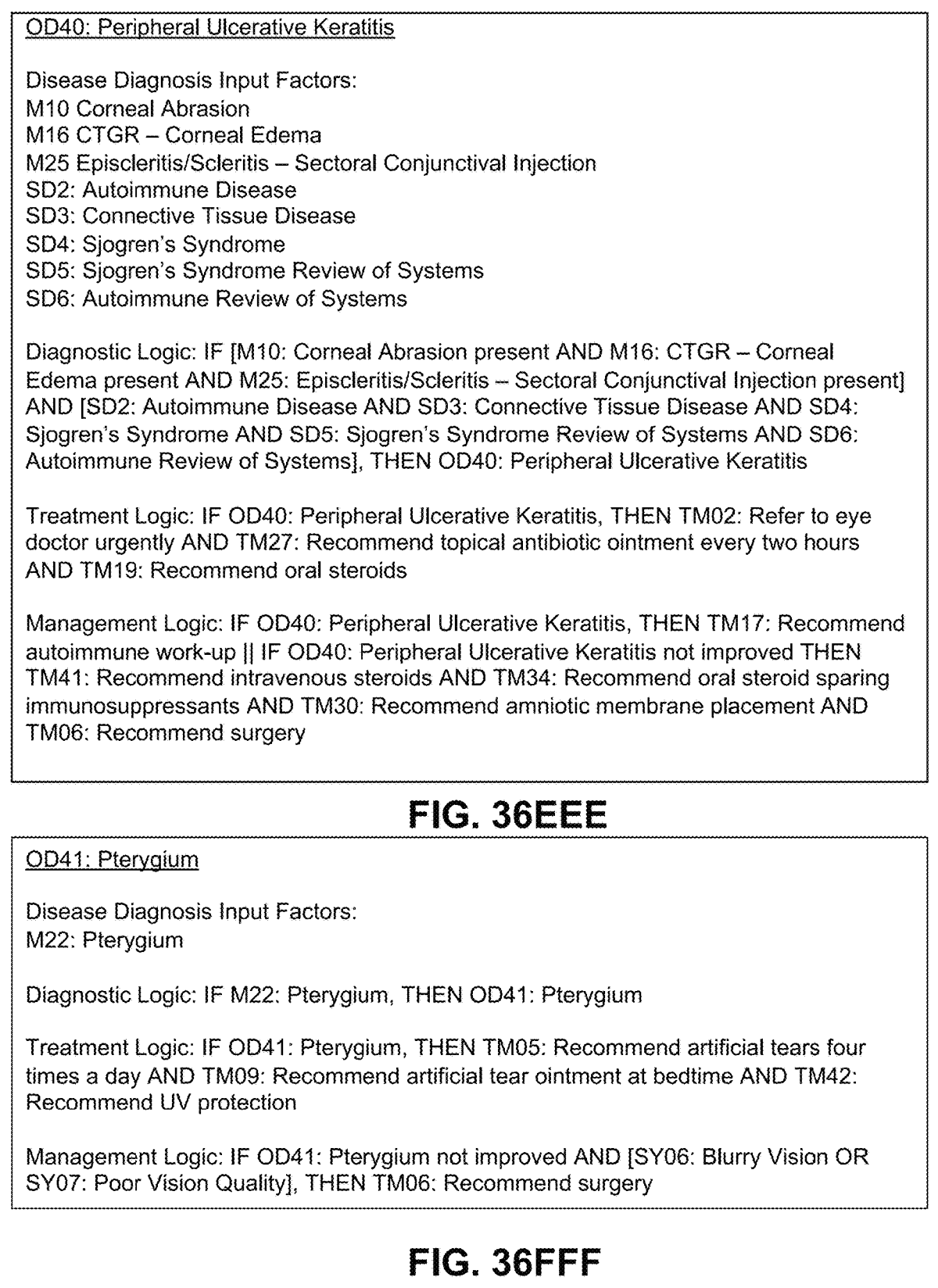

OD40: Peripheral Ulcerative Keratitis

Disease Diagnosis Input Factors:
M10 Corneal Abrasion
M16 CTGR – Corneal Edema
M25 Episcleritis/Scleritis – Sectoral Conjunctival Injection
SD2: Autoimmune Disease
SD3: Connective Tissue Disease
SD4: Sjogren's Syndrome
SD5: Sjogren's Syndrome Review of Systems
SD6: Autoimmune Review of Systems Diagnostic Logic: IF [M10: Corneal Abrasion present AND M16: CTGR – Corneal Edema present AND M25: Episcleritis/Scleritis – Sectoral Conjunctival Injection present] AND [SD2: Autoimmune Disease AND SD3: Connective Tissue Disease AND SD4: Sjogren's Syndrome AND SD5: Sjogren's Syndrome Review of Systems AND SD6: Autoimmune Review of Systems], THEN OD40: Peripheral Ulcerative Keratitis Treatment Logic: IF OD40: Peripheral Ulcerative Keratitis, THEN TM02: Refer to eye doctor urgently AND TM27: Recommend topical antibiotic ointment every two hours AND TM19: Recommend oral steroids Management Logic: IF OD40: Peripheral Ulcerative Keratitis, THEN TM17: Recommend autoimmune work-up || IF OD40: Peripheral Ulcerative Keratitis not improved THEN TM41: Recommend intravenous steroids AND TM34: Recommend oral steroid sparing immunosuppressants AND TM30: Recommend amniotic membrane placement AND TM06: Recommend surgery

FIG. 36EEE

OD41: Pterygium

Disease Diagnosis Input Factors:
M22: Pterygium

Diagnostic Logic: IF M22: Pterygium, THEN OD41: Pterygium

Treatment Logic: IF OD41: Pterygium, THEN TM05: Recommend artificial tears four times a day AND TM09: Recommend artificial tear ointment at bedtime AND TM42: Recommend UV protection Management Logic: IF OD41: Pterygium not improved AND [SY06: Blurry Vision OR SY07: Poor Vision Quality], THEN TM06: Recommend surgery

FIG. 36FFF

Figure 36:
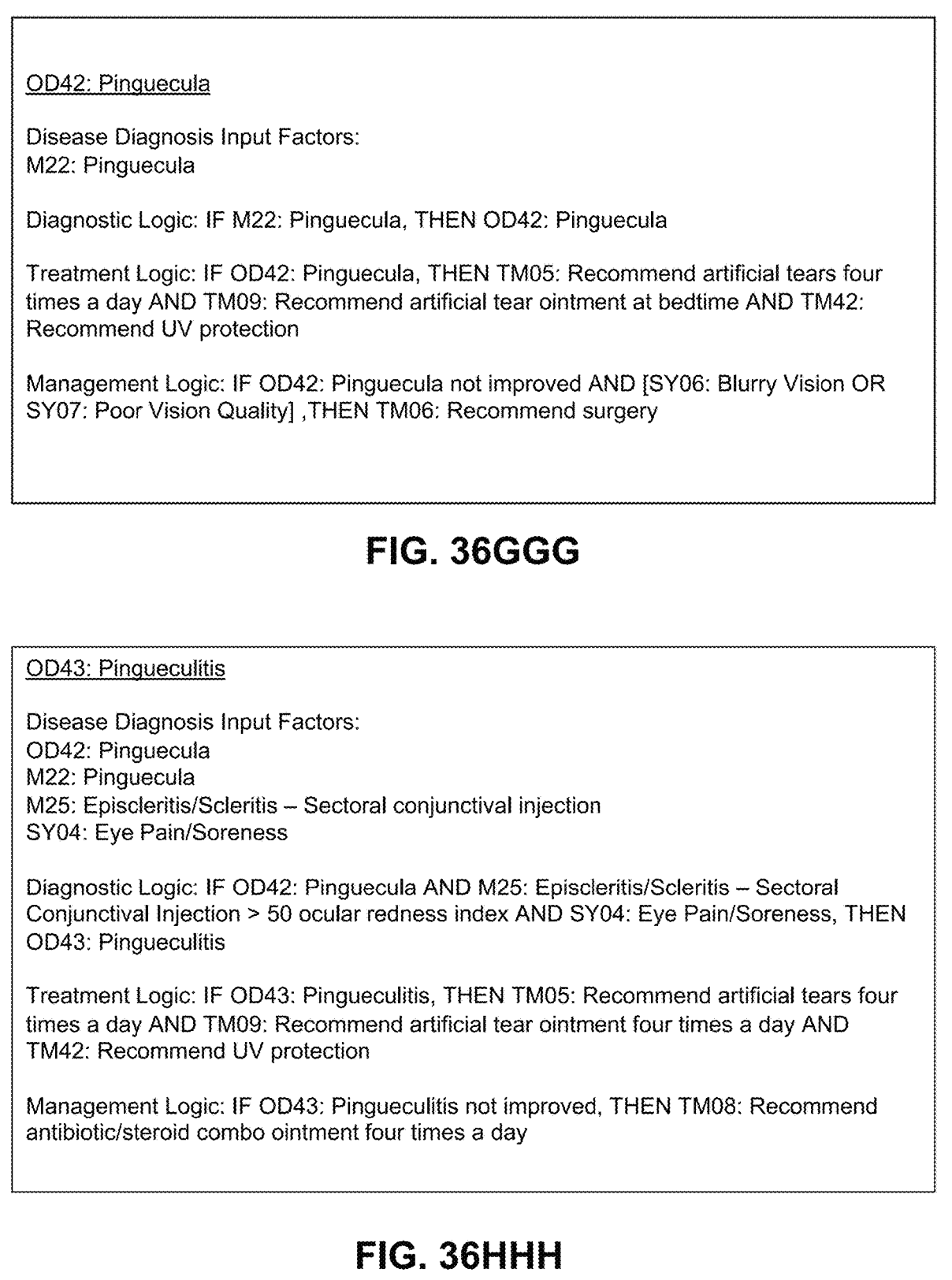

OD42: Pinguecula

Disease Diagnosis Input Factors:
M22: Pinguecula

Diagnostic Logic: IF M22: Pinguecula, THEN OD42: Pinguecula

Treatment Logic: IF OD42: Pinguecula, THEN TM05: Recommend artificial tears four times a day AND TM09: Recommend artificial tear ointment at bedtime AND TM42: Recommend UV protection Management Logic: IF OD42: Pinguecula not improved AND [SY06: Blurry Vision OR SY07: Poor Vision Quality] ,THEN TM06: Recommend surgery

FIG. 36GGG

OD43: Pingueculitis

Disease Diagnosis Input Factors:
OD42: Pinguecula
M22: Pinguecula
M25: Episcleritis/Scleritis – Sectoral conjunctival injection
SY04: Eye Pain/Soreness Diagnostic Logic: IF OD42: Pinguecula AND M25: Episcleritis/Scleritis – Sectoral Conjunctival Injection > 50 ocular redness index AND SY04: Eye Pain/Soreness, THEN OD43: Pingueculitis Treatment Logic: IF OD43: Pingueculitis, THEN TM05: Recommend artificial tears four times a day AND TM09: Recommend artificial tear ointment four times a day AND TM42: Recommend UV protection Management Logic: IF OD43: Pingueculitis not improved, THEN TM08: Recommend antibiotic/steroid combo ointment four times a day

FIG. 36HHH

Figure 36:
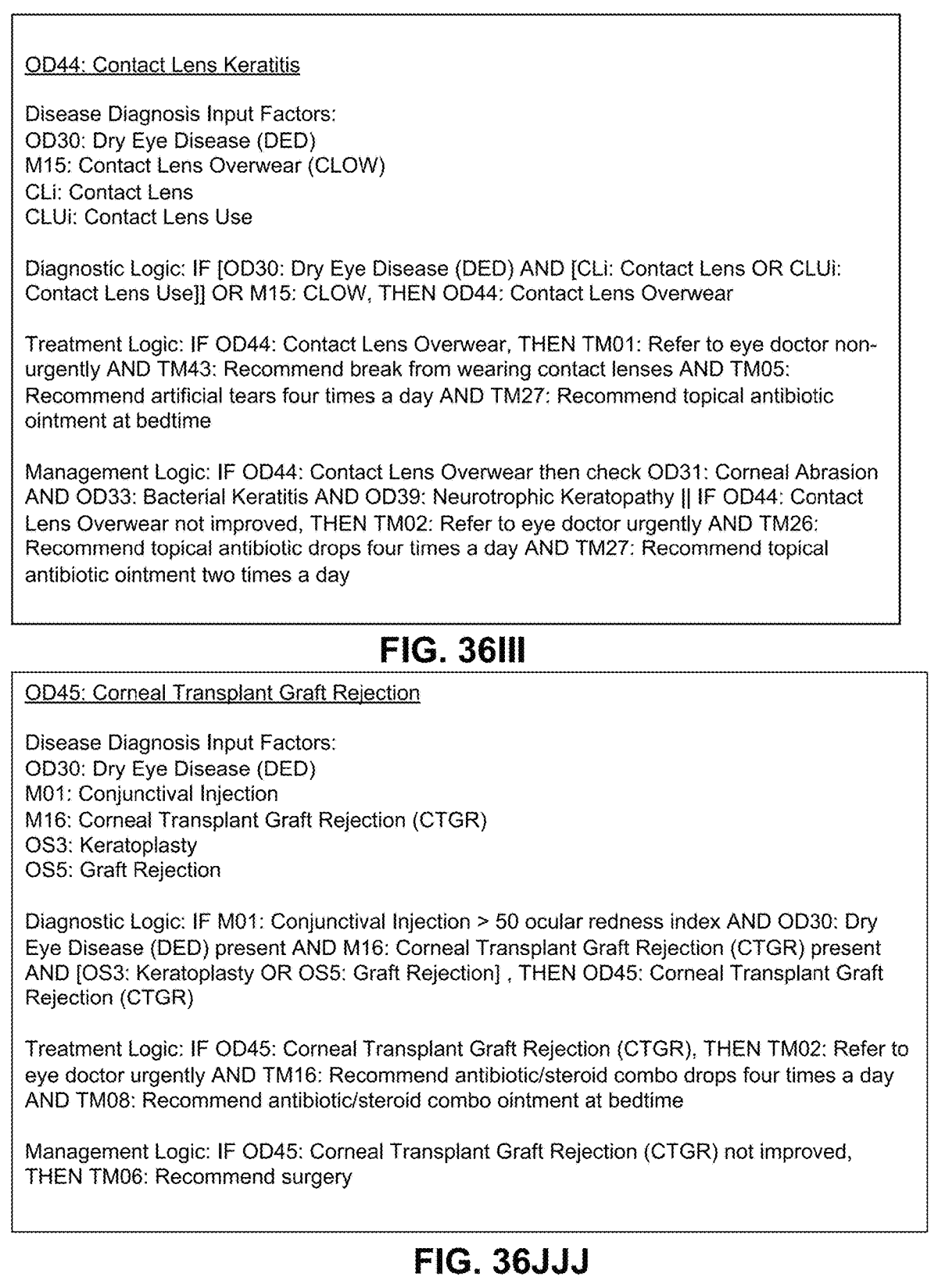

OD44: Contact Lens Keratitis

Disease Diagnosis Input Factors:
OD30: Dry Eye Disease (DED)
M15: Contact Lens Overwear (CLOW)
CLi: Contact Lens
CLUi: Contact Lens Use Diagnostic Logic: IF [OD30: Dry Eye Disease (DED) AND [CLi: Contact Lens OR CLUi: Contact Lens Use]] OR M15: CLOW, THEN OD44: Contact Lens Overwear Treatment Logic: IF OD44: Contact Lens Overwear, THEN TM01: Refer to eye doctor non-urgently AND TM43: Recommend break from wearing contact lenses AND TM05: Recommend artificial tears four times a day AND TM27: Recommend topical antibiotic ointment at bedtime Management Logic: IF OD44: Contact Lens Overwear then check OD31: Corneal Abrasion AND OD33: Bacterial Keratitis AND OD39: Neurotrophic Keratopathy || IF OD44: Contact Lens Overwear not improved, THEN TM02: Refer to eye doctor urgently AND TM26: Recommend topical antibiotic drops four times a day AND TM27: Recommend topical antibiotic ointment two times a day

FIG. 36III

OD45: Corneal Transplant Graft Rejection

Disease Diagnosis Input Factors:
OD30: Dry Eye Disease (DED)
M01: Conjunctival Injection
M16: Corneal Transplant Graft Rejection (CTGR)
OS3: Keratoplasty
OS5: Graft Rejection Diagnostic Logic: IF M01: Conjunctival Injection > 50 ocular redness index AND OD30: Dry Eye Disease (DED) present AND M16: Corneal Transplant Graft Rejection (CTGR) present AND [OS3: Keratoplasty OR OS5: Graft Rejection] , THEN OD45: Corneal Transplant Graft Rejection (CTGR)

Treatment Logic: IF OD45: Corneal Transplant Graft Rejection (CTGR), THEN TM02: Refer to eye doctor urgently AND TM16: Recommend antibiotic/steroid combo drops four times a day AND TM08: Recommend antibiotic/steroid combo ointment at bedtime Management Logic: IF OD45: Corneal Transplant Graft Rejection (CTGR) not improved, THEN TM06: Recommend surgery

FIG. 36JJJ

Figure 36:
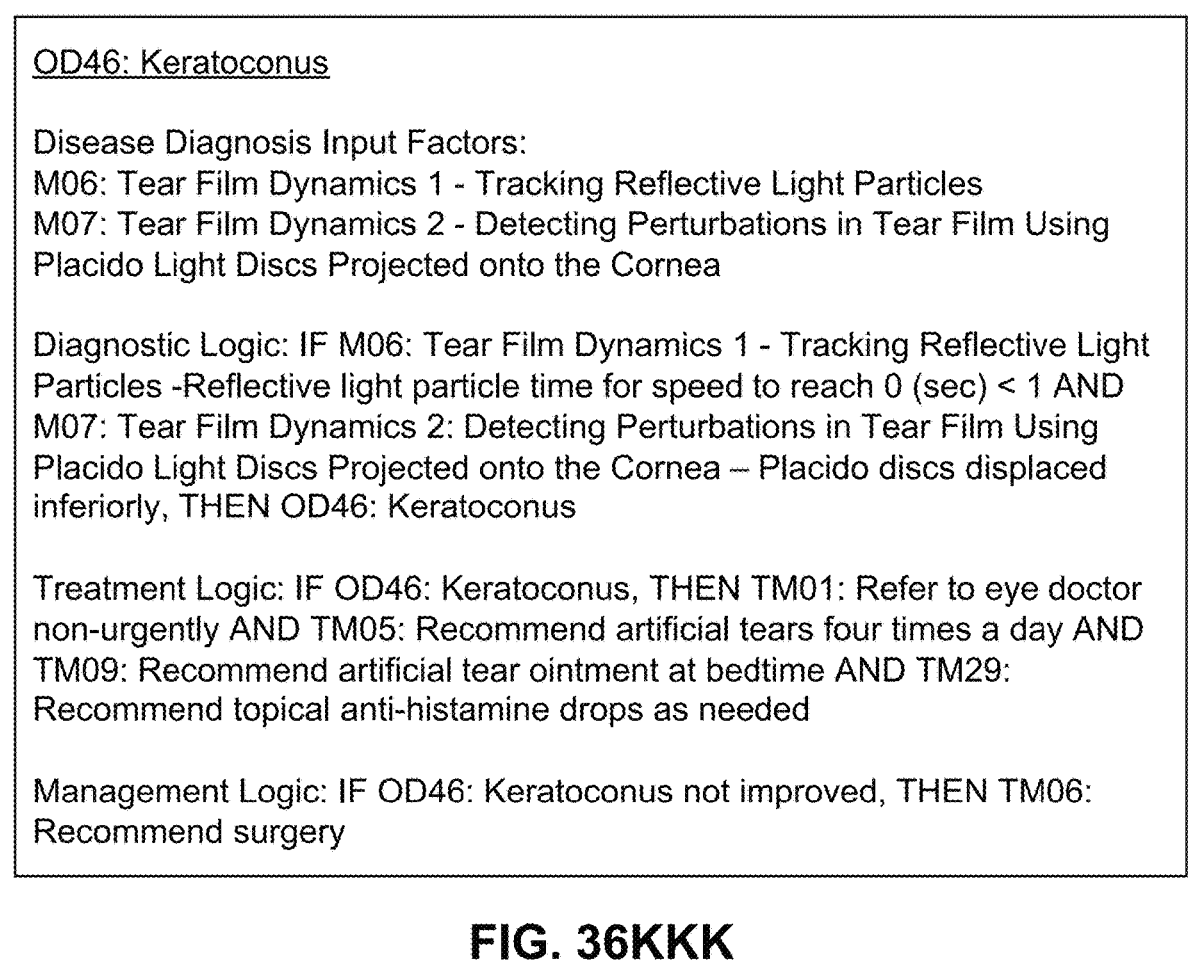

OD46: Keratoconus

Disease Diagnosis Input Factors:
M06: Tear Film Dynamics 1 - Tracking Reflective Light Particles
M07: Tear Film Dynamics 2 - Detecting Perturbations in Tear Film Using
Placido Light Discs Projected onto the Cornea Diagnostic Logic: IF M06: Tear Film Dynamics 1 - Tracking Reflective Light
Particles -Reflective light particle time for speed to reach 0 (sec) < 1 AND
M07: Tear Film Dynamics 2: Detecting Perturbations in Tear Film Using
Placido Light Discs Projected onto the Cornea – Placido discs displaced
inferiorly, THEN OD46: Keratoconus Treatment Logic: IF OD46: Keratoconus, THEN TM01: Refer to eye doctor
non-urgently AND TM05: Recommend artificial tears four times a day AND
TM09: Recommend artificial tear ointment at bedtime AND TM29:
Recommend topical anti-histamine drops as needed Management Logic: IF OD46: Keratoconus not improved, THEN TM06:
Recommend surgery

FIG. 36KKK

Figure 36:
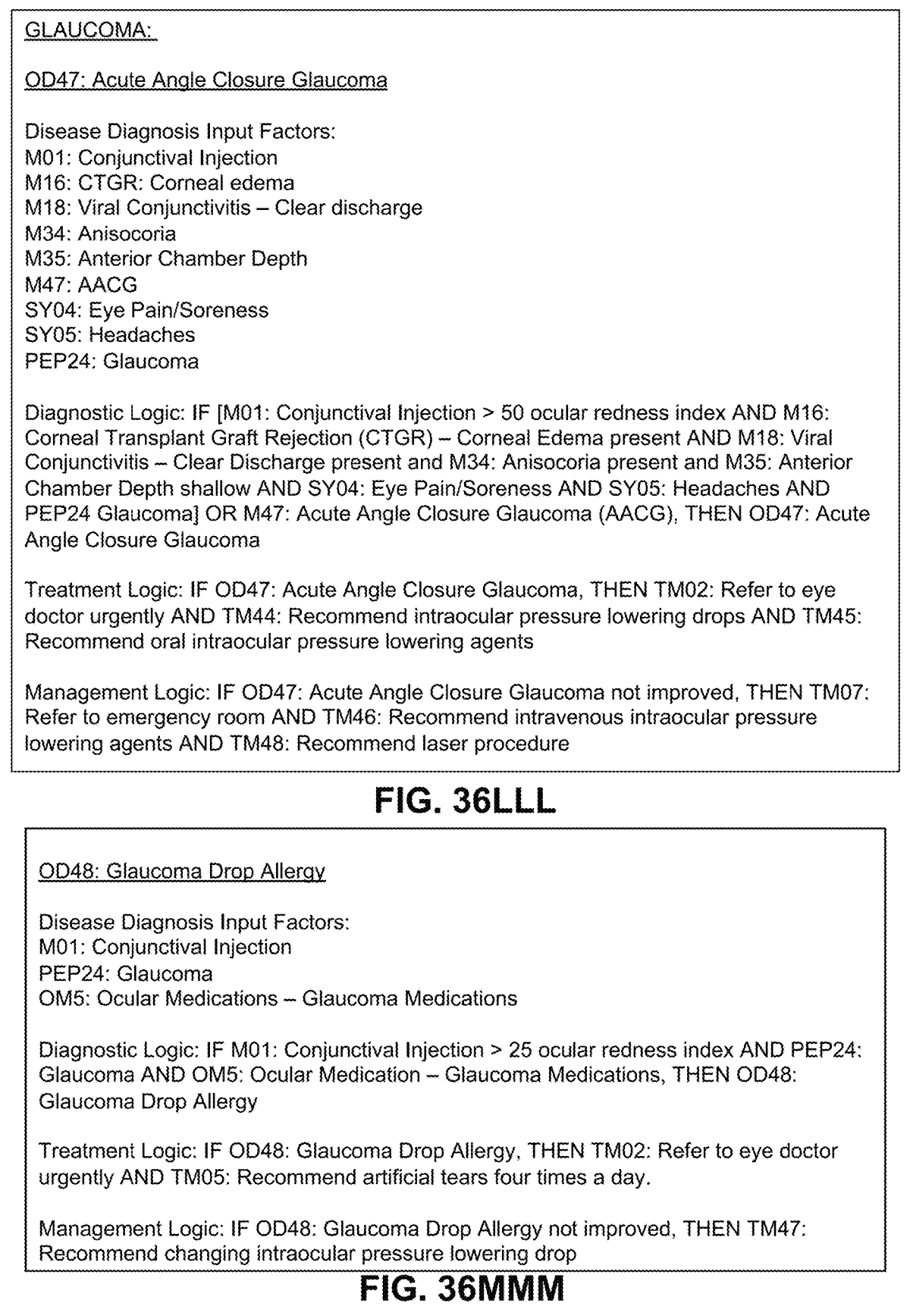

GLAUCOMA:

OD47: Acute Angle Closure Glaucoma

Disease Diagnosis Input Factors:
M01: Conjunctival Injection
M16: CTGR: Corneal edema
M18: Viral Conjunctivitis – Clear discharge
M34: Anisocoria
M35: Anterior Chamber Depth
M47: AACG
SY04: Eye Pain/Soreness
SY05: Headaches
PEP24: Glaucoma Diagnostic Logic: IF [M01: Conjunctival Injection > 50 ocular redness index AND M16: Corneal Transplant Graft Rejection (CTGR) – Corneal Edema present AND M18: Viral Conjunctivitis – Clear Discharge present and M34: Anisocoria present and M35: Anterior Chamber Depth shallow AND SY04: Eye Pain/Soreness AND SY05: Headaches AND PEP24 Glaucoma] OR M47: Acute Angle Closure Glaucoma (AACG), THEN OD47: Acute Angle Closure Glaucoma Treatment Logic: IF OD47: Acute Angle Closure Glaucoma, THEN TM02: Refer to eye doctor urgently AND TM44: Recommend intraocular pressure lowering drops AND TM45: Recommend oral intraocular pressure lowering agents Management Logic: IF OD47: Acute Angle Closure Glaucoma not improved, THEN TM07: Refer to emergency room AND TM46: Recommend intravenous intraocular pressure lowering agents AND TM48: Recommend laser procedure

FIG. 36LLL

OD48: Glaucoma Drop Allergy

Disease Diagnosis Input Factors:
M01: Conjunctival Injection
PEP24: Glaucoma
OM5: Ocular Medications – Glaucoma Medications Diagnostic Logic: IF M01: Conjunctival Injection > 25 ocular redness index AND PEP24: Glaucoma AND OM5: Ocular Medication – Glaucoma Medications, THEN OD48: Glaucoma Drop Allergy Treatment Logic: IF OD48: Glaucoma Drop Allergy, THEN TM02: Refer to eye doctor urgently AND TM05: Recommend artificial tears four times a day.

Management Logic: IF OD48: Glaucoma Drop Allergy not improved, THEN TM47: Recommend changing intraocular pressure lowering drop

FIG. 36MMM

Figure 36:
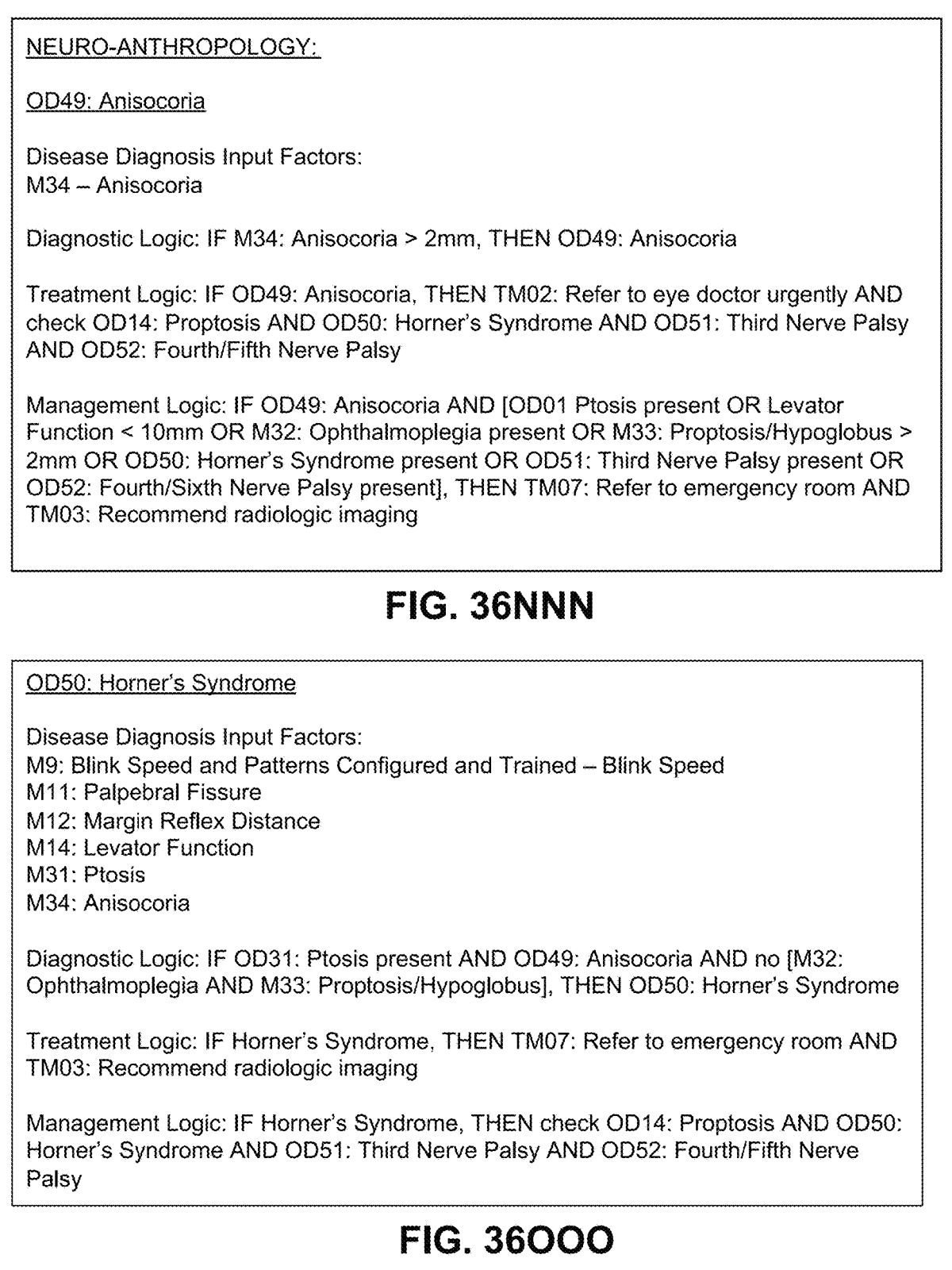

NEURO-ANTHROPOLOGY:

OD49: Anisocoria

Disease Diagnosis Input Factors:
M34 – Anisocoria

Diagnostic Logic: IF M34: Anisocoria > 2mm, THEN OD49: Anisocoria

Treatment Logic: IF OD49: Anisocoria, THEN TM02: Refer to eye doctor urgently AND check OD14: Proptosis AND OD50: Horner's Syndrome AND OD51: Third Nerve Palsy AND OD52: Fourth/Fifth Nerve Palsy Management Logic: IF OD49: Anisocoria AND [OD01 Ptosis present OR Levator Function < 10mm OR M32: Ophthalmoplegia present OR M33: Proptosis/Hypoglobus > 2mm OR OD50: Horner's Syndrome present OR OD51: Third Nerve Palsy present OR OD52: Fourth/Sixth Nerve Palsy present], THEN TM07: Refer to emergency room AND TM03: Recommend radiologic imaging

FIG. 36NNN

OD50: Horner's Syndrome

Disease Diagnosis Input Factors:
M9: Blink Speed and Patterns Configured and Trained – Blink Speed
M11: Palpebral Fissure
M12: Margin Reflex Distance
M14: Levator Function
M31: Ptosis
M34: Anisocoria Diagnostic Logic: IF OD31: Ptosis present AND OD49: Anisocoria AND no [M32: Ophthalmoplegia AND M33: Proptosis/Hypoglobus], THEN OD50: Horner's Syndrome Treatment Logic: IF Horner's Syndrome, THEN TM07: Refer to emergency room AND TM03: Recommend radiologic imaging Management Logic: IF Horner's Syndrome, THEN check OD14: Proptosis AND OD50: Horner's Syndrome AND OD51: Third Nerve Palsy AND OD52: Fourth/Fifth Nerve Palsy

FIG. 36OOO

Figure 36:
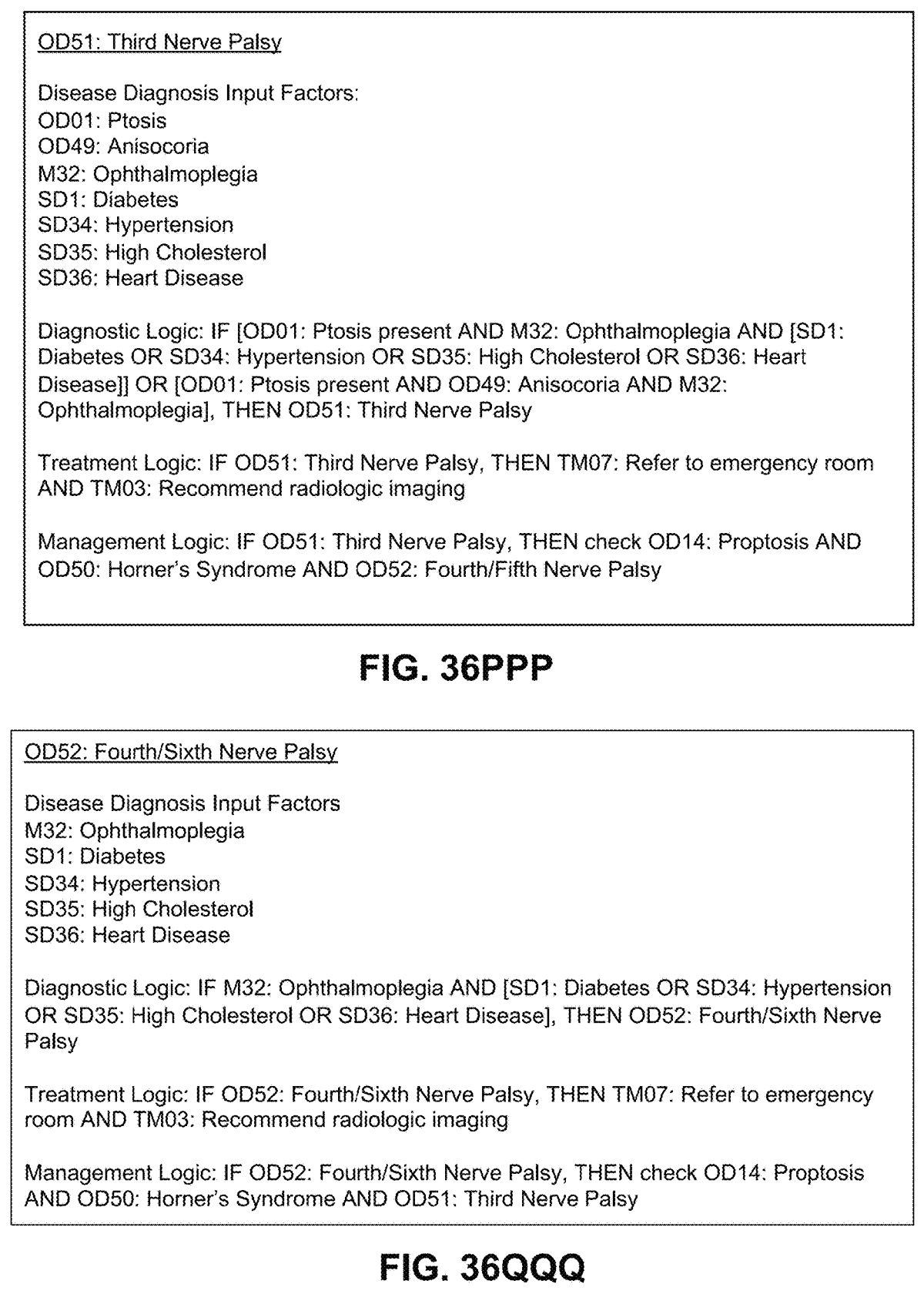

OD51: Third Nerve Palsy

Disease Diagnosis Input Factors:
OD01: Ptosis
OD49: Anisocoria
M32: Ophthalmoplegia
SD1: Diabetes
SD34: Hypertension
SD35: High Cholesterol
SD36: Heart Disease Diagnostic Logic: IF [OD01: Ptosis present AND M32: Ophthalmoplegia AND [SD1: Diabetes OR SD34: Hypertension OR SD35: High Cholesterol OR SD36: Heart Disease]] OR [OD01: Ptosis present AND OD49: Anisocoria AND M32: Ophthalmoplegia], THEN OD51: Third Nerve Palsy Treatment Logic: IF OD51: Third Nerve Palsy, THEN TM07: Refer to emergency room AND TM03: Recommend radiologic imaging Management Logic: IF OD51: Third Nerve Palsy, THEN check OD14: Proptosis AND OD50: Horner's Syndrome AND OD52: Fourth/Fifth Nerve Palsy

FIG. 36PPP

OD52: Fourth/Sixth Nerve Palsy

Disease Diagnosis Input Factors
M32: Ophthalmoplegia
SD1: Diabetes
SD34: Hypertension
SD35: High Cholesterol
SD36: Heart Disease Diagnostic Logic: IF M32: Ophthalmoplegia AND [SD1: Diabetes OR SD34: Hypertension OR SD35: High Cholesterol OR SD36: Heart Disease], THEN OD52: Fourth/Sixth Nerve Palsy Treatment Logic: IF OD52: Fourth/Sixth Nerve Palsy, THEN TM07: Refer to emergency room AND TM03: Recommend radiologic imaging Management Logic: IF OD52: Fourth/Sixth Nerve Palsy, THEN check OD14: Proptosis AND OD50: Horner's Syndrome AND OD51: Third Nerve Palsy

FIG. 36QQQ

Figure 36:
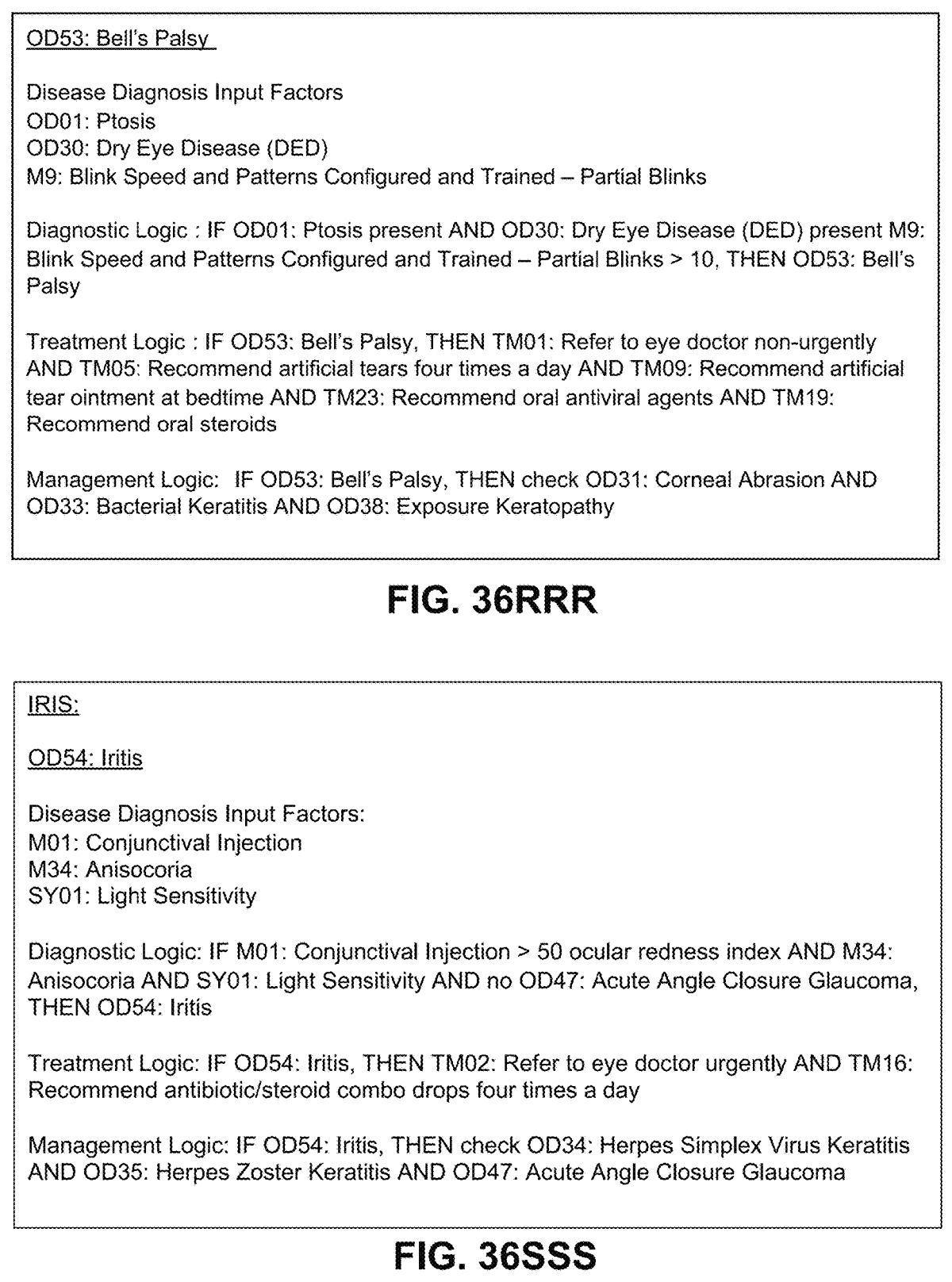

OD53: Bell's Palsy

Disease Diagnosis Input Factors
OD01: Ptosis
OD30: Dry Eye Disease (DED)
M9: Blink Speed and Patterns Configured and Trained – Partial Blinks Diagnostic Logic : IF OD01: Ptosis present AND OD30: Dry Eye Disease (DED) present M9: Blink Speed and Patterns Configured and Trained – Partial Blinks > 10, THEN OD53: Bell's Palsy Treatment Logic : IF OD53: Bell's Palsy, THEN TM01: Refer to eye doctor non-urgently AND TM05: Recommend artificial tears four times a day AND TM09: Recommend artificial tear ointment at bedtime AND TM23: Recommend oral antiviral agents AND TM19: Recommend oral steroids Management Logic:  IF OD53: Bell's Palsy, THEN check OD31: Corneal Abrasion AND OD33: Bacterial Keratitis AND OD38: Exposure Keratopathy

FIG. 36RRR

IRIS:

OD54: Iritis

Disease Diagnosis Input Factors:
M01: Conjunctival Injection
M34: Anisocoria
SY01: Light Sensitivity Diagnostic Logic: IF M01: Conjunctival Injection > 50 ocular redness index AND M34: Anisocoria AND SY01: Light Sensitivity AND no OD47: Acute Angle Closure Glaucoma, THEN OD54: Iritis Treatment Logic: IF OD54: Iritis, THEN TM02: Refer to eye doctor urgently AND TM16: Recommend antibiotic/steroid combo drops four times a day Management Logic: IF OD54: Iritis, THEN check OD34: Herpes Simplex Virus Keratitis AND OD35: Herpes Zoster Keratitis AND OD47: Acute Angle Closure Glaucoma

FIG. 36SSS

Figure 36:
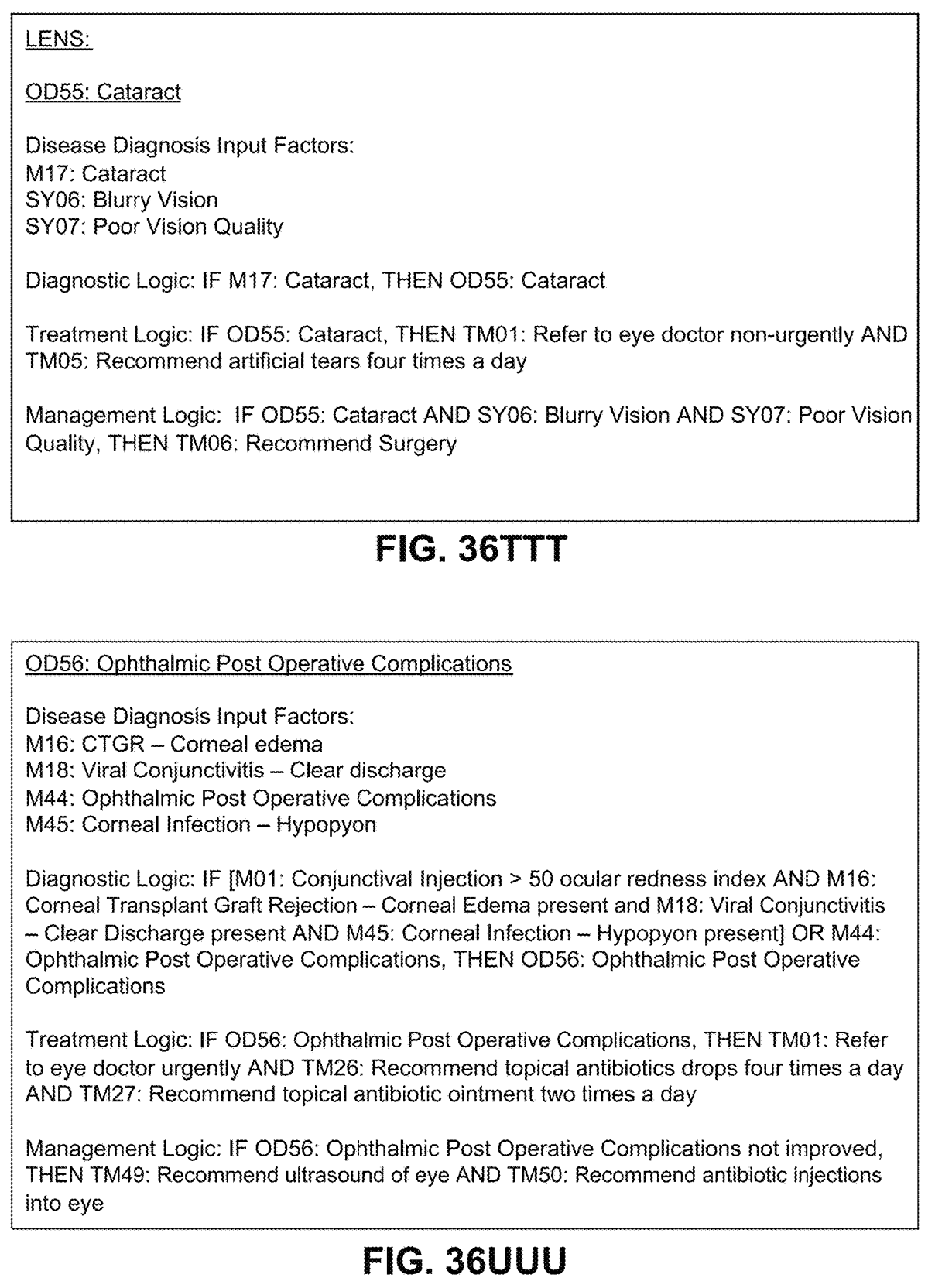

LENS:

OD55: Cataract

Disease Diagnosis Input Factors:
M17: Cataract
SY06: Blurry Vision
SY07: Poor Vision Quality Diagnostic Logic: IF M17: Cataract, THEN OD55: Cataract Treatment Logic: IF OD55: Cataract, THEN TM01: Refer to eye doctor non-urgently AND TM05: Recommend artificial tears four times a day Management Logic:  IF OD55: Cataract AND SY06: Blurry Vision AND SY07: Poor Vision Quality, THEN TM06: Recommend Surgery

FIG. 36TTT

OD56: Ophthalmic Post Operative Complications

Disease Diagnosis Input Factors:
M16: CTGR – Corneal edema
M18: Viral Conjunctivitis – Clear discharge
M44: Ophthalmic Post Operative Complications
M45: Corneal Infection – Hypopyon Diagnostic Logic: IF [M01: Conjunctival Injection > 50 ocular redness index AND M16: Corneal Transplant Graft Rejection – Corneal Edema present and M18: Viral Conjunctivitis – Clear Discharge present AND M45: Corneal Infection – Hypopyon present] OR M44: Ophthalmic Post Operative Complications, THEN OD56: Ophthalmic Post Operative Complications Treatment Logic: IF OD56: Ophthalmic Post Operative Complications, THEN TM01: Refer to eye doctor urgently AND TM26: Recommend topical antibiotics drops four times a day AND TM27: Recommend topical antibiotic ointment two times a day Management Logic: IF OD56: Ophthalmic Post Operative Complications not improved, THEN TM49: Recommend ultrasound of eye AND TM50: Recommend antibiotic injections into eye

FIG. 36UUU

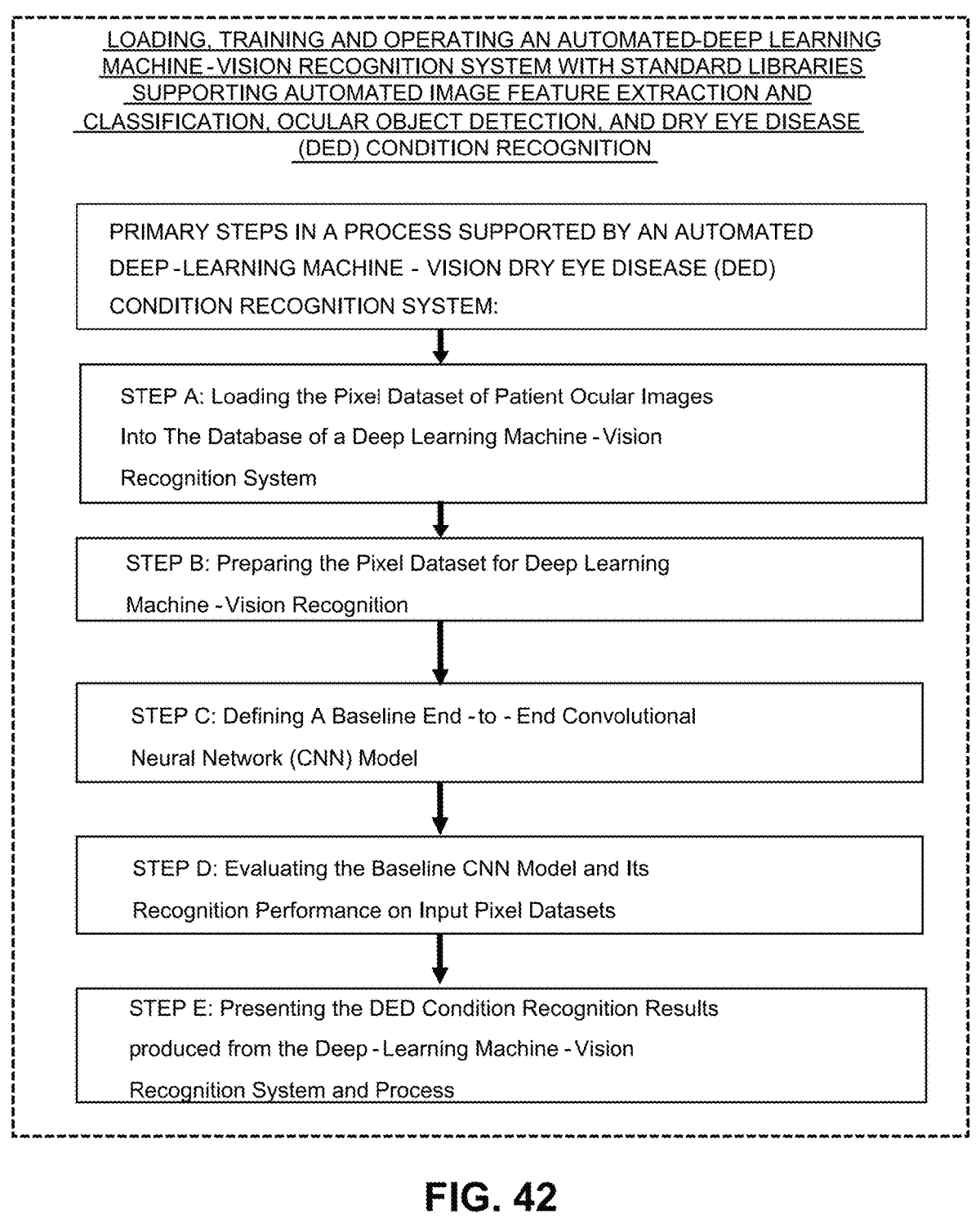

LOADING, TRAINING AND OPERATING AN AUTOMATED-DEEP LEARNING
MACHINE-VISION RECOGNITION SYSTEM WITH STANDARD LIBRARIES
SUPPORTING AUTOMATED IMAGE FEATURE EXTRACTION AND
CLASSIFICATION, OCULAR OBJECT DETECTION, AND DRY EYE DISEASE
(DED) CONDITION RECOGNITION

PRIMARY STEPS IN A PROCESS SUPPORTED BY AN AUTOMATED
DEEP-LEARNING MACHINE - VISION DRY EYE DISEASE (DED)
CONDITION RECOGNITION SYSTEM:

STEP A: Loading the Pixel Dataset of Patient Ocular Images
Into The Database of a Deep Learning Machine-Vision
Recognition System STEP B: Preparing the Pixel Dataset for Deep Learning
Machine-Vision Recognition STEP C: Defining A Baseline End-to-End Convolutional
Neural Network (CNN) Model STEP D: Evaluating the Baseline CNN Model and Its
Recognition Performance on Input Pixel Datasets STEP E: Presenting the DED Condition Recognition Results
produced from the Deep-Learning Machine-Vision
Recognition System and Process

FIG. 42

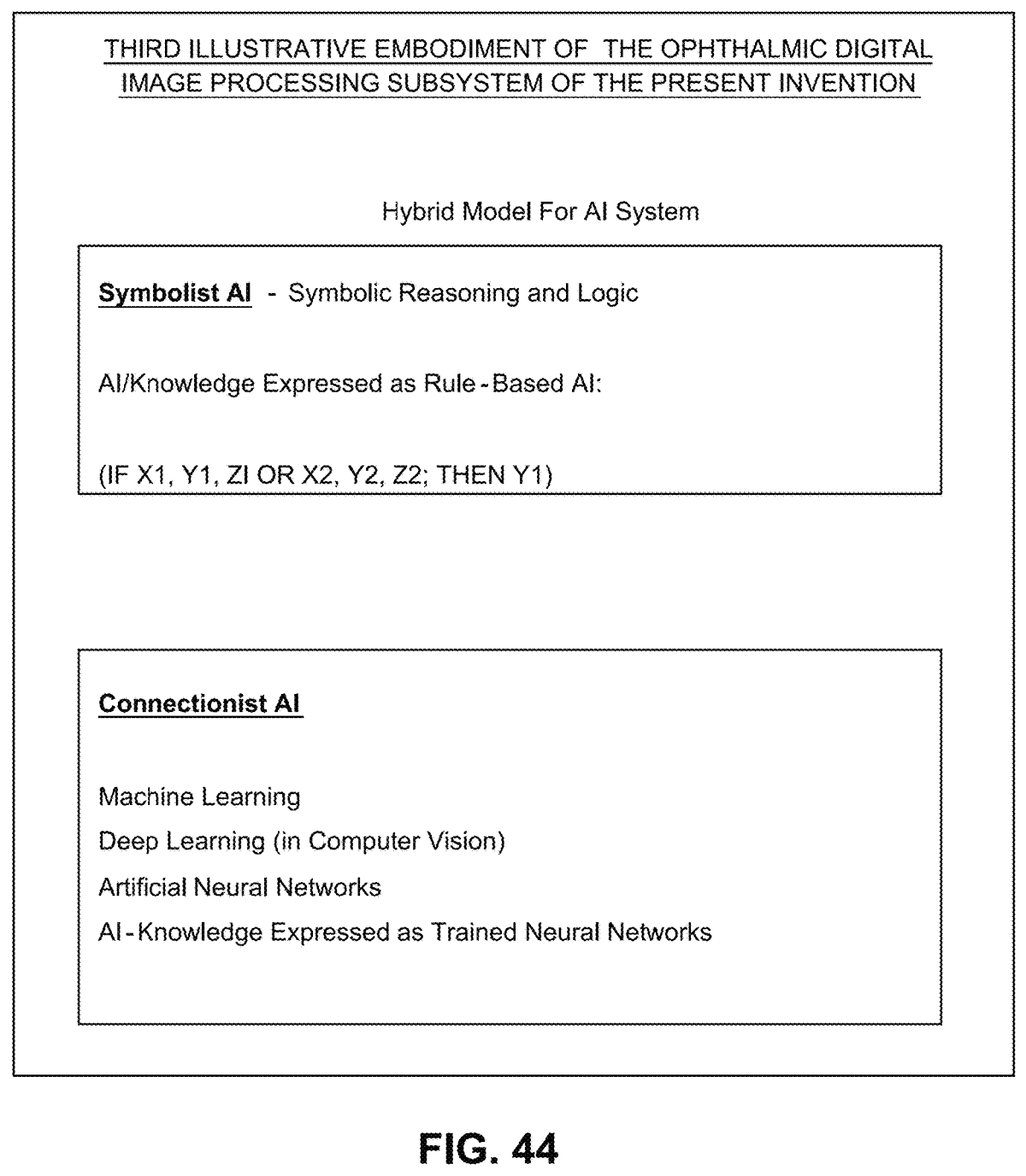

THIRD ILLUSTRATIVE EMBODIMENT OF THE OPHTHALMIC DIGITAL IMAGE PROCESSING SUBSYSTEM OF THE PRESENT INVENTION

Hybrid Model For AI System

Symbolist AI - Symbolic Reasoning and Logic

AI/Knowledge Expressed as Rule-Based AI:

(IF X1, Y1, ZI OR X2, Y2, Z2; THEN Y1)

Connectionist AI

Machine Learning

Deep Learning (in Computer Vision)

Artificial Neural Networks

AI-Knowledge Expressed as Trained Neural Networks

FIG. 44

Figure 45:
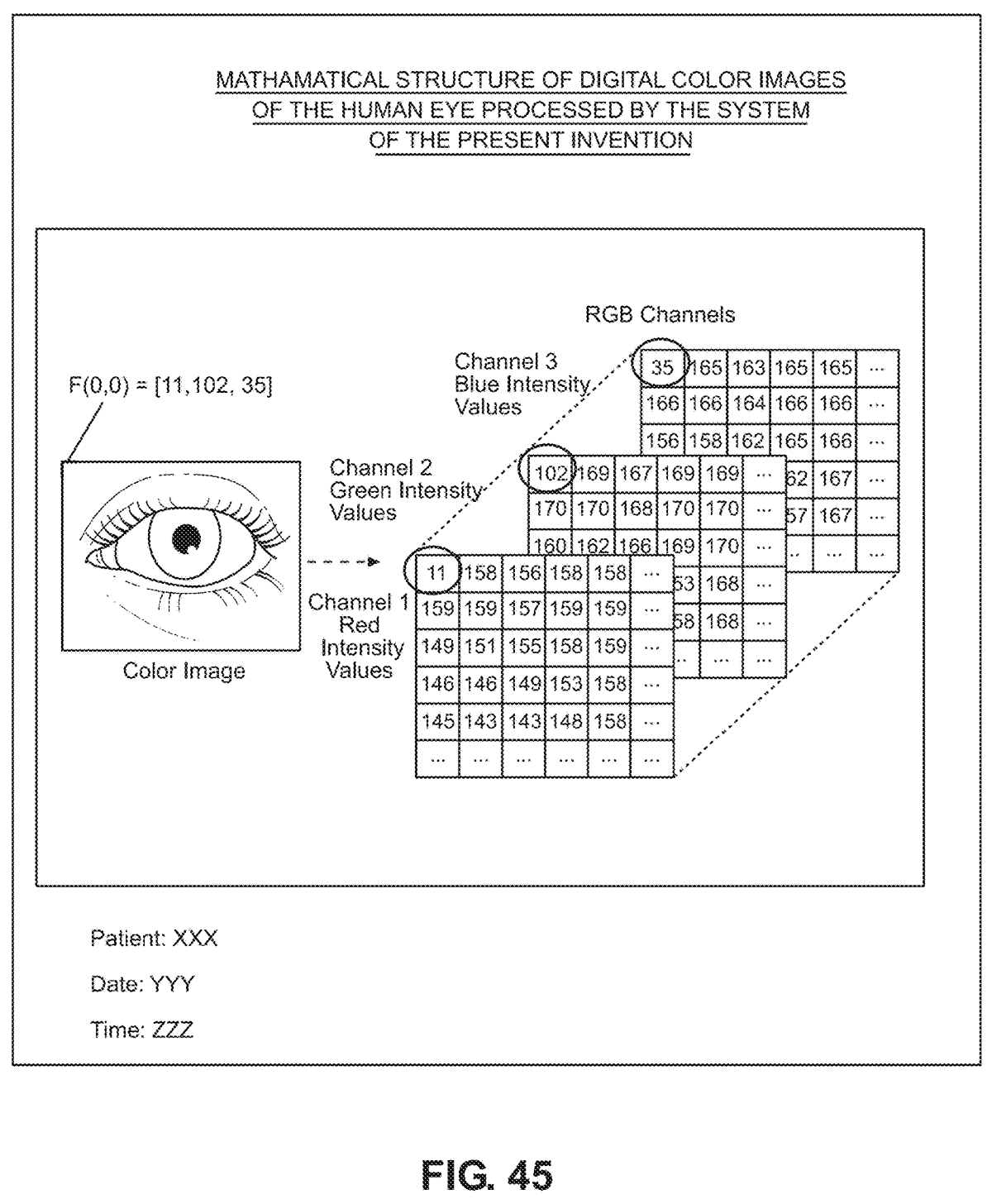

MATHAMATICAL STRUCTURE OF DIGITAL COLOR IMAGES
OF THE HUMAN EYE PROCESSED BY THE SYSTEM
OF THE PRESENT INVENTION

RGB Channels

Channel 3
Blue Intensity
Values

| 35 | 165 | 163 | 165 | 165 | ... |
|----|-----|-----|-----|-----|-----|
| 166 | 166 | 164 | 166 | 166 | ... |
| 156 | 158 | 162 | 165 | 166 | ... |

Channel 2
Green Intensity
Values

| 102 | 169 | 167 | 169 | 169 | ... | 62 | 167 |
| 170 | 170 | 168 | 170 | 170 | ... | 57 | 167 |
| 160 | 162 | 166 | 169 | 170 | ... |

F(0,0) = [11,102, 35]

Channel 1
Red
Intensity
Values

| 11 | 158 | 156 | 158 | 158 | ... | 53 | 168 |
| 159 | 159 | 157 | 159 | 159 | ... | 58 | 168 |
| 149 | 151 | 155 | 158 | 159 | ... |
| 146 | 146 | 149 | 153 | 158 | ... |
| 145 | 143 | 143 | 148 | 158 | ... |
| ... | ... | ... | ... | ... | ... |

Color Image

Patient: XXX

Date: YYY

Time: ZZZ

AUTOMATICALLY DETECTING AND MEASURING
CONJUNCTIVITIS (CJ) USING A REAL-TIME OPHTALMIC IMAGE
PROCESSING ENGINE OPERATING ON FRONT VIEW DIGITAL IMAGES
OF THE HUMAN EYE

Conjunctival
Injection

SCHEMATIC MODEL SUPPORTING THE AUTOMATED DETECTION AND MEASUREMENT OF CONJUNCTIVAL INJECTION (CI) IN HUMAN EYES USING A REAL-TIME OPHTALMIC IMAGE PROCESSING ENGINE OPERATING ON FRONTAL VIEW DIGITAL IMAGES OF THE HUMAN EYES

METHOD NO. 1

MACHINE-VISION BASED METHOD OF DETECTING,
MEASURING, AND GENERATING A DATABASE OF IMAGES
INDICATIVE OF CONJUNCTIVAL INJECTION (CI)

Step 1: Capture a series of color digital images, with each color
digital image having a set of pixels;

Step 2: Process the pixels in each digital image and classify the following
structures in the human eye, including eyelids, iris,
pupil, and sclera;

Step 3: Use sclera and non-sclera digital images to train a system to detect
the sclera;

Step 4: Use the above structures and the trained system for automatic region of
interest (ROI) segmentation of the sclera using non-parametric methods, including but
not limited to, random decision forests such as Breiman's random forest algorithm,
gray scale probability maps, binary thresholds, morphological operators and
Bresenham'sline algorithm;

Step 5: Use region of interest matching to measure conjunctival injection across a
series of digital images reproducibly using methods including, but not limited to,
a feature detection algorithm(e.g. scale invariant feature transform) and an
iterative Parameter estimation method (e.g. random sample consensus);

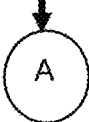

FIG. 49A

METHOD NO. 1

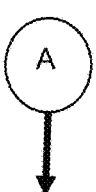

Step 6: Measure conjunctival injection in region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: If the conjunctival injection value is greater than 30, then generate output data indicative of such determined ocular disease factors and index the processed image(s) therewith to indicate the same.

AUTOMATICALLY MEASURING TEAR MENISCUS HEIGHT (TMH)
USING REAL-TIME OPHTALMIC IMAGE PROCESSING ENGINE
OPERATING ON FRONT VIEW DIGITAL IMAGES OF THE HUMAN EYE

Tear Meniscus
Height

SCHEMATIC MODEL SUPPORTING THE AUTOMATED DETECTION
AND MEASUREMENT OF THE TEAR MENISCUS PARAMETERS IN HUMAN EYES
USING A REAL-TIME OPHTHALMIC IMAGE PROCESSING ENGINE
OPERATING ON FRONTAL VIEW DIGITAL IMAGES
OF THE HUMAN EYES

METHOD NO. 2

MACHINE-VISION BASED METHOD OF DETECTING,
MEASURING, AND GENERATING A DATABASE OF IMAGES
INDICATIVE OF TEAR MENISCUS HEIGHT (TMH)

Step 1: Capture a series of color digital images, with each color digital image having a set of pixels;

Step 2: Process the pixels in each digital image and classify the following structures in the human eye, including eyelids, iris, pupil, and sclera;

Step 3: eyelid and non-eyelid digital images to train a system to detect eyelids;

Step 4: Use the above structures and the trained system for automatic region of interest segmentation of lower eyelid using non-parametric methods, including but not limited to, random decision forests such as Breiman's random forest algorithm, gray scale probability maps, binary thresholds, morphological operators and Bresenham'sline algorithm;

Step 5: Use region of interest matching to measure tear meniscus height (TMH) parameter across a series of digital images reproducibly using methods including, but not limited to, scale invariant feature transform and random sample consensus;

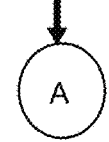

FIG. 53A

METHOD NO. 2

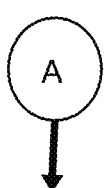

Step 6: Differentiate tear meniscus reflective line from lower eyelid
by using methods, including, but not limited to, edge detection,
k-means clustering, region growing and thresholding methods;

Step 7: Measure tear meniscus height in millimeters by using
pixel-by-pixel size;

Step 8: If the tear meniscus height is less than 0.2mm right after a blink,
then generate output data indicative of such determined ocular disease
factors and index the processed image(s) therewith to indicate the same.

<u>AUTOMATICALLY DETECTING MEIBOMIAN GLAND DYSFUNCTION (MGD) AND SCRUFF AT EYELASHES USING A REAL-TIME OPHTALMIC IMAGE PROCESSING ENGINE OPERATING ON FRONT VIEW DIGITAL IMAGES OF THE HUMAN EYE</u>

Meibomian gland dysfunction/scruff at eyelashes

Patient: XXX

Date: YYY

Time: ZZZ

M3

SCHEMATIC MODEL SUPPORTING THE AUTOMATED DETECTION
AND MEASUREMENT OF THE MEIBOMIAN GLAND AND SCRUFF IN HUMAN
EYES USING A REAL-TIME OPHTHALMIC IMAGES PROCESSING
ENGINE OPERATING OF FRONTAL VIEW DIGITAL IMAGES OF THE HUMAN EYES

METHOD NO. 3
MACHINE-VISION BASED METHOD OF DETECTING,
MEASURING, AND GENERATING A DATABASE OF IMAGES INDICATIVE
OF MEIBOMIAN GLAND DYSFUNCTION  (MGD) AND SCRUFF AT EYELASHES

Step 1: Capture a series of color digital images each color digital image having a set of pixels;

Step 2: Process the pixels in each digital image and classify the  following structures in the human eye, including  eyelids, iris, pupil, and sclera;

Step 3: Use eyelid and non -eyelid digital images to train a system to detect eyelids;

Step 4: Use the above structures and the trained system for automatic region of interest segmentation of eyelid margins using non-parametric methods, including but not limited to, random decision forests such as Breiman's random forest algorithm, binary thresholds, morphological operators and Bresenham's line algorithm;

Step 5: Use region of interest matching to measure meibomian gland dysfunction and scruff at eyelashes across a series of digital images reproducibly using methods including, but not limited to, scale invariant feature transform and random sample consensus;

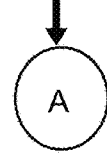

METHOD NO. 3

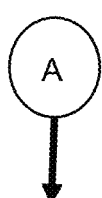

Step 6: Identify and count meibomian glands, and identify scruff at eyelashes using methods, including, but not limited to, edge detection, k-means clustering, region growing and thresholding methods;

Step 7: A change in edges, clusters or regions at the on the lower eyelid margin and in the eyelashes are meibomian glands or scruff at eyelashes; and Step 8: If the meibomian glands or scruff visible at eyelashes is 25% of the eyelid margin, then generate output data indicative of such determined ocular disease factors and index the processed image(s) therewith to indicate the same.

AUTOMATICALLY MEASURING CONJUNCTIVOCHALASIS
USING A REAL-TIME OPHTALMIC IMAGE PROCESSING ENGINE
OPERATING ON FRONT VIEW DIGITAL IMAGES OF THE HUMAN EYE

AUTOMATICALLY MEASURING CONJUCTIVOCHALASIS
USING A REAL-TIME OPHTALMIC IMAGE PROCESSING ENGINE
OPERATING ON FRONT VIEW DIGITAL IMAGES OF THE HUMAN EYE

M4

<u>SCHEMATIC MODEL SUPPORTING THE AUTOMATED DETECTION
AND MEASUREMENT OF CONJUNCTIVOCHALASIS IN HUMAN EYES
USING A REAL-TOME OPHTHALMIC IMAGE PROCESSING ENGINE
OPERATING ON FRONTAL VIEW DIGITAL IMAGES OF THE HUMAN EYES</u>

<u>CONJUNCTIVOCHALASIS  (M4)</u>

Process

CONJUNCTIVOCHALASIS

METHOD NO. 4
MACHINE-VISION BASED METHOD OF DETECTING,
MEASURING, AND GENERATING A DATABASE OF IMAGES
INDICATIVE OF CONJUNCTIVOCHALASIS

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train a system to detect sclera;

Step 4: Use the above structures and the trained system for automatic region of interest segmentation of sclera using non-parametric methods, including but not limited to, random decision forests such as Breiman's random forest algorithm, gray scale probability maps, binary thresholds, morphological operators and Bresenham'sline algorithm;

Step 5: Use region of interest matching to measure conjunctivochalasis across a series of digital images reproducibly using methods including, but not limited to, scale invariant feature transform and random sample consensus;

FIG. 60A

METHOD NO. 4

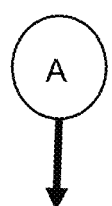

Step 6: Identify conjunctivochalasis using methods, including, but not limited to, edge detection, k-means clustering, region growing and thresholding methods;

Step 7: A detectable edge, cluster or region above the lower eyelid margin overlying the sclera is considered conjunctivochalasis; and Step 8: If conjunctivochalasis is greater than the single fold in the conjunctiva, then generate output data indicative of such determined ocular disease factors and index the processed image(s) therewith to indicate the same.

AUTOMATICALLY DETECTING AND MEASURING DERMATOCHALASIS
USING A REAL-TIME OPHTALMIC IMAGE PROCSSING ENGINE
OPERATING ON FRONT VIEW DIGITAL IMAGES OF THE HUMAN EYE

Patient: XXX
Date: YYY
Time: ZZZ

M5

SCHEMATIC MODEL SUPPORTING THE AUTOMATED DETECTION
AND MEASUREMENT OF DERMATOCHALASIS IN HUMAN EYES
USING A REAL-TIME OPHTALMIC IMAGE PROCESSING ENGINE
OPERATING ON FRONTAL AND/OR SIDE VIEW DIGITAL IMAGES
OF THE HUMAN EYES

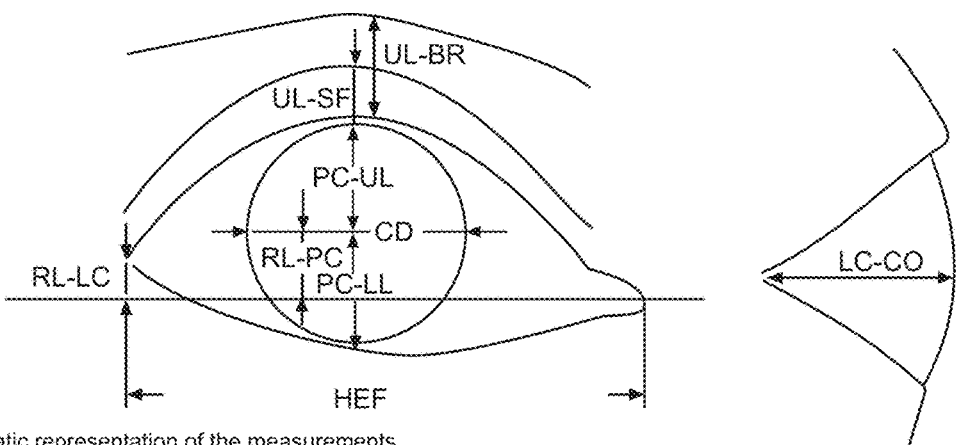

Schematic representation of the measurements.

Left: frontal slides. A reference line was drawn through the medial canthus on both sides, vertical lines were drawn through the pupil centre and through the lateral canthal angle. HEF= horizontal eyelid fissure, RL-PC=reference line to pupil centre, PC-UL=pupil centre to upper eyelid margin, PC-LL=pupil centre to lower eyelid margin; the sum of the latter two measurements represents the vertical eyelid fissure. RL-LC=reference line to lateral cathaus, UL-SF=upper eyelid margin to skin fold, UL-BR=upper eyelid margin to lower margin of eyebrow, CD=corneal diameter.

Right: lateral slides, LC-CO=distance between lateral canthus and anterior corneal surface.

FIG. 63

METHOD NO. 5

MACHINE-VISION BASED METHOD OF DETECTING,
MEASURING, AND GENERATING A DATABASE OF IMAGES
INDICATIVE OF DERMATOCHALASIS

Step 1: Capture a series of color digital images each color digital
image having a set of pixels;

Step 2: Process the pixels in each digital image and classify the
following structures in the human eye, including eyelids, iris,
pupil, and sclera;

Step 3: Use eyelid and non -eyelid digital images to train a system
to detect eyelids;

Step 4: Use the above structures and the trained system for automatic region of
interest segmentation of eyelid using non-parametric methods, including
but not limited to, random decision forests such as Breiman's random
forest algorithm, gray scale probability maps, binary thresholds, morphological
operators and Bresenham's line algorithm;

Step 5: Use region of interest matching to measure dermatochalasis across
a series of digital images reproducibly using methods including, but not
limited to, scale invariant feature transform and random sample consensus;

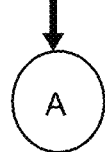

FIG. 64A

METHOD NO. 5

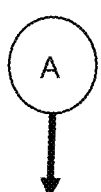

Step 6: Identify dermatochalasis using methods, including, but not limited to, edge detection, k-means clustering, region growing and thresholding methods;

Step 7: Detection of edges, clusters or regions separate from the upper eyelid margin are considered dermatochalasis; and Step 8: If dermatochalasis is greater than the upper eyelid hang over the eyelid margin, then generate output data indicative of such determined ocular disease factors and index the processed image(s) therewith to indicate the same.

AUTOMATICALLY MEASURING TEAR FILM DYNAMICS (TFD) BY TRACKING LIGHT REFLECTIVE PARTICLES ON THE CORNEAL SURFACE DETECTED BETWEEN EYE BLINKS IN TEAR FILM OF A HUMAN EYE USING A REAL-TIME OPHTALMIC IMAGE PROCESSING ENGINE OPERATING ON FRONT VIEW DIGITAL HUMAN EYE

METHOD NO. 6

MACHINE-VISION BASED METHOD OF DETECTING,
MEASURING, AND GENERATING A DATABASE OF IMAGES
INDICATING TEAR FILM DYNAMICS USING REFLECTIVE LIGHT PARTICLES

Step 1: Capture a color digital video having a set of frames per second, and
decompose the video into 0.1 second intervals, over the course of user
keeping the eye open;

Step 2: Process the individual image frames and classify the following structures
in the human eye, including eyelids, iris, pupil, and sclera;

Step 3: Use cornea and non-cornea digital images to train a system to detect eyelids;

Step 4: Use the above structures and the trained system for automatic region
of interest segmentation of inferior cornea using non-parametric methods, including
but not limited to, random decision forests such as Breiman's random
forest algorithm, gray scale probability maps, binary thresholds, morphological
operators and Bresenham's line algorithm;

Step 5: Use region of interest to identify mobile reflective light particles visible in the
film using k-means clustering methods;

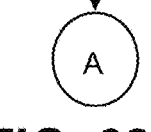

FIG. 68A

METHOD NO. 6

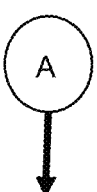

Step 6: Follow the movement of the reflective light particles on subsequent 0.1 sec intervals using pixel-based loci for a total of 2 sec;

Step 7: Measure speed and direction of movement of reflective light particles over a 2 second interval, with movement superiorly and nasally indicating positive displacement;

Step 8: Measure the initial speed of reflective light particles, i.e., speed immediately after blink, of less than 7 mm/sec, or the time for reflective light particles to stop moving, i.e., reach speed of 0 mm/sec, of less than 1 sec, is suggestive of ocular pathology;

Step 8: If the initial speed of reflective light particles is less than 7mm/sec, or if the time for reflective might particles to stop moving is less than 1 second, then generate output data indicative of such determined ocular disease factors and index the processed image(s) therewith to indicate the same.

AUTOMATICALLY MEASURING TEAR FILM DYNAMICS BY DETECTING
CONCENTRIC PLACIDO DISCS USING A REAL-TIME OPHTHALMIC IMAGE
PROCESSING ENGINE OPERATING ON FRONT VIEW DIGITAL VIDEO
IMAGES OF THE HUMAN EYE

Connectric
Placido Light Discs

Connectric
Placido Light Discs

M7

AUTOMATICALLY MEASURING TEAR FILM DYNAMICS BY DETECTING
CONCENTRIC PLACIDO DISCS USING A REAL-TIME OPHTHALMIC IMAGE
PROCESSING ENGINE OPERATING ON FRONT VIEW DIGITAL VIDEO
IMAGES OF THE HUMAN EYE

Connectric
Placido Light Discs

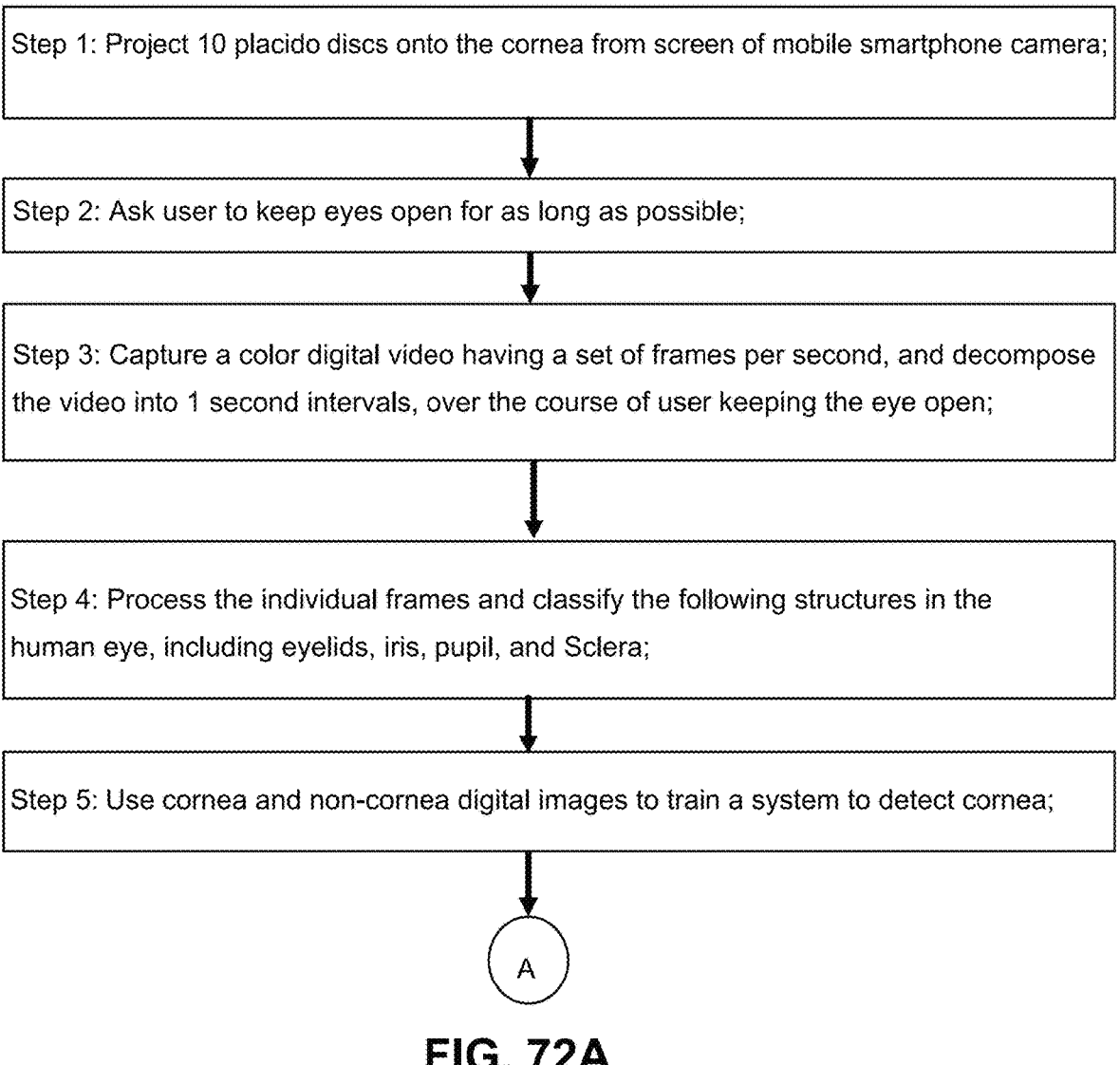

METHOD NO. 7

MACHINE -VISION BASED METHOD OF DETECTING,
MEASURING, AND GENERATING A DATABASE OF IMAGES
INDICATING  TEAR FILM DYNAMICS USING CONCENTRIC PLACIDO DISCS

Step 1: Project 10 placido discs onto the cornea from screen of mobile smartphone camera;

Step 2: Ask user to keep eyes open for as long as possible;

Step 3: Capture a color digital video having a set of frames per second, and decompose the video into 1 second intervals, over the course of user keeping the eye open;

Step 4: Process the individual frames and classify the following structures in the human eye, including eyelids, iris, pupil, and Sclera;

Step 5: Use cornea and non-cornea digital images to train a system to detect cornea;

METHOD NO. 7

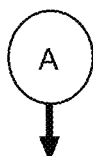

Step 6: Use the above structures and the trained system for automatic region of interest segmentation of cornea using non -parametric methods, including but not limited to, random decision forests such as Breiman's random forest algorithm, gray scale probability maps, binary thresholds, morphological operators and Bresenham's line algorithm;

Step 7: Use region of interest to identify placido discs on the cornea using k-means clustering and edge detection methods;

Step 8: Track the placido discs at 1 second intervals using pixel-based loci for 10 seconds;

Step 9: If tear film break up is less than 10 seconds, then generate output data indicative of such determined ocular disease factors and index the processed image(s) therewith to indicate the same.

AUTOMATICALLY MEASURING TEAR FILM DYNAMICS BY MEASURING
TEAR MENISCUS HEIGHT USING A REAL-TIME OPHTALMIC IMAGE
PROCESSING ENGINE OPERATING ON FRONT VIEW DIGITAL IMAGES
OF THE HUMAN EYE

Patient: XXX
Date: YYY
Time: ZZZ

M8

AUTOMATICALLY MEASURING TEAR FILM DYNAMICS BY MEASURING
TEAR MENISCUS HEIGHT USING A REAL-TIME OPHTALMIC IMAGE
PROCESSING ENGINE OPERATING ON FRONT VIEW DIGITAL IMAGES
OF THE HUMAN EYE

Patient: XXX
Date: YYY
Time: ZZZ

M8

SCHEMATIC MODEL SUPPORTING THE AUTOMATED DETECTION
AND MEASUREMENT OF THE INCREASE IN TEAR MENISCUS HEIGHT
(TMH) AFTER FULL EYE BLINK DURING VIDEO IMAGING OF THE EYE
USING A REAL-TIME OPHTALMIC PROCESSING ENGINE
OPERATING ON FRONTAL VIEW DIGITAL IMAGES
OF THE HUMAN EYES

Tear Meniscus Height (TMH1) Before Full Blink

Tear Meniscus Height (TMH2) After Full Blink

METHOD NO. 8

MACHINE-VISION BASED METHOD OF DETECTING,
MEASURING, AND GENERATING A DATABASE OF IMAGES
INDICATING TEAR FILM DYNAMICS USING TEAR MENISCUS HEIGHT

Step 1: Ask user to keep eyes open for as long as possible;

Step 2: Capture a color digital video having a set of frames per second, and decompose the video into 0.1 second intervals, over the course of user keeping the eye open;

Step 3: Process the individual frames and classify the following structures in the human eye, including eyelids, iris, pupil, and Sclera;

Step 4: Use eyelid and non-eyelid digital images to train a system to detect eyelids;

Step 5: Use the above structures and the trained system for automatic region of interest segmentation of lower eyelid using non-parametric methods, including but not limited to, random decision forests such as Breiman's random forest algorithm, gray scale probability maps, binary thresholds, morphological operators and Bresenham's line algorithm;

FIG. 76A

METHOD NO. 8

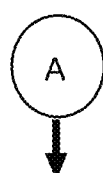

Step 6: Use region of interest matching to measure tear meniscus height across a series of digital images reproducibly using methods including, but not limited to, scale invariant feature transform and random sample consensus;

Step 7: Differentiate tear meniscus reflective line from lower eyelid by using methods, including, but not limited to, edge detection, k-means clustering, region growing and thresholding methods;

Step 8: Measure tear meniscus height in millimeters by using pixel-by-pixel size;

Step 9: If tear meniscus height right after a blink is less than 0.2mm, and/or the tear meniscus height increases is less than 0.2mm from baseline over the course of keeping the eye open, then generate output data indicative of such determined ocular disease factors and index the processed image(s) therewith to indicated the same.

AUTOMATICALLY MEASURING EYELID POSITION FOR BLINK
ANALYSIS USING A REAL-TIME OPHTHALMIC IMAGE PROCESSING ENGINE
OPERATING ON FRONT VIEW DIGITAL IMAGES OF THE HUMAN EYE

Patient: XXX
Date: YYY
Time: ZZZ

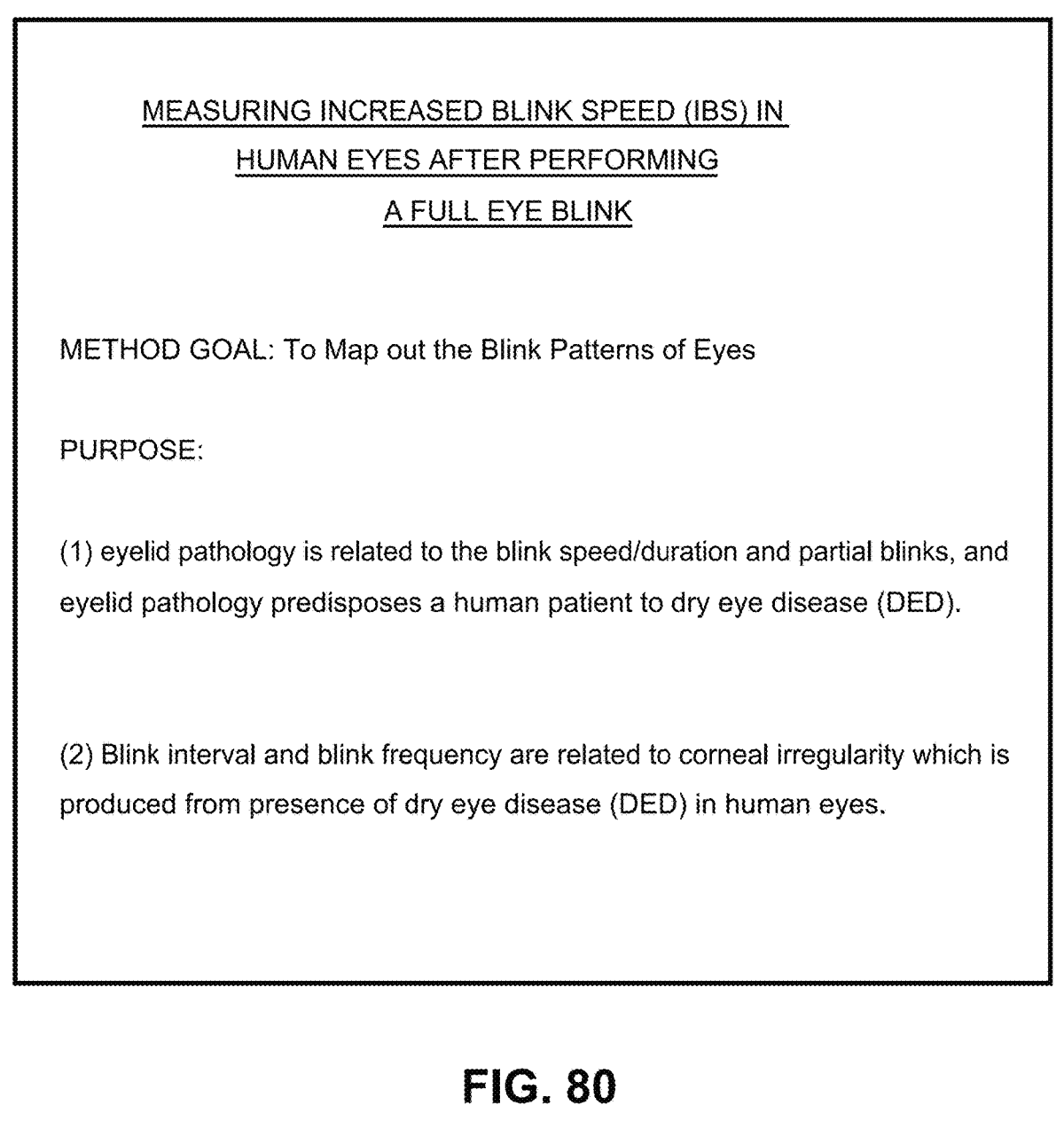

MEASURING INCREASED BLINK SPEED (IBS) IN
HUMAN EYES AFTER PERFORMING
A FULL EYE BLINK

METHOD GOAL: To Map out the Blink Patterns of Eyes

PURPOSE:

(1) eyelid pathology is related to the blink speed/duration and partial blinks, and eyelid pathology predisposes a human patient to dry eye disease (DED).

(2) Blink interval and blink frequency are related to corneal irregularity which is produced from presence of dry eye disease (DED) in human eyes.

FIG. 80

METHOD NO. 9

MACHINE-VISION BASED METHOD OF DETECTING,
MEASURING, AND GENERATING A DATABASE OF IMAGES
INDICATIVE OF EYELID POSITION FOR INCREASED BLINK ANALYSIS

Step 1: Capture a color digital video having a set of frames per Second, and each color digital image having a set of pixels;

Step 2: Process the individual frames and classify the following structures in the human eye, including eyelids, iris, pupil, and Sclera;

Step 3: Use eyelid and non-eyelid digital images to train a system to detect upper and lower eyelid;

Step 4: Use region of interest matching across a series of digital images reproducibly using methods including, but not limited to, scale invariant feature transform and random sample consensus;

Step 5: Edge detection is used to mark and track the upper and lower eyelid to determine palpebral opening height and measure the number of blinks;

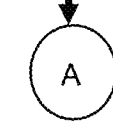

METHOD NO. 9

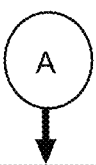

Step 6: Blinking is plotted over time to calculate the blinks per minute, duration of individual blinks and to calculate the interval between blinks;

Step 7: Blink speed is measured using the distance between the upper and lower eyelid divided by the time to blink;

Step 8: Partial blinks are determined using non -parametric methods, including but not limited to, random decision forests such as   Breiman's random forest algorithm, gray scale probability maps, binary thresholds, morphological operators, Bresenham's line algorithm, and marked location of upper and lower eyelid using edge detection;

Step 9: Detecting a >1mm difference between the upper and lower eyelid or greater than 10% difference in grayscale binary images on blinking suggests a partial blink;

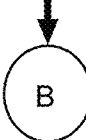

FIG. 81B

METHOD NO. 9

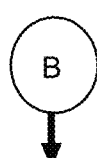

Step 10: If measured blinking rate is greater than 20 blinks per minute, then generate output data indicative of such determined ocular disease factors and index the processed image(s) therewith to indicate the same;

Step 11: If measured blinking rate is greater than 12 partial blinks per minute, then generate output data indicative of such determined ocular disease factors and index the processed image(s) therewith to indicate the same;

Step 12: If measured blink duration is greater than 0.5 secs per blink, then generate output data indicative of such determined ocular disease factors and index the processed image(s) therewith to indicate the same;

Step 13: If the duration of lid closure is greater than 0.5 secs per blink, then generate output data indicative of such determined ocular disease factors and index the processed image(s) therewith to indicate the same.

AUTOMATICALLY DETECTING AND MEASURING
CORNEAL ABRASION (CA) USING A REAL-TIME OPHTHALMIC
IMAGE PROCESSING ENGINE OPERATING ON FRONT VIEW
DIGITAL IMAGES OF THE HUMAN EYE

Corneal
Abrasion

METHOD NO. 10

MACHINE-VISION BASED METHOD OF DETECTING,
MEASURING, AND GENERATING A DATABASE OF IMAGES
INDICATING CORNEAL ABRASION

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of the cornea using non - parametric methods, including but not limited to, random decision forests such as Breiman's random forest algorithm, gray scale probability maps, binary thresholds, morphological operators and Bresenham's line algorithm;

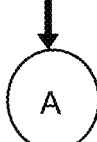

METHOD NO. 10

Step 5: Use region of interest matching to detect cornea across a series of digital images reproducibly using methods including, but not limited to, scale invariant feature transform and random sample consensus;

Step 6: Identify corneal abrasion using edge detection, region growing, k-means clustering and thresholding;

Step 7: Measure corneal abrasion height and width and respective surface areas using pixel-by-pixel size;

Step 8: If the corneal abrasion height and corneal abrasion width are greater than 0.1 mm, then generate output data indicative of such determined ocular disease factors and index the processed image(s) therewith to indicate the same.

SCHEMATIC MODEL SUPPORTING THE AUTOMATED DETECTION AND
MEASUREMENT OF THE PALPEBRAL FISSURE OF HUMAN EYES
USING A REAL-TIME OPTHALMIC IMAGE PROCESSING ENGINE OPERATING ON
FRONT VIEW DIGITAL IMAGES OF THE HUMAN EYES

Palpebral Fissure

Processing

PFH

PFW

PFH - Palpebral Fissure Height

PFW - Palpebral Fissure Width

METHOD NO. 11

MACHINE-VISION BASED METHOD OF DETECTING,
MEASURING, AND GENERATING A DATABASE OF IMAGES
INDICATING THE PALPEBRAL FISSURE

Step 1: Capture a series of color digital images each color digital image having a set of pixels;

Step 2: Process the pixels in each digital image and classify the following structures in the human eye, including eyelids, iris, pupil, and sclera;

Step 3: Process the individual frames and classify the following structures in the human eye, including eyelids, iris, pupil, and sclera;

Step 4: Use eyelid and non-eyelid digital images to train a system to detect eyelids;

Step 5: Use the above structures and the trained system for automatic region of interest segmentation of eyelid margins, using non -parametric methods, including but not limited to, random decision forests such as Breiman's random forest algorithm, gray scale probability maps, binary thresholds, morphological operators and Bresenham's line algorithm

METHOD NO. 11

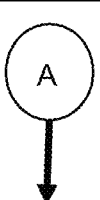

Step 6: Use region of interest matching to detect eyelid margins across a series of digital images reproducibly using methods including, but not limited to, scale invariant feature transform and random sample consensus;

Step 7: Identify the eyelid margin to eyelid margin distance, i.e., the palpebral fissure height, using methods, including, but not limited to, edge detection, k-means clustering and thresholding methods;

Step 8: Measure palpebral fissure height and palpebral fissure width in millimeters using pixel-by-pixel size;

Step 9: If the Palpebral fissure height is greater than 12mm or the palpebral fissure height is less than 8mm, then generate output data indicative of such determined ocular disease factors and index the processed image(s) therewith to indicate the same Step 10: If the Palpebral fissure height is greater than 33mm or the palpebral fissure height is less than 28mm, then generate output data indicative of such determined ocular disease factors and index the processed image(s) therewith to indicate the same.

FIG. 89B

M12
<u>SCHEMATIC MODEL SUPPORTING THE AUTMATED DETECTION AND
MEASUREMENT OF THE MARGIN REFLEX DISTANCE (MRD) OF HUMAN EYES
USING A REAL-TIME OPTHALMIC IMAGE PROCSSING ENGINE OPERATING
ON FRONT VIEW DIGITAL IMAGES OF THE HUMAN EYES</u>
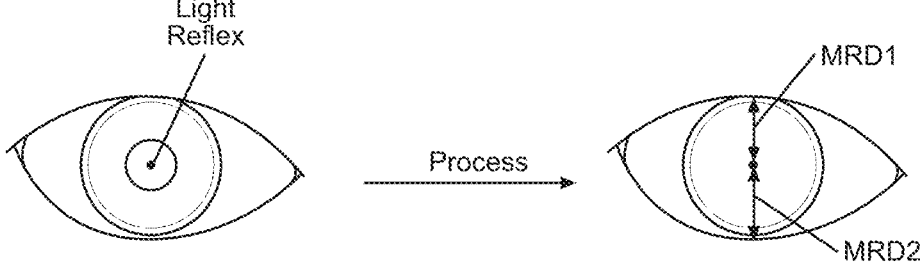
MRD1 / MRD2: Margin Reflex Distance 1 / 2
FIG. 92

METHOD NO. 12

MACHINE-VISION BASED METHOD OF DETECTING,
MEASURING, AND GENERATING A DATABASE OF IMAGES
INDICATING MARGIN REFLEX DISTANCE (MRD)

Step 1: Capture a series of color digital images each color digital
image having a set of pixels;

Step 2: Process the pixels in each individual digital frames and
classify the following structures in the human eye, including eyelids,
iris, pupil, and sclera;

Step 3: Use eyelid and non-eyelid digital images to train the system
to detect eyelids;

Step 4: Use the above structures and trained system for automatic
region of interest segmentation of eyelid margins using non-
parametric methods, including but not limited to, random
decision forests such as Breiman's random forest algorithm, gray
scale probability maps, binary thresholds, morphological
operators and Bresenham's line algorithm;

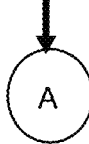

METHOD NO. 12

Step 5: Use region of interest matching to detect eyelid margins across a series of digital images reproducibly using methods including, but not limited to, scale invariant feature transform and random sample consensus;

Step 6: Identify the eyelid margin to eyelid margin distance using methods, including, but not limited to, edge detection, k- means clustering and thresholding methods;

Step 7:Use region of interest to identify light reflex using k-means Clustering methods;

Step 8: Measure margin reflex distance 1 from light reflex to upper eyelid margin and margin reflex distance 2 from light reflex to lower eyelid margin in millimeters using pixel- by -pixel size;

Step 9: If the margin reflex distance 1 is less than 3.5mm or greater than 4.5mm, then generate output data indicative of such determined ocular disease factors and index the processed image(s) therewith to indicate the same Step 10: If the margin reflex distance 2 is less than 4.5mm or greater than 5.5mm, then generate output data indicative of such determined ocular disease factors and index the processed image(s) therewith to indicate the same.

SCHEMATIC MODEL SUPPORING THE AUTOMATED DETECTION AND
MEASUREMENT OF THE SCLERAL SHOW OF HUMAN EYES
USING A REAL-TIME OPTHALMIC IMAGE PROCESSING ENGINE
OPERATING ON FRONT VIEW DIGITAL IMAGES OF THE HUMAN EYES

Scleral Show

<u>METHOD NO. 13</u>

<u>MACHINE-VISION BASED METHOD OF DETECTING,
MEASURING, AND GENERATING A DATABASE OF IMAGES
INDICATING SCLERAL SHOW</u>

Step 1: Capture a series of color digital images each color digital image having a set of pixels;

Step 2: Process the pixels in each digital image and classify the Following structures in the human eye, including eyelids, iris, pupil, and sclera;

Step 3: Use sclera and non-sclera digital images to train the system to detect sclera;

Step 4: Use the above structures and the trained system for automatic region of interest segmentation of sclera using non-parametric methods, including but not limited to, random decision forests such as Breiman's random forest algorithm, gray scale probability maps, binary thresholds, morphological operators and Bresenham's line algorithm;

FIG. 97A

METHOD NO. 13

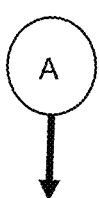

Step 5: Use region of interest matching to detect sclera across a
series of digital images reproducible using methods including,
but not limited to, scale invariant feature transform and random
sample consensus;

Step 6: Apply Steps 3 to 5 for automated and reproducible detection
of the eyelid margin;

Step 7: Measure inferior scleral show from inferior cornea to lower
eyelid margin, and superior scleral show from superior cornea to
upper eyelid margin in millimeters using pixel-by-pixel size;

Step 8: If the superior scleral show is greater than 0.00 mm or the
inferior scleral show is greater than 1.0mm, then generate output
data indicative of such determined ocular disease factors and index
the processed image(s) therewith to indicate the same.

AUTOMATICALLY DETECTING AND MEASURING
LEVATOR FUNCTION USING A REAL-TIME OPTHALMIC
IMAGE PROCESSING ENGINE OPERATING ON FRONT
VIEW DIGITAL IMAGES OF THE HUMAN EYE

METHOD NO. 14

MACHINE-VISION BASED METHOD OF DETECTING, MEASURING, AND GENERATING A DATABASE OF IMAGES INDICATING LEVATOR FUNCTION

Step 1: User is asked to look down and then up

Step 2:  Capture a series of color digital images each color digital image having a set of pixels Step 3: Process the pixels in each digital image and classify the following structures in the human eye, including  eyelids, iris, pupil, and sclera;

Step 4: Use eyelid and non -eyelid digital images to train the system to detect eyelids;

Step 5: Use the above structures and trained system for automatic region of interest segmentation of eyelid margins using non - parametric methods, including but not limited to, random decision forests such as Breiman's random forest algorithm, gray scale probability maps, binary thresholds, morphological operators and Bresenham's line algorithm;

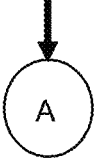

METHOD NO. 14

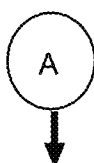

Step 6: Use region of interest matching to detect eyelid margins across a series of digital images reproducibly using methods including, but not limited to, scale invariant feature transform and random sample consensus;

Step 7: Identify the eyelid margin to eyelid margin distance using methods, including, but not limited to, edge detection, k-means clustering and thresholding methods;

Step 8: Measure the distance from the upper eyelid on downgaze to the upper eyelid on upgaze in millimeters using pixel-by-pixel size to obtain levator function;

Step 9: If the levator function is less than 12mm, then generate output data indicative of such determined ocular disease factors and index the processed image(s) therewith to indicate the same.

SCHEMATIC MODEL SUPPORTING THE AUTOMATED DETECTION AND
MEASUREMENT OF THE CORNEAL LENS OVERWEAR (CLOW) OF HUMAN
EYES USING A REAL-TIME OPHTHALMIC IMAGE PROCESSING ENGINE
OPERATING ON FRONT VIEW DIGITAL IMAGES OF THE HUMAN EYES

Contact Lens Overwear

METHOD NO. 15

MACHINE-VISION BASED METHOD OF DETECTING,
MEASURING, AND GENERATING A DATABASE OF IMAGES
INDICATING CORNEAL LENS OVERWEAR (CLOW)

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

METHOD NO. 15

Step 5: Use region of interest matching to detect cornea across a series of digital images reproducibly using methods including, but not limited to, scale invariant feature transform and random sample consensus;

Step 6: Identify contact lens, corneal neovascularization and corneal subepithelial infiltrates using edge detection, region growing, k-means clustering and thresholding methods;

Step 7: Differentiate corneal subepithelial infiltrates from corneal infection, abrasion and foreign body using contrast- limited adaptive histogram equalization, hue-saturation -value, product of saturation and hue maps, and maximal values of saturation and hue values;

Step 8: If corneal neovascularization is greater than 10% of the cornea, then generate output data indicative of such determined ocular disease factors and index the processed image(s) therewith to indicate the same;

Step 9: If the corneal subepithelial layer infiltrates greater than 0.1mm, then generate output data indicative of such determined ocular disease factors and index the processed image(s) therewith to indicate the same.

AUTOMATICALLY MEASURING TEAR FILM DYNAMICS BY MEASURING
CORNEAL TRANSPLANT GRAFT REJECTION (CTGR) USING A REAL-TIME
OPHTHALMIC IMAGE PROCESSING ENGINE OPERATING ON
FRONT VIEW DIGITAL IMAGES OF THE HUMAN EYE

Sutures

Khodadoust Line

Corenal
Edema

Stomal Infiltrates

Corneal
Neovascularization

Keratic
Precipitates

FIG. 109

METHOD NO. 16

MACHINE-VISION BASED METHOD OF DETECTING,
MEASURING, AND GENERATING A DATABASE OF IMAGES
INDICATING CORNEAL TRANSPLANT GRAFT REJECTION (CTGR)

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and the trained system for automatic region of interest segmentation of using non-parametric methods, including but not limited to, random decision forests such as Breiman's random forest algorithm, gray scale probability maps, binary thresholds, morphological operators and Bresenham's line algorithm;

METHOD NO. 16

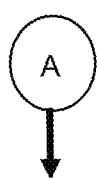

Step 5: Use region of interest matching to detect cornea across a series of digital images reproducibly using methods including, but not limited to, scale invariant feature transform and random sample consensus;

Step 6: Identify sutures, keratic precipitates, stromal infiltrates, corneal edema, and Khodadoust line (accumulation of inflammatory cells on the corneal endothelium) using edge detection, region growing, k-means clustering and thresholding methods;

Step 7: Differentiate corneal transplant graft rejection features using contrast -limited adaptive histogram equalization, hue -saturation -value, product of saturation and hue maps, and maximal values of saturation and hue values; and Step 8: If sutures are present or keratic precipitates are greater than 0.1mm, or stromal infiltrates are greater than 0.1 mm, or corneal edema is greater than 0.1% of the cornea, or the Khodadoust line is 0.1mm, then generate output data indicative of such determined ocular disease factors and index the processed image(s) therewith to indicate the same.

FIG. 110B

M17
<u>AUTOMATICALLY DETECTING AND MEASURING A CATARACT</u>
<u>USING A REAL-TIME OPHTHALMIC IMAGE PROCESSING ENGINE</u>
<u>OPERATING ON FRONT VIEW DIGITAL IMAGES</u>
<u>OF THE HUMAN EYE</u>
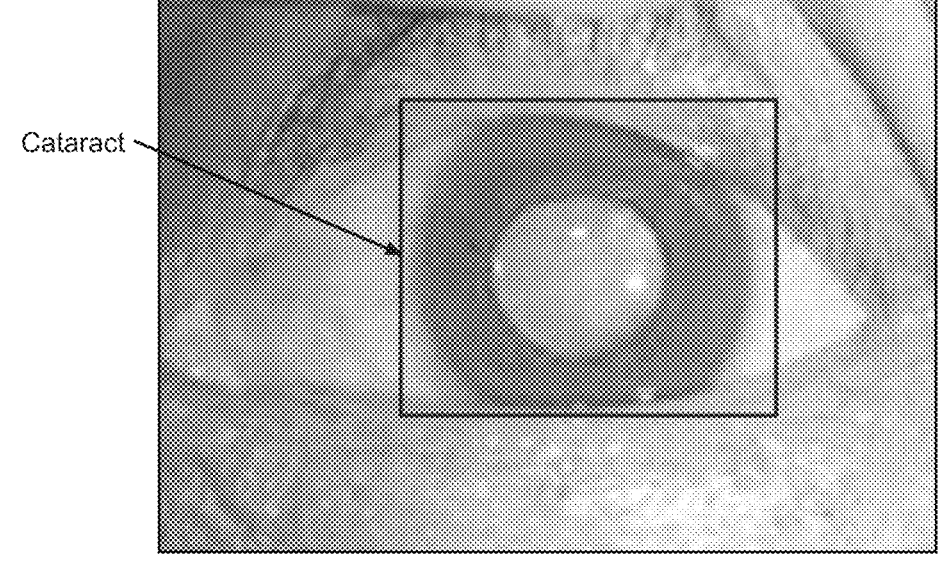
Cataract
FIG. 112

FIG. 113

METHOD NO. 17

MACHINE -VISION BASED METHOD OF DETECTING,
MEASURING, AND GENERATING A DATABASE OF IMAGES
INDICATING EXISTENCE OF CATARACT

Step 1: Capture a series of color digital images each color digital
image having a set of pixels;

Step 2: Process the pixels in each digital image and classify the
following structures in the human eye, including eyelids, iris, pupil,
and sclera;

Step 3: Use cornea and non-cornea digital images to train the
system to detect cornea;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm;

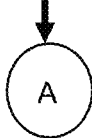

METHOD NO. 17

Step 5: Use region of interest matching to detect cornea across a series of digital images reproducibly using methods including, but not limited to, scale invariant feature transform and random sample consensus;

Step 6: Identify the pupillary margin using edge detection, region growing, k-means clustering and thresholding method;

Step 7: Identify cataract (e.g. degree of lens opacification) using contrast-limited adaptive histogram equalization, hue-saturation-value, product of saturation and hue maps, and maximal values of saturation and hue values; and Step 8: If lens opacification is greater than 50%, then generate output data indicative of such determined ocular disease factors and index the processed image(s) therewith to indicate the same.

FIG. 114B

Figure 118A:
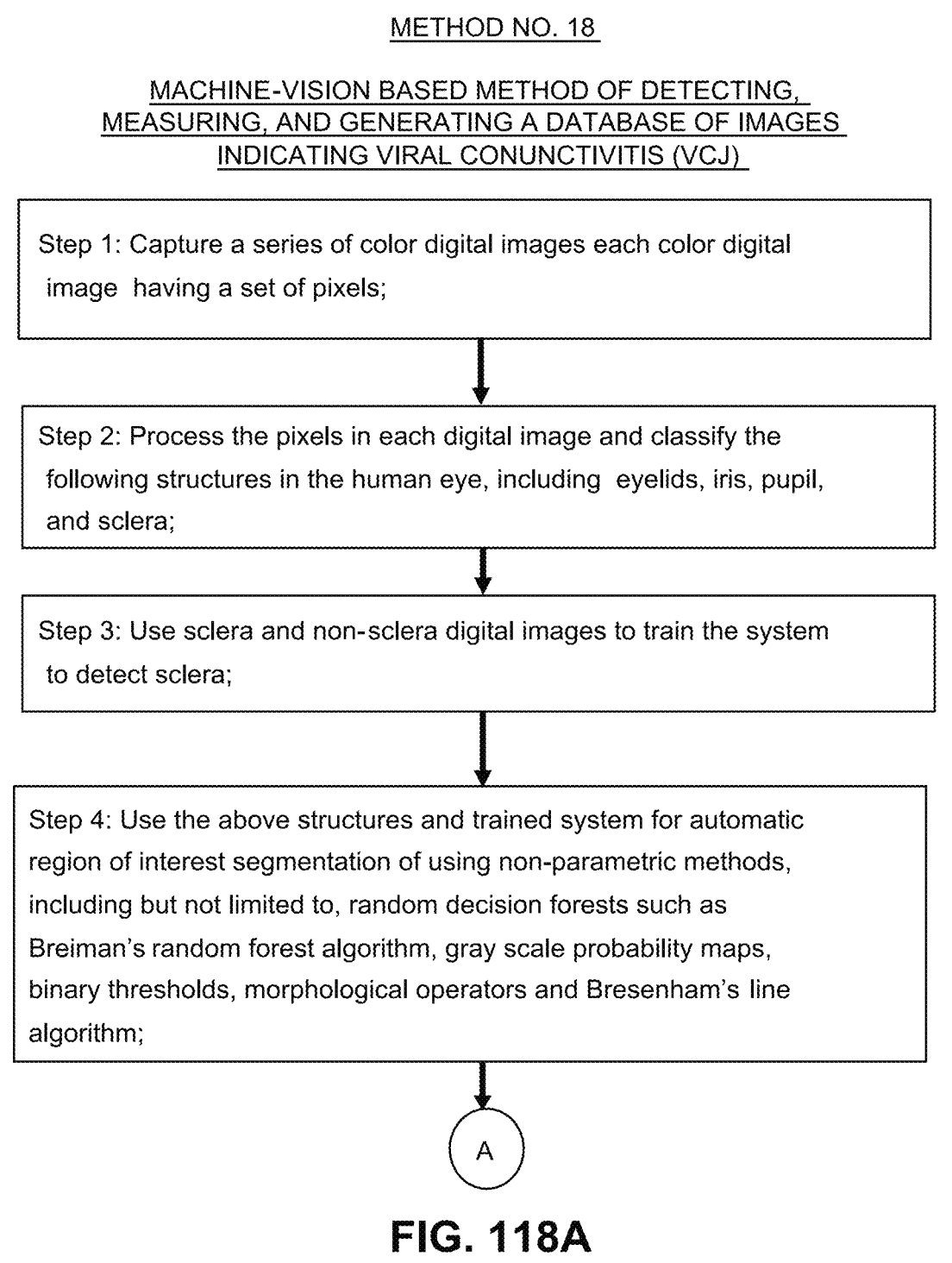

METHOD NO. 18

MACHINE-VISION BASED METHOD OF DETECTING,
MEASURING, AND GENERATING A DATABASE OF IMAGES
INDICATING VIRAL CONUNCTIVITIS (VCJ)

Step 1: Capture a series of color digital images each color digital
image  having a set of pixels;

Step 2: Process the pixels in each digital image and classify the
following structures in the human eye, including  eyelids, iris, pupil,
and sclera;

Step 3: Use sclera and non-sclera digital images to train the system
to detect sclera;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm;

METHOD NO. 18

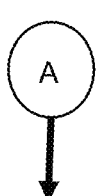

Step 5: Use region of interest matching to detect sclera across a series of digital images reproducibly using methods including, but not limited to, scale invariant feature transform and random sample consensus;

Step 6: Measure conjunctival injection in region of interest using methods including, but not limited to, contrast- limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: Detect clear discharge using edge detection, region growing, k- means clustering and thresholding methods; and Step 8: If clear discharge is greater than 0.1mm, then generate output data indicative of such determined ocular disease factors and index the processed image(s) therewith to indicate the same.

<u>SCHEMATIC MODEL SUPPORTING THE AUTOMATED DETECTION
AND MEASUREMENT OF BACTERIAL CONJUNCTIVITIS (BCJ) OF
HUMAN EYES USING A REAL-TIME OPHTHALMIC IMAGE
PROCESSING ENGINE OPERATING ON FRONT VIEW DIGITAL
IMAGES OF THE HUMAN EYES</u>

Bacterial

Process

Conjunctival Injection
(M1)

Purulent Discharge

METHOD NO. 19

MACHINE-VISION BASED METHOD OF DETECTING,
MEASURING, AND GENERATING A DATABASE OF IMAGES
INDICATING BACTERIAL CONJUNCTIVITIS (BCJ)

Step 1: Capture a series of color digital images each color digital
image having a set of pixels;

Step 2: Process the pixels in each digital image and classify the
following structures in the human eye, including eyelids, iris, pupil,
and sclera;

Step 3: Use sclera and non-sclera digital images to train the system
to detect sclera;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm;

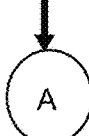

FIG. 122A

METHOD NO. 19

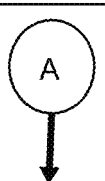

Step 5: Use region of interest matching to detect sclera across a series of digital images reproducibly using methods including, but not limited to, scale invariant feature transform and random sample consensus;

Step 6: Measure conjunctival injection in the region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: Detect purulent discharge using edge detection, region growing, k-means clustering and thresholding methods; and Step 8: If detected purulent discharge is greater than 0.1mm, then generate output data indicative of such determined ocular disease factors and index the processed image(s) therewith to indicate the same.

FIG. 122B

METHOD NO. 20

MACHINE-VISION BASED METHOD OF DETECTING,
MEASURING, AND GENERATING A DATABASE OF IMAGES
INDICATING ALLERGIC CONJUNCTIVITIS (ACJ)

Step 1: Capture a series of color digital images each color digital
image having a set of pixels;

Step 2: Process the pixels in each digital image and classify the
following structures in the human eye, including eyelids, iris,
pupil, and sclera;

Step 3: Use sclera and non-sclera digital images to train the system
to detect sclera;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm;

METHOD NO. 20

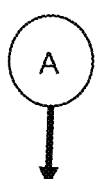

Step 5: Use region of interest matching to detect sclera across a series of digital images reproducibly using methods including, but not limited to, scale invariant feature transform and random sample consensus;

Step 6: Measure conjunctival injection in region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: Detect clear discharge and chemosis using edge detection, region growing, k-means clustering and thresholding methods;

Step 8: If conjunctival injection is greater than 75 and clear discharge is greater than 0.1mm in both eyes, then generate output data indicative of such determined ocular disease factors and index the processed image(s) therewith to indicate the same.

FIG. 126B

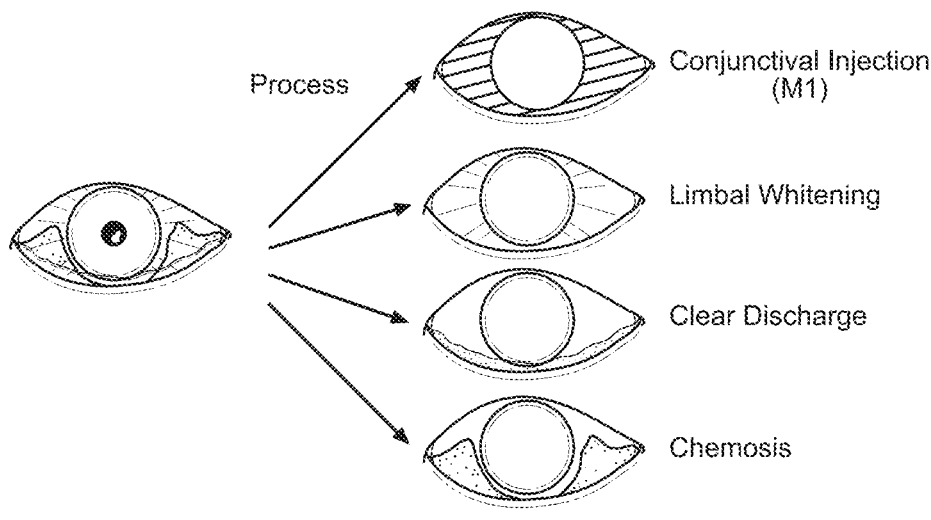

M21

SUPPORTING THE AUTOMATED DETECTION AND MEASUREMENT OF CHEMICAL BURN CONJUNCTIVITIS (CBCJ) OF HUMAN EYES USING A REAL-TIME OPHTHALMIC IMAGE PROCESSING ENGINE OPERATING ON FRONT VIEW DIGITAL IMAGES OF THE HUMAN EYES

Chemical Burn Conjunctivitis (CBCJ)

Chemical Burn Conjunctivitis (M21)

Process

Conjunctival Injection (M1)

Limbal Whitening

Clear Discharge

Chemosis

FIG. 129

Figure 130A:
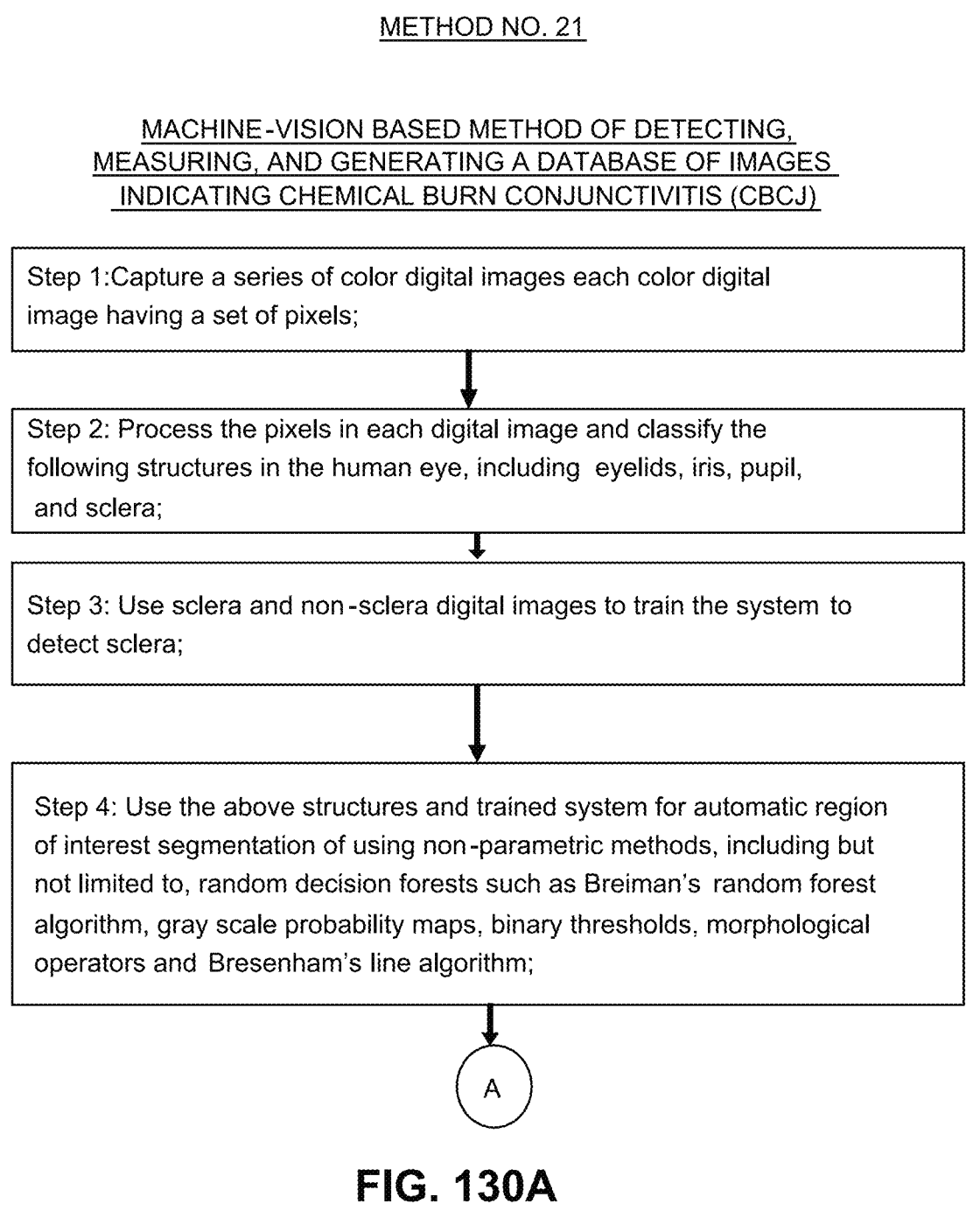

METHOD NO. 21

MACHINE-VISION BASED METHOD OF DETECTING,
MEASURING, AND GENERATING A DATABASE OF IMAGES
INDICATING CHEMICAL BURN CONJUNCTIVITIS (CBCJ)

Step 1:Capture a series of color digital images each color digital
image having a set of pixels;

Step 2: Process the pixels in each digital image and classify the
following structures in the human eye, including  eyelids, iris, pupil,
 and sclera;

Step 3: Use sclera and non-sclera digital images to train the system to
detect sclera;

Step 4: Use the above structures and trained system for automatic region
of interest segmentation of using non-parametric methods, including but
not limited to, random decision forests such as Breiman's  random forest
algorithm, gray scale probability maps, binary thresholds, morphological
operators and  Bresenham's line algorithm;

METHOD NO. 21

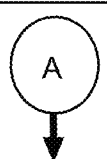

Step 5: Use region of interest matching to detect sclera across a series of digital images reproducibly using methods including, but not limited to, scale invariant feature transform and random sample consensus;

Step 6: Measure conjunctival injection in region of interest using methods including, but not limited to, contrast- limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: Detect clear discharge, chemosis and limbal whitening using edge detection, region growing, k-means clustering and thresholding methods;

Step 8: If detected conjunctival injection is greater than 75 and clear discharge is greater than 0.1mm in both eyes, then generate output data indicative of such determined ocular disease factors and index the processed image(s) therewith to indicate the same;

Step 9: If detected limbal whitening is greater than 0.1 % of cornea, then generate output data indicative of such determined ocular disease factors and index the processed image(s) therewith to indicate the same

Step 10: If detected chemosis is greater than 5 % of conjunctiva, then generate output data indicative of such determined ocular disease factors and index the processed image(s) therewith to indicate the same.

<u>AUTOMATICALLY DETECTING AND MEASURING
PTERYGIUM / PINGUECULA (PP) USING A REAL-TIME OPHTHALMIC IMAGE
PROCESSING ENGINE OPERATING ON FRONT VIEW DIGITAL IMAGES
OF THE HUMAN EYE</u>

Pterygium                      Pinguecula

METHOD NO. 22

MACHINE-VISION BASED METHOD OF DETECTING,
MEASURING, AND GENERATING A DATABASE OF IMAGES
INDICATING PTERYGIUM/PINGUECULA

Step 1: Capture a series of color digital images each color digital
image having a set of pixels;

Step 2: Process the pixels in each digital image and classify the
following structures in the human eye, including eyelids, iris, pupil,
and sclera;

Step 3: Use sclera and non-sclera digital images to train the system
to detect sclera;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm;

METHOD NO. 22

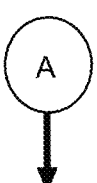

Step 5: Detect pterygium or pinguecula in the region of interest using edge detection, region growing, k-means clustering and thresholding methods;

Step 6: Differentiate pterygium or pinguecula using methods including, but not limited to, contrast- limited adaptive histogram equalization, hue-saturation-value, product of saturation and hue maps, and maximal values of saturation and hue values;

Step 7: If detected pterygium or pinguecula are greater than 0.1 mm, then generate output data indicative of such determined ocular disease factors and index the processed image(s) therewith to indicate the same.

AUTOMATICALLY DETECTING AND MEASURING
SUBCONJUNCTIVAL HEMORRHAGE (SCH) USING A
REAL-TIME OPHTHALMIC IMAGE PROCESSING ENGINE OPERATING
ON FRONT VIEW DIGITAL IMAGES OF THE HUMAN EYE

Subconjunctival
Hemorrhage

M23

SCHEMATIC MODEL SUPPORTING THE AUTOMATED DETECTION
AND MEASUREMENT OF SUBCONJUNCTIVAL HEMORRHAGE (SCH)
OF HUMAN EYES USING A REAL-TIME OPHTHALMIC IMAGE
PROCSSING ENGINE OPERATING ON FRONT VIEW DIGITAL
IMAGES OF THE HUMAN EYES

Subconjunctival Hemorrhage

Process

Subconjunctival
Hemorrhage

METHOD NO. 23

MACHINE-VISION BASED METHOD OF DETECTING,
MEASURING, AND GENERATING A DATABASE OF IMAGES
INDICATING SUBCONJUNCTIVAL HEMORRHAGE (SCH)

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

FIG. 138A

METHOD NO. 23

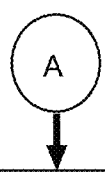

Step 5: Use region of interest matching to detect sclera across a series of digital images reproducibly using methods including, but not limited to, scale invariant feature transform and random sample consensus;

Step 6: Detect subconjunctival hemorrhage borders using edge detection, k-means clustering, region growing and thresholding methods;

Step 7: Differentiate subconjunctival hemorrhage from conjunctival injection using methods including, but not limited to, contrast-limited adaptive histogram equalization, hue-saturation-value, product of saturation and hue maps, and maximal values of saturation and hue values;

Step 8: If detected subconjunctival hemorrhage is greater than 0.1 mm, then generate output data indicative of such determined ocular disease factors and index the processed image(s) therewith to indicate the same.

FIG. 138B

METHOD NO. 24

MACHINE-VISION BASED METHOD OF DETECTING,
MEASURING, AND GENERATING A DATABASE OF IMAGES
INDICATING CONJUNCTIVAL LACERATION (CJL)

Step 1: capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

FIG. 142A

METHOD NO. 24

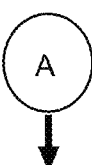

Step 5: Use region of interest matching to detect sclera across a
series of digital images reproducibly using methods including,
but not limited to, scale invariant feature transform and random
sample consensus;

Step 6: Detect conjunctival laceration borders using edge
detection, k-means clustering, region growing and thresholding
methods;

Step 7: Differentiate conjunctival laceration from chemosis and
subconjunctival hemmorhage using methods including, but not
limited to, contrast- limited adaptive histogram equalization, hue-
saturation-value, product of saturation and hue maps, and
maximal values of saturation and hue values;

Step 8: If detected conjunctival laceration is greater than 0.1 mm,
then generate output data indicative of such determined ocular
disease factors and index the processed image(s) therewith to
indicate the same.

AUTOMATICALLY DETECTING AND MEASURING
EPISCLERTIS / SCLERITIS USING A REAL-TIME OPHTHALMIC IMAGE
PROCESSING ENGINE OPERATING ON FRONT VIEW DIGITAL IMAGES
OF THE HUMAN EYE

Sectoral
Conjunctival
Injection

M25

<u>SCHEMATIC MODEL SUPPORTING THE AUTOMATED DETECTION AND
MEASUREMENT OF EPISCLERTIS / SCLERITIS OF HUMAN EYES USING A
REAL-TIME OPHTHALMIC IMAGE PROCSSING ENGINE OPERATING ON
FRONT VIEW DIGITAL IMAGES OF THE HUMAN EYES</u>

Episclertis / Scleritis

Process

Sectoral
Conjunctival
Injection

METHOD NO. M25

MACHINE-VISION BASED METHOD OF DETECTING,
MEASURING, AND GENERATING A DATABASE OF IMAGES
INDICATING EPISCLERTIS/SCLERITIS

Step 1: Capture a series of color digital images each color digital
image having a set of pixels;

Step 2: Process the pixels in each digital image and classify the
following structures in the human eye, including  eyelids, iris, pupil,
and sclera;

Step 3: Use sclera and non-sclera digital images to train the system
to detect sclera;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm;

METHOD NO. 25

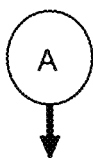

Step 5: Use region of interest matching to detect sclera across a series of digital images reproducibly using methods including, but not limited to, scale invariant feature transform and random sample consensus;

Step 6: Detect sectoral conjunctival injection using edge detection, region growing, k-means clustering and thresholding methods;

Step 7: Measure sectoral conjunctival injection in region of interest using methods including, but not limited to, contrast-limited adaptive histogram equalization, hue-saturation-value, product of saturation and hue maps, and maximal values of saturation and hue values; sectoral conjunctival injection is measured on scale 0 to 100, with higher numbers corresponding with greater conjunctival injection;

Step 8: If sectoral conjunctival injection is greater than 75, then generate output data indicative of such determined ocular disease factors and index the processed image(s) therewith to indicate the same.

FIG. 146B

METHOD NO. 26

MACHINE-VISION BASED METHOD OF DETECTING,
MEASURING, AND GENERATING A DATABASE OF IMAGES
INDICATING SUPERIOR LIMBIC KERATOCONJUNCTIVITIS (SLK)

Step 1: Capture a series of color digital images each color digital
image having a set of pixels;

Step 2: Process the pixels in each digital image and classify the
following structures in the human eye, including  eyelids, iris, pupil,
 and sclera;

Step 3: Use sclera and non-sclera digital images to train the system
 to detect sclera;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm;

FIG. 150A

METHOD NO. 26

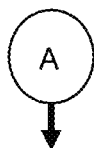

Step 5: Use region of interest matching to detect sclera across a series of digital images reproducibly using methods including, but not limited to, scale invariant feature transform and random sample consensus;

Step 6: Detect superior conjunctival injection and redundant conjunctiva superiorly using edge detection, region growing, k-means clustering and thresholding methods;

Step 7: Measure superior conjunctival injection in region of interest using methods including, but not limited to, contrast-limited adaptive histogram equalization, hue-saturation-value, product of saturation and hue maps, and maximal values of saturation and hue values; wherein conjunctival injection is measured on scale 0 to 100, with higher numbers corresponding with greater conjunctival injection;

Step 8: If detected superior conjunctival injection is greater than 75, then generate output data indicative of such determined ocular disease factors and index the processed image(s) therewith to indicate the same.

Step 9: If detected redundant conjunctival superior is greater than one fold in the conjunctiva, then generate output data indicative of such determined ocular disease factors and index the processed image(s) therewith to indicate the same.

FIG. 150B

METHOD NO. 27

MACHINE-VISION BASED METHOD OF DETECTING, MEASURING, AND
GENERATING A DATABASE OF IMAGES INDICATING BLEPHARITIS

Step 1: Capture a series of color digital images each color digital
image having a set of pixels;

Step 2: Process the pixels in each digital image and classify the
following structures in the human eye, including eyelids, iris, pupil,
and sclera;

Step 3: Use eyelid and non -eyelid digital images to train the system
to detect eyelids;

Step 4: Use the above structures and trained system for automatic
region of interest segmentation of eyelid margins using non -
parametric methods, including but not limited to, random decision
forests such as Breiman's random forest algorithm, gray scale
probability maps, binary thresholds, morphological operators and
Bresenham's line algorithm;

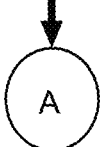

METHOD NO. 27

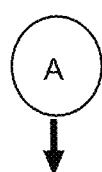

Step 5: Use region of interest matching to measure meibomian gland dysfunction and scruff at eyelashes across a series of digital images reproducibly using methods including, but not limited to, scale invariant feature transform and random sample consensus;

Step 6: Detect, Identify and count meibomian glands, and identify scruff at eyelashes using methods, including, but not limited to, edge detection, k-means clustering, region growing and thresholding methods;

Step 7: Any change in edges, clusters or regions at the on the lower eyelid margin and in the eyelashes are meibomian glands or scruff at eyelashes;

Step 8: If the meibomian glands or visible scruff at eyelids is greater than 50% of eyelid margin, then generate output data indicative of such determined ocular disease factors and index the processed image(s) therewith to indicate the same.

SCHEMATIC MODEL SUPPORTING THE AUTOMATED DETECTION AND
MEASUREMENT OF CHALAZION STYES OF HUMAN EYES USING A REAL-TIME
OPHTHALMIC IMAGE PROCESSING ENGINE OPERATING ON FRONT VIEW
DIGITAL IMAGES OF THE HUMAN EYES

Chalazion Stye

Process

Chalazion
Stye

METHOD NO. 28

MACHINE -VISION BASED METHOD OF DETECTING, MEASURING, AND
GENERATING A DATABASE OF IMAGES INDICATING CHALAZION STYES (CS)

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non -eyelid digital images to train the system to detect eyelids;

Step 4: Use the above structures and trained system for automatic region of interest segmentation of eyelid margins using non - parametric methods, including but not limited to, random decision forests such as Breiman's random forest algorithm, gray scale probability maps, binary thresholds, morphological operators and Bresenham's line algorithm;

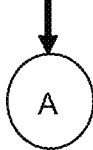

METHOD NO. 28

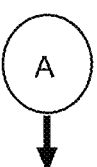

Step 5: Use region of interest matching to detect eyelid across a
series of digital images reproducibly using methods including,
but not limited to, scale invariant feature transform and random
 sample consensus;

Step 6: Detect and Identify chalazion using methods, including,
but not limited to, edge detection, k-means clustering, region
growing and thresholding methods;

Step 7: If a detected chalazion is greater than 1 mm, then
generate output data indicative of such determined ocular
disease factors and index the processed image(s) therewith to
indicate the same.

AUTOMATICALLY DETECTING AND MEASURING
EYELID CYSTS USING A REAL-TIME OPHTHALMIC IMAGE
PROCESSING ENGINE OPERATING ON FRONT VIEW DIGITAL IMAGES
OF THE HUMAN EYE

Eyelid Cyst

M29

SCHEMATIC MODEL SUPPORTING THE AUTOMATED DETECTION AND MEASUREMENT OF EYELID CYSTS (EC) OF HUMAN EYES USING A REAL-TIME OPHTHALMIC IMAGE PROCESSING ENGINE OPERATING ON FRONT VIEW DIGITAL IMAGES OF THE HUMAN EYES

Eyelid Cyst

Process

Eyelid Cyst

METHOD NO. 29

MACHINE -VISION BASED METHOD OF DETECTING,  MEASURING, AND
GENERATING A DATABASE OF IMAGES  INDICATING EYELID CYSTS (EC)

Step 1: Capture a series of color digital images each color digital image having a set of pixels;

Step 2: Process the pixels in each digital image and classify the following structures
the human eye, including  eyelids, iris, pupil, and sclera;

Step 3: Use eyelid and non -eyelid digital images to train the system to detect eyelids;

Step 4: Use the above structures and trained system for automatic region of interest
segmentation of eyelid margins using non-parametric methods, including but not
limited to, random decision forests such as Breiman's random forest  algorithm, gray
scale probability maps, binary thresholds, morphological operators and
Bresenham's  line algorithm;

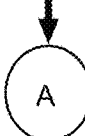

METHOD NO. 29

Step 5: Use region of interest matching to detect eyelid across a series of digital images reproducibly using methods including, but not limited to, scale invariant feature transform and random sample consensus;

Step 6: Detect and Identify eyelid cyst using methods, including, but not limited to, edge detection, k-means clustering, region growing and thresholding methods;

Step 7: Differentiate an eyelid cyst from chalazion by using methods including, but not limited to, contrast- limited adaptive histogram equalization, hue-saturation-value, product of saturation and hue maps, and maximal values of saturation and hue values;

Step 8: If a detected eyelid cyst is greater than 1mm, then generate output data indicative of such determined ocular disease factors and index the processed image(s) therewith to indicate the same.

AUTOMATICALLY DETECTING AND MEASURING
PRESEPTAL CELLULITIS (PC) USING A REAL-TIME OPHTHALMIC IMAGE
PROCESSING ENGINE OPERATING ON FRONT VIEW DIGITAL IMAGES
OF THE HUMAN EYE

Eyelid Swelling

M30

SCHEMATIC MODEL SUPPORTING THE AUTOMATED DETECTION AND
MEASUREMENT OF PRESEPTAL CELLULITIS (PC) OF HUMAN EYES
USING A REAL-TIME OPHTHALMIC IMAGE PROCESSING ENGINE
OPERATING ON FRONT VIEW DIGITAL IMAGES OF THE HUMAN EYES

Preseptal Cellulitis

Process

Eyelid Swelling

METHOD NO. 30

MACHINE-VISION BASED METHOD OF DETECTING,
MEASURING, AND GENERATING A DATABASE OF IMAGES
INDICATING PRESEPTAL CELLULITIS (PC)

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train the system to detect eyelids;

Step 4: Use the above structures and trained system for automatic region of interest segmentation of eyelid margins using non - parametric methods, including but not limited to, random decision forests such as Breiman's random forest algorithm, gray scale probability maps, binary thresholds, morphological operators and Bresenham's line algorithm;

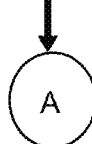

METHOD NO. 30

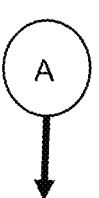

Step 5: Use region of interest matching to detect eyelid across a series of digital images reproducibly using methods including, but not limited to, scale invariant feature transform and random sample consensus;

Step 6: Identify eyelid swelling using methods, including, but not limited to, edge detection, k-means clustering, region growing and thresholding methods;

Step 7: Differentiate eyelid swelling from eyelid cyst and chalazion by using methods including, but not limited to, contrast- limited adaptive histogram equalization, hue-saturation-value, product of saturation and hue maps, and maximal values of saturation and hue values;

Step 8: If detected eyelid swelling is greater than 50% of upper or lower eyelid, then generate output data indicative of such determined ocular disease factors and index the processed image(s) therewith to indicate the same.

<u>AUTOMATICALLY DETECTING AND MEASURING PTOSIS (PT) USING A REAL-TIME
OPHTHALMIC IMAGE PROCESSING ENGINE OPERATING ON FRONT VIEW DIGITAL
IMAGES OF THE HUMAN EYE</u>

Ptotic Eyelid

M31

<u>SCHEMATIC MODEL SUPPORTING THE AUTOMATED DETECTION AND MEASUREMENT OF PTOSIS (PT) OF HUMAN EYES USING A REAL-TIME OPHTHALMIC IMAGE PROCESSING ENGINE OPERATING ON FRONT VIEW DIGITAL IMAGES OF THE HUMAN EYES</u>

<u>Ptosis</u>

MRD1 / 2: Margin Reflex Distance 1 / 2
PFH: Palpebral Fissure Height
PFW: Palpebral Fissure Width

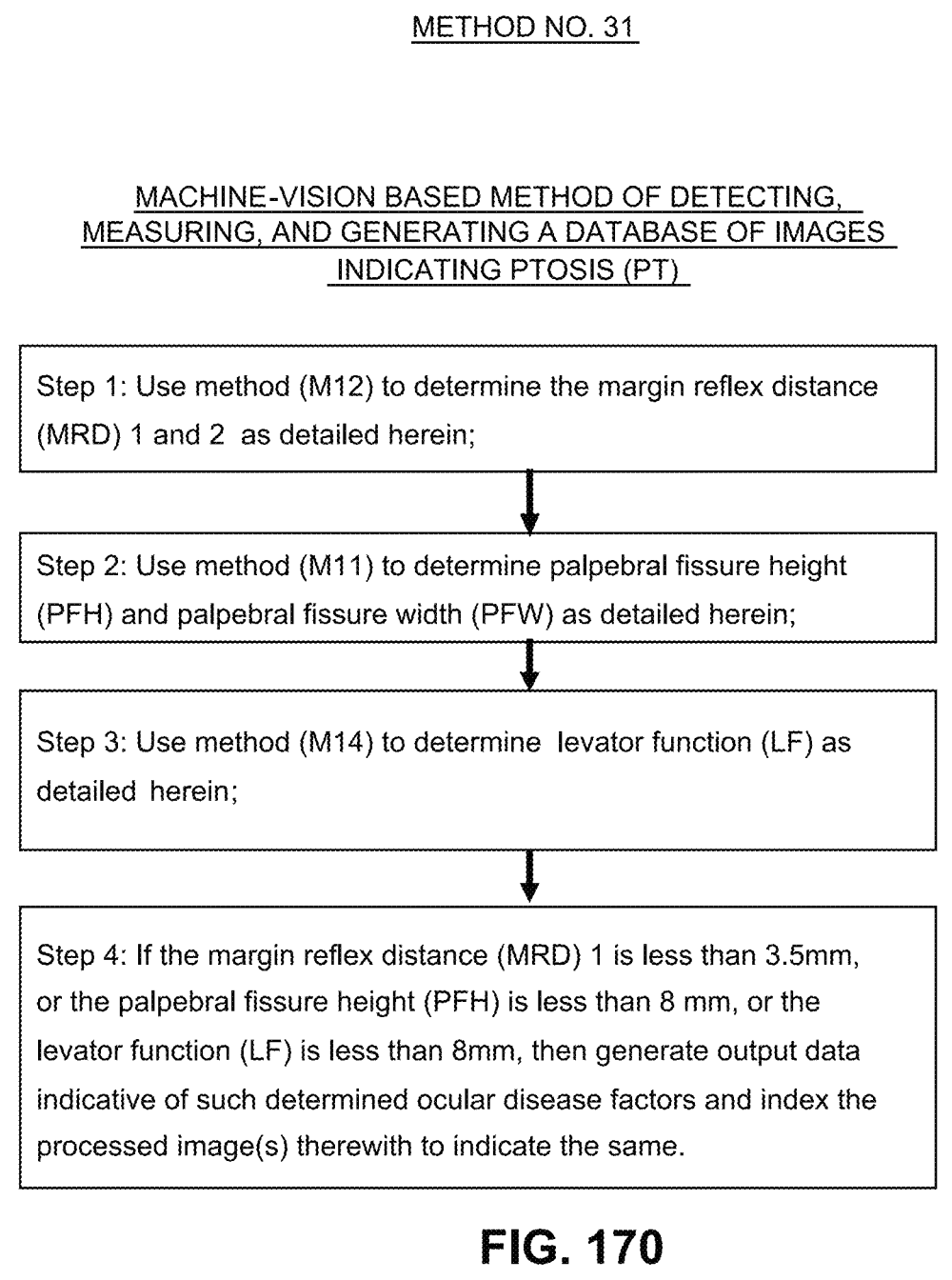

METHOD NO. 31

MACHINE-VISION BASED METHOD OF DETECTING,
MEASURING, AND GENERATING A DATABASE OF IMAGES
INDICATING PTOSIS (PT)

Step 1: Use method (M12) to determine the margin reflex distance (MRD) 1 and 2  as detailed herein;

Step 2: Use method (M11) to determine palpebral fissure height (PFH) and palpebral fissure width (PFW) as detailed herein;

Step 3: Use method (M14) to determine  levator function (LF) as detailed  herein;

Step 4: If the margin reflex distance (MRD) 1 is less than 3.5mm, or the palpebral fissure height (PFH) is less than 8 mm, or the levator function (LF) is less than 8mm, then generate output data indicative of such determined ocular disease factors and index the processed image(s) therewith to indicate the same.

FIG. 170

METHOD NO. 32

MACHINE-VISION BASED METHOD OF DETECTING,
MEASURING, AND GENERATING A DATABASE OF IMAGES
INDICATING OPHTHALMOPLEGIA (OPM)

Step 1: Capture a color digital video having a set of frames per second, and decompose the video into 1 second intervals; use is asked to look left, right, up and down; wherein each image each color digital image having a set of pixels;

Step 2: Process the pixels in the individual frames and classify the following structures in the human eye, including eyelids, iris, pupil, and sclera;

Step 3:Use cornea and non-cornea digital images to train the system to detect pupillary margin;

Step 4: Use the above structures and trained system for automatic region of interest segmentation of pupillary margin using non-parametric methods, including but not limited to, random decision forests such as Breiman's random forest algorithm, gray scale probability maps, binary thresholds, morphological operators and Bresenham's line algorithm;

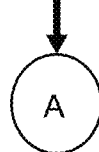

METHOD NO. 32

Step 5: Use region of interest matching to recognize pupillary margin across a series of digital images reproducibly using methods including, but not limited to, scale invariant feature transform and random sample consensus;

Step 6: Use pixel-by-pixel location to map pupillary margin onto a grid and detect movement of each eye pupillary margin as user looks left, right, up and down;

Step 7: If the absolute difference in movement between one eye pupillary margin compared to the adjacent eye pupillary margin is greater than 0.00 mm, then generate output data indicative of such determined ocular disease factors and index the processed image(s) therewith to indicate the same.

FIG. 174B

METHOD NO. 33

MACHINE-VISION BASED METHOD OF DETECTING,
MEASURING, AND GENERATING A DATABASE OF IMAGES
INDICATING PROPTOSIS/HYPOGLOBUS (HP)

Step 1: Capture a series of color digital images each color digital
image having a set of pixels captured from front, side, above
and below angles (i.e. views);

Step 2: Process the pixels in each digital image and classify the
following structures in the human eye, including eyelids, iris, pupil,
and sclera, brow and lateral canthus and facial landmarks,
including tragus and tip of nose;

Step 3: Use digital images to train the system to detect the above
structures;

Step 4: Use the above structures and trained system for automatic
region of interest segmentation using non-parametric methods,
including but not limited to, random decision forests such as
Breiman's random forest algorithm, gray scale probability maps,
binary thresholds, morphological operators and Bresenham's line
algorithm;

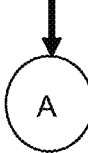

FIG. 178A

METHOD NO. 33

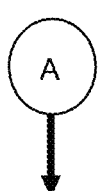

Step 5: Use region of interest matching to detect the above
structures across a series of digital images reproducibly using
methods including, but not limited to, scale invariant feature
transform and random sample consensus;

Step 6: Use pixel -by -pixel location to map: pupillary margin and
corneal surface onto a grid; and a mismatch in pupillary margin
position or corneal surface position;

Step 7: To standardize location of corneal surface and account for
head tilt, the medial canthus is used on front angle images,
the lateral canthus and tragus is used on side angled images, and
the tip of the nose is used on above and below angled photos;

Step 8: If the difference in pupillary margin is greater than 1 mm
or the difference in corneal surface location from eye to eye is
greater than 1 mm from one eye to the other, then generate
output data indicative of such determined ocular disease factors
and index the processed image(s) therewith to indicate the
same.

AUTOMATICALLY DETECTING AND MEASURING ANISOCORIA (ACR) USING A
REAL-TIME OPHTHALMIC IMAGE PROCESSING ENGINE OPERATING ON FRONT
VIEW DIGITAL IMAGES OF THE HUMAN EYE

Mismatch in Pupil Size

METHOD NO. 34

MACHINE-VISION BASED METHOD OF DETECTING,
MEASURING, AND GENERATING A DATABASE OF IMAGES
INDICATING ANISOCORIA

Step 1: Capture a color digital images and video having a set of
frames per second, and decompose the video into 1 second
intervals;

Step 2: Process the individual frames and classify the following
Structures in the human eye, including eyelids, iris, pupil, and sclera;

Step 3: Use cornea and non-cornea digital images to train the
system to detect pupillary margin;

Step 4: Use the above structures and trained system for automatic
region of interest segmentation of pupillary margin using non -
parametric methods, including but not limited to, random decision
forests such as Breiman's random forest algorithm, gray scale
probability maps, binary thresholds, morphological operators and
Bresenham's line algorithm;

FIG. 182A

METHOD NO. 34

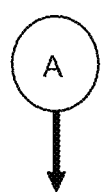

Step 5: Use region of interest matching to recognize pupillary margin across a series of digital images reproducibly using methods including, but not limited to, scale invariant feature transform and random sample consensus;

Step 6: Use pixel-by-pixel size to determine the pupillary margin size;

Step 7: Vary the intensity of light source on mobile device to detect how pupillary margin change in size;

Step 8: If the difference in pupil size from one eye to the other eye is greater than 1mm, then generate output data indicative of such determined ocular disease factors and index the processed image(s) therewith to indicate the same;

Step 9: If there is no change is detected in pupil size with light stimulus, then generate output data indicative of such determined ocular disease factors and index the processed image(s) therewith to indicate the same.

FIG. 182B

AUTOMATICALLY DETECTING AND MEASURING
ANTERIOR CHAMBER DEPTH (ACD) USING A REAL-TIME
OPHTHALMIC IMAGE PROCESSING ENGINE OPERATING ON
FRONT VIEW DIGITAL IMAGES OF THE HUMAN EYE

M35

Anterior Chamber
Having Normal
Depth

M35

Anterior Chamber
Having Moderate
Depth

M35

Anterior
Chamber
Having
Shallow
Depth

M35

AUTOMATICALLY DETECTING AND MEASURING
ANTERIOR CHAMBER DEPTH (ACD) USING A REAL-TIME
OPHTHALMIC IMAGE PROCESSING ENGINE OPERATING ON
FRONT VIEW DIGITAL IMAGES OF THE HUMAN EYE

Normal - note light
illuminating both sides of iris

Shallow - nasal side of iris is
in darkness

M35

AUTOMATICALLY DETECTING AND MEASURING
ANTERIOR CHAMBER DEPTH (ACD) USING A REAL-TIME
OPHTHALMIC IMAGE PROCESSING ENGINE OPERATING ON
FRONT VIEW DIGITAL IMAGES OF THE HUMAN EYE

Z = Distance from
limbus to corneal
surface

E = Distance from
limbus to center of
pupil

METHOD NO. 35

MACHINE-VISION BASED METHOD OF DETECTING, MEASURING, AND GENERATING A DATABASE OF IMAGES MEASURING ANTERIOR CHAMBER DEPTH (ACD)

Step 1: Capture a color digital images and video having a set of frames per second, and decompose the video into 1 second intervals;

Step 2: Process the individual frames and classify the following structures in the human eye, including eyelids, iris, pupil, and sclera;

Step 3: Use cornea and non-cornea digital images to train the system to detect pupillary margin;

Step 4: Use the above structures and trained system for automatic region of interest segmentation of pupillary margin using non - parametric methods, including but not limited to, random decision forests such as Breiman's random forest algorithm, gray scale probability maps, binary thresholds, morphological operators and Bresenham's line algorithm;

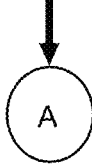

METHOD NO. 35

Step 5: Use region of interest matching to recognize pupillary margin across a series of digital images reproducibly using methods including, but not limited to, scale invariant feature transform and random sample consensus;

Step 6: For front-facing images, detect shadow on the iris, by projecting light on the cornea and casting a shadow on the underlying iris, which is detected using edge detection and k-means clustering methods;

Step 7: Determine iris with and without shadow using methods including, but not limited to, contrast-limited adaptive histogram equalization, hue-saturation-value, product of saturation and hue maps, maximal values of saturation and hue values;

Step 8: For side-facing images of the eye, measure the distance from limbus to corneal surface (Z) in millimeters, and the distance from the limbus to the center of pupil (E) in millimeters, using pixel-by-pixel size;

Step 9: Calculate the anterior chamber depth (ACD) using the following equation: ACD (mm) = -3.3 x EZ ratio + 4.2 ;

Step 10: If ACD (mm) is less than 2.5 mm, then generate output data indicative of such determined ocular disease factors and index the processed image(s) to indicate the same; and Step 11: If the iris casts a shadow nasally or temporally, then generate output data indicative of such determined ocular disease factors and index the processed image(s) therewith to indicate the same.

FIG. 187B

METHOD NO. 36

MACHINE-VISION BASED METHOD OF DETECTING,
MEASURING, AND GENERATING A DATABASE OF IMAGES
INDICATING ORBITAL POSTSEPTAL CELLULITIS (OPSC)

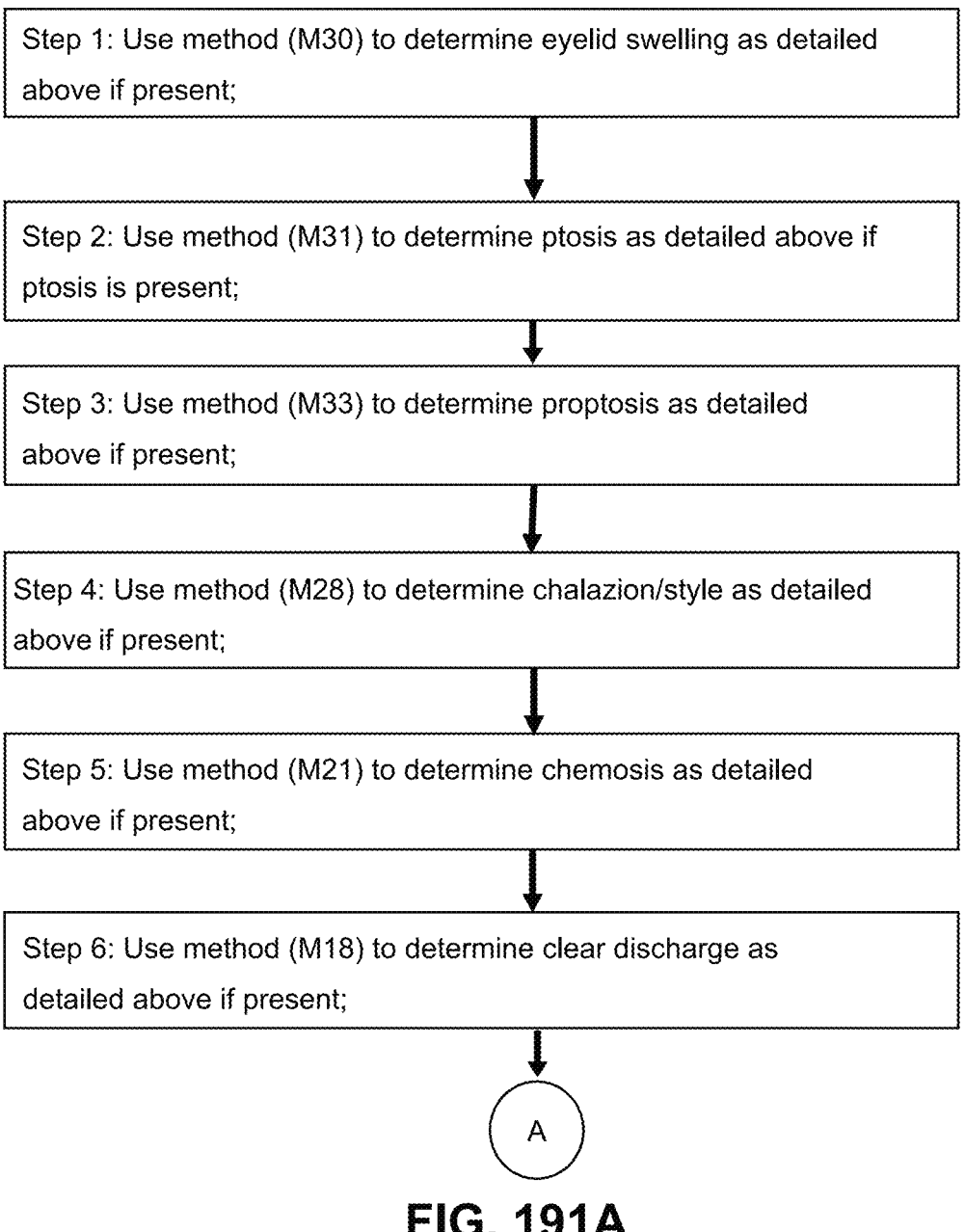

Step 1: Use method (M30) to determine eyelid swelling as detailed above if present;

Step 2: Use method (M31) to determine ptosis as detailed above if ptosis is present;

Step 3: Use method (M33) to determine proptosis as detailed above if present;

Step 4: Use method (M28) to determine chalazion/style as detailed above if present;

Step 5: Use method (M21) to determine chemosis as detailed above if present;

Step 6: Use method (M18) to determine clear discharge as detailed above if present;

METHOD NO. 36

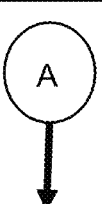

Step 7: Use method (M19) to determine purulent discharge as detailed above if present;

Step 8: Use method (M1) to determine conjunctival injection as detailed above if present;

Step 9: Use method (M23) to determine subconjunctival hemorrhage as detailed above if present;

Step 10: Use method (M32) to determine ophthalmoplegia as detailed above if present; and Step 11: If proptosis is present, and eyelid swelling is present, and conjunctival injection is present, and ophthalmoplegia is present, and (either ptosis is present or chalazion/stye is present, or chemosis is present or clear discharge present or purulent discharge is present or subconjunctival hemorrhage is present), then determine that Orbital Postseptal Cellulitis (OPSC) is present, and generate output data indicative of such determined ocular disease factors and index the processed image(s) therewith to indicate the same.

FIG. 191B

M37
SCHEMATIC MODEL SUPPORTING THE AUTOMATED DETECTION AND MEASUREMENT OF THYROIDAL EYE DISEASE OF HUMAN EYES USING A REAL-TIME OPTHALMIC IMAGE PROCESSING ENGINE OPERATING ON FRONT VIEWS OF DIGITAL IMAGES OF THE HUMAN EYES
Thyroid Eye Disease (M37)
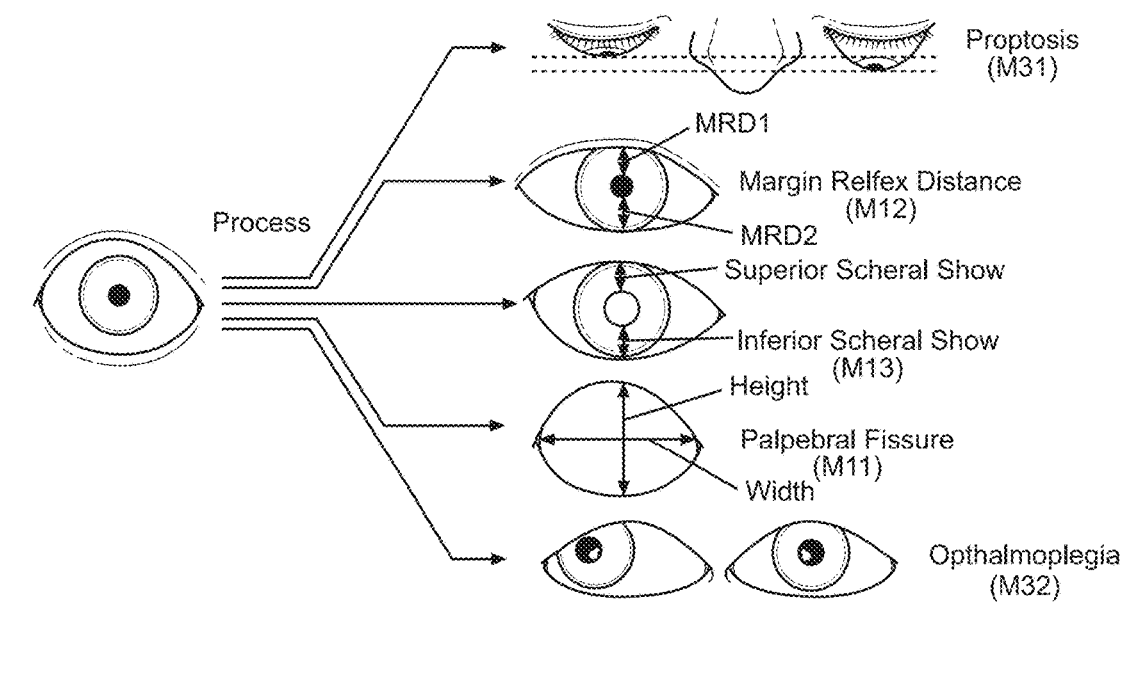
FIG. 194

METHOD NO. 37

MACHINE-VISION BASED METHOD OF DETECTING,
MEASURING, AND GENERATING A DATABASE OF IMAGES
INDICATING THYROID EYE DISEASE (TED)

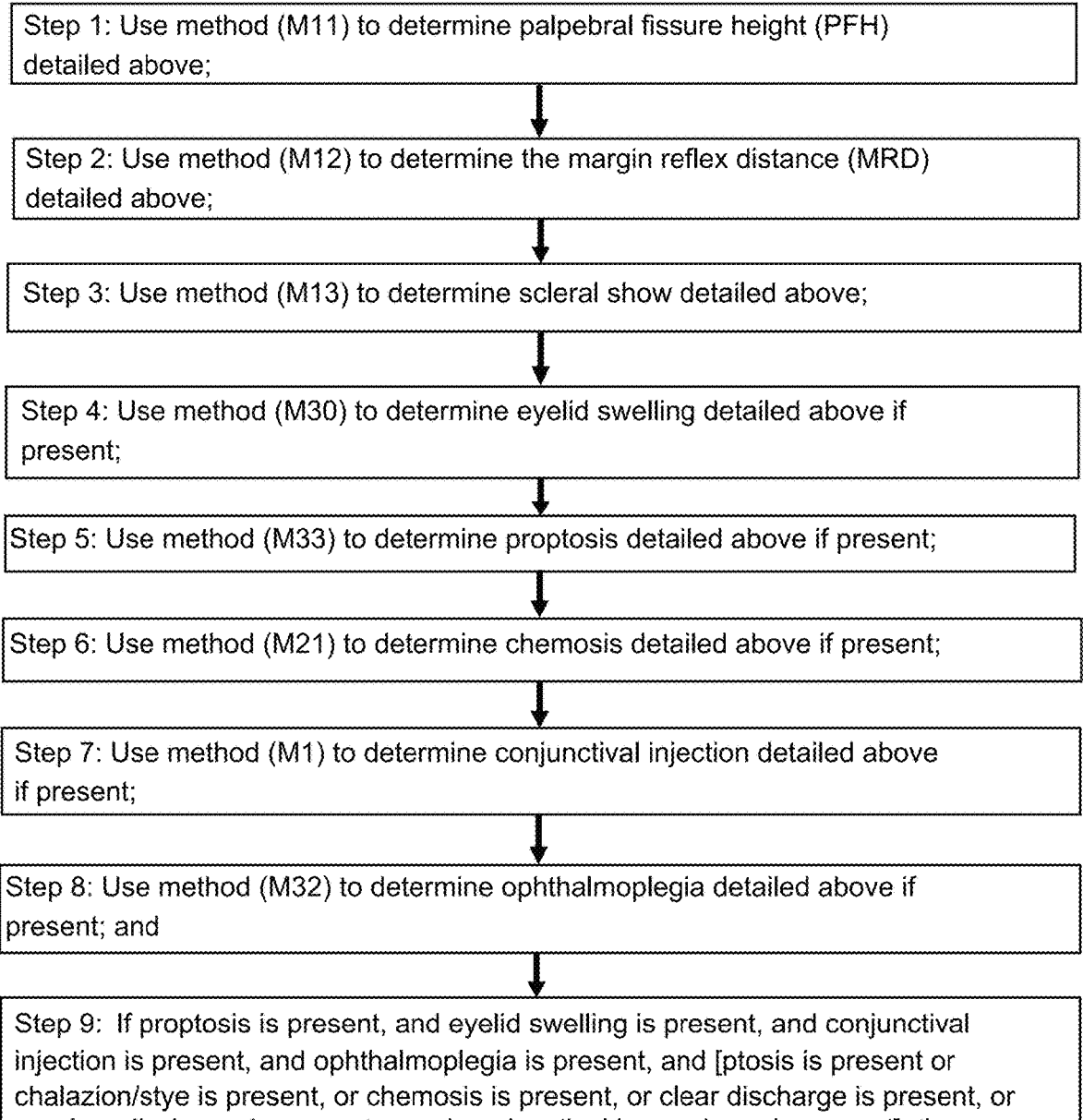

Step 1: Use method (M11) to determine palpebral fissure height (PFH) detailed above;

Step 2: Use method (M12) to determine the margin reflex distance (MRD) detailed above;

Step 3: Use method (M13) to determine scleral show detailed above;

Step 4: Use method (M30) to determine eyelid swelling detailed above if present;

Step 5: Use method (M33) to determine proptosis detailed above if present;

Step 6: Use method (M21) to determine chemosis detailed above if present;

Step 7: Use method (M1) to determine conjunctival injection detailed above if present;

Step 8: Use method (M32) to determine ophthalmoplegia detailed above if present; and Step 9: If proptosis is present, and eyelid swelling is present, and conjunctival injection is present, and ophthalmoplegia is present, and [ptosis is present or chalazion/stye is present, or chemosis is present, or clear discharge is present, or purulent discharge is present, or subconjunctival hemorrhage is present], then determine that Thyroidal Eye Disease (TED) is present and generate output data indicative of such determined ocular disease factors, and index the processed image(s) therewith to indicate the same.

FIG. 195

METHOD NO. 38

MACHINE-VISION BASED METHOD OF DETECTING,
MEASURING, AND GENERATING A DATABASE OF IMAGES
INDICATING ECTROPION / ENTROPION (EE)

Step 1: Capture a series of color digital images each color digital image having a set of pixels from front and side angles;

Step 2:Process the pixels in each digital image and classify the following structures in the human eye, including eyelids, iris, pupil, and sclera;

Step 3: Use eyelid and non-eyelid digital images to train the system to detect eyelids;

Step 4 Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: Use region of interest matching to detect eyelid margins across a series of digital images reproducibly using methods including, but not limited to, scale invariant feature transform and random sample consensus;

Step 6: Detect entropion and ectropion using region growing, k-means clustering and thresholding methods; and Step 7: If entropion is present, or ectropion is present, then generate output data indicative of such determined ocular disease factors and index the processed image(s) therewith to indicate the same.

M39
AUTOMATICALLY DETECTING AND MEASURING TRICHIASIS / DISTICHIASIS USING A REAL-TIME OPTHALMIC IMAGE PROCESSING ENGINE OPERATING ON FRONT VIEW DIGITAL IMAGES OF THE HUMAN EYE
Trichiasis:
Lash in normal
anatomical
location but
turned inward
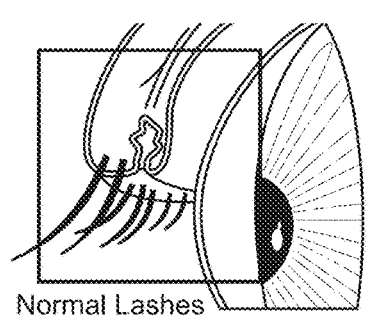
Normal Lashes
Distichiasis:
Lash growing
out of
meibomian
gland and
turned inward
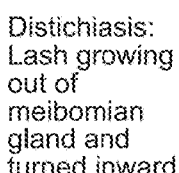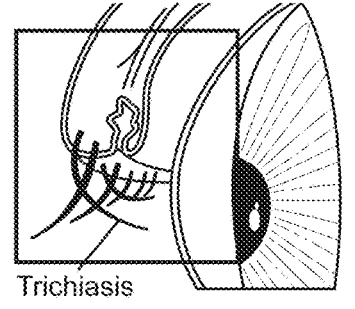
Trichiasis
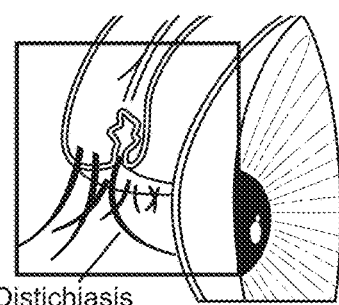
Distichiasis
FIG. 201

METHOD NO. 39

MACHINE-VISION BASED METHOD OF DETECTING,
MEASURING, AND GENERATING A DATABASE OF IMAGES
INDICATING TRICHIASIS/DISTICHIASIS

Step 1: Capture a series of color digital images each color digital
image having a set of pixels from front and side angles;

Step 2: Process the pixels in each digital image and classify the
following structures in the human eye, including eyelids, iris,
pupil, and sclera;

Step 3: Use eyelid and non-eyelid digital images to train the system
to detect eyelids;

Step 4: Use the above structures and trained system for automatic region of
interest segmentation of eyelid margins using non-parametric methods,
including but not limited to, random decision forests such as Breiman's random
forest algorithm, gray scale probability maps, binary thresholds, morphological
operators and Bresenham'sline algorithm;

FIG. 203A

METHOD NO. 39

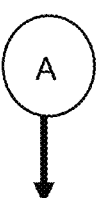

Step 5: Use region of interest matching to detect eyelid margins across a series of digital images reproducibly using methods including, but not limited to, scale invariant feature transform and random sample consensus;

Step 6: Detect trichiasis and distichiasis using region growing, k-means clustering and thresholding methods; and Step 7: If detected trichiasis is greater than 1.0%, or detected distichiasis is greater than 1.0%, then generate output data indicative of such determined ocular disease factors and index the processed image(s) therewith to indicate the same.

AUTOMATICALLY DETECTING AND MEASURING
FLOPPY EYELID SYNDROME (FES) USING A REAL-TIME OPTHALMIC IMAGE
PROCESSING ENGINE OPERATING ON FRONT VIEW DIGITAL IMAGES
OF THE HUMAN EYE

M40

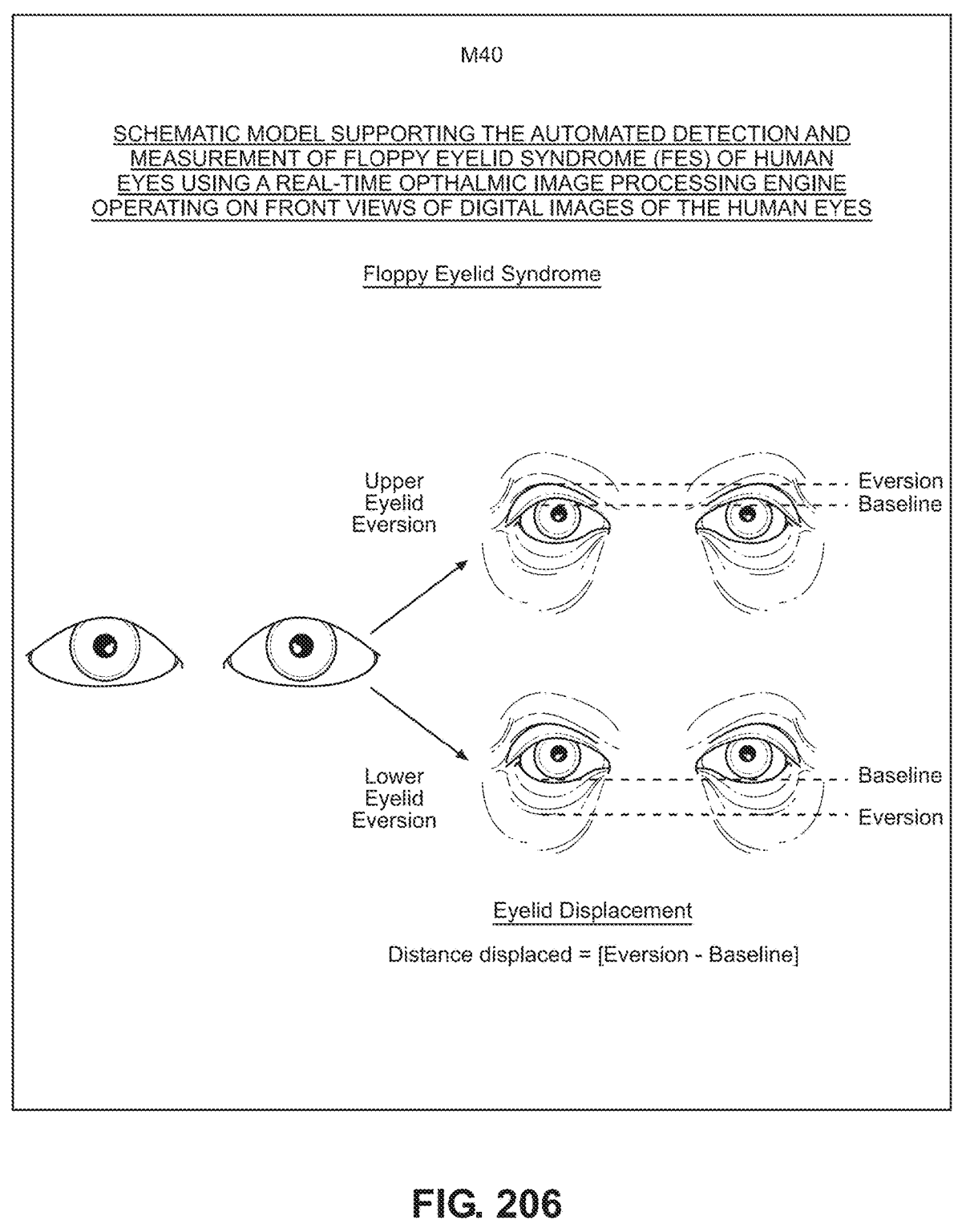

M40

SCHEMATIC MODEL SUPPORTING THE AUTOMATED DETECTION AND
MEASUREMENT OF FLOPPY EYELID SYNDROME (FES) OF HUMAN
EYES USING A REAL-TIME OPTHALMIC IMAGE PROCESSING ENGINE
OPERATING ON FRONT VIEWS OF DIGITAL IMAGES OF THE HUMAN EYES

Floppy Eyelid Syndrome

Upper
Eyelid
Eversion

Eversion
Baseline

Lower
Eyelid
Eversion

Baseline
Eversion

Eyelid Displacement

Distance displaced = [Eversion - Baseline]

FIG. 206

METHOD NO. 40

MACHINE-VISION BASED METHOD OF DETECTING,
MEASURING, AND GENERATING A DATABASE OF IMAGES
INDICATING FLOPPY EYELID SYNDROME (FES)

Step 1: Capture a series of color digital images each color digital
image having a set of pixels;

Step 2: Process the pixels in each digital image and classify the
following structures in the human eye, including eyelids, iris,
pupil, and sclera;

Step 3: Use eyelid and non-eyelid digital images to train the system
to detect eyelids;

Step 4: Use the above structures and trained system for
automatic region of interest segmentation of eyelid margins
using non-parametric methods, including but not limited to,
random decision forests such as Breiman's random forest
algorithm, gray scale probability maps, binary thresholds,
morphological operators and Bresenham's line algorithm;

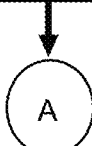

FIG. 207A

METHOD NO. 40

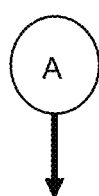

Step 5: Use region of interest matching to detect eyelid margins across a series of digital images reproducibly using methods including, but not limited to, scale invariant feature transform and random sample consensus;

Step 6: Have user patient to evert the upper eyelid up and the lower eyelid down; and Step 7: If the displacement of eyelid margin from the baseline location is greater than 10 mm, or orbital fat prolapse is present, or the time required for eyelid to snap back to baseline location from eversion is greater than 1 second, then determine that Floppy Eyelid Syndrome (FES) is present, and generate output data indicative of such determined ocular disease factors and index the processed image(s) therewith to indicate the same.

AUTOMATICALLY DETECTING AND MEASURING
HERPES ZOSTER DERMATITIS (HZD) USING A REAL-TIME
OPTHALMIC IMAGE PROCESSING ENGINE OPERATING ON FRONT VIEW
DIGITAL IMAGES OF THE HUMAN EYE

Shingles Rash

Figure 211:
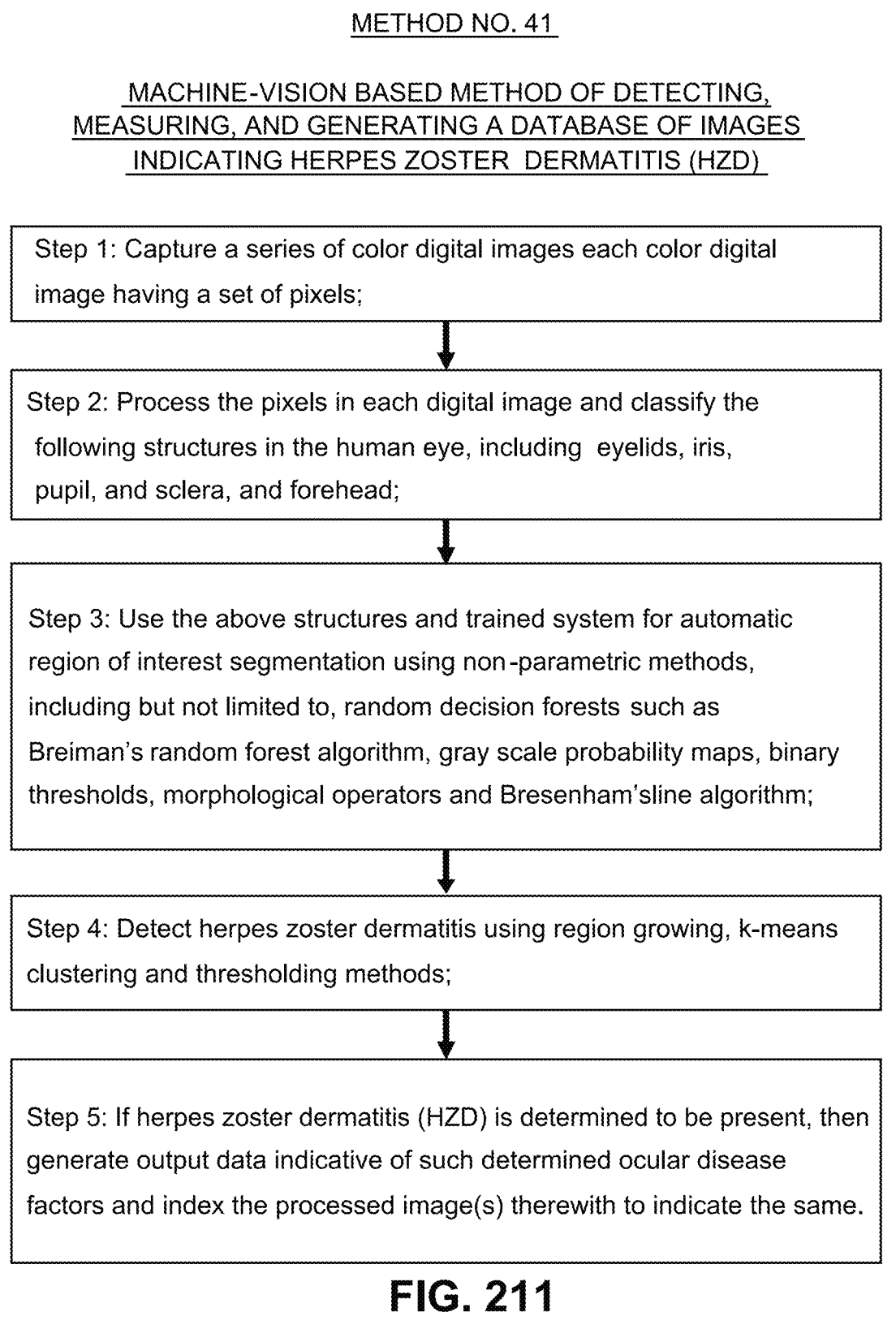

METHOD NO. 41

MACHINE-VISION BASED METHOD OF DETECTING,
MEASURING, AND GENERATING A DATABASE OF IMAGES
INDICATING HERPES ZOSTER  DERMATITIS (HZD)

Step 1: Capture a series of color digital images each color digital
image having a set of pixels;

Step 2: Process the pixels in each digital image and classify the
following structures in the human eye, including  eyelids, iris,
pupil, and sclera, and forehead;

Step 3: Use the above structures and trained system for automatic
region of interest segmentation using non-parametric methods,
including but not limited to, random decision forests such as
Breiman's random forest algorithm, gray scale probability maps, binary
thresholds, morphological operators and Bresenham'sline algorithm;

Step 4: Detect herpes zoster dermatitis using region growing, k-means
clustering and thresholding methods;

Step 5: If herpes zoster dermatitis (HZD) is determined to be present, then
generate output data indicative of such determined ocular disease
factors and index the processed image(s) therewith to indicate the same.

AUTOMATICALLY DETECTING AND MEASURING HERPES
ZOSTER KERATITIS (HZK) USING A REAL-TIME OPHTHALMIC
IMAGE PROCESSING ENGINE OPERATING ON FRONT VIEW
DIGITAL IMAGES OF THE HUMAN EYE

Herpes Zoster
Keratitis

M42

SCHEMATIC MODEL SUPPORTING THE AUTOMATED DETECTION AND
MEASUREMENT OF HERPES ZOSTER KERATITIS (HZK) OF HUMAN EYES
USING A REAL-TIME OPHTHALMIC IMAGE PROCESSING ENGINE OPERATING
ON FRONT VIEW DIGITAL IMAGES OF THE HUMAN EYES

Herpes Zoster Keratitis (M42)

Herpes Zoster Dermatitis
(M41)

Conjunctival Injection
(M1)

Corneal Infection
(M45)

Corneal Edema
(M16)

METHOD NO. 42

MACHINE-VISION BASED METHOD OF DETECTING,
MEASURING, AND GENERATING A DATABASE OF
IMAGES INDICATING HERPES ZOSTER KERATITIS (HZK)

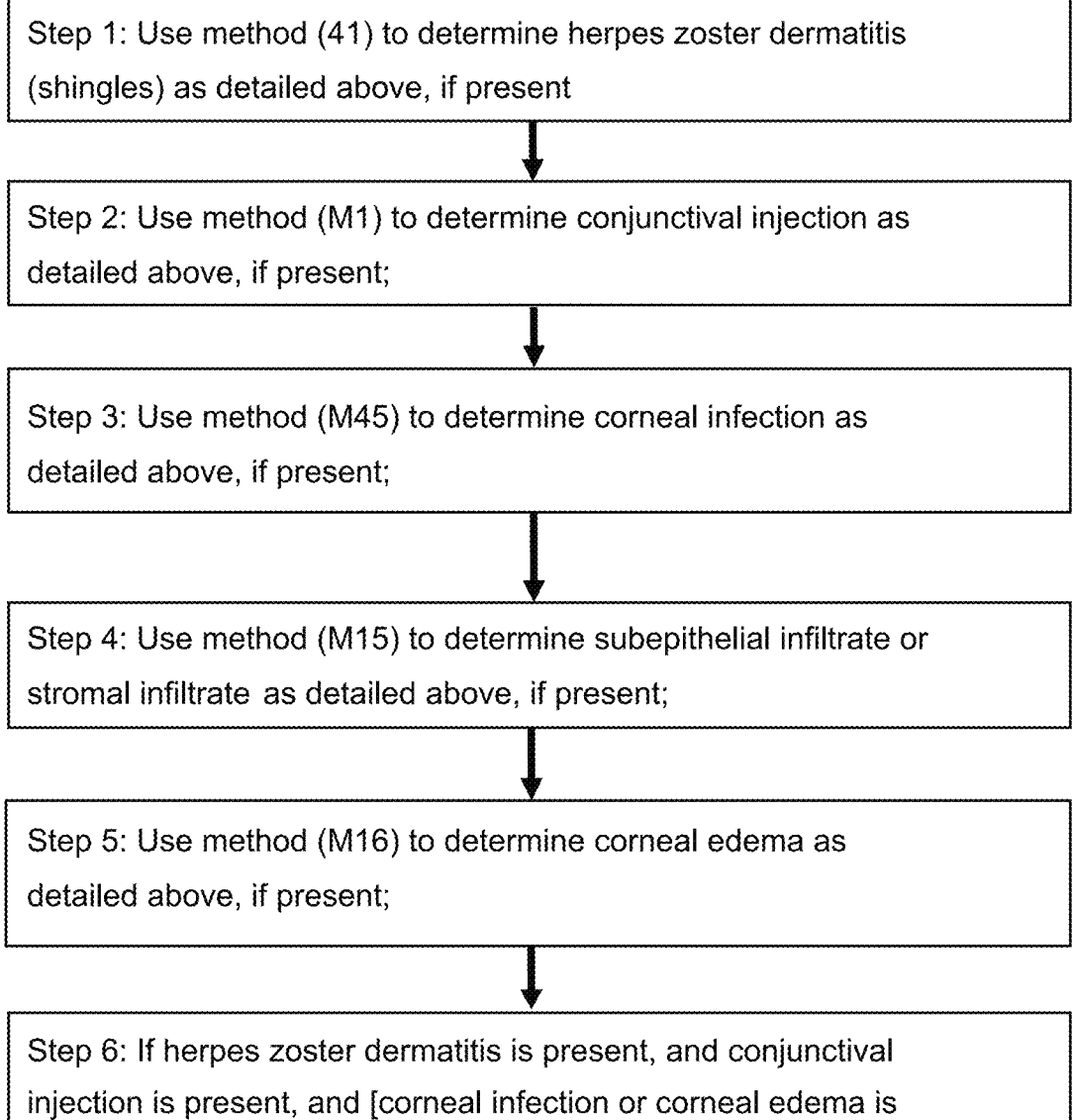

Step 1: Use method (41) to determine herpes zoster dermatitis (shingles) as detailed above, if present Step 2: Use method (M1) to determine conjunctival injection as detailed above, if present;

Step 3: Use method (M45) to determine corneal infection as detailed above, if present;

Step 4: Use method (M15) to determine subepithelial infiltrate or stromal infiltrate as detailed above, if present;

Step 5: Use method (M16) to determine corneal edema as detailed above, if present;

Step 6: If herpes zoster dermatitis is present, and conjunctival injection is present, and [corneal infection or corneal edema is present], then determine that Herpes Zoster Keratitis (HZK) is present, and generate output data indicative of such determined ocular disease factors and index the processed image(s) therewith to indicate the same.

AUTOMATICALLY DETECTING AND MEASURING
HERPES SIMPLEX VIRUS KERATITIS (HSVK) USING A REAL-TIME
OPHTHALMIC IMAGE PROCESSING ENGINE OPERATING ON FRONT VIEW
DIGITAL IMAGES OF THE HUMAN EYE

HSV Infection

Figure 219:
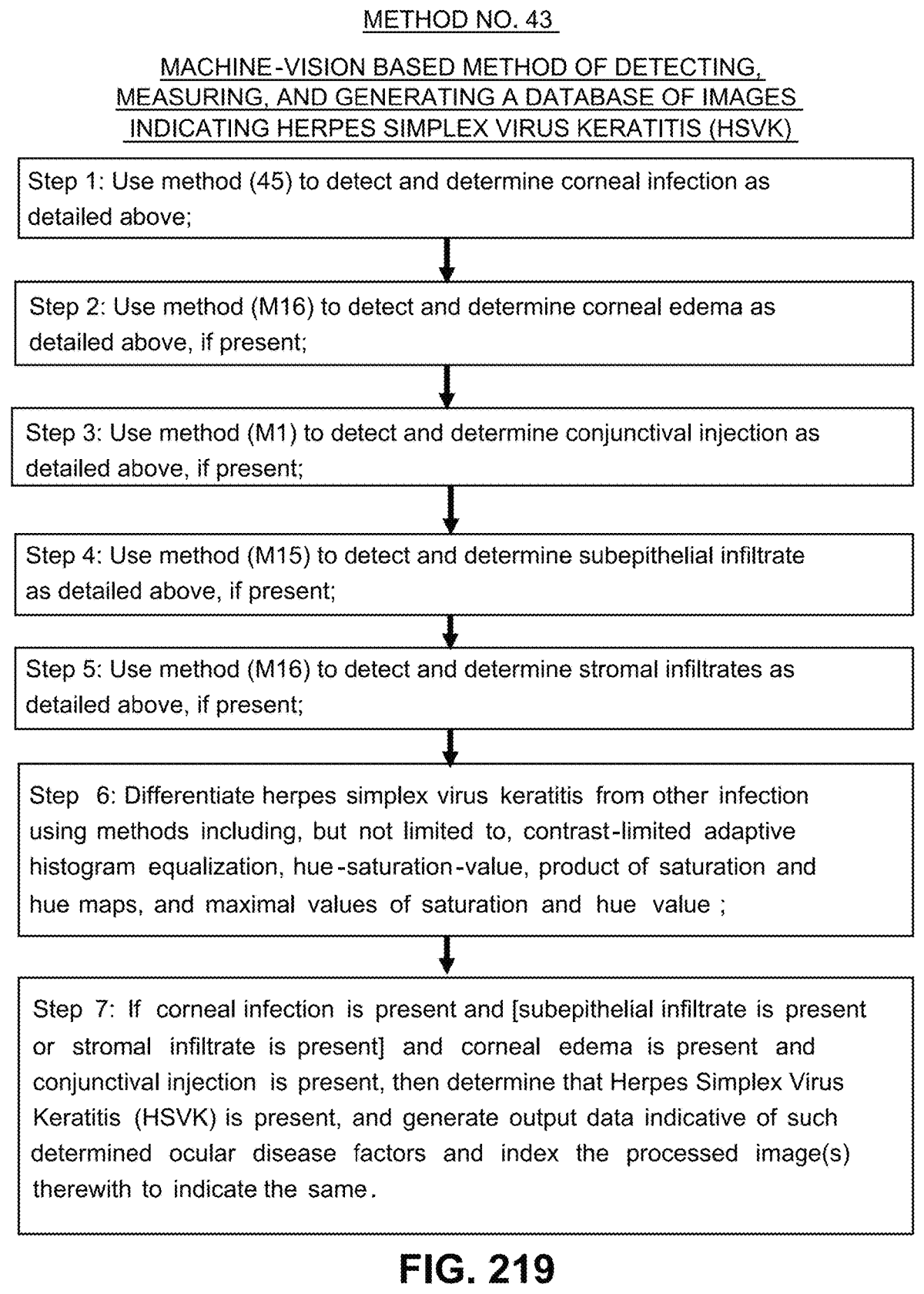

METHOD NO. 43

MACHINE-VISION BASED METHOD OF DETECTING,
MEASURING, AND GENERATING A DATABASE OF IMAGES
INDICATING HERPES SIMPLEX VIRUS KERATITIS (HSVK)

Step 1: Use method (45) to detect and determine corneal infection as detailed above;

Step 2: Use method (M16) to detect and determine corneal edema as detailed above, if present;

Step 3: Use method (M1) to detect and determine conjunctival injection as detailed above, if present;

Step 4: Use method (M15) to detect and determine subepithelial infiltrate as detailed above, if present;

Step 5: Use method (M16) to detect and determine stromal infiltrates as detailed above, if present;

Step 6: Differentiate herpes simplex virus keratitis from other infection using methods including, but not limited to, contrast-limited adaptive histogram equalization, hue-saturation-value, product of saturation and hue maps, and maximal values of saturation and hue value ;

Step 7: If corneal infection is present and [subepithelial infiltrate is present or stromal infiltrate is present] and corneal edema is present and conjunctival injection is present, then determine that Herpes Simplex Virus Keratitis (HSVK) is present, and generate output data indicative of such determined ocular disease factors and index the processed image(s) therewith to indicate the same.

SCHEMATIC MODEL SUPPORTING THE AUTOMATED DETECTION AND
MEASUREMENT OF OPHTHALMIC POST OPERATIVE COMPLICATIONS (OPOC)
OF HUMAN EYES USING A REAL-TIME OPHTHALMIC IMAGE PROCESSING
ENGINE OPERATING ON FRONT VIEW DIGITAL IMAGES OF THE HUMAN EYES

Ophthalmic Post Operative Complications (OPOC) (M44)

METHOD NO. 44

MACHINE-VISION BASED METHOD OF DETECTING,
MEASURING, AND GENERATING A DATABASE OF IMAGES
INDICATING OPHTHALMIC POST OPERATIVE COMPLICATIONS (OPOC)

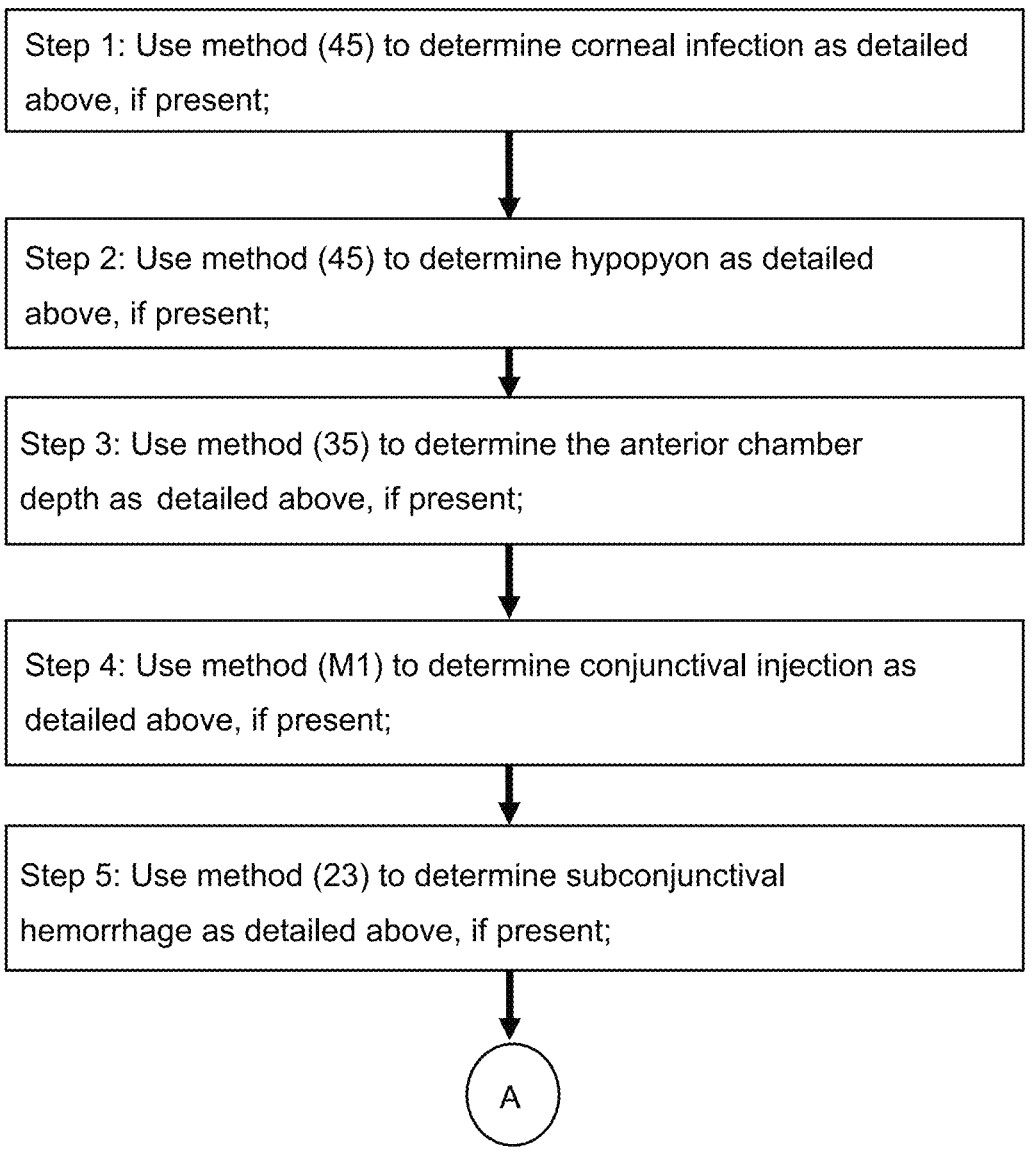

Step 1: Use method (45) to determine corneal infection as detailed above, if present;

Step 2: Use method (45) to determine hypopyon as detailed above, if present;

Step 3: Use method (35) to determine the anterior chamber depth as detailed above, if present;

Step 4: Use method (M1) to determine conjunctival injection as detailed above, if present;

Step 5: Use method (23) to determine subconjunctival hemorrhage as detailed above, if present;

METHOD NO. 44

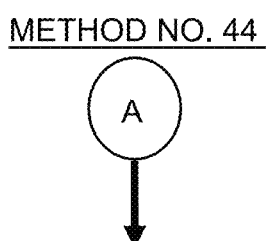

Step 6:  Use method (M10) to determine corneal abrasion as
Detailed above, if present;

Step 7:  Use method (M33) to determine proptosis as
Detailed above, if present;

Step 8:  Use method (M19) to determine purulent discharge as
Detailed above, if present;

Step 9:  Use method (M16) to determine sutures, keratic
preciptates, stromal infiltrates and corneal edema as detailed
above, if present.

Step 10:  If [corneal infection is present and corenal abrasion
is present], or hypopyon is present or the anterior chamber
(acd) depth is less than 2.5mm, or conjunctival injection is
present, or subconjunctival hermorrhage is present, or
proptosis is present, or purulent discharge is present, then
determine that Ophthalmic Post Operative Complications (OPOC)
are present, and output data is indicative of such determined
ocular disease factors and indext the process image(s) to
indicate the same.

<u>SCHEMATIC MODEL SUPPORTING THE AUTOMATED DETECTION AND
MEASUREMENT OF CORNEAL INFECTION OF HUMAN EYES USING A
REAL-TIME OPHTHALMIC IMAGE PROCESSING ENGINE OPERATING ON
FRONT VIEW DIGITAL IMAGES OF THE HUMAN EYES</u>

Corneal Infection (M45)

Process

Corneal Infection
(M45)

Hypopyon (M45)

Conjunctival Injection (M1)

METHOD NO. 45

MACHINE-VISION BASED METHOD OF DETECTING,
MEASURING, AND GENERATING A DATABASE OF IMAGES
INDICATING CORNEAL INFECTION

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm

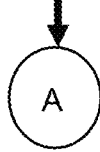

METHOD NO. 45

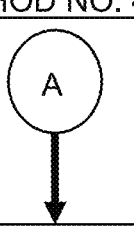

Step 5: Use region of interest matching to detect cornea across a series of digital images reproducibly using methods including, but not limited to, scale invariant feature transform and random sample consensus;

Step 6: Identify corneal infection and hypopyon using edge detection, region growing, k-means clustering and thresholding methods;

Step 7: Measure corneal infection height and width, and hypopyon height and respective surface areas using pixel-by-pixel size;

Step 8: If corneal infection height is greated than 0.1mm, or corneal infection width is greater than 0.1mm, then generate output data indicative of such determined ocular disease factors and index the processed image(s) to indicate the same;

Step 9: If hypopyon is greater than 0.1mm, then generate output data indicative of such determined ocular disease factors and index the processed image(s) to indicate the same

<u>AUTOMATICALLY DETECTING AND MEASURING
MEASURING CORNEAL FOREIGN BODY USING A REAL-TIME
OPHTHALMIC IMAGE PROCESSING ENGINE OPERATING ON FRONT VIEW
DIGITAL IMAGES OF THE HUMAN EYE</u>

Corneal
Foreign Body

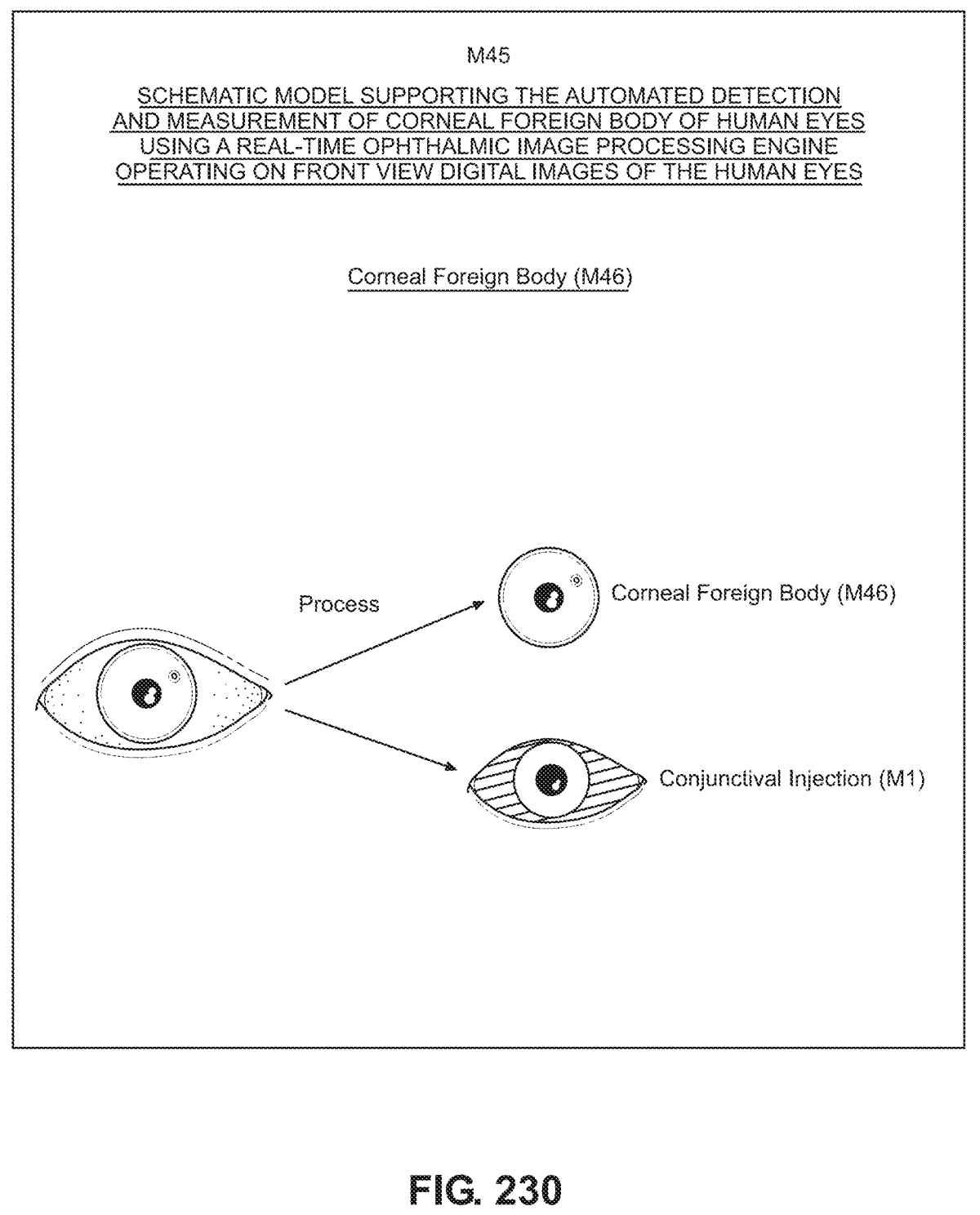

M45

SCHEMATIC MODEL SUPPORTING THE AUTOMATED DETECTION
AND MEASUREMENT OF CORNEAL FOREIGN BODY OF HUMAN EYES
USING A REAL-TIME OPHTHALMIC IMAGE PROCESSING ENGINE
OPERATING ON FRONT VIEW DIGITAL IMAGES OF THE HUMAN EYES

Corneal Foreign Body (M46)

Process

Corneal Foreign Body (M46)

Conjunctival Injection (M1)

FIG. 230

METHOD NO. 46

MACHINE-VISION BASED METHOD OF DETECTING,
MEASURING, AND GENERATING A DATABASE OF IMAGES
INDICATING CORNEAL FOREIGN BODY

Step 1: Capture a series of color digital images each color digital
image having a set of pixels;

Step 2: Process the pixels in each digital image and classify the
following structures in the human eye, including eyelids, iris, pupil,
and sclera;

Step 3: Use cornea and non-cornea digital images to train the
system to detect cornea;

Step 4: Use the above structures and trained system for automatic
region of interest segmentation of using non-parametric methods,
including but not limited to, random decision forests such as
Breiman's random forest algorithm, gray scale probability maps,
binary thresholds, morphological operators and Bresenham's line
algorithm

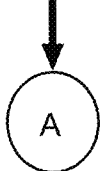

METHOD NO. 46

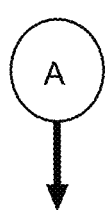

Step 5: Use region of interest matching to detect cornea across a series of digital images reproducibly using methods including, but not limited to, scale invariant feature transform and random sample consensus;

Step 6: Detect and identify a corneal foreign body (CFB) using edge detection, region growing, k-means clustering and thresholding methods;

Step 7: Differentiate corneal foreign body (CFB) from corneal infection and abrasion using contrast-limited adaptive histogram equalization, hue-saturation-value, product of saturation and hue maps, and maximal values of saturation and hue values; and Ste 8: If a detected corneal foreign body is greater than 0.1mm, then generate output data indicative of such determined ocular disease factors and index the processed image(s) to indicate the same

SCHEMATIC MODEL SUPPORTING THE AUTOMATED DETECTION AND MEASUREMENT OF ACUTE ANGLE CLOSURE GLAUCOMA (AACG) OF HUMAN EYES USING A REAL-TIME OPHTHALMIC IMAGE PROCESSING ENGINE OPERATING ON FRONT VIEW DIGITAL IMAGES OF THE HUMAN EYES

Acute Angle Closure Glaucoma (M47)

Process

Conjunctival Injection (M1)

Anisocoria (M34)

Corenal Edema (M16)

Anterior Chamber Depth (M35)

METHOD NO. 47

MACHINE-VISION BASED METHOD OF DETECTING,
MEASURING, AND GENERATING A DATABASE OF IMAGES
INDICATING ACUTE ANGLE CLOSURE GLAUCOMA

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of using non-parametric methods, including but not limited to, random decision forests such as Breiman's random forest algrithm, gray scale probability maps, binary thresholds, morphological operators and Bresenham's line algorithm

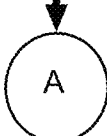

METHOD NO. 47

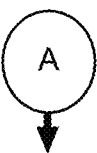

Step 5: Use region of interest matching to detect cornea across a series of digital images reproducibly using methods including, but not limited to, scale invariant feature transform and random sample consensus;

Step 6: Use method (M34) to determine anisocoria as detailed above;

Step 7: Use method (M16) to determine corneal edema as detailed above;

Step 8: Use method (M1) to determine conjunctival injection as detailed previously;

Step 9: Use method (M35) to determine the anterior chamber depth (ACD) as detailed previously;

Step 10: If anterior chamber depth (ACD) is less than 2.5mm and anisociria is present, and [corneal edema is present or conjuntival injection is present], then determine that Acute Angle Closure Glaucoma (AACG) is present, and generate output data indicative of such determined ocular disease factors and index the processed image(s) to indicate the same.

FIG. 235B

METHODS OF CAPTURING OPHTHALMIC IMAGES OF HUMAN EYES
USING A SMARTPHONE CAMERA SYSTEM OPERATING
IN A BIRD'S EYE SELFIE MODE + AR
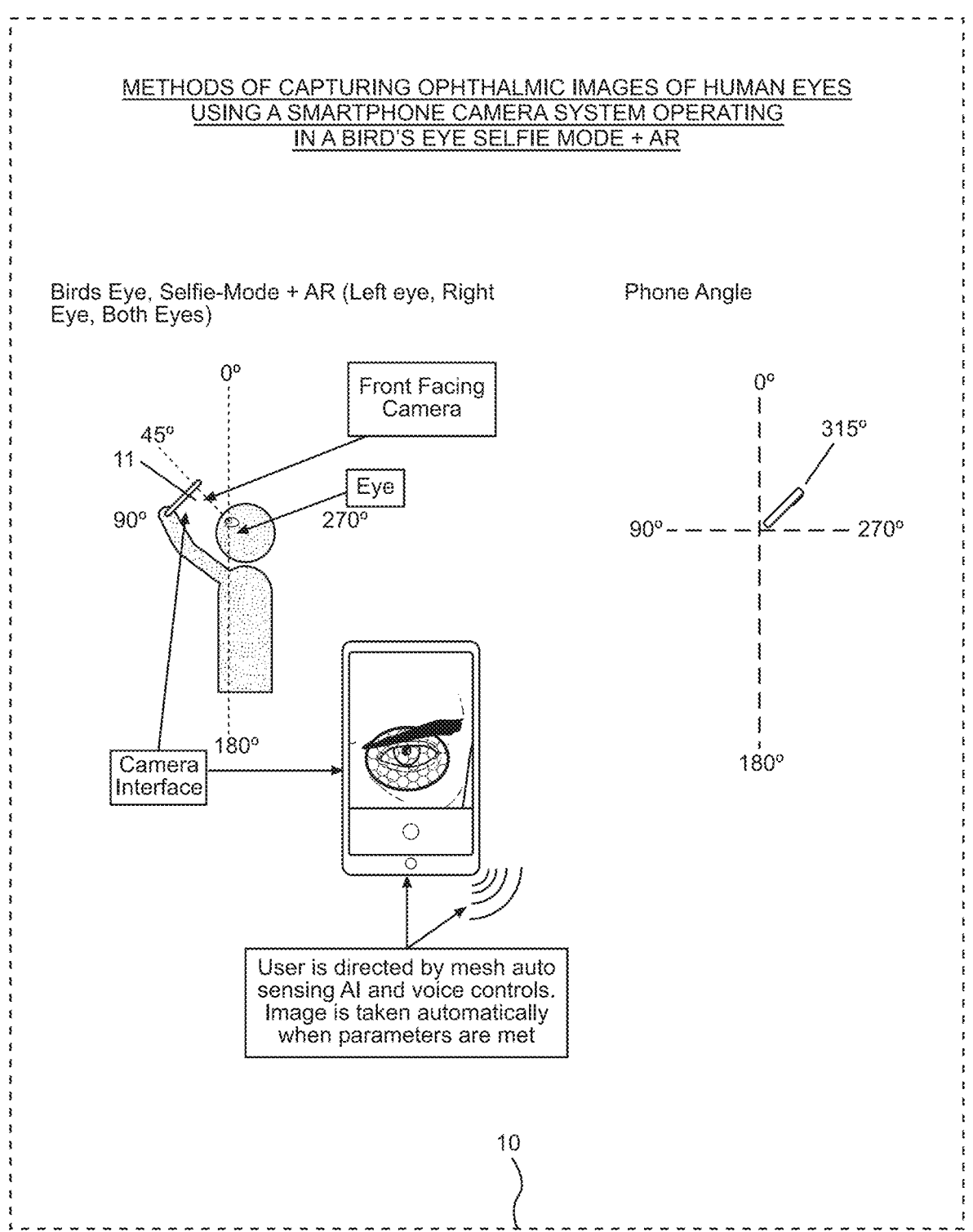
FIG. 236A1

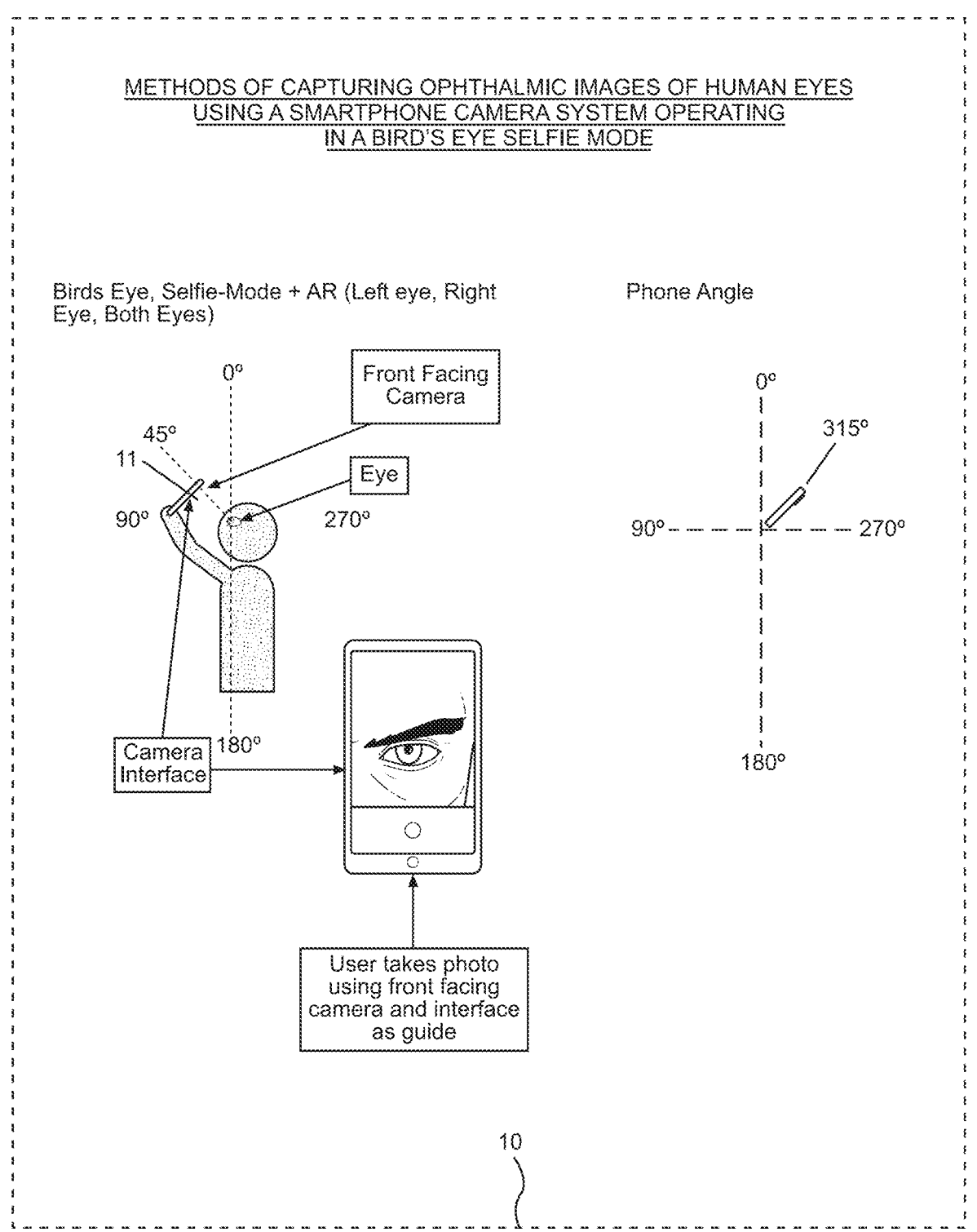
METHODS OF CAPTURING OPHTHALMIC IMAGES OF HUMAN EYES
USING A SMARTPHONE CAMERA SYSTEM OPERATING
IN A BIRD'S EYE SELFIE MODE
Birds Eye, Selfie-Mode + AR (Left eye, Right Eye, Both Eyes)
Phone Angle
Front Facing Camera
Eye
Camera Interface
User takes photo using front facing camera and interface as guide
10
FIG. 236A2

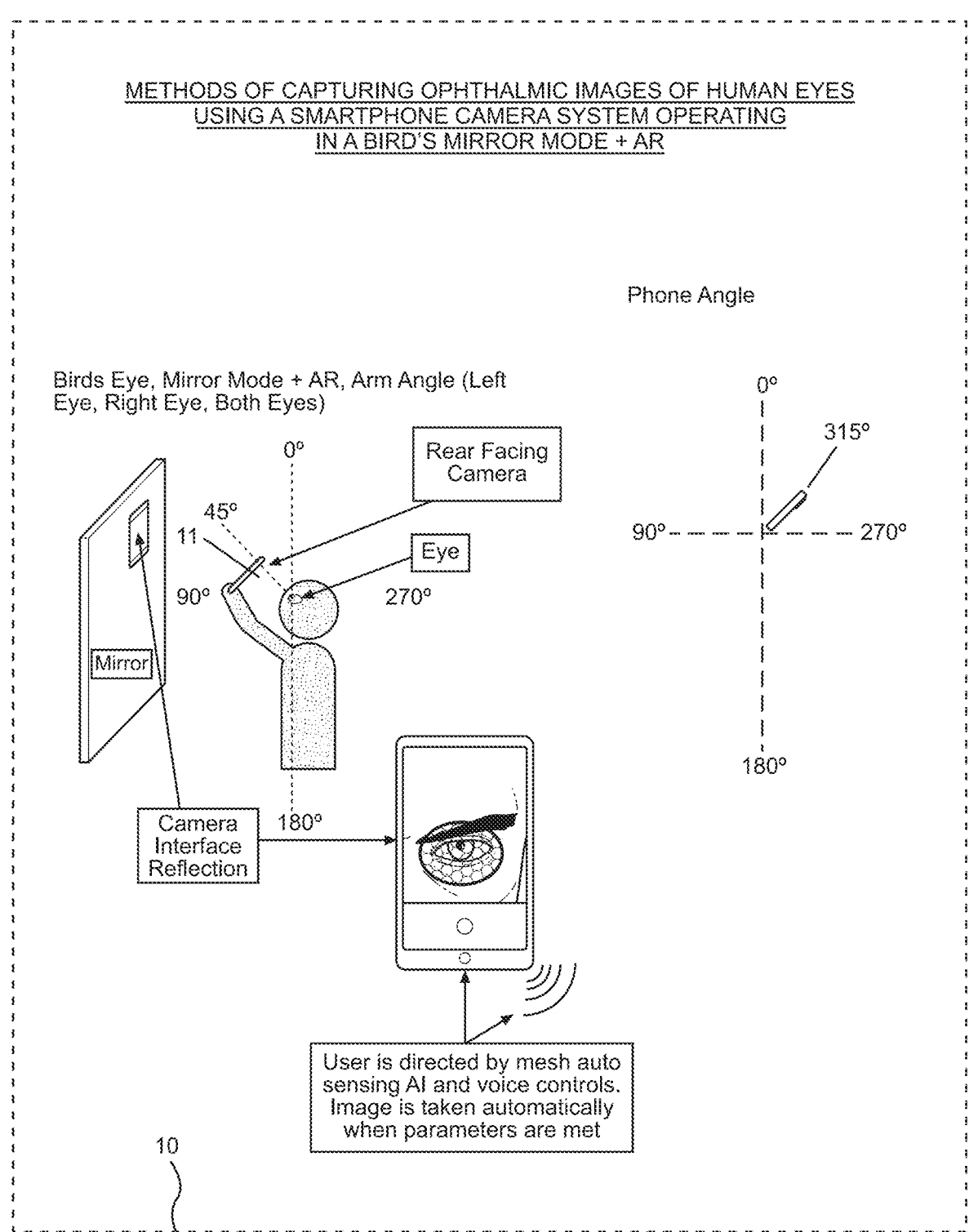
FIG. 236A3

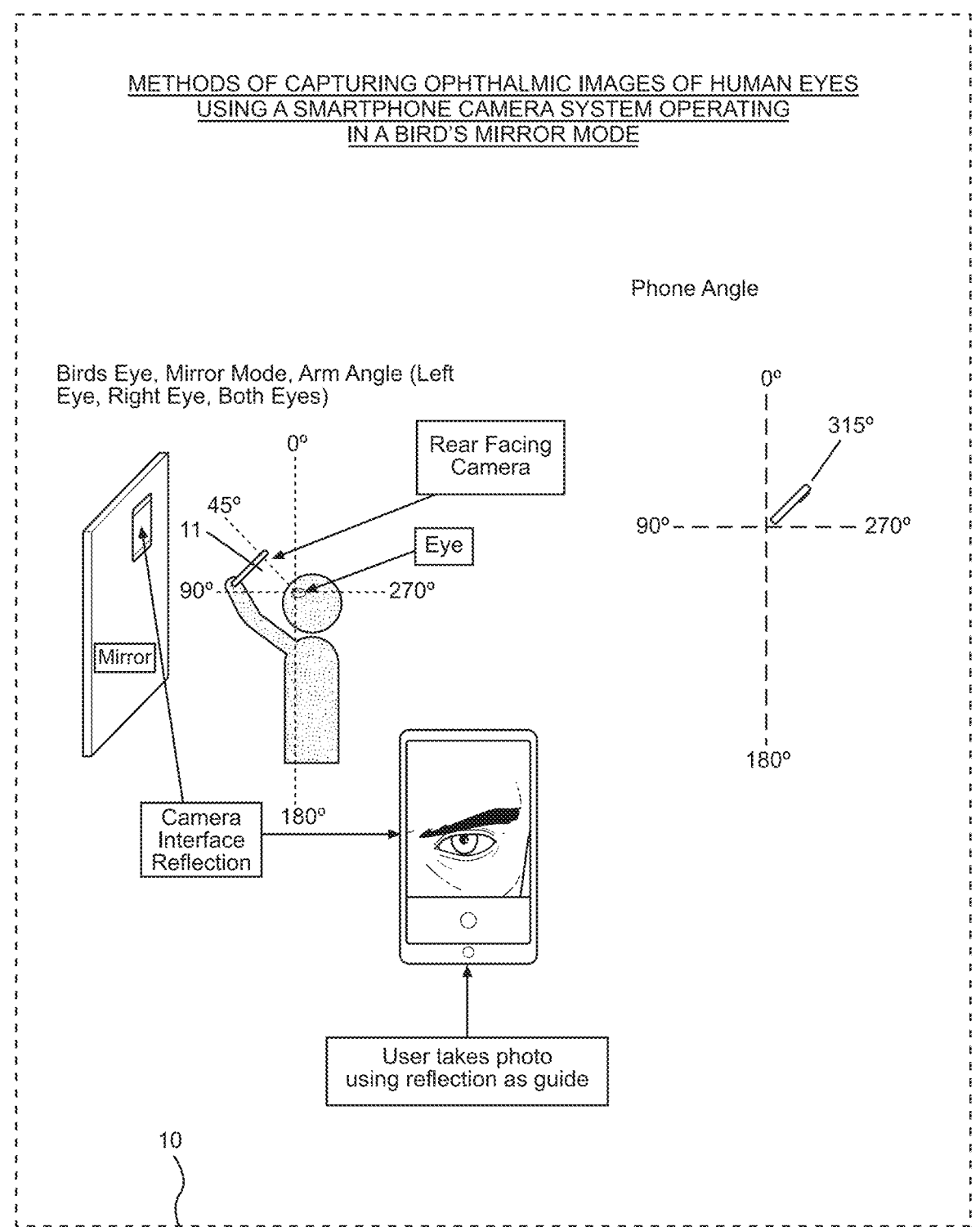
FIG. 236A4

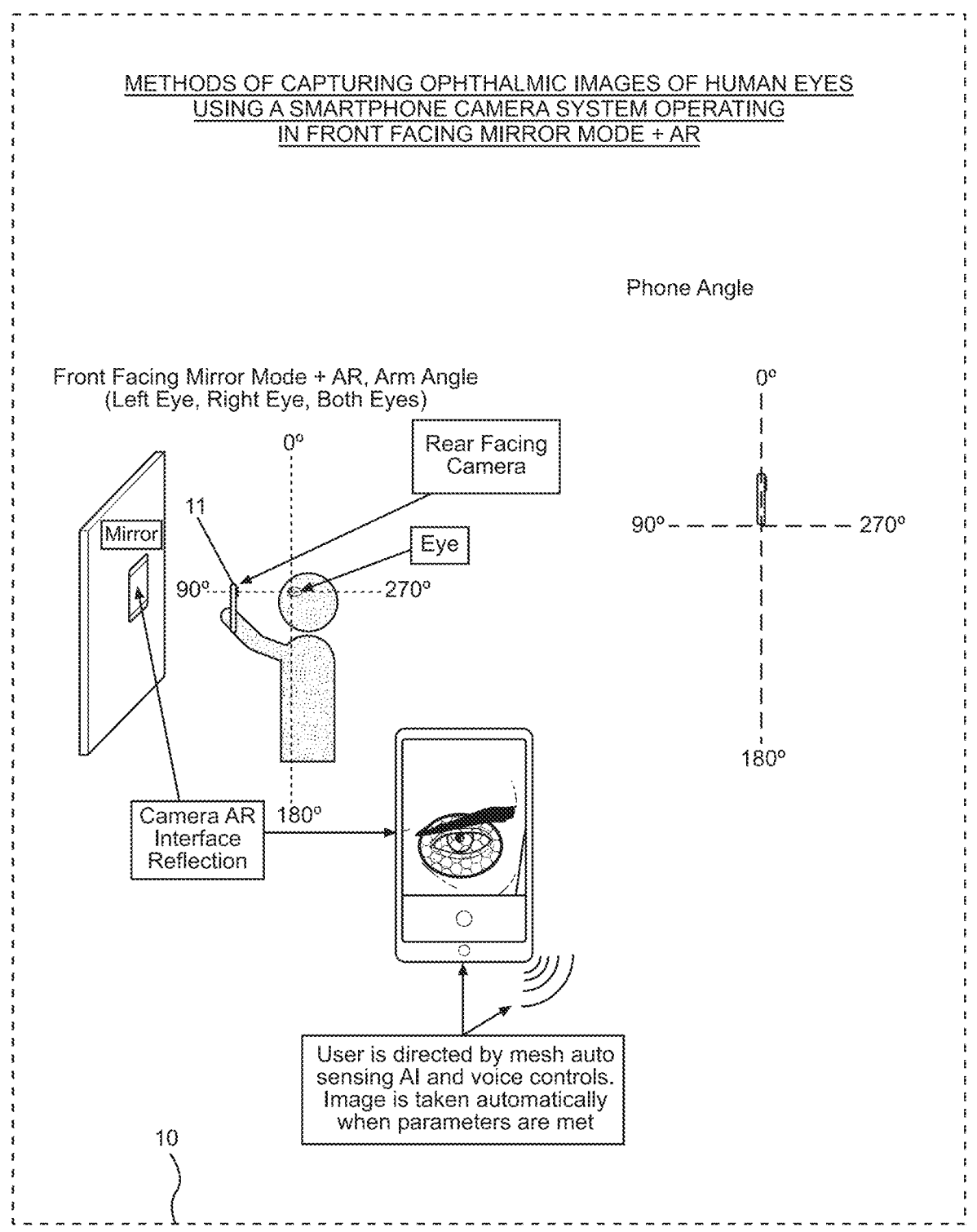
FIG. 236B1

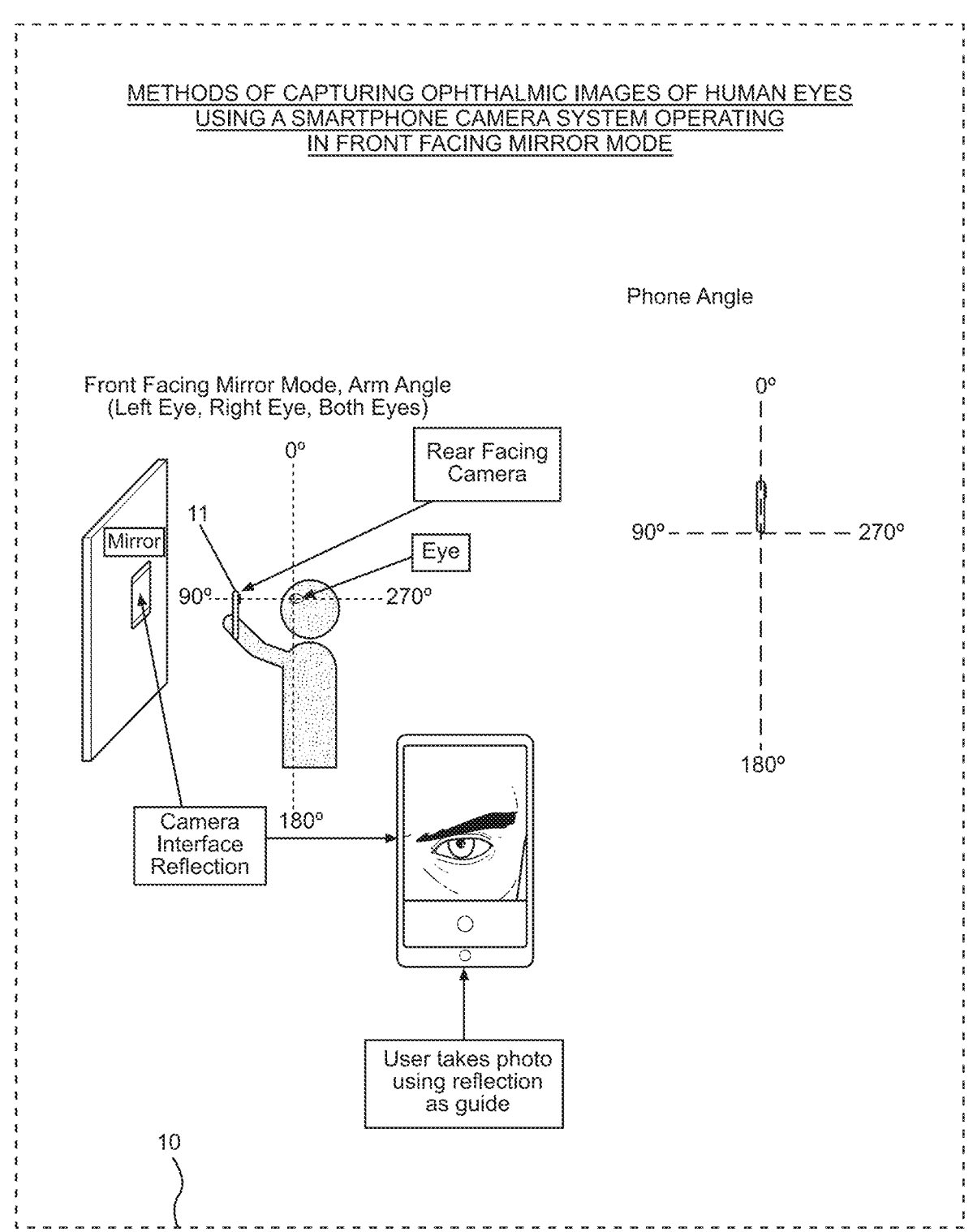
METHODS OF CAPTURING OPHTHALMIC IMAGES OF HUMAN EYES
USING A SMARTPHONE CAMERA SYSTEM OPERATING
IN FRONT FACING MIRROR MODE
Phone Angle
Front Facing Mirror Mode, Arm Angle
(Left Eye, Right Eye, Both Eyes)
Rear Facing Camera
Eye
Mirror
Camera Interface Reflection
User takes photo using reflection as guide
FIG. 236B2

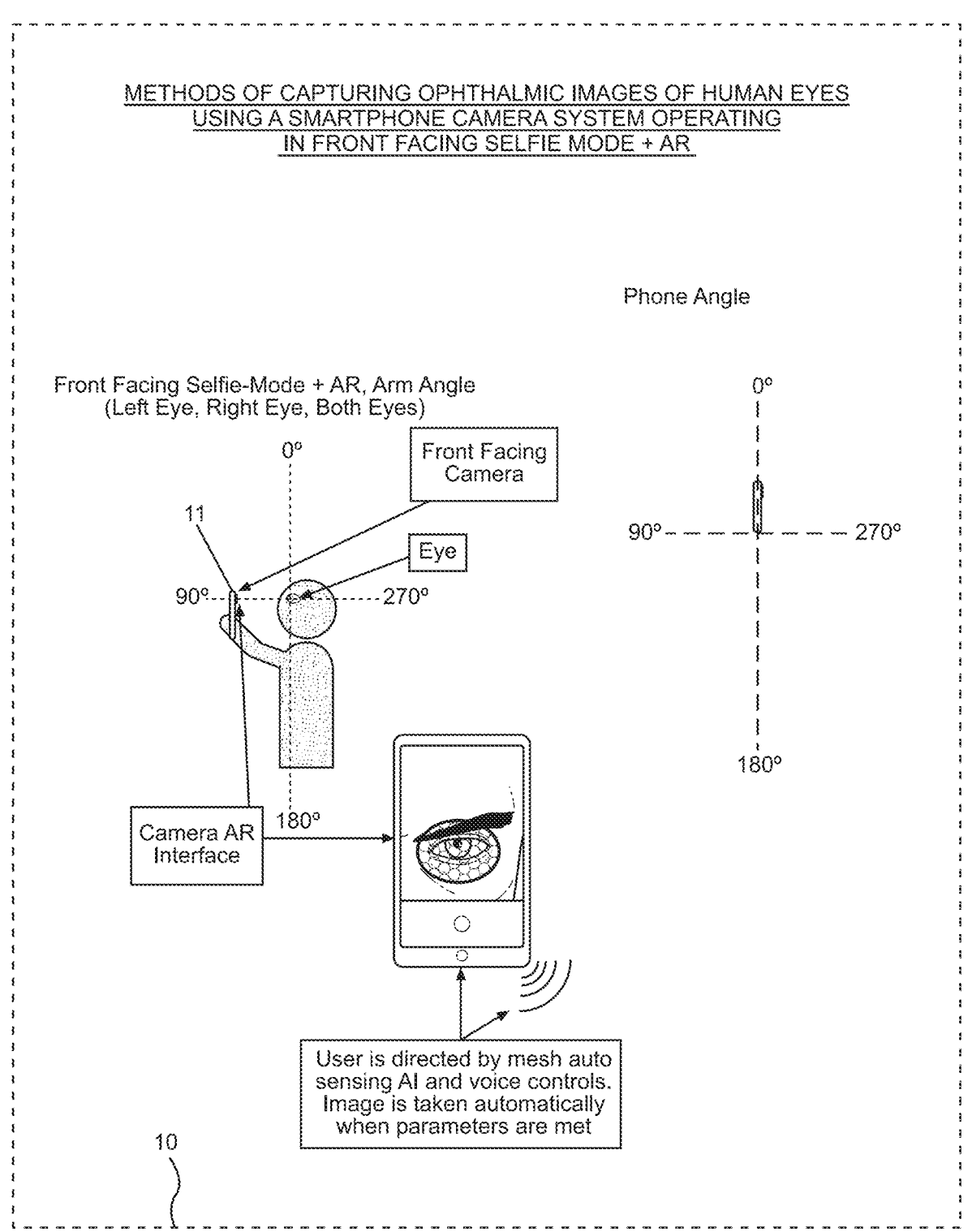
FIG. 236B3

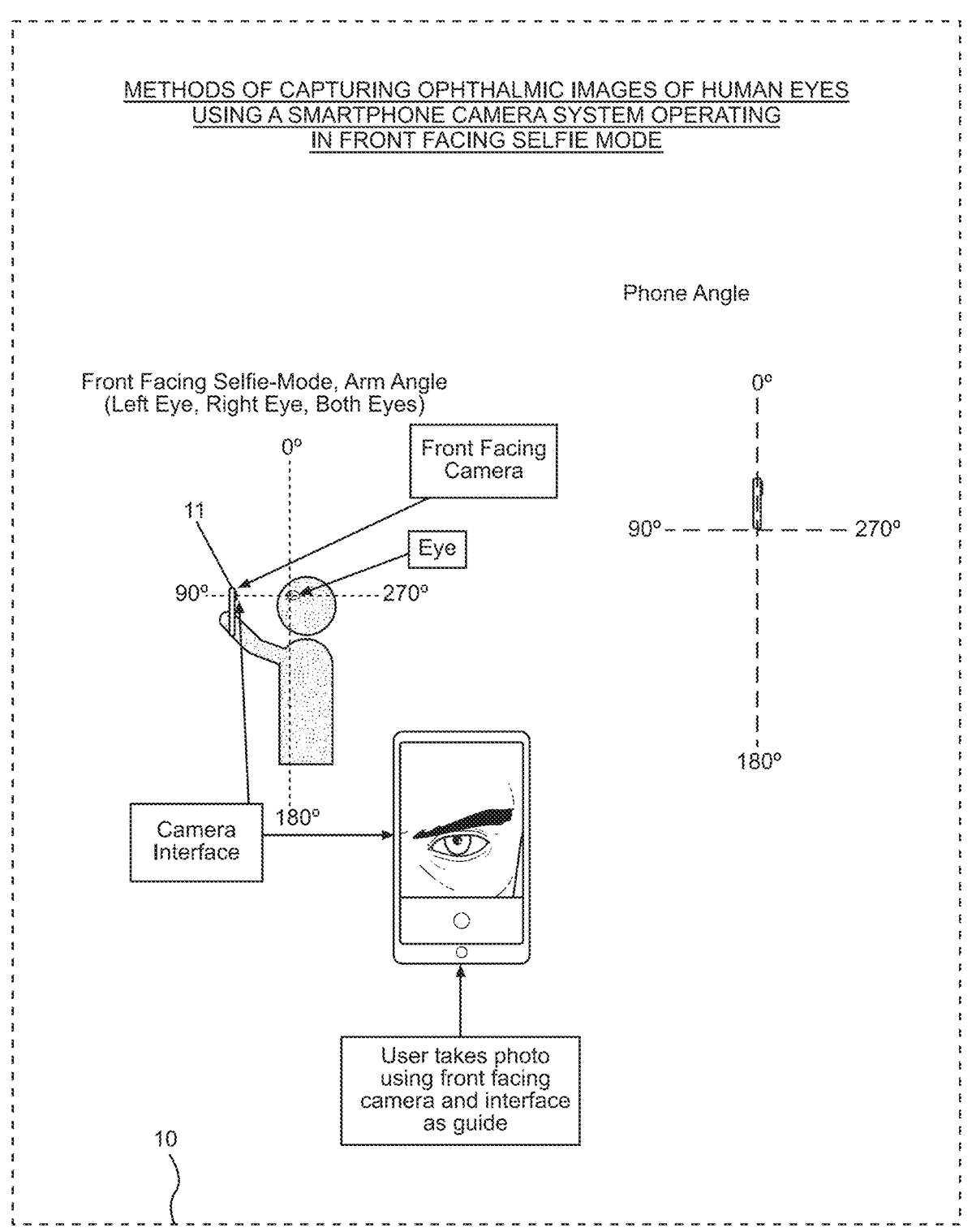
FIG. 236B4

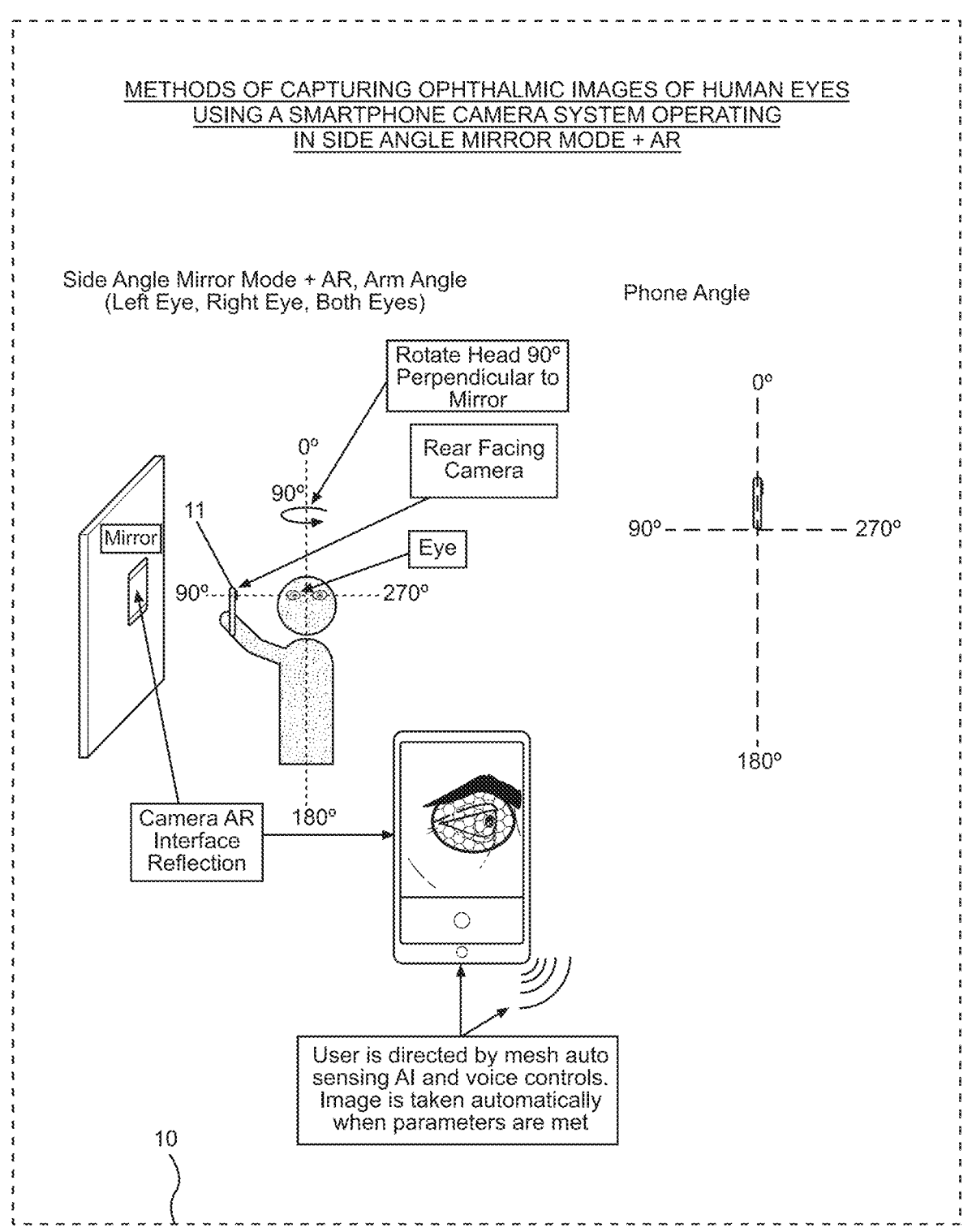
FIG. 236C1

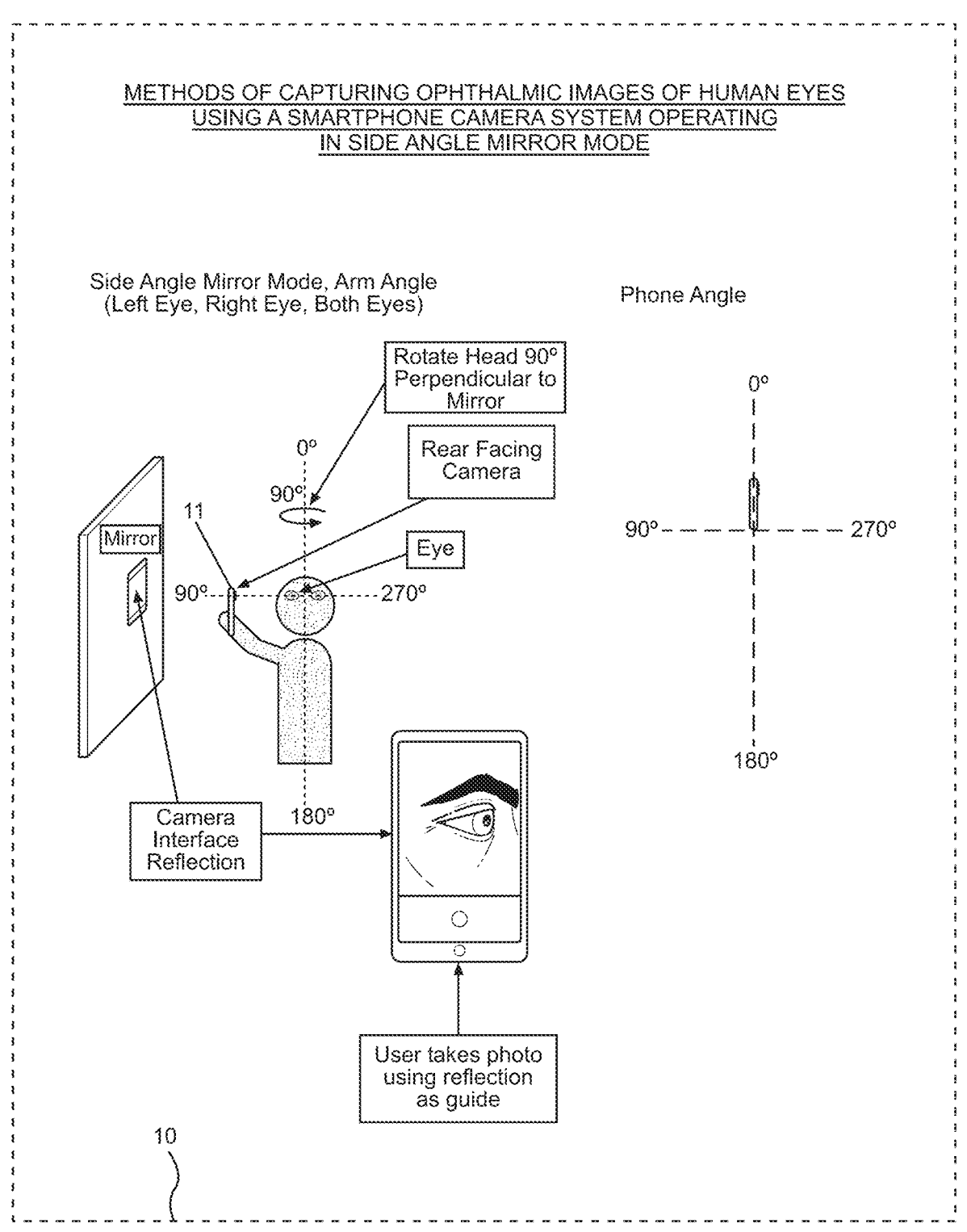
FIG. 236C2

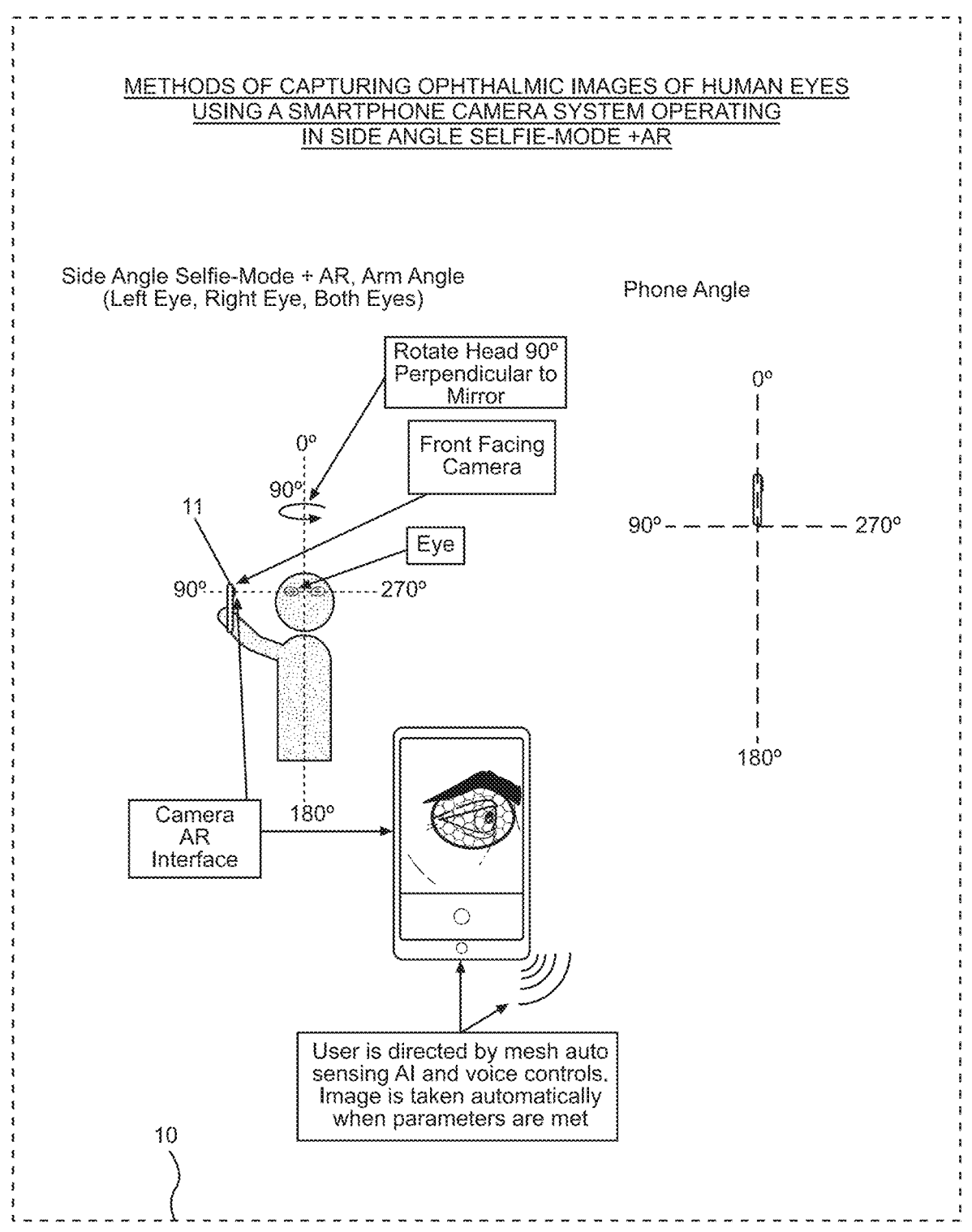
FIG. 236C3

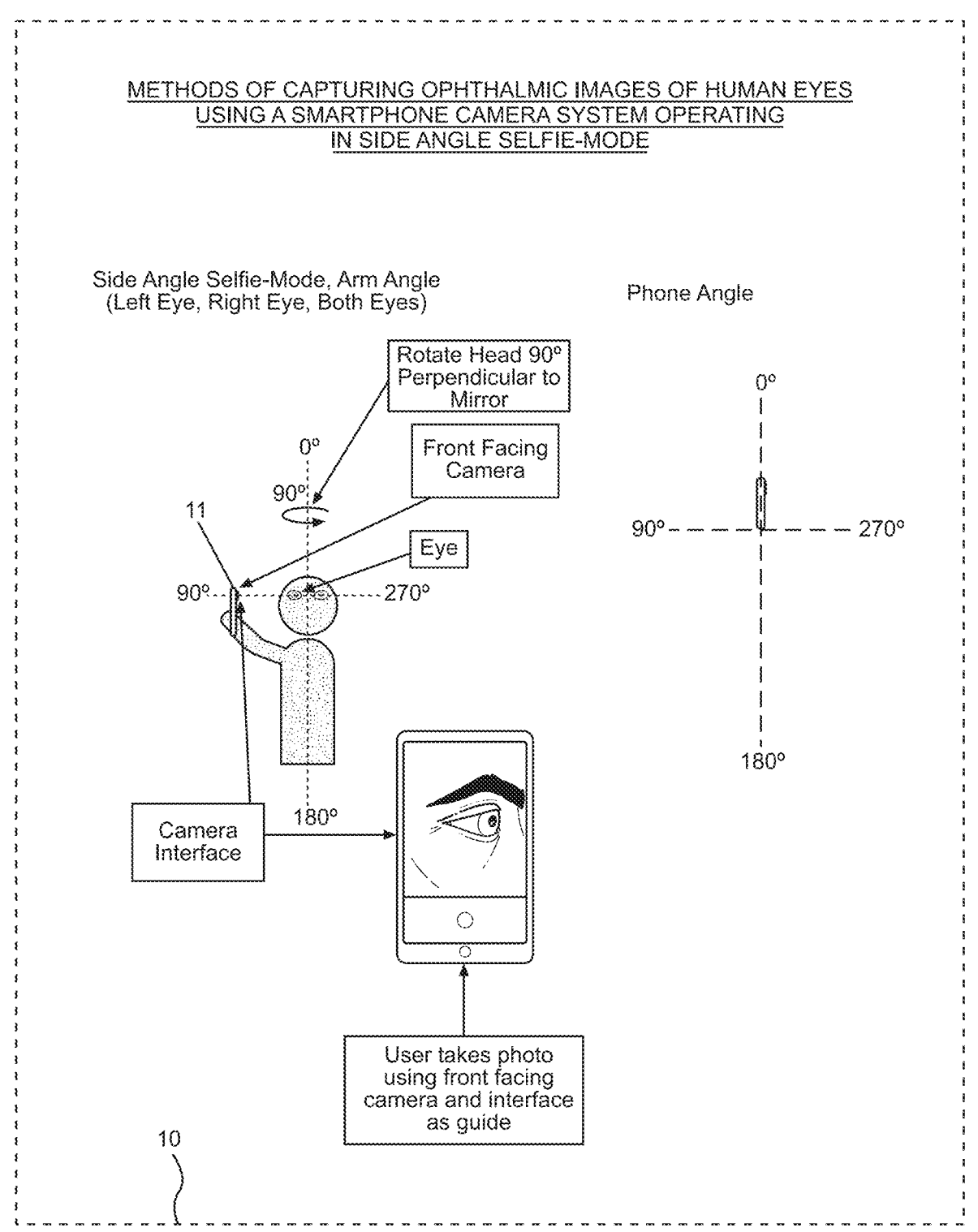
FIG. 236C4

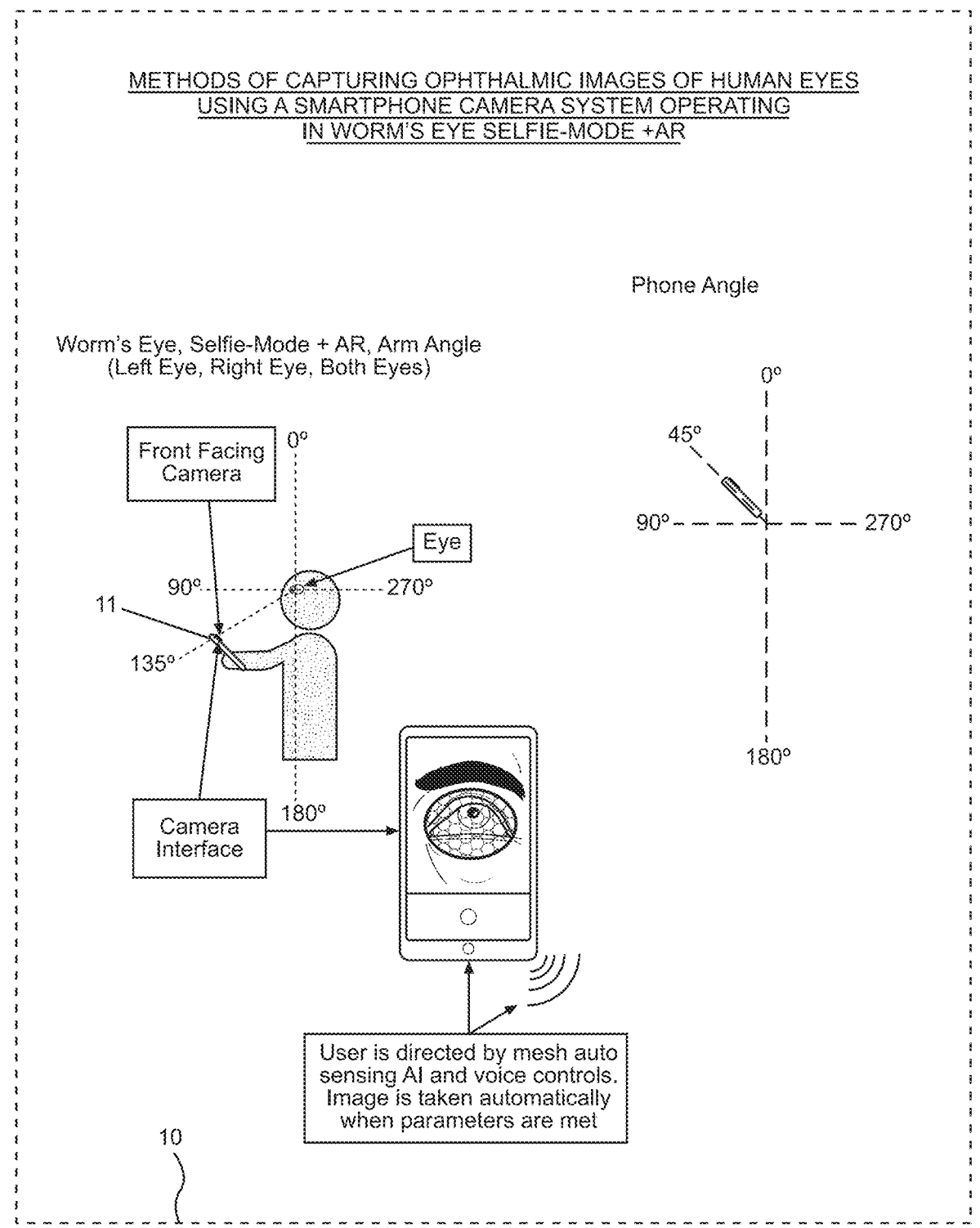
FIG. 236D1

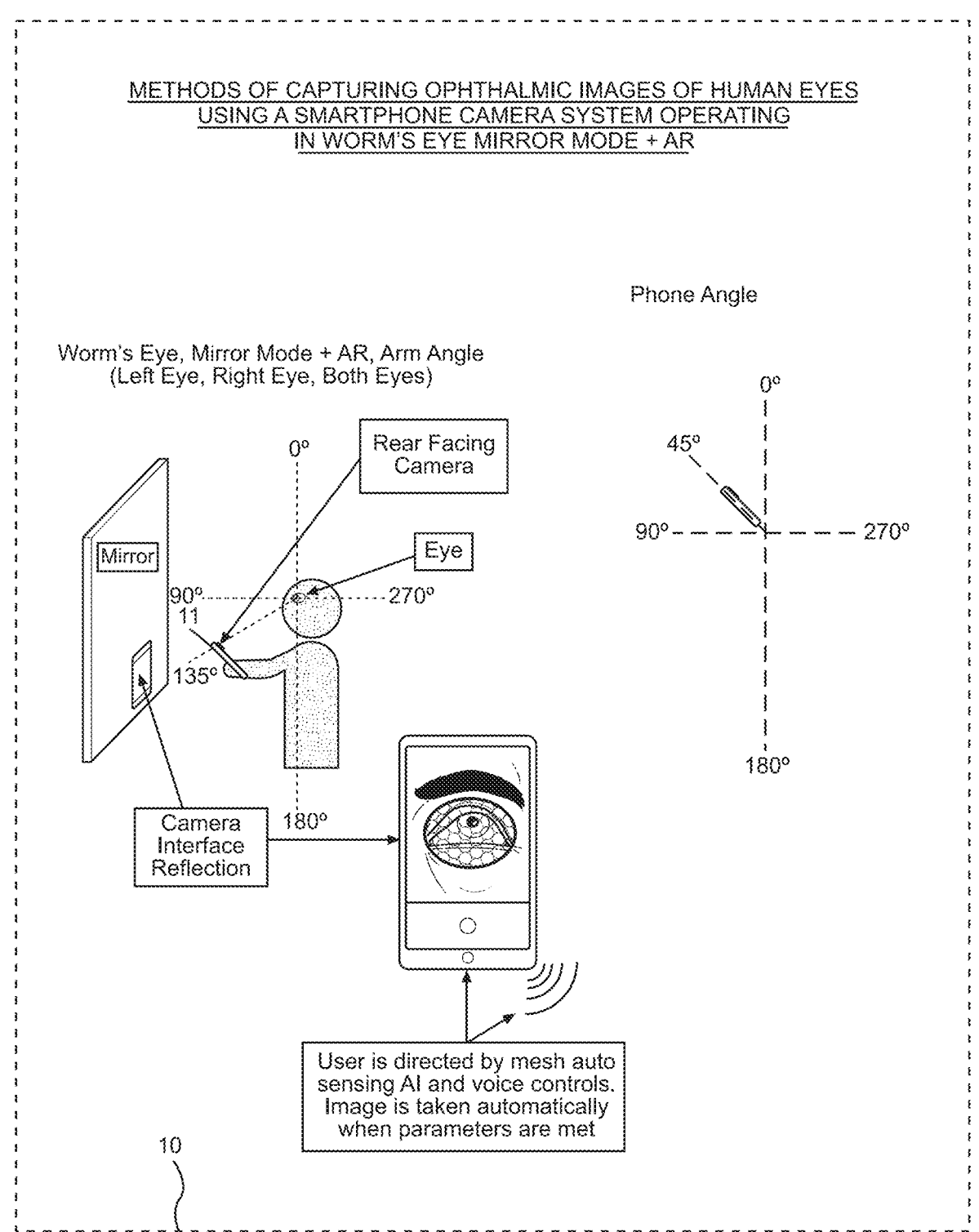
FIG. 236D2

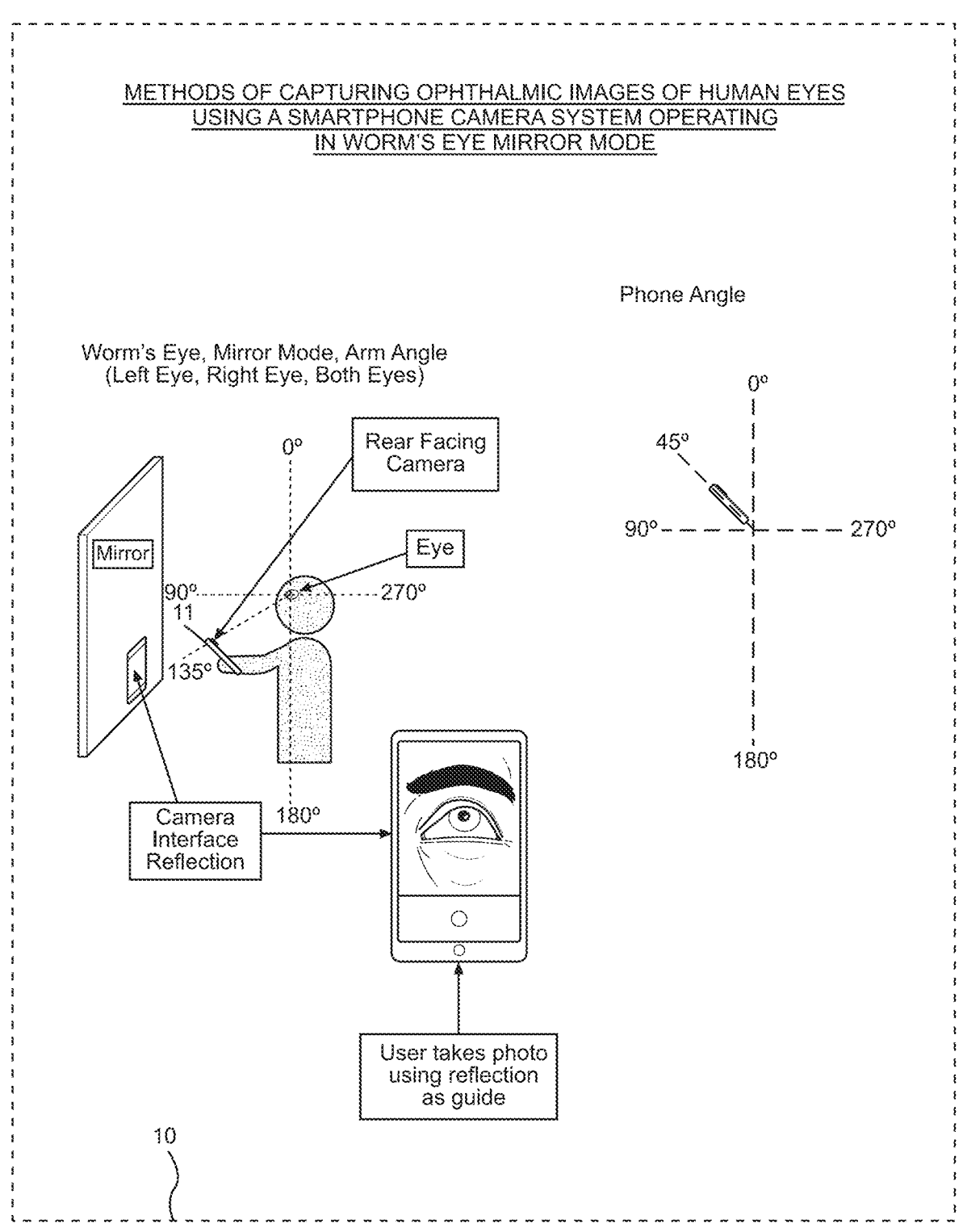
FIG. 236D3

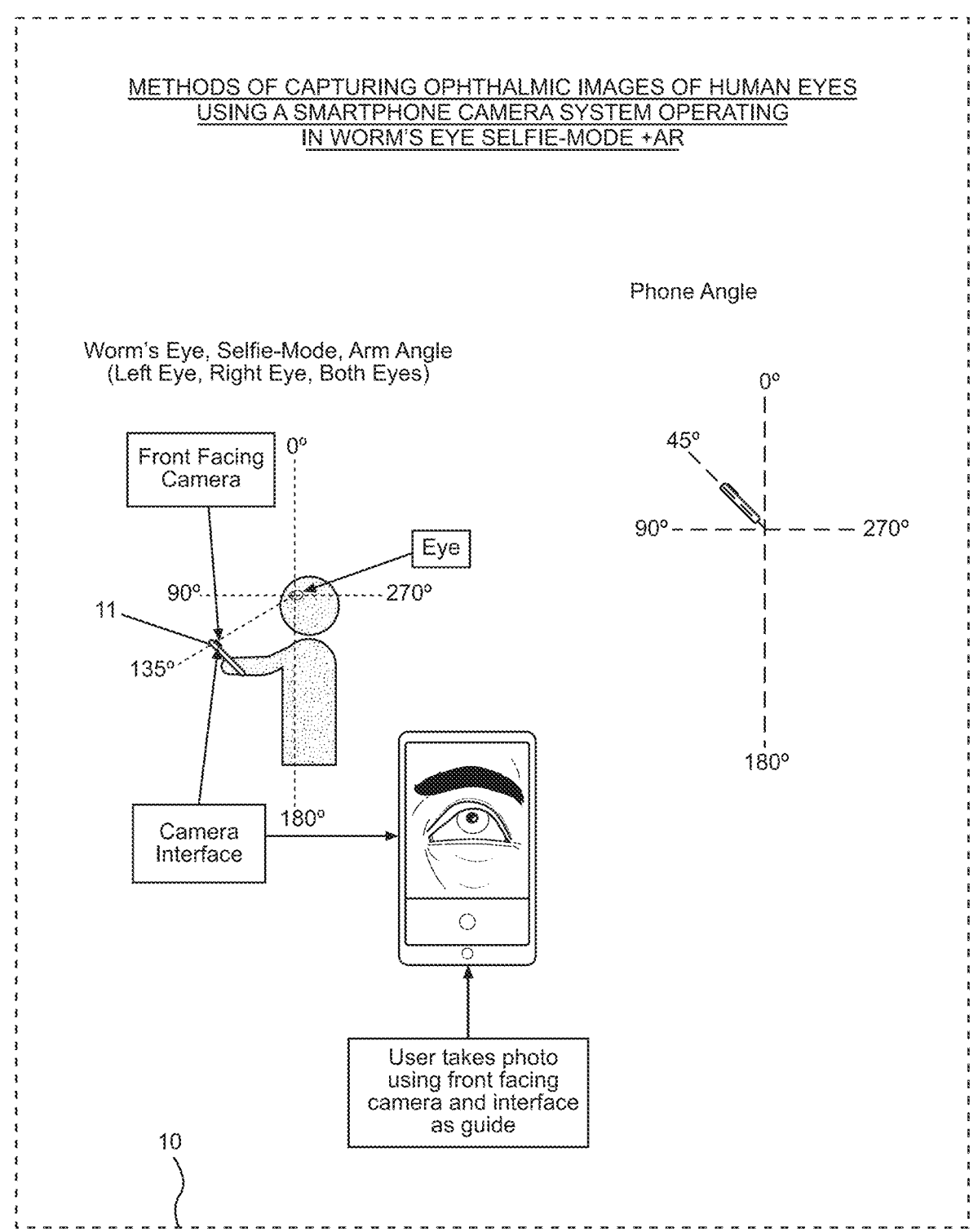
FIG. 236D4

<u>METHOD OF OPERATING AN AUTOMATED OPHTHALMIC IMAGE CAPTURING AND PROCESSING SYSTEM TO ENABLE AUTOMATED MACHINE-ASSISTED DETECTION OF DRY EYE CONDITIONS IN THE HUMAN EYE, PRESCRIPTION OF TREATMENT, AND ASSESSMENT OF PRESCRIBED TREATMENT, BY PROCESSING A SERIES OF DIGITAL IMAGES OF THE HUMAN EYE CAPTURED BY A MOBILE SMARTPHONE CAMERA SYSTEM</u>

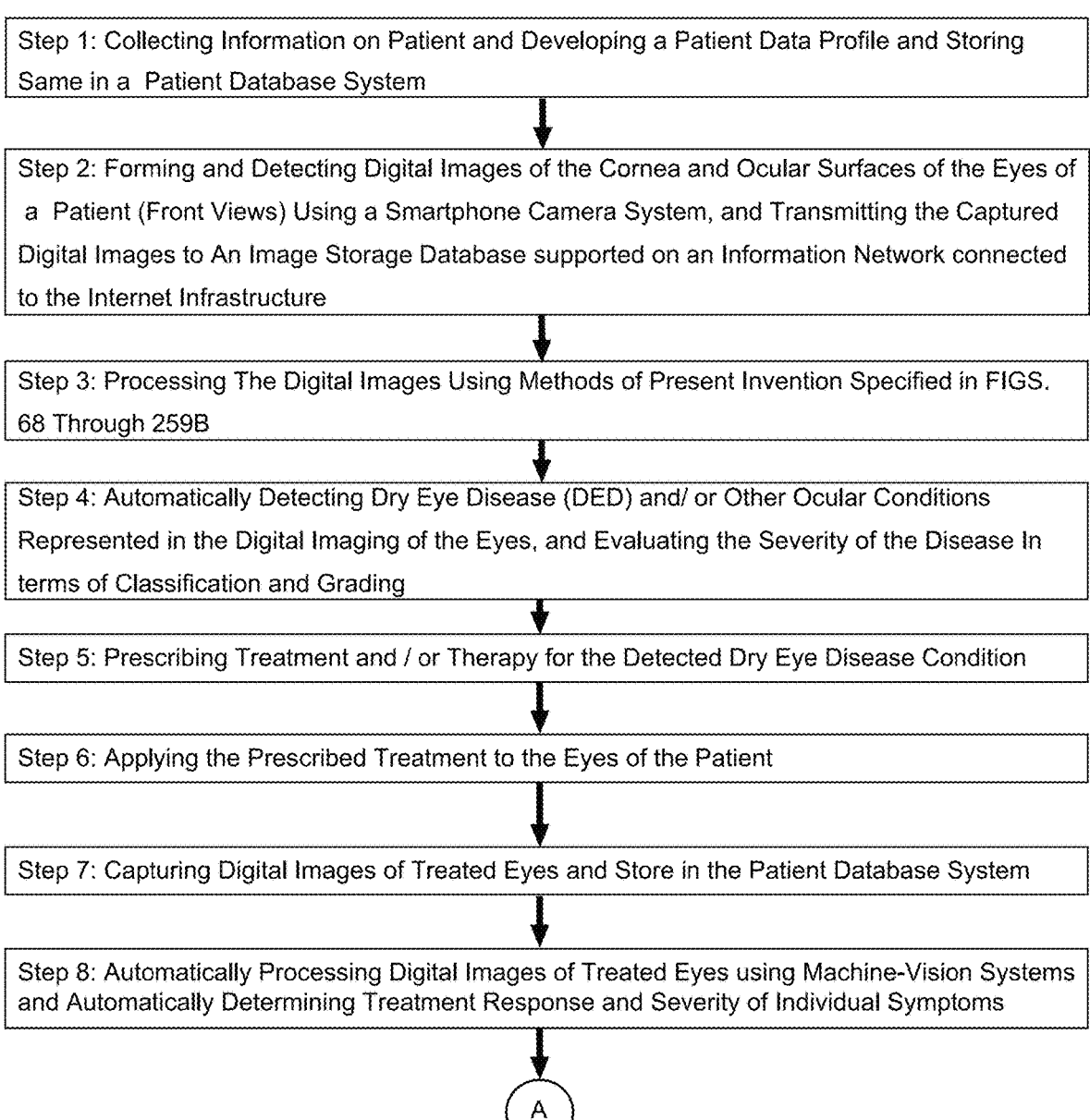

Step 1: Collecting Information on Patient and Developing a Patient Data Profile and Storing Same in a Patient Database System Step 2: Forming and Detecting Digital Images of the Cornea and Ocular Surfaces of the Eyes of a Patient (Front Views) Using a Smartphone Camera System, and Transmitting the Captured Digital Images to An Image Storage Database supported on an Information Network connected to the Internet Infrastructure Step 3: Processing The Digital Images Using Methods of Present Invention Specified in FIGS. 68 Through 259B Step 4: Automatically Detecting Dry Eye Disease (DED) and/ or Other Ocular Conditions Represented in the Digital Imaging of the Eyes, and Evaluating the Severity of the Disease In terms of Classification and Grading Step 5: Prescribing Treatment and / or Therapy for the Detected Dry Eye Disease Condition Step 6: Applying the Prescribed Treatment to the Eyes of the Patient Step 7: Capturing Digital Images of Treated Eyes and Store in the Patient Database System Step 8: Automatically Processing Digital Images of Treated Eyes using Machine-Vision Systems and Automatically Determining Treatment Response and Severity of Individual Symptoms

METHOD OF OPERATING AN AUTOMATED OPHTHALMIC IMAGE CAPTURING AND
PROCESSING SYSTEM AND TRAINING THE SAME USING DIGITAL IMAGES OF THE
HUMAN EYE CAPTURED BY A MOBILE SMARTPHONE CAMERA SYSTEM, AND
MANUALLY INDEXED BY AN OPTHALMOLOGIST

Step 1: Collecting Information on Patient and Developing a Patient Data Profile and
Storing Same in a Patient Database System

Step 2: Forming and Detecting Digital Images of the Cornea and Ocular Surfaces of the
Eyes of a Patient (Front Views) Using a Smartphone Camera System, and Transmitting
the Captured Digital Images to An Image Storage Database supported on an
Information Network connected to the Internet Infrastructure

Step 3: Processing The Digital Images Using Methods of Present Invention (Mi)
Specified in FIGS. 46 Through 235B

Step 4: Using A Machine-Vision System To Automatically Detect Dry Eye Disease (DED)
and/or Other Ocular Conditions Represented in the Digital Imaging of the Eyes and
Evaluate the Severity of the Disease In terms of Classification and Grading

Step 5: Sending Digital Images to an Ophthalmologist to Assess and Diagnosis Dry Eye
Disease (DED) and/or Other Ocular Conditions Represented in the Digital Images, and
Indexing the Digital Images to Reflected the Ocular Conditions Confirmed by the
Ophthalmologist

Step 6: Prescribing Treatment and/or Therapy for the Detected Dry Eye Disease Condition

Step 7: Applying the Prescribed Treatment to the Eyes of the Patient

Step 8: Using Condition-Indexed Digital Images Produced in Step 5 to Train The Machine-
Vision System Step 9: Capturing Digital Images of Treated Eyes and Store in the Patient Database System Step 10: Processing Digital Images of Treated Eyes and Automatically Determining
Treatment Response and Severity of Individual Symptoms

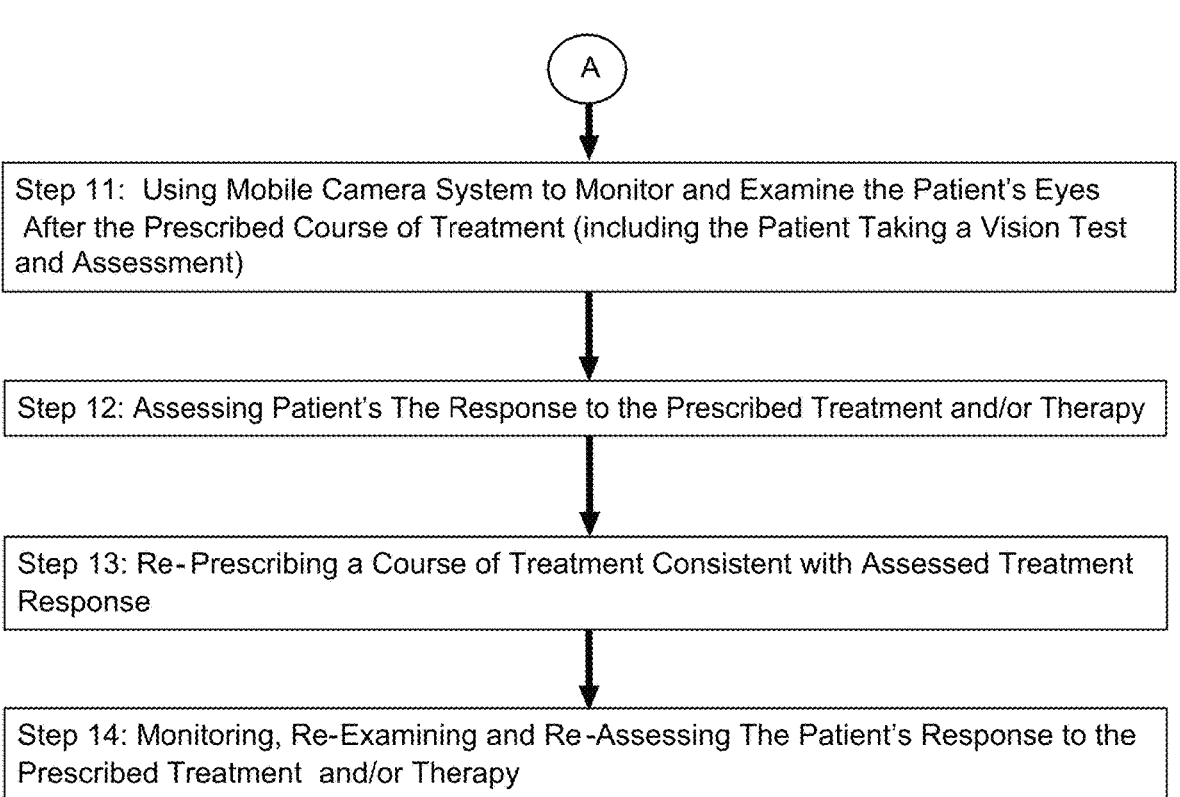

A

Step 11: Using Mobile Camera System to Monitor and Examine the Patient's Eyes After the Prescribed Course of Treatment (including the Patient Taking a Vision Test and Assessment)

Step 12: Assessing Patient's The Response to the Prescribed Treatment and/or Therapy Step 13: Re-Prescribing a Course of Treatment Consistent with Assessed Treatment Response Step 14: Monitoring, Re-Examining and Re-Assessing The Patient's Response to the Prescribed Treatment and/or Therapy

FIG. 239B

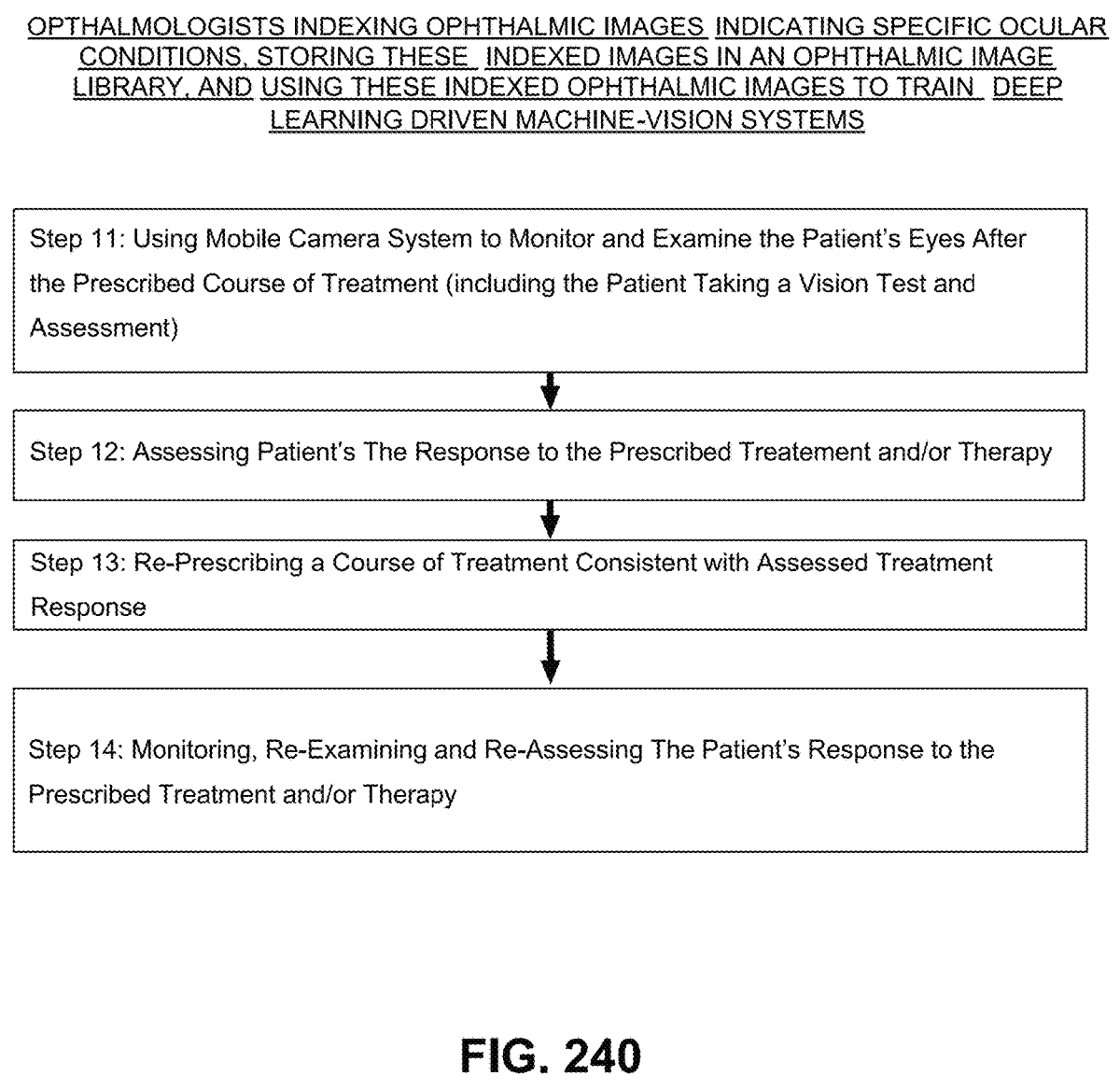

OPTHALMOLOGISTS INDEXING OPHTHALMIC IMAGES INDICATING SPECIFIC OCULAR CONDITIONS, STORING THESE INDEXED IMAGES IN AN OPHTHALMIC IMAGE LIBRARY, AND USING THESE INDEXED OPHTHALMIC IMAGES TO TRAIN DEEP LEARNING DRIVEN MACHINE-VISION SYSTEMS

Step 11: Using Mobile Camera System to Monitor and Examine the Patient's Eyes After the Prescribed Course of Treatment (including the Patient Taking a Vision Test and Assessment)

↓

Step 12: Assessing Patient's The Response to the Prescribed Treatement and/or Therapy

↓

Step 13: Re-Prescribing a Course of Treatment Consistent with Assessed Treatment Response

↓

Step 14: Monitoring, Re-Examining and Re-Assessing The Patient's Response to the Prescribed Treatment and/or Therapy

FIG. 240

MOBILE VISION TESTING OPERATIONS

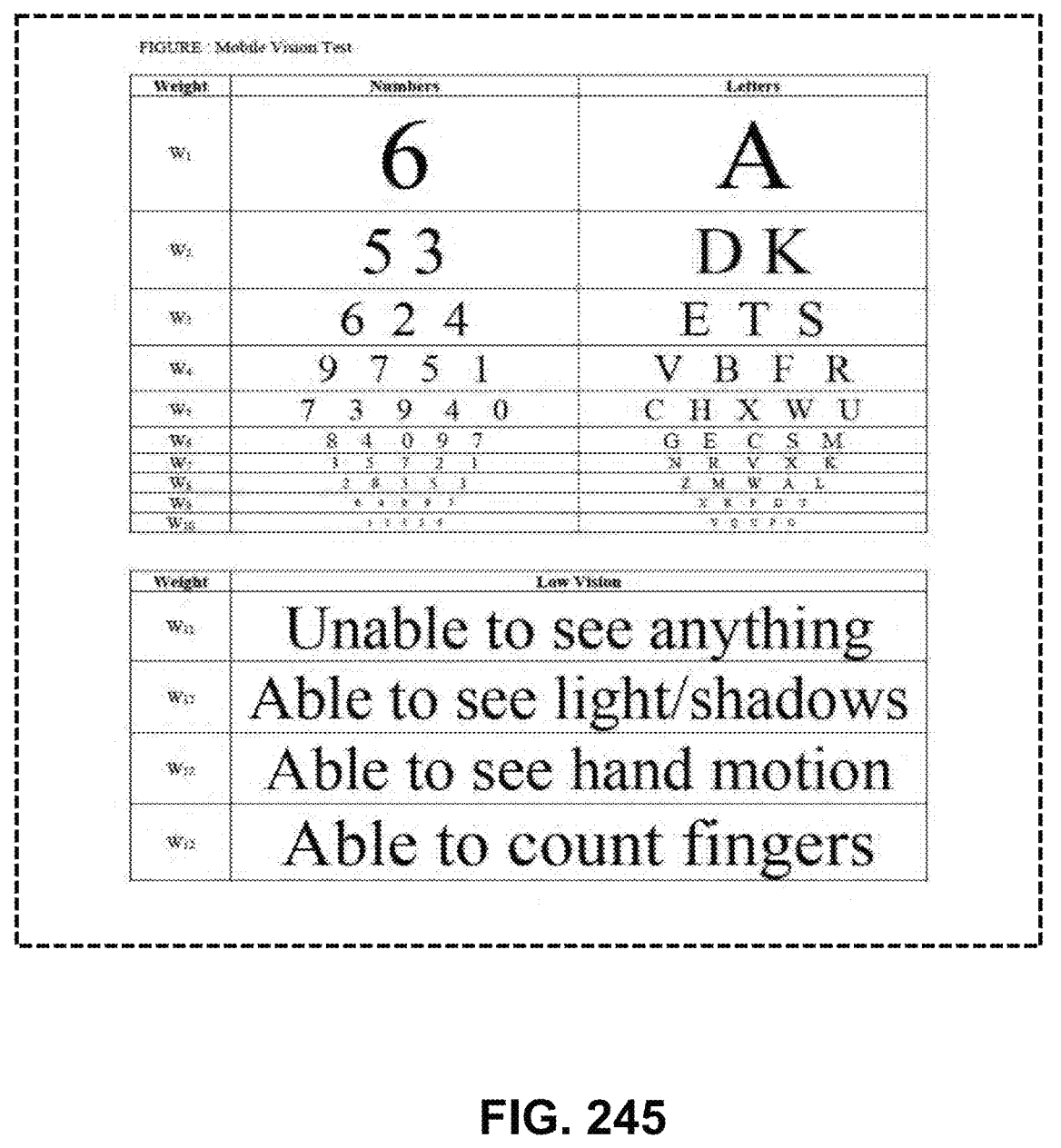

FIGURE : Mobile Vision Test

| Weight | Numbers | Letters |
|---|---|---|
| W₁ | 6 | A |
| W₂ | 5 3 | D K |
| W₃ | 6 2 4 | E T S |
| W₄ | 9 7 5 1 | V B F R |
| W₅ | 7 3 9 4 0 | C H X W U |
| W₆ | 8 4 0 9 7 | G E C S M |
| W₇ | 1 5 7 7 1 | N R V R K |
| W₈ | 2 8 1 5 7 | Z M W A L |
| W₉ | 6 3 8 9 7 | Y B P O T |
| W₁₀ | 1 3 5 2 4 | V O S T Q |

| Weight | Low Vision |
|---|---|
| W₁₀ | Unable to see anything |
| W₁₁ | Able to see light/shadows |
| W₁₂ | Able to see hand motion |
| W₁₃ | Able to count fingers |

FIG. 245

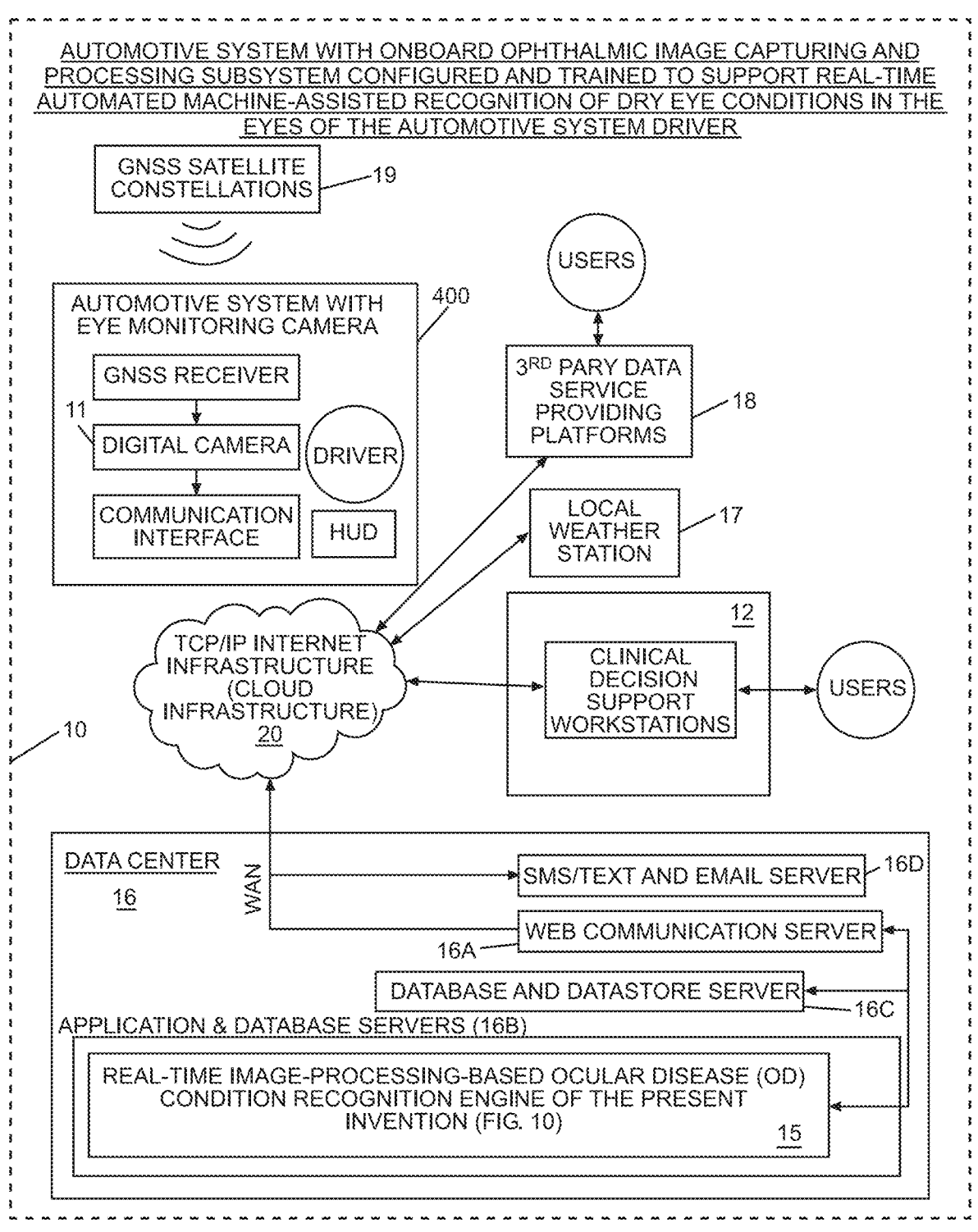

AUTOMOTIVE SYSTEM WITH ONBOARD OPHTHALMIC IMAGE CAPTURING AND PROCESSING SUBSYSTEM CONFIGURED AND TRAINED TO SUPPORT REAL-TIME AUTOMATED MACHINE-ASSISTED RECOGNITION OF DRY EYE CONDITIONS IN THE EYES OF THE AUTOMOTIVE SYSTEM DRIVER

GNSS SATELLITE CONSTELLATIONS — 19

USERS

AUTOMOTIVE SYSTEM WITH EYE MONITORING CAMERA — 400

GNSS RECEIVER

11

DIGITAL CAMERA    DRIVER

COMMUNICATION INTERFACE    HUD

3RD PARY DATA SERVICE PROVIDING PLATFORMS — 18

LOCAL WEATHER STATION — 17

TCP/IP INTERNET INFRASTRUCTURE (CLOUD INFRASTRUCTURE) 20

10

CLINICAL DECISION SUPPORT WORKSTATIONS 12

USERS

DATA CENTER 16

WAN

SMS/TEXT AND EMAIL SERVER — 16D

WEB COMMUNICATION SERVER

16A

DATABASE AND DATASTORE SERVER — 16C

APPLICATION & DATABASE SERVERS (16B)

REAL-TIME IMAGE-PROCESSING-BASED OCULAR DISEASE (OD) CONDITION RECOGNITION ENGINE OF THE PRESENT INVENTION (FIG. 10) 15

FIG. 252

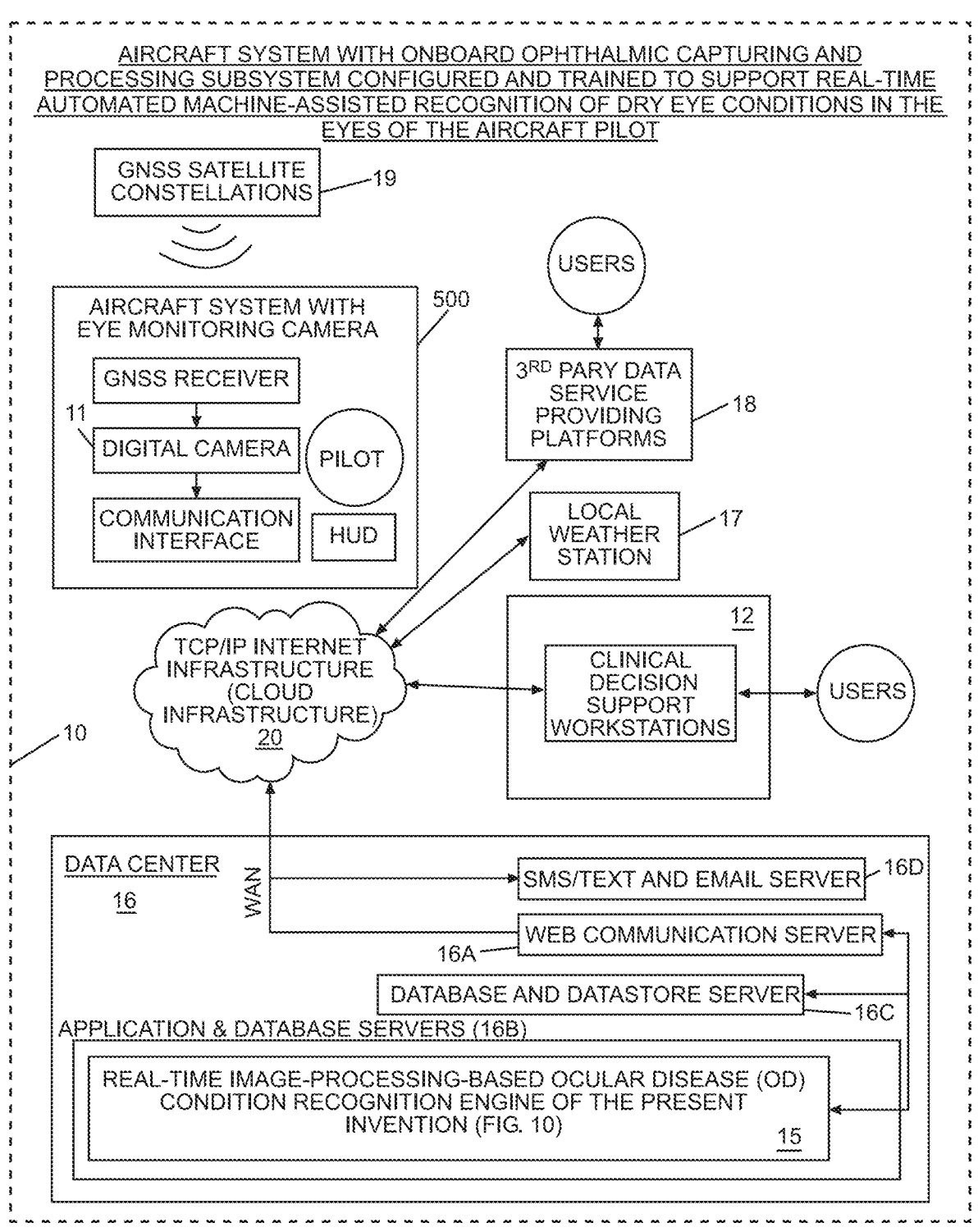

AIRCRAFT SYSTEM WITH ONBOARD OPHTHALMIC CAPTURING AND PROCESSING SUBSYSTEM CONFIGURED AND TRAINED TO SUPPORT REAL-TIME AUTOMATED MACHINE-ASSISTED RECOGNITION OF DRY EYE CONDITIONS IN THE EYES OF THE AIRCRAFT PILOT

GNSS SATELLITE CONSTELLATIONS — 19

USERS

AIRCRAFT SYSTEM WITH EYE MONITORING CAMERA — 500

GNSS RECEIVER

11

DIGITAL CAMERA   PILOT

COMMUNICATION INTERFACE   HUD

3RD PARY DATA SERVICE PROVIDING PLATFORMS — 18

LOCAL WEATHER STATION — 17

TCP/IP INTERNET INFRASTRUCTURE (CLOUD INFRASTRUCTURE) 20

10

CLINICAL DECISION SUPPORT WORKSTATIONS — 12

USERS

DATA CENTER 16

WAN

SMS/TEXT AND EMAIL SERVER — 16D

WEB COMMUNICATION SERVER

16A

DATABASE AND DATASTORE SERVER — 16C

APPLICATION & DATABASE SERVERS (16B)

REAL-TIME IMAGE-PROCESSING-BASED OCULAR DISEASE (OD) CONDITION RECOGNITION ENGINE OF THE PRESENT INVENTION (FIG. 10) 15

FIG. 253

OFFICE WORKSTATION SYSTEM WITH ONBOARD OPHTHALMIC IMAGE CAPTURING AND PROCESSING SUBSYSTEM CONFIGURED AND TRAINED TO SUPPORT REAL-TIME AUTOMATED MACHINE-ASSISTED RECOGNITION OF DRY EYE CONDITIONS IN THE EYES OF THE OFFICE WORKER

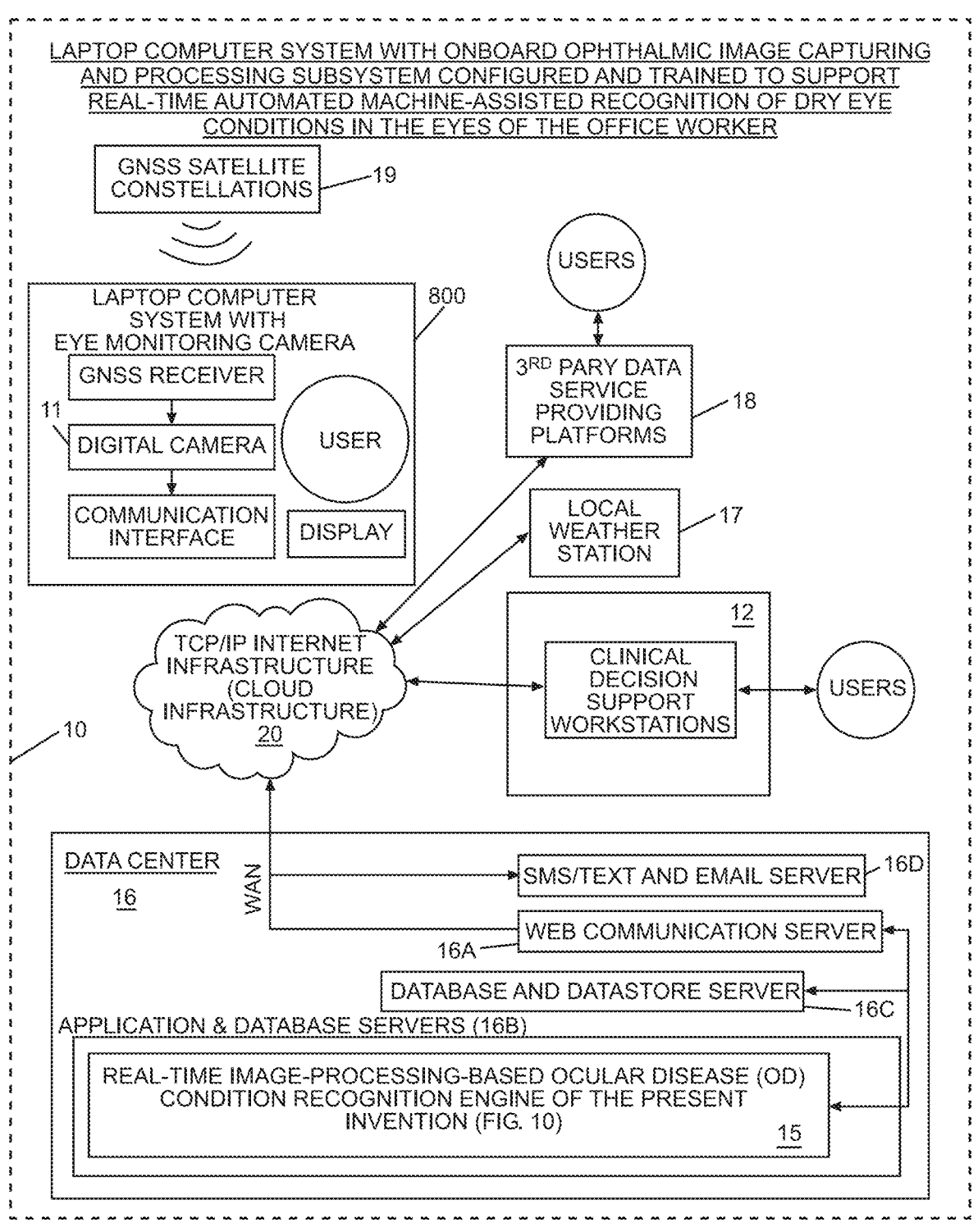

LAPTOP COMPUTER SYSTEM WITH ONBOARD OPHTHALMIC IMAGE CAPTURING AND PROCESSING SUBSYSTEM CONFIGURED AND TRAINED TO SUPPORT REAL-TIME AUTOMATED MACHINE-ASSISTED RECOGNITION OF DRY EYE CONDITIONS IN THE EYES OF THE OFFICE WORKER

GNSS SATELLITE CONSTELLATIONS — 19

LAPTOP COMPUTER SYSTEM WITH EYE MONITORING CAMERA — 800
GNSS RECEIVER
11
DIGITAL CAMERA          USER
COMMUNICATION INTERFACE          DISPLAY

USERS

3RD PARY DATA SERVICE PROVIDING PLATFORMS — 18

LOCAL WEATHER STATION — 17

TCP/IP INTERNET INFRASTRUCTURE (CLOUD INFRASTRUCTURE) 20

10

CLINICAL DECISION SUPPORT WORKSTATIONS — 12

USERS

DATA CENTER 16          WAN

SMS/TEXT AND EMAIL SERVER — 16D

WEB COMMUNICATION SERVER
16A

DATABASE AND DATASTORE SERVER — 16C

APPLICATION & DATABASE SERVERS (16B)

REAL-TIME IMAGE-PROCESSING-BASED OCULAR DISEASE (OD) CONDITION RECOGNITION ENGINE OF THE PRESENT INVENTION (FIG. 10) — 15

FIG. 256

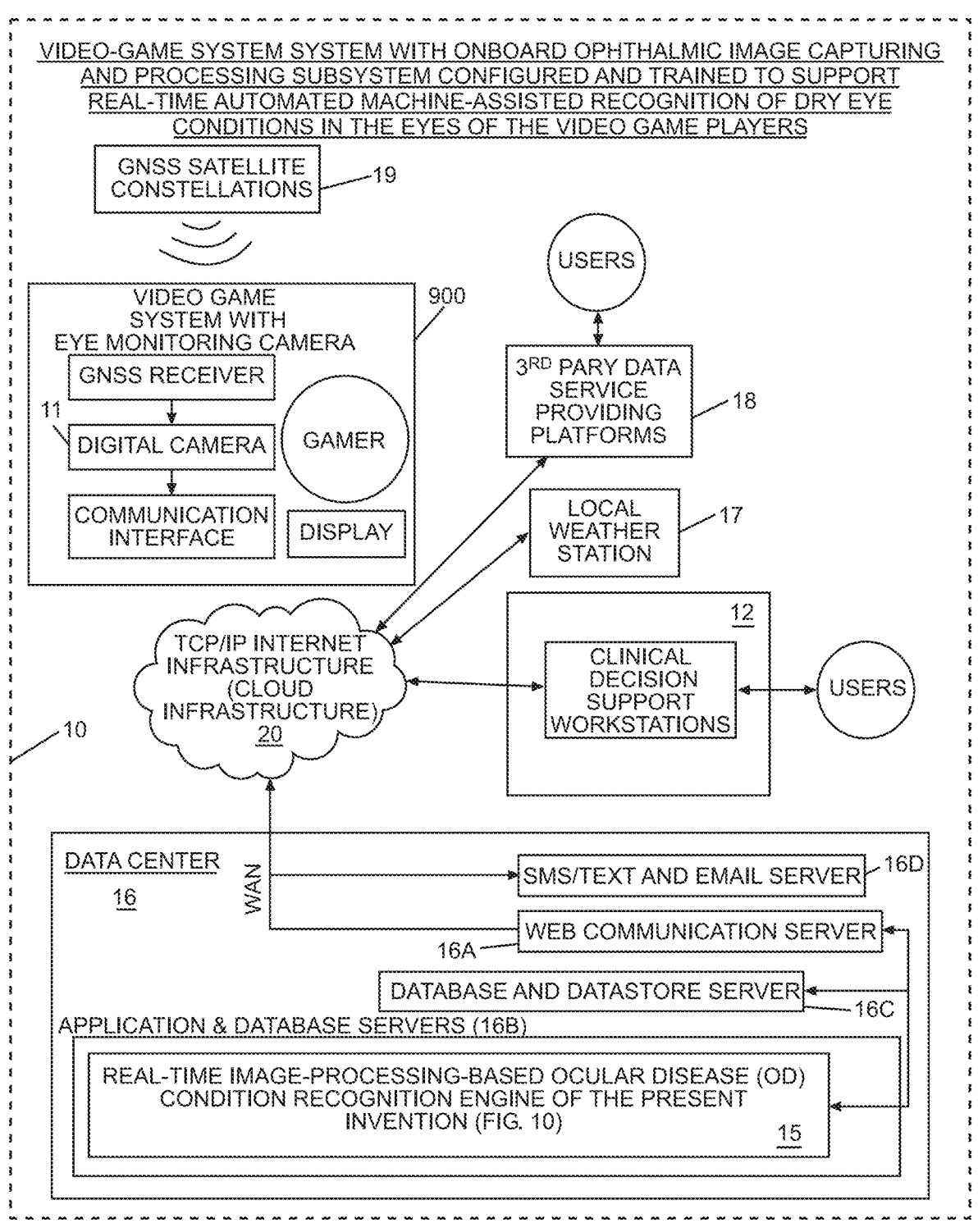

VIDEO-GAME SYSTEM SYSTEM WITH ONBOARD OPHTHALMIC IMAGE CAPTURING AND PROCESSING SUBSYSTEM CONFIGURED AND TRAINED TO SUPPORT REAL-TIME AUTOMATED MACHINE-ASSISTED RECOGNITION OF DRY EYE CONDITIONS IN THE EYES OF THE VIDEO GAME PLAYERS

GNSS SATELLITE CONSTELLATIONS — 19

USERS

VIDEO GAME SYSTEM WITH EYE MONITORING CAMERA — 900

GNSS RECEIVER

11

DIGITAL CAMERA    GAMER

COMMUNICATION INTERFACE    DISPLAY

3RD PARY DATA SERVICE PROVIDING PLATFORMS — 18

LOCAL WEATHER STATION — 17

TCP/IP INTERNET INFRASTRUCTURE (CLOUD INFRASTRUCTURE) 20

10

CLINICAL DECISION SUPPORT WORKSTATIONS — 12

USERS

DATA CENTER 16

WAN

SMS/TEXT AND EMAIL SERVER — 16D

WEB COMMUNICATION SERVER

16A

DATABASE AND DATASTORE SERVER — 16C

APPLICATION & DATABASE SERVERS (16B)

REAL-TIME IMAGE-PROCESSING-BASED OCULAR DISEASE (OD) CONDITION RECOGNITION ENGINE OF THE PRESENT INVENTION (FIG. 10) 15

FIG. 257

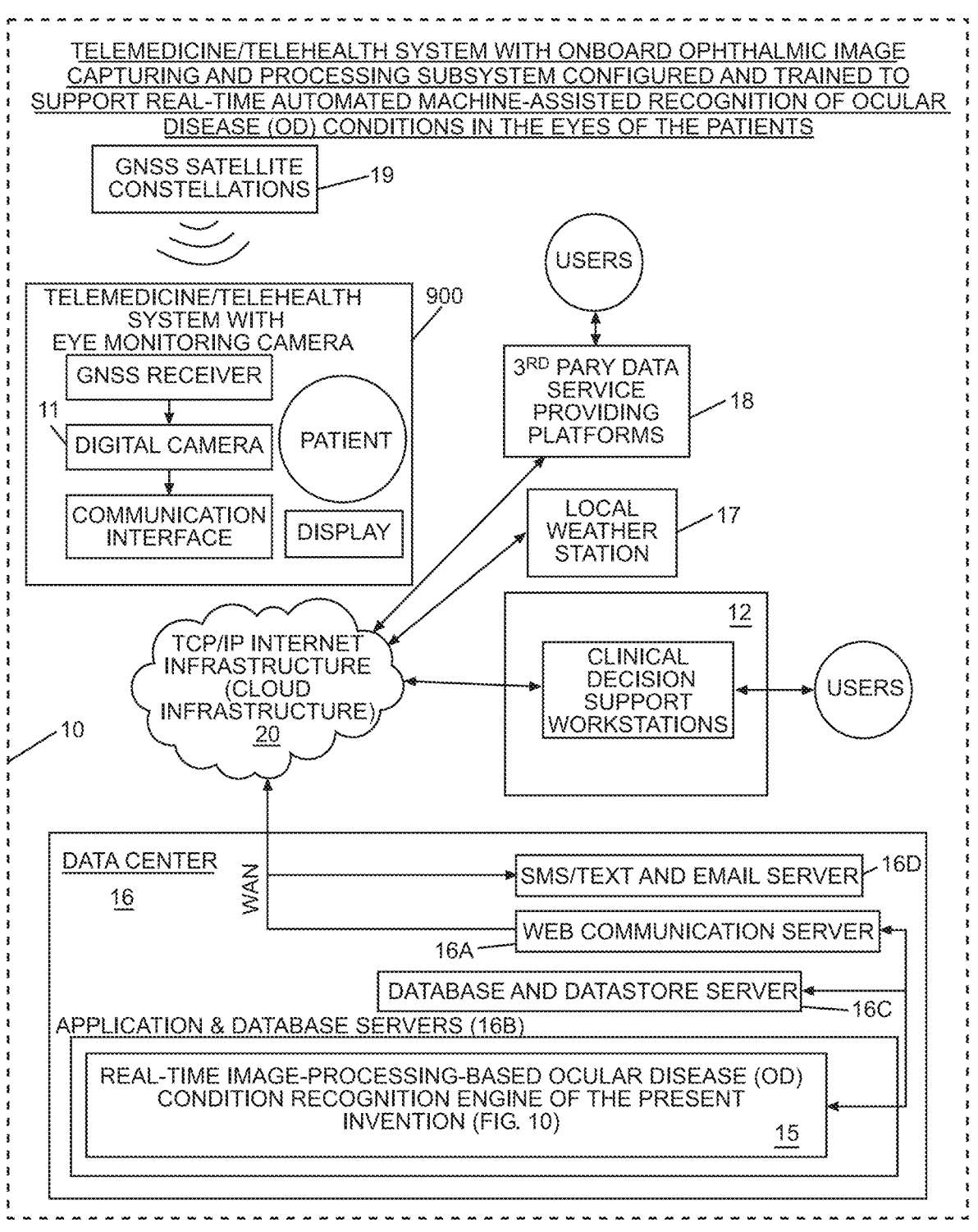

TELEMEDICINE/TELEHEALTH SYSTEM WITH ONBOARD OPHTHALMIC IMAGE CAPTURING AND PROCESSING SUBSYSTEM CONFIGURED AND TRAINED TO SUPPORT REAL-TIME AUTOMATED MACHINE-ASSISTED RECOGNITION OF OCULAR DISEASE (OD) CONDITIONS IN THE EYES OF THE PATIENTS

GNSS SATELLITE CONSTELLATIONS — 19

USERS

TELEMEDICINE/TELEHEALTH SYSTEM WITH EYE MONITORING CAMERA — 900

GNSS RECEIVER

11

DIGITAL CAMERA

PATIENT

COMMUNICATION INTERFACE

DISPLAY

3RD PARY DATA SERVICE PROVIDING PLATFORMS — 18

LOCAL WEATHER STATION — 17

TCP/IP INTERNET INFRASTRUCTURE (CLOUD INFRASTRUCTURE) 20

CLINICAL DECISION SUPPORT WORKSTATIONS — 12

USERS

10

DATA CENTER 16

WAN

SMS/TEXT AND EMAIL SERVER — 16D

WEB COMMUNICATION SERVER

16A

DATABASE AND DATASTORE SERVER — 16C

APPLICATION & DATABASE SERVERS (16B)

REAL-TIME IMAGE-PROCESSING-BASED OCULAR DISEASE (OD) CONDITION RECOGNITION ENGINE OF THE PRESENT INVENTION (FIG. 10) — 15

FIG. 258

SMART CONTACT LENS SYSTEM WITH ONBOARD OPHTHALMIC IMAGE CAPTURING AND PROCESSING SUBSYSTEM CONFIGURED AND TRAINED TO SUPPORT REAL-TIME AUTOMATED MACHINE-ASSISTED RECOGNITION OF OCULAR DISEASE (OD) CONDITIONS IN THE EYES OF THE WEARER

METHOD OF AND SYSTEM FOR AUTOMATED MACHINE-ASSISTED DETECTION OF OCULAR DISEASE CONDITIONS IN HUMAN EYES CAPTURED USING VISIBLE ILLUMINATION LIGHT SOURCES AND DIGITAL CAMERA SYSTEMS

BACKGROUND OF INVENTION

Field of Invention

The present invention is related to new and improved methods, systems and technologies for forming, capturing, and processing digital images of human eyes in patients in flexible and distributed ways so as to support the automated detection, recognition and/or prediction of the existence of conditions indicative of particular diseases, such as dry eye disease, and prescribed treatment and care to restore and/or preserve human vision.

Brief Description of the State of Art

Vision is an essential capacity to human life and survival, only second to vital functions such as respiration and consciousness. And yet hundreds of millions of individuals around the world suffer daily from dry eye disease (DED) which is now identified as one of the most common ocular disorders worldwide. To better understand the nature of this complex disease, it is helpful to have a basic understanding of the anatomy and physiology of the human eye.

In the human eye, the anterior segment of the eye is defined as the front third of the eye that includes the conjunctiva, cornea, iris, pupil, and the lens. The conjunctiva, iris, pupil, cornea, retina, lens, vitreous, optic nerve, choroid and sclera of the human eye are illustrated in FIG. 1A. The epithelium, Bowman's membrane, stroma, Descemet's membrane, and endothelium of the human cornea are illustrated in FIG. 1B. These structures constitute the path of light through the eye and the ocular refractive system. The primary function is to form clear and converging images on the retina in the back of the eye, which generate a pattern of impulses that are transmitted along the optic nerve to the visual cortex in the human brain where human perception and vision is realized.

FIG. 2 shows the lacrimal sac, canaliculi, the puncta, the tear duct (i.e. nasolacrimal duct), and the tear gland (i.e. lacrimal gland) above the eye. FIG. 3 shows the lacrimal gland, meibomian glands, and the goblet cells in the conjunctiva, with an expanded view of the tear film showing the lipid layer supplied by the meibomian glands, an aqueous layer supplied by the lacrimal glands, and the mucin layer provided by the epithelial cells. These structures produce the components of the tear film membrane, namely: aqueous saline liquid layer closest to the ocular surfaces; and lipids and oils that mix with the saline liquid to produce an outer film that inhibits evaporation of aqueous layer from the corneal surface. Any disturbance within the tear film is likely to contribute to what is called dry eye disease (DED) condition. For example, a deficiency in aqueous layer production will lead to inadequate lubrication of the corneal surface, whereas a deficient or a dysfunctional lipid layer will lead to rapid evaporation of the tear film from the corneal surface.

FIG. 4 lists some common symptoms of dry eye disease (DED), including, redness, stinging or burning, blurred vision, sensitivity to light, excessive tearing, foreign body sensation, itchiness, and eyelid asymmetry. Based on abnormalities of the tear film composition, dry eye disease (DED) has been broadly classified into two categories: (i) aqueous-deficient dry eye (ADDE); and (ii) evaporative dry eye (EDE), corresponding to disorders of the lacrimal and meibomian glands, respectively.

(i) ADDE can be classified into: (i) Sjögren's syndrome (SS), and (ii) non-Sjögren's syndrome (NSS) dry eye.

(ii) EDE can be classified into intrinsic and extrinsic causes, with meibomian gland dysfunction (MGD) being the most common cause of EDE.

As ADDE and EDE are not mutually exclusive and may act together to produce signs and symptoms, it may be challenging to identify pure forms of each disease due to mixed forms of DED using the current system of classification. In addition, the initial underlying dry eye mechanism may lead to involvement of additional mechanisms, thus resulting in misclassification of the initial etiology at different stages of disease. Thus, with time and progression of disease severity, it is possible that the clinical phenotype of DED may be altered as well, which can lead to mixed clinical phenotypes.

Currently, dry eye disease severity is graded into four categories based on a combination of patient symptoms and clinical signs. However, several studies have demonstrated the lack of correlation between the severity of symptoms experienced by the patient and physical findings on clinical examination. For example, patients in early stages of DED may demonstrate symptoms, without clear clinical signs. Conversely, patients may show mild or severe objective clinical signs of DED, but may be symptom free. The disparity between signs and symptoms is multifactorial but may be explained in part by the reduction of corneal nerve density with dry eye disease. Reduced or loss of corneal sensation, secondary to reduced corneal sub-basal nerve density from nerve damage in DED, may explain the presence of clinical signs of ocular surface damage in the absence of concordant symptoms of ocular discomfort. To establish a definite diagnosis of anterior segment eye/ocular diseases, conventional practice involves evaluating both anatomy and function, typically using specialized instruments such as: slit-lamp bio-microscopy, optical coherence tomography, corneal topography, tonometry, perimetry, etc. For such historical reasons, when developing computer assisted or artificial intelligence (AI) methods of detecting such ocular diseases, various forms of data besides slit-lamp images, AS-OCT images, tear film lipid layer interference images (e.g. image), including videos, formatted parameters and texts, have been used for such purposes.

In the paper titled "IMAGE-GUIDED EVALUATION AND MONITORING OF TREATMENT RESPONSE IN PATIENTS WITH DRY EYE DISEASE (2014)" by Yureeda Qazi, et al, working in the Cornea and Ocular Surface Imaging Center, in the Department of Ophthalmology—Cornea Service, at the Massachusetts Eye and Ear Infirmary, Harvard Medical School, Boston, MA, acknowledged that the pathophysiological mechanisms involved in the development of DED are not well understood, and thus treating DED has been a significant challenge for ophthalmologists and optometrist. Most of the currently available diagnostic tests demonstrate low correlation to patient symptoms and have low reproducibility. Conventional methods propose using non-invasive in vivo imaging modalities during patient care, namely, in vivo confocal microscopy (IVCM) and optical coherence tomography (OCT), which allow real-time visualization of cellular and anatomical structures of the cornea and ocular surface. By providing both qualitative and quantitative assessment, these techniques can be used to demonstrate early subclinical disease, grade layer-by-layer severity, and allow monitoring of disease severity by cellular alterations. Imaging-guided stratification of patients may also be possible in conjunction with clinical examination methods. Visualization of subclinical changes and stratification of patients in vivo, allows objective image-guided evaluation of tailored treatment response based on cellular morphological alterations specific to each patient. This image-guided approach to DED may ultimately improve patient outcomes and allow studying the efficacy of novel therapies in clinical trials.

FIG. 5 lists primary prior art imaging modalities that are currently being used to image features in the anterior segment of the human eye during particular AI-supported diagnostic applications, and are relevant to the Background of the Present Invention. As shown in FIG. 5, conventional imaging modalities include: (i) slit-lamp microscopes where slit light 1A is used to produce slit lamp images 1B during cataract detection and grading, where diffuse light 1C is used during conjunctival hyperemia grading, high intraocular pressure detection, and identification, localization of conjunctiva and cornea and lens diseases, and where retro-illumination 1D is used during posterior capsule opacification progress prediction; (ii) optical coherence tomography (OCT) for producing AS-OCT images 1E for angle closure detection; (iii) tear film lipid layer interference images 1F for tear film lipid layer classification dry eye diagnosis (DED); (iv) frontal eye videos 1G for use during fluorescein instillation, during dry eye detection, with tear break up time (TBUT) calculation; (v) retinal fundus images 1H for use during cataract grading and detecting gross macular or optic nerve abnormalities; and (vi) visible wavelength images 1I captured by a digital camera for use during corneal arcus and a cataract detection. Notably, visible wavelength images are modes of imaging of great interest in view of the fact that there are billions of mobile smartphone camera systems currently in use around the world.

FIG. 6 illustrates a typical workflow and system environment 2 used when constructing models for use in deep learning (AI) systems and applications. As illustrated during the data preparation stage 3, models are developed to train deep learning systems 5 using both traditional learning and more modern deep learning techniques 5, as well as combinations of the same, to detect and recognize objects, and then evaluate system performance using various techniques 6 well known in the art.

In recent times, a number of researchers have suggested using the digital camera subsystem integrated in mobile smartphone systems to capture visible-wavelength images (1A) for use in detecting dry eye disease (DED) conditions in the human eyes. However, most prior art proposals have required the addition of specialized optical and/or illumination apparatus outfitted to the smartphone camera to detect specific features with specialized imaging modalities, other than visible wavelength imaging. Most proposals have been aspirational in nature, identifying the use of mobile smartphone camera devices in dry eye disease (DED) detection and treatment as an industry aim, without disclosing, teaching or offering any adequate means for, way of, or enabling knowledge on how to actually and reliably realize such an important objective in the global medical industry.

Rather, the prior art has identified that there are many significant limitations and hurdles to be overcome for widespread clinical implementation of AI-assisted applications in anterior segment ocular diseases.

At the same time, the prior art has clearly recognized the need for a number of things, namely: (i) algorithms that can learn with less image data and achieve quality assessment during system training; (ii) integrative analysis of multi-modal data (e.g. videos, images, formatting parameters, texts, etc.) to diagnose complicated ocular diseases (e.g. dry eye disease) which currently remains an unsolved challenge in the field; (iii) methods that will allow smartphone photography to serve as a diagnostic tool for anterior segment ocular diseases in the near future; (iv) AI systems that that can be used in clinical settings and employing systemic AI models trained on multimodal and heterogeneous data using less data-intensive algorithms; and (v) home-based systems that use AI methods for diagnosis and management of ocular diseases and related eye care problems.

Accordingly, there is a great need in the art for new and improved ways of and means for (i) capturing and processing digital images of human eyes using conventional visible-wavelength mobile smartphone camera systems, and (ii) automatically recognizing specific ocular disease conditions such as dry eye disease (DED) and other ocular pathologies, and prescribing treatment thereof and managing the ocular care needs of human beings and other animals, in both remote/distributed telemedicine and clinical care environments alike.

OBJECTS AND SUMMARY OF THE PRESENT INVENTION

Accordingly, it is a primary object of the present invention to provide a new and improved digital imaging processing system and method to automatically recognize ocular disease (OD) conditions in humans by (i) processing 2D digital images of the human eyes in real-time formed, captured and detected using a visible-wavelength operating mobile smartphone camera system, (ii) detecting the presence and location of specific objects in the ocular surfaces in the human eye, and (iii) confirming that specific conditions have been satisfied during image processing to support automated ocular disease condition recognition.

Another object of the present invention is to provide new and improved machine-learning based systems and methods to support and enable the reliable computer-aided diagnosis and treatment of ophthalmic/ocular diseases and disorders afflicting millions of human beings around the world.

Another object of the present invention is to provide such a new and improved system which uses mobile smartphone cameras and machine-vision systems, image processing and deep learning processes.

Another object of the present invention is to provide new and improved automated machine-vision processing system that automatically identifies, localizes, and extracts specific pixel content of ocular objects represented in digital images of human eyes formed and captured using visible-wavelength operating smartphone camera systems, to support automated recognition of various ocular disease (OD) conditions, including dry eye disease (DED), and prescription of subclinical treatment thereof, and thereafter monitor a prescribed course's treatment response, and continue with and/or adapt the prescribed course of treatment with minimal or no human input required, while enhancing the preclinical and/or clinical management of ocular disease conditions around the world.

Another object of the present invention is to provide new and improved automated eye-care diagnostics, treatment & management applications using visible-wavelength operating digital camera systems.

Another object of the present invention is to provide new and improved automated computer-based automated eye-care diagnostic, treatment & management applications using visible-wavelength digital camera systems.

Another object of the present invention is to provide new and improved automated automotive-based eye-care diagnostics, treatment & management applications using visible-wavelength operating digital camera systems.

Another object of the present invention is to provide new and improved automated video-gaming-based automated eye-care diagnostics, treatment & management applications using visible-wavelength digital camera systems.

Another object of the present invention is to provide new and improved automated aircraft-based automated eye-care diagnostic, treatment & management applications using visible-wavelength digital camera systems.

Another object of the present invention is to provide new and improved automated telemedicine eye care system using visible-wavelength digital camera systems.

Another object of the present invention is to provide a novel system network in which a mobile ophthalmic image capturing and processing system is deployed and adapted for automated machine-assisted recognition of ocular disease (OD) conditions, and other anterior eye segment diseases, including automated prescription of disease treatment, and managed assessment of treatment response care.

Another object of the present invention is to provide a novel system network in which a mobile ophthalmic image capturing and processing system is deployed and adapted for automated machine-assisted recognition of dry eye disease and other anterior eye segment diseases, prescription of treatment, and assessment of treatment response, comprising (i) smartphone mobile image capturing systems for use by patients and users whose eyes are to be monitored and cared for using the system, (ii) clinical ophthalmic decision workstations, and real-time ophthalmic image driven ocular disease (DOD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel ecosystem of system networks and medical instruments and systems deployable in a large, medium or small scale hospital management system covering hospitals, clinics and medical practices, including slit-lamp microscope systems, fundus camera systems, fluorescence imaging systems, X-Ray, PET and imaging systems, PCR-based diagnostic and genetic and diagnostic instruments and systems, functional imaging systems, AI and deep-learning medical diagnostic, analytics and decision support systems, and including the mobile ophthalmic image capturing and processing system, that produce and supply patient data for use by the system network of the present invention to support automated ocular disease recognition, treatment and managed care.

Another object of the present invention is to provide a novel mobile ophthalmic image capturing and processing system comprising a system input/output subsystem, a patient history data processing subsystem, a patient eye image data processing subsystem, a patient eye video data processing subsystem, mobile vision testing data processing subsystem, a patient symptom data processing subsystem, a vision functionality data processing subsystem, an environmental factors data processing subsystem, a risk factors data processing subsystem, an exam and in-office testing data processing subsystem, an automated ocular disease (OD) recognition engine, an automated OD treatment prescription engine of the present invention, and a OD treatment compliance data processing subsystem (e.g. treatment compliance engine), configured and integrated into a single system network supporting the innovative remote, mobile and distributed methods of ocular disease diagnosis, treatment and managed care.

Another object of the present invention is to provide a novel digital image and video capturing and processing subsystem comprising an array of mobile smartphone camera systems and an automated digital image processing server realized within one or more enterprise-level data center(s), supporting machine learning and predictive analytics subsystems, a clinical decision support subsystem realized as workstations, tablet computers and laptop workstations, a geolocation (GPS) tracking and linking subsystem to chains of pharmacies, drugstores and health care vendors around the globe, and a database subsystem for storing data and maintaining data records for patients, users, medical and health care providers and medicine vendors across the entire enterprise.

Another object of the present invention is to provide a novel mobile smart phone function used to capture digital images of a patient's eyes using an augmented reality (AR) overlay graphical user interface (GUI) displayed on the screen of the mobile phone, for directing the user to capture images and videos of their eyes in a guided manner to support the advanced machine-vision image capture and processing methods enabled in smart phones used by patients, at workstations in the clinic and hospital setting, and at other remote data centers connected together over a global wireless system network.

Another object of the present invention is to provide a novel machine-vision based digital image processing system employed within the system network, and which is organized, arranged and configured according to traditional machine-vision models employing feature engineering and feature classifiers with shallow structure, so as to classify input digital images as being representative of a particular ocular disease (OD) condition, from many possible trained ocular disease conditions, including dry eye disease (DED) conditions in the human eye.

Another object of the present invention is to provide a novel machine-vision based digital image processing system comprising in its training pipeline, an image/video input module, a pre-processing module, a segmentation module, a post-processing module, feature measurements added to a database, and in a classification pipeline, an image/video input module, an image pre-processing module, an image segmentation module, a post-processing module, a feature extraction module, and a classification/recognition module to support automated ocular disease recognition, treatment and manage care, including predicting dry eye disease (DED) class and grade of severity.

Another object of the present invention is to provide a novel machine-vision based digital image processing system employed within a system network, and is organized, arranged and configured according to a deep learning machine-vision models employing convolutional neural networks having deep structure, so as to provide an end-to-end system for classifying input digital images as being representative of a particular ocular disease (OD) condition.

Another object of the present invention is to provide a novel automated deep neural network module, for implementing a machine-vision based digital image processing system employed within a system network, comprising feature extraction involving convolution and pooling, and classification to produce automated classification outputs, achieved using digital images captured using visible-wavelength operating digital camera systems.

Another object of the present invention is to provide a novel unified framework of deep structure convolutional neural networks (CNNs) specially configured to automatically classify object candidates into specific categories of ocular disease conditions, wherein the deep-learning machine-vision based digital image processing system comprises (i) a faster recurrent-CNN (R-CNN) for carrying out image convolutional layers and producing feature maps from input images, (ii) a regional proposal network (RPN) for producing proposed regions of interest (ROI), and (iii) a faster R-CNN for classifying the proposed ROIs to support automated ocular disease recognition, treatment and manage care, including predicting dry eye disease (DED) class and grade of severity using digital images captured using visible-wavelength digital camera systems.

Another object of the present invention is to provide a novel deep neural network using a TensorFlow 2.0 ecosystem consisting of Python libraries to build an automated deep-learning machine-vision recognition system capable of automatically recognizing specific categories of dry eye conditions from a set of ocular images captured using a standard visible-wavelength operating digital camera system.

Another object of the present invention is to provide a novel deep neural network machine-vision based digital ocular image processing system deployed on a distributed ocular health care system network, employing a hybrid architecture when practicing the system and methods, consisting of (i) a symbolist AI component employing symbolic reasoning and logic (e.g. Rule Based Logic, IF X, then Y), and (ii) a connectionist AI component employing connected statistical models such as machine learning, deep-learning neural networks in computer vision, natural language processing (NLP), and speech recognition, and artificial neural networks (ANNs).

Another object of the present invention is to provide a novel deep neural network method of operating an automated ophthalmic image capturing and processing system configured to enable automated machine-assisted detection and recognition of dry eye disease (DED) conditions in the human eye, automated prescription of disease treatment, and managed assessment of prescribed treatment, by processing a series of digital images of the human eye formed, captured and detected by a mobile visible-wavelength operating digital camera system.

Another object of the present invention is to provide a visible-wavelength mobile smartphone camera system, for use by a patient to capture image data of the patient's eyes and provide the same to the system for image processing using automated machine vision processing to detect and/or measure ocular conditions, including but not limited to, tear meniscus height (TMH), conjunctival injection (CI), scruff at eyelashes, meibomian gland dysfunction (MGD), dermatochalasis, and conjunctivochalasis.

Another object of the present invention is to provide a novel ophthalmic image system for automatically detecting and classifying in collected images of the patient's eyes using the machine-vision imaging processing methods operating on digital images of human eyes formed and captured using visible-wavelength operating digital camera systems.

Another object of the present invention is to provide a novel mobile smartphone camera system, for use by a patient to capture video data of the patient's eyes and provide the same to the system for image processing using automated machine vision processing, to automatically detect and measure ocular functions such as, but not limited to, blink rate, blink interval, blink duration, blink speed and partial blinks per minute, that are used in the automated recognition of ocular disease conditions, including dry eye disease conditions in human eyes.

Another object of the present invention is to provide a novel ophthalmic image processing system for automatically detecting and classifying in collected video of the patient's eyes using the machine-vision imaging processing methods of the present invention, to measure blink rate, blink interval, blink duration, blink speed and partial blinks per minute.

Another object of the present invention is to provide a novel ophthalmic image processing system that uses primary patient diagnostic factors to automatically recognize the type or class of dry eye disease, and its grade/severity experienced by the patient, automatically determined using the machine-vision imaging processing methods operating on digital images of human eyes formed and captured using visible-wavelength operating digital camera systems.

Another object of the present invention is to provide a novel ophthalmic image processing system that employs an automated machine-vision based dry eye disease recognition engine of the present invention, operating on digital images of human eyes formed and captured using visible-wavelength operating digital camera systems.

Another object of the present invention is to provide a novel system network, in which a mobile digital camera system is used by a patient to receive a dry eye disease treatment prescription generated by the system using automated machine vision processing supporting the automated measurement of ocular conditions such as, but not limited to, tear meniscus height (TMH), conjunctival injection, scruff at eyelashes, meibomian gland dysfunction, dermatochalasis, and/or conjunctivochalasis.

Another object of the present invention is to provide a novel ophthalmic image processing system, in which a mobile digital camera system is used by a patient to capture data about the patient and the patient's eyes and provide the same to the system for automated image processing using an automated machine-vision processing system and methods.

Another object of the present invention is to provide a novel mobile smartphone camera system used by a patient to capture digital image and video data about the patient's eyes, and provide the same to an automated machine-vision processing system for automated machine-vision processing.

Another object of the present invention is to provide a novel ophthalmic image processing system for use in automatically monitoring and supporting automated and/or semi-automated decisions and prescription updates for effective treatment and remotely managed care of the dry eye disease condition automatically recognized by the machine-vision imaging processing methods.

Another object of the present invention is to provide a novel automated machine-vision based dry eye disease recognition engine for use in continuously monitoring the patient's ocular disease condition and response to prescribed treatment.

Another object of the present invention is to provide a novel ophthalmic image processing system, wherein compliance factors that are continuously monitored, updated and supplied to the system of the present invention to automatically measure prescribed treatment compliance and support decisions and prescription updates for effective treatment of an ocular disease condition automatically recognized by the machine-vision imaging processing methods.

Another object of the present invention is to provide a novel automated machine-vision based dry eye disease recognition engine for use in monitoring the patient's ocular disease condition and response to prescribed treatment.

Another object of the present invention is to provide a novel dry eye disease (DED) recognition engine deployed within a system, wherein the various detectable ocular/ patient factors that are known to contribute to each different class of dry eye disease conditions that the automated DED condition recognition engine of the present invention is configured to automatically recognize during system operation.

Another object of the present invention is to provide a novel automated dry eye disease (DED) condition recognition engine, wherein each rule specifies the various input ocular factors which, if detected by the system for a given set of patient images, then the system will automatically classify the patient images as indicating a particular dry eye disease condition present in the eyes of the patient.

Another object of the present invention is to provide a novel dry eye disease (DED) recognition engine deployed within a system, wherein the various detectable ocular/ patient factors that are known to contribute to the specific grading of the severity of a dry eye disease condition classified by the automated DED condition recognition engine.

Another object of the present invention is to provide a novel automated dry eye disease (DED) condition recognition engine, wherein each rule specifies the various input ocular factors which, if detected by the system for a given set of patient images, then the system will automatically specify the grade of severity to be automatically assigned to the particular dry eye disease condition automatically recognized by the system.

Another object of the present invention is to provide a novel dry eye disease (DED) treatment compliance engine deployed within a system having various system inputs continuously supplied to the engine from the treatment prescription engine and various subsystems supporting the system, and the system outputs of the compliance engine being vector inputs to the treatment prescription engine that is being continuously reconfigured as needed to provide optimal treatment to the automatically recognized dry eye disease condition recognized by the system.

Another object of the present invention is to provide a novel automated dry eye disease (DED) treatment compliance engine, wherein each rule specifies the various input ocular factors which, if detected by the system for a prescribed course of dry eye disease treatment, then the system will automatically specify how the prescribed course of treatment should be modified if at all, given the treatment response data factors provided to the system.

Another object of the present invention is to provide a novel deep-learning machine-vision ocular image processing and classification system (i.e. "engine") configured and trained for use and deployment on a system network configured to support and enable automated detection and measurement of conjunctival injection (CI) of eyes photographically represented in digital images of a front view of human eyes formed, captured and detected by mobile smartphone camera system.

Another object of the present invention is to provide a novel machine-vision based method of processing time and date stamped digital images of a human eye captured by a mobile smartphone camera system, so as to automatically detect and measure conjunctival injection present in the human eye of a patient at a specific time and date to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on the system network to support and enable automated detection and measurement of tear meniscus height (TMH) of eyes photographically represented in digital images of a front view of human eyes formed, captured and detected by a mobile smartphone camera system.

Another object of the present invention is to provide a novel method of automatically detecting dry eye disease conditions, including measuring the retention of tears at the interface between the corneal surface and the eyelid of the human eye, via the meniscus effect, to form a collection of tears having a tear meniscus height (TMH) measured by the method.

Another object of the present invention is to provide a novel machine-vision based method of processing time and date stamped digital images of a human eye captured by a mobile smartphone camera system, so as to automatically detect and measure the tear meniscus height (TMH) in the human eye at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network designed to support and enable automated detection and measurement of meibomian gland dysfunction (MGD) and scruff at the eyelashes of the human eyes photographically represented in digital images of a front view of human eyes formed, captured and detected by a mobile smartphone camera system.

Another object of the present invention is to provide a novel method of processing digital images of human eyes so as to indicate (i) where meibomian gland dysfunction (MGD) and scruff at the eyelashes are detected in the photographic image of the human eye, and (ii) which pixel region of interest (ROI) requires pixel data processing according to a method of digital image processing using a machine-based ophthalmic image processing engine operating on one or more front view digital images of the human eye, so as to automatically detect meibomian gland dysfunction (MGD) and scruff, as an indication of ocular disease recognition, treatment and manage care, including predicting dry eye disease (DED) class and grade of severity by the automated system.

Another object of the present invention is to provide a novel machine-vision based method of processing time and date stamped digital images of a human eye formed, captured and detected by a mobile smartphone camera system and processed to automatically detect meibomian gland dysfunction (MGD) and scruff at the eyelashes in the human eye at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network designed to support and enable automated detection and measurement of conjunctivochalasis of the human eyes photographically represented in digital images of a front view of human eyes formed and captured by a mobile smartphone camera system.

Another object of the present invention is to provide a novel method of automatically processing digital images of a patient human eyes so as to indicate (i) where conjunctivochalasis is detected in the photographic image of the human eyes, and (ii) which pixel region of interest (ROI) requires pixel data processing according to a method of digital image processing using a machine-based ophthalmic image processing engine operating on one or more front view digital images of the human eye, so as to automatically detect conjunctivochalasis, as an indication of ocular disease recognition, treatment and manage care, including predicting dry eye disease (DED) class and grade of severity by the automated system.

Another object of the present invention is to provide a novel method of automatically detecting dry eye disease conditions, and showing the existence of conjunctivochalasis on the lower eyelid of the human eye, preventing the normal replenishment of tears at the meniscus interface between the cornea surface and the lower eyelid.

Another object of the present invention is to provide a novel machine-vision based method of processing time and date stamped digital images of a human eye formed, captured and detected by a mobile smartphone camera system and processed to automatically detect conjunctivochalasis in the human eye at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network designed to support and enable automated detection and measurement of dermatochalasis of the human eyes photographically represented in digital images of a front view of human eyes formed and captured by a mobile smartphone camera system.

Another object of the present invention is to provide a novel method of processing digital images of a patient's human eyes so as to indicate (i) where dermatochalasis is detected in the upper eyelids of the human eyes in the photographic image, and (ii) which pixel region of interest (ROI) requires pixel data processing according to a method of digital image processing using a machine-based ophthalmic image processing engine operating on one or more front view digital images of the human eye, so as to automatically detect dermatochalasis, as an indication of ocular disease recognition, treatment and manage care, including predicting dry eye disease (DED) class and grade of severity by the automated system.

Another object of the present invention is to provide a novel machine-vision based method of processing time and date stamped digital images of a human eye formed, captured and detected by a mobile smartphone camera system and processed to automatically detect a dermatochalasis condition in the human eyes at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network designed to support and enable automated detection and measurement of tear film dynamics (TFD1) of the human eyes photographically represented in a time series set of digital images of a front view of human eyes formed and captured by a mobile smartphone camera system.

Another object of the present invention is to provide a novel method of automatically recognizing dry eye disease (DED) conditions, (i) where light reflective particles are detected in the photographic image of the tear film of a human eye between eye blinks, and (ii) which pixel region of interest (ROI) requires pixel data processing according to a method of digital image processing using a machine-based ophthalmic image processing engine operating on one or more front view digital images of the human eye, so as to automatically detect the light reflective particles in the tear film of a human eye during eye blinks, as an indication of ocular disease recognition, treatment and manage care, including predicting dry eye disease (DED) class and grade of severity by the automated system.

Another object of the present invention is to provide a novel machine-vision based method of processing time and date stamped digital images of a human eye formed, captured and detected by a mobile smartphone camera system and processed to automatically detect and measure tear film dynamics in human eyes at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network designed to support and enable automated detection and measurement of tear film dynamics (TFD2) of human eyes photographically represented in a time series set of digital images of a front view of human eyes formed and captured by a mobile smartphone camera system.

Another object of the present invention is to provide a novel method of recognizing dry eye disease (DED) conditions, (i) where the tear film dynamics (TFD2) of the tear film on human eyes are detected in the human eyes in a series of digital photographic images, and (ii) which pixel region of interest (ROI) requires pixel data processing according to a method of digital image processing using a machine-based ophthalmic image processing engine operating on one or more front view digital images of the human eye, so as to automatically detect and measure the tear film dynamics, by virtue of detected perturbations in concentric placido light discs projected on the cornea from the display screen of a mobile smartphone, as an indication of ocular disease recognition, treatment and manage care, including predicting dry eye disease (DED) class and grade of severity by the automated system.

Another object of the present invention is to provide a novel method of projecting concentric placido light discs onto the human eye from the display screen of a smartphone camera system capturing images of the human eyes during tear film dynamics testing.

Another object of the present invention is to provide a novel machine-vision based method of processing time and date stamped digital images of a human eye formed, captured and detected by a mobile smartphone camera system and processed to automatically detect and measure tear film dynamics in the human eye at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network designed to support and enable automated detection and measurement of tear film dynamics (TFD3) of the human eyes photographically represented in a times series of digital images of a front view of human eyes formed and captured by a mobile smartphone camera system.

Another object of the present invention is to provide a novel method of recognizing dry eye disease (DED) conditions, (i) where the tear film dynamics in the human eye are measured by analysis of eye blinks during a time series of digital photographic images, and (ii) which pixel region of interest (ROI) requires pixel data processing according to a method of digital image processing using the machine-based ophthalmic image processing engine operating on one or more front view digital images of the human eye, so as to automatically detect and measure tear film dynamics of the human eyes, as an indication of ocular disease recognition, treatment and manage care, including predicting dry eye disease (DED) class and grade of severity by the automated system.

Another object of the present invention is to provide a novel machine-vision based method of processing time and date stamped digital images of a human eye formed, captured and detected by a mobile smartphone camera system, and processed to automatically detect and measure the tear film dynamics in the human eye at a particular time and date by real-time changes in the measurement of tear meniscus height (TMH) in between eye blinks, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network designed to support and enable automated detection and measurement and mapping of the speed of blinking in the human eyes photographically represented in a times series of digital images (e.g. video recording) of a front view of human eyes formed and captured by a mobile smartphone camera.

Another object of the present invention is to provide a novel method of automated recognition of dry eye disease (DED) conditions, (i) where the speed of eye blinks are detected, and measured in the human eye in the photographic image, and (ii) which pixel region of interest (ROI) requires pixel data processing according to a method of digital image processing using the machine-based ophthalmic image processing engine of the present invention operating on one or more front view digital images of the human eye, so as to automatically map changes in eye blinking speed, as an indication of ocular disease recognition, treatment and manage care, including predicting dry eye disease (DED) class and grade of severity by the automated system.

Another object of the present invention is to provide a novel machine-vision based method of processing time and date stamped digital images of a human eye captured by a mobile smartphone camera system, so as to automatically detect the speed and patterns of eye blinking in the human eye at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network to support and enable automated detection and measurement of corneal abrasions in the human eyes photographically represented in digital images of a front view of human eyes formed and captured by a mobile smartphone camera system.

Another object of the present invention is to provide a novel deep-learning machine-vision ocular image processing and classification system (i.e. "engine") configured and trained for use and deployment on a system network, to support and enable an automated method (M10) of detection and measurement of corneal abrasions scratches in the human eyes photographically represented in digital images of a front view of human eyes formed, captured and detected by a mobile smartphone camera system configured and operating in accordance with the principles of the present invention.

Another object of the present invention is to provide a new and improved machine-vision based method of processing time and date stamped digital images of a human eye formed, captured and detected by a mobile smartphone camera system and processed to automatically detect and measure corneal abrasions in the human eye at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") configured and trained for use and deployment on a system network, to support and enable an automated method (M11) of method of detection and measurement of palpebral fissure (PF) in the human eyes photographically represented in digital images of a front view of human eyes formed and captured by a mobile smartphone camera system in accordance with the principles of the present invention.

Another object of the present invention is to provide a novel machine-vision based method of processing time and date stamped digital images of a human eye captured by a mobile smartphone camera system and processed to automatically detect palpebral fissure (PF) in the human eye at a particular time and date, to support automated ocular disease recognition, treatment and manage care, including predicting dry eye disease (DED) class and grade of severity by the automated system.

Another object of the present invention is to provide a deep-learning machine-vision ocular image processing and classification system (i.e. "engine") of the present invention configured and trained for use and deployment on a system network, to support and enable automated method (M12) of detection and measurement of the margin reflex distance (MRD) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect margin reflex distance (MRD) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on the system network, to support and enable automated method (M13) of detection and measurement of scleral show (SS) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect scleral show (SS) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M14) of detection and measurement of levator function (LF) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect the levator function in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M15) of detection and measurement of the contact lens overwear (CLOW) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect contact lens overwear (CLOW) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M16) of detection and measurement of corneal transplant graft rejection (CTGR) of the human eyes photographically represented in digital images of a front view of human eyes formed and captured by a mobile smartphone camera system.

Another object of the present invention is to provide a new and improved a machine-vision based method of processing time and date stamped digital images of a human eye captured by a mobile smartphone camera system and processed to automatically detect corneal transplant graft rejection (CTGR) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on the system network, to support and enable an automated method (M18) of detection and measurement of a cataract in the human eye photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect a cataract in the human eye at a particular time and date, to support automated ocular disease recognition, treatment and manage care, including predicting dry eye disease (DED) class and grade of severity.

Another object of the present invention is to provide a new and improved deep-learning machine-vision ocular image processing and classification system (i.e. "engine") configured and trained for use and deployment on a system network, to support and enable an automated method (M18) of method of detection and measurement of viral conjunctivitis (VCJ) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect viral conjunctivitis (VCJ) in the human eye at a particular time and date to support automated ocular disease recognition, treatment and manage care, including predicting dry eye disease (DED) class and grade of severity by the automated system by the automated system.

Another object of the present invention is to provide a new and improved deep-learning machine-vision ocular image processing and classification system (i.e. "engine") configured and trained for use and deployment on the system network, to support and enable an automated method (M19) of detection and measurement of bacterial conjunctivitis (BCJ) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect bacterial conjunctivitis (BCJ) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M20) of method of detection and measurement of allergic conjunctivitis (ACJ) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect allergic conjunctivitis (ACJ) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") of the present invention configured and trained for use and deployment on a system network, to support and enable an automated method (M21) of detection and measurement of chemical burn conjunctivitis (CBCJ) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect chemical burn conjunctivitis (CBCJ) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M22) of detection and measurement of pterygium/pinguecula (PP) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect pterygium/pinguecula (PP) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M23)

of detection and measurement of subconjunctival hemorrhage (SCH) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect subconjunctival hemorrhage (SCH) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M24) of detection and measurement of subconjunctival laceration (CJL) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect subconjunctival laceration (CJL) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M25) of detection and measurement of episcleritis/scleritis in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect episcleritis/scleritis in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M26) of detection and measurement of superior limbic keratoconjunctivitiskeratoconjunctivitis (SLK) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect superior limbic keratoconjunctivitiskeratoconjunctivitis (SLK) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M27) of detection and measurement of blepharitisblepharitis (BH) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect blepharitisblepharitis (BH) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M28) of detection and measurement of chalazion/styes (CS) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect chalazion/styes in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M29) of detection and measurement of eyelid cysts (EC) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect eyelid cysts (EC) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M30) of detection and measurement of preseptal cellulitis (PC) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect preseptal cellulitis (PC) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M31) of detection and measurement of ptosis (PT) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect ptosis in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M32) of method of detection and measurement of ophthalmoplegiaophthalmoplegia (OPM) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect ophthalmoplegiaophthalmoplegia (OPM) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M33) of method of detection and measurement of proptosis/hypoglobus (HP) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect proptosis/hypoglobus (HP) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M34) of method of detection and measurement of anisocoria (ACR) of the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect anisocoria (ACR) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M35) of detection and measurement of anterior chamber depth (ACD) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect anterior chamber depth (ACD) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M36) of detection and measurement of orbital post septal cellulitis (OPSC) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect orbital post septal cellulitis (OPSC) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M37) of detection and measurement of thyroid eye disease (TED) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect thyroid eye disease (TED) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on the system network, to support and enable an automated method (M38) of method of detection and measurement of entropion/ ectropion in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect entropion/ectropion in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M39) of detection and measurement of trichiasistrichiasis/disti- chiasis (T/D) in the human eyes photographically repre- sented in digital images of a front view of human eyes formed and captured by a mobile smartphone camera sys- tem.

Another object of the present invention is to provide a new and improved machine-vision based method of pro- cessing time and date stamped digital images of a human eye captured by a mobile smartphone camera system and pro- cessed to automatically detect trichiasistrichiasis/distichiasis (T/D) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M40) of detection and measurement of floppy eyelid syndrome (FES) in the human eyes photographically represented in digital images of a front view of human eyes formed and captured by a mobile smartphone camera system.

Another object of the present invention is to provide a new and improved machine-vision based method of pro- cessing time and date stamped digital images of a human eye captured by a mobile smartphone camera system and pro- cessed to automatically detect floppy eyelid syndrome (FES) in the human eye at a particular time and date, to support automated ocular disease recognition, treatment and manage care, including predicting dry eye disease (DED) class and grade of severity by the automated system by the automated system.

Another object of the present invention is to provide a new and improved deep-learning machine-vision ocular image processing and classification system (i.e. "engine") configured and trained for use and deployment on a system network, to support and enable an automated method (M41) of detection and measurement of herpes zoster dermatitis (HZD) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect herpes zoster dermatitis (HZD) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M42) of detection and measurement of herpes zoster keratitis (HZK) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect herpes zoster keratitis (HZK) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M43) of method of detection and measurement of herpes simplex virus keratitis (HSVK) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect herpes simplex virus keratitis (HSVK) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M44) of detection and measurement of ophthalmic postoperative complications (OPOS) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect ophthalmic postoperative complications (OPOS) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M45) of detection and measurement of corneal infection (CI) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect corneal infection (CI) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M46) of detection and measurement of corneal foreign body (CFB) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect corneal foreign body (CFB) in the human eye at a particular time and date, to support automated ocular disease recognition, treatment and manage care, including predicting dry eye disease (DED) class and grade of severity by the automated system.

Another object of the present invention is to provide a new and improved deep-learning machine-vision ocular image processing and classification system (i.e. "engine") configured and trained for use and deployment on a system network, to support and enable an automated method (M47) of detection and measurement of acute angle closure glaucoma (AACG) in the human eyes photographically represented in digital images of a front view of human eyes formed and captured by a mobile smartphone camera system.

Another object of the present invention is to provide a new and improved machine-vision based method of processing time and date stamped digital images of a human eye captured by a mobile smartphone camera system and processed to automatically detect acute angle closure glaucoma (AACG) in the human eye at a particular time and date, to support automated ocular disease recognition, treatment and manage care, including predicting dry eye disease (DED) class and grade of severity by the automated system.

Another object of the present invention is to provide a novel deep-learning machine-vision ocular image processing and classification system (i.e. "engine") with convolutional neural networks (CNNs) configured and trained for use and deployment on a system network designed to support and enable automated detection and measurement of dry eye disease (DED) condition in the human eyes photographically represented in digital images of human eyes formed and captured by a mobile smartphone camera system.

Another object of the present invention is to provide a novel process of loading, training and operating an automated deep-learning machine-vision recognition system supported by standard Python libraries supporting automated image feature extraction and classification, ocular object detection, and dry eye disease (DED) condition recognition, comprising the steps of (a) loading the pixel dataset of patient ocular images into the database of a deep learning machine-vision recognition system, (b) preparing the pixel dataset for deep learning machine-vision recognition, (c) defining a baseline end-to-end convolutional neural network (CNN) model, (d) evaluating the baseline CNN model and its recognition performance on input pixel datasets, and (e) presenting the DED condition recognition results produced from the deep-learning machine-vision recognition system.

Another object of the present invention is to provide a novel system network for deploying the automotive system with onboard ophthalmic image capturing and processing subsystem supporting real-time automated machine-assisted recognition of ocular conditions in the eyes of the automotive system driver, comprising (i) mobile visible-wavelength operating digital image capturing systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers supporting the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the aircraft system with onboard ophthalmic image capturing and processing subsystem supporting real-time automated machine-assisted recognition of ocular conditions in the eyes of the aircraft pilot, comprising (i) mobile visible-wavelength operating digital image capturing systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the industrial machinery system with onboard ophthalmic image capturing and processing subsystem supporting real-time automated machine-assisted recognition of ocular conditions in the eyes of the operator, comprising (i) mobile visible-wavelength operating digital image capturing (i.e. camera) systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the office workstation system with onboard ophthalmic image capturing and processing subsystem supporting real-time automated machine-assisted recognition of ocular conditions in the eyes of the worker, comprising (i) mobile visible-wavelength operating digital image capturing systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the portable workstation system with onboard ophthalmic image capturing and processing subsystem supporting real-time automated machine-assisted recognition of dry eye conditions in the eyes of the worker, comprising (i) mobile visible-wavelength operating digital image capturing systems for use by patients and users whose eyes are to be monitored and care for using the system, (ii) clinical ophthalmic decision workstations, and real-time ophthalmic image driven dry eye disease (DED) condition recognition engines realized and supported within data centers deployed around the world, (iii) local environmental monitoring stations and third-party data provider platforms, (iv) a global navigation satellite system (GNSS)

comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the telemedicine or tele-health system with onboard ophthalmic image capturing and processing subsystem supporting real-time automated machine-assisted recognition of ocular conditions in the eyes of the worker, comprising (i) mobile visible-wavelength operating smartphone image capturing systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the laptop computer system with onboard ophthalmic image capturing and processing subsystem supporting real-time automated machine-assisted recognition of ocular conditions in the eyes of the user, comprising (i) mobile visible-wavelength operating digital image capturing systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the video game system, including mobile, computer and console, with onboard ophthalmic image capturing and processing subsystem supporting real-time automated machine-assisted recognition of dry eye conditions in the eyes of the gamer, comprising (i) mobile visible-wavelength operating digital image capturing systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the smart television system with onboard ophthalmic image capturing and processing subsystem supporting real-time automated machine-assisted recognition of ocular conditions in the eyes of the viewers, comprising (i) visible-wavelength operating digital image capturing systems embedded within the television system for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the virtual reality and/or augmented reality headset systems with onboard ophthalmic image capturing and processing subsystem supporting real-time automated machine-assisted recognition of ocular conditions in the eyes of the users, comprising (i) visible-wavelength operating digital image capturing systems embedded within the headset systems for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the smart eye glasses system with onboard ophthalmic image capturing and processing subsystem supporting real-time automated machine-assisted recognition of dry eye conditions in the eyes of the viewers, comprising (i) visible-wavelength operating digital image capturing systems embedded within the smart eye glasses for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

Another object of the present invention is to provide a novel system network deploying the smart contact lens system with onboard ophthalmic image capturing and processing subsystem supporting real-time automated machine-assisted recognition of dry eye conditions in the eyes of the viewers, comprising (i) visible-wavelength operating digital image capturing systems embedded within the smart contact lens for use by patients and users whose eyes are to be monitored and care for using the system, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network.

These and other objects will become more apparent hereinafter in view of the Detailed Description and pending Claims to Invention.

BRIEF DESCRIPTION OF THE DRAWINGS

In order to more fully understand the Objects, the following Detailed Description of the illustrative embodiments should be read in conjunction with the accompanying Drawings, wherein:

FIG. 5 is a table listing various prior art imaging modalities used to image features in the anterior segment of the human eye, often employed in particular AI-supported diagnostic applications;

FIG. 8A is a schematic representation of the mobile ophthalmic image capturing and processing system network of the present invention illustrated in FIG. 7, and adapted for automated machine-vision assisted recognition of ocular diseases, including dry eye disease and other anterior eye segment diseases, prescription of ocular disease treatment, and assessment of treatment response, showing in greater detail subsystems including (i) mobile visible-wavelength operating digital image capturing systems (e.g. smartphone camera systems) for use by patients and users whose eyes are to be monitored and care for using the system of the present invention, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 11 is a table listing the various functions supported by the automated ocular disease (OD) condition recognition methods and supporting wireless system network of the present invention;

Figure 14D:
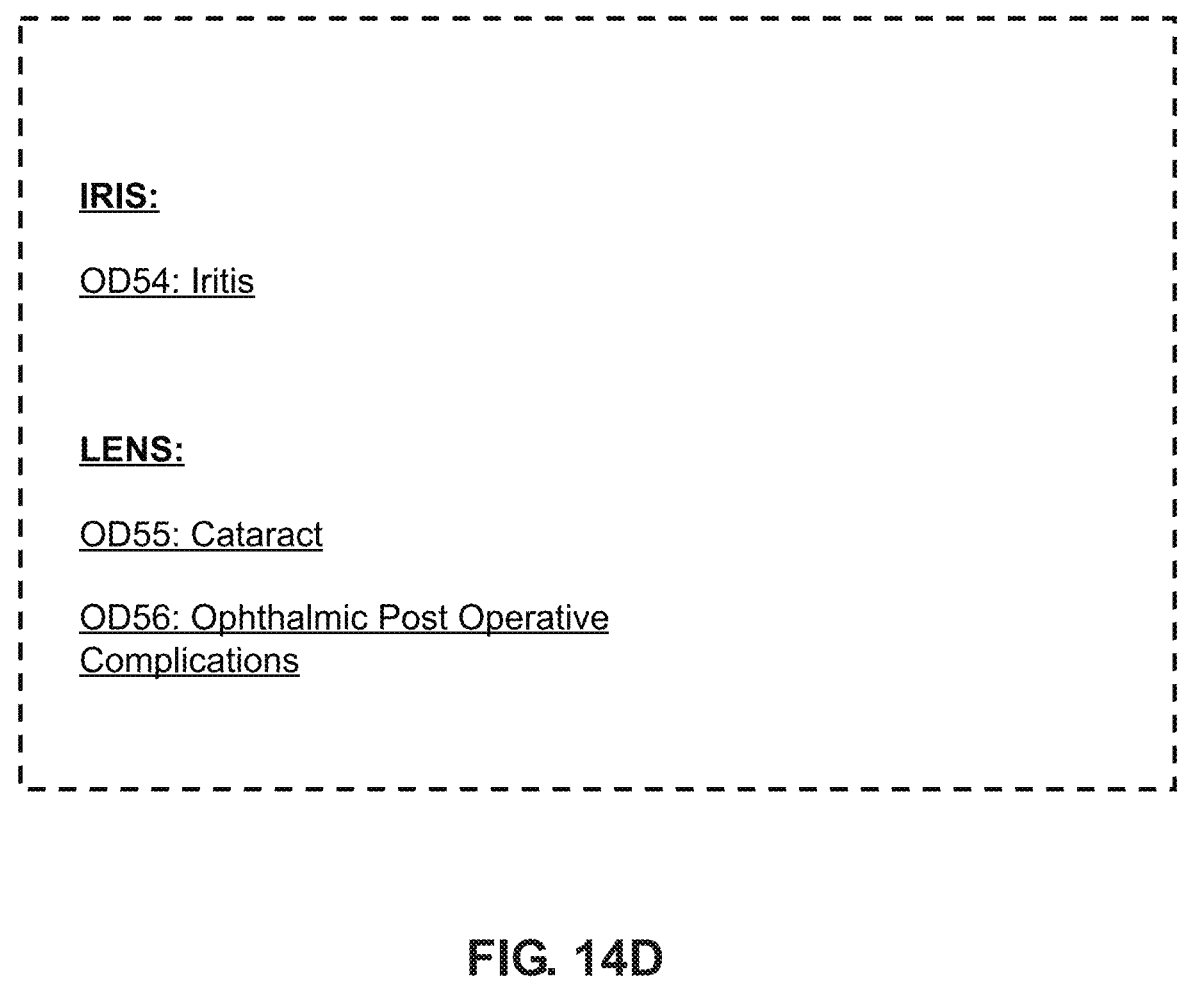

FIGS. 14A, 14B, 14C and 14D, taken together, show a list of exemplary ocular diseases (OD) associated with the anterior segment of the human eye, that can be automatically recognized, treated and managed with care by the system network of the present invention upon processing the various patient data input factors provided to the system network using the patient's mobile visible-wavelength operating smartphone camera device registered with the system network;

FIG. 15 is a schematic representation of a data record of the personal and demographic data of a patient, used as ocular disease factors to support the system network of the present invention;

FIG. 16 is a schematic representation of a data record on the contact lens worn by a patient, and content lens use, used as ocular disease factors to support the system network of the present invention;

FIG. 17 is a schematic representation of a data record of the eye pathology of a patient; used as ocular disease factors to support the system network of the present invention;

FIG. 18 is a schematic representation of a data record of the ocular medications taken by a patient, used as ocular disease factors to support the system network of the present invention;

FIG. 19 is a schematic representation of a data record of the ophthalmic surgery of a patient, used as ocular disease factors to support the system network of the present invention;

FIG. 20 is a schematic representation of a data record of the systemic disease of a patient, used as ocular disease factors to support the system network of the present invention;

FIG. 21 is a schematic representation of a data record of the systemic surgery of a patient, used as ocular disease factors to support the system network of the present invention;

FIG. 22 is a schematic representation of a data record of the systemic medications of a patient, used as ocular disease factors to support the system network of the present invention;

FIG. 25 is a schematic representation of a data record of the environment of a patient, used as ocular disease factors to support the system network of the present invention;

FIG. 26 is a schematic representation of a data record of the vision functionality of a patient, used as ocular disease factors to support the system network of the present invention;

FIG. 27 is a schematic representation of a data record of a summary of risk factors (e.g. demographic, contact lens, trauma, surgery, ocular medications, systemic medication, eye disease, systemic disease and other) experienced by a patient and used as ocular disease factors to support the system network of the present invention;

FIG. 28 is a schematic representation of a data record of the symptoms experienced by a patient, used as ocular disease factors to support the system network of the present invention;

FIG. 29 is a schematic representation of a data record of the in-office exam of a patient, used as ocular disease factors to support the system network of the present invention;

FIG. 30 is a table consisting of the data elements of the exam and in-office testing data records shown in FIG. 29, used as ocular disease factors to support the system network of the present invention

FIG. 33 is a schematic representation of a data record of the compliance factors of a patient (e.g. medication, image/video, symptoms, vision and depression), used as ocular disease factors to support the system network of the present invention;

FIGS. 34A and 34B, taken together, shows a list describing the various kinds of ocular disease (OD) conditions that can be automatically detected and recognized using the image-based machine-vision processing methods described in FIGS. 34A and 34B, and specified in FIGS. 68 through 64B, and FIGS. 46 through 68A, and FIGS. 82 through 239B;

FIG. 34C shows a list describing the various kinds of ocular disease conditions that can be automatically detected and recognized using video-based machine-vision processing methods as described in in FIG. 34C, and specified in FIGS. 69 through 81C;

FIGS. 35A, 35B and 35C, taken together, show a table listing ocular disease condition treatment and management prescriptions/recommendations that may be automatically determined by the system network of the present invention, wherein each treatment and management recommendation is coded for logical application and management within the system;

FIG. 36A is a schematic specification of a logic package installed and operative within the automated ocular disease (OD) recognition, treatment and compliance management system of the present invention, biomedically-engineered for the ocular disease afflicting the eyelids/orbit, specifically—Ptosis—and assigned ocular disease code OD01, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36B is a schematic specification of logic packages installed and operative within the automated ocular disease (OD) recognition, treatment and compliance management system of the present invention, biomedically-engineered for (a) the ocular disease afflicting the eyelids/orbit, specifically—Chalazion/Stye—and assigned ocular disease code OD02, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36C is a schematic specification of logic packages installed and operative within the automated ocular disease (OD) recognition, treatment and compliance management system of the present invention, biomedically-engineered for the ocular disease afflicting the eyelids/orbit, specifically—Eyelid Cyst—and assigned ocular disease code OD03, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36D is a schematic specification of a logic package installed and operative within the automated ocular disease (OD) recognition, treatment and compliance management system of the present invention, biomedically-engineered for the ocular disease afflicting the eyelids/orbit, specifically—Ectropion—and assigned ocular disease code OD4, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36E is a schematic specification of a logic package installed and operative within the automated ocular disease (OD) recognition, treatment and compliance management system of the present invention, biomedically-engineered for the ocular disease afflicting the eyelids/orbit, specifically—Entropion—and assigned ocular disease code OD5, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36F is a schematic specification of a logic package installed and operative within the automated ocular disease (OD) recognition, treatment and compliance management system of the present invention, biomedically-engineered for the ocular disease afflicting the eyelids/orbit, specifically—Trichiasis—and assigned ocular disease code OD6, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36G is a schematic specification of a logic package installed and operative within the automated ocular disease (OD) recognition, treatment and compliance management system of the present invention, biomedically-engineered for the ocular disease afflicting the eyelids/orbit, specifically—Distichiasis—and assigned ocular disease code OD7, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36H is a schematic specification of a logic package installed and operative within the automated ocular disease (OD) recognition, treatment and compliance management system of the present invention, biomedically-engineered for the ocular disease afflicting the eyelids/orbit, specifically—Floppy Eyelid Syndrome—and assigned ocular disease code OD8, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36I is a schematic specification of a logic package installed and operative within the automated ocular disease (OD) recognition, treatment and compliance management system of the present invention, biomedically-engineered for the ocular disease afflicting the eyelids/orbit, specifically—Blepharospasm—and assigned ocular disease code OD9, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36J is a schematic specification of a logic package installed and operative within the automated ocular disease (OD) recognition, treatment and compliance management system of the present invention, biomedically-engineered for the ocular disease afflicting the eyelids/orbit, specifically—Dacryocystitis—and assigned ocular disease code OD10, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36K is a schematic specification of a logic package installed and operative within the automated ocular disease (OD) recognition, treatment and compliance management system of the present invention, biomedically-engineered for the ocular disease afflicting the eyelids/orbit, specifically—Canaliculitis—and assigned ocular disease code OD11, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36L is a schematic specification of a logic package installed and operative within the automated ocular disease (OD) recognition, treatment and compliance management system of the present invention, biomedically-engineered for the ocular disease afflicting the eyelids/orbit, specifically—Preseptal Cellulitis (i.e. Eyelid Swelling)—and assigned ocular disease code OD12, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36M is a schematic specification of a logic package installed and operative within the automated ocular disease (OD) recognition, treatment and compliance management system of the present invention, biomedically-engineered for the ocular disease afflicting the eyelids/orbit, specifically—Orbital Postseptal Cellulitis—and assigned ocular disease code OD13, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36N is a schematic specification of a logic package installed and operative within the automated ocular disease (OD) recognition, treatment and compliance management system of the present invention, biomedically-engineered for the ocular disease afflicting the eyelids/orbit, specifically—Proptosis—and assigned ocular disease code OD14, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36O is a schematic specification of a logic package installed and operative within the automated ocular disease (OD) recognition, treatment and compliance management system of the present invention, biomedically-engineered for the ocular disease afflicting the eyelids/orbit, specifically—Orbital Fracture—and assigned ocular disease code OD15, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36P is a schematic specification of a logic package installed and operative within the automated ocular disease (OD) recognition, treatment and compliance management system of the present invention, biomedically-engineered for the ocular disease afflicting the eyelids/orbit, specifically—Thyroid Eye Disease—and assigned ocular disease code OD16, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36Q is a schematic specification of a logic package installed and operative within the automated ocular disease (OD) recognition, treatment and compliance management system of the present invention, biomedically-engineered for the ocular disease afflicting the eyelids/orbit, specifically—Blepharitis—and assigned ocular disease code OD17, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36R is a schematic specification of a logic package installed and operative within the automated ocular disease (OD) recognition, treatment and compliance management system of the present invention, biomedically-engineered for the ocular disease afflicting the eyelids/orbit, specifically—Herpes Zoster Dermatitis (i.e. Shingles)—and assigned ocular disease code OD18, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36S is a schematic specification of a logic package installed and operative within the automated ocular disease (OD) recognition, treatment and compliance management system of the present invention, biomedically-engineered for the ocular disease afflicting the eyelids/orbit, specifically—Retrobulbar Hemorrhage—and assigned ocular disease code OD19, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36T is a schematic specification of a logic package installed and operative within the automated ocular disease (OD) recognition, treatment and compliance management system of the present invention, biomedically-engineered for the ocular disease afflicting the sclera/conjunctiva, specifically—Viral Conjunctivitis—and assigned ocular disease code OD20, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36U is a schematic specification of a logic package installed and operative within the automated ocular disease (OD) recognition, treatment and compliance management system of the present invention, biomedically-engineered for the ocular disease afflicting the sclera/conjunctiva, specifically—Bacterial Conjunctivitis—and assigned ocular disease code OD21, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36V is a schematic specification of a logic package installed and operative within the automated ocular disease (OD) recognition, treatment and compliance management system of the present invention, biomedically-engineered for the ocular disease afflicting the sclera/conjunctiva, specifically—Allergic Conjunctivitis—and assigned ocular disease code OD22, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36W is a schematic specification of a logic package installed and operative within the automated ocular disease (OD) recognition, treatment and compliance management system of the present invention, biomedically-engineered for the ocular disease afflicting the sclera/conjunctiva, specifically—Chemical Burn Conjunctivitis—and assigned ocular disease code OD23, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36X is a schematic specification of a logic package installed and operative within the automated ocular disease (OD) recognition, treatment and compliance management system of the present invention, biomedically-engineered for the ocular disease afflicting the sclera/conjunctiva, specifically—Superior Limbic Keratoconjunctivititis—and assigned ocular disease code OD24, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36Y is a schematic specification of a logic package installed and operative within the automated ocular disease (OD) recognition, treatment and compliance management system of the present invention, biomedically-engineered for the ocular disease afflicting the sclera/conjunctiva, specifically—Subconjunctival Hemorrhage—and assigned ocular disease code OD25, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36Z is a schematic specification of a logic package installed and operative within the automated ocular disease (OD) recognition, treatment and compliance management system of the present invention, biomedically-engineered for the ocular disease afflicting the sclera/conjunctiva, specifically—Episceritis/Scleritis—and assigned ocular disease code OD26, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36AA is a schematic specification of a logic package installed and operative within the automated ocular disease (OD) recognition, treatment and compliance management system of the present invention, biomedically-engineered for the ocular disease afflicting the sclera/conjunctiva, specifically—Conjunctivival Laceration—and assigned ocular disease code OD27, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36BB is a schematic specification of a logic package installed and operative within the automated ocular disease (OD) recognition, treatment and compliance management system of the present invention, biomedically-engineered for the ocular disease afflicting the sclera/conjunctiva, specifically—Herpes Zoster Conjunctivitis—and assigned ocular disease code OD28, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36CC is a schematic specification of a logic package installed and operative within the automated ocular disease (OD) recognition, treatment and compliance management system of the present invention, biomedically-engineered for the ocular disease afflicting the sclera/conjunctiva, specifically—Pemphigold—and assigned ocular disease code OD29, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36DD is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36EE is a schematic specification of a logic package for staged management installed and operative within the automated ocular disease (OD) recognition, treatment and compliance management system of the present invention, biomedically-engineered for the ocular disease afflicting the cornea, specifically—Dry Eye Disease (DED) Staged Management—and assigned ocular disease code OD30-DED (i.e. staged treatment code TM63), wherein the logic package specifies staged management logic rules for the various ocular disease conditions under dry eye disease (DED);

FIG. 36FF is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED01 Primary Sjogren's Disease, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36GG is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED02 Secondary Sjogren's Disease, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36HH is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED03 Lacrimal Gland Dysfunction, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36II is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED04 Lacrimal Gland Duct Dysfunction, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36JJ is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED05 Corneal Reflex Block, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36KK is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED06 Systemic Medications Side Effect, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36LL is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED07 Meibomian Gland Dysfunction, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36MM is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED08 Lid Aperture Abnormality, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36NN is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED09 Lid Function Abnormality, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36OO is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED10 Blink Abnormality, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36PP is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED11 Topical Drop Toxicity, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36QQ is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED12 Contact Lens Overwear, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36RR is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED13 Ocular Surface Disease, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36SS is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED14 Vitamin A Deficiency, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36TT is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED15 Occupational Dry Eye, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36UU is a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD31-DED 16 Environmental Dry Eye, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36VV is a schematic specification of a logic package installed and operative within the automated ocular disease (OD) recognition, treatment and compliance management system of the present invention, biomedically-engineered for the ocular disease afflicting the cornea, specifically—Corneal Abrasion—and assigned ocular disease code OD31, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36WW is a schematic specification of a logic package installed and operative within the automated ocular disease (OD) recognition, treatment and compliance management system of the present invention, biomedically-engineered for the ocular disease afflicting the cornea, specifically—Corneal Foreign Body—and assigned ocular disease code OD32, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36XX is a schematic specification of a logic package installed and operative within the automated ocular disease (OD) recognition, treatment and compliance management system of the present invention, biomedically-engineered for the ocular disease afflicting the cornea, specifically—Bacterial Keratitis—and assigned ocular disease code OD33, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36YY is a schematic specification of a logic package installed and operative within the automated ocular disease (OD) recognition, treatment and compliance management system of the present invention, biomedically-engineered for the ocular disease afflicting the cornea, specifically—Herpes Simplex Virus Keratitis—and assigned ocular disease code OD34, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36ZZ is a schematic specification of a logic package installed and operative within the automated ocular disease (OD) recognition, treatment and compliance management system of the present invention, biomedically-engineered for the ocular disease afflicting the cornea, specifically—Herpes Zoster Keratitis—and assigned ocular disease code OD35, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36AAA is a schematic specification of a logic package installed and operative within the automated ocular disease (OD) recognition, treatment and compliance management system of the present invention, biomedically-engineered for the ocular disease afflicting the cornea, specifically—Acanthamoeba Keratitis—and assigned ocular disease code OD36, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36BBB is a schematic specification of a logic package installed and operative within the automated ocular disease (OD) recognition, treatment and compliance management system of the present invention, biomedically-engineered for the ocular disease afflicting the cornea, specifically—Recurrent Corneal Erosion—and assigned ocular disease code OD37, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36CCC is a schematic specification of a logic package installed and operative within the automated ocular disease (OD) recognition, treatment and compliance management system of the present invention, biomedically-engineered for the ocular disease afflicting the cornea, specifically—Exposure Keratopathy—and assigned ocular disease code OD38, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36DDD is a schematic specification of a logic package installed and operative within the automated ocular disease (OD) recognition, treatment and compliance management system of the present invention, biomedically-engineered for the ocular disease afflicting the cornea, specifically—Neurotrophic Keratopathy—and assigned ocular disease code OD39, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36EEE is a schematic specification of a logic package installed and operative within the automated ocular disease (OD) recognition, treatment and compliance management system of the present invention, biomedically-engineered for the ocular disease afflicting the cornea, specifically—Peripheral Ulcerative Keratitis—and assigned ocular disease code OD40, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36FFF is a schematic specification of a logic package installed and operative within the automated ocular disease (OD) recognition, treatment and compliance management system of the present invention, biomedically-engineered for the ocular disease afflicting the cornea, specifically—Pterygium—and assigned ocular disease code OD41, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36GGG is a schematic specification of a logic package installed and operative within the automated ocular disease (OD) recognition, treatment and compliance management system of the present invention, biomedically-engineered for the ocular disease afflicting the cornea, specifically—Pinguecula—and assigned ocular disease code OD42, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36HHH is a schematic specification of a logic package installed and operative within the automated ocular disease (OD) recognition, treatment and compliance management system of the present invention, biomedically-engineered for the ocular disease afflicting the cornea, specifically—Pinguecultitis—and assigned ocular disease code OD43, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36III is a schematic specification of a logic package installed and operative within the automated ocular disease (OD) recognition, treatment and compliance management system of the present invention, biomedically-engineered for the ocular disease afflicting the cornea, specifically—Contact Lens Keratitis—and assigned ocular disease code OD44, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36JJJ is a schematic specification of a logic package installed and operative within the automated ocular disease (OD) recognition, treatment and compliance management system of the present invention, biomedically-engineered for the ocular disease afflicting the cornea, specifically—Corneal Transplant Grant Rejection—and assigned ocular disease code OD45, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36KKK is a schematic specification of a logic package installed and operative within the automated ocular disease (OD) recognition, treatment and compliance management system of the present invention, biomedically-engineered for the ocular disease afflicting the cornea, specifically—Keratoconus—and assigned ocular disease code OD46, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36LLL is a schematic specification of a logic package installed and operative within the automated ocular disease (OD) recognition, treatment and compliance management system of the present invention, biomedically-engineered for the ocular disease afflicting the eye, specifically—Acute Angle Closure Glaucoma—and assigned ocular disease code OD47, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36MMM is a schematic specification of a logic package installed and operative within the automated ocular disease (OD) recognition, treatment and compliance management system of the present invention, biomedically-engineered for the ocular disease afflicting the eye, specifically—Glaucoma Drop Allergy—and assigned ocular disease code OD48, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36NNN is a schematic specification of a logic package installed and operative within the automated ocular disease (OD) recognition, treatment and compliance management system of the present invention, biomedically-engineered for the ocular disease afflicting the eye, specifically—Anisocoria—and assigned ocular disease code OD49, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36OOO is a schematic specification of a logic package installed and operative within the automated ocular disease (OD) recognition, treatment and compliance management system of the present invention, biomedically-engineered for the ocular disease afflicting the eye, specifically—Homer's Syndrome—and assigned ocular disease code OD50, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36PPP is a schematic specification of a logic package installed and operative within the automated ocular disease (OD) recognition, treatment and compliance management system of the present invention, biomedically-engineered for the ocular disease afflicting the eye, specifically—Third Nerve Palsy—and assigned ocular disease code OD51, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36QQQ is a schematic specification of a logic package installed and operative within the automated ocular disease (OD) recognition, treatment and compliance management system of the present invention, biomedically-engineered for the ocular disease afflicting the eye, specifically—Fourth/Sixth Nerve Palsy—and assigned ocular disease code OD52, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36RRR is a schematic specification of a logic package installed and operative within the automated ocular disease (OD) recognition, treatment and compliance management system of the present invention, biomedically-engineered for the ocular disease afflicting the eye, specifically—Bell's Palsy—and assigned ocular disease code OD53, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36SSS is a schematic specification of a logic package installed and operative within the automated ocular disease (OD) recognition, treatment and compliance management system of the present invention, biomedically-engineered for the ocular disease afflicting the iris, specifically—Irisitis—and assigned ocular disease code OD54, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36TTT is a schematic specification of a logic package installed and operative within the automated ocular disease (OD) recognition, treatment and compliance management system of the present invention, biomedically-engineered for the ocular disease afflicting the lens, specifically—Cataract—and assigned ocular disease code OD55, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

FIG. 36UUU is a schematic specification of a logic package installed and operative within the automated ocular disease (OD) recognition, treatment and compliance management system of the present invention, biomedically-engineered for the ocular disease afflicting the lens, specifically—Ophthalmic Post Operative Complications—and assigned ocular disease code OD56, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease;

Figure 9A:
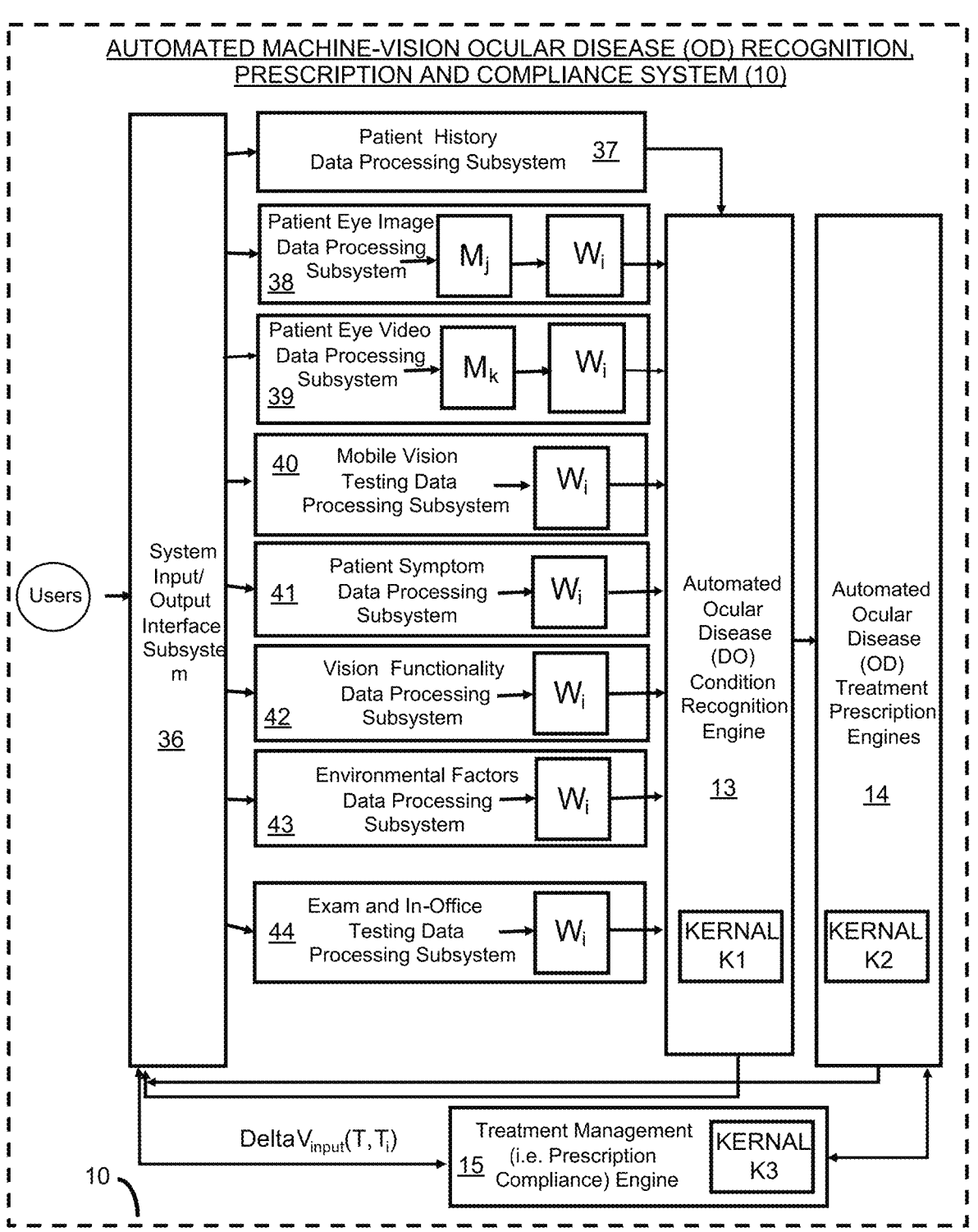
FIG. 9A is schematic representation of the system architecture of the automated machine-vision driven ocular disease (OD) recognition, treatment and compliance system of the present invention.
Figure 39:
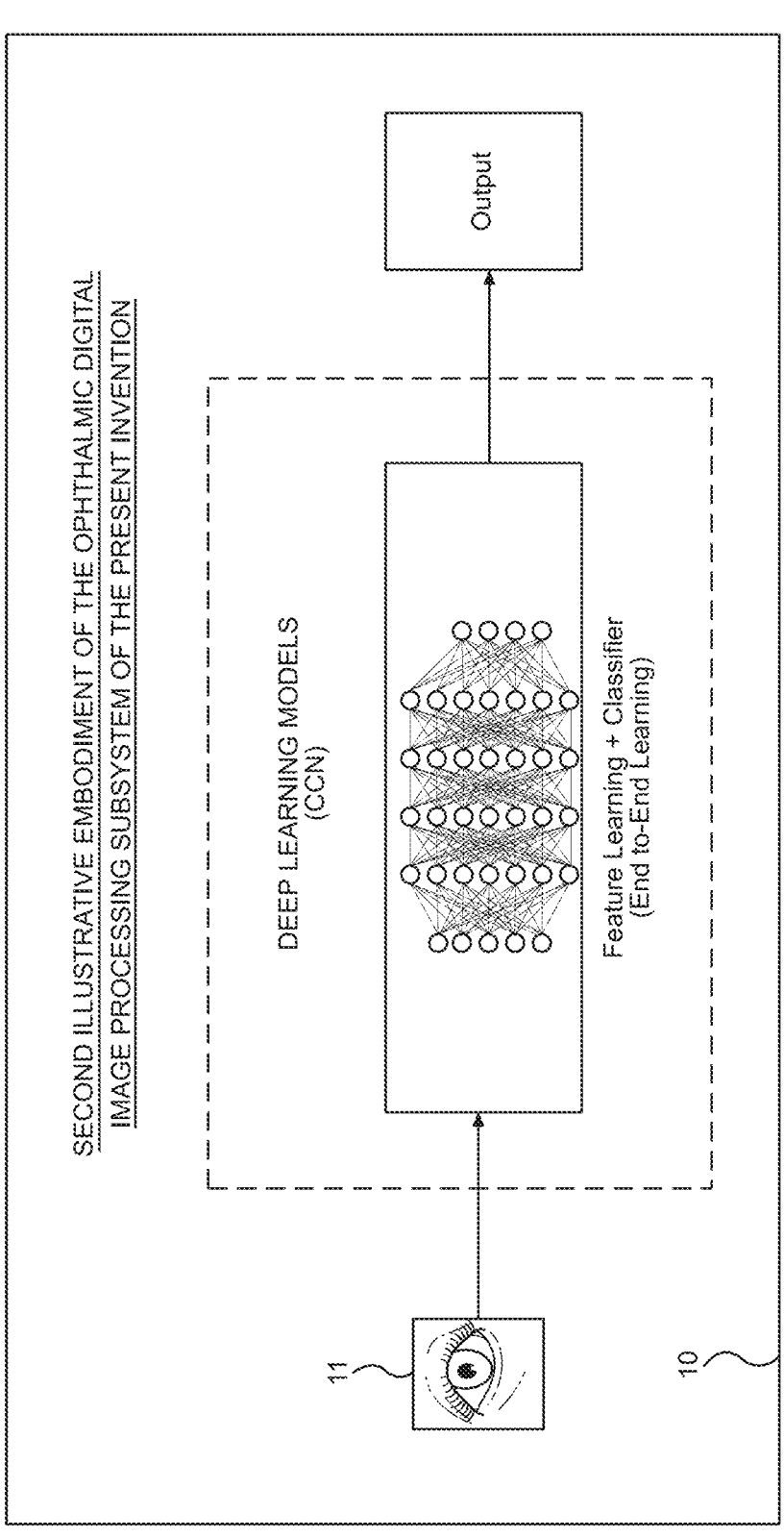
Figure 40A:
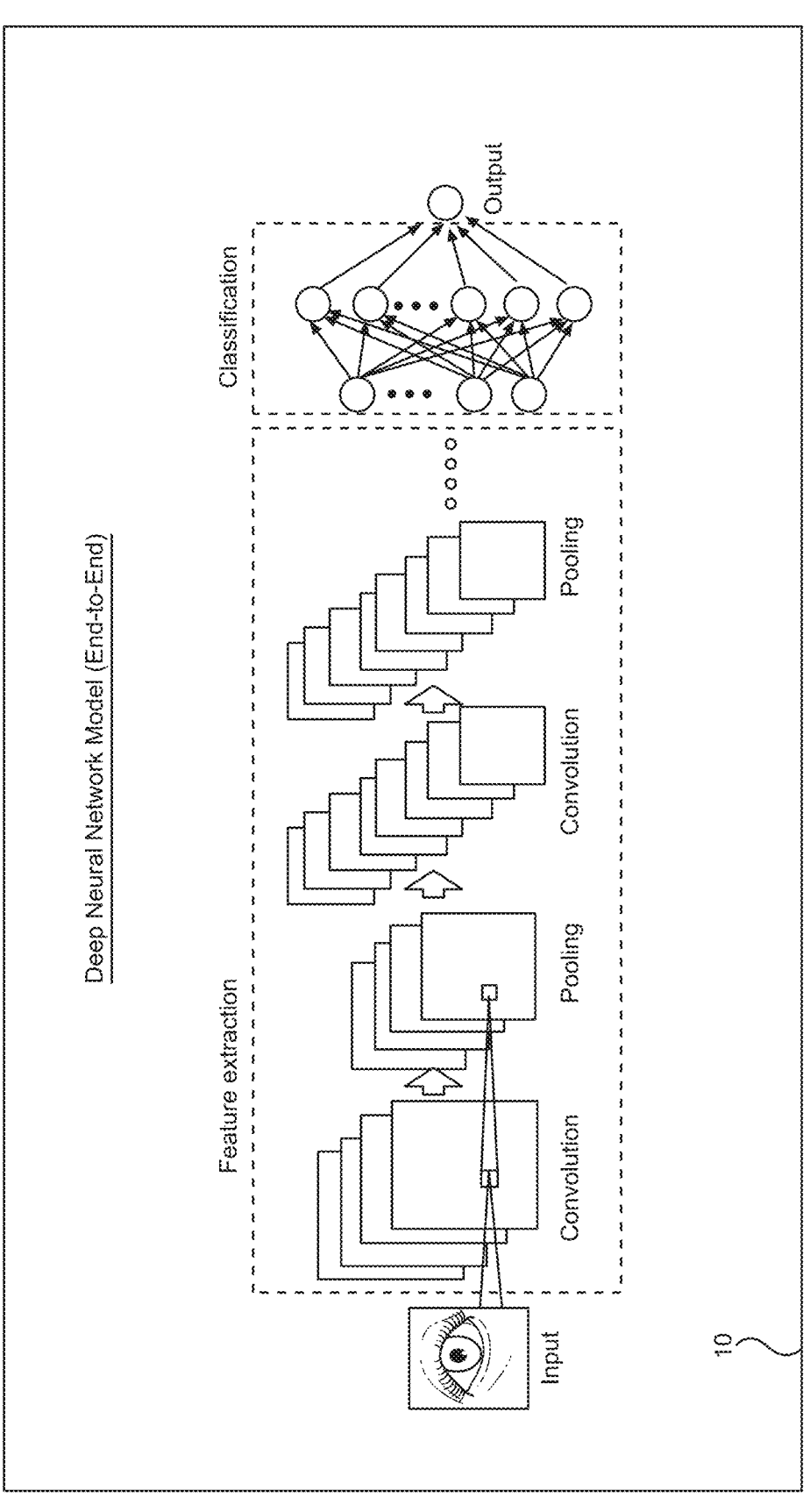
Figure 40B:
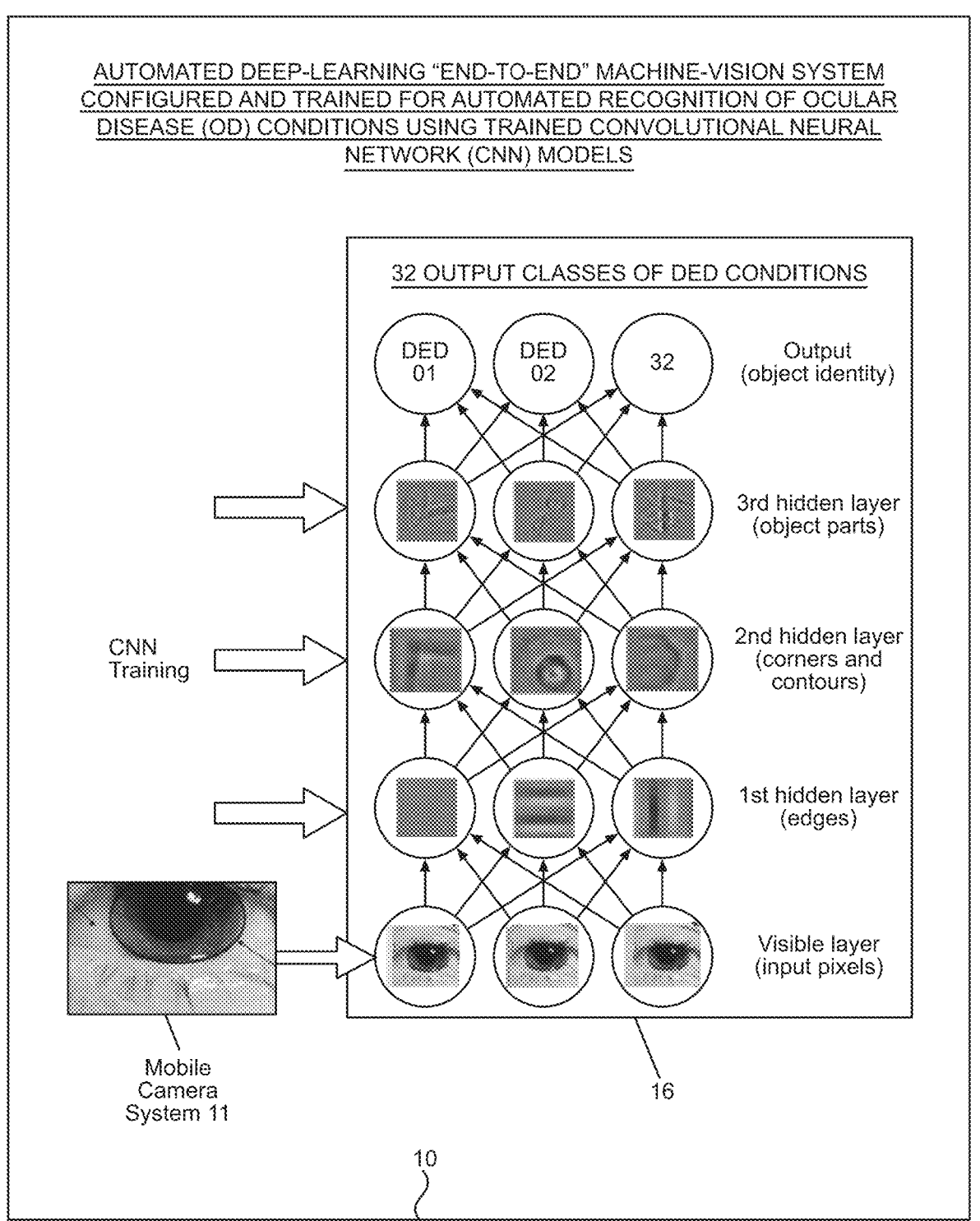
Figure 41:
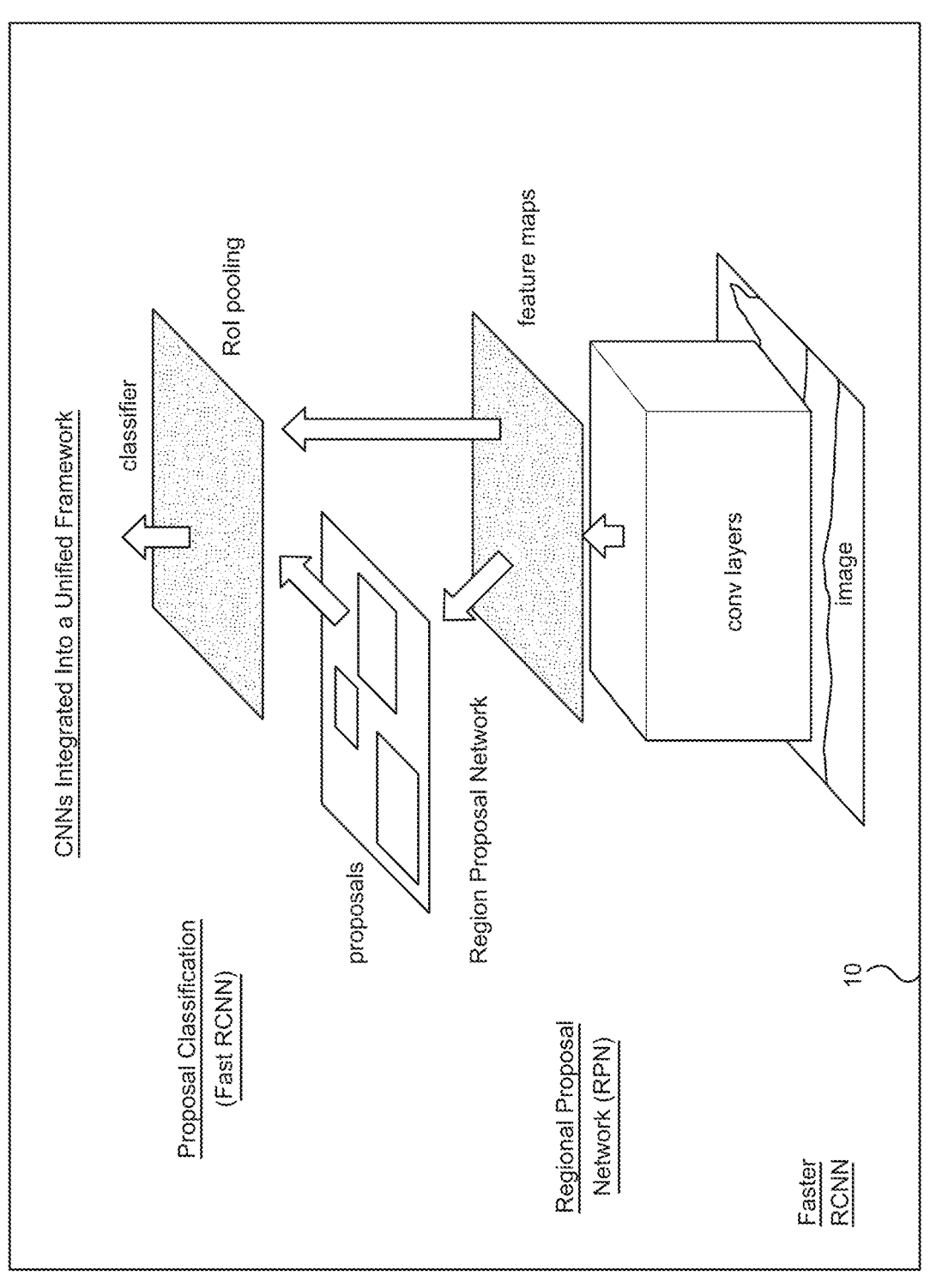
Figure 43:
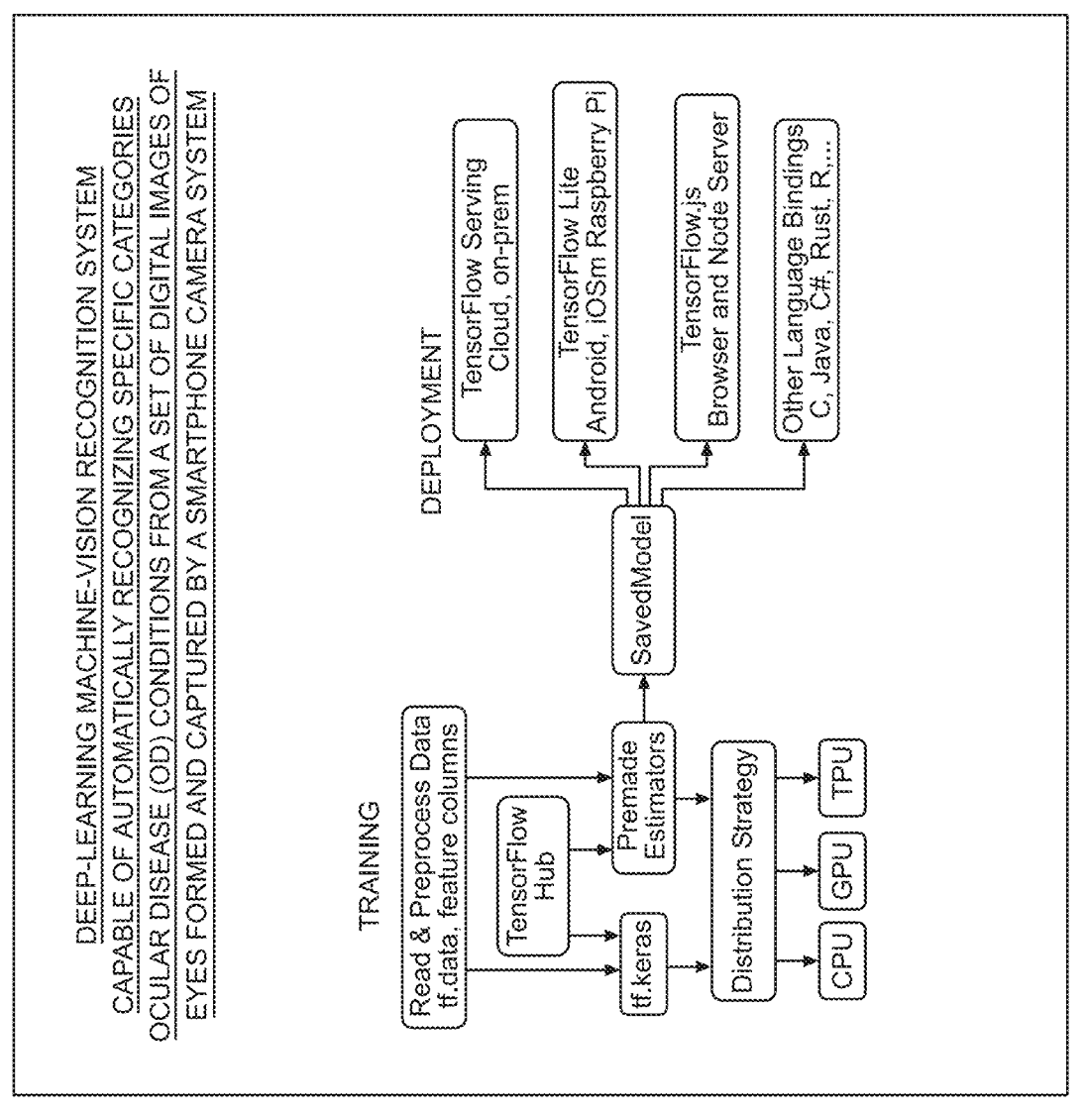
Figure 46:
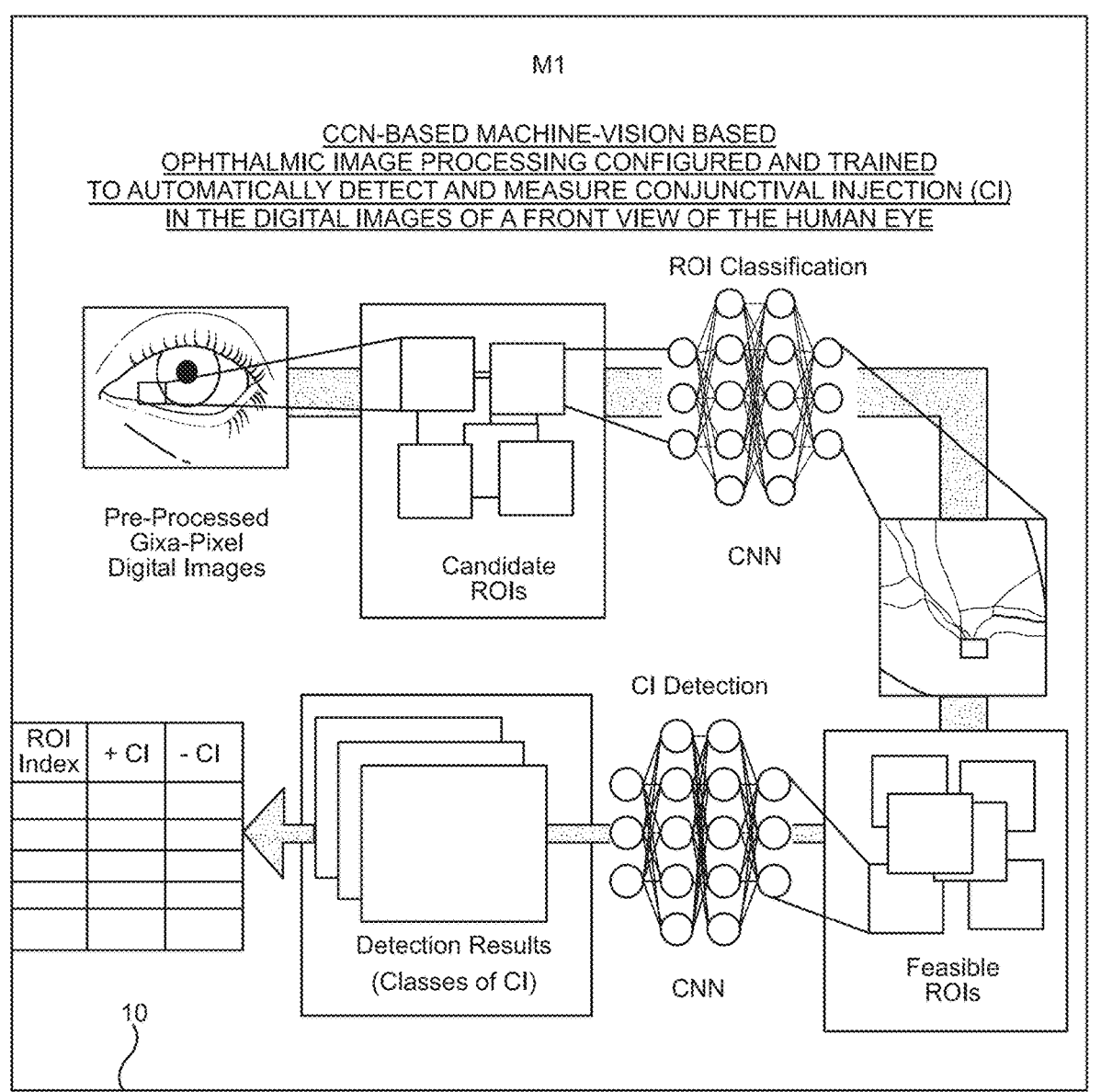
Figure 47:
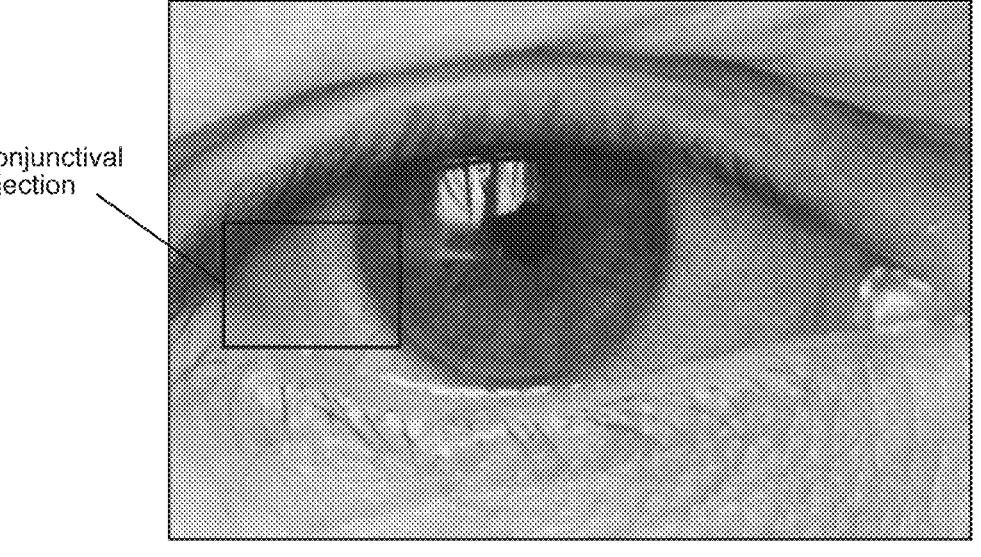
Figure 48:
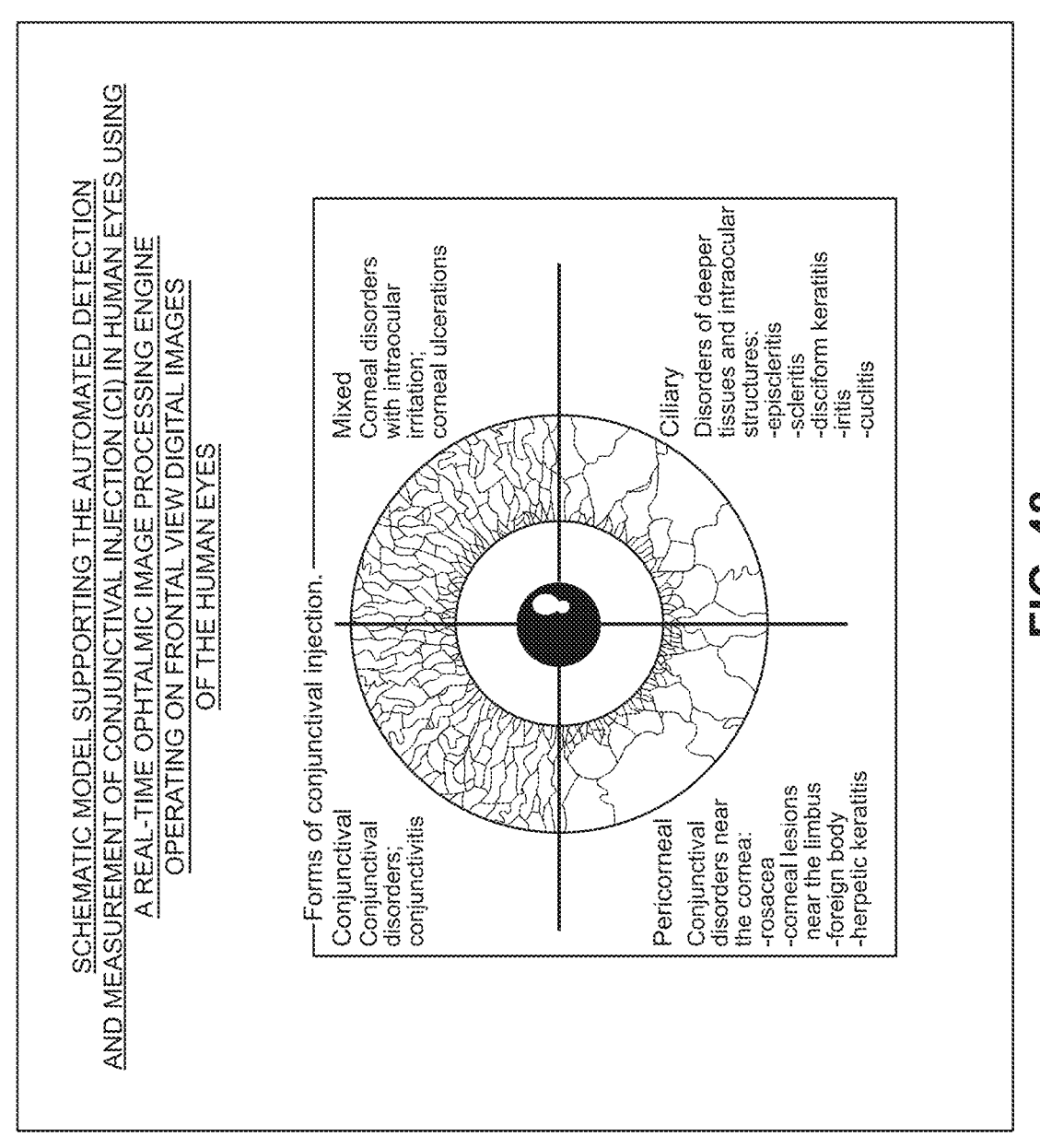
Figure 50:
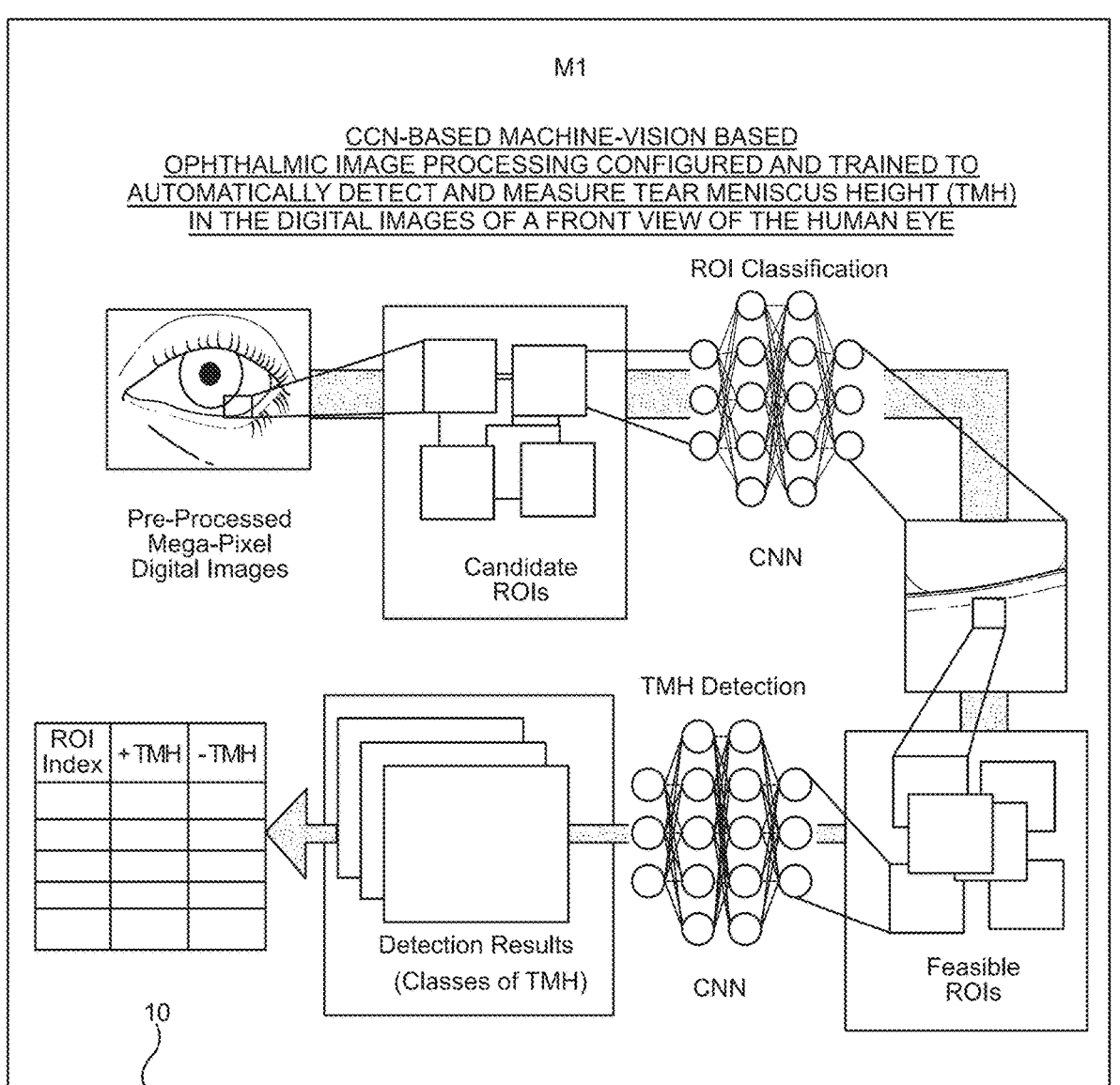
Figure 51:
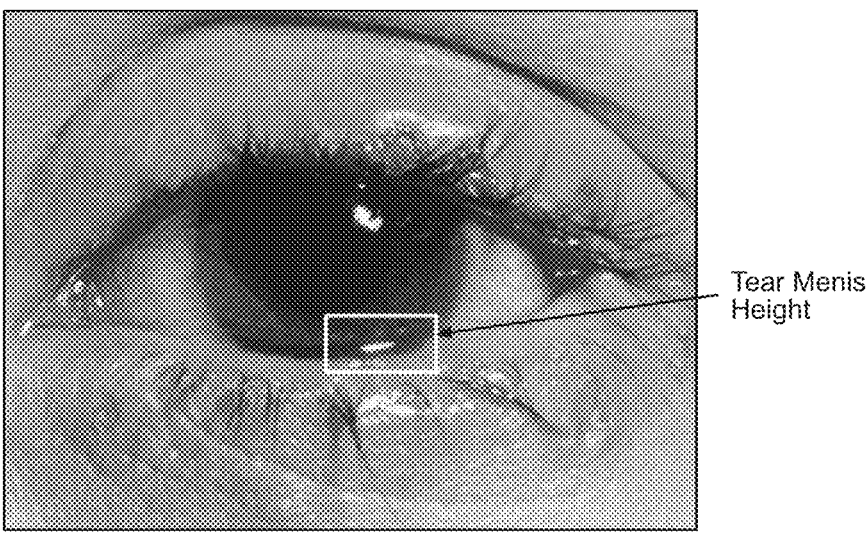
Figure 52A:
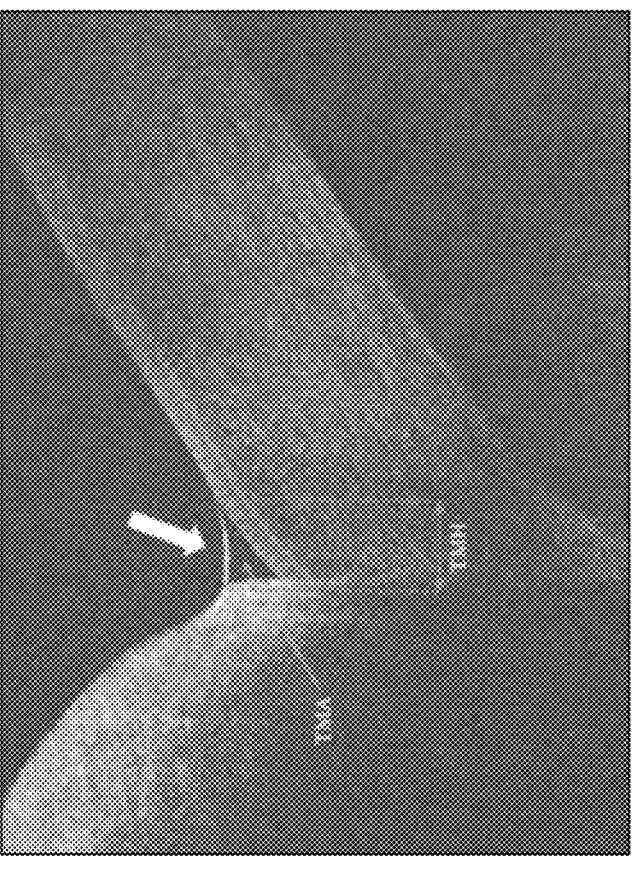
Figure 52B:
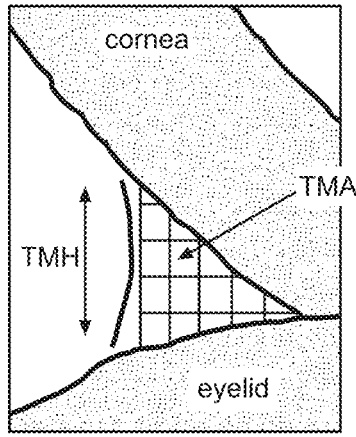
Figure 54:
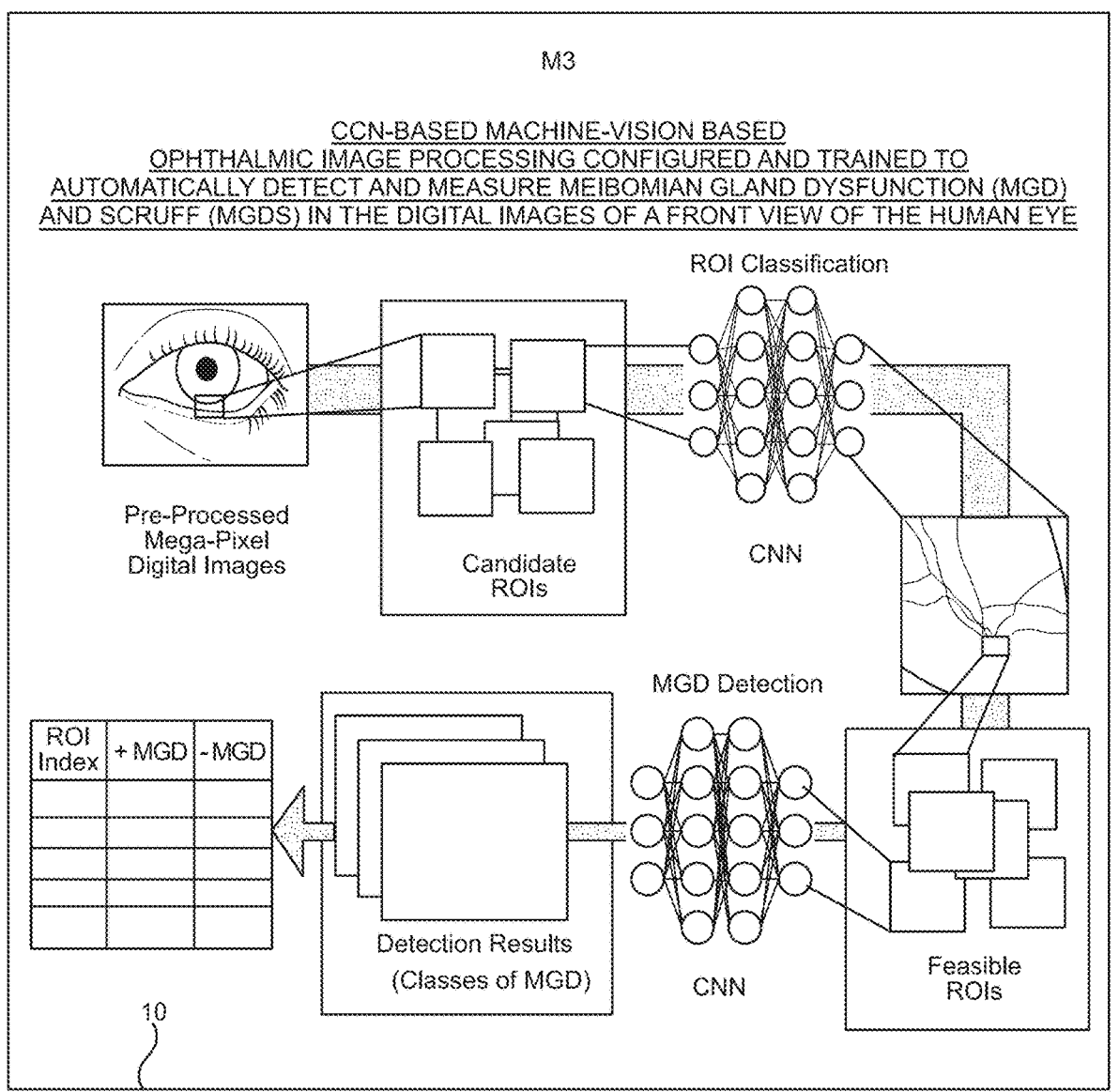
Figure 55A:
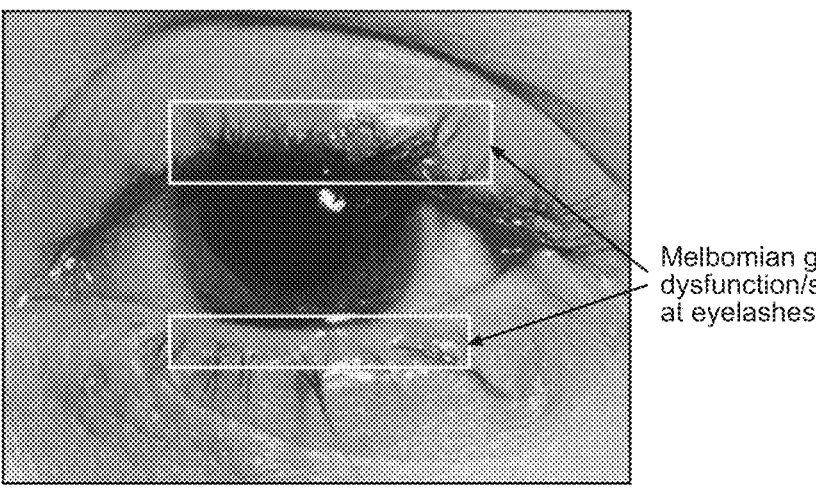
Figure 55B:
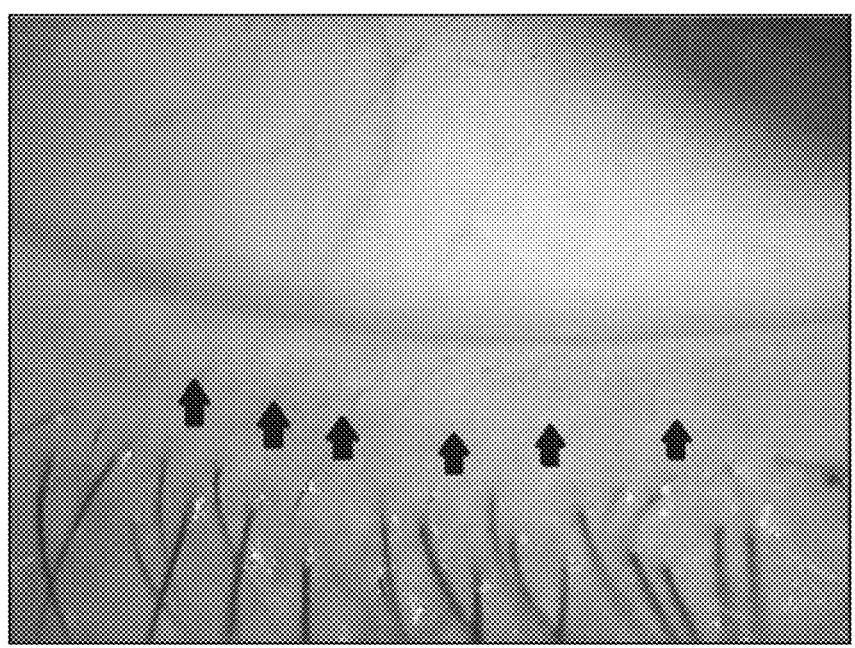
Figure 57:
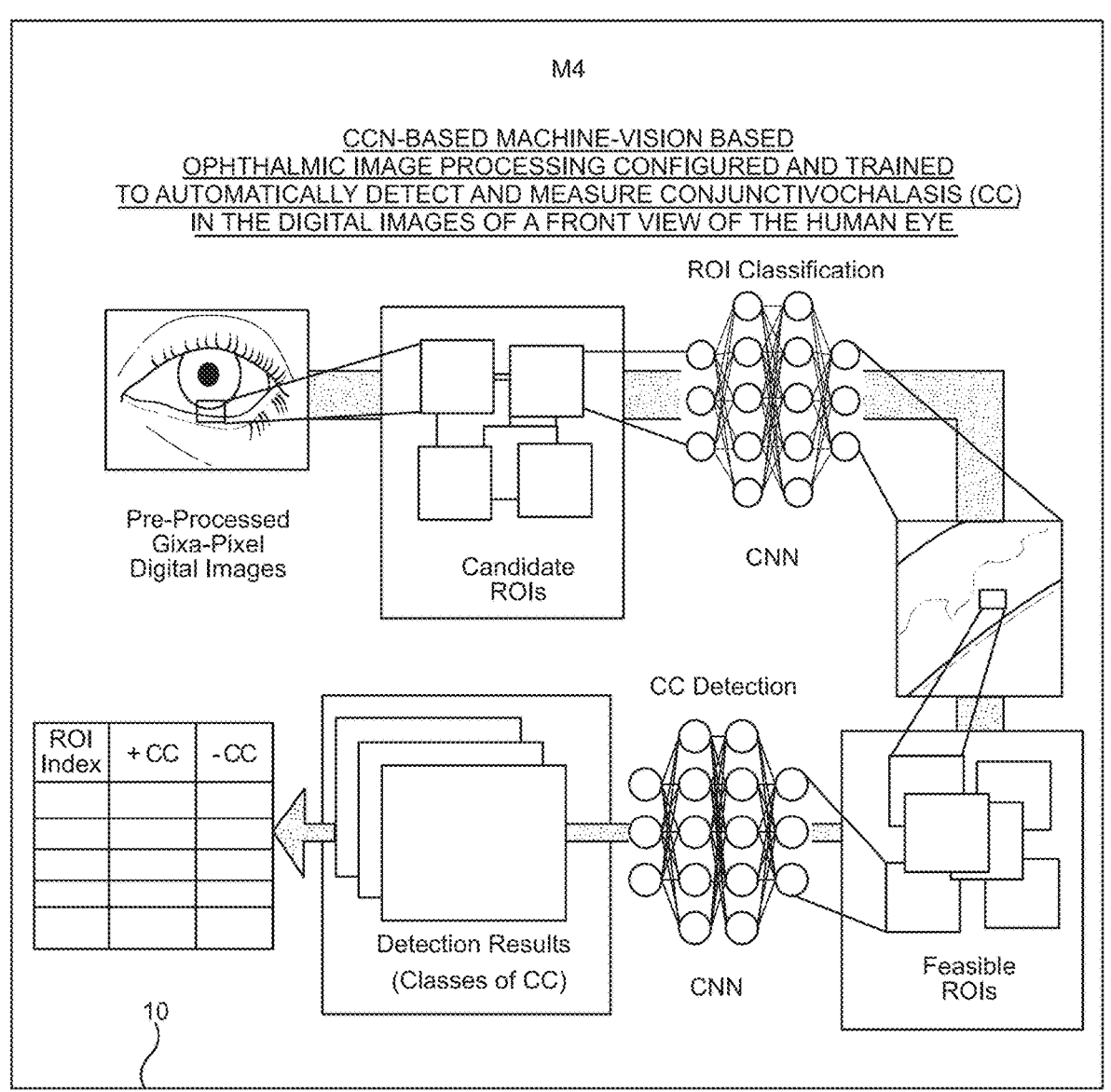
Figure 58A:
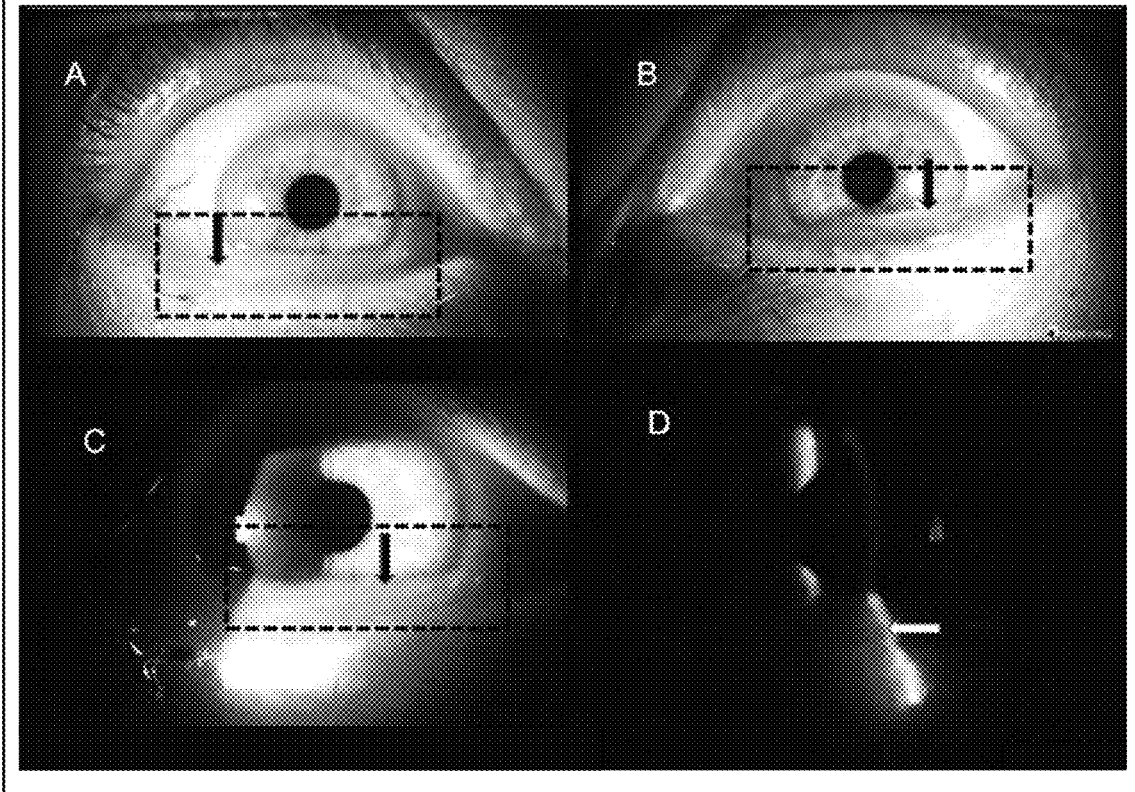
Figure 58B:
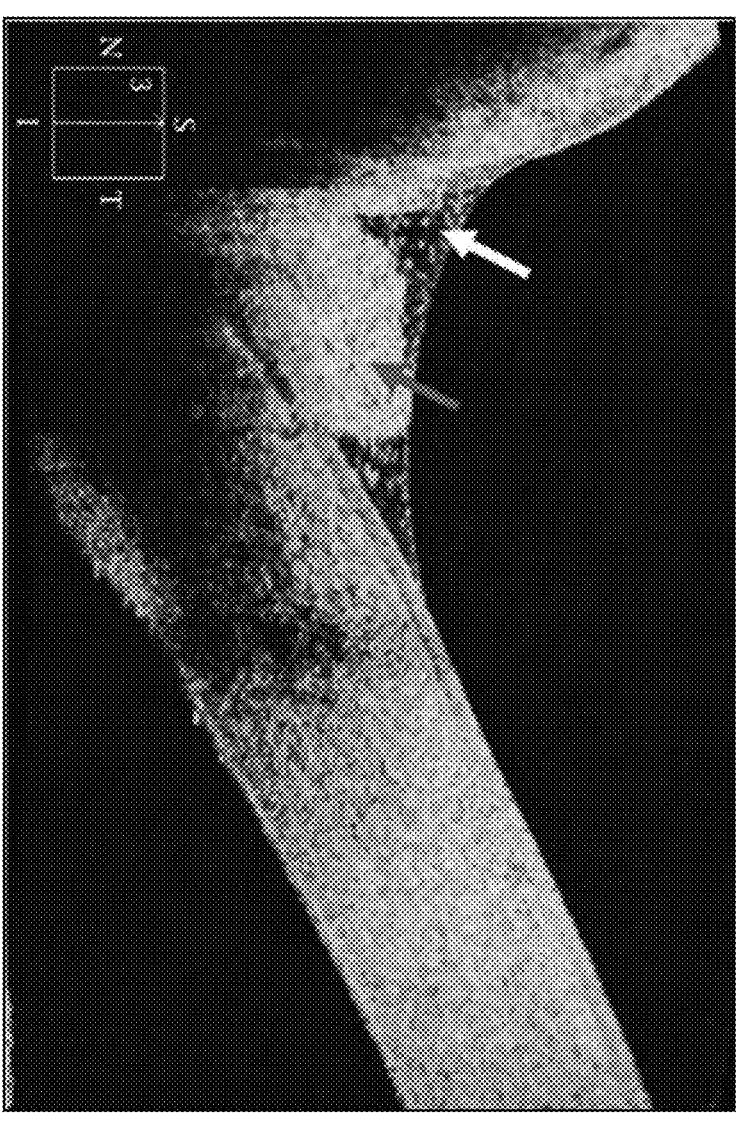
Figure 59:
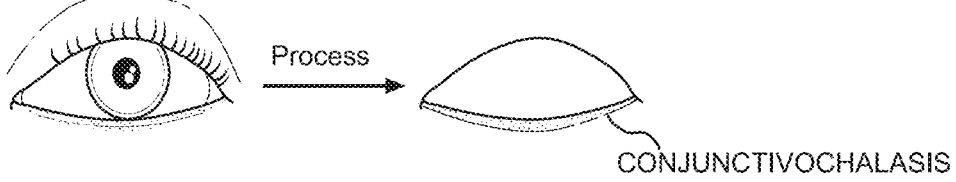
Figure 61:
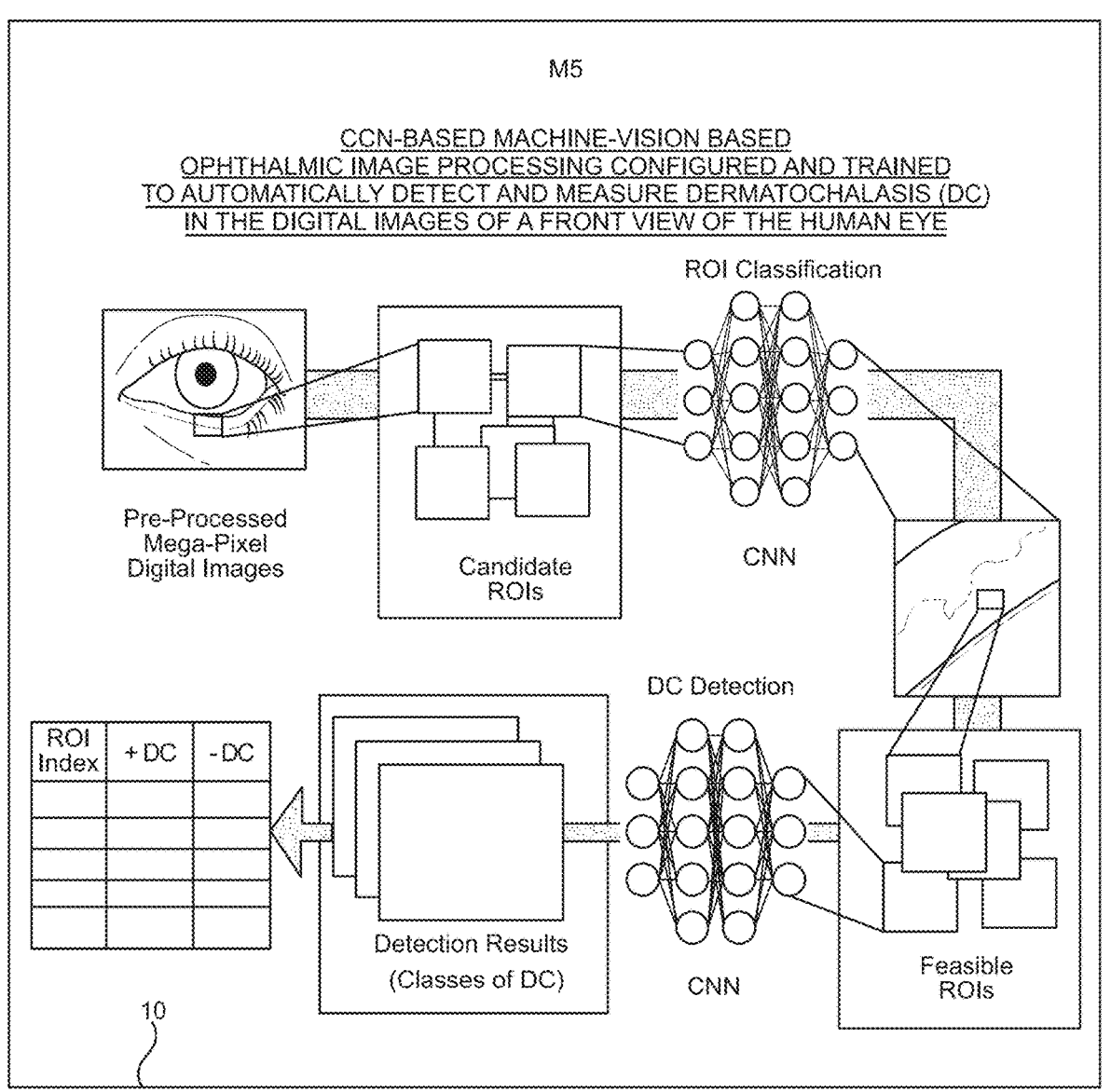
Figure 62:
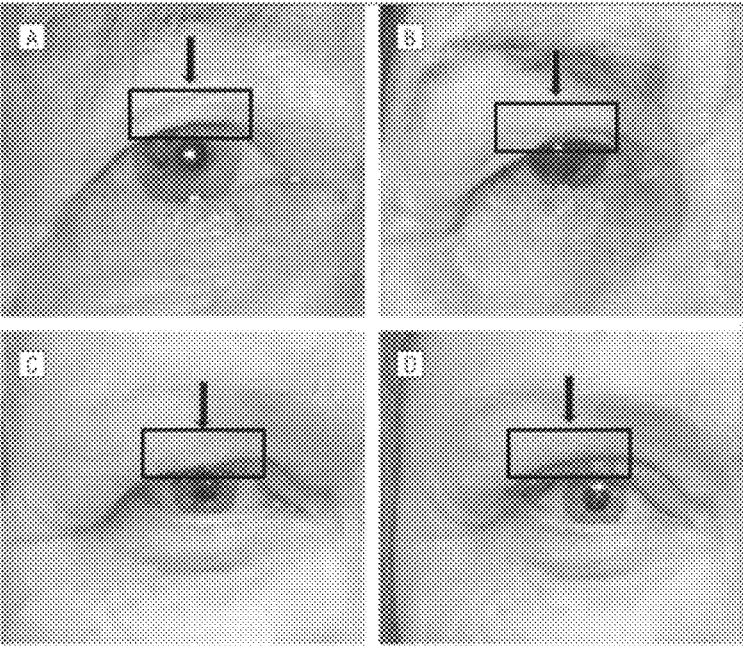
Figure 65:
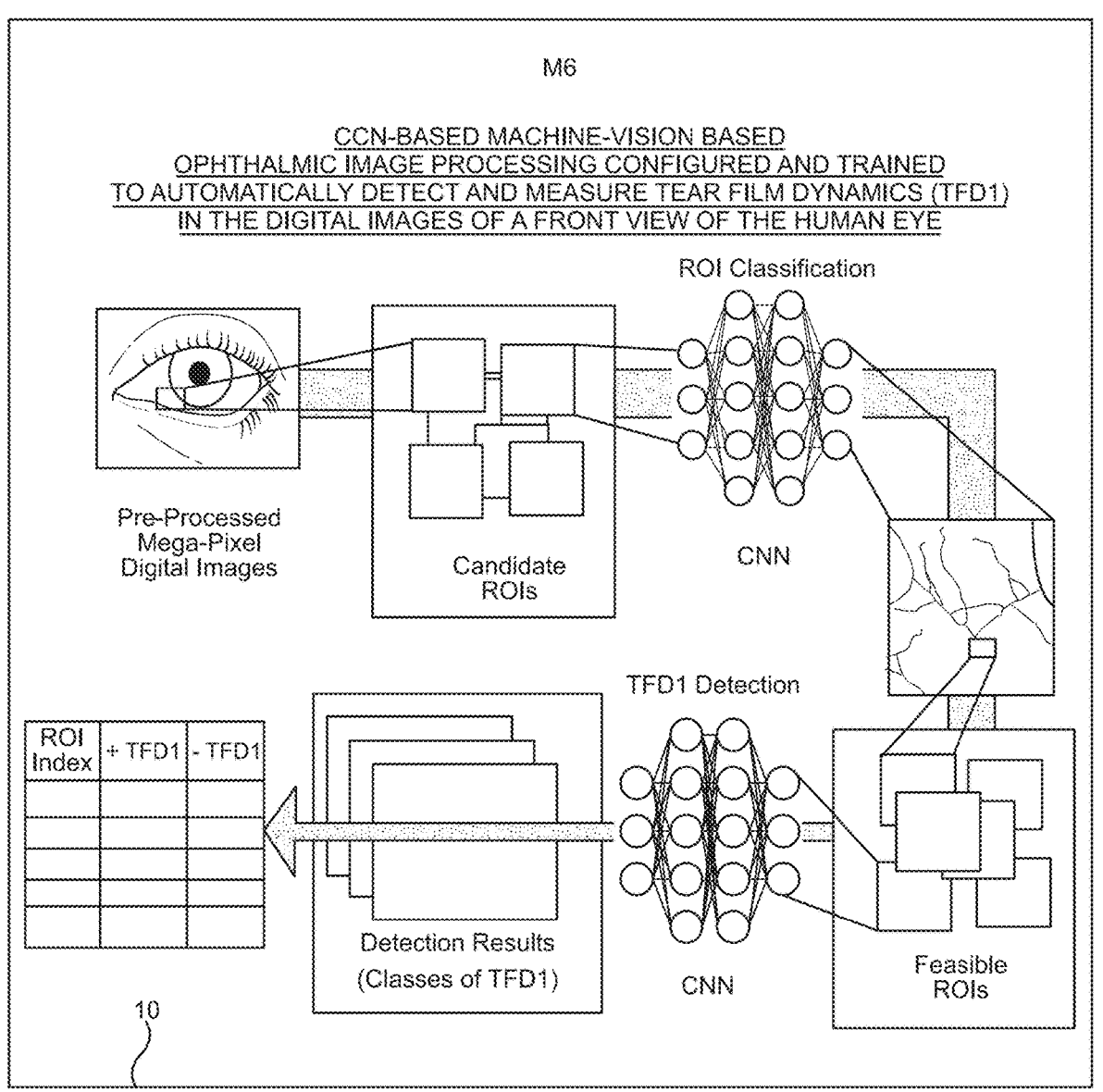
Figure 66A:
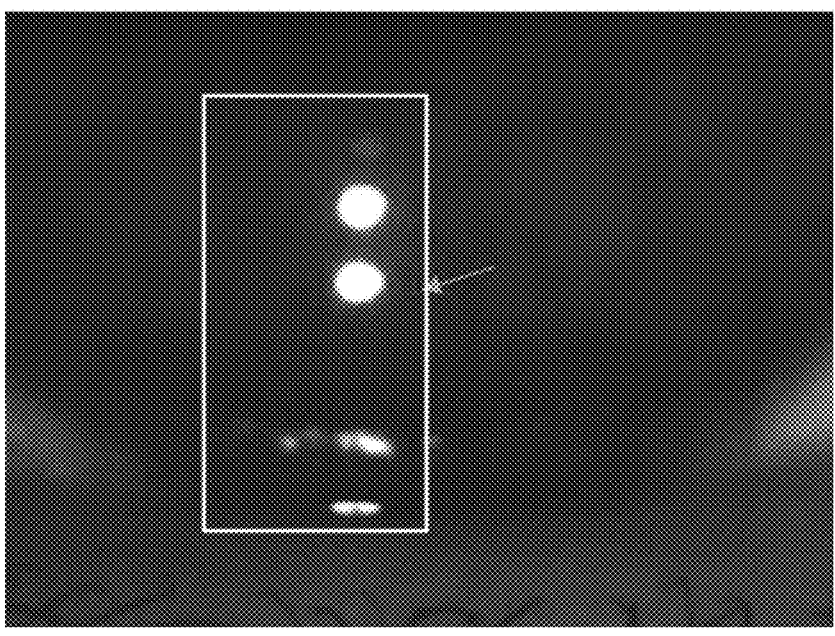
Figure 66B:
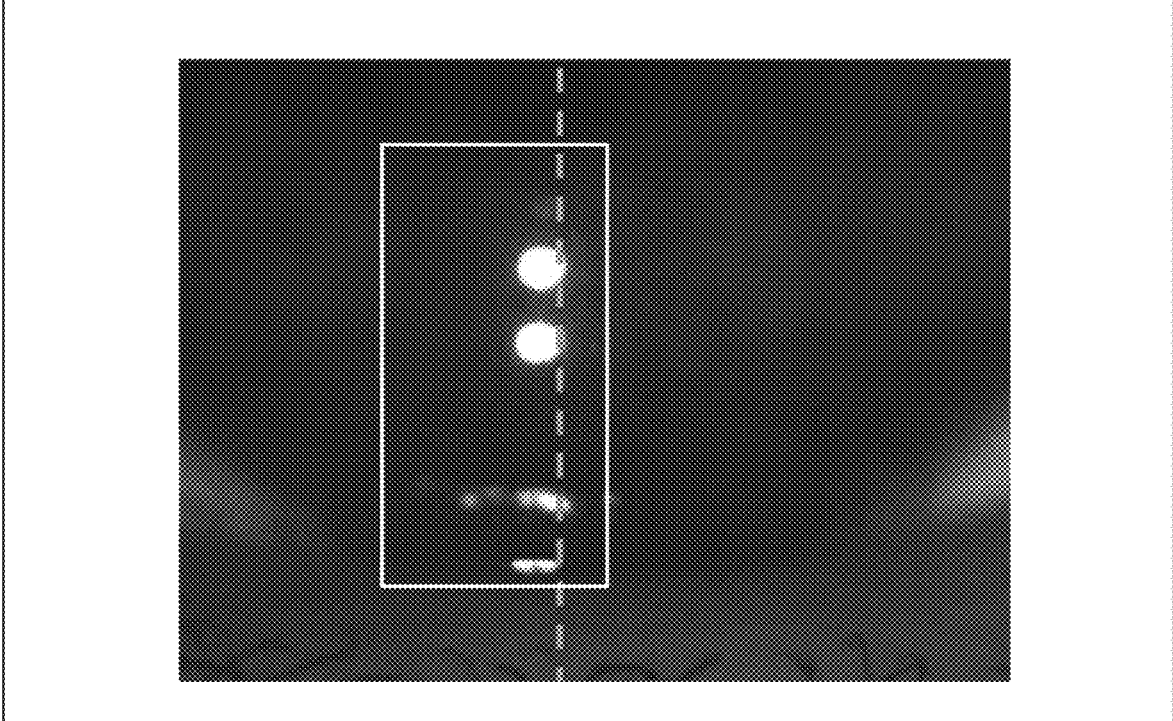
Figure 67:
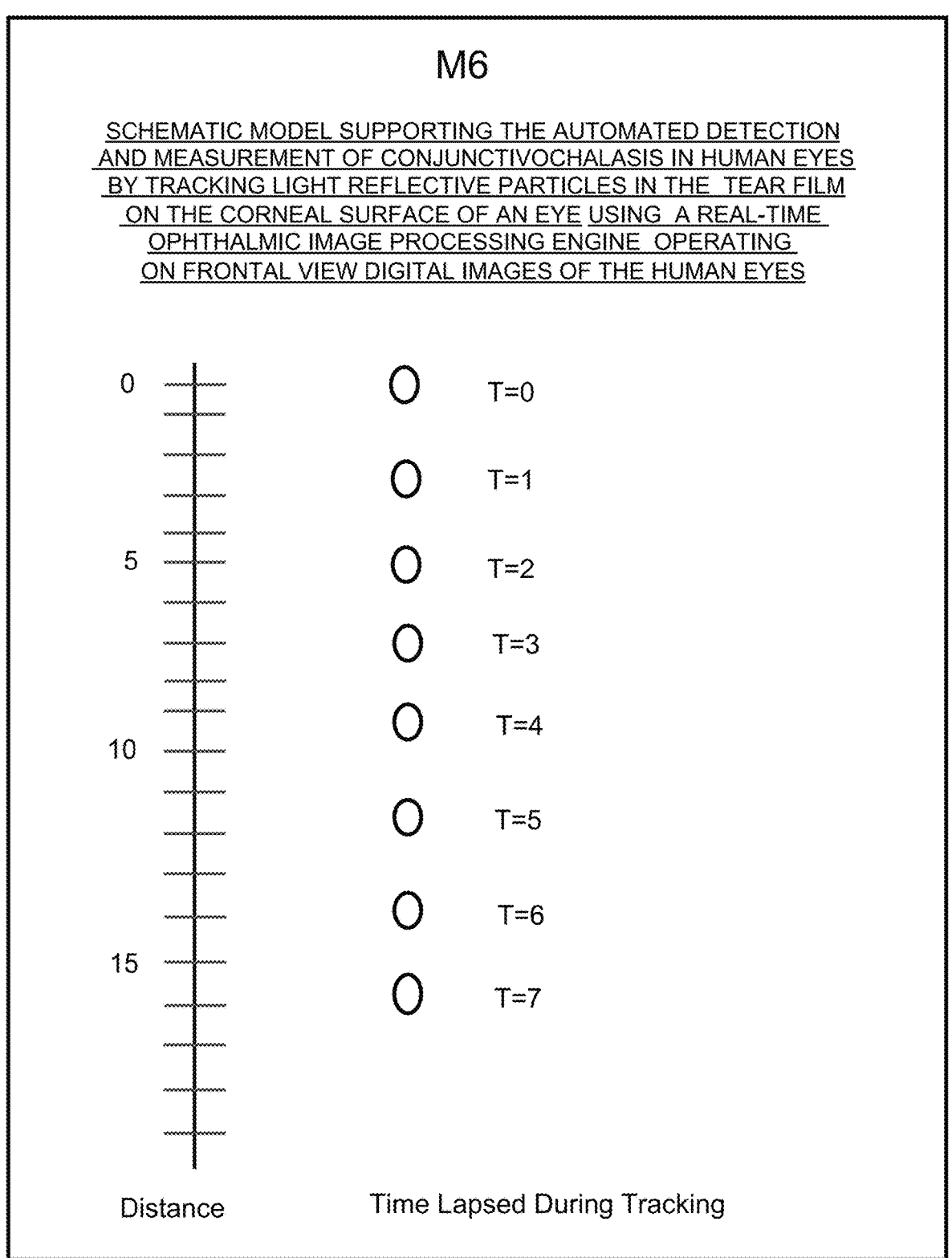
Figure 69:
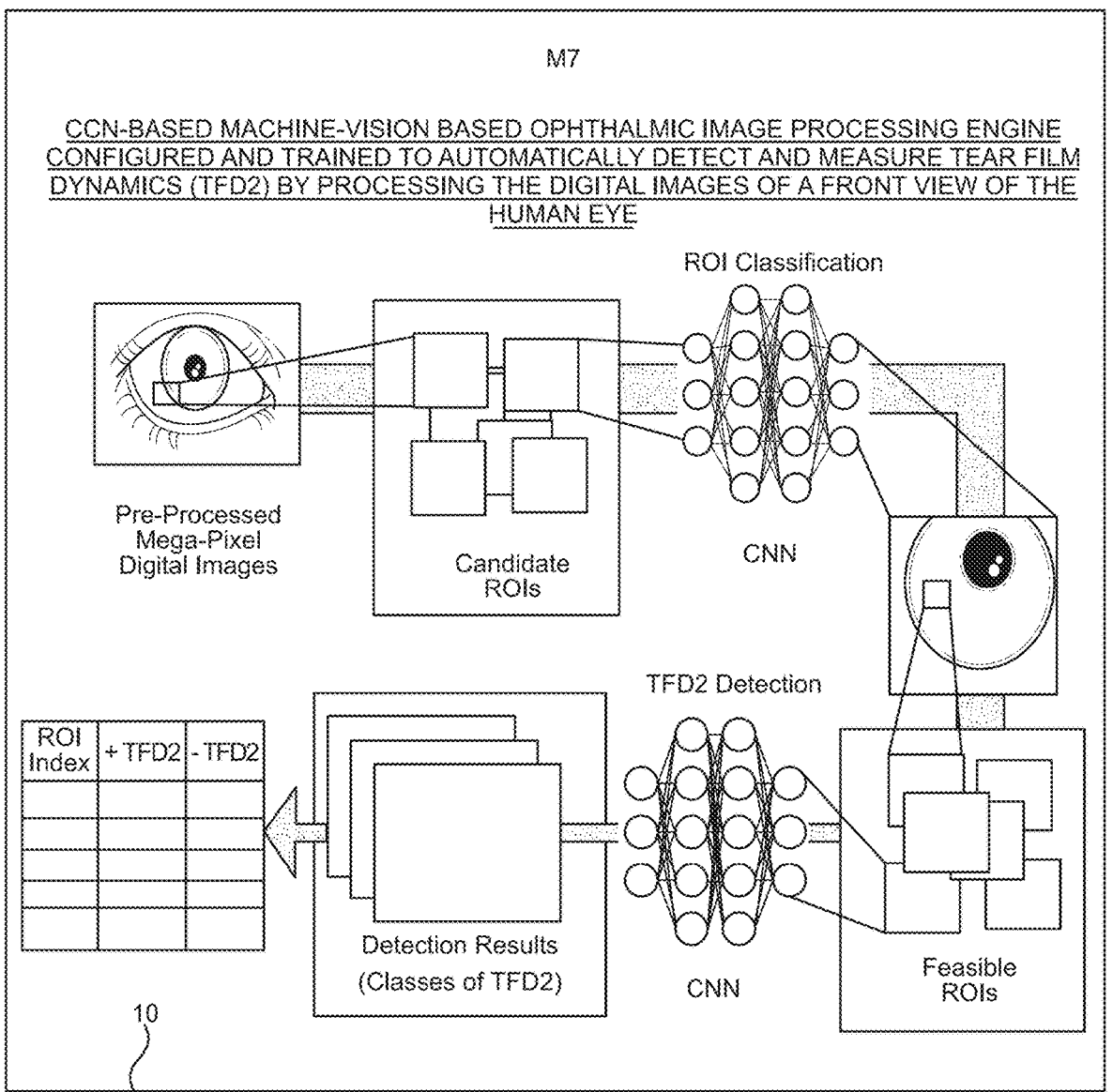
Figure 70A:
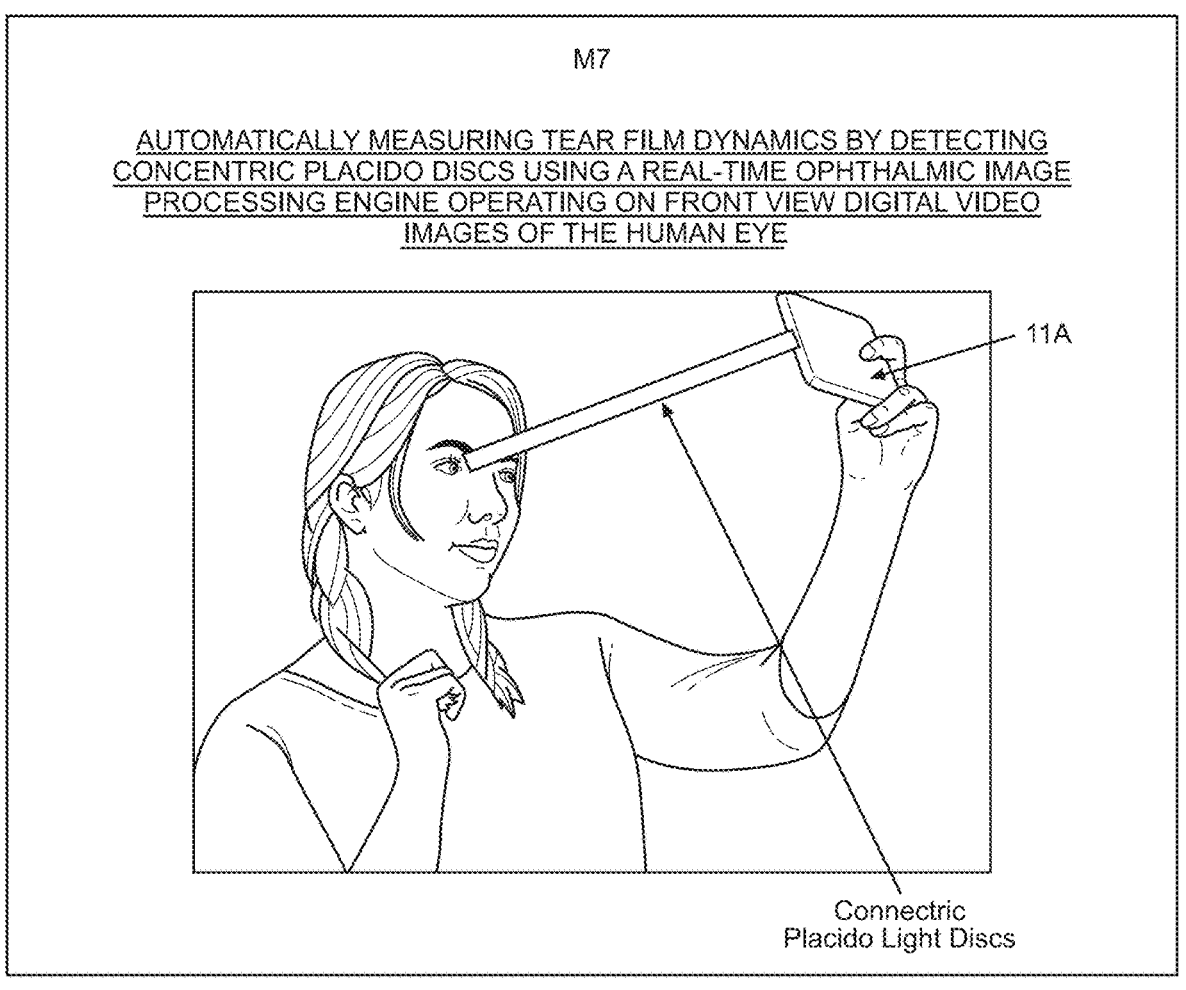
Figure 70B:
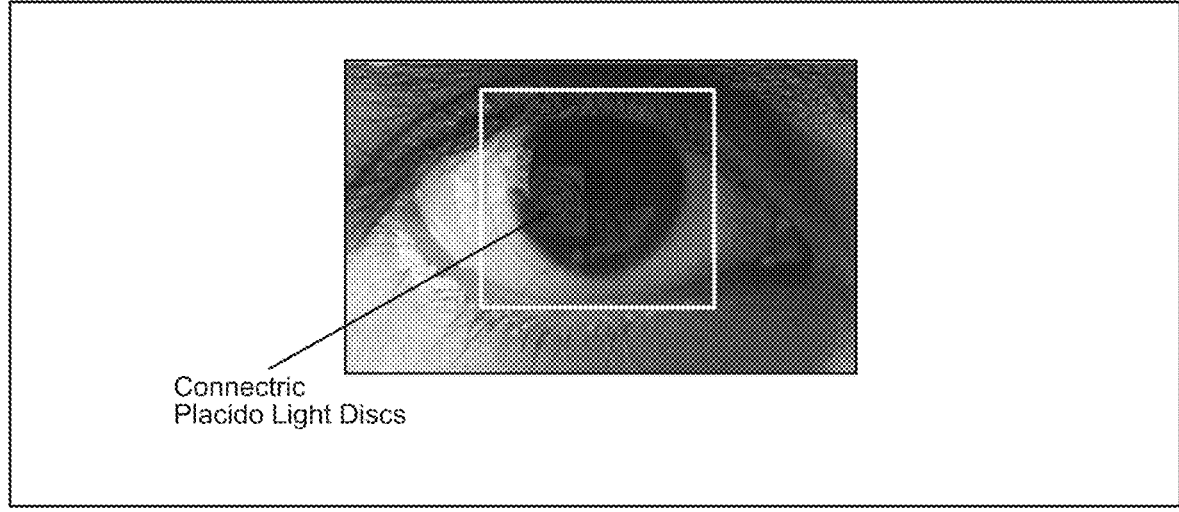
Figure 70C:
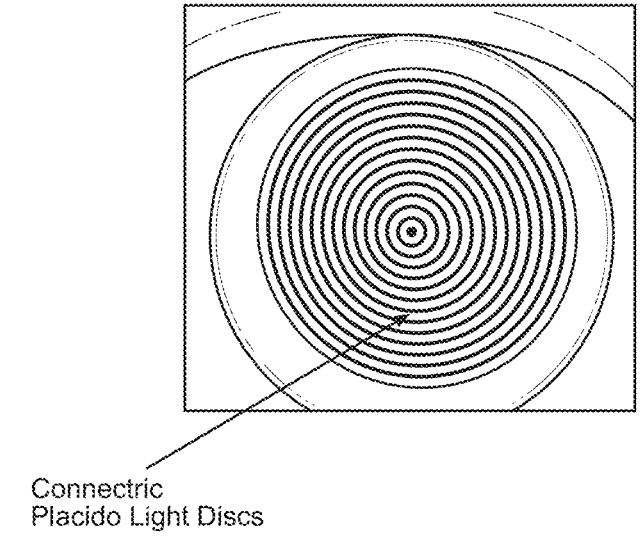
Figure 71:
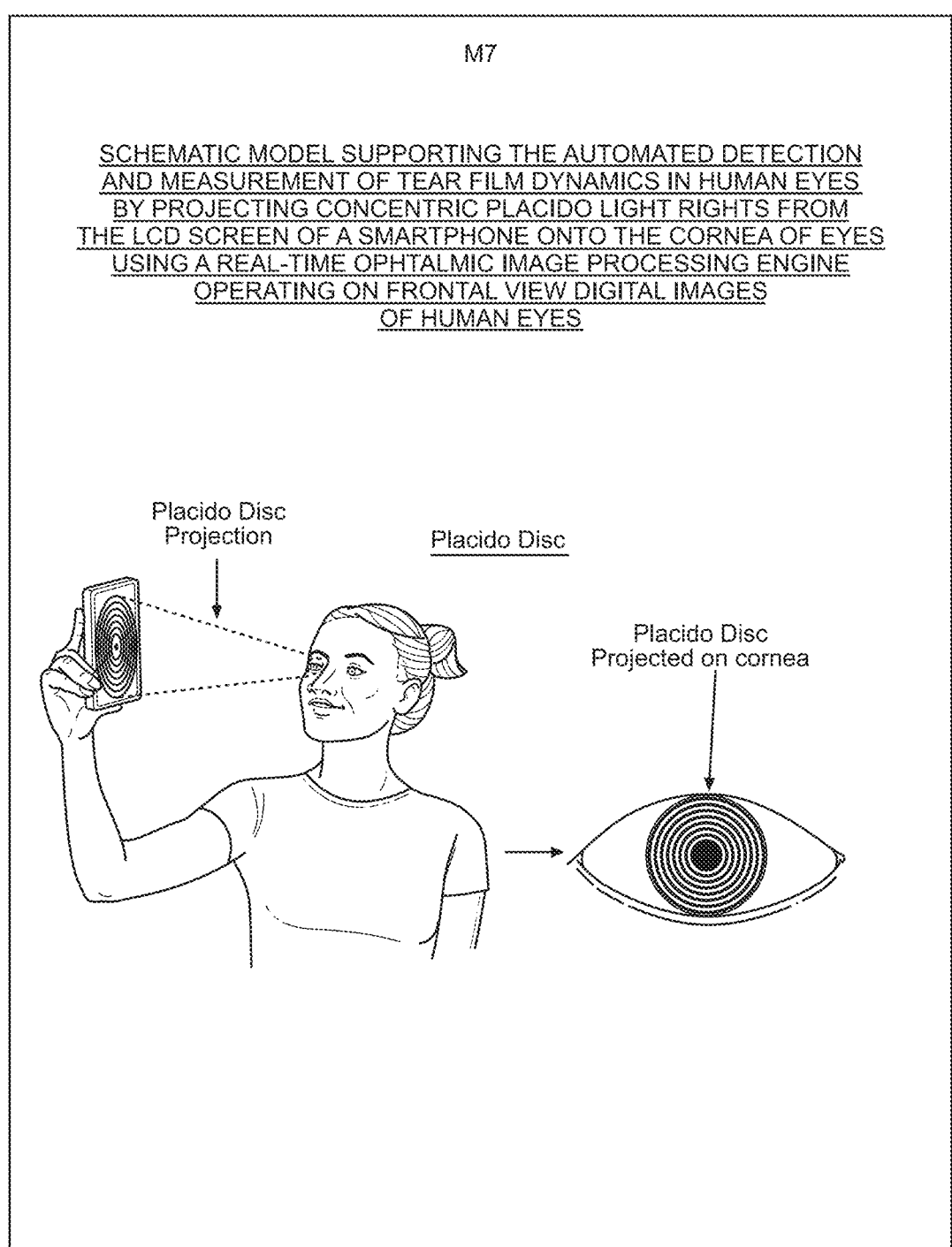
Figure 73:
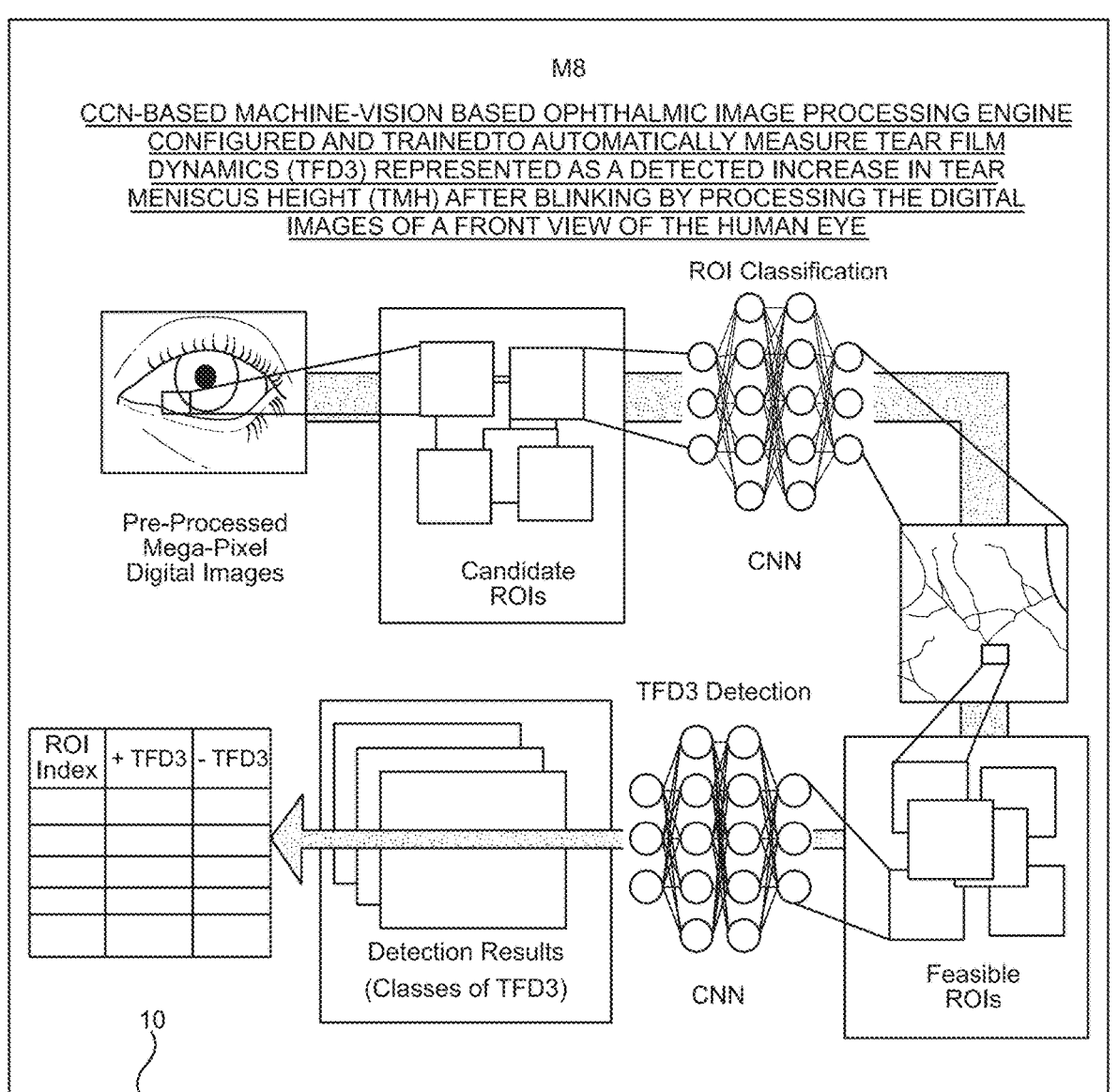
Figure 74A:
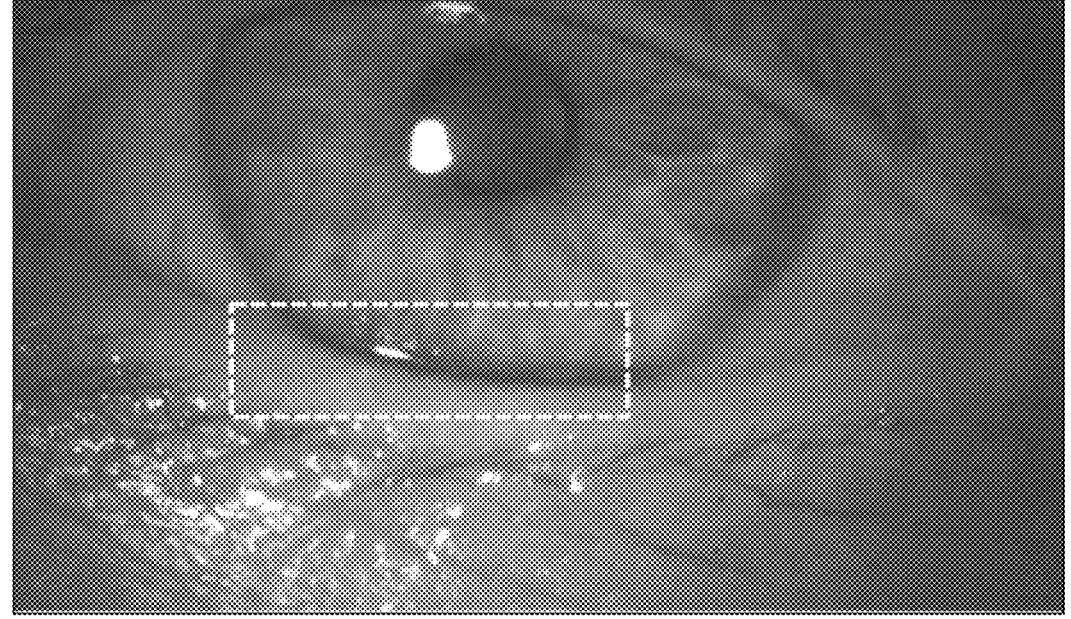
Figure 74B:
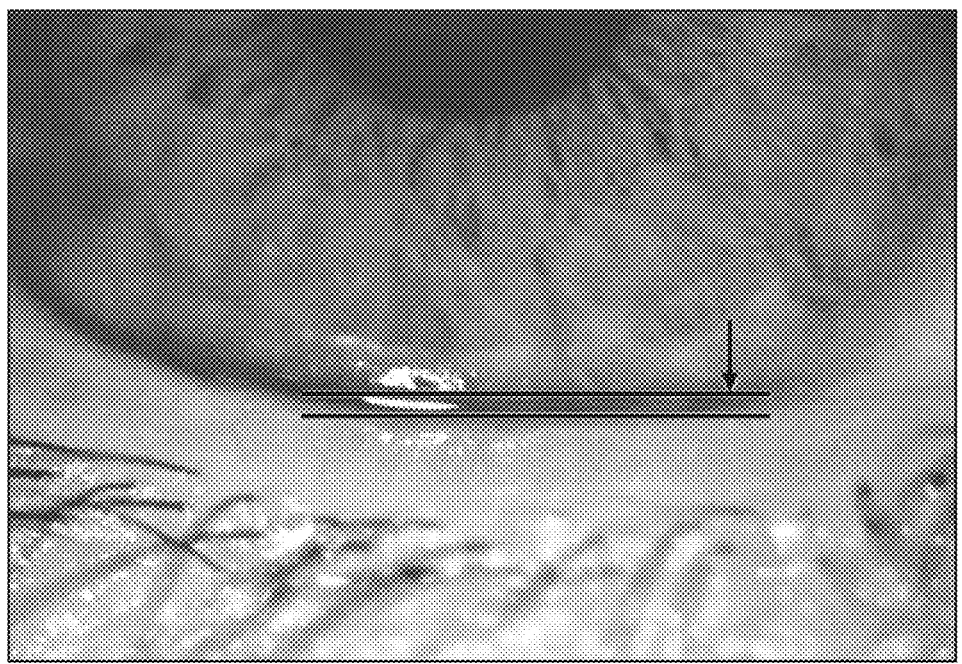
Figure 75A:
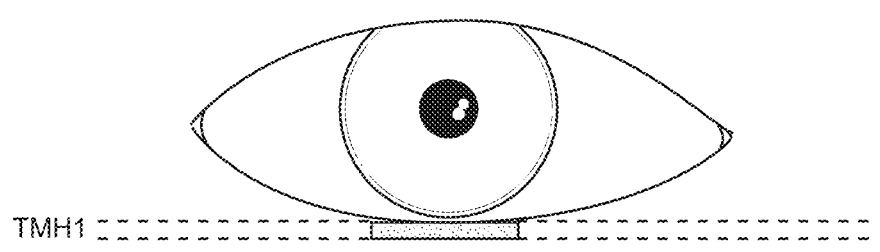
Figure 75B:
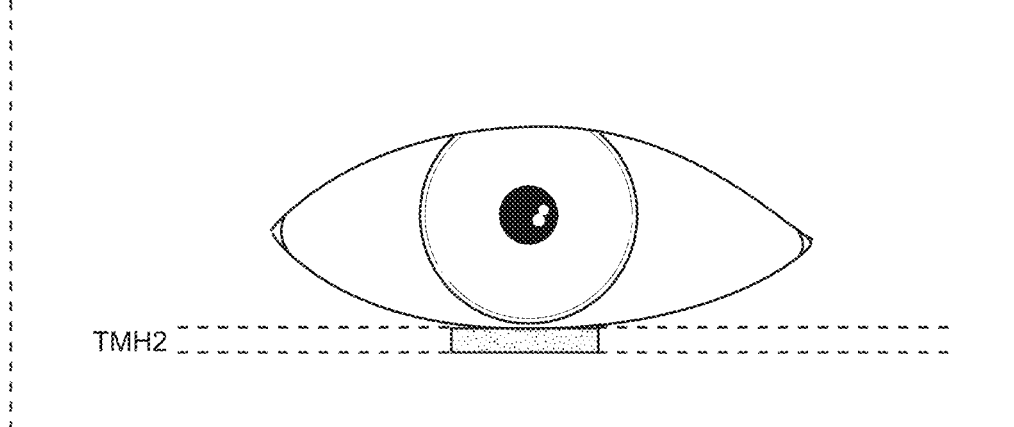
Figure 75C:
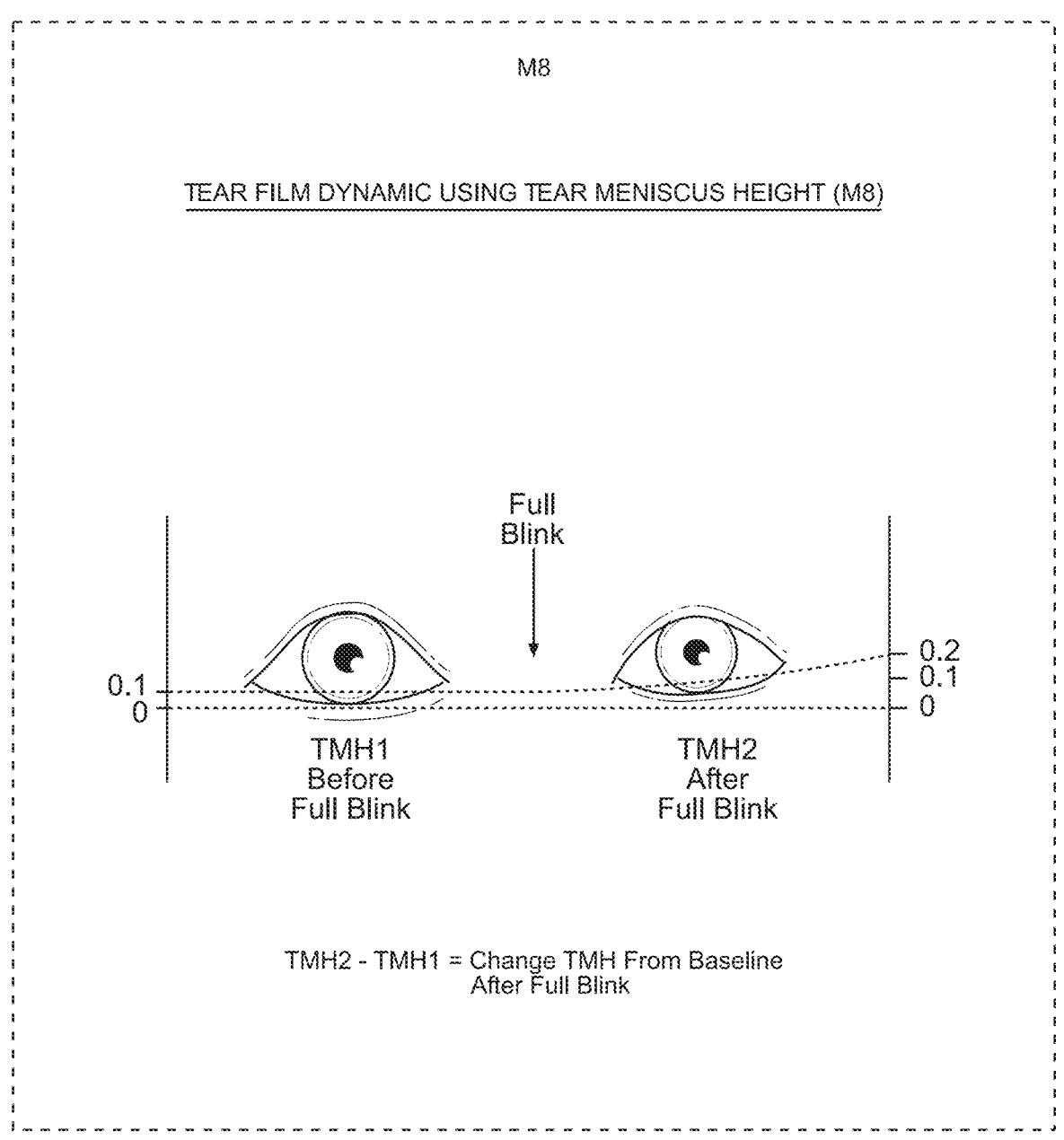
Figure 77:
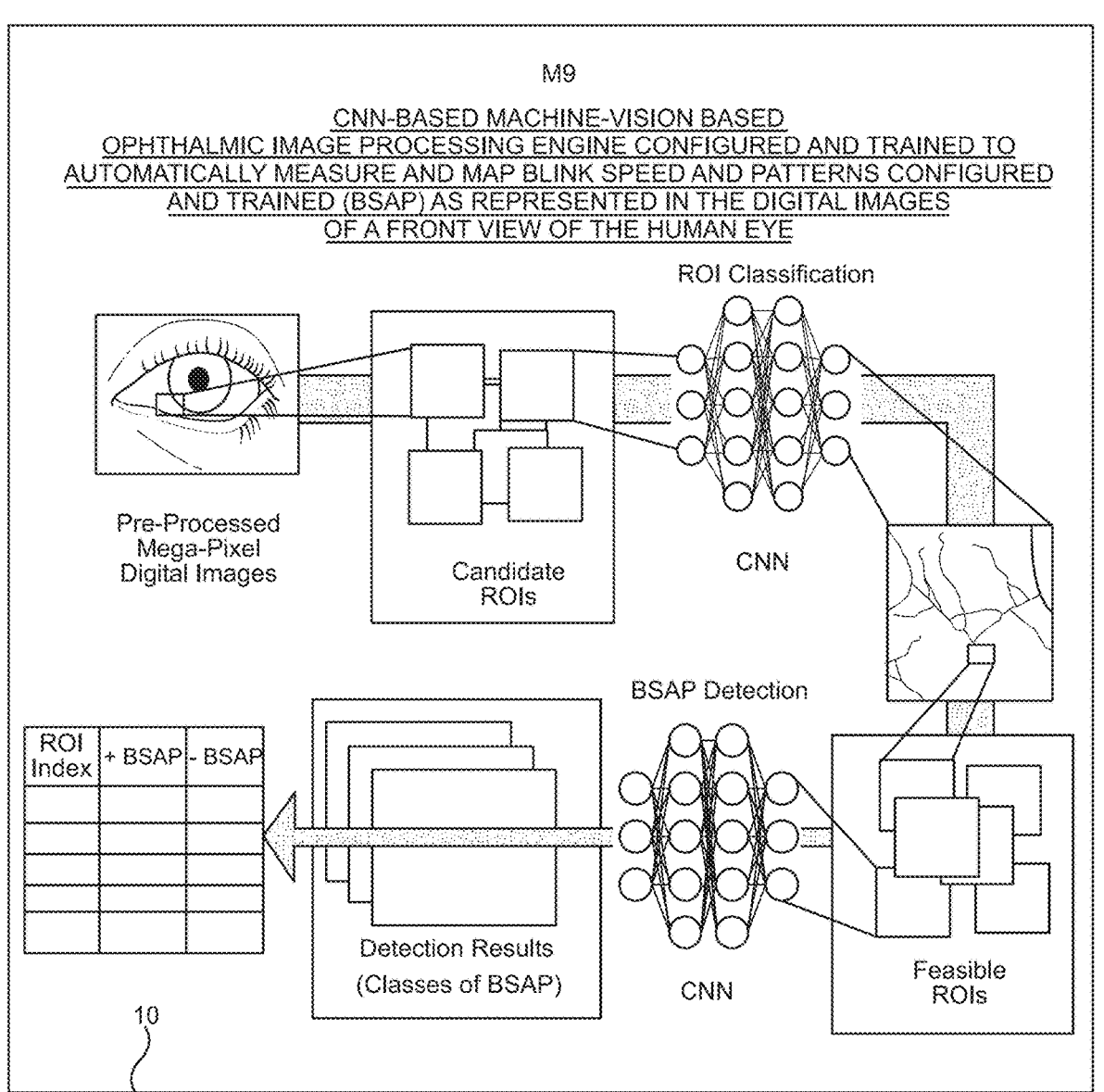
Figure 78:
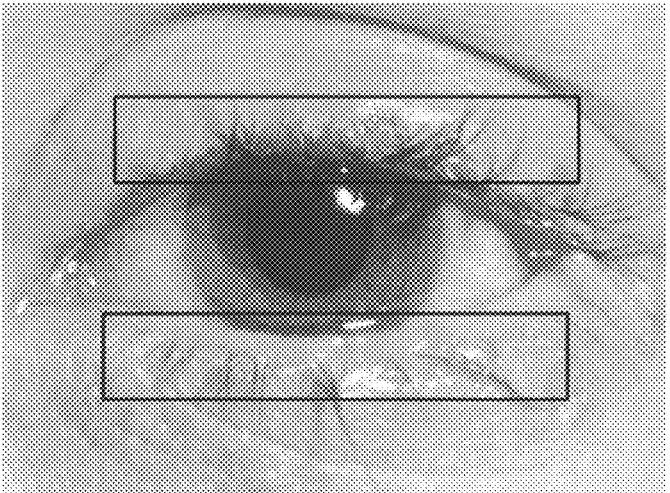
Figure 79A:
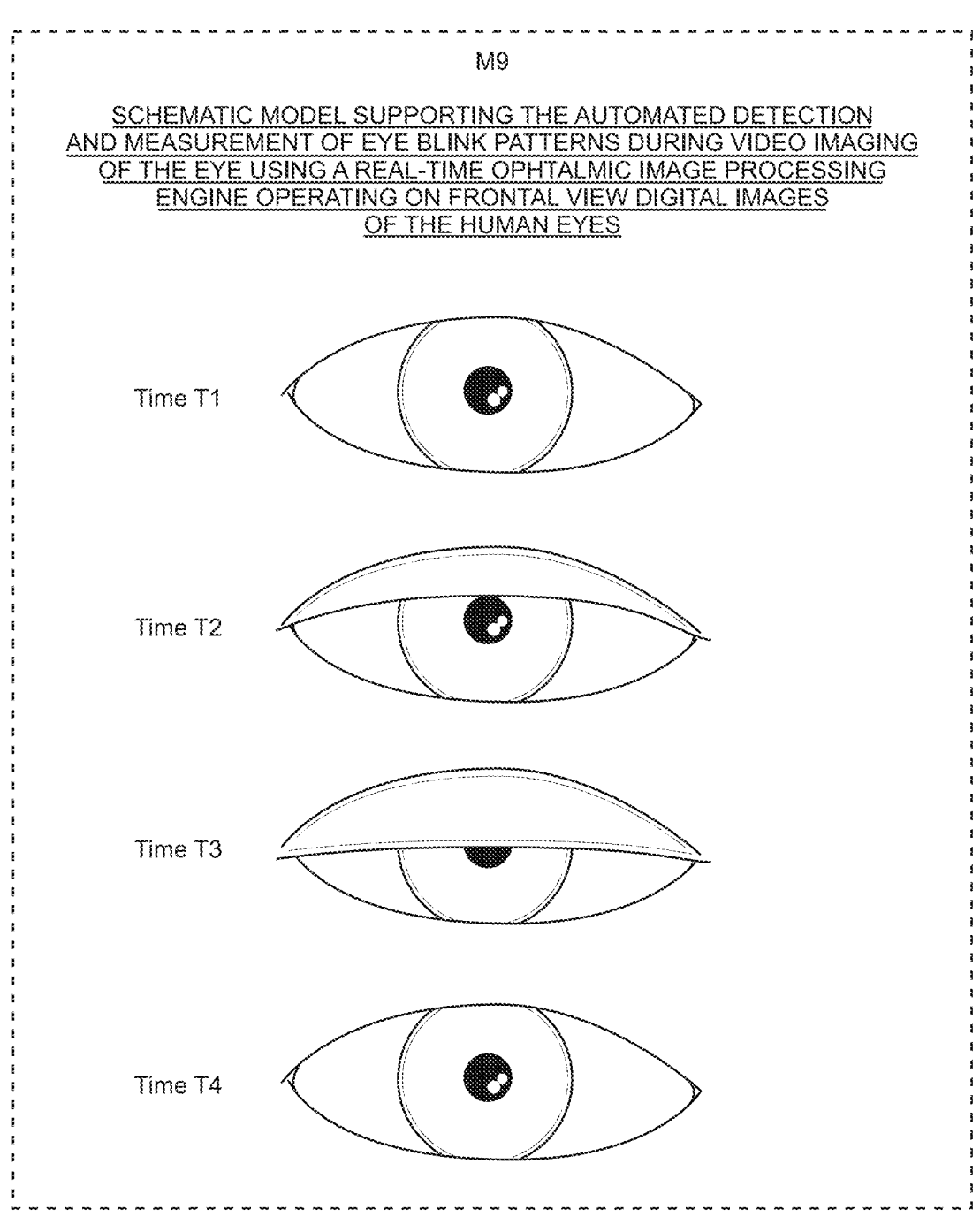
Figure 79B:
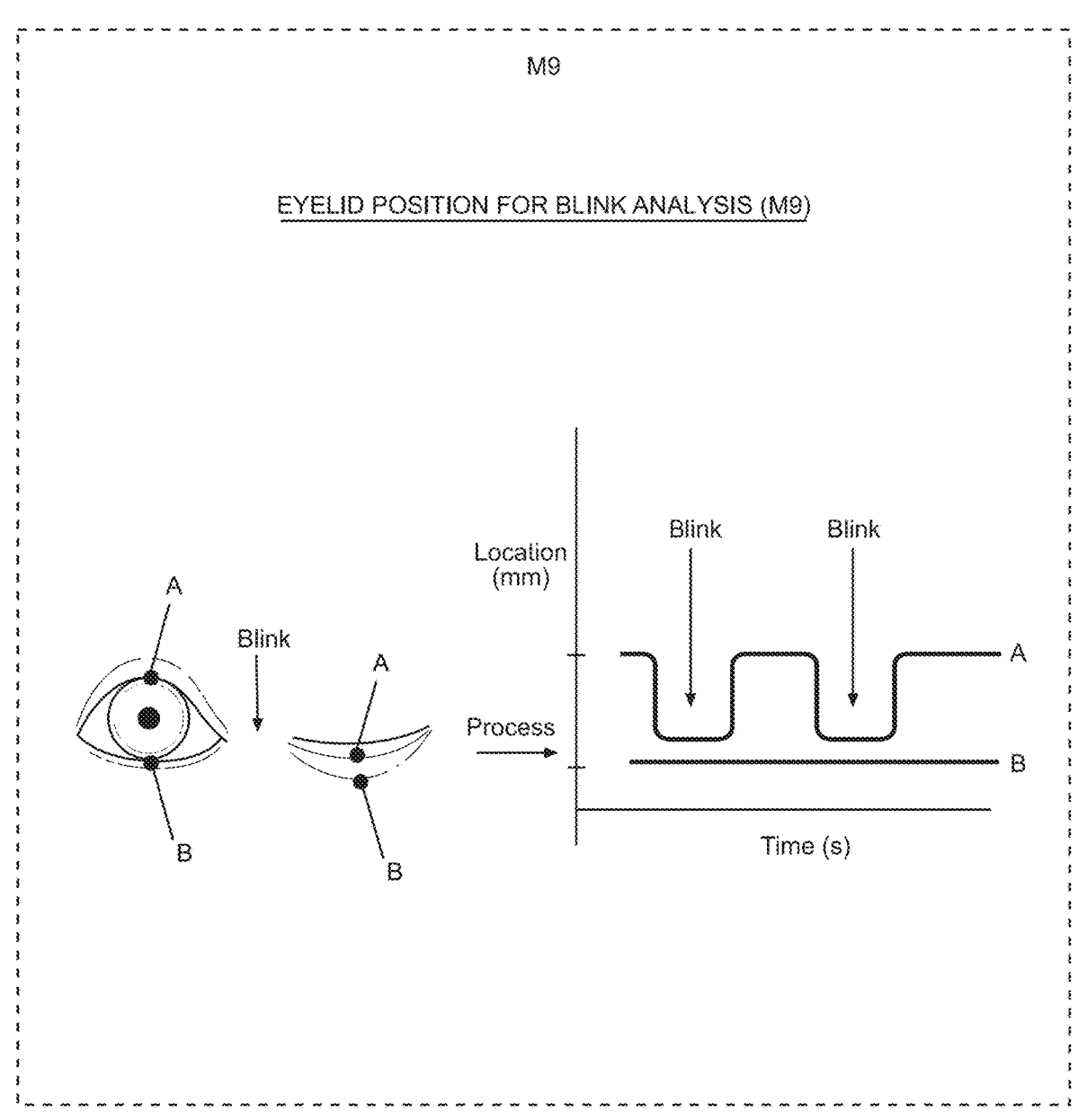
Figure 82:
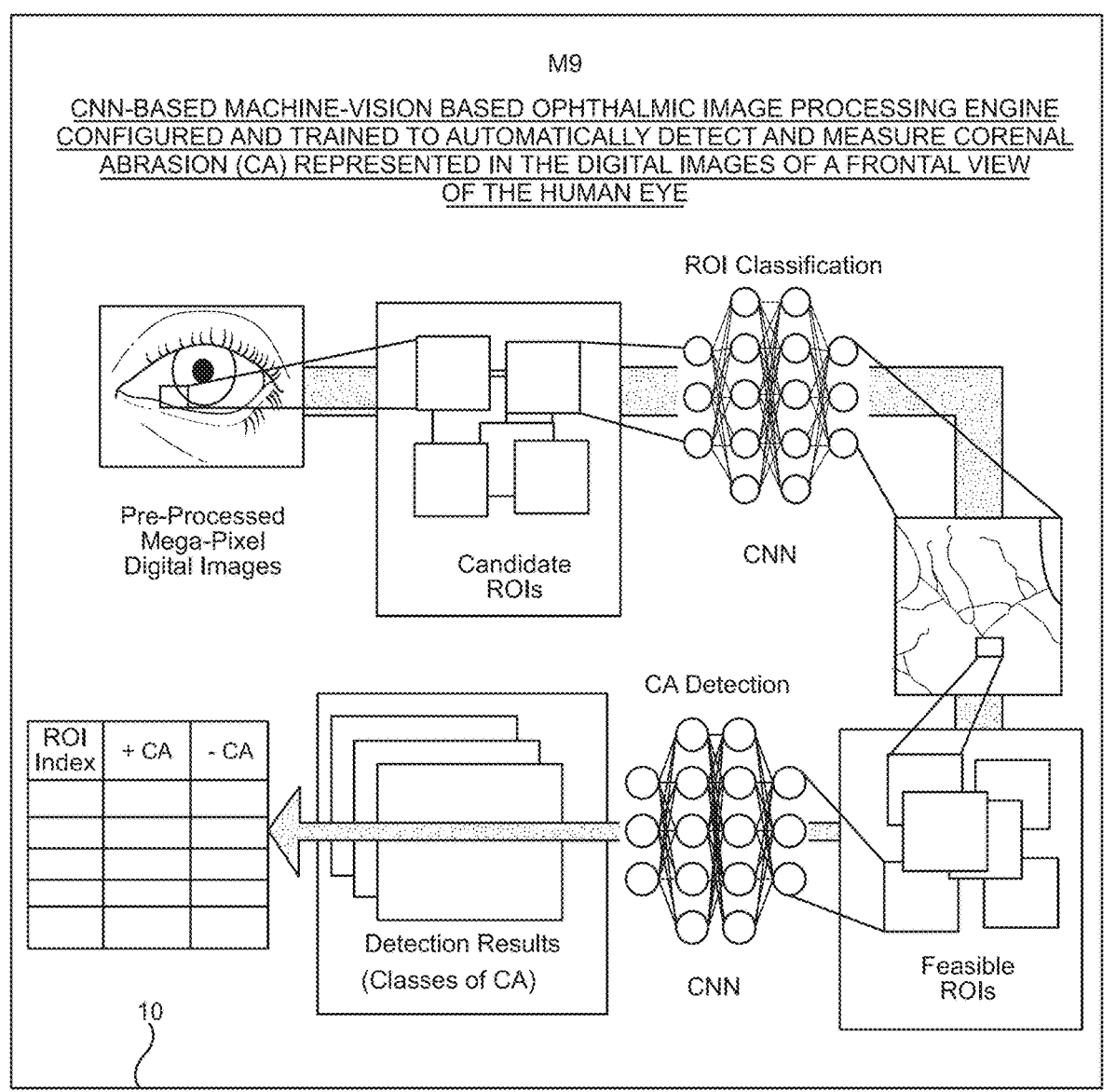
Figure 83:
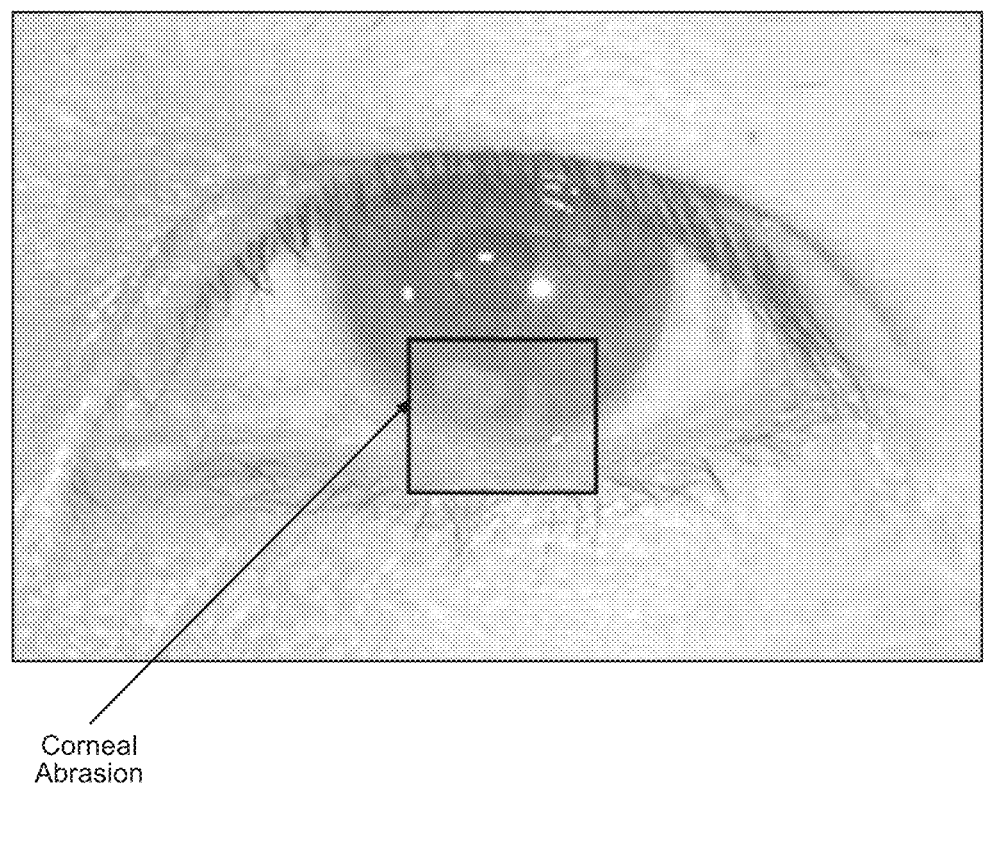
Figure 84:
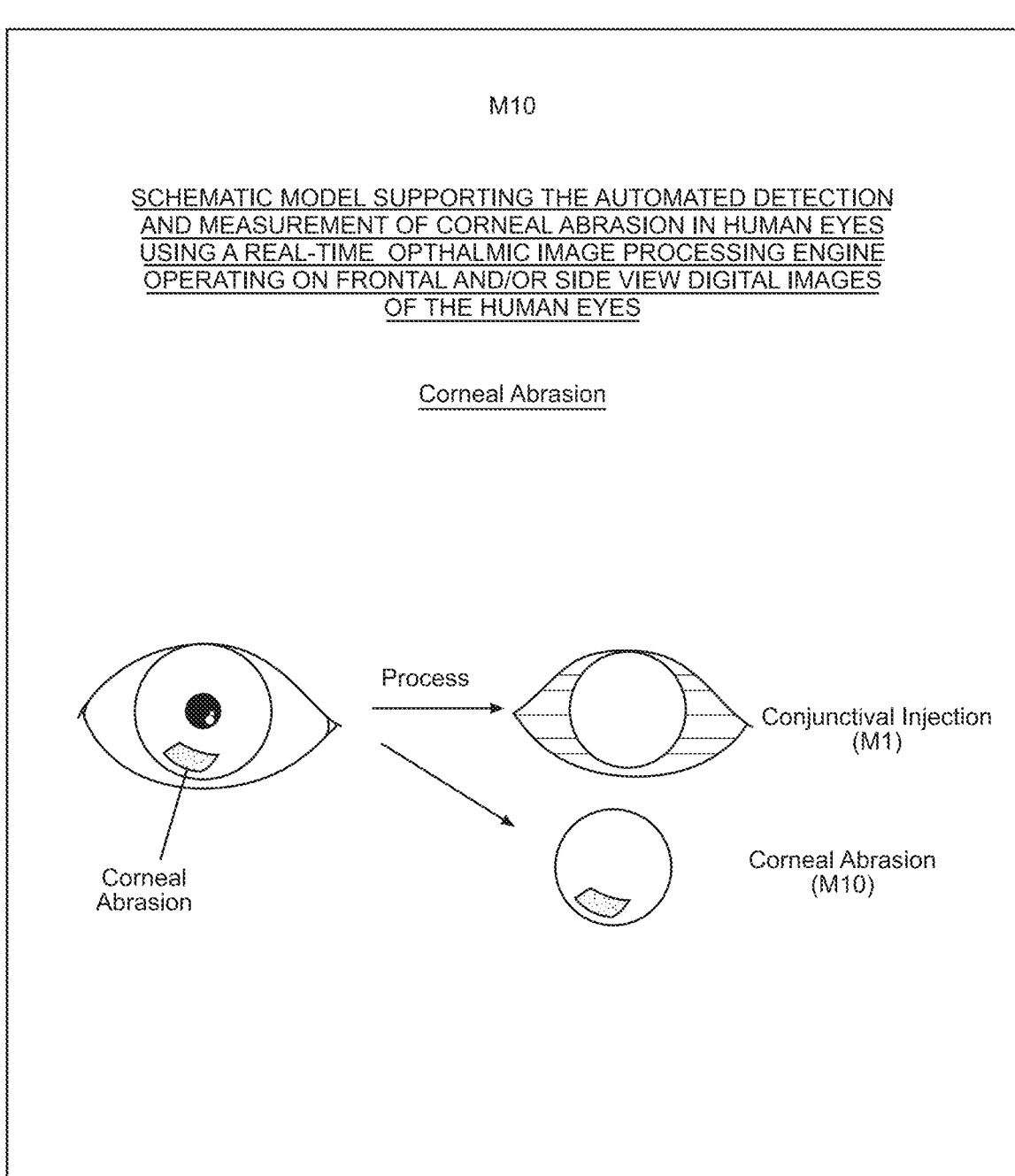
Figure 86:
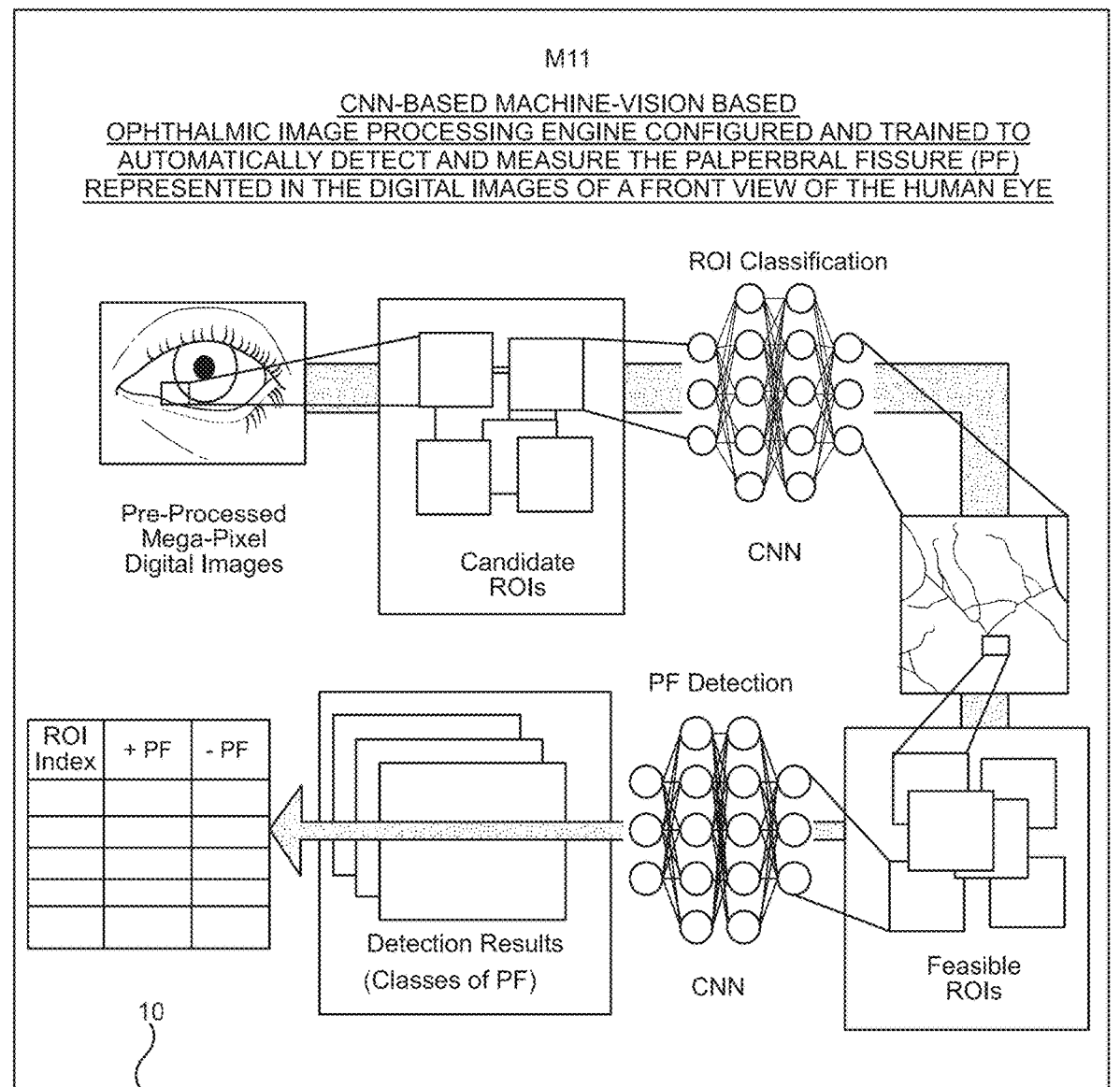
Figure 87:
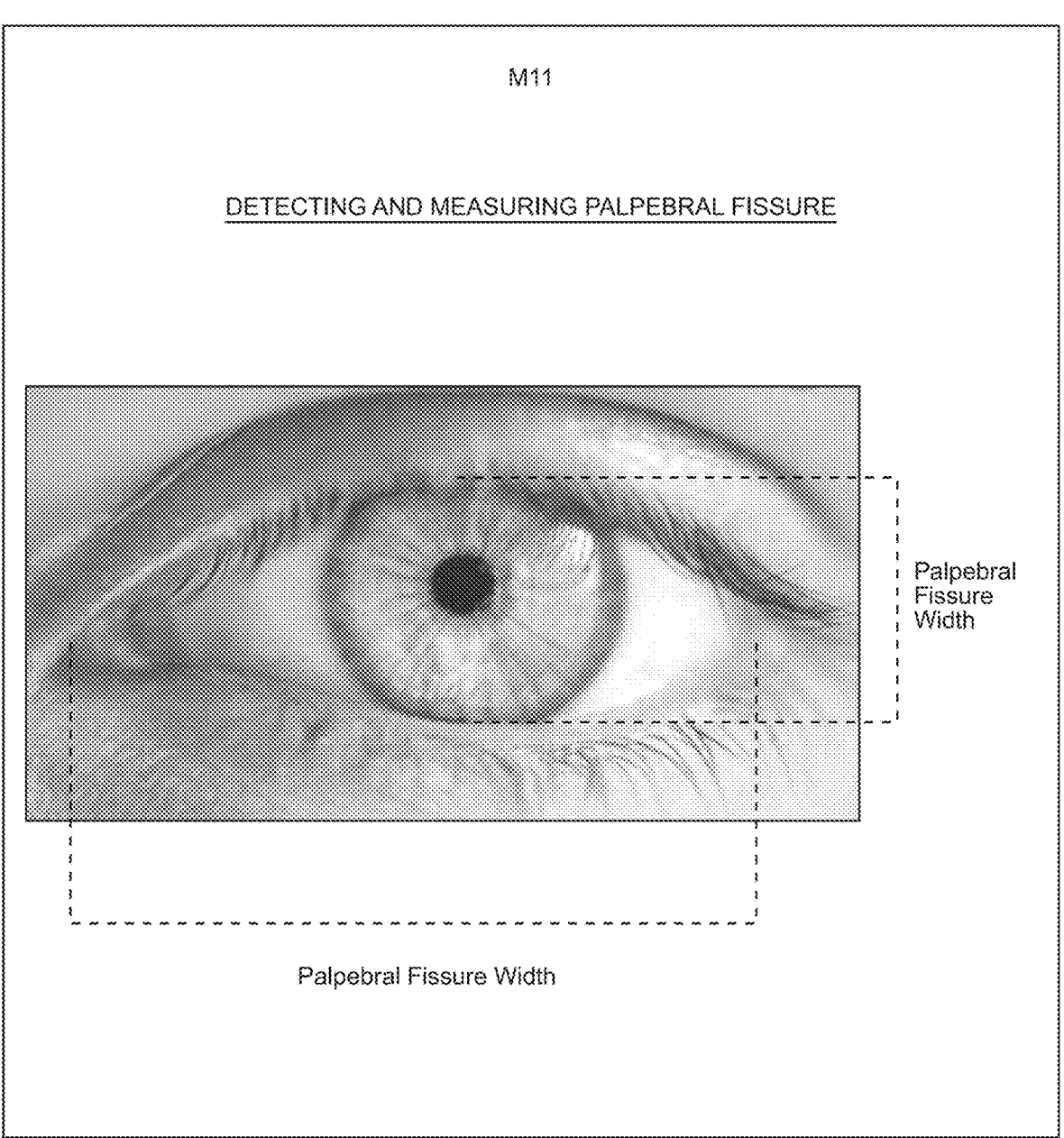
Figure 88:
Figure 90:
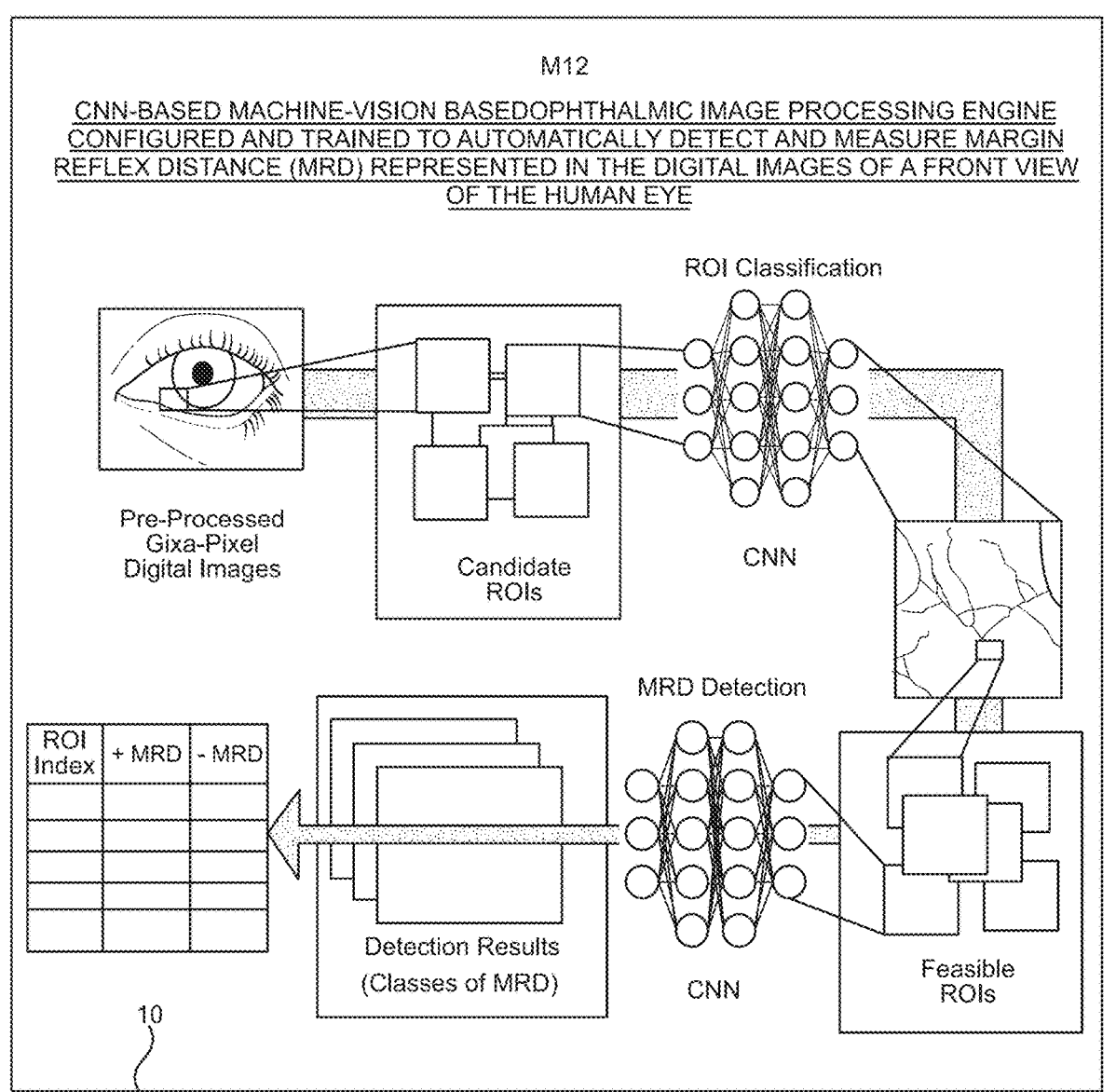
Figure 91:
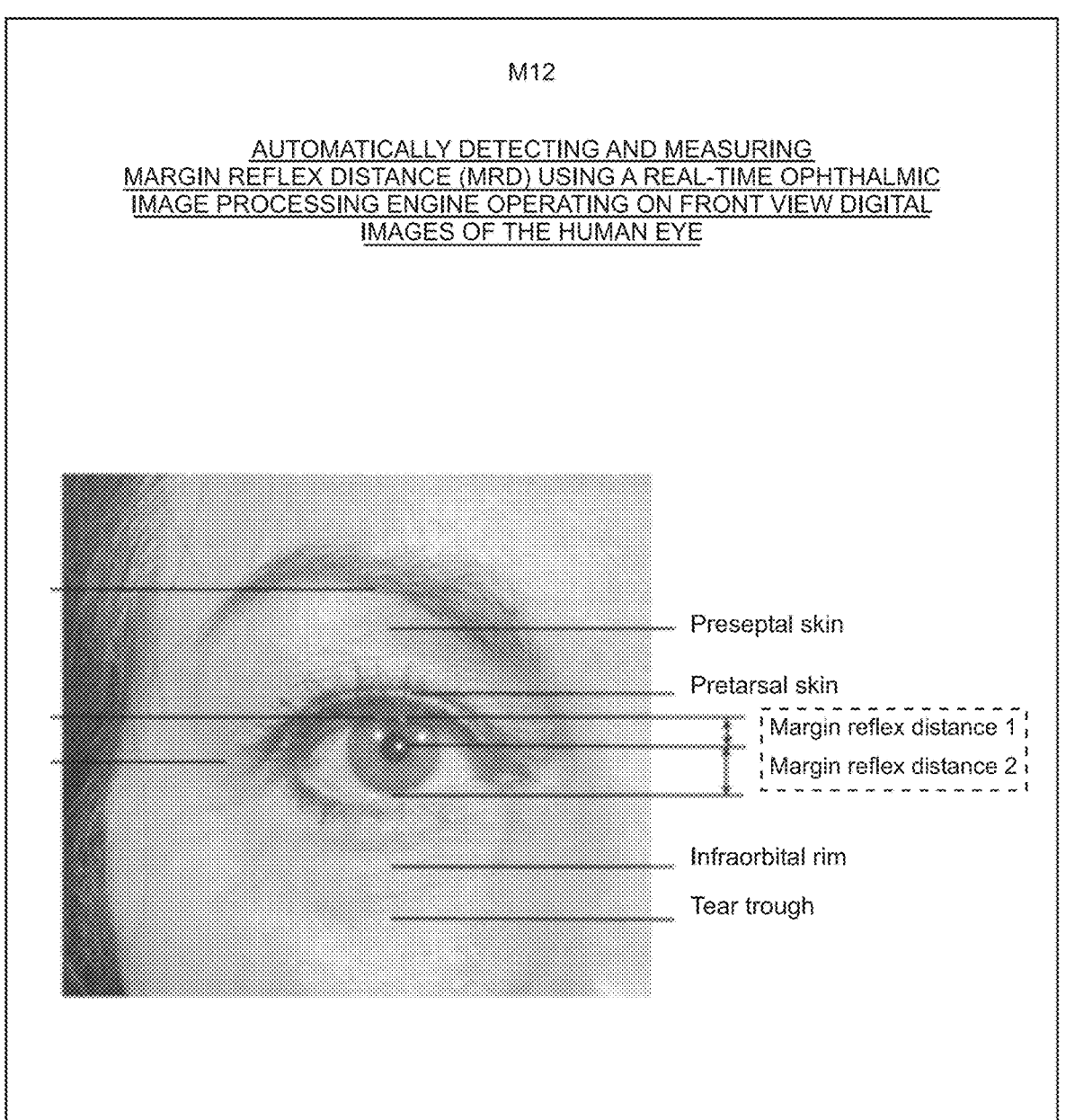
Figure 94:
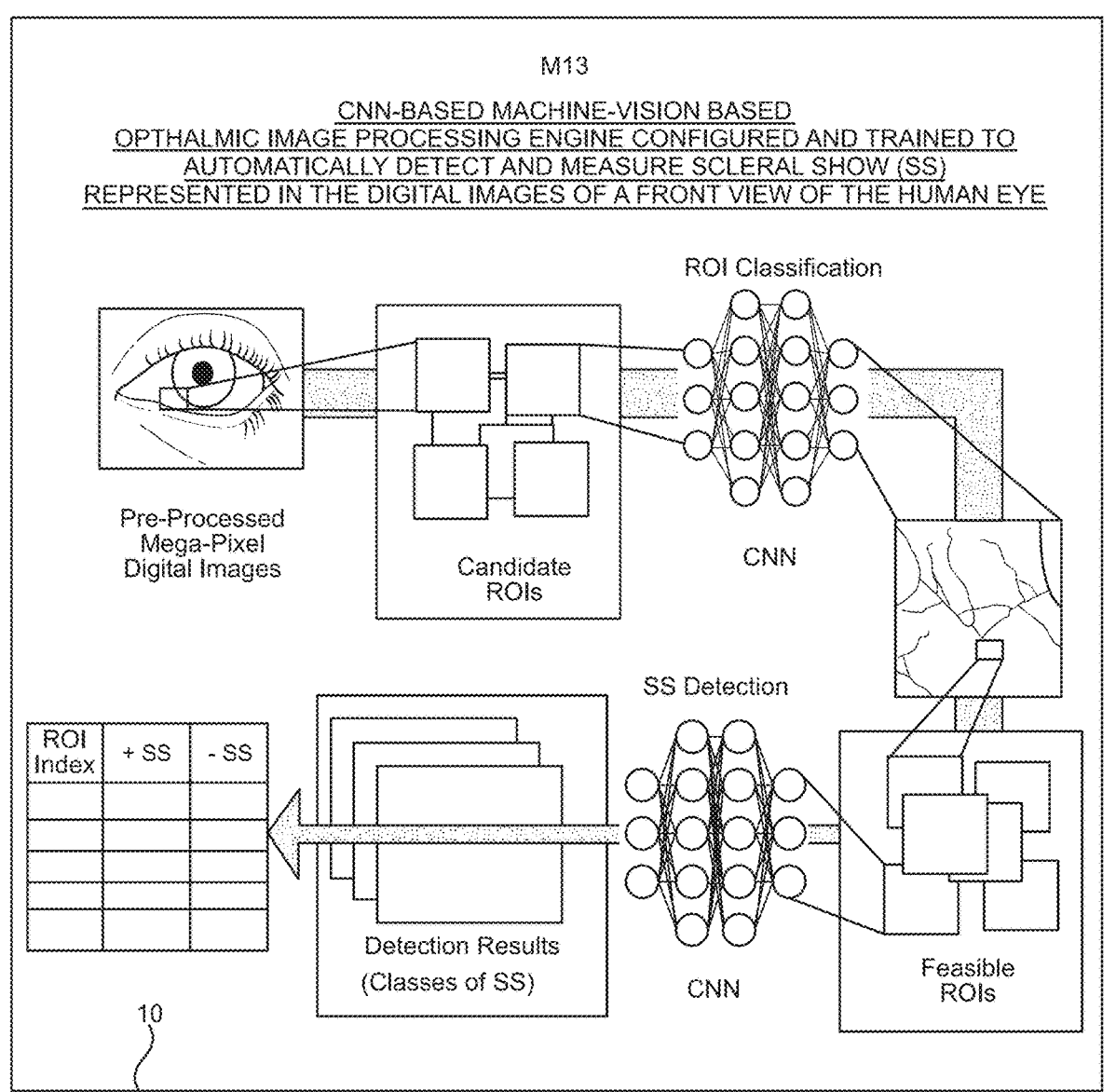
Figure 95:
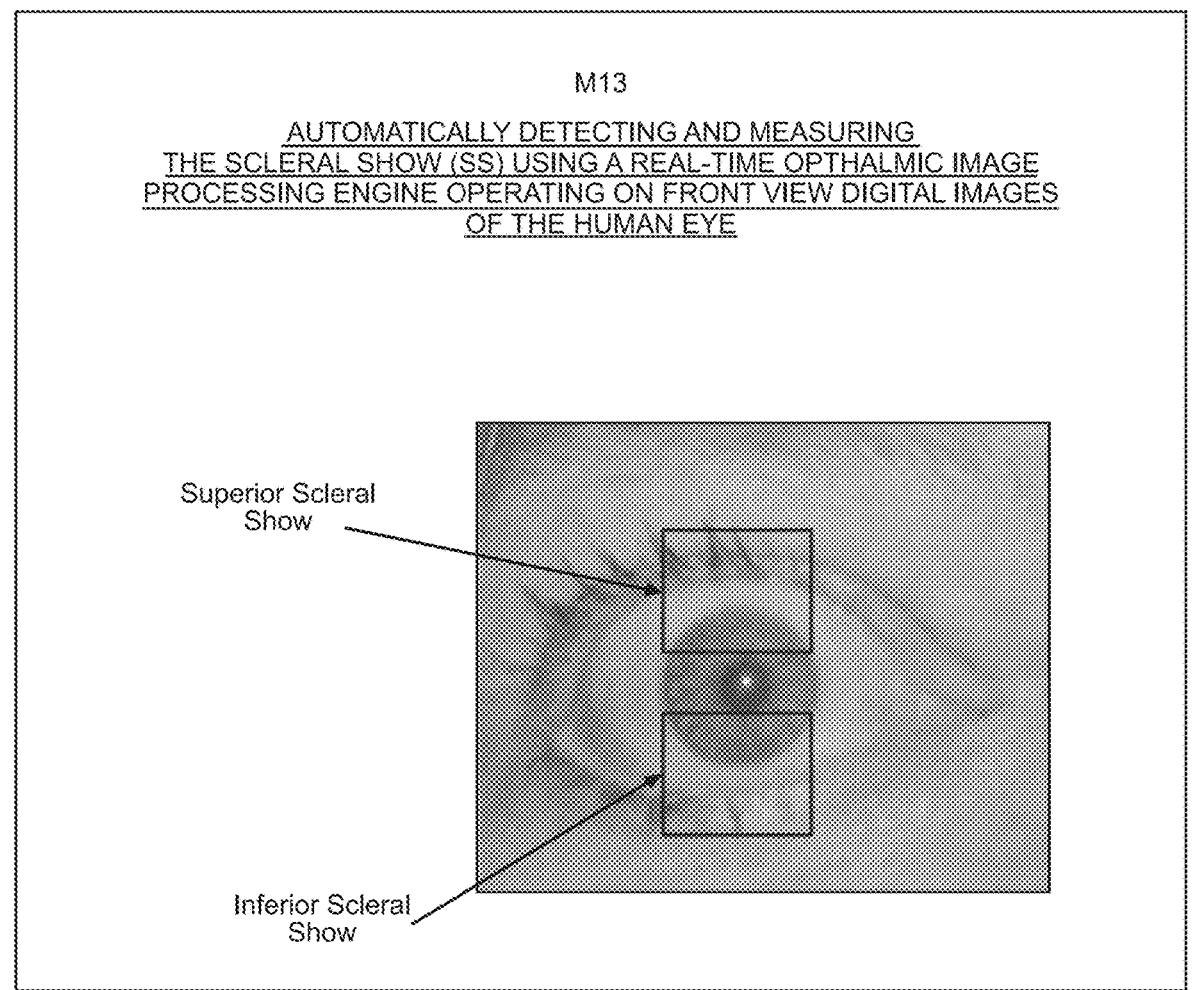
Figure 96:
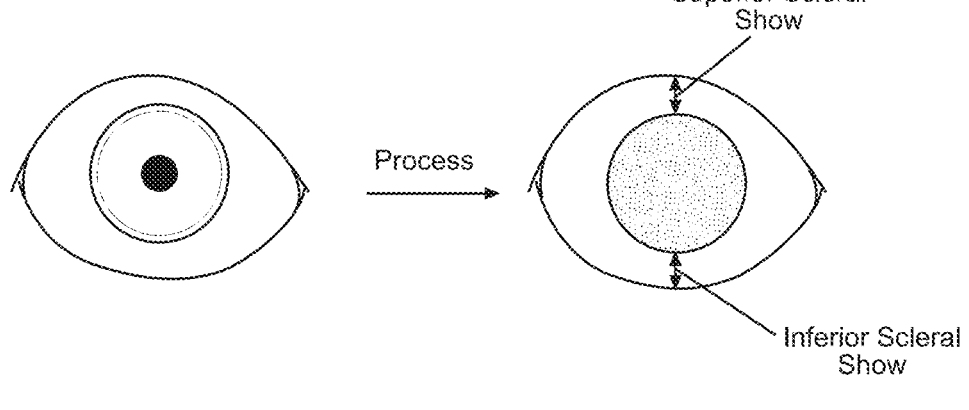
Figure 98:
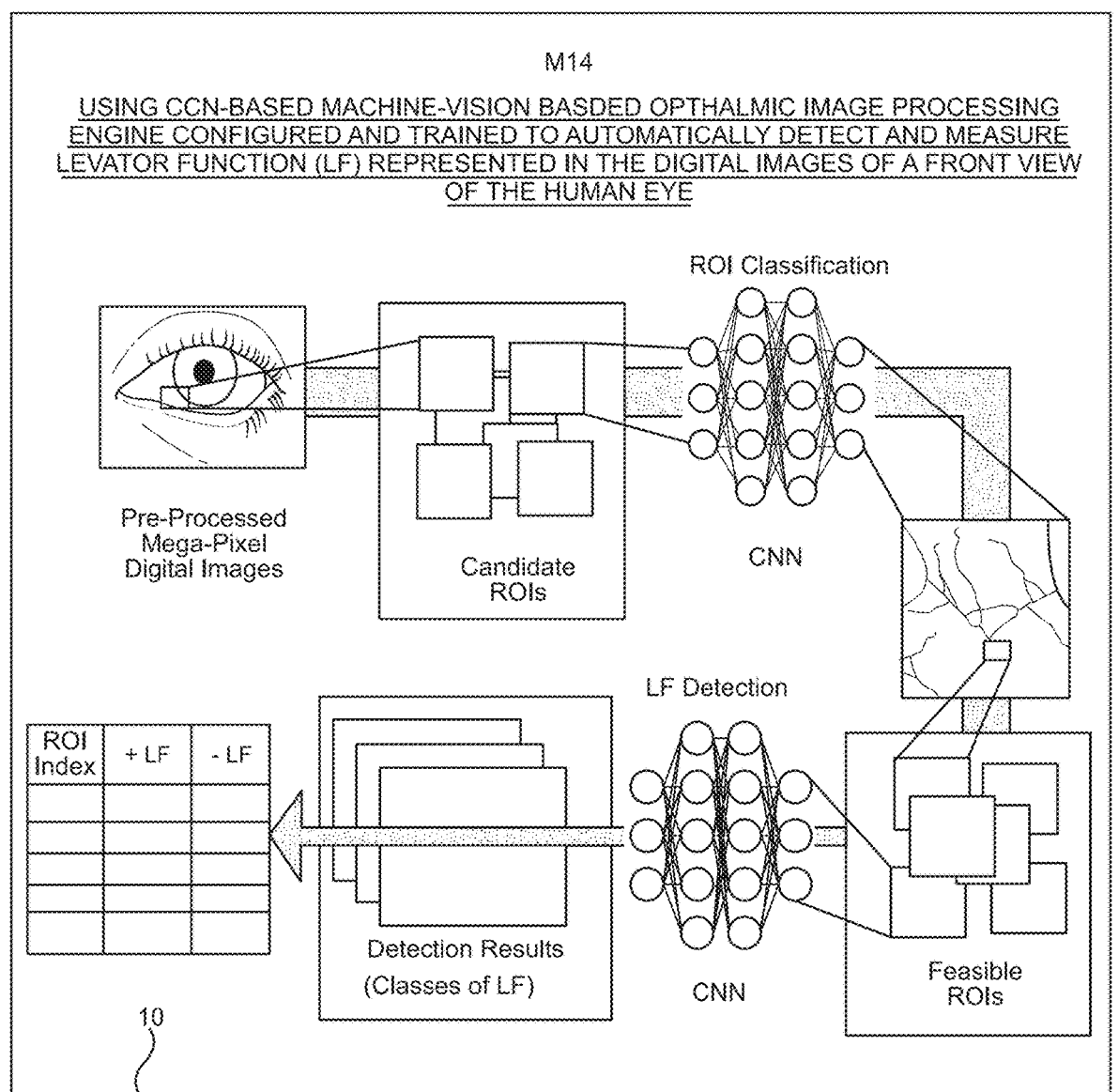
Figure 99:
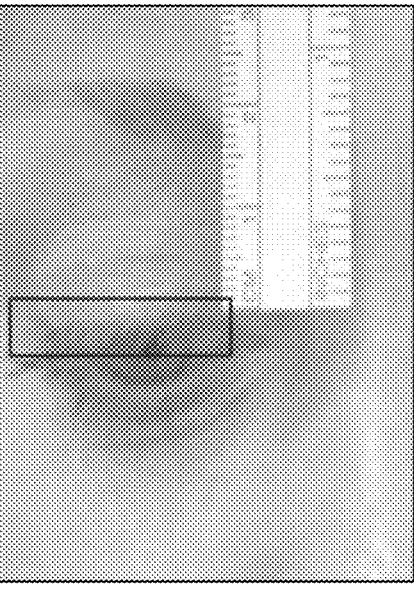
Figure 100:
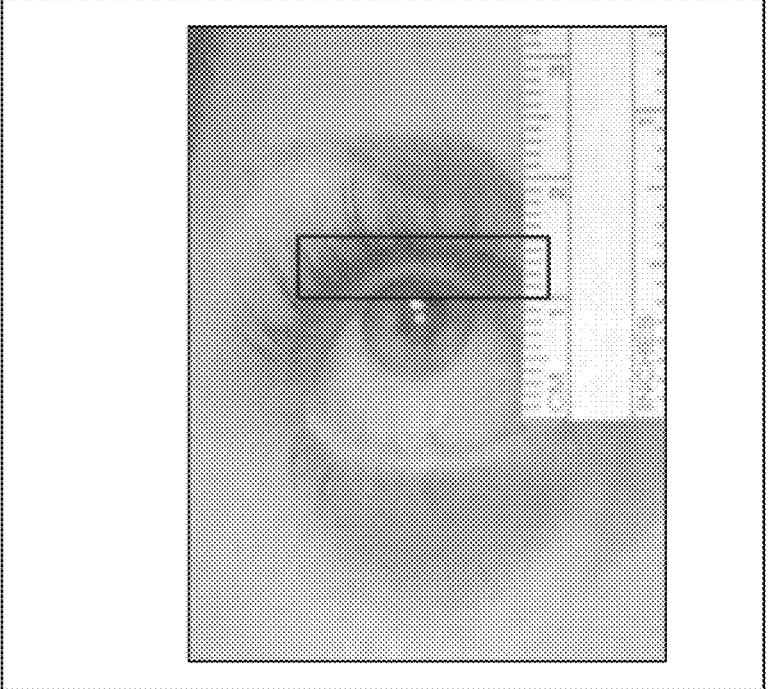
Figure 101:
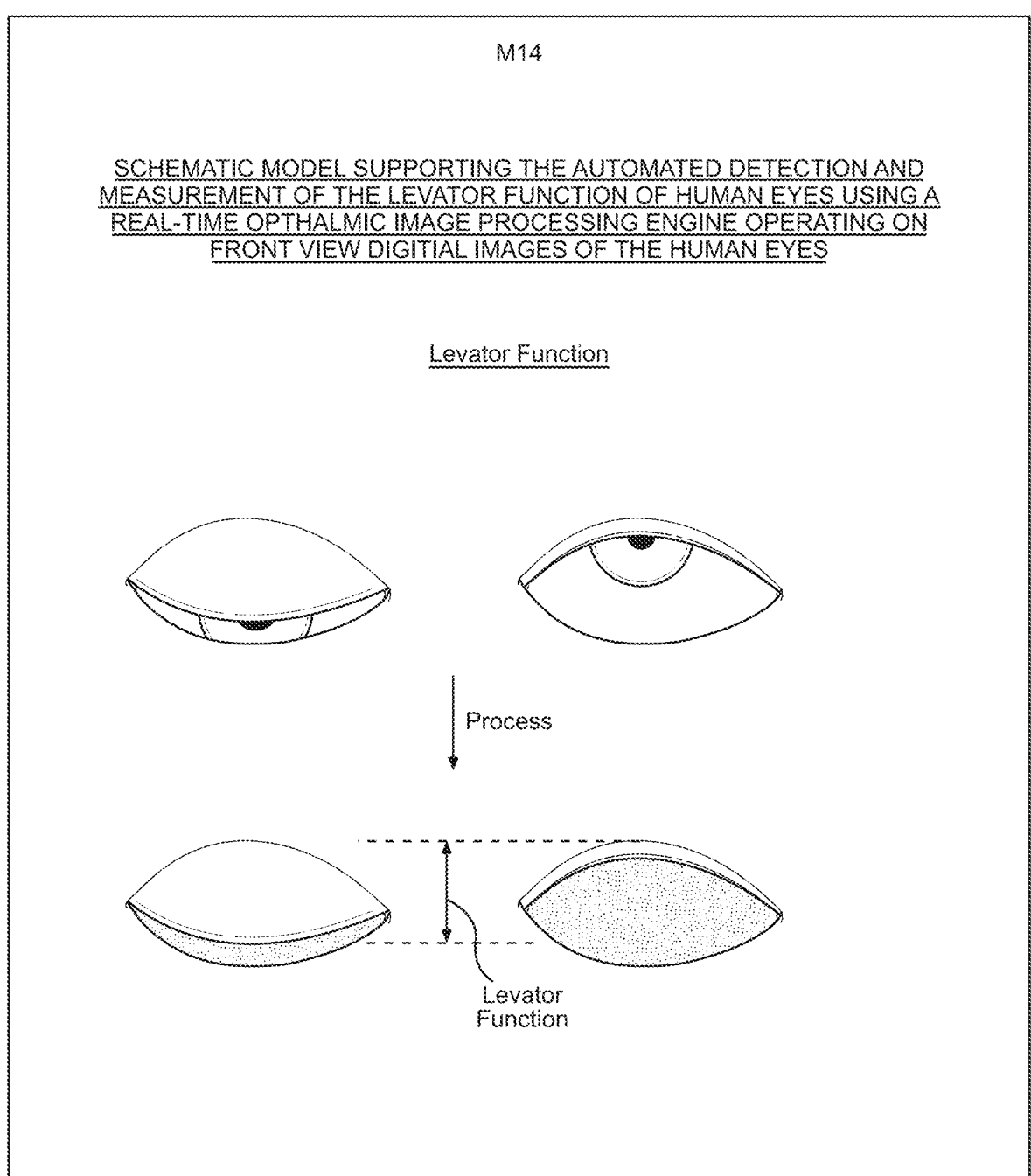
Figure 103:
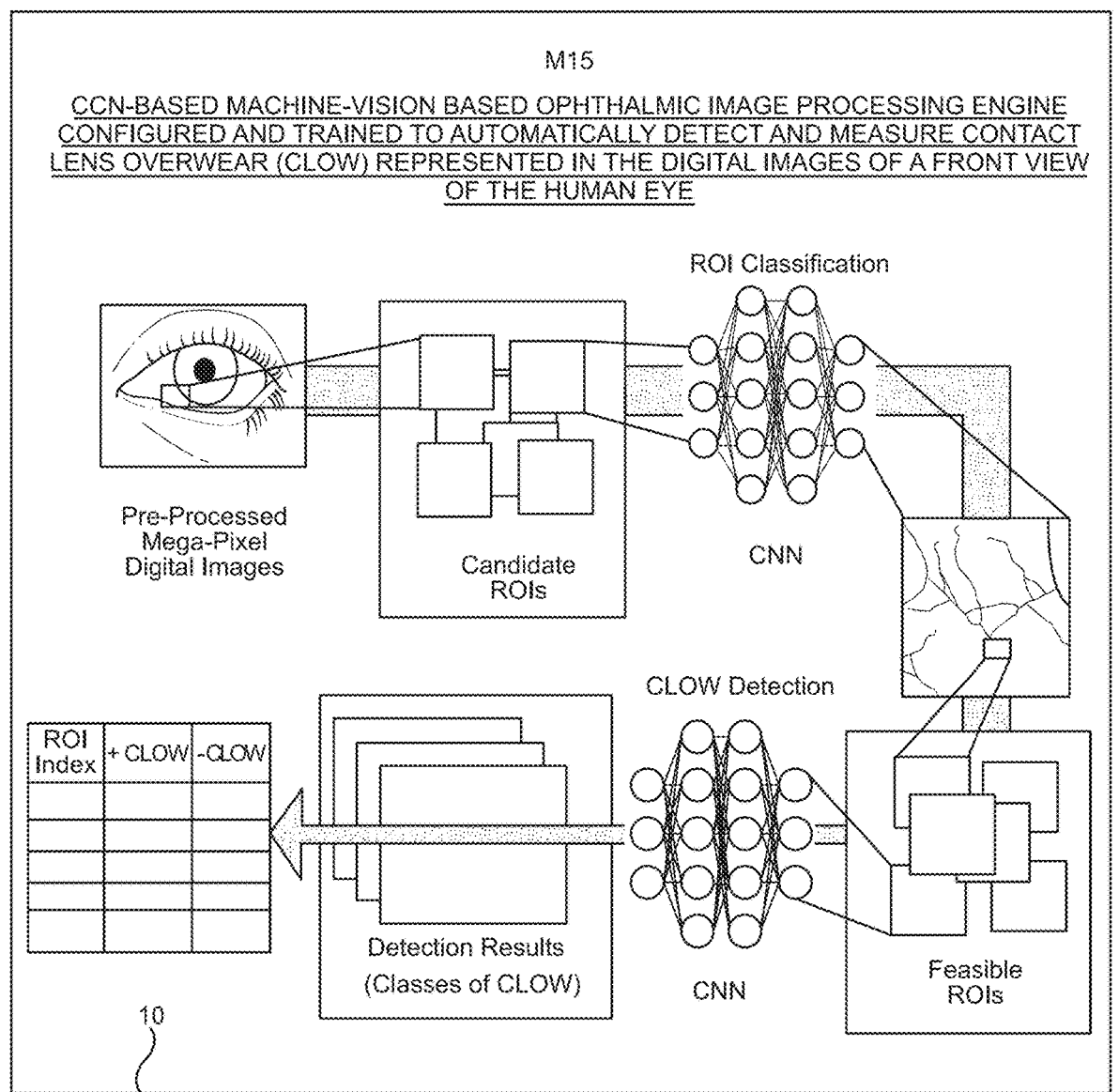
Figure 105:
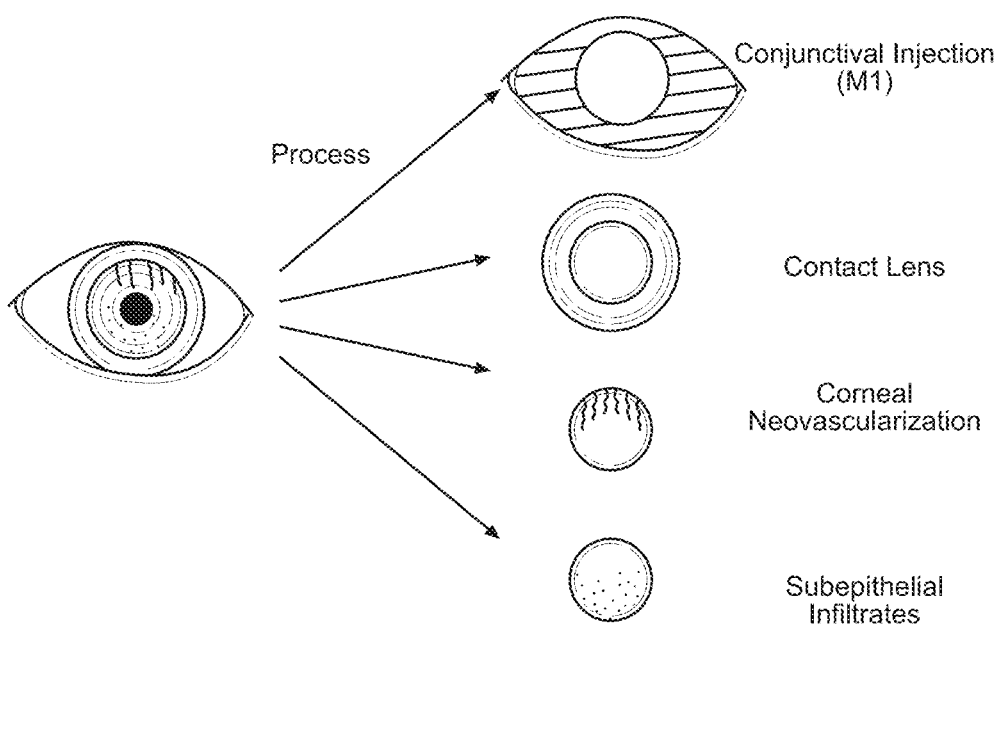
Figure 107:
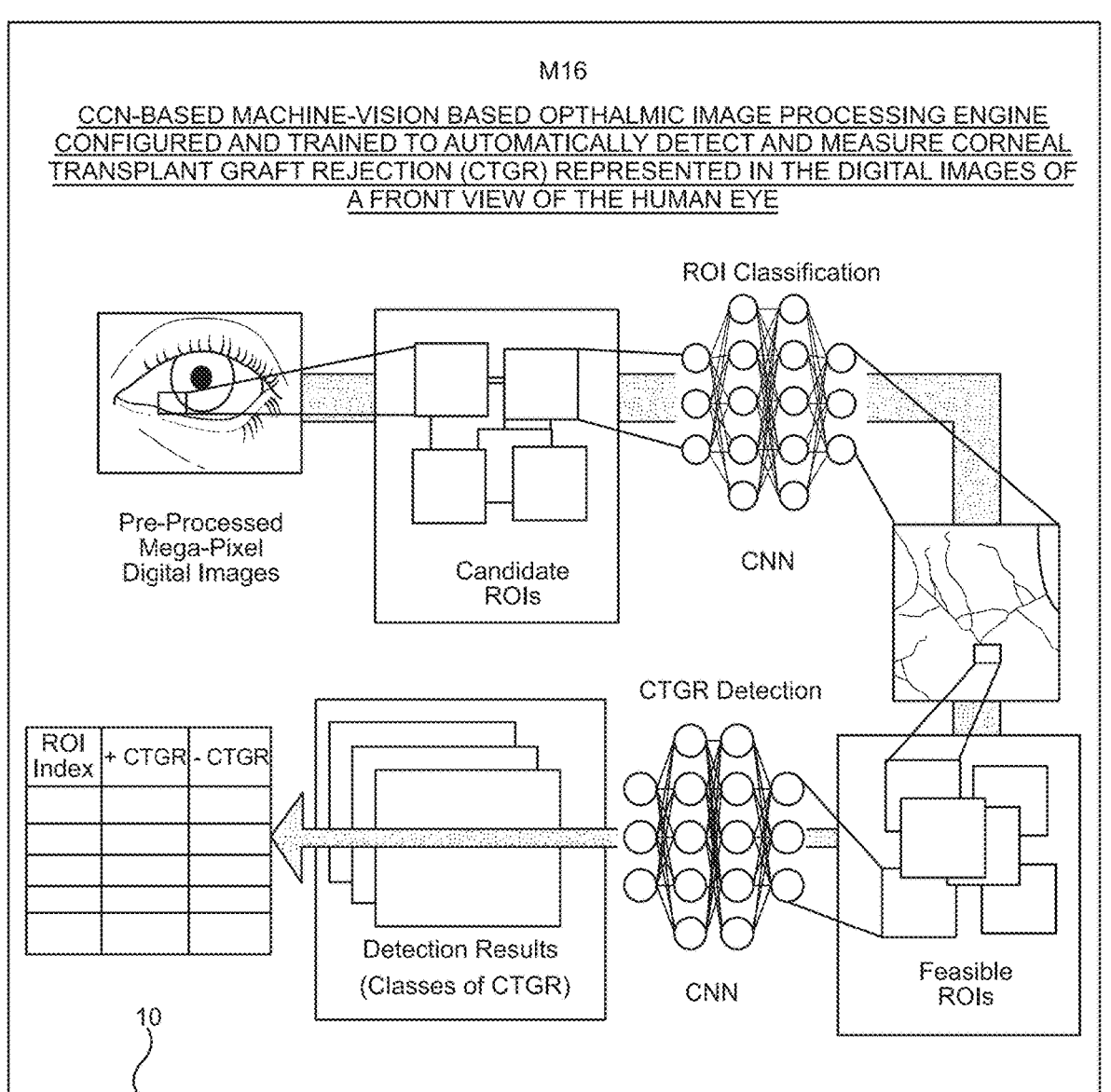
Figure 108:
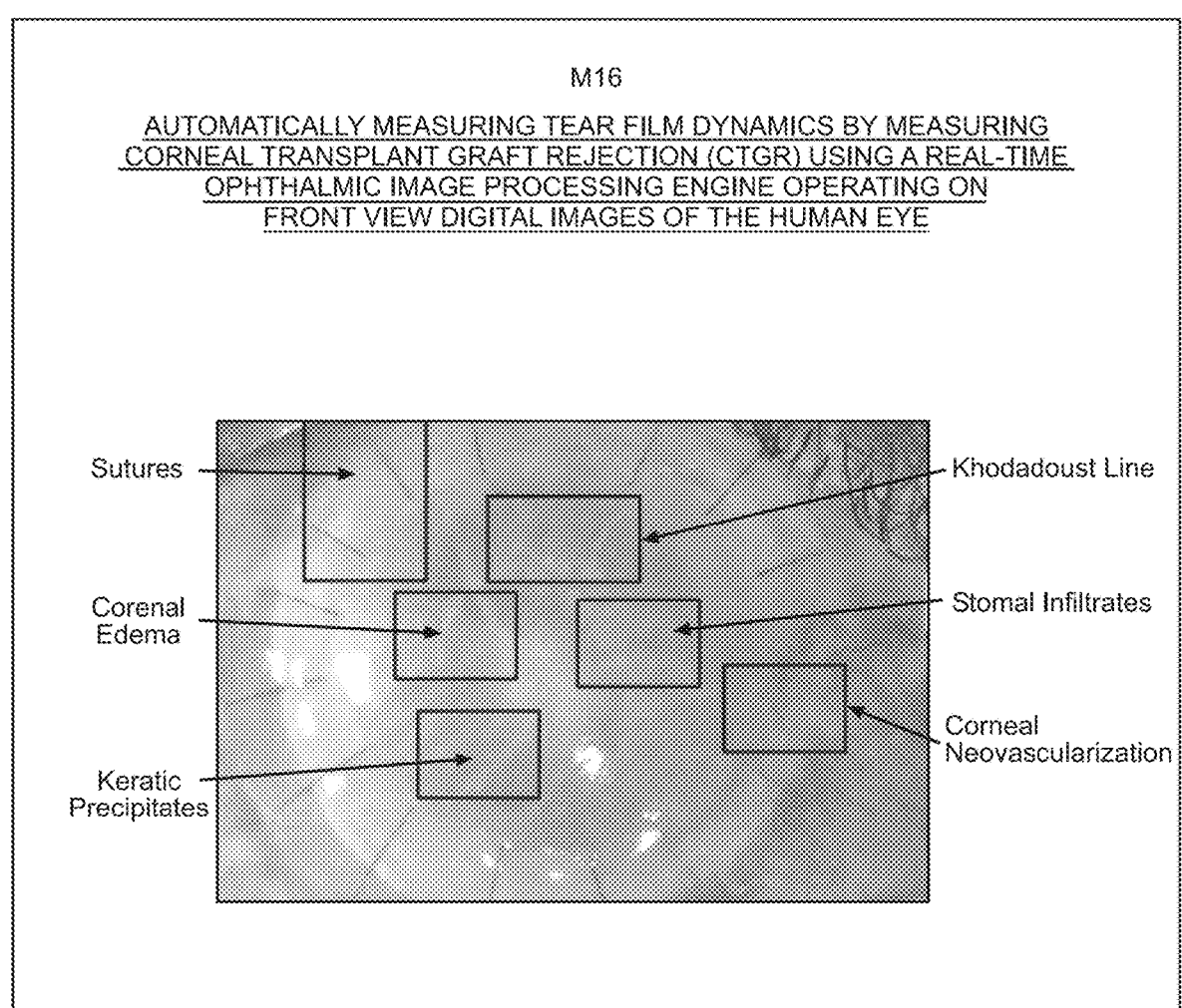
Figure 111:
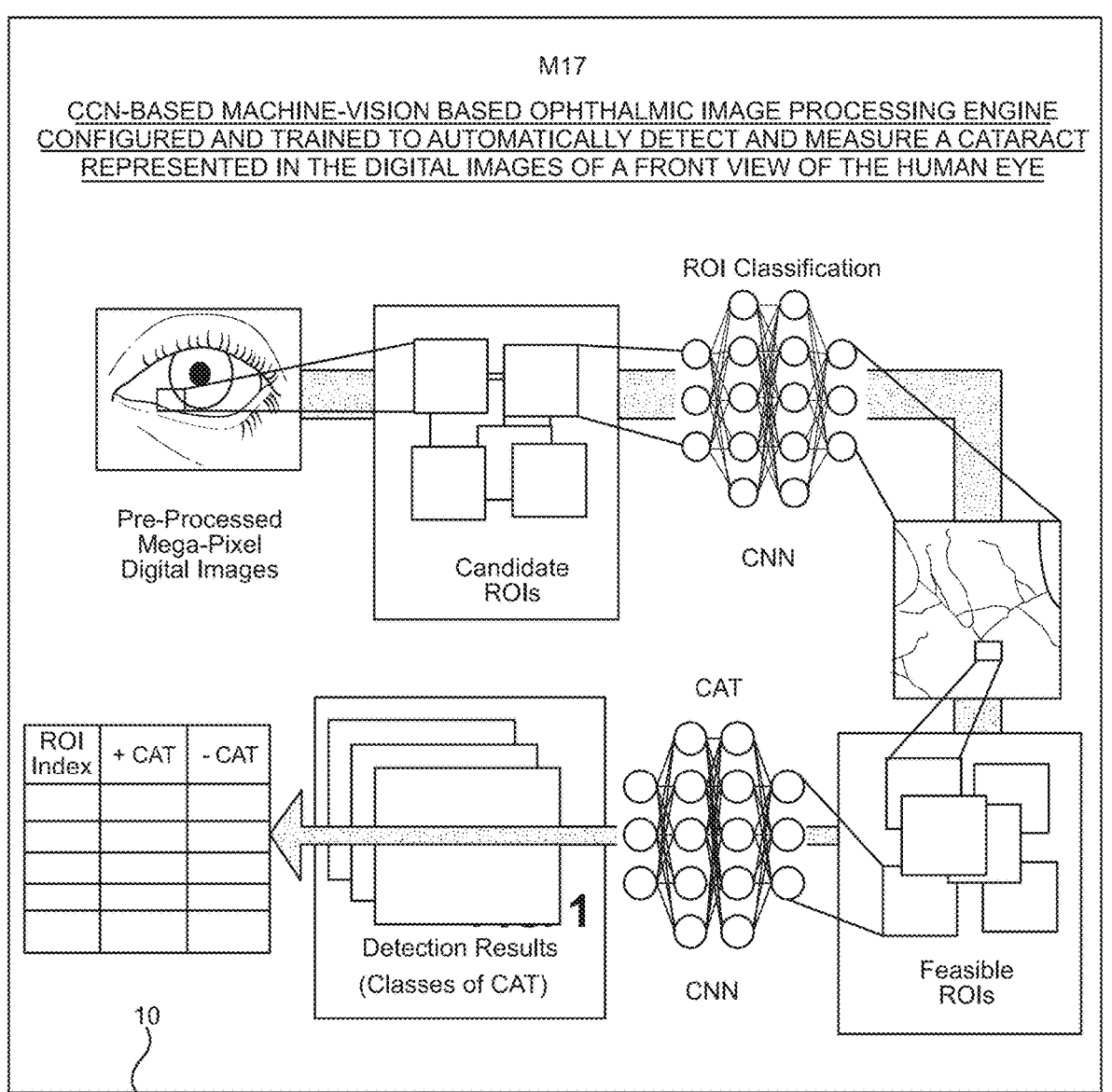
Figure 115:
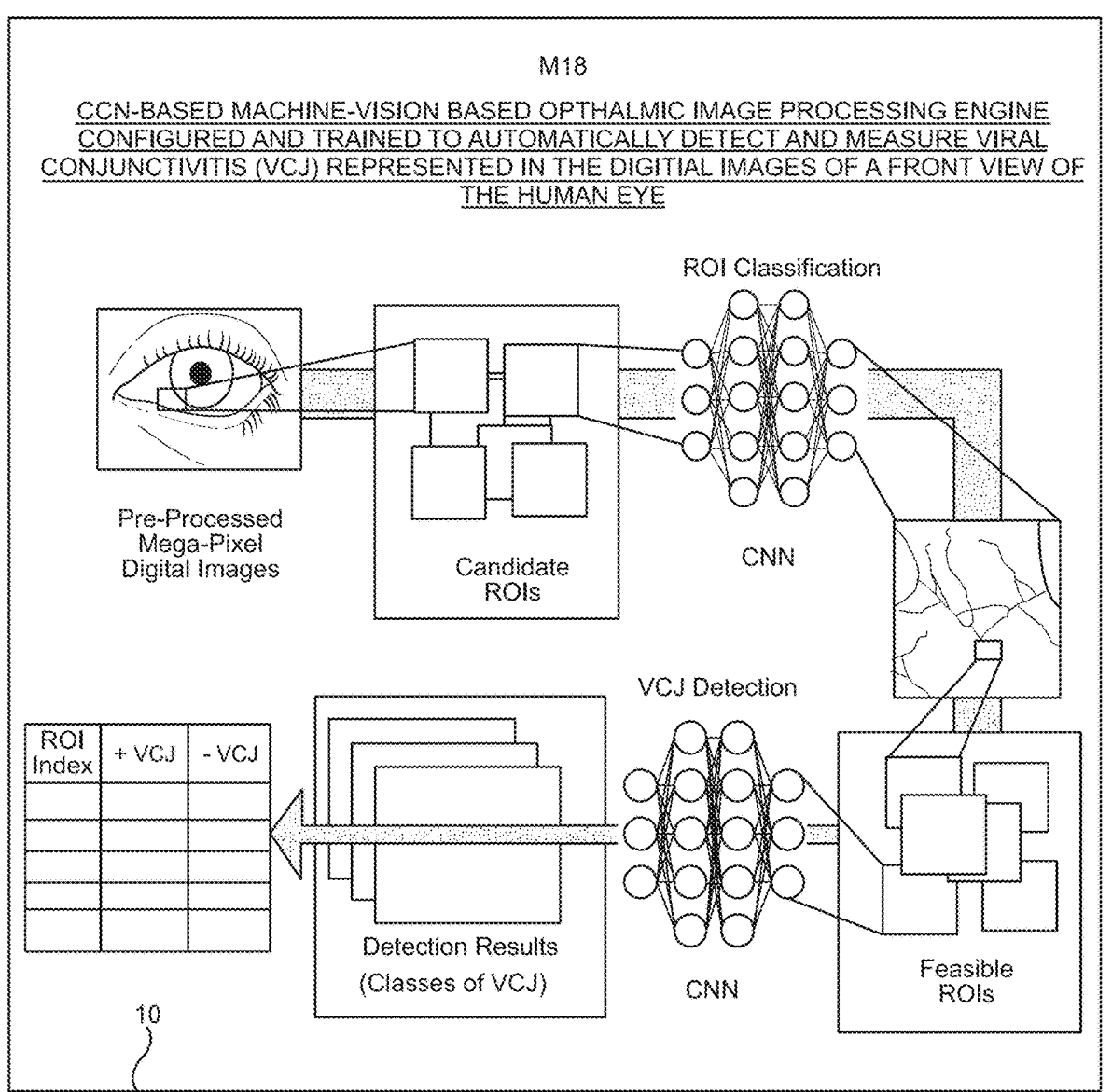
Figure 116:
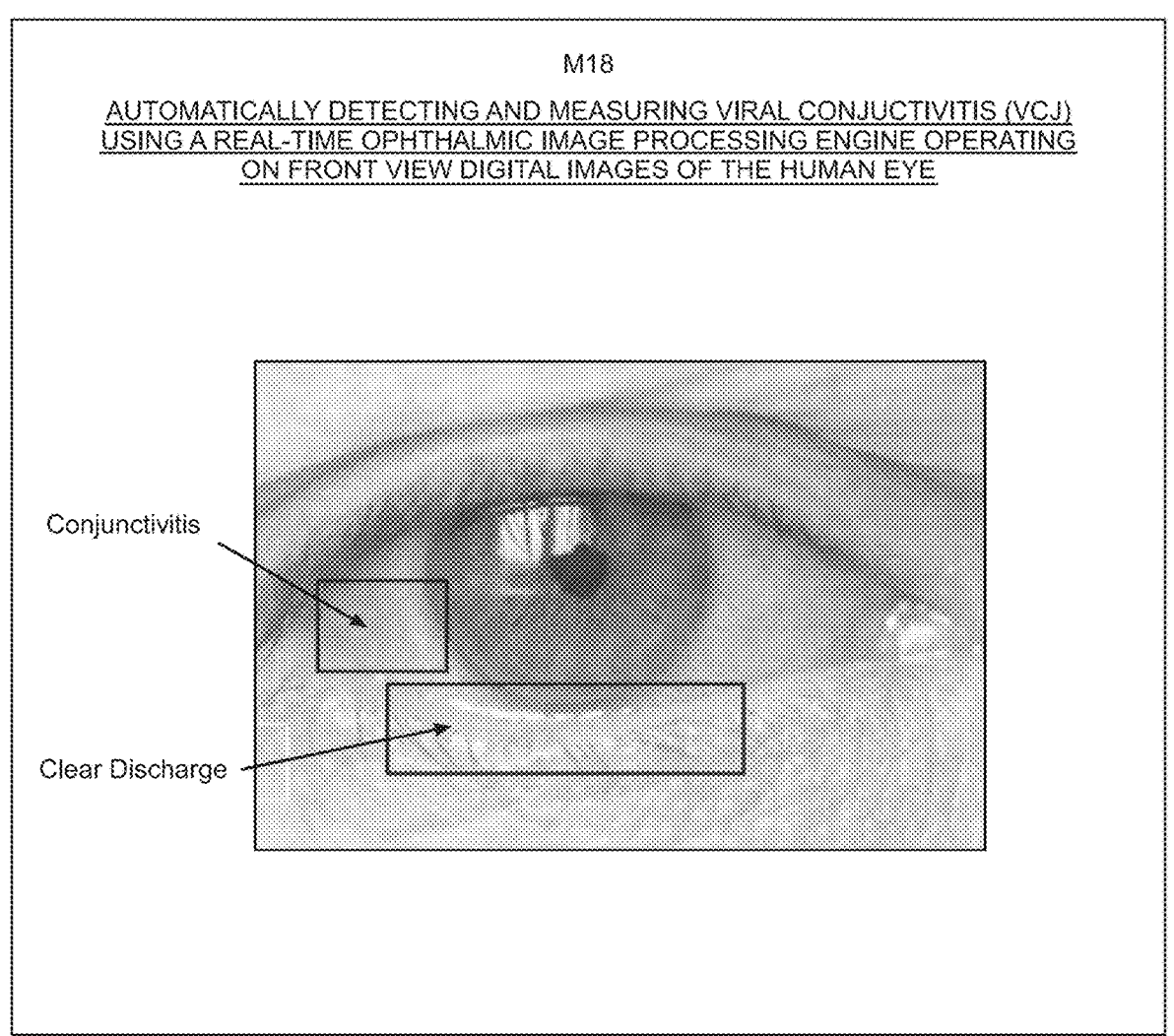
Figure 117:
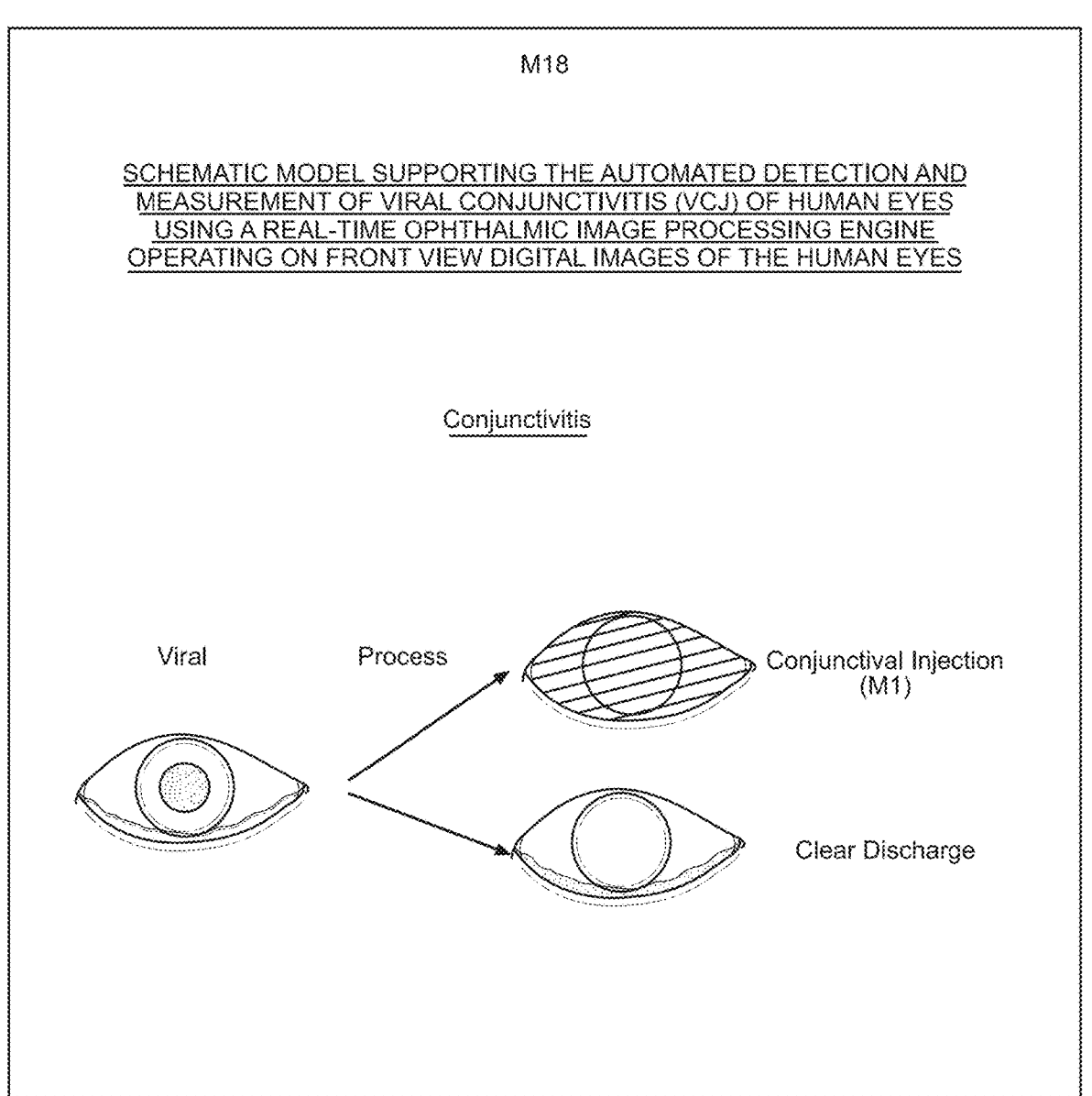
Figure 119:
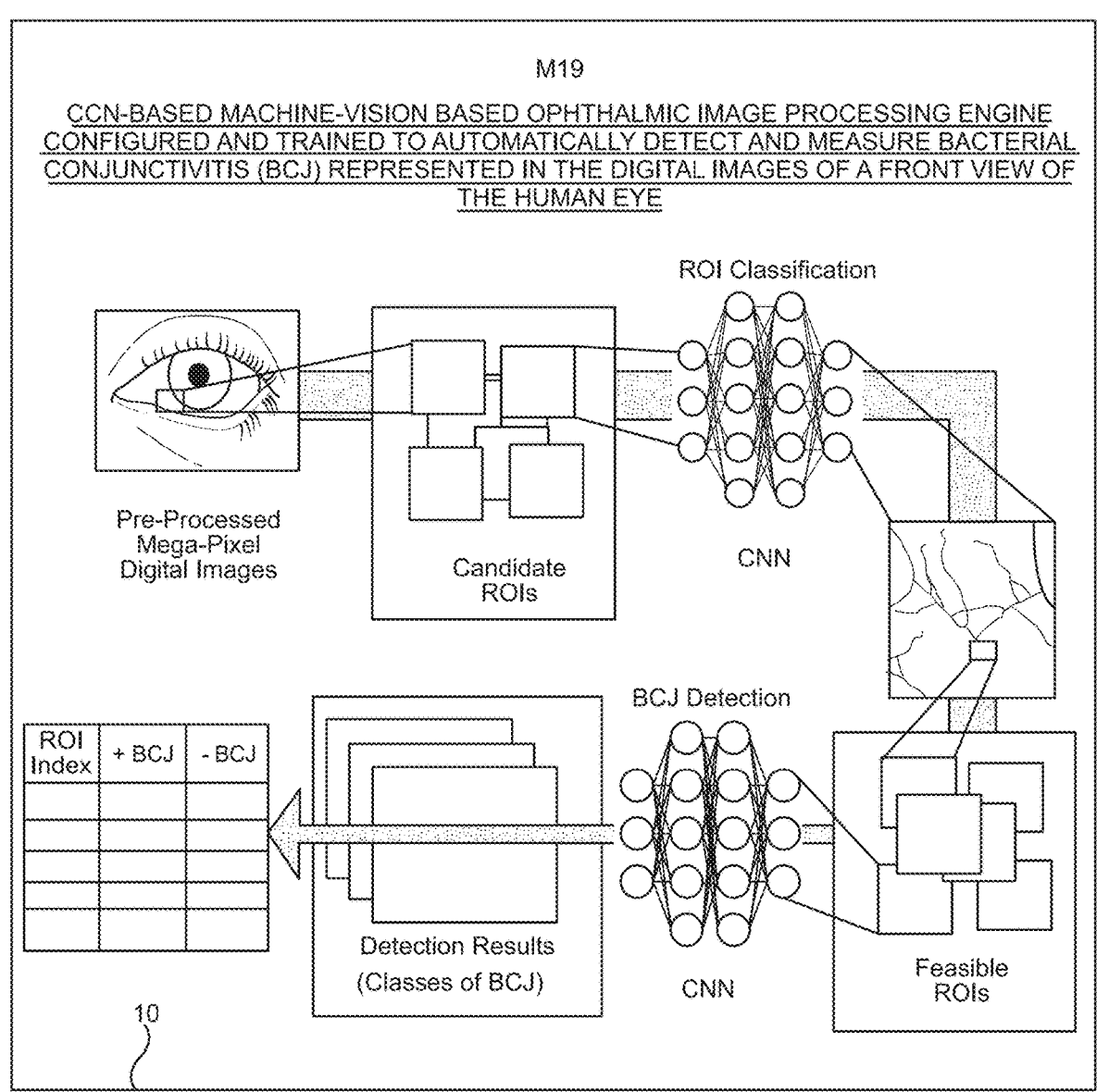
Figure 120:
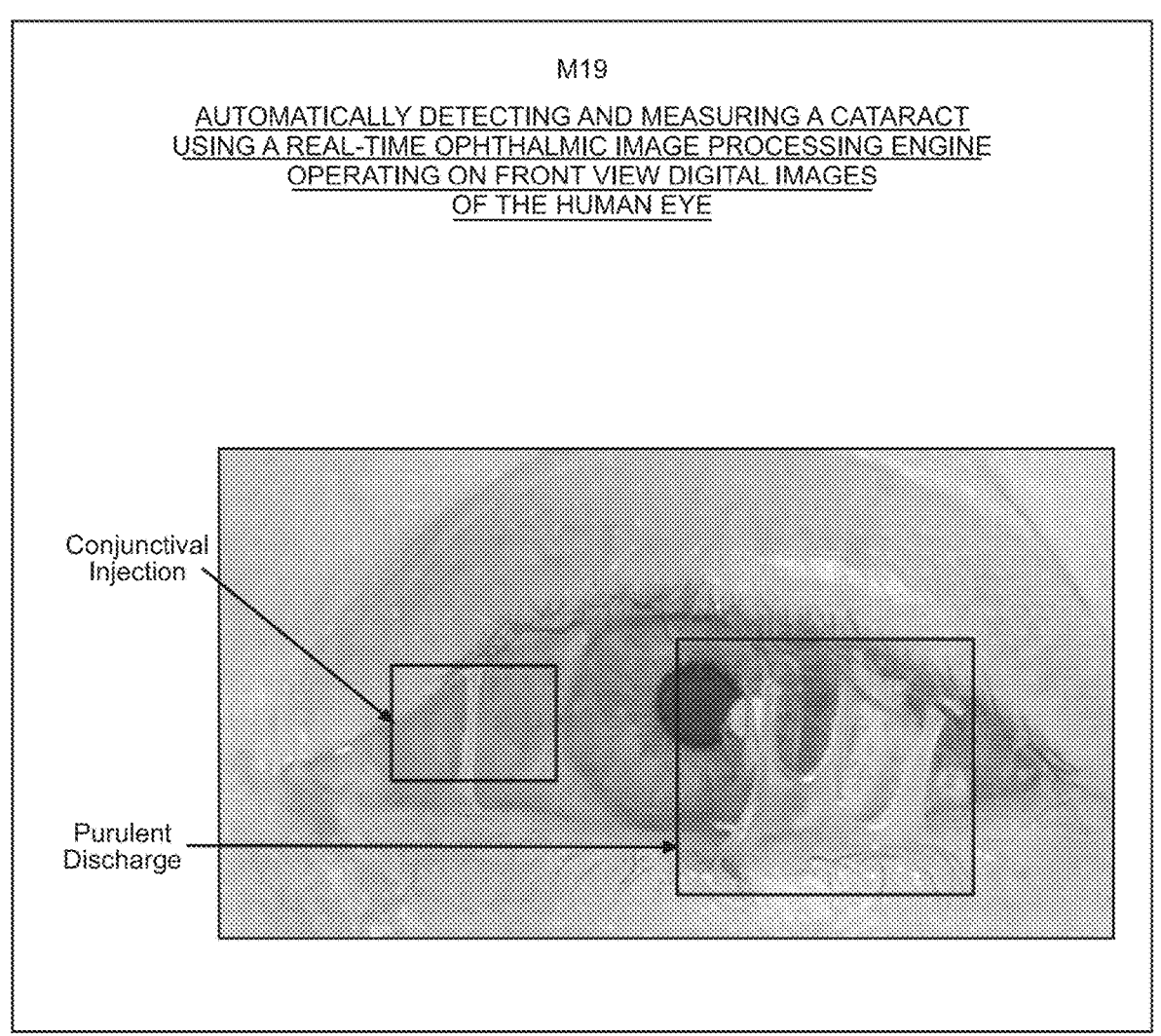
Figure 121:
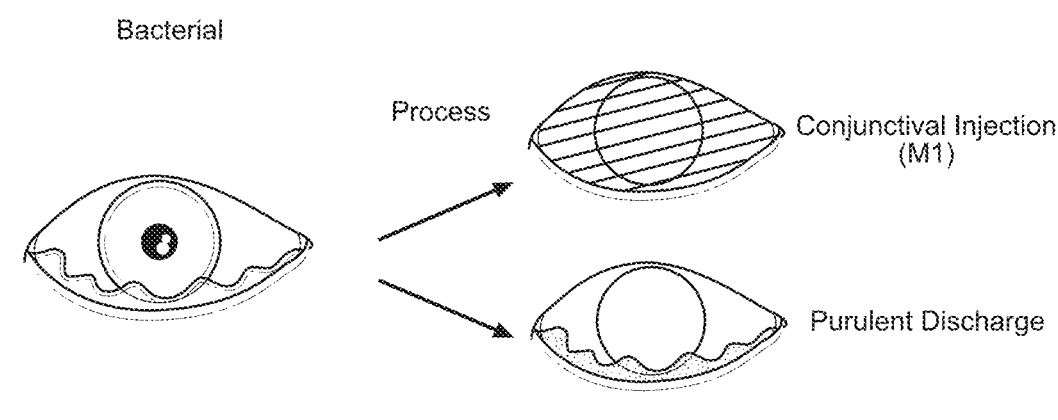
Figure 123:
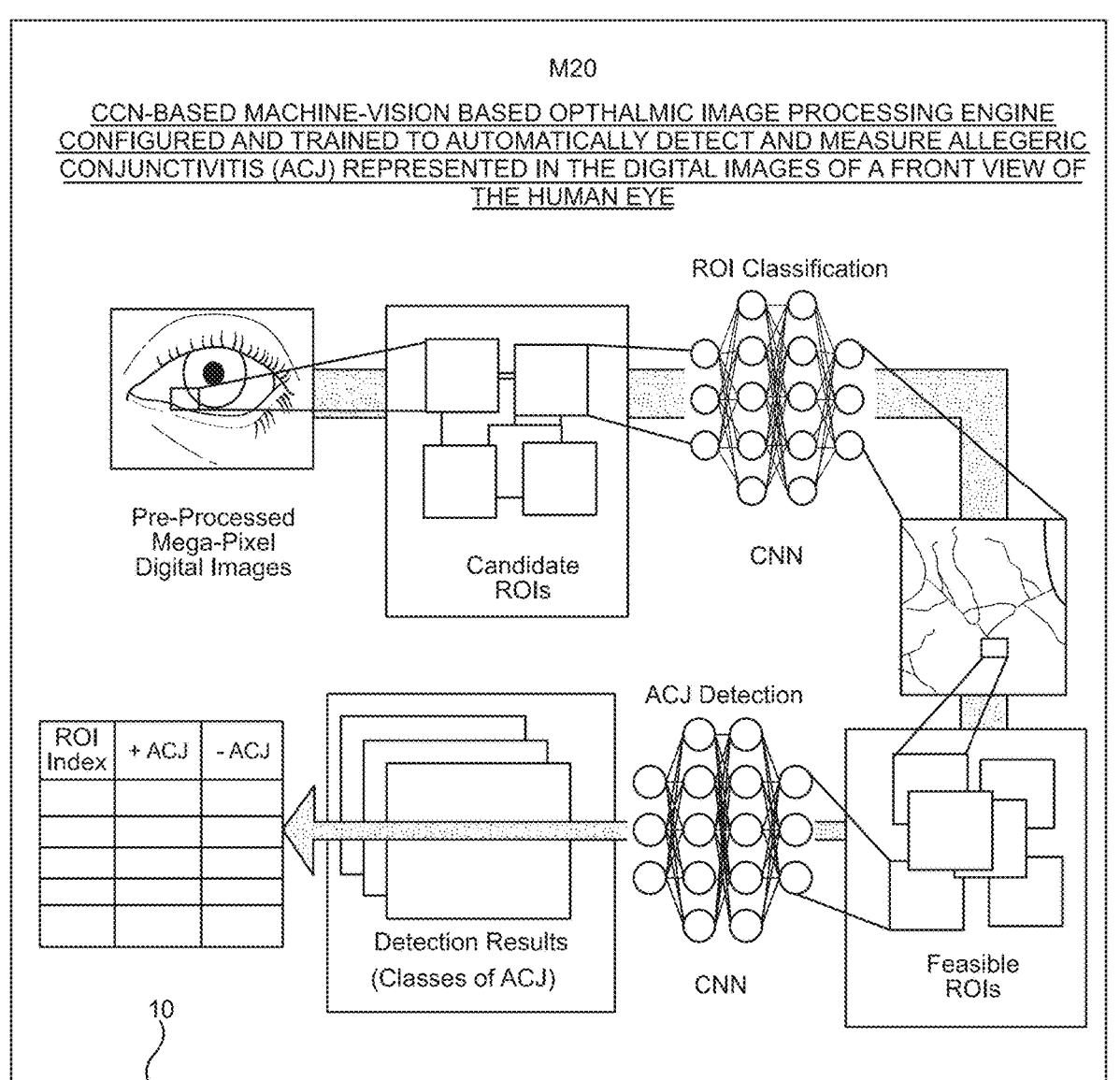
Figure 124:
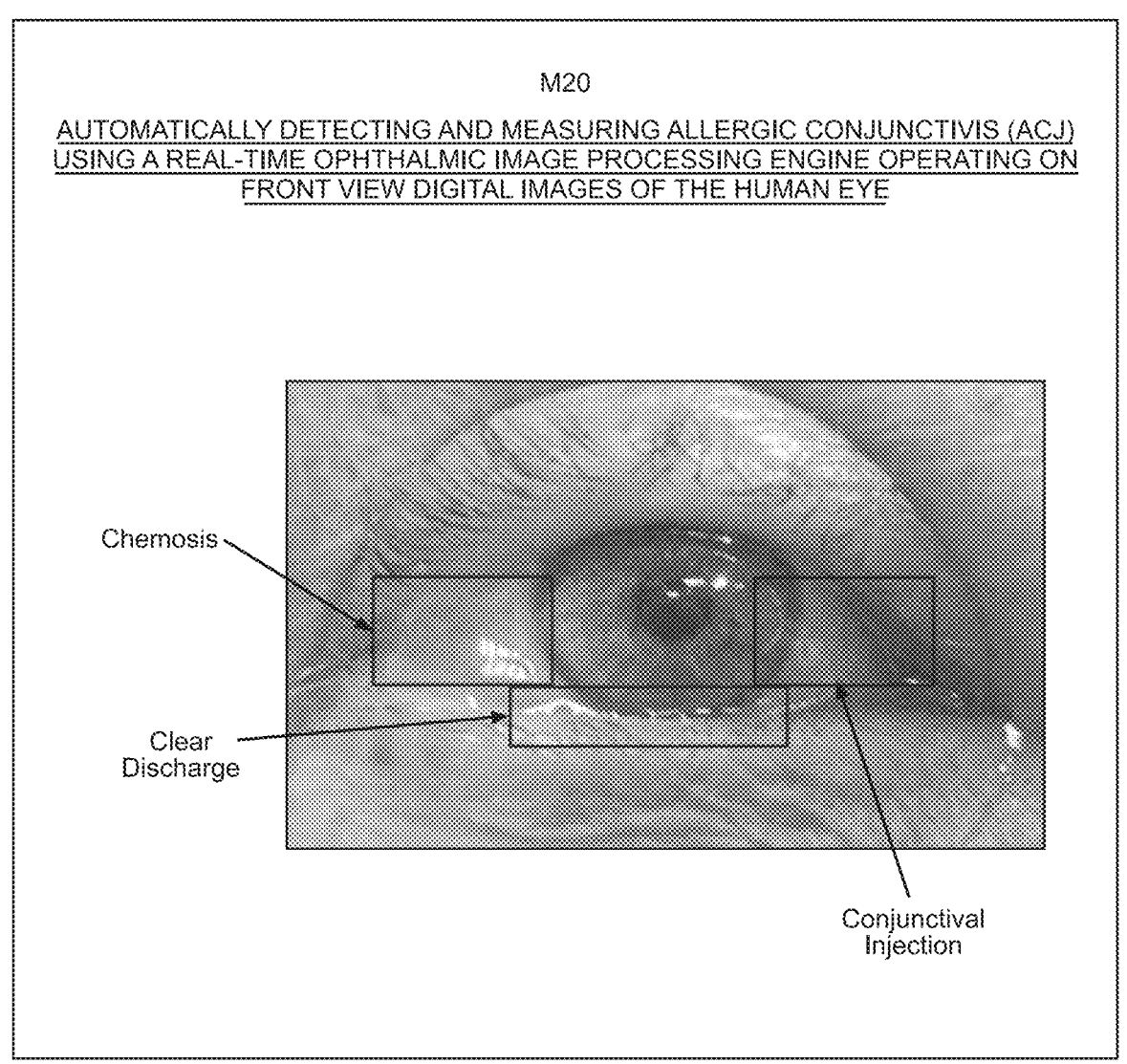
Figure 125:
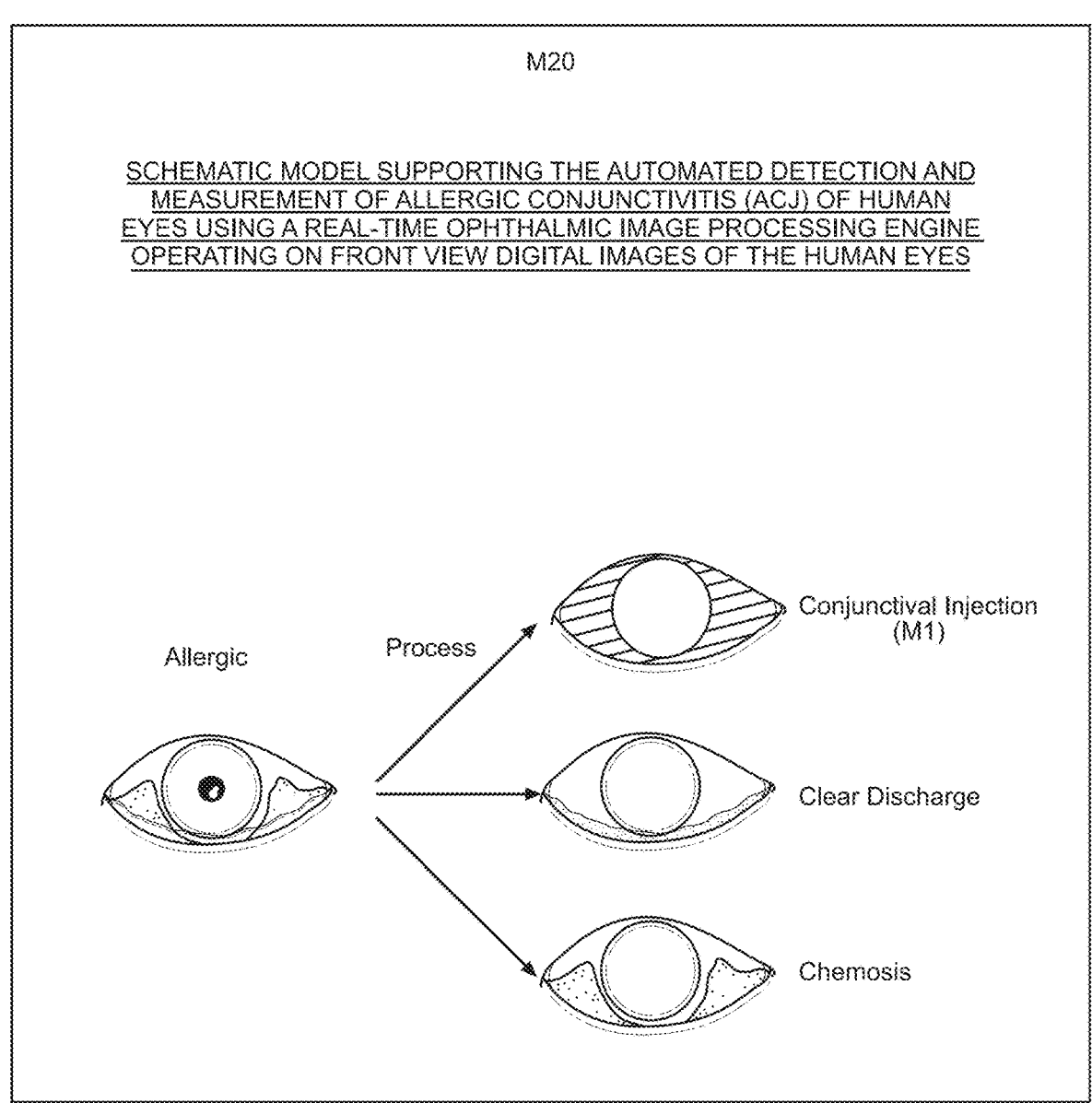
Figure 127:
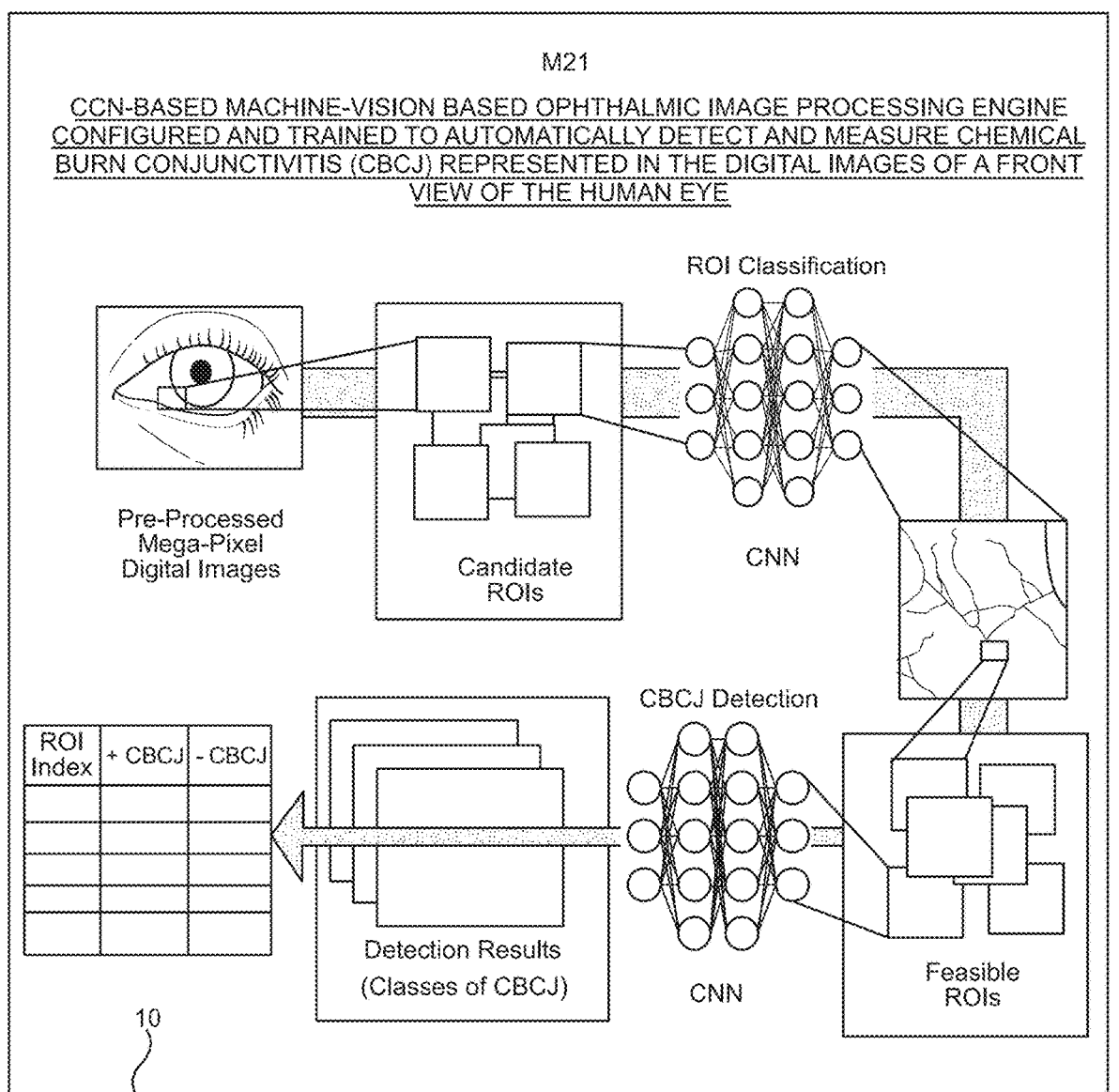
Figure 128:
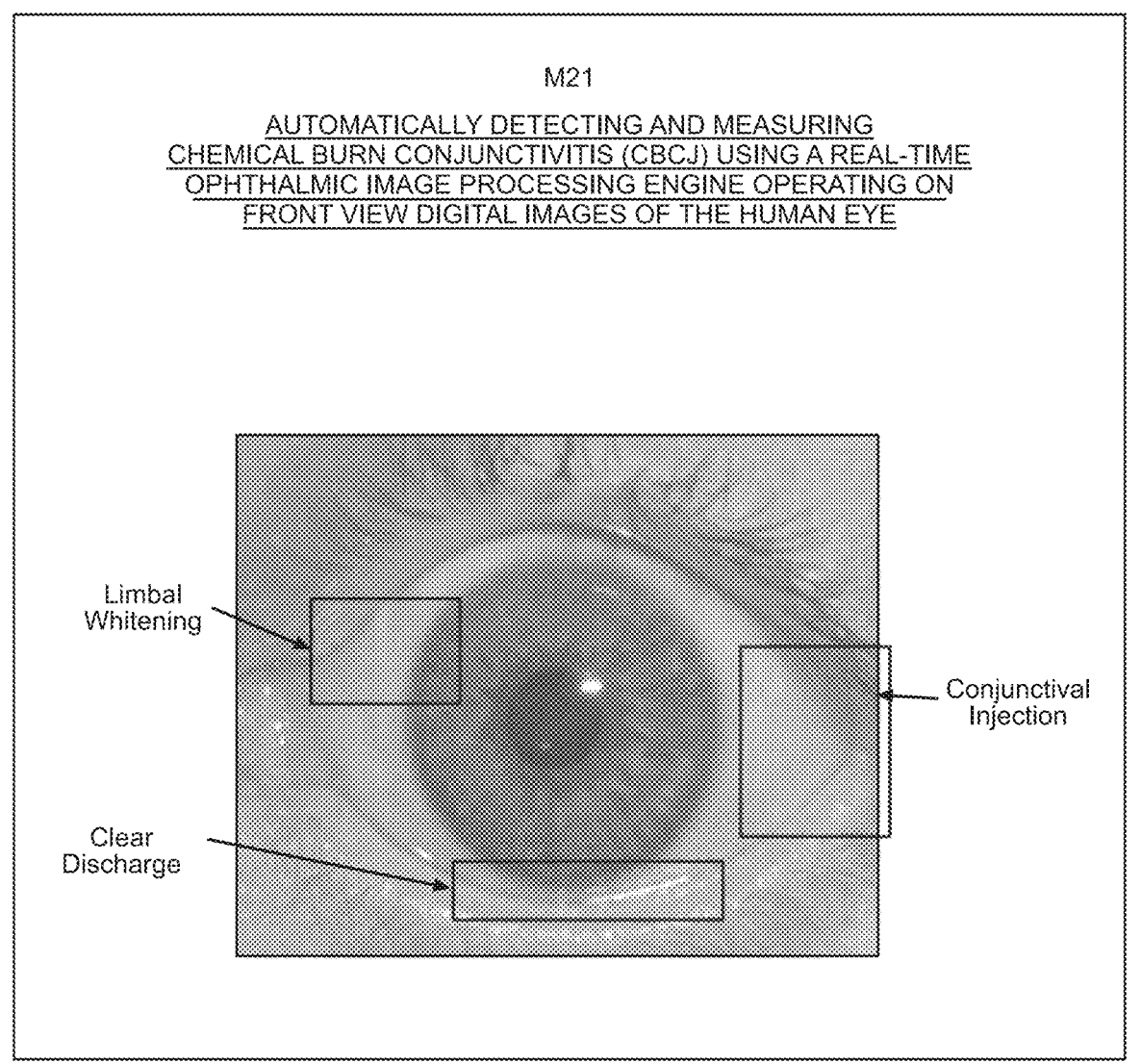
Figure 131:
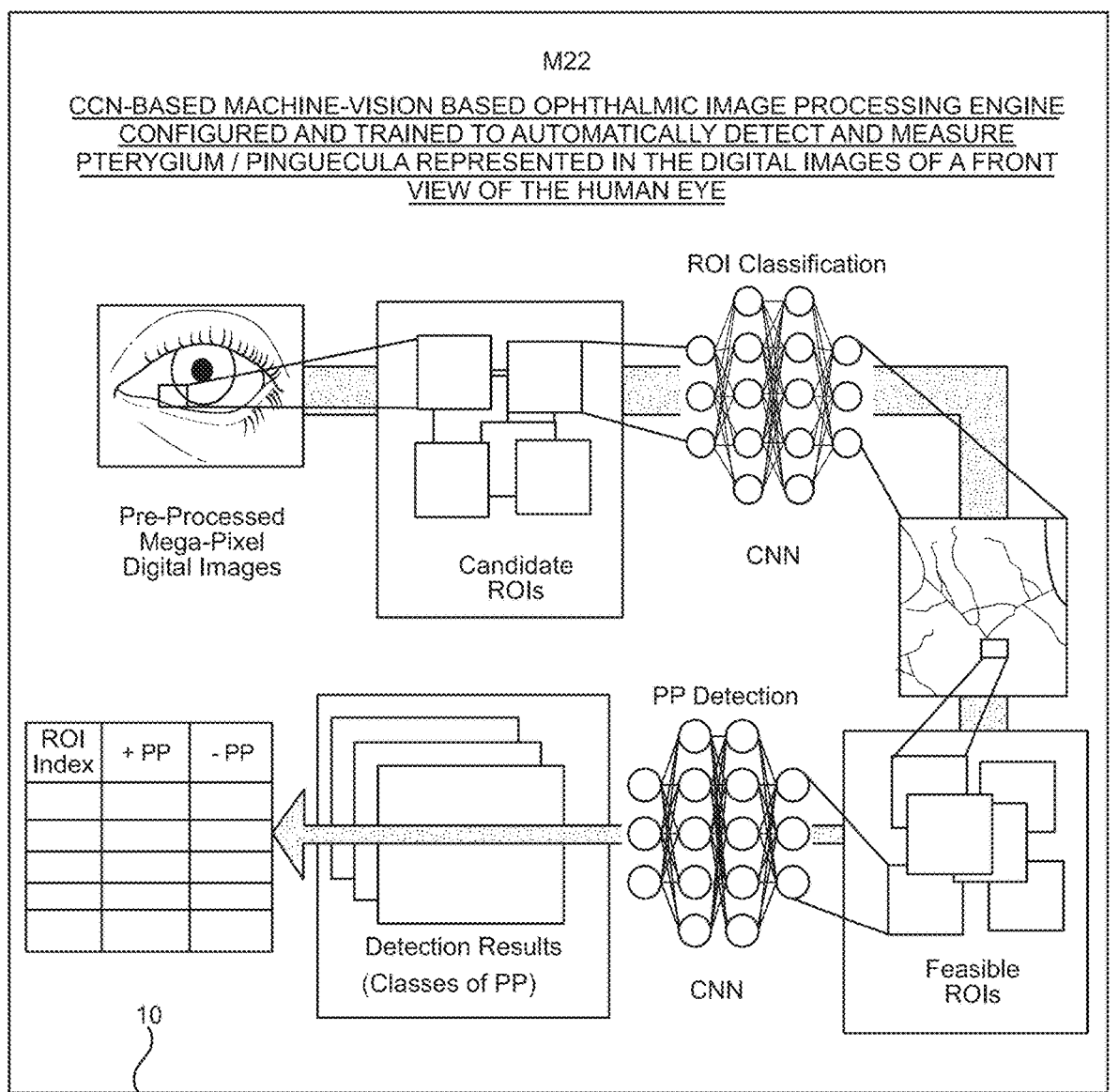
Figure 132:
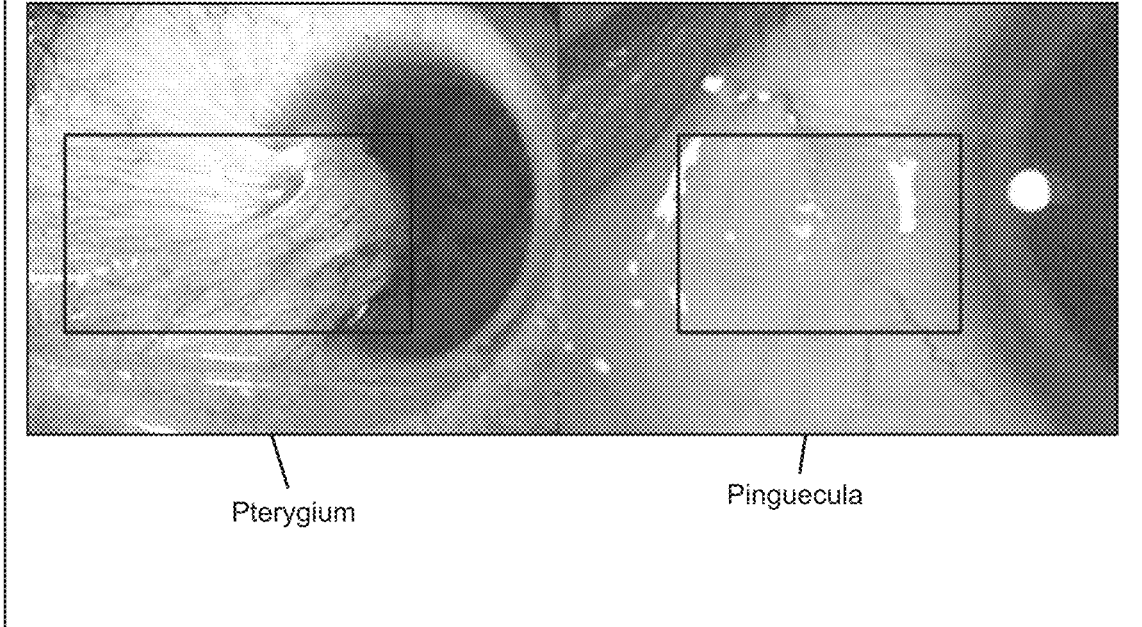
Figure 133:
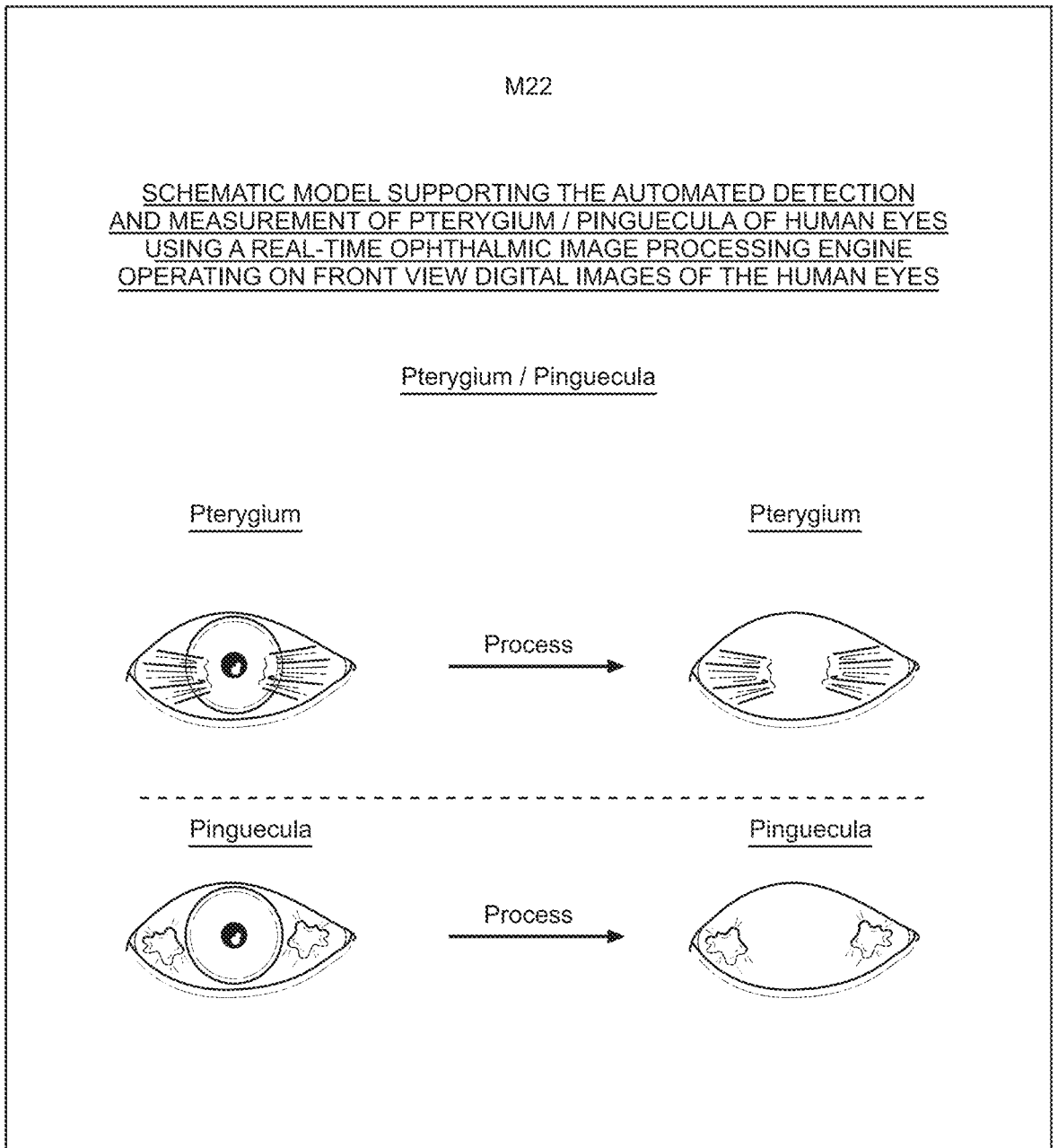
Figure 135:
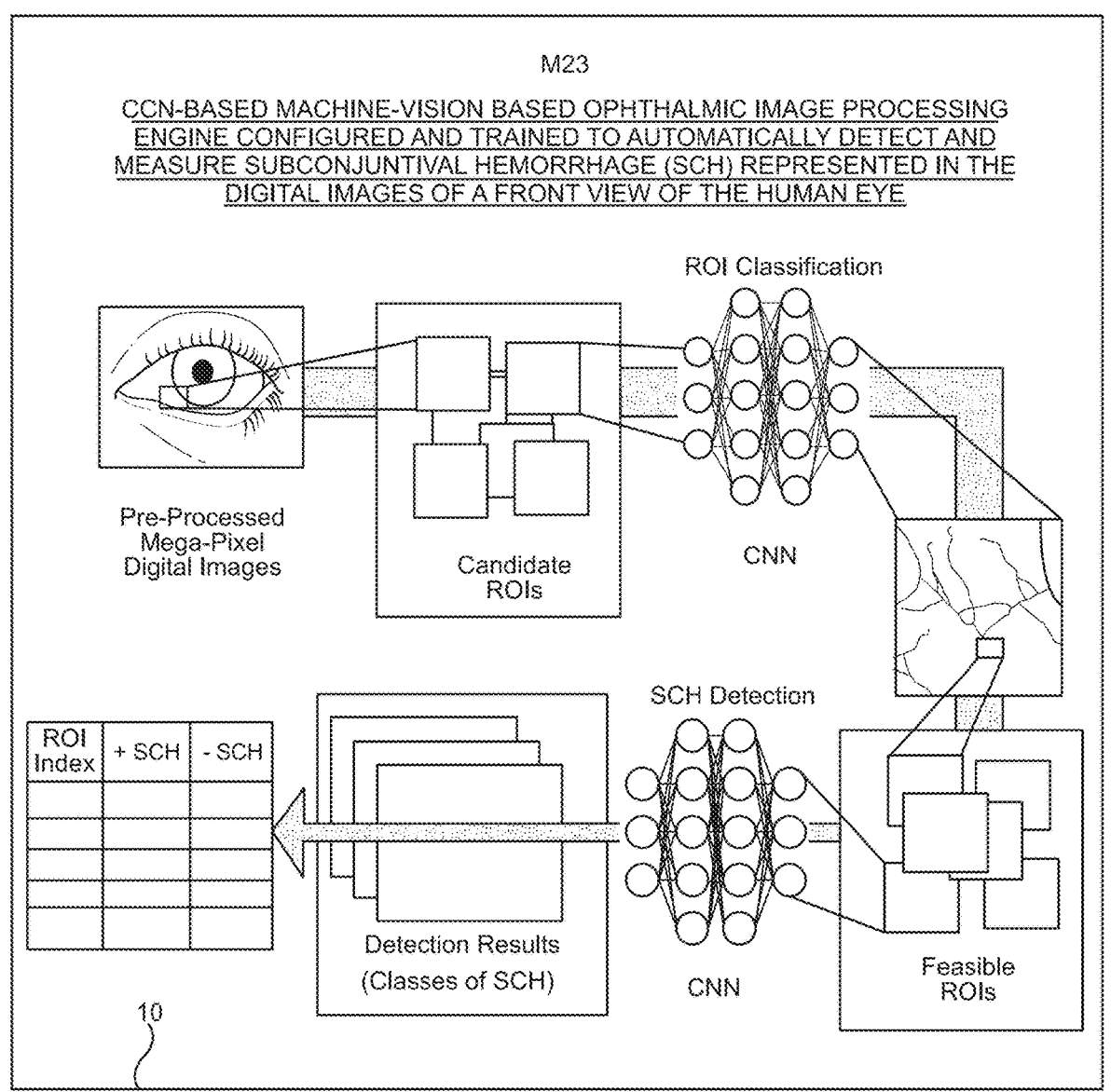
Figure 136:
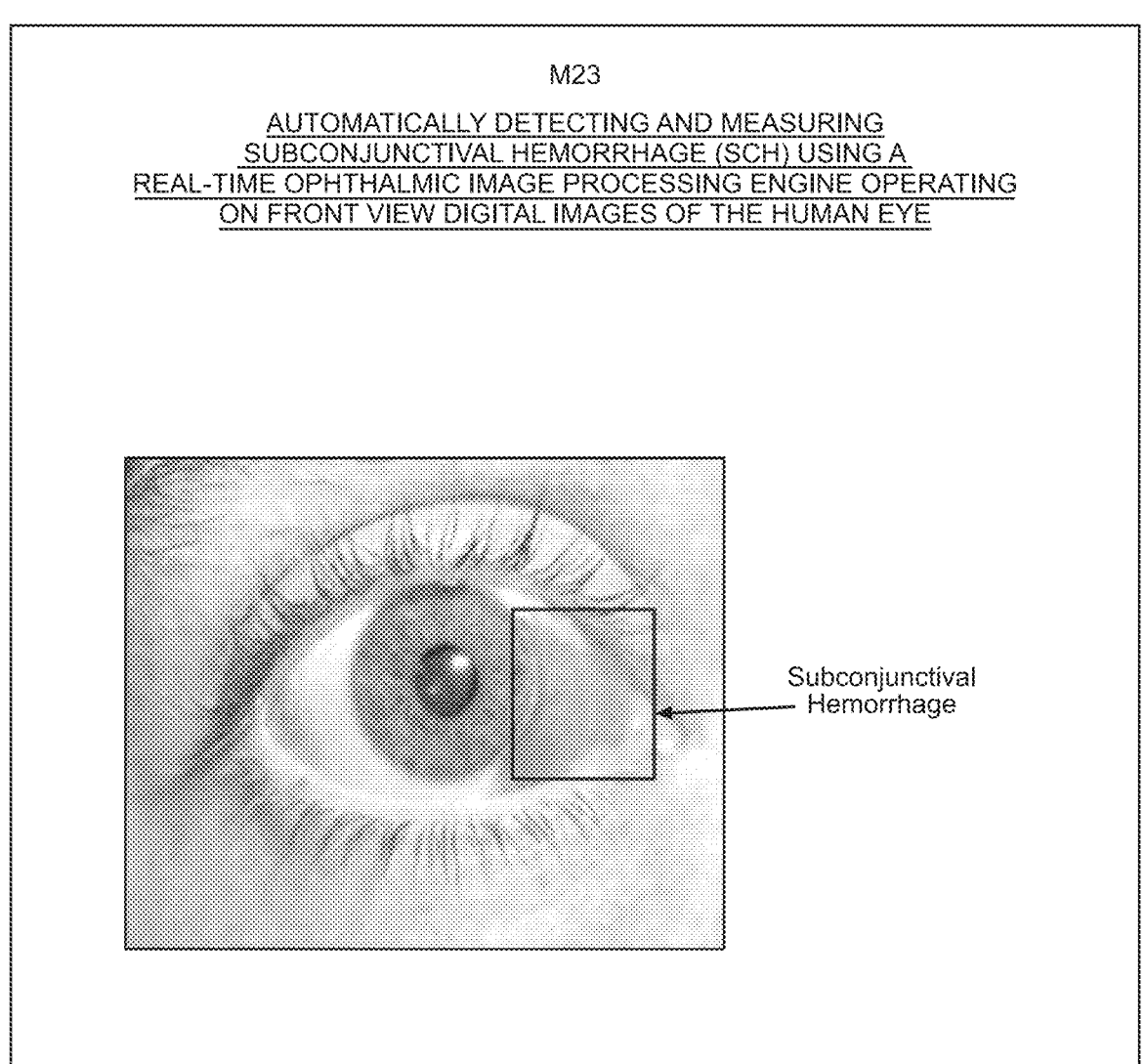
Figure 137:
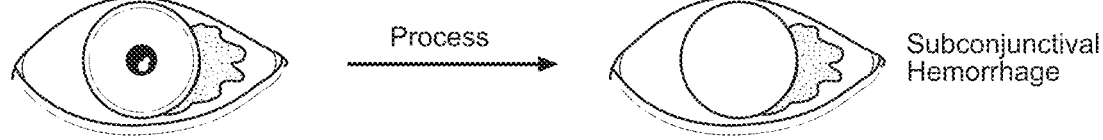
Figure 139:
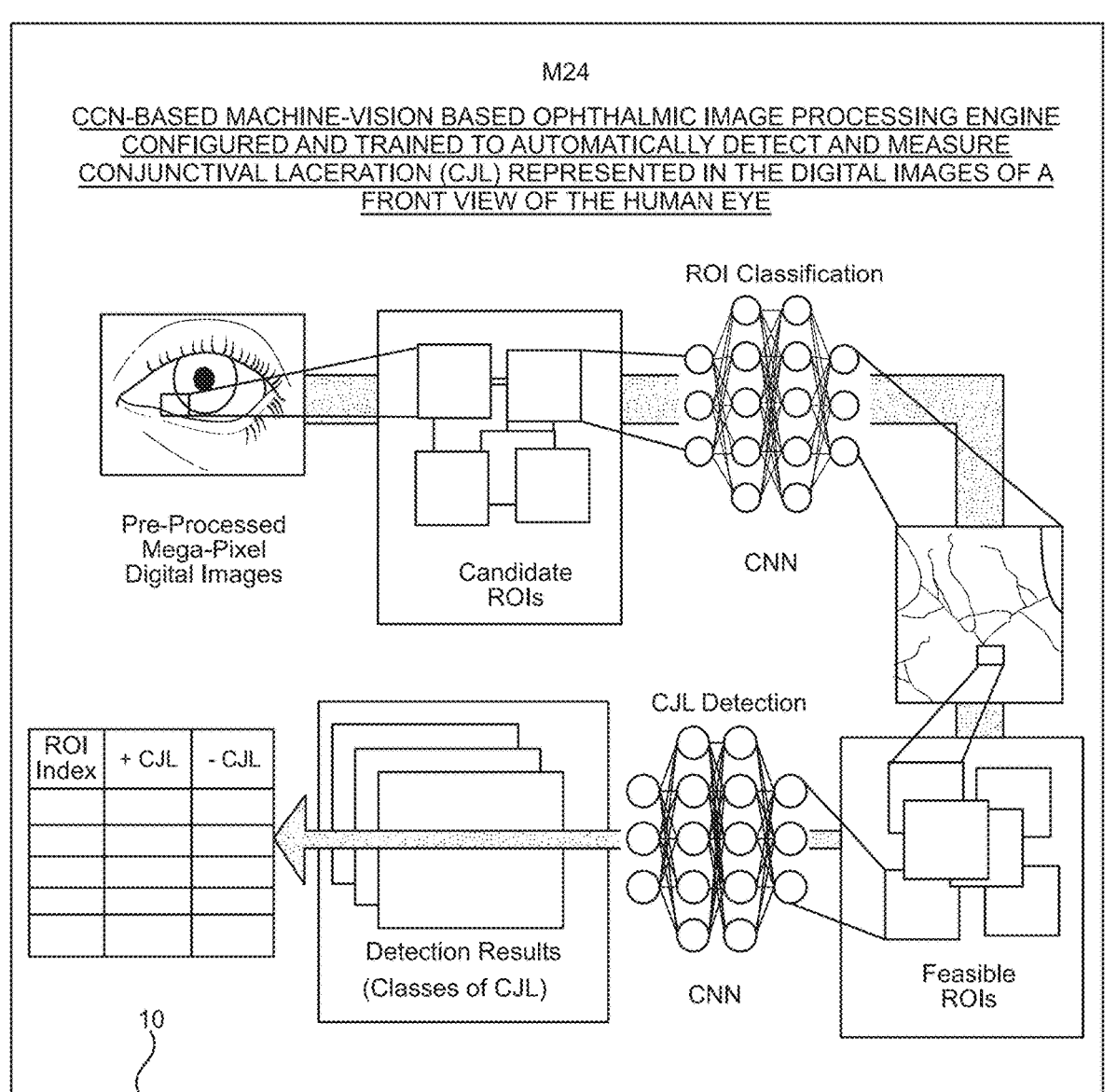
Figure 140:
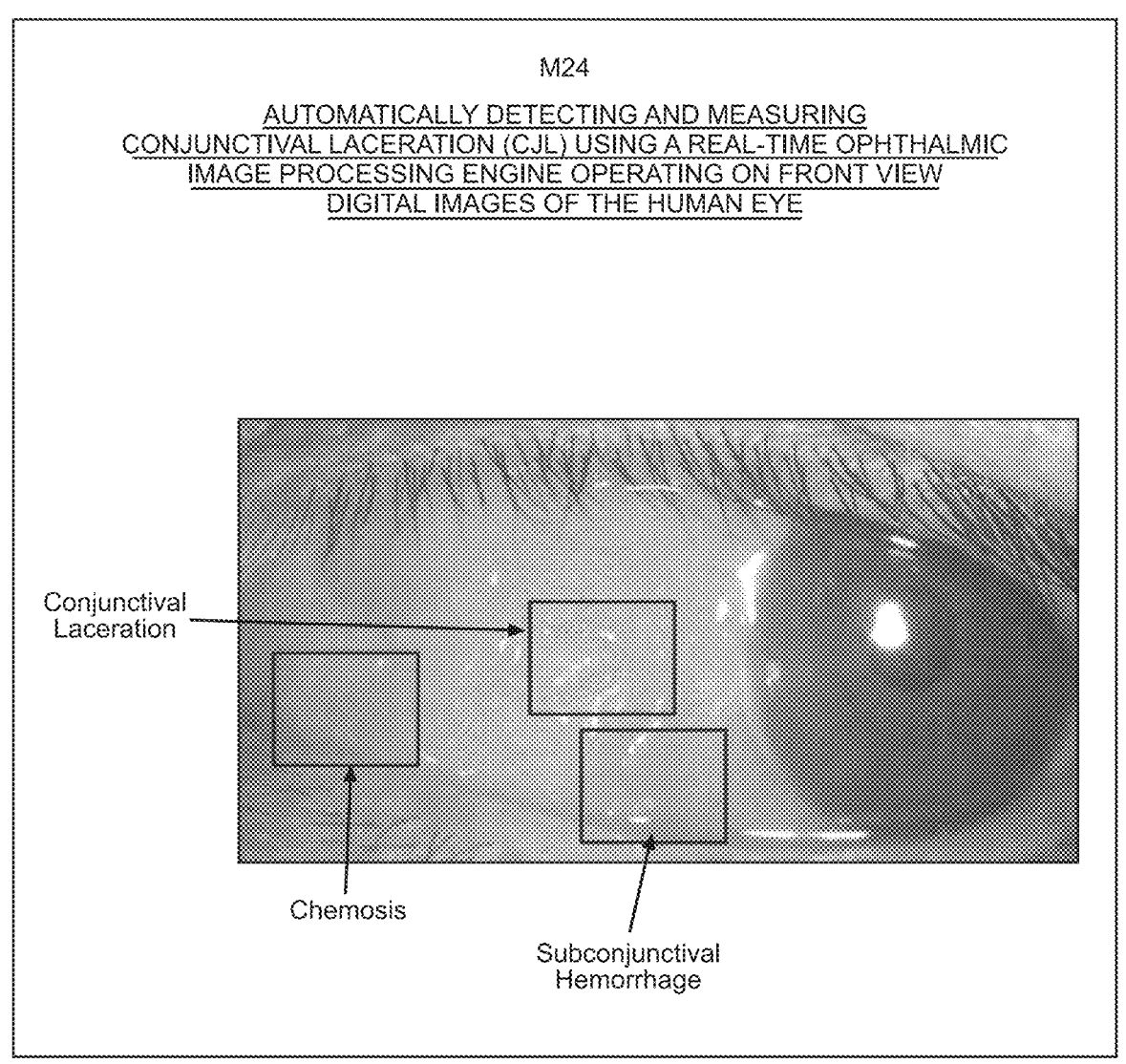
Figure 141:
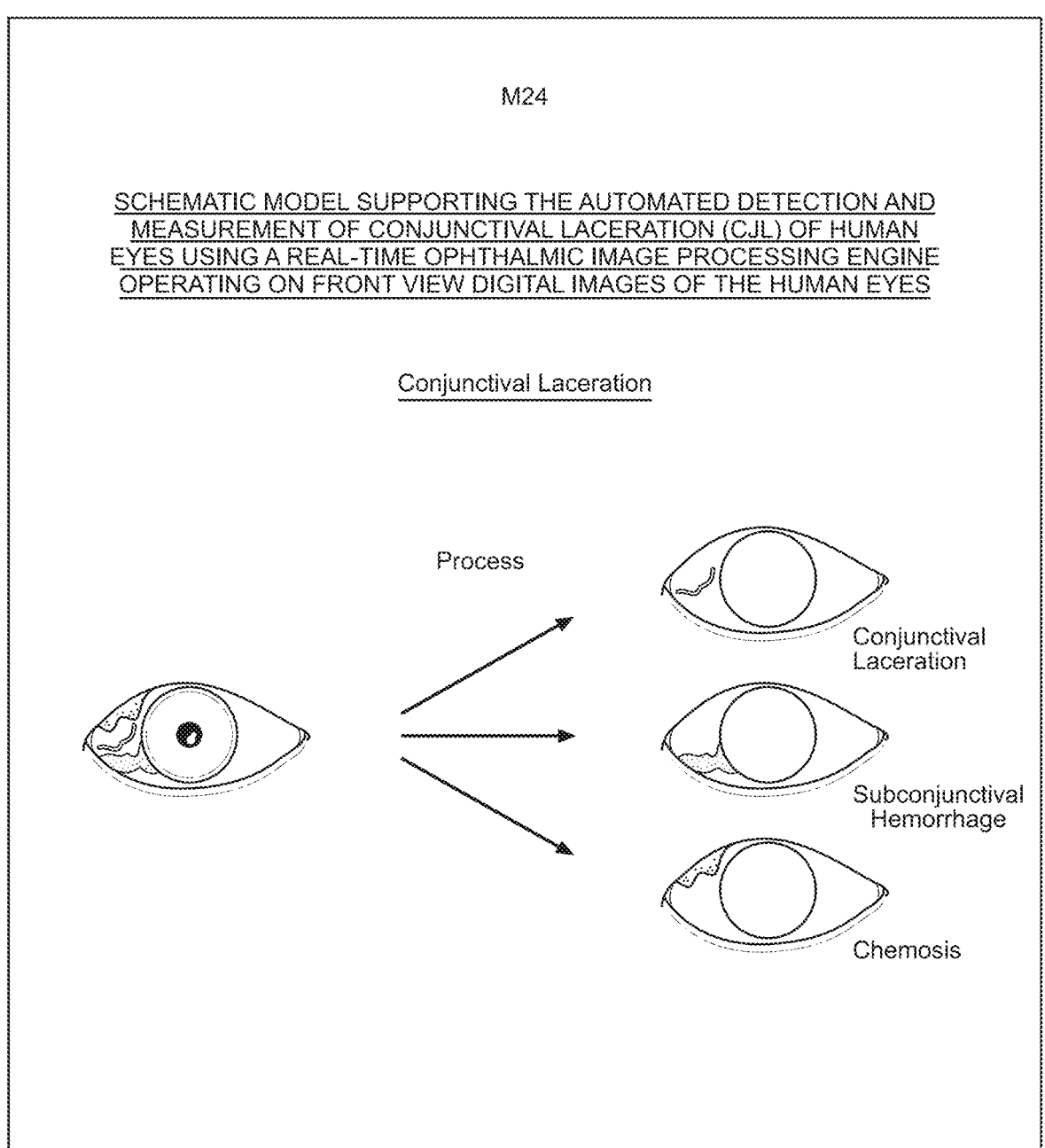
Figure 143:
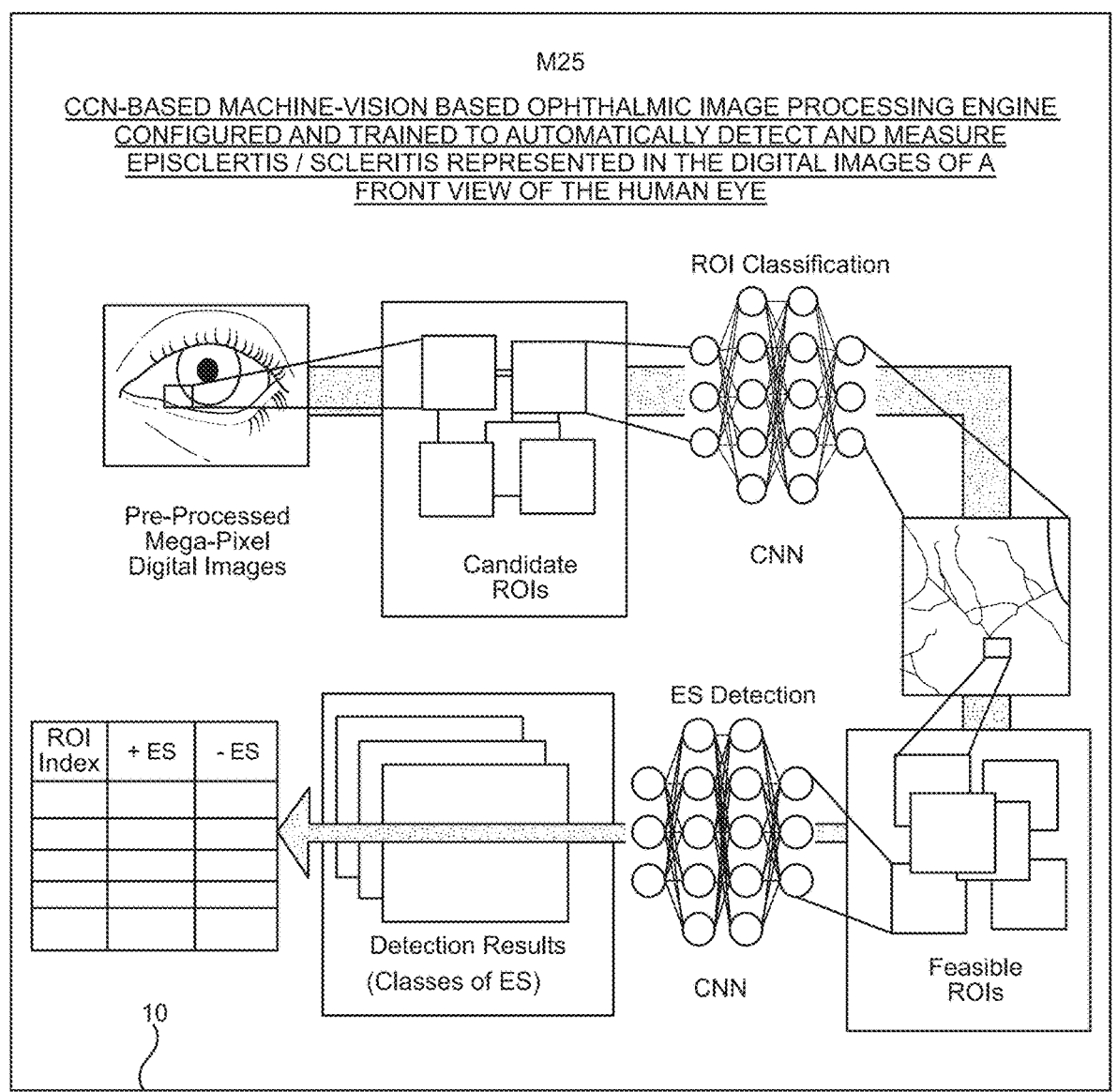
Figure 144:
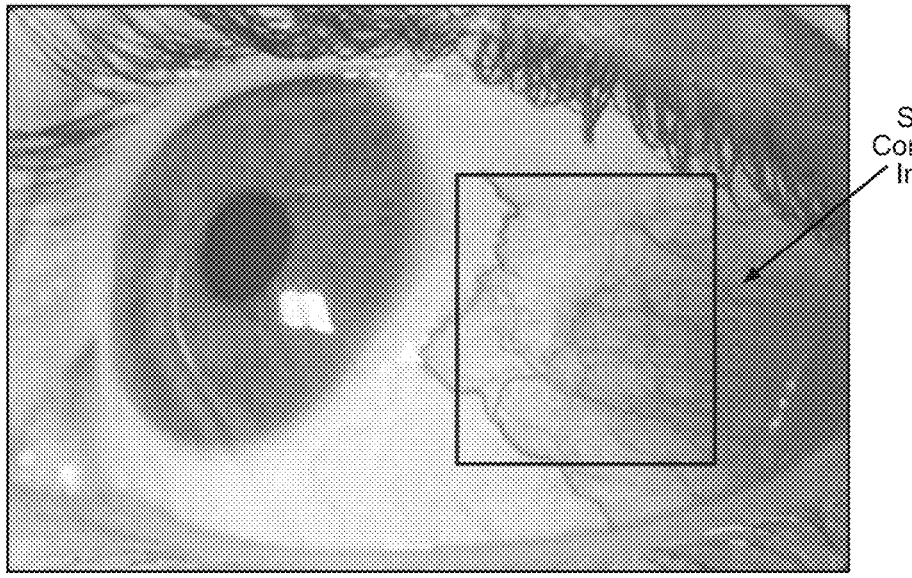
Figure 145:
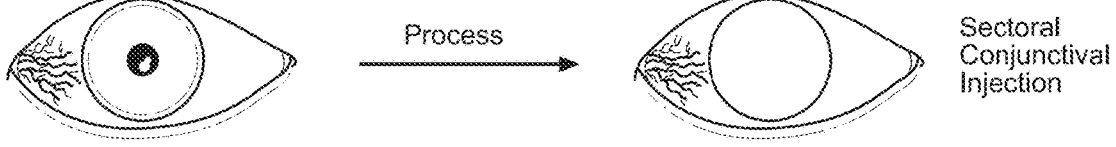
Figure 147:
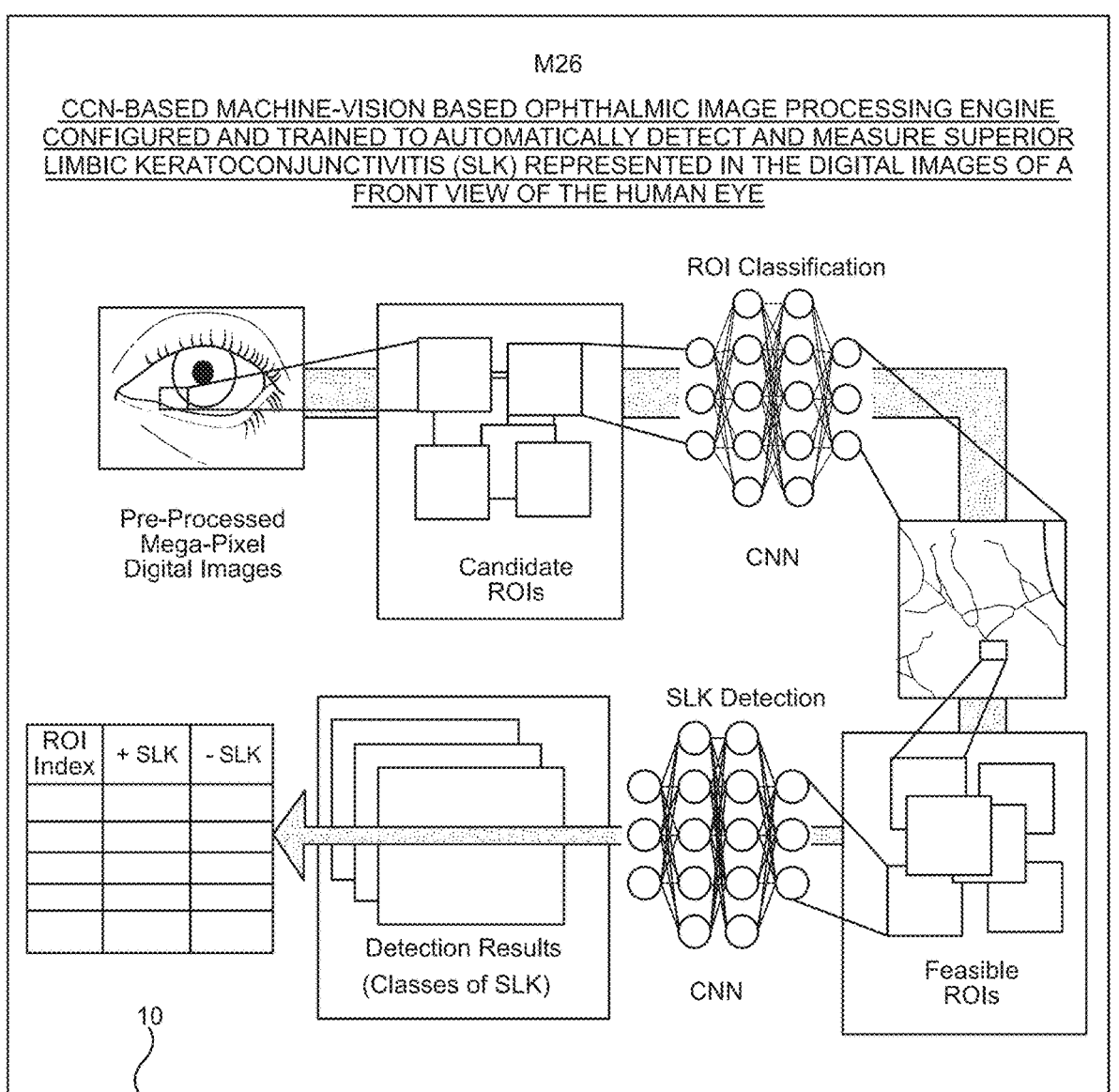
Figure 148:
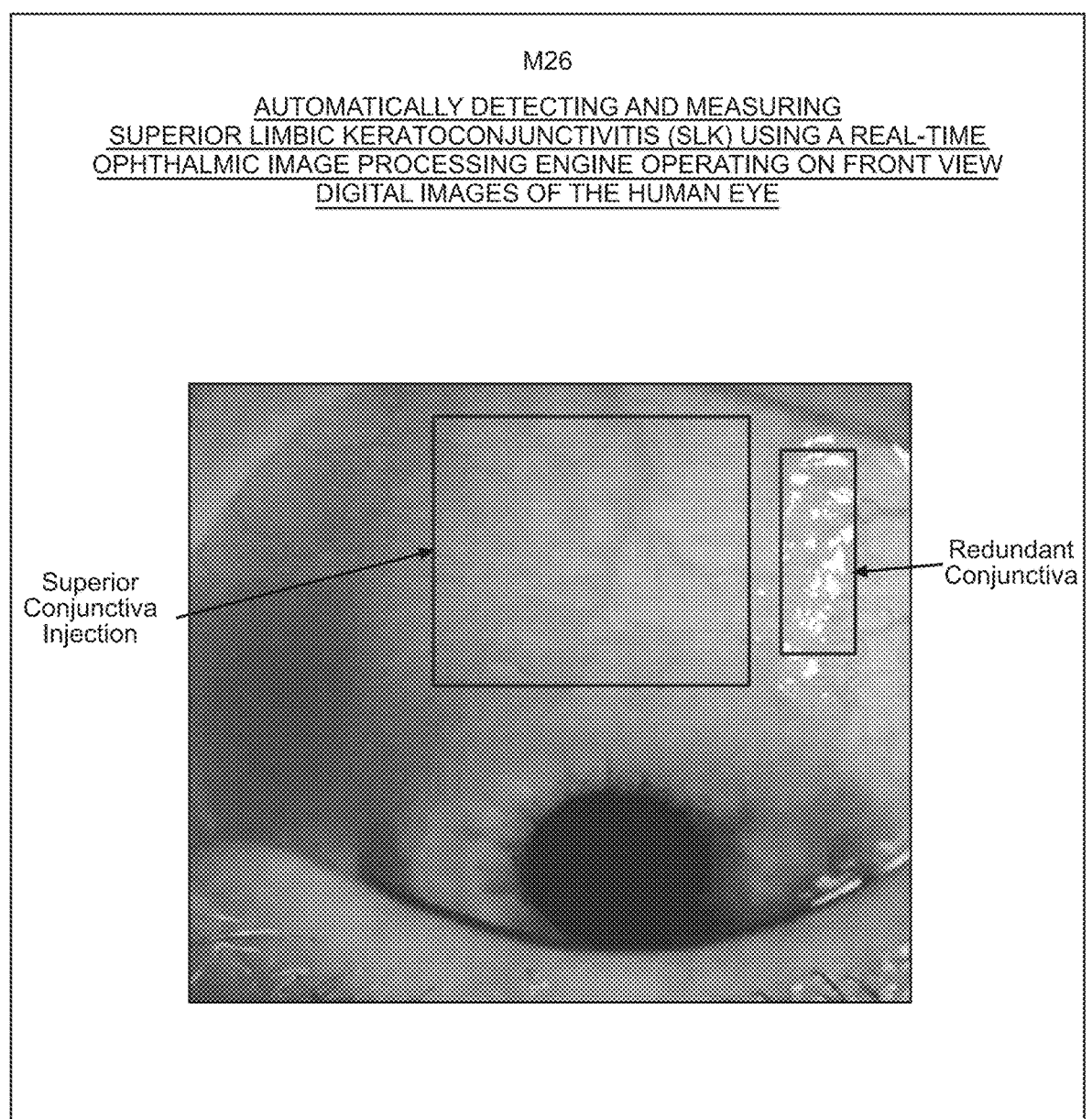

FIG. 39 is a schematic representation of a second illustrative embodiment of the machine-vision based digital image processing system of the present invention, organized, arranged and configured according to a deep learning machine-vision models employing convolutional networks with deep structure, to provide an end-to-end learning system for classifying input digital images as representative of a particular ocular disease (OD);

FIG. 40A is a schematic presentation showing the deep neural network (end-to-end) model, for implementing the second illustrative embodiment of the machine-vision based digital image processing system, comprising feature extraction involving convolution and pooling, and classification to produce classification output;

FIG. 40B is a schematic representation of a deep-learning machine-vision ocular image processing and classification system (i.e. "engine") of the present invention employing Convolutional Neural Networks (CNNs) configured and trained for use and deployment on the system network shown in FIG. 8A, to support and enable automated detection and measurement of ocular disease (OD) condition in the human eyes photographically represented in digital images of human eyes formed, captured and detected by a mobile smartphone camera system configured and operating in accordance with the principles of the present invention;

FIG. 41 is a schematic representation showing the use of an unified framework of deep CNNs to classify object candidates into specific categories of ocular disease conditions, wherein the deep-learning machine-vision based digital image processing system comprises (i) a faster RCNN for carrying out image convolutional layers and producing feature maps from input images, (ii) a regional proposal network (RPN) for producing proposed regions of interest (ROI), and (iii) a Fast RCNN for classifying the proposed ROIs and producing a predicted ocular disease (OD) class and grade of severity;

FIG. 42 is a flow chart describing the steps of the process of the present invention involving the loading, training and operating an automated deep-learning machine-vision ocular disease (OD) recognition system constructed using standard Python (e.g. Keras and TensorFlow 2) libraries supporting automated image feature extraction and classification, ocular object detection, and ocular disease (OD) condition recognition, comprising the steps of (a) loading the pixel dataset of patient ocular images into the database of a deep learning machine-vision recognition system, (b) preparing the pixel dataset for deep learning machine-vision recognition, (c) defining a baseline end-to-end convolutional neural network (CNN) model, (d) evaluating the baseline CNN model and its recognition performance on input pixel datasets, and (e) presenting the OD condition recognition results produced from the deep-learning machine-vision recognition system and process;

FIG. 43 is a schematic representation showing the use of a TensorFlow 2.0 ecosystem consisting of Python libraries to build a deep-learning machine-vision ocular disease recognition system of the present invention reflected in FIG. 42, and being capable of recognizing specific categories of ocular disease conditions (including dry eye disease conditions) from an automated intelligent analysis of the pixel data contained in a set of ocular images captured by a standard visible-wavelength operating camera system employed in mobile smartphones, tablet computers, laptop computers, desktop computers and many other kinds of portable and stationary telecommunication products supporting the advanced methods of telemedicine according to the principles of the present invention;

FIG. 44 shows a schematic representation of the subsystem architecture of the third illustrative embodiment of an automated machine-vision based ocular disease recognition system of the present invention, wherein the automated system employs a hybrid architecture when practicing the system and methods of the present invention, consisting of (i) a symbolist AI component employing symbolic reasoning and logic (e.g. Rule Based Logix, IF X, then Y), and (ii) a connectionist AI component employing connected statistical models such as machine learning, deep-learning neural networks in computer vision, natural language processing (NLP), and speech recognition, and artificial neural networks (ANNs);

FIG. 45 is a graphical representation illustrating the mathematical structure of the digital color images of the human eye processed by the machine-vision ocular disease recognition systems deployed on the system network of the present invention;

FIG. 46 is a schematic representation of a deep-learning machine-vision ocular image processing and classification system (i.e. "engine") of the present invention configured and trained for use and deployment on the system network shown in FIG. 9A, to support and enable an automated method (M1) of detection and measurement of conjunctival injection (CI) of eyes photographically represented in digital images of a front view of human eyes formed and captured by a mobile smartphone camera system configured and operated in accordance with the principles of the present invention;

FIG. 47 is a front view digital image representation of a human eye augmented with graphical indications superimposed on the digital image to indicate (i) where conjunctival injection appears to be present on the sclera of the human eye in the photographic image, and (ii) which pixel region of interest (ROI) requires pixel data processing according to an automated method of digital image processing using a machine-vision based ophthalmic image processing engine operating on one or more front view digital images of the human eye, so as to automatically measure conjunctival injection, to support automated ocular disease recognition, treatment and manage care, including predicting dry eye disease (DED) class and grade of severity by the automated system;

FIG. 48 showing a schematic model supporting the automated detection and measurement of conjunctival injection (CI) in human eyes using a real-time ophthalmic image processing engine of FIG. 47 operating on frontal view digital images of the human eyes formed using a visible wavelength light source;

FIGS. 49A and 49B, taken together, set forth a flow chart describing the primary steps carried out when practicing the machine-vision based method of FIG. 47 involving the processing of time and date stamped digital images of a human eye captured by a mobile smartphone camera system and processed to automatically detect and measure conjunctival injection (CI) present in the human eye of a patient at a specific time and date, to support automated ocular disease recognition, treatment and manage care, including predicting dry eye disease (DED) class and grade of severity by the automated system;

FIG. 50 is a schematic representation of a deep-learning machine-vision ocular image processing and classification system (i.e. "engine") of the present invention configured and trained for use and deployment on the system network shown in FIG. 8A, to support and enable an automated method (M2) of detection and measurement of tear meniscus height (TMH) of eyes photographically represented in digital images of a front view of human eyes formed and captured by a mobile smartphone camera system configured and operated in accordance with the principles of the present invention;

FIG. 51 is a front view digital image representation of a human eye augmented with graphical indications superimposed on the digital image to indicate (i) where tear meniscus height (TMH) is measured in the human eye in the photographic image, and (ii) which pixel region of interest (ROI) requires pixel data processing according to an automated method of digital image processing using a machine-based ophthalmic image processing engine of FIG. 50 operating on one or more front view digital images of the human eye to automatically detect and measure the tear meniscus height (TMH), as an indication of ocular disease recognition, treatment and manage care, including predicting dry eye disease (DED) class and grade of severity by the automated system;

FIG. 52A is a first side view digital image representation of the human eye showing the retention of tears at the interface between the cornea surface and the eyelid of the human eye, via the meniscus effect, to form a collection of tears having a tear meniscus height (TMH) indicated by the measure TMH schematically depicted in the illustration;

FIG. 52B is a second side view digital image representation of the human eye showing the retention of tears at the interface between the cornea surface and the eyelid of the human eye, via the meniscus effect, to form a collection of tears having a first tear meniscus height indicated by the measure TMH schematically depicted in the illustration;

FIGS. 53A and 53B, taken together, set forth a flow chart describing the primary steps carried out when practicing the machine-vision based method of FIG. 50 involving the processing of time and date stamped digital images of a human eye captured by a mobile smartphone camera system and processed to automatically detect and measure the tear meniscus height (TMH) in the human eye at a particular time and date, to support automated ocular disease recognition, treatment and manage care, including predicting dry eye disease (DED) class and grade of severity by the automated system;

FIG. 54 is a schematic representation of a deep-learning machine-vision ocular image processing and classification system (i.e. "engine") of the present invention configured and trained for use and deployment on the system network shown in FIG. 8A, to support and enable an automated method (M3) of detection and measurement of meibomian gland dysfunction (MGD) and scruff at eyelashes of the human eyes photographically represented in digital images of a front view of human eyes formed and captured by a mobile smartphone camera system configured and operated in accordance with the principles of the present invention;

FIG. 55A is a front view digital image representation of a human eye augmented with graphical indications superimposed on the digital image to indicate (i) where meibomian gland dysfunction (MGD) and scruff at eyelashes are detected in the photographic image of the human eye, and (ii) which pixel region of interest (ROI) requires pixel data processing according to an automated method of digital image processing using the machine-based ophthalmic image processing engine of FIG. 54 operating on one or more front view digital images of the human eye, so as to automatically detect meibomian gland dysfunction (MGD) and scruff, as an indication of ocular disease recognition, treatment and manage care, including predicting dry eye disease (DED) class and grade of severity by the automated system;

FIG. 55B is a front view digital image representation of the human eye showing the location of the meibomian glands on the lower eyelid of the human eye for automated detection;

FIGS. 56A and 56B, taken together, set forth a flow chart describing the primary steps carried out when practicing the machine-vision based method of FIG. 50 involving the processing of time and date stamped digital images of a human eye captured by a mobile smartphone camera system and processed to automatically detect and assess meibomian gland dysfunction (MGD) and scruff at eyelashes in the human eye at a particular time and date, to support automated ocular disease recognition, treatment and manage care, including predicting dry eye disease (DED) class and grade of severity by the automated system;

FIG. 57 is a schematic representation of a deep-learning machine-vision ocular image processing and classification system (i.e. "engine") of the present invention configured and trained for use and deployment on the system network shown in FIG. 8A, to support and enable an automated method (M4) of method of detection and measurement of conjunctivochalasis of the human eyes photographically represented in digital images of a front view of human eyes formed and captured by a mobile smartphone camera system in accordance with the principles of the present invention;

FIG. 58A is a front view digital image representation of a human eye augmented with graphical indications superimposed on the digital image to indicate (i) where conjunctivochalasis is detected in the photographic image of the human eye, and (ii) which pixel region of interest (ROI) requires pixel data processing according to an automated method of digital image processing using the machine-based ophthalmic image processing engine of FIG. 57 operating on one or more front view digital images of the human eye, so as to automatically detect conjunctivochalasis, as an indication of ocular disease recognition, treatment and manage care, including predicting dry eye disease (DED) class and grade of severity by the automated system;

FIG. 58B is a side view digital image representation of the human eye showing the existence of conjunctivochalasis on the lower eyelid of the human eye, preventing the normal replenishment of tears at the meniscus interface between the cornea surface and the lower eyelid;

FIG. 59 is a schematic model supporting the automated detection and measurement of conjunctivochalasis in human eyes using a real-time ophthalmic image processing engine operating on frontal view digital images of the human eyes formed using a visible wavelength light source;

FIGS. 60A and 60B, taken together, set forth a flow chart describing the primary steps carried out when practicing the machine-vision based method of FIG. 57 involving the processing of time and date stamped digital images of a human eye captured by a mobile smartphone camera system and processed to automatically detect conjunctivochalasis in the human eye at a particular time and date, to support automated ocular disease recognition, treatment and manage care, including predicting dry eye disease (DED) class and grade of severity by the automated system;

FIG. 61 is a schematic representation of a deep-learning machine-vision ocular image processing and classification system (i.e. "engine") of the present invention configured and trained for use and deployment on the system network shown in FIG. 8A, to support and enable an automated method (M5) of detection and measurement of dermatochalasis of the human eyes photographically represented in digital images of a front view of human eyes formed and captured by a mobile smartphone camera system in accordance with the principles of the present invention;

FIG. 62 is a front view digital image representation of a human eye augmented with graphical indications superimposed on the digital image to indicate (i) where dermatochalasis detected in the upper eyelids of the human eyes in the photographic image, and (ii) which pixel region of interest (ROI) requires pixel data processing according to an automated method of digital image processing using the machine-based ophthalmic image processing engine of FIG. 61 operating on one or more front view digital images of the human eye, so as to automatically detect dermatochalasis, as an indication of ocular disease recognition, treatment and manage care, including predicting dry eye disease (DED) class and grade of severity by the automated system;

FIG. 63 is a schematic representation of the human eye showing the location of dermatochalasis on the upper eye-lids of the human eye formed using a visible wavelength light source;

FIGS. 64A and 64B, taken together, set forth a flow chart describing the primary steps carried out when practicing the machine-vision based method of FIG. 61 involving the processing of time and date stamped digital images of a human eye captured by a mobile smartphone camera system, so as to automatically detect dermatochalasis condition in the human eyes at a particular time and date, to support automated ocular disease recognition, treatment and manage care, including predicting dry eye disease (DED) class and grade of severity by the automated system;

FIG. 65 is a schematic representation of a deep-learning machine-vision ocular image processing and classification system (i.e. "engine") of the present invention configured and trained for use and deployment on the system network shown in FIG. 8A, to support and enable automated method (M6) of detection and measurement of tear film dynamics (TFD1) of the human eyes photographically represented in a time series set of digital images of a front view of human eyes formed and captured by a mobile smartphone camera system in accordance with the principles of the present invention;

FIGS. 66A and 66B is a time series of front view digital image representations of a human eye augmented with graphical indications superimposed on the digital image to indicate (i) where light reflective particle are detected in the photographic image of the tear film of a human eye between eye blinks, and (ii) which pixel region of interest (ROI) requires pixel data processing according to an automated method of digital image processing using the machine-based ophthalmic image processing engine of FIG. 65 operating on one or more front view digital images of the human eye, so as to automatically detect the light reflective particles in the tear film of a human eye during eye blinks, as an indication of ocular disease recognition, treatment and manage care, including predicting dry eye disease (DED) class and grade of severity by the automated system;

FIG. 67 schematic model supporting the automated detection and measurement of conjunctivochalasis in human eyes by tracking light reflective particles in the tear film on the corneal surface of an eye using a real-time ophthalmic image processing engine as shown in FIG. 65 operating on frontal view digital images of the human eyes formed using a visible wavelength light source;

FIGS. 68A and 68B, taken together, set forth a flow chart describing the primary steps carried out when practicing the machine-vision based method of FIG. 65 involving the processing of time and date stamped digital images of a human eye captured by a mobile smartphone camera system, so as to automatically detect and measure tear film dynamics in human eyes at a particular time and date, to support automated ocular disease recognition, treatment and manage care, including predicting dry eye disease (DED) class and grade of severity by the automated system;

FIG. 69 is a schematic representation of a deep-learning machine-vision ocular image processing and classification system (i.e. "engine") of the present invention configured and trained for use and deployment on the system network shown in FIG. 8A, to support and an enable automated method (M7) of detection and measurement of tear film dynamics (TFD2) of human eyes photographically represented in a time series set of digital images of a front view of human eyes formed and captured by a mobile smartphone camera system in accordance with the principles of the present invention;

FIG. 70A is an illustrating showing the projection of placido light discs onto the human eye from the display screen of a smartphone camera system capturing images of the human eyes during teal film dynamics testing, in accordance with the principles of the present invention;

FIG. 70B is digital image of the front view of the human eye of FIG. 93A captured using a visible wavelength light source while the placido light discs are projected onto the human eye from the display screen of a smartphone camera system during teal film dynamics testing, in accordance with the principles of the present invention;

FIG. 70C is a front view of the human eye of FIG. 70B captured using a visible wavelength light source while the placido light discs are projected onto the human eye from the display screen of a smartphone camera system during teal film dynamics testing, automatically measuring tear film dynamics by detecting concentric placido discs using the real-time ophthalmic image processing engine of FIG. 69 operating on front view digital video images of the human eye;

FIG. 71 shows a schematic model supporting the automated detection and measurement of tear film dynamics in human eyes by projecting concentric placido light rights from the LCD screen of a smartphone onto the cornea of eyes using a real-time ophthalmic image processing engine operating on frontal view digital images of the human eyes formed using a visible wavelength light source, (i) wherein the tear film dynamics (TF D2) of the tear film on human eyes are detected in the human eyes in a series of digital photographic images, and (ii) wherein the pixel region of interest (ROI) requires pixel data processing according to an automated method of digital image processing using the machine-based ophthalmic image processing engine operating on one or more front view digital images of the human eye, so as to automatically detect and measure the tear film dynamics, by virtue of detected perturbations in concentric placido light discs projected on the cornea from the display screen of a mobile smartphone, as an indication of ocular disease recognition, treatment and manage care, including predicting dry eye disease (DED) class and grade of severity by the automated system;

FIGS. 72A and 72B, taken together, set forth a flow chart describing the primary steps carried out when practicing the machine-vision based method of processing time and date stamped digital images of a human eye formed, captured and detected by a mobile smartphone camera system and processed to automatically detect and measure tear film dynamics in the human eye at a particular time and date, to support automated ocular disease recognition, treatment and manage care, including predicting dry eye disease (DED) class and grade of severity by the automated system;

FIG. 73 is a schematic representation of a deep-learning machine-vision ocular image processing and classification system (i.e. "engine") of the present invention configured and trained for use and deployment on the system network shown in FIG. 8A, to support and enable an automated method (M8) of detection and measurement of tear film dynamics (TFD3) of the human eyes photographically represented in a times series of digital images of a front view of human eyes formed and captured by a mobile smartphone camera system formed using a visible wavelength light source, in accordance with the principles of the present invention;

FIGS. 74A and 74B each show front view digital image representations of a human eye augmented with graphical indications superimposed on the digital image to indicate (i) where the tear film dynamics (TFD3) in the human eye are measured by analysis of eye blinks during a time series of digital photographic images, and (ii) which pixel region of interest (ROI) requires pixel data processing according to an automated method of digital image processing using the machine-based ophthalmic image processing engine of FIG. 73 operating on one or more front view digital images of the human eye, so as to automatically detect and measure tear film dynamics of the human eyes, as an indication of ocular disease recognition, treatment and manage care, including predicting dry eye disease (DED) class and grade of severity by the automated system;

FIGS. 75A, 75B and 75C provide schematic representations for a schematic model supporting the automated detection and measurement of the increase in tear meniscus height (TMH) after full eye blink during video imaging of the eye using a real-time ophthalmic image processing engine operating on frontal view digital images of the human eyes formed using a visible wavelength light source;

FIGS. 76A and 76B, taken together, set forth a flow chart describing the primary steps carried out when practicing the machine-vision based method of FIG. 73 involving the processing of time and date stamped digital images of a human eye formed, captured and detected by a mobile smartphone camera system and processed to automatically detect and measure the tear film dynamics in the human eye at a particular time and date by real-time changes in the measurement of tear meniscus height (TMH) in between eye blinks, to support automated ocular disease recognition, treatment and manage care, including predicting dry eye disease (DED) class and grade of severity by the automated system;

FIG. 77 is a schematic representation of a deep-learning machine-vision ocular image processing and classification system (i.e. "engine") of the present invention configured and trained for use and deployment on the system network shown in FIG. 8A, to support and enable an automated method (M9) of detection and measurement and mapping of the speed of blinking in the human eyes photographically represented in a times series of digital images of a front view of human eyes formed and captured by a mobile smartphone camera system in accordance with the principles of the present invention;

FIG. 78 is a front view digital image representation of a human eye augmented with graphical indications superimposed on the digital image to indicate (i) where the speed of eye blinks are detected, measured and in the human eye in the photographic image, and (ii) which pixel region of interest (ROI) requires pixel data processing according to an automated method of digital image processing using the machine-based ophthalmic image processing engine of FIG. 77 operating on one or more front view digital images of the human eye, so as to automatically map changes in eye blinking speed, as an indication of ocular disease recognition, treatment and manage care, including predicting dry eye disease (DED) class and grade of severity by the automated system;

FIGS. 79A and 79B are schematic representations showing the mapping of eye blink speed and patterns in the human eye exhibiting dry eye disease conditions, taken over a period of time samples T1, T2, T3 . . . ;

FIG. 80 is a schematic representation indicating that the goal of measuring increased blink speed (IBS) after each full blink of a patient's eye;

FIGS. 81A, 81B, and 81C, taken together, set forth a flow chart describing the primary steps carried out when practicing the machine-vision based method of FIG. 77 involving the processing of time and date stamped digital images of a human eye formed, captured and detected by a mobile smartphone camera system and processed to automatically detect and measure the speed and patterns of eye blinking (B SAP) in the human eye at a particular time and date, to support automated ocular disease recognition, treatment and manage care, including predicting dry eye disease (DED) class and grade of severity by the automated system;

FIG. 82 is a schematic representation of a deep-learning machine-vision ocular image processing and classification system (i.e. "engine") of the present invention configured and trained for use and deployment on the system network shown in FIG. 8A, to support and enable an automated method (M10) of detection and measurement of corneal scratches in the human eyes photographically represented in digital images of a front view of human eyes formed using a visible wavelength light source, and captured and detected by a mobile smartphone camera system configured and operating in accordance with the principles of the present invention;

FIG. 83 is a front view digital image representation of a human eye augmented with graphical indications superimposed on the digital image to indicate (i) where corneal scratches are detected and measured in the human eye in the photographic image, and (ii) which pixel region of interest (ROI) requires pixel data processing according to an automated method of digital image processing using the machine-based ophthalmic image processing engine of FIG. 82 operating on one or more front view digital images of the human eye, so as to automatically detect corneal scratches in the human eye;

FIG. 84 is schematic model supporting the automated detection and measurement of corneal abrasion in human eyes using a real-time ophthalmic image processing engine operating on frontal and/or side view digital images of the human eyes formed using a visible wavelength light source;

FIGS. 85A and 85B, taken together, set forth a flow chart describing the primary steps carried out when practicing the machine-vision based method of FIG. 82 involving the processing of time and date stamped digital images of a human eye formed, captured and detected by a mobile smartphone camera system and processed to automatically detect and measure corneal scratches in the human eye at a particular time and date, to support automated ocular disease recognition, treatment and manage care, including predicting dry eye disease (DED) class and grade of severity by the automated system;

FIG. 86 is a schematic representation of a deep-learning machine-vision ocular image processing and classification system (i.e. "engine") of the present invention configured and trained for use and deployment on the system network shown in FIG. 8A, to support and enable automated method (M11) of method of detection and measurement of palpebral fissure (PF) in the human eyes photographically represented in digital images of a front view of human eyes formed and captured by a mobile smartphone camera system in accordance with the principles of the present invention;

FIG. 87 is a front view digital image representation of a human eye augmented with graphical indications superimposed on the digital image to indicate (i) where a palpebral fissure (PF) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect palpebral fissure (PF) as an indication of ocular disease recognition, treatment and manage care, including predicting dry eye disease (DED) class and grade of severity by the automated system;

FIG. 88 is a schematic model supporting the automated detection and measurement of palpebral fissure (PF) in the human eyes using a real-time ophthalmic image processing engine operating on front view digital images of the human eyes formed using a visible wavelength light source;

FIGS. 89A and 89B, taken together, set forth a flow chart describing the primary steps carried out when practicing the machine-vision based method of FIG. 87 involving the processing of time and date stamped digital images of a human eye captured by a mobile smartphone camera system and processed to automatically detect palpebral fissure (PF) in the human eye at a particular time and date, to support automated ocular disease recognition, treatment and manage care, including predicting dry eye disease (DED) class and grade of severity by the automated system;

FIG. 90 is a schematic representation of a deep-learning machine-vision ocular image processing and classification system (i.e. "engine") of the present invention configured and trained for use and deployment on the system network shown in FIG. 8A, to support and enable an automated method (M12) of method of detection and measurement of the margin reflex distance (MRD) in the human eyes photographically represented in digital images of a front view of human eyes formed using a visible wavelength light source and captured by a mobile smartphone camera system in accordance with the principles of the present invention;

FIG. 91 is a front view digital image representation of a human eye augmented with graphical indications superimposed on the digital image to indicate (i) where margin reflex distance (MRD) is detected and measured in the human eye in the photographic image, and (ii) which pixel region of interest (ROI) requires pixel data processing according to an automated method of digital image processing using the machine-based ophthalmic image processing engine of FIG. 90 operating on one or more front view digital images of the human eye, so as to automatically detect and measure margin reflex distance (MRD) as an indication of ocular disease recognition, treatment and manage care, including predicting dry eye disease (DED) class and grade of severity by the automated system;

FIG. 92 is a schematic model supporting the automated detection and measurement of margin reflex distance (MRD) in the human eyes using a real-time ophthalmic image processing engine operating on front view digital images of the human eyes formed using a visible wavelength light source;

FIGS. 93A and 93B, taken together, set forth a flow chart describing the primary steps carried out when practicing the machine-vision based method of FIG. 91 involving the processing of time and date stamped digital images of a human eye captured by a mobile smartphone camera system and processed to automatically detect margin reflex distance (MRD) in the human eye at a particular time and date, to support automated ocular disease recognition, treatment and manage care, including predicting dry eye disease (DED) class and grade of severity by the automated system;

FIG. 94 is a schematic representation of a deep-learning machine-vision ocular image processing and classification system (i.e. "engine") of the present invention configured and trained for use and deployment on the system network shown in FIG. 8A, to support and enable an automated method (M13) of method of detection and measurement of scleral show (SS) of the human eyes photographically represented in digital images of a front view of human eyes formed using a visible wavelength light source and captured by a mobile smartphone camera system in accordance with the principles of the present invention;

FIG. 95 is a front view digital image representation of a human eye augmented with graphical indications superimposed on the digital image to indicate (i) where scleral show (SS) is detected in the photographic image of the human eye, and (ii) which pixel region of interest (ROI) requires pixel data processing according to an automated method of digital image processing using the machine-based ophthalmic image processing engine of FIG. 94 operating on one or more front view digital images of the human eye, so as to automatically detect scleral show (SS) as an indication of ocular disease recognition, treatment and manage care, including predicting dry eye disease (DED) class and grade of severity by the automated system;

FIG. 96 is a schematic model supporting the automated detection and measurement of scleral show (SS) in the human eyes using a real-time ophthalmic image processing engine operating on front view digital images of the human eyes formed using a visible wavelength light source;

FIGS. 97A and 97B, taken together, set forth a flow chart describing the primary steps carried out when practicing the machine-vision based method of FIG. 94 involving the processing of time and date stamped digital images of a human eye captured by a mobile smartphone camera system and processed to automatically detect scleral show (SS) in the human eye at a particular time and date, to support automated ocular disease recognition, treatment and manage care, including predicting dry eye disease (DED) class and grade of severity by the automated system;

FIG. 98 is a schematic representation of a deep-learning machine-vision ocular image processing and classification system (i.e. "engine") of the present invention configured and trained for use and deployment on the system network shown in FIG. 8A, to support and enable an automated method (M14) of method of detection and measurement of levator function (LF) in the human eyes photographically represented in digital images of a front view of human eyes formed and captured by a mobile smartphone camera system in accordance with the principles of the present invention;

FIGS. 99 and 100 is a set of front view digital image representations of a human eye captured while looking up and looking down respectively, and augmented with graphical indications superimposed on the digital image to indicate (i) where the levator function (LF) is detected in the photographic image of the human eye, and (ii) which pixel region of interest (ROI) requires pixel data processing according to an automated method of digital image processing using the machine-based ophthalmic image processing engine of FIG. 98 operating on one or more front view digital images of the human eye, so as to automatically detect the levator function as an indication of ocular disease recognition, treatment and manage care, including predicting dry eye disease (DED) class and grade of severity by the automated system;

FIG. 101 is a schematic model supporting the automated detection and measurement of the levator function in the human eyes using a real-time ophthalmic image processing engine operating on front view digital images of the human eyes;

FIGS. 102A and 102B, taken together, set forth a flow chart describing the primary steps carried out when practicing the machine-vision based method of FIG. 98 involving the processing of time and date stamped digital images of a human eye captured by a mobile smartphone camera system and processed to automatically detect the levator function in the human eye at a particular time and date, to support automated ocular disease recognition, treatment and manage care, including predicting dry eye disease (DED) class and grade of severity by the automated system;

FIG. 103 is a schematic representation of a deep-learning machine-vision ocular image processing and classification system (i.e. "engine") of the present invention configured and trained for use and deployment on the system network shown in FIG. 8A, to support and enable an automated method (M15) of method of detection and measurement of the contact lens overwear (CLOW) in the human eyes photographically represented in digital images of a front view of human eyes formed using a visible wavelength light source and captured by a mobile smartphone camera system in accordance with the principles of the present invention;

FIGS. 104A and 104B are front view digital image representations of a human eye augmented with graphical indications superimposed on the digital image to indicate (i) where the contact lens overwear (CLOW) is detected in the photographic image of the human eye with corneal neovascularization shown in FIG. 10A and subepithelial infiltrates shown in FIG. 104B, and (ii) which pixel regions of interest (ROI) requires pixel data processing according to an automated method of digital image processing using the machine-based ophthalmic image processing engine of FIG. 103 operating on one or more front view digital images of the human eye, so as to automatically detect contact lens overwear (CLOW) as an indication of ocular disease recognition, treatment and manage care, including predicting dry eye disease (DED) class and grade of severity by the automated system;

FIG. 105 is a schematic model supporting the automated detection and measurement of contact lens overwear (CLOW) in the human eyes using a real-time ophthalmic image processing engine operating on front view digital images of the human eyes formed using a visible wavelength light source;

FIGS. 106A and 106B, taken together, set forth a flow chart describing the primary steps carried out when practicing the machine-vision based method of FIG. 103 involving the processing of time and date stamped digital images of a human eye captured by a mobile smartphone camera system and processed to automatically detect contact lens overwear (CLOW) in the human eye at a particular time and date, to support automated ocular disease recognition, treatment and manage care, including predicting dry eye disease (DED) class and grade of severity by the automated system;

FIG. 107 is a schematic representation of a deep-learning machine-vision ocular image processing and classification system (i.e. "engine") of the present invention configured and trained for use and deployment on the system network shown in FIG. 8A, to support and enable an automated method (M16) of method of detection and measurement of corneal transplant graft rejection (CTGR) of the human eyes photographically represented in digital images of a front view of human eyes formed using a visible wavelength light source and captured by a mobile smartphone camera system in accordance with the principles of the present invention;

FIG. 108 is a front view digital image representation of a human eye augmented with graphical indications superimposed on the digital image to indicate (i) where corneal transplant graft rejection (CTGR) is detected in the photographic image of the human eye, and (ii) which pixel region of interest (ROI) requires pixel data processing according to an automated method of digital image processing using the machine-based ophthalmic image processing engine of FIG. 107 operating on one or more front view digital images of the human eye, so as to automatically detect corneal transplant graft rejection (CTGR) as an indication of ocular disease recognition, treatment and manage care, including predicting dry eye disease (DED) class and grade of severity by the automated system;

Figure 109:
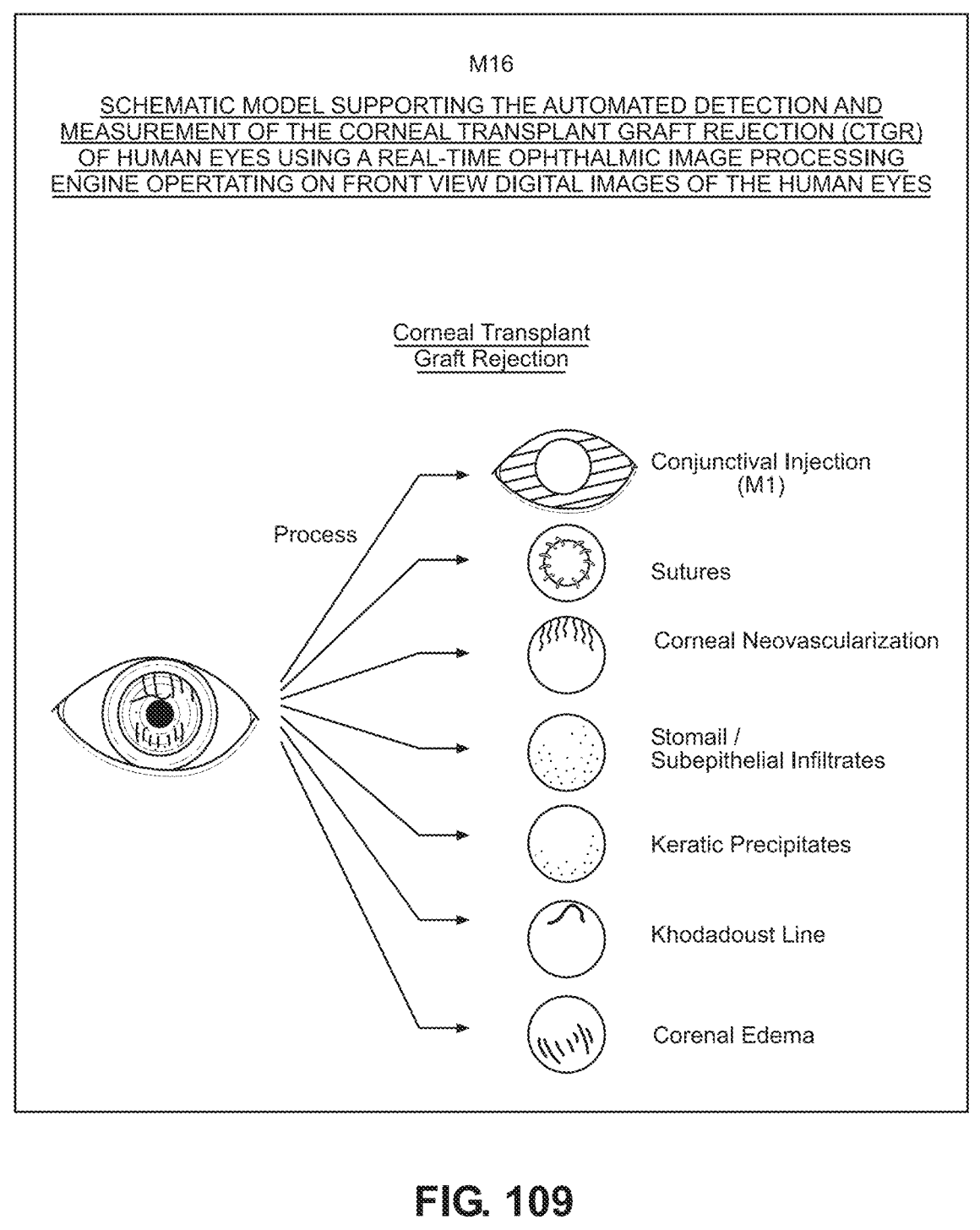

FIG. 109 is a schematic model supporting the automated detection and measurement of corneal transplant graft rejection (CTGR) in the human eyes using a real-time ophthalmic image processing engine operating on front view digital images of the human eyes;

FIGS. 110A and 110B, taken together, set forth a flow chart describing the primary steps carried out when practicing the machine-vision based method of FIG. 107 involving the processing of time and date stamped digital images of a human eye captured by a mobile smartphone camera system and processed to automatically detect corneal transplant graft rejection (CTGR) in the human eye at a particular time and date, to support automated ocular disease recognition, treatment and manage care, including predicting dry eye disease (DED) class and grade of severity by the automated system;

FIG. 111 is a schematic representation of a deep-learning machine-vision ocular image processing and classification system (i.e. "engine") of the present invention configured and trained for use and deployment on the system network shown in FIG. 8A, to support and enable an automated method (M18) of method of detection and measurement of cataract in the human eyes photographically represented in digital images of a front view of human eyes formed and captured by a mobile smartphone camera system in accordance with the principles of the present invention;

FIG. 112 is a front view digital image representation of a human eye augmented with graphical indications superimposed on the digital image to indicate (i) where a cataract is detected and measured in the human eye in the photographic image, and (ii) which pixel region of interest (ROI) requires pixel data processing according to an automated method of digital image processing using the machine-based ophthalmic image processing engine of FIG. 111 operating on one or more front view digital images of the human eye, so as to automatically detect cataract as an indication of ocular disease recognition, treatment and manage care, including predicting dry eye disease (DED) class and grade of severity by the automated system;

Figure 113:
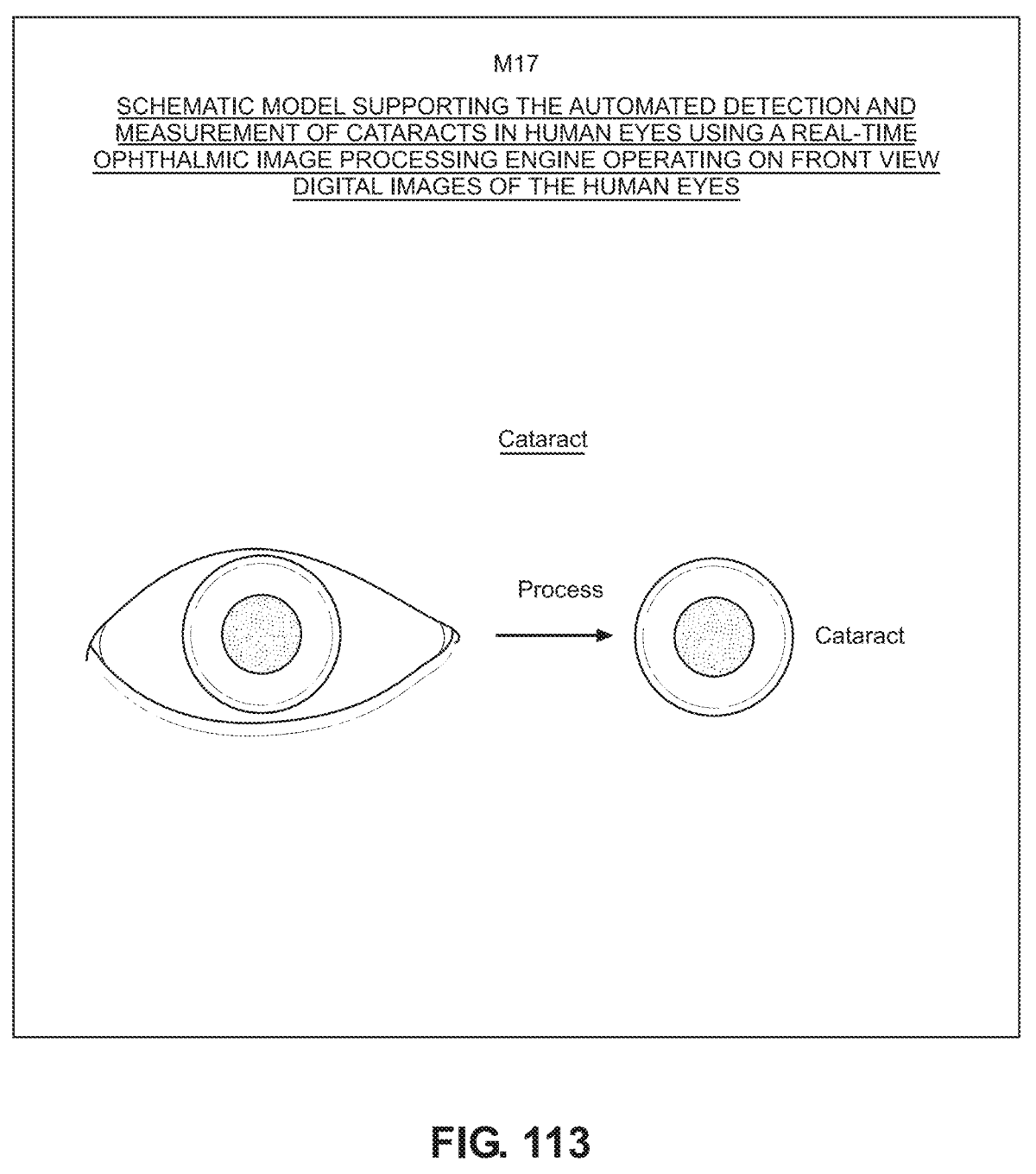

FIG. 113 is a schematic model supporting the automated detection and measurement of cataract in the human eyes using a real-time ophthalmic image processing engine operating on front view digital images of the human eyes formed using a visible wavelength light source;

FIGS. 114A and 114B, taken together, set forth a flow chart describing the primary steps carried out when practicing the machine-vision based method of FIG. 111 involving the processing of time and date stamped digital images of a human eye captured by a mobile smartphone camera system and processed to automatically detect a cataract in the human eye at a particular time and date, to support automated ocular disease recognition, treatment and manage care, including predicting dry eye disease (DED) class and grade of severity by the automated system;

FIG. 115 is a schematic representation of a deep-learning machine-vision ocular image processing and classification system (i.e. "engine") of the present invention configured and trained for use and deployment on the system network shown in FIG. 8A, to support and enable an automated method (M18) of method of detection and measurement of viral conjunctivitis (VCJ) in the human eyes photographically represented in digital images of a front view of human eyes formed and captured by a mobile smartphone camera system in accordance with the principles of the present invention;

FIG. 116 is a front view digital image representation of a human eye augmented with graphical indications superimposed on the digital image to indicate (i) where viral conjunctivitis (VCJ) is detected in the photographic image of the human eye, and (ii) which pixel region of interest (ROI) requires pixel data processing according to an automated method of digital image processing using the machine-based ophthalmic image processing engine of FIG. 115 operating on one or more front view digital images of the human eye, so as to automatically detect viral conjunctivitis (VCJ) as an indication of ocular disease recognition, treatment and manage care, including predicting dry eye disease (DED) class and grade of severity by the automated system;

FIG. 117 is a schematic model supporting the automated detection and measurement of viral conjunctivitis (VCJ) in the human eyes using a real-time ophthalmic image processing engine operating on front view digital images of the human eyes formed using a visible wavelength light source;

FIGS. 118A and 118B, taken together, set forth a flow chart describing the primary steps carried out when practicing the machine-vision based method of FIG. 115 involving the processing of time and date stamped digital images of a human eye captured by a mobile smartphone camera system and processed to automatically detect viral conjunctivitis (VCJ) in the human eye at a particular time and date, to support automated ocular disease recognition, treatment and manage care, including predicting dry eye disease (DED) class and grade of severity by the automated system;

FIG. 119 is a schematic representation of a deep-learning machine-vision ocular image processing and classification system (i.e. "engine") of the present invention configured and trained for use and deployment on the system network shown in FIG. 8A, to support and enable an automated method (M19) of method of detection and measurement of bacterial conjunctivitis (BCJ) of the human eyes photographically represented in digital images of a front view of human eyes formed and captured by a mobile smartphone camera system in accordance with the principles of the present invention;

FIG. 120 is a front view digital image representation of a human eye augmented with graphical indications superimposed on the digital image to indicate (i) where bacterial conjunctivitis (BCJ) is detected in the photographic image of the human eye, and (ii) which pixel region of interest (ROI) requires pixel data processing according to an automated method of digital image processing using the machine-based ophthalmic image processing engine of FIG. 119 operating on one or more front view digital images of the human eye, so as to automatically detect bacterial conjunctivitis (BCJ) as an indication of ocular disease recognition, treatment and manage care, including predicting dry eye disease (DED) class and grade of severity by the automated system;

FIG. 121 is a schematic model supporting the automated detection and measurement of bacterial conjunctivitis (BCJ) in the human eyes using a real-time ophthalmic image processing engine operating on front view digital images of the human eyes formed using a visible wavelength light source;

FIGS. 122A and 122B, taken together, set forth a flow chart describing the primary steps carried out when practicing the machine-vision based method of FIG. 119 involving the processing of time and date stamped digital images of a human eye captured by a mobile smartphone camera system and processed to automatically detect bacterial conjunctivitis (BCJ) in the human eye at a particular time and date, to support automated ocular disease recognition, treatment and manage care, including predicting dry eye disease (DED) class and grade of severity by the automated system;

FIG. 123 is a schematic representation of a deep-learning machine-vision ocular image processing and classification system (i.e. "engine") of the present invention configured and trained for use and deployment on the system network shown in FIG. 8A, to support and enable an automated method (M20) of method of detection and measurement of allergic conjunctivitis (ACJ) of the human eyes photographically represented in digital images of a front view of human eyes formed and captured by a mobile smartphone camera system in accordance with the principles of the present invention;

FIG. 124 is a front view digital image representation of a human eye augmented with graphical indications superimposed on the digital image to indicate (i) where allergic conjunctivitis (ACJ) is detected in the photographic image of the human eye, and (ii) which pixel region of interest (ROI) requires pixel data processing according to an automated method of digital image processing using the machine-based ophthalmic image processing engine of FIG. 123 operating on one or more front view digital images of the human eye, so as to automatically detect allergic conjunctivitis (ACJ) as an indication of ocular disease recognition, treatment and manage care, including predicting dry eye disease (DED) class and grade of severity by the automated system;

FIG. 125 is a schematic model supporting the automated detection and measurement of allergic conjunctivitis (ACJ) in the human eyes using a real-time ophthalmic image processing engine operating on front view digital images of the human eyes formed using a visible wavelength light source;

FIGS. 126A and 126B, taken together, set forth a flow chart describing the primary steps carried out when practicing the machine-vision based method of FIG. 123 involving the processing of time and date stamped digital images of a human eye captured by a mobile smartphone camera system and processed to automatically detect allergic conjunctivitis (ACJ) in the human eye at a particular time and date, to support automated ocular disease recognition, treatment and manage care, including predicting dry eye disease (DED) class and grade of severity by the automated system;

FIG. 127 is a schematic representation of a deep-learning machine-vision ocular image processing and classification system (i.e. "engine") of the present invention configured and trained for use and deployment on the system network shown in FIG. 8A, to support and enable an automated method (M21) of method of detection and measurement of chemical burn conjunctivitis (CBCJ) of the human eyes photographically represented in digital images of a front view of human eyes formed and captured by a mobile smartphone camera system in accordance with the principles of the present invention;

FIG. 128 is a front view digital image representation of a human eye augmented with graphical indications superimposed on the digital image to indicate (i) where chemical burn conjunctivitis (CBCJ) is detected in the photographic image of the human eye, and (ii) which pixel region of interest (ROI) requires pixel data processing according to an automated method of digital image processing using the machine-based ophthalmic image processing engine of FIG. 127 operating on one or more front view digital images of the human eye, so as to automatically detect chemical burn conjunctivitis (CBCJ) as an indication of ocular disease recognition, treatment and manage care, including predicting dry eye disease (DED) class and grade of severity by the automated system;

FIG. 129 is a schematic model supporting the automated detection and measurement of chemical burn conjunctivitis (CBCJ) in the human eyes using a real-time ophthalmic image processing engine operating on front view digital images of the human eyes formed using a visible wavelength light source;

FIGS. 130A and 130B, taken together, set forth a flow chart describing the primary steps carried out when practicing the machine-vision based method of FIG. 127 involving the processing of time and date stamped digital images of a human eye captured by a mobile smartphone camera system and processed to automatically detect chemical burn conjunctivitis (CBCJ) in the human eye at a particular time and date, to support automated ocular disease recognition, treatment and manage care, including predicting dry eye disease (DED) class and grade of severity by the automated system;

FIG. 131 is a schematic representation of a deep-learning machine-vision ocular image processing and classification system (i.e. "engine") of the present invention configured and trained for use and deployment on the system network shown in FIG. 8A, to support and enable an automated method (M22) of method of detection and measurement of pterygium/pinguecula (PP) in the human eyes photographically represented in digital images of a front view of human eyes formed and captured by a mobile smartphone camera system in accordance with the principles of the present invention;

FIG. 132 is a front view digital image representation of a human eye augmented with graphical indications superimposed on the digital image to indicate (i) where pterygium/pinguecula (PP) is detected in the photographic image of the human eye, and (ii) which pixel region of interest (ROI) requires pixel data processing according to an automated method of digital image processing using the machine-based ophthalmic image processing engine of FIG. 131 operating on one or more front view digital images of the human eye, so as to automatically detect pterygium/pinguecula (PP) as an indication of ocular disease recognition, treatment and manage care, including predicting dry eye disease (DED) class and grade of severity by the automated system;

FIG. 133 is a schematic model supporting the automated detection and measurement of pterygium/pinguecula (PP) in the human eyes using a real-time ophthalmic image processing engine operating on front view digital images of the human eyes formed using a visible wavelength light source;

FIGS. 134A and 134B, taken together, set forth a flow chart describing the primary steps carried out when practicing the machine-vision based method of FIG. 131 involving the processing of time and date stamped digital images of a human eye captured by a mobile smartphone camera system and processed to automatically detect pterygium/pinguecula (PP) in the human eye at a particular time and date, to support automated ocular disease recognition, treatment and manage care, including predicting dry eye disease (DED) class and grade of severity by the automated system;

FIG. 135 is a schematic representation of a deep-learning machine-vision ocular image processing and classification system (i.e. "engine") of the present invention configured and trained for use and deployment on the system network shown in FIG. 8A, to support and enable an automated method (M23) of method of detection and measurement of subconjunctival hemorrhage (SCH) of the human eyes photographically represented in digital images of a front view of human eyes formed and captured by a mobile smartphone camera system in accordance with the principles of the present invention;

FIG. 136 is a front view digital image representation of a human eye augmented with graphical indications superimposed on the digital image to indicate (i) where subconjunctival hemorrhage (SCH) is detected in the photographic image of the human eye, and (ii) which pixel region of interest (ROI) requires pixel data processing according to an automated method of digital image processing using the machine-based ophthalmic image processing engine of FIG. 135 operating on one or more front view digital images of the human eye, so as to automatically detect subconjunctival hemorrhage (SCH) as an indication of ocular disease recognition, treatment and manage care, including predicting dry eye disease (DED) class and grade of severity by the automated system;

FIG. 137 is a schematic model supporting the automated detection and measurement of subconjunctival hemorrhage (SCH) in the human eyes using a real-time ophthalmic image processing engine operating on front view digital images of the human eyes formed using a visible wavelength light source;

FIGS. 138A and 138B, taken together, set forth a flow chart describing the primary steps carried out when practicing the machine-vision based method of FIG. 135 involving the processing of time and date stamped digital images of a human eye captured by a mobile smartphone camera system and processed to automatically detect subconjunctival hemorrhage (SCH) in the human eye at a particular time and date, to support automated ocular disease recognition, treatment and manage care, including predicting dry eye disease (DED) class and grade of severity by the automated system;

FIG. 139 is a schematic representation of a deep-learning machine-vision ocular image processing and classification system (i.e. "engine") of the present invention configured and trained for use and deployment on the system network shown in FIG. 8A, to support and enable an automated method (M24) of method of detection and measurement of subconjunctival laceration (CJL) of the human eyes photographically represented in digital images of a front view of human eyes formed and captured by a mobile smartphone camera system in accordance with the principles of the present invention;

FIG. 140 is a front view digital image representation of a human eye augmented with graphical indications superimposed on the digital image to indicate (i) where subconjunctival laceration (CJL) is detected in the photographic image of the human eye, and (ii) which pixel region of interest (ROI) requires pixel data processing according to an automated method of digital image processing using the machine-based ophthalmic image processing engine of FIG. 139 operating on one or more front view digital images of the human eye, so as to automatically detect subconjunctival laceration (CJL) as an indication of ocular disease recognition, treatment and manage care, including predicting dry eye disease (DED) class and grade of severity by the automated system;

FIG. 141 is a schematic model supporting the automated detection and measurement of subconjunctival laceration (CJL) in the human eyes using a real-time ophthalmic image processing engine operating on front view digital images of the human eyes formed using a visible wavelength light source;

FIGS. 142A and 142B, taken together, set forth a flow chart describing the primary steps carried out when practicing the machine-vision based method of FIG. 139 involving the processing time and date stamped digital images of a human eye captured by a mobile smartphone camera system and processed to automatically detect subconjunctival laceration (CJL) in the human eye at a particular time and date, to support automated ocular disease recognition, treatment and manage care, including predicting dry eye disease (DED) class and grade of severity by the automated system;

FIG. 143 is a schematic representation of a deep-learning machine-vision ocular image processing and classification system (i.e. "engine") of the present invention configured and trained for use and deployment on the system network shown in FIG. 8A, to support and enable an automated method (M25) of method of detection and measurement of episcleritis/scleritis in the human eyes photographically represented in digital images of a front view of human eyes formed and captured by a mobile smartphone camera system in accordance with the principles of the present invention;

FIG. 144 is a front view digital image representation of a human eye augmented with graphical indications superimposed on the digital image to indicate (i) where episcleritis/scleritis is detected in the photographic image of the human eye, and (ii) which pixel region of interest (ROI) requires pixel data processing according to an automated method of digital image processing using the machine-based ophthalmic image processing engine of FIG. 143 operating on one or more front view digital images of the human eye, so as to automatically detect episcleritis/scleritis as an indication of ocular disease recognition, treatment and manage care, including predicting dry eye disease (DED) class and grade of severity by the automated system;

FIG. 145 is a schematic model supporting the automated detection and measurement of episcleritis/scleritis in the human eyes using a real-time ophthalmic image processing engine operating on front view digital images of the human eyes formed using a visible wavelength light source;

FIGS. 146A and 146B, taken together, set forth a flow chart describing the primary steps carried out when practicing the machine-vision based method of FIG. 143 involving the processing of time and date stamped digital images of a human eye captured by a mobile smartphone camera system and processed to automatically detect episcleritis/scleritis in the human eye at a particular time and date, to support automated ocular disease recognition, treatment and manage care, including predicting dry eye disease (DED) class and grade of severity by the automated system;

FIG. 147 is a schematic representation of a deep-learning machine-vision ocular image processing and classification system (i.e. "engine") of the present invention configured and trained for use and deployment on the system network shown in FIG. 8A, to support and enable an automated method (M26) of method of detection and measurement of superior limbic keratoconjunctivitis (SLK) in the human eyes photographically represented in digital images of a front view of human eyes formed and captured by a mobile smartphone camera system in accordance with the principles of the present invention;

FIG. 148 is a front view digital image representation of a human eye augmented with graphical indications superimposed on the digital image to indicate (i) where superior limbic keratoconjunctivitis (SLK) is detected in the photographic image of the human eye, and (ii) which pixel region of interest (ROI) requires pixel data processing according to an automated method of digital image processing using the machine-based ophthalmic image processing engine of FIG.

Figure 1A:
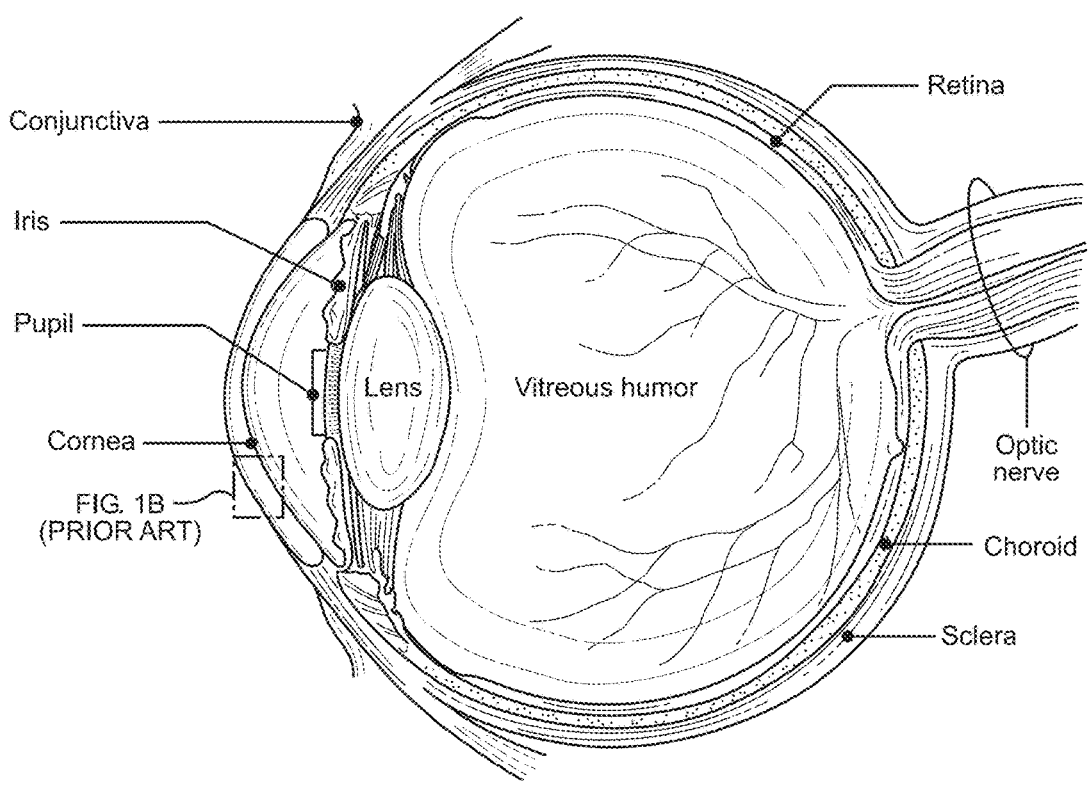
FIG. 1A is a prior art schematic representation of the human eye illustrating the conjunctiva, iris, pupil, cornea, retina, lens, vitreous humor, optic nerve, choroid and sclera.
Figure 1B:
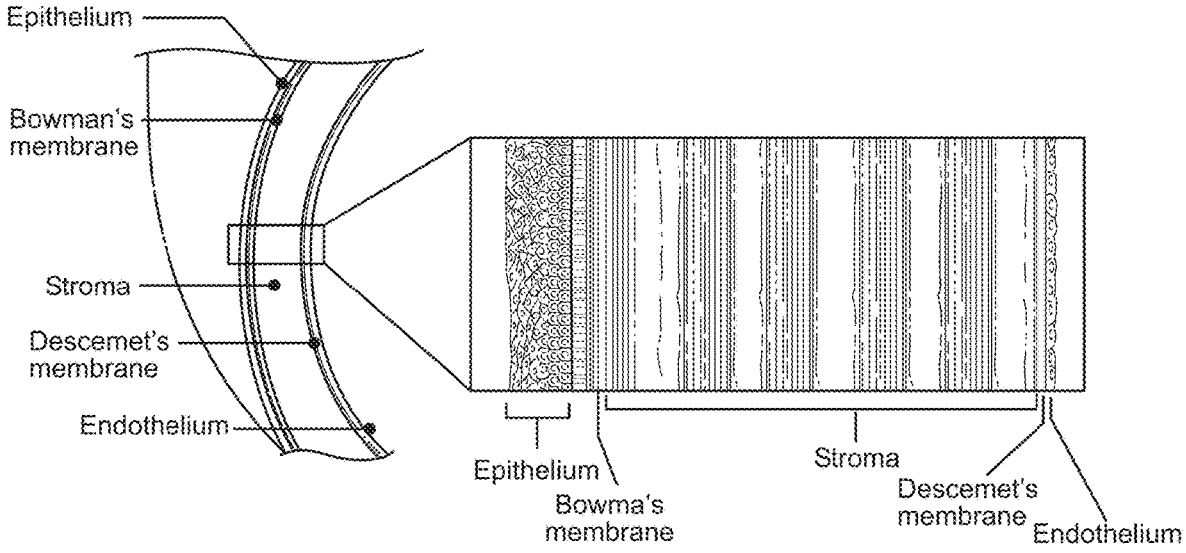
FIG. 1B is a prior art schematic representation of the cross-sectional structure of the cornea illustrating the epithelium, Bowman's membrane, stroma, Descemet's membrane, and endothelium.
Figure 2:
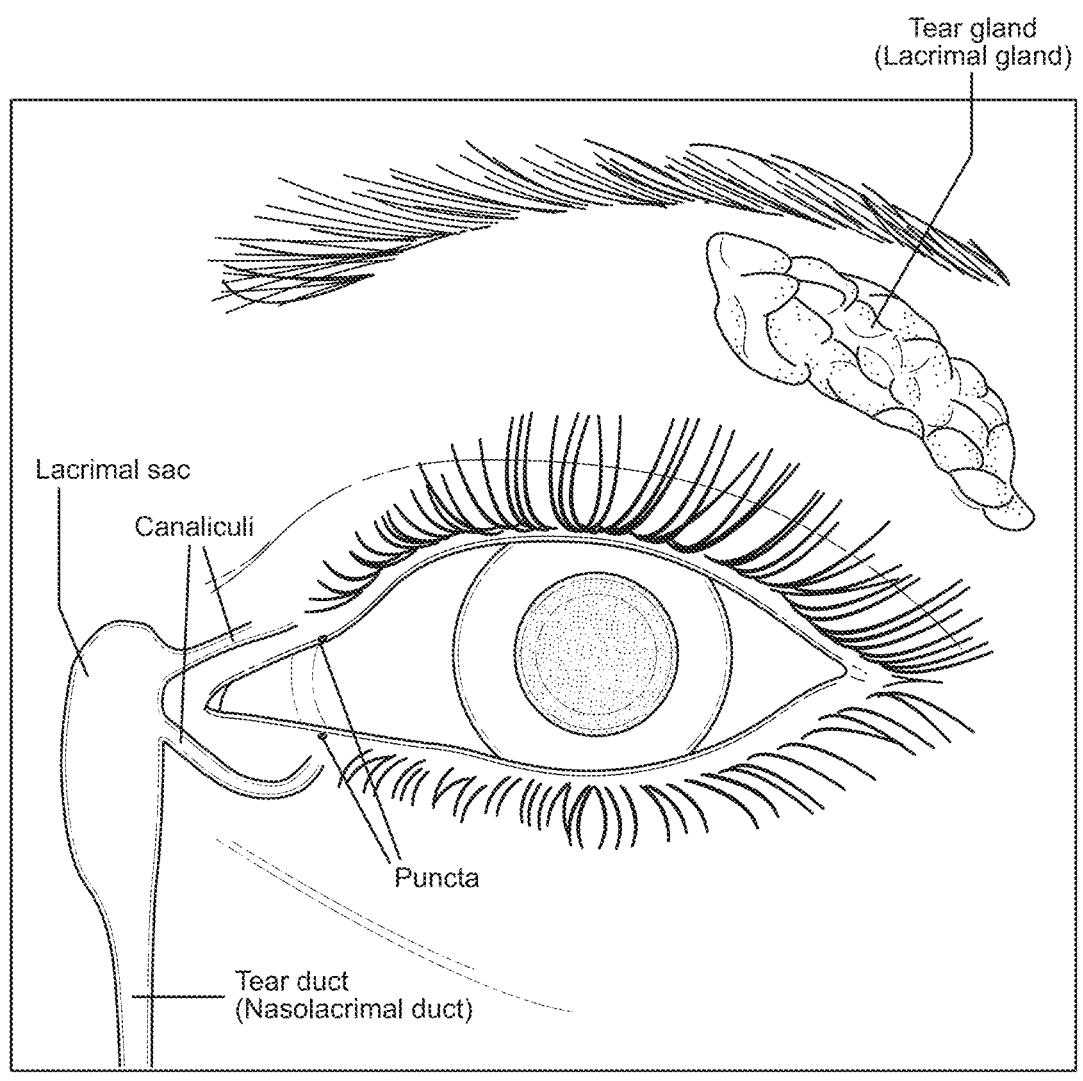
FIG. 2 is prior art graphical illustration of the front view of the human eye showing the Lacrimal sac, Canaliculi, the Puncta, the tear duct (i.e. Nasolacrimal duct), and the tear gland (i.e. Lacrimal gland) above the eye.
Figure 3:
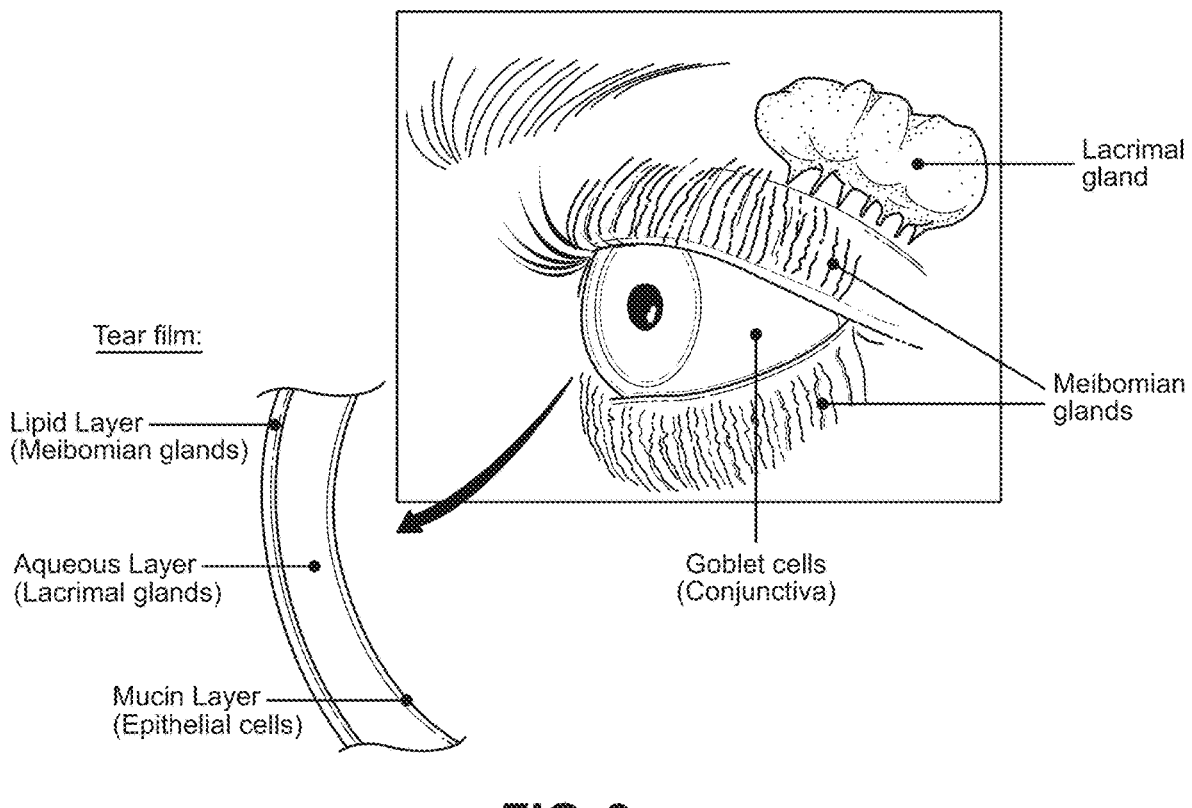
FIG. 3 is prior art graphical illustration of the side view of the human eye showing the Lacrimal gland, Meibomian glands, and the Goblet cells in the Conjunctiva, with an expanded view of the Tear film showing its lipid layer supplied by the Meibomian glands, its aqueous layer supplied by the Lacrimal glands, and its Mucin layer provided by the epithelial cells.
Figure 4:
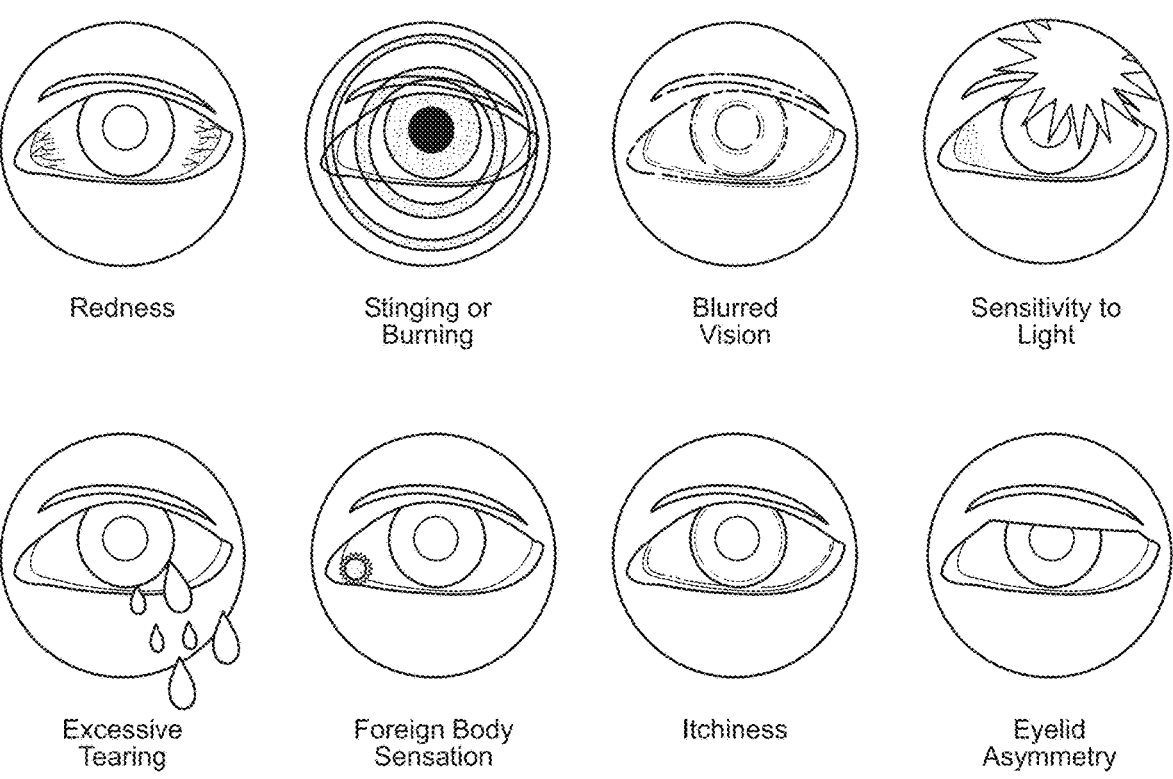
FIG. 4 are graphical illustrations of the human eye in different states indicating common symptoms of dry eye disease, including, redness, stinging or burning, blurred vision, sensitivity to light, excessive tearing, foreign body sensation, itchiness, and eyelid asymmetry.
Figure 6:
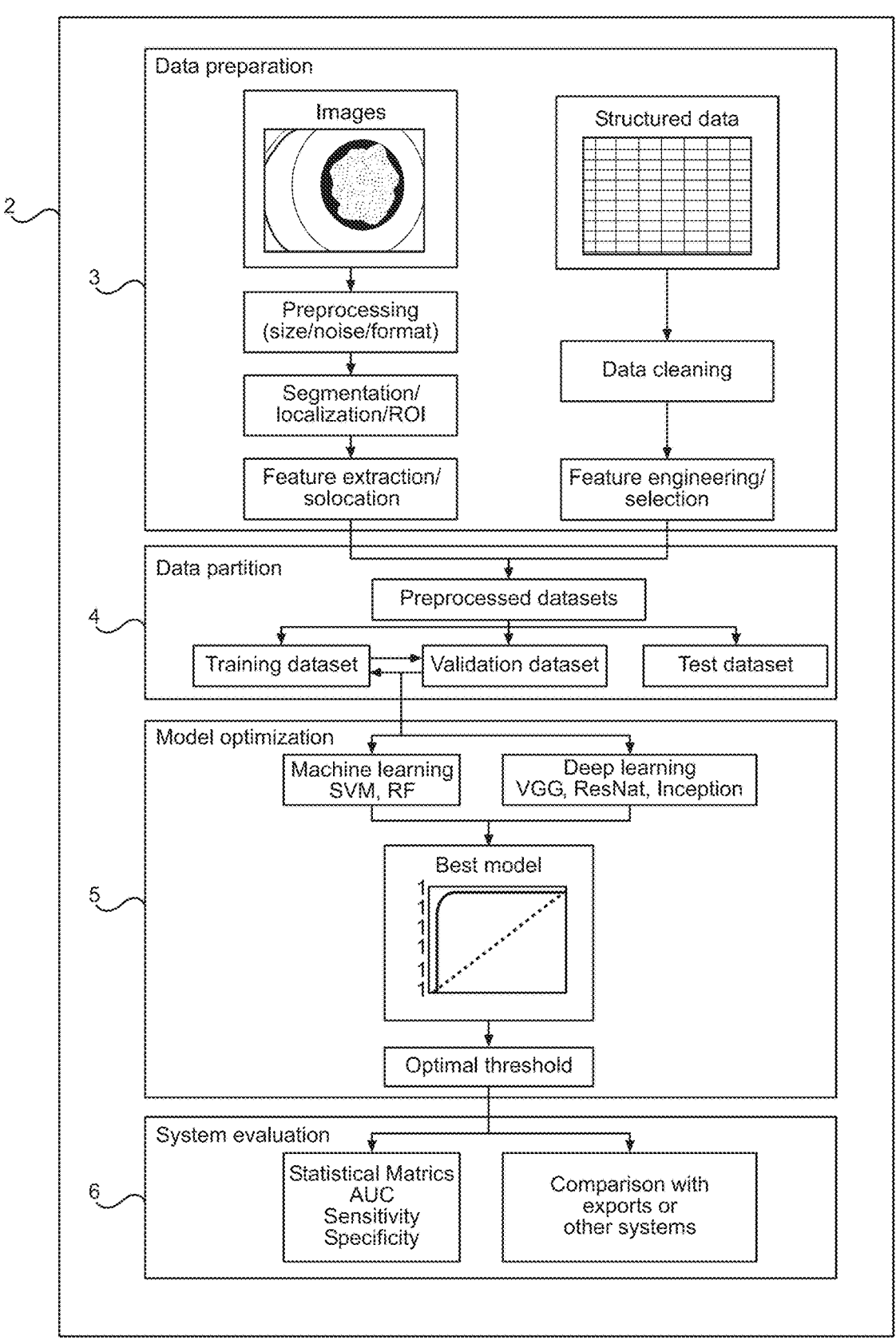
FIG. 6 is a prior art schematic representation illustrating an exemplary workflow that may be used to construct models used in deep learning (AI) systems and applications in the ophthalmological arts.
Figures 12A, 12B, 12C, 12D:
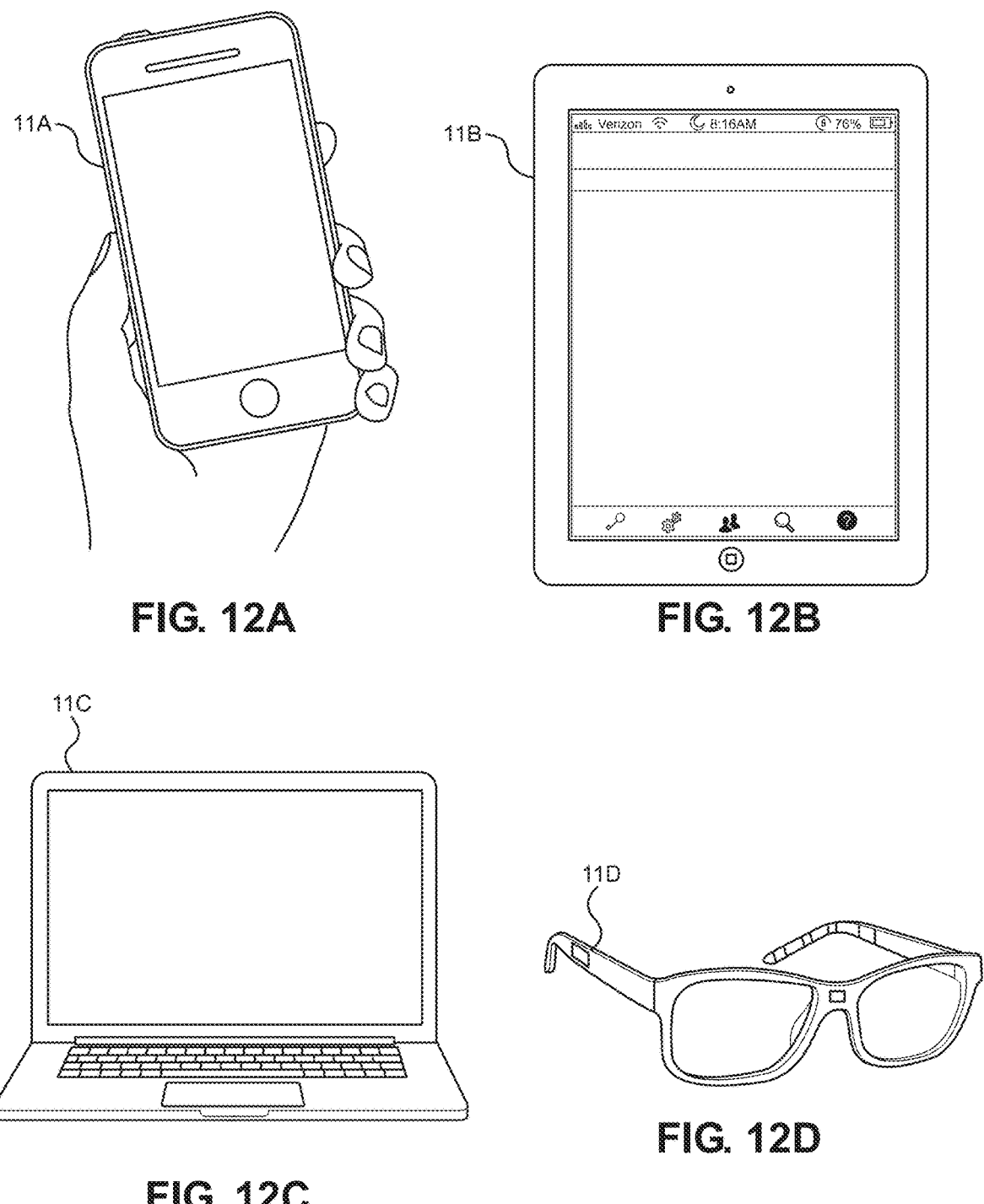
FIG. 12A is a perspective view of a mobile smartphone-based camera system of the present invention for deployment and use in the system network of the present invention depicted in FIGS. 7, 8, 9A, 9B and 10.
FIG. 12B is a perspective view of a mobile tablet-based camera system for deployment and use in the system network of the present invention depicted in FIGS. 7, 8A, 8B, 9A, 9B and 10.
FIG. 12C is a perspective view of a mobile laptop-based camera system for deployment and use in the system network of the present invention depicted in FIGS. 7, 8A, 8B 9A, 9B and 10.
FIG. 12D is a perspective view of a mobile eyeglasses computing system for deployment and use in the system network of the present invention depicted in FIGS. 7, 8A, 8B, 9A, 9B and 10.
Figure 149:
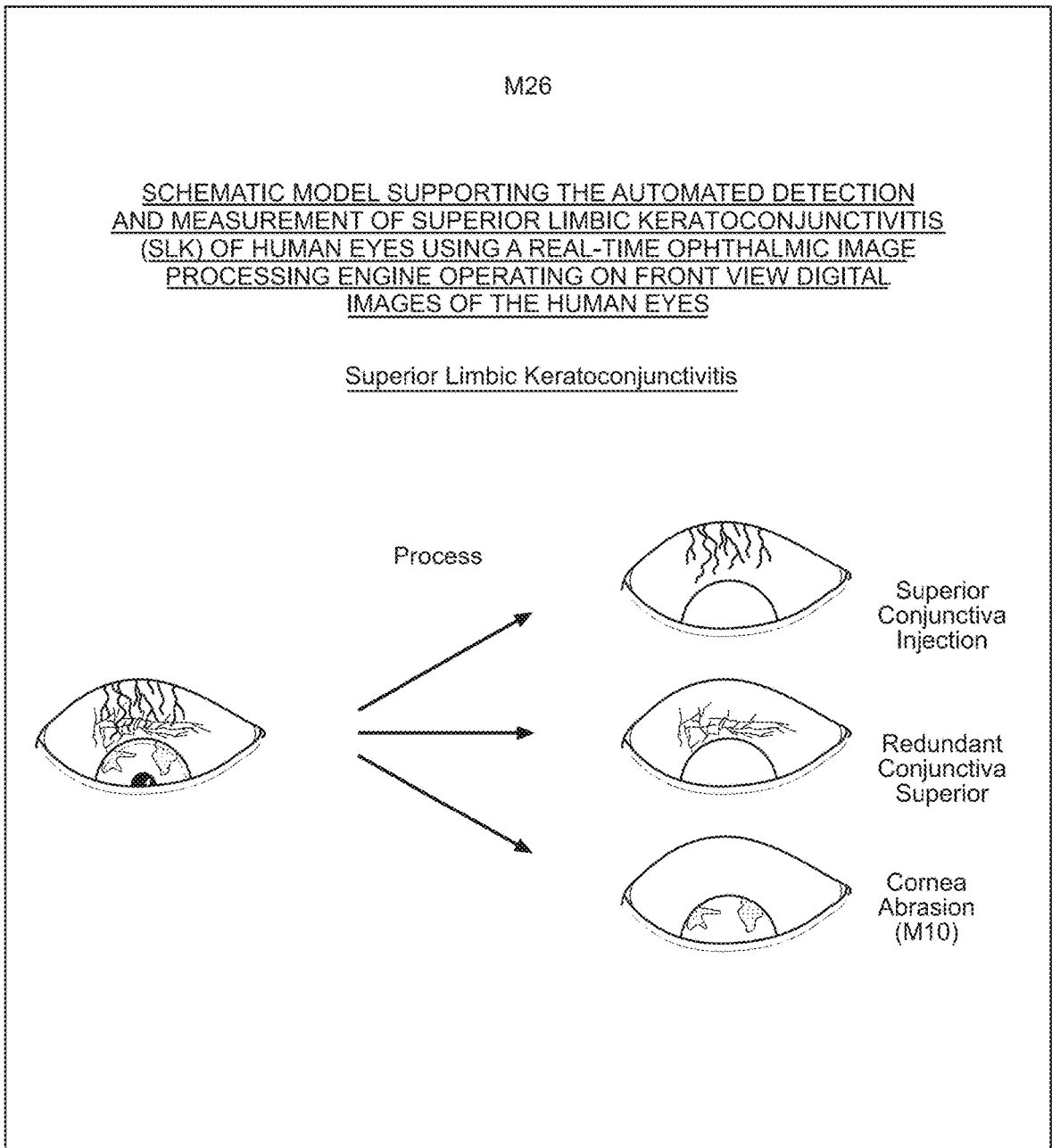
Figure 151:
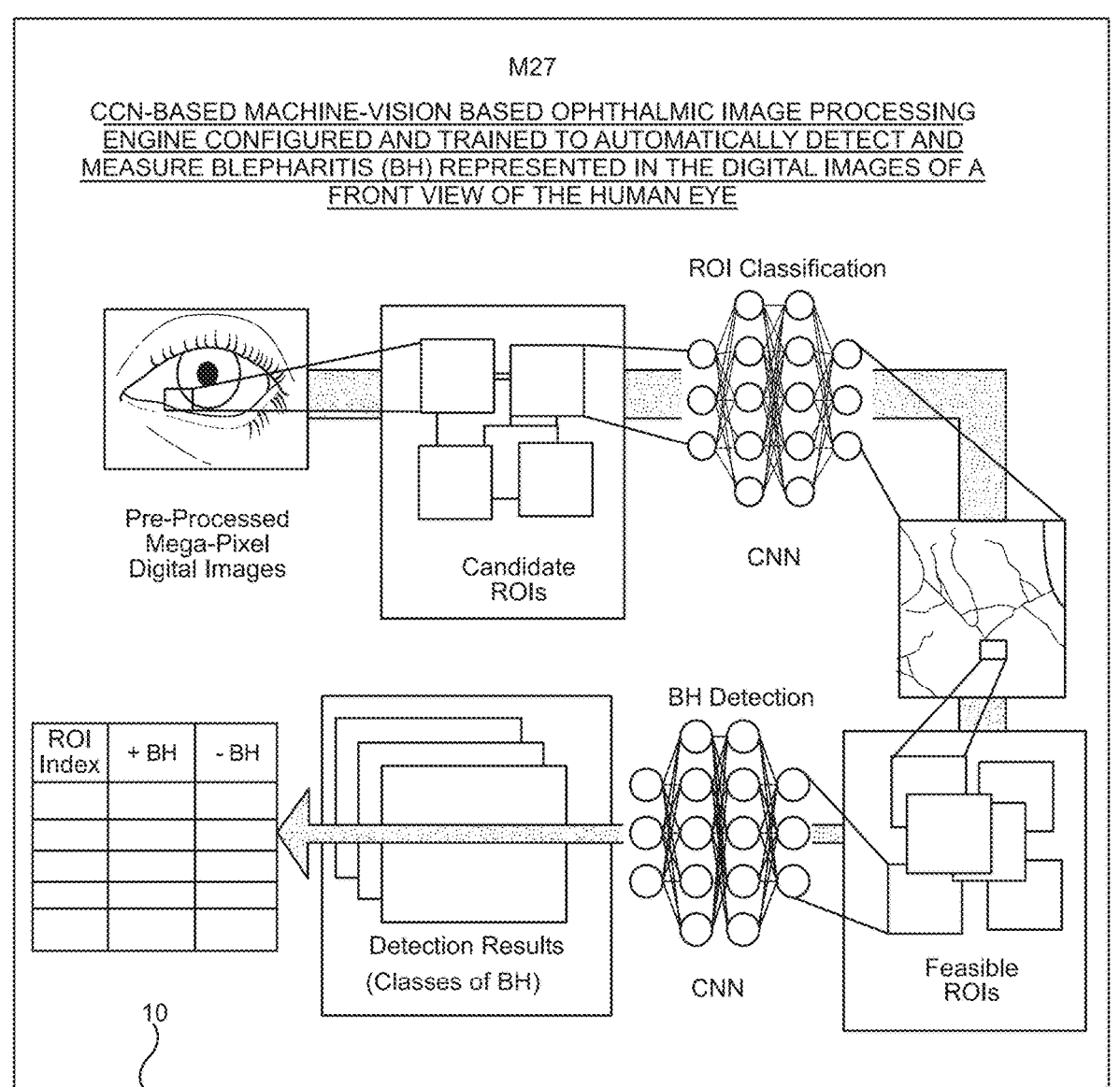
Figure 152:
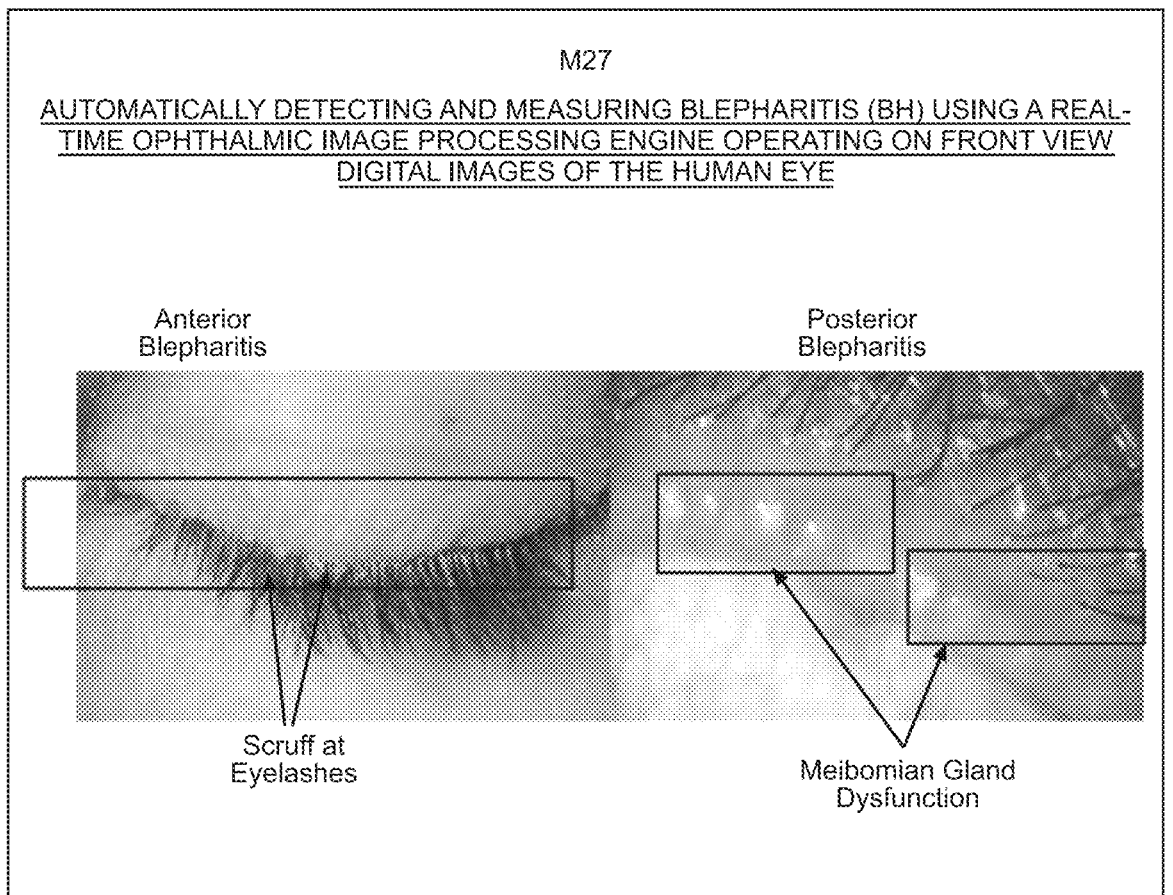
Figure 153:
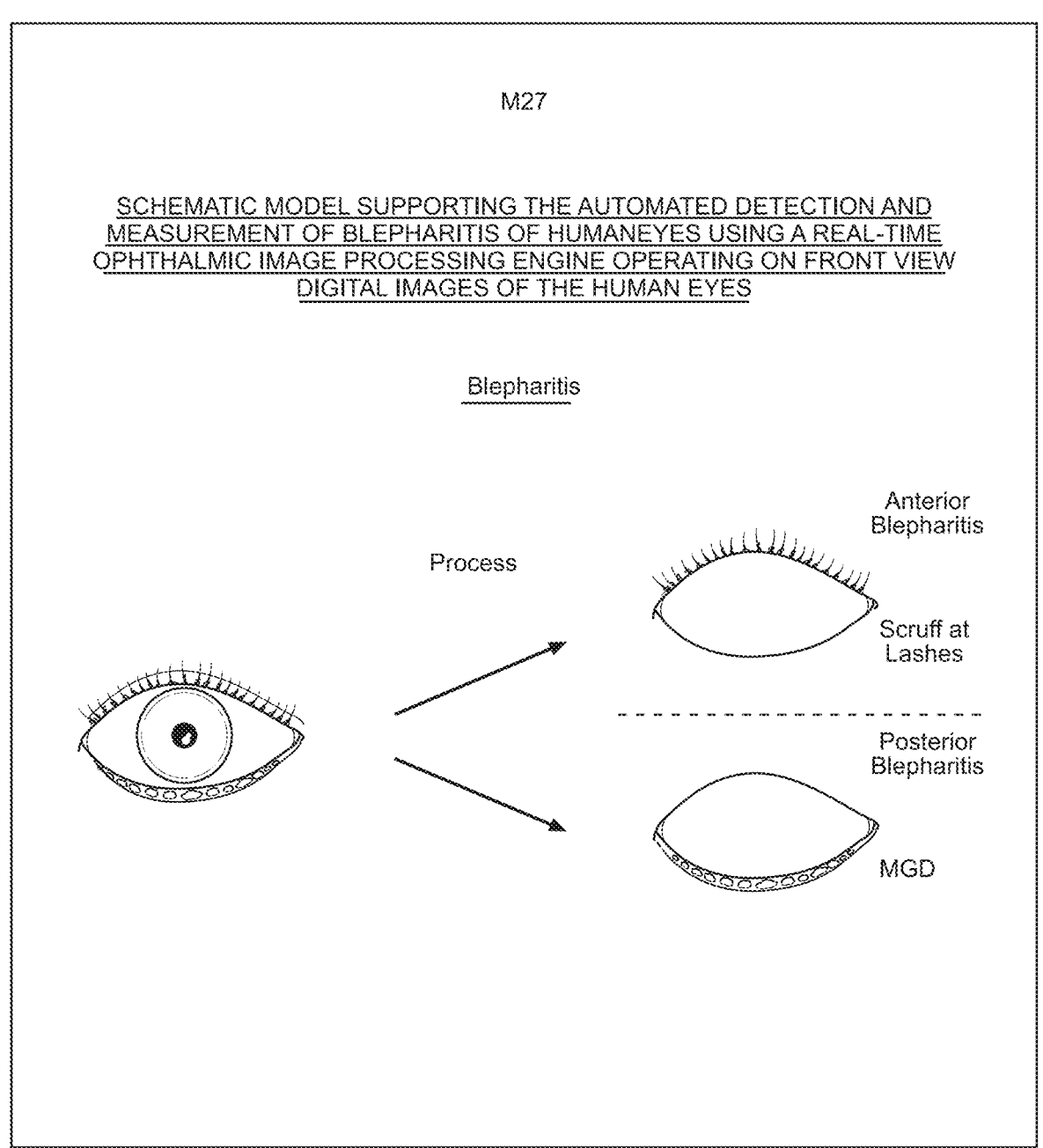
Figure 155:
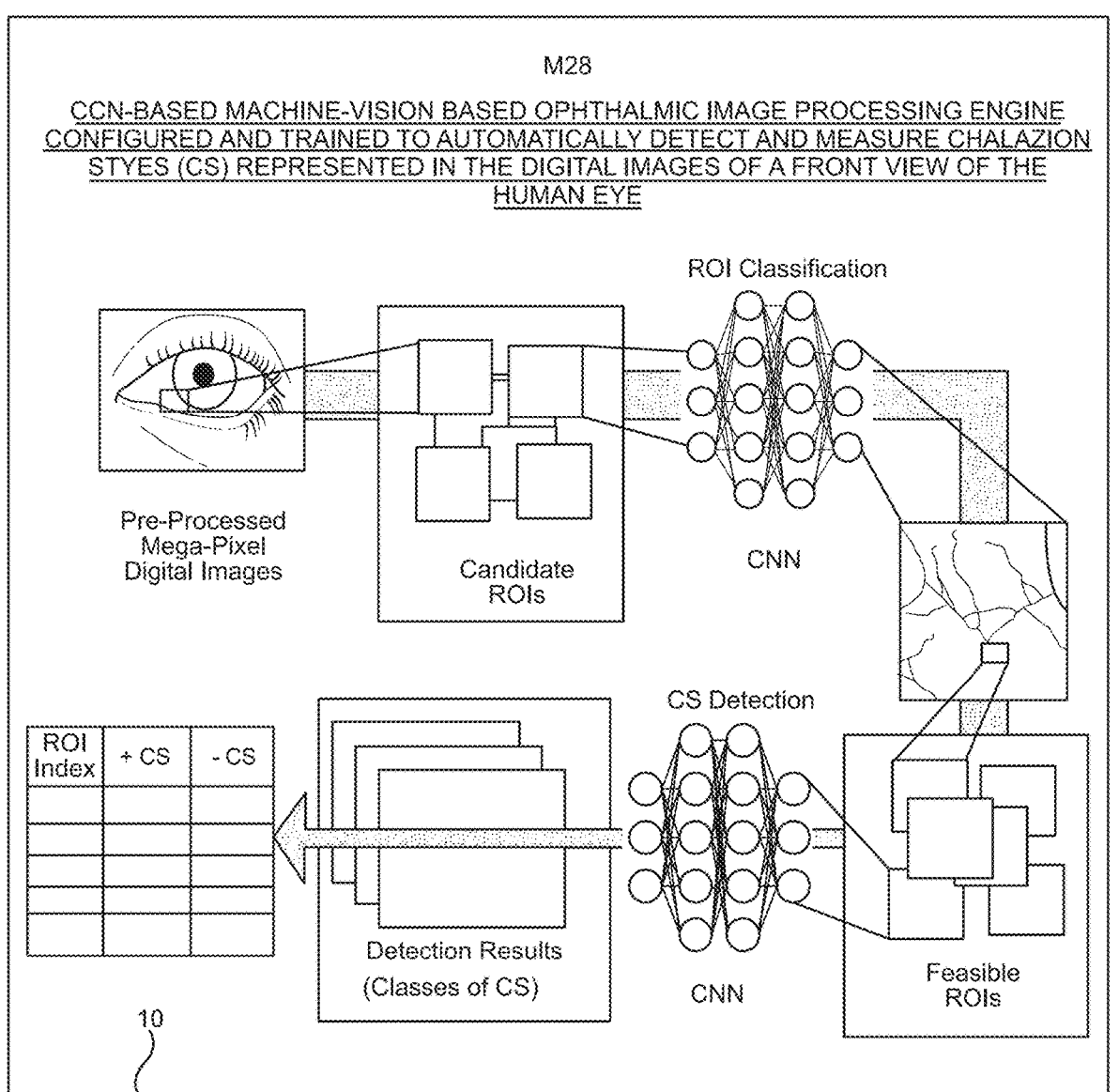
Figure 156:
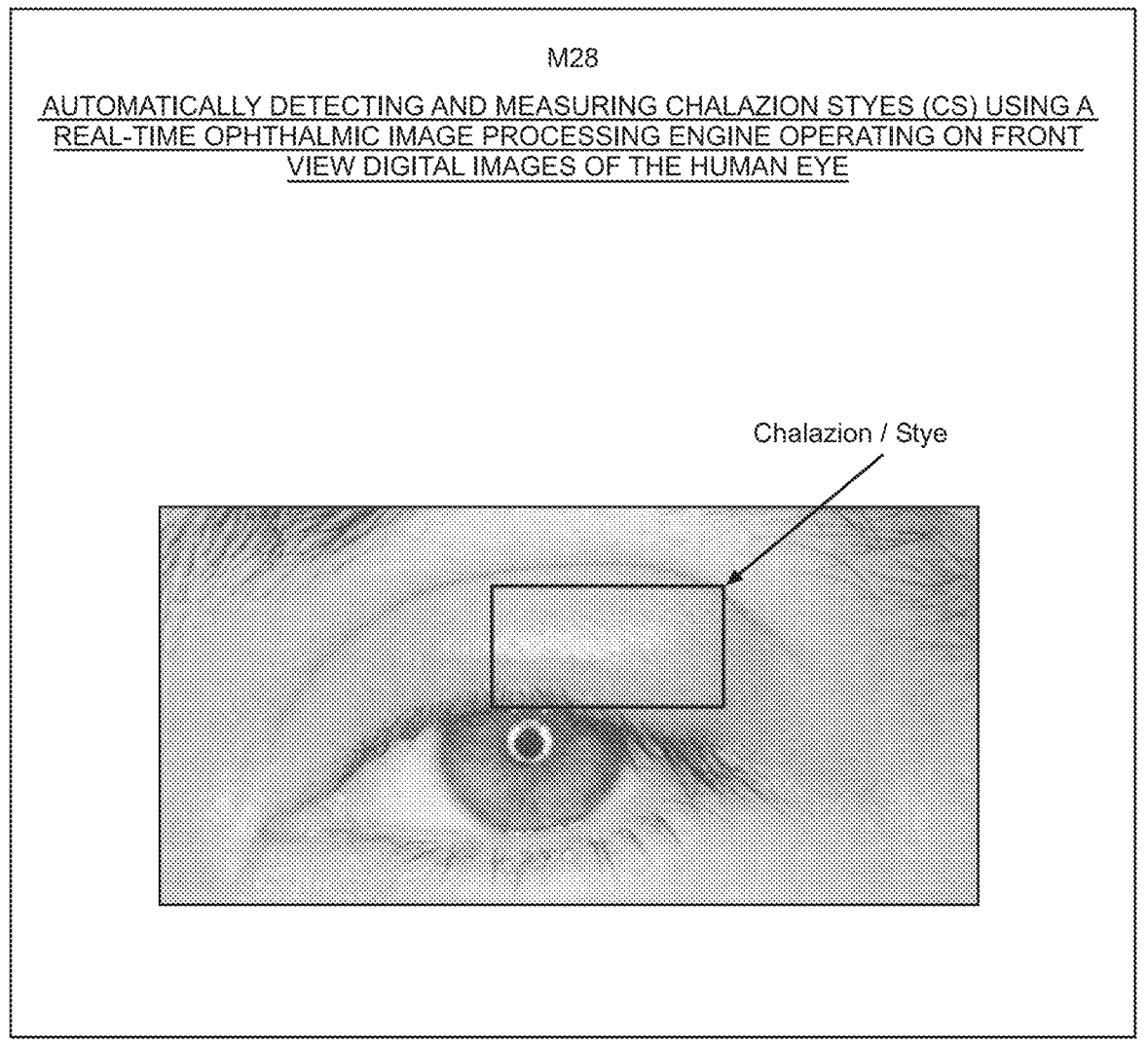
Figure 157:
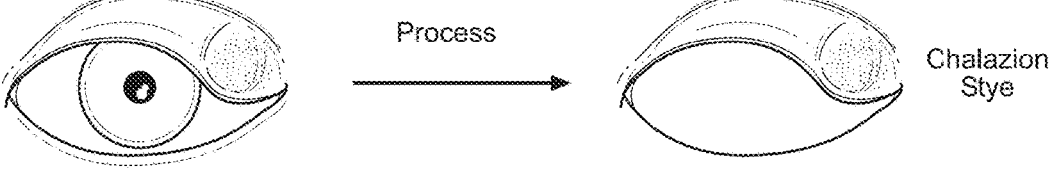
Figure 159:
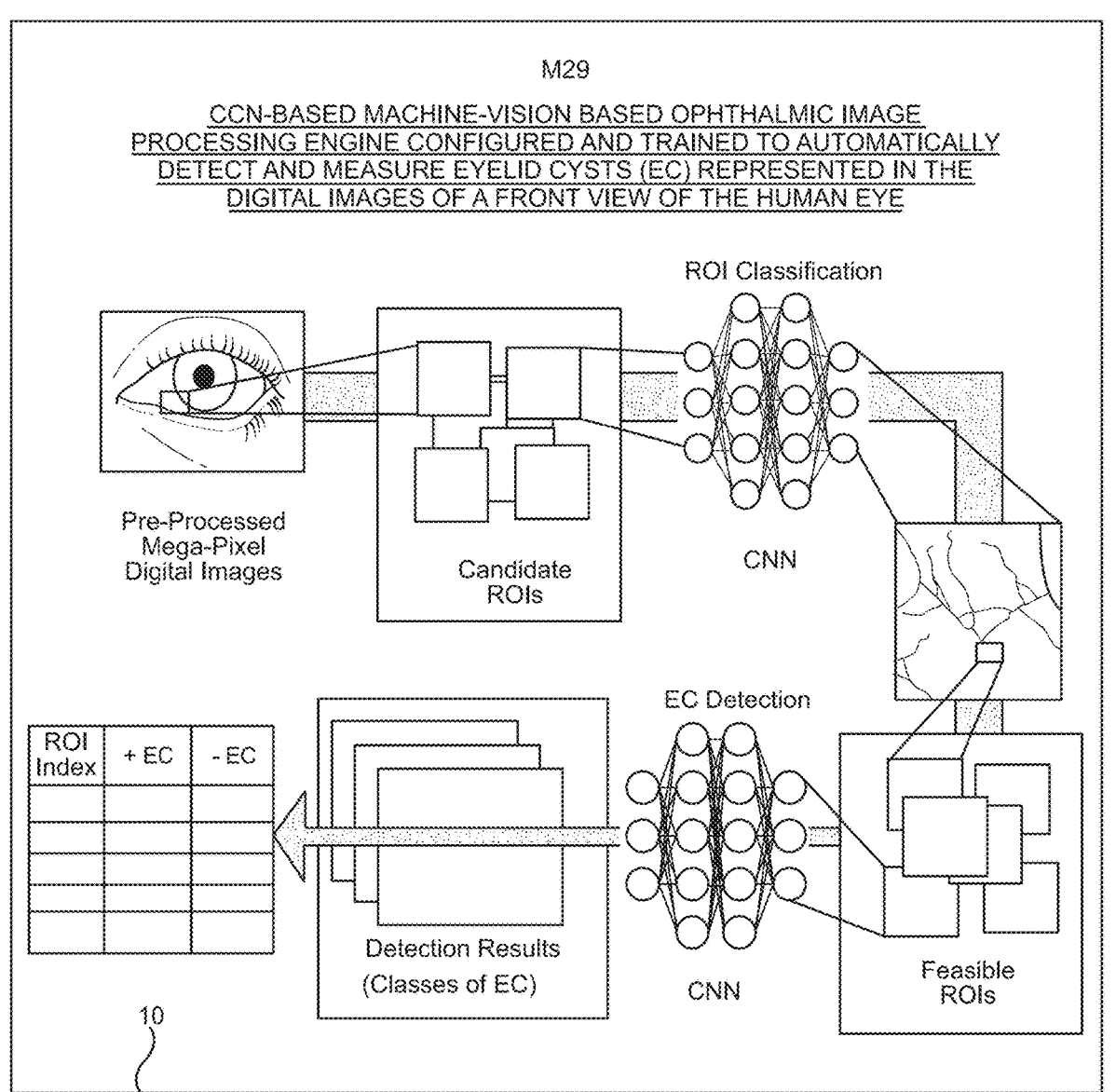
Figure 160:
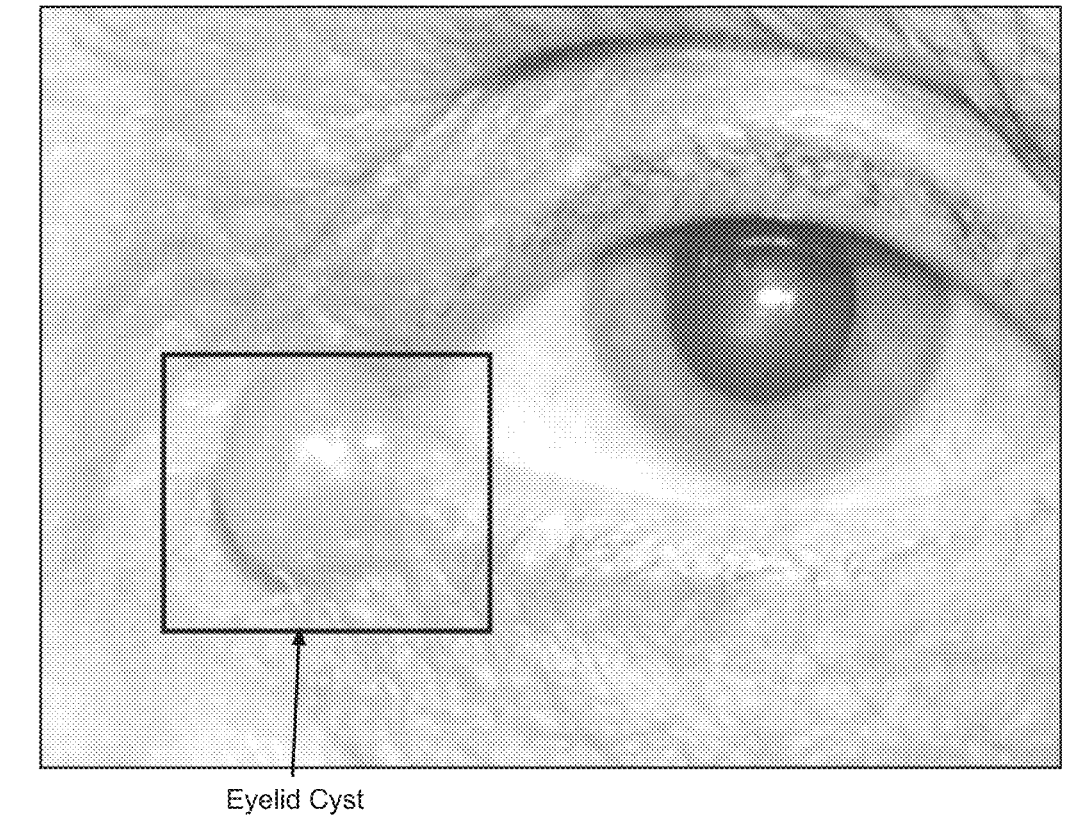
Figure 161:
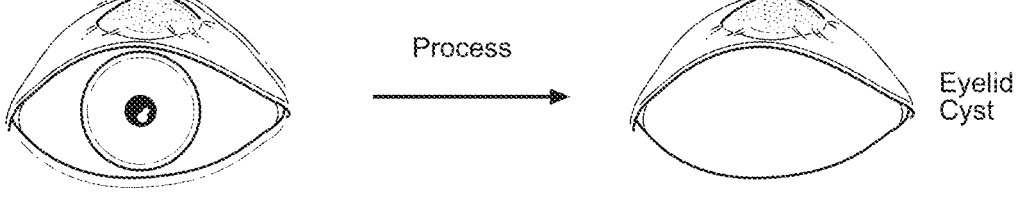
Figure 163:
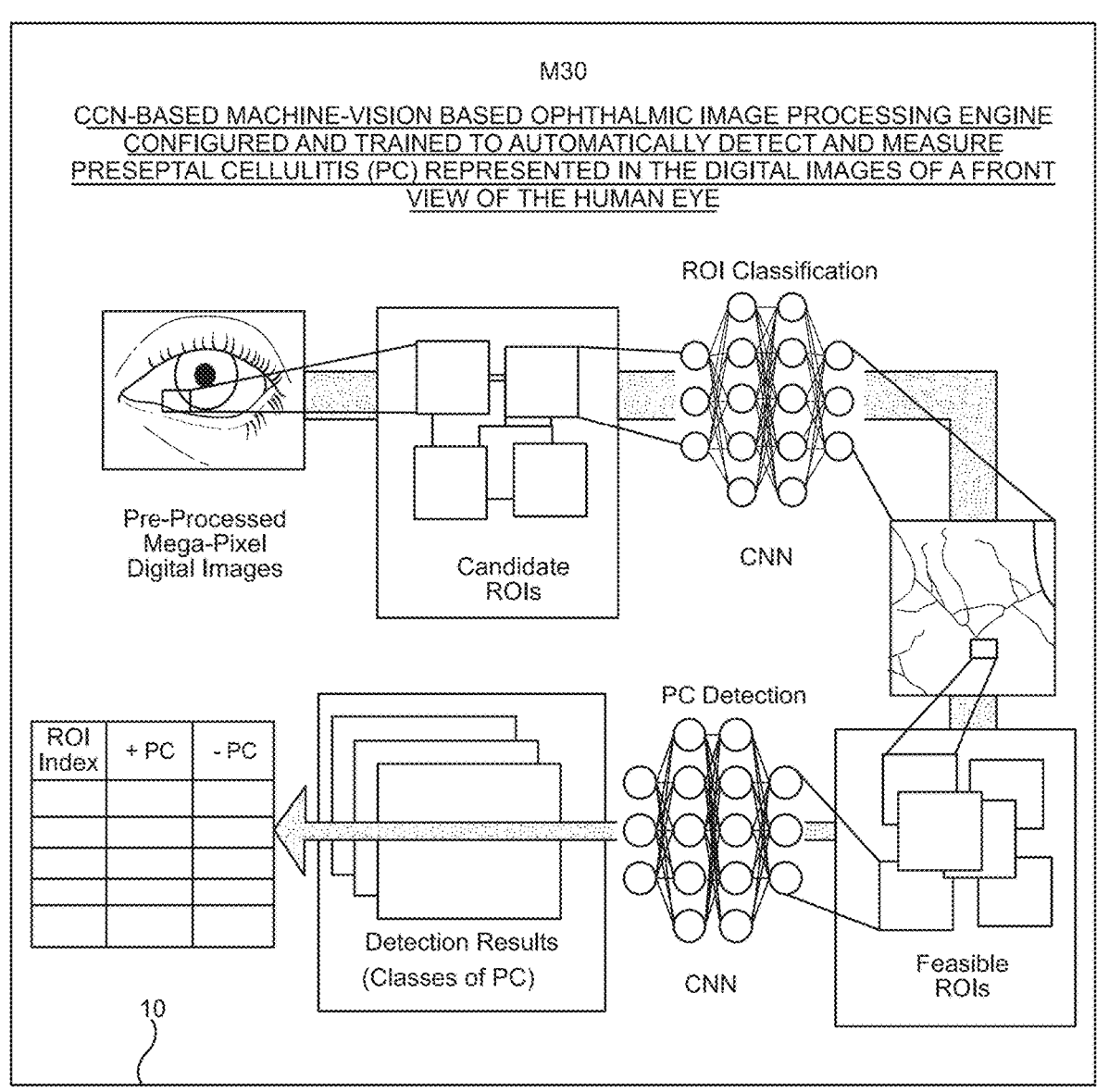
Figure 164:
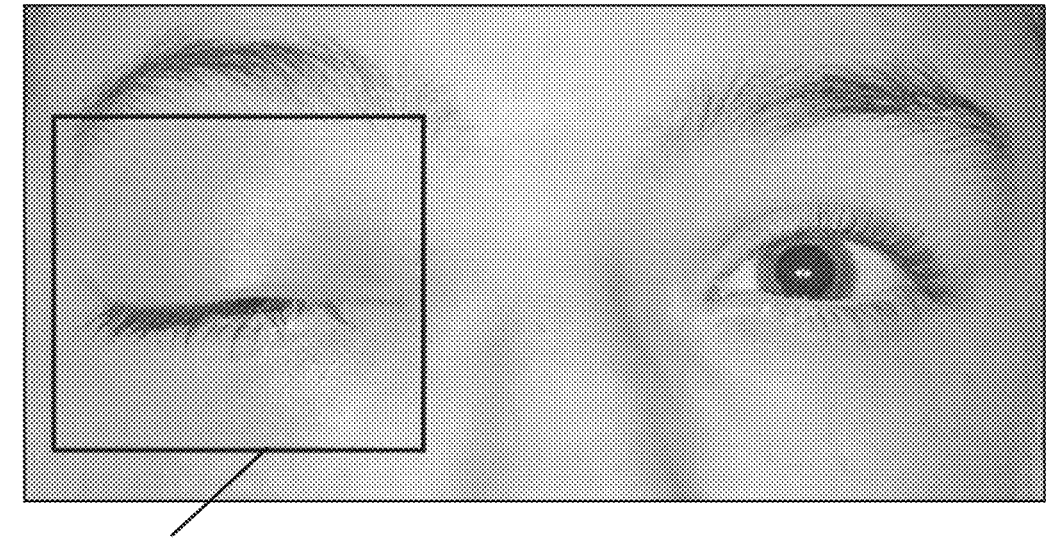
Figure 165:
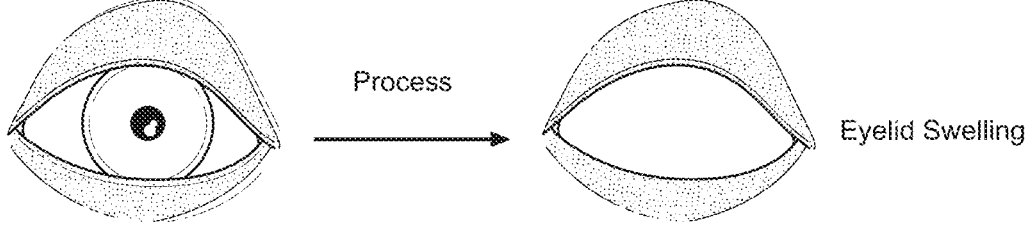
Figure 167:
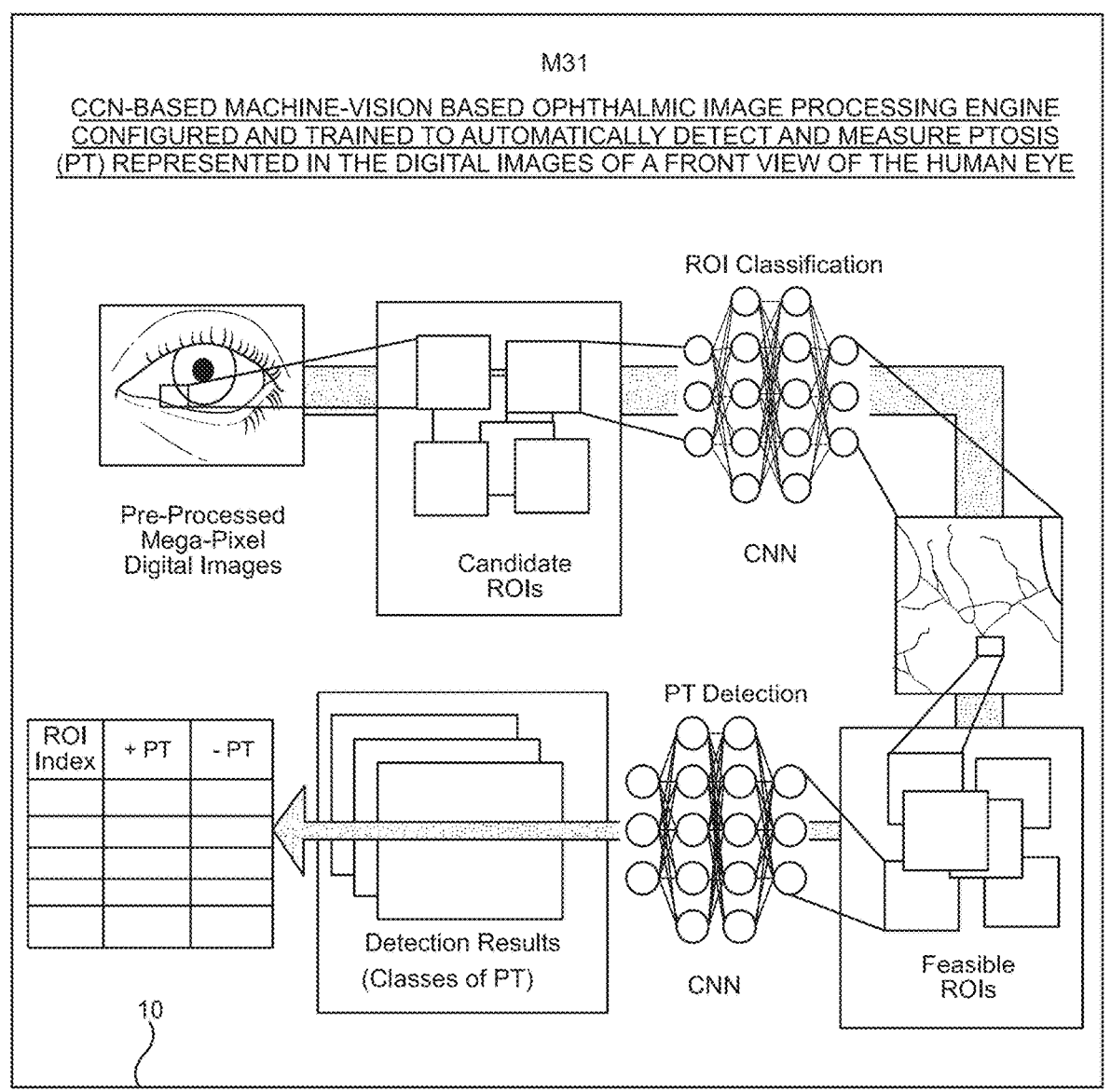
Figure 168:
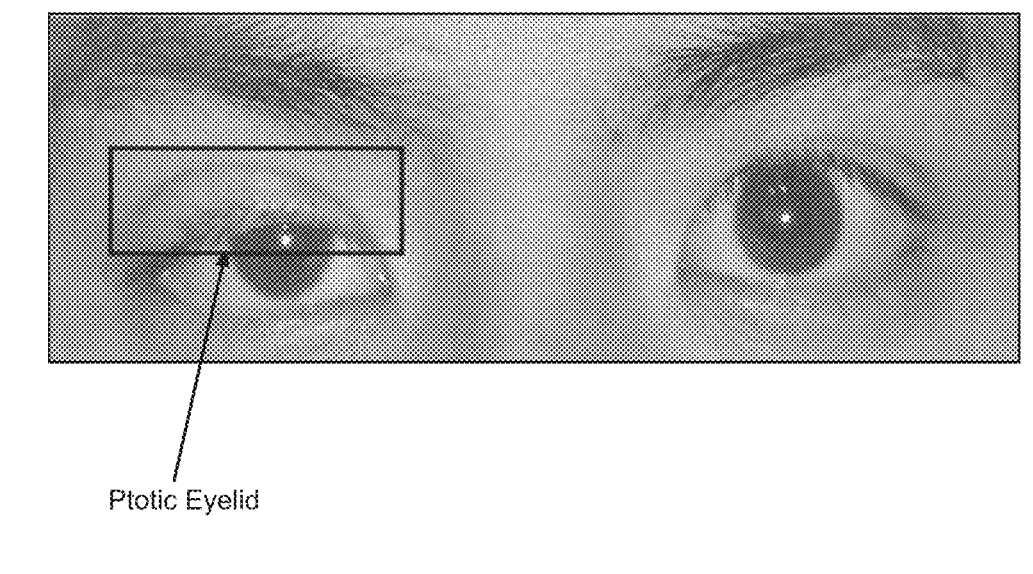
Figure 169:
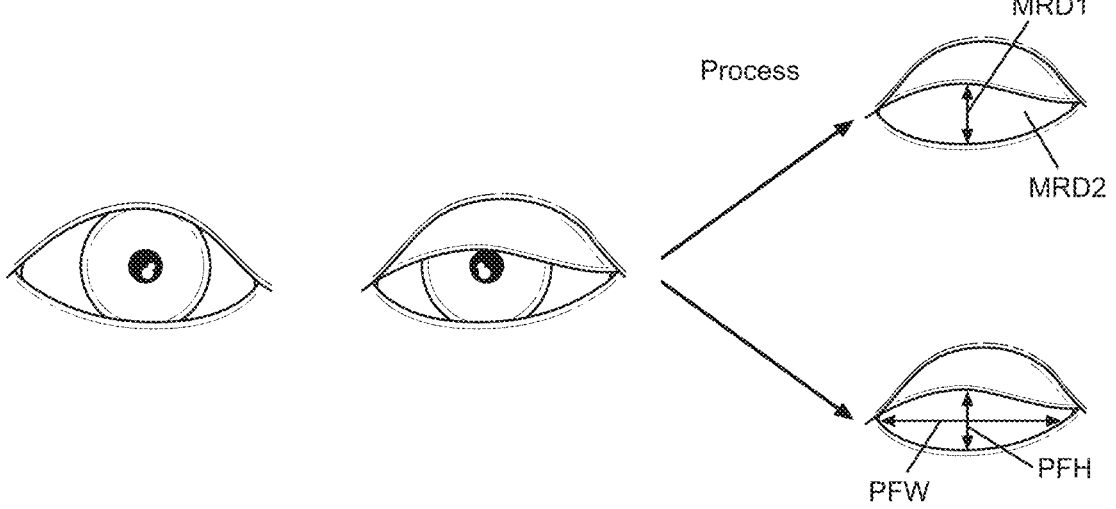
Figure 171:
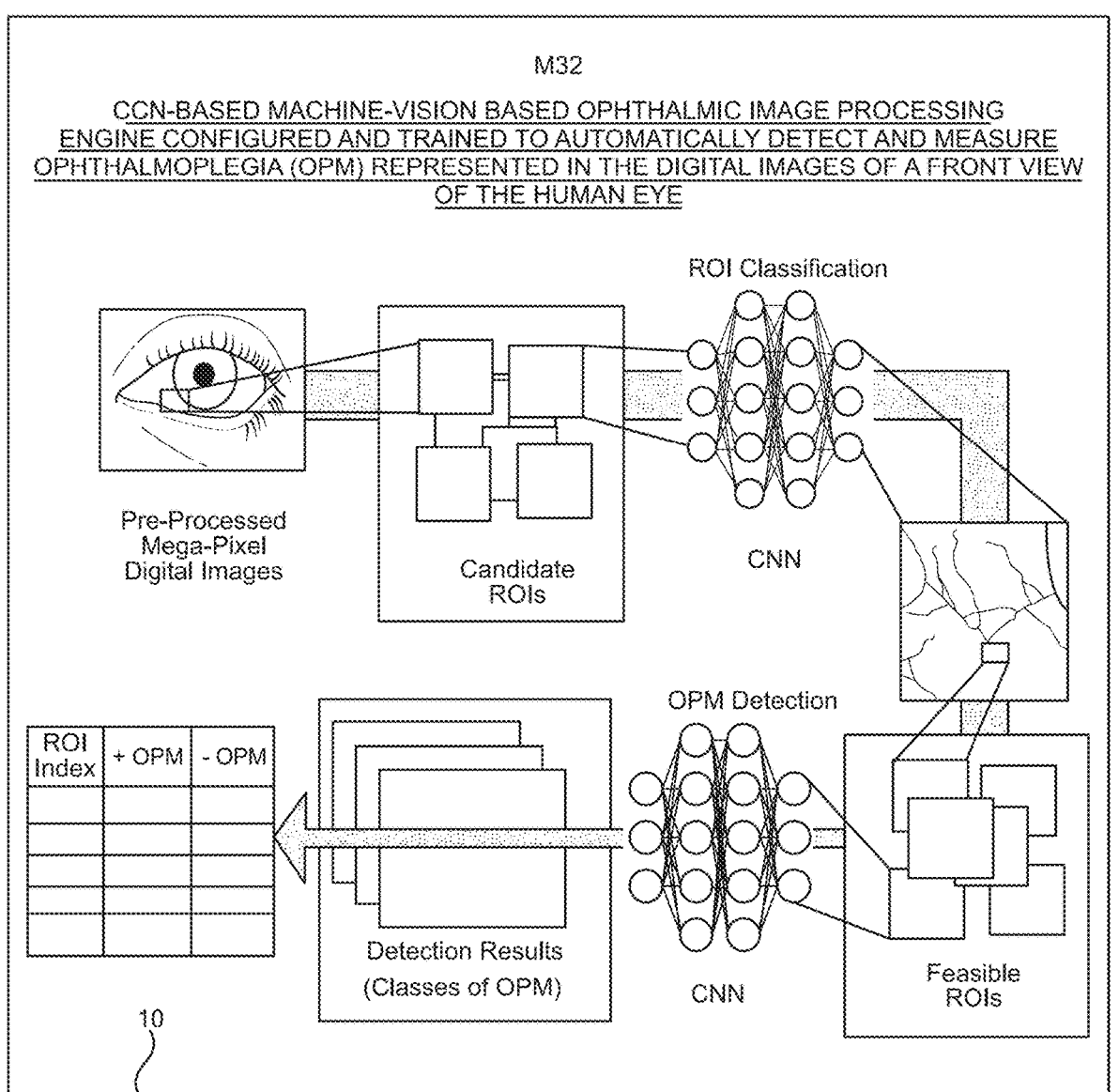
Figure 172:
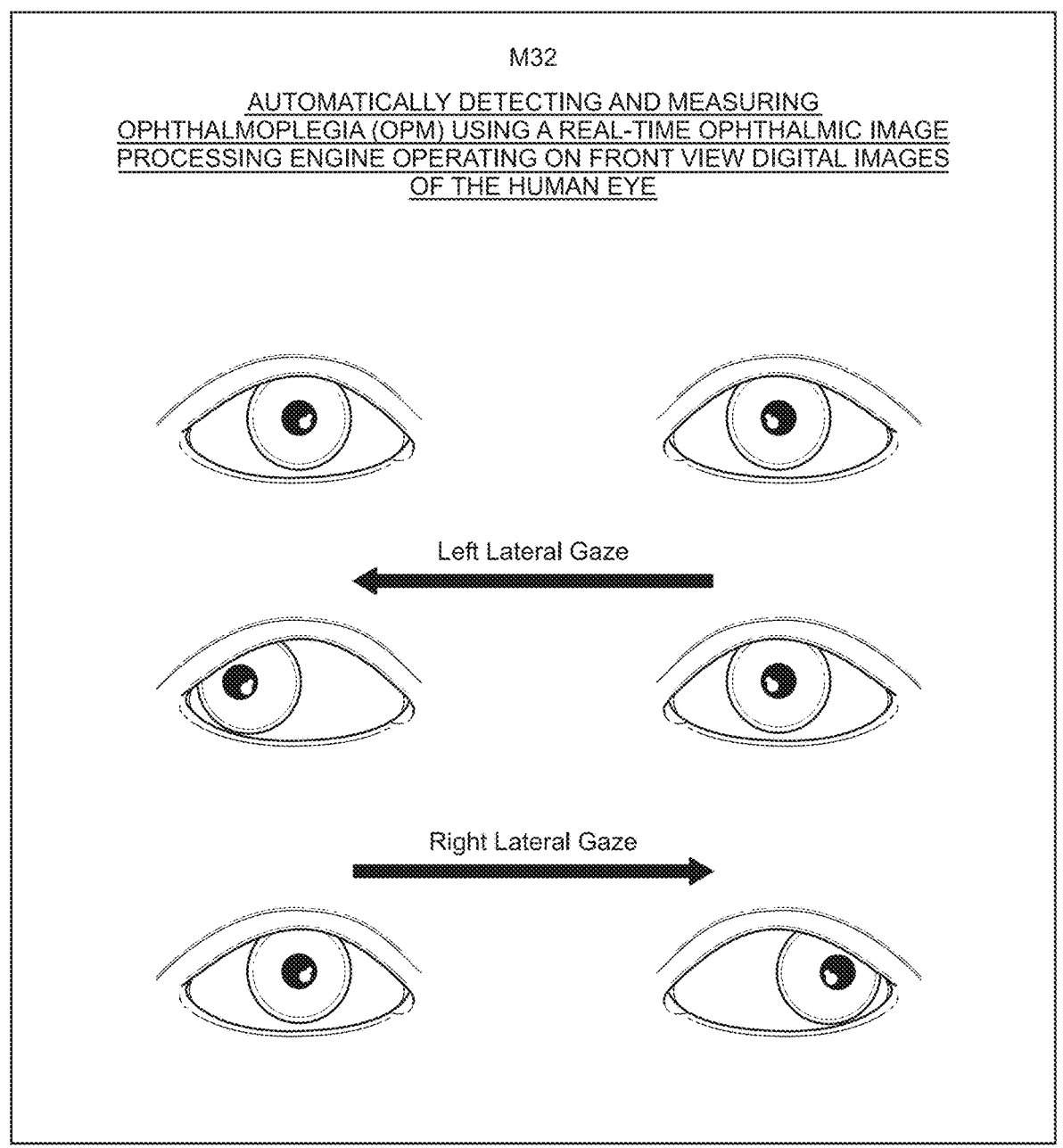
Figure 173:
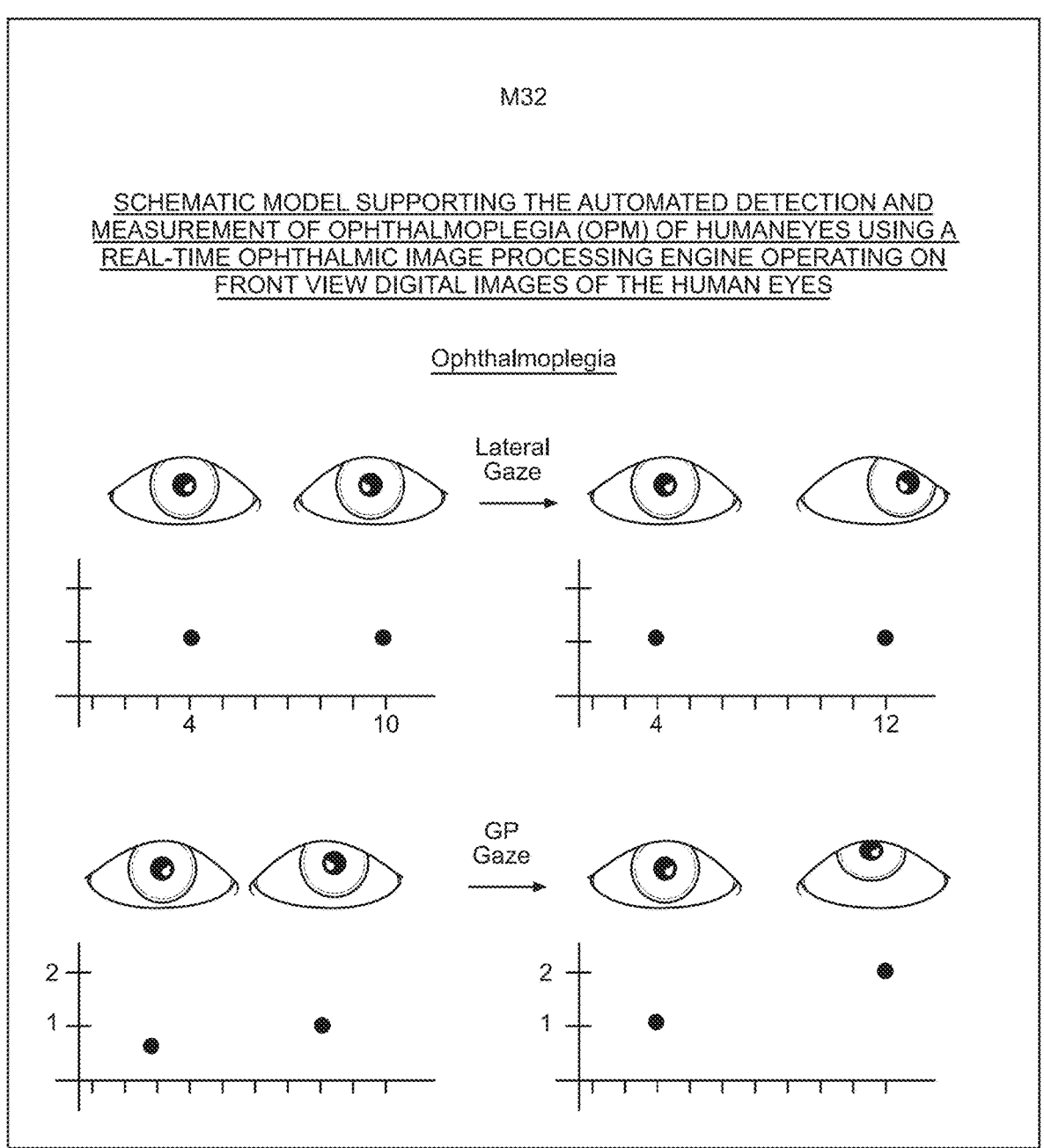
Figure 175:
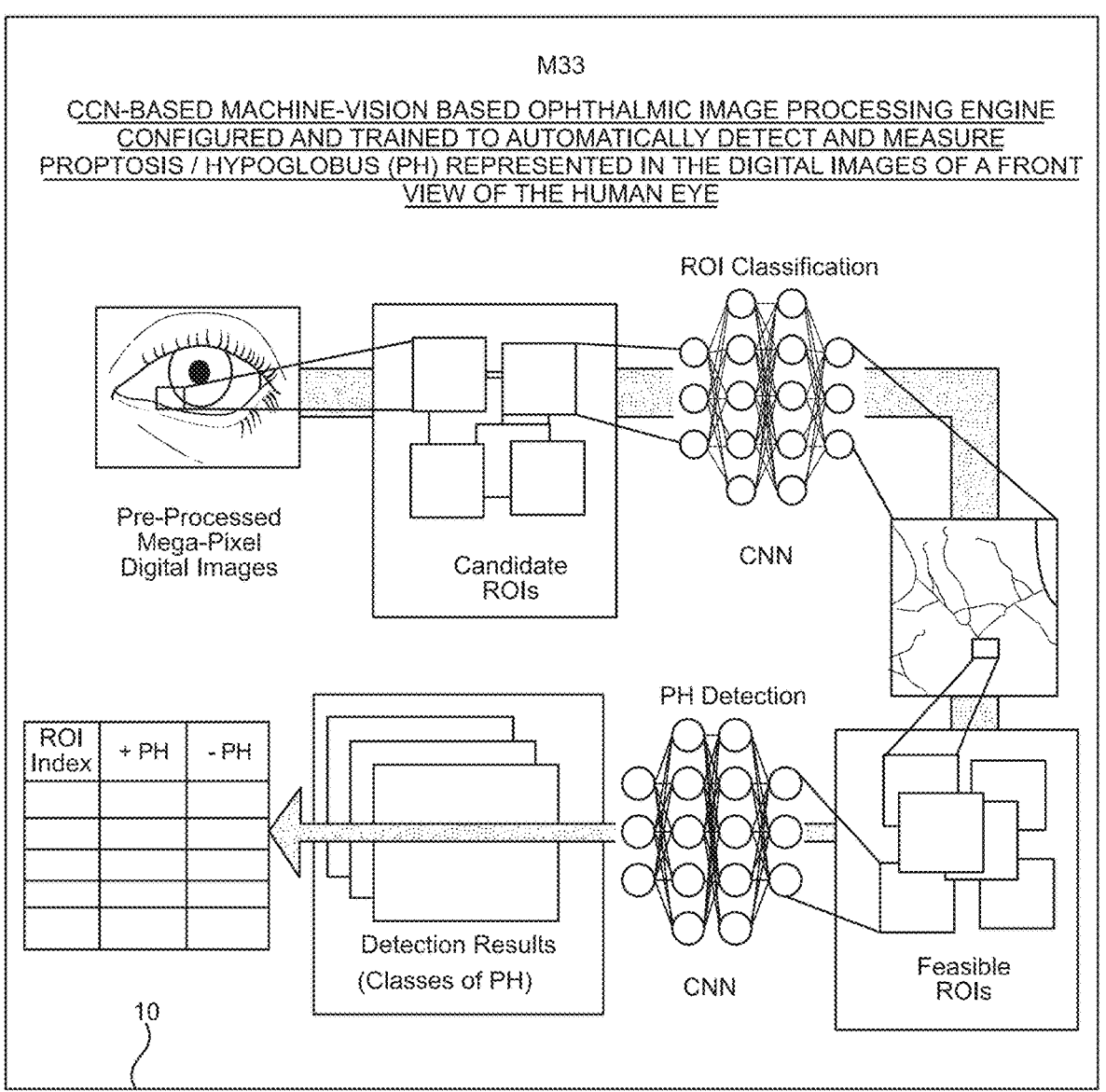
Figure 176:
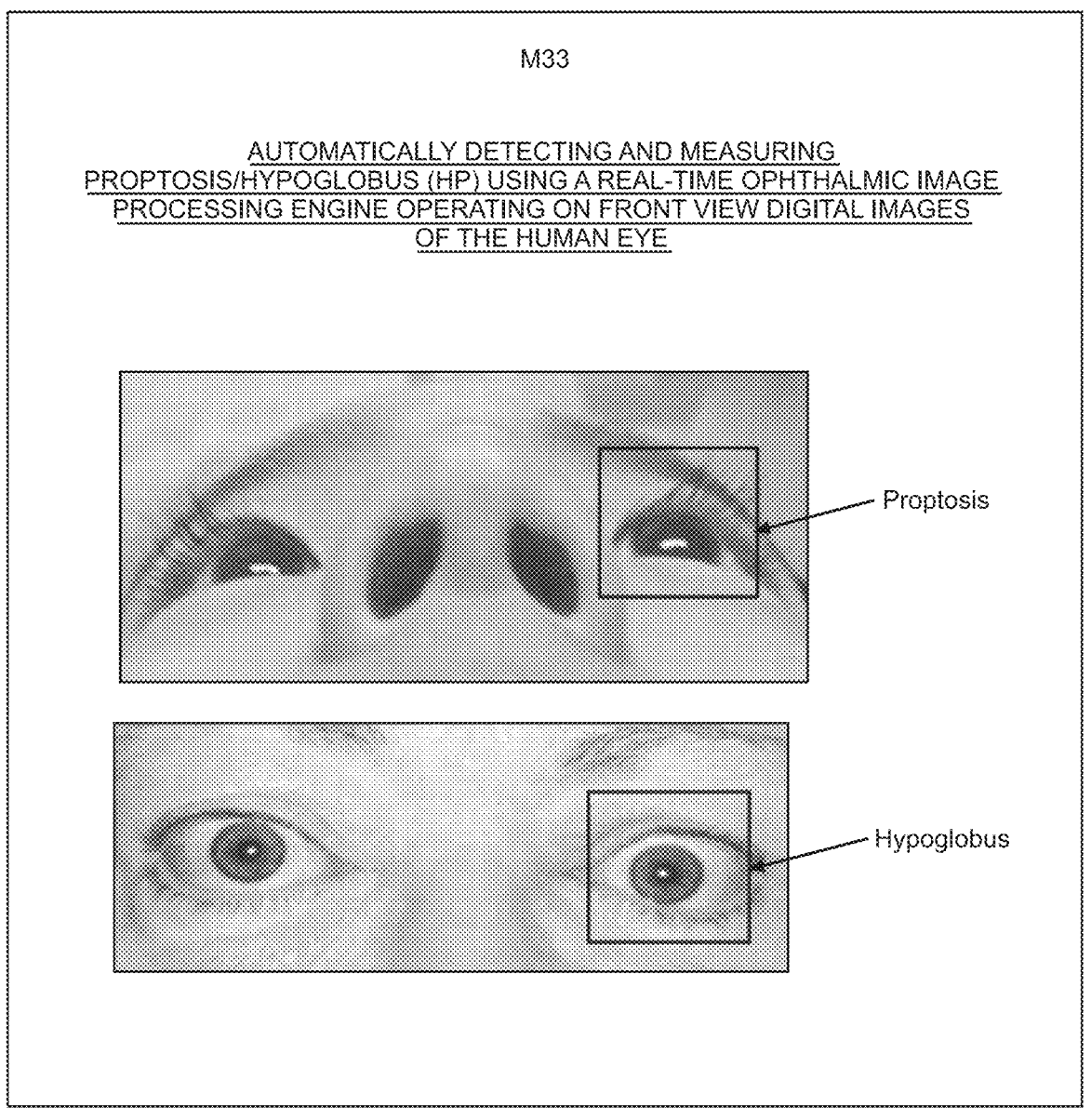
Figure 177:
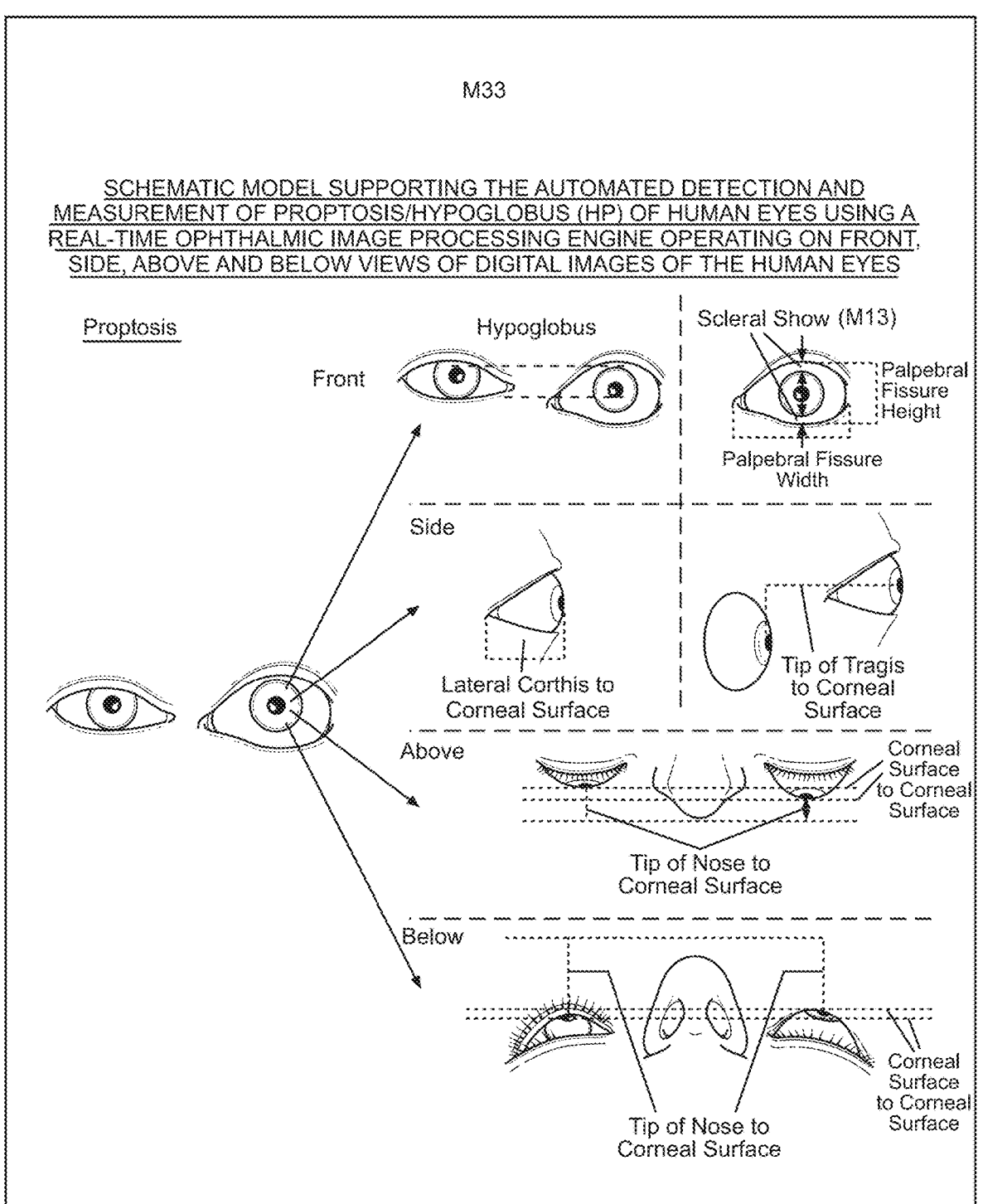
Figure 179:
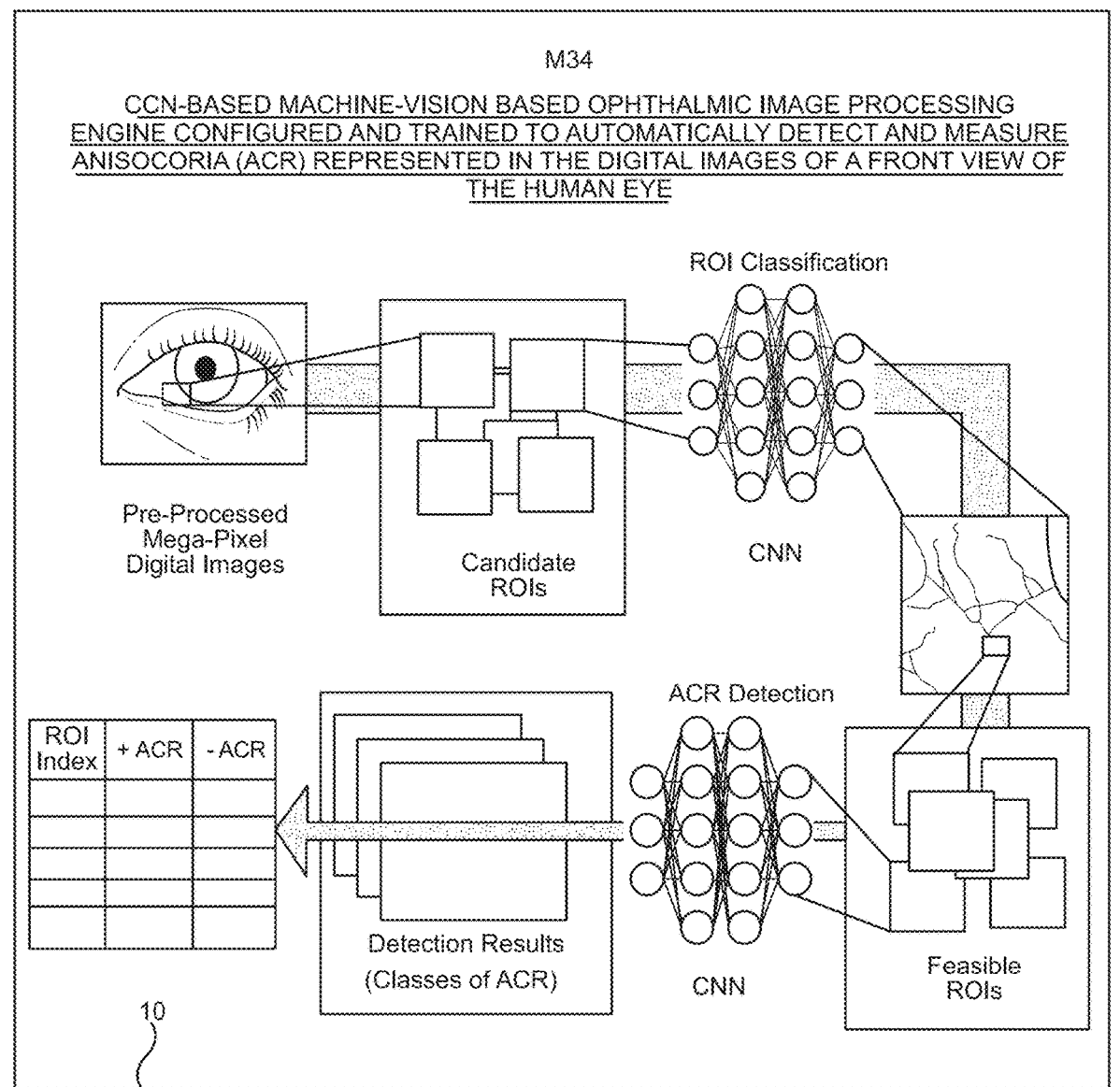
Figure 180:
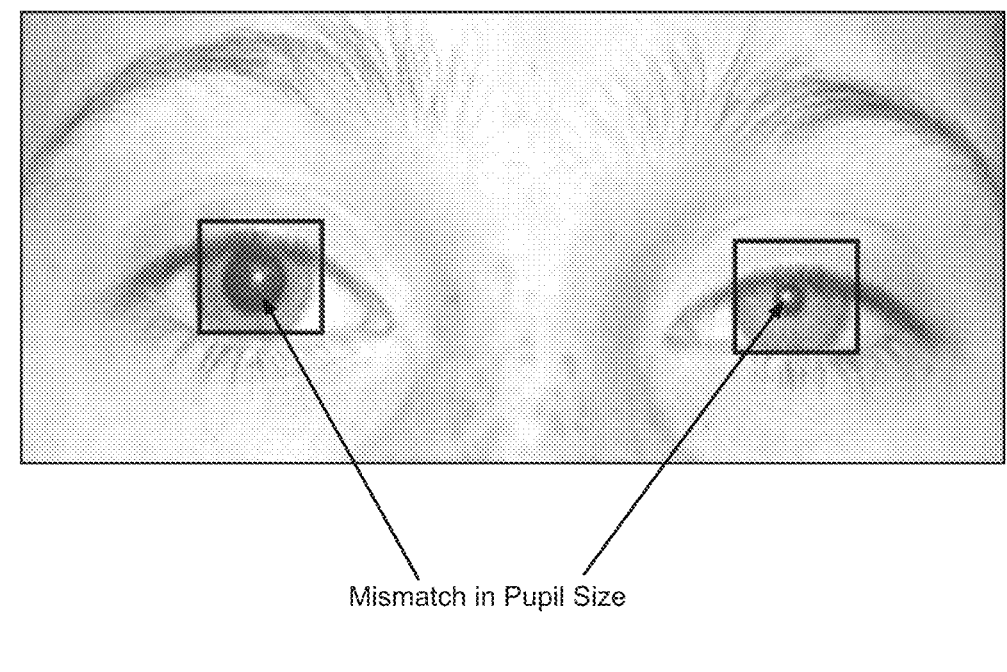
Figure 181:
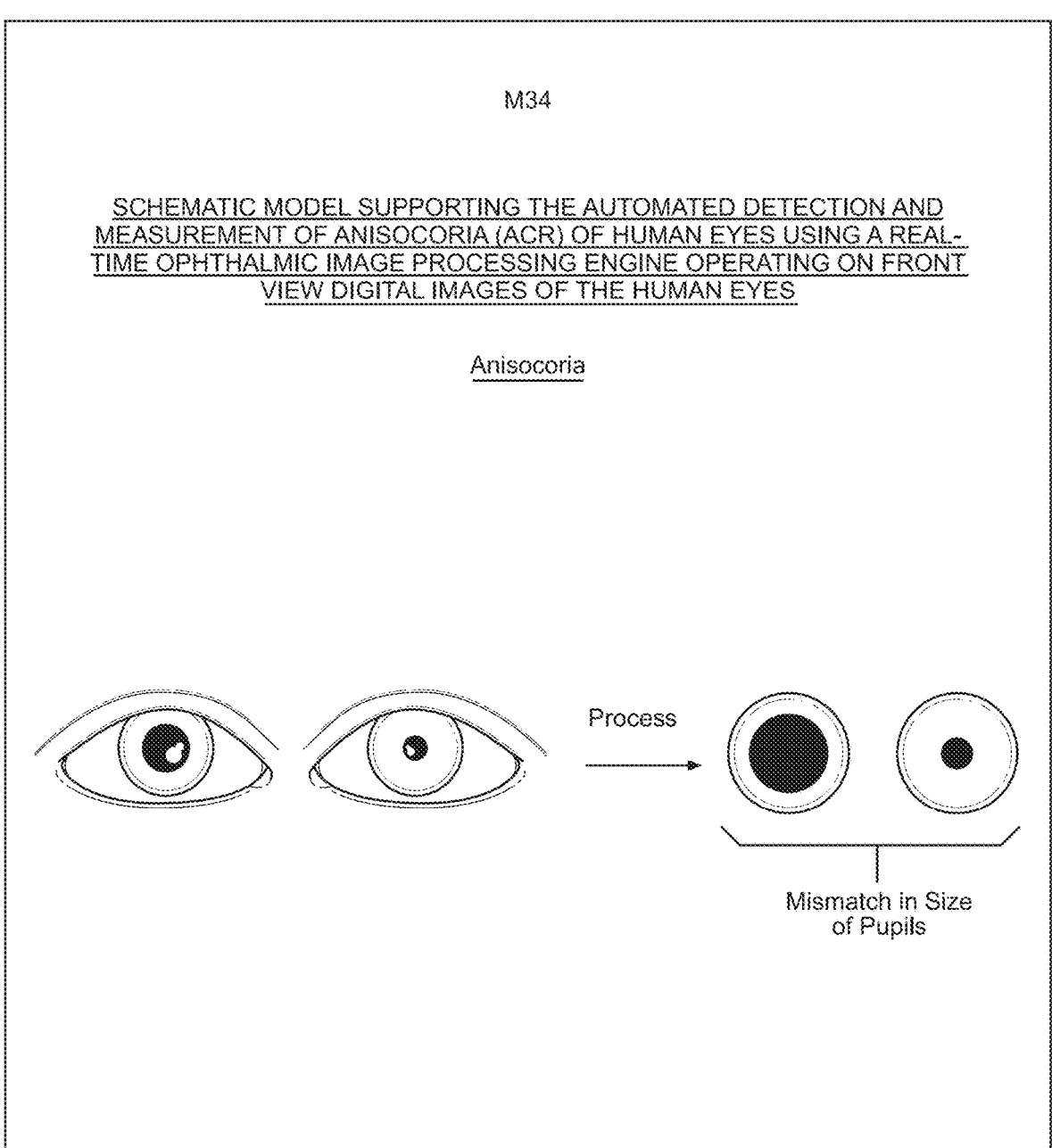
Figure 183:
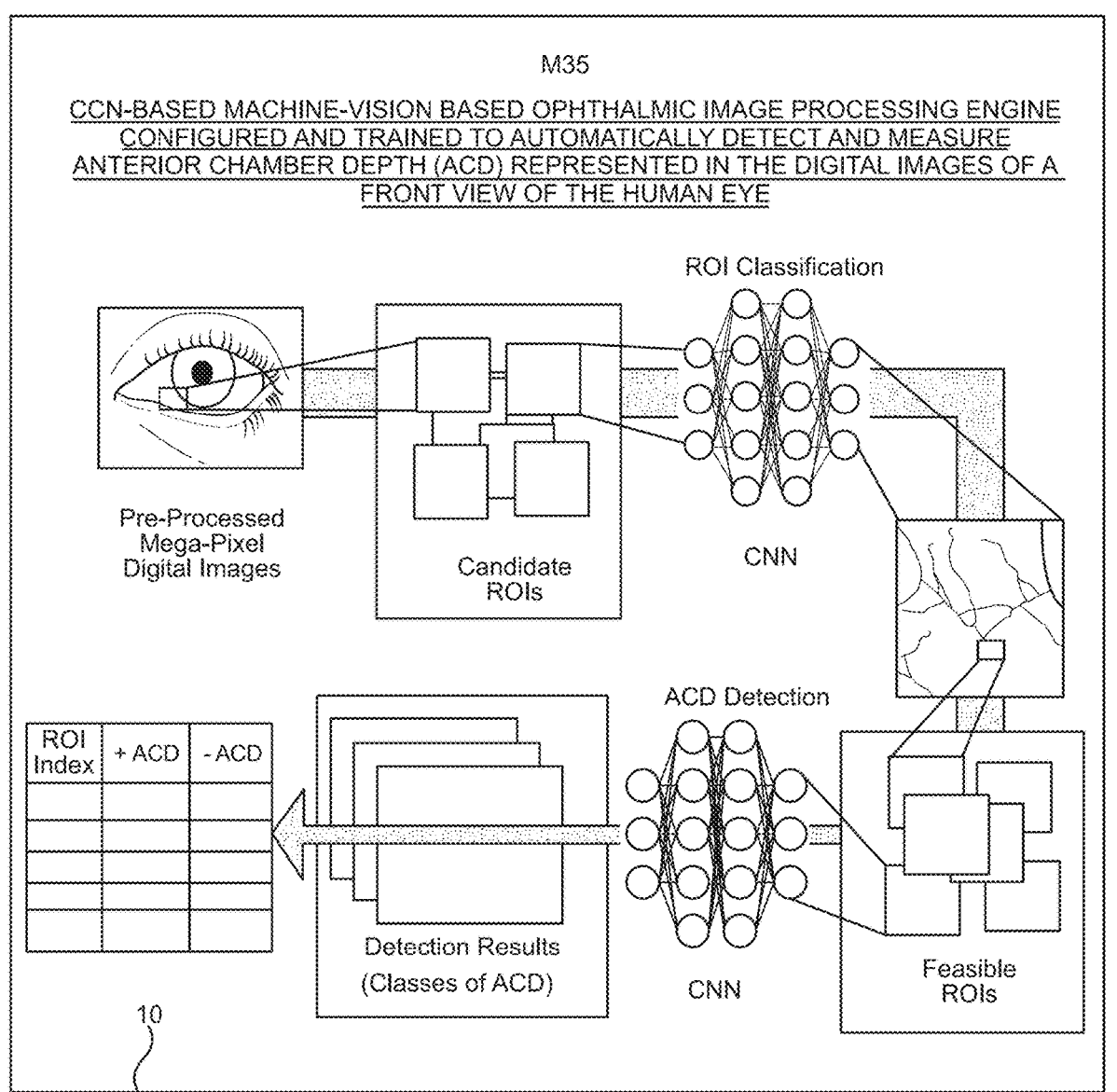
Figure 184A:
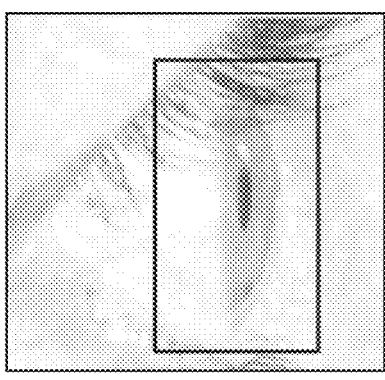
Figure 184B:
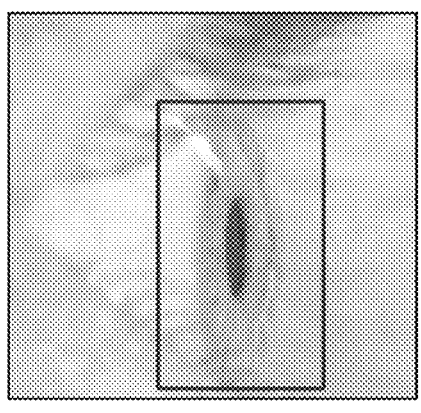
Figure 184C:
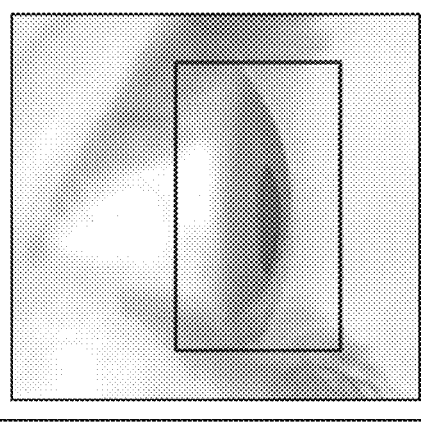
Figure 184D:
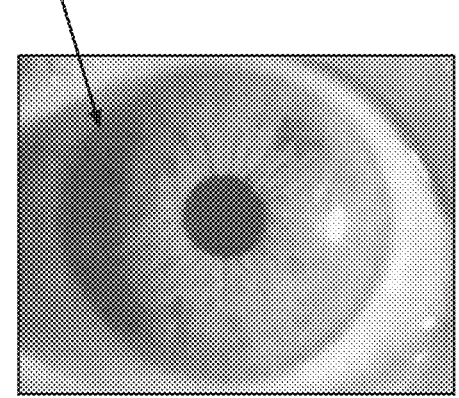
Figure 185A:
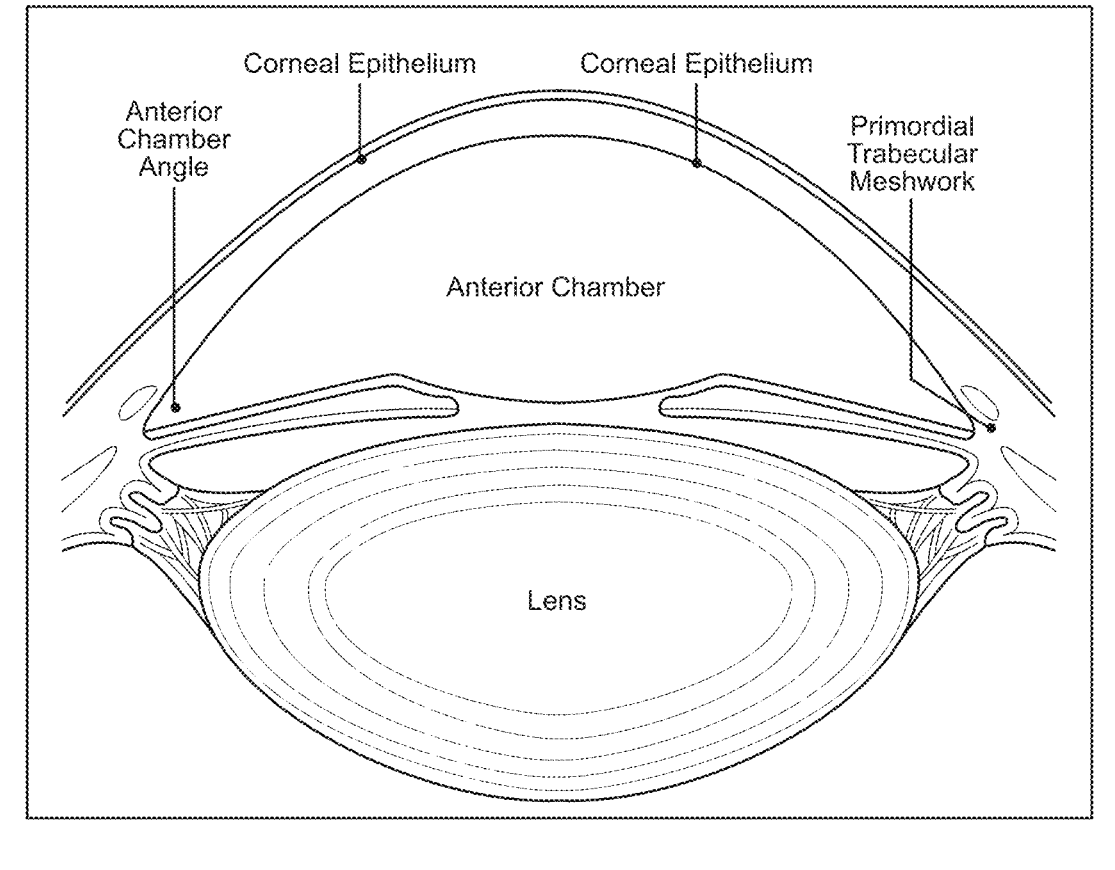
Figure 186:
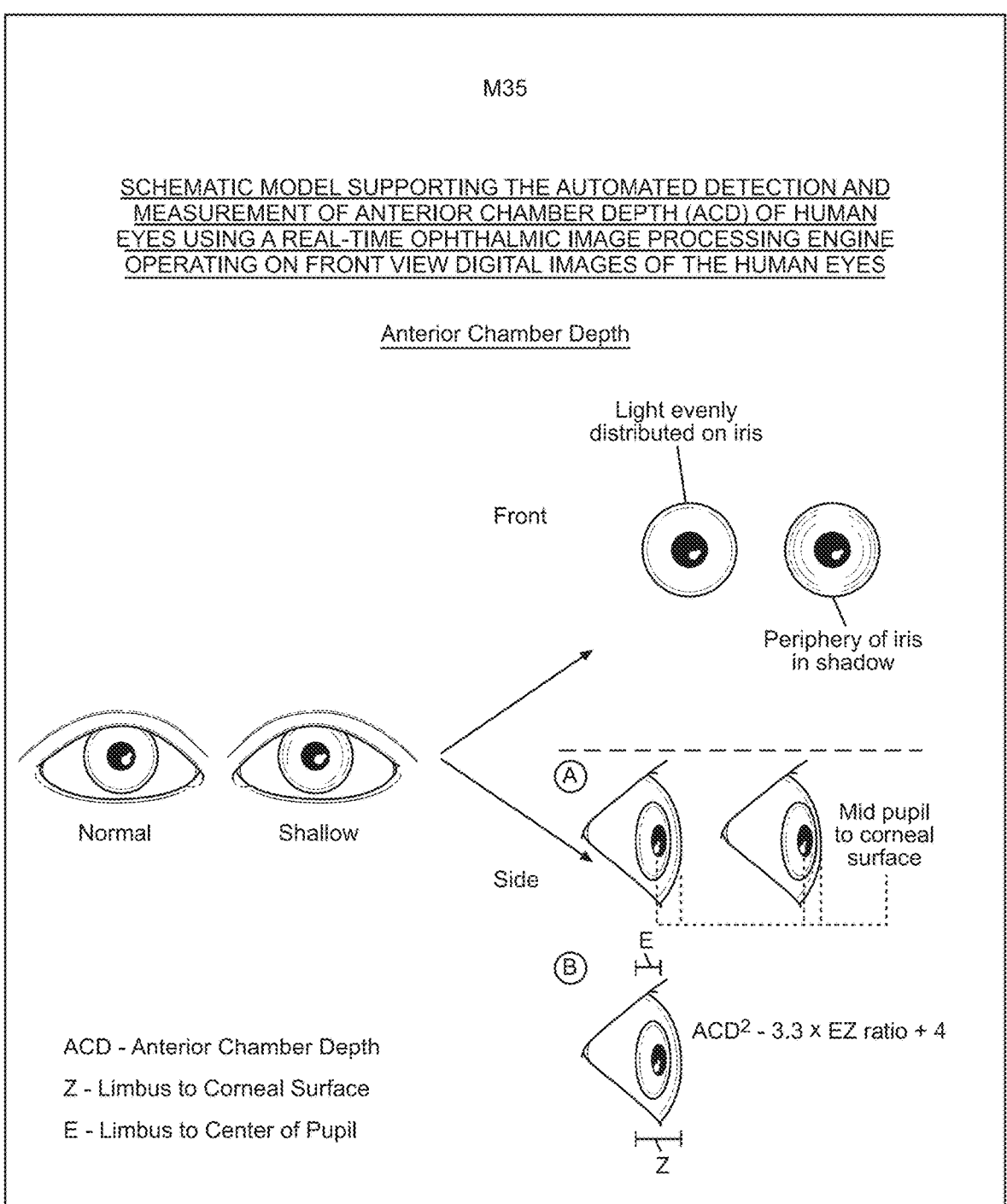
Figure 188:
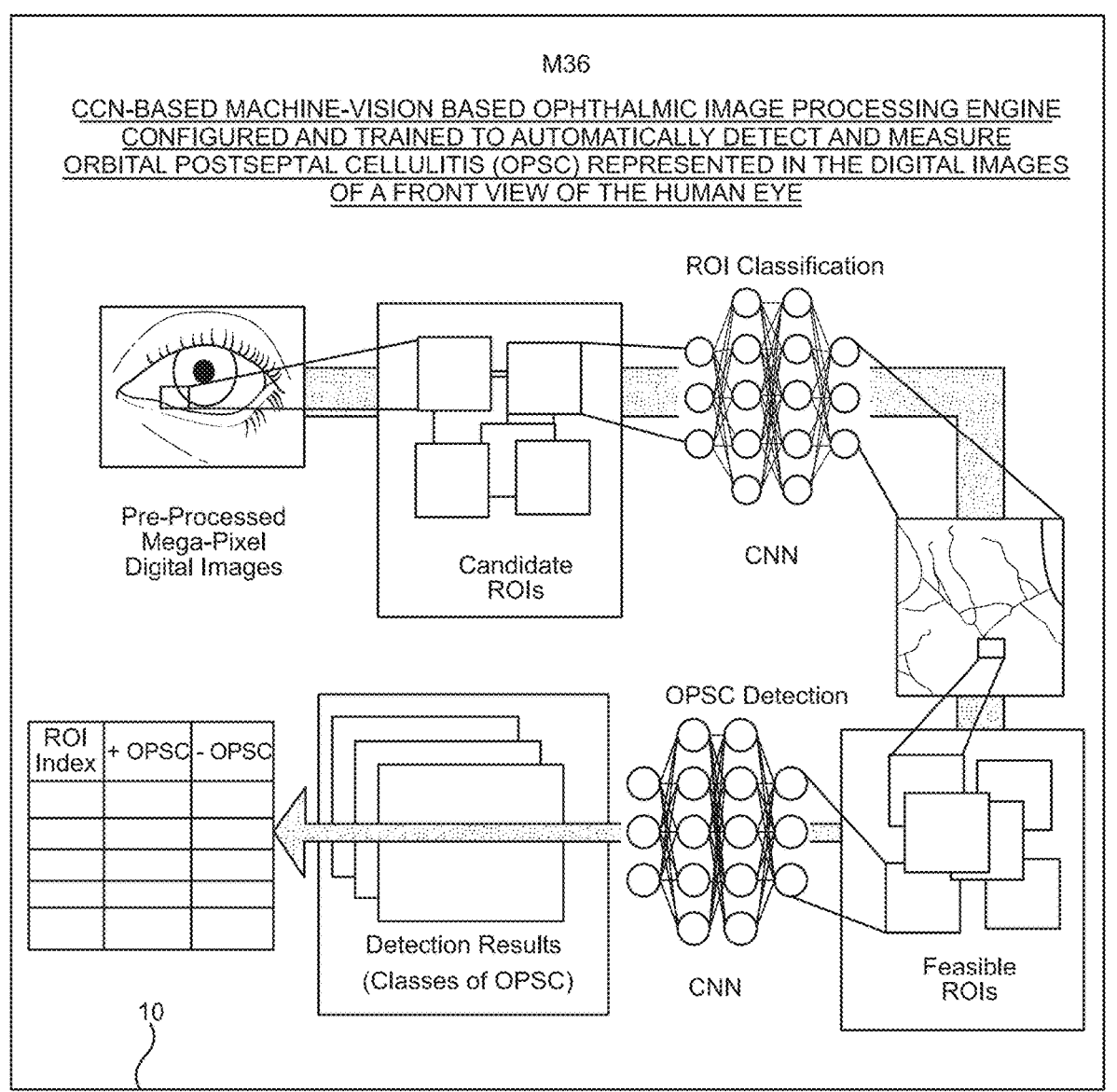
Figure 189:
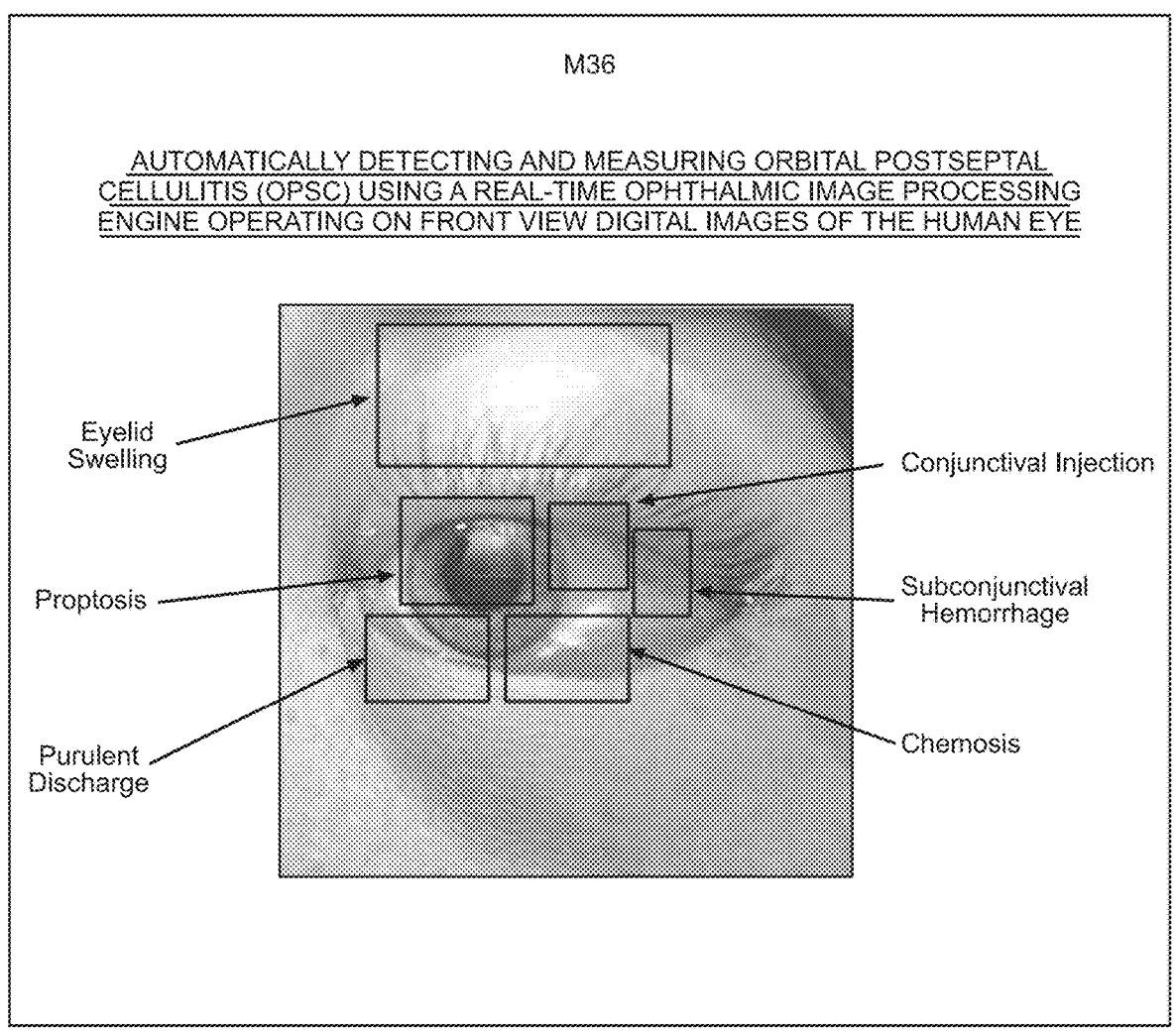
Figure 190:
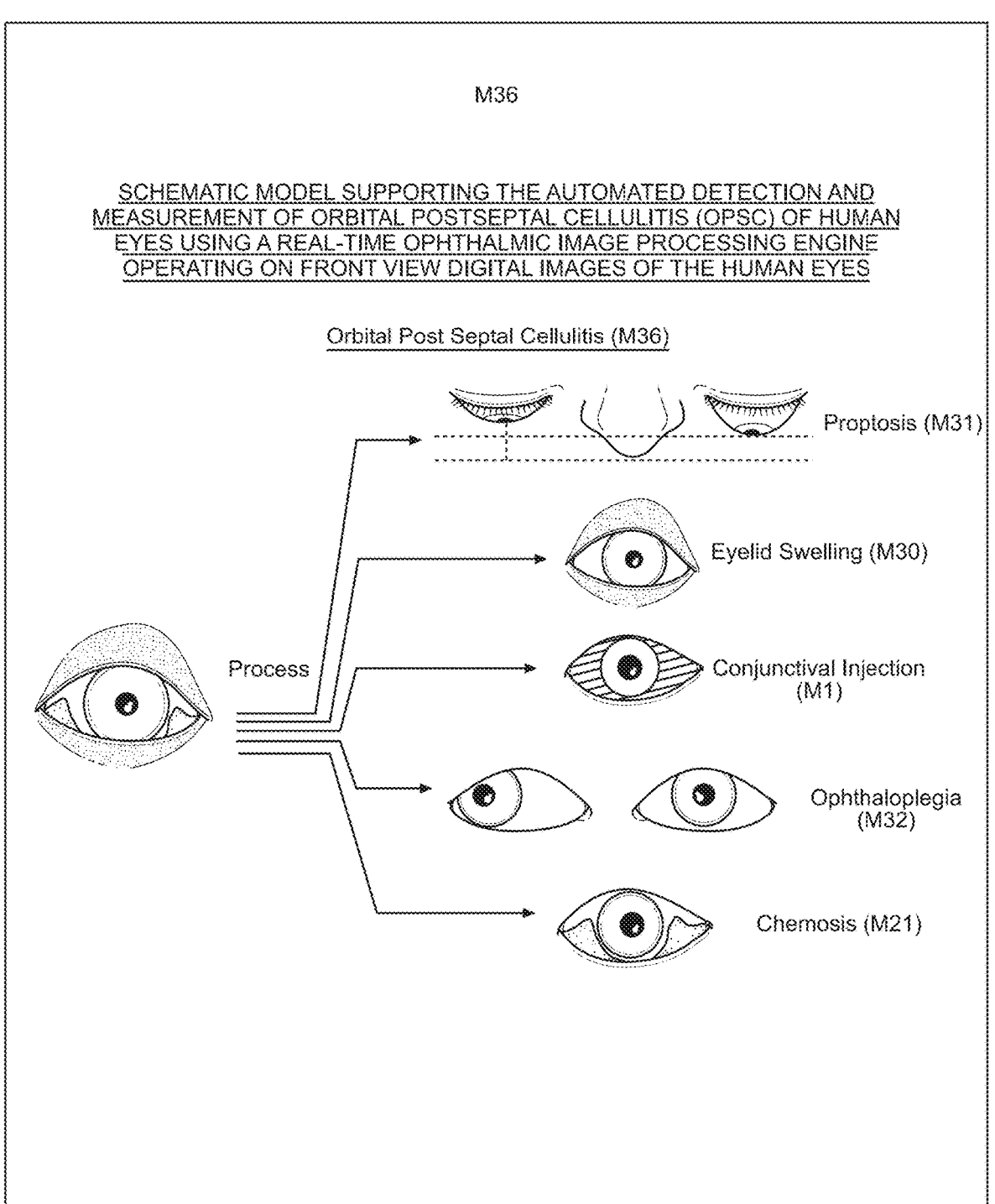
Figure 192:
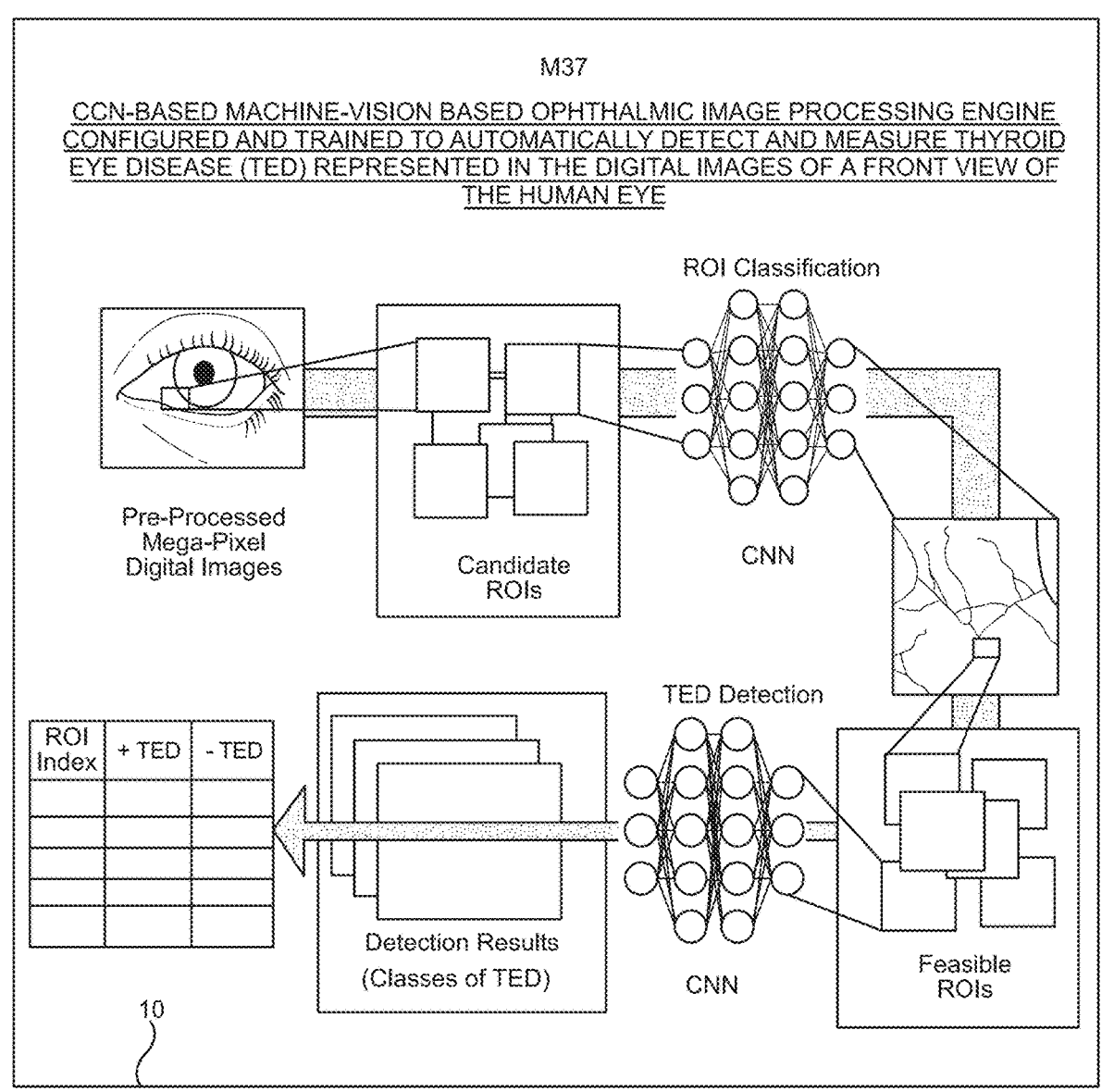
Figure 193:
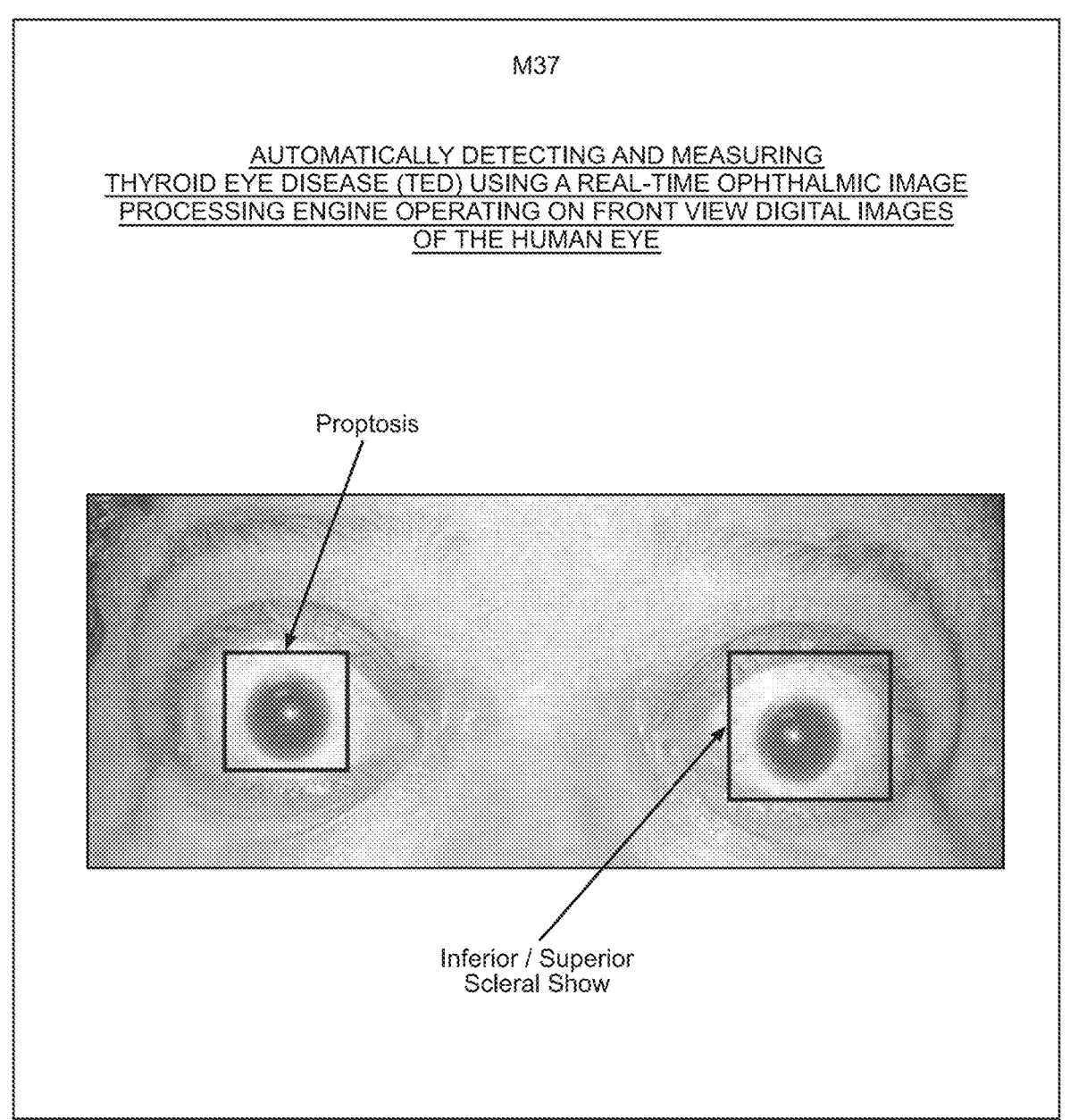
Figure 196:
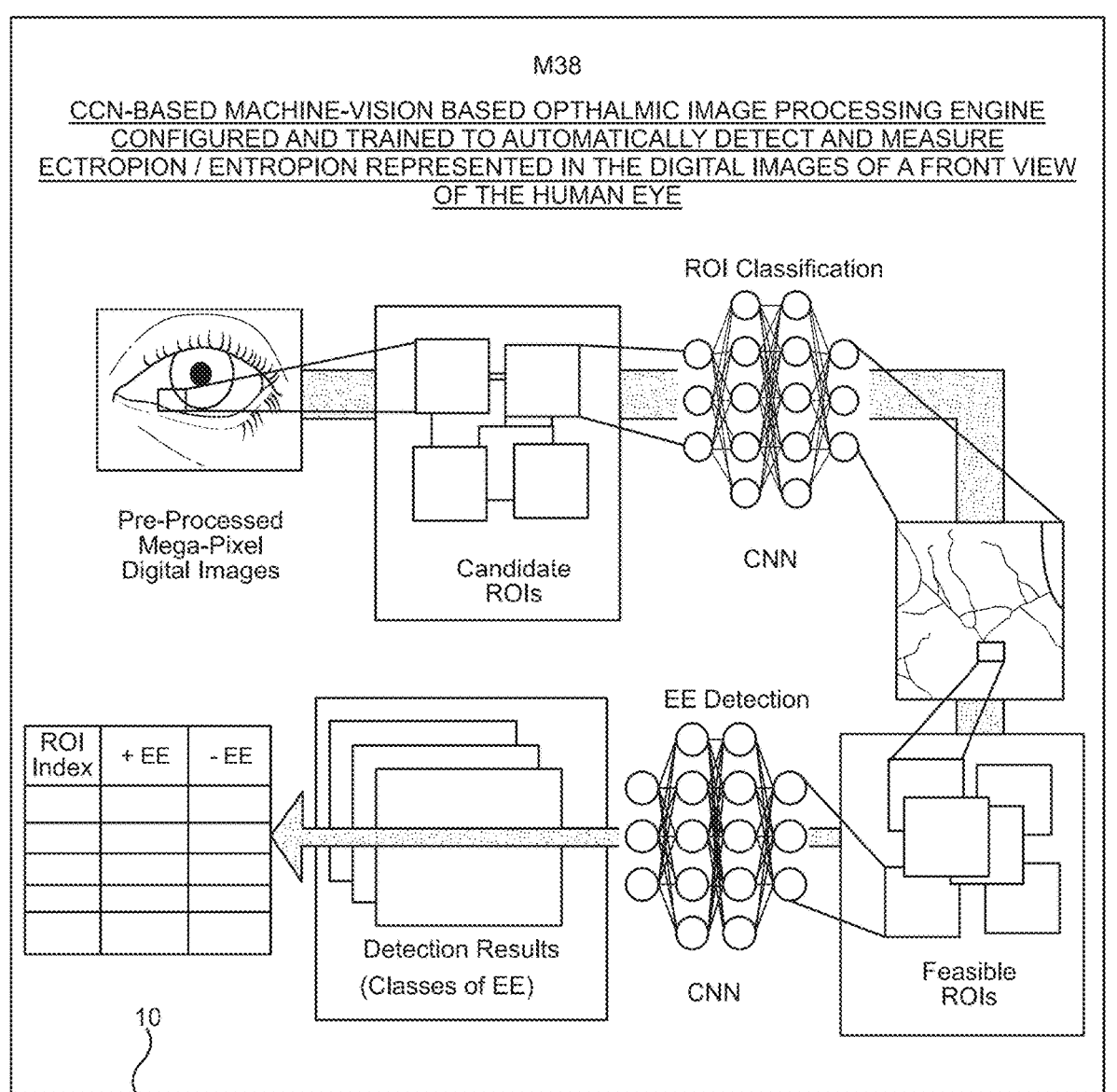
Figure 197:
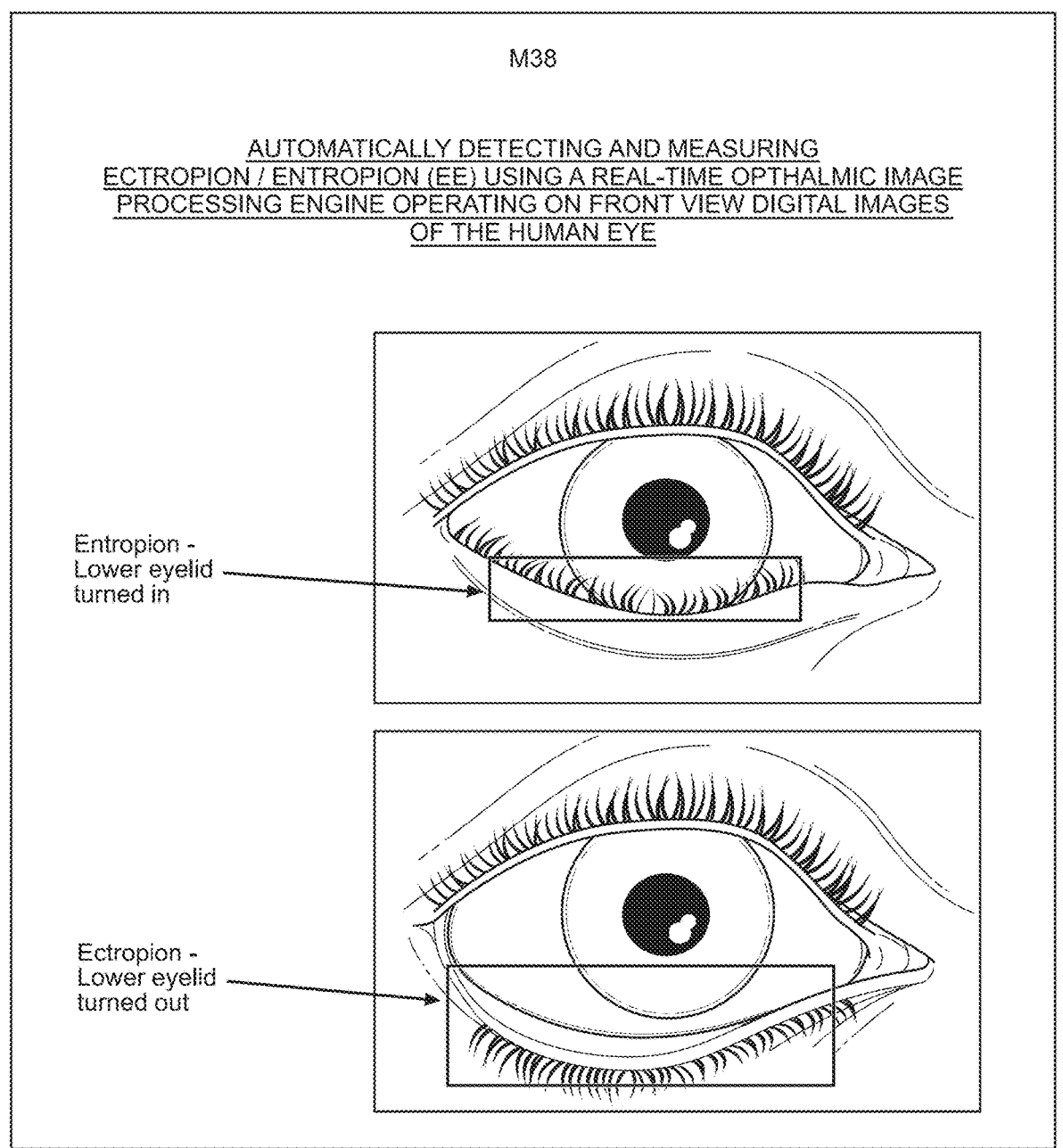
Figure 198:
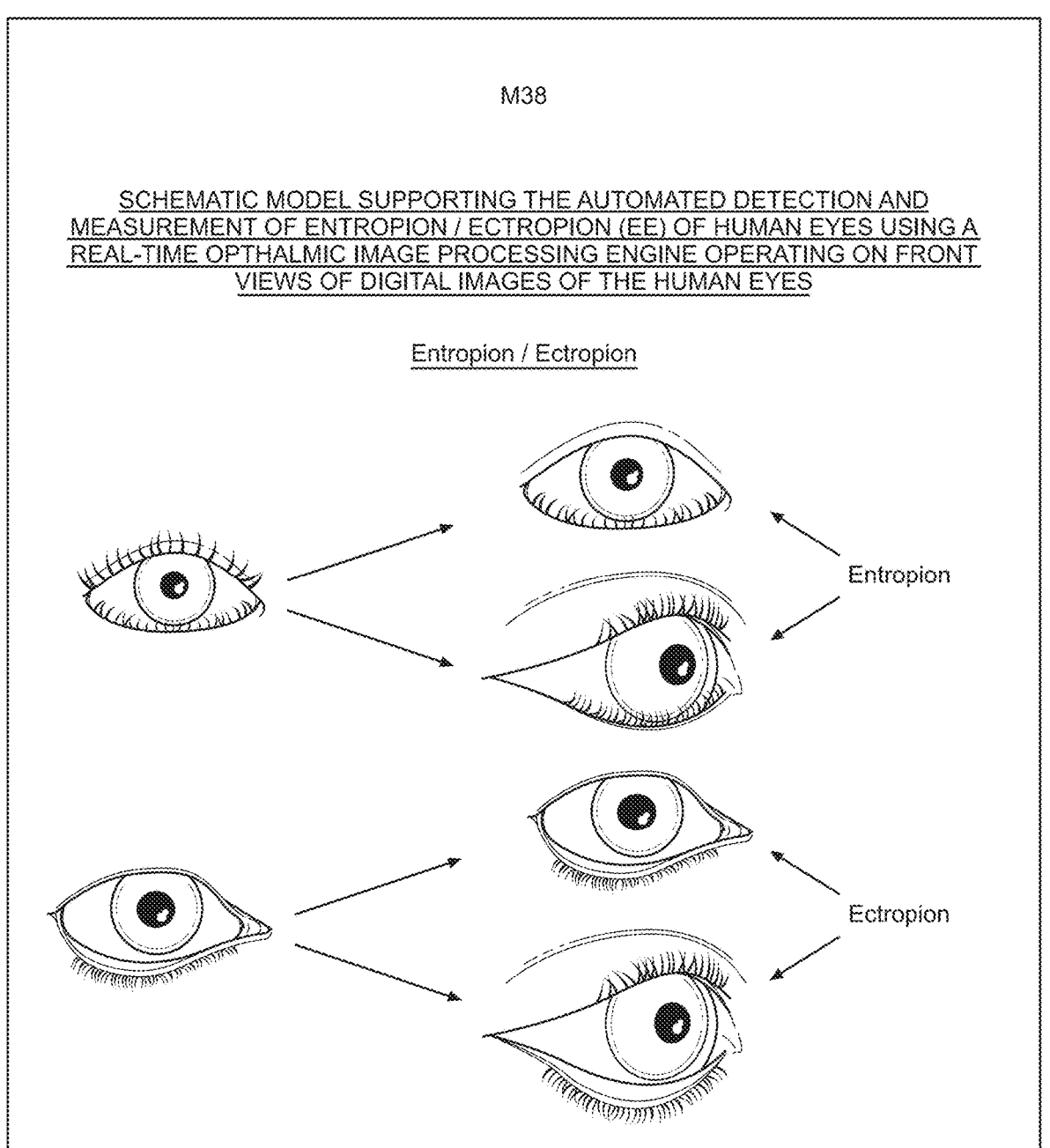
Figure 199B:
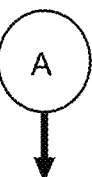
Figure 200:
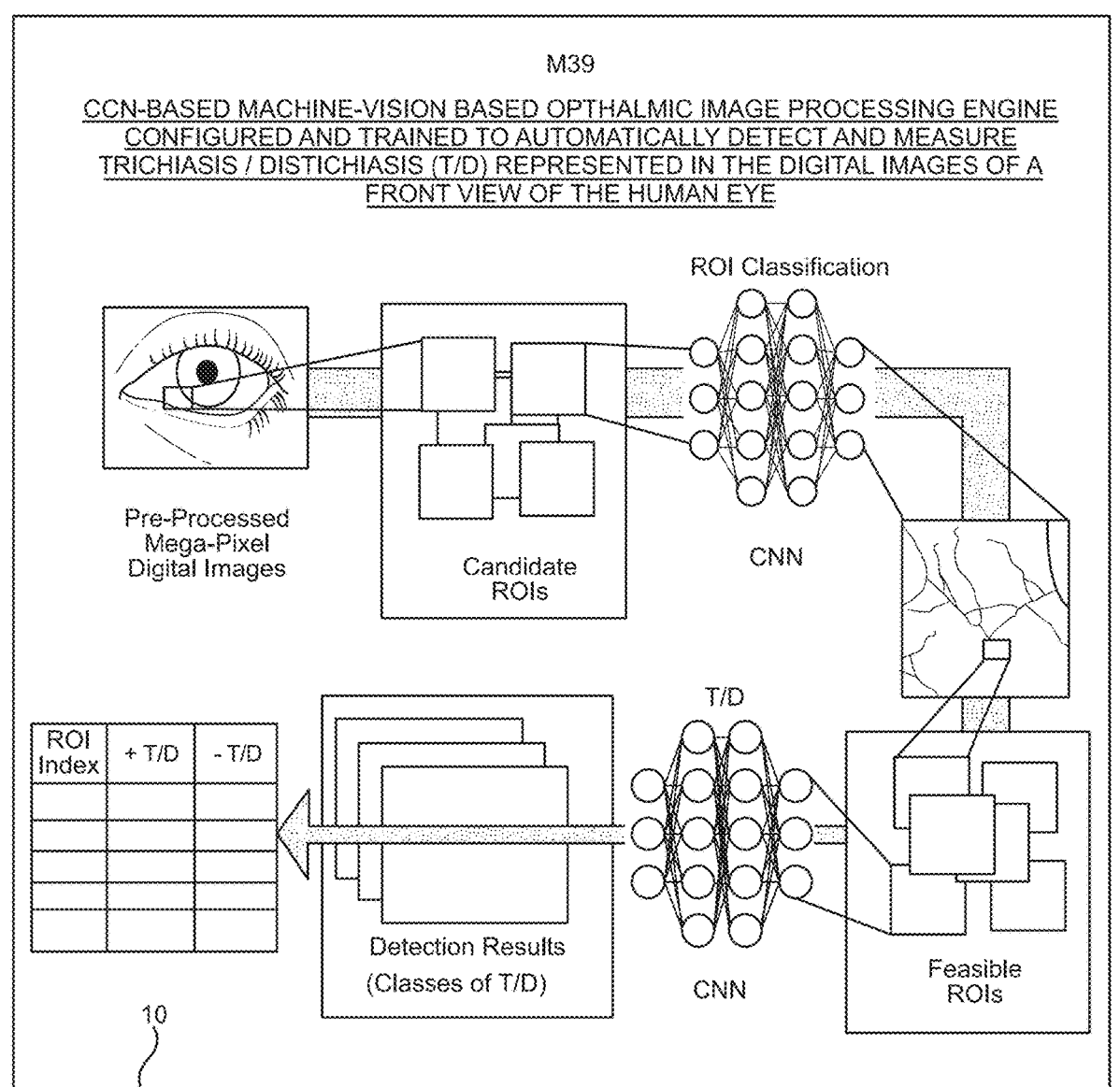
Figure 202:
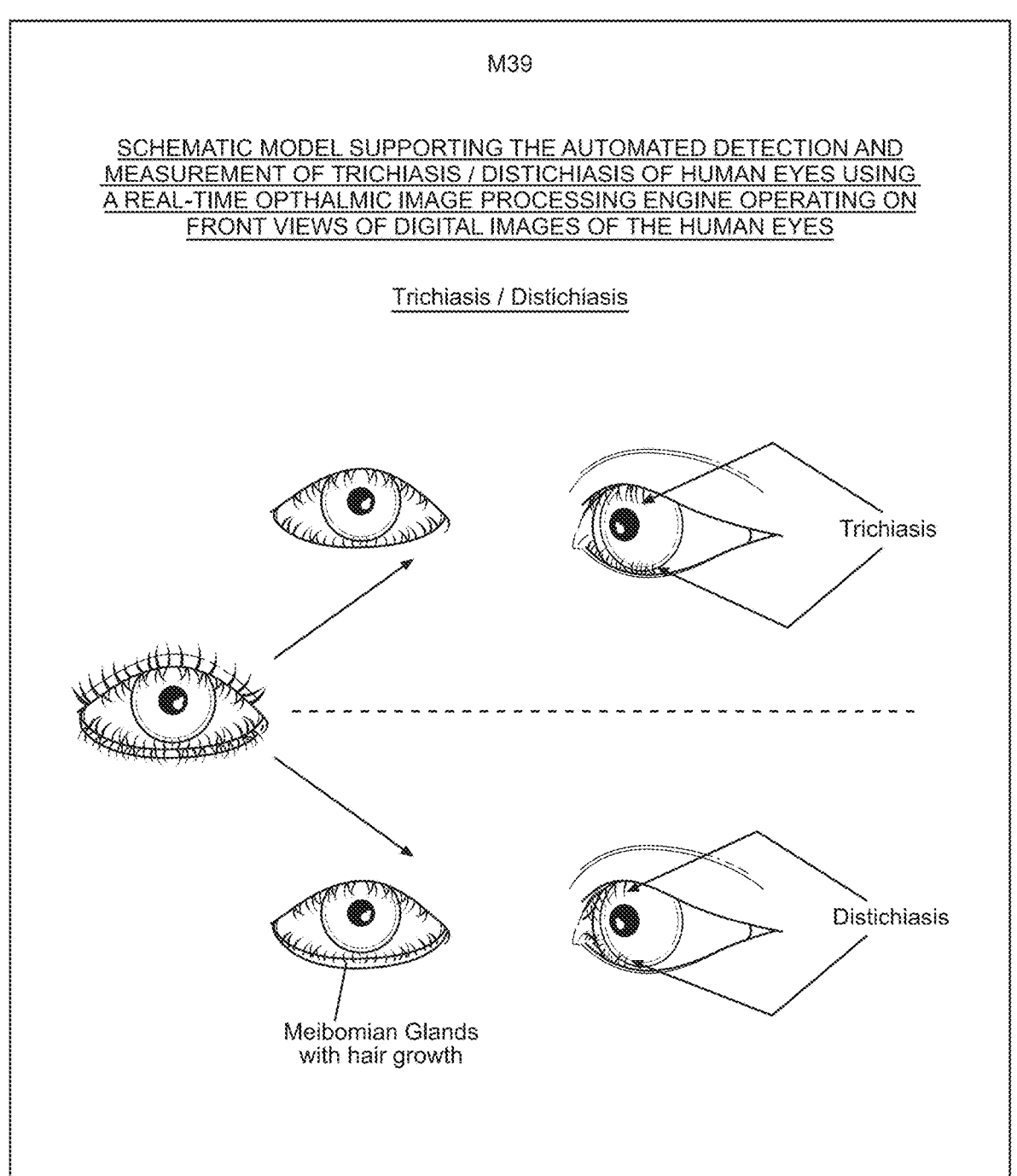
Figure 204:
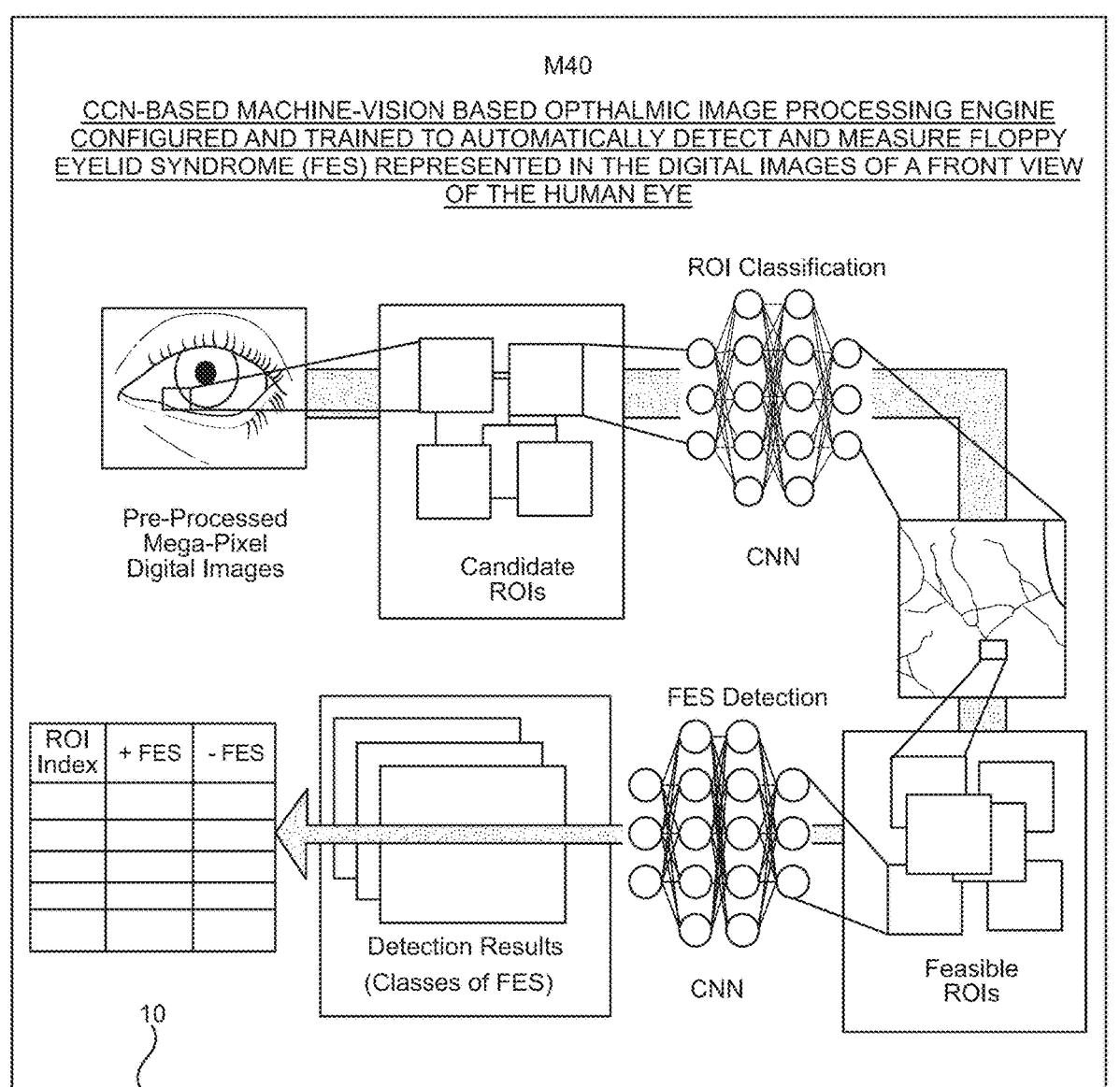
Figure 205A:
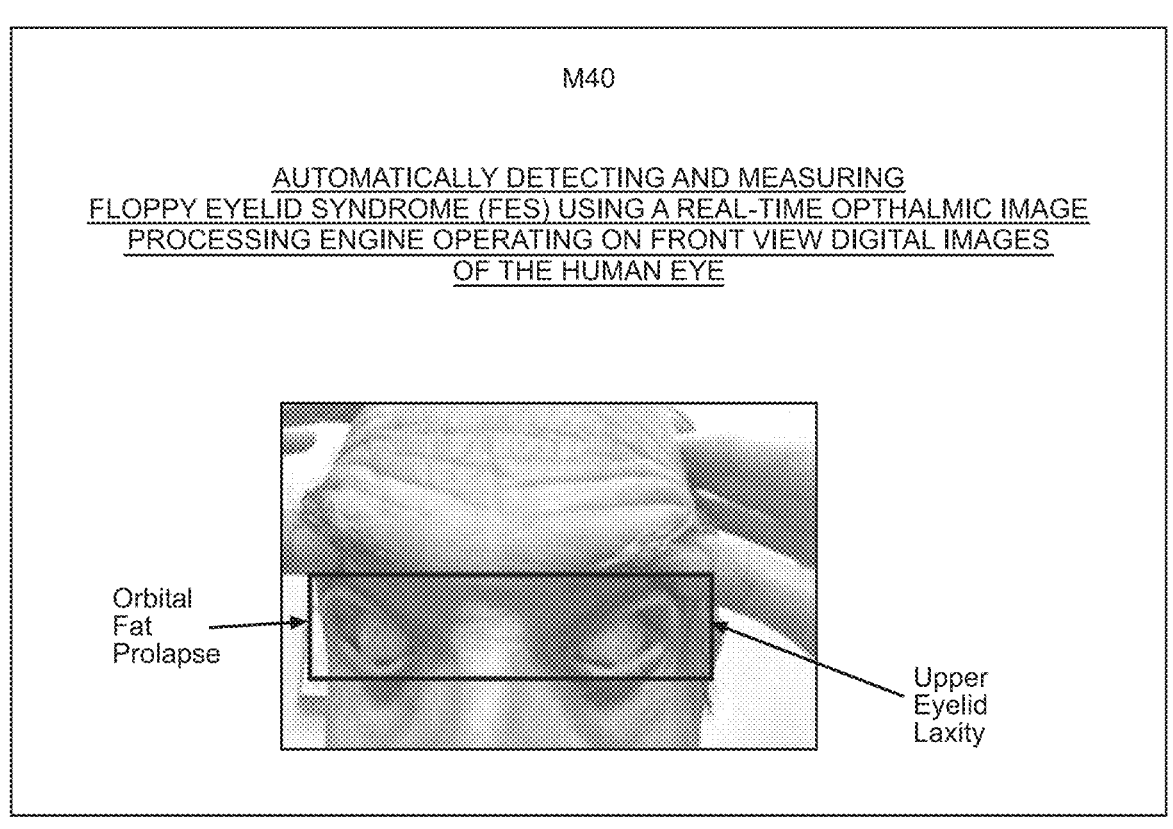
Figure 205B:
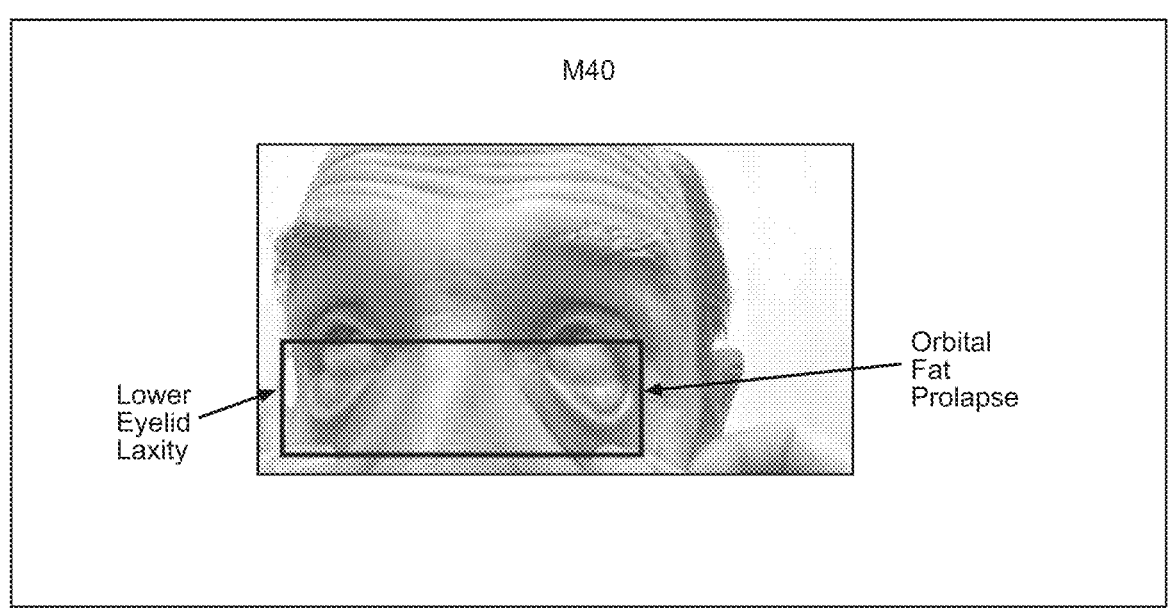
Figure 208:
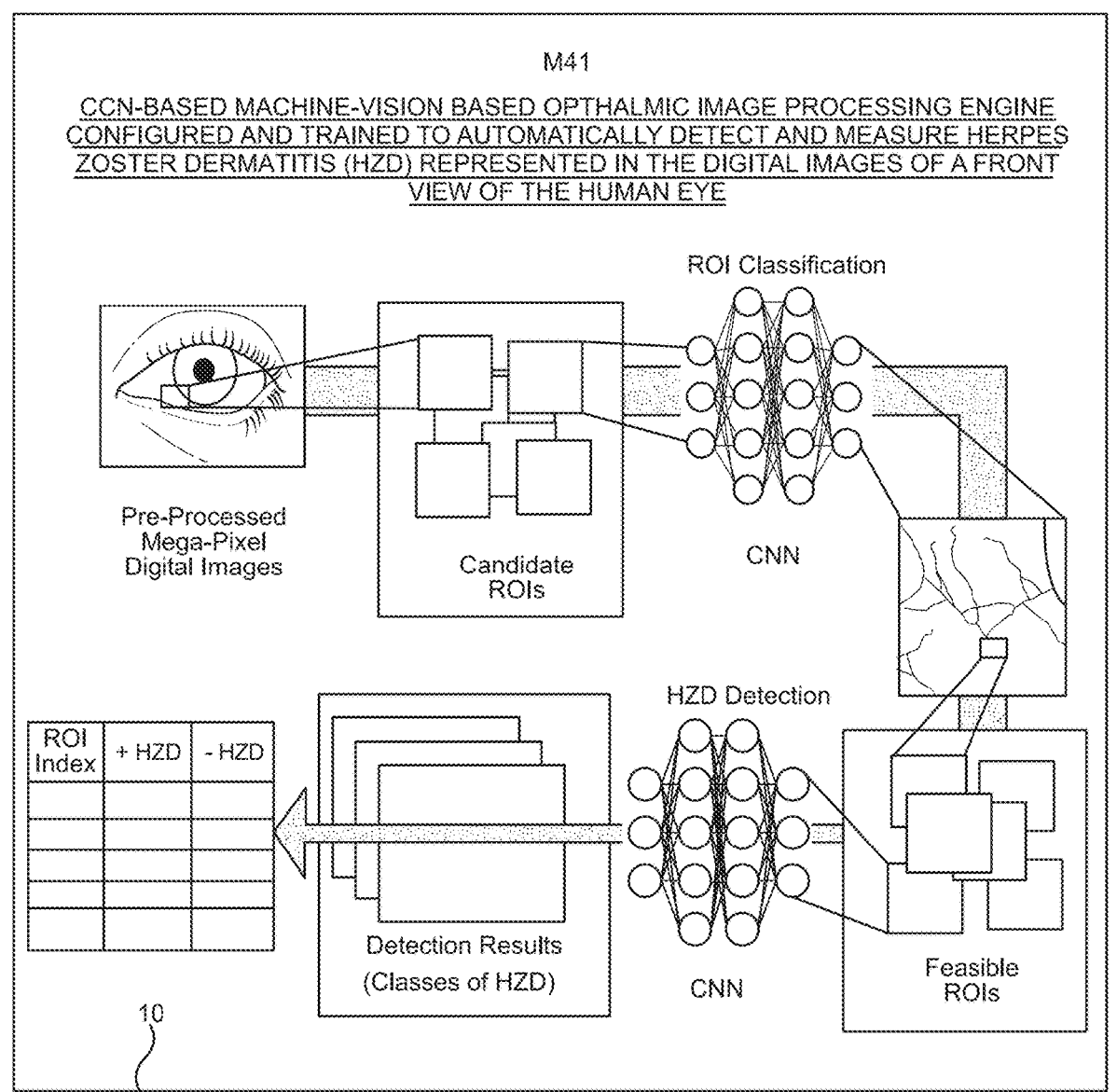
Figure 209:
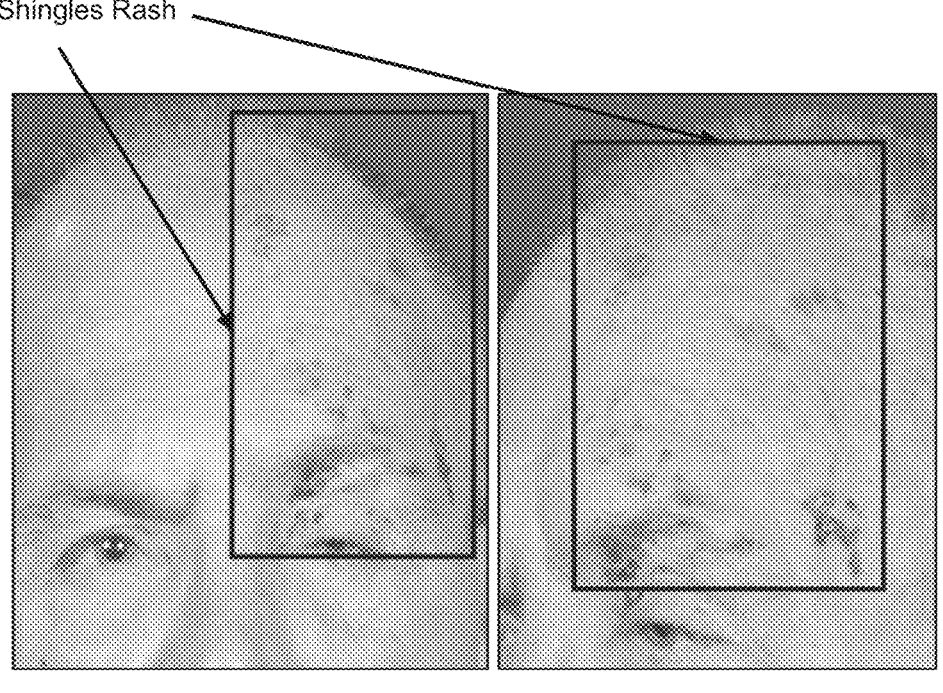
Figure 210:
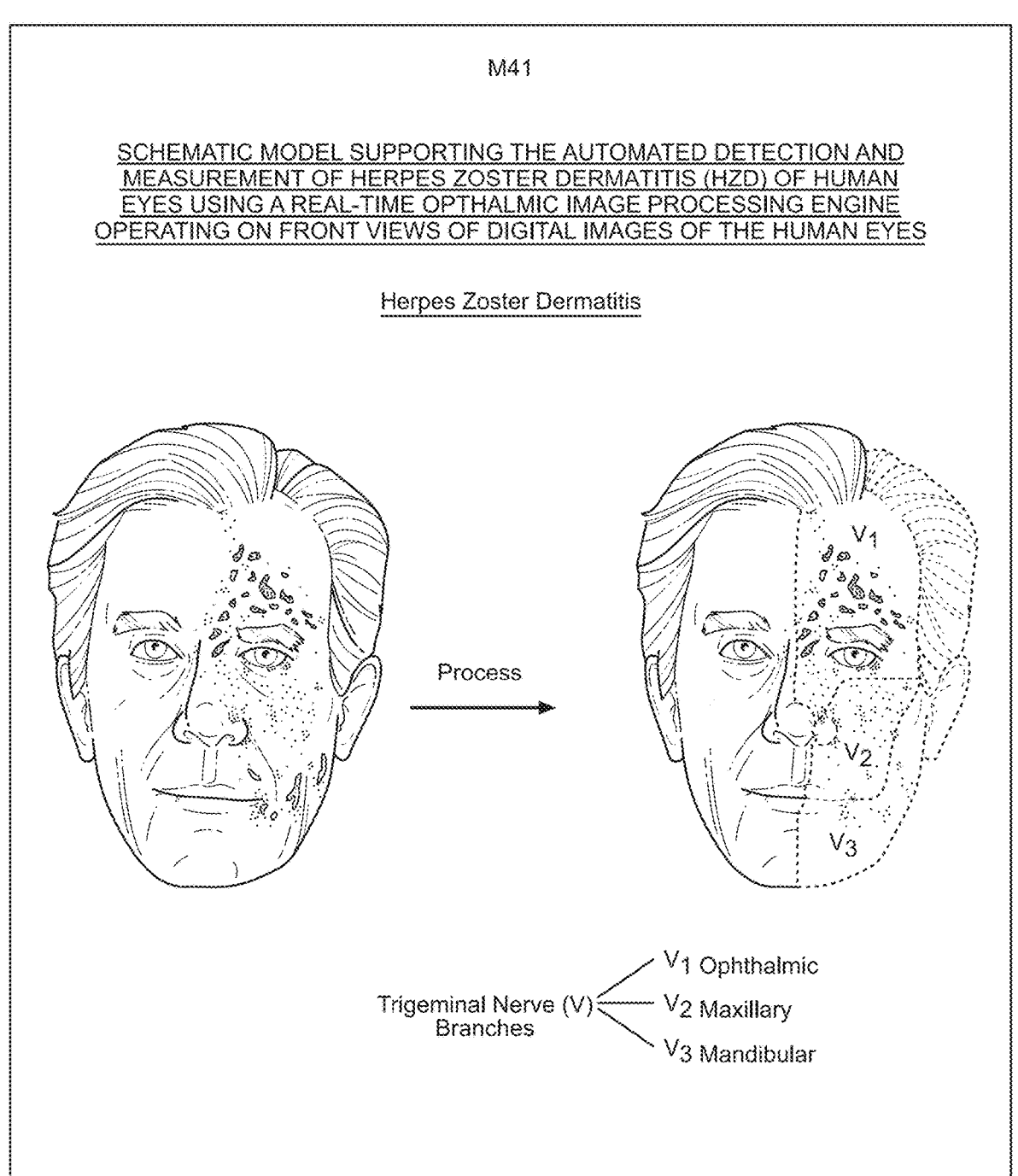
Figure 212:
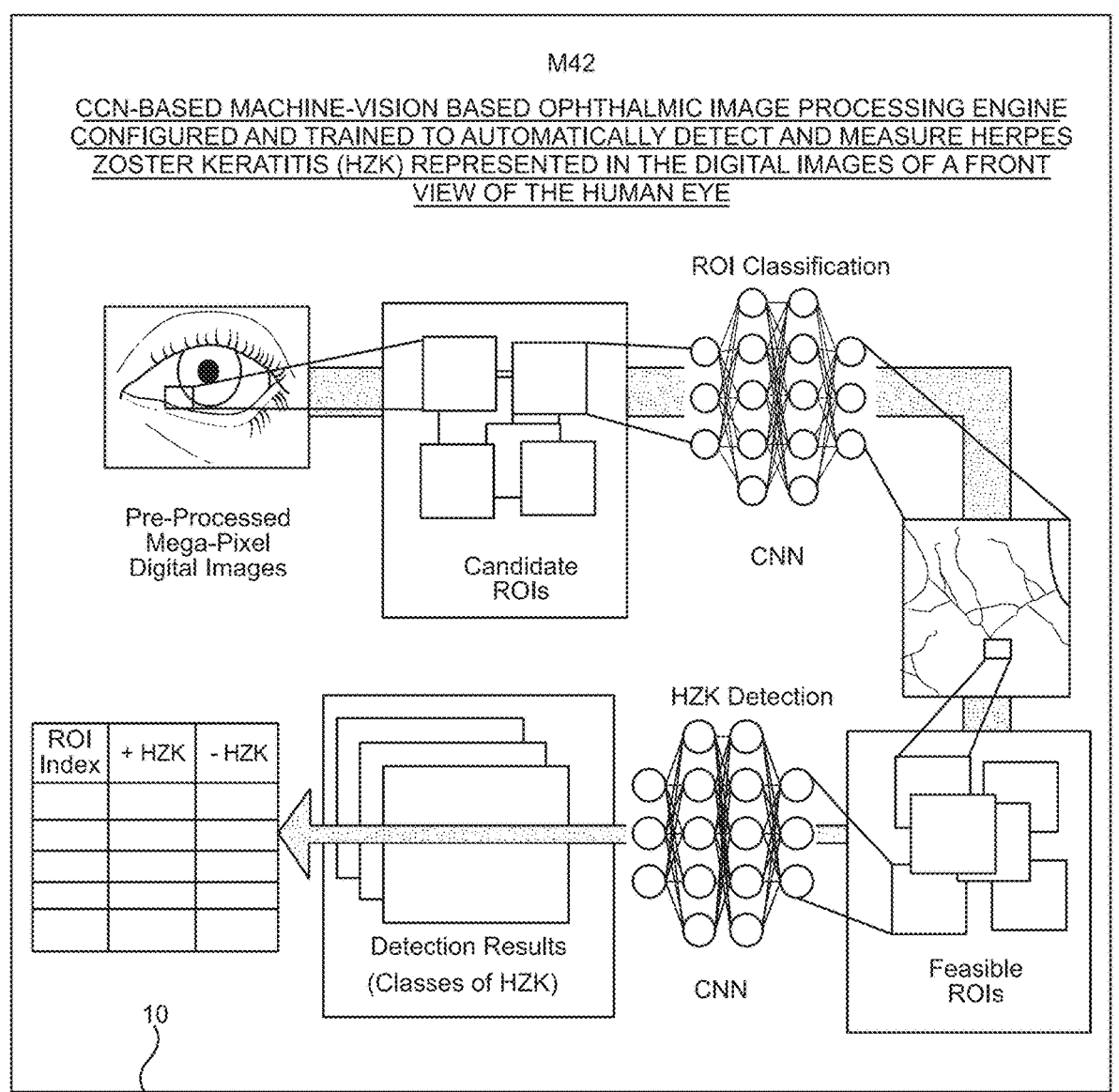
Figure 213A:
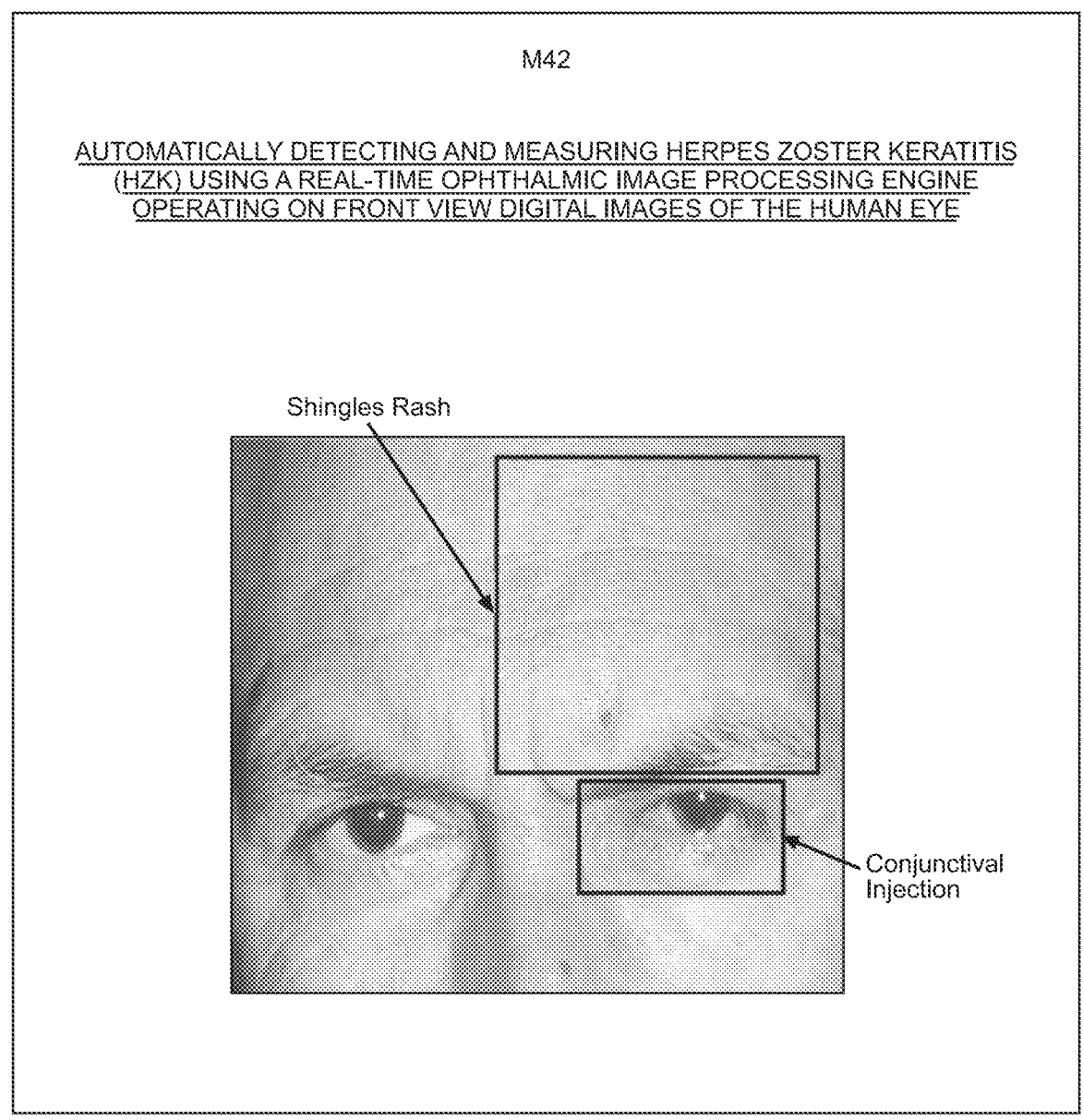
Figure 213B:
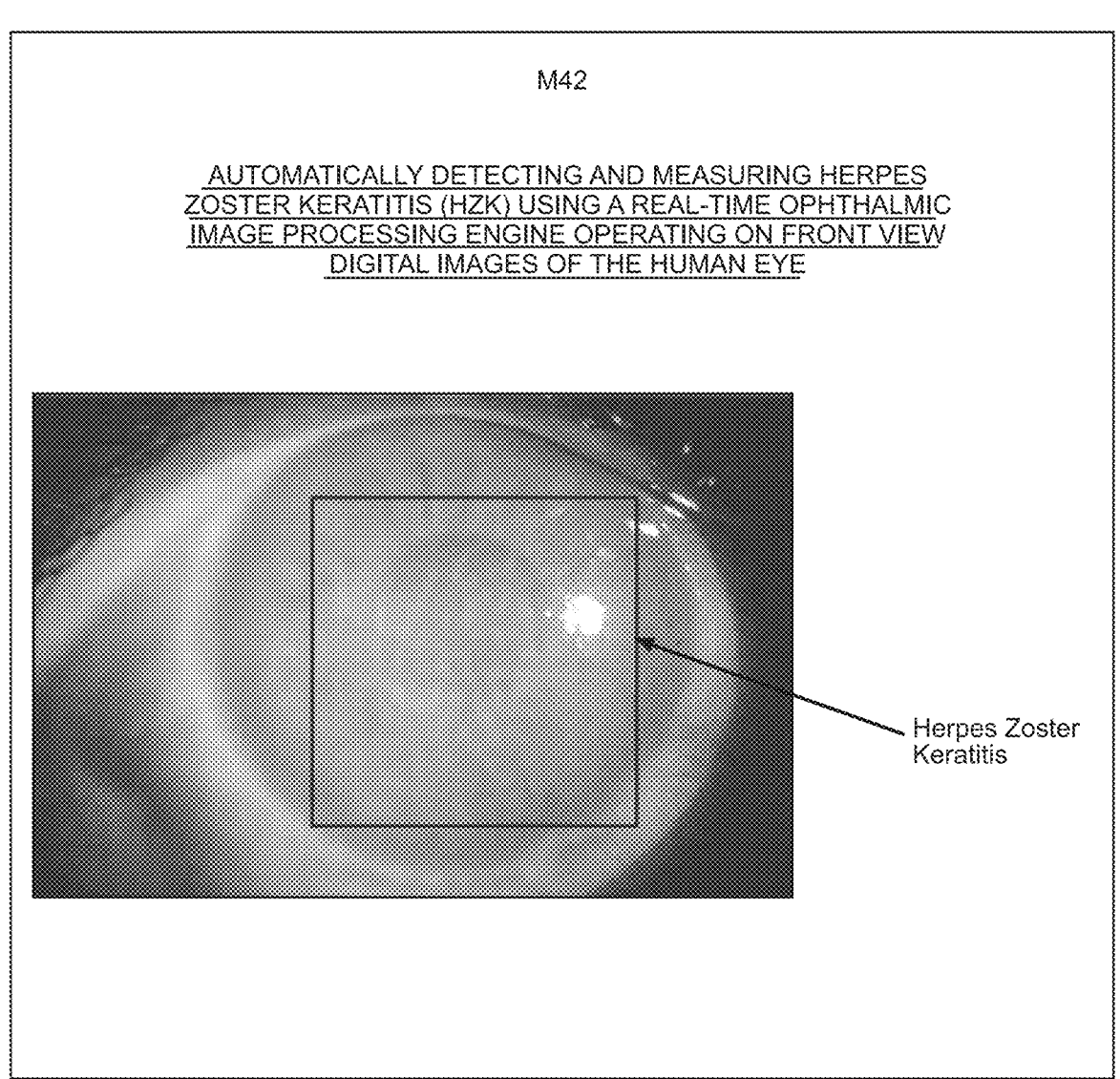
Figure 214:
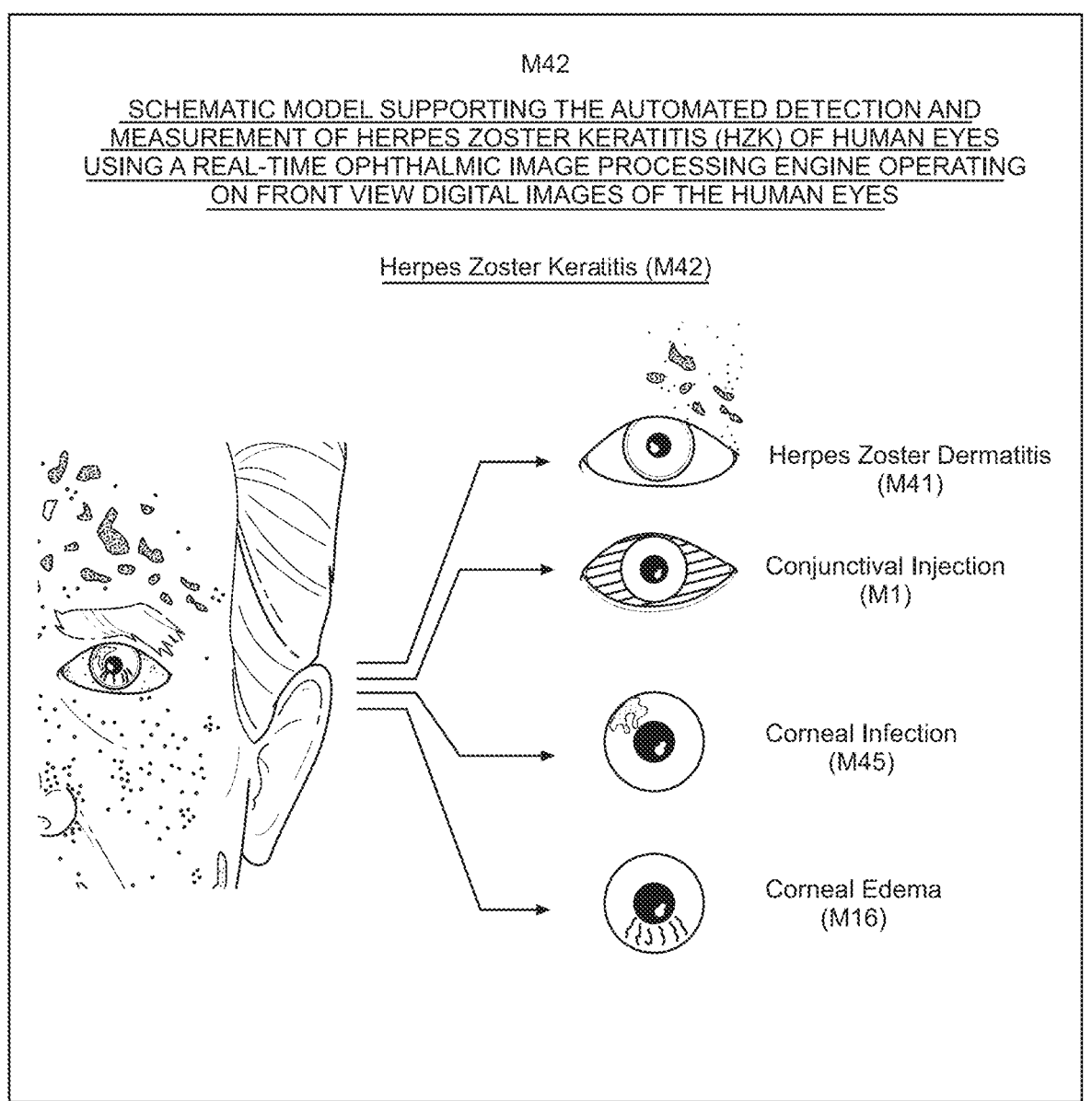
Figure 216:
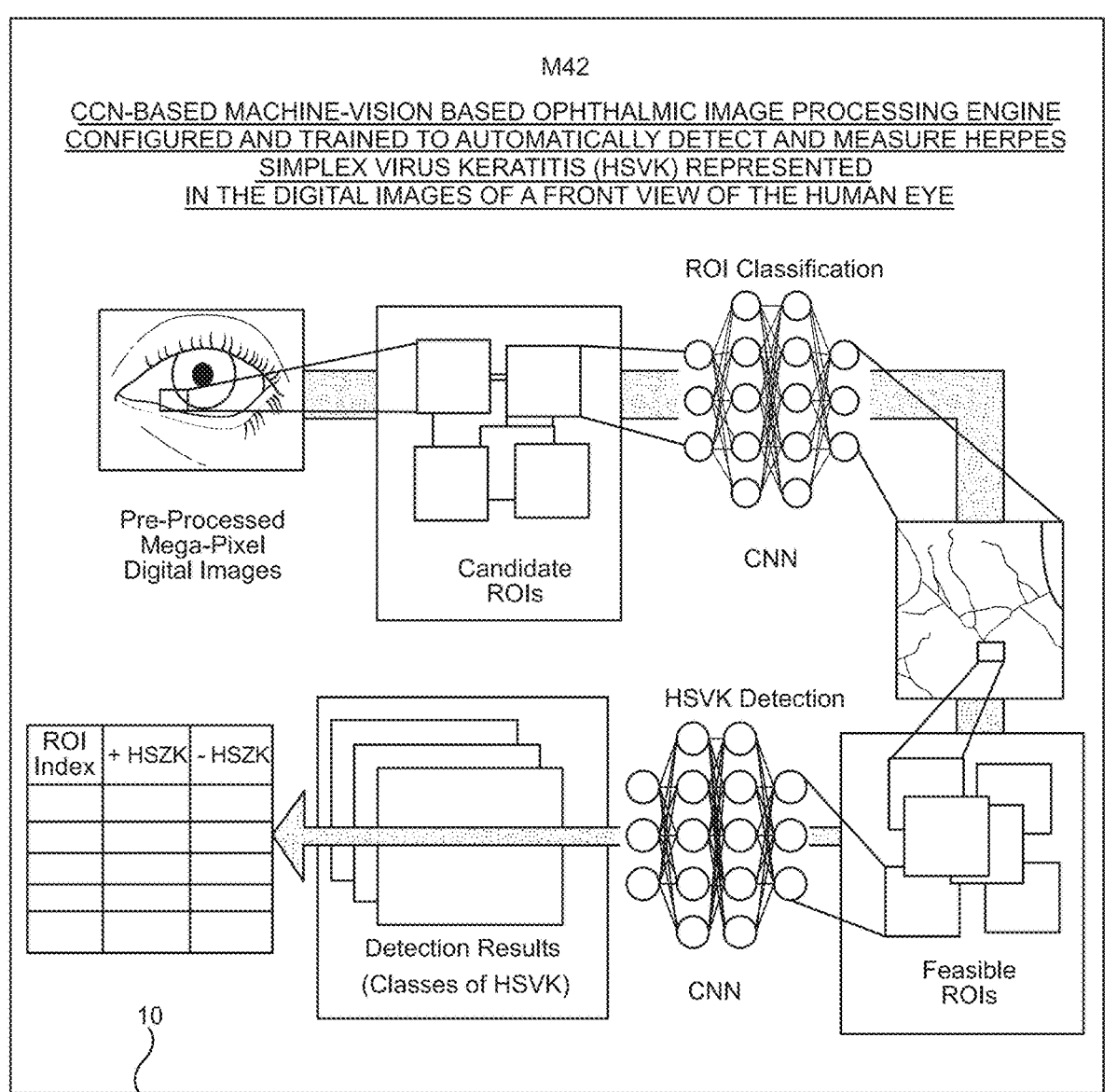
Figure 217:
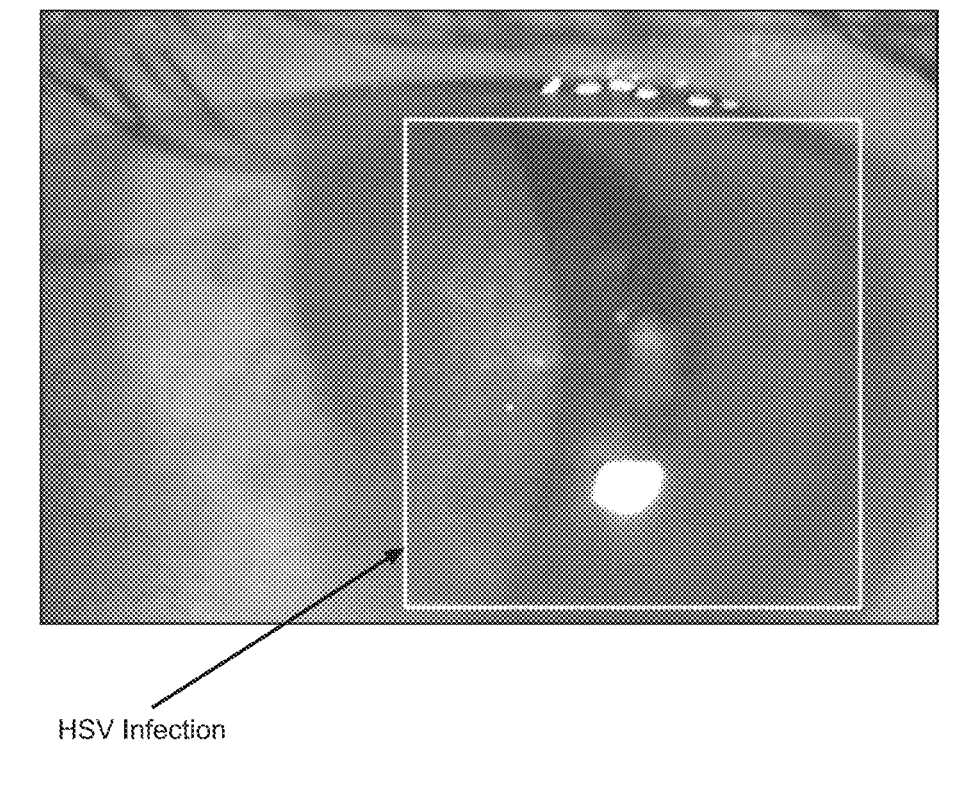
Figure 218:
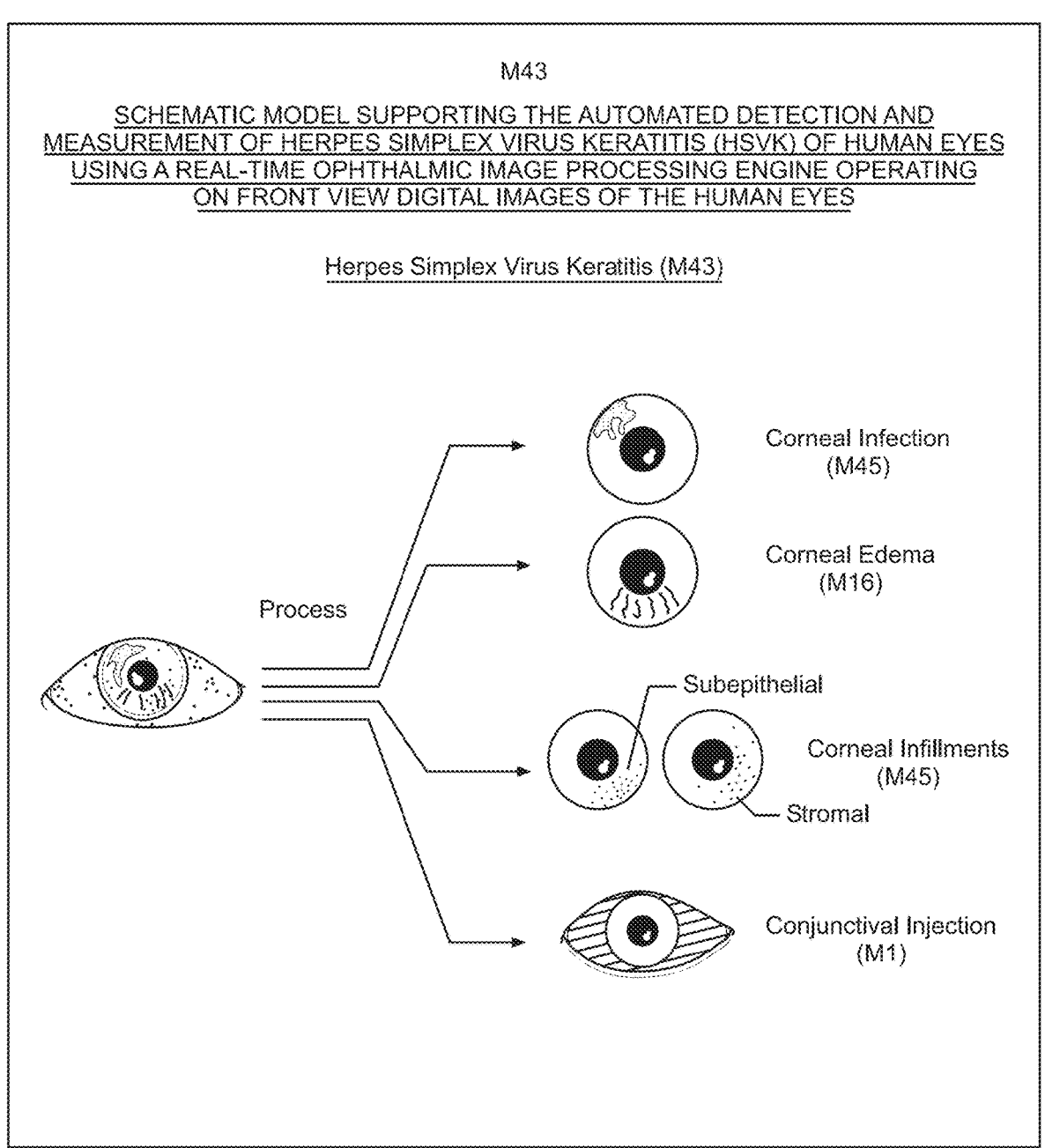
Figure 220:
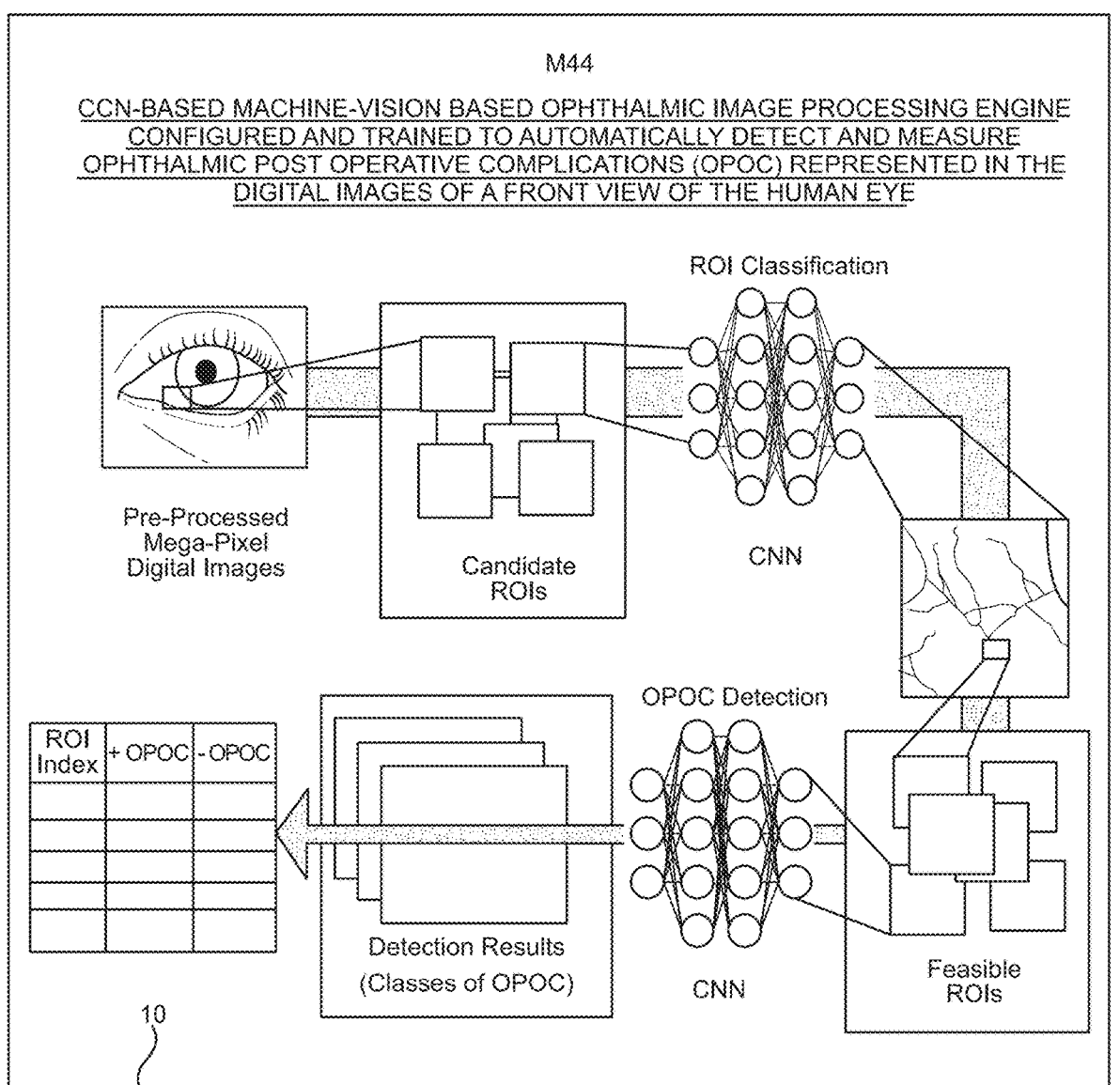
Figure 221:
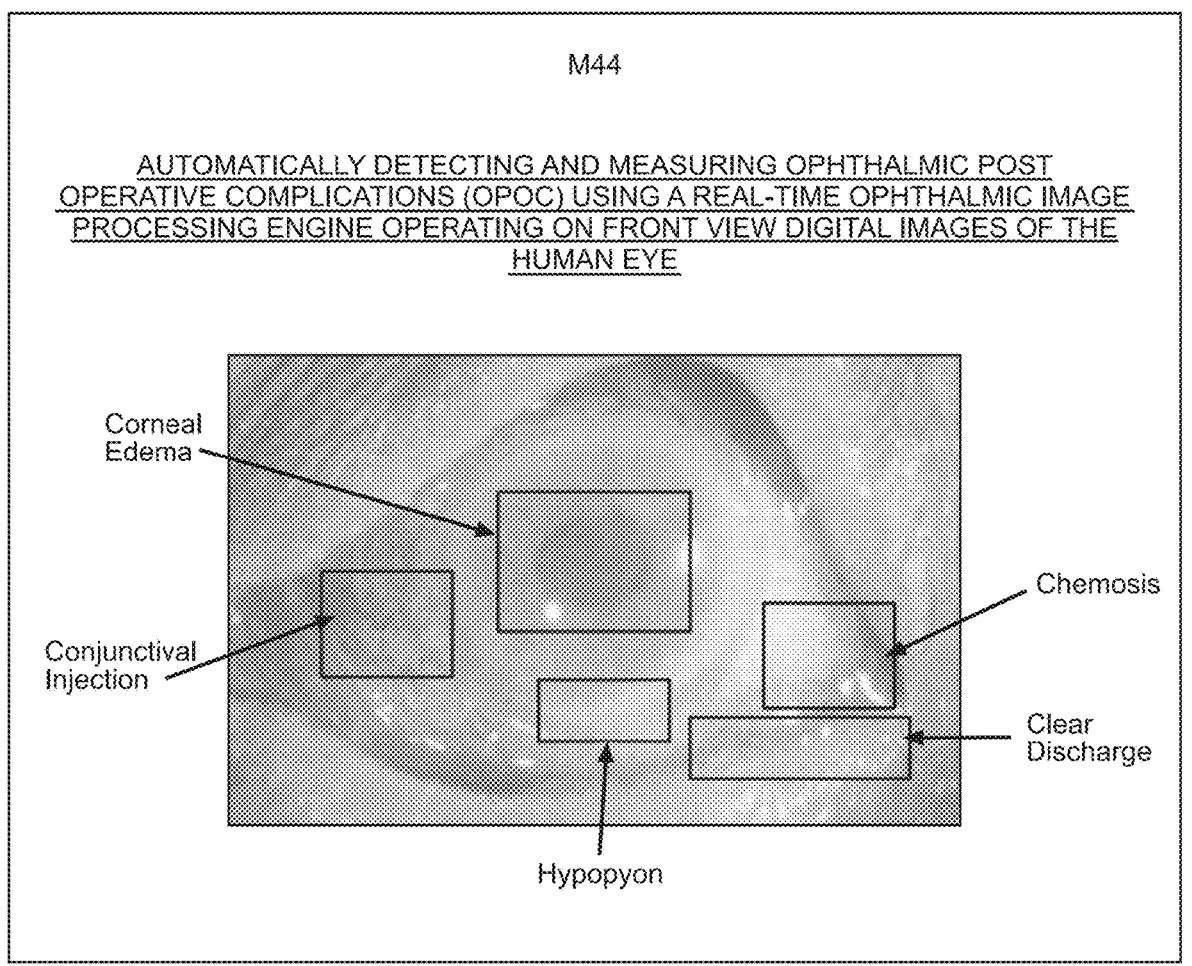
Figure 222:
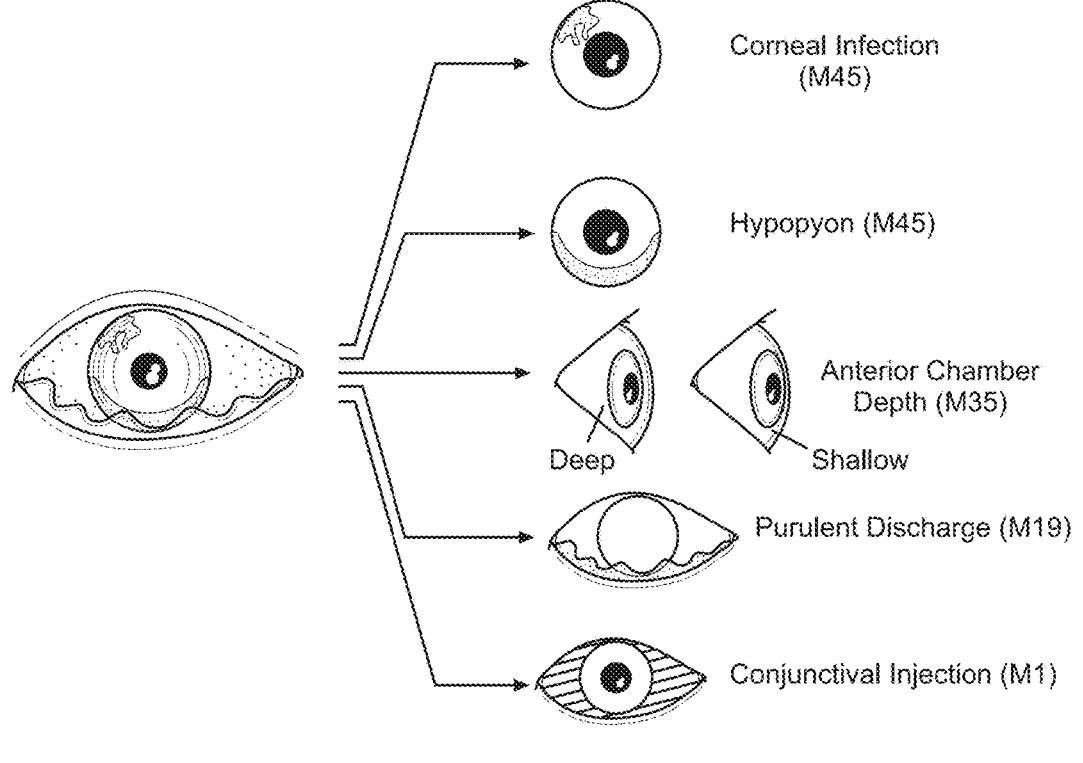
Figure 224:
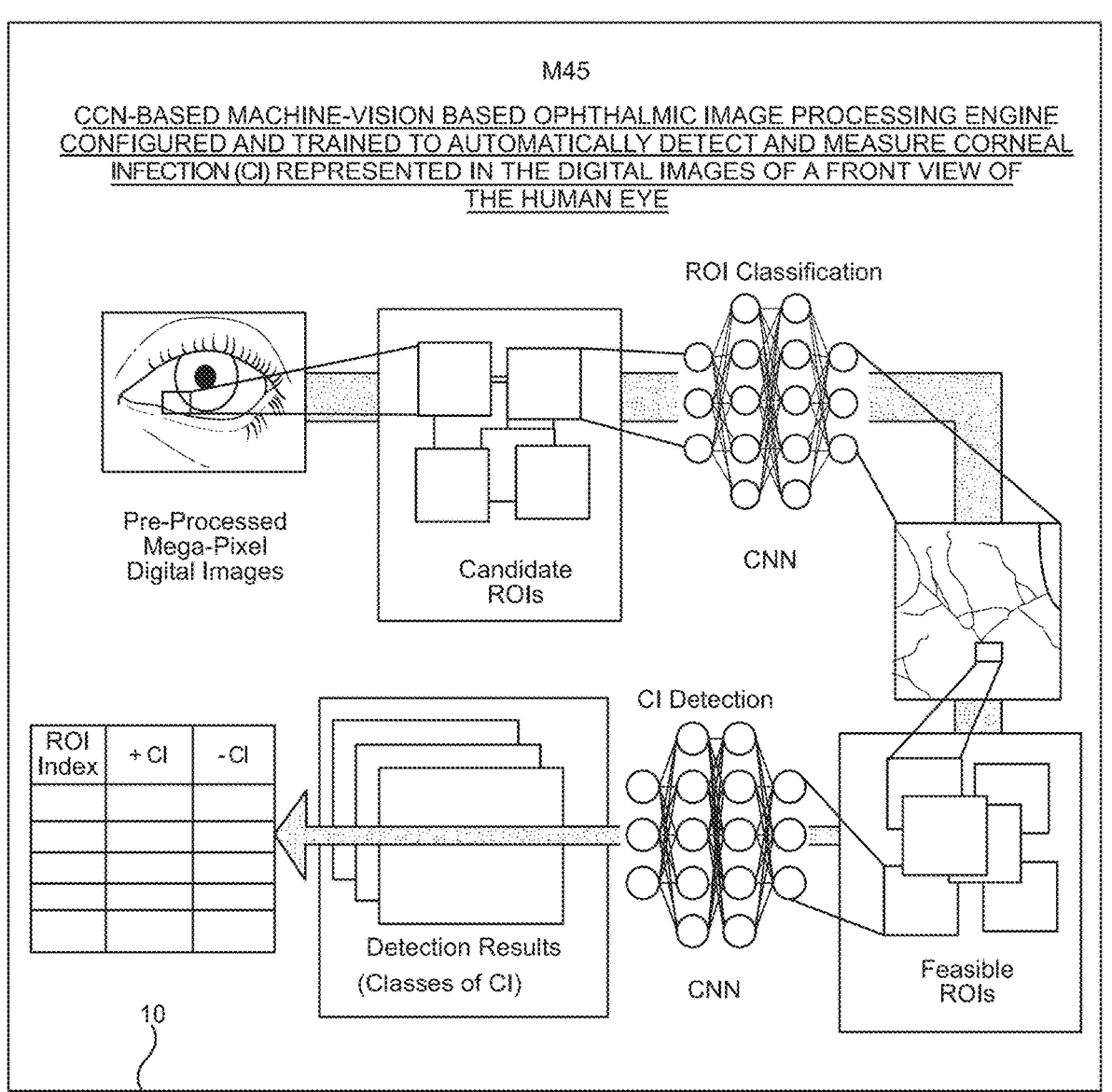
Figure 225:
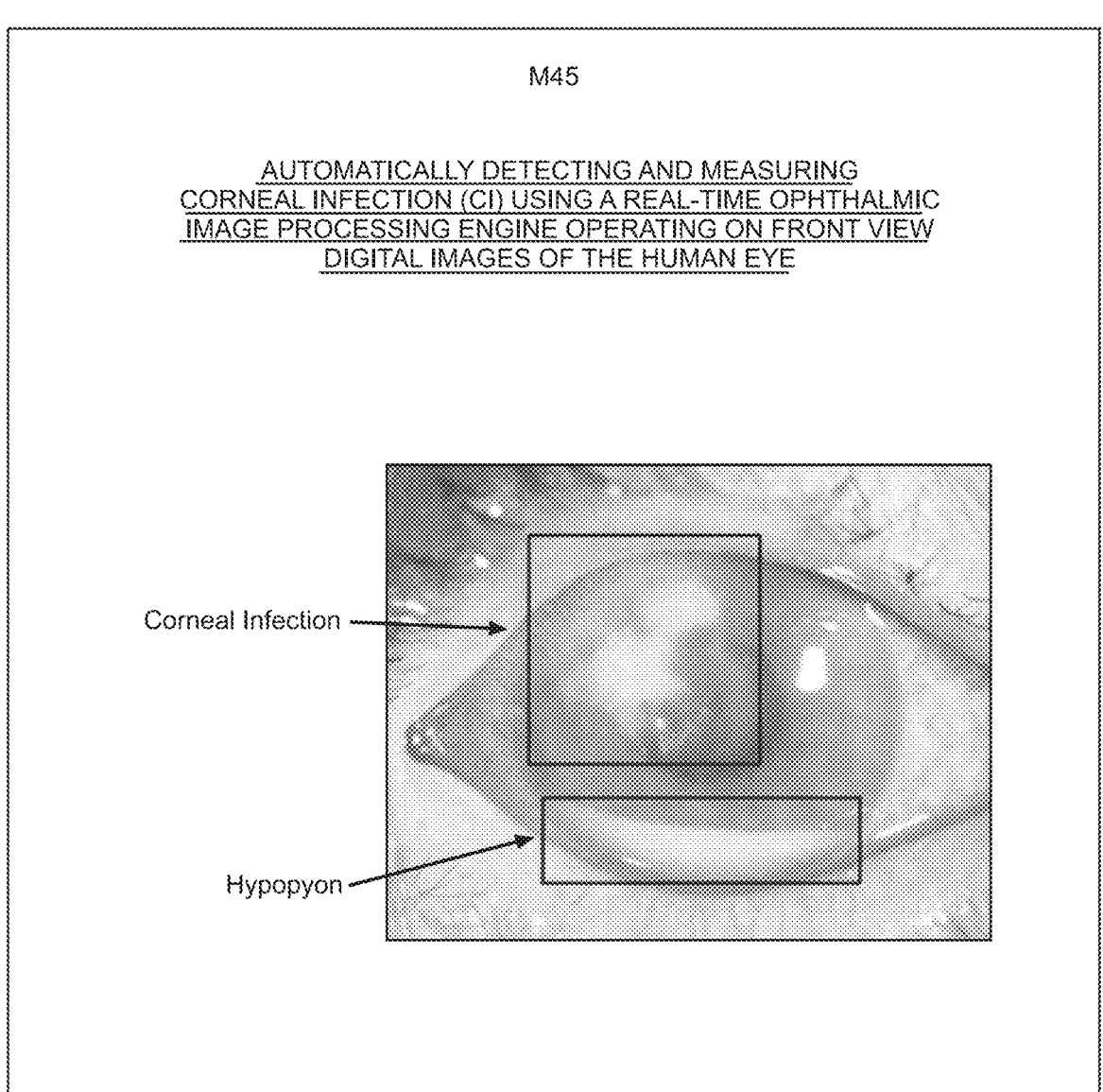
Figure 226:
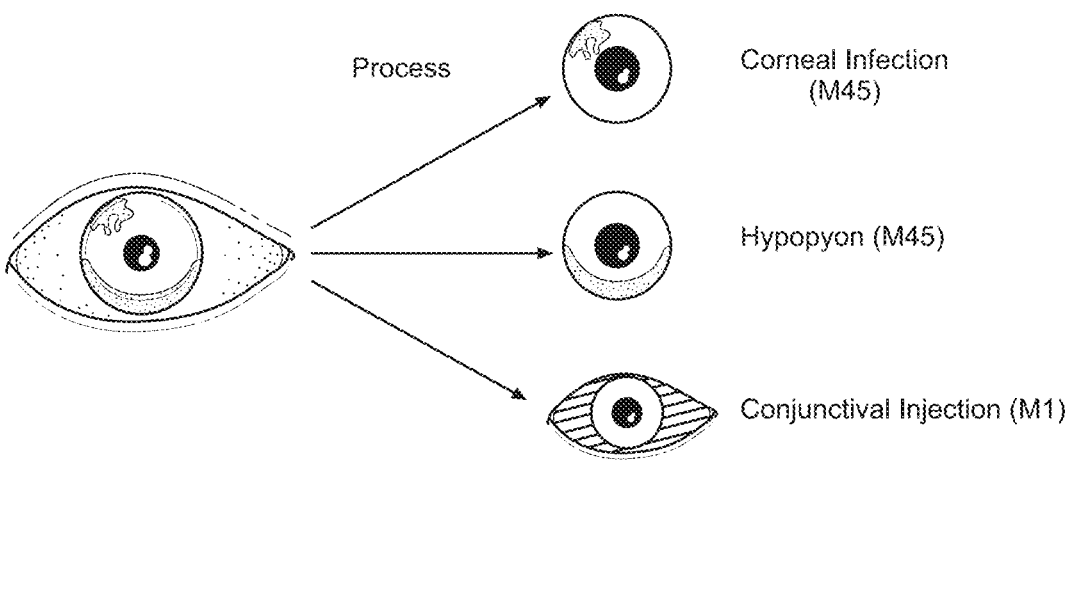
Figure 228:
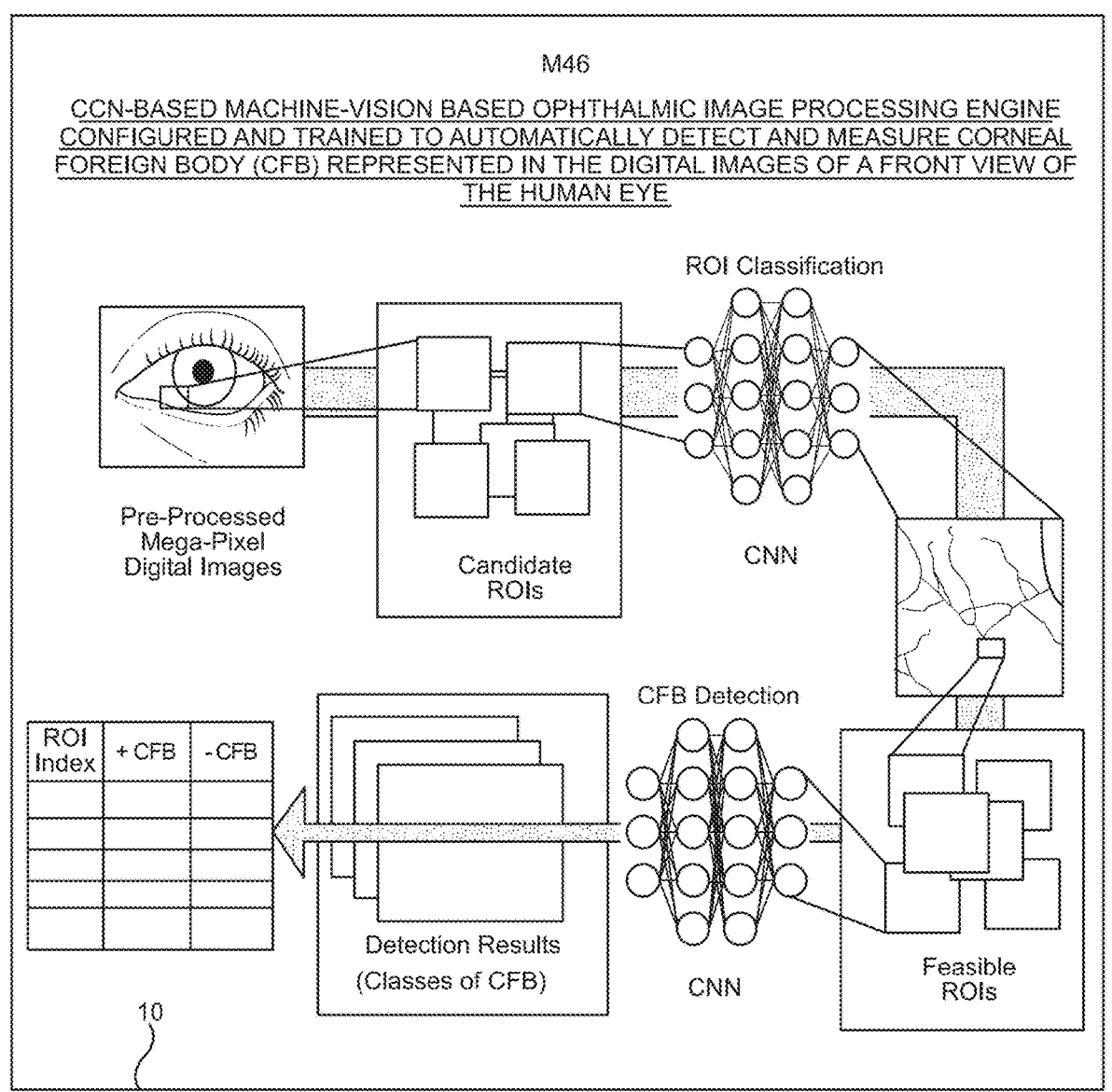
Figure 229:
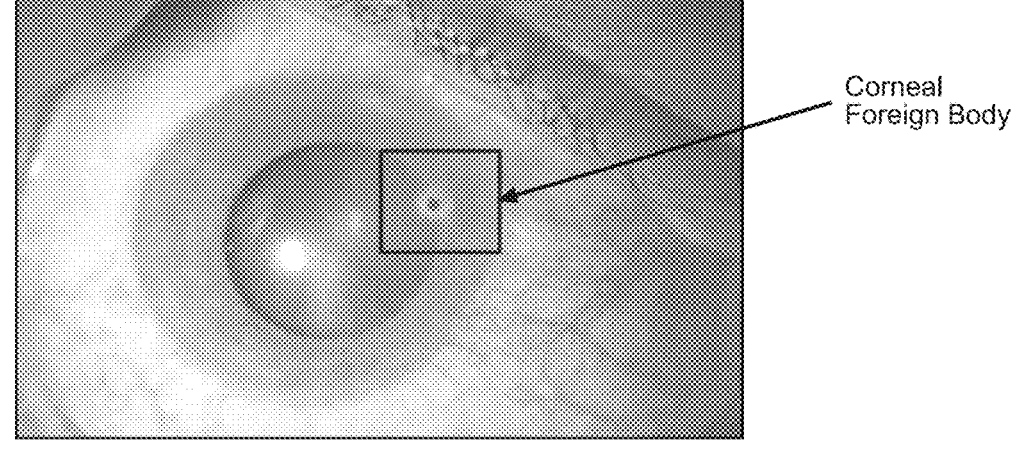
Figure 232:
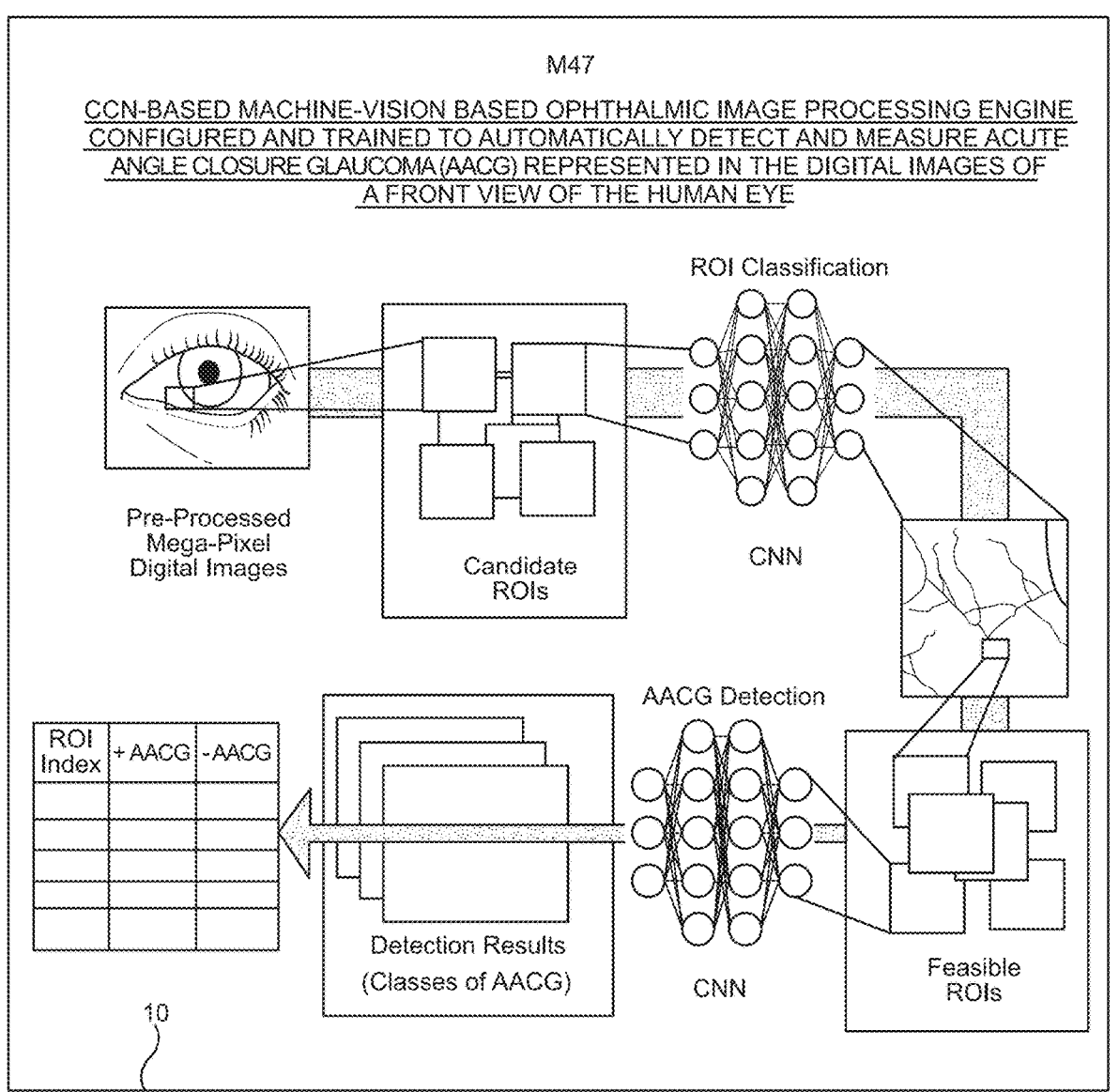
Figure 233:
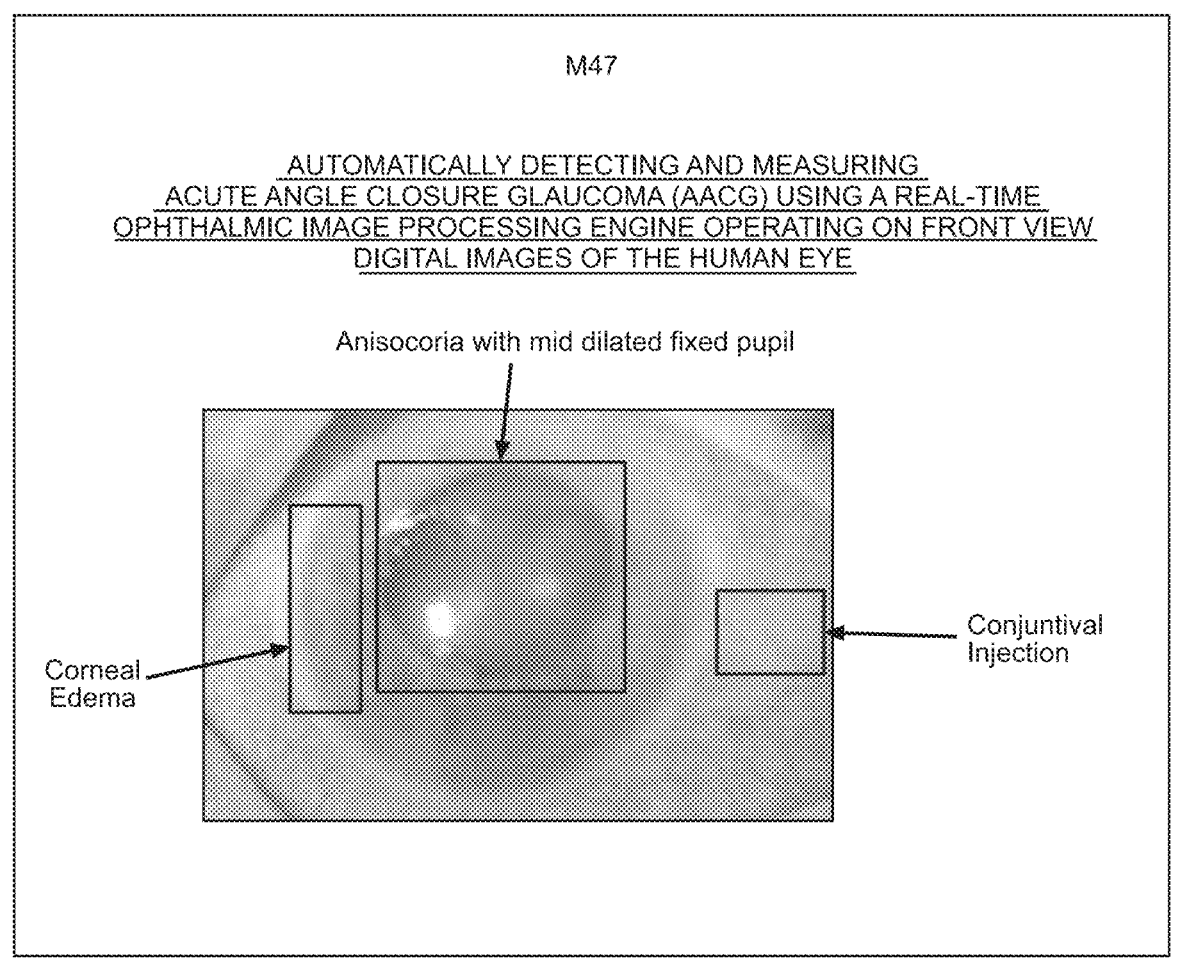
Figure 234:
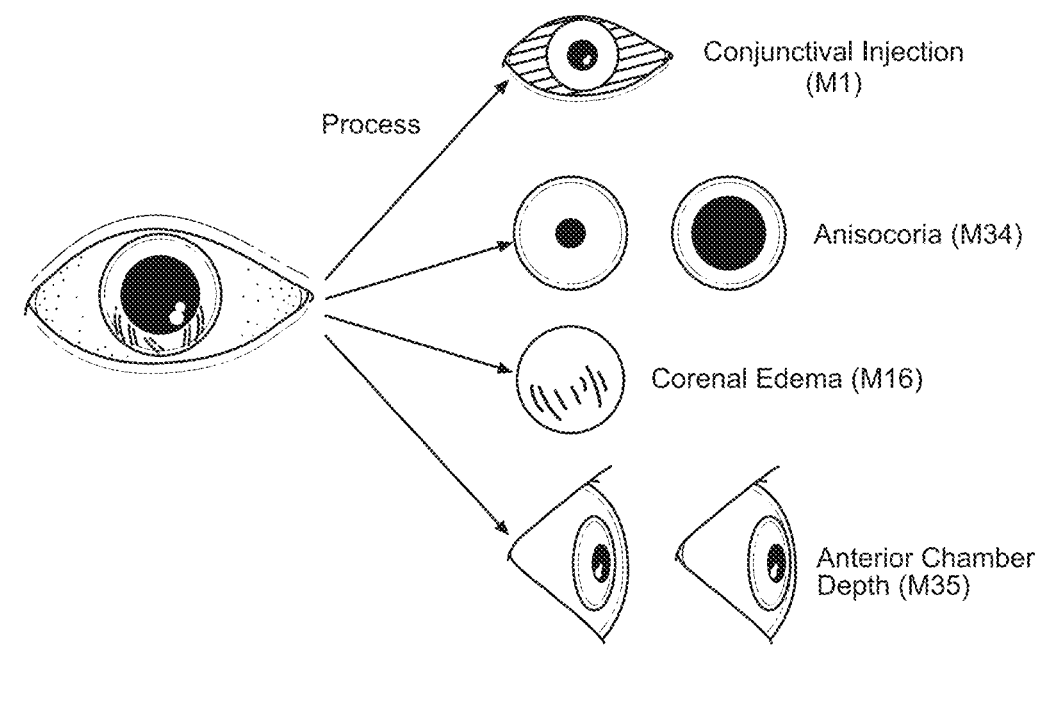
Figure 237:
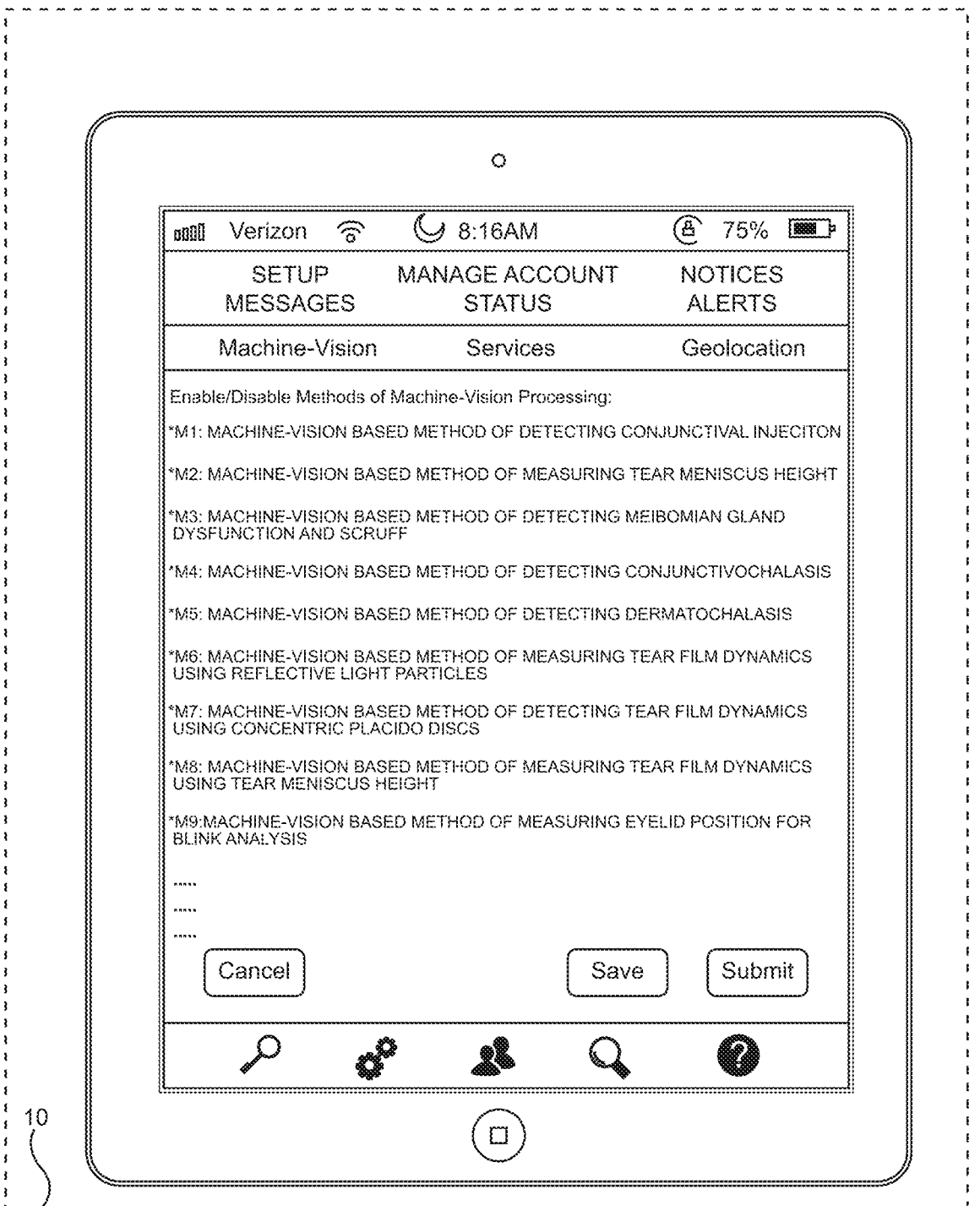
Figure 238B:
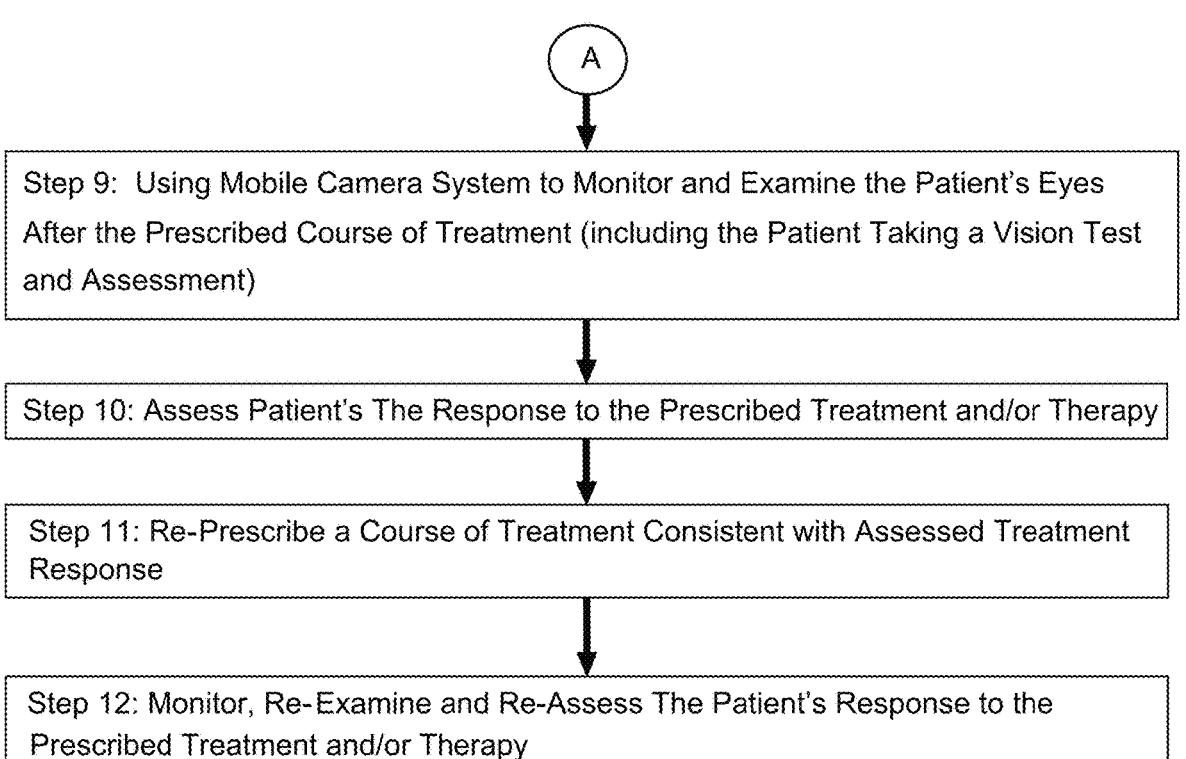
Figure 241:
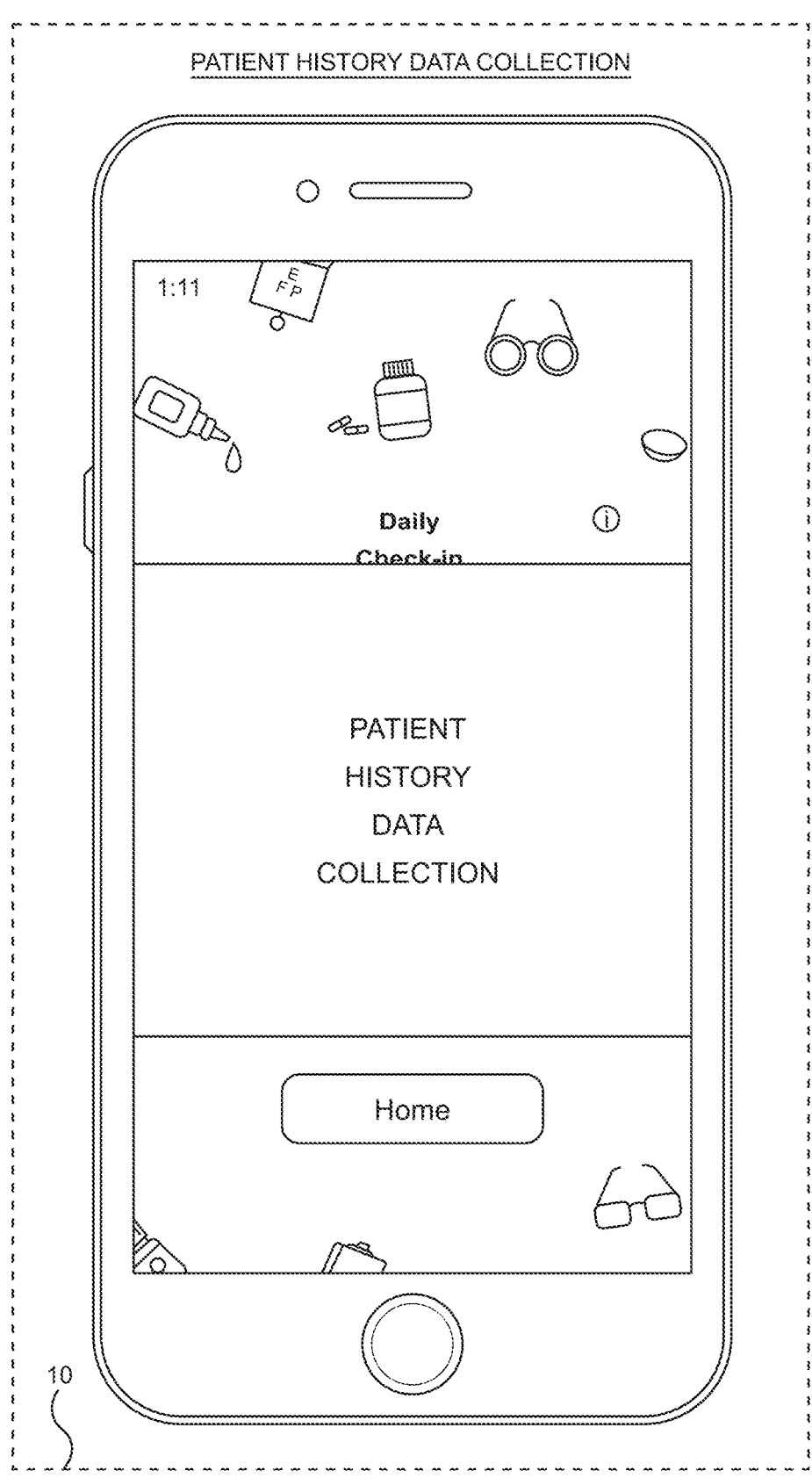
Figure 242:
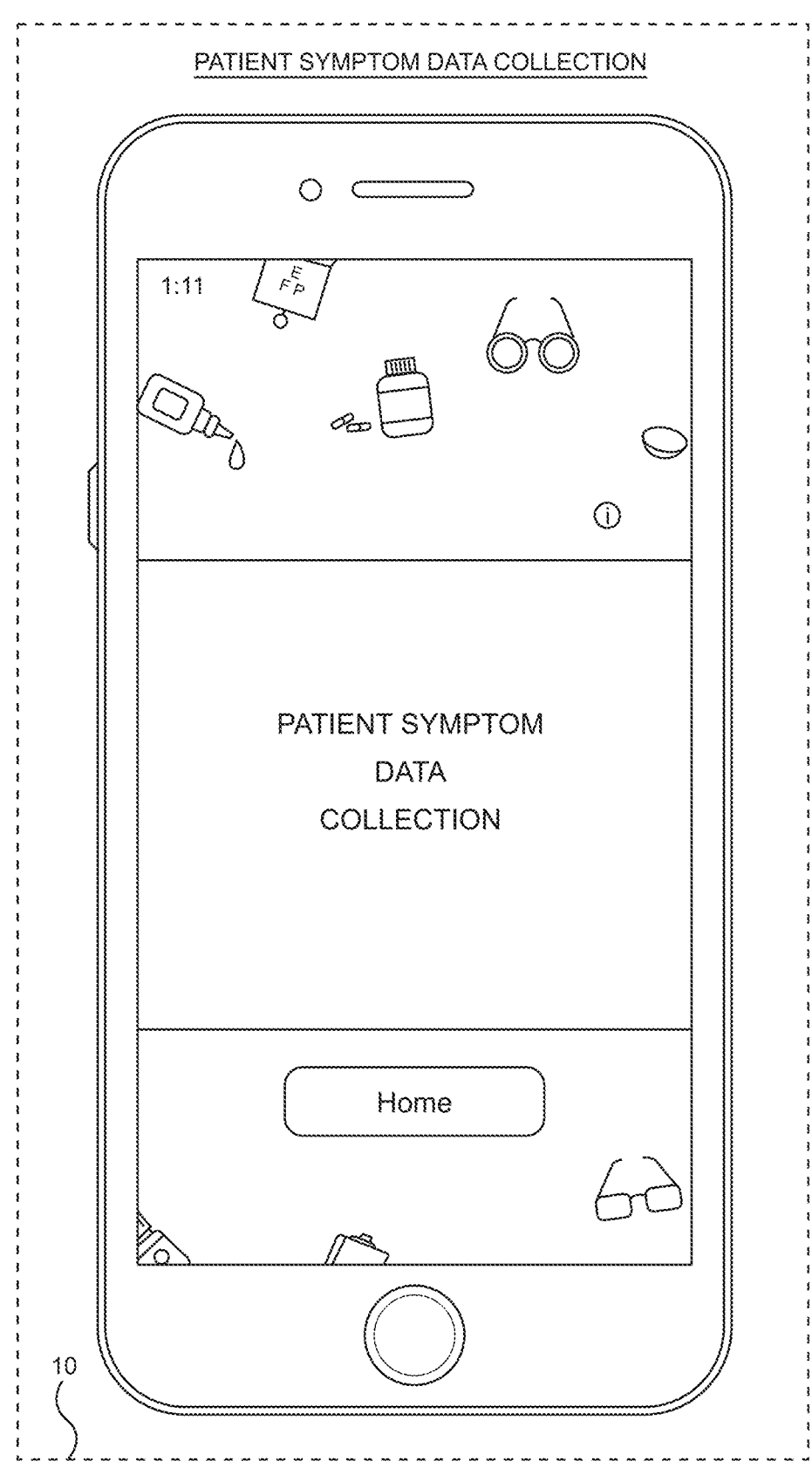
Figure 243:
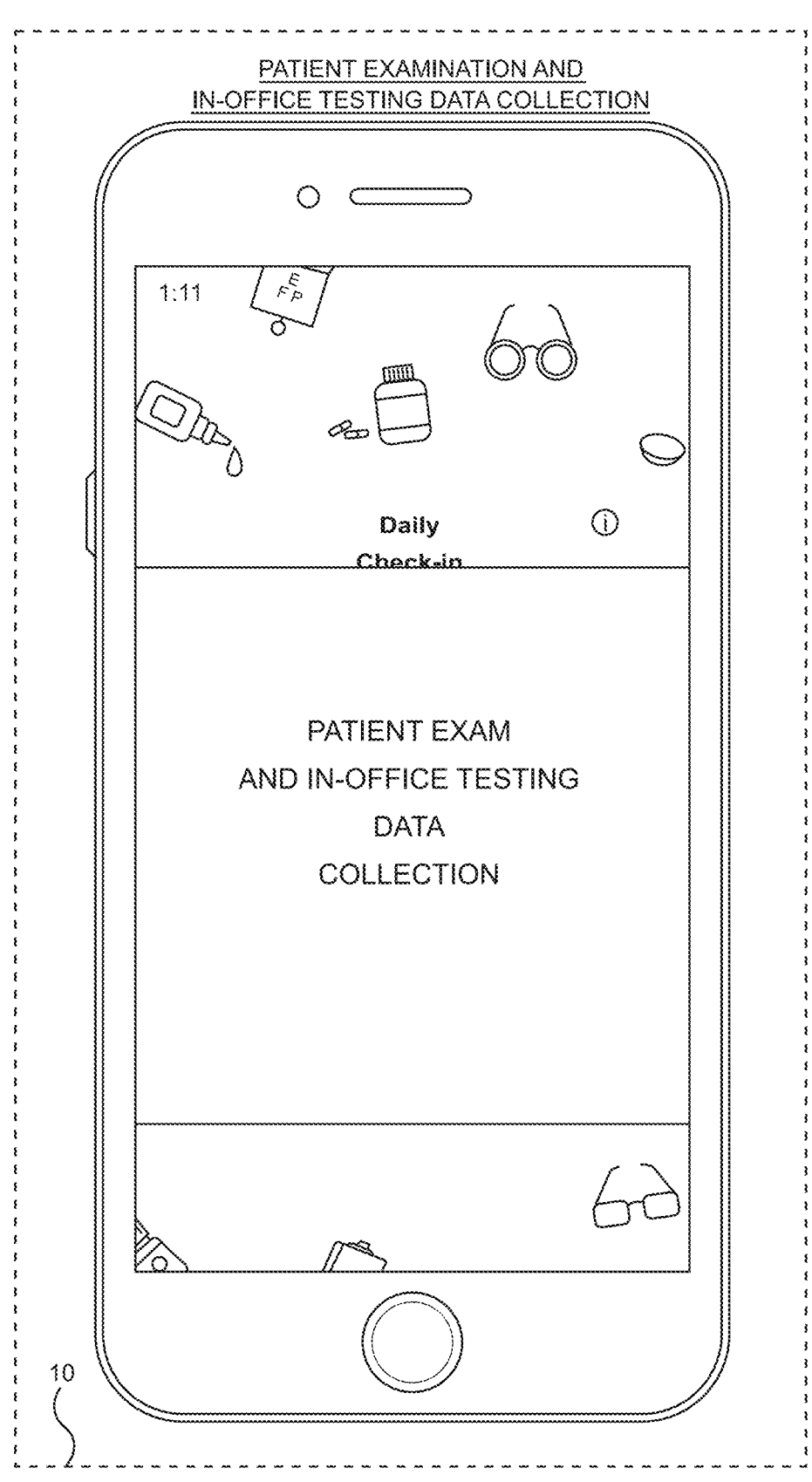
Figure 244:
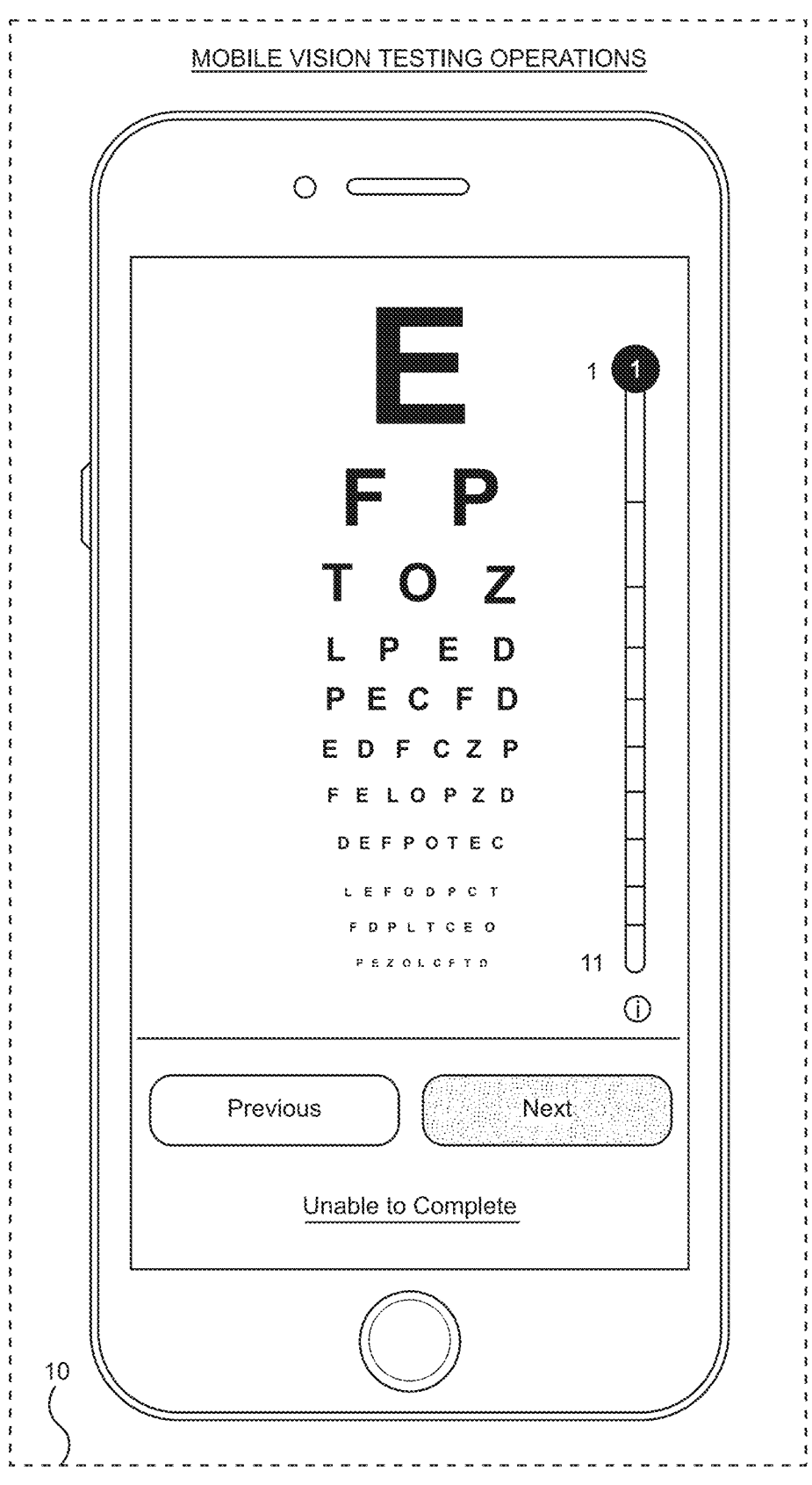
Figure 246:
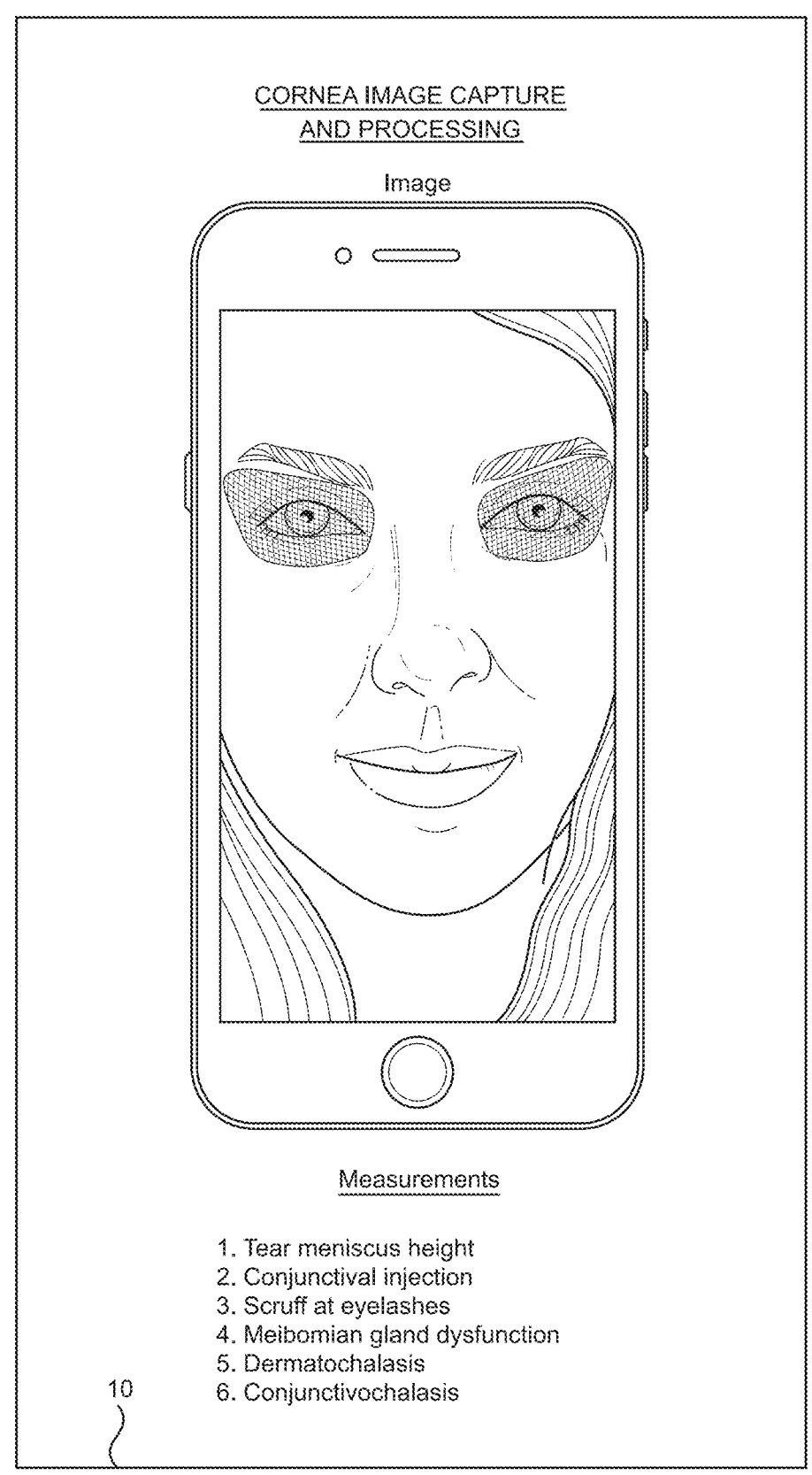
Figure 247:
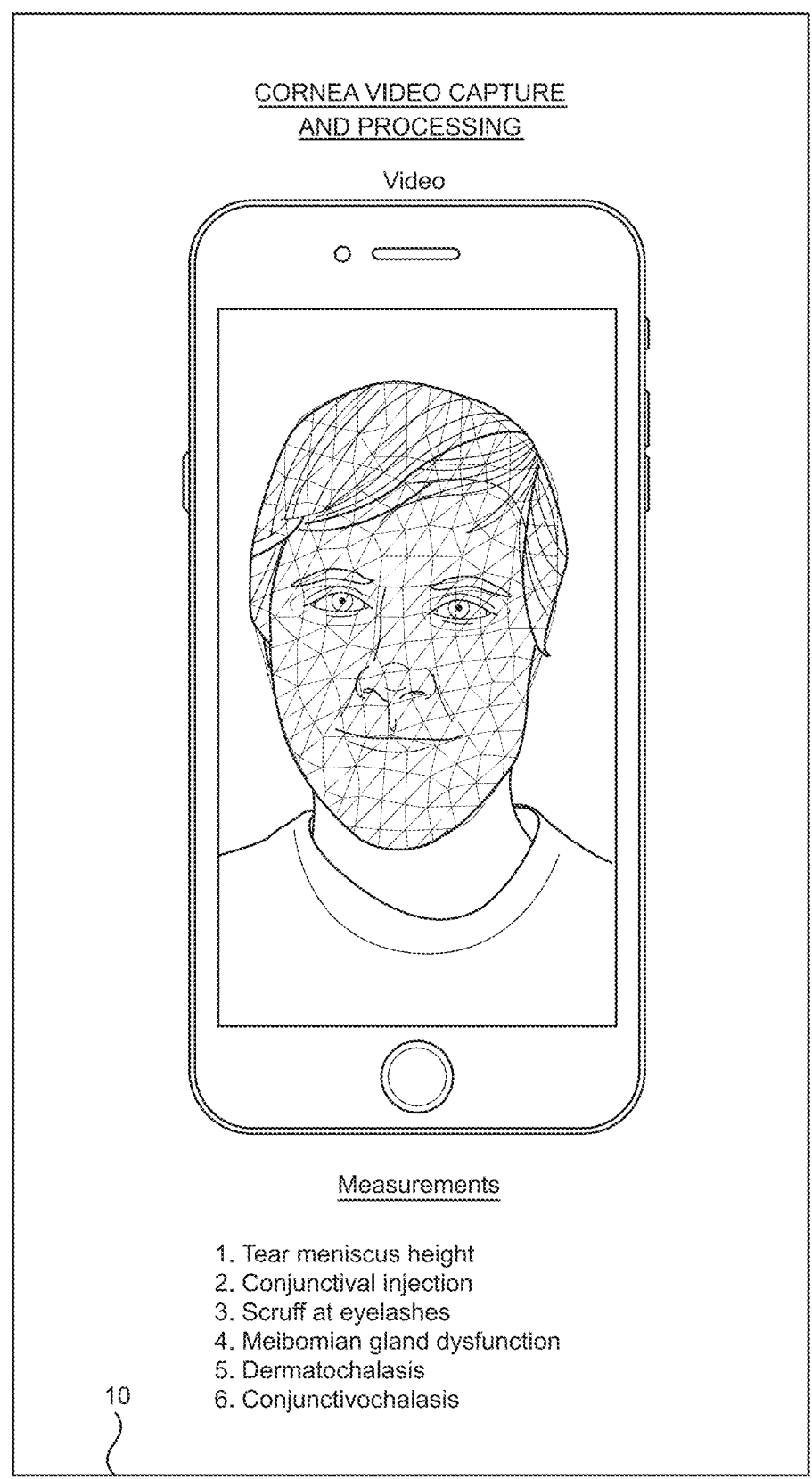
Figure 248:
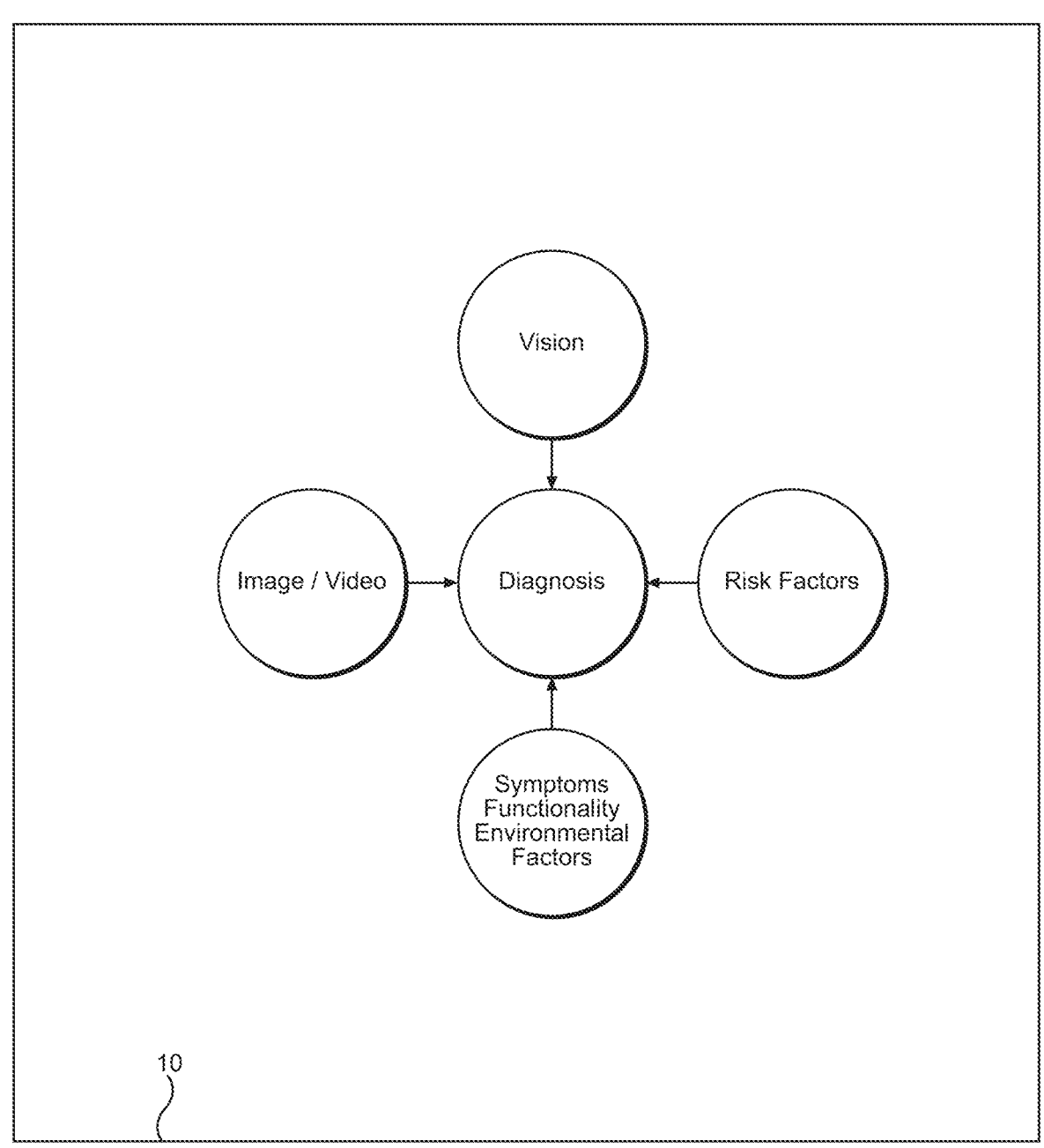
Figure 249:
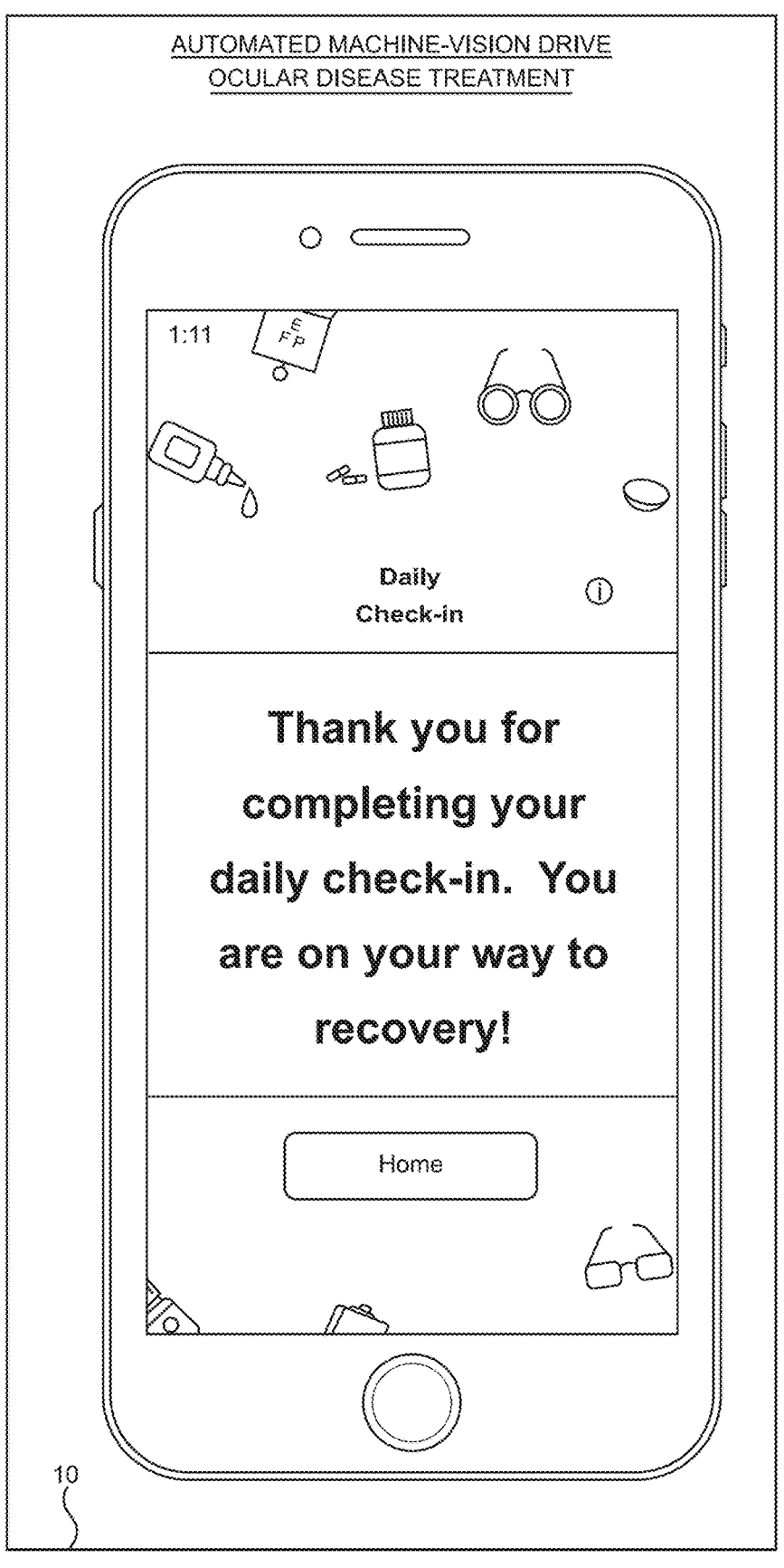
Figure 250:
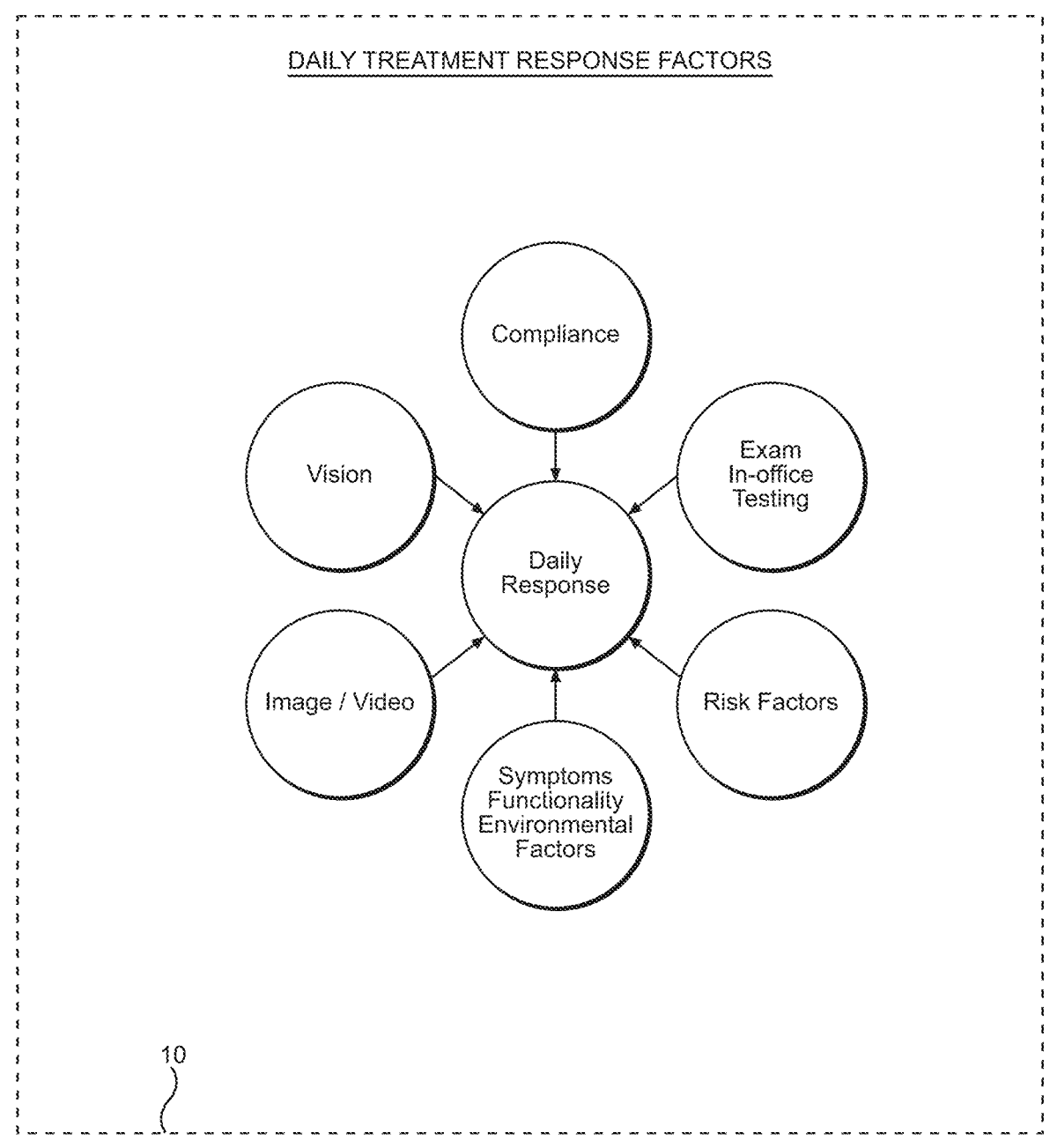
Figure 251:
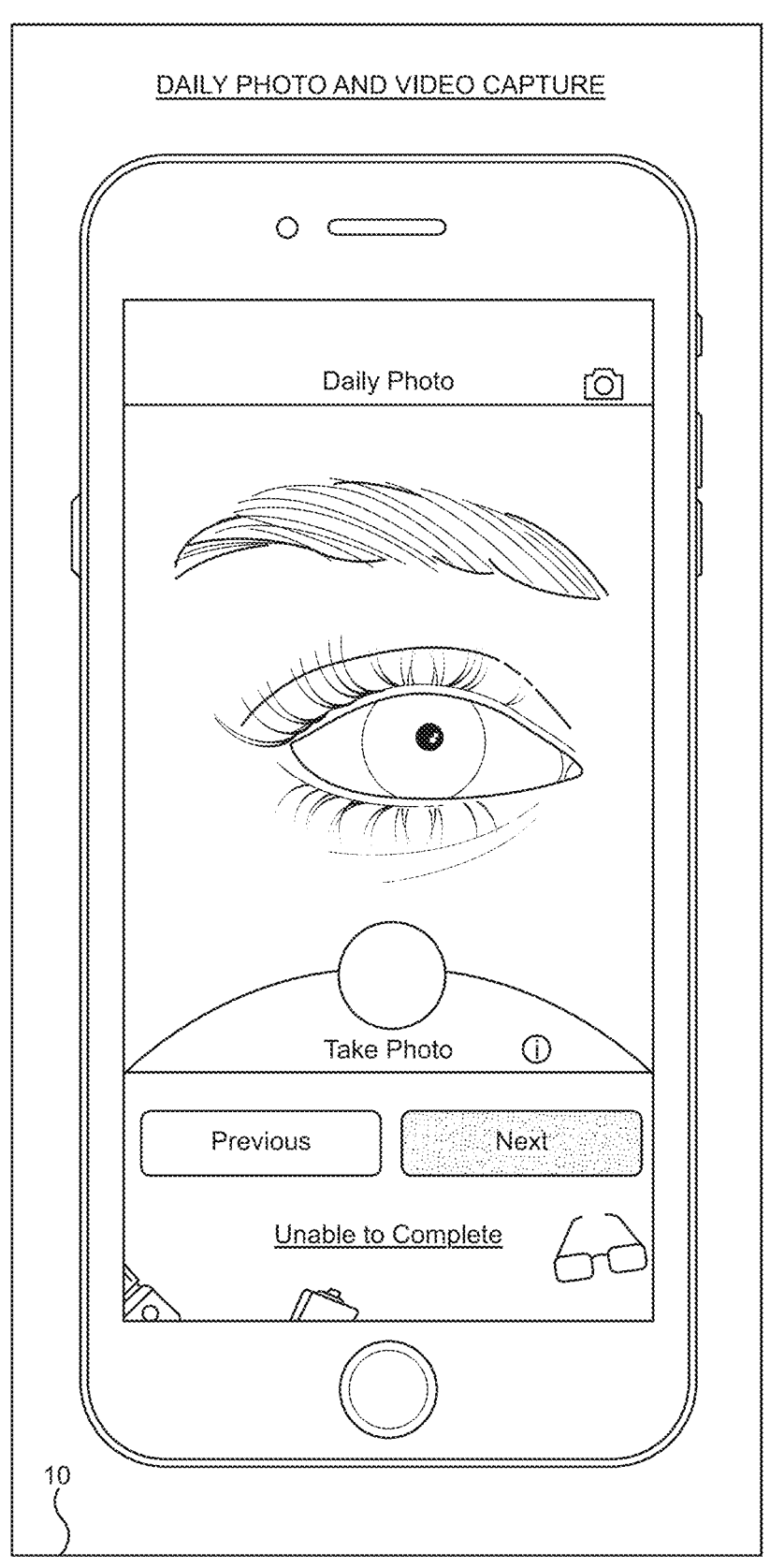
Figure 254:
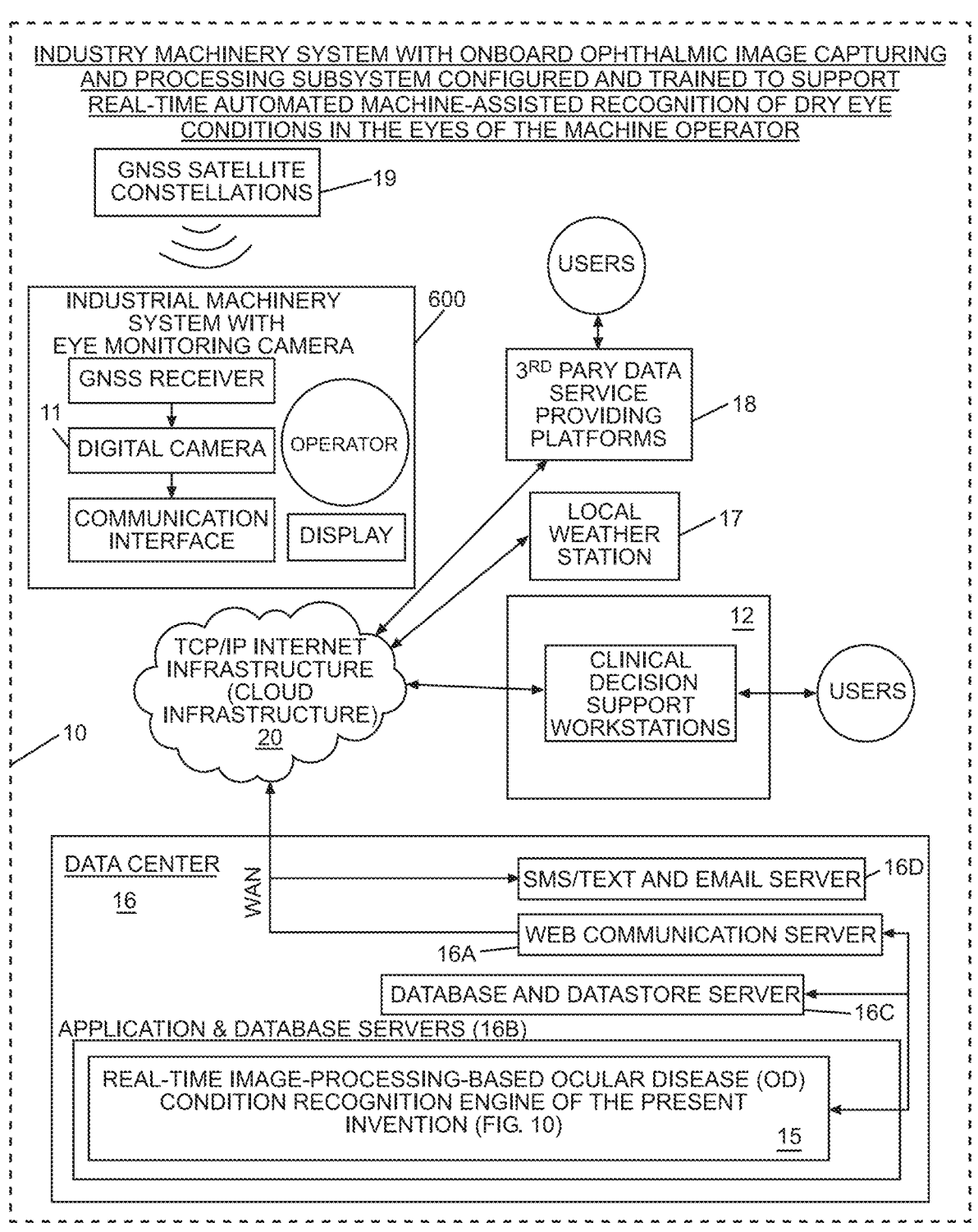
Figure 255:
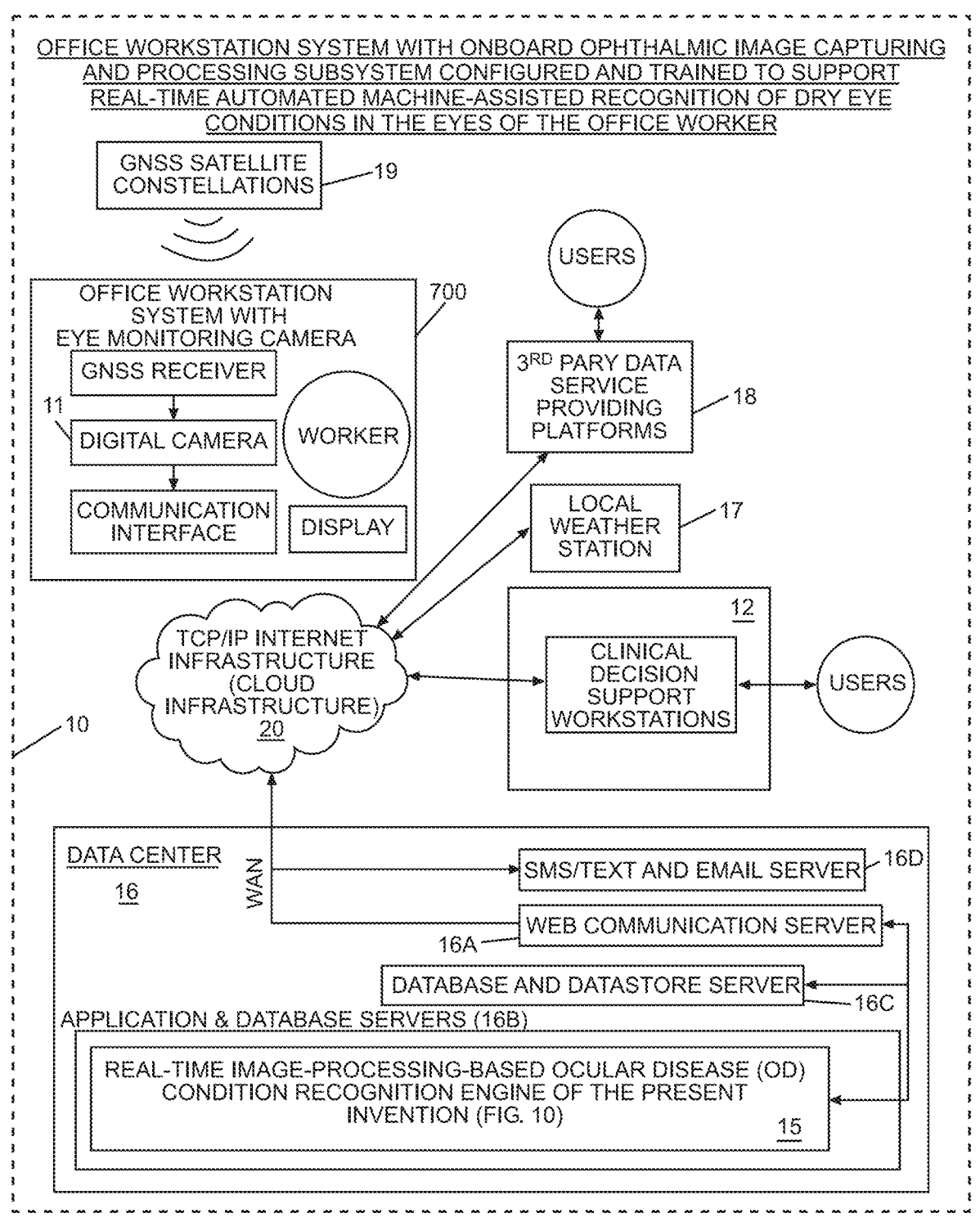
Figure 259:
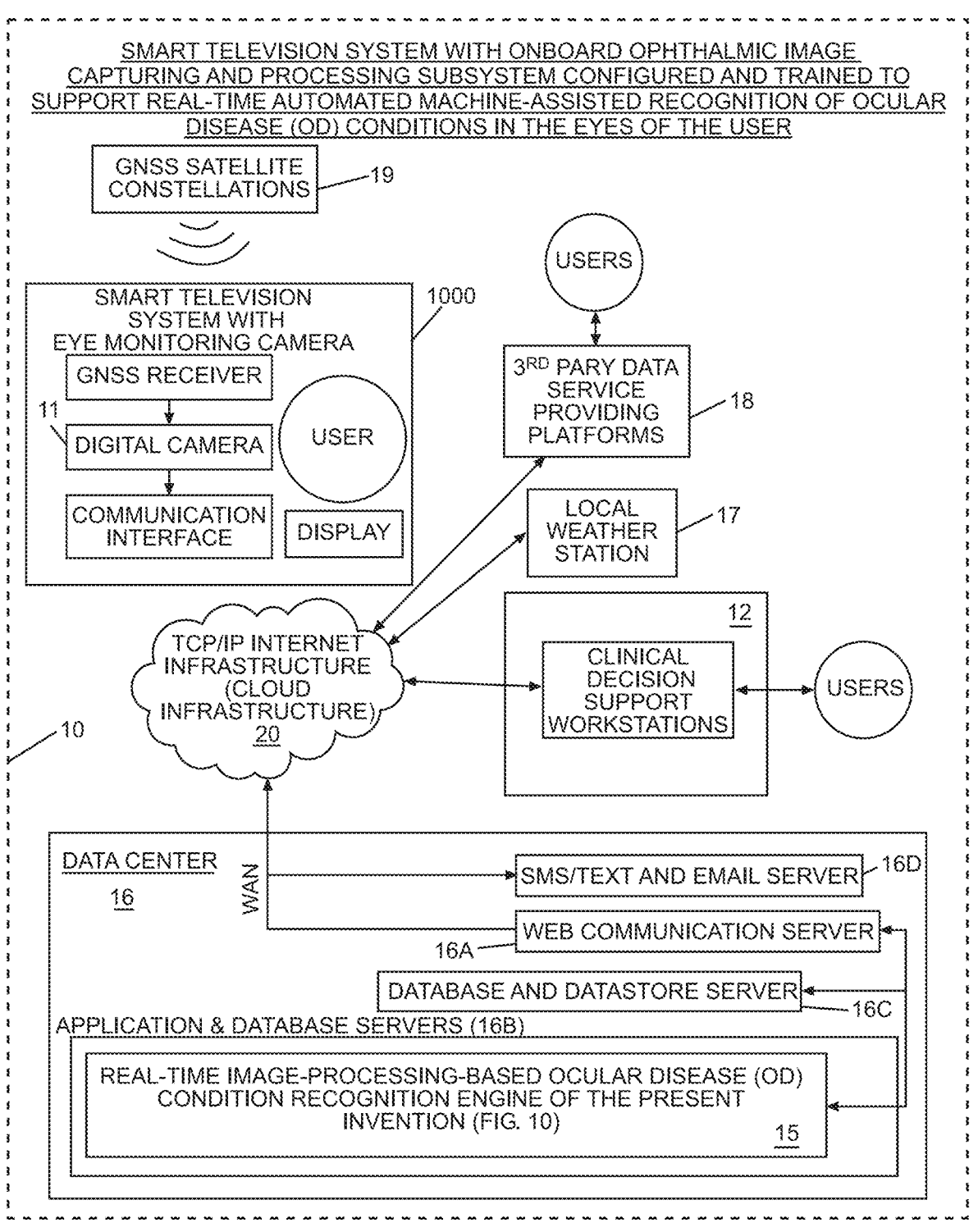
Figure 260:
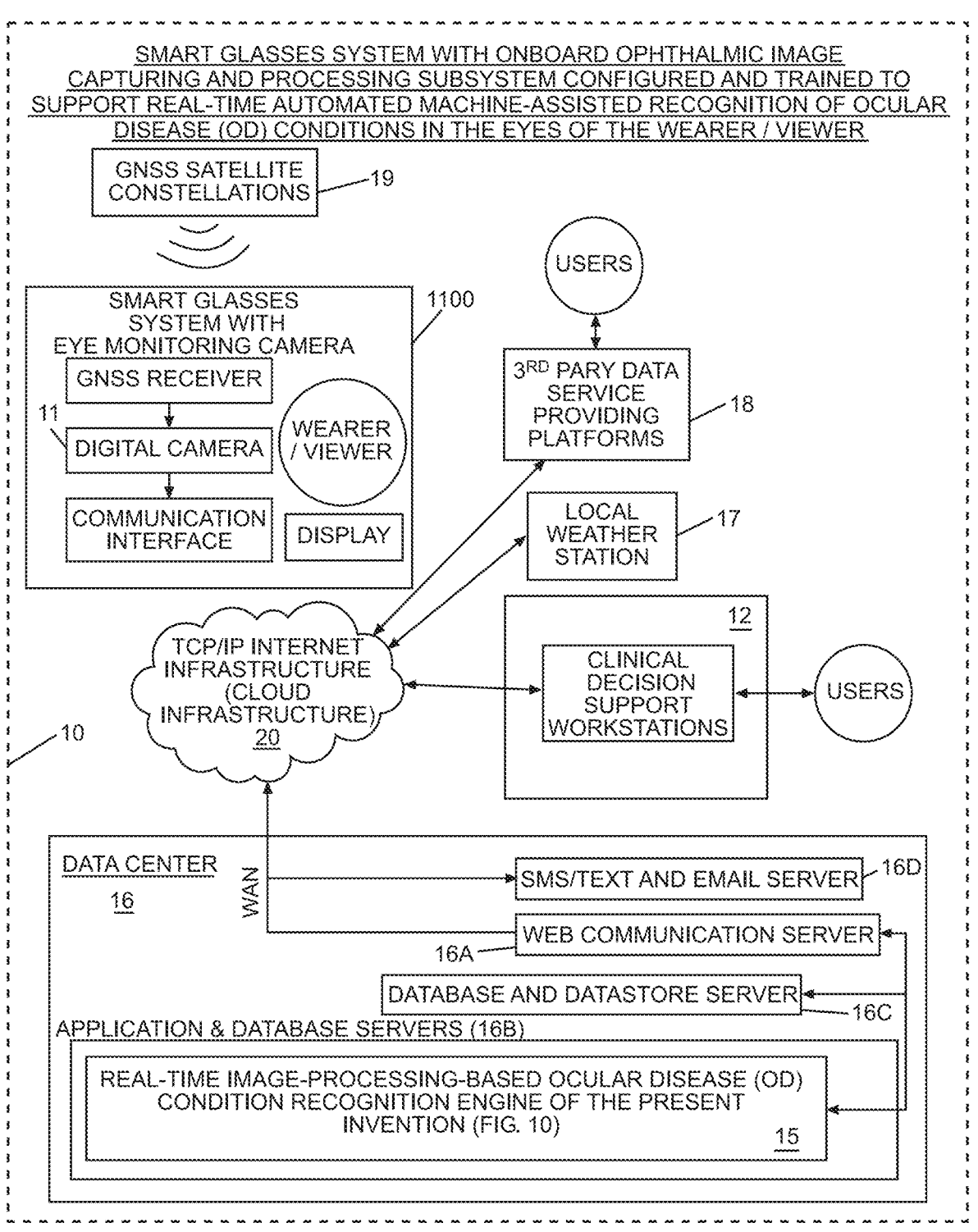
Figure 261:
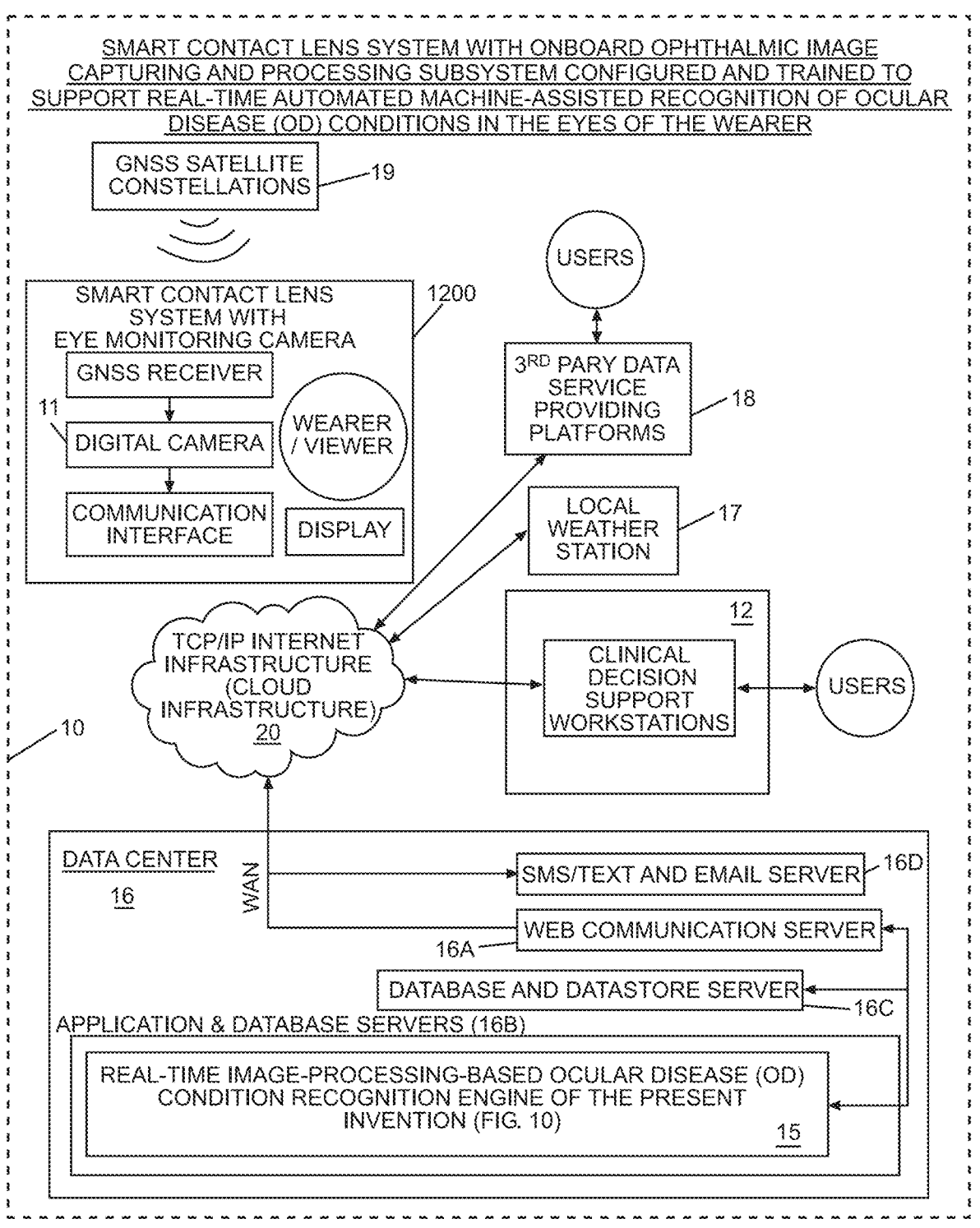
Figure 262:
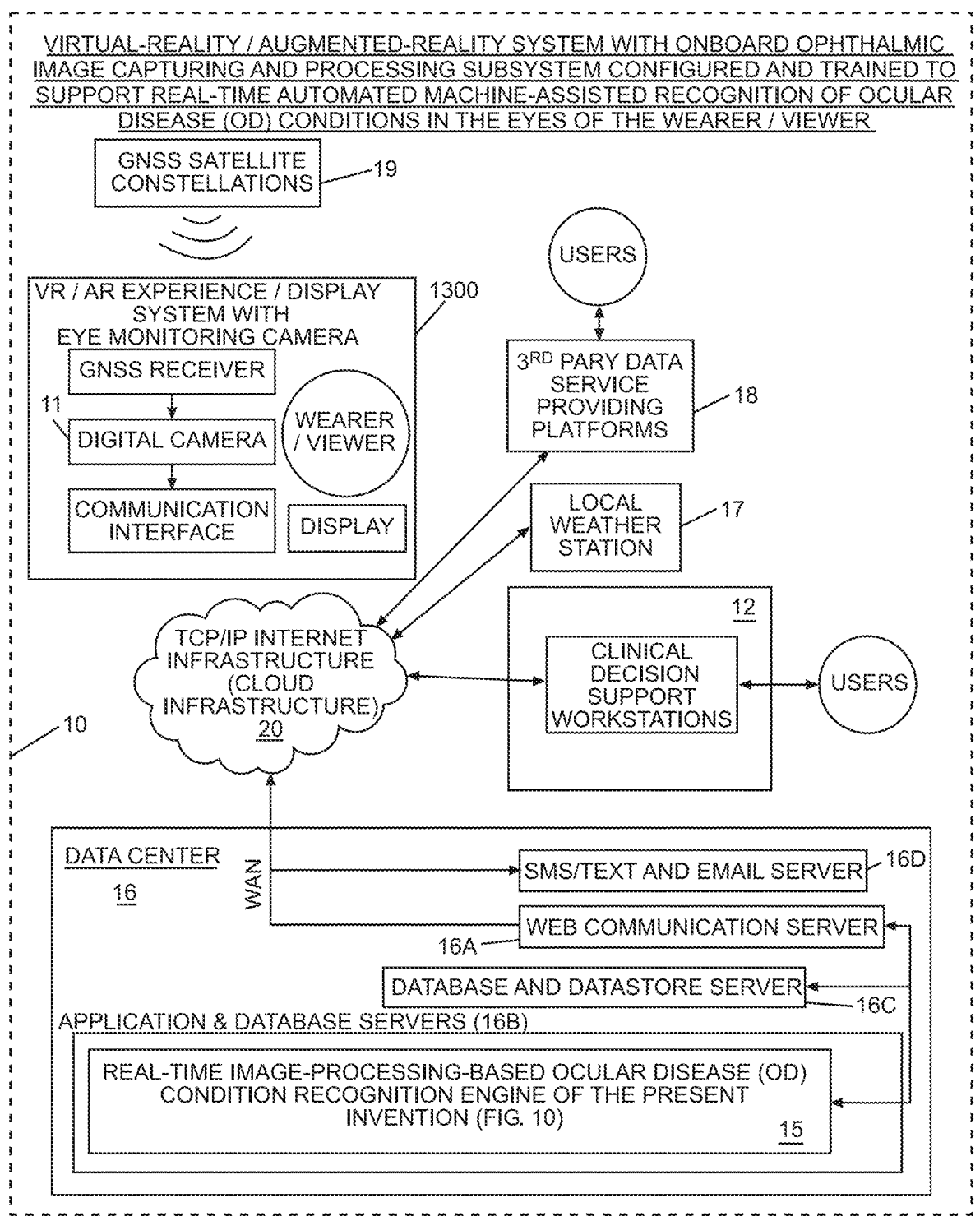

147 operating on one or more front view digital images of the human eye, so as to automatically detect superior limbic keratoconjunctivitis (SLK) as an indication of ocular disease recognition, treatment and manage care, including predicting dry eye disease (DED) class and grade of severity by the automated system;

FIG. 149 is a schematic model supporting the automated detection and measurement of superior limbic keratoconjunctivitis (SLK) in the human eyes using a real-time ophthalmic image processing engine operating on front view digital images of the human eyes formed using a visible wavelength light source;

FIGS. 150A and 150B, taken together, set forth a flow chart describing the primary steps carried out when practicing the machine-vision based method of FIG. 147 involving the processing of time and date stamped digital images of a human eye captured by a mobile smartphone camera system and processed to automatically detect superior limbic keratoconjunctivitis (SLK) in the human eye at a particular time and date, to support automated ocular disease recognition, treatment and manage care, including predicting dry eye disease (DED) class and grade of severity by the automated system;

FIG. 151 is a schematic representation of a deep-learning machine-vision ocular image processing and classification system (i.e. "engine") of the present invention configured and trained for use and deployment on the system network shown in FIG. 8A, to support and enable an automated method (M27) of method of detection and measurement of blepharitis (BH) of the human eyes photographically represented in digital images of a front view of human eyes formed and captured by a mobile smartphone camera system in accordance with the principles of the present invention;

FIG. 152 is a front view digital image representation of a human eye augmented with graphical indications superimposed on the digital image to indicate (i) where blepharitis (BH) is detected in the photographic image of the human eye, and (ii) which pixel region of interest (ROI) requires pixel data processing according to an automated method of digital image processing using the machine-based ophthalmic image processing engine of FIG. 151 operating on one or more front view digital images of the human eye, so as to automatically detect blepharitis (BH) as an indication of ocular disease recognition, treatment and manage care, including predicting dry eye disease (DED) class and grade of severity by the automated system;

FIG. 153 is a schematic model supporting the automated detection and measurement of blepharitis (BH) in the human eyes using a real-time ophthalmic image processing engine operating on front view digital images of the human eyes formed using a visible wavelength light source;

FIGS. 154A and 154B, taken together, set forth a flow chart describing the primary steps carried out when practicing the machine-vision based method of FIG. 151 involving the processing of time and date stamped digital images of a human eye captured by a mobile smartphone camera system and processed to automatically detect blepharitis (BH) in the human eye at a particular time and date, to support automated ocular disease recognition, treatment and manage care, including predicting dry eye disease (DED) class and grade of severity by the automated system;

FIG. 155 is a schematic representation of a deep-learning machine-vision ocular image processing and classification system (i.e. "engine") of the present invention configured and trained for use and deployment on the system network shown in FIG. 9A, to support and enable automated method (M28) of method of detection and measurement of chalazion/styes (CS) in the human eyes photographically represented in digital images of a front view of human eyes formed and captured by a mobile smartphone camera system in accordance with the principles of the present invention;

FIG. 156 is a front view digital image representation of a human eye augmented with graphical indications superimposed on the digital image to indicate (i) where chalazion/styes (CS) are detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect chalazion/styes (CS) as an indication of ocular disease recognition, treatment and manage care, including predicting dry eye disease (DED) class and grade of severity by the automated system;

FIG. 157 is a schematic model supporting the automated detection and measurement of chalazion/styes (CS) in the human eyes using a real-time ophthalmic image processing engine operating on front view digital images of the human eyes formed using a visible wavelength light source;

FIGS. 158A and 158B, taken together, set forth a flow chart describing the primary steps carried out when practicing the machine-vision based method of processing time and date stamped digital images of a human eye captured by a mobile smartphone camera system and processed to automatically detect chalazion/styes in the human eye at a particular time and date, to support automated ocular disease recognition, treatment and manage care, including predicting dry eye disease (DED) class and grade of severity by the automated system;

FIG. 159 is a schematic representation of a deep-learning machine-vision ocular image processing and classification system (i.e. "engine") of the present invention configured and trained for use and deployment on the system network shown in FIG. 8A, to support and enable an automated method (M29) of method of detection and measurement of eyelid cysts (EC) in the human eyes photographically represented in digital images of a front view of human eyes formed and captured by a mobile smartphone camera system in accordance with the principles of the present invention;

FIG. 160 is a front view digital image representation of a human eye augmented with graphical indications superimposed on the digital image to indicate (i) where eyelid cysts (EC) are detected in the photographic image of the human eye, and (ii) which pixel region of interest (ROI) requires pixel data processing according to an automated method of digital image processing using the machine-based ophthalmic image processing engine of FIG. 159 operating on one or more front view digital images of the human eye, so as to automatically detect eyelid cysts (EC) as an indication of ocular disease recognition, treatment and manage care, including predicting dry eye disease (DED) class and grade of severity by the automated system;

FIG. 161 is a schematic model supporting the automated detection and measurement of eyelid cysts (EC) in the human eyes using a real-time ophthalmic image processing engine operating on front view digital images of the human eyes formed using a visible wavelength light source;

FIGS. 162A and 162B, taken together, set forth a flow chart describing the primary steps carried out when practicing the machine-vision based method of FIG. 159 involving the processing of time and date stamped digital images of a human eye captured by a mobile smartphone camera system and processed to automatically detect eyelid cysts (EC) in the human eye at a particular time and date, to support automated ocular disease recognition, treatment and manage care, including predicting dry eye disease (DED) class and grade of severity by the automated system;

FIG. 163 is a schematic representation of a deep-learning machine-vision ocular image processing and classification system (i.e. "engine") of the present invention configured and trained for use and deployment on the system network shown in FIG. 8A, to support and enable an automated method (M30) of method of detection and measurement of preseptal cellulitis (PC) in the human eyes photographically represented in digital images of a front view of human eyes formed and captured by a mobile smartphone camera system in accordance with the principles of the present invention;

FIG. 164 is a front view digital image representation of a human eye augmented with graphical indications superimposed on the digital image to indicate (i) where preseptal cellulitis (PC) is detected in the photographic image of the human eye, and (ii) which pixel region of interest (ROI) requires pixel data processing according to an automated method of digital image processing using the machine-based ophthalmic image processing engine of FIG. 163 operating on one or more front view digital images of the human eye, so as to automatically detect preseptal cellulitis (PC) as an indication of ocular disease recognition, treatment and manage care, including predicting dry eye disease (DED) class and grade of severity by the automated system;

FIG. 165 is a schematic model supporting the automated detection and measurement of preseptal cellulitis (PC) in the human eyes using a real-time ophthalmic image processing engine operating on front view digital images of the human eyes formed using a visible wavelength light source;

FIGS. 166A and 166B, taken together, set forth a flow chart describing the primary steps carried out when practicing the machine-vision based method of FIG. 163 involving the processing of time and date stamped digital images of a human eye captured by a mobile smartphone camera system and processed to automatically detect preseptal cellulitis (PC) in the human eye at a particular time and date, to support automated ocular disease recognition, treatment and manage care, including predicting dry eye disease (DED) class and grade of severity by the automated system;

FIG. 167 is a schematic representation of a deep-learning machine-vision ocular image processing and classification system (i.e. "engine") of the present invention configured and trained for use and deployment on the system network shown in FIG. 8A, to support and enable an automated method (M31) of method of detection and measurement of ptosis (PT) of the human eyes photographically represented in digital images of a front view of human eyes formed and captured by a mobile smartphone camera system in accordance with the principles of the present invention;

FIG. 168 is a front view digital image representation of a human eye augmented with graphical indications superimposed on the digital image to indicate (i) where ptosis is detected in the photographic image of the human eye, and (ii) which pixel region of interest (ROI) requires pixel data processing according to an automated method of digital image processing using the machine-based ophthalmic image processing engine of FIG. 167 operating on one or more front view digital images of the human eye, so as to automatically detect ptosis as an indication of ocular disease recognition, treatment and manage care, including predicting dry eye disease (DED) class and grade of severity by the automated system;

FIG. 169 is a schematic model supporting the automated detection and measurement of ptosis in the human eyes using a real-time ophthalmic image processing engine operating on front view digital images of the human eyes formed using a visible wavelength light source;

FIG. 170 sets forth a flow chart describing the primary steps carried out when practicing the machine-vision based method of FIG. 167 involving the processing of time and date stamped digital images of a human eye captured by a mobile smartphone camera system and processed to automatically detect ptosis in the human eye at a particular time and date, to support automated ocular disease recognition, treatment and manage care, including predicting dry eye disease (DED) class and grade of severity by the automated system;

FIG. 171 is a schematic representation of a deep-learning machine-vision ocular image processing and classification system (i.e. "engine") of the present invention configured and trained for use and deployment on the system network shown in FIG. 8A, to support and enable an automated method (M32) of method of detection and measurement of ophthalmoplegia (OPM) in the human eyes photographically represented in digital images of a front view of human eyes formed and captured by a mobile smartphone camera system in accordance with the principles of the present invention;

FIG. 172 is a front view digital image representation of a human eye augmented with graphical indications superimposed on the digital image to indicate (i) where ophthalmoplegia (OPM) is detected in the photographic image of the human eye, and (ii) which pixel region of interest (ROI) requires pixel data processing according to an automated method of digital image processing using the machine-based ophthalmic image processing engine of FIG. 171 operating on one or more front view digital images of the human eye, so as to automatically detect ophthalmoplegia (OPM) as an indication of ocular disease recognition, treatment and manage care, including predicting dry eye disease (DED) class and grade of severity by the automated system;

FIG. 173 is a schematic model supporting the automated detection and measurement of ophthalmoplegia (OPM) in the human eyes using a real-time ophthalmic image processing engine operating on front view digital images of the human eyes formed using a visible wavelength light source;

FIGS. 174A and 174B, taken together, set forth a flow chart describing the primary steps carried out when practicing the machine-vision based method of FIG. 171 involving the processing of time and date stamped digital images of a human eye captured by a mobile smartphone camera system and processed to automatically detect ophthalmoplegia (OPM) in the human eye at a particular time and date, to support automated ocular disease recognition, treatment and manage care, including predicting dry eye disease (DED) class and grade of severity by the automated system;

FIG. 175 is a schematic representation of a deep-learning machine-vision ocular image processing and classification system (i.e. "engine") of the present invention configured and trained for use and deployment on the system network shown in FIG. 8A, to support and enable an automated method (M33) of method of detection and measurement of proptosis/hypoglobus (HP) in the human eyes photographically represented in digital images of a front view of human eyes formed and captured by a mobile smartphone camera system in accordance with the principles of the present invention;

FIG. 176 is a front view digital image representation of a human eye augmented with graphical indications superimposed on the digital image to indicate (i) where proptosis/hypoglobus (HP) is detected in the photographic image of the human eye, and (ii) which pixel region of interest (ROI)

requires pixel data processing according to an automated method of digital image processing using the machine-based ophthalmic image processing engine of FIG. 175 operating on one or more front view digital images of the human eye, so as to automatically detect proptosis/hypoglobus (HP) as an indication of ocular disease recognition, treatment and manage care, including predicting dry eye disease (DED) class and grade of severity by the automated system;

FIG. 177 is a schematic model supporting the automated detection and measurement of proptosis/hypoglobus (HP) in the human eyes using a real-time ophthalmic image processing engine operating on front/worm's eye view digital images of the human eyes formed using a visible wavelength light source;

FIGS. 178A and 178B, taken together, set forth a flow chart describing the primary steps carried out when practicing the machine-vision based method of FIG. 175 involving the processing of time and date stamped digital images of a human eye captured by a mobile smartphone camera system and processed to automatically detect proptosis/hypoglobus (HP) in the human eye at a particular time and date, to support automated ocular disease recognition, treatment and manage care, including predicting dry eye disease (DED) class and grade of severity by the automated system;

FIG. 179 is a schematic representation of a deep-learning machine-vision ocular image processing and classification system (i.e. "engine") of the present invention configured and trained for use and deployment on the system network shown in FIG. 8A, to support and enable an automated method (M34) of method of detection and measurement of anisocoria (ACR) of the human eyes photographically represented in digital images of a front view of human eyes formed and captured by a mobile smartphone camera system in accordance with the principles of the present invention;

FIG. 180 is a front view digital image representation of a human eye augmented with graphical indications superimposed on the digital image to indicate (i) where anisocoria (ACR) is detected in the photographic image of the human eye, and (ii) which pixel region of interest (ROI) requires pixel data processing according to an automated method of digital image processing using the machine-based ophthalmic image processing engine of FIG. 179 operating on one or more front view digital images of the human eye, so as to automatically detect anisocoria (ACR) as an indication of ocular disease recognition, treatment and manage care, including predicting dry eye disease (DED) class and grade of severity by the automated system;

FIG. 181 is a schematic model supporting the automated detection and measurement of anisocoria (ACR) in the human eyes using a real-time ophthalmic image processing engine operating on front view digital images of the human eyes formed using a visible wavelength light source;

FIGS. 182A and 182B, taken together, set forth a flow chart describing the primary steps carried out when practicing the machine-vision based method of FIG. 179 involving the processing of time and date stamped digital images of a human eye captured by a mobile smartphone camera system and processed to automatically detect anisocoria (ACR) in the human eye at a particular time and date, to support automated ocular disease recognition, treatment and manage care, including predicting dry eye disease (DED) class and grade of severity by the automated system;

FIG. 183 is a schematic representation of a deep-learning machine-vision ocular image processing and classification system (i.e. "engine") of the present invention configured and trained for use and deployment on the system network shown in FIG. 8A, to support and enable an automated method (M35) of method of detection and measurement of anterior chamber depth (ACD) in the human eyes photographically represented in digital images of a front view of human eyes formed and captured by a mobile smartphone camera system in accordance with the principles of the present invention;

FIGS. 184A, 184B, 184C and 184D are side view digital image representations of a human eye exhibiting dry eye disease (DED) conditions, and augmented with graphical indications superimposed on the digital image to indicate (i) where anterior chamber depth (ACD) is detected in the photographic image of the human eye, and (ii) which pixel region of interest (ROI) requires pixel data processing according to an automated method of digital image processing using the machine-based ophthalmic image processing engine of FIG. 183 operating on one or more front view digital images of the human eye, so as to automatically detect anterior chamber depth (ACD) as an indication of ocular disease recognition, treatment and manage care, including predicting dry eye disease (DED) class and grade of severity by the automated system;

FIG. 185 is a schematic representation for a schematic model supporting the automated detection and measurement of anterior chamber depth (ACD) in the human eyes using a real-time ophthalmic image processing engine operating on front view digital images of the human eyes formed using a visible wavelength light source;

FIG. 186 is a schematic representation for a schematic model supporting the automated detection and measurement of anterior chamber depth (ACD) in the human eyes using a real-time ophthalmic image processing engine operating on front view digital images of the human eyes formed using a visible wavelength light source;

FIGS. 187A and 187B, taken together, set forth a flow chart describing the primary steps carried out when practicing the machine-vision based method of FIG. 183 involving the processing of time and date stamped digital images of a human eye captured by a mobile smartphone camera system and processed to automatically detect anterior chamber depth (ACD) in the human eye at a particular time and date, to support automated ocular disease recognition, treatment and manage care, including predicting dry eye disease (DED) class and grade of severity by the automated system;

FIG. 188 is a schematic representation of a deep-learning machine-vision ocular image processing and classification system (i.e. "engine") of the present invention configured and trained for use and deployment on the system network shown in FIG. 8A, to support and enable an automated method (M36) of method of detection and measurement of orbital post septal cellulitis (OPSC) in the human eyes photographically represented in digital images of a front view of human eyes formed using a visible wavelength light source and captured by a mobile smartphone camera system in accordance with the principles of the present invention;

FIG. 189 is a front view digital image representation of a human eye augmented with graphical indications superimposed on the digital image to indicate (i) where orbital post septal cellulitis (OPSC) is detected in the photographic image of the human eye, and (ii) which pixel region of interest (ROI) requires pixel data processing according to an automated method of digital image processing using the machine-based ophthalmic image processing engine of FIG. 188 operating on one or more front view digital images of the human eye, so as to automatically detect orbital post septal cellulitis (OPSC) as an indication of ocular disease recognition, treatment and manage care, including predicting dry eye disease (DED) class and grade of severity by the automated system;

FIG. 190 is a schematic model supporting the automated detection and measurement of orbital post septal cellulitis (OPSC) in the human eyes using a real-time ophthalmic image processing engine operating on front view digital images of the human eyes formed using a visible wavelength light source;

FIGS. 191A and 191B, taken together, set forth a flow chart describing the primary steps carried out when practicing the machine-vision based method of FIG. 188 involving the processing of time and date stamped digital images of a human eye captured by a mobile smartphone camera system and processed to automatically detect orbital post septal cellulitis (OPSC) in the human eye at a particular time and date, to support automated ocular disease recognition, treatment and manage care, including predicting dry eye disease (DED) class and grade of severity by the automated system;

FIG. 192 is a schematic representation of a deep-learning machine-vision ocular image processing and classification system (i.e. "engine") of the present invention configured and trained for use and deployment on the system network shown in FIG. 8A, to support and enable an automated method (M37) of method of detection and measurement of thyroid eye disease (TED) in the human eyes photographically represented in digital images of a front view of human eyes formed using a visible wavelength light source and captured by a mobile smartphone camera system in accordance with the principles of the present invention;

FIG. 193 is a front view digital image representation of a human eye augmented with graphical indications superimposed on the digital image to indicate (i) where thyroid eye disease (TED) is detected in the photographic image of the human eye, and (ii) which pixel region of interest (ROI) requires pixel data processing according to an automated method of digital image processing using the machine-based ophthalmic image processing engine of FIG. 192 operating on one or more front view digital images of the human eye, so as to automatically detect thyroid eye disease (TED) as an indication of ocular disease recognition, treatment and manage care, including predicting dry eye disease (DED) class and grade of severity by the automated system;

FIG. 194 is a schematic model supporting the automated detection and measurement of thyroid eye disease (TED) in the human eyes using a real-time ophthalmic image processing engine operating on front view digital images of the human eyes formed using a visible wavelength light source;

FIG. 195 sets forth a flow chart describing the primary steps carried out when practicing the machine-vision based method of FIG. 192 involving the processing of time and date stamped digital images of a human eye captured by a mobile smartphone camera system and processed to automatically detect thyroid eye disease (TED) in the human eye at a particular time and date, to support automated ocular disease recognition, treatment and manage care, including predicting dry eye disease (DED) class and grade of severity by the automated system;

FIG. 196 is a schematic representation of a deep-learning machine-vision ocular image processing and classification system (i.e. "engine") of the present invention configured and trained for use and deployment on the system network shown in FIG. 8A, to support and enable an automated method (M38) of method of detection and measurement of entropion/ectropion in the human eyes photographically represented in digital images of a front view of human eyes formed and captured by a mobile smartphone camera system in accordance with the principles of the present invention;

FIG. 197 is a front view digital image representation of a human eye augmented with graphical indications superimposed on the digital image to indicate (i) where entropion/ectropion (E/E) is detected in the photographic image of the human eye, and (ii) which pixel region of interest (ROI) requires pixel data processing according to an automated method of digital image processing using the machine-based ophthalmic image processing engine of FIG. 196 on one or more front view digital images of the human eye, so as to automatically detect entropion/ectropion as an indication of ocular disease recognition, treatment and manage care, including predicting dry eye disease (DED) class and grade of severity by the automated system;

FIG. 198 is a schematic model supporting the automated detection and measurement of entropion/ectropion in the human eyes using a real-time ophthalmic image processing engine operating on front view digital images of the human eyes formed using a visible wavelength light source;

FIGS. 199A and 199B, taken together, set forth a flow chart describing the primary steps carried out when practicing the machine-vision based method of FIG. 196 involving the processing of time and date stamped digital images of a human eye captured by a mobile smartphone camera system and processed to automatically detect entropion/ectropion in the human eye at a particular time and date, to support automated ocular disease recognition, treatment and manage care, including predicting dry eye disease (DED) class and grade of severity by the automated system;

FIG. 200 is a schematic representation of a deep-learning machine-vision ocular image processing and classification system (i.e. "engine") of the present invention configured and trained for use and deployment on the system network shown in FIG. 8A, to support and enable an automated method (M39) of method of detection and measurement of trichiasis/distichiasis (T/D) in the human eyes photographically represented in digital images of a front view of human eyes formed using a visible wavelength light source and captured by a mobile smartphone camera system in accordance with the principles of the present invention;

FIG. 201 is a front view digital image representation of a human eye augmented with graphical indications superimposed on the digital image to indicate (i) where trichiasis/distichiasis (T/D) is detected in the photographic image of the human eye, and (ii) which pixel region of interest (ROI) requires pixel data processing according to an automated method of digital image processing using the machine-based ophthalmic image processing engine of FIG. 200 operating on one or more front view digital images of the human eye, so as to automatically detect trichiasis/distichiasis (T/D) as an indication of ocular disease recognition, treatment and manage care, including predicting dry eye disease (DED) class and grade of severity by the automated system;

FIG. 202 is a schematic model supporting the automated detection and measurement of trichiasis/distichiasis (T/D) in the human eyes using a real-time ophthalmic image processing engine operating on front view digital images of the human eyes formed using a visible wavelength light source;

FIGS. 203A and 203B, taken together, set forth a flow chart describing the primary steps carried out when practicing the machine-vision based method of FIG. 200 involving the processing of time and date stamped digital images of a human eye captured by a mobile smartphone camera system and processed to automatically detect trichiasis/distichiasis (T/D) in the human eye at a particular time and date, to support automated ocular disease recognition, treatment and manage care, including predicting dry eye disease (DED) class and grade of severity by the automated system;

FIG. 204 is a schematic representation of a deep-learning machine-vision ocular image processing and classification system (i.e. "engine") of the present invention configured and trained for use and deployment on the system network shown in FIG. 8A, to support and enable an automated method (M40) of method of detection and measurement of floppy eyelid syndrome (FES) in the human eyes photographically represented in digital images of a front view of human eyes formed and captured by a mobile smartphone camera system in accordance with the principles of the present invention;

FIGS. 205A and 205B show a pair of front view digital image representations of a human eye augmented with graphical indications superimposed on the digital images to indicate (i) where floppy eyelid syndrome (FES) is detected in the photographic image of the human eye, and (ii) which pixel region of interest (ROI) requires pixel data processing according to an automated method of digital image processing using the machine-based ophthalmic image processing engine of FIG. 204 on one or more front view digital images of the human eye, so as to automatically detect floppy eyelid syndrome (FES) as an indication of ocular disease recognition, treatment and manage care, including predicting dry eye disease (DED) class and grade of severity by the automated system;

FIG. 206 is a schematic model supporting the automated detection and measurement of floppy eyelid syndrome (FES) in the human eyes using a real-time ophthalmic image processing engine operating on front view digital images of the human eyes formed using a visible wavelength light source;

FIGS. 207A and 207B, taken together, set forth a flow chart describing the primary steps carried out when practicing the machine-vision based method of FIG. 204 involving the processing of time and date stamped digital images of a human eye captured by a mobile smartphone camera system and processed to automatically detect floppy eyelid syndrome (FES) in the human eye at a particular time and date, to support automated ocular disease recognition, treatment and manage care, including predicting dry eye disease (DED) class and grade of severity by the automated system;

FIG. 208 is a schematic representation of a deep-learning machine-vision ocular image processing and classification system (i.e. "engine") of the present invention configured and trained for use and deployment on the system network shown in FIG. 8A, to support and enable an automated method (M41) of method of detection and measurement of herpes zoster dermatitis (HZD) in the human eyes photographically represented in digital images of a front view of human eyes formed and captured by a mobile smartphone camera system in accordance with the principles of the present invention;

FIG. 209 is a front view digital image representation of a human eye augmented with graphical indications superimposed on the digital image to indicate (i) where herpes zoster dermatitis (HZD) is detected in the photographic image of the human eye, and (ii) which pixel region of interest (ROI) requires pixel data processing according to an automated method of digital image processing using the machine-based ophthalmic image processing engine of FIG. 208 operating on one or more front view digital images of the human eye, so as to automatically detect herpes zoster dermatitis (HZD) as an indication of ocular disease recognition, treatment and manage care, including predicting dry eye disease (DED) class and grade of severity by the automated system;

FIG. 210 is a schematic model supporting the automated detection and measurement of herpes zoster dermatitis (HZD) in the human eyes using a real-time ophthalmic image processing engine operating on front view digital images of the human eyes formed using a visible wavelength light source;

FIG. 211 sets forth a flow chart describing the primary steps carried out when practicing the machine-vision based method of FIG. 208 involving the processing of time and date stamped digital images of a human eye captured by a mobile smartphone camera system and processed to automatically detect herpes zoster dermatitis (HZD) in the human eye at a particular time and date, to support automated ocular disease recognition, treatment and manage care, including predicting dry eye disease (DED) class and grade of severity by the automated system;

FIG. 212 is a schematic representation of a deep-learning machine-vision ocular image processing and classification system (i.e. "engine") of the present invention configured and trained for use and deployment on the system network shown in FIG. 8A, to support and enable an automated method (M42) of method of detection and measurement of herpes zoster keratitis (HZK) in the human eyes photographically represented in digital images of a front view of human eyes formed and captured by a mobile smartphone camera system in accordance with the principles of the present invention;

FIG. 213A is a front view digital image representation of a human face exhibiting herpes zoster keratitis (HZK) in the photographic image of the human eye, and wherein the pixel region of interest (ROI) requires pixel data processing according to an automated method of digital image processing using the machine-based ophthalmic image processing engine of FIG. 212 operating on one or more front view digital images of the human eye, so as to automatically detect herpes zoster keratitis (HZK) as an indication of ocular disease recognition, treatment and manage care, including predicting dry eye disease (DED) class and grade of severity by the automated system;

FIG. 213B is a front view digital image representation of a human eye augmented with graphical indications superimposed on the digital image to indicate (i) where herpes zoster keratitis (HZK) is detected in the photographic image of the human eye, and (ii) which pixel region of interest (ROI) requires pixel data processing according to an automated method of digital image processing using the machine-based ophthalmic image processing engine of FIG. 212 operating on one or more front view digital images of the human eye, so as to automatically detect herpes zoster keratitis (HZK) as an indication of ocular disease recognition, treatment and manage care, including predicting dry eye disease (DED) class and grade of severity by the automated system;

FIG. 214 is a schematic model supporting the automated detection and measurement of herpes zoster keratitis (HZK) in the human eyes using a real-time ophthalmic image processing engine operating on front view digital images of the human eyes formed using a visible wavelength light source;

FIG. 215 set forth a flow chart describing the primary steps carried out when practicing the machine-vision based method of processing time and date stamped digital images of a human eye captured by a mobile smartphone camera system and processed to automatically detect herpes zoster keratitis (HZK) in the human eye at a particular time and date, to support automated ocular disease recognition, treatment and manage care, including predicting dry eye disease (DED) class and grade of severity by the automated system;

FIG. 216 is a schematic representation of a deep-learning machine-vision ocular image processing and classification system (i.e. "engine") of the present invention configured and trained for use and deployment on the system network shown in FIG. 8A, to support and enable an automated method (M43) of method of detection and measurement of herpes simplex virus keratitis (HSVK) in the human eyes photographically represented in digital images of a front view of human eyes formed and captured by a mobile smartphone camera system in accordance with the principles of the present invention;

FIG. 217 is a front view digital image representation of a human eye augmented with graphical indications superimposed on the digital image to indicate (i) where herpes simplex virus keratitis (HSVK) is detected in the photographic image of the human eye, and (ii) which pixel region of interest (ROI) requires pixel data processing according to an automated method of digital image processing using the machine-based ophthalmic image processing engine of FIG. 16 operating on one or more front view digital images of the human eye, so as to automatically detect herpes simplex virus keratitis (HSVK) as an indication of ocular disease recognition, treatment and manage care, including predicting dry eye disease (DED) class and grade of severity by the automated system;

FIG. 218 is a schematic model supporting the automated detection and measurement of herpes simplex virus keratitis (HSVK) in the human eyes using a real-time ophthalmic image processing engine operating on front view digital images of the human eyes formed using a visible wavelength light source;

FIG. 219 sets forth a flow chart describing the primary steps carried out when practicing the machine-vision based method of FIG. 216 involving the processing of time and date stamped digital images of a human eye captured by a mobile smartphone camera system and processed to automatically detect herpes simplex virus keratitis (HSVK) in the human eye at a particular time and date, to support automated ocular disease recognition, treatment and manage care, including predicting dry eye disease (DED) class and grade of severity by the automated system;

FIG. 220 is a schematic representation of a deep-learning machine-vision ocular image processing and classification system (i.e. "engine") of the present invention configured and trained for use and deployment on the system network shown in FIG. 8A, to support and enable an automated method (M44) of method of detection and measurement of ophthalmic post operative complications (OPOS) in the human eyes photographically represented in digital images of a front view of human eyes formed and captured by a mobile smartphone camera system in accordance with the principles of the present invention;

FIG. 221 is a front view digital image representation of a human eye augmented with graphical indications superimposed on the digital image to indicate (i) where ophthalmic post operative complications (OPOS) is detected in the photographic image of the human eye, and (ii) which pixel region of interest (ROI) requires pixel data processing according to an automated method of digital image processing using the machine-based ophthalmic image processing engine of FIG. 220 operating on one or more front view digital images of the human eye, so as to automatically detect ophthalmic post operative complications (OPOS) as an indication of ocular disease recognition, treatment and manage care, including predicting dry eye disease (DED) class and grade of severity by the automated system;

FIG. 222 is a schematic model supporting the automated detection and measurement of ophthalmic post operative complications (OPOS) in the human eyes using a real-time ophthalmic image processing engine operating on front view digital images of the human eyes formed using a visible wavelength light source;

FIGS. 223A and 223B, taken together, set forth a flow chart describing the primary steps carried out when practicing the machine-vision based method of FIG. 220 involving the processing of time and date stamped digital images of a human eye captured by a mobile smartphone camera system and processed to automatically detect ophthalmic post operative complications (OPOS) in the human eye at a particular time and date, to support automated ocular disease recognition, treatment and manage care, including predicting dry eye disease (DED) class and grade of severity by the automated system;

FIG. 224 is a schematic representation of a deep-learning machine-vision ocular image processing and classification system (i.e. "engine") of the present invention configured and trained for use and deployment on the system network shown in FIG. 8A, to support and enable an automated method (M45) of detection and measurement of corneal infection (CI) in the human eyes photographically represented in digital images of a front view of human eyes formed and captured by a mobile smartphone camera system in accordance with the principles of the present invention;

FIG. 225 is a front view digital image representation of a human eye augmented with graphical indications superimposed on the digital image to indicate (i) where ophthalmic post operative complications (OPOS) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect ophthalmic post operative complications (OPOS) as an indication of ocular disease recognition, treatment and manage care, including predicting dry eye disease (DED) class and grade of severity by the automated system;

FIG. 226 is a schematic model supporting the automated detection and measurement of ophthalmic post operative complications (OPOS) in the human eyes using a real-time ophthalmic image processing engine operating on front view digital images of the human eyes formed using a visible wavelength light source;

FIGS. 227A and 227B, taken together, set forth a flow chart describing the primary steps carried out when practicing the machine-vision based method of FIG. 224 involving the processing of time and date stamped digital images of a human eye captured by a mobile smartphone camera system and processed to automatically detect ophthalmic post operative complications (OPOS) in the human eye at a particular time and date, to support automated ocular disease recognition, treatment and manage care, including predicting dry eye disease (DED) class and grade of severity by the automated system;

FIG. 228 is a schematic representation of a deep-learning machine-vision ocular image processing and classification system (i.e. "engine") of the present invention configured and trained for use and deployment on the system network shown in FIG. 8A, to support and enable an automated method (M46) of detection and measurement of corneal foreign body (CFB) in the human eyes photographically represented in digital images of a front view of human eyes formed and captured by a mobile smartphone camera system in accordance with the principles of the present invention;

FIG. 229 is a front view digital image representation of a human eye augmented with graphical indications superimposed on the digital image to indicate (i) where corneal foreign body (CFB) is detected in the photographic image of the human eye, and (ii) which pixel region of interest (ROI) requires pixel data processing according to an automated method of digital image processing using the machine-based ophthalmic image processing engine of FIG. 228 operating on one or more front view digital images of the human eye, so as to automatically detect corneal foreign body (CFB) as an indication of ocular disease recognition, treatment and manage care, including predicting dry eye disease (DED) class and grade of severity by the automated system;

FIG. 230 is a schematic model supporting the automated detection and measurement of corneal foreign body (CFB) in the human eyes using a real-time ophthalmic image processing engine operating on front view digital images of the human eyes formed using a visible wavelength light source;

FIGS. 231A and 231B, taken together, set forth a flow chart describing the primary steps carried out when practicing the machine-vision based method of FIG. 228 involving the processing of time and date stamped digital images of a human eye captured by a mobile smartphone camera system and processed to automatically detect corneal foreign body (CFB) in the human eye at a particular time and date, to support automated ocular disease recognition, treatment and manage care, including predicting dry eye disease (DED) class and grade of severity by the automated system;

FIG. 232 is a schematic representation of a deep-learning machine-vision ocular image processing and classification system (i.e. "engine") of the present invention configured and trained for use and deployment on the system network shown in FIG. 8A, to support and enable an automated method (M47) of method of detection and measurement of acute angle closure glaucoma (AACG) in the human eyes photographically represented in digital images of a front view of human eyes formed and captured by a mobile smartphone camera system in accordance with the principles of the present invention;

FIG. 233 is a front view digital image representation of a human eye augmented with graphical indications superimposed on the digital image to indicate (i) where acute angle closure glaucoma (AACG) is detected in the photographic image of the human eye, and (ii) which pixel region of interest (ROI) requires pixel data processing according to an automated method of digital image processing using the machine-based ophthalmic image processing engine of FIG. 232 operating on one or more front view digital images of the human eye, so as to automatically detect acute angle closure glaucoma (AACG) as an indication of ocular disease recognition, treatment and manage care, including predicting dry eye disease (DED) class and grade of severity by the automated system;

FIG. 234 is a schematic model supporting the automated detection and measurement of acute angle closure glaucoma (AACG) in the human eyes using a real-time ophthalmic image processing engine operating on front view digital images of the human eyes formed using a visible wavelength light source;

FIGS. 235A and 235B, taken together, set forth a flow chart describing the primary steps carried out when practicing the machine-vision based method of FIG. 232 processing time and date stamped digital images of a human eye captured by a mobile smartphone camera system and processed to automatically detect acute angle closure glaucoma (AACG) in the human eye at a particular time and date, to support automated ocular disease recognition, treatment and manage care, including predicting dry eye disease (DED) class and grade of severity by the automated system;

FIG. 236A1 is a schematic illustration showing a mobile visible-wavelength operating smartphone system being used to capture digital images of a user's eyes using the front facing camera in the smartphone camera system so the user can capture images of the user's left eye, right eye or both eyes using the smartphone camera system operating in a bird's eye selfie mode with augmented reality (AR) graphical instructions displayed on the display screen of the smartphone system, for example, in the form of mesh structure using auto-sensing and voice controls, with the image taken automatically when parameters are satisfied;

FIG. 236A2 is a schematic illustration showing a mobile visible-wavelength operating smartphone system being used to capture digital images of a user's eyes using the front facing camera in the smartphone so the user can capture images of the user's left eye, right eye or both eyes using the smartphone camera system operating in a bird's eye selfie mode;

FIG. 236A3 is a schematic illustration showing a mobile visible-wavelength operating smartphone system being used to capture digital images of a user's eyes using the rear facing camera in the smartphone so the user can capture a mirror image of the user's left eye, right eye or both eyes using the smartphone camera system operating in a bird's eye mirror mode with augmented reality (AR) graphical instructions displayed on the display screen of the smartphone system, for example, in the form of mesh structure using auto-sensing and voice controls, with the image taken automatically when parameters are satisfied;

FIG. 236A4 is a schematic illustration showing a mobile visible-wavelength operating smartphone system being used to capture digital images of a user's eyes using the rear facing camera in the smartphone system so the user can capture mirror images of the user's left eye, right eye or both eyes using the smartphone camera system operating in a bird's eye mirror mode using the smartphone camera system operating in a bird's eye mirror mode;

FIG. 236B1 is a schematic illustration showing a mobile visible-wavelength operating smartphone system being used to capture digital images of a patient's eyes using the rear facing camera in the smartphone and a mirror surface, so the user can capture a mirror image of the user's left eye, right eye or both eyes reflected on the mirror surface with augmented reality (AR) graphical instructions displayed on the display screen of the smartphone system, for example, in the form of mesh structure using auto-sensing and voice controls, with the image taken automatically when parameters are satisfied;

FIG. 236B2 is a schematic illustration showing a mobile visible-wavelength operating smartphone system being used to capture digital images of a patient's eyes using the front facing camera in the mobile smartphone and a mirror surface, so the user can capture a mirror image of the user's left eye, right eye or both eyes using the smartphone camera system operating in front facing selfie mode on the display screen of the smartphone;

FIG. 236B3 is a schematic illustration showing a mobile visible-wavelength operating smartphone system being used to capture digital images of a patient's eyes using the front facing camera in the phone and a mirror surface, so the user can capture an image of the user's left eye, right eye or both eyes using the smartphone camera system operating in a front facing selfie mode, with augmented reality (AR) graphical instructions displayed on the display screen of the smartphone system, for example, in the form of mesh structure using auto-sensing and voice controls, with the image taken automatically when parameters are satisfied;

FIG. 236B4 is a schematic illustration showing a mobile visible-wavelength operating smartphone system being used to capture digital images of a patient's eyes using the front facing camera in the phone so the user can capture an image of the user's left eye, right eye or both eyes using the smartphone camera system operating in front facing selfie mode on the display screen of the smartphone;

FIG. 236C1 is a schematic illustration showing a mobile visible-wavelength operating smartphone system being used to capture digital images of a user's eyes using the front facing camera in the phone so the user can capture an image of the user's left eye, right eye or both eyes using the smartphone camera system operating in a side angle mirror mode with augmented reality (AR) graphical instructions displayed on the display screen of the smartphone system, for example, in the form of mesh structure using auto-sensing and voice controls, with the image taken automatically when parameters are satisfied;

FIG. 236C2 is a schematic illustration showing a mobile visible-wavelength operating smartphone system being used to capture digital images of a user's eyes using the front facing camera in the phone so the user can capture an image of the user's left eye, right eye or both eyes using the smartphone camera system operating in a side angle mirror mode;

FIG. 236C3 is a schematic illustration showing a mobile visible-wavelength operating smartphone system being used to capture digital images of a user's eyes using the rear facing camera in the phone so the user can capture a mirror image of the user's left eye, right eye or both eyes using the smartphone camera system operating in a side angle selfie mode with augmented reality (AR) graphical instructions displayed on the display screen of the smartphone system, for example, in the form of mesh structure using auto-sensing and voice controls, with the image taken automatically when parameters are satisfied;

FIG. 236C4 is a schematic illustration showing a mobile visible-wavelength operating smartphone system being used to capture digital images of a user's eyes using the rear facing camera in the phone so the user can capture a mirror image of the user's left eye, right eye or both eyes using the smartphone camera system operating in a side angle selfie mode using the smartphone camera system operating in a side angle selfie mode;

FIG. 236D1 is a schematic illustration showing a mobile visible-wavelength operating smartphone system being used to capture digital images of a user's eyes using the front facing camera in the phone so the user can capture an image of the user's left eye, right eye or both eyes using the smartphone camera system operating in a worm's eye selfie mode with augmented reality (AR) graphical instructions displayed on the display screen of the smartphone system, for example, in the form of mesh structure using auto-sensing and voice controls, with the image taken automatically when parameters are satisfied;

FIG. 236D2 is a schematic illustration showing a mobile visible-wavelength operating smartphone system being used to capture digital images of a user's eyes using the rear facing camera in the phone so the user can capture a mirror image of the user's left eye, right eye or both eyes using the smartphone camera system operating in a worm's eye selfie mode with augmented reality (AR) graphical instructions displayed on the display screen of the smartphone system, for example, in the form of mesh structure using auto-sensing and voice controls, with the image taken automatically when parameters are satisfied;

FIG. 236D3 is a schematic illustration showing a mobile visible-wavelength operating smartphone system being used to capture digital images of a user's eyes using the rear facing camera in the phone so the user can capture a mirror image of the user's left eye, right eye or both eyes using the smartphone camera system operating in a worm's eye mirror mode;

FIG. 236D4 is a schematic illustration showing a mobile visible-wavelength operating smartphone system being used to capture digital images of a user's eyes using the front facing camera in the phone so the user can capture a mirror image of the user's left eye, right eye or both eyes using the smartphone camera system operating in a worm's eye selfie mode using the smartphone camera system operating in a worm's eye selfie mode;

FIG. 237 is a graphical representation of an exemplary graphical user interface (GUI) displayed on the mobile tablet computer shown in FIG. 12B, and used by an ophthalmologist and/or medical administrator in a clinical or like setting, or on the road, to enable/disable the machine-vision based methods of image processing, indexed as M1 through M47 and illustrated in FIGS. 46 through 235B, and/or other services supported on the system network of the present invention;

FIGS. 238A and 238B, taken together, set forth a flow chart describing the primary steps of a method of operating an automated ophthalmic image capturing and processing system of the present invention configured to enable automated machine-assisted detection of dry eye conditions in the human eye, prescription of treatment, and response assessment of prescribed treatment, by processing a series of digital images of the human eye captured by a mobile digital camera system used by anyone, including an ophthalmologist, optometrist and lay people alike;

FIGS. 239A and 239B, taken together, set forth a flow chart describing the primary steps of a method of operating an automated ophthalmic image capturing and processing system and training the same using digital images of the human eye captured by a mobile smartphone camera system and manually indexed by an ophthalmologist;

FIG. 240 is a sets forth a flow chart describing the primary steps of a method of operating an automated ophthalmic image capturing and processing system and training the same using ophthalmic images indexed with specific ocular conditions determined by eye specialists (e.g. ophthalmologists, optometrists, or other subject matter experts) and storing these indexed images in an indexed ophthalmic image library, and using these indexed ophthalmic images to train deep learning driven machine-vision systems;

FIG. 241 is a wireframe model of a graphical user interface (GUI) displayed on the mobile smartphone camera system, for use by a patient to collect patient history data and supply the same to the system;

FIG. 242 is a wireframe model of a graphical user interface (GUI) displayed on the mobile smartphone camera system, for use by a patient to provide patient symptom data (e.g. pain experienced) to the system;

FIG. 243 is a wireframe model of a graphical user interface (GUI) displayed on the mobile smartphone camera system, for use by a patient to provide patient exam and in-office testing data collection to the system;

FIG. 244 is a wireframe model of an exemplary graphical user interface (GUI) displayed on the mobile smartphone camera system, for use by a patient during mobile vision testing operations, and providing such vision testing data to the system network accordance with the present invention;

FIG. 245 is a schematic representation of a mobile vision test supported by the mobile smartphone camera system;

FIG. 246 is a wireframe model of a graphical user interface (GUI) displayed on the mobile smartphone camera system, for use by a patient to capture image data from the patient's eyes from different smartphone camera viewing angles specified in FIGS. 14A1 through 14D4, and provide the same to the system network for image processing using the automated machine-vision image processing methods according to the principles of the present invention described in FIGS. 34A, 34B, 46-64B and 82-237B to automatically detect, recognize and/or measure ocular disease conditions, including but not limited to, tear meniscus height (TMH), conjunctival injection, scruff at eyelashes, meibomian gland dysfunction, dermatochalasis, and conjunctivochalasis;

FIG. 247 is a wireframe model of a graphical user interface (GUI) displayed on the mobile smartphone camera system, for use by a patient to capture video data of the patient's eyes and provide the same to the system for image processing using automated machine-vision video processing methods according to the principles of the present invention described in FIGS. 34C, and 65-81 to automatically detect, recognize and measure ocular disease conditions such as, but not limited to, blink rate per minute, blink interval, blink duration, blink speed and partial blinks per minute;

FIG. 248 is a schematic representation illustrating some of the primary patient diagnostic factors that are used by the system of the present invention using images/videos, vision test, symptoms, risk factors, functionality, environmental factors to automatically recognize the patient's ocular disease, and its grade/severity experience by the patient automatically determined using the machine-vision imaging processing methods of the present invention;

FIG. 249 is a wireframe model of a graphical user interface (GUI) displayed on the mobile smartphone camera system, for use by a patient to receive an ocular disease treatment prescription generated by from the system network using automated machine-vision processing methods according to the principles of the present invention;

FIG. 250 is a schematic representation of the daily treatment response supported by the system of the present invention, in response to patient data factors such as risk factors, exam and in-office testing, vision functionality, image/video data, symptoms, and treatment compliance;

FIG. 251 is a wireframe model of a graphical user interface (GUI) displayed on the mobile smartphone camera system, for use by a patient to capture daily digital image and video data about the current condition of the patient's eyes, from different smartphone camera viewing angles specified in FIGS. 236A1 through 236D4, and to provide the same to the automated machine-vision image processing system (i.e. engines) for image processing in accordance with the principles of the present invention;

FIG. 252 is a schematic representation of the system network of the present invention deploying one or more automotive systems, each provided with an onboard ophthalmic image capturing and processing subsystem supporting real-time automated machine-assisted recognition of ocular disease (OD), and other ocular disease conditions in the eyes of the automotive system driver, and showing (i)

digital image capturing systems operating a visible-wavelengths and/or IR wavelengths, embedded and/or integrated into the automotive system, for use by driver/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 253 is a schematic representation of the system network of the present invention deploying one or more aircraft systems, each provided an with onboard ophthalmic image capturing and processing subsystem supporting real-time automated machine-assisted recognition of dry eye and other ocular disease conditions in the eyes of the aircraft pilot, and showing (i) digital image capturing systems operating a visible-wavelengths and/or IR wavelengths, and embedded or integrated into the aircraft system, for use by the pilot/users whose eyes are to be monitored and cared for using the system of the present invention, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 254 is a schematic representation of the system network of the present invention deploying one or more industrial machinery systems, each provided with an onboard ophthalmic image capturing and processing subsystem supporting real-time automated machine-assisted recognition of dry eye and other ocular disease conditions in the eyes of the operator, and showing (i) digital image capturing systems operating a visible-wavelengths and/or IR wavelengths, embedded or integrated into the systems, for use by operator/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 255 is a schematic representation of the system network of the present invention deploying one or more office workstation systems, each provided with an onboard ophthalmic image capturing and processing subsystem supporting real-time automated machine-assisted recognition of dry eye and other ocular disease conditions in the eyes of the worker, and showing (i) digital image capturing systems operating a visible-wavelengths and/or IR wavelengths, and embedded or integrated into the systems, for use by worker/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 256 is a schematic representation of the system network of the present invention deploying one or more laptop computer systems, each provided with an onboard ophthalmic image capturing and processing subsystem supporting real-time automated machine-assisted recognition of dry eye and other ocular disease conditions in the eyes of the user, and showing (i) digital image capturing systems operating a visible-wavelengths and/or IR wavelengths, and embedded or integrated into the systems, for use by users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 257 is a schematic representation of the system network of the present invention deploying one or more video game systems, each provided with an onboard ophthalmic image capturing and processing subsystem supporting real-time automated machine-assisted recognition of dry eye and other ocular disease conditions in the eyes of the gamer, and showing (i) digital image capturing systems operating a visible-wavelengths and/or IR wavelengths, and embedded or integrated into the systems, for use by gamer/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (DOD) recognition engine, and (v) a TCP/IP internet infrastructure (i.e. cloud infrastructure) supporting a wireless digital data packet-switched communication infrastructure to support the many systems integrated within the system network of the present invention;

FIG. 258 is a schematic representation of the system network of the present invention deploying one or more telemedicine/telehealth systems, each provided with an onboard ophthalmic image capturing and processing subsystem supporting real-time automated machine-assisted recognition of dry eye and other ocular disease conditions in the eyes of the gamer, and showing (i) mobile digital image capturing systems for use by patient/users whose eyes are to be monitored and cared for using the system of the present invention, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 259 is a schematic representation of the system network of the present invention deploying one or more smart television TV systems, each provided with an onboard ophthalmic image capturing and processing subsystem supporting real-time automated machine-assisted recognition of dry eye and other ocular disease conditions in the eyes of the gamer, and showing (i) digital image capturing systems operating a visible-wavelengths and/or IR wavelengths, and embedded or integrated into the smart television systems, for use by for use by viewer/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 260 is a schematic representation of the system network of the present invention deploying one or more smart glasses systems, each provided with an onboard ophthalmic image capturing and processing subsystem supporting real-time automated machine-assisted recognition of dry eye and other ocular disease conditions in the eyes of the gamer, and showing (i) digital image capturing systems operating a visible-wavelengths and/or IR wavelengths, and embedded or integrated into the smart glasses systems, for use by viewer/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention;

FIG. 261 is a schematic representation of the system network of the present invention deploying one or more smart contact lens systems, each provided with an onboard ophthalmic image capturing and processing subsystem supporting real-time automated machine-assisted recognition of dry eye and other ocular disease conditions in the eyes of the gamer, and showing (i) digital image capturing systems operating a visible-wavelengths and/or IR wavelengths, and embedded or integrated into the smart contact lens systems, for use by wearer/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention; and FIG. 262 is a schematic representation of the system network of the present invention deploying one or more VR/AR headset systems, each provided with an onboard ophthalmic image capturing and processing subsystem supporting real-time automated machine-assisted recognition of dry eye and other ocular disease conditions in the eyes of the gamer, and showing (i) digital image capturing systems operating a visible-wavelengths and/or IR wavelengths, and embedded or integrated into the AR/VR headsets, for use by wearer/users whose eyes are to be monitored and cared for using the system of the present invention, (ii) remote clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention.

DETAILED DESCRIPTION OF THE ILLUSTRATIVE EMBODIMENTS OF THE PRESENT INVENTION

Referring to the figures in the accompanying Drawings, the illustrative embodiments of the system and will be described in great detail, wherein like elements will be indicated using like reference numerals.

Figure 7:
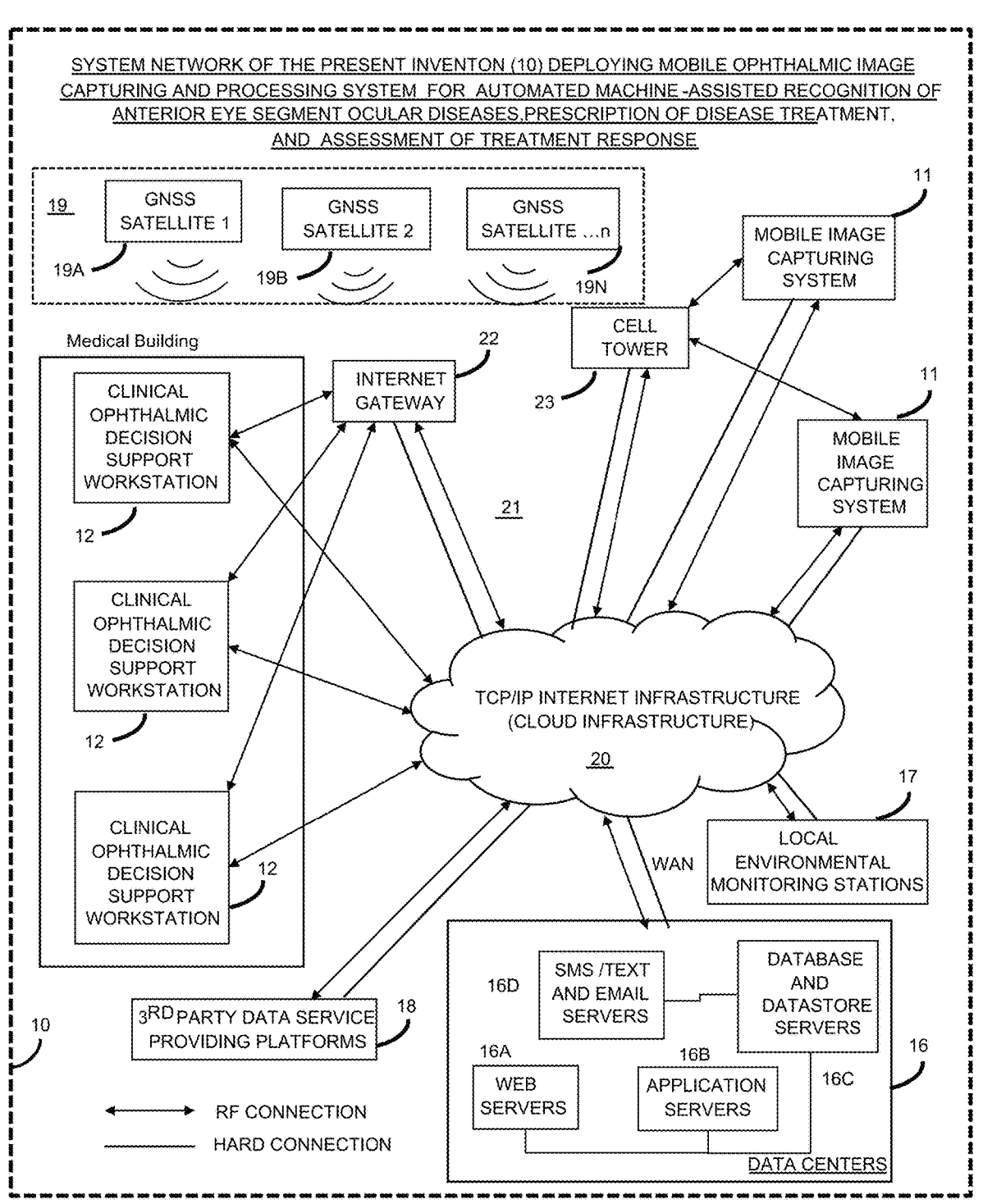
FIG. 7 is a schematic representation of a mobile ophthalmic image capturing and processing system network of the present invention adapted for automated machine-vision assisted recognition of ocular diseases and ocular disease (OD) conditions including, but not limited to, dry eye disease (DED) and other anterior eye segment ocular diseases (OD), prescription of ocular disease treatment, and managed assessment of the treatment response, comprising (i) mobile visible-wavelength operating smartphone image capturing systems for use by patients and users whose eyes are to be monitored and cared for using the system of the present invention, (ii) clinical ophthalmic decision workstations, and real-time ophthalmic image driven ocular disease (OD) condition recognition engines realized and supported within data centers deployed around the world, (iii) local environmental monitoring stations and third-party data provider platforms, (iv) a global navigation satellite system (GNSS) comprising a constellation of GNSS satellites orbiting around the earth for GPS positioning of objects carrying GNSSS receivers (or GNSS transceivers), (v) a data center supporting web, application and database servers to support the functions and services to be delivered by the system network of the present invention including a machine-vision driven ocular disease (OD) recognition engine, and (v) a TCP/IP internet infrastructure (i.e. cloud infrastructure) supporting a wireless digital data packet-switched communication infrastructure to support the many systems integrated within the system network of the present invention.

Specification of a System Network of the Present Invention Deploying the Mobile Ophthalmic Image Capturing and Processing System of the Present Invention Adapted for Automated Machine-Assisted Recognition of Dry Eye Disease and Other Anterior Eye Segment Diseases, Prescription of Treatment, and Assessment of Treatment Response FIG. 7 shows the mobile ophthalmic image capturing and processing system of the present invention 10 adapted for automated machine-assisted recognition of dry eye disease and other anterior eye segment diseases, prescription of treatment, and assessment of treatment response. As shown, the system network 10 comprises: (i) smartphone mobile image capturing systems 11 for use by patients and users whose eyes are to be monitored and care for using the system of the present invention; (ii) clinical ophthalmic decision workstations 12, and real-time ophthalmic image driven dry eye disease (DED) condition recognition engines 13 and automated treatment prescription engines 14 and treatment compliance management engines 15, realized and supported within data centers 16 deployed around the world; (iii) local environmental monitoring stations 17 and third-party data provider platforms 18; (iv) a global navigation satellite system (GNSS) 19 comprising a constellation of GNSS satellites orbiting around the earth for GPS position-ing of objects carrying GNSSS receivers (or GNSS trans-ceivers); (v) a data center 16 supporting web, application and database servers 16A, 16B, 16C to support the functions and services to be delivered by the system network 10 of the present invention including a machine-vision driven dry eye disease (DED) recognition engine 13, treatment engine 14 and treatment management and compliance engine 15; and (v) a TCP/IP internet infrastructure (i.e. cloud infrastructure) 20 supporting a wireless digital data packet-switched com-munication infrastructure to support the many systems inte-grated within the system network of the present invention.

As shown in FIG. 7, the system network 10 further comprises: (i) a cloud-based TCP/IP network architecture 20 supporting a plurality of GNSS satellites 19 transmitting GNSS signals towards the earth 21 and objects below; an Internet Gateway 22 providing the mobile smartphones 11 and clinical workstations 12 wireless and/or wired access to the Internet communication infrastructure 20; a cell tower 23 for supporting cellular data communications across the system network 10 and providing the mobile smartphones 11 and clinical workstations 12 wireless access to the Internet infrastructure 20; a local weather station 17 (e.g. including NOAA, and other national and state weather services) and numerous media servers 18 (e.g. Google, Facebook, NOAA, etc.) operably connected to the infrastructure of the Internet.

In general, the network of mobile computing systems 11 will run enterprise-level mobile application software, oper-ably connected to the TCP/IP infrastructure of the Internet 20. The industrial-strength data centers 16, are preferably mirrored with each other and running Border Gateway Protocol (BGP) between its router gateways, in a manner well known in the data center art. Each mobile computing system 11 is provided with GPS-tracking and having wire-less internet connectivity with the TCP/IP infrastructure of the Internet 20, using various communication technologies (e.g. GSM, Bluetooth and other wireless networking proto-cols well known in the wireless communications arts).

As shown in FIG. 7, each data center 16 comprises: a cluster of communication servers 16A for supporting http and other TCP/IP based communication protocols on the Internet; cluster of application servers 16B; a cluster of email processing servers 16D; cluster of SMS servers 16E; and a cluster of RDBMS servers 16C configured within an distributed file storage and retrieval ecosystem/system, and interfaced around the TCP/IP infrastructure of the Internet 20 well known in the art.

As shown in FIG. 8A, the mobile ophthalmic image capturing and processing system network 10 comprises: (i) mobile image capturing systems 11 (e.g. smartphones, lap-tops, tablets, etc.) for use by patients and users whose eyes are to be monitored and care for using the system of the present invention; (ii) clinical ophthalmic decision worksta-tions 12, and real-time ophthalmic image driven dry eye disease (DED) condition recognition, treatment and man-agement engines 13, 14 and 15, respectively, realized and supported within data centers 16 deployed around the world; (iii) local environmental monitoring stations 17 and third-party data provider platforms 18; (iv) a global navigation satellite system (GNSS) 19 comprising a constellation of GNSS satellites orbiting around the earth for GPS position-ing of objects carrying GNSS/GPS transceivers; (v) a data center 16 supporting web, application and database servers 16A, 16B and 16C to support the functions and services to be delivered by the system network of the present invention including a machine-vision driven dry eye disease (DED) recognition engine 13; and (v) a TCP/IP internet infrastruc-ture (i.e. cloud infrastructure) 20 supporting a wireless digital data packet-switched communication infrastructure to support the many systems integrated within the system network of the present invention.

As shown in FIG. 8A, the web, application and database servers 16A, 16B and 16C, respectively, support and realize the following image and information processing engines of the present invention, namely: a real-time ocular disease (OD) condition recognition engine 13 provided with logic kernel K1; a real-time OD treatment prescription engine 14 provided with logic kernel K2; and a real-time image-processing based OD treatment compliance engine 15 provided with logic kernel K3; and other analytical engines described herein; each of which is specified in great technical detail hereinbelow.

Specification of the Real-Time Ocular Disease (OD) Condition Recognition Engine of the Present Invention, Supported by Logic Kernel K1 and Capable of Auto-Recognizing Many Different Classes of Ocular Disease (OD) Conditions in Response to Patient Data and Ocular Image Input The Disease Diagnosis Input Factors and Diagnostic Logic contained in the machine-based logic packages specified in FIGS. 36A through 36UUU provide the logic kernel K1 that is installed within the real-time ocular disease (OD) condition recognition engine 13 deployed within the system of the present invention shown in FIG. 8A. As shown in each logic package, the logic kernel K1 specifies two key components of the logic kernel K1, namely: (i) the various detectable patient/ocular disease data factors that are known to contribute to each of the many different classes of ocular disease (OD) conditions automatically recognizable by the automated OD condition recognition engine of the present invention 13 once properly trained and configured to do so as taught herein; and (ii) the various machine-vision image/video processing methods (indexed as M1 through 48) which the machine-vision processing engine 13 of the present invention is configured to perform for the purpose of automatically recognizing specific ocular disease conditions, using the extensive library of machine-vision image processing methods (M1 through M47) specified in great detail in FIGS. 47 through 239B.

Notably, the Diagnostic Logic provides a set of symbolic rules for the logic kernel K1, executed within the automated ocular disease (OD) condition recognition engine of the present invention 13. As shown, each rule specifies the various input factors (i.e. using patent data and detected ocular features in the machine-vision processed images) which, if detected by the system for a given set of patient ophthalmic images, then the system will automatically classify the patient images as indicating a particular ocular disease (DED) or other specified ocular condition present in the examined eyes of the patient or system user. Ideally, the real-time ocular disease recognition engine 13 will include logic indicating the various detectable input factors (i.e. patient data and detectable image features) that are known to contribute to the specific grading of the severity of a particular ocular disease (OD) condition classified by the automated OD recognition engine of the present invention 13.

Thus, in the present embodiment of the present invention, the logic kernel K1 will support automated grading of the severity of a dry eye disease (DED) condition automatically classified by the automated OD condition recognition engine of the present invention. Symbolic class grading rules can be executed within the automated ocular disease (OD) condition recognition engine, for automatically grading the specific severity of the classified DED condition based on the input factors automatically detected by the system. Based on current conventions in the ophthalmic practice, there are four grades of severity: I; II; III; and IV, where grade I is the least severe, and grade IV the most severe. Notably, according to current conventions, there are at least 27 different factors that may contribute to the four grades of severity in the illustrative embodiment of the present invention. More or less factors may contribute to, or factor into, any particular embodiment of the present invention.

Specification of the Real-Time Ocular Disease (OD) Treatment Prescription Engine of the Present Invention, Supported by Logic Kernel K2 and Capable of Automatically Prescribing Recommended Treatment Different Classes of Ocular Disease (OD) Automatically Recognized by the Automated Ocular Disease Condition Recognition Engine of the Present Invention The Treatment Logic contained in the machine-based packages specified in FIGS. 36A through 36UUU provides the logic kernel K2 that is installed and executed within the automated ocular disease treatment prescription engine 14 deployed within the system of the present invention shown in FIG. 8A. As shown in each logic package, each rule specifies a recommended course of prescribed treatment for a given set of detected input patient data factors and/or automatically classified OD conditions, applicable over a specified period of time while being managed by the system network using the automated treatment compliance engine 15 of the present invention.

Specification of the Real-Time Ocular Disease (OD) Treatment Compliance Engine of the Present Invention, Supported by Logic Kernel K3 and Capable of Automatically Monitoring and Managing Patient Compliance with Respect to Different Classes of Ocular Disease (OD) Treatment Automatically Prescribed by the Treatment Prescription Engine of the Present Invention The Management Logic contained in the machine-based logic packages specified in FIGS. 36A through 36UUU provides the logic kernel K3 that is installed and executed within the ocular disease treatment management (i.e. compliance) engine of the present invention 15 shown in FIG. 8A. As shown in each logic package, each rule specifies various classification-based modifications to OD condition treatments prescribed by the treatment prescription engine, and these recommended modifications will be automatically triggered and applied upon automated detection of the specified antecedent conditions during machine-vision examination operations and treatment compliance operations, to automatically specify how the prescribed course of treatment should be modified and managed, if at all, given the treatment response data factors collected and provided to the system network.

Figure 8B:
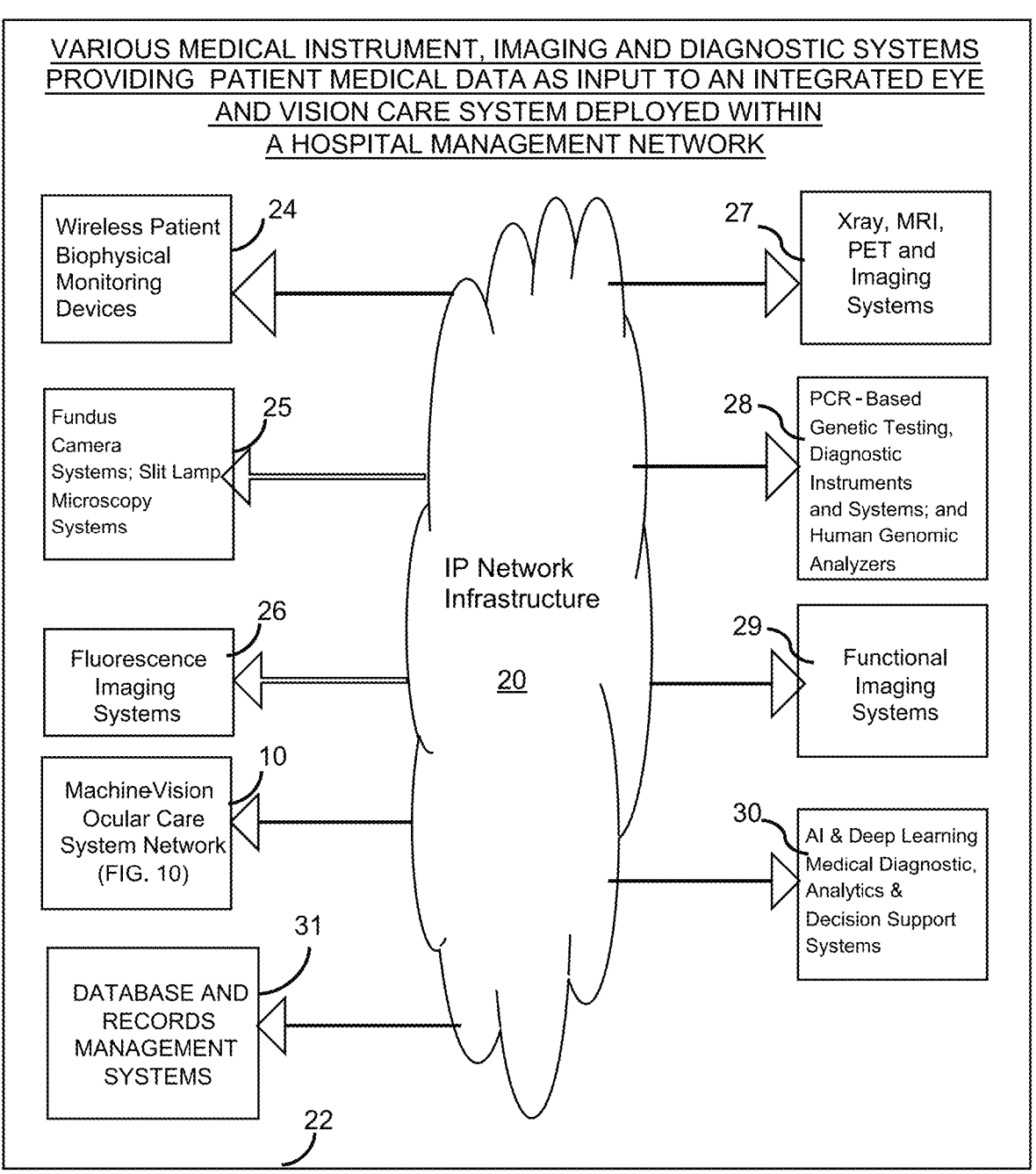
FIG. 8B is a schematic representation showing an ecosystem of systems, networks and medical instruments deployed in a large scale hospital management system covering many hospitals, clinics and medical practices, and including slit-lamp microscope systems, fundus camera systems, fluorescence imaging systems, X-Ray systems, Mill systems, PET systems and imaging systems, functional imaging systems, PCR-based diagnostic systems, genetic/genome diagnostic instruments and systems, AI deep-learning medical diagnostic, analytics and decision support systems, and the mobile machine-vision ocular care image system of the present invention shown in FIGS. 7 and 8A, described throughout the Drawings in the present Patent Specification, comprising a system input/output subsystem, a patient history data processing subsystem, a patient eye image data processing subsystem, a patient eye video data processing subsystem, mobile vision testing data processing subsystem, a patient symptom data processing subsystem, a vision functionality data processing subsystem, an environmental factors data processing subsystem, an exam and in-office testing data processing subsystem, an automated ocular disease (OD) recognition engine, an automated OD treatment prescription engine of the present invention, and a DED treatment compliance data processing subsystem (e.g. treatment compliance engine), configured as shown therein.

Specification of the Ecosystem of System Networks and Medical Instruments and Systems Deployed in a Large Scale Hospital Management System Covering Many Hospitals, Clinics and Medical Practices, Wherein the Systems of the Present Invention May be Installed and Deployed As shown in FIG. 8B, an ecosystem 22 of system networks and medical instruments and systems are deployed in a large scale hospital management system 23 covering many hospitals, clinics and medical practices 23, including wireless patient biophysical monitoring devices (e.g. Apple® watch, FitBit® device, etc.) 24, slit-lamp microscope systems and fundus camera systems 25, fluorescence imaging systems 26, X-Ray, machine-vision ocular care systems 10, PET and imaging systems 27, PCR-based diagnostic and genetic and diagnostic instruments and systems 28, functional imaging systems 29, AI and deep-learning medical diagnostic, analytics and decision support systems 30, and including the mobile machine-vision based ocular care image capturing and processing systems of the present invention shown in FIGS. 7, 8A, 8B, 9A and 10A and described throughout the Drawings in the Present Application; and database and records management systems 31, integrated within the infrastructure of the Internet 20.

As shown in FIG. 9A, the mobile ophthalmic image capturing and processing system 35 comprises: a system input/output subsystem 36; a patient history data processing subsystem 37; a patient eye image data processing subsystem 38; a patient eye video data processing subsystem 39; a mobile vision testing data processing subsystem 40; a patient symptom data processing subsystem 41: a vision functionality data processing subsystem 42; an environmental factors data processing subsystem 43: an exam and in-office testing data processing subsystem 44; an automated ocular disease (OD) recognition engine 13; an automated OD treatment prescription engine 14: and an OD treatment compliance data processing subsystem (e.g. treatment compliance engine) 15 configured as shown therein.

Figure 9B:
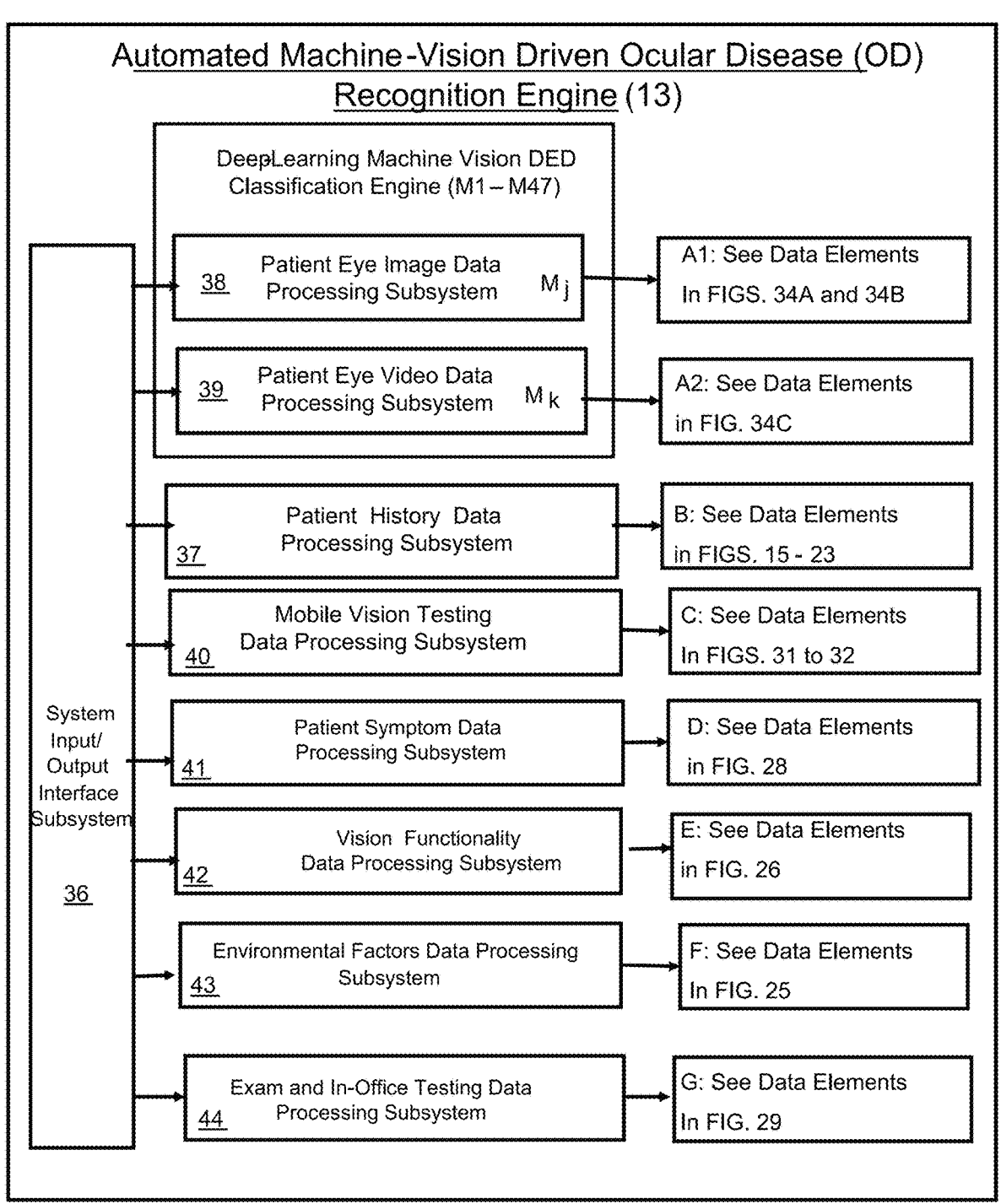
FIG. 9B is a schematic representation of the system architecture of FIG. 9A, illustrating the various data inputs provided continuously to the automated machine-vision driven ocular disease (OD) recognition engine of the present invention.
Figure 10:
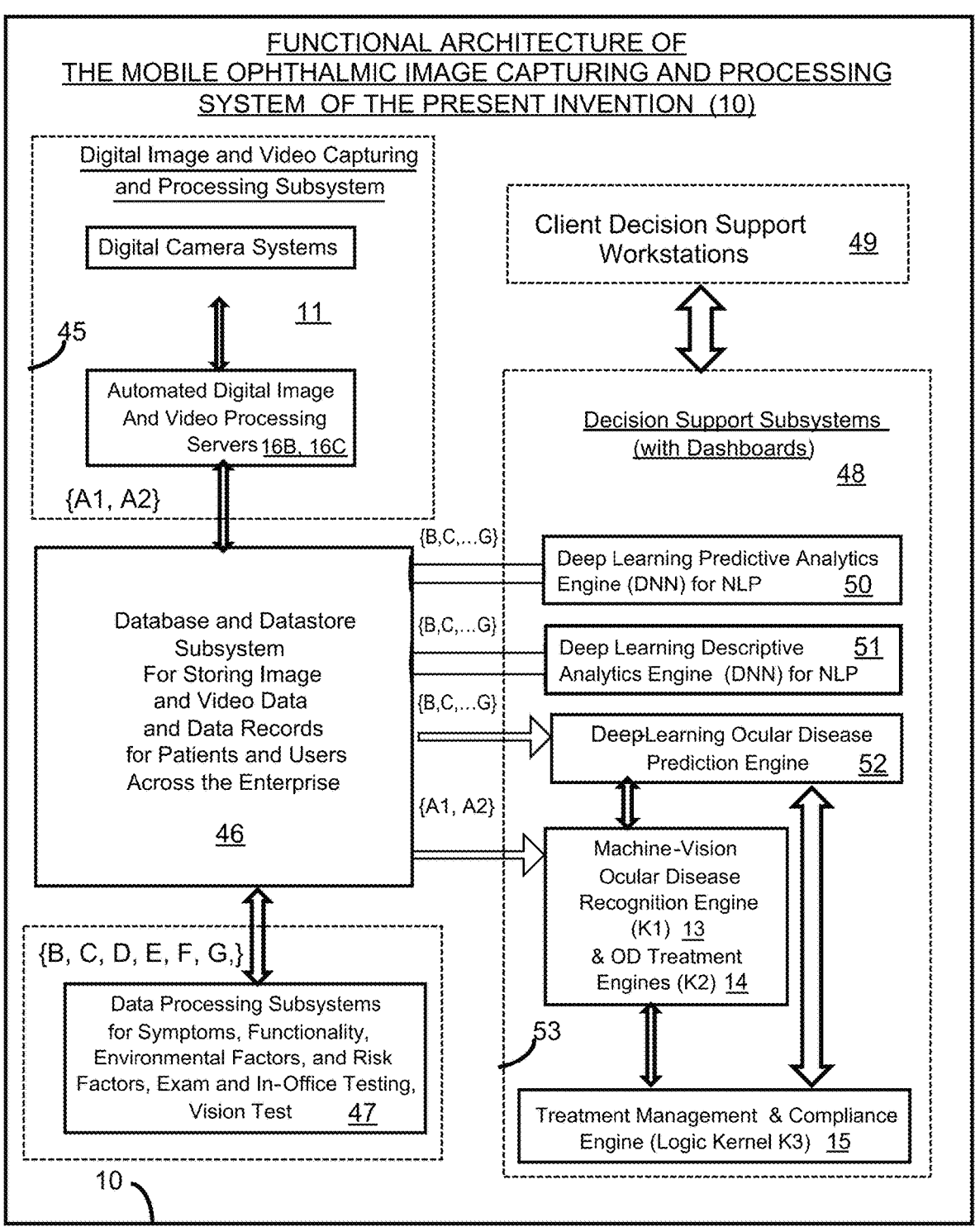
FIG. 10 is a schematic representation of the functional subsystems supported within the mobile ophthalmic image capturing and processing system of the present invention shown in FIGS. 7, 8A, 8B 9A, 9B, namely, a digital image and video capturing and processing subsystem comprising an array of mobile digital (e.g. smartphone) camera systems in wireless communication with an automated digital image processing server(s) realized within an enterprise-level data center having a database subsystem for storing data and maintaining data records for patients and users across the entire enterprise, and supporting decision support subsystems including a deep-learning predictive analytics subsystem, a deep-learning descriptive analytics engine, a deep-learning ocular disease prediction engine, a deep-learning machine-vision ocular disease recognition engine, and a treatment management and compliance engine subsystem, each being accessible via workstations, tablet computers and laptop workstations deployed across the system network.

FIG. 9B illustrates the various data inputs provided continuously to the automated ocular disease (OD) recognition engine 13 of the present invention. As shown, patient eye image data elements A1 is described in FIGS. 34A and 34B. Patient eye video data elements A2 are described in FIG. 34C. Patent history data elements B are described in FIGS. 15 through 23. Mobile vision testing data elements C are described in FIGS. 31 through 32. Patient symptom data elements D are described in FIG. 28. Vision functionality data elements E are described in FIG. 26. Environmental factors data elements F are described in FIG. 25. Exam and in-office Testing Data Elements G are described in FIG. 29. Specification of Primary Functional Subsystems Supported within the Mobile Ophthalmic Image Capturing and Processing System of the Present Invention FIG. 10 shows the functional subsystems supported within the mobile ophthalmic image capturing and processing system of the present invention 10 shown in FIGS. 7, 8A, 8B, 9A and 9B, namely: (i) a digital image and video capturing and processing subsystem 45 comprising an array of mobile smartphone camera systems 11 supported by an array of an automated digital image processing servers 41 realized within the enterprise-level data center 16 having communication (e.g. Web), application and database servers; (ii) a database and datastore subsystem 46 for storing data and maintaining data records for patients and users across the entire mobile enterprise; (iii) data processing subsystems 47 for receiving and processing data relating to patient symptoms, vision functionality, patient environmental factors, patient risk factors, patient examination and in-office testing, and patient mobile vision testing, {B, C, D, E, F G}, and storing output data elements in the database and datastore subsystem 42 for use by the other system; (iv) decision support subsystems 48 with dashboards, including a deep-learning predictive analytics engine 49 (i.e. Deep Neural Networks—DNNs) configured and trained for national language processing (NLP) receiving and processing data elements {B, C, . . . , G}, a deep-learning descriptive analytics engine (DNN) 51 configured and trained for NLP receiving and processing data elements {B, C, . . . , G}, a deep-learning ocular disease (OD) prediction engine 52 receiving and processing data elements {B, C, . . . , G}, a deep-learning machine-vision ocular disease (OD) recognition and treatment engine 35, including an OD recognition engine 13 for receiving and processing data elements {A1, A2}, and an OD treatment prescription engine 14, and a treatment management compliance engine 15; and (v) a clinical decision support subsystems 49 realized as workstations, tablet computers and laptop workstations, each with geolocation (GPS) tracking and brick-and-mortar commerce linking capabilities, to make finding stores selling eye care products in the vicinity of specific GPS-coordinates resolved on any given mobile computing system (e.g. mobile smartphone camera system).

FIG. 11 lists the various functions supported by the system network of the present invention 10, namely: Collecting Patient History Data; Supporting Exam and In-Office Testing; Supporting Mobile Vision Testing; Collecting Symptom Data; Collecting Vision Functionality Data; Collecting Environmental Factor Data; Collecting Risk Factors Data; Supporting Image and Video Capture; Capturing Dry Eye Image Features; Capturing Dry Eye Video Features; Clinical Decision Support System for Diagnosis; Supporting Clinical Decisions for Monitoring and Assessing Treatment Response in Patients; Supporting Clinical Decisions for Therapeutics & Prevention; Automated Alerts from System; Compliance Monitoring; Machine-Vision Image and Video Analysis; Teleconsultation; Geolocation; and Data Integration. These functions will be described in greater detail hereinafter.

Methods of Design and Implementation of the System Network of the Present Invention In general, regardless of the method of implementation employed, the system network of the present invention 10 will be in almost all instances, realized as an industrial-strength, carrier-class Internet-based network of having a cloud-based distributed computing and data storage architecture. Also, the system network will be deployed over a global data packet-switched communication network comprising numerous computing systems and networking components, as shown. As such, the information network of the present invention is often referred to herein as the "system" or "system network".

Preferably, although not necessary, the system network 10 would be designed according to object-oriented systems engineering (DOSE) methods using UML-based modeling tools such as ROSE by Rational Software, Inc. using an industry-standard Rational Unified Process (RUP) or Enterprise Unified Process (EUP), both well known in the art. Implementation programming languages can include C, Objective C, C, Java, PHP, Python, Google's GO, and other computer programming languages known in the art. The Internet-based system network can be implemented using any integrated development environment (IDE) such as for example: the Java Platform, Enterprise Edition, or Java EE (formerly J2EE); Websphere IDE by IBM; Weblogic IDE by BEA; a non-Java IDE such as Microsoft's .NET IDE; or other suitably configured development and deployment environment well known in the art. Preferably, the system network 10 is deployed as a three-tier server architecture with a double-firewall, and appropriate network switching and routing technologies well known in the art. In some deployments, private/public/hybrid cloud service providers, such Amazon Web Services (AWS), may be used to deploy Kubernetes, an open-source software container/cluster management/orchestration system, for automating deployment, scaling, and management of containerized software applications, such as the mobile enterprise-level application described above. Such practices are well known in the computer programming, networking and digital communication arts.

Specification of Database Schema for the Database Component Used on the System Network of the Present Invention During the design and development of the system network 10, a data schema will be created for the object-oriented system-engineered (DOSE) software component thereof, for execution on a client-server architecture. In general, the software component of the system network will consist of classes, and these classes can be organized into frameworks or libraries that support the generation of graphical interface objects within GUI screens, control objects within the application or middle layer of the enterprise-level application, and enterprise or database objects represented within the system database (RDBMS) 16C.

Preferably, the RDBMS maintained within the database server 16C will be structured according to a database schema comprising enterprise objects, represented within the system database (e.g. RDBMS), and including, for example: patient; doctor; clinic; medical practice; hospital; system user ID; patient ID; workstation ID for workstation deployed on the system network; mobile smartphone system ID; patient history data code; ocular disease (OD) code; OD treatment code; machine-vision image recognition processing method code (Mi); logic kernel code (Ki); and many other objects used to model the many different aspects of the system being developed. These objects and the database schema will be used and reflected in a set of object-oriented software modules developed for the system.

Each software module contains classes (e.g. written in an object-oriented programming language) supporting the system network of the present invention 10 including, for example: the user registration module; mobile client registration module; user account management module; log-in module; settings and preferences module; contacts module; search module; data synchronization module; help module; image and video processing module; patient data processing module; ocular disease recognition module; ocular disease treatment prescription module; ocular disease treatment management care module; ocular disease treatment compliance module; deep-learning data descriptive analytics natural language processing (NLP) module; deep-learning ocular disease prediction module; and many other modules supporting the selection, delivery and monitoring of system related services supported on the system network of the present invention, reflected in the schematic illustrations shown and described in FIGS. 7 through 11.

Specification of a Mobile Smartphone-Based Camera System for Deployment and Use in the System Network of the Present Invention FIG. 12A shows a mobile smartphone-based camera system 11A for deployment and use in the system network of the present invention depicted in in FIGS. 7, 8A, 8B, 9A, 9B and 10. Such mobile systems may be realized using Apple iPhone devices, Samsung Android smartphones, and many other smartphone device made and sold around the world.

FIG. 12B shows a mobile tablet-based camera system 11B for deployment and use in the system network of the present invention depicted in in FIGS. 7, 8A, 8B, 9A, 9B and 10. Such mobile tablet systems may be realized using Apple iPad devices, and many other tablet computer devices made and sold around the world.

FIG. 12C shows a mobile laptop-based camera system 11C for deployment and use in the system network of the present invention depicted in in FIGS. 7, 8A, 8B, 9A, 9B and 10. A similar camera system can be deployed on a desktop computer.

FIG. 12D shows a mobile eyeglasses computing system 11D, wherein a mobile computer ad services are embedded within a pair of eyeglasses, for deployment and use in the system network of the present invention depicted in FIGS. 7, 8A, 8B, 9A, 9B and 10.

Figure 13A:
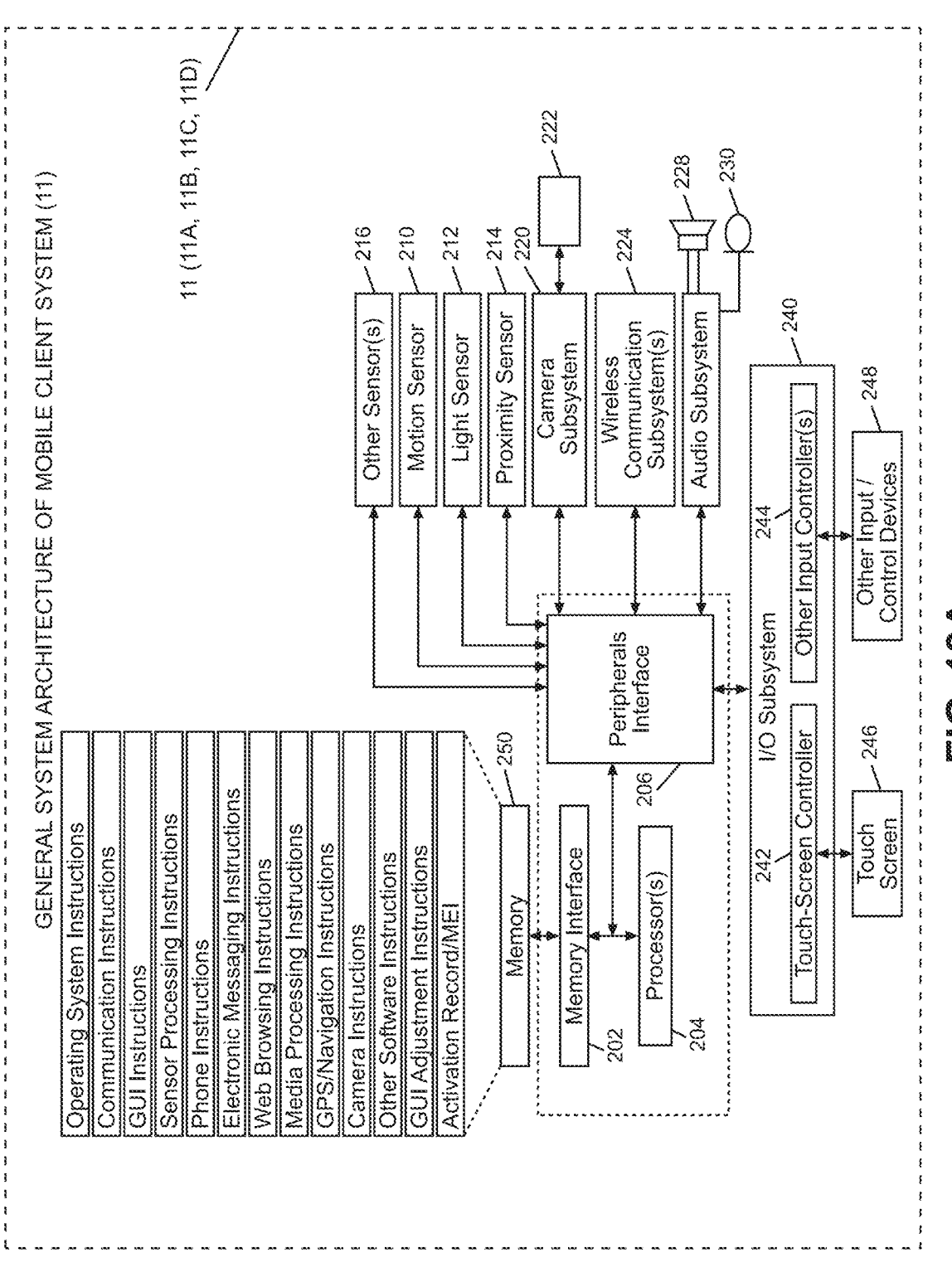
FIG. 13A is a schematic system diagram for the mobile computing systems shown in FIGS. 12A, 12B, 12C, 12C, and 13 and each supporting a high-resolution color digital camera system having optics illustrated in FIG. 13A.

FIG. 13A illustrates the system architecture of an exemplary mobile smartphone, tablet, laptop, desktop and/or eyeglasses computing system (e.g. system component) 11 (i.e. 11A, 11B, 11C and 11D) that may be deployed on the system network. As shown, each mobile computing device 11 (i.e. 11A, 1B, 11C, 1D), regardless of its form factor, can and will typically include a memory interface 202, one or more data processors, image processors and/or central processing units 204, and a peripherals interface 206. The memory interface 202, the one or more processors 204 and/or the peripherals interface 206 can be separate components or can be integrated in one or more integrated circuits. One or more communication buses or signal lines can couple the various components in the mobile device. Sensors, devices, and subsystems can be coupled to the peripherals interface 206 to facilitate multiple functionalities. For example, a motion sensor 210, a light sensor 212, and a proximity sensor 214 can be coupled to the peripherals interface 206 to facilitate the orientation, lighting, and proximity functions. Other sensors 216 can also be connected to the peripherals interface 206, such as a positioning system (e.g., GPS receiver), a temperature sensor, a biometric sensor, a gyroscope, or other sensing device, to facilitate related functionalities. A camera subsystem 70, its image formation optics 260, and its optical sensor (e.g. high-resolution image detection array) 212, e.g., a charged coupled device (CCD) or a complementary metal-oxide semiconductor (CMOS) optical sensor, can be utilized to facilitate camera functions, such as recording photographs and video clips. Communication functions can be facilitated through one or more wireless communication subsystems 224, which can include radio frequency receivers and transmitters and/or optical (e.g. infrared) receivers and transmitters.

The specific design and implementation of the communication subsystem 224 can depend on the communication network(s) over which the mobile computing device 11 is intended to operate. For example, a mobile device 11 may include communication subsystems 224 designed to operate over a GSM network, a GPRS network, an EDGE network, a Wi-Fi or WiMax network, and a Bluetooth™ network. In particular, the wireless communication subsystems 224 may include hosting protocols such that the mobile computing device 11 may be configured as a base station for other wireless devices. An audio subsystem 216 can be coupled to a speaker 228 and a microphone 230 to facilitate voice-enabled functions, such as voice recognition, voice replication, digital recording, and telephony functions. The I/O subsystem 240 can include a touch screen controller 242 and/or other input controller(s) 244. The touch-screen controller 242 can be coupled to a touch screen 246. The touch screen 246 and touch screen controller 242 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen 246. The other input controller(s) 244 can be coupled to other input/control devices 248, such as one or more buttons, rocker switches, thumb-wheel, infrared port, USB port, and/or a pointer device such as a stylus. The one or more buttons (not shown)

can include an up/down button for volume control of the speaker 228 and/or the microphone 230. Such buttons and controls can be implemented as a hardware objects, or touch-screen graphical interface objects, touched and controlled by the system user. Additional features of mobile computing device 11 can be found in U.S. Pat. No. 8,631, 358 incorporated herein by reference in its entirety.

Figure 13B:
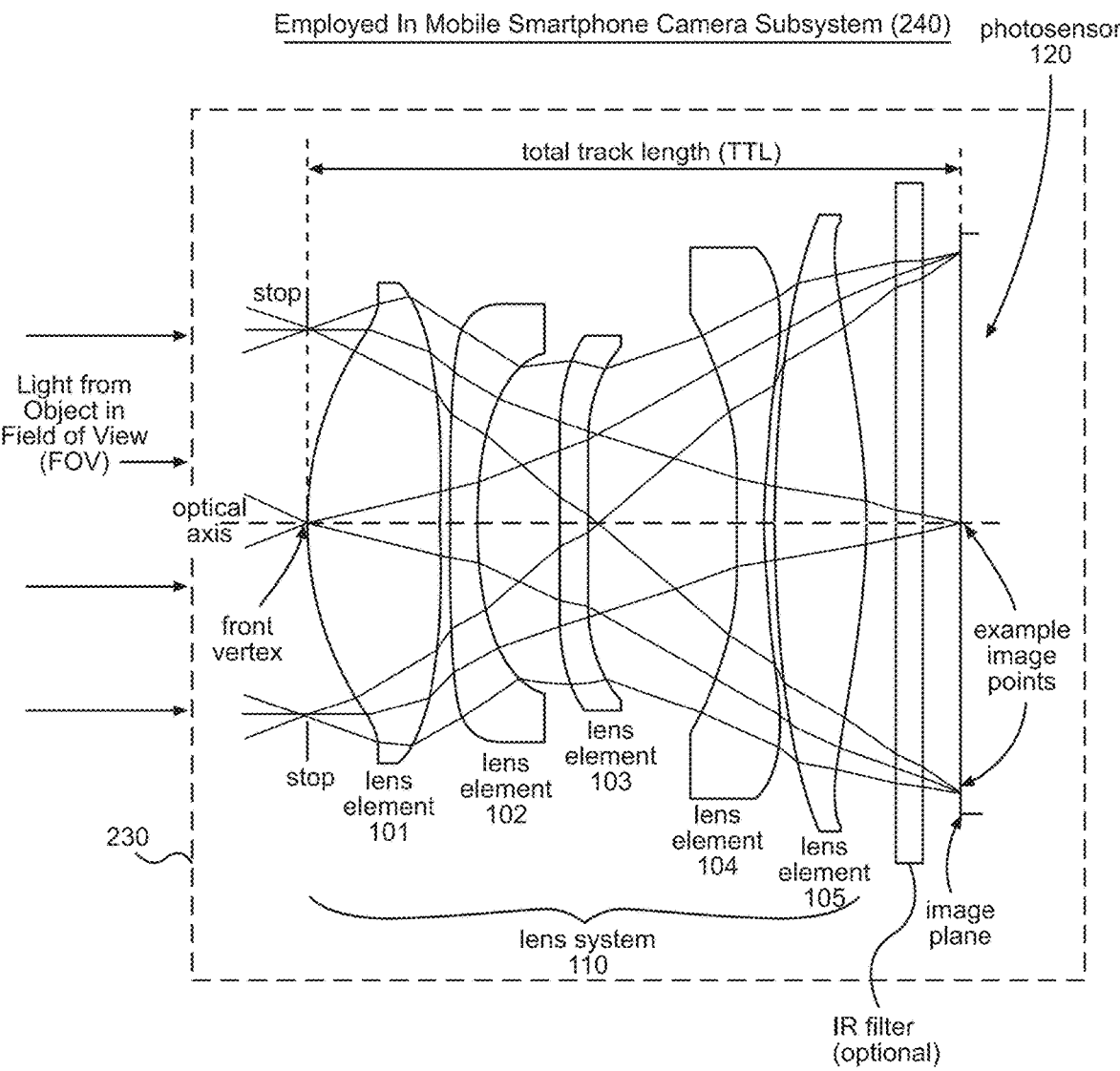
FIG. 13B is a schematic representation of an exemplary high-resolution optical subsystem that may be employed in the color digital camera in the mobile computing systems shown in FIGS. 13, 12A, 12B, 12C and 12D.

FIG. 13B shows an exemplary illustrative optical-based image formation subsystem 260 that may be employed in any mobile digital video camera system 11 deployed on the system network of the present invention 10. The optical subsystem 260 can include fixed or variable image focusing optics, as well as variable or fixed field of view (FOV) forming optics as the application requires. By providing appropriate image formation optics to the mobile smartphone camera system 11 or other mobile computing device illustrated in FIGS. 12A through 12D, it is possible to provide the optical flexibility required when capturing digital images of a patient's eyes preferably using a visible wavelength light source, and any of the image capturing methods illustrated in FIGS. 240A1 through 240D4.

In the illustrative embodiments, the enterprise-level system network of the present invention 10 is supported by a robust suite of hosted services delivered to millions of mobile Web-enable client systems (e.g. mobile smart phones, iPads, tablet computers, etc.) 11 using an application service provider (ASP) model, micro-services model, and/or another service model that is supported on the TCP/IP infrastructure of the Internet. In these illustrative embodiments, the mobile client systems 11 can be realized using a web-browser application running on the operating system (OS) of the mobile computing device 11 (e.g. Linux, Application IOS, etc.) to support online modes of system operation. It is understood, however, that some or all of the services provided by the system network can be accessed using Java clients, or a native client application, running on the operating system (OS) of the mobile client computing device 11 to support both online and limited off-line modes of system operation. Such modifications will occur to those skilled in the art having the benefit of the present invention disclosure.

General Overview Specification of the Automated Ophthalmic Image and Video Capture and Processing Machine Vision Systems of Present Invention In general, the automated ophthalmic image and video capturing and processing methods of present invention support the use of: (i) mobile visible-wavelength operating smartphone image capturing (i.e. camera) systems to form, capture and detect digital images and videos of any human eye while situated at home, in the office, on the road, or in a clinical setting; (ii) traditional machine learning (ML) techniques and technology such as scalar vector machines (SVMs), machines using logistic regression decision trees and random forests; and also (iii) deep-learning (DL) machine-vision (ML) technologies employing deep neural networks such as convolutional neural networks (CCNs) or recurrent neural networks (RNNs), configured and trained to process digital images of human eyes and support fully-automated feature detection, object detection, image analysis, image classification, and ocular disease recognition processes that are supported on the system network to enable the automated ocular disease condition recognition methods of the present invention.

In general, during the training stage of the image and video processing system, digital images and videos of human eyes go through pre-processing, segmentation, post-processing and feature measurements (often performed by ophthalmology trained experts) to generate a database of reliable datasets of training images. Once trained, a deep learning machine vision system of the present invention then analyzes new images and videos to determine if the system is able to classify and measure accurately the desired image and video features. Correct classifications (determined by an ophthalmology trained expert) automatically added to the database, influence the prior classification steps, leading to adaptation, and allowing the classification to be performed faster and with greater accuracy. Over time, with the help and training of expert ophthalmologists, the deep-learning machine-vision ocular disease recognition system should be able to reliably and automatically recognize a broad set (e.g. at least 32 or more) classes of dry eye disease (DED) conditions in the human eyes, and other ocular disease conditions as well, based only on digital images and videos formed, captured and detected by visible-wavelength operating digital image capturing systems operably connected to the system network of the present invention as illustrated in FIGS. 7, 8A, 8B, 9A and 9A.

The various kinds of machine-vision systems that may be used to practice the present invention are shown in great detail throughout the Patent Specification in FIGS. 8A, 9A, 1B, 10, 37A, 37B, 38, 39A, 39B, 40A, 41, 42, 43 and 44 described herein. However, it is understood that other suitable enabling technologies well known in the art, or to be developed in the future, may be used to practice the various embodiments of the present invention.

Specification of Exemplary Ocular Disease (OD) Conditions Associated with the Anterior Segment of the Human Eye, that can be Automatically Recognized by the System of the Present Invention FIGS. 14A, 14B, 14C and 14D show a list of exemplary ocular disease (OD) conditions associated with the anterior segment of the human eye, that can be automatically recognized by the system network of the present invention upon processing the various patient data input factors provided to the system using a patient's mobile smartphone device when registered with the system network 10.

As shown, the OD condition list includes numerous ocular diseases, including cornea-based dry eye diseases, organized by particular parts of the anterior segment of the human eye, namely as shown below:

Eyelids/Orbit:
    OD01: Ptosis
    OD02: Chalazion/Stye
    OD03: Eyelid Cyst
    OD04: Ectropion
    OD05: Entropion
    OD06: Trichiasis
    OD07: Distichiasis
    OD08: Floppy Eyelid Syndrome
    OD09: Blepharospasm
    OD10: Dacryocystitis
    OD11: Canaliculitis
    OD12: Preseptal Cellulitis
    OD13: Orbital Post Septal Cellulitis
    OD14: Proptosis
    OD15: Orbital Floor Fracture
    OD16: Thyroid Eye Disease
    OD17: Blepharitis
    OD18: Herpes Zoster Dermatitis (Shingles)
    OD 19: Retrobulbar Hemorrhage
Sclera/Conjunctiva:
    OD20: Viral Conjunctivitis
    OD21: Bacterial Conjunctivitis
    OD22: Allergic Conjunctivitis OD23: Chemical Burn Conjunctivitis
OD24: Superior Limbic Keratoconjunctivitis
OD25: Subconjunctival Hemorrhage
OD26: Episcleritis/Scleritis
OD27: Conjunctival Laceration
OD28: Herpes Zoster Conjunctivitis
OD29: Pemphigoid
Cornea:
OD30: Dry Eye Disease (DED)
OD31: Corneal Abrasion
OD32: Cornea Foreign Body
OD33: Bacterial Keratitis
OD34: Herpes Simplex Virus Keratitis
OD35: Herpes Zoster Keratitis
OD36: Acanthamoeba Keratitis
OD37: Recurrent Corneal Erosion
OD38: Exposure Keratopathy
OD39: Neurotrophic Keratopathy
OD40: Peripheral Ulcerative Keratitis
OD41: Pterygium
OD42: Pinguecula
OD43: Pingueculitis
OD44: Contact Lens Overwear
OD45: Corneal Transplant Graft Rejection
OD46: Keratoconus
Glaucoma:
OD47: Acute Angle Closure Glaucoma
OD48: Glaucoma Drop Allergy
Neuro-Anthropology:
OD49: Anisocoria
OD50: Horner
OD51: Third Nerve Palsy
OD52: Fourth/Sixth Nerve Palsy
OD52: Bell's Palsy
Iris:
OD54: Iritis
Lens:
OD55: Cataract
OD56: Ophthalmic Post Operative Complications Using the mobile distributed system network of the present invention, each of these ocular disease (OD) conditions can be automatically detected and recognized, and then treated and managed using machine-vision based methods of processing images and videos of human eyes requiring examination and remotely managed ocular care in accordance with the principles of the present invention. As will be described and explained below, various patient-related data elements identified and specified in FIGS. 15 through 33 will be collected by the system network using mobile smartphone systems and other computing systems, and then processes using machine-vision based methods identified in FIGS. 34A through 34C and specified in FIGS. 67 through 259B. In automated response to ocular disease (OD) conditions recognized by the system network, alone and/or with the assistance of a human ophthalmologist or ocular technician, as the case may be, the system network automatically generates treatment recommendations as listed, for example, in FIGS. 35A, 35B and 35C, and according to treatment management procedures and practices reflected in the management logic specified in the logic packages described in FIGS. 36A through 36UUU.

Specification of Patient Data Records that Function as Factors in the Automated Recognition of Ocular Disease Conditions Using the Automated Methods and System of the Present Invention FIG. 15 provides a schematic representation for a data record of the personal and demographic data of a patient, used as ocular disease factors to support the system network of the present invention. In the illustrative embodiment, personal and Demographic Data is encoded as follows: D01 Age; D02 Sex-Male; D03 Sex-Female; D04 Sex—Other; D05 Race—White; D06 Race—Hispanic or Latino; D07 Race—Black or African American; D08 Race—Native American or American Indian; D09 Race—Asian or Pacific Islander; D10 Race—Other; D11 Height—Feet; D12 Height—Inches; and D13 Weight—Pounds.

FIG. 16 provides a schematic representation for a data record on the contact lens worn by a patient, and content lens use, used as ocular disease factors to support the system network of the present invention. In the illustrative embodiment, Contact Lens and Contact Lens Wearing data is encoded as follows: CL01 Ever Use: Yes or No; CL02—If Use, How Often Replaced; CL03—If Use, How Many Hours Per Day; CL04—If Use, How Many Years Worn; CLU01—Overnight Wear; CLU02—Overwear; CLU03—Inadequate Disinfection of Contact Lenses; CLU04—Contamination of Contact Solution; CLU05—Contamination of Contact Lens Case; CLU06—Rising Contacts in Water; CLU07—Sharing Contact Lenses; CLU08—Cosmetic Contact Lenses; CLU09—Swimming While Wearing Contact Lenses; and CLU10—Showering While Wearing Contact Lenses.

FIG. 17 provides a schematic representation for a data record of the eye pathology of a patient used as ocular disease factors to support the system network of the present invention. In the illustrative embodiment, Previous Eye Pathology Data is encoded as follows: PEP01 Dry Eyes; PEP02 Poor Eyelid Closure; PEP03 Poor Bell's Phenomenon; PEP04 Eye Lash Misdirection; PEP05 Blepharitis; PEP06 Conjunctivitis; PEP07 Blepharoconjunctivitis; PEP08—Canalicultitis; PEP09—Dacryocystitis; PEP10 Neurotrophic keratopathy; PEP11 Viral Keratitis; PEP12 Corneal dystrophy; PEP13 Corneal edema; PEP14 Trigeminal lesion; PEP15 Acoustic neuroma; PEP16 Ciliary nerves lesion; PEP17 Orbital tumor; PEP18 Orbital surgery; PEP19 Corneal nerve lesion; PEP20 Pterygium; PEP21 Allergic Conjunctivitis; PEP22 Demodex; PEP23 Recurrent Corneal Erosion; PEP24 Glaucoma; PEP25 Bilateral Involvement; PEP26 Chemical Exposure; PEP27 Trachoma; PEP28 Pemphigoid; PEP29 Erythema multiforme; PEP30 Burns; PEP31 Bells Palsy; PEP32 Swimming in lake or ocean recently.

FIG. 18 provides a schematic representation for a data record of the ocular medications taken by a patient, used as ocular disease factors to support the system network of the present invention. In the illustrative embodiment, Ocular Medications Data is encoded as follows: OM01 Containment Ocular Meds; OM02 Topical SAIDs; OM03 Topical Anesthetics; OM04 Topical 19; OM05 Glaucoma medications; OM06 Anti-VEGF agents; and OM07 Botox.

FIG. 19 provides a schematic representation for a data record of the ophthalmic surgery of a patient, used as ocular disease factors to support the system network of the present invention. In the illustrative embodiment, Ophthalmic Surgery Data is encoded as follows: OS01 Refractive Surgery; OS02 Cataract Surgery; OS03 Keratoplasty; OS04 Loose Corneal Sutures; OS05: Graft Rejection; S06 PRP; OS07 Cyclocoagulation; and OS08 Botox.

FIG. 20 provides a schematic representation for a data record of the systemic disease of a patient, used as ocular disease factors to support the system network of the present invention. In the illustrative embodiment, Systemic Disease data is encoded as follows: SD01 Diabetes; SD02 Autoimmune Disease; OS03 Connective Tissue Disease; OS04

Sjogren; Syndrome; SD05 Siogen's review of systems; SD06 Autoimmune review of systems; SD07 Stevens-Johnson syndrome; SD08 Pemphigold; SD09 HIV/AIDS; SD10 Vitamin A deficiency; SD11 Low fatty acids intake; SD12 Malnourished; SD13 Dermatitis; SD14 Rosacea; SD15 Transplant; SD16 Measles; SD17 Atrophy; SD18 Stroke; SD19 Brainstem lesion; SD20 Multiple sclerosis; SD21 Facial trauma; SD22 Androgen deficiency; SD23 Hormone replacement therapy; SD24 Hematopoietic stem cell transplantation; SD25 Thyroid disease; SD26 Viral injection; SD27 Psychiatric condition; SD28 Acne; SD29 Sarcoidosis; SD30 Menopause; SD31 Cold Systems; SD32 Sleep Apnea; and SD33 Atopy.

FIG. 21 provides a schematic representation for a data record of the systematic surgery of a patient, used as ocular disease factors to support the system network of the present invention. In the illustrative embodiment, System Surgery Data is encoded as follows: SS01 Heart Surgery; SS02 Joint Surgery; SS03 Endocrine Surgery; SS04 Lung Surgery; SS05 Breast Surgery; and SS06 Colorectal Surgery.

FIG. 22 provides a schematic representation for a data record of the systemic medications of a patient, used as ocular disease factors to support the system of the present invention. In the illustrative embodiment, Systemic Medication Data is encoded as follows: SM01 Immunosuppressive medication; SM02 Antihistamines; SM03; Antidepressants; SM04 Anxiolytics; SM05 Isotretinoin; SM06 Anticholinergics; SM07 Diuretics; SM08 Beta Blockers; and SM09 Oral Contraception.

Figures 23, 24:
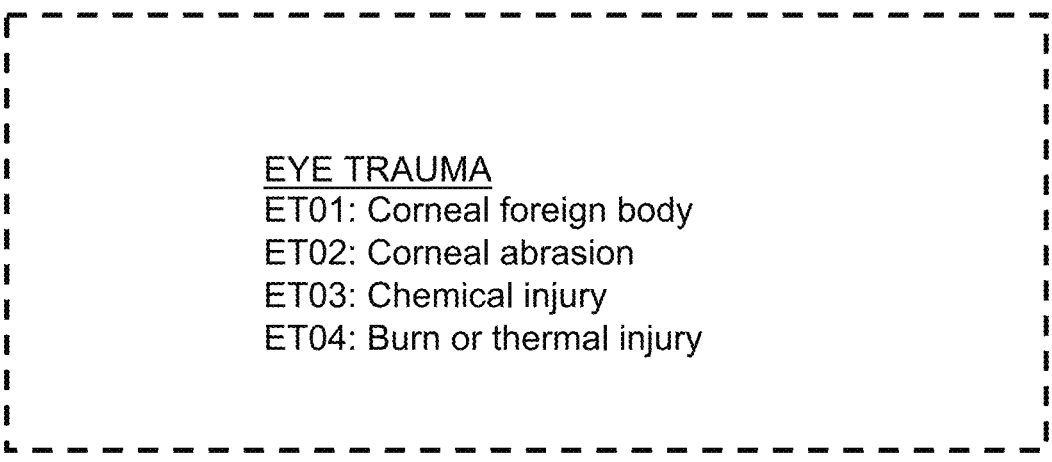
FIG. 23 is a schematic representation of a data record of the eye trauma of a patient, used as ocular disease factors to support the system network of the present invention.
FIG. 24 is a schematic representation of a data record of the living situation of a patient, used as ocular disease factors to support the system network of the present invention.

FIG. 23 provides a schematic representation for a data record of the eye trauma of a patient, used as ocular disease factors to support the system network of the present invention. In the illustrative embodiment, Eye Trauma Data is encoded as follows: ET01 Corneal Foreign Body; ET02 Corneal Abrasion; ET03 Chemical Injury; and ET04 Burn or Thermal Injury.

FIG. 24 provides a schematic representation for a data record of the living situation of a patient, used as ocular disease factors to support the system network of the present invention. In the illustrative embodiment, Living Situation Data is encoded as follows: LST01 Sleep Under Fan; LST02 Humidified Air at Home; LST03 Humidified Air at Work; LST04 Geolocation—Urban; LST05 Geolocation—Suburban; LST06 Rural; LST07 High Pollution Area; LST08 Dry Climate Area; and LST09 Low Humidity Area.

Figures 25, 26:
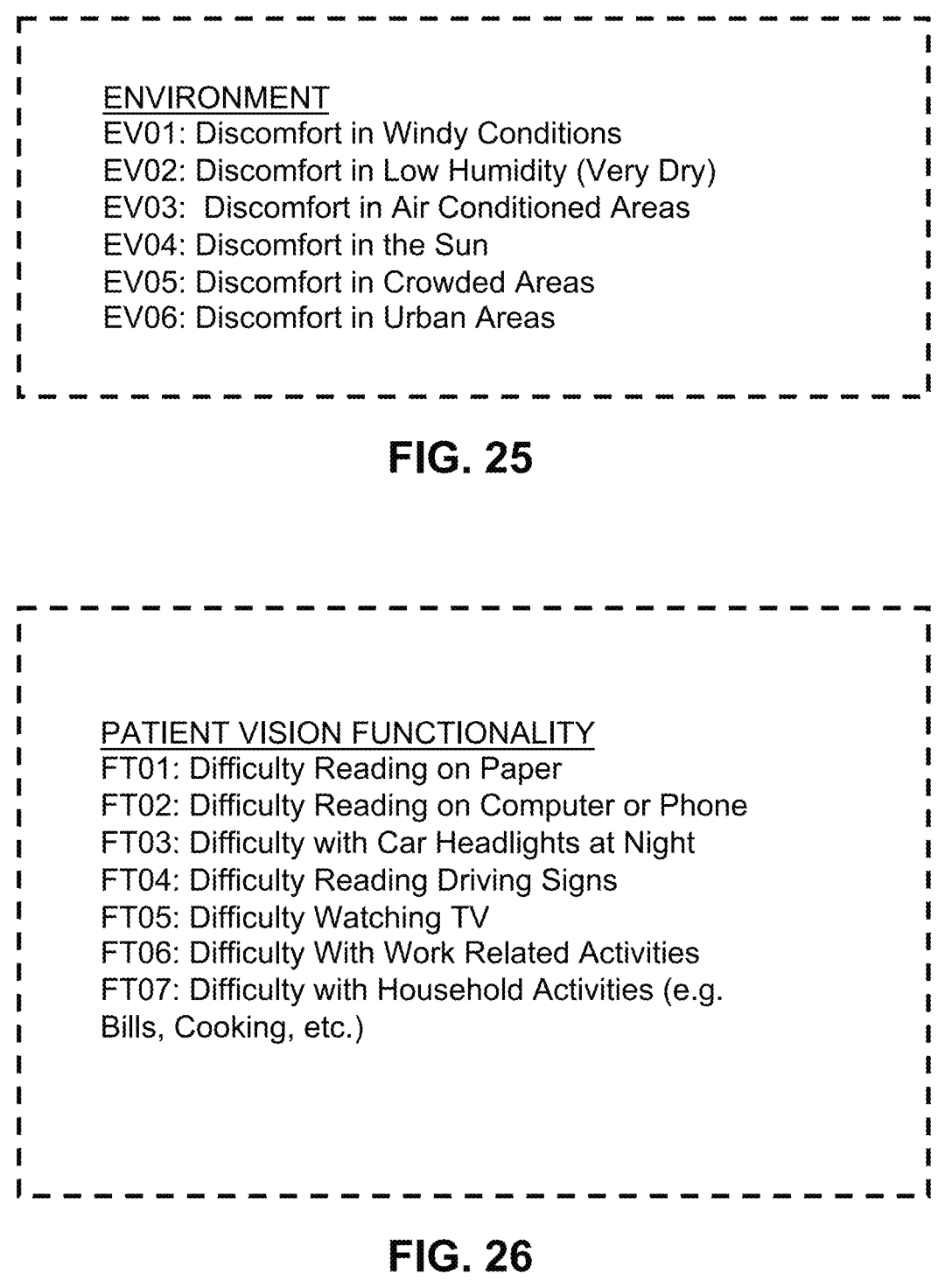

FIG. 25 provides a schematic representation for a data record of the environment of a patient, used as ocular disease factors to support the system network of the present invention. In the illustrative embodiment, Environment Data is encoded as follows: EV01 Discomfort in Windy Conditions; EV02 Discomfort in Lower Humidity (Very Dry); EV03 Discomfort in Air Conditioned Areas; EV04 Discomfort in the Sun; EV05 Discomfort in Crowded Areas; and EV06 Discomfort in Urban Areas.

FIG. 26 provides a schematic representation for a data record of the vision functionality of a patient, used as ocular disease factors to support the system network of the present invention. In the illustrative embodiment, Vision Functionality Data is encoded as follows: FT01 Difficulty Reading on Paper; FT02 Difficulty Reading on Computer or Phone; FT03 Difficulty With Car Headlights at Night; FT04 Difficulty Reading Driving Signs; FT05 Difficulty Watching TV; FT06 Difficulty with Work Related Activities; and FT07 Difficulty with Household Activities (e.g. Bills, Cooking, etc.)

FIG. 27 provides a schematic representation for a data record of summary of risk factors (e.g. demographic, contact lens, trauma, surgery, ocular medications, systemic medication, eye disease, systemic disease and other) experienced by a patient of a patient, used as ocular disease factors to support the system network of the present invention. In the illustrative embodiment, Summary of Risk Factor Data is shown in a table organized under the following data classifications, with corresponding risk factors: demographic covering age, sex, race, and menopause; contact lens covering; trauma; surgery; ocular medications; systemic medications; eye disease; systemic disease; and other.

Specification of Mobile Smartphone Systems and Mobile Services for Collecting Patient Symptom Data for Delivery to the System Network of the Present Invention FIG. 28 provides a schematic representation for a data record of the symptoms experienced by a patient, used as ocular disease factors to support the system network of the present invention. In the illustrative embodiments of the present invention, the symptom data is coded as follows: SY01 Light Sensitivity; SY02 Gritty or Scratchy Sensation; SY03 Sandy or Foreign Body Sensation; SY04 Eye Pain/Soreness; SY05 Headaches; SY06 Blurry Vision; SY07 Poor Vision Quality; SY08 Burning or Stinging; SY09 Itching; SY10 Tearing or Discharge; SY11 Frequent Blinking; SY12 Redness; SY13 Heavy Eyelids or Eye Fatigue; and SY14 Mattering or Caking of the Eyelashes (usually worse upon Waking).

Specification of Mobile Smartphone Systems and Mobile Services for Collecting Patient In-Office Examination Data for Delivery to the System Network of the Present Invention FIG. 29 provides a schematic representation for a data record on the in-office examination data collected from a patient, used as ocular disease factors to support the system network of the present invention. In the illustrative embodiments of the present invention, the In-Office Exam (IOE) data element is coded as follows: IOE01 Visual Acuity; IOE02 Intraocular Pressure; IOE03 Conjunctival Injection; IOE04 Conjunctivochalasis; IOE05 Meibomian Gland Dysfunction; IOE06 Blepharitis; IOE07 Dermatochalasis; IOE08 Floppy Eyelid; IOE09 Anterior Basement Membrane Dystrophy; IOE10 Poor Bell's Phenomenon; IOE11 Corneal Staining; IOE12 Tearfilm Break-Up Time (BUT); IOE13 Schirmer's Test; IOE14 Osmolarity; IOE15 Matrix Metalloproteinase 9; and IOE16 Meibography.

Figures 31, 32:
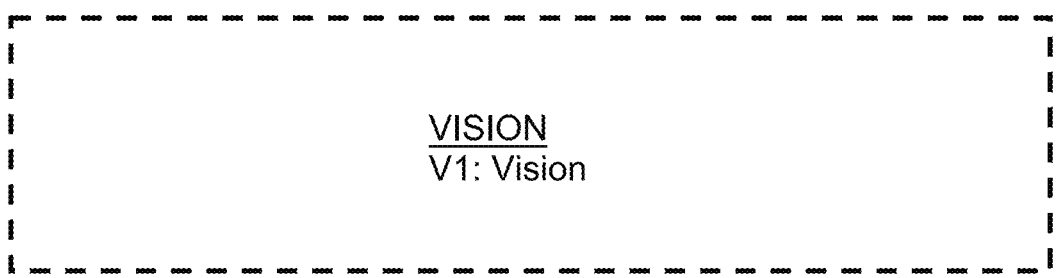
FIG. 31 is a schematic representation a data record for vision testing of a patient, used as ocular disease factors to support the system network of the present invention.
FIG. 32 is a schematic representation of a mobile vision test supported by the mobile smartphone camera system.

FIG. 31 provides a table of the data elements creating a vision test data record shown in FIG. 30. As shown in FIG. 30, each IOE data element is provided a range of values for use during the in-office examination, and also a binary test determining when each condition should be indicated as present or existing in the patient during the in-office examination.

Specification of Mobile Smartphone Systems and Mobile Services Supporting Mobile Patient Vision Examination and Delivery of Collected Vision Data to the System Network of the Present Invention FIG. 32 shows an exemplary graphical user interface (GUI) displayed on the mobile smartphone camera system, for use by a patient during mobile vision testing of the user's eyes and collecting patient vision testing data for delivery to the system network in accordance with the present invention. As shown, this vision test measures a patient's ability to read numbers and letters of particular sizes, and provides a quantification of the user's power of vision from low to high.

Figure 33:
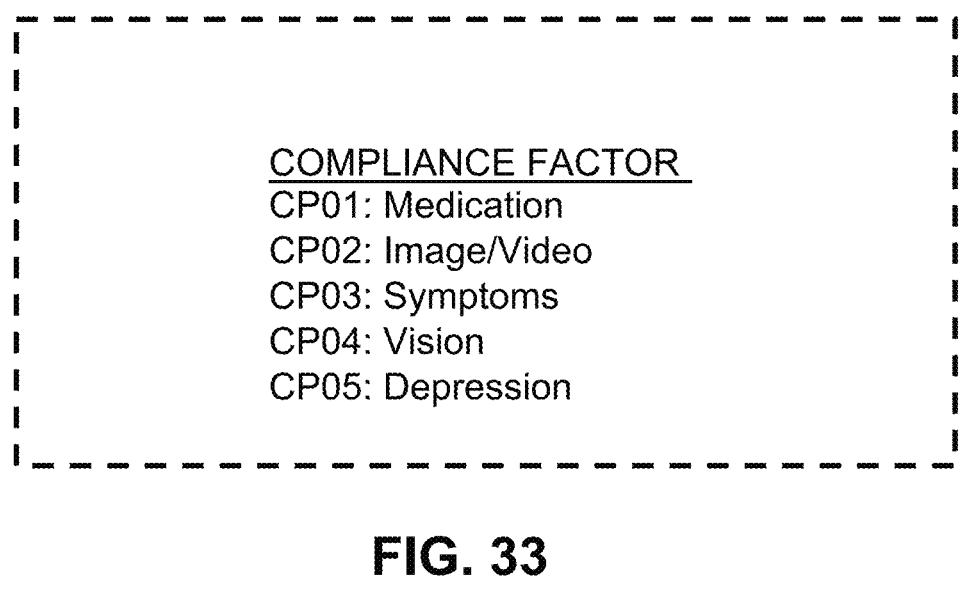

FIG. 33 provides a data record for the compliance factors of a patient (e.g. medication, image/video, symptoms, vision and depression) that are used as ocular disease compliance factors to support the system network of the present invention.

Specification of Mobile Smartphone Systems and Mobile Services for Collecting Patient Mobile Vision Test Data for Delivery to the System Network of the Present Invention FIGS. 34A and 34B show a list describing the various kinds of ocular conditions (i.e. diseases) that can be automatically detected and recognized using machine-vision image-based processing methods of the present invention. Each of these methods involve automated processing of digital images of human eyes captured by a mobile smartphone system, as described and taught in great detail in FIGS. 67 through 256.

In the illustrative embodiments of the present invention, these various machine-vision based methods of digital image processing (Mi) are coded as follows: M1 Conjunctival Injection; M2 Tear Meniscus Height (TMH); M3 Meibomian Gland Dysfunction; M4 Conjunctivochalasis; M5 Dermatochalasis; M10 Corneal Abrasion; M11 Palpebral; M12 Margin Reflex Distance (MRD); M13 Scleral Show (SS); M14 Levator Function (LF); M15 Contact Lens Over Wear (CLOW): M16 Corneal Transplant Graft Rejection (CTGR); M17 Cataract; M18 Viral Conjunctivitis; M19 Bacterial Conjunctivitis; M20 Allergic Conjunctivitis; M21 Chemical Burn Conjunctivitis; M22 Pterygium/Pinguecula; M23 Subconjunctival Hemorrhage; M24 Subconjunctival Laceration; M25 Episcleritis/Scleritis; M26 Superior Limbic Keratoconjunctivitis; M27 Blepharitis; M28 Chalazion/Stye; M29 Eyelid Cysts; M30 Preseptal Cellulitis; M31 Ptosis; M32 Ophthalmoplegia; M33 Proptosis/Hypoglobus; M34 Anisocoria; M35 Anterior Chamber Depth; M36 Orbital Post Septal Cellulitis; M37 Thyroid Eye Disease; M38 Ectropion/Entropion; M39 Trichiasis/Distichiasis; M40 Floppy Eye Syndrome; M41 Herpes Zoster Dermatitis; M42 Herpes Zoster Keratitis; M43 Herpes Simplex Virus Keratitis; M44 Ophthalmic Post Operative Complications; M45 Corneal Infection; M46 Corneal Foreign Body; and M47 Acute Angle Closure Glaucoma.

Specification of Mobile Smartphone Systems and Mobile Services for Collecting Patient Eye Image Capture Data for Delivery to the System Network of the Present Invention FIG. 34C shows a list describing the various kinds of ocular conditions (e.g. diseases) are can be automatically detected and recognized using machine-vision video frame processing methods of the present invention (i.e. M6, M7, M8 and M9) designed for processing digital images of human eyes captured by a mobile visible-wavelength operating smartphone camera system as described and taught in great detail in FIGS. 65 through 81C.

In the illustrative embodiments of the present invention, these various machine-vision based methods of digital image processing (Mi) are coded as follows: M6 Tear Film Dynamics 1—Tracking Reflective Light Particles; M7 Tear Film Dynamics 2—Detecting Perturbations in Tear Film Using Placido Light Discs Projected onto the Cornea; M8 Tear Film Dynamics 3—Detecting Changes in Tear Meniscus Height (TMH) During Blinking Operations; and M9 Detecting and Analyzing Blink Speed and Patterns Configured and Trained—Partial Blink.

Specification of the Various Kinds of Treatment and Management Recommendations that the System Network of the Present Invention can Automatically Prescribe for Specific Ocular Disease Conditions Automatically Detected and Recognized Using the Machine-Vision Imaging Processing Methods of the Present Invention Applied to the Digital Images of Human Eyes Captured by a Mobile Smartphone System FIGS. 35A, 35B and 35C describe a robust coded list of treatment and management recommendations that the system network of the present invention 10 can automatically prescribe to patients for specific ocular disease conditions that are automatically detected and recognized using the automated machine-vision imaging processing methods of the present invention applied to the digital images of human eyes captured by a mobile smartphone system and supplied as patient data input to the system network.

In the illustrative embodiments of the present invention, these various machine-vision based methods of treatment and management are coded as with the character string TMi as follows: TM01 Refer to eye doctor non-urgently; TM02 Refer to eye doctor urgently; TM03 Recommend warm compresses; TM05 Recommend artificial tears; TM06 Recommend surgery; TM07 Refer to emergency room; TM08 Recommend antibiotic/steroid combo ointment; TM09 Recommend artificial tear ointment; TM10 Recommend epilation (removal of eye lashes); TM11 Recommend cryotherapy to eyelashes; TM12 Botulinum toxin injection; TM13 Recommend cold compresses; TM14 Recommend oral antibiotics; TM15 Recommend lacrimal system probe and irrigation; TM16 Recommend antibiotic/steroid combo drops; TM17 Recommend autoimmune work-up; TM18 Recommend intravenous antibiotics; TM19 Recommend oral steroids; TM20 Recommend cool compresses; TM21 Recommend endocrine work-up; TM22 Recommend eyelid hygiene; TM23 Recommend oral antiviral agents; TM24 Recommend intravenous antiviral agent; TM25 Recommend topical antiviral drops; TM26 Recommend topical antibiotics drops; TM27 Recommend topical antibiotic ointment; TM28 Recommend oral anti-histamine; TM29 Recommend topical anti-histamine drops; TM30 Recommend amniotic membrane placement; TM31 Recommend topical cyclosporine drops; TM32 Recommend oral ibuprofen; TM33 Recommend steroid drops; TM34 Recommend Oral Steroid sparing immune-suppressants; TM32 Recommend oral ibuprofen; TM33 Recommend steroid drops; TM34 Recommend oral steroid sparing immunosuppressants, TM35 Recommend corneal cultures; TM36 Recommend fortified topical antibiotic drops; TM37 Recommend topical anti-parasitic drops; TM38 Recommend topical propamidine isethionate drops; TM39 Recommend topical polyhexamethylene biguanide drops; TM40 Recommend diamond burr procedure; TM41 Recommend intravenous steroids; TM42 Recommend UV protection; TM43 Recommend break from wearing contact lenses; TM44 Recommend intraocular pressure lowering drops; TM45 Recommend oral intraocular pressure lowering agents; TM46 Recommend intravenous intraocular pressure lowering drop; TM47 Recommend changing intraocular pressure lowering drop; TM48 Recommend laser procedure; TMTM49 Recommend ultrasound of eye; TM50 Recommend antibiotic injections into the eye; TM51 Recommend oral omega-3 supplement, TM52 Recommend oral vitamin C supplement; TM53 Recommend indoor humidification; TM54 recommend preservative free artificial tears; TM55 Recommend re-esterified omega-3/6 supplement, TM56 Recommend dry eye disease (DED) prescription drop; TM57 Recommend punctal plugs, TM58 Recommend office-based procedures for Meibomian gland dysfunction; TM59 Recommend serum tears; TM60 Recommend contact lens trial; TM61 Recommend surgical punctal occlusion; TM62 Recommend compounded N-acetylcysteine drops; TM63 Recommend Dry Eye Disease (DED) Staged Management; TM64 Recommend dry eye disease classification determination; TM65 Recommend corneal sensitivity testing; TM66 Recommend systemic medication evaluation; TM67 Recommend Demodex treatment; TM68 Recommend blink exercises; TM69 Recommend evaluation with primary care physician; TM70 Recommend a sleep study; TM71 Recommend topical drop evaluation; TM72 Recommend contact lens fitting; TM73 Recommend oral vitamin A supplement; TM74 Recommend blue-light blocking glasses; and TM75 Recommend moisture-chamber glasses.

As will be described in the machine-based logic packages specified in FIGS. 36A through 36UUU, one or more of the ocular disease (OD) treatment and management recommendations, listed in FIGS. 35A through 35C, may be prescribed for any given ocular disease condition recognition/diagnosis automatically performed by the system network, and then assigned an associated method of care management, as may be required and reflected in the Management Logic provided in each logic package provided for the recognized ocular disease condition.

Specification of the Various Kinds of Ocular Disease (OD) Conditions that can be Automatically Detected and Recognized Using Machine-Vision Imaging Processing Methods of the Present Invention for Automatically Processing Digital Images of the Human Eyes of a Patient Captured by a Mobile Visible-Wavelength Operating Smartphone Camera System FIGS. 36A through 36UUU lists the various kinds of ocular disease (OD) conditions are can be automatically detected and recognized using machine-vision imaging processing methods of the present invention, for processing digital images of human eyes captured by a mobile visible-wavelength operating smartphone image capturing systems 11A, 11B, 11C and 11D, as described and taught herein. Below is a detailed specification of the machine-based logic packages used by the system network in enabling the automated recognition, treatment and care management operations provided for the many ocular diseases conditions supported by the system network of the illustrative embodiments of the present invention 10.

Specification of Machine-Based Logic Packages Used in the Automated Recognition, Treatment and Care Management of Ocular Disease OD01—PTOSIS FIG. 36A provides a schematic specification of a logic package installed and operative within the automated ocular disease (OD) recognition, treatment and compliance management system of the present invention 10, biomedically-engineered for the ocular disease afflicting the eyelids/orbit, specifically—Ptosis—and assigned ocular disease code OD01. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

Eyelids/Orbit:
  OD01: Ptosis
Disease Diagnosis Input Factors:
  M11: Palpebral Fissure
  M12: Margin Reflex Distance
  M31: Ptosis
  Diagnostic Logic: IF M11: Palpebral Fissure Height <8 mm OR M12: Margin Reflex Distance 1<2.5 mm OR M31: Ptosis present, THEN OD01: Ptosis.

This Diagnostic Rule expressed in canonical form, having a compact syntactical structure, should be understood as follows: IF [the diagnostic Method M11 disclosed herein and executed on the processed image(s) determines that the Palpebral Fissure Height detected and measured within the processed images is less than 8 mm, OR the diagnostic Method M12 disclosed herein and executed on the processed images determines that the Margin Reflex Distance detected and measured within the processed images is less than 2.5 mm, OR the diagnostic Method M31 disclosed herein and executed on the process images determines that the Ptosis is detected and present], THEN determine that the Ocular Disease OD01 "Ptosis" is reflected by the detected conditions in the processed digital image(s).

Treatment Logic: IF OD01: Ptosis chronic, THEN TM01: Refer to eye doctor non-urgently AND TM06: Recommend surgery‖(i.e. alternatively, if required conditions are satisfied or otherwise apply") IF OD01: Ptosis acute onset, THEN TM02: Refer to eye doctor urgently.

This Treatment Rule expressed in canonical form, having a compact syntactical structure, should be understood as follows: IF [the Ocular Disease OD01 Ptosis chronic is determined by the system], THEN [execute Treatment Management TM01: Refer to eye doctor non-urgently AND Treatment Management TM06: Recommend surgery.] Alternatively, IF [the Ocular Disease OD01: Ptosis acute onset is determined by the system], THEN [execute Treatment Management TM01: Refer to eye doctor urgently].

Management Logic: IF Ptosis AND [M16: Levator Function <10 mm OR M32: Ophthalmoplegia present OR M33: Proptosis/Hypoglobus >2 mm OR M34: Anisocoria >2 mm OR OD50: Horner's Syndrome present OR OD51: Third Nerve Palsy present OR OD52: Fourth/Sixth Nerve Palsy present] THEN TM07: Refer to emergency room AND TM03: Recommend radiologic imaging.

This Treatment Management Rule expressed in canonical form, having a compact syntactical structure, should be understood as follows: IF [the Ocular Disease is OD01: Ptosis, AND Diagnostic Method M16 determines that the Levator Function is less than 10 mm OR the Diagnostic Method M32: determines that Ophthalmoplegia is present, OR the Diagnostic Method M33 determines that Proptosis/Hypoglobus is greater than 2 mm, OR the Diagnostic Method M34 determines that Anisocoria is 2 mm, OR Ocular Disease OD50: Horner's Syndrome has been determined as present, OR Ocular Disease OD51: Third Nerve Palsy has been determined as present, OR Ocular Disease OD52: Fourth/Sixth Nerve Palsy has been determined as present], THEN [execute Treatment Management TM07 which Refers emergency room treatment, AND Treatment Management TM03 which Recommends radiologic imaging].

These rules and guidelines for interpretation should be used when interpretation all Diagnostic Logic, Treatment Logic, and Management Logic disclosed herein with regards to the various aspects of the present invention.

Specification of Machine-Based Logic Packages Used in the Automated Recognition, Treatment and Care Management of Ocular Disease OD02—CHALAZION/STYE FIG. 36B provides a schematic specification of logic packages installed and operative within the automated ocular disease (OD) recognition, treatment and compliance management system of the present invention 10, biomedically-engineered for (a) the ocular disease afflicting the eyelids/orbit, specifically—Chalazion/Stye—and assigned ocular disease code OD02. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD02: Chalazion/Stye

Disease Diagnosis Input Factors:

M03: Meibomian Gland Dysfunction

M11: Palpebral Fissure

M27: Blepharitis—Scruff at Eyelashes

M28: Chalazion/Stye

M30: Preseptal Cellulitis—Eyelid Swelling

Diagnostic Logic: IF [M3: Meibomian Gland Dysfunction >50% of eyelid OR M27: Blepharitis—Scruff at Eyelashes upper or lower eyelid] AND [M11: Palpebral Fissure <8 mm OR M30: Preseptal Cellulitis—Eyelid Swelling upper or lower eyelid] OR [M28: Chalazion/Stye present], THEN OD02: Chalazion/Stye.

Treatment Logic: IF OD02: Chalazion/Stye THEN TM04: Recommend warm compresses four times a day to affected eyelid AND TM05: Recommend artificial tears four times a day to the affected eye.

Management Logic: IF OD02: Chalazion/Stye AND no improvement with T04: Warm compresses OR TM05: Artificial tears, THEN TM01: Refer to eye doctor non-urgently AND TM08: Recommend antibiotic/steroid ointment two times a day to affected eyelid‖IF OD02: Chalazion/Stye AND SY15: Fevers OR chills THEN TM02: Refer to eye doctor urgently.

Specification of Machine-Based Logic Packages Used in the Automated Recognition, Treatment and Care Management of Ocular Disease OD03—EYELID CYST FIG. 36C provides a schematic specification of logic packages installed and operative within the automated ocular disease (OD) recognition, treatment and compliance management system of the present invention 10, biomedically-engineered for the ocular disease afflicting the eyelids/ orbit, specifically—Eyelid Cyst—and assigned ocular disease code OD03. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD03: Eyelid Cyst

Disease Diagnosis Input Factors:

M11: Palpebral Fissure

M29: Eyelid Cyst

M30: Preseptal Cellulitis—Eyelid Swelling

Diagnostic Logic: IF [M11: Palpebral Fissure <8 mm AND [M30: Preseptal Cellulitis—Eyelid swelling upper OR lower eyelid] AND NOT OD02: Chalazion/Stye] OR M29: Eyelid Cyst present, THEN OD03: Eyelid Cyst.

Treatment Logic: IF OD03: Eyelid Cyst, THEN TM04: Recommend warm compresses four times a day to affected eyelid.

Management Logic: IF OD03: Eyelid Cyst AND no improvement with warm compresses THEN TM01: Refer to eye doctor AND TM06: Surgery‖IF OD03: Eyelid Cyst AND SY15: Fevers OR chills, THEN TM02: Refer to eye doctor urgently.

Specification of Machine-Based Logic Packages Used in the Automated Recognition, Treatment and Care Management of Ocular Disease OD04—ECTROPION FIG. 36D provides a schematic specification of a logic package installed and operative within the automated ocular disease (OD) recognition, treatment and compliance management system of the present invention 10, biomedically-engineered for the ocular disease afflicting the eyelids/orbit, specifically—Ectropion—and assigned ocular disease code OD4. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD04: Ectropion

Disease Diagnosis Input Factors:

M09: Blink Speed Patterns Configured and Trained— Partial Blinks

M13: Scleral Show

M38: Ectropion

M40: FES—Lower Eyelid Prolapse

PEP31: Bell's Palsy

PEP28: Pemphigoid

SD32: Sleep Apnea

Diagnostic Logic: IF M9: Blink Speed Patterns Configured and Trained—Partial Blinks >10 AND [[M40: FES— Lower Eye Prolapse present AND SD32: Sleep Apnea present] OR [[PEP28: Pemphigoid present OR PEP31 Bell's Palsy present] AND M13: Scleral Show inferior scleral show >2 mm]] OR M38: Ectropion present, THEN OD04: Ectropion.

Treatment Logic: IF OD04: Ectropion, THEN TM01: Refer to eye doctor AND TM05: Recommend artificial tears four times a day to the affected eye AND TM09: Recommend artificial tear ointment AND TM06: Recommend surgery.

Management Logic: IF OD04: Ectropion, THEN check OD08: Floppy Eyelid Syndrome AND OD09: Blepharospasm AND OD29: Pemphigoid AND OD38: Exposure Keratopathy.

Specification of Machine-Based Logic Packages Used in the Automated Recognition, Treatment and Care Management of Ocular Disease OD05—ENTROPION FIG. 36E provides a schematic specification of a logic package installed and operative within the automated ocular disease (OD) recognition, treatment and compliance management system of the present invention 10, biomedically-engineered for the ocular disease afflicting the eyelids/orbit, specifically—Entropion—and assigned ocular disease code OD5. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD05: Entropion

Disease Diagnosis Input Factors:

M09: Blink Speed Patterns Configured and Trained— Partial Blinks

M38: Entropion

ET3: Chemical Injury

ET4: Burn or Thermal Injury

ET5: Blunt Eye Trauma

SD21: Facial Trauma

PEP28: Pemphigoid

PEP29: Erythema Multiforme

PEP30: Burns

Diagnostic Logic: IF M9: Blink Speed Patterns Configured and Trained—Partial Blinks>10 blinks AND [ET3: Chemical Injury present OR ET4: Burn or Thermal Injury present OR ET5: Blunt Eye Trauma present OR SD21: Facial Trauma present OR PEP28: Pemphigoid present OR PEP29: Erythema Multiforme present OR PEP30: Burns present] OR M39: Entropion present, THEN OD05: Entropion.

Treatment Logic: IF OD05: Entropion, THEN TM01: Refer to eye doctor AND TM05: Recommend artificial tears four times a day to the affected eye AND TM09: Recommend artificial tear ointment AND [TM06: Recommend surgery OR TM11: Recommend cryotherapy to eyelashes].

Management Logic: IF OD05: Entropion, THEN check OD06: Trichiasis AND OD07: Distichiasis AND OD08: Floppy Eyelid Syndrome AND OD09: Blepharospasm AND OD29: Pemphigoid.

Specification of Machine-Based Logic Packages Used in the Automated Recognition, Treatment and Care Management of Ocular Disease OD06—TRICHIASIS FIG. 36F provides a schematic specification of a logic package installed and operative within the automated ocular disease (OD) recognition, treatment and compliance management system of the present invention 10, biomedically-engineered for the ocular disease afflicting the eyelids/orbit, specifically—Trichiasis—and assigned ocular disease code OD6. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD06: Trichiasis

Disease Diagnosis Input Factors:

M06: Tear Film Dynamics 1: Tracking Reflective Light Particles

M07: Tear Film Dynamics 2: Detecting Perturbations in Tear Film Using Placido Light Discs Projected onto the Cornea M39: Trichiasis PEP28: Pemphigoid PEP29: Erythema Multiforme PEP30: Burns Diagnosis Logic: IF [M06: Tear Film Dynamics 1: Tracking Reflective Light Particle speed after opening eyes <7 mm/sec OR M06: Tear Film Dynamics 1: Tracking Reflective Light Particle time for speed to reach 0 mm/sec<1 sec] AND M07: Tear Film Dynamics 2: Detecting Perturbations in Tear Film Using Placido Light Discs Projected onto the cornea tear film break-up time <4 secs AND [PEP28: Pemphigoid present OR PEP29: Erythema Multiforme present OR PEP30: Burns present] OR M39: Trichiasis present, THEN OD06: Trichiasis Treatment Logic: IF OD06: Trichiasis, THEN TM01: Refer to eye doctor AND TM05: Recommend artificial tears four times a day to the affected eye AND TM09: Recommend artificial tear ointment AND [TM06: Recommend surgery OR TM11: Recommend cryotherapy to eyelashes].

Management Logic: IF OD06: Trichiasis, THEN check OD05: Entropion AND OD07: Distichiasis AND OD08: Floppy Eyelid Syndrome AND OD09: Blepharospasm AND OD29: Pemphigoid.

Specification of Machine-Based Logic Packages Used in the Automated Recognition, Treatment and Care Management of Ocular Disease OD07— DISTICHIASIS FIG. 36G provides a schematic specification of a logic package installed and operative within the automated ocular disease (OD) recognition, treatment and compliance management system of the present invention 10, biomedically-engineered for the ocular disease afflicting the eyelids/orbit, specifically—Distichiasis—and assigned ocular disease code OD7. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD07: Distichiasis

Disease Diagnosis Input Factors:

M03: Meibomian Gland Dysfunction

M06: Tear Film Dynamics 1: Tracking Reflective Light Particles

M07: Tear Film Dynamics 2: Detecting Perturbations in Tear Film Using Placido Light Discs Projected onto the Cornea M39: Distichiasis Diagnosis Logic: IF [M06: Tear Film Dynamics 1: Tracking Reflective Light Particle speed after opening eyes <7 mm/sec OR M06: Tear Film Dynamics 1: Tracking Reflective Light Particle time for speed to reach 0 mm/sec<1 sec] AND M07: Tear Film Dynamics 2: Detecting Perturbations in Tear Film Using Placido Light Discs Projected onto the cornea tear film break-up time <4 secs AND M03: Meibomian Gland Dysfunction >50% of eyelid OR M39: Distichiasis present, THEN OD07: Distichiasis.

Treatment Logic: IF OD07: Distichiasis, THEN TM01: Refer to eye doctor AND TM05: Recommend artificial tears four times a day to the affected eye AND TM09: Recommend artificial tear ointment AND [TM06: Recommend surgery OR TM11: Recommend cryotherapy to eyelashes].

Management Logic: IF OD07: Distichiasis, THEN check OD06: Trichiasis AND OD07: Distichiasis AND OD08: Floppy Eyelid Syndrome AND OD09: Blepharospasm AND OD29: Pemphigoid.

Specification of Machine-Based Logic Packages Used in the Automated Recognition, Treatment and Care Management of Ocular Disease OD08—FLOPPY EYELID SYNDROME FIG. 36H provides a schematic specification of a logic package installed and operative within the automated ocular disease (OD) recognition, treatment and compliance management system of the present invention 10, biomedically-engineered for the ocular disease afflicting the eyelids/orbit, specifically—Floppy Eyelid Syndrome—and assigned ocular disease code OD8. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD08: Floppy Eyelid Syndrome

Disease Diagnosis Input Factors:

M5: Dermatochalasis

M9: Blink Speed and Patterns Configured and Trained—Partial Blink

M38: Ectropion

M40: FES Upper Eyelid Laxity

M40: FES Lower Eyelid Laxity

M40: FES Orbital Fat Prolapse

SD32: Sleep Apnea

Diagnostic Logic: IF (M5: Blink Speed and Patterns Configured and Trained—Partial Blink >10 blinks OR M38 Ectropion present OR M5: Dermatochalasis upper eyelid overhand over eyelid margin] AND [M40: FES Upper Eyelid Laxity OR FES Lower Eyelid Laxity OR FES Orbital Fat Prolapse], THEN OD08: Floppy Eyelid Syndrome.

Treatment Logic: IF OD08: Floppy Eyelid Syndrome, THEN check OD38: Exposure Keratopathy AND TM05: Recommend artificial tears four times a day to both eyes AND TM09: Recommend artificial tear ointment at bedtime to both eyes AND TM01: Refer to eye doctor non-urgently.

Management Logic: IF OD08: Floppy Eyelid Syndrome, THEN check SD32: Sleep Apnea.

Specification of Machine-Based Logic Packages Used in the Automated Recognition, Treatment and Care Management of Ocular Disease OD09—BLEPHAROSPASM FIG. 36I provides a schematic specification of a logic package installed and operative within the automated ocular disease (OD) recognition, treatment and compliance management system of the present invention 10, biomedically-engineered for the ocular disease afflicting the eyelids/orbit, specifically—Blepharospasm—and assigned ocular disease code OD9. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD09: Blepharospasm

Disease Diagnosis Input Factors:

M9: Blink Speed Patterns Configured and Trained—Partial Blinks

M9: Blink Speed Patterns Configured and Trained—Blink Frequency

Diagnostic Logic: IF M9: Blink Speed Patterns Configured and Trained—Partial Blinks >15 OR M9: Blink Speed Patterns Configured and Trained—Blink Frequency >30, THEN OD09: Blepharospasm.

Treatment Logic: IF OD09: Blepharospasm, THEN TM01: Refer to eye doctor non-urgently AND TM05: Recommend artificial tears four times a day AND TM06: Recommend surgery AND TM13: Recommend cold compresses.

Management Logic: IF OD09: Blepharospasm, THEN check OD04: Entropion AND OD16: Thyroid Eye Disease AND OD30: Dry Eye Disease.

Specification of Machine-Based Logic Packages Used in the Automated Recognition, Treatment and Care Management of Ocular Disease OD10—DACRYOCYSTITIS FIG. 36J provides a schematic specification of a logic package installed and operative within the automated ocular disease (OD) recognition, treatment and compliance management system of the present invention 10, biomedically-engineered for the ocular disease afflicting the eyelids/orbit, specifically—Dacryocystitis—and assigned ocular disease code OD10. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD10: Dacryocystitis

Disease Diagnosis Input Factors:

M01: Conjunctival Injection

M18: Bacterial Conjunctivitis—Purulent Discharge

M28: Chalazion/Stye

M30: Preseptal Cellulitis—Eyelid Swelling

PEP8: Dacryocystitis

Diagnostic Logic: IF M01: Conjunctival Injection >25 ocular redness index AND M18: Bacterial Conjunctivitis—Purulent Discharge present AND M28: Chalazion/Stye present located medial lower eyelid AND M30: Preseptal Cellulitis—Eyelid Swelling lower eyelid present, THEN OD10: Dacryocystitis.

Treatment Logic: IF OD10: Dacryocystitis, THEN TM02: Refer to eye doctor urgently AND TM03: Recommend radiologic imaging AND TM04: Recommend warm compresses four times a day AND TM05: Recommend artificial tears four times a day AND TM14: Recommend oral antibiotics.

Management Logic: IF OD10: Dacryocystitis improved, THEN TM15: Recommend lacrimal system probe and irrigation||IF TM15: Lacrimal system with 25-75% reflux THEN TM16: Recommend antibiotic/steroid combo drops||IF TM15: Lacrimal system with >75% reflux THEN TM06: Recommend surgery. IF OD10: Dacryocystitis AND PEP29: Dacryocystitis THEN TM17: Recommend autoimmune work-up.

Specification of Machine-Based Logic Packages Used in the Automated Recognition, Treatment and Care Management of Ocular Disease OD11—CANALICULITIS FIG. 36K provides a schematic specification of a logic package installed and operative within the automated ocular disease (OD) recognition, treatment and compliance management system of the present invention 10, biomedically-engineered for the ocular disease afflicting the eyelids/orbit, specifically—Canaliculitis—and assigned ocular disease code OD11. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD11: Canaliculitis

Disease Diagnosis Input Factors:

M01: Conjunctival Injection

M19: Bacterial Conjunctivitis—Purulent Discharge

M30: Preseptal Cellulitis—Eyelid Swelling

PEP8: Canaliculitis

Diagnostic Logic: IF M01: Conjunctival Injection >25 ocular redness index AND M18: Bacterial Conjunctivitis—Purulent Discharge present AND M30: Preseptal Cellulitis—Eyelid Swelling medial upper or lower eyelid present, THEN OD11: Canaliculitis, Treatment Logic: IF OD11: Canaliculitis, THEN TM02: Refer to eye doctor urgently AND TM04: Recommend warm compresses four times a day AND TM05: Recommend artificial tears four times a day.

Management Logic: IF OD11: Canaliculitis not improved, THEN TM14: Recommend oral antibiotics AND TM16: Recommend antibiotic/steroid combo drops||IF OD11: Canaliculitis improved THEN TM15: Recommend lacrimal system probe and irrigation||IF TM15: Lacrimal system with >50% reflux then check OD10: Dacryocystitis.

Specification of Machine-Based Logic Packages Used in the Automated Recognition, Treatment and Care Management of Ocular Disease OD12—PRESEPTAL CELLULITIS FIG. 36L provides a schematic specification of a logic package installed and operative within the automated ocular disease (OD) recognition, treatment and compliance management system of the present invention 10, biomedically-engineered for the ocular disease afflicting the eyelids/orbit, specifically—Preseptal Cellulitis—and assigned ocular disease code OD12. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD12: Preseptal Cellulitis

Disease Diagnosis Input Factors:

M01: Conjunctival Injection

M30: Preseptal Cellulitis—Eyelid Swelling

Diagnostic Logic: IF M01: Conjunctival Injection >25 ocular redness index AND M30: Preseptal Cellulitis—Eyelid Swelling entire upper or lower eyelid, THEN OD12: Preseptal Cellulitis.

Treatment Logic: IF OD12: Preseptal Cellulitis, THEN TM02: Refer to eye doctor urgently AND TM04: Recommend warm compresses four times a day AND TM05: Recommend artificial tears four times a day AND TM14: Recommend oral antibiotics.

Management Logic: IF OD12: Preseptal Cellulitis not improved, THEN TM07: Refer to emergency room AND TM03: Recommend radiologic imaging AND TM18: Recommend intravenous antibiotics AND check OD13: Orbital Postseptal Cellulitis.

Specification of Machine-Based Logic Packages Used in the Automated Recognition, Treatment and Care Management of Ocular Disease OD13—ORBITAL POSTSEPTAL CELLULITIS FIG. 36M provides a schematic specification of a logic package installed and operative within the automated ocular disease (OD) recognition, treatment and compliance management system of the present invention 10, biomedically-engineered for the ocular disease afflicting the eyelids/orbit, specifically—Orbital Postseptal Cellulitis—and assigned ocular disease code OD13. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD13: Orbital Postseptal Cellulitis

Disease Diagnosis Input Factors:

M01: Conjunctival Injection
M11: Palpebral Fissure
M12: Margin Reflex Distance
M14: Levator Function
M18: Viral Conjunctivitis—Clear Discharge
M19: Bacterial Conjunctivitis—Purulent Discharge
M20: Allergic Conjunctivitis—Chemosis
M30: Preseptal Cellulitis—Eyelid Swelling
M31: Ptosis
M36: Orbital Postseptal Cellulitis Diagnostic Logic: IF M01: Conjunctival Injection >25 ocular redness index AND [M11: Palpebral Fissure <8 mm OR M12: Margin Reflex Distance 1<2 mm OR M14: Levator Function <8 mm] AND [M18: Viral Conjunctivitis—Clear Discharge present OR M19: Bacterial Conjunctivitis—Purulent Discharge present] AND M20: Allergic Conjunctivitis—Chemosis present AND M30: Preseptal Cellulitis—Eyelid Swelling upper and lower eyelid present AND M31: Ptosis AND M32: Proptosis OR M39: Orbital Postseptal Cellulitis, THEN OD13: Orbital Postseptal Cellulitis.

Treatment Logic: IF OD13: Orbital Post Septal Cellulitis, THEN TM07: Refer to emergency room AND TM03: Recommend radiologic imaging AND TM04: Recommend warm compresses four times a day AND TM05: Recommend artificial tears four times a day AND TM18: Recommend intravenous antibiotics.

Management Logic: IF OD13: Orbital Postseptal Cellulitis not improved, THEN TM06: Recommend surgery.

Specification of Machine-Based Logic Packages Used in the Automated Recognition, Treatment and Care Management of Ocular Disease OD14—PROPTOSIS FIG. 36N provides a schematic specification of a logic package installed and operative within the automated ocular disease (OD) recognition, treatment and compliance management system of the present invention 10, biomedically-engineered for the ocular disease afflicting the eyelids/orbit, specifically—Proptosis—and assigned ocular disease code OD14. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD14: Proptosis

Disease Diagnosis Input Factors:

M11: Palpebral Fissure
M12: Margin Reflex Distance
M13: Scleral Show
M33: Proptosis Diagnostic Logic: IF M11: Palpebral Fissure >12 mm OR M12: Margin Reflex Distance 1 >6 mm OR M12: Margin Reflex Distance 2 >6 mm OR M12: Scleral Show >2 mm OR M33: Proptosis, THEN OD14: Proptosis.

Treatment Logic: IF OD14: Proptosis, THEN TM02: Refer to eye doctor urgent AND TM03: Recommend radiologic imaging.

Management Logic: IF OD14: Proptosis, THEN check OF13: Orbital Post Septal Cellulitis AND OD16: Thyroid Eye Disease AND OD19: Retrobulbar Hemorrhage.

Specification of Machine-Based Logic Packages Used in the Automated Recognition, Treatment and Care Management of Ocular Disease OD15—ORBITAL FRACTURE FIG. 36O provides a schematic specification of a logic package installed and operative within the automated ocular disease (OD) recognition, treatment and compliance management system of the present invention 10, biomedically-engineered for the ocular disease afflicting the eyelids/orbit, specifically—Orbital Fracture—and assigned ocular disease code OD15. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD15: Orbital Fracture

Disease Diagnosis Input Factors:

M30: Preseptal cellulitis—Eyelid Swelling
M32: Ophthalmoplegia
M33: Hypoglobus
ET5: Blunt Eye Trauma
SD21: Facial Trauma Diagnostic Logic: IF [M30: Preseptal cellulitis—Eyelid Swelling present OR M32: Ophthalmoplegia present OR M33: Hypoglobus] AND [ET5: Blunt Eye Trauma OR SD21: Facial Trauma], THEN OD15: Orbital Fracture.

Treatment Logic: IF OD15: Orbital Fracture, THEN TM07: Refer to emergency room AND TM03: Recommend radiologic imaging AND TM14: Recommend oral antibiotics AND TM20: Recommend cool compresses.

Management Logic: IF OD15: Orbital Fracture, THEN check OD14: Proptosis AND OD19: Retrobulbar Hemorrhage.

Specification of Machine-Based Logic Packages Used in the Automated Recognition, Treatment and Care Management of Ocular Disease OD16—THYROID EYE DISEASE FIG. 36P provides a schematic specification of a logic package installed and operative within the automated ocular disease (OD) recognition, treatment and compliance management system of the present invention 10, biomedically-engineered for the ocular disease afflicting the eyelids/orbit, specifically—Thyroid Eye Disease—and assigned ocular disease code OD16. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD16: Thyroid Eye Disease

Disease Diagnosis Input Factors:

M32: Ophthalmoplegia
M33: Proptosis
M37: Thyroid Eye Disease

PEP33: Thyroid Eye Disease

SD25: Thyroid Disease

Diagnostic Logic: IF [M32: Ophthalmoplegia present OR M33: Proptosis present OR M37: Thyroid Eye Disease] AND [PEP33: Thyroid Eye Disease OR SD25: Thyroid Disease], THEN OD16: Thyroid Eye Disease.

Treatment Logic: IF OD16: Thyroid Eye Disease chronic, THEN TM01: Refer to eye doctor non-urgently||IF OD16: Thyroid Eye Disease acute, THEN TM02: Refer to eye doctor urgently AND TM03: Recommend radiologic imaging AND TM19: Recommend oral steroids.

Management Logic: IF OD16: Thyroid Eye Disease, THEN TM21: Recommend endocrine work-up.

Specification of Machine-Based Logic Packages Used in the Automated Recognition, Treatment and Care Management of Ocular Disease OD17—BLEPHARITIS FIG. 36Q provides a schematic specification of a logic package installed and operative within the automated ocular disease (OD) recognition, treatment and compliance management system of the present invention 10, biomedically-engineered for the ocular disease afflicting the eyelids/orbit, specifically—Blepharitis—and assigned ocular disease code OD17. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD17: Blepharitis

Disease Diagnosis Input Factors

M3: Meibomian Gland Dysfunction

M27: Blepharitis—Scruff at Eyelashes

PEP22: Demodex

Diagnostic Logic: IF [M3: Meibomian Gland Dysfunction >25% OR M27: Blepharitis—Scruff at Eyelashes] AND PEP22: Demodex, THEN OD17: Blepharitis.

Treatment Logic: IF OD17: Blepharitis, THEN TM01: Refer to eye doctor non-urgently AND TM04: Recommend warm compresses two times a day AND TM05: Recommend artificial tears four times a day AND TM22: Recommend eyelid hygiene.

Management Logic: IF OD17: Blepharitis not improved, THEN TM14: Recommend oral antibiotics AND TM16: Recommend antibiotic/steroid combo drops.

Specification of Machine-Based Logic Packages Used in the Automated Recognition, Treatment and Care Management of Ocular Disease OD18—HERPES ZOSTER DERMATITIS (SHINGLES)

FIG. 36R provides a schematic specification of a logic package installed and operative within the automated ocular disease (OD) recognition, treatment and compliance management system of the present invention, biomedically-engineered for the ocular disease afflicting the eyelids/orbit, specifically—Herpes Zoster Dermatitis (Shingles)—and assigned ocular disease code OD18, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD18: Herpes Zoster Dermatitis (Shingles)

Disease Diagnosis Input Factors

M41: Herpes Zoster Dermatitis

Diagnostic Logic: IF M41: Herpes Zoster Dermatitis on face, THEN OD18: Herpes Zoster Dermatitis (Shingles).

Treatment Logic: IF M41: Herpes Zoster Dermatitis (Shingles), THEN TM02: Refer to eye doctor urgently AND TM23: Recommend oral antiviral agents AND TM27: Recommend topical antibiotic ointment two times a day.

Management Logic: IF M41: Herpes Zoster Dermatitis (Shingles) not improved, THEN TM07: Refer to emergency room AND TM24: Recommend intravenous antiviral agent.

Specification of Machine-Based Logic Packages Used in the Automated Recognition, Treatment and Care Management of Ocular Disease OD19—RETROBULBAR HEMORRHAGE FIG. 36S provides a schematic specification of a logic package installed and operative within the automated ocular disease (OD) recognition, treatment and compliance management system of the present invention 10, biomedically-engineered for the ocular disease afflicting the eyelids/orbit, specifically—Retrobulbar Hemorrhage—and assigned ocular disease code OD19. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD19: Retrobulbar Hemorrhage

Disease Diagnosis Input Factors:

M32: Ophthalmoplegia

M33: Proptosis

ET5: Blunt Eye Trauma

SD21: Facial Trauma

Diagnostic Logic: IF [M32: Ophthalmoplegia present OR M33: Proptosis present] AND [ET5: Blunt Eye Trauma OR SD21: Facial Trauma], THEN OD19: Retrobulbar Hemorrhage.

Treatment Logic: IF OD19: Retrobulbar Hemorrhage, THEN TM07: Refer to emergency room AND TM03: Recommend radiologic imaging.

Management Logic: IF OD19: Retrobulbar Hemorrhage not improved, THEN TM06: Recommend surgery.

Specification of Machine-Based Logic Packages Used in the Automated Recognition, Treatment and Care Management of Ocular Disease OD20—VIRAL CONJUNCTIVITIS FIG. 36T is a schematic specification of a logic package installed and operative within the automated ocular disease (OD) recognition, treatment and compliance management system of the present invention 10, biomedically-engineered for the ocular disease afflicting the sclera/conjunctiva, specifically—Viral Conjunctivitis—and assigned ocular disease code OD20. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

Sclera/Conjunctiva:

OD20: Viral Conjunctivitis

Disease Diagnosis Input Factors:

M01: Conjunctival Injection

M18: Viral Conjunctivitis—Clear Discharge

SD31: Cold Symptoms

PEP25: Bilateral Involvement

Diagnostic Logic: IF M01: Conjunctival Injection >25 ocular redness index AND M18: Viral Conjunctivitis—Clear Discharge present AND SD31: Cold Symptoms AND PEP25: Bilateral Involvement, THEN OD20: Viral Conjunctivitis.

Treatment Logic: IF OD20: Viral Conjunctivitis, THEN TM05: Recommend artificial tears four times a day AND TM20: Recommend cool compresses.

Management Logic: IF OD20: Viral Conjunctivitis not improved, THEN TM01: Refer to doctor non-urgently.

Specification of Machine-Based Logic Packages Used in the Automated Recognition, Treatment and Care Management of Ocular Disease OD21—BACTERIAL CONJUNCTIVITIS FIG. 36U provides a schematic specification of a logic package installed and operative within the automated ocular disease (OD) recognition, treatment and compliance management system of the present invention 10, biomedically-engineered for the ocular disease afflicting the sclera/conjunctiva, specifically—Bacterial Conjunctivitis—and assigned ocular disease code OD21. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD21: Bacterial Conjunctivitis

Disease Diagnosis Input Factors:

M01: Conjunctival Injection

M19: Bacterial Conjunctivitis—Purulent Discharge

Diagnostic Logic: IF M01: Conjunctival Injection >25 ocular redness index AND M19: Bacterial Conjunctivitis—Purulent Discharge, THEN OD21: Bacterial Conjunctivitis.

Treatment Logic: IF OD21: Bacterial Conjunctivitis, THEN TM02: Refer to eye doctor urgently AND TM26: Recommend topical antibiotic drops four times a day AND Tm27: Recommend topical antibiotic ointment at bedtime.

Management Logic: IF OD21: Bacterial Conjunctivitis not improved, THEN TM07: Refer to emergency room AND TM26: Recommend topical antibiotic drops every hour during the day.

Specification of Machine-Based Logic Packages Used in the Automated Recognition, Treatment and Care Management of Ocular Disease OD22—ALLERGIC CONJUNCTIVITIS FIG. 36V provides a schematic specification of a logic package installed and operative within the automated ocular disease (OD) recognition, treatment and compliance management system of the present invention 10, biomedically-engineered for the ocular disease afflicting the sclera/conjunctiva, specifically—Allergic Conjunctivitis—and assigned ocular disease code OD22. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD22: Allergic Conjunctivitis

Disease Diagnosis Input Factors:

M01: Conjunctival Injection

M18: Viral Conjunctivitis: Clear Discharge

M20: Allergic Conjunctivitis—Chemosis

PEP21: Allergic Conjunctivitis

SD17: Atopy

SD33: Seasonal Allergies

Diagnostic Logic: IF M01: Conjunctival Injection >25 ocular redness index AND M18: Viral Conjunctivitis: Clear Discharge present AND M20: Allergic Conjunctivitis—Chemosis present AND PEP21: Allergic Conjunctivitis AND SD17: Atopy AND SD33: Seasonal Allergies, THEN OD22: Allergic Conjunctivitis.

Treatment Logic: IF OD22: Allergic Conjunctivitis, THEN TM28: Recommend oral anti-histamine once a day AND TM29: Recommend topical anti-histamine drops two times a day.

Management Logic: IF OD22: Allergic Conjunctivitis not improved, THEN TM01: Refer to eye doctor non-urgently AND TM16: Recommend antibiotic/steroid combo drops.

Specification of Machine-Based Logic Packages Used in the Automated Recognition, Treatment and Care Management of Ocular Disease OD23—CHEMICAL BURN CONJUNCTIVITIS FIG. 36W provides a schematic specification of a logic package installed and operative within the automated ocular disease (OD) recognition, treatment and compliance management system of the present invention 10, biomedically-engineered for the ocular disease afflicting the sclera/conjunctiva, specifically—Chemical Burn Conjunctivitis—and assigned ocular disease code OD23. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD23: Chemical Burn Conjunctivitis

Disease Diagnosis Input Factors:

M01: Conjunctival Injection

M18: Viral Conjunctivitis—Clear Discharge

M20: Allergic Conjunctivitis—Chemosis

M21: Chemical Burn Conjunctivitis—Limbal Whitening

PEP26: Chemical Exposure

Diagnostic Logic: IF M01: Conjunctival Injection >25 ocular redness index AND [M18: Viral Conjunctivitis—Clear Discharge present OR M20: Allergic Conjunctivitis—Chemosis] AND M21: Chemical Burn Conjunctivitis—Limbal Whitening AND PEP26: Chemical Exposure, THEN OD23: Chemical Burn Conjunctivitis.

Treatment Logic: IF OD23: Chemical Burn Conjunctivitis, THEN TM02: Refer to eye doctor urgently AND TM16: Recommend antibiotic/steroid combo drop every hour while awake AND TM08: Recommend antibiotic/steroid combo ointment at bedtime.

Management Logic: IF OD23: Chemical Burn Conjunctivitis not improved, THEN TM03: Recommend amniotic membrane placement.

Specification of Machine-Based Logic Packages Used in the Automated Recognition, Treatment and Care Management of Ocular Disease OD24—SUPERIOR LIMBIC KERATO-CONJUNCTIVITIS FIG. 36X provides a schematic specification of a logic package installed and operative within the automated ocular disease (OD) recognition, treatment and compliance management system of the present invention 10, biomedically-engineered for the ocular disease afflicting the sclera/conjunctiva, specifically—Superior Limbic Keratoconjunctivitis—and assigned ocular disease code OD24. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD24: Superior Limbic Keratoconjunctivitis

Disease Diagnosis Input Factors:

M01: Conjunctival Injection

M10: Corneal Abrasion

M18: Viral Conjunctivitis—Clear Discharge

M26: Superior Limbic Keratoconjunctivitis (SLK)

Diagnostic Logic: IF [M01: Conjunctival Injection >50 in superior conjunctiva AND M10: Corneal abrasion present superior cornea AND M18: Viral Conjunctivitis—Clear Discharge present] OR M26: Superior Limbic Keratoconjunctivitis (SLK), THEN OD24: Superior Limbic Keratoconjunctivitis (SLK).

Treatment Logic: IF OD24: Superior Limbic Keratoconjunctivitis (SLK), THEN TM02: Refer to eye doctor urgently AND TM05: Recommend artificial tears four times a day AND TM09: Recommend artificial tear ointment at bedtime.

Management Logic: IF OD24: Superior Limbic Kerato-conjunctivitis (SLK) not improved, THEN TM31: Recommend topical cyclosporine drops OR TM16: Recommend antibiotic/steroid combo drops||IF OD24: Superior Limbic Keratoconjunctivitis (SLK), THEN check SD25: Thyroid Disease AND TM21: Recommend endocrine work-up.

Specification of Machine-Based Logic Packages Used in the Automated Recognition, Treatment and Care Management of Ocular Disease OD25—SUBCONJUNCTIVAL HEMORRHAGE FIG. 36Y provides a schematic specification of a logic package installed and operative within the automated ocular disease (OD) recognition, treatment and compliance management system of the present invention 10, biomedically-engineered for the ocular disease afflicting the sclera/conjunctiva, specifically—Subconjunctival Hemorrhage—and assigned ocular disease code OD25. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD25: Subconjunctival Hemorrhage
Disease Diagnosis Input Factors:
    M25: Episcleritis/Scleritis—Sectoral Conjunctival Injection
    M23: Subconjunctival Hemorrhage
    ET5: Blunt Eye Trauma
    SD21: Facial Trauma Diagnostic Logic: IF [M25: Episcleritis/Scleritis—Sectoral Conjunctival Injection >75 ocular redness index in one sector without vessel differentiation AND [ET5: Blunt Eye Trauma OR SD21: Facial Trauma]] OR M23: Subconjunctival Hemorrhage, THEN OD25: Subconjunctival Hemorrhage.

Treatment Logic: IF OD25: Subconjunctival Hemorrhage, THEN TM05: Recommend artificial tears four times a day AND TM20: Recommend cool compresses.

Management Logic: IF OD25: Subconjunctival Hemorrhage, THEN check OD27: Conjunctival Laceration.

Specification of Machine-Based Logic Packages Used in the Automated Recognition, Treatment and Care Management of Ocular Disease OD26—EPISCLERITIS/SCLERITIS FIG. 36Z provides a schematic specification of a logic package installed and operative within the automated ocular disease (OD) recognition, treatment and compliance management system of the present invention 10, biomedically-engineered for the ocular disease afflicting the sclera/conjunctiva, specifically—Episcleritis/Scleritis—and assigned ocular disease code OD26. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD26: Episcleritis/Scleritis
Disease Diagnosis Input Factors:
    SD2: Autoimmune Disease
    SD3: Connective Tissue Disease
    SD4: Sjogren's Syndrome
    SD5: Sjogren's Syndrome Review of Systems
    SD6: Autoimmune Review of Systems Diagnostic Logic: IF M25: Episcleritis/Scleritis—Sectoral Conjunctival Injection >50 ocular redness index AND

[SD2: Autoimmune Disease OR SD3: Connective Tissue Disease OR SD4: Sjogren's Syndrome OR SD5: Sjogren's Syndrome of Systems OR SD6: Autoimmune Review of Systems, THEN OD26: Episcleritis/Scleritis.

Treatment Logic: IF OD26: Episcleritis/Scleritis, THEN TM02: Refer to eye doctor urgently AND TM32: Recommend oral ibuprofen AND TM05: Recommend artificial tears four times a day.

Management Logic: IF OD26: Episcleritis/Scleritis not improved, THEN TM19: Recommend oral steroids AND TM16: Recommend antibiotic/steroid combo drops||IF OD26: Episcleritis/Scleritis, THEN TM17: Recommend autoimmune work-up.

Specification of Machine-Based Logic Packages Used in the Automated Recognition, Treatment and Care Management of Ocular Disease OD27—CONJUNCTIVAL LACERATION FIG. 36AA provides a schematic specification of a logic package installed and operative within the automated ocular disease (OD) recognition, treatment and compliance management system of the present invention 10, biomedically-engineered for the ocular disease afflicting the sclera/conjunctiva, specifically—Conjunctival Laceration—and assigned ocular disease code OD27. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD27: Conjunctival Laceration
Disease Diagnosis Input Factors:
    M23: Subconjunctival Hemorrhage
    M24: Conjunctival Laceration
    M25: Episcleritis/Scleritis—Sectoral Conjunctival Injection
    ET5: Blunt Eye Trauma
    SD21: Facial Trauma Diagnostic Logic: IF [[M23: Subconjunctival Hemorrhage OR M25: Episcleritis/Scleritis—Sectoral Conjunctival Injection >50 ocular redness index] AND [ET5: Blunt Eye Trauma OR SD21: Facial Trauma]] OR M24: Conjunctival Laceration, THEN OD27: Conjunctival Laceration.

Treatment Logic: IF OD27: Conjunctival Laceration, THEN TM02: Refer to eye doctor urgently AND TM27: Recommend topical antibiotic ointment four times a day.

Management Logic: IF OD27: Conjunctival Laceration not improved, THEN TM06: Recommend surgery.

Specification of Machine-Based Logic Packages Used in the Automated Recognition, Treatment and Care Management of Ocular Disease OD28—HERPES ZOSTER CONJUNCTIVITIS FIG. 36BB provides a schematic specification of a logic package installed and operative within the automated ocular disease (OD) recognition, treatment and compliance management system of the present invention 10, biomedically-engineered for the ocular disease afflicting the sclera/conjunctiva, specifically—Herpes Zoster Conjunctivitis—and assigned ocular disease code OD28. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD28: Herpes Zoster Conjunctivitis
Disease Diagnosis Input Factors:
    M01: Conjunctival Injection
    M18: Viral Conjunctivitis—Clear Discharge
    M41: Herpes Zoster Dermatitis Diagnostic Logic: IF M01: Conjunctival Injection >25 ocular redness index AND M18: Viral Conjunctivitis—Clear Discharge AND M41: Herpes Zoster Dermatitis, THEN OD28: Herpes Zoster Conjunctivitis.

Treatment Logic: IF OD28: Herpes Zoster Conjunctivitis, THEN TM02: Refer to eye doctor urgently AND TM23: Recommend oral antivirals AND TM05: Recommend artificial tears four times a day AND TM27: Recommend antibiotic ointment three times a day.

Management Logic: IF OD28: Herpes Zoster Conjunctivitis THEN check OD35: Herpes Zoster Keratitis‖IF OD28: Herpes Zoster Conjunctivitis not improved, THEN TM07: Refer to emergency room AND check [M32: Ophthalmoplegia AND M33: Proptosis/Hypoglobus]‖‖IF OD28: Herpes Zoster Conjunctivitis AND M32: Ophthalmoplegia present OR M33: Proptosis present, THEN TM24: Recommend intravenous antiviral agents.

Specification of Machine-Based Logic Packages Used in the Automated Recognition, Treatment and Care Management of Ocular Disease OD29—PEMPHIGOID FIG. 36CC provides a schematic specification of a logic package installed and operative within the automated ocular disease (OD) recognition, treatment and compliance management system of the present invention 10, biomedically-engineered for the ocular disease afflicting the sclera/conjunctiva, specifically—Pemphigoid—and assigned ocular disease code OD29. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD29: Pemphigoid

Disease Diagnosis Input Factors:

M01: Conjunctival Injection

M07: Tear Film Dynamics 2: Detecting Perturbations in Tear Film Using Placido Light Discs Projected onto the Cornea M09: Blink Speed and Patterns Configured and Trained—Partial Blinks M11: Palpebral Fissure M12: Margin Reflex Distance M38: Ectropion/Entropion M39: Trichiasis Diagnostic Logic: IF Conjunctival Injection >50 ocular redness index AND [M07: Tear Film Dynamics 2: Detecting Perturbations in Tear Film Using Placido Light Discs Projected onto the Cornea present OR M09: Blink Speed and Patterns Configured and Trained—Partial Blinks >10] AND [M11: Palpebral Fissure Height <8 mm OR M12: Margin Reflex Distance 1<2.5 mm] AND [M38: Ectropion/Entropion OR M39: Trichiasis], THEN OD29: Pemphigoid.

Treatment Logic: IF OD29: Pemphigoid, THEN TM02: Refer to eye doctor urgently AND TM08: Recommend antibiotic/steroid combo ointment four times a day AND TM14: Recommend oral antibiotics AND TM17: Recommend autoimmune work-up.

Management Logic: IF OD29: Pemphigoid not improved, THEN TM34: Recommend oral steroid sparing immunosuppressants.

Specification of Machine-Based Logic Packages Used in the Automated Recognition, Treatment and Care Management of Ocular Disease OD30—DRY EYE DISEASE (DED)

FIG. 36DD provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

FIG. 36EE is a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED) Staged Management—and assigned ocular disease code OD30. As shown, the logic package specifies staged treatment logic rules for the specified ocular disease.

Cornea:

OD30: Dry Eye Disease (DED)

Disease Diagnosis Input Factors:

M01: Conjunctival Injection

M2: Tear Meniscus Height

M3: Meibomian Gland Dysfunction

M4: Conjunctivochalasis

M5: Dermatochalasis

M6: Tear Film Dynamics 1

M7: Tear Film Dynamics 2

M8: Tear Film Dynamics 3

M9: Blink Speed and Patterns Configured and Trained

CLi: Contact Lens

CLUi: Contact Lens Use

SD1: Diabetes

SD2: Autoimmune Disease

SD4: Sjogren's Syndrome

SD5: Sjogren's Syndrome Review of Systems

SD6: Autoimmune Review of Systems

SD7: Stevens-Johnson's Syndrome

SD32: Sleep Apnea

SD34: Hypertension

SD35: High Cholesterol

SD36: Heart Disease

OSi: Ophthalmic Surgery

PEPi: Previous Eye Pathology

OMi: Ocular Medications

SMi: Systemic Medications

LTi: Lifestyle

LSi: Living Situation

SYi: Symptoms

FTi: Functionality

EVi: Environment

Diagnostic Logic: IF SYi OR [FTi AND EVi], THEN OD30: Dry Eye Disease (DED).

Treatment Logic: IF OD30: Dry Eye Disease (DED), THEN TM63: Dry eye disease staged management.

Management Logic: IF OD30: Dry Eye Disease (DED), THEN TM64: Dry eye disease classification determination.

TM63: Dry Eye Disease (DED)—Staged Management—OD30.

IF OD30: Dry Eye Disease (DED) THEN TM01: Refer to eye doctor non-urgently AND TM05: Recommend artificial tears four times a day AND TM04: Recommend warm compresses two times a day AND TM51: Recommend oral omega-3 supplement AND TM52: Recommend oral vitamin C supplement AND TM53: Recommend indoor humidification.

IF no improvement after 4 weeks, THEN TM54: Recommend preservative free artificial tears six times a day AND TM04: Recommend warm compresses two times a day AND TM22: Recommend eyelid hygiene two times a day AND TM09: Recommend artificial tear ointment at bedtime AND TM55: Recommend re-esterified omega-3/6 supplement AND TM52: Recommend oral vitamin C supplement AND TM53: Recommend indoor humidification.

IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND [TM56: Recommend dry eye disease prescription drops OR TM57: Recommend punctal plugs OR TM08: Recommend antibiotic/steroid combo ointment two times a day].

IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND [TM58: Recommend office-based procedures for Meibomian gland dysfunction OR TM33: Recommend steroid drops four week tapering course OR TM14: Recommend oral antibiotics].

IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND TM59: Recommend serum tears four times a day.

IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND TM60: Recommend contact lens trial.

IF no improvement after 8 weeks, THEN TM54: Recommend preservative free artificial tears six times a day AND TM04: Recommend warm compresses two times a day AND TM22: Recommend eyelid hygiene two times a day AND TM55: Recommend re-esterified omega-3/6 supplement AND TM52: Recommend oral vitamin C supplement AND TM53: Recommend indoor humidification AND TM56: Recommend dry eye disease prescription drops AND [TM61: Recommend surgical punctal occlusion OR TM62: Recommend compounded N-acetylcysteine drops OR TM30: Recommend amniotic membrane placement].

Specification of Machine-Based Logic Packages Used in the Automated Recognition, Treatment and Care Management of Ocular Disease OD30-DED01—SJOGREN's DISEASE FIG. 36FF provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED01 Primary Sjogren's Disease. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED01: Primary Sjogren's Disease

Diagnostic Logic: IF M2: Tear Meniscus Height <0.2 mm AND [M6: Tear Film Dynamics 1—Reflective light particles velocity <7 mm/sec OR M7: Tear Film Dynamics 2—Placido disc with aberrations OR M8: Tear Film Dynamics 3—Change in tear meniscus height after blinking <0.2 mm] AND [S4: Sjogren's Syndrome OR SD5: Sjogren's Syndrome Review of Systems], THEN OD30-DED01: Primary Sjogren's Disease.

Treatment Logic: IF OD30-DED01: Primary Sjogren's Disease, THEN TM63: Dry eye disease staged management.

Management Logic: IF OD30-DED01: Primary Sjogren's Disease, THEN TM17: Recommend autoimmune work-up.

Specification of Machine-Based Logic Packages Used in the Automated Recognition, Treatment and Care Management of Ocular Disease OD30-DED02—SECONDARY SJOGREN's DISEASE FIG. 36GG provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED02 Secondary Sjogren's Disease. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED02: Secondary Sjogren's Disease

Diagnostic Logic: IF M2: Tear Meniscus Height <0.2 mm AND [M6: Tear Film Dynamics 1—Reflective light particles velocity <7 mm/sec OR M7: Tear Film Dynamics 2—Placido disc with aberrations OR M8: Tear Film Dynamics 3—Change in tear meniscus height after blinking <0.2 mm] AND [SD6: Autoimmune Review of Systems OR SD2: Autoimmune Disorder], THEN OD30-DED02: Secondary Sjogren's Disease.

Treatment Logic: IF OD30-DED02: Secondary Sjogren's Disease, THEN TM63: Dry eye disease staged management.

Management Logic: IF OD30-DED02: Secondary Sjogren's Disease, THEN TM17: Recommend autoimmune work-up.

Specification of Machine-Based Logic Packages Used in the Automated Recognition, Treatment and Care Management of Ocular Disease OD30-DED03—LACRIMAL GLAND DYSFUNCTION FIG. 36HH provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED03 Lacrimal Gland Dysfunction. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED03: Lacrimal Gland Dysfunction

Diagnostic Logic: IF M2: Tear Meniscus Height <0.2 mm AND [M6: Tear Film Dynamics 1—Reflective light particles velocity <7 mm/sec OR M7: Tear Film Dynamics 2—Placido disc with aberrations OR M8: Tear Film Dynamics 3—Change in tear meniscus height after blinking <0.2 mm], THEN OD30-DED03: Lacrimal Gland Dysfunction Treatment Logic: IF OD30-DED03: Lacrimal Gland Dysfunction, THEN TM63: Dry eye disease staged management.

Management Logic: IF OD30-DED03: Lacrimal Gland Dysfunction. THEN TM17: Recommend autoimmune work-up AND TM03: Recommend radiologic imaging.

Specification of Machine-Based Logic Packages Used in the Automated Recognition, Treatment and Care Management of Ocular Disease OD30-DED04—LACRIMAL GLAND DUCT DYSFUNCTION FIG. 36II provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED04 Lacrimal Gland Duct Dysfunction. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED04: Lacrimal Gland Duct Obstruction

Diagnostic Logic: IF M2: Tear Meniscus Height <0.2 mm AND [M6: Tear Film Dynamics 1—Reflective light particles velocity <7 mm/sec OR M7: Tear Film Dynamics 2—Placido disc with aberrations OR M8: Tear Film Dynamics 3—Change in tear meniscus height after blinking <0.2 mm] AND [PEP27: Trachoma OR PEP28: Pemphigoid OR PEP29: Erythema Multiforme OR PEP30: burns], THEN OD30-DED04: Lacrimal Gland Duct Obstruction.

Treatment Logic: IF OD30-DED04: Lacrimal Gland Duct Obstruction, THEN TM63: Dry eye disease staged management.

Management Logic: IF OD30-DED04: Lacrimal Gland Duct Obstruction, THEN TM17: Recommend autoimmune work-up AND TM03: Recommend radiologic imaging.

Specification of Machine-Based Logic Packages Used in the Automated Recognition, Treatment and Care Management of Ocular Disease OD30-DED05—CORNEAL REFLEX BLOCK FIG. 36JJ provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED05 Corneal Reflex Block. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED05: Corneal Reflex Block

Diagnostic Logic: IF M2: Tear Meniscus Height <0.2 mm AND [M6: Tear Film Dynamics 1—Reflective light particles velocity <7 mm/sec OR M7: Tear Film Dynamics 2—Placido disc with aberrations OR M8: Tear Film Dynamics 3—Change in tear meniscus height after blinking <0.2 mm] AND [CLi: Contact Lens OR CLUi: Contact Lens Use OR ETi: Eye Trauma OR OSi: Ophthalmic Surgery OR PEPi: Previous Eye Pathology], THEN OD30-DED05: Corneal Reflex Block.

Treatment Logic: IF OD30-DED05: Corneal Reflex Block, THEN TM63: Dry eye disease staged management.

Management Logic: IF OD30-DED05: Corneal Reflex Block, THEN TM65: Recommend corneal sensitivity testing.

Specification of Machine-Based Logic Packages Used in the Automated Recognition, Treatment and Care Management of Ocular Disease OD30-DED06—SYSTEMIC MEDICATIONS SIDE EFFECT FIG. 36KK provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED06 Systemic Medications Side Effect. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED06: Systemic Medications Side Effect

Diagnostic Logic: IF M2: Tear Meniscus Height <0.2 mm AND [M6: Tear Film Dynamics 1—Reflective light particles velocity <7 mm/sec OR M7: Tear Film Dynamics 2—Placido disc with aberrations OR M8: Tear Film Dynamics 3—Change in tear meniscus height after blinking <0.2 mm] AND SMi: Systemic Medications, THEN OD30-DED06: Systemic Medications Side Effect.

Treatment Logic: IF OD30-DED06: Systemic Medications Side Effect, THEN TM63: Dry eye disease staged management.

Management Logic: IF OD30-DED06: Systemic Medications Side Effect, THEN TM66: Recommend systemic medication evaluation.

Specification of Machine-Based Logic Packages Used in the Automated Recognition, Treatment and Care Management of Ocular Disease OD30-DED07—MEIBOMIAN GLAND DYSFUNCTION FIG. 36LL provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED07 Meibomian Gland Dysfunction. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED07: Meibomian Gland Dysfunction

Diagnostic Logic: IF M3: Meibomian Gland Dysfunction >0% of glands OR M27: Blepharitis—Scruff at eyelashes, THEN OD30-DED07: Meibomian Gland Dysfunction.

Treatment Logic: IF OD30-DED07: Meibomian Gland Dysfunction, THEN TM63: Dry eye disease staged management.

Management Logic: IF OD30-DED07: Meibomian Gland Dysfunction, THEN TM67: Recommend Demodex treatment.

Specification of Machine-Based Logic Packages Used in the Automated Recognition, Treatment and Care Management of Ocular Disease OD30-DED08—LID APERTURE ABNORMALITY FIG. 36MM provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED08 Lid Aperture Abnormality. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED08: Lid Aperture Abnormality

Diagnostic Logic: IF M5: Dermatochalasis OR M11: Palpebral Fissure >10 mm or <8 mm OR M13: Scleral Show >1 mm OR M9: Blink Speed and Patterns Configured and Trained—Partial blinks >10, THEN OD30-DED08: Lid Aperture Abnormality.

Treatment Logic: IF OD30-DED08: Lid Aperture Abnormality, THEN TM63: Dry eye disease staged management.

Management Logic: IF OD30-DED08: Lid Aperture Abnormality THEN TM68: Recommend blink exercises.

Specification of Machine-Based Logic Packages Used in the Automated Recognition, Treatment and Care Management of Ocular Disease OD30-DED09—LID FUNCTION ABNORMALITY FIG. 36NN provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED09 Lid Function Abnormality. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED09: Lid Function Abnormality

Diagnostic Logic: IF [M11: Palpebral Fissure >10 mm or <8 mm AND M14: Levator Function <15 mm] OR M9: Blink Speed and Patterns Configured and Trained—Blink duration >0.5 sec OR M9: Blink Speed and Patterns Configured and Trained—Blink speed <20 mm/sec OR M40: Floppy Eyelid Syndrome OR PEP31: Bell's Palsy, THEN OD30-DED09: Lid Function Abnormality.

Treatment Logic: IF OD30-DED09: Lid Function Abnormality, THEN TM63: Dry eye disease staged management.

Management Logic: IF OD30-DED09: Lid Function Abnormality, THEN TM68: Recommend blink exercises AND TM69: Recommend evaluation with primary care physician AND TM70: Recommend a sleep study.

Specification of Machine-Based Logic Packages Used in the Automated Recognition, Treatment and Care Management of Ocular Disease OD30-DED10—BLINK ABNORMALITY FIG. 36OO provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED10 Blink Abnormality. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED10: Blink Abnormality

Diagnostic Logic: IF [M9: Blink Speed and Patterns Configured and Trained—Partial blinks >10 AND M9: Blink Speed and Patterns Configured and Trained—Lid closure time >0.5 sec] OR [M9: Blink Speed and Patterns Configured and Trained—Blink interval <2.5 sec AND M9: Blink Speed and Patterns Configured and Trained—Blink frequency >20] OR [M9: Blink Speed and Patterns Configured and Trained—Blink duration >0.5 sec AND M9: Blink Speed and Patterns Configured and Trained—Blink speed <20 mm/sec] AND no other classifications, THEN OD30-DED10: Blink Abnormality.

Treatment Logic: IF OD30-DED10: Blink Abnormality, THEN TM63: Dry eye disease staged management.

Management Logic: IF OD30-DED10: Blink Abnormality, THEN TM68: Recommend blink exercises.

Specification of Machine-Based Logic Packages Used in the Automated Recognition, Treatment and Care Management of Ocular Disease OD30-DED11—TOPICAL DROP TOXICITY FIG. 36PP provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED11 Topical Drop Toxicity. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED11: Topical Drop Toxicity

Diagnostic Logic: IF M1: Conjunctival Injection >50 ocular redness index AND Omi, THEN OD30-DED11: Topical Drop Toxicity.

Treatment Logic: IF OD30-DED11: Topical Drop Toxicity, THEN TM63: Dry eye disease staged management.

Management Logic: IF OD30-DED11: Topical Drop Toxicity, THEN TM71: Recommend topical drop evaluation.

Specification of Machine-Based Logic Packages Used in the Automated Recognition, Treatment and Care Management of Ocular Disease OD30-DED12—CONTACT LENS OVERWEAR FIG. 36QQ provides a schematic specification of a logic package installed and operative within the automated ocular disease (OD) recognition, treatment and compliance management system of the present invention, biomedically-engineered for the ocular disease afflicting the cornea, specifically—Dry Eye Disease (DED)—and assigned ocular disease code OD30-DED12 Contact Lens Overwear, wherein the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED12: Contact Lens Overwear

Diagnostic Logic: IF CLi: Contact Lens OR CLUi: Contact Lens Use, THEN OD30-DED12: Contact Lens Overwear.

Treatment Logic: IF OD30-DED12: Contact Lens Overwear, THEN TM63: Dry eye disease staged management.

Management Logic: IF OD30-DED12: Contact Lens Overwear, THEN TM43: Recommend break from wearing contact lenses AND TM72: Recommend contact lens fitting/

Specification of Machine-Based Logic Packages Used in the Automated Recognition, Treatment and Care Management of Ocular Disease OD30-DED13—OCULAR SURFACE DISEASE FIG. 36RR is a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED13 Ocular Surface Disease. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED13: Ocular Surface Disease

Diagnostic Logic: IF [PEPi: Previous Eye Pathology OR ETi: Eye Trauma OR OSi: Ophthalmic Surgery] AND [M9: Blink Speed and Patterns Configured and Trained—Blink interval <2.5 sec OR M9: Blink Speed and Patterns Configured and Trained—Blink duration >0.5 sec OR M9: Blink Speed and Patterns Configured and Trained—Blink frequency]>20, THEN OD30-DED13: Ocular Surface Disease.

Treatment Logic: IF OD30-DED13: Ocular Surface Disease, THEN TM63: Dry eye disease staged management.

Management Logic: IF OD30-DED13: Ocular Surface Disease, THEN TM65: Recommend corneal sensitivity testing.

Specification of Machine-Based Logic Packages Used in the Automated Recognition, Treatment and Care Management of Ocular Disease OD30-DED14—VITAMIN A DEFICIENCY FIG. 36SS provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED14 Vitamin A Deficiency. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED14: Vitamin A Deficiency

Diagnostic Logic: IF M4: Conjunctivochalasis AND M5: Dermatochalasis AND [SD10: Vitamin A Deficiency OR SD12: Malnourished OR SD37: Weight Loss OR SD38: Bariatric Surgery], THEN OD30-DED14: Vitamin A Deficiency.

Treatment Logic: IF OD30-DED14: Vitamin A Deficiency, THEN TM63: Dry eye disease staged management.

Management Logic: IF OD30-DED14: Vitamin A Deficiency, THEN TM73: Recommend oral vitamin A supplement AND TM69: Recommend evaluation with primary care physician.

Specification of Machine-Based Logic Packages Used in the Automated Recognition, Treatment and Care Management of Ocular Disease OD30-DED15—OCCUPATIONAL DRY EYE FIG. 36TT provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD30-DED15 Occupational Dry Eye. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED15: Occupational Dry Eye

Diagnostic Logic: IF LFS1: Hours of Screen Time Daily >3 hours AND [[M9: Blink Speed and Patterns Configured and Trained—Partial blinks >10 AND M9: Blink Speed and Patterns Configured and Trained—Lid closure time >0.5 sec] OR [M9: Blink Speed and Patterns Configured and Trained—Blink interval <2.5 sec AND M9: Blink Speed and Patterns Configured and Trained—Blink frequency >20] OR [M9: Blink Speed and Patterns Configured and Trained—Blink duration >0.5 sec AND M9: Blink Speed and Patterns Configured and Trained—Blink speed <20 mm/sec]], THEN OD30-DED15: Occupational Dry Eye.

Treatment Logic: IF OD30-DED15: Occupational Dry Eye, THEN TM63: Dry eye disease staged management.

Management Logic: IF OD30-DED15: Occupational Dry Eye, THEN TM68: Recommend blink exercises AND TM74: Recommend blue-light blocking glasses.

Specification of Machine-Based Logic Packages Used in the Automated Recognition, Treatment and Care Management of Ocular Disease OD30-DED16—ENVIRONMENTAL DRY EYE FIG. 36UU provides a schematic specification of a logic package installed and operative within the automated ocular disease (OD) recognition, treatment and compliance management system of the present invention 10, biomedically-engineered for the ocular disease afflicting the cornea, specifically—Dry Eye Disease (DED)—and assigned ocular disease code OD31-DED 16 Environmental Dry Eye. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD30-DED16: Environmental Dry Eye

Diagnostic Logic: IF LSTi: Living Situation AND no other classification, THEN OD30-DED16: Environmental Dry Eye Treatment Logic: IF OD30-DED16: Environmental Dry Eye, THEN TM63: Dry eye disease staged management Management Logic: IF OD30-DED16: Environmental Dry Eye, THEN TM68: Recommend blink exercises AND TM75: Recommend moisture-chamber glasses.

Specification of Machine-Based Logic Packages Used in the Automated Recognition, Treatment and Care Management of Ocular Disease OD31—CORNEAL ABRASION FIG. 36VV provides a schematic specification of a logic package installed and operative within the automated ocular disease (OD) recognition, treatment and compliance management system of the present invention 10, biomedically-engineered for the ocular disease afflicting the cornea, specifically—Corneal Abrasion—and assigned ocular disease code OD31. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD31: Corneal Abrasion

Disease Diagnosis Input Factors:

M01: Conjunctival Injection

M10: Corneal Abrasion

M18: Viral Conjunctivitis—Clear discharge

ETi: Eye Trauma

Diagnostic Logic: IF [M01: Conjunctival Injection >25 ocular redness index AND M18: Viral Conjunctivitis—Clear Discharge present AND ETi: Eye Trauma] OR M10: Corneal Abrasion, THEN OD31: Corneal Abrasion.

Treatment Logic: IF OD31: Corneal Abrasion, THEN TM02: Refer to eye doctor urgently AND TM26: Recommend topical antibiotic drops four times a day and TM27: Recommend topical antibiotic ointment at bedtime.

Management Logic: IF OD31: Corneal Abrasion not improved, THEN check OD33: Bacterial Keratitis AND OD34: Herpes Simplex Virus Keratitis AND OD35: Herpes Zoster Keratitis AND OD36: Acanthamoeba Keratitis AND OD37: Recurrent Corneal Erosion.

Specification of Machine-Based Logic Packages Used in the Automated Recognition, Treatment and Care Management of Ocular Disease OD32—CORNEAL FOREIGN BODY FIG. 36WW provides a schematic specification of a logic package installed and operative within the automated ocular disease (OD) recognition, treatment and compliance management system of the present invention 10, biomedically-engineered for the ocular disease afflicting the cornea, specifically—Corneal Foreign Body—and assigned ocular disease code OD32. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD32: Cornea Foreign Body
Disease Diagnosis Input Factors:
    M01: Conjunctival Injection
    M18: Viral Conjunctivitis—Clear discharge
    M45: Corneal Foreign Body
    Diagnostic Logic: IF M01: Conjunctival Injection >25 ocular redness index AND M18 Viral Conjunctivitis—Clear Discharge AND M45: Corneal Foreign Body, THEN OD32: Corneal Foreign Body.

Treatment Logic: IF OD32: Corneal Foreign Body, THEN TM02: Refer to eye doctor urgently AND TM26: Recommend topical antibiotic drops four times a day and TM27: Recommend topical antibiotic ointment at bedtime.

Management Logic: IF OD32: Corneal Foreign Body not improved, THEN check OD33: Bacterial Keratitis.

Specification of Machine-Based Logic Packages Used in the Automated Recognition, Treatment and Care Management of Ocular Disease OD33—BACTERIAL KERATITIS FIG. 36XX provides a schematic specification of a logic package installed and operative within the automated ocular disease (OD) recognition, treatment and compliance management system of the present invention 10, biomedically-engineered for the ocular disease afflicting the cornea, specifically—Bacterial Keratitis—and assigned ocular disease code OD33. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD33: Bacterial Keratitis
Disease Diagnosis Input Factors:
    M01: Conjunctival Injection
    M10: Corneal Abrasion
    M16: CTGR—Corneal Edema
    M18: Viral Conjunctivitis—Clear discharge
    M45: Corneal Infection
    Diagnostic Logic: IF M01: Conjunctival Injection >50 ocular redness index AND M10: Corneal Abrasion present AND M16: CTGR—Corneal Edema present AND M18:

Viral Conjunctivitis—Clear Discharge present AND M45: Corneal Infection, THEN OD33: Bacterial Keratitis.

Treatment Logic: IF OD33: Bacterial Keratitis, THEN TM02: Refer to eye doctor urgently AND TM26: Recommend topical antibiotic drops every hour while awake AND TM27: Recommend topical antibiotic ointment at bedtime.

Management Logic: IF OD33: Bacterial Keratitis not improved, THEN TM35: Recommend corneal cultures AND TM36: Recommend fortified topical antibiotic drops every hour around the clock.

Specification of Machine-Based Logic Packages Used in the Automated Recognition, Treatment and Care Management of Ocular Disease OD34—HERPES SIMPLEX VIRUS KERATITIS FIG. 36YY provides a schematic specification of a logic package installed and operative within the automated ocular disease (OD) recognition, treatment and compliance management system of the present invention 10, biomedically-engineered for the ocular disease afflicting the cornea, specifically—Herpes Simplex Virus Keratitis—and assigned ocular disease code OD34. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD34: Herpes Simplex Virus Keratitis
Disease Diagnosis Input Factors:
    M01: Conjunctival Injection
    M16: CTGR—Corneal Edema
    M18: Viral Conjunctivitis—Clear discharge
    PEP11: Viral Keratitis
    SD39: Cold Sores
    Diagnostic Logic: IF M01: Conjunctival Injection >25 ocular redness index AND M16: CTGR—Cornea Edema present AND M18: Viral Conjunctivitis—Clear Discharge present AND SD39: Cold Sores, THEN OD34: Herpes Simplex Virus Keratitis.

Treatment Logic: IF OD34: Herpes Simplex Virus Keratitis, THEN TM02: Refer to eye doctor urgently AND TM23: Recommend oral antiviral agents AND TM26: Recommend topical antibiotic drops four times a day AND TM27: Recommend topical antibiotic ointment at bedtime.

Management Logic: IF OD34 Herpes Simplex Virus Keratitis not improved, THEN TM35: Recommend corneal cultures AND TM25: Recommend topical antiviral drops four times a day. TM16: Recommend antibiotic/steroid combo drops four times a day IFF no OD31: Corneal Abrasion.

Specification of Machine-Based Logic Packages Used in the Automated Recognition, Treatment and Care Management of Ocular Disease OD35—HERPES ZOSTER KERATITIS FIG. 36ZZ provides a schematic specification of a logic package installed and operative within the automated ocular disease (OD) recognition, treatment and compliance management system of the present invention 10, biomedically-engineered for the ocular disease afflicting the cornea, specifically—Herpes Zoster Keratitis—and assigned ocular disease code OD35. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD35: Herpes Zoster Keratitis
Disease Diagnosis Input Factors:
    M01: Conjunctival Injection
    M10: Corneal Abrasion M16: CTGR—Corneal Edema M18: Viral Conjunctivitis—Clear discharge M41: Herpes Zoster Dermatitis M42: Herpes Zoster Keratitis M45: Corneal Infection Diagnostic Logic: IF [M01: Conjunctival Injection >25 ocular redness index AND M10: Corneal Abrasion present AND M16: CTGR—Corneal Edema present and M18: Viral Conjunctivitis—Clear Discharge present AND M42: Herpes Zoster Dermatitis present] OR M42: Herpes Zoster Keratitis, THEN OD35: Herpes Zoster Keratitis.

Treatment Logic: IF OD35: Herpes Zoster Keratitis, THEN TM02: Refer to eye doctor urgently AND TM23: Recommend oral antiviral agents AND TM26: Recommend topical antibiotic drops four times a day AND TM27: Recommend topical antibiotic ointment at bedtime.

Management Logic: IF OD35 Herpes Zoster Keratitis not improved, THEN TM35: Recommend corneal cultures AND TM25: Recommend topical antiviral drops four times a day AND TM16: Recommend antibiotic/steroid combo drops four times a day IFF no OD31: Corneal Abrasion.

Specification of Machine-Based Logic Packages Used in the Automated Recognition, Treatment and Care Management of Ocular Disease OD36—ACANTHAMOEBA KERATITIS FIG. 36AAA provides a schematic specification of a logic package installed and operative within the automated ocular disease (OD) recognition, treatment and compliance management system of the present invention 10, biomedically-engineered for the ocular disease afflicting the cornea, specifically—Acanthamoeba Keratitis—and assigned ocular disease code OD36. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD36: Acanthamoeba Keratitis

Disease Diagnosis Input Factors:

M01: Conjunctival Injection

M10: Corneal Abrasion

M16: CTGR—Corneal Edema

M18: Viral Conjunctivitis—Clear discharge

PEP32: Swim in Lake or Ocean Recently

Diagnostic Logic: IF M01: Conjunctival Injection >25 ocular redness index AND M10: Corneal Abrasion present AND M16: CTGR—Corneal Edema present and M18: Viral Conjunctivitis—Clear Discharge present AND PEP32: Swim in Lake or Ocean Recently, THEN OD36: Acanthamoeba Keratitis.

Treatment Logic: IF OD35: Acanthamoeba Keratitis, THEN TM02: Refer to eye doctor urgently AND TM35: Recommend corneal cultures AND TM37: Recommend topical anti-parasitic drops every hour around the clock AND TM36: Recommend fortified topical antibiotic drops around the clock.

Management Logic: IF OD35: Acanthamoeba Keratitis not improved, THEN TM38: Recommend topical propamidine isethionate drops every hour around the clock AND TM39: Recommend topical polyhexamethylene biguanide drops around the clock.

Specification of Machine-Based Logic Packages Used in the Automated Recognition, Treatment and Care Management of Ocular Disease OD37—RECURRENT CORNEAL EROSION FIG. 36BBB provides a schematic specification of a logic package installed and operative within the automated ocular disease (OD) recognition, treatment and compliance management system of the present invention 10, biomedically-engineered for the ocular disease afflicting the cornea, specifically—Recurrent Corneal Erosion—and assigned ocular disease code OD37. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD37: Recurrent Corneal Erosion

Disease Diagnosis Input Factors:

M01: Conjunctival Injection

M10: Corneal Abrasion

M16: CTGR: Corneal Edema

M18: Viral Conjunctivitis—Clear discharge

PEP23: Recurrent Corneal Erosions

Diagnostic Logic: IF M01: Conjunctival Injection >25 ocular redness index AND M10: Corneal Abrasion present AND M16: CTGR— Corneal Edema present and M18: Viral Conjunctivitis—Clear Discharge present AND PEP23: Recurrent Corneal Erosion, THEN OD37: Recurrent Corneal Erosion.

Treatment Logic: IF OD37: Recurrent Corneal Erosion, THEN TM02: Refer to eye doctor urgently AND TM26: Recommend topical antibiotic drops four times a day AND TM27: Recommend topical antibiotic ointment at bedtime.

Management Logic: IF OD37: Recurrent Corneal Erosion not improved, THEN TM40: Recommend diamond burr procedure.

Specification of Machine-Based Logic Packages Used in the Automated Recognition, Treatment and Care Management of Ocular Disease OD38—EXPOSURE KERATOPATHY FIG. 36CCC provides a schematic specification of a logic package installed and operative within the automated ocular disease (OD) recognition, treatment and compliance management system of the present invention 10, biomedically-engineered for the ocular disease afflicting the cornea, specifically—Exposure Keratopathy—and assigned ocular disease code OD38. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD38: Exposure Keratopathy

Disease Diagnosis Input Factors:

OD30: Dry Eye Disease (DED)

M09: Blink Speed and Patterns Configured and Trained

M10: Cornea Abrasion

M33: Proptosis/Hypoglobus

M37: Ectropion/Entropion

M38: Ectropion/Entropion

M39: Trichiasis/Distichiasis

M40: Floppy Eyelid Syndrome

M45: Corneal Infection

PEP28: Pemphigoid

PEP29: Erythema Multiforme

PEP30: Burns

PEP31: Bells Palsy

PEP33: Thyroid Eye Disease

SD32: Sleep Apnea

Diagnostic Logic: IF OD30: Dry Eye Disease (DED) present AND [M10: Cornea Abrasion present OR M45: Corneal Infection present] AND [M09: Blink Speed and Patterns Configured and Trained—Partial Blinks >10 OR M33: Proptosis/Hypoglobus OR M38: Ectropion/Entropion OR M39: Trichiasis/Distichiasis OR M40: Floppy Eyelid Syndrome] AND [PEP28: Pemphigoid OR PEP29: Erythema Multiforme OR PEP30: Burns OR PEP31: Bells Palsy OR PEP33: Thyroid Eye Disease AND SD32: Sleep Apnea], THEN OD38: Exposure Keratopathy.

Treatment Logic: IF OD38: Exposure Keratopathy, THEN TM01: Refer to eye doctor non-urgently AND TM05: Recommend artificial tears four times a day AND TM09: Recommend artificial tear ointment at bedtime.

Management Logic: IF OD38: Exposure Keratopathy, THEN check OD39: Neurotrophic Keratopathy AND OD14: Proptosis AND OD16: Thyroid Eye Disease AND OD31: Corneal Abrasion AND OD33: Bacterial Keratitis AND OD53: Bell's Palsy||IF OD38: Exposure Keratopathy not improved THEN TM02: Refer to eye doctor urgently AND TM27: Recommend topical antibiotic ointment four times a day.

Specification of Machine-Based Logic Packages Used in the Automated Recognition, Treatment and Care Management of Ocular Disease OD39—NEUROTROPHIC KERA-TOPATHY FIG. 36DDD provides a schematic specification of a logic package installed and operative within the automated ocular disease (OD) recognition, treatment and compliance management system of the present invention 10, biomedically-engineered for the ocular disease afflicting the cornea, specifically—Neurotrophic Keratopathy—and assigned ocular disease code OD39. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD39: Neurotrophic Keratopathy
Disease Diagnosis Input Factors:
    OD30: Dry Eye Disease (DED)
    M15 CLOW— Corneal Neovascularization
    OSi: Ocular Surgery
    ETi: Eye Trauma
    PEPi: Previous Eye pathology
    Diagnostic Logic: IF OD30: Dry Eye Disease (DED) present AND [M10: Cornea Abrasion present OR M45: Corneal Infection present] AND M15: CLOW— Corneal Neovascularization present AND [OSi: Ocular Surgery OR ETi: Eye Trauma OR PEPi: Previous Eye pathology], THEN OD39: Neurotrophic Keratopathy.

Treatment Logic: IF OD39: Neurotrophic Keratopathy, THEN TM02: Refer to eye doctor urgently AND TM05: Recommend artificial tears four times a day AND TM27: Recommend topical antibiotic ointment four times a day.

Management Logic: IF OD39: Neurotrophic Keratopathy, THEN check OD38: Exposure Keratopathy AND OD31: Corneal Abrasion AND OD33: Bacterial Keratitis AND OD34: Herpes Simplex Virus Keratitis AND OD35: Herpes Zoster Keratitis||IF OD39: Neurotrophic Keratopathy not improved, THEN TM26: Recommend topical antibiotic drops four times a day AND TM27: Recommend topical antibiotic ointment four times a day.

Specification of Machine-Based Logic Packages Used in the Automated Recognition, Treatment and Care Management of Ocular Disease OD40—PERIPHERAL ULCERATIVE KERATITIS FIG. 36EEE provides a schematic specification of a logic package installed and operative within the automated ocular disease (OD) recognition, treatment and compliance management system of the present invention 10, biomedically-engineered for the ocular disease afflicting the cornea, specifically—Peripheral Ulcerative Keratitis—and assigned ocular disease code OD40. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD40: Peripheral Ulcerative Keratitis
Disease Diagnosis Input Factors:
    M10 Corneal Abrasion
    M16 CTGR— Corneal Edema
    M25 Episcleritis/Scleritis—Sectoral Conjunctival Injection
    SD2: Autoimmune Disease
    SD3: Connective Tissue Disease
    SD4: Sjogren's Syndrome
    SD5: Sjogren's Syndrome Review of Systems
    SD6: Autoimmune Review of Systems
    Diagnostic Logic: IF [M10: Corneal Abrasion present AND M16: CTGR— Corneal Edema present AND M25: Episcleritis/Scleritis—Sectoral Conjunctival Injection present] AND [SD2: Autoimmune Disease AND SD3: Connective Tissue Disease AND SD4: Sjogren's Syndrome AND SD5: Sjogren's Syndrome Review of Systems AND SD6: Autoimmune Review of Systems], THEN OD40: Peripheral Ulcerative Keratitis.

Treatment Logic: IF OD40: Peripheral Ulcerative Keratitis, THEN TM02: Refer to eye doctor urgently AND TM27: Recommend topical antibiotic ointment every two hours AND TM19: Recommend oral steroids.

Management Logic: IF OD40: Peripheral Ulcerative Keratitis, THEN TM17: Recommend autoimmune work-up||IF OD40: Peripheral Ulcerative Keratitis not improved THEN TM41: Recommend intravenous steroids AND TM34: Recommend oral steroid sparing immunosuppressants AND TM30: Recommend amniotic membrane placement AND TM06: Recommend surgery.

Specification of Machine-Based Logic Packages Used in the Automated Recognition, Treatment and Care Management of Ocular Disease OD41—PTERYGIUM FIG. 36FFF provides a schematic specification of a logic package installed and operative within the automated ocular disease (OD) recognition, treatment and compliance management system of the present invention 10, biomedically-engineered for the ocular disease afflicting the cornea, specifically—Pterygium—and assigned ocular disease code OD41. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD41: Pterygium
Disease Diagnosis Input Factors:
    M22: Pterygium
    Diagnostic Logic: IF M22: Pterygium, THEN OD41: Pterygium.

Treatment Logic: IF OD41: Pterygium, THEN TM05: Recommend artificial tears four times a day AND TM09: Recommend artificial tear ointment at bedtime AND TM42: Recommend UV protection.

Management Logic: IF OD41: Pterygium not improved AND [SY06: Blurry Vision OR SY07: Poor Vision Quality], THEN TM06: Recommend surgery.

Specification of Machine-Based Logic Packages Used in the Automated Recognition, Treatment and Care Management of Ocular Disease OD42—PINGUECULA FIG. 36GGG provides a schematic specification of a logic package installed and operative within the automated ocular disease (OD) recognition, treatment and compliance management system of the present invention 10, biomedically-engineered for the ocular disease afflicting the cornea, specifically—Pinguecula—and assigned ocular disease code OD42. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD42: Pinguecula

Disease Diagnosis Input Factors:

M22: Pinguecula

Diagnostic Logic: IF M22: Pinguecula, THEN OD42: Pinguecula.

Treatment Logic: IF OD42: Pinguecula, THEN TM05: Recommend artificial tears four times a day AND TM09: Recommend artificial tear ointment at bedtime AND TM42: Recommend UV protection.

Management Logic: IF OD42: Pinguecula not improved AND [SY06: Blurry Vision OR SY07: Poor Vision Quality], THEN TM06: Recommend surgery.

Specification of Machine-Based Logic Packages Used in the Automated Recognition, Treatment and Care Management of Ocular Disease OD43—PING UECULTITIS FIG. 36HHH provides a schematic specification of a logic package installed and operative within the automated ocular disease (OD) recognition, treatment and compliance management system of the present invention 10, biomedically-engineered for the ocular disease afflicting the cornea, specifically—Pinguecultitis—and assigned ocular disease code OD43. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD43: Pingueculitis

Disease Diagnosis Input Factors:

OD42: Pinguecula

M22: Pinguecula

M25: Episcleritis/Scleritis—Sectoral conjunctival injection

SY04: Eye Pain/Soreness

Diagnostic Logic: IF OD42: Pinguecula AND M25: Episcleritis/Scleritis—Sectoral Conjunctival Injection >50 ocular redness index AND SY04: Eye Pain/Soreness, THEN OD43: Pingueculitis.

Treatment Logic: IF OD43: Pingueculitis, THEN TM05: Recommend artificial tears four times a day AND TM09: Recommend artificial tear ointment four times a day AND TM42: Recommend UV protection.

Management Logic: IF OD43: Pingueculitis not improved, THEN TM08: Recommend antibiotic/steroid combo ointment four times a day.

Specification of Machine-Based Logic Packages Used in the Automated Recognition, Treatment and Care Management of Ocular Disease OD44—CONTACT LENS KERATITIS FIG. 36III provides a schematic specification of a logic package installed and operative within the automated ocular disease (OD) recognition, treatment and compliance management system of the present invention 10, biomedically-engineered for the ocular disease afflicting the cornea, specifically—Contact Lens Keratitis—and assigned ocular disease code OD44. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD44: Contact Lens Keratitis

Disease Diagnosis Input Factors:

OD30: Dry Eye Disease (DED)

M15: Contact Lens Overwear (CLOW)

CLi: Contact Lens

CLUi: Contact Lens Use

Diagnostic Logic: IF [OD30: Dry Eye Disease (DED) AND [CLi: Contact Lens OR CLUi: Contact Lens Use]] OR M15: CLOW, THEN OD44: Contact Lens Overwear.

Treatment Logic: IF OD44: Contact Lens Overwear, THEN TM01: Refer to eye doctor non-urgently AND TM43: Recommend break from wearing contact lenses AND TM05: Recommend artificial tears four times a day AND TM27: Recommend topical antibiotic ointment at bedtime.

Management Logic: IF OD44: Contact Lens Overwear then check OD31: Corneal Abrasion AND OD33: Bacterial Keratitis AND OD39: Neurotrophic Keratopathy‖ IF OD44: Contact Lens Overwear not improved, THEN TM02: Refer to eye doctor urgently AND TM26: Recommend topical antibiotic drops four times a day AND TM27: Recommend topical antibiotic ointment two times a day.

Specification of Machine-Based Logic Packages Used in the Automated Recognition, Treatment and Care Management of Ocular Disease OD45—CORNEAL TRANSPLANT GRAFT REJECTION FIG. 36JJJ provides a schematic specification of a logic package installed and operative within the automated ocular disease (OD) recognition, treatment and compliance management system of the present invention 10, biomedically-engineered for the ocular disease afflicting the cornea, specifically—Corneal Transplant Graft Rejection—and assigned ocular disease code OD45. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD45: Corneal Transplant Graft Rejection

Disease Diagnosis Input Factors:

OD30: Dry Eye Disease (DED)

M01: Conjunctival Injection

M16: Corneal Transplant Graft Rejection (CTGR)

OS3: Keratoplasty

OS5: Graft Rejection

Diagnostic Logic: IF M01: Conjunctival Injection >50 ocular redness index AND OD30: Dry Eye Disease (DED) present AND M16: Corneal Transplant Graft Rejection (CTGR) present AND [OS3: Keratoplasty OR OS5: Graft Rejection], THEN OD45: Corneal Transplant Graft Rejection (CTGR).

Treatment Logic: IF OD45: Corneal Transplant Graft Rejection (CTGR), THEN TM02: Refer to eye doctor urgently AND TM16: Recommend antibiotic/steroid combo drops four times a day AND TM08: Recommend antibiotic/steroid combo ointment at bedtime.

Management Logic: IF OD45: Corneal Transplant Graft Rejection (CTGR) not improved, THEN TM06: Recommend surgery.

Specification of Machine-Based Logic Packages Used in the Automated Recognition, Treatment and Care Management of Ocular Disease OD46—KERATOCONUS FIG. 36KKK provides a schematic specification of a logic package installed and operative within the automated ocular disease (OD) recognition, treatment and compliance management system of the present invention 10, biomedically-engineered for the ocular disease afflicting the cornea, specifically—Keratoconus—and assigned ocular disease code OD46. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD46: Keratoconus

Disease Diagnosis Input Factors:

M06: Tear Film Dynamics 1—Tracking Reflective Light Particles

M07: Tear Film Dynamics 2—Detecting Perturbations in Tear Film Using Placido Light Discs Projected onto the Cornea Diagnostic Logic: IF M06: Tear Film Dynamics 1—Tracking Reflective Light Particles-Reflective light particle time for speed to reach 0 (sec)<1 AND M07: Tear Film Dynamics 2: Detecting Perturbations in Tear Film Using Placido Light Discs Projected onto the Cornea—Placido discs displaced inferiorly, THEN OD46: Keratoconus.

Treatment Logic: IF OD46: Keratoconus, THEN TM01: Refer to eye doctor non-urgently AND TM05: Recommend artificial tears four times a day AND TM09: Recommend artificial tear ointment at bedtime AND TM29: Recommend topical anti-histamine drops as needed.

Management Logic: IF OD46: Keratoconus not improved, THEN TM06: Recommend surgery.

Specification of Machine-Based Logic Packages Used in the Automated Recognition, Treatment and Care Management of Ocular Disease OD47—ACUTE ANGLE CLOSURE GLAUCOMA FIG. 36LLL provides a schematic specification of a logic package installed and operative within the automated ocular disease (OD) recognition, treatment and compliance management system of the present invention 10, biomedically-engineered for the ocular disease afflicting the eye, specifically—Acute Angle Closure Glaucoma—and assigned ocular disease code OD47. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

Glaucoma:

OD47: Acute Angle Closure Glaucoma

Disease Diagnosis Input Factors:

M01: Conjunctival Injection

M16: CTGR: Corneal edema

M18: Viral Conjunctivitis—Clear discharge

M34: Anisocoria

M35: Anterior Chamber Depth

M47: AACG

SY04: Eye Pain/Soreness

SY05: Headaches

PEP24: Glaucoma

Diagnostic Logic: IF [M01: Conjunctival Injection >50 ocular redness index AND M16: Corneal Transplant Graft Rejection (CTGR)—Corneal Edema present AND M18: Viral Conjunctivitis—Clear Discharge present and M34: Anisocoria present and M35: Anterior Chamber Depth shallow AND SY04: Eye Pain/Soreness AND SY05: Headaches AND PEP24 Glaucoma] OR M47: Acute Angle Closure Glaucoma (AACG), THEN OD47: Acute Angle Closure Glaucoma.

Treatment Logic: IF OD47: Acute Angle Closure Glaucoma, THEN TM02: Refer to eye doctor urgently AND TM44: Recommend intraocular pressure lowering drops AND TM45: Recommend oral intraocular pressure lowering agents.

Management Logic: IF OD47: Acute Angle Closure Glaucoma not improved, THEN TM07: Refer to emergency room AND TM46: Recommend intravenous intraocular pressure lowering agents AND TM48: Recommend laser procedure.

Specification of Machine-Based Logic Packages Used in the Automated Recognition, Treatment and Care Management of Ocular Disease OD48—GLAUCOMA DROP ALLERGY FIG. 36MMM provides a schematic specification of a logic package installed and operative within the automated ocular disease (OD) recognition, treatment and compliance management system of the present invention 10, biomedically-engineered for the ocular disease afflicting the eye, specifically—Glaucoma Drop Allergy—and assigned ocular disease code OD48. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD48: Glaucoma Drop Allergy

Disease Diagnosis Input Factors:

M01: Conjunctival Injection

PEP24: Glaucoma

OM5: Ocular Medications—Glaucoma Medications

Diagnostic Logic: IF M01: Conjunctival Injection >25 ocular redness index AND PEP24: Glaucoma AND OM5: Ocular Medication—Glaucoma Medications, THEN OD48: Glaucoma Drop Allergy.

Treatment Logic: IF OD48: Glaucoma Drop Allergy, THEN TM02: Refer to eye doctor urgently AND TM05: Recommend artificial tears four times a day.

Management Logic: IF OD48: Glaucoma Drop Allergy not improved, THEN TM47: Recommend changing intraocular pressure lowering drop.

Specification of Machine-Based Logic Packages Used in the Automated Recognition, Treatment and Care Management of Ocular Disease OD49—ANISOCORIA FIG. 36NNN is a schematic specification of a logic package installed and operative within the automated ocular disease (OD) recognition, treatment and compliance management system of the present invention 10, biomedically-engineered for the ocular disease afflicting the eye, specifically—Anisocoria—and assigned ocular disease code OD49. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

Neuro-Anthropology:

OD49: Anisocoria

Disease Diagnosis Input Factors:

M34—Anisocoria

Diagnostic Logic: IF M34: Anisocoria >2 mm, THEN OD49: Anisocoria.

Treatment Logic: IF OD49: Anisocoria, THEN TM02: Refer to eye doctor urgently AND check OD14: Proptosis AND OD50: Homer's Syndrome AND OD51: Third Nerve Palsy AND OD52: Fourth/Fifth Nerve Palsy.

Management Logic: IF OD49: Anisocoria AND [OD01 Ptosis present OR Levator Function <10 mm OR M32: Ophthalmoplegia present OR M33: Proptosis/Hypoglobus >2 mm OR OD50: Homer's Syndrome present OR OD51: Third Nerve Palsy present OR OD52: Fourth/Sixth Nerve Palsy present], THEN TM07: Refer to emergency room AND TM03: Recommend radiologic imaging.

Specification of Machine-Based Logic Packages Used in the Automated Recognition, Treatment and Care Management of Ocular Disease OD50—HORNER's SYNDROME FIG. 36OOO provides a schematic specification of a logic package installed and operative within the automated ocular disease (OD) recognition, treatment and compliance management system of the present invention 10, biomedically-engineered for the ocular disease afflicting the eye, specifically—Horner's Syndrome—and assigned ocular disease code OD50. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD50: Horner's Syndrome
Disease Diagnosis Input Factors:
    M9: Blink Speed and Patterns Configured and Trained—Blink Speed
    M11: Palpebral Fissure
    M12: Margin Reflex Distance
    M14: Levator Function
    M31: Ptosis
    M34: Anisocoria
    Diagnostic Logic: IF OD31: Ptosis present AND OD49: Anisocoria AND no [M32: Ophthalmoplegia AND M33: Proptosis/Hypoglobus], THEN OD50: Homer's Syndrome.
    Treatment Logic: IF Homer's Syndrome, THEN TM07: Refer to emergency room AND TM03: Recommend radiologic imaging.
    Management Logic: IF Horner's Syndrome, THEN check OD14: Proptosis AND OD50: Homer's Syndrome AND OD51: Third Nerve Palsy AND OD52: Fourth/Fifth Nerve Palsy.

Specification of Machine-Based Logic Packages Used in the Automated Recognition, Treatment and Care Management of Ocular Disease OD51—THIRD NERVE PALSY FIG. 36PPP provides a schematic specification of a logic package installed and operative within the automated ocular disease (OD) recognition, treatment and compliance management system of the present invention 10, biomedically-engineered for the ocular disease afflicting the eye, specifically—Third Nerve Palsy—and assigned ocular disease code OD51. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD51: Third Nerve Palsy
Disease Diagnosis Input Factors:
    OD01: Ptosis
    OD49: Anisocoria
    M32: Ophthalmoplegia
    SD1: Diabetes
    SD34: Hypertension
    SD35: High Cholesterol
    SD36: Heart Disease
    Diagnostic Logic: IF [OD01: Ptosis present AND M32: Ophthalmoplegia AND [SD1: Diabetes OR SD34: Hypertension OR SD35: High Cholesterol OR SD36: Heart Disease]] OR [OD01: Ptosis present AND OD49: Anisocoria AND M32: Ophthalmoplegia], THEN OD51: Third Nerve Palsy.
    Treatment Logic: IF OD51: Third Nerve Palsy, THEN TM07: Refer to emergency room AND TM03: Recommend radiologic imaging.

Management Logic: IF OD51: Third Nerve Palsy, THEN check OD14: Proptosis AND OD50: Homer's Syndrome AND OD52: Fourth/Fifth Nerve Palsy.

Specification of Machine-Based Logic Packages Used in the Automated Recognition, Treatment and Care Management of Ocular Disease OD52—FOURTH/SIXTH NERVE PALSY FIG. 36QQQ provides a schematic specification of a logic package installed and operative within the automated ocular disease (OD) recognition, treatment and compliance management system of the present invention 10, biomedically-engineered for the ocular disease afflicting the eye, specifically—Fourth/Sixth Nerve Palsy—and assigned ocular disease code OD52. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD52: Fourth/Sixth Nerve Palsy
Disease Diagnosis Input Factors
    M32: Ophthalmoplegia
    SD1: Diabetes
    SD34: Hypertension
    SD35: High Cholesterol
    SD36: Heart Disease
    Diagnostic Logic: IF M32: Ophthalmoplegia AND [SD1: Diabetes OR SD34: Hypertension OR SD35: High Cholesterol OR SD36: Heart Disease], THEN OD52: Fourth/Sixth Nerve Palsy.
    Treatment Logic: IF OD52: Fourth/Sixth Nerve Palsy, THEN TM07: Refer to emergency room AND TM03: Recommend radiologic imaging.
    Management Logic: IF OD52: Fourth/Sixth Nerve Palsy, THEN check OD14: Proptosis AND OD50: Horner's Syndrome AND OD51: Third Nerve Palsy.

Specification of Machine-Based Logic Packages Used in the Automated Recognition, Treatment and Care Management of Ocular Disease OD53—BELL's PALSY FIG. 36RRR provides a schematic specification of a logic package installed and operative within the automated ocular disease (OD) recognition, treatment and compliance management system of the present invention 10, biomedically-engineered for the ocular disease afflicting the eye, specifically—Bell's Palsy—and assigned ocular disease code OD53. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD53: Bell's Palsy
Disease Diagnosis Input Factors
    OD01: Ptosis
    OD30: Dry Eye Disease (DED)
    M9: Blink Speed and Patterns Configured and Trained—Partial Blinks
    Diagnostic Logic: IF OD01: Ptosis present AND OD30: Dry Eye Disease (DED) present M9: Blink Speed and Patterns Configured and Trained—Partial Blinks >10, THEN OD53: Bell's Palsy.
    Treatment Logic: IF OD53: Bell's Palsy, THEN TM01: Refer to eye doctor non-urgently AND TM05: Recommend artificial tears four times a day AND TM09: Recommend artificial tear ointment at bedtime AND TM23: Recommend oral antiviral agents AND TM19: Recommend oral steroids.
    Management Logic: IF OD53: Bell's Palsy, THEN check OD31: Corneal Abrasion AND OD33: Bacterial Keratitis AND OD38: Exposure Keratopathy.

US 12,697,024 B2

139

Specification of Machine-Based Logic Packages Used in the Automated Recognition, Treatment and Care Management of Ocular Disease OD54—IRITIS FIG. 36SSS provides a schematic specification of a logic package installed and operative within the automated ocular disease (OD) recognition, treatment and compliance management system of the present invention 10, biomedically-engineered for the ocular disease afflicting the iris, specifically—Iritis—and assigned ocular disease code OD54. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

Iris:
OD54: Iritis
Disease Diagnosis Input Factors:
    M01: Conjunctival Injection
    M34: Anisocoria
    SY01: Light Sensitivity
    Diagnostic Logic: IF M01: Conjunctival Injection >50 ocular redness index AND M34: Anisocoria AND SY01: Light Sensitivity AND no OD47: Acute Angle Closure Glaucoma, THEN OD54: Iritis.
    Treatment Logic: IF OD54: Iritis, THEN TM02: Refer to eye doctor urgently AND TM16: Recommend antibiotic/steroid combo drops four times a day.
    Management Logic: IF OD54: Iritis, THEN check OD34: Herpes Simplex Virus Keratitis AND OD35: Herpes Zoster Keratitis AND OD47: Acute Angle Closure Glaucoma.

Specification of Machine-Based Logic Packages Used in the Automated Recognition, Treatment and Care Management of Ocular Disease OD55—CATARACT FIG. 36TTT provides a schematic specification of a logic package installed and operative within the automated ocular disease (OD) recognition, treatment and compliance management system of the present invention 10, biomedically-engineered for the ocular disease afflicting the lens, specifically—Cataract—and assigned ocular disease code OD55. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

Lens:
OD55: Cataract
Disease Diagnosis Input Factors:
    M17: Cataract
    SY06: Blurry Vision
    SY07: Poor Vision Quality
    Diagnostic Logic: IF M17: Cataract, THEN OD55: Cataract.
    Treatment Logic: IF OD55: Cataract, THEN TM01: Refer to eye doctor non-urgently AND TM05: Recommend artificial tears four times a day.
    Management Logic: IF OD55: Cataract AND SY06: Blurry Vision AND SY07: Poor Vision Quality, THEN TM06: Recommend Surgery.

Specification of Machine-Based Logic Packages Used in the Automated Recognition, Treatment and Care Management of Ocular Disease OD56—OPHTHALMIC POST OPERATIVE COMPLICATIONS FIG. 36UUU provides a schematic specification of a logic package installed and operative within the automated ocular disease (OD) recognition, treatment and compliance management system of the present invention 10, biomedically-engineered for the ocular disease afflicting the lens, specifically—Ophthalmic Post Operative Complications—and assigned ocular disease code OD56. As shown, the logic package specifies (i) the primary disease diagnosis input factors for this ocular disease, (ii) diagnostic logic rules for this particular ocular disease, (iii) treatment logic rules for the ocular disease, and (iv) management logic rules for the ocular disease.

OD56: Ophthalmic Post Operative Complications
Disease Diagnosis Input Factors:
    M16: CTGR— Corneal edema
    M18: Viral Conjunctivitis—Clear discharge
    M44: Ophthalmic Post Operative Complications
    M45: Corneal Infection—Hypopyon
    Diagnostic Logic: IF [M01: Conjunctival Injection >50 ocular redness index AND M16: Corneal Transplant Graft Rejection—Corneal Edema present and M18: Viral Conjunctivitis—Clear Discharge present AND M45: Corneal Infection—Hypopyon present] OR M44: Ophthalmic Post Operative Complications, THEN OD56: Ophthalmic Post Operative Complications.
    Treatment Logic: IF OD56: Ophthalmic Post Operative Complications, THEN TM01: Refer to eye doctor urgently AND TM26: Recommend topical antibiotics drops four times a day AND TM27: Recommend topical antibiotic ointment two times a day.
    Management Logic: IF OD56: Ophthalmic Post Operative Complications not improved, THEN TM49: Recommend ultrasound of eye AND TM50: Recommend antibiotic injections into eye.

Figure 37A:
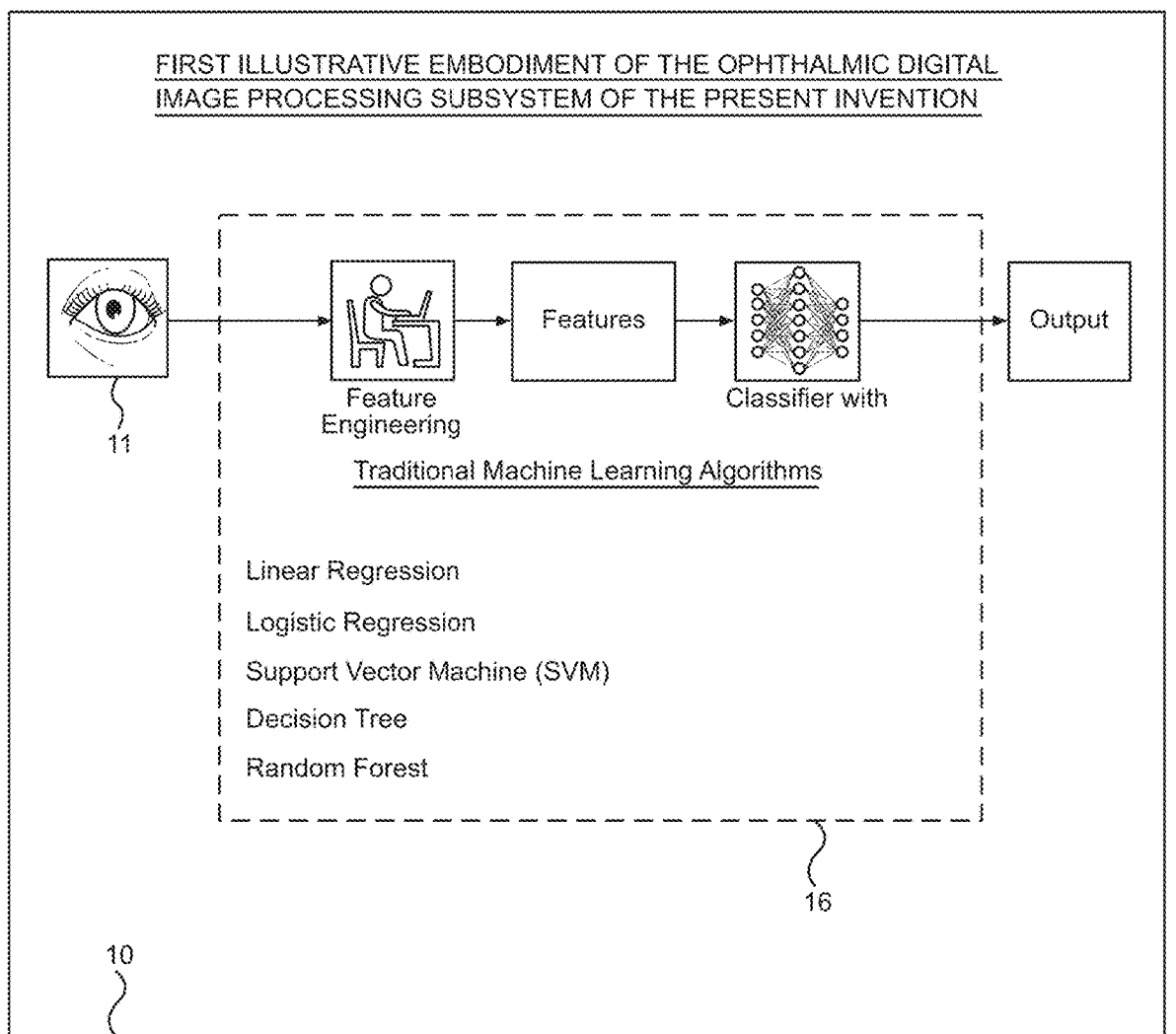
FIG. 37A is a schematic representation of a first illustrative embodiment of the machine-vision based digital image processing system employed within the system network of the present invention, which is organized, arranged and configured according to traditional machine-vision models (e.g. traditional machine learning algorithms including linear regression, logistic regression, support vector machine (SVM), decision trees, and random forest models) employing feature engineering and feature classifiers with shallow structure, to classify input digital images as representative of a particular ocular disease (OD)

First Illustrative Embodiment of the Ophthalmic Digital Image Processing Subsystem of the Present Invention: Using Traditional Machine Learning Technologies to Enable Automated Object Detection and Classification within Sets of Digital Ophthalmic Images Formed, Captured and Detected by Mobile Visible-Wavelength Operating Smartphone Camera Systems FIG. 37A shows a first illustrative embodiment of the machine-vision based digital image processing system employed within the system of the present invention. As shown, this illustrative embodiment is organized, arranged and configured according to traditional machine-vision models employing feature engineering and feature classifiers designed with shallow structure, to classify input digital images as being representative or indicative of a particular ocular disease (OD) among a large class of possible classes (i.e. a machine for solving a multi-classification problem).

Figure 37B:
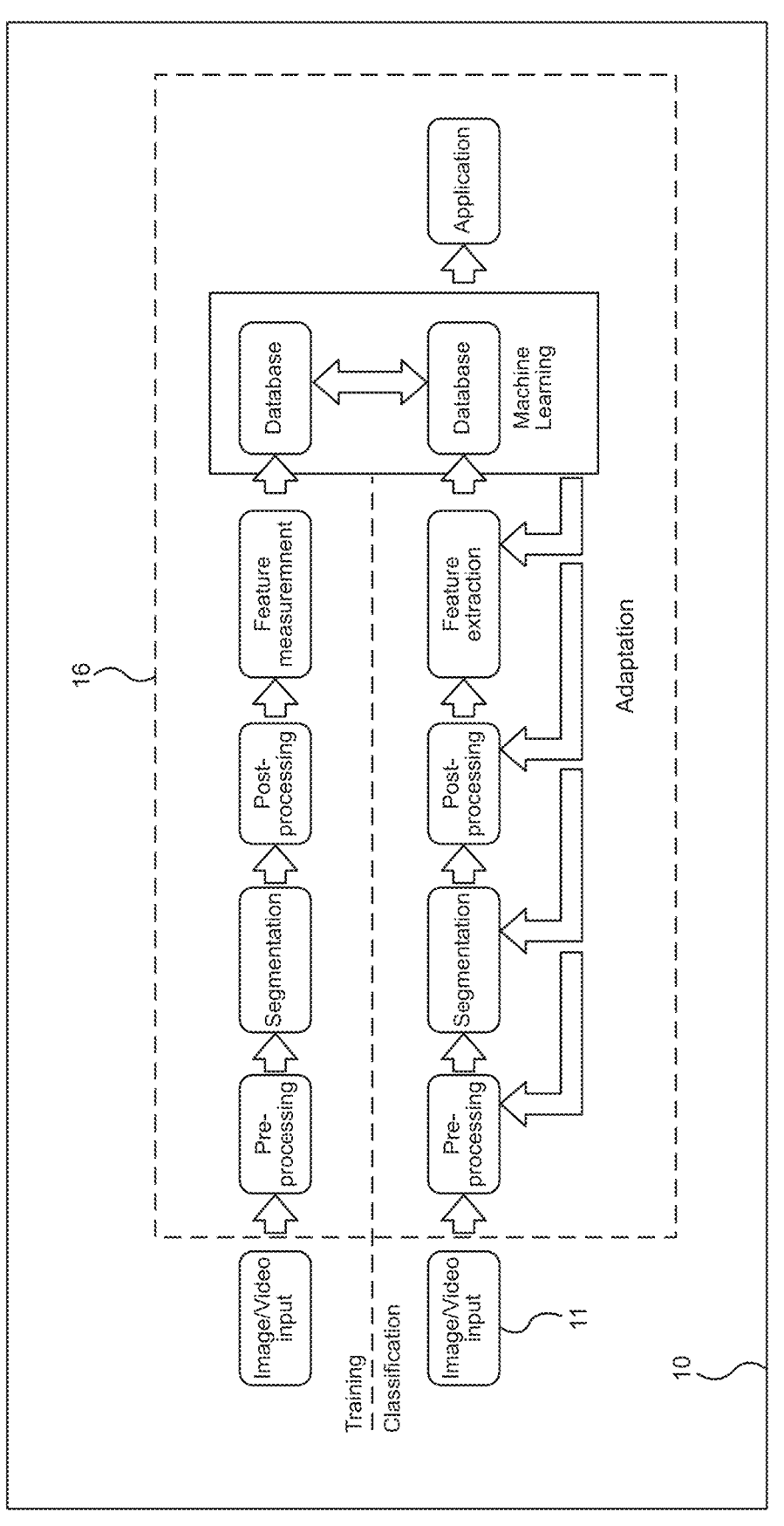
FIG. 37B is a schematic representation showing the subsystem architecture of the first illustrative embodiment of the machine-vision based digital image processing system employed within the system of the present invention, comprising in its training pipeline, an image image/video input module, a pre-processing module, a segmentation module, a post-processing module, feature measurements added to a database, and in a classification pipeline, an image/video input module, an image pre-processing module, an image segmentation module, a post-processing module, a feature extraction module, and classification/recognition module to produce a predicted ocular disease class and grade of severity.

When using more traditional machine-vision technologies for enabling automated image classification, such as support vector machines (SVM) and machines using linear regression, logistic regression, decision trees, and random forest testing as shown in FIGS. 37A and 37B, there is the general need to (i) discriminate and extract features in a scene of a digital image in order to build reference models, and then (ii) classify the extracted features so as to form specific "classified" objects.

When using traditional learning methods, the "logistic model" can be used to model the probability of a certain class or event existing in view of the observed image, using measures such as pass/fail, win/lose, alive/dead or healthy/sick. This statistical model can be extended to model several classes of events such as determining whether an image contains a cat, a dog, a bird, a frog, etc. Each object that is being detected in the image is assigned a probability between 0 and 1, with a sum of all possible classes or outcomes being equal to one. The image classifier ultimately makes a decision on the most likely class of object reflected in the image, based on its computed probability.

As is well known, logistic regression is a predictive analysis algorithm that is used often in solving classification problems. This method operates by describing data and explaining the relationship between variables. Logistic regression is applied to an input variable (X) where the output variable (y) is a discrete value which ranges between 1 (yes) and 0 (no). It uses a logistic (sigmoid) function to find the relationship between variables. The sigmoid function is an S-shaped curve that can take any real-valued number and map it to a value between 0 and 1, but never exactly at those limits.

The support vector machine (SVM) is a model often used for both classification and regression problems, though mostly to solve classification problems. The SVM algorithm creates a hyperplane or line (i.e. a decision boundary) which separates data into classes. SVM uses the "kernel trick" method to find the best line separator which is a decision boundary that has the same distance from the boundary point of both classes. SVM provides a clear and more powerful way of learning complex non-linear functions. While SVM tries to find the "best" margin (distance between the line and the support vectors) that separates the classes and reduces the risk of making an error when classifying the data, logistic regression does not find the best decision margin. Instead, logical regression can have different decision boundaries with different weights that are near the optimal point. While SVM is based on geometrical properties of the data, logistic regression is based on a statistical approach, and the risk of overfitting is less in SVM, while logistic regression is vulnerable to overfitting. While SVM works well with unstructured and semi-structured data like text and images, logistic regression works with already identified independent variables.

As illustrated in FIG. 37B, images and videos of eyes are captured by mobile systems 11 and analyzed using computer vision methods employing convolutional or recurrent neural networks and machine learning. This includes, but is not limited to, object detection, recognition and verification, facial recognition, edge detection, image classification and analysis, feature detection and pattern recognition. An exemplary data pathway for image and video analysis is shown in FIG. 37B. During training, the image and video analysis software, images and videos go through pre-processing, segmentation, post-processing and feature measurements (done by an ophthalmology trained experts) to generate a database of images maintained 16C on the system network 10. The analysis software is then used on new images and videos to determine if it is able to classify and measure accurately the desired image and video features. The correct classifications (determined by an ophthalmology trained expert) are automatically added to the database, and also influence the prior classification steps, leading to adaptation and allowing the classification to be done faster and with greater accuracy.

Figure 38:
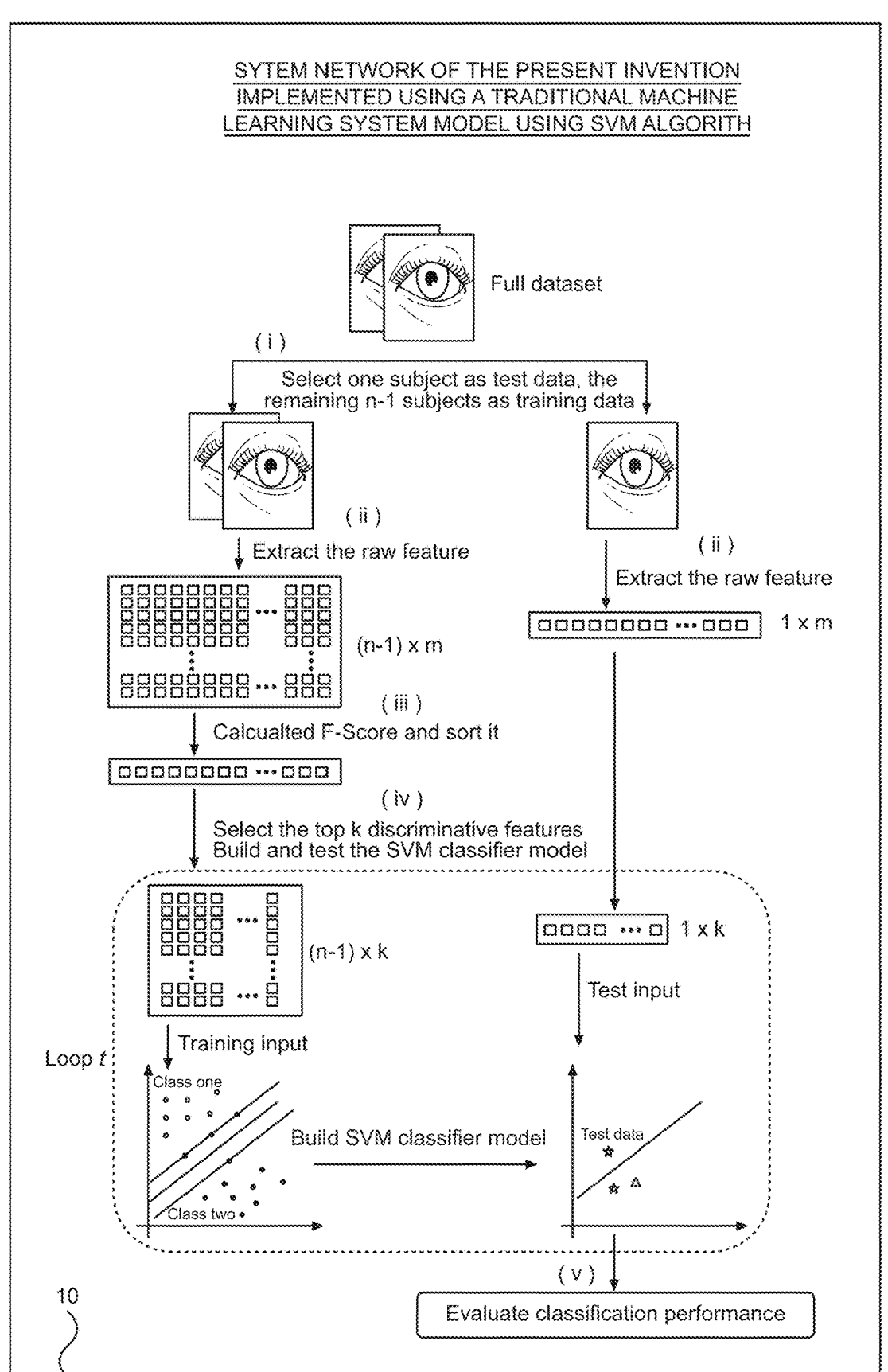
FIG. 38 is a schematic representation of the machine-vision based digital image processing system of the present invention employing a traditional SVM-based machine learning model.

In FIG. 38, an SVM-based machine-learning ocular disease (OD) classifier/recognizer model is shown being used to process digital images taken from the front view of human eyes formed, captured and detected using a visible-wavelength operating smartphone camera system, and then provided for preprocessing and storage in the system network database 16C.

As shown in FIG. 38, the SVM-based machine-learning process comprises five primary steps, namely: (i) splitting the entire full image dataset into two parts, specifically—a first image dataset serving as the test set, and the remaining second part comprising the training set; (ii) extracting the features from the digital images (e.g. data sets) of human eyes; (iii) calculating the Fisher scores of each feature in the image, and ranking the features; (iv) selecting the top k discriminative features to build the SVM classifier model and testing the SVM classifier model; and (v) evaluating the performance of the SVM classifier model during the task of machine learning classification.

In general, the SVM-based DED Condition Classifier model can be implemented in computer programming code using any suitable programming language, such as Python, or the LibSVM toolbox of MATLAB. In the flowchart shown in FIG. 38, where the system is trained and configured for automated recognition of ocular disease, including dry eye disease (DED) conditions, the illustrated process would be repeated n times, where n (e.g. n=32) is the number of possible ocular diseases, including dry eye disease (DED) conditions, that can be rationally recognized by the system using machine-learning principles practiced in accordance with the present invention.

In step (ii) of FIG. 38, the feature vector is extracted from the digital image for each class (of DED condition) to form the raw feature matrices. The dimensions of the feature matrices are set to m1 and m2, for the training and test datasets, respectively. In the presence of the unrelated or redundant features, the SVM learning model will tend to overfit, which in turn will degrade the classification performance. In step (iii) of FIG. 38, the Fisher score (F-Score) algorithm is a supervised feature selection method that can effectively measure data discrimination from ocular diseases, including multiple classes of DED conditions, and assign the higher score to the feature, which has more discriminative ability.

The F-score for each feature can be calculated independently based on the Fisher or other suitable criterion. The top k features with the highest ranking F-scores are then selected. Apparently, the greater the Fisher score, the stronger the discriminative power of the feature. The Fisher score for the qth feature can be defined in a manner well known in the SVM modeling arts.

The features are sorted in descending order according to the pre-calculated Fisher scores. Then, some of these features should be selected as the input to build and test the SVM classifier model. FIG. 38 shows that the dotted box indicates a loop within the machine learning process. For each loop, the ranked features are selected with an increase in length. Feature sorting and selection should be built in a nested leave-one-out procedure to promote model generalization, by which the training input and test input are obtained. Based on these inputs, the SVM classifier model is trained and tested. While the SVM model is a binary classification algorithm, it can be adapted to support multiple classes computed based on multiple class labels.

In summary, traditional computer vision methods have been focused on detecting and extracting features from digital images. Extracted features provide the context for inference about an image, and often the richer the features, the better the inference. Sophisticated hand-designed features such as scale-invariant feature transform (SIFT), Gabor filters, and histogram of oriented gradients (HOG) can be used to support feature extraction with good success. Second Illustrative Embodiment of the Ophthalmic Digital Image Processing Subsystem of the Present Invention: Using Deep Learning Machine Vision Technologies to Enable Automated Object Detection and Classification within Digital Ophthalmic Images Captured by Mobile Visible-Wavelength Operating Smartphone Camera Systems When using "deep learning" machine-vision technologies to perform automated image recognition operations using, for example, Deep Neural Network (DNN) classifiers, as shown in FIG. 39, there is the need to (i) discriminate and extract features in a scene to build reference models, and then (ii) classify the extracted features to form the specific "classified" objects. These classifiers can be used on large multimedia data sets (e.g. images, videos and sounds). Neural networks (employing convolutional kernels) are used to extract non-linear features from training data sets. The nonlinear features are extracted/constructed through convolutional processing layers that are generated and maintained when processing the training data set. As the training dataset contains richer and more complex objects (e.g. ocular disease conditions) to be recognized, additional convolutional processing layers are generated, and the deeper the structure of the deep-learning machine-vision system becomes in order to support the automated image recognition tasks presented to the system network and its many users.

Specification of the Second Illustrative Embodiment of the Machine-Vision Based Digital Image Processing System Employed within the System Network of the Present Invention Employing an Automated Deep-Learning "End-to-End" Machine-Vision System Configured and Trained for Automated Recognition of Dry Eye Disease (DED) and Other Ocular Conditions Using Trained Convolutional Neural Network (CNN) Models FIG. 40A shows another implementation of a deep-learning machine-vision ocular image processing and classification/recognition system (i.e. "engine") of the present invention 10. As shown, this engine uses Convolutional Neural Networks (CNNs) configured and trained for use and deployment on the system network shown in FIG. 8A, to support and enable automated detection and measurement of dry eye disease (DED) conditions in the human eyes photographically represented in digital images of human eyes formed, captured and detected by mobile visible-wavelength operating smartphone camera systems configured and operated in accordance with the principles of the present invention. As shown, this embodiment is organized, arranged and configured according to a deep-learning machine-vision models employing convolutional networks with deep structure, to provide an end-to-end system for classifying input digital images as representative of a particular ocular disease (OD) condition, including dry eye disease (DED) conditions well known in the field of ophthalmology.

FIG. 40A shows a deep neural network (DNN) module for implementing a machine-vision based digital ocular image processing system employed within the system network of the present invention. As shown, the DNN module comprises: feature extraction operations involving convolution; pooling operations; and classification/recognition operations realized by convolution and pooling, to produce the desired classification output.

When practicing the present invention, deep learning (DL) and machine learning (DL) technologies can be applied to implement the ophthalmic image and video data processing subsystems and automated ocular disease (OD) condition recognition engine (i.e. subsystems) of the present invention disclosed herein. For greater technical details about the art of deep learning and machine learning, reference should be made to the DIVE INTO DEEP LEARNING textbook (dated Nov. 6, 2020) at https://d21.ai/d21-en.pdf and Courses CS229 Machine Learning and CS230 Deep Learning offered at Stanford University, California, USA, https://cs230.stanford.edu, incorporated herein by reference in its entirety.

Such deep learning (DL) methods enable automated learning of complex and useful features directly from large image datasets of human eyes in different conditions, collected from a human population. Using multiple deep layers of neural network models, deep learning methods can automatically learn and extract a deep hierarchy of rich features from images captured by mobile smartphone cameras 11 disclosed herein, as illustrated in FIG. 40B. DL methods support deeper architectures and have the capacity to learn more complex features than the shallow ones. Also training algorithms allow DL systems to learn informative object representations without the need to design features manually, as required by traditional learning methods.

While traditional computer vision methods have involved using a system of modular models, wherein each model was designed for a specific task, such as feature extraction, image alignment, or classification. These models are used in a pipeline with a raw image dataset entering the system at one end, and an outcome, such as a prediction or classification, exiting at the other end of the system. This pipeline approach can and is still used within deep learning models, where a feature detector model can be replaced with a deep neural network.

Alternatively, deep neural networks allow a single model to subsume two or more traditional models, such as feature extraction and classification, to develop and deploy a single end-to-end model based deep learning system. It is common to use a single model trained directly on raw pixel values for image classification, and there has been a trend toward replacing pipelines that use a deep neural network model with a single model trained end-to-end directly. With the availability of so much training data (along with an efficient algorithmic implementation and GPU computing resources), it became possible to develop neural networks directly from the image data, without needing to create multi-stage hand-tuned pipelines of extracted features and discriminative classifiers, as conventionally employed in traditional deep learning methods and systems.

In general, there are five (5) different kinds of deep learning (DL) architectures currently available for use in implementing the ophthalmic image and video processing subsystems and ocular condition recognition engines of the present invention, namely: Stacked Autoencoders (SAEs); Deep Belief Networks (DBNs); Convolutional Neural Networks (CCNs); Recurrent Neural Networks (RNNs) and Generative Adversarial Networks (GANS). Deep Learning Architectures can be used to automatically process image and video data sets as described and taught in great detail herein.

In the illustrative embodiment, FIG. 41 shows the use of a unified framework of deep learning CNNs to classify object candidates (e.g. ocular diseases) into specific categories of ocular disease conditions (e.g. DED conditions). As shown in FIG. 41, the deep-learning machine-vision based digital image processing system comprises: (i) a faster RCNN for carrying out image convolutional layers and producing feature maps from input images; (ii) a regional proposal network (RPN) for producing proposed regions of interest (ROI); and (iii) a Fast RCNN for classifying the proposed ROIs and producing a predicted dry eye disease (DED) class and grade of severity, or a predicted ocular disease (OD) class and grade of severity, as the case and application at hand may require.

Specification of the Process of the Present Invention Involving the Loading, Training and Operating an Automated Deep-Learning Machine-Vision Ocular Disease (OD) Recognition System Supported by Standard Python Libraries Supporting Automated Image Feature Extraction and Classification, Ocular Object Detection, and Ocular Disease (OD) Condition Recognition/Classification FIG. 42 describes the primary steps of a process used to train an automated deep-learning machine-vision ocular disease recognition system according to the present invention. As shown, the method involves the loading, training and operating an automated deep-learning machine-vision recognition system supported by standard Python (e.g. Keras and TensorFlow 2) libraries supporting automated image feature extraction and classification, ocular object detection, and ocular disease (OD) condition recognition/classification.

As shown in FIG. 42, the training and operating process comprises the steps of: (a) loading the pixel dataset of patient ocular images into the database of a deep learning machine-vision recognition system; (b) preparing the pixel dataset for deep learning machine-vision recognition; (c) defining a baseline end-to-end convolutional neural network (CNN) model); (d) evaluating the baseline CNN model and its recognition performance on input pixel datasets; and (e) presenting the ocular disease condition recognition results produced from the deep-learning machine-vision recognition system and process. Each of these steps in FIG. 42 will be described in greater technical detail below.

STEP A: Loading the Pixel Dataset of Patient Ocular Images into the Database of a Deep Learning Machine-Vision Recognition System Pre-segment each captured image of human eyes so that all digital images all have the same square size of N×M pixels, and that the images are grayscale (i.e. load the images and reshape the data arrays to have a single color channel).

In the illustrative embodiment, the system supports X=32 number of ocular disease (e.g. dry eye disease (DED)) conditions, i.e. classes, supported by the ocular condition (OD) recognition process, and that the classes are represented as unique integers. Each integer can be transformed into a 10 element binary vector with a 1 for the index of the class value. This can be achieved using the categorical( ) utility function. The Python load dataset( ) function implements these behaviors and can be used to load the dataset.

STEP B: Preparing the Pixel Dataset for Deep Learning Machine-Vision Recognition In the illustrative embodiment, the pixel values for each image in the dataset are unsigned integers in the range between black and white, or 0 and 255. A good starting point to scale the pixel values is to normalize the pixel values of grayscale images, e.g. rescale them to the range [0,1]. This step involves first converting the data type from unsigned integers to floats, then dividing the pixel values by the maximum value. The prep pixels( ) function below implements these behaviors and is provided with the pixel values for both the train and test datasets that will need to be scaled.

STEP C: Defining a Baseline End-to-End Convolutional Neural Network (CNN) Model

The next step involves defining a baseline convolutional neural network (CNN) model for the problem. The model has two main components: (i) a feature extraction front-end portion comprised of convolutional and pooling layers; and (ii) a classification back-end portion that will make a prediction on what class of ocular disease condition the input images best predict, all things considered. For the convolutional front end portion, a single convolutional layer is used with a small filter size (3,3) and a modest number of filters (64) followed by a max pooling layer. The filter maps can then be flattened to provide features to the classier component. Given that the problem is a multiclass classification problem, the output layer will require at least 64 nodes in order to predict the probability distribution of an input image belonging to each of the 64 classes of possible ocular diseases. Between the feature extractor and the output layer, a dense layer can be added to interpret the features, in this case with multiple nodes. All layers will use the ReLU activation function and the He weight initialization scheme, that satisfies best practices in deep learning.

STEP D: Evaluating the Baseline CNN Model and its Recognition Performance on Input Pixel Datasets After the CNN Model is defined, it needs to be evaluated. The Model will be evaluated using 5-fold cross validation. The value of k=5 was chosen to provide a baseline for both repeated evaluation and to not be too large as to require a long running time. Each test set will be 20% of the training dataset, or about 12,000 examples, close to the size of the actual test set for the problem. The training dataset is shuffled prior to being split and the sample shuffling is performed each time so that any model we evaluate will have the same train and test datasets in each fold, providing an apples-to-apples comparison.

The Baseline Model will be trained for a modest 10 training epochs with a default batch size of 32 examples. The test set for each fold will be used to evaluate the model both during each epoch of the training run, to later create learning curves, and at the end of the run, to estimate the performance of the model. As such, the resulting history from each run will be tracked, as well as the classification accuracy of the fold. An evaluate model( ) function can be used to implement these behaviors, taking the training dataset as arguments and returning a list of accuracy scores and training histories that can be later summarized, as well known in the art.

STEP E: Presenting the Ocular Disease Condition Recognition Results Produced from the Deep-Learning Machine-Vision Recognition System and Process Once the model has been evaluated, the results can be presented. There are two key aspects to present in the model: (i) the diagnostics of the learning behavior of the model during training; and (ii) the estimation of the performance of the deep-learning model. These evaluations of the deep-learning model can be implemented using separate functions.

First, the diagnostics of learning behavior involves creating a line plot showing model performance on the train and test set during each fold of the k-fold cross-validation. These plots are valuable for getting an idea of whether a model is overfitting, under-fitting, or has a good score for the dataset. A single figure will be created with two subplots, one for loss and one for accuracy. Blue lines will indicate model performance on the training dataset and orange lines will indicate performance on the hold out test dataset. The summarize diagnostics( ) function creates and shows this plot given the collected training histories.

Second, an estimation of performance can be gained by collecting and summarizing the classification accuracy scores during each fold, by calculating the mean and standard deviation. This provides an estimate of the average expected performance of the model trained on the dataset, with an estimate of the average variance in the mean. Also the distribution of performance scores can be summarized by creating and showing a box and whisker plot. The summarize performance( ) function implements this for a given list of scores collected during model evaluation.

Deep-Learning Machine-Vision Recognition System Capable of Automatically Recognizing Specific Categories Ocular Disease (OD) Conditions from a Set of Digital Images of Eyes Formed and Captured by Mobile Visible-Wavelength Operating Smartphone Camera Systems FIG. 43 shows the use of a TensorFlow 2.0 ecosystem consisting of Python libraries used to build a deep-learning machine-vision ocular disease (OD) condition recognition system. In the illustrative embodiments, this deep-learning machine-vision system is capable of automatically recognizing specific categories of ocular disease (OD) conditions from a set of digital images of a patient's eyes captured using a mobile or stationary visible-wavelength operating digital camera system, and provided to the system network as input to the machine-vision processing engine of the present invention. In view of the present invention disclosure, this system architecture is capable of supporting automated recognition of the full class of ocular diseases listed in FIGS. 14A through 14D, for the anterior segment of the human eye. Other illustrative embodiments, this class of ocular diseases can be extended to cover other parts of the human eye and its supporting human vision system.

Among the core automated machine-vision tasks, there are (i) object detection, and (ii) object recognition. Automated machine-vision systems using deep neural network (DNN) classifiers need to (i) discriminate and extract features in a scene or digital image (for the purpose of building reference models), and then (ii) classify the extracted features so as to form or recognize specific "classified" objects. These classifiers can be used on large image-based data sets (e.g. images and videos). Typically, Deep Neural Networks (DNNs) employ convolutional kernels to extract non-linear features from training data sets. The non-linear features are extracted/constructed through convolutional processing layers generated when processing the training data set. Typically, Deep Neural Networks (DNNs) are implemented as "end-to-end" systems, implying that input images are received as input, processed, and then classified objects are produced as output from the system, based on the system input.

Currently, there are several different types of deep learning algorithms that may be used for image classification, where each algorithm is adapted to learn to classify an image into a set of predefined categories. These different types of deep learning algorithms include: large scale (deep) neural networks; artificial neural networks (ANNs); convolutional neural networks (CNNs); and recurrent neural networks (RNNs). Typically, CNNs are used for Classification (e.g. VGG, ResNet Inception, Inception, REsNet). Deep Neural Networks can be used to perform Object Detection. This focuses on what an image is and on the position of the objects of interest (ROI). Examples of popular Deep Neural Networks include: Faster RCNN, You Only Look Once (YOLO), and Single Shot Multibox Detector (SSD).

Deep Neural Networks can be used to perform two stage methods of object detection, for example: (a) Step 1, extracting proposals for possible objects; and (b) Step 2: classifying the possible objects to achieve object detection (e.g. R-CNN, Fast RCNN, Faster RCNN).

Also, deep Neural Networks can be used to perform one stage methods of object detection, for example: Step 1, Predicting the position and category of an object simultaneously (e.g. OverFeat, YOLO, SSD, RetinaNet).

Deep learning algorithms have solved these computer vision tasks (i.e. image classification and object detection) with an increasing level of difficulty. Deep neural networks can also be used as semantic segmentation algorithms (e.g. Fully Convolutional Network (FCN), U-Net, and Google's DeepLabPopular). The image semantic segmentation challenge consists in classifying each pixel of an image (or just several ones) into an instance, wherein each instance (or predefined category) corresponds to an object or a part of the image (road, sky, . . . ). This task is part of the concept of scene understanding: how a deep learning model can better learn the global context of a visual content?

The object detection task has exceeded the image classification/recognition task in term of complexity. The object detection task consists in creating bounding boxes around the objects contained in an image, and then classifying each one of them. Most of the object detection models use anchor boxes and proposals to detect bounding boxes disposed around objects.

Specification of the Third Illustrative Embodiment of the Machine-Vision Based Digital Image Processing System Employed within the System Network of the Present Invention FIG. 44 show a third illustrative embodiment of the machine-vision based digital image processing system employed within the system of the present invention. As shown, this illustrative embodiment employs a hybrid architecture for practicing the system and methods of the present invention. Specifically, this method consists of two different components, namely: (i) a symbolist AI component employing symbolic reasoning and logic (e.g. Rule Based Logix, IF X, then Y); and (ii) a connectionist AI component employing connected statistical models such as machine learning, deep-learning neural networks in computer vision, natural language processing (NLP), and speech recognition, and artificial neural networks (ANNs).

FIG. 44 lists various AI components that may be used to support the machine-vision based digital image processing system employed within the system of the present invention, namely: machine learning; deep learning (machine vision); artificial neural networks; and AI knowledge expressed and captured as trained neural networks. Notably, the hybrid approach has many practical advantages when practicing the systems and methods of the present invention described herein. Notably, the symbolic reasoning and logic supported in such hybrid models provides a very useful and convenient way to capture the knowledge and know-how possessed by experts who have deep experience and expertise in the domain of ocular disease diagnosis, treatment and care management.

The machine-based logic packages specified and described in FIGS. 36A through 36UUU clearly reflect the use of symbolic reasoning and logic to design and implement the machine-vision expert systems of the present invention, and indicate a hybrid architecture of Symbolist AI and Connectionist AI Technology employed in such illustrative embodiments of the present invention.

Overview of Mathematical Nature of the Digital Images of Human Eyes Captured by Mobile Smartphone Camera Systems and Processed Using Machine-Vision Image Processing Engines of the Present Invention FIG. 45 simply illustrates the mathematical (matrix) structure of digital color images of the human eye that are captured by mobile visible-wavelength operating (VWO) smartphone camera systems and processed by the machine-vision systems supported on the system network of the present invention. Specifically, each captured digital image consists of millions of color pixels, and each color pixel in a three color system is represented by a matrix of numbers representing the intensity of the pixel color value at the (x,y,z) pixel location in the digital image In FIG. 45, there is shown a photographic representation of a human eye suffering from dry eye disease (DED)

conditions (e.g. conjunctival injection, conjunctivochalasis, tear meniscus height (TMH), scruff at eyelashes, meibomian gland dysfunction, dermatochalasis, and scruff at eyelashes). This exemplary photographic image is represented by three matrices each containing its respective color pixel data which collectively constitutes the color values of each image pixel at the (x,y,y) pixel location in the digital image. It is understood, however, that captured digital images handled and processed by the system network of the present invention can be views taken of any aspect of the anterior segment of the human eye, captured using a mobile visible-wavelength operating smartphone camera system provided with standardized optics and image detection capabilities, operating within the visible-wavelength region of the electromagnetic spectrum. By doing so, the system network of the present invention has widespread applicability around the world, empowering every mobile smartphone owner with a new level of service, enabling remote ophthalmic examination, automated machine-vision supported ocular disease diagnosis and care management, backed by advanced deep-learning and machine-learning technologies, capable of revolutionizing the ocular health care industry at large.

Specification of the Deep-Learning Machine-Vision Ocular Image Processing and Classification System of the Present Invention Configured and Trained for Use and Deployment on the System Network to Support and Enable Automated Detection and Measurement of Conjunctival Injection (CI) of Human Eyes Photographically Represented in Digital Images Formed and Captured by a Mobile Smartphone Camera System FIG. 46 shows a deep-learning machine-vision ocular image processing and classification system (i.e. "engine") of the present invention configured and trained for use and deployment on the system network shown in FIG. 8A. This system is configured and deployed to support and enable an automated method (M1) of detection and measurement of conjunctival injection (CI) in one or more human eyes photographically represented in digital images of a front view of the human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 47 shows a front view digital image representation of a human eye exhibiting conjunctival injection. As shown, the digital image of the human eye is augmented with graphical indications superimposed on the digital image to indicate (i) where conjunctival injection appears to be present on the sclera of the human eye in the photographic image. The digital image also indicates which pixel region of interest (ROI) requires pixel data processing according to a method of digital image processing using the machine-vision based ophthalmic image processing engine operating on one or more front view digital images of the human eye, so as to automatically measure conjunctival injection, as an indication of ocular disease recognition, treatment and manage care, including predicting dry eye disease (DED) class and grade of severity by the automated system, in accordance with the method specified in FIGS. 49A and 49B FIG. 48 show a schematic illustration of the human eye with various degrees of conjunctival injection (CI).

FIGS. 49A and 49B describe the primary steps carried out when practicing the machine-vision based method of processing time and date stamped digital images of a human eye captured by a mobile smartphone camera system, so as to automatically detect and measure conjunctival injection present in the human eye of a patient at a specific time and date, to support automated ocular disease recognition, treatment and manage care, including predicting dry eye disease (DED) class and grade of severity by the automated system. Automated Machine-Vision Based Image Processing Method #1 (M1)

As shown and described in FIGS. 49A and 49B, the machine-vision based method of detecting, measuring, and generating a database of images indicating conjunctival injection (CI), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train a system to detect the sclera;

Step 4: Use the above structures and the trained system for automatic region of interest (ROI) segmentation of the sclera using non-parametric methods, including but not limited to, random decision forests such as Breiman's random forest algorithm, gray scale probability maps, binary thresholds, morphological operators and Bresenham's line algorithm;

Step 5: Use region of interest matching to measure conjunctival injection across a series of digital images reproducibly using methods including, but not limited to, a feature detection algorithm (e.g. scale invariant feature transform) and an iterative parameter estimation method (e.g. random sample consensus);

Step 6: Measure conjunctival injection in region of interest using methods including, but not limited to, contrast-limited adaptive histogram equalization, hue-saturation-value, product of saturation and hue maps, and maximal values of saturation and hue values, wherein conjunctival injection is measured on scale 0 to 100, with higher numbers corresponding with greater degrees of conjunctival injection; and Step 7: If conjunctival injection is greater than 30, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Measurement of Tear Meniscus Height (TMH) of Human Eyes Photographically Represented in Digital Images Formed and Captured by a Mobile Smartphone Camera System FIG. 50 shows a deep-learning machine-vision ocular image processing and classification system (i.e. "engine") of the present invention 10 configured and trained for use and deployment on the system network shown in FIG. 8A, to support and enable an automated method (M2) of detection and measurement of tear meniscus height (TMH)) of eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 51 shows a front view digital image representation of a human eye exhibiting tear meniscus height, and augmented with graphical indications superimposed on the digital image to indicate where tear meniscus height is measured in the human eye in the photographic image. The digital image also indicates which pixel region of interest (ROI) requires pixel data processing according to a method of digital image processing using the machine-based ophthalmic image processing engine operating on one or more front view digital images of the human eye, so as to automatically measure the tear meniscus height (TMH), as an indication of ocular disease recognition, treatment and manage care, including predicting dry eye disease (DED) class and grade of severity by the automated system, in accordance with the method specified in FIGS. 53A and 53B.

FIG. 52A shows a first side view digital image representation of the human eye exhibiting tear meniscus height, and showing the retention of tears at the interface between the cornea surface and the eyelid of the human eye, via the meniscus effect, to form a collection of tears having a tear meniscus height indicated by the measure TMH schematically depicted in the illustration.

FIG. 52B shows a second side view digital image representation of the human eye exhibiting tear meniscus height, and showing the retention of tears at the interface between the cornea surface and the eyelid of the human eye, via the meniscus effect, to form a collection of tears having a first tear meniscus height indicated by the measure TMH1 schematically depicted in the illustration, and a second tear meniscus height indicated by the measure TMH2 schematically depicted in the illustration, indicating the need to replenish this surface reserve of tears.

FIGS. 53A and 53B describe the primary steps carried out when practicing the machine-vision based method of processing time and date stamped digital images of a human eye captured by a mobile smartphone camera system, so as to automatically detect and measure the tear meniscus height (TMH) in the human eye at a particular time and date, as an indication of ocular disease recognition, treatment and manage care, including predicting dry eye disease (DED) class and grade of severity by the automated system.

Automated Machine-Vision Based Image Processing Method #2 (M2)

As shown and described in FIGS. 53A and 53B, the machine-vision based method of detecting, measuring, and generating a database of images indicating tear meniscus height (TMH), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train a system to detect eyelids;

Step 4: Use the above structures and the trained system for automatic region of interest segmentation of eyelid, using non-parametric methods, including but not limited to, random decision forests such as Breiman's random forest algorithm, gray scale probability maps, binary thresholds, morphological operators and Bresenham's line algorithm;

Step 5: Use region of interest matching to measure tear meniscus height (TMH) parameter across a series of digital images reproducibly using methods including, but not limited to, scale invariant feature transform and random sample consensus;

Step 6: Differentiate tear meniscus reflective line from the lower eyelid by using methods, including, but not limited to, edge detection, k-means clustering, region growing and thresholding;

Step 7: Measure tear meniscus height (TMH) in millimeters by using pixel-by-pixel size; and Step 8: If tear meniscus height (TMH) is less than 0.2 mm immediately after an eye blink, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Measurement of Meibomian Gland Dysfunction (MGD) and Scruff in Human Eyes Photographically Represented in Digital Images Formed and Captured by a Mobile Smartphone Camera System FIG. 54 shows a deep-learning machine-vision ocular image processing and classification system (i.e. "engine") of the present invention 10 configured and trained for use and deployment on the system network shown in FIG. 8A. As configured and deployed, the system supports and enables an automated method (M3) of detection and measurement of meibomian gland dysfunction (MGD) and scruff of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 55A shows a front view digital image representation of a human eye exhibiting meibomian glad dysfunction (MGD), and augmented with graphical indications superimposed on the digital image to indicate where meibomian gland dysfunction (MGD) and scruff are detected in the photographic image of the human eye. As shown, the digital image also indicated which pixel region of interest (ROI) requires pixel data processing according to a method of digital image processing using the machine-based ophthalmic image processing engine operating on one or more front view digital images of the human eye, so as to automatically detect meibomian gland dysfunction (MGD) and scruff, as an indication of ocular disease recognition, treatment and manage care, including predicting dry eye disease (DED) class and grade of severity by the automated system, in accordance with the method specified in FIGS. 78A and 78B.

FIG. 55B shows a front view digital image representation of the human eye exhibiting meibomian gland dysfunction (MGD), and showing the location of the meibomian glands on the lower eyelid of the human eye, not suggestive of dysfunction.

FIGS. 56A and 56B describe the primary steps carried out when practicing the machine-vision based method of processing time and date stamped digital images of a human eye captured by a mobile smartphone camera system, so as to automatically detect meibomian gland dysfunction (MGD) and scruff in the human eye at a particular time and date, to support automated ocular disease recognition, treatment and manage care, including predicting dry eye disease (DED) class and grade of severity by the automated system.

Automated Machine-Vision Based Image Processing Method #3 (M3)

As shown and described in FIGS. 56A and 56B, the machine-vision based method of detecting, measuring, and generating a database of images indicating a meibomian gland dysfunction (MGD) condition, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train a system to detect eyelids;

Step 4: Use the above structures and the trained system for automatic region of interest segmentation of eyelid margins, using non-parametric methods, including but not limited to, random decision forests such as Breiman's random forest algorithm, gray scale probability maps, binary thresholds, morphological operators and Bresenham's line algorithm;

Step 5: Use region of interest matching to measure meibomian gland dysfunction (MGD) and visible scruff at eyelashes across a series of digital images reproducibly using methods including, but not limited to, scale invariant feature transform and random sample consensus;

Step 6: Identify and count meibomian glands, and identify scruff at eyelashes using methods, including, but not limited to, edge detection, k-means clustering, region growing and thresholding methods;

Step 7: A change in edges, clusters or regions at the on the lower eyelid margin and in the eyelashes are meibomian glands or scruff at eyelashes; and Step 8: If meibomian glands or visible scruff at eyelashes is greater than 25% of eyelid margin, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Measurement of Conjunctivochalasis in Human Eyes Photographically Represented in Digital Images Formed and Captured by a Mobile Smartphone Camera System FIG. 57 shows a deep-learning machine-vision ocular image processing and classification system (i.e. "engine") of the present invention 10 configured and trained for use and deployment on the system network shown in FIG. 8A. As configured and deployed, the system supports and enables an automated method (M4) of detection and measurement of conjunctivochalasis of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 58A shows a front view digital image representation of a human eye exhibiting conjunctivochalasis, and augmented with graphical indications superimposed on the digital image to indicate where conjunctivochalasis is detected in the photographic image of the human eye. Also, the digital image indicates which pixel region of interest (ROI) requires pixel data processing according to a method of digital image processing using the machine-based ophthalmic image processing engine operating on one or more front view digital images of the human eye, so as to automatically detect conjunctivochalasis, as an indication of ocular disease recognition, treatment and manage care, including predicting dry eye disease (DED) class and grade of severity by the automated system, in accordance with the method specified in FIGS. 82A and 83B.

FIG. 58B shows a side view digital image representation of the human eye exhibiting conjunctivochalasis, and showing the existence of conjunctivochalasis on the lower eyelid of the human eye, preventing the normal replenishment of tears at the meniscus interface between the cornea surface and the lower eyelid.

FIG. 59 provides a schematic representation of the human eye exhibiting conjunctivochalasis with conjunctivochalasis on the lower eyelid.

FIGS. 60A and 60B describe the primary steps carried out when practicing the machine-vision based method of processing time and date stamped digital images of a human eye captured by a mobile smartphone camera system, so as to automatically detect conjunctivochalasis on the lower eyelid of the human eye at a particular time and date, to support automated ocular disease recognition, treatment and manage care, including predicting dry eye disease (DED) class and grade of severity by the automated system.

Automated Machine-Vision Based Image Processing Method #4 (M4)

As shown and described in FIGS. 60A and 60B, the machine-vision based method of detecting, measuring, and generating a database of images indicating conjunctivochalasis, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train a system to detect eyelids;

Step 4: Use the above structures and the trained system for automatic region of interest segmentation of sclera using non-parametric methods, including but not limited to, random decision forests such as Breiman's random forest algorithm, gray scale probability maps, binary thresholds, morphological operators and Bresenham's line algorithm;

Step 5: Use region of interest matching to measure conjunctivochalasis across a series of digital images reproducibly using methods including, but not limited to, scale invariant feature transform and random sample consensus;

Step 6: Identify conjunctivochalasis using methods, including, but not limited to, edge detection, k-means clustering, region growing and thresholding methods;

Step 7: A detectable edge, cluster or region above the lower eyelid margin overlying the sclera is considered conjunctivochalasis; and Step 8: If conjunctivochalasis greater than single fold in conjunctiva, then generate output data indicative of such determined ocular disease factors and index the processed image(s) to indicate the same Once each digital image is processed according to the image-processing method described above, and a specified ocular condition is detected/recognized as reflected in the digital image, then the digital image is indexed with the recognized condition (e.g. using suitable image indexing methods and coding), and then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Measurement of Dermatochalasis in Human Eyes Photographically Represented in Digital Images Formed and Captured by a Mobile Smartphone Camera System FIG. 61 shows a schematic representation of a deep-learning machine-vision ocular image processing and classification system (i.e. "engine") of the present invention 10 configured and trained for use and deployment on the system network shown in FIG. 8A. As configured and deployed, the system supports and enables an automated method (M5) of detection and measurement of dermatochalasis of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 62 shows a front view digital image representation of a human eye exhibiting dermatochalasis, and augmented with graphical indications superimposed on the digital image to indicate where dermatochalasis detected in the upper eye lids of the human eyes in the photographic image. Also, the digital image indicates which pixel region of interest (ROI) requires pixel data processing according to a method of digital image processing using the machine-based ophthalmic image processing engine operating on one or more front view digital images of the human eye, so as to automatically detect dermatochalasis, as an indication of ocular disease recognition, treatment and manage care, including predicting dry eye disease (DED) class and grade of severity by the automated system, in accordance with the method specified in FIGS. 86A and 86B.

FIG. 63 shows a schematic representation of the human eye specifying the location of dermatochalasis on the upper eyelids of the human eye, within the captured digital image thereof.

FIGS. 64A and 64B describe the primary steps carried out when practicing the machine-vision based method of processing time and date stamped digital images of a human eye captured by a mobile smartphone camera system, so as to automatically detect dermatochalasis condition in the human eyes at a particular time and date, to support automated ocular disease recognition, treatment and manage care, including predicting dry eye disease (DED) class and grade of severity by the automated system.

Automated Machine-Vision Based Image Processing Method #5 (M5)

As shown and described in FIGS. 64A and 64B, the machine-vision based method of detecting, measuring, and generating a database of images indicating dermatochalasis, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train a system to detect eyelids;

Step 4: Use the above structures and the trained system for automatic region of interest segmentation of eyelid using non-parametric methods, including but not limited to, random decision forests such as Breiman's random forest algorithm, gray scale probability maps, binary thresholds, morphological operators and Bresenham's line algorithm;

Step 5 Use region of interest matching to measure dermatochalasis across a series of digital images reproducibly using methods including, but not limited to, scale invariant feature transform and random sample consensus;

Step 6: Identify dermatochalasis using methods, including, but not limited to, edge detection, k-means clustering, region growing and thresholding;

Step 7: Detection of edges, clusters or regions separate from the upper eyelid margin are considered dermatochalasis; and Step 8: If dermatochalasis is greater than upper eyelid hang (UELH) over the eyelid margin (ELM), then generate output data indicative of such determined ocular disease factors and index the processed image(s) to indicate the same Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Measurement of Tear Film Dynamics (TFD1)

in Human Eyes Photographically Represented in Digital Images Formed and Captured by a Mobile Smartphone Camera System FIG. 65 shows a schematic representation of a deep-learning machine-vision ocular image processing and classification system (i.e. "engine") of the present invention 10 configured and trained for use and deployment on the system network shown in FIG. 8A. As configured and deployed, the system supports and enables an automated method (M6) of detection and measurement of tear film dynamics (TFD1) of the human eyes photographically represented in a time series set of digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIGS. 66A and 66B show a set of time series digital images of a front view digital image representation of a human eye exhibiting tear film dynamics (TFD1), and augmented with graphical indications superimposed on the digital image to indicate where light reflective particle are detected in the photographic image of the tear film of a human eye between eye blinks. Also, the digital images indicate which pixel region of interest (ROI) requires pixel data processing according to a method of digital image processing using the machine-based ophthalmic image processing engine of the present invention operating on one or more front view digital images of the human eye, so as to automatically detect the light reflective particles in the tear film of a human eye during eye blinks, as an indication of ocular disease recognition, treatment and manage care, including predicting dry eye disease (DED) class and grade of severity by the automated system, in accordance with the method specified in FIGS. 68A and 68B.

FIG. 67 shows a schematic representation of the set of time series digital images of the front view of the human eye exhibiting tear film dynamics (TFD1), and showing the tracked movement of light reflective particles within the tear film on the cornea of a human eye being video imaged during testing so as to measure the tear film dynamics of the tear film, in the context of determining ocular disease conditions and grades of severity in the human eye.

FIGS. 68A and 68B describe the primary steps carried out when practicing the machine-vision based method of processing time and date stamped digital images of a human eye captured by a mobile smartphone camera system, so as to automatically detect and measure tear film dynamics in human eyes at a particular time and date, to support automated ocular disease recognition, treatment and manage care, including predicting dry eye disease (DED) class and grade of severity by the automated system.

Automated Machine-Vision Based Image Processing Method #6 (M6)

As shown and described in FIGS. 68A and 68B, the machine-vision based method of detecting, measuring, and generating a database of images indicating tear film dynamics (TFD1) suggestive of ocular pathology, comprises the following steps:

Step 1: Capture a color digital video having a set of frames per second, and decompose the video into 0.1 second intervals, over the course of user keeping the eye open;

Step 2: Process the individual image frames and classify the following structures in the human eye, including eyelids, iris, pupil, and sclera;

Step 3: Use cornea and non-cornea digital images to train a system to detect eyelids;

Step 4: Use the above structures and the trained system for automatic region of interest segmentation of inferior cornea using non-parametric methods, including but not limited to, random decision forests such as Breiman's random forest algorithm, gray scale probability maps, binary thresholds, morphological operators and Bresenham's line algorithm;

Step 5: Use region of interest to identify mobile reflective light particles visible in the tear film using k-means clustering;

Step 6: Follow the movement of the reflective light particles on subsequent 0.1 sec intervals using pixel-based loci for a total of 2 second;

Step 7: Measure speed and direction of movement of reflective light particles over a 2 second interval, with movement superiorly and nasally indicating positive displacement;

Step 8: Measure initial speed of reflective light particles, i.e., speed right after blink and time for reflective light particles to stop moving, i.e., reach speed of 0 mm/sec; and Step 9: If initial speed of reflective light particles is less than 7 mm/sec, or the time for reflective light particles is to stop moving less than 1 second, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Measurement of Tear Film Dynamics (TFD2) in Human Eyes Photographically Represented in Digital Images Formed and Captured by a Mobile Smartphone Camera System FIG. 69 shows a deep-learning machine-vision ocular image processing and classification system (i.e. "engine") of the present invention 10 configured and trained for use and deployment on the system network shown in FIG. 8. As configured and deployed, the system supports and enables an automated method (M7) of detection and measurement of tear film dynamics (TFD2) of human eyes photographically represented in a time series set of digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 70A shows a front view digital image representation of a human eye exhibiting tear film dynamics (TFD2) and augmented with graphical indications superimposed on the digital image to indicate where the tear film dynamics (TFD2) of the tear film on human eyes are detected in the human eyes in a series of digital photographic images. Also, the digital images indicate pixel region of interest (ROI) requires pixel data processing according to a method of digital image processing using the machine-based ophthalmic image processing engine operating on one or more front view digital images of the human eye, so as to automatically detect and measure the tear film dynamics, by virtue of detected perturbations in concentric placido light discs projected on the cornea from the display screen of a mobile smartphone, as an indication of ocular disease recognition, treatment and manage care, including predicting dry eye disease (DED) class and grade of severity by the automated system, in accordance with the method specified in FIGS. 72A and 72B.

FIG. 70B shows a digital image of the front view of the human eye of FIG. 70A captured while the placido light discs are projected onto the human eye from the display screen of a smartphone camera system during teal film dynamics testing, in accordance with the principles of the present invention.

FIG. 70C shows an enlarged view of the digital image of the human eye shown in FIG. 70B showing in greater detail, the placido light discs projected onto the human eye from the display screen of a smartphone camera system during teal film dynamics testing.

FIG. 71 shows an illustration showing the projection of placido light discs onto the human eye from the display screen of a smartphone camera system capturing images of the human eyes during teal film dynamics testing, in accordance with the principles of the present invention.

FIGS. 72A and 72B describe the primary steps carried out when practicing the machine-vision based method of processing time and date stamped digital images of a human eye captured by a mobile smartphone camera system, so as to automatically detect and measure tear film dynamics in the human eye at a particular time and date, to support automated ocular disease recognition, treatment and manage care, including predicting dry eye disease (DED) class and grade of severity by the automated system.

Automated Machine-Vision Based Image Processing Method #7 (M7)

As shown and described in FIGS. 72A and 72B, the machine-vision based method of detecting, measuring, and generating a database of images indicating tear film dynamics (TFD2) suggestive of ocular pathology, comprises the following steps:

Step 1: Project 10 placido discs onto the cornea from screen of mobile smartphone camera;

Step 2: Ask user to keep eyes open for as long as possible;

Step 3: Capture a color digital video having a set of frames per second, and decompose the video into 1 second intervals, over the course of user keeping the eye open;

Step 4: Process the individual frames and classify the following structures in the human eye, including eyelids, iris, pupil, and sclera;

Step 5: Use cornea and non-cornea digital images to train a System to detect cornea;

Step 6: Use the above structures and the trained system for automatic region of interest segmentation of cornea using non-parametric methods, including but not limited to, random decision forests such as Breiman's random forest algorithm, gray scale probability maps, binary thresholds, morphological operators and Bresenham's line algorithm;

Step 7: Use region of interest to identify placido discs on the cornea using k-means clustering and edge detection;

Step 8: Track the placido discs at 1 second intervals using pixel-based loci for 10 seconds;

Step 9: Perturbations in the placido discs, including loss of circularity or indiscrete placido discs, indicate tear film break up; and Step 10: If tear film break up time (TFBUT) is less than 10 seconds, then generate output data indicative of such determined ocular disease factors and index the processed image(s) to indicate the same Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Measurement of Detectable Increases in Tear Meniscus Height (TMH) after Blinking in Human Eyes Photographically Represented in Digital Images Formed and Captured by a Mobile Smartphone Camera System FIG. 73 shows a deep-learning machine-vision ocular image processing and classification system (i.e. "engine") of the present invention 10 configured and trained for use and deployment on the system network shown in FIG. 8A. As configured and deployed, the system supports and enables an automated method (M8) of detection and measurement of tear film dynamics (TFD3) of the human eyes photographically represented in a times series of digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIGS. 74A and 74B show front view digital image representations of a human eye exhibiting tear film dynamics (TFD3), and augmented with graphical indications superimposed on the digital image to indicate where the tear film dynamics in the human eye are measured by analysis of eye blinks during a time series of digital photographic images. Also, the digital image indicates which pixel region of interest (ROI) requires pixel data processing according to a method of digital image processing using the machine-based ophthalmic image processing engine operating on one or more front view digital images of the human eye, so as to automatically detect and measure tear film dynamics of the human eyes, as an indication of ocular disease recognition, treatment and manage care, including predicting dry eye disease (DED) class and grade of severity by the automated system, in accordance with the method specified in FIGS. 76A and 76B.

FIGS. 75A, 75B and 75C schematic representations of the human eye exhibiting tear film dynamics (TFD3), and showing the location of tears accumulating in the tear meniscus region of the human eye, at the interface between the cornea surface and the lower eyelid of the human eye, and measuring the change of tear meniscus height. (TMH) from baseline after a full eye blink.

FIGS. 76A and 76B describe the primary steps carried out when practicing the machine-vision based method of processing time and date stamped digital images of a human eye captured by a mobile smartphone camera system, so as to automatically detect and measure the tear film dynamics in the human eye at a particular time and date by real-time changes in the measurement of tear meniscus height (TMH) in between eye blinks, to support automated ocular disease recognition, treatment and manage care, including predicting dry eye disease (DED) class and grade of severity by the automated system.

Automated Machine-Vision Based Image Processing Method #8 (M8)

As shown and described in FIGS. 76A and 76B, the machine-vision based method of detecting, measuring, and generating a database of images indicating tear meniscus height (TMH) and its change in height over time, comprises the following steps:

Step 1: Ask user to keep eyes open for as long as possible;

Step 2: Capture a color digital video having a set of frames per second, and decompose the video into 0.1 second intervals, over the course of user keeping the eye open;

Step 3: Process the individual frames and classify the following structures in the human eye, including eyelids, iris, pupil, and sclera;

Step 4: Use eyelid and non-eyelid digital images to train a system to detect eyelids;

Step 5: Use the above structures and the trained system for automatic region of interest segmentation of lower eyelid using non-parametric methods, including but not limited to, random decision forests such as Breiman's random forest algorithm, gray scale probability maps, binary thresholds, morphological operators and Bresenham's line algorithm;

Step 6: Use region of interest matching to measure tear meniscus height (TMH) across a series of digital images reproducibly using methods including, but not limited to, scale invariant feature transform and random sample consensus;

Step 7: Differentiate tear meniscus reflective line from lower eyelid by using methods, including, but not limited to, edge detection, k-means clustering, region growing and thresholding;

Step 8: Measure tear meniscus height (TMH) in millimeters by using pixel-by-pixel size;

Step 9: Tear meniscus height right after a blink of less than 0.2 mm is suggestive of ocular pathology; and Step 10: If the tear meniscus height (TMH) increase is less than 0.2 mm measured from baseline over the course of keeping the eye open, then generate output data indicative of such determined ocular disease factors and index the processed image(s) to indicate the same Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection and Mapping of Blink Speed Patterns (BSP) in Human Eyes Photographically Represented in Digital Images Formed and Captured by a Mobile Smartphone Camera System FIG. 77 shows a deep-learning machine-vision ocular image processing and classification system (i.e. "engine") of the present invention 10 configured and trained for use and deployment on the system network shown in FIG. 8A. As configured and deployed, the system supports and enables an automated method (M9) of detection and measurement and mapping of the speed of blinking in the human eyes photographically represented in a times series of digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 78 shows a front view digital image representation of a human eye, augmented with graphical indications superimposed on the digital image to indicate where the speed of eye blinks are detected, measured and in the human eye in the photographic image. Also, the digital images indicate which pixel region of interest (ROI) requires pixel data processing according to the second method of digital image processing using the machine-based ophthalmic image processing engine of the present invention operating on one or more front view digital images of the human eye, so as to automatically map changes in eye blinking speed, as an indication of ocular disease recognition, treatment and manage care, including predicting dry eye disease (DED) class and grade of severity by the automated system, in accordance with the method specified in FIGS. 102A, 102B and 102C.

FIGS. 79A and 79B show schematics mapping of eye blink speed and patterns in the human eye, taken at different time samples T1, T2, T3, T4.

FIG. 80 shows a table describing the reasons to measure the increased blink speed (IDS) after a full blink of a patient's eyes, namely: (i) the blink speed/duration and partial blinks are related to eyelid pathology which predisposes to ocular disease conditions; and (ii) the blink interval and frequency are related to corneal irregularity from ocular disease conditions.

FIGS. 81A, 81B and 81C describe the primary steps carried out when practicing the machine-vision based method of processing time and date stamped digital images of a human eye captured by a mobile smartphone camera system, so as to automatically detecting the speed and patterns of eye blinking in the human eye at a particular time and date, to support automated ocular disease recognition, treatment and manage care, including predicting dry eye disease (DED) class and grade of severity by the automated system.

Automated Machine-Vision Based Image Processing Method #9 (M9)

As shown and described in FIGS. 81A, 81B and 81C, the machine-vision based method of detecting, measuring, and generating a database of images indicating blink speed patterns (BSP) suggestive of ocular pathology, comprises the following steps:

Step 1: Capture a color digital video having a set of frames per second, and each color digital image having a set of pixels;

Step 2: Process the individual frames and classify the following structures in the human eye, including eyelids, iris, pupil, and sclera;

Step 3: Use eyelid and non-eyelid digital images to train a system to detect upper and lower eyelid;

Step 4: Use region of interest matching across a series of digital images reproducibly using methods including, but not limited to, scale invariant feature transform and random sample consensus;

Step 5: Edge detection is used to mark and track the upper and lower eyelid to determine palpebral opening height and measure the number of blinks;

Step 6: Blinking is plotted over time to calculate the blinks per minute, duration of individual blinks and to calculate the interval between blinks;

Step 7: Blink speed is measured using the distance between the upper and lower eyelid divided by the time to blink;

Step 8: Partial blinks are determined using non-parametric methods, including but not limited to, random decision forests such as Breiman's random forest algorithm, gray scale probability maps, binary thresholds, morphological operators, Bresenham's line algorithm, and marked location of upper and lower eyelid using edge detection;

Step 8: Use method for conjunctival injection recognition as detailed previously;

Step 9: Detecting a >1 mm difference between the upper and lower eyelid or greater than 10% difference in grayscale binary images on blinking suggests a partial blink;

Step 10: If greater than 20 blinks per minute, then generate output data indicative of such determined ocular disease factors and index the processed image(s) to indicate the same;

Step 11: If greater than 12 partial blinks per minute, then generate output data indicative of such determined ocular disease factors and index the processed image(s) to indicate the same;

Step 12: If blink duration greater than 0.5 secs per blink, then generate output data indicative of such determined ocular disease factors and index the processed image(s) to indicate the same; and Step 13: If lid closure is greater than 0.5 secs per blink, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Corneal Abrasions in Human Eyes Photographically Represented in Digital Images Formed and Captured by a Mobile Smartphone Camera System FIG. 82 shows a deep-learning machine-vision ocular image processing and classification system (i.e. "engine") of the present invention 10 configured and trained for use and deployment on the system network shown in FIG. 8A. As configured and deployed, the system supports and enables an automated method (M10) of detection and measurement of corneal abrasions (e.g. scratches) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 83 shows a front view digital image representation of a human eye and augmented with graphical indications superimposed on the digital image to indicate where corneal scratches are detected and measured in the human eye in the photographic image. Also, the digital images indicate which pixel region of interest (ROI) requires pixel data processing according to an automated method of digital image processing using the machine-based ophthalmic image processing engine of the present invention operating on one or more front view digital images of the human eye, so as to automatically detect corneal scratches in the human eye, in accordance with the method specified in FIGS. 85A and 85B.

FIG. 84 shows a model supporting the automated detection and measurement of corneal abrasion in human eyes using a real-time ophthalmic image processing engine operating on frontal and/or side view digital images of the human eyes.

FIGS. 85A and 85B describe the primary steps carried out when practicing the machine-vision based method of processing time and date stamped digital images of a human eye captured by a mobile smartphone camera system, so as to automatically detecting the corneal scratches in the human eye at a particular time and date using the automated system of the present invention.

Automated Machine-Vision Based Image Processing Method #10 (M10)

As shown and described in FIGS. 85A and 85B, the machine-vision based method of detecting, measuring, and generating a database of images indicating corneal abrasion (CA), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of cornea using non-parametric methods, including but not limited to, random decision forests such as Breiman's random forest algorithm, gray scale probability maps, binary thresholds, morphological operators and Bresenham's line algorithm;

Step 5: Use region of interest matching to measure cornea across a series of digital images reproducibly using methods including, but not limited to, scale invariant feature transform and random sample consensus;

Step 6: Identify corneal abrasion using edge detection, region growing, k-means clustering and thresholding;

Step 7: Measure corneal abrasion height (CAH) and corneal abrasion width (CAW) and respective surface areas using pixel-by-pixel size measurements; and Step 8: If the corneal abrasion height (CAH) and corneal abrasion width (CAW) are greater than 0.1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention. Specification of the Deep-Learning Machine-Vision Ocular Image Processing and Classification System of the Present Invention Configured and Trained for Use and Deployment on the System Network to Support and Enable Automated Detection of Palpebral Fissures in Human Eyes Photographically Represented in Digital Images Formed and Captured by a Mobile Smartphone Camera System FIG. 86 shows a deep-learning machine-vision ocular image processing and classification system (i.e. "engine") of the present invention 10 configured and trained for use and deployment on the system network shown in FIG. 8A, to support and enable an automated method (M11) of detection and measurement of palpebral fissures (PF) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 87 shows a front view digital image representation of a human eye, and augmented with graphical indications superimposed on the digital image to indicate (i) where a palpebral fissure (PF) is detected in the photographic image of the human eye, and (ii) which pixel region of interest (ROI) requires pixel data processing according to an auto-mated method of digital image processing using the machine-based ophthalmic image processing engine of the present invention operating on one or more front view digital images of the human eye, so as to automatically detect palpebral fissure (PF) as an indication of ocular disease recognition, treatment and manage care, including predicting dry eye disease (DED) class and grade of severity by the automated system.

FIG. 88 provides a schematic model supporting the auto-mated detection and measurement of palpebral fissure (PF) in the human eyes using a real-time ophthalmic image processing engine operating on front view digital images of the human eyes.

FIGS. 89A and 89B describe the primary steps carried out when practicing the machine-vision based method of pro-cessing time and date stamped digital images of a human eye captured by a mobile smartphone camera system and pro-cessed to automatically detect palpebral fissure (PF) in the human eye at a particular time and date, to support auto-mated ocular disease recognition, treatment and manage care, including predicting dry eye disease (DED) class and grade of severity by the automated system.

Automated Machine-Vision Based Image Processing Method #11 (M11)

As shown and described in FIGS. 89A and 89B, the machine-vision based method of detecting, measuring, and generating a database of images indicating palpebral fissure suggestive of ocular pathology, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Process the individual frames and classify the following structures in the human eye, including eye-lids, iris, pupil, and sclera;

Step 4: Use eyelid and non-eyelid digital images to train a system to detect eyelids;

Step 5: Use the above structures and the trained system for automatic region of interest segmentation of eyelid margins, using non-parametric methods, including but not limited to, random decision forests such as Bre-iman's random forest algorithm, gray scale probability maps, binary thresholds, morphological operators and Bresenham's line algorithm;

Step 6: Use region of interest matching to detect eyelid margins across a series of digital images reproducibly using methods including, but not limited to, scale invariant feature transform and random sample con-sensus;

Step 7: Identify the eyelid margin to eyelid margin distance, i.e., the palpebral fissure height, using meth-ods, including, but not limited to, edge detection, k-means clustering and thresholding;

Step 8: Measure palpebral fissure height (PFH) and palpe-bral fissure width (PFW) measured in millimeters using pixel-by-pixel size;

Step 9: If the palpebral fissure height (PFW) is greater than 12 mm or palpebral fissure height (PFW) is less than 8 mm, then generate output data indicative of such determined ocular disease factors and index the pro-cessed image(s) to indicate the same; and Step 10: If palpebral fissure width (PFW) is greater than 33 mm or palpebral fissure width (PFW) is less than 28 mm, then generate output data indicative of such deter-mined ocular disease factors and index the processed image(s) to indicate the same Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention. Specification of the Deep-Learning Machine-Vision Ocular Image Processing and Classification System of the Present Invention Configured and Trained for Use and Deployment on the System Network to Support and Enable Automated Detection of the Margin Reflect Distance (MRD) in Human Eyes Photographically Represented in Digital Images Formed and Captured by a Mobile Smartphone Camera System FIG. 90 shows a deep-learning machine-vision ocular image processing and classification system (i.e. "engine") of the present invention 10 configured and trained for use and deployment on the system network shown in FIG. 8A, to support and enable an automated method (M12) of detection and measurement of the margin reflex distance (MRD) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 91 shows a front view digital image representation of a human eye, and augmented with graphical indications superimposed on the digital image to indicate (i) where margin reflex distance (MRD) is detected and measured in the human eye in the photographic image, and (ii) which pixel region of interest (ROI) requires pixel data processing according to an automated method of digital image processing using the machine-based ophthalmic image processing engine of the present invention operating on one or more front view digital images of the human eye, so as to automatically detect and measure margin reflex distance (MRD) as an indication of ocular disease recognition, treatment and manage care, including predicting dry eye disease (DED) class and grade of severity by the automated system.

FIG. 92 provides a schematic model supporting the automated detection and measurement of margin reflex distance (MRD) in the human eyes using a real-time ophthalmic image processing engine operating on front view digital images of the human eyes.

FIGS. 93A and 93B describes the primary steps carried out when practicing the machine-vision based method of processing time and date stamped digital images of a human eye captured by a mobile smartphone camera system and processed to automatically detect margin reflex distance (MRD) in the human eye at a particular time and date, to support automated ocular disease recognition, treatment and manage care, including predicting dry eye disease (DED) class and grade of severity by the automated system.

Automated Machine-Vision Based Image Processing Method #12 (M12)

As shown and described in FIGS. 93A and 93B, the machine-vision based method of detecting, measuring, and generating a database of images indicating margin reflex distance (MRD) suggestive of ocular pathology, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train the system to detect eyelid;

Step 4: Use the above structures and trained system for automatic region of interest segmentation of eyelid using non-parametric methods, including but not limited to, random decision forests such as Breiman's random forest algorithm, gray scale probability maps, binary thresholds, morphological operators and Bresenham's line algorithm;

Step 5: Use region of interest matching to detect eyelid margins across a series of digital images reproducibly using methods including, but not limited to, scale invariant feature transform and random sample consensus;

Step 6: Identify the eyelid margin to eyelid margin (EM-EM) distance using methods, including, but not limited to, edge detection, k-means clustering and thresholding;

Step 7: Use region of interest to identify light reflex using k-means clustering methods;

Step 8: Measure margin reflex distance 1 from light reflex to upper eyelid margin and margin reflex distance 2 from light reflex to lower eyelid margin in millimeters using pixel-by-pixel size;

Step 9: If the margin reflex distance (MRD) 1 is less than 3.5 mm, or the margin reflex distance (MRD) 1 is greater than 4.5 mm, then generate output data indicative of such determined ocular disease factors and index the processed image(s) to indicate the same; and Step 10: If the margin reflex distance MRD) 2 is less than 4.5 mm, or the margin reflex distance (MRD) 2 is greater than 5.5 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of the Scleral Show (SS) in Human Eyes Photographically Represented in Digital Images Formed and Captured by a Mobile Smartphone Camera System FIG. 94 shows a deep-learning machine-vision ocular image processing and classification system (i.e. "engine") of the present invention 10 configured and trained for use and deployment on the system network shown in FIG. 8A, to support and enable an automated method (M13) of method of detection and measurement of scleral show (SS) of the human eyes photographically represented in digital images of a front view of human eyes formed and captured by a mobile smartphone camera system in accordance with the principles of the present invention.

FIG. 95 shows a front view digital image representation of a human eye, and augmented with graphical indications superimposed on the digital image to indicate (i) where scleral show (SS) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect scleral show (SS) as an indication of ocular disease recognition, treatment and manage care, including predicting dry eye disease (DED) class and grade of severity by the automated system.

FIG. 96 provides a schematic model supporting the automated detection and measurement of scleral show (SS) in the human eyes using a real-time ophthalmic image processing engine operating on front view digital images of the human eyes.

FIGS. 97A and 97B describe the primary steps carried out when practicing the machine-vision based method of processing time and date stamped digital images of a human eye captured by a mobile smartphone camera system and processed to automatically detect scleral show (SS) in the human eye at a particular time and date, to support automated ocular disease recognition, treatment and manage care, including predicting dry eye disease (DED) class and grade of severity by the automated system.

Automated Machine-Vision Based Image Processing Method #13 (M13)

As shown and described in FIGS. 97A and 97B, the machine-vision based method of detecting, measuring, and generating a database of images indicating scleral show (SS), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and the trained system for automatic region of interest segmentation of sclera using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducible using methods including, but not limited to, scale invariant feature transform and random sample consensus;

Step 6: Apply Steps 3 to 5 for automated and reproducible detection of the eyelid margin; and Step 7: Measure inferior scleral show (ISS) from the inferior cornea to the lower eyelid margin, and measure the superior scleral show (SSS) from the superior cornea to the upper eyelid margin in millimeters using pixel-by-pixel size measurements.

Step 8: If the superior scleral show is greater than 0.00 mm, or the inferior scleral show is greater than 1.0 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of the Levator Function in Human Eyes Photographically Represented in Digital Images Formed and Captured by a Mobile Smartphone Camera System FIG. 98 shows a deep-learning machine-vision ocular image processing and classification system (i.e. "engine") of the present invention 10 configured and trained for use and deployment on the system network shown in FIG. 8A, to support and enable an automated method (M14) of method of detection and measurement of levator function (LF) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIGS. 99 and 100 show a set of front view digital image representation of a human eye, while looking up and looking down respectively, and augmented with graphical indications superimposed on the digital image to indicate (i) where the levator function is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect the levator function as an indication of ocular disease recognition, treatment and manage care, including predicting dry eye disease (DED) class and grade of severity by the automated system.

FIG. 101 provide a schematic model supporting the automated detection and measurement of the levator function in the human eyes using a real-time ophthalmic image processing engine operating on front view digital images of the human eyes.

FIGS. 102A and 102B describe the primary steps carried out when practicing the machine-vision based method of processing time and date stamped digital images of a human eye captured by a mobile smartphone camera system and processed to automatically detect the levator function in the human eye at a particular time and date, to support automated ocular disease recognition, treatment and manage care, including predicting dry eye disease (DED) class and grade of severity by the automated system.

Automated Machine-Vision Based Image Processing Method #14 (M14)

As shown and described in FIGS. 102A and 102B, the machine-vision based method of detecting, measuring, and generating a database of images indicating levator function (LF), comprises the following steps:

Step 1: User is asked to look down and then up;

Step 2: Capture a series of color digital images each color digital image having a set of pixels;

Step 3: Process the pixels in each digital image and classify the following structures in the human eye, including eyelids, iris, pupil, and sclera;

Step 4: use eyelid and non-eyelid digital images to train the system to detect eyelid;

Step 4: use the above structures and trained system for automatic region of interest segmentation of eyelid using non-parametric methods, including but not limited to, random decision forests such as Breiman's random forest algorithm, gray scale probability maps, binary thresholds, morphological operators and Bresenham's line algorithm;

Step 5: Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 6: Use region of interest matching to detect eyelid margins across a series of digital images reproducibly using methods including, but not limited to, scale invariant feature transform and random sample consensus;

Step 7: Identify the eyelid margin to eyelid margin distance using methods, including, but not limited to, edge detection, k-means clustering and thresholding;

Step 8: Measure the distance from the upper eyelid on downgaze to the upper eyelid on up gaze in millimeters using pixel-by-pixel size measurement to obtain the levator function (LF) measure of the human eyes;

Step 9: IF the levator function is determined to be less than 12 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Contact Lens Overwear (CLOW) in Human Eyes Photographically Represented in Digital Images Formed and Captured by a Mobile Smartphone Camera System FIG. 103 shows a deep-learning machine-vision ocular image processing and classification system (i.e. "engine") of the present invention 10 configured and trained for use and deployment on the system network shown in FIG. 8A, to support and enable an automated method (M15) of method of detection and measurement of the contact lens overwear (CLOW) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

Figure 104:
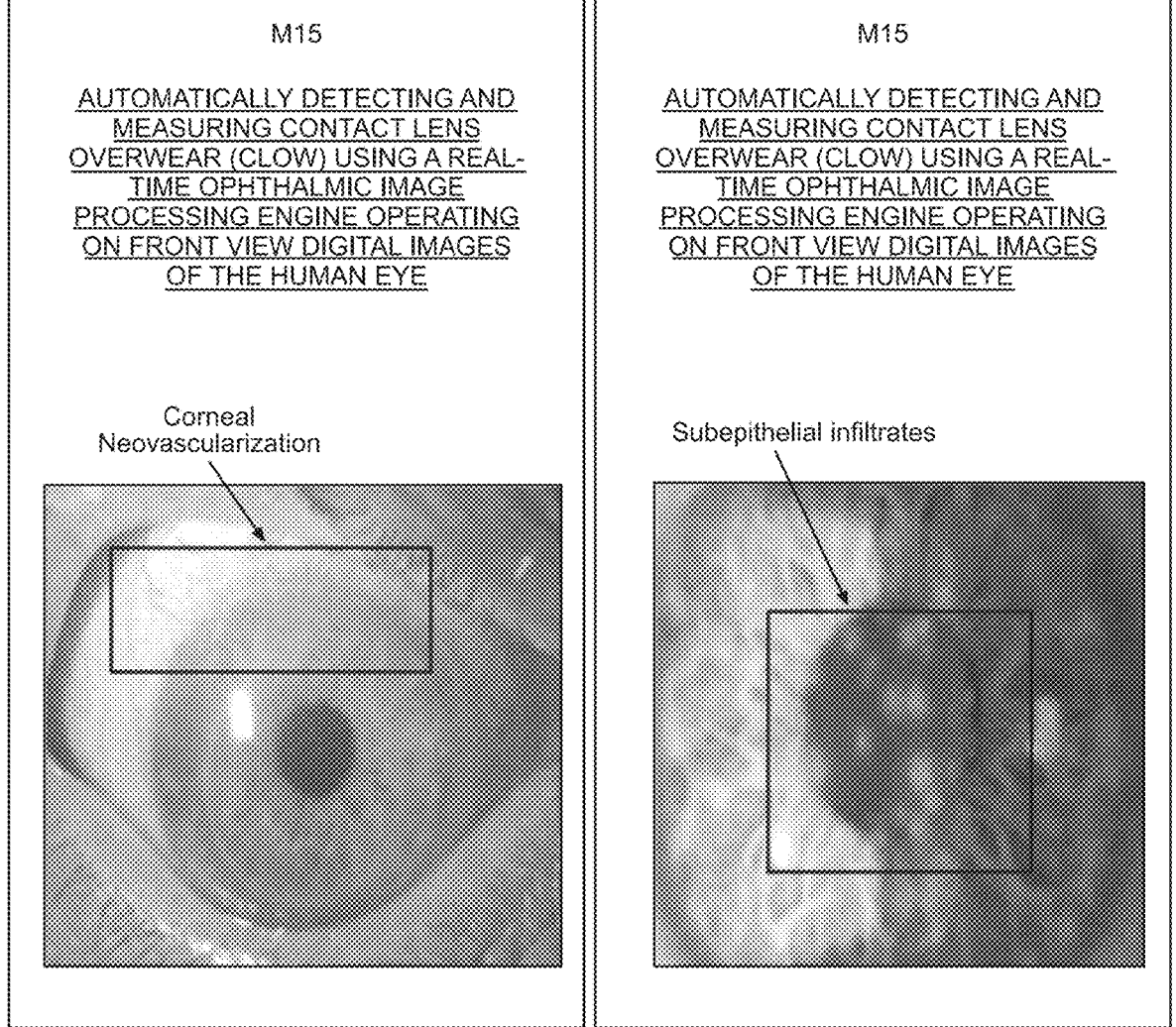

FIG. 104 shows a front view digital image representation of a human eye exhibiting contact lens overwear (CLOW), and augmented with graphical indications superimposed on the digital image to indicate (i) where the contact lens overwear (CLOW) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect contact lens overwear (CLOW) as an indication of ocular disease recognition, treatment and manage care, including predicting dry eye disease (DED) class and grade of severity by the automated system.

FIG. 105 provides a schematic model supporting the automated detection and measurement of contact lens overwear (CLOW) in the human eyes using a real-time ophthalmic image processing engine operating on front view digital images of the human eyes.

FIGS. 106A and 106B describe the primary steps carried out when practicing the machine-vision based method of processing time and date stamped digital images of a human eye captured by a mobile smartphone camera system and processed to automatically detect contact lens overwear (CLOW) in the human eye at a particular time and date, to support automated ocular disease recognition, treatment and manage care, including predicting dry eye disease (DED) class and grade of severity by the automated system.

Automated Machine-Vision Based Image Processing Method #15

As shown and described in FIGS. 106A and 106B, the machine-vision based method of detecting, measuring, and generating a database of images indicating contact lens overwear (CLOW), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation using non-parametric methods, including but not limited to, random decision forests such as Breiman's random forest algorithm, gray scale probability maps, binary thresholds, morphological operators and Bresenham's line algorithm;

Step 5: Use region of interest matching to detect cornea across a series of digital images reproducibly using methods including, but not limited to, scale invariant feature transform and random sample consensus;

Step 6: Identify contact lens, corneal neovascularization and corneal subepithelial infiltrates using edge detection, region growing, k-means clustering and thresholding;

Step 7: Differentiate the corneal subepithelial infiltrates from corneal infection, abrasion and foreign body as illustrated in FIG. 105 using contrast-limited adaptive histogram equalization, hue-saturation-value, product of saturation and hue maps, and maximal values of saturation and hue values;

Step 8: If corneal neovascularization is greater than 10% of cornea, then generate output data indicative of such determined ocular disease factors and index the processed image(s) to indicate the same; and Step 9: If the corneal subepithelial infiltrates is greater than 0.1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Corneal Transplant Graft Rejection (CTGR) in Human Eyes Photographically Represented in Digital Images Formed and Captured by a Mobile Smartphone Camera System FIG. 107 shows a deep-learning machine-vision ocular image processing and classification system (i.e. "engine") of the present invention 10 configured and trained for use and deployment on the system network shown in FIG. 8A, to support and enable an automated method (M16) of method of detection and measurement of corneal transplant graft rejection (CTGR) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 108 shows a front view digital image representation of a human eye exhibiting corneal transplant graft rejection (CTGR), and augmented with graphical indications superimposed on the digital image to indicate (i) where corneal transplant graft rejection (CTGR) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect corneal transplant graft rejection (CTGR) as an indication of ocular disease recognition, treatment and manage care, including predicting dry eye disease (DED) class and grade of severity by the automated system.

FIG. 109 provides a schematic model supporting the automated detection and measurement of corneal transplant graft rejection (CTGR) in the human eyes using a real-time ophthalmic image processing engine operating on front view digital images of the human eyes.

FIGS. 110A and 110B describe the primary steps carried out when practicing the machine-vision based method of processing time and date stamped digital images of a human eye captured by a mobile smartphone camera system and processed to automatically detect corneal transplant graft rejection (CTGR) in the human eye at a particular time and date, to support automated ocular disease recognition, treatment and manage care, including predicting dry eye disease (DED) class and grade of severity by the automated system.

Automated Machine-Vision Based Image Processing Method #16 (M16)

As shown and described in FIGS. 110A and 110B, the machine-vision based method of detecting, measuring, and generating a database of images indicating corneal transplant graft rejection (CTGR) comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation using nonparametric methods, including but not limited to, random decision forests such as Breiman's random forest algorithm, gray scale probability maps, binary thresholds, morphological operators and Bresenham's line algorithm;

Step 5: Use region of interest matching to detect cornea across a series of digital images reproducibly using methods including, but not limited to, scale invariant feature transform and random sample consensus;

Step 6: As illustrated in FIG. 109, detect and identify sutures, keratic precipitates, stromal infiltrates, corneal edema, and the Khodadoust line (i.e. accumulation of inflammatory cells on the corneal endothelium) in the digital images, using edge detection, region growing, k-means clustering and thresholding methods;

Step 7: Differentiate the corneal transplant graft rejection (CTGR) features from others using contrast-limited adaptive histogram equalization, hue-saturation-value, product of saturation and hue maps, and maximal values of saturation and hue values; and Step 8: If sutures are present, or detected keratic precipitates are greater than 0.1 mm, or stromal infiltrates are greater than 0.1 mm, or corneal edema is greater than 0.1% of cornea, or the Khodadoust line is greater 0.1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of a Cataract in Human Eyes Photographically Represented in Digital Images Formed and Captured by a Mobile Smartphone Camera System FIG. 111 shows a deep-learning machine-vision ocular image processing and classification system (i.e. "engine") of the present invention 10 configured and trained for use and deployment on the system network shown in FIG. 8A, to support and enable the automated method (M17) of detection and measurement of cataract in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 112 is a front view digital image representation of a human eye exhibiting cataract, and augmented with graphical indications superimposed on the digital image to indicate (i) where a cataract is detected and measured in the human eye in the photographic image, and (ii) which pixel region of interest (ROI) requires pixel data processing according to an automated method of digital image processing using the machine-based ophthalmic image processing engine of the present invention operating on one or more front view digital images of the human eye, so as to automatically detect cataract as an indication of ocular disease recognition, treatment and manage care, including predicting dry eye disease (DED) class and grade of severity by the automated system.

FIG. 113 provides a schematic model supporting the automated detection and measurement of cataract in the human eyes using a real-time ophthalmic image processing engine operating on front view digital images of the human eyes.

FIGS. 114A and 114B describe the primary steps carried out when practicing the machine-vision based method of processing time and date stamped digital images of a human eye captured by a mobile smartphone camera system and processed to automatically detect a cataract in the human eye at a particular time and date, to support automated ocular disease recognition, treatment and manage care, including predicting dry eye disease (DED) class and grade of severity by the automated system.

Automated Machine-Vision Based Image Processing Method #17 (M17)

As shown and described in FIGS. 114A and 114B, the machine-vision based method of detecting, measuring, and generating a database of images indicating a cataract, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: As illustrated in FIG. 113, use region of interest (ROI) matching to detect the cornea across a series of digital images reproducibly using methods including, but not limited to, scale invariant feature transform and random sample consensus;

Step 6: Identify the pupillary margin using edge detection, region growing, k-means clustering and thresholding methods;

Step 7: Identify a cataract (i.e. degree of lens opacification) using contrast-limited adaptive histogram equalization, hue-saturation-value, product of saturation and hue maps, and maximal values of saturation and hue values; and Step 8: If lens opacification is greater than 50%, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Viral Conjunctivitis (VCJ) in Human Eyes Photographically Represented in Digital Images Formed and Captured by a Mobile Smartphone Camera System FIG. 115 shows a deep-learning machine-vision ocular image processing and classification system (i.e. "engine") of the present invention configured and trained for use and deployment on the system network shown in FIG. 8A, to support and enable an automated method (M18) of detection and measurement of viral conjunctivitis (VCJ) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 116 is a front view digital image representation of a human eye exhibiting viral conjunctivitis (VCJ), and augmented with graphical indications superimposed on the digital image to indicate (i) where viral conjunctivitis (VCJ) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect viral conjunctivitis (VCJ) as an indication of ocular disease recognition, treatment and manage care, including predicting dry eye disease (DED) class and grade of severity by the automated system.

FIG. 117 is a schematic model supporting the automated detection and measurement of viral conjunctivitis (VCJ) in the human eyes using a real-time ophthalmic image processing engine operating on front view digital images of the human eyes.

FIGS. 118A and 118B describe the primary steps carried out when practicing the machine-vision based method of processing time and date stamped digital images of a human eye captured by a mobile smartphone camera system and processed to automatically detect viral conjunctivitis (VCJ) in the human eye at a particular time and date, to support automated ocular disease recognition, treatment and manage care, including predicting dry eye disease (DED) class and grade of severity by the automated system.

Automated Machine-Vision Based Image Processing Method #18 (M18)

As shown and described in FIGS. 118A and 118B, the machine-vision based method of detecting, measuring, and generating a database of images indicating viral conjunctivitis (VCJ), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducibly using methods including, but not limited to, scale invariant feature transform and random sample consensus;

Step 6: As illustrated in FIG. 117, measure conjunctival injection in the region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: As illustrated in FIG. 117, detect clear discharge using edge detection, region growing, k-means clustering and thresholding methods; and Step 8: If detected clear discharge is greater than 0.1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Bacterial Conjunctivitis (BCJ) in Human Eyes Photographically Represented in Digital Images Formed and Captured by a Mobile Smartphone Camera System FIG. 119 show a deep-learning machine-vision ocular image processing and classification system (i.e. "engine") of the present invention configured and trained for use and deployment on the system network shown in FIG. A, to support and enable automated method (M19) of method of detection and measurement of bacterial conjunctivitis (BCJ) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 120 show a front view digital image representation of a human eye exhibiting bacterial conjunctivitis (BCJ), and augmented with graphical indications superimposed on the digital image to indicate (i) where bacterial conjunctivitis (BCJ) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect bacterial conjunctivitis (BCJ) as an indication of ocular disease recognition, treatment and manage care, including predicting dry eye disease (DED) class and grade of severity by the automated system.

FIG. 121 provides a schematic model supporting the automated detection and measurement of bacterial conjunctivitis (BCJ) in the human eyes using a real-time ophthalmic image processing engine operating on front view digital images of the human eyes.

FIGS. 122A and 122B describe the primary steps carried out when practicing the machine-vision based method of processing time and date stamped digital images of a human eye captured by a mobile smartphone camera system and processed to automatically detect bacterial conjunctivitis (BCJ) in the human eye at a particular time and date, to support automated ocular disease recognition, treatment and manage care, including predicting dry eye disease (DED) class and grade of severity by the automated system.

Automated Machine-Vision Based Image Processing Method #19

As shown and described in FIGS. 122A and 122B, the machine-vision based method of detecting, measuring, and generating a database of images indicating bacterial conjunctivitis (BCJ) comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to measure dermatochalasis across a series of digital images reproducibly using methods including, but not limited to, scale invariant feature transform and random sample consensus;

Step 6: As illustrated in FIG. 121, measure conjunctival injection in region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: As illustrated in FIG. 121, detect purulent discharge using edge detection, region growing, k-means clustering and thresholding methods; and Step 8: If detected purulent discharge is greater than 0.1 mm, then generate output data indicative of such determined ocular disease factors and index the processed image(s) to indicate the same Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Allergic Conjunctivitis (ACJ) in Human Eyes Photographically Represented in Digital Images Formed and Captured by a Mobile Smartphone Camera System FIG. 123 shows a deep-learning machine-vision ocular image processing and classification system (i.e. "engine") of the present invention 10 configured and trained for use and deployment on the system network shown in FIG. 8A, to support and enable an automated method (M20) of detection and measurement of allergic conjunctivitis (ACJ) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 124 shows a front view digital image representation of a human eye exhibiting allergic conjunctivitis (ACJ), and augmented with graphical indications superimposed on the digital image to indicate (i) where allergic conjunctivitis (ACJ) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect allergic conjunctivitis (ACJ) as an indication of ocular disease recognition, treatment and manage care, including predicting dry eye disease (DED) class and grade of severity by the automated system.

FIG. 125 provides a schematic model supporting the automated detection and measurement of allergic conjunctivitis (ACJ) in the human eyes using a real-time ophthalmic image processing engine operating on front view digital images of the human eyes.

FIGS. 126A and 126B describe the primary steps carried out when practicing the machine-vision based method of processing time and date stamped digital images of a human eye captured by a mobile smartphone camera system and processed to automatically detect allergic conjunctivitis (ACJ) in the human eye at a particular time and date, to support automated ocular disease recognition, treatment and manage care, including predicting dry eye disease (DED) class and grade of severity by the automated system.

Automated Machine-Vision Based Image Processing Method #20 (M20)

As shown and described in FIGS. 126A and 126B, machine-vision based method of detecting, measuring, and generating a database of images indicating allergic conjunctivitis (ACJ), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducibly using methods including, but not limited to, scale invariant feature transform and random sample consensus;

Step 6: As illustrated in FIG. 125, measure conjunctival injection in region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 7: As illustrated in FIG. 125, detect clear discharge and chemosis using edge detection, region growing, k-means clustering and thresholding methods; and Step 8: If detected conjunctival injection is greater than 75, and detected clear discharge is greater than 0.1 mm in both eyes, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Chemical Burn Conjunctivitis (BCJ) in Human Eyes Photographically Represented in Digital Images Formed and Captured by a Mobile Smartphone Camera System FIG. 127 shows a deep-learning machine-vision ocular image processing and classification system (i.e. "engine") of the present invention configured and trained for use and deployment on the system network shown in FIG. 8A, to support and enable an automated method (M21) of detection and measurement of chemical burn conjunctivitis (CBCJ) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 128 shows a front view digital image representation of a human eye exhibiting chemical burn conjunctivitis (CBCJ), and augmented with graphical indications superimposed on the digital image to indicate (i) where chemical burn conjunctivitis (CBCJ) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect chemical burn conjunctivitis (CBCJ) as an indication of ocular disease recognition, treatment and manage care, including predicting dry eye disease (DED) class and grade of severity by the automated system.

FIG. 129 provides a schematic model supporting the automated detection and measurement of chemical burn conjunctivitis (CBCJ) in the human eyes using a real-time ophthalmic image processing engine operating on front view digital images of the human eyes.

FIGS. 130A and 130B describe the primary steps carried out when practicing the machine-vision based method of processing time and date stamped digital images of a human eye captured by a mobile smartphone camera system and processed to automatically detect chemical burn conjunctivitis (CBCJ) in the human eye at a particular time and date, to support automated ocular disease recognition, treatment and manage care, including predicting dry eye disease (DED) class and grade of severity by the automated system.

Automated Machine-Vision Based Image Processing Method #21 (M21)

As shown and described in FIGS. 130A and 130B, machine-vision based method of detecting, measuring, and generating a database of images indicating chemical burn conjunctivitis (CBCJ), comprises the following steps:

Step 1: capture a series of color digital images each color digital image having a set of pixels;

Step 2: process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducibly using methods including, but not limited to, scale invariant feature transform and random sample consensus;

Step 6: As illustrated in FIG. 129, measure conjunctival injection in region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection; and Step 7: As illustrated in FIG. 129, detect clear discharge, chemosis and limbal whitening using edge detection, region growing, k-means clustering and thresholding methods;

Step 8: If detected conjunctival injection is greater than 75, and detected clear discharge is greater than 0.1 mm in both eyes, then generate output data indicative of such determined ocular disease factors and index the processed image(s) to indicate the same; and Step 9: If detected limbal whitening is greater than 0.1% of cornea, then generate output data indicative of such determined ocular disease factors and index the processed image(s) to indicate the same; and Step 10: If detected chemosis is greater than 5% of conjunctiva, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Pterygium/Pinguecula (PP) in Human Eyes Photographically Represented in Digital Images Formed and Captured by a Mobile Smartphone Camera System FIG. 131 shows a deep-learning machine-vision ocular image processing and classification system (i.e. "engine") of the present invention 10 configured and trained for use and deployment on the system network shown in FIG. 8A, to support and enable an automated method (M22) of detection and measurement of pterygium/pinguecula (PP) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 132 shows a front view digital image representation of a human eye exhibiting pterygium/pinguecula (PP), and augmented with graphical indications superimposed on the digital image to indicate (i) where pterygium/pinguecula (PP) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect pterygium/pinguecula (PP) as an indication of ocular disease recognition, treatment and manage care, including predicting dry eye disease (DED) class and grade of severity by the automated system.

FIG. 133 provides a schematic model supporting the automated detection and measurement of pterygium/pinguecula (PP) in the human eyes using a real-time ophthalmic image processing engine operating on front view digital images of the human eyes.

FIGS. 134A and 134B describe the primary steps carried out when practicing the machine-vision based method of processing time and date stamped digital images of a human eye captured by a mobile smartphone camera system and processed to automatically detect pterygium/pinguecula (PP) in the human eye at a particular time and date, to support automated ocular disease recognition, treatment and manage care, including predicting dry eye disease (DED) class and grade of severity by the automated system.

Automated Machine-Vision Based Image Processing Method #22 (M22)

As shown and described in FIGS. 134A and 134B, machine-vision based method of detecting, measuring, and generating a database of images indicating pterygium/pinguecula, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: As illustrated in FIG. 133, detect pterygium or pinguecula in region of interest using edge detection, region growing, k-means clustering and thresholding methods;

Step 6: Differentiate pterygium or pinguecula using methods including, but not limited to, contrast-limited adaptive histogram equalization, hue-saturation-value, product of saturation and hue maps, and maximal values of saturation and hue values; and Step 7: If detected pterygium or detected pinguecula is greater than 0.1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Subconjunctival Hemorrhage (SCH) in Human Eyes Photographically Represented in Digital Images Formed and Captured by a Mobile Smartphone Camera System FIG. 135 shows a deep-learning machine-vision ocular image processing and classification system (i.e. "engine") of the present invention 10 configured and trained for use and deployment on the system network shown in FIG. 8A, to support and enable the automated method (M23) of detection and measurement of subconjunctival hemorrhage (SCH) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 136 shows a front view digital image representation of a human eye exhibiting subconjunctival hemorrhage (SCH), and augmented with graphical indications superimposed on the digital image to indicate (i) where subconjunctival hemorrhage (SCH) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect subconjunctival hemorrhage (SCH) as an indication of ocular disease recognition, treatment and manage care, including predicting dry eye disease (DED) class and grade of severity by the automated system.

FIG. 137 provides a schematic model supporting the automated detection and measurement of subconjunctival hemorrhage (SCH) in the human eyes using a real-time ophthalmic image processing engine operating on front view digital images of the human eyes.

FIGS. 138A and 138B describe the primary steps carried out when practicing the machine-vision based method of processing time and date stamped digital images of a human eye captured by a mobile smartphone camera system and processed to automatically detect subconjunctival hemorrhage (SCH) in the human eye at a particular time and date, to support automated ocular disease recognition, treatment and manage care, including predicting dry eye disease (DED) class and grade of severity by the automated system.

Automated Machine-Vision Based Image Processing Method #23 (M23)

As shown and described in FIGS. 138A and 138B, machine-vision based method of detecting, measuring, and generating a database of images indicating subconjunctival hemorrhage (SCH), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducibly using methods including, but not limited to, scale invariant feature transform and random sample consensus;

Step 6: As illustrated in FIG. 137, detect subconjunctival hemorrhage borders using edge detection, K-means clustering, region growing and thresholding methods; and Step 7: Differentiate subconjunctival hemorrhage from conjunctival injection using methods including, but not limited to, contrast-limited adaptive histogram equalization, hue-saturation-value, product of saturation and hue maps, and maximal values of saturation and hue values; and Step 8: If detected subconjunctival hemorrhage is greater than 0.1 mm, then generate output data indicative of such determined ocular disease factors and index the processed image(s) to indicate the same.

Specification of the Deep-Learning Machine-Vision Ocular Image Processing and Classification System of the Present Invention Configured and Trained for Use and Deployment on the System Network to Support and Enable Automated Detection of Conjunctival Laceration (SCJL) in Human Eyes Photographically Represented in Digital Images Formed and Captured by a Mobile Smartphone Camera System FIG. 139 shows a deep-learning machine-vision ocular image processing and classification system (i.e. "engine") of the present invention 10 configured and trained for use and deployment on the system network shown in FIG. 8A, to support and enable an automated method (M24) of detection and measurement of conjunctival laceration (CJL) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B,

40A, 41, 42, 43 and 44 described herein, as well as any other suitable enabling technologies well known in the arts or to be developed in the future.

FIG. 140 shows a front view digital image representation of a human eye exhibiting conjunctival laceration (CJL), and augmented with graphical indications superimposed on the digital image to indicate (i) where conjunctival laceration (CJL) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect conjunctival laceration (CJL) as an indication of ocular disease recognition, treatment and manage care, including predicting dry eye disease (DED) class and grade of severity by the automated system.

FIG. 141 provides a schematic model supporting the automated detection and measurement of conjunctival laceration (CJL) in the human eyes using a real-time ophthalmic image processing engine operating on front view digital images of the human eyes.

FIGS. 162A and 142B describe the primary steps carried out when practicing the machine-vision based method of processing time and date stamped digital images of a human eye captured by a mobile smartphone camera system and processed to automatically detect subconjunctival laceration (CIL) in the human eye at a particular time and date, to support automated ocular disease recognition, treatment and manage care, including predicting dry eye disease (DED) class and grade of severity by the automated system.

Automated Machine-Vision Based Image Processing Method #24 (M24)

As shown and described in FIGS. 142A and 142B, machine-vision based method of detecting, measuring, and generating a database of images indicating conjunctival laceration (CIL), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducibly using methods including, but not limited to, scale invariant feature transform and random sample consensus;

Step 6: As illustrated in FIG. 141, detect conjunctival laceration borders using edge detection, K-means clustering, region growing and thresholding methods;

Step 7: As illustrated in FIG. 141, differentiate conjunctival laceration from chemosis and subconjunctival hemorrhage using methods including, but not limited to, contrast-limited adaptive histogram equalization, hue-saturation-value, product of saturation and hue maps, and maximal values of saturation and hue values; and Step 8: If a detected conjunctival laceration is greater than 0.1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Episcleritis/Scleritis in Human Eyes Photographically Represented in Digital Images Formed and Captured by a Mobile Smartphone Camera System FIG. 143 shows a deep-learning machine-vision ocular image processing and classification system (i.e. "engine") of the present invention configured and trained for use and deployment on the system network shown in FIG. 8A, to support and enable an automated method (M25) of method of detection and measurement of episcleritis/scleritis in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 144 show a front view digital image representation of a human eye exhibiting episcleritis/scleritis, and augmented with graphical indications superimposed on the digital image to indicate (i) where episcleritis/scleritis is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect episcleritis/scleritis as an indication of ocular disease recognition, treatment and manage care, including predicting dry eye disease (DED) class and grade of severity by the automated system.

FIG. 145 provide a schematic model supporting the automated detection and measurement of episcleritis/scleritis in the human eyes using a real-time ophthalmic image processing engine operating on front view digital images of the human eyes.

FIGS. 146A and 146B describe the primary steps carried out when practicing the machine-vision based method of processing time and date stamped digital images of a human eye captured by a mobile smartphone camera system and processed to automatically detect episcleritis/scleritis in the human eye at a particular time and date, to support automated ocular disease recognition, treatment and manage care, including predicting dry eye disease (DED) class and grade of severity by the automated system.

Automated Machine-Vision Based Image Processing Method #25 (M25)

As shown and described in FIGS. 146A and 146B, machine-vision based method of detecting, measuring, and generating a database of images indicating episcleritis/scleritis, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducibly using methods including, but not limited to, scale invariant feature transform and random sample consensus;

Step 6: As illustrated in FIG. 145, detect sectoral conjunctival injection using edge detection, region growing, k-means clustering and thresholding methods;

Step 7: Measure sectoral conjunctival injection in the region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection; and Step 8: If detected sectoral conjunctival injection is greater than 75, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Superior Limbic Keratoconjunctivitis (SLK) in Human Eyes Photographically Represented in Digital Images Formed and Captured by a Mobile Smartphone Camera System FIG. 147 shows a deep-learning machine-vision ocular image processing and classification system (i.e. "engine") of the present invention configured and trained for use and deployment on the system network shown in FIG. 8A, to support and enable an automated method (M26) of detection and measurement of superior limbic keratoconjunctivitis (SLK) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 148 shows a front view digital image representation of a human eye exhibiting superior limbic keratoconjunctivitis (SLK), and augmented with graphical indications superimposed on the digital image to indicate (i) where superior limbic keratoconjunctivitis (SLK) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect superior limbic keratoconjunctivitis (SLK) as an indication of ocular disease recognition, treatment and manage care, including predicting dry eye disease (DED) class and grade of severity by the automated system.

FIG. 149 provides a schematic model supporting the automated detection and measurement of superior limbic keratoconjunctivitis (SLK) in the human eyes using a real-time ophthalmic image processing engine operating on front view digital images of the human eyes.

FIGS. 150A and 150B describes the primary steps carried out when practicing the machine-vision based method of processing time and date stamped digital images of a human eye captured by a mobile smartphone camera system and processed to automatically detect superior limbic keratoconjunctivitis (SLK) in the human eye at a particular time and date, to support automated ocular disease recognition, treatment and manage care, including predicting dry eye disease (DED) class and grade of severity by the automated system.

Automated Machine-Vision Based Image Processing Method #26 (M26)

As shown and described in FIGS. 150A and 150B, machine-vision based method of detecting, measuring, and generating a database of images indicating superior limbic keratoconjunctivitis (SLK), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use sclera and non-sclera digital images to train the system to detect sclera;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect sclera across a series of digital images reproducibly using methods including, but not limited to, scale invariant feature transform and random sample consensus;

Step 6: As illustrated in FIG. 149, detect superior conjunctival injection and redundant conjunctiva superiorly using edge detection, region growing, k-means clustering and thresholding methods;

Step 7: Measure superior conjunctival injection in the region of interest using methods including, but not limited to, contrast-limited adaptive histogram equalization, hue-saturation-value, product of saturation and hue maps, and maximal values of saturation and hue values; conjunctival injection is measured on scale 0 to 100, with higher numbers corresponding with greater conjunctival injection;

Step 8: If detected superior conjunctival injection is greater than 75, then generate output data indicative of such determined ocular disease factors and index the processed image(s) to indicate the same; and Step 9: If detected redundant conjunctiva superiorly is greater than one fold in the conjunctiva, then generate output data indicative of such determined ocular disease factors and index the processed image(s) to indicate the same.

Once each digital image is processed according to the image-processing method described above, and a specified ocular condition is detected/recognized as reflected in the digital image, then the digital image is indexed with the recognized condition (e.g. using suitable image indexing methods and coding), and then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Blepharitis in Human Eyes Photographically Represented in Digital Images Formed and Captured by a Mobile Smartphone Camera System FIG. 151 shows a deep-learning machine-vision ocular image processing and classification system (i.e. "engine") of the present invention configured and trained for use and deployment on the system network shown in FIG. 8A, to support and enable an automated method (M27) of detection and measurement of blepharitis (BH) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 152 shows a front view digital image representation of a human eye exhibiting blepharitis (BH), and augmented with graphical indications superimposed on the digital image to indicate (i) where blepharitis (BH) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect blepharitis (BH) as an indication of ocular disease recognition, treatment and manage care, including predicting dry eye disease (DED) class and grade of severity by the automated system.

FIG. 153 provides a schematic model supporting the automated detection and measurement of blepharitis (BH) in the human eyes using a real-time ophthalmic image processing engine operating on front view digital images of the human eyes.

FIGS. 154A and 154B describe the primary steps carried out when practicing the machine-vision based method of processing time and date stamped digital images of a human eye captured by a mobile smartphone camera system and processed to automatically detect blepharitis (BH) in the human eye at a particular time and date, to support automated ocular disease recognition, treatment and manage care, including predicting dry eye disease (DED) class and grade of severity by the automated system Automated Machine-Vision Based Image Processing Method #27 (M27)

As shown and described in FIGS. 154A and 154B, machine-vision based method of detecting, measuring, and generating a database of images indicating blepharitis, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train the system to detect eyelids;

Step 4: Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: Use region of interest matching to measure meibomian gland dysfunction and scruff at eyelashes across a series of digital images reproducibly using methods including, but not limited to, scale invariant feature transform and random sample consensus;

Step 6: As illustrated in FIG. 153, detect, identify and count meibomian glands, and detect and identify scruff at eyelashes using methods, including, but not limited to, edge detection, k-means clustering, region growing and thresholding methods;

Step 7: Any change in edges, clusters or regions at or on the lower eyelid margin and in the eyelashes are considered meibomian glands or scruff at the eyelashes; and Step 8: IF the meibomian glands or visible scruff at eyelashes is greater than 50% of the eyelid margin, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Chalazion/Styes in Human Eyes Photographically Represented in Digital Images Formed and Captured by a Mobile Smartphone Camera System FIG. 155 shows a deep-learning machine-vision ocular image processing and classification system (i.e. "engine") of the present invention configured and trained for use and deployment on the system network shown in FIG. 8A, to support and enable an automated method (M28) of detection and measurement of chalazion/styes (CS) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 156 shows a front view digital image representation of a human eye exhibiting chalazion/styes (CS), and augmented with graphical indications superimposed on the digital image to indicate (i) where chalazion/styes (CS) are detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect chalazion/styes (CS) as an indication of ocular disease recognition, treatment and manage care, including predicting dry eye disease (DED) class and grade of severity by the automated system.

FIG. 157 provides a schematic model supporting the automated detection and measurement of chalazion/styes (CS) in the human eyes using a real-time ophthalmic image processing engine operating on front view digital images of the human eyes.

FIGS. 158A and 158B describe the primary steps carried out when practicing the machine-vision based method of processing time and date stamped digital images of a human eye captured by a mobile smartphone camera system and processed to automatically detect chalazion/styes in the human eye at a particular time and date, to support automated ocular disease recognition, treatment and manage care, including predicting dry eye disease (DED) class and grade of severity by the automated system.

Automated Machine-Vision Based Image Processing Method #28 (M28)

As shown and described in FIGS. 158A and 158B, machine-vision based method of detecting, measuring, and generating a database of images indicating chalazion/styes, comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train the system to detect eyelids;

Step 4: Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: Use region of interest (ROI) matching to detect eyelid across a series of digital images reproducibly using methods including, but not limited to, scale invariant feature transform and random sample consensus;

Step 6: As illustrated in FIG. 157, detect and identify chalazion using methods, including, but not limited to, edge detection, k-means clustering, region growing and thresholding; and Step 7: IF a detected chalazion is greater than 1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Eyelid Cysts in Human Eyes Photographically Represented in Digital Images Formed and Captured by a Mobile Smartphone Camera System FIG. 159 shows a deep-learning machine-vision ocular image processing and classification system (i.e. "engine") of the present invention configured and trained for use and deployment on the system network shown in FIG. 8A, to support and enable an automated method (M29) of method of detection and measurement of eyelid cysts (EC) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 160 shows a front view digital image representation of a human eye exhibiting eyelid cysts (EC), and augmented with graphical indications superimposed on the digital image to indicate (i) where eyelid cysts (EC) are detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect eyelid cysts (EC) as an indication of ocular disease recognition, treatment and manage care, including predicting dry eye disease (DED) class and grade of severity by the automated system.

FIG. 161 provides a schematic model supporting the automated detection and measurement of eyelid cysts (EC) in the human eyes using a real-time ophthalmic image processing engine operating on front view digital images of the human eyes.

FIGS. 162A and 162B describe the primary steps carried out when practicing the machine-vision based method of processing time and date stamped digital images of a human eye captured by a mobile smartphone camera system and processed to automatically detect eyelid cysts (EC) in the human eye at a particular time and date, to support automated ocular disease recognition, treatment and manage care, including predicting dry eye disease (DED) class and grade of severity by the automated system.

Automated Machine-Vision Based Image Processing Method #29 (M29)

As shown and described in FIGS. 162A and 162B, machine-vision based method of detecting, measuring, and generating a database of images indicating eyelid cysts (EC) comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train the system to detect eyelids;

Step 4: Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: Use region of interest matching to detect eyelid across a series of digital images reproducibly using methods including, but not limited to, scale invariant feature transform and random sample consensus;

Step 6: As illustrated in FIG. 161, detect and identify eyelid cyst using methods, including, but not limited to, edge detection, k-means clustering, region growing and thresholding;

Step 7: As illustrated in FIG. 161, differentiate eyelid cyst from chalazion by using methods including, but not limited to, contrast-limited adaptive histogram equalization, hue-saturation-value, product of saturation and hue maps, and maximal values of saturation and hue values; and Step 8: If a detected eyelid cyst is greater than 1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition, i.e. preseptal cellulitis (PC), using suitable image indexing methods and coding, is then stored in the system network database 16C for future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Preseptal Cellulitis (PC) in Human Eyes Photographically Represented in Digital Images Formed and Captured by a Mobile Smartphone Camera System FIG. 163 shows a deep-learning machine-vision ocular image processing and classification system (i.e. "engine") of the present invention configured and trained for use and deployment on the system network shown in FIG. 8A, to support and enable automated method (M30) of detection and measurement of preseptal cellulitis (PC) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 164 shows a front view digital image representation of a human eye exhibiting preseptal cellulitis (PC), and augmented with graphical indications superimposed on the digital image to indicate (i) where preseptal cellulitis (PC) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect preseptal cellulitis (PC) as an indication of ocular disease recognition, treatment and manage care, including predicting dry eye disease (DED) class and grade of severity by the automated system.

FIG. 165 shows a schematic model supporting the automated detection and measurement of preseptal cellulitis (PC) in the human eyes using a real-time ophthalmic image processing engine operating on front view digital images of the human eyes.

FIGS. 166A and 166B describe the primary steps carried out when practicing the machine-vision based method of processing time and date stamped digital images of a human eye captured by a mobile smartphone camera system and processed to automatically detect preseptal cellulitis (PC) in the human eye at a particular time and date, to support automated ocular disease recognition, treatment and manage care, including predicting dry eye disease (DED) class and grade of severity by the automated system.

Automated Machine-Vision Based Image Processing Method #30 (M30)

As shown and described in FIGS. 166A and 166B, machine-vision based method of detecting, measuring, and generating a database of images indicating preseptal cellulitis (PC), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train the system to detect eyelids;

Step 4: Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: Use region of interest matching to detect eyelid across a series of digital images reproducibly using methods including, but not limited to, scale invariant feature transform and random sample consensus;

Step 6: As illustrated in FIG. 165, detect and identify eyelid swelling (in terms of upper and lower eyelid size) using methods, including, but not limited to, edge detection, k-means clustering, region growing and thresholding;

Step 7: Differentiate eyelid swelling from eyelid cyst and chalazion by using methods including, but not limited to, contrast-limited adaptive histogram equalization, hue-saturation-value, product of saturation and hue maps, and maximal values of saturation and hue values; and Step 8: If detected eyelid swelling (based on pixel measurements) is greater than 50% of the upper or lower eyelid, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Ptosis (PT) in Human Eyes Photographically Represented in Digital Images Formed and Captured by a Mobile Smartphone Camera System FIG. 167 shows a deep-learning machine-vision ocular image processing and classification system (i.e. "engine") of the present invention configured and trained for use and deployment on the system network shown in FIG. 8A, to support and enable automated method (M31) of detection and measurement of ptosis (PT) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 168 shows a front view digital image representation of a human eye exhibiting ptosis, and augmented with graphical indications superimposed on the digital image to indicate (i) where ptosis is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect ptosis as an indication of ocular disease recognition, treatment and manage care, including predicting dry eye disease (DED) class and grade of severity by the automated system.

FIG. 169 provides a schematic model supporting the automated detection and measurement of ptosis in the human eyes using a real-time ophthalmic image processing engine operating on front view digital images of the human eyes.

FIGS. 170A and 170B describes the primary steps carried out when practicing the machine-vision based method of processing time and date stamped digital images of a human eye captured by a mobile smartphone camera system and processed to automatically detect ptosis in the human eye at a particular time and date, to support automated ocular disease recognition, treatment and manage care, including predicting dry eye disease (DED) class and grade of severity by the automated system.

Automated Machine-Vision Based Image Processing Method #31 (M31)

As shown and described in FIGS. 170A and 170B, machine-vision based method of detecting, measuring, and generating a database of images indicating ptosis, comprising the following steps:

Step 1: As illustrated in FIG. 169, use method (M12) to determine margin reflex distance (MRD) 1 and 2 as detailed above;

Step 2: As illustrated in FIG. 169, use method (M11) to determine palpebral fissure height (PFH) and palpebral fissure width (PFW) as detailed above;

Step 3 As illustrated in FIG. 169, use method (M14) to determine levator function (LF) as detailed above; and Step 4: If the margin reflex distance (MRD) 1 is less than 3.5 mm, or the palpebral fissure height (PFH) is less than 8 mm, of the levator function (LF) is less than 8 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Ophthalmoplegia (OPM) in Human Eyes Photographically Represented in Digital Images Formed and Captured by a Mobile Smartphone Camera System FIG. 171 shows a deep-learning machine-vision ocular image processing and classification system (i.e. "engine") of the present invention configured and trained for use and deployment on the system network shown in FIG. 8A, to support and enable an automated method (M32) of detection and measurement of ophthalmoplegia (OPM) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 172 shows a front view digital image representation of a human eye exhibiting ophthalmoplegia (OPM), and augmented with graphical indications superimposed on the digital image to indicate (i) where ophthalmoplegia (OPM) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect ophthalmoplegia (OPM) as an indication of ocular disease recognition, treatment and manage care, including predicting dry eye disease (DED) class and grade of severity by the automated system.

FIG. 173 provides a schematic model supporting the automated detection and measurement of ophthalmoplegia (OPM) in the human eyes using a real-time ophthalmic image processing engine operating on front view digital images of the human eyes.

FIGS. 174A and 174B describe the primary steps carried out when practicing the machine-vision based method of processing time and date stamped digital images of a human eye captured by a mobile smartphone camera system and processed to automatically detect ophthalmoplegia (OPM) in the human eye at a particular time and date, to support automated ocular disease recognition, treatment and manage care, including predicting dry eye disease (DED) class and grade of severity by the automated system.

Automated Machine-Vision Based Image Processing Method #32 (M32)

As shown and described in FIGS. 174A and 174B, machine-vision based method of detecting, measuring, and generating a database of images indicating ptosis, comprises the following steps:

Step 1: Capture a color digital video having a set of frames per second, and decompose the video into 1 second intervals; use is asked to look left, right, up and down; wherein each image each color digital image having a set of pixels;

Step 2: Process the pixels in the individual frames and classify the following structures in the human eye, including eyelids, iris, pupil, and sclera;

Step 3: Use cornea and non-cornea digital images to train the System to detect pupillary margin;

Step 4: Use the above structures and trained system for automatic region of interest segmentation of pupillary margin using non-parametric methods, including but not limited to, random decision forests such as Breiman's random forest algorithm, gray scale probability maps, binary thresholds, morphological operators and Bresenham's line algorithm;

Step 5: As illustrated in FIGS. 172 and 173, use region of interest (ROI) matching to recognize pupillary margin across a series of digital images reproducibly using methods including, but not limited to, scale invariant feature transform and random sample consensus;

Step 6: As illustrated in FIGS. 172 and 173, use pixel-by-pixel location to map pupillary margin onto a grid and detect movement of each eye pupillary margin as user looks left, right, up and down; and Step 7: If the absolute difference in movement between one eye pupillary margin compared to the adjacent eye pupillary margin is greater than 0.00 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Proptosis/Hypoglobus (PH) in Human Eyes Photographically Represented in Digital Images Formed and Captured by a Mobile Smartphone Camera System FIG. 175 shows a deep-learning machine-vision ocular image processing and classification system (i.e. "engine") of the present invention configured and trained for use and deployment on the system network shown in FIG. 8A, to support and enable an automated method (M33) of detection and measurement of proptosis/hypoglobus (PH) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 176 shows a front view digital image representation of a human eye exhibiting proptosis/hypoglobus (PH), and augmented with graphical indications superimposed on the digital image to indicate (i) where proptosis/hypoglobus (PH) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect proptosis/hypoglobus (HP) as an indication of ocular disease recognition, treatment and manage care, including predicting dry eye disease (DED) class and grade of severity by the automated system.

FIG. 177 provides a schematic model supporting the automated detection and measurement of proptosis/hypoglobus (PH) in the human eyes using a real-time ophthalmic image processing engine operating on front/worm's eye view digital images of the human eyes.

FIGS. 178A and 178B describe the primary steps carried out when practicing the machine-vision based method of processing time and date stamped digital images of a human eye captured by a mobile smartphone camera system and processed to automatically detect proptosis/hypoglobus (PH) in the human eye at a particular time and date, to support automated ocular disease recognition, treatment and manage care, including predicting dry eye disease (DED) class and grade of severity by the automated system.

Automated Machine-Vision Based Image Processing Method #33 (M33)

As shown and described in FIGS. 178A and 178B, machine-vision based method of detecting, measuring, and generating a database of images indicating proptosis/hypoglobus (HP), comprises the following steps:

Step 1: Capture a series of color digital images each color digital image having a set of pixels captured from front, side, above and below;

Step 2: Process the pixels in each digital image and classify the following structures in the human eye, including eyelids, iris, pupil, and sclera, brow and lateral canthus and facial landmarks, including tragus and tip of nose;

Step 3: Use digital images to train the system to detect the above structures;

Step 4: Use the above structures and trained system for automatic region of interest segmentation using non-parametric methods, including but not limited to, random decision forests such as Breiman's random forest algorithm, gray scale probability maps, binary thresholds, morphological operators and Bresenham's line algorithm;

Step 5: As illustrated in FIG. 177, use region of interest matching to detect the above structures across a series of digital images reproducibly using methods including, but not limited to, scale invariant feature transform and random sample consensus;

Step 6: As illustrated in FIG. 177, use pixel-by-pixel location to map pupillary margin and corneal surface onto a grid, and a mismatch in pupillary margin position or corneal surface position;

Step 7: As illustrated in FIG. 177, to standardize location of corneal surface and account for head tilt, the medial canthus is used on front angle images, the lateral canthus and tragus is used on side angled images, and the tip of the nose is used on above and below angled photos; and Step 7: If difference in pupillary margin greater than 1 mm, or difference in corneal surface greater than 1 mm from one eye to the other, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Anisocoria in Human Eyes Photographically Represented in Digital Images Formed and Captured by a Mobile Smartphone Camera System FIG. 179 shows a deep-learning machine-vision ocular image processing and classification system (i.e. "engine") of the present invention configured and trained for use and deployment on the system network shown in FIG. 8A, to support and enable an automated method (M34) of detection and measurement of anisocoria (ACR) of the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 180 shows a front view digital image representation of a human eye exhibiting anisocoria (ACR) and augmented with graphical indications superimposed on the digital image to indicate (i) where anisocoria (ACR) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect anisocoria (ACR) as an indication of ocular disease recognition, treatment and manage care, including predicting dry eye disease (DED) class and grade of severity by the automated system.

FIG. 181 provides a schematic model supporting the automated detection and measurement of anisocoria (ACR) in the human eyes using a real-time ophthalmic image processing engine operating on front view digital images of the human eyes.

FIGS. 182A and 182B describe the primary steps carried out when practicing the machine-vision based method of processing time and date stamped digital images of a human eye captured by a mobile smartphone camera system and processed to automatically detect anisocoria (ACR) in the human eye at a particular time and date, to support automated ocular disease recognition, treatment and manage care, including predicting dry eye disease (DED) class and grade of severity by the automated system.

Automated Machine-Vision Based Image Processing Method #34 (M34)

As shown and described in FIGS. 182A and 182B, the machine-vision based method of detecting, measuring, and generating a database of images indicating anisocoria, comprises the following steps:

Step 1: Capture a color digital images and video having a set of frames per second, and decompose the video into 1 second intervals;

Step 2: process the pixels in each digital image and classify the following structures in the human eye, including eyelids, iris, pupil, and sclera;

Step 3: Use cornea and non-cornea digital images to train the system to detect pupillary margin;

Step 4: Use the above structures and trained system for automatic region of interest segmentation of pupillary margin using non-parametric methods, including but not limited to, random decision forests such as Breiman's random forest algorithm, gray scale probability maps, binary thresholds, morphological operators and Bresenham's line algorithm;

Step 5: Use region of interest matching to recognize pupillary margin across a series of digital images reproducibly using methods including, but not limited to, scale invariant feature transform and random sample consensus;

Step 6: As illustrated in FIG. 181, use pixel-by-pixel location to map Use pixel-by-pixel size to determine the pupillary margin size;

Step 7: Vary the intensity of light source on mobile device to detect how pupillary margin change size;

Step 8: If the difference in pupil size from one eye to the other eye is greater than 1 mm, then generate output data indicative of such determined ocular disease factors and index the processed image(s) to indicate the same; and Step 9: If there is no change in pupil size with light stimulus, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Anterior Chamber Depth (ACD) in Human Eyes Photographically Represented in Digital Images Formed and Captured by a Mobile Smartphone Camera System FIG. 183 shows a deep-learning machine-vision ocular image processing and classification system (i.e. "engine") of the present invention configured and trained for use and deployment on the system network shown in FIG. 8A, to support and enable an automated method (M35) of method of detection and measurement of anterior chamber depth (ACD) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIGS. 184A, 184B, 184C and 184D show side view digital image representations of a human eye exhibiting anterior chamber depth (ACD), and augmented with graphical indications superimposed on the digital image to indicate (i) where anterior chamber depth (ACD) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect anterior chamber depth (ACD) as an indication of ocular disease recognition, treatment and manage care, including predicting dry eye disease (DED) class and grade of severity by the automated system.

FIG. 185 provides a schematic representation for a schematic model supporting the automated detection and measurement of anterior chamber depth (ACD) in the human eyes using a real-time ophthalmic image processing engine operating on front view digital images of the human eyes.

FIG. 186 provides a schematic representation for a schematic model supporting the automated detection and measurement of anterior chamber depth (ACD) in the human eyes using a real-time ophthalmic image processing engine operating on front view digital images of the human eyes.

FIGS. 187A and 187B describe the primary steps carried out when practicing the machine-vision based method of processing time and date stamped digital images of a human eye captured by a mobile smartphone camera system and processed to automatically detect anterior chamber depth (ACD) in the human eye at a particular time and date, to support automated ocular disease recognition, treatment and manage care, including predicting dry eye disease (DED) class and grade of severity by the automated system.

Automated Machine-Vision Based Image Processing Method #35 (M35)

Figure 185B:
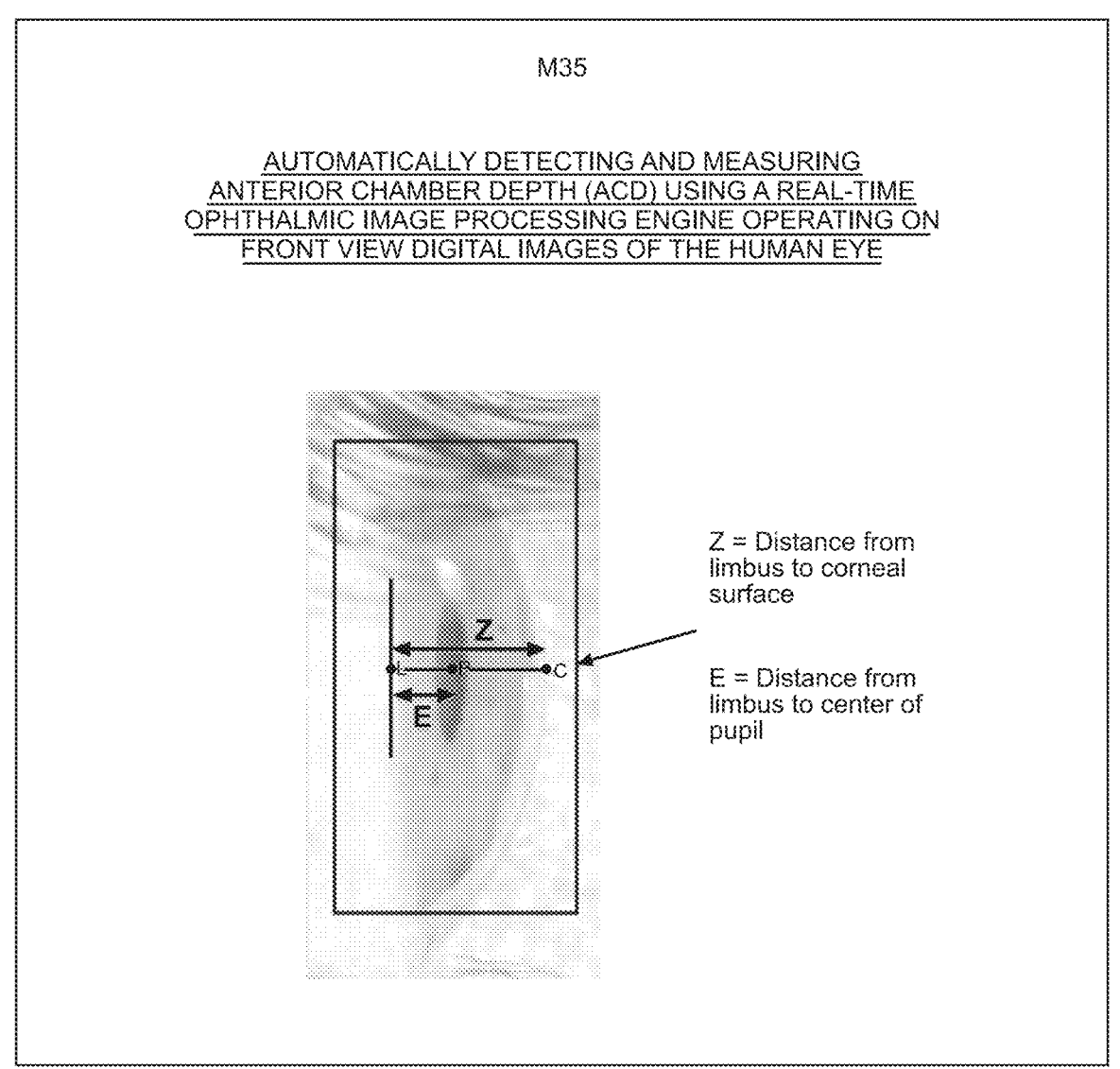

As shown and described in FIGS. 187A and 187B, machine-vision based method of detecting, measuring, and generating a database of images indicating and measuring the anterior chamber depth (ACD), comprises the following steps:

Step 1: Capture a color digital images and video from front-facing and side-facing angles having a set of frames per second, and decompose the video into 1 second intervals;

Step 2: Process the individual frames and classify the following structures in the human eye, including eyelids, iris, pupil, and sclera;

Step 3: Use cornea and non-cornea digital images to train the system to detect pupillary margin;

Step 4: Use the above structures and trained system for automatic region of interest segmentation of pupillary margin using non-parametric methods, including but not limited to, random decision forests such as Breiman's random forest algorithm, gray scale probability maps, binary thresholds, morphological operators and Bresenham's line algorithm; and Step 5: Use region of interest matching to recognize pupillary margin across a series of digital images reproducibly using methods including, but not limited to, scale invariant feature transform and random sample consensus;

Step 6: For front-facing images, detect shadow on the iris, which is cast by light hitting the cornea and casting a shadow on the underlying iris, using edge detection and k-means clustering;

Step 7: Determine iris with shadow and without using methods including, but not limited to, contrast-limited adaptive histogram equalization, hue-saturation-value, product of saturation and hue maps, maximal values of saturation and hue values;

Step 8: As illustrated in FIGS. 185B and 186, use pixel-by-pixel location to map For side-facing images, measure the distance from limbus to corneal surface (Z) in millimeters and limbus to center of pupil (E) in millimeters using pixel-by-pixel size;

Step 9: Calculate anterior chamber depth (ACD) using the following equation:

$$ACD(mm) = -3.3 \times EZ \text{ ration} + 4.2$$

Step 10: If the ACD less than 2.5 mm, then generate output data indicative of such determined ocular disease factors and index the processed image(s) to indicate the same; and Step 11: If the iris casts a shadow nasally or a shadow temporally, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Orbital Post Septal (OPSC) in Human Eyes Photographically Represented in Digital Images Formed and Captured by a Mobile Smartphone Camera System FIG. 188 shows a deep-learning machine-vision ocular image processing and classification system (i.e. "engine") of the present invention configured and trained for use and deployment on the system network shown in FIG. 8A, to support and enable an automated method (M36) of detection and measurement of orbital post septal cellulitis (OPSC) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 189 shows a front view digital image representation of a human eye exhibiting orbital post septal cellulitis (OPSC), and augmented with graphical indications superimposed on the digital image to indicate (i) where orbital post septal cellulitis (OPSC) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect orbital post septal cellulitis (OPSC) as an indication of ocular disease recognition, treatment and manage care, including predicting dry eye disease (DED) class and grade of severity by the automated system.

FIG. 190 provides a schematic model supporting the automated detection and measurement of orbital post septal cellulitis (OPSC) in the human eyes using a real-time ophthalmic image processing engine operating on front view digital images of the human eyes.

FIGS. 191A and 191B describe the primary steps carried out when practicing the machine-vision based method of processing time and date stamped digital images of a human eye captured by a mobile smartphone camera system and processed to automatically detect orbital post septal cellulitis (OPSC) in the human eye at a particular time and date, to support automated ocular disease recognition, treatment and manage care, including predicting dry eye disease (DED) class and grade of severity by the automated system.

Automated Machine-Vision Based Image Processing Method #36 (M36)

As shown and described in FIGS. 191A and 191B, the machine-vision based method of detecting, measuring, and generating a database of images indicating orbital post septal cellulitis (OPSC), comprises the following steps:

Step 1: As illustrated in FIG. 190, use method (M30) to determine eyelid swelling as detailed above if present;

Step 2: As illustrated in FIG. 190, use method (M31) to determine ptosis as detailed above if ptosis is present;

Step 3: As illustrated in FIG. 190, use method (M33) to determine proptosis as detailed above if present;

Step 4: As illustrated in FIG. 190, use method (M28) to determine chalazion/stye s detailed above if present;

Step 5: As illustrated in FIG. 190, use method (M21) to determine chemosis as detailed above if present;

Step 6: As illustrated in FIG. 190, use method (M18) to determine clear discharge as detailed above, if present;

Step 7: As illustrated in FIG. 190, use method (M19) to determine purulent discharge as detailed above, if present;

Step 8: As illustrated in FIG. 190, use method (M1) to determine conjunctival injection as detailed above if present;

Step 9: As illustrated in FIG. 190, use method (M23) to determine subconjunctival hemorrhage as detailed above if present;

Step 10: As illustrated in FIG. 190, use method (M32) to determine ophthalmoplegia as detailed above if present; and Step 11: If proptosis is present, and eyelid swelling is present, and conjunctival injection is present, and ophthalmoplegia is present, and [ptosis present is present, or chalazion/stye is present, or chemosis is present, or clear discharge is present, or purulent discharge is present, or subconjunctival hemorrhage is present], then determine that Orbital Postseptal Cellulitis (OPSC) is present, and generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the net0work database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Thyroid Eye Disease (TED) in Human Eyes Photographically Represented in Digital Images Formed and Captured by a Mobile Smartphone Camera System FIG. 192 shows a deep-learning machine-vision ocular image processing and classification system (i.e. "engine") of the present invention configured and trained for use and deployment on the system network shown in FIG. 8A, to support and enable an automated method (M37) of detection and measurement of thyroid eye disease (TED) in the human eyes photographically represented in digital images of a front view of human eyes formed and captured by a mobile smartphone camera system in accordance with the principles of the present invention.

FIG. 193 shows a front view digital image representation of a human eye exhibiting thyroid eye disease (TED), and augmented with graphical indications superimposed on the digital image to indicate (i) where thyroid eye disease (TED) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect thyroid eye disease (TED) as an indication of ocular disease recognition, treatment and manage care, including predicting dry eye disease (DED) class and grade of severity by the automated system.

FIG. 194 provides a schematic model supporting the automated detection and measurement of thyroid eye disease (TED) in the human eyes using a real-time ophthalmic image processing engine operating on front view digital images of the human eyes.

FIG. 195 describes the primary steps carried out when practicing the machine-vision based method of processing time and date stamped digital images of a human eye captured by a mobile smartphone camera system and processed to automatically detect thyroid eye disease (TED) in the human eye at a particular time and date, to support automated ocular disease recognition, treatment and manage care, including predicting dry eye disease (DED) class and grade of severity by the automated system.

Automated Machine-Vision Based Image Processing Method #37 (M37)

As shown and described in FIG. 195, the machine-vision based method of detecting, measuring, and generating a database of images indicating thyroid eye disease (TED), comprises the following steps:

Step 1: As illustrated in FIG. 195, use method (M11) to determine palpebral fissure height (PFH) and palpebral fissure width (PFW) as detailed above;

Step 2: As illustrated in FIG. 195, use method (M12) to determine margin reflex distance 1 and 2 as detailed above;

Step 3: As illustrated in FIG. 195, use method (M13) to determine scleral show as detailed above;

Step 4: As illustrated in FIG. 195, use method (M30) to determine eyelid swelling as detailed above if present;

Step 5: As illustrated in FIG. 195, use method (M33) to determine proptosis as detailed above if present;

Step 6: As illustrated in FIG. 195, use method (M21) to determine chemosis as detailed above if present;

Step 7: As illustrated in FIG. 195, use method (M1) to determine conjunctival injection recognition as detailed above if present;

Step 8: As illustrated in FIG. 195, use method (M32) to determine ophthalmoplegia as detailed above if present; and Step 9: If ophthalmoplegia is present, and proptosis is present, and [palpebral fissure height is greater than 12 mm, or margin reflex distance is 1 greater than 4.5 mm, or scleral show is greater than 2 mm], and [eyelid swelling is present, or chemosis is present, or conjunctival injection is present], then determine that Thyroid Eye Disease (TED) is present, and generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Entropion/Ectropion in Human Eyes Photographically Represented in Digital Images Formed and Captured by a Mobile Smartphone Camera System FIG. 196 shows a deep-learning machine-vision ocular image processing and classification system (i.e. "engine") of the present invention configured and trained for use and deployment on the system network shown in FIG. 8A, to support and enable an automated method (M38) of detection and measurement of entropion/ectropion in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 197 shows a front view digital image representation of a human eye exhibiting entropion/ectropion (E/E), and augmented with graphical indications superimposed on the digital image to indicate (i) where entropion/ectropion (E/E) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect entropion/ectropion as an indication of ocular disease recognition, treatment and manage care, including predicting dry eye disease (DED) class and grade of severity by the automated system.

FIG. 198 provides a schematic model supporting the automated detection and measurement of entropion/ectropion in the human eyes using a real-time ophthalmic image processing engine operating on front view digital images of the human eyes.

FIGS. 199A and 199B describes the primary steps carried out when practicing the machine-vision based method of processing time and date stamped digital images of a human eye captured by a mobile smartphone camera system and processed to automatically detect entropion/ectropion in the human eye at a particular time and date, to support automated ocular disease recognition, treatment and manage care, including predicting dry eye disease (DED) class and grade of severity by the automated system.

Automated Machine-Vision Based Image Processing Method #38 (M38)

As shown and described in FIGS. 199A and 199B, the machine-vision based method of detecting, measuring, and generating a database of images indicating entropion/ectropion, comprises the following steps:

Step 1: Capture a series of color digital images each color digital image having a set of pixels from front and side angles;

Step 2: Process the pixels in each digital image and classify the following structures in the human eye, including eyelids, iris, pupil, and sclera;

Step 3: Use eyelid and non-eyelid digital images to train the system to detect eyelids;

Step 4 Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: As illustrated in FIG. 198, use region of interest matching to detect eyelid margins across a series of digital images reproducibly using methods including, but not limited to, scale invariant feature transform and random sample consensus;

Step 6: As illustrated in FIG. 198, detect entropion and ectropion using region growing, k-means clustering and thresholding; and Step 7: IF entropion is present, or ectropion is present, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Trichiasis/Distichiasis (T/D) in Human Eyes Photographically Represented in Digital Images Formed and Captured by a Mobile Smartphone Camera System FIG. 200 shows a deep-learning machine-vision ocular image processing and classification system (i.e. "engine") of the present invention configured and trained for use and deployment on the system network shown in FIG. 8A, to support and enable an automated method (M39) of detection and measurement of trichiasis/distichiasis (T/D) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 201 provides a front view digital image representation of a human eye exhibiting trichiasis/distichiasis (T/D), and augmented with graphical indications superimposed on the digital image to indicate (i) where trichiasis/distichiasis (T/D) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect trichiasis/distichiasis (T/D) as an indication of ocular disease recognition, treatment and manage care, including predicting dry eye disease (DED) class and grade of severity by the automated system.

FIG. 202 provides a schematic model supporting the automated detection and measurement of trichiasis/distichiasis (T/D) in the human eyes using a real-time ophthalmic image processing engine operating on front view digital images of the human eyes.

FIGS. 203A and 203B describe the primary steps carried out when practicing the machine-vision based method of processing time and date stamped digital images of a human eye captured by a mobile smartphone camera system and processed to automatically detect trichiasis/distichiasis (T/D) in the human eye at a particular time and date, to support automated ocular disease recognition, treatment and manage care, including predicting dry eye disease (DED) class and grade of severity by the automated system.

Automated Machine-Vision Based Image Processing Method #39 (M39)

As shown and described in FIGS. 203A and 203B, machine-vision based method of detecting, measuring, and generating a database of images indicating trichiasis/distichiasis (T/D), comprises the following steps:

Step 1: Capture a series of color digital images each color digital image having a set of pixels from front and side angles;

Step 2: Process the pixels in each digital image and classify the following structures in the human eye, including eyelids, iris, pupil, and sclera;

Step 3: Use eyelid and non-eyelid digital images to train the system to detect eyelids;

Step 4: Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: As illustrated in FIG. 202, use region of interest (ROI) matching to detect eyelid margins across a series of digital images reproducibly using methods including, but not limited to, scale invariant feature transform and random sample consensus;

Step 6: Detect trichiasis and distichiasis using region growing, k-means clustering and thresholding methods; and Step 7: If detected trichiasis is greater than 1.0%, or detected distichiasis is greater than 1.0%, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the system network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Floppy Eyelid Syndrome (FES) in Human Eyes Photographically Represented in Digital Images Formed and Captured by a Mobile Smartphone Camera System FIG. 204 shows a deep-learning machine-vision ocular image processing and classification system (i.e. "engine") of the present invention configured and trained for use and deployment on the system network shown in FIG. 8A, to support and enable an automated method (M40) of detection and measurement of floppy eyelid syndrome (FES) in the human eyes photographically represented in digital images of a front view of human eyes formed and captured by a mobile smartphone camera system in accordance with the principles of the present invention.

The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIGS. 205A and 205B show front view digital image representations of a human eye exhibiting floppy eyelid syndrome (FES), augmented with graphical indications superimposed on the digital image to indicate (i) where floppy eyelid syndrome (FES) is detected in the photographic image of the human eye in the presence of upper and lower eyelid laxity and orbital fat prolapse as shown, and (ii) which pixel region of interest (ROI) requires pixel data processing according to an automated method of digital image processing using the machine-based ophthalmic image processing engine of the present invention operating on one or more front view digital images of the human eye, so as to automatically detect floppy eyelid syndrome (FES) as an indication of ocular disease recognition, treatment and manage care, including predicting dry eye disease (DED) class and grade of severity by the automated system.

FIG. 206 provides a schematic model supporting the automated detection and measurement of floppy eyelid syndrome (FES) in the human eyes using a real-time ophthalmic image processing engine operating on front view digital images of the human eyes.

FIGS. 207A and 207B describe the primary steps carried out when practicing the machine-vision based method of processing time and date stamped digital images of a human eye captured by a mobile smartphone camera system and processed to automatically detect floppy eyelid syndrome (FES) in the human eye at a particular time and date, to support automated ocular disease recognition, treatment and manage care, including predicting dry eye disease (DED) class and grade of severity by the automated system.

Automated Machine-Vision Based Image Processing Method #40 (M40)

As shown and described in FIGS. 207A and 207B, the machine-vision based method of detecting, measuring, and generating a database of images indicating floppy eyelid syndrome (FES), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use eyelid and non-eyelid digital images to train the system to detect eyelids;

Step 4: Use the above structures and trained system for automatic region of interest segmentation of eyelid margins using non-parametric methods, including but not limited to, random decision forests such as Breiman's random forest algorithm, gray scale probability maps, binary thresholds, morphological operators and Bresenham's line algorithm;

Step 5: As illustrated in FIG. 206A, use region of interest matching to detect eyelid margins across a series of digital images reproducibly using methods including, but not limited to, scale invariant feature transform and random sample consensus;

Step 6: Ask user to evert the upper eyelid up and the lower eyelid down; and

Step 7: If the displacement of eyelid margin from the baseline location is greater than 10 mm, or orbital fat prolapse is present, or greater than 1 second of time is required for eyelid to snap back to baseline location from eversion, then determine that Floppy Eyelid Syndrome (FES) is present, and generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Herpes Zoster Dermatitis (HZD) in Human Eyes Photographically Represented in Digital Images Formed and Captured by a Mobile Smartphone Camera System FIG. 208 shows a deep-learning machine-vision ocular image processing and classification system (i.e. "engine") of the present invention configured and trained for use and deployment on the system network shown in FIG. 8A, to support and enable an automated method (M41) of detection and measurement of herpes zoster dermatitis (HZD) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 209 shows a front view digital image representation of a human eye exhibiting herpes zoster dermatitis (HZD), and augmented with graphical indications superimposed on the digital image to indicate (i) where herpes zoster dermatitis (HZD) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect herpes zoster dermatitis (HZD) as an indication of ocular disease recognition, treatment and manage care, including predicting dry eye disease (DED) class and grade of severity by the automated system.

FIG. 210 provides a schematic model supporting the automated detection and measurement of herpes zoster dermatitis (HZD) in the human eyes using a real-time ophthalmic image processing engine operating on front view digital images of the human eyes.

FIG. 211 describes the primary steps carried out when practicing the machine-vision based method of processing time and date stamped digital images of a human eye captured by a mobile smartphone camera system and processed to automatically detect herpes zoster dermatitis (HZD) in the human eye at a particular time and date, to support automated ocular disease recognition, treatment and manage care, including predicting dry eye disease (DED) class and grade of severity by the automated system.

Automated Machine-Vision Based Image Processing Method #41 (M41)

As shown and described in FIG. 211, the machine-vision based method of detecting, measuring, and generating a database of images indicating herpes zoster dermatitis/shingles (HZD), comprises the following steps:

Step 1: Capture a series of color digital images each color digital image having a set of pixels;

Step 2: Process the pixels in each digital image and classify the following structures in the human eye, including eyelids, iris, pupil, and sclera, and forehead;

Step 3: Use the above structures and trained system for automatic region of interest segmentation using non-parametric methods, including but not limited to, random decision forests such as Breiman's random forest algorithm, gray scale probability maps, binary thresholds, morphological operators and Bresenham's line algorithm;

Step 4: As illustrated in FIG. 210, detect herpes zoster dermatitis using region growing, k-means clustering and thresholding methods; and Step 5: If herpes zoster dermatitis is present, then generate output data indicative of such determined ocular disease factors and index the processed image(s) to indicate the same Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Herpes Zoster Keratitis (HZK) in Human Eyes Photographically Represented in Digital Images Formed and Captured by a Mobile Smartphone Camera System FIG. 212 shows a deep-learning machine-vision ocular image processing and classification system (i.e. "engine") of the present invention configured and trained for use and deployment on the system network shown in FIG. 8A, to support and enable an automated method (M42) of detection and measurement of herpes zoster keratitis (HZK) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 213A shows a front view digital image representation of a human face and eye exhibiting herpes zoster keratitis (HZK), and augmented with graphical indications superimposed on the digital image to indicate (i) where herpes zoster keratitis (HZK) is detected in the photographic image of the human face and eye, and (ii) which pixel region of interest (ROI) requires pixel data processing according to an automated method of digital image processing using the machine-based ophthalmic image processing engine of the present invention operating on one or more front view digital images of the human eye, so as to automatically detect herpes zoster keratitis (HZK) as an indication of ocular disease recognition, treatment and manage care, including predicting dry eye disease (DED) class and grade of severity by the automated system.

FIG. 213B shows a front view digital image representation of a human eye exhibiting dry eye disease (DED) conditions, and augmented with graphical indications superimposed on the digital image to indicate (i) where herpes zoster keratitis (HZK) is detected in the photographic image of the human face and eye, and (ii) which pixel region of interest (ROI) requires pixel data processing according to an automated method of digital image processing using the machine-based ophthalmic image processing engine of the present invention operating on one or more front view digital images of the human eye, so as to automatically detect herpes zoster keratitis (HZK) as an indication of ocular disease recognition, treatment and manage care, including predicting dry eye disease (DED) class and grade of severity by the automated system.

FIG. 214 provides a schematic model supporting the automated detection and measurement of herpes zoster keratitis (HZK) in the human eyes using a real-time ophthalmic image processing engine operating on front view digital images of the human eyes.

FIG. 215 describes the primary steps carried out when practicing the machine-vision based method of processing time and date stamped digital images of a human eye captured by a mobile smartphone camera system and processed to automatically detect herpes zoster keratitis (HZK) in the human eye at a particular time and date, to support automated ocular disease recognition, treatment and manage care, including predicting dry eye disease (DED) class and grade of severity by the automated system.

Automated Machine-Vision Based Image Processing Method #42 (M42)

As shown and described in FIG. 215, the machine-vision based method of detecting, measuring, and generating a database of images indicating herpes zoster keratitis (HZK), comprises the following steps:

Step 1: Use method (M41) to determine herpes zoster dermatitis (i.e. shingles) as detailed above;

Step 2: Use method (M1) to determine conjunctival injection as detailed above, if present;

Step 3: Use method (M45) to determine for corneal infection as detailed above, if present;

Step 4: Use method (M15) to determine subepithelial infiltrate as detailed above, if present;

Step 5: Use method (M16) to determine corneal edema (i.e. swelling) as detailed above, if present; and Step 6: If herpes zoster dermatitis (i.e. shingles) is detected as present, and conjunctival injection is present, and [corneal infection is present, or subepithelial infiltrate is present, or corneal edema present], then determine that Herpes Zoster Keratitis (HZK) is present, and generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Herpes Simplex Virus Keratitis (HSVK) in Human Eyes Photographically Represented in Digital Images Formed and Captured by a Mobile Smartphone Camera System FIG. 216 shows a deep-learning machine-vision ocular image processing and classification system (i.e. "engine") of the present invention configured and trained for use and deployment on the system network shown in FIG. 8A, to support and enable an automated method (M43) of detection and measurement of herpes simplex virus keratitis (HSVK) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 217 shows a front view digital image representation of a human eye exhibiting herpes simplex virus keratitis (HSVK), and augmented with graphical indications superimposed on the digital image to indicate (i) where herpes simplex virus keratitis (HSVK) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect herpes simplex virus keratitis (HSVK) as an indication of ocular disease recognition, treatment and manage care, including predicting dry eye disease (DED) class and grade of severity by the automated system.

FIG. 218 provides a schematic model supporting the automated detection and measurement of herpes simplex virus keratitis (HSVK) in the human eyes using a real-time ophthalmic image processing engine operating on front view digital images of the human eyes.

FIG. 219 describes the primary steps carried out when practicing the machine-vision based method of processing time and date stamped digital images of a human eye captured by a mobile smartphone camera system and processed to automatically detect herpes simplex virus keratitis (HSVK) in the human eye at a particular time and date, to support automated ocular disease recognition, treatment and manage care, including predicting dry eye disease (DED) class and grade of severity by the automated system.

Automated Machine-Vision Based Image Processing Method #43 (M43)

As shown and described in FIG. 219, the machine-vision based method of detecting, measuring, and generating a database of images indicating herpes simplex virus keratitis (HSVK), comprises the following steps:

Step 1: As illustrated in FIG. 218, use method (M45) to determine corneal infection as detailed above;

Step 2: As illustrated in FIG. 218, use method (M16) to determine corneal edema as detailed above, if present;

Step 3: As illustrated in FIG. 218, use method (M1) to determine conjunctival injection as detailed above, if present;

Step 4: As illustrated in FIG. 218, use method (M15) to determine subepithelial infiltrate as detailed above, if present;

Step 5: As illustrated in FIG. 218, use method (M16) to determine stromal infiltrates as detailed above, if present;

Step 6: As illustrated in FIG. 218, differentiate herpes simplex virus keratitis from other infection using methods including, but not limited to, contrast-limited adaptive histogram equalization, hue-saturation-value, product of saturation and hue maps, and maximal values of saturation and hue values; and Step 7: If corneal infection is present, and [subepithelial infiltrate is present, or stromal infiltrate is present] and corneal edema is present, and conjunctival injection is present, then determine that Herpes Simplex Virus Keratitis (HSVK) is present, and generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Ophthalmic Post Operative Complications (OPOS) in Human Eyes Photographically Represented in Digital Images Formed and Captured by a Mobile Smartphone Camera System FIG. 220 shows a deep-learning machine-vision ocular image processing and classification system (i.e. "engine") of the present invention configured and trained for use and deployment on the system network shown in FIG. 8A, to support and enable automated method (M44) of detection and measurement of ophthalmic post operative complications (OPOS) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 221 shows a front view digital image representation of a human eye exhibiting ophthalmic post operative complications (OPOS), and augmented with graphical indications superimposed on the digital image to indicate (i) where ophthalmic post operative complications (OPOS) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect ophthalmic post operative complications (OPOS) as an indication of ocular disease recognition, treatment and manage care, including predicting dry eye disease (DED) class and grade of severity by the automated system.

FIG. 222 provides a schematic model supporting the automated detection and measurement of ophthalmic post operative complications (OPOS) in the human eyes using a real-time ophthalmic image processing engine operating on front view digital images of the human eyes.

FIGS. 223A and 223B describe the primary steps carried out when practicing the machine-vision based method of processing time and date stamped digital images of a human eye captured by a mobile smartphone camera system and processed to automatically detect ophthalmic post operative complications (OPOS) in the human eye at a particular time and date, to support automated ocular disease recognition, treatment and manage care, including predicting dry eye disease (DED) class and grade of severity by the automated system.

Automated Machine-Vision Based Image Processing Method #44 (M44)

As shown and described in FIGS. 223A and 223B, the machine-vision based method of detecting, measuring, and generating a database of images indicating ophthalmic post operative (OPOS), comprises the following steps:

Step 1: As illustrated in FIG. 223, use method (M45) to determine corneal infection as detailed above, if present Step 2: As illustrated in FIG. 222, use method (M45) to determine hypopyon as detailed above, if present;

Step 3: As illustrated in FIG. 222, use method (M35) to determine anterior chamber depth as detailed above;

Step 4: As illustrated in FIG. 222, use method (M1) to determine conjunctival injection as detailed above, if present;

Step 5: As illustrated in FIG. 222, use method (M23) to determine subconjunctival hemorrhage as detailed above, if present;

Step 6: As illustrated ins FIG. 222, use method (M10) to determine corneal abrasion as detailed above, if present;

Step 7: As illustrated in FIG. 222, use method (M33) to determine proptosis as detailed above, if present;

Step 8: As illustrated in FIG. 222, use method (M19) to determine purulent discharge as detailed above, if present;

Step 9: As illustrated ins FIG. 222, use method (M16) to determine sutures, keratic precipitates, stromal infiltrates and corneal edema as detailed above, if present; and Step 10: If [corneal infection present AND corneal abrasion present] or hypopyon is present, or anterior chamber depth is less than 2.5 mm, or conjunctival injection is present, or subconjunctival hemorrhage is present, or proptosis is present, or purulent discharge is present, then determine that Ophthalmic Post Operative Complications (OPOS) are present, and generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Corneal Infection (CI) in Human Eyes Photographically Represented in Digital Images Formed and Captured by a Mobile Smartphone Camera System FIG. 224 shows a deep-learning machine-vision ocular image processing and classification system (i.e. "engine") of the present invention configured and trained for use and deployment on the system network shown in FIG. 8A, to support and enable an automated method (M45) of detection and measurement of corneal infection (CI) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 225 shows a front view digital image representation of a human eye exhibiting corneal infection (CI), and augmented with graphical indications superimposed on the digital image to indicate (i) where of corneal infection (CI) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect of corneal infection (CI) as an indication of ocular disease recognition, treatment and manage care, including predicting dry eye disease (DED) class and grade of severity by the automated system.

FIG. 226 provides a schematic model supporting the automated detection and measurement of corneal infection (CI) in the human eyes using a real-time ophthalmic image processing engine operating on front view digital images of the human eyes.

FIGS. 227A and 227B describe the primary steps carried out when practicing the machine-vision based method of processing time and date stamped digital images of a human eye captured by a mobile smartphone camera system and processed to automatically detect of corneal infection (CI) in the human eye at a particular time and date, to support automated ocular disease recognition, treatment and manage care, including predicting dry eye disease (DED) class and grade of severity by the automated system.

Automated Machine-Vision Based Image Processing Method #45 (M45)

As shown and described in FIGS. 227A and 227B, the machine-vision based method of detecting, measuring, and generating a database of images indicating of corneal infection (CI), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: As illustrated ins FIG. 226, use region of interest matching to detect cornea across a series of digital images reproducibly using methods including, but not limited to, scale invariant feature transform and random sample consensus;

Step 6: As illustrated ins FIG. 226, use Identify corneal infection and hypopyon using edge detection, region growing, k-means clustering and thresholding methods (M45);

Step 7: As illustrated ins FIG. 226, measure corneal infection height and width, and hypopyon height and respective surface areas using pixel-by-pixel size;

Step 8: If corneal infection height is greater than 0.1 mm, or corneal infection width is greater than 0.1 mm, then generate output data indicative of such determined ocular disease factors and index the processed image(s) to indicate the same; and Step 9: If hypopyon is greater than 0.1 mm, then generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of a Corneal Foreign Body (CFB) in Human Eyes Photographically Represented in Digital Images Formed and Captured by a Mobile Smartphone Camera System FIG. 228 shows a deep-learning machine-vision ocular image processing and classification system (i.e. "engine") of the present invention configured and trained for use and deployment on the system network shown in FIG. 8A, to support and enable an automated method (M46) of detection and measurement of a corneal foreign body (CFB) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 229 shows a front view digital image representation of a human eye exhibiting corneal foreign body (CFB), and augmented with graphical indications superimposed on the digital image to indicate (i) where corneal foreign body (CFB) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect corneal foreign body (CFB) as an indication of ocular disease recognition, treatment and manage care, including predicting dry eye disease (DED) class and grade of severity by the automated system.

FIG. 230 provides a schematic model supporting the automated detection and measurement of corneal foreign body (CFB) in the human eyes using a real-time ophthalmic image processing engine operating on front view digital images of the human eyes.

FIGS. 231A and 231B describes the primary steps carried out when practicing the machine-vision based method of processing time and date stamped digital images of a human eye captured by a mobile smartphone camera system and processed to automatically detect corneal foreign body (CFB) in the human eye at a particular time and date, to support automated ocular disease recognition, treatment and manage care, including predicting dry eye disease (DED) class and grade of severity by the automated system.

Automated Machine-Vision Based Image Processing Method #46 (M46)

As shown and described in FIGS. 231A and 231B, the machine-vision based method of detecting, measuring, and generating a database of images indicating corneal foreign body (CFB), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: Use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: Use region of interest matching to detect cornea across a series of digital images reproducibly using methods including, but not limited to, scale invariant feature transform and random sample consensus;

Step 6: As illustrated in FIG. 230, detect and identify a corneal foreign body (CFB) using edge detection, region growing, k-means clustering and thresholding methods (M46);

Step 7: As illustrated in FIG. 230, differentiate a corneal foreign body (CFB) from corneal infection and abrasion using contrast-limited adaptive histogram equalization, hue-saturation-value, product of saturation and hue maps, and maximal values of saturation and hue values; and Step 8: If a detected corneal foreign body (CFB) is greater than 0.1 mm, then generate output data indicative of such determined ocular disease factors and index the processed image(s) to indicate the same, for subsequent storage in the database.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Specification of the Deep-Learning Machine-Vision Ocular Image Processing and Classification System of the Present Invention Configured and Trained for Use and Deployment on the System Network to Support and Enable Automated Detection of Acute Angle Closure Glaucoma (AACG) in Human Eyes Photographically Represented in Digital Images Formed and Captured by a Mobile Smartphone Camera System FIG. 232 shows a deep-learning machine-vision ocular image processing and classification system (i.e. "engine") of the present invention configured and trained for use and deployment on the system network shown in FIG. 8A, to support and enable an automated method (M47) of detection and measurement of acute angle closure glaucoma (AACG) in the human eyes photographically represented in digital images of a front view of human eyes formed and captured by a mobile smartphone camera system in accordance with the principles of the present invention. The machine-vision engine of this illustrative embodiment of the present invention may be realized using any of the system architectures described in FIGS. 8A, 9A, 1B, 10, 37A, 37B, 38, 39A, 39B, 40A, 41, 42, 43 and 44 described herein, as well as any other suitable enabling technologies well known in the arts or to be developed in the future.

FIG. 233 shows a front view digital image representation of a human eye exhibiting acute angle closure glaucoma (AACG), and augmented with graphical indications superimposed on the digital image to indicate (i) where acute angle closure glaucoma (AACG) is detected in the photographic image of the human eye, and (ii) which pixel region of interest (ROI) requires pixel data processing according to an automated method of digital image processing using the machine-based ophthalmic image processing engine of the present invention operating on one or more front view digital images of the human eye, so as to automatically detect acute angle closure glaucoma (AACG) as an indication of ocular disease recognition, treatment and manage care, including predicting dry eye disease (DED) class and grade of severity by the automated system.

FIG. 234 provides a schematic model supporting the automated detection and measurement of acute angle closure glaucoma (AACG) in the human eyes using a real-time ophthalmic image processing engine operating on front view digital images of the human eyes.

FIGS. 235A and 235B describes the primary steps carried out when practicing the machine-vision based method of processing time and date stamped digital images of a human eye captured by a mobile smartphone camera system and processed to automatically detect acute angle closure glaucoma (AACG) in the human eye at a particular time and date, to support automated ocular disease recognition, treatment and manage care, including predicting dry eye disease (DED) class and grade of severity by the automated system.

Automated Machine-Vision Based Image Processing Method #47 (M47)

As shown and described in FIGS. 235A and 235B, the machine-vision based method of detecting, measuring, and generating a database of images indicating Acute Angle Closure Glaucoma (AACG), comprises the following steps:

Step 1: Capture a series of color digital images each color digital image having a set of pixels;

Step 2: Process the pixels in each digital image and classify the following structures in the human eye, including eyelids, iris, pupil, and sclera;

Step 3: Use cornea and non-cornea digital images to train the system to detect cornea;

Step 4: As illustrated in FIG. 234, use the above structures and trained system for automatic region of interest segmentation of using non-parametric methods, including but not limited to, random decision forests such as Breiman's random forest algorithm, gray scale probability maps, binary thresholds, morphological operators and Bresenham's line algorithm;

Step 5: As illustrated in FIG. 234, use region of interest matching to detect cornea across a series of digital images reproducibly using methods including, but not limited to, scale invariant feature transform and random sample consensus;

Step 6: As illustrated in FIG. 234, use method (M34) to determine anisocoria as detailed above;

Step 7: As illustrated in FIG. 234, use method (M16) to determine corneal edema as detailed above;

Step 8: As illustrated in FIG. 234, use method (M1) to determine conjunctival injection (CI) as detailed previously;

Step 9: As illustrated in FIG. 234, use method (M35) to determine anterior chamber depth (ACD) as detailed previously; and Step 10: If anterior chamber depth is less than 2.5 mm, and anisocoria is present, and [corneal edema is present, or conjunctival injection is present], then determine that Acute Angle Closure Glaucoma (AACG) is present, and generate output data indicative of such determined ocular disease factors and index the processed image(s) to indicate the same.

Once each digital image is processed according to the image-processing method described above, and a specified ocular condition is detected/recognized as reflected in the digital image, then the digital image indexed with the recognized condition (e.g. using suitable image indexing methods and coding), is then stored in the network database 16C for use future training of the automated machine-vision engine systems of the present invention.

Applications for the Automated Machine-Vision Methods of Recognizing Specific Ocular Disease Conditions Beyond the System Network of the Present Invention The various automated machine-vision methods of ocular disease condition (ODC) recognition disclosed in FIGS. 67 through 239B were shown as playing a critical role by providing automated ocular disease (OD) condition recognition intelligence services to system users of the system network of the present invention, illustrated in FIG. 8A. However, it is understood that such automated machine-vision methods and recognition services may be deployed in diverse applications independent and separate from any ocular health care system network as disclosed herein. Instead, such recognition services may be supported on local and/or remote computing servers, and provided within stand-alone diagnostic instruments and systems deployed in diverse settings such as medical clinics, hospitals, emergency rooms, as well as business offices, and consumer homes. Such applications will be explained in greater detail with references to system applications shown in FIGS. 256 through 261.

Specification of the Different Ways of Capturing Digital Images and Videos of the Patient's Eyes Using a Mobile Smart Phone Camera System of the Present Invention The deep-learning machine-vision systems employed in the system network disclosed and taught herein can be trained with, and operated upon using, front, side, top and/or bottom view images of human eyes being examined, analyzed and treated using the various methods supported by such systems. Conventions will be followed when preprocessing and using image data sets to train deep learning convolutional neural networks (CNNs) to automatically recognize specific classes of ocular disease conditions, with a given severity. Various methods described below have been developed for use with mobile smartphone camera systems and tablet devices to form and capture front, side, top and/or bottom view images of the human eyes being examined, analyzed and treated using the system network of the present invention.

Methods of Capturing Digital Images of Eyes Using a Mobile Smartphone Camera System Employing Bird's Eye View Imaging Modes Selfie Mode+Augmented Reality: Using the Front Facing Camera Viewing the Eyes of the User FIG. 236A1 illustrates a mobile smartphone system 11 being used on the system network to capture digital images of a user's eyes using the front facing camera in the visible-wavelength operating smartphone camera system. This viewing mode is used so that the user can capture an image of the user's left eye, right eye or both eyes using the smartphone camera system operating in a bird's eye selfie mode with augmented reality (AR) graphical instructions displayed on the display screen of the smartphone camera system. As illustrated below, these AR instructions can be realized in the form of mesh-work graphics, while supporting the use of auto-sensing and voice controls, with digital images taken automatically when selected parameters are met.

As shown in FIG. 236A1, the method of ocular image capture using a mobile smartphone system 11 configured in this mode, comprises a series of steps, namely:

Step 1: User is instructed to place the camera at eye level, approximately 6-12 inches from eye, with front-facing camera facing them;

Step 2: User is instructed to bring the mobile phone to approximately 45 degrees above the horizontal axis at eye level;

Step 3: In the preferred embodiment of the present invention, the mobile smartphone camera system 11 uses its gyroscope functionalities to instruct the user/patient to angle the smartphone camera system at approximately 315 degrees downward from the vertical axis of the smartphone camera system; and Step 4: Preferably, the smartphone GUI screen also utilizes augmented reality (AR) graphics realized as a superimposed mesh-work region of interest (ROI) for eye placement and computer vision, which includes, but is not limited to, object detection, recognition and verification, facial recognition, eye tracking, edge detection, image classification and analysis, feature detection and pattern recognition, as described in great detail hereinafter.

Bird's Eye: Selfie Mode

FIG. 236A2 illustrates a mobile smart phone being used on the system camera network to capture digital images of a user's eyes using the front facing camera in the smartphone camera system. This viewing mode is used so that so the user can capture an image of the user's left eye, right eye or both eyes using the smartphone camera system operating in a bird's eye selfie mode.

As shown in FIG. 236A2, the method of ocular image capture using a mobile smartphone camera system 11 configured in this mode, comprises a series of steps, namely:

Step 1: User is instructed to place the smartphone camera system at eye level, approximately 6-12 inches from eye, with front-facing camera facing them;

Step 2: User is instructed to bring the smartphone camera system to approximately 45 degrees above the horizontal axis at eye level;

Step 3: User is instructed to angle the smartphone camera downwards at approximately 315 degrees from vertical axis of the smartphone camera system; and Step 3: User then takes a digital image of the eye using the smartphone camera system.

This viewing method is suited for capturing top view images of a user's eyes which are ideal for use in the machine-vision based methods disclosed herein requiring top view images of human eyes.

Mirror Mode+Augmented Reality: Using the Rear Facing Camera Viewing the Eyes of the User FIG. 236A3 illustrates a mobile smartphone camera system being used to capture digital images of a user's eyes using the rear facing camera in the visible-wavelength operating smartphone camera system. This viewing mode is used so that the user can capture a mirror image of the user's left eye, right eye or both eyes using the smartphone camera system operating in a bird's eye mirror mode with augmented reality (AR) graphical instructions displayed on the display screen of the smartphone camera system.

As shown in FIG. 236A1, the method of ocular image capture using a mobile smartphone system 11 configured in this mode, comprises a series of steps, namely:

Step 1: User is instructed to stand in front of a mirror, with the rear-facing camera on the back of the smartphone camera system directed towards the user, at eye level, approximately 6-12 inches from eye, and the phone's screen is reflected on the mirror;

Step 2: User is instructed to bring the mobile smartphone camera system to approximately 45 degrees above the horizontal axis at eye level;

Step 3: In the preferred embodiment of the present invention, the mobile smartphone camera system 11 uses its gyroscope capability to instruct patient to angle the camera at approximately 315 degrees downward from the vertical axis of the smartphone camera system;

Step 4: The smartphone GUI screen utilizes augmented reality (AR) graphics realized as a superimposed mesh-work region of interest (ROI) for eye placement and computer vision, which includes, but is not limited to, object detection, recognition and verification, facial recognition, eye tracking, edge detection, image classification and analysis, feature detection and pattern recognition, as described in great detail hereinafter; and Step 5: The mobile smartphone camera system runs application software that detects and recognizes the user, guides the user on camera placement using audible commands and does an image classification to check if image or video quality is optimized. If quality is optimized, assessed using k-means clustering and mean-squared, then the software automatically takes the image or starts the video. If the quality is not optimized, then the software guides the patient to retake another image or video until optimal quality is obtained.

This viewing method is suited for capturing top view images of a user's eyes which are ideal for use in the machine-vision based methods disclosed herein requiring top view images of human eyes.

Bird's Eye Angle: Mirror Mode: Using the Rear Facing Camera Viewing the Eyes of the User FIG. 236A4 illustrates a mobile smartphone system being used to capture digital images of a user's eyes using the rear facing camera in the visible-wavelength operating smartphone camera system. This viewing mode is used so that the user can capture a mirror image of the user's left eye, right eye or both eyes using the smartphone camera system operating in a bird's eye mirror mode.

This method of ocular image capture using a mobile smartphone camera system 11 comprises a series of steps, namely:

Step 1: User is instructed to stand in front of a mirror, with the rear-facing camera on the back of the smartphone system directed towards the user, at eye level, approximately 6-12 inches from eye, and the smartphone's display screen is reflected on the mirror;

Step 2: User is instructed to bring the phone to approximately 45 degrees above the horizontal axis at eye level;

Step 3: User is instructed to angle the phone downwards at approximately 315 degrees from vertical axis of the smartphone camera system; and Step 4: User then uses his or her reflection and the phone's screen reflection on the mirror to guide the rear-facing camera to take an image of the eye.

This viewing method is suited for capturing top view images of a user's eyes which are ideal for use in the machine-vision based methods disclosed herein requiring top view images of human eyes.

Methods of Capturing Digital Images of Eyes Using a Mobile Smartphone Camera System Employing Front View Imaging Modes Mirror Mode+Augmented Reality: Rear Facing Camera Viewing Eyes of the User FIG. 236B1 illustrates a visible-wavelength operating mobile smartphone camera system being used to capture digital images of a patient's eyes using the rear facing camera in the phone and a mirror surface. This viewing mode is used so that the user can capture a mirror image of the user's left eye, right eye or both eyes reflected on the mirror surface with augmented reality (AR) graphical instructions displayed on the display screen of the smartphone camera system.

This method of ocular image capture using a mobile smartphone camera system 11 comprises a series of steps, namely:

Step 1: User is instructed to stand in front of a mirror, with the rear-facing camera on the back of the smartphone camera system directed towards the user, at eye level, approximately 6-12 inches from eye, and the smartphone's display screen is reflected on the mirror;

Step 2: User then uses his or her reflection and the smartphone's display screen reflection on the mirror to guide the rear-facing camera; and Step 3: The smartphone GUI screen utilizes augmented reality (AR) graphics realized as a superimposed mesh-work region of interest (ROI) for eye placement and computer vision, which includes, but is not limited to, object detection, recognition and verification, facial recognition, eye tracking, edge detection, image classification and analysis, feature detection and pattern recognition, as described in great detail herein.

This viewing method is suited for capturing front view images of a user's eyes which are ideal for use in the machine-vision based methods disclosed herein requiring front view images of human eyes.

Mirror Mode: Rear Facing Camera Viewing Eyes of the User

FIG. 236B2 illustrates a visible-wavelength operating mobile smartphone system being used to capture digital images of a patient's eyes using the front facing camera in the mobile smart phone and a mirror surface. This viewing mode is used so that the user can capture a mirror image of the user's left eye, right eye or both eyes user's eye reflected on the mirror surface.

This method of ocular image capture using a mobile smartphone system 11 comprises a series of steps, namely:

Step 1: User is instructed to stand in front of a mirror, with the rear-facing camera on the back of the smartphone camera system directed towards the user, at eye level, approximately 6-12 inches from eye, and the phone's display screen is reflected on the mirror; and Step 2: User then uses his or her reflection and the smartphone's display screen reflection on the mirror to guide the rear-facing camera to take an image of the eye.

This viewing method is suited for capturing front view images of a user's eyes which are ideal for use in the machine-vision based methods disclosed herein requiring front view images of human eyes.

Selfie Mode+Augmented Reality: Front Facing Camera Viewing Eyes of the User

FIG. 236B3 illustrates a visible-wavelength operating mobile smartphone camera system being used to capture digital images of a patient's eyes using the front facing camera in the smartphone camera system and a mirror surface. This viewing mode is used so that the user can capture an image of the user's left eye, right eye or both eyes using the smartphone camera system operating in a front facing selfie mode, with augmented reality (AR) graphical instructions displayed on the display screen of the smartphone.

This method of ocular image capture using a mobile smartphone system 11 configured in this mode, comprises a series of steps, namely:

Step 1: User is instructed to place the smartphone camera system at eye level, approximately 6-12 inches from eye, with front-facing camera facing them;

Step 2: The smartphone GUI screen utilizes augmented reality as a superimposed mesh-work region of interest for eye placement and computer vision, which includes, but is not limited to, object detection, recognition and verification, facial recognition, eye tracking, edge detection, image classification and analysis, feature detection and pattern recognition; and Step 3: The smartphone camera system runs application software that detects and recognizes the user, guides the user on camera placement using audible commands and does an image classification to check if image or video quality is optimized. If quality is optimized and assessed using k-means clustering and mean-squared, then the software automatically takes the image or starts the video. If the quality is not optimized, then the software guides the patient to retake another image or video until optimal quality is obtained.

This viewing method is suited for capturing front view images of a user's eyes which are ideal for use in the machine-vision based methods disclosed herein requiring front view images of human eyes.

Selfie Mode: Front Facing Camera Viewing Eyes of the User

FIG. 236B4 illustrates a visible-wavelength operating mobile smartphone system being used to capture digital images of a patient's eyes using the front facing camera in the smartphone system. This viewing mode is used so that the user can capture an image of the user's left eye, right eye or both eyes using the smartphone camera system operating in a front facing selfie mode.

This method of ocular image capture using a mobile smartphone system 11 configured in this mode, comprises a series of steps, namely:

Step 1: User is instructed to place the smartphone camera system, at eye level, approximately 6-12 inches from eye, with front-facing camera facing them; and Step 2: User takes a photo using the front-facing camera of the smartphone camera system.

This viewing method is suited for capturing front view images of a user's eyes which are ideal for use in the machine-vision based methods disclosed herein requiring front view images of human eyes.

Methods of Capturing Digital Images of Eyes Using a Mobile Smartphone Camera System Employing Side View Imaging Modes Side Angle/Mirror Mode+Augmented Reality: Using Front Facing Camera Viewing Eyes of the User FIG. 236C1 is a schematic illustration showing a visible-wavelength operating mobile smartphone camera system being used to capture digital images of a user's eyes using the front facing camera in the smartphone camera system. This viewing mode is used so that the user can capture an image of the user's left eye, right eye or both eyes using the smartphone camera system operating in a side angle mirror mode. As shown, augmented reality (AR) graphical instructions are displayed on the display screen of the smartphone, in the form of mesh using auto-sensing and voice controls, with the image taken automatically when selected parameters are met.

This method of ocular image capture using a mobile smartphone system 11 configured in this mode, comprises a series of steps, namely:

Step 1: User is instructed to stand in front of a mirror, with the rear-facing camera on the back of the smartphone camera system directed towards the user, at eye level, approximately 6-12 inches from eye, and the smartphone's display screen is reflected on the mirror;

Step 2: The user is then asked to turn their head at 90 degrees to left;

Step 3: The smartphone GUI screen utilizes augmented reality (AR) graphics realized as a superimposed mesh-work region of interest for eye placement and computer vision, which includes, but is not limited to, object detection, recognition and verification, facial recognition, eye tracking, edge detection, image classification and analysis, feature detection and pattern recognition, as described in detail herein;

Step 4: The smartphone system runs operating software that detects and recognizes the user, guides the user on camera placement using audible commands and does an image classification to check if image or video quality is optimized. If the quality is optimized and assessed using k-means clustering and mean-squared, then the software automatically takes the image or starts the video. If the quality is not optimized, the software guides the patient to retake another image or video until optimal quality is obtained; and Step 5: The same method is repeated with the user turning their head 90 degrees to the right.

This viewing method is suited for capturing side view images of a user's eyes which are ideal for use in the machine-vision based methods disclosed herein requiring side view images of human eyes.

Side Angle Mirror Mode: Using the Front Facing Camera Viewing the Eyes of the User FIG. 236C2 is a schematic illustration showing a mobile smart phone system being used to capture digital images of a user's eyes using the front facing camera in the phone. This viewing mode is used so that the user can capture an image of the user's left eye, right eye or both eyes using the smartphone camera system operating in a side angle mirror mode.

This method of ocular image capture using a mobile smartphone system 11 comprises a series of steps, namely:

Step 1: User is instructed to stand in front of a mirror, with the rear-facing camera on the back of the phone directed towards the user, at eye level, approximately 6-12 inches from eye, and the phone's screen is reflected on the mirror; and Step 2: The user is then asked to turn their head at 90 degrees to left.

The same method is repeated with the user turning their head 90 degrees to the right.

This viewing method is suited for capturing side view images of a user's eyes which are ideal for use in the machine-vision based methods disclosed herein requiring side view images of human eyes.

Side Angle Selfie Mode+Augmented Reality: Using Rear Facing Camera Viewing the Eyes of the User FIG. 236C3 is a schematic illustration showing a visible-wavelength operating mobile smartphone system being used to capture digital images of a user's eyes using the rear facing camera in the phone. This viewing mode is used so that the user can capture a mirror image of the user's left eye, right eye or both eyes using the smartphone camera system operating in a side angle selfie mode with augmented reality (AR) graphical instructions displayed on the display screen of the smartphone.

This method of ocular image capture using a mobile smartphone system 11 comprises a series of steps, namely:

Step 1: User is instructed to stand in front of a mirror, with the front-facing camera directed towards the user, at eye level, approximately 6-12 inches from eye;

Step 2: The user is then asked to turn their head at 90 degrees to left;

Step 3: The smartphone GUI screen utilizes augmented reality (AR) graphics realized as a superimposed mesh-work region of interest for eye placement and computer vision, which includes, but is not limited to, object detection, recognition and verification, facial recognition, eye tracking, edge detection, image classification and analysis, feature detection and pattern recognition, as described in great detail herein;

Step 4: The smartphone system runs application software that detects and recognizes the user, guides the user on camera placement using audible commands and does an image classification to check if image or video quality is optimized. If quality is optimized and assessed using k-means clustering and mean-squared, then the software automatically takes the image or starts the video. If the quality is not optimized, the software guides the patient to retake another image or video until optimal quality is obtained; and Step 5: The same method is repeated with the user turning their head 90 degrees to the right.

This viewing method is suited for capturing side view images of a user's eyes which are ideal for use in the machine-vision based methods disclosed herein requiring side view images of human eyes.

Side Angle Selfie Mode: Using Rear Facing Camera Viewing Eyes of the User

FIG. 236C4 is a schematic illustration showing a visible-wavelength operating mobile smart phone being used to capture digital images of a user's eyes using the rear facing camera in the phone. This viewing mode is used so that the user can capture a mirror image of the user's left eye, right eye or both eyes using the smartphone camera system operating in a side angle selfie mode.

This method of ocular image capture using a mobile smartphone system 11 comprises a series of steps, namely:

Step 1: User is instructed to place the camera at eye level, approximately 6-12 inches from eye, with front-facing camera facing them;

Step 2: The user is then asked to turn their head at 90 degrees to left; then the User takes an image of the eye.

The same method is repeated with the user turning their head 90 degrees to the right.

This viewing method is suited for capturing side view images of a user's eyes which are ideal for use in the machine-vision based methods disclosed herein requiring side view images of human eyes.

Methods of Capturing Digital Images of Eyes Using a Mobile Smartphone Camera System Employing Worm's Eye View Imaging Modes Selfie Mode+Augmented Reality:

FIG. 236D1 is a schematic illustration showing a visible-wavelength operating mobile smartphone being used to capture digital images of a user's eyes using the front facing camera in the phone. This viewing mode is used so that the user can capture an image of the user's left eye, right eye or both eyes using the smartphone camera system operating in a worm's eye Selfie Mode with Augmented Reality (AR) graphical instructions displayed on the display screen of the smartphone, in the form of mesh using auto-sensing and voice controls, with the image taken automatically when parameters are met.

This method of ocular image capture using a mobile smartphone system 11 comprises a series of steps, namely:

Step 1: User is instructed to place the camera at eye level, approximately 6-12 inches from eye, with front-facing camera facing them;

Step 2: User is instructed to bring the phone to approximately 135 degrees below the horizontal axis at eye level;

Step 3: The smartphone system runs software uses its gyroscope capability to instruct user/patient to angle the smartphone camera at approximately 45 degrees upward from the vertical axis of the smartphone;

Step 4: The smartphone GUI screen utilizes augmented reality (AR) graphics realized as a superimposed mesh-work region of interest for eye placement and computer vision, which includes, but is not limited to, object detection, recognition and verification, facial recognition, eye tracking, edge detection, image classification and analysis, feature detection and pattern recognition; and Step 5: The smartphone system runs application software that detects and recognizes the user, guides the user on camera placement using audible commands and does an image classification to check if image or video quality is optimized. If quality is optimized, assessed using k-means clustering and mean-squared, the software automatically takes the image or starts the video. If the quality is not optimized, the software guides the patient to retake another image or video until optimal quality is obtained.

This viewing method is suited for capturing bottom view images of a user's eyes which are ideal for use in the machine-vision based methods disclosed herein requiring bottom view images of human eyes, taken using worm's eye selfie mode as disclosed in FIG. 176.

Mirror Mode+Augmented Reality: Rear Facing Camera Viewing Eyes of User

FIG. 236D2 is a schematic illustration showing a visible-wavelength operating mobile smart phone being used to capture digital images of a user's eyes using the rear facing camera in the phone. This viewing mode is used so that the user can capture a mirror image of the user's left eye, right eye or both eyes using the smartphone camera system operating in a worm's eye selfie mode with augmented reality (AR) graphical instructions displayed on the GUI display screen of the smartphone system, in the form of mesh using auto-sensing and voice controls, with the image taken automatically when parameters are met.

This method of ocular image capture using a mobile smartphone system 11 comprises a series of steps, namely:

Step 1: User is instructed to stand in front of a mirror, with the rear-facing camera on the back of the phone directed towards the user, at eye level, approximately 6-12 inches from eye, and the phone's screen is reflected on the mirror;

Step 2: User is instructed to bring the phone to approximately 135 degrees below the horizontal axis at eye level;

Step 3: The smartphone system runs software uses its gyroscope capability to instruct patient to angle the camera at approximately 45 degrees upward from the vertical axis of the phone;

Step 4: The smartphone GUI screen utilizes augmented reality (AR) graphics realized as a superimposed mesh-work region of interest for eye placement and computer vision, which includes, but is not limited to, object detection, recognition and verification, facial recognition, eye tracking, edge detection, image classification and analysis, feature detection and pattern recognition, as described in great detail hereinafter; and Step 5: The smartphone system runs application software that detects and recognizes the user, guides the user on camera placement using audible commands and does an image classification to check if image or video quality is optimized. If quality is optimized and assessed using k-means clustering and mean-squared, then the software automatically takes the image or starts the video. If the quality is not optimized, then the software guides the patient to retake another image or video until optimal quality is obtained.

This viewing method is suited for capturing bottom view images of a user's eyes which are ideal for use in the machine-vision based methods disclosed herein requiring bottom view images of human eyes, such as disclosed in FIG. 176.

Worm's Eye Angle/Mirror Mode: Using Front Facing Camera Viewing Eyes of the User FIG. 236D3 is a schematic illustration showing a visible-wavelength operating mobile smartphone system being used to capture digital images of a user's eyes using the rear facing camera in the phone. This viewing mode is used so that the user can capture a mirror image of the user's left eye, right eye or both eyes using the smartphone camera system operating in a Worm's Eye Mirror Mode.

This method of ocular image capture using a mobile smartphone system 11 comprises a series of steps, namely:

Step 1: User is instructed to stand in front of a mirror, with the rear-facing camera on the back of the smartphone directed towards the user, at eye level, approximately 6-12 inches from eye, and the smartphone's GUI screen is reflected on the mirror;

Step 2: User is instructed to bring the smartphone to approximately 135 degrees below the horizontal axis at eye level;

Step 3: User is instructed to angle the phone approximately 45 degrees upward from vertical axis of the smartphone system; and Step 4: User then uses his or her reflection and the phone's screen reflection on the mirror to guide the rear-facing camera to take an image of the eye.

This viewing method is suited for capturing bottom view images of a user's eyes which are ideal for use in the machine-vision based methods disclosed herein requiring bottom view images of human eyes, such as disclosed in FIG. 176.

Selfie Mode: Using Front Facing Camera Viewing Eyes of the User

FIG. 236D4 is a schematic illustration showing a visible-wavelength operating mobile smart phone being used to capture digital images of a user's eyes using the front facing camera in the phone. This viewing mode is use so that the user can capture a mirror image of the user's left eye, right eye or both eyes using the smartphone camera system operating in a worm's eye selfie mode.

This method of ocular image capture using a mobile smartphone system 11 configured in this mode, comprises a series of steps, namely:

Step 1: User is instructed to place the camera at eye level, approximately 6-12 inches from eye, with front-facing camera facing them;

Step 2: User is instructed to bring the smartphone system to approximately 135 degrees below the horizontal axis at eye level;

Step 3: User is instructed to angle the phone approximately 45 degrees upward from vertical axis of the smartphone system; and Step 5: User then takes an image of the eye using the smartphone system arranged as described above according to the method of image capture.

This viewing method is suited for capturing bottom view images of a user's eyes which are ideal for use in the machine-vision based methods disclosed herein requiring bottom view images of human eyes, such as disclosed in FIG. 176.

Specification of Mobile Tablet Computer Used by a Medical Administrator or Doctor in a Clinical or Like Setting to Enable/Disable the Machine-Vision Based Methods of Image Processing FIG. 237 shows an exemplary graphical user interface (GUI) displayed on the mobile computers depicted in FIGS. 12A, 12B and 12C, displaying a list of the various machine-vision methods of ocular image processing (M1 through M47) supported by the system network of the present invention, described in detail in FIGS. 46 through 235B, and which methods the system or medical administrator wishes to enable and activate on the system user's smartphone system and patient user account. Typically, this GUI screen will be used by a medical administrator or doctor in a clinical or like setting to enable/disable the machine-vision based methods of image processing illustrated in FIGS. 46 through 235B.

Specification of a Human Eye Represented in a Front View Digital Image Thereof Captured by a Smartphone Camera System Supported by the System Network of the Present Invention FIGS. 238A and 238B describe the primary steps of a method of operating an automated ophthalmic image capturing and processing system of the present invention described herein to enable the following core functions: (i) automated machine-assisted detection of ocular disease (OD) conditions in the human eye; (ii) automated prescription of treatment and management; and (iii) automated assessment of the prescribed treatment and management.

As described below, this method of operation is carried out by providing requested patient data into the system via a mobile smartphone system, and processing a series of digital images of the human eye captured by a mobile visible-wavelength operating (VWO) smartphone camera system deployed on the system network anywhere on and around the Earth, with full GPS-tracking and indexing enabled during system operation.

As indicated in FIG. 238A, Step 1 of the method of operation involves collecting information on a patient and developing a patient data profile and storing same in a database system 16C connected to the system network.

As indicated in FIG. 238A, Step 2 of the method involves forming and detecting digital images of the cornea and ocular surfaces of the eyes of a patient (front views) using a smartphone camera system, and transmitting the captured digital images to the database system 16C over the wireless data communication network.

As indicated in FIG. 238A, Step 3 of the method involves processing the digital images using methods of present invention specified in FIGS. 46 through 239B.

As indicated in FIG. 238A, Step 4 of the method involves automatically detecting dry eye disease (DED) and/or other ocular disease (OD) conditions represented in the digital imaging of the eyes, and also evaluating the severity of the disease conditions in terms of classification and grading.

As indicated in FIG. 238A, Step 5 of the method involves prescribing treatment and/or therapy for the detected ocular disease (OD) condition.

As indicated in FIG. 238A, Step 6 of the method involves applying the prescribed treatment to the eyes of the patient.

As indicated in FIG. 238A, Step 7 of the method involves capturing digital images of treated eyes and storing in the patient database system 16C.

As indicated in FIG. 238A, Step 8 of the method involves automatically processing digital images of treated eyes using machine-vision systems and automatically determining treatment response and severity of individual symptoms.

As indicated in FIG. 238B, Step 9 of the method involves using a mobile camera system 11 to monitor and examine the patient's eyes after the prescribed course of treatment (including the patient taking a mobile vision test and assessment as described herein).

As indicated in FIG. 238B, Step 10 of the method involves assessing patient's the response to the prescribed treatment and/or therapy.

As indicated in FIG. 238B, Step 11 of the method involves assessing re-prescribe a course of treatment consistent with assessed treatment response.

As indicated in FIG. 238B, Step 12 of the method involves monitoring, re-examining and re-assessing the patient's response to the prescribed treatment and/or therapy.

Specification of Mobile Smartphone Systems and Mobile Services for Collecting Patient History Data for Delivery to the System Network of the Present Invention FIGS. 239A and 239B describe the primary steps of a method of operating an automated ophthalmic image capturing and processing system of the present invention 10, and training the same using digital images of the human eye that are (i) captured by a mobile visible-wavelength operating smartphone camera system 11, and (ii) manually indexed by an ophthalmologist or subject matter expert in a remote or clinical environment as the case may be, to reflect the underlying ocular disease condition diagnosed by the ophthalmologist or subject matter expert.

As indicated in FIG. 239A, Step 1 of the method involves collecting information on a patient and developing a patient data profile and storing same in the database system.

As indicated in FIG. 239A, Step 2 of the method involves forming and detecting digital images of the cornea and ocular surfaces of the eyes of a patient (front views) using a smartphone camera system, and transmitting the captured digital images to the database system supported on an system network connected of the present invention.

As indicated in FIG. 239A, Step 3 of the method involves processing the digital images using methods of present invention specified in FIGS. 46 through 235B.

As indicated in FIG. 239A, Step 4 of the method involves using a machine-vision system to automatically detect dry eye disease (DED) and/or other ocular conditions represented in the digital imaging of the eyes and evaluate the severity of the disease in terms of classification and grading.

As indicated in FIG. 239A, Step 5 of the method involves sending digital images to an ophthalmologist to assess and diagnosis dry eye disease (DED) and/or other ocular disease (OD) conditions represented in the digital images, and indexing the digital images to reflected the ocular conditions confirmed by the ophthalmologist.

As indicated in FIG. 239A, Step 6 of the method involves prescribing treatment and/or therapy for the detected dry eye disease condition.

As indicated in FIG. 239A, Step 7 of the method involves applying the prescribed treatment to the eyes of the patient.

As indicated in FIG. 239A, Step 8 of the method involves using condition-indexed digital images produced in Step 5 to train the machine-vision system.

As indicated in FIG. 239A, Step 9 of the method involves capturing digital images of treated eyes and store in the patient database system.

As indicated in FIG. 239A, Step 10 of the method involves processing digital images of treated eyes and automatically determining treatment response and severity of individual symptoms.

As indicated in FIG. 243B, Step 11 of the method involves using mobile camera system to monitor and examine the patient's eyes after the prescribed course of treatment (including the patient taking a vision test and assessment).

As indicated in FIG. 239B, Step 12 of the method involves assessing patient's the response to the prescribed treatment and/or therapy.

As indicated in FIG. 239B, Step 13 of the method involves re-prescribing a course of treatment consistent with assessed treatment response.

As indicated in FIG. 239B, Step 14 of the method involves monitoring, re-examining and re-assessing the patient's response to the prescribed treatment and/or therapy.

Specification of Method of Indexing Ophthalmic Images Indicating Specific Ocular Conditions, Storing these Indexed Images in an Ophthalmic Image Library, and Using these Indexed Ophthalmic Images to Train Deep-Learning Driven Machine-Vision Systems FIG. 240 describes a method for ophthalmologists to use to index ophthalmic images indicating specific ocular conditions, and storing these indexed images in an ophthalmic image library system, so that these indexed ophthalmic images can be used to train deep learning driven machine-vision systems deployed on the system network of the present invention This method is described in greater detail below.

As indicated in FIG. 240, Step 1 of the method involves using a mobile smartphone or computing device to form and capture ophthalmic color digital images of the eyes of a patient, indicating specific ocular disease (OD) conditions.

As indicated in FIG. 240, Step 2 of the method involves one or more ophthalmologists to index the captured ophthalmic images indicating specific ocular conditions.

As indicated in FIG. 240, Step 3 of the method involves storing these indexed ophthalmic images in an ophthalmic image library system.

As indicated in FIG. 240, Step 4 of the method involves using these indexed ophthalmic images to train deep learning driven machine-vision systems to automatically recognize the specific ocular conditions indicated in the ophthalmic images.

Specification of Mobile Smartphone Systems and Mobile Services for Collecting Patient History Data for Delivery to the System Network of the Present Invention FIG. 241 shows an exemplary GUI screen displayed on a mobile smartphone system of the present invention during patient history data collection operations on the system network of the present invention.

Specification of Mobile Smartphone Systems and Mobile Services for Collecting Patient Symptom Data for Delivery to the System Network of the Present Invention FIG. 242 shows an exemplary GUI screen displayed on a mobile smartphone system of the present invention, for use by a patient to provide patient symptom data (e.g. pain experienced) to the system network of the present invention.

Specification of Mobile Smartphone Systems and Mobile Services for Collecting Patient Examination and In-Office Examination Data for Delivery to the System Network of the Present Invention FIG. 243 shows an exemplary GUI screen displayed on a mobile smartphone system of the present invention during patient examination and in-office examination data collection operations on the system network of the present invention.

Specification of Mobile Smartphone Systems and Mobile Services for Supporting Mobile Vision Testing Operations Using a Mobile Smartphone Device Deployed on the System Network of the Present Invention FIG. 244 shows an exemplary GUI screen displayed on a mobile smartphone system of the present invention during patient mobile vision testing operations on the system network of the present invention. FIG. 245 shows a mobile vision testing screen that is displayed on the patient's mobile phone screen during exemplary mobile vision testing operations. Various vision testing screens can be created by those skilled in the vision testing arts, and displayed from the display screen of the smartphone camera system to perform the required vision testing on the patient's eyes using the mobile smartphone camera system while remotely-situated from the machine-vision processing servers at the data center, as described in detail herein.

Specification of the Mobile Smartphone Camera System for Use by a Patient to Capture Image-Based Data from the Patient's Eyes and Provide the Same to the System for Image Processing Using Automated Machine Vision Processing Methods Provided According to the Principles of the Present Invention FIG. 246 shows a graphical user interface (GUI) displayed on a mobile smartphone camera system deployed on the system network of FIG. 8A, for use by any patient to capture image/video-based data from the patient's eyes and provide the same to the system network for remote image processing, using automated machine-vision processing methods (M1 through M47) according to the principles of the present invention described in FIGS. 34A, 34B, 67-64B, and 86-235B. The objective of these image-frame based processing methods is to automatically detect, recognize, and/or measure specific ocular disease conditions, including but not limited to, tear meniscus height (TMH), conjunctival injection, scruff at eyelashes, meibomian gland dysfunction, dermatochalasis, conjunctivochalasis, and the numerous other ocular disease conditions described herein, by analyzing single frames of image data representative of the patient's eyes captured while in a stationary gazing mode.

Specification of the Mobile Smartphone Camera System for Use by a Patient to Capture Image-Based Data from the Patient's Eyes and Provide the Same to the System for Image Processing Using Automated Machine Vision Processing According to the Principles of the Present Invention FIG. 247 shows a graphical user interface (GUI) displayed on the mobile smartphone camera system, for use by a patient to capture video-based data of the patient's eyes and provide the same to the system network for image processing using automated machine-vision video-based processing methods according to the principles of the present invention described in FIGS. 34C, and 65-85. The objective of these video-based processing methods is to automatically detect, recognize, and/or measure specific ocular disease conditions, including but not limited to, blink rate per minute, blink interval, blink duration, blink speed and partial blinks per minute, by analyzing sequential frames of video data recording the behavior of the patient's eyes while blinking.

Specification of the Primary Diagnostic Factors Used by the System Network of the Present Invention to Automatically Recognize the Type or Class of Ocular Disease, and its Grade/Severity Experienced by the Patient, Automatically Determined Using the Machine-Vision Processing Methods of the Present Invention FIG. 248 illustrates the primary diagnostic factors that are used by the system network of the present invention to automatically recognize the patient's ocular disease, and its grade/severity experienced by the patient, using the machine-vision imaging processing methods of the present invention, along with the other patient data collected as specified in FIGS. 15 through 26, and 28 through 33, described hereinabove. As shown, these primary diagnostic factors include: image and video data sets captured by mobile smartphone camera systems and automatically processed using the machine-vision based systems and methods specified in FIGS. 67 through 235B; environmental factors specified in FIGS. 24-25; the various risk factors summarized in FIG. 27 and described hereinabove; patient symptom data specified in FIG. 28; vision functionality data specified in FIG. 26; in-office exam data specified in FIGS. 29-30; and mobile vision testing performance data specified in FIGS. 31-32, using the smartphone application described hereinabove.

Specification of Mobile Smartphone Systems and Mobile Services for Automated Ocular Disease (OD) Recognition for Delivery to Mobile Systems Deployed on the System Network of the Present Invention Once the system network has processed the collected patient data and images and videos of the patient's eyes for processing by the machine-vision systems of the present invention, the system network servers generate and serve GUI screens to the patient's mobile smartphone system for display of information pertaining to the automatically recognized ocular disease conditions discovered in the images of the patient's eyes.

Various graphical user interfaces (GUIs) similar in style to the ones illustrated herein will be designed and generated from system network servers to the mobile smartphone camera systems deployed on the system network, for use by a patient to receive an ocular disease diagnoses generated by from the system using automated machine vision processing methods according to the principles of the present invention. As described herein, these methods support the automated detection and measurement of ocular conditions such as, but not limited to, tear meniscus height (TMH), conjunctival injection, scruff at eyelashes, meibomian gland dysfunction, dermatochalasis, and/or conjunctivochalasis.

FIGS. 14A through 14D show a list of exemplary ocular diseases (OD) associated with the anterior segment of the human eye, that can be automatically recognized by the system of the present invention upon processing the various input factors provided to the system using the patient's mobile smartphone device registered with the system. In the illustrative embodiments of the present invention, these various ocular diseases (OD) are coded as follows: OD01 Ptosis; OD02 Chalazion/Stye; OD03 Eyelid Cyst; OD04 Ectropion; OD05 Entropion; OD06 Trichiasis; OD07 Distichiasis; OD08 Floppy Eyelid Syndrome; OD09 Blepharospasm; OD10 Dacryocystitis; OD11 Canaliculitis; OD12 Preseptal Cellulitis; OD13 Orbital Post Septal Cellulitis; OD14 Proptosis; OD15 Orbital Floor Fracture; OD16 Thyroid Eye Disease; OD17 Blepharitis; OD18 Herpes Zoster Dermatitis (Shingles); OD19 Retrobulbar Hemorrhage; OD20 Viral Conjunctivitis; OD21 Bacterial Conjunctivitis; OD22 Allergic Conjunctivitis; OD23 Chemical Burn Conjunctivitis; OD24 Superior Limbic Hemorrhage; OD25 Subconjunctival Hemorrhage; OD26 Episcleritis/Scleritis; OD27 Conjunctival Laceration; OD28 Herpes Zoster Conjunctivitis; OD29 Pemphigoid; OD30 Dry Eye Disease (DED); OD31 Corneal Abrasion; OD32 Cornea Foreign Body; OD33 Bacterial Keratitis; OD34 Herpes Simplex Virus Keratitis; OD35 Herpes Zoster Keratitis; OD36 Acanthamoeba Keratitis; OD37 Recurrent Corneal Erosion; OD38 Exposure Keratopathy; OD39 Neurotrophic Keratopathy; OD40 Peripheral Ulcerative Keratitis; OD41 Pterygium; OD42 Pinguecula; OD43 Pinguecultitis; OD44 Contact Lens Overwear; OD45 Corneal Transplant Graft Rejection (CTGR); OD46 Keratoconus; OD47 Acute Angle Closure Glaucoma; OD48 Glaucoma Drop Allergy; OD49 Anisocoria; OD50 Homer; OD51 Third Nerve Palsy; OD52 Fourth/Fifth Nerve Palsy; OD53 Bell's Palsy; OD54 Iritis; OD55 Cataract; and OD56 Ophthalmic Post Operative Complications.

Specification of Mobile Smartphone Systems and Mobile Services for Automated Ocular Disease (OD) Treatment and Management Prescription to the Mobile Smartphone Systems Deployed on the System Network of the Present Invention Along with the automatically recognized ocular disease condition, the system will automatically prescribe and display an appropriate course of treatment and management for the system to track and help manage in response to the patient's compliance with the prescribed course of treatment and staged management. FIGS. 57A, 57B and 57C show a list of exemplary prescriptions and treatments for ocular diseases (OD) associated with the anterior segment of the human eye, that can be automatically prescribed by the system of the present invention using the patient's mobile smartphone device registered with the system. In the illustrative embodiments of the present invention, these various ocular disease (OD) treatment and management recommendations are coded as follows:

Treatment and Management Recommendations

TM01: Refer to eye doctor non-urgently

TM02: Refer to eye doctor urgently

TM03: Recommend radiologic imaging

TM04: Recommend warm compresses

TM05: Recommend artificial tears

TM06: Recommend surgery

TM07: Refer to emergency room

TM08: Recommend antibiotic/steroid combo ointment

TM09: Recommend artificial tear ointment

TM10: Recommend epilation (removal of eye lashes)

TM11: Recommend cryotherapy to eyelashes

TM12: Botulinum toxin injection

TM13: Recommend cold compresses

TM14: Recommend oral antibiotics

TM15: Recommend lacrimal system probe and irrigation

TM16: Recommend antibiotic/steroid combo drops

TM17: Recommend autoimmune work-up

TM18: Recommend intravenous antibiotics

TM19: Recommend oral steroids

TM20: Recommend cool compresses

TM21: Recommend endocrine work-up

TM22: Recommend eyelid hygiene

TM23: Recommend oral antiviral agents

TM24: Recommend intravenous antiviral agents

TM25: Recommend topical antiviral drops

TM26: Recommend topical antibiotic drops

TM27: Recommend topical antibiotic ointment

TM28: Recommend oral anti-histamine

TM29: Recommend topical anti-histamine drops

TM30: Recommend amniotic membrane placement

TM31: Recommend topical cyclosporine drops

TM32: Recommend oral ibuprofen

TM33: Recommend steroid drops

TM34: Recommend oral steroid sparing immunosuppressants

TM35: Recommend corneal cultures

TM36: Recommend fortified topical antibiotic drops

TM37: Recommend topical anti-parasitic drops

TM38: Recommend topical propamidine isethionate drops

TM39: Recommend topical polyhexamethylene biguanide drops

TM40: Recommend diamond burr procedure

TM41: Recommend intravenous steroids

TM42: Recommend UV protection

TM43: Recommend break from wearing contact lenses

TM44: Recommend intraocular pressure lowering drops

TM45: Recommend oral intraocular pressure lowering agents

TM46: Recommend intravenous intraocular pressure lowering agents

TM47: Recommend changing intraocular pressure lowering drop

TM48: Recommend laser procedure

TM49: Recommend ultrasound of eye

TM50: Recommend antibiotic injections into eye

TM26: Recommend topical antibiotic drops

TM27: Recommend topical antibiotic ointment

TM28: Recommend oral anti-histamine

TM29: Recommend topical anti-histamine drops

TM30: Recommend amniotic membrane placement

TM31: Recommend topical cyclosporine drops

TM32: Recommend oral ibuprofen

TM33: Recommend steroid drops

TM34: Recommend oral steroid sparing immunosuppressants

TM35: Recommend corneal cultures

TM36: Recommend fortified topical antibiotic drops

TM37: Recommend topical anti-parasitic drops

TM38: Recommend topical propamidine isethionate drops

TM39: Recommend topical polyhexamethylene biguanide drops

TM40: Recommend diamond burr procedure

TM41: Recommend intravenous steroids

TM42: Recommend UV protection

TM43: Recommend break from wearing contact lenses

TM44: Recommend intraocular pressure lowering drops

TM45: Recommend oral intraocular pressure lowering agents

TM46: Recommend intravenous intraocular pressure lowering agents

TM47: Recommend changing intraocular pressure lowering drop

TM48: Recommend laser procedure

TM49: Recommend ultrasound of eye

TM50: Recommend antibiotic injections into eye

Specification of Mobile Smartphone Systems and Mobile Services Used to Collect and Deliver Daily Treatment Response Data to the System Network of the Present Invention FIG. 249 shows an exemplary GUI screen displayed on a mobile smartphone system of the present invention for use when managing daily ocular disease treatment response operations over the system network of the present invention.

FIG. 250 shows a data records collected from the patient during this phase of treatment/management care using the system network, namely: Compliance (CP01 Medication, CP02 Image/Video, CP03 Symptoms, CP04 Vision, and CP05 Depression); Exam In-Office Testing; Risk Factors; Systems Functionality and Environmental Factors; Image and Videos of the Eyes of the Patient; and Remote/Mobile Vision Testing using the patient's smartphone system deployed on and linked to the system network.

Specification of Mobile Smartphone Systems and Mobile Services Used to Collect Daily Image and Video Capture of the Patient's Eyes for Transmission and Delivery to the System Network of the Present Invention FIG. 251 shows an exemplary GUI screen displayed on a mobile smartphone system of the present invention for use during daily photo and video capture of the patient's eyes and transmittal to the machine-vision processing servers maintained on the system network of the present invention.

Specification of the System Network of the Present Invention Deploying the Automotive Systems with Onboard Ophthalmic Image Capturing and Processing Subsystems Configured and Trained to Support Real-Time Automated Machine-Assisted Recognition of Ocular Disease (OD) Conditions in the Eyes of the Automotive System Drivers FIG. 252 shows the system network of the present invention 10 deploying one or more automotive systems 400, each provided with an onboard ophthalmic image capturing and processing subsystem 10 supporting real-time automated machine-assisted recognition of dry eye conditions in the eyes of the automotive system driver, including dry eye disease. As shown in FIG. 252, the system 10 comprises: (i) digital image (i.e. video) capturing systems 11 embedded within automotive systems and configured for use by patients/drivers whose eyes are to be automatically monitored and cared for using the automated system of the present invention, and its automated methods of machine-vision processing of digital images (i.e. video) of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the automotive vehicles carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 252, each automotive system 400 deployed on and served by the system network 10 comprises: an automotive vehicle 400; a digital image (i.e. video) capturing system 11 mounted within the automotive vehicle (e.g. visor or vehicle cabin) adapted for capturing digital images of the eyes of the driver the automotive system while driving the vehicle; and automated ophthalmic image capturing and processing system 13, 14 and 15 for receiving and processing the digital images so as to support automated machine-assisted recognition of ocular disease conditions in the eyes of the automotive system driver, including dry eye disease (DED) conditions, as described herein. The digital image capturing system 11 can be embedded within a heads-up display (HUD) unit installed in the automobile, or anywhere within or outside the automobile so as to provide a field of view (FOV) onto the eyes of the driver for digital image formation and capture using visible wavelengths of light, and/or infra-red wavelengths of light, as the application may require during night-time vehicle driving. User/driver authentication systems can be provided within the automobile system to authenticate the user/driver during each driving session, and then using this authentication to identify and index all digital images captured from a specified identified driver, and transmitted to the remote (or embedded) machine-vision servers 13, 14, 15 in compliance with health and medical record laws that may be operational within the jurisdiction where the present invention is being practiced.

Such automotive systems can be passenger vehicles, public and private buses, tractor-trailer vehicles, and any kind of automotive vehicle carrying passengers and/or cargo, or simple a single driver. The onboard ophthalmic vision systems of the present invention could also be installed in autonomous vehicles driven by robotic systems, sensors, GPS-navigation and like systems, where human passengers are either passengers and/or supervisors.

Specification of the System Network of the Present Invention Deploying the Aircraft Systems with Onboard Ophthalmic Image Capturing and Processing Subsystems Configured and Trained to Support Real-Time Automated Machine-Assisted Recognition of Ocular Disease (OD) Conditions in the Eyes of the Aircraft Pilots FIG. 253 shows the system network of the present invention 10 deploying one or more aircraft systems. 500, each provided with an onboard ophthalmic image capturing and processing subsystem 10 supporting real-time automated machine-assisted recognition of ocular disease (OD) conditions in the eyes of the aircraft pilot, including dry eye disease. As shown the system 10 comprises: (i) digital image capturing systems 11 embedded within the aircraft systems for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the aircraft vehicles carrying GNSS receivers adapted for GNSS signal processing and geolocation services; (v) a data center 16 supporting web, application and database servers 16A, 16B 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 253, each aircraft system deployed on and serviced by the system network 10 comprises: an aircraft vehicle 500; a digital image capturing system 11 mounted within the aircraft vehicle for capturing digital images of the eyes of the pilot of the aircraft system; and automated ophthalmic image capturing and processing system 13, 14 and 15 receiving and processing the digital images so as to support automated machine-assisted recognition of ocular disease conditions in the eyes of the aircraft pilot. The digital image capturing system 11 can be embedded within a heads-up display (HUD) unit installed in the aircraft, or anywhere within or outside the aircraft so as to provide a field of view (FOV) onto the eyes of the pilot for digital image formation and capture using visible wavelengths of light, and/or infra-red wavelengths of light, as the application may require during night-time flying. User/driver authentication systems can be provided within the aircraft system to authenticate the user/driver during each flight session, and then using this authentication to identify and index all digital images captured from a specified identified piolet, and transmitted to the remote (or embedded) machine-vision servers 13, 14, 15 in compliance with health and medical record laws that may be operational within the jurisdiction where the present invention is being practiced.

Such aircraft systems can be passenger aircraft systems, public and private passenger aircrafts, and any kind of automotive vehicle carrying passengers and/or cargo, or simple a single solo flying pilot as the case may be. The onboard ophthalmic vision systems of the present invention can also be installed in autonomously navigated aircraft systems driven by robotic flight systems, sensors, GPS-navigation and like systems, where human pilots are either copilots and/or supervisors.

Specification of the System Network of the Present Invention Deploying the Industrial Machinery Systems with Onboard Ophthalmic Image Capturing and Processing Subsystems Configured and Trained to Support Real-Time Automated Machine-Assisted Recognition of Ocular Disease (OD) Conditions in the Eyes of the Machinery Operators FIG. 254 shows the system network of the present invention 10 deploying one or more industrial machinery systems 600, each provided with an onboard ophthalmic image capturing and processing subsystem 10 supporting real-time automated machine-assisted recognition of ocular disease (OD) conditions in the eyes of the operator. As shown, the system 10 comprises: (i) digital image capturing systems 11 embedded within the industrial machinery systems for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations and third-party data provider platforms; (iv) a global navigation satellite system (GNSS) 19 comprising a constellation of GNSS satellites 19A, 19B, 19C, 19D orbiting around the earth for GPS positioning of objects carrying GNSSS receivers (or GNSS transceivers); (v) a data center 16 supporting web, application and database servers 16A, 16B 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 254, each industrial machinery system deployed on and serviced by the system network 10 comprises: an industrial machinery 600; a digital image capturing system 11 mounted about the industrial machine for capturing digital images of the eyes of the operator of the industrial machinery; and automated ophthalmic image capturing and processing system 13, 14 and 15 receiving and processing the digital images so as to support automated machine-assisted recognition of ocular disease conditions in the eyes of the operator. The digital image capturing system 11 can be embedded within a heads-up display (HUD) unit installed in the machinery system, or anywhere within or outside the machinery so as to provide a field of view (FOV) onto the eyes of the operator for digital image formation and capture using visible wavelengths of light, and/or infra-red wavelengths of light, as the application may require during night-time operation. User/driver authentication systems can be provided within the machinery system to authenticate the user/driver during each working session, and then using this authentication to identify and index all digital images captured from a specified identified operator, and transmitted to the remote machine-vision servers 13, 14, 15 in compliance with health and medical record laws that may be operational within the jurisdiction where the present invention is being practiced.

Such industrial machinery systems may be forklift vehicular systems used to move freight around in warehouses, on docks and at airports, as well as heavy equipment such as payloaders, dump trucks, cranes, cement mixers, trailers, as the case may be. The onboard ophthalmic vision monitoring systems of the present invention can also be installed in in any kind of industrial or commercial equipment where human operators require good quality vision to safely operate their equipment without undue risk of injury, accident or harm.

Specification of the System Network of the Present Invention Deploying the Office Workstation Systems with Onboard Ophthalmic Image Capturing and Processing Subsystems Configured and Trained to Support Real-Time Automated Machine-Assisted Recognition of Ocular Disease (OD) Conditions in the Eyes of the Workstation Workers FIG. 255 shows of the system network of the present invention 10 deploying one or more office workstation systems 700, each provided with an onboard ophthalmic image capturing and processing subsystem 10 supporting real-time automated machine-assisted recognition of dry eye conditions in the eyes of the worker. As shown, the system 10 comprises: (i) digital image capturing systems 11 embedded within an office or workplace/office workstation system, for use by human users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven dry eye disease (DED) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of objects carrying GNSSS receivers (or GNSS transceivers); (v) a data center 16 supporting web, application and database servers 16A, 16B 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 255, each office computer workstation 700 deployed on and serviced by the system network 10 comprises: an computer workstation 700 having a video display monitor and computer graphics engine with graphical processing units (GPUs); a digital image capturing system 11 mounted within the computer workstation for capturing digital images of the eyes of the operator of the computer workstation; and automated ophthalmic image capturing and processing system 13, 14 and 15 receiving and processing the digital images so as to support automated machine-assisted recognition of ocular disease conditions in the eyes of the operator. The digital image capturing system

11 can be embedded within a heads-up display (HUD) unit installed in the computer workstation system, or anywhere nearby the system, so as to provide a field of view (FOV) onto the eyes of the operator for digital image formation and capture using visible wavelengths of light, and/or infra-red wavelengths of light, as the application may require during night-time operation. User/driver authentication systems can be provided within the workstation system to authenticate the user/driver during each working session, and then using this authentication to identify and index all digital images captured from a specified identified worker, and transmitted to the remote machine-vision servers 13, 14, 15 in compliance with health and medical record laws that may be operational within the jurisdiction where the present invention is being practiced.

Such office workstation systems may be ordinary computer workstation systems used business offices, health centers, schools, hospitals, and even remote office workstations, as the case may be. The onboard ophthalmic vision monitoring systems of the present invention can also be installed in any kind of computer workstation that supports a visual display monitor, with an embedded digital camera system, configured for supporting video-conferencing, as well as the video and image capturing functions required by ophthalmic monitoring, diagnostic and care system of the present invention.

Specification of the System Network of the Present Invention Deploying the Laptop Computer Systems with Onboard Ophthalmic Image Capturing and Processing Subsystems Configured and Trained to Support Real-Time Automated Machine-Assisted Recognition of Ocular Disease (OD) Conditions in the Eyes of the System Users FIG. 256 shows the system network of the present invention 10 deploying one or more laptop computer systems 800, each provided with an onboard ophthalmic image capturing and processing subsystem 10 supporting real-time automated machine-assisted recognition of dry eye conditions in the eyes of the user. As shown, the system 10 comprises: (i) digital image capturing systems 11 embedded in the laptop computer systems, for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS 19A, 19B, 19C, 19D orbiting around the earth for GPS positioning of the laptop computers carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 256, each mobile laptop computer system 800 deployed on and serviced by the system network 10 of the present invention comprises: a mobile computer 800 having a video display and computer graphics engine with graphical processing units (GPUs); a digital image capturing system 11 mounted within the computer system for capturing digital images of the eyes of the operator of the computer system; and automated ophthalmic image capturing and processing system 13, 14 and 15 receiving and processing the digital images so as to support automated machine-assisted recognition of ocular disease conditions in the eyes of the operator. The digital image capturing system 11 can be embedded within a display unit installed in the laptop computer system, so as to provide a field of view (FOV) onto the eyes of the pilot for digital image formation and capture using visible wavelengths of light, and/or infra-red wavelengths of light, as the application may require during night-time use. User/driver authentication systems can be provided within the laptop system to authenticate the user during each work session, and then using this authentication to identify and index all digital images captured from a specified identified user, and transmitted to the remote (or embedded) machine-vision servers 13, 14, 15 in compliance with health and medical record laws that may be operational within the jurisdiction where the present invention is being practiced.

Such laptop systems may be ordinary laptop computer systems, as well as tablet computer systems, that may be used business offices, health centers, schools, hospitals, and even remote office workstations, as the case may be, as well as on the road by remote employees and consultants. The onboard ophthalmic vision monitoring systems of the present invention can also be installed in any kind of laptop computer system that supports a visual display monitor, with an embedded digital camera system, configured for supporting video-conferencing, as well as the video and image capturing functions required by ophthalmic monitoring, diagnostic and care system of the present invention.

Specification of the System Network of the Present Invention Deploying the Video Game Systems with Onboard Ophthalmic Image Capturing and Processing Subsystems Configured and Trained to Support Real-Time Automated Machine-Assisted Recognition of Ocular Disease (OD) Conditions in the Eyes of the Video System Gamers FIG. 257 shows the system network of the present invention 10 deploying one or more video game systems 900, each provided with an onboard ophthalmic image capturing and processing subsystem 10 supporting real-time automated machine-assisted recognition of dry eye conditions in the eyes of the gamer. As shown, the system 10 comprises: (i) digital image capturing systems 11 embedded within the video game systems, for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the video game consoles carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 257, each video game system 900 deployed on and serviced by the system network of the present invention 10 comprises: an video game workstation 900 having a video display and computer graphics engine with graphical processing units (GPUs); a digital image capturing system 11 mounted within the video game workstation for capturing digital images of the eyes of the gamer using the video game workstation; and automated ophthalmic image capturing and processing system 13, 14 and 15 receiving and processing said digital images so as to support automated machine-assisted recognition of ocular disease conditions in the eyes of the gamer. The digital image capturing system 11 can be embedded within a display unit installed in or with the video game system, so as to provide a field of view (FOV) onto the eyes of the gamer for digital image formation and capture using visible wavelengths of light, and/or infra-red wavelengths of light, as the application may require during night-time use. User authentication systems can be provided within the video game system to authenticate the user during each play session, and then using this authentication to identify and index all digital images captured from a specified identified user, and transmitted to the remote (or embedded) machine-vision servers 13, 14, 15 in compliance with health and medical record laws that may be operational within the jurisdiction where the present invention is being practiced.

Such video game systems may be conventional video game systems, as well as video simulation training systems, that are used in homes, schools, military, industry, and elsewhere around the world. Such video game systems may or may not support virtual reality and/or augmented reality (AR) applications, including the use of VR/AR display headsets (e.g. Facebook Occulas™ VR Display System), smart glasses (e.g. Google Glass™ Smart Glasses System)—optical head-mounted display designed in the shape of a pair of glasses), and smart contact lens systems well known and continually emerging in the art. The embedded ophthalmic vision monitoring systems of the present invention can also be installed in any kind of video game system that supports a visual display monitor, with an embedded and/or external digital camera system, configured for supporting video-game play, as well as the video and image capturing functions required by ophthalmic monitoring, diagnostic and care system of the present invention.

Specification of the System Network of the Present Invention Deploying the Telemedicine/Telehealth Systems with Onboard Ophthalmic Image Capturing and Processing Subsystems Configured and Trained to Support Real-Time Automated Machine-Assisted Recognition of Ocular Disease (OD) Conditions in the Eyes of the Remote Patients/Users FIG. 258 is a schematic representation of the system network of the present invention deploying one or more telemedicine/telehealth systems, each provided with an onboard ophthalmic image capturing and processing subsystem supporting real-time automated machine-assisted recognition of dry eye and other ocular disease conditions in the eyes of the patient/user, and showing: (i) digital image capturing systems 11 (e.g. smartphone camera system) for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the video game consoles carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 258, each telemedicine/telehealth system deployed on and serviced by the system network 10 of the present invention comprises: a mobile computing system (e.g. having a video display and computer graphics engine with graphical processing units (GPUs); a digital image capturing system 11 mounted within the mobile computing system for capturing digital images of the eyes of the patient/user; and automated ophthalmic image capturing and processing system 13, 14 and 15 receiving and remotely processing the digital images so as to support automated machine-assisted recognition of ocular disease conditions in the eyes of the patient/user.

Such telemedicine/telehealth systems may be deployed in homes, schools, businesses, retail stores, nursing homes, athletic fields, the outdoors or wilderness, almost anywhere human beings live, work or play and may require routine and/or emergency eye case. The onboard ophthalmic vision monitoring systems of the present invention can also be deployed from in any kind of mobile computing system or device (e.g. mobile smartphone device) that supports a visual display, and an embedded digital camera system, configured for supporting video-conferencing, as well as the video and image capturing functions required by ophthalmic monitoring, diagnostic and care system of the present invention.

Specification of the System Network of the Present Invention Deploying the Smart Television Systems with an Onboard Ophthalmic Image Capturing and Processing Subsystem Configured and Trained to Support Real-Time Automated Machine-Assisted Recognition of Ocular Disease (OD) Conditions in the Eyes of the Smart Television Viewer/User FIG. 259 is a schematic representation of the system network of the present invention deploying one or more smart television (TV) systems 1000, each provided with an onboard ophthalmic image capturing and processing subsystem 13, 14 and 15 supporting real-time automated machine-assisted recognition of dry eye and other ocular disease conditions in the eyes of the viewer, and showing: (i) digital image capturing systems 11 embedded within the television system, for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the video game consoles carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 259, each smart television (TV) system 1000 deployed on and serviced by the system network 10 comprises: a smart television module 1000 having a video display and computer graphics engine with graphical processing units (GPUs); a digital image capturing system 11 mounted within the video display monitor for capturing digital images of the eyes of the viewer of the smart television system; and automated ophthalmic image capturing and processing system 13, 14 and 15 receiving and processing the digital images so as to support automated machine-assisted recognition of ocular disease conditions in the eyes of the viewer. The digital image capturing system 11 can be embedded within the smart television system, or anywhere near the system, so as to provide a field of view (FOV) onto the eyes of the operator for digital image formation and capture using visible wavelengths of light, and/or infra-red wavelengths of light, as the application may require during night-time operation. User/driver authentication systems can be provided within the smart television system to authenticate the user/driver during each viewing session, and then using this authentication to identify and index all digital images captured from a specified identified operator, and transmitted to the remote machine-vision servers 13, 14, 15 in compliance with health and medical record laws that may be operational within the jurisdiction where the present invention is being practiced.

Such smart television systems may be deployed in homes, schools, businesses, retail stores, nursing homes, almost anywhere human beings live, work or play and may require routine and/or emergency eye case. The onboard ophthalmic vision monitoring systems of the present invention can also be deployed from in any kind of smart television system that supports a visual display, and an embedded digital camera system, configured for supporting video-conferencing, as well as the video and image capturing functions required by ophthalmic monitoring, diagnostic and care system of the present invention.

Specification of the System Network of the Present Invention Deploying the Smart Glasses Systems with Onboard Ophthalmic Image Capturing and Processing Subsystems Configured and Trained to Support Real-Time Automated Machine-Assisted Recognition of Ocular Disease (OD) Conditions in the Eyes of the Smart Glasses Wearer/User FIG. 260 is a schematic representation of the system network of the present invention deploying one or more smart glasses systems 1100, each provided with an onboard ophthalmic image capturing and processing subsystem 13, 14 and 15 supporting real-time automated machine-assisted recognition of dry eye and other ocular disease conditions in the eyes of the wearer, and showing (i) digital image capturing systems 11 embedded into the smart glasses, for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the video game consoles carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 260, each smart glasses system 1100 deployed on and serviced by the system network 10 of the present invention comprises: a smart glasses 1100 having a small video display mounted within a framework, adapted to be worn by a user, and micro-computing system with a computer graphics engine having graphical processing units (GPUs); a digital image capturing system 11 mounted within the framework worn by the user for capturing digital images of the eyes of the user; and automated ophthalmic image capturing and processing system 13, 14 and 15 receiving and remotely processing the digital images so as to support automated machine-assisted recognition of ocular disease conditions in the eyes of the user. In this illustrative embodiment, the digital capturing system 11 can be embedded within the smart glasses (e.g. Google Glass™ head-mounted display system) so as to provide a field of view (FOV) onto the eyes of the wearer for digital image formation and capture using visible wavelengths of light, and/or infra-red wavelengths of light, as the application may require during night-time operation. User/wearer authentication systems can be provided within the smart glasses system to authenticate the user/driver during each session, and then using this authentication to identify and index all digital images captured from a specified identified users/wearer, and transmitted to the remote machine-vision servers 13, 14, 15 in compliance with health and medical record laws that may be operational within the jurisdiction where the present invention is being practiced.

Such smart glasses systems may be deployed in homes, schools, businesses, retail stores, nursing homes, athletic fields, the outdoors or wilderness, almost anywhere human beings live, work or play and may require routine and/or emergency eye case. Exemplary smart glasses headsets that can be adapted, modified and operated in accordance with the principles of the present invention include the Google Glass™ Smart Glasses System, and other smart VR/AR glasses being developed, commercially available or otherwise well known in the art. In general, the embedded ophthalmic vision monitoring systems of the present invention can also be deployed from in any kind of smart glasses system that supports a visual display typically in head-supported framework, and an embedded digital camera system, configured for supporting video-conferencing, as well as the video and image capturing functions required by ophthalmic monitoring, diagnostic and care system of the present invention.

Specification of the System Network of the Present Invention Deploying the Smart Contact Lens Systems with Onboard Ophthalmic Image Capturing and Processing Subsystems Configured and Trained to Support Real-Time Automated Machine-Assisted Recognition of Ocular Disease (OD) Conditions in the Eyes of the Smart Contact Lens Wearer/User FIG. 261 is a schematic representation of the system network of the present invention deploying one or more smart contact lens systems 1200, each provided with an onboard ophthalmic image capturing and processing subsystem 13, 14 and 15 supporting real-time automated machine-assisted recognition of dry eye and other ocular disease conditions in the eyes of the wearer, and showing: (i) digital image capturing systems 11 embedded into the smart contact lens, for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the video game consoles carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 261, each smart contact lens system 1200 deployed on and serviced by the system network of the present invention 10 comprises: a smart (soft) contact lens 1200 adapted to be worn on the eye of a user to provide a support framework for other components; an embedded miniature display surface supported within or by the contact lens for displaying images to the retina of the user/wearer; a micro-computing system with a computer graphics engine having graphical processing units (GPUs) for generating and rendering digital images to be displayed on the embedded miniature display surface; a miniature digital image capturing system 11 embedded within or supported by the smart contact lens, adapted for capturing digital images of the eyes of the user while wearing the soft contact lens on the user's eye; and automated ophthalmic image capturing and processing system 13, 14 and 15 receiving and remotely processing the digital images so as to support automated machine-assisted recognition of ocular disease conditions in the eyes of the user. In this application, the digital image capturing system 11 provides a field of view (FOV) onto the eyes of the operator for digital image formation and capture using visible wavelengths of light, and/or infra-red wavelengths of light, as the application may require during night-time operation. User/wearer authentication systems can be provided within the system to authenticate the user/wearer during each session, and then using this authentication to identify and index all digital images captured from a specified identified wearer, and transmitted to the remote machine-vision servers 13, 14, 15 in compliance with health and medical record laws that may be operational within the jurisdiction where the present invention is being practiced.

Such smart contact lens systems may be worn by anyone and deployed in homes, schools, military, businesses, retail stores, nursing homes, athletic fields, the outdoors or wilderness, almost anywhere human beings live, work or play and may require routine and/or emergency eye case. In general, the embedded ophthalmic vision monitoring system of the present invention can also be deployed in any kind of smart contact lens device that supports a visual display, and an embedded digital camera system, configured for supporting video and image capturing functions required by ophthalmic monitoring, diagnostic and care system of the present invention.

Specification of the System Network of the Present Invention Deploying the Virtual Reality (VR)/Augmented Reality (AR) Systems with Onboard Ophthalmic Image Capturing and Processing Subsystems Configured and Trained to Support Real-Time Automated Machine-Assisted Recognition of Ocular Disease (OD) Conditions in the Eyes of the VR/AR Equipment Wearer/User FIG. 262 is a schematic representation of the system network of the present invention deploying one or more VR/AR headset systems 1300, each provided with an onboard ophthalmic image capturing and processing subsystem supporting real-time automated machine-assisted recognition of dry eye and other ocular disease conditions in the eyes of the AR/VR equipment wearer/user, and showing: (i) digital image capturing systems 11 embedded within an AR/VR headset, for use by patients and users whose eyes are to be automatically monitored and cared for using the automated system of the present invention, and its automated methods of machine-vision processing of digital images of the user's eyes in accordance with the principles of the present invention; (ii) remote clinical ophthalmic decision workstations 12, and real-time ophthalmic image driven ocular disease (OD) condition recognition engines 13, 14 and 15 realized and supported within data centers 16 deployed around the world; (iii) local environmental monitoring stations 17 and third-party data provider platforms 18; (iv) a global navigation satellite system (GNSS) 19 comprising a constellation of GNSS satellites 19A, 19B, 19C, 19D orbiting around the earth for GPS positioning of the video game consoles carrying GNSS receivers adapted for GNSS signal processing and geolocation services; (v) a data center 16 supporting web, application and database servers 16A, 16B, 16C to support the functions and services to be delivered by the system network of the present invention including a machine-vision driven ocular disease (OD) recognition engines 13, 14 and 15; and (v) a TCP/IP internet infrastructure (i.e. cloud infrastructure) 20 supporting a wireless digital data packet-switched communication infrastructure to support the many systems integrated within the system network of the present invention.

As shown in FIG. 262, each VR/AR display/experience system 1300 deployed on and serviced by the system network of the present invention 10 comprises: a computing system 1300 having a video display and computer graphics engine with graphical processing units (GPUs); a digital image capturing system 11 mounted within a headset worn by a user of the computing system for capturing digital images of the eyes of the user; and an automated ophthalmic image capturing and processing system 13, 14 and 15 receiving and remotely processing the digital images so as to support automated machine-assisted recognition of ocular disease conditions in the eyes of the user. In this application, the digital image capturing system 11 provides a field of view (FOV) onto the eyes of the operator for digital image formation and capture using visible wavelengths of light, and/or infra-red wavelengths of light, as the application may require during night-time operation. User/wearer authentication systems can be provided within the system to authenticate the user/wearer during each session, and then using this authentication to identify and index all digital images captured from a specified identified wearer, and transmitted to the remote machine-vision servers 13, 14, 15 in compliance with health and medical record laws that may be operational within the jurisdiction where the present invention is being practiced.

Such VR/AR systems may be deployed in homes, schools, businesses, retail stores, nursing homes, athletic fields, the outdoors or wilderness, almost anywhere human beings live, work or play and may require routine and/or emergency eye case. Exemplary VR/AR display headsets that can be adapted, modified and operated in accordance with the principles of the present invention include, but are not limited to, the popular Facebook Occulas™ VR Display System, and other VR/AR systems commercially available or otherwise known in the art.

Specification of Applications for Systems, Methods, Devices and Networks of the Present Invention While visible-wavelength operating smartphone camera systems are shown in disclosed as being used to capture digital images of patient and system user eyes throughout the various illustrative embodiments of the present invention, it is understood that in alternative embodiments of the present invention, camera systems with image spectral bandwidth outside the visible band (e.g. infrared wavelengths and even ultra-violet) may be used to capture digital images of human eyes for processing, recognition, treatment and managed care, within accordance with the spirit of the present invention. In some applications, this would provide some advantages because various micro-vascular structures in the human eye are responsive and detectable at infrared wavelengths of light.

In the case of embedded-type ocular care systems, as illustrated in FIGS. 252 through 262, the use of infrared illumination and imaging in combination with visible-wavelength light illumination and imaging will offer many advantages including real-time diagnostic testing of eyes while subjects are operating or present in low levels of ambient illumination (i.e. lighting). Where desired or required, these supplemental illumination sources may be used to practice the many illustrative embodiments of the present invention as disclosed and taught herein, including the capturing and recording digital images embodying detailed structural features of human eyes that may be afflicted by any of the many ocular disease (OD) identified and specified herein, and for which detailed methods of automated ocular disease recognition, based on automated machine-vision pixel data processing, have been disclosed and taught herein for the specific applications and purposes described.

While the systems, methods, devices and networks of the present invention disclosed herein were shown and disclosed for use in remote/distributed and clinical telemedicine environments, it is understood that such systems, methods and devices can be used in many other applications, such as, including, for example: clinical trial support applications; pre-operative eye care environments; telemedicine diagnostics and application; urgent care centers; veterinary medicine; and any environment in which human beings work live, work and play.

Modifications of the Illustrative Embodiments of the Present Invention

The present invention has been described in great detail with reference to the above illustrative embodiments. It is understood, however, that numerous modifications will readily occur to those with ordinary skill in the art having had the benefit of reading the present disclosure.

For example, in alternative embodiments of the present invention described hereinabove, the system can be realized as a stand-alone application, or integrated as part of a larger system network possibly offering new and improved services to others. Such alternative system configurations will depend on particular end-user applications and target markets for products and services using the principles and technologies of the present invention.

These and all other such modifications and variations are deemed to be within the scope and spirit of the present invention as defined by the accompanying Claims to Invention.

What is claimed is:

1. A cloud-based system network for (i) machine-vision supported recognition, treatment and management of ocular conditions detected in the one or both eyes of human beings being treated as patients, specifically for dry eye disease (DED) conditions detected in the eyes of the human beings and severity of the detected DED conditions, and (ii) delivery of ocular care to the human beings as patients situated remotely on the Earth, including prescription of treatment and assessment of treatment response, said cloud-based system network comprising:

a plurality of mobile image capturing systems, selected from the group consisting of mobile smartphone camera systems, mobile camera systems and mobile image capturing devices, each said mobile image capturing system having an integrated camera subsystem with image formation optics and an optical sensor for forming and detecting said digital images using visible-wavelength sources of light illumination, and a graphical user interface (GUI) display surface supporting communication and augmented reality (AR) with a patient and/or user whose eyes are to be monitored using said integrated camera subsystem, and cared for using services supported over said cloud-based system network;

a data center supporting web, application and database servers connected to infrastructure of the Internet, to support functions and services to be delivered to patients and users by said cloud-based system network including an automated machine-vision driven ocular disease (OD) recognition engine;

a geolocation (GPS) tracking and linking subsystem for GPS-specified location tracking of systems and subsystems and workstations deployed on said cloud-based system network;

wherein said automated machine-vision driven ocular disease (OD) recognition engine comprises:

an automated digital image processing server realized within said data center, supporting processing of said digital images of said human eyes, and one or more clinical ophthalmic decision support subsystems realized as workstations, tablet computers and/or laptop workstations; and a database subsystem for storing data and maintaining data records for patients and users across the cloud-based system network;

wherein, in order to realize automated recognition of dry eye disease (DED) conditions present in human eyes, said automated machine-vision driven ocular disease (OD) recognition engine supports and enables one or more methods of automated detection and/or measurement selected from the group consisting of:

an automated detection and/or measurement of hyperemia of the human eyes;

an automated detection and/or measurement of tear film in the human eyes;

an automated detection and/or measurement of oily lid margin in the human eyes;

an automated detection and/or measurement of capped meibomian glands in the human eyes;

an automated detection and/or measurement of conjunctivochalasis in the human eyes;

an automated detection and/or measurement of eyelash crusting in the human eyes; and an automated detection and/or measurement of eyelid redness in the human eyes;

wherein said automated machine-vision driven ocular disease (OD) recognition engine comprises a deep neural network operating to process a series of digital images of the human eye formed, captured and detected by said mobile image capturing system, so as to enable automated machine-assisted recognition of (i) detected ocular disease (OD) conditions in the human eye including dry eye disease (DED) conditions and the severity thereof, and also the automated treatment and management of the detected ocular disease (OD) conditions;

wherein said automated machine-vision driven ocular disease (OD) recognition engine includes deep-learning machine-vision models employing multi-layer convolutional networks trained using digital images of eyes captured using visible wavelengths of light illumination, to provide an end-to-end system for processing and recognizing input digital images captured by said mobile image capturing system and indicating particular ocular diseases (OD), including dry eye disease (DED);

wherein said automated machine-vision ocular disease (OD) recognition engine further processes patient symptom data, and other ocular/patient factors, that contribute to specific grading of the severity of the dry eye disease (DED) condition recognized by said automated machine-vision driven ocular disease (OD) recognition engine;

wherein machine-based logic packages are installed and operative within said automated machine-vision driven ocular disease (OD) recognition engine and include (i) diagnostic logic for determining ocular diseases (OD)

based on disease diagnosis input factors provided to as input to said automated machine-vision driven ocular disease (OD) recognition engine, (ii) treatment logic for determining prescription of one or more of the ocular disease (OD) treatment and management recommendations for each ocular disease (OD) condition automatically determined by said automated machine-vision driven ocular disease (OD) recognition engine, and (iii) management logic for managing treatment of each recognized ocular disease condition recognized by said automated machine-vision driven ocular disease (OD) recognition engine; and wherein said one or more clinical ophthalmic decision support subsystems are operably connected to the Internet infrastructure, for use by eye care professionals, including doctors and medical technicians, for the purpose of reviewing and managing patient records maintained by said cloud-based system network and providing patient decision support in connection with delivery of dry eye disease (DED) diagnosis, treatment and management care services to human patients situated remotely on the Earth.

2. The cloud-based system network of claim 1, wherein each said mobile image capturing system is a mobile smartphone camera system, and said automated machine-vision driven ocular disease (OD) recognition engine supports practice of a digital imaging processing method for automatically recognizing dry eye disease (DED) conditions in humans comprising the steps of:

(a) automatically processing 2D in vivo digital images of the human eyes formed, captured and detected using visible-wavelength sources of light illumination and said mobile image capturing system;

(b) using said automated machine-vision driven ocular disease (OD) recognition engine for automatically processing said digital images and automatically detecting presence and location of specific objects in ocular surfaces in the human eye; and (c) confirming that specific conditions have been satisfied during said image processing to support automated dry eye disease (DED) condition recognition.

3. The cloud-based system network of claim 1, wherein said automated machine-vision driven ocular disease (OD) recognition engine supports displaying an augmented reality (AR) overlay GUI on the display screen of said mobile image capturing system for guiding capture of said digital images of the human eyes using visible wavelengths of light and said mobile image capturing system, and processing the digital images of the human eyes to detect and recognize dry eye disease (DED) conditions in the patient's eyes.

4. The cloud-based system network of claim 1, wherein said automated machine-vision driven ocular disease (OD) recognition engine comprises a deep neural network for building a deep-learning machine-vision recognition system capable of recognizing specific categories of ocular conditions (OD), including dry eye disease (DED), from a set of digital ocular images formed, captured and detected by said mobile image capturing system.

5. The cloud-based system network of claim 4, wherein said deep neural network operating to process a series of digital images of the human eye formed, captured and detected by said mobile image capturing system, so as to enable automated machine-assisted recognition of (i) dry eye disease (DED) conditions in the human eye and the severity thereof, and (ii) prescription of treatment of the dry eye disease (DED) conditions.

6. The cloud-based system network of claim 4, said deep neural network operating to process a series of digital images of the human eye formed, captured and detected by said mobile image capturing system, so as to enable automated machine-assisted recognition of (i) dry eye disease (DED) conditions in the human eye and the severity thereof, and (ii) prescribed treatment of said dry eye disease (DED) conditions, and (iii) assessment of said prescribed treatment.

7. The cloud-based system network of claim 1, wherein said automated machine-vision driven ocular disease (OD) recognition engine uses patient symptom data to automatically recognize a grade/severity of the dry eye disease (DED) condition(s) experienced by the patient.

8. The cloud-based system network of claim 1, wherein said mobile image capturing system is a mobile smartphone system configured for use by a patient to receive a dry eye disease (DED) diagnosis and course of prescribed treatment generated by said automated machine-vision driven ocular disease (OD) recognition engine.

9. The cloud-based system network of claim 1, wherein said automated machine-vision driven ocular disease (OD) recognition engine is configured for use in automatically monitoring and supporting decisions and prescription updates for effective treatment of the dry eye disease (DED) condition automatically recognized by said automated machine-vision driven ocular disease (OD) recognition engine.

10. The cloud-based system network of claim 1, wherein said automated machine-vision driven ocular disease (OD) recognition engine is configured for use in continuously monitoring the patient's DED condition and response to prescribed treatment, using said mobile image capturing system for forming and detecting digital images of patient's eyes that are processed by said automated machine-vision driven ocular disease recognition engine using visible-wavelength sources of light illumination.

11. The cloud-based system network of claim 1, wherein said automated machine-vision driven ocular disease (OD) recognition engine is configured so that compliance factors are continuously monitored, updated and supplied to the cloud-based system network so as to automatically measure prescribed treatment compliance and support decisions and prescription updates for effective treatment of a recognized dry eye disease (DED) condition.

12. The cloud-based system network of claim 1, wherein said automated detection and measurement of hyperemia (i.e. conjunctival injection) of the human eyes employs one or more methods selected from the group consisting of a method of detecting conjunctival injection, a method of detecting subconjunctival hemorrhage, a method of detecting episcleritis/scleritis, and a method of detecting superior limbic keratoconjunctivitis;

wherein said automated detection and measurement of tear film in the human eyes employs a method of detecting tear meniscus height;

wherein said automated detection and measurement of oily lid margin in the human eyes employs a method of detecting meibomian gland dysfunction;

wherein said automated detection and measurement of capped meibomian glands in the human eyes employs a method of detecting meibomian gland dysfunction;

wherein said automated detection and measurement of conjunctivochalasis in the human eyes employs a method of detecting conjunctivochalasis;

wherein said automated detection and measurement of eyelash crusting in the human eyes employs a method of detecting blepharitis; and wherein said automated detection and measurement of eyelid redness in the human eyes employs a method of detecting chalazion/stye, a method of detecting eyelid cysts and a method of detecting preseptal cellulitis.

13. The cloud-based system network of claim 1, wherein said automated machine-vision driven ocular disease (OD) recognition engine employs convolutional neural networks (CNNs) configured and trained for use and deployment on said cloud-based system network, and designed to support and enable automated detection and measurement of dry eye disease (DED) condition in the human eyes photographically represented in digital images of human eyes formed, captured and detected by said mobile image capturing system.

\* \* \* \* \*